(12) United States Patent
Takahashi et al.

(10) Patent No.: US 12,012,389 B2
(45) Date of Patent: Jun. 18, 2024

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO., LTD., Tokyo (JP)

(72) Inventors: Yusuke Takahashi, Sodegaura (JP); Tasuku Haketa, Sodegaura (JP); Shota Tanaka, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 18/329,687

(22) Filed: Jun. 6, 2023

(65) Prior Publication Data
US 2023/0312501 A1    Oct. 5, 2023

Related U.S. Application Data

(63) Continuation of application No. 17/810,443, filed on Jul. 1, 2022, now Pat. No. 11,795,155, which is a
(Continued)

(30) Foreign Application Priority Data

Nov. 5, 2020   (JP) .................. 2020-185314

(51) Int. Cl.
*C07D 307/91*   (2006.01)
*C07C 15/28*    (2006.01)
(Continued)

(52) U.S. Cl.
CPC ............ *C07D 307/91* (2013.01); *C07C 15/28* (2013.01); *C07C 15/38* (2013.01); *H10K 50/15* (2023.02);
(Continued)

(58) Field of Classification Search
CPC .. C07D 307/91; C07D 307/77; C07D 409/14; C07D 405/12; C07D 405/14;
(Continued)

(56) References Cited

U.S. PATENT DOCUMENTS

2010/0001636 A1   1/2010   Yabunouchi
2012/0112169 A1*  5/2012   Mizuki ................ H10K 85/633
                                               257/E51.026
(Continued)

FOREIGN PATENT DOCUMENTS

CN    108658932 A   10/2018
CN    108689972 A   10/2018
(Continued)

OTHER PUBLICATIONS

Office Action dated Jan. 6, 2023 in co-pending U.S. Appl. No. 17/810,443.
(Continued)

*Primary Examiner* — Caleb E Henry
(74) *Attorney, Agent, or Firm* — Oblon, McClelland, Maier & Neustadt, L.L.P.

(57) ABSTRACT

A compound represented by the following formula (1):

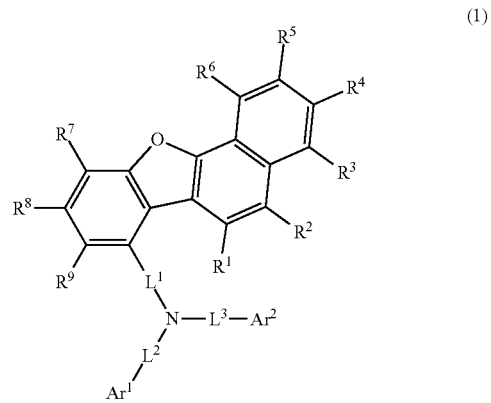

The $R^1$ to $R^9$, $L^1$ to $L^3$, and $Ar^1$ to $Ar^2$ in the formula (1) are as defined in the description. An organic electrolumines-
(Continued)

cence device contains the compound, and an electronic instrument includes the organic electroluminescence device.

36 Claims, 1 Drawing Sheet

Related U.S. Application Data continuation of application No. PCT/JP2021/040498, filed on Nov. 4, 2021.

(51) Int. Cl.
*C07C 15/38* (2006.01)
*H10K 50/12* (2023.01)
*H10K 50/15* (2023.01)
*H10K 85/60* (2023.01)

(52) U.S. Cl.
CPC ....... *H10K 85/622* (2023.02); *H10K 85/6574* (2023.02); *H10K 50/12* (2023.02)

(58) Field of Classification Search
CPC .... C07D 409/12; C07D 407/12; C07C 15/28; C07C 15/38; H10K 50/15; H10K 85/622; H10K 85/6574; H10K 50/12; H10K 50/156; H10K 85/615; H10K 85/626; H10K 85/631; H10K 85/633; H10K 85/636; H10K 85/6572; H10K 85/6576; H01L 51/5064; H01L 51/0072; H01L 51/0073; H01L 51/0074; H01L 51/0058; H01L 51/006; H01L 51/0061; H01L 51/0059; H01L 51/0052; H01L 51/0054; H01L 51/5056

See application file for complete search history.

(56) References Cited

U.S. PATENT DOCUMENTS

| 2013/0306945 | A1* | 11/2013 | Seo ........................ H10K 50/16 257/40 |
| 2014/0034930 | A1* | 2/2014 | Seo ........................ H10K 50/16 257/40 |
| 2015/0340623 | A1* | 11/2015 | Kawamura ........... C09B 69/008 257/40 |
| 2016/0028022 | A1* | 1/2016 | Seo ...................... C07D 403/14 257/40 |
| 2016/0093812 | A1* | 3/2016 | Stoessel ................. H10K 85/30 438/46 |
| 2018/0072695 | A1 | 3/2018 | Byun et al. |
| 2018/0083197 | A1 | 3/2018 | Park et al. |
| 2018/0130968 | A1* | 5/2018 | Ikeda ...................... C07C 15/28 |
| 2018/0277765 | A1* | 9/2018 | Yen ...................... H10K 85/624 |
| 2019/0006591 | A1 | 1/2019 | Yamaki et al. |
| 2019/0229270 | A1* | 7/2019 | Yen ...................... C07D 413/14 |
| 2020/0111965 | A1* | 4/2020 | Nakano ................ H10K 85/633 |
| 2020/0144516 | A1* | 5/2020 | Cao ...................... H10K 85/633 |
| 2020/0317637 | A1* | 10/2020 | Cooper ................ C07D 233/84 |
| 2021/0043850 | A1* | 2/2021 | Maeda ............... H10K 85/6574 |
| 2021/0122723 | A1 | 4/2021 | Zhang et al. |
| 2021/0167304 | A1* | 6/2021 | Scholz ................ H10K 85/611 |
| 2022/0255018 | A1* | 8/2022 | Takahashi ............ H10K 85/626 |
| 2023/0024273 | A1* | 1/2023 | Takahashi ............. C07C 211/54 |
| 2023/0047512 | A1* | 2/2023 | Ito ...................... H10K 85/6576 |

FOREIGN PATENT DOCUMENTS

| CN | 108947902 A | 12/2018 |
| CN | 110746391 A | 2/2020 |
| CN | 111253377 A | 6/2020 |
| JP | 2018-524289 A | 8/2018 |
| KR | 2019-0007789 A | 1/2019 |
| KR | 10-2076958 B1 | 2/2020 |
| KR | 2020-0053284 A | 5/2020 |
| KR | 2020-0056059 A | 5/2020 |
| WO | WO2009/145016 A1 | 12/2009 |
| WO | WO 2016/148425 A2 | 9/2016 |
| WO | WO 2017/022730 A1 | 2/2017 |
| WO | WO 2020/231197 A1 | 11/2020 |
| WO | WO 2021/060865 A1 | 4/2021 |
| WO | WO 2021/133016 A2 | 7/2021 |
| WO | WO 2022/009999 A2 | 1/2022 |

OTHER PUBLICATIONS

International Search Report dated Dec. 28, 2021, in PCT/JP2021/040498, filed Nov. 4, 2021 (3 pages).
Japanese Office Action dated Aug. 16, 2022, in Japanese Patent Application No. 2022-506515 (with English Translation).
Japanese Office Action dated Oct. 4, 2022, in Japanese Patent Application No. 2022-506515 (with English Translation).
Official Communication issued Feb. 20, 2024, in Japanese Patent Application No. 2022-198944 w/Attached Concise English Explanation.

* cited by examiner

COMPOUND, MATERIAL FOR ORGANIC ELECTROLUMINESCENT ELEMENT, ORGANIC ELECTROLUMINESCENT ELEMENT, AND ELECTRONIC DEVICE

CROSS-REFERENCE TO RELATED APPLICATIONS

This application is a continuation of U.S. patent application Ser. No. 17/810,443 filed on Jul. 1, 2022, which is a continuation of International Application No. PCT/JP2021/040498 filed on Nov. 4, 2021, and claims priority to Japanese Application No. 2020-185314 filed on Nov. 5, 2020, the disclosures of all of which are incorporated herein by reference in their entireties.

TECHNICAL FIELD

The present invention relates to a compound, a material for organic electroluminescence devices, an organic electroluminescence device, and an electronic instrument including the organic electroluminescence device.

BACKGROUND ART

In general, an organic electroluminescence device (hereinafter sometimes referred to as "organic EL device") is composed of an anode, a cathode, and an organic layer interposed between the anode and the cathode. In application of a voltage between the two electrodes, electrons from the cathode side and holes from the anode side are injected into a light emitting region, and the injected electrons and holes are recombined in the light emitting region to generate an excited state, which then returns to the ground state to emit light. Accordingly it is important, for providing a high-performance organic EL device, to develop a material that efficiently transports electrons or holes into a light emitting region to promote recombination of the electrons and holes.

PTLs 1 to 8 disclose compounds for use as a material for organic electroluminescence devices.

CITATION LIST

Patent Literature

PTL 1: KR 2076958 B1
PTL 2: KR 2019-0007789 A
PTL 3: CN 108689972 A
PTL 4: CN 108658932 A
PTL 5: CN 108947902 A
PTL 6: KR 2020-0056059 A
PTL 7: KR 2020-0053284 A
PTL 8: US 2018/0083197 A1

SUMMARY OF INVENTION

Technical Problem

Although many compounds for organic EL devices have conventionally been reported, a compound that further enhances performance of an organic EL device is still desired.

The present invention has been made for solving the above problem, and has an object to provide a compound that further improves performance of an organic EL device, an organic EL device having further improved device performance, and an electronic instrument including such an organic EL device.

Solution to Problem

As a result of intensive and extensive studies about the compounds disclosed in the above patent literatures and the performance of organic EL devices including the compounds, the present inventors have found that a monoamine represented by the following formula (1) provides an organic EL device having further improved device performance.

In an aspect, the present invention provides a compound represented by the following formula (1):

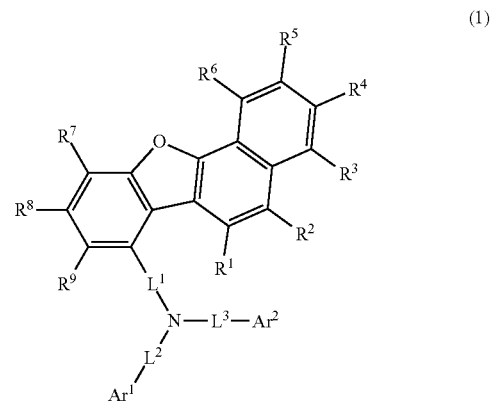

(1)

wherein
$R^1$ to $R^9$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, or a substituted or unsubstituted heterocyclic group having 5 to 50 ring atoms,
provided that
adjacent two selected from $R^1$ to $R^9$ are not bonded to each other, thus forming no ring structure,
$L^1$ is a substituted or unsubstituted arylene group having 6 to 30 ring carbon atoms or a substituted or unsubstituted divalent heterocyclic group having 5 to 30 ring atoms, and
$L^2$ and $L^3$ are each independently a single bond, a substituted or unsubstituted divalent heterocyclic group having 5 to 30 ring atoms, or a group represented by any of the following formulae (i) to (iii):

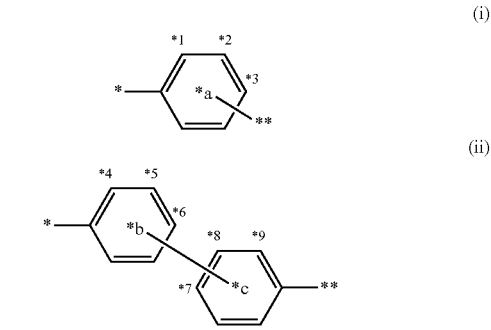

-continued

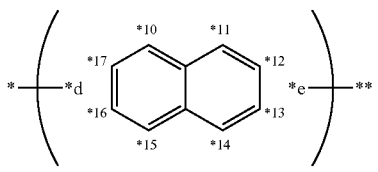
(iii)

wherein
*a is bonded to one selected from the carbon atoms *1 to *3,
*b is bonded to one selected from the carbon atoms *4 to *6,
*c is bonded to one selected from the carbon atoms *7 to *9,
*d is bonded to one selected from the carbon atoms *10 to *17, *e is bonded to another one selected from the carbon atoms *10 to *17,
\* represents a bonding site to the central nitrogen atom, and
\*\* represents a bonding site to $Ar^1$ or $Ar^2$, $Ar^1$ and $Ar^2$ are each independently a group represented by any of the following formulae (a) to (e):

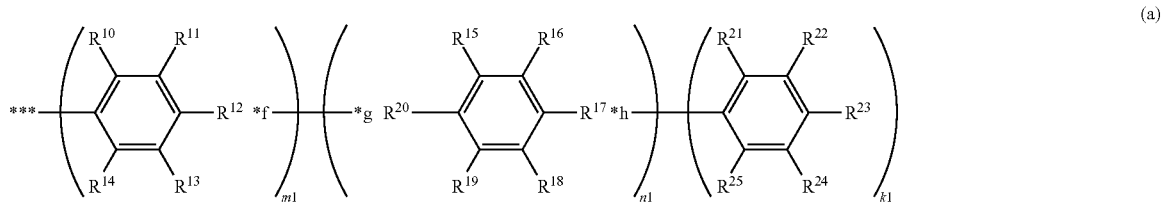
(a)

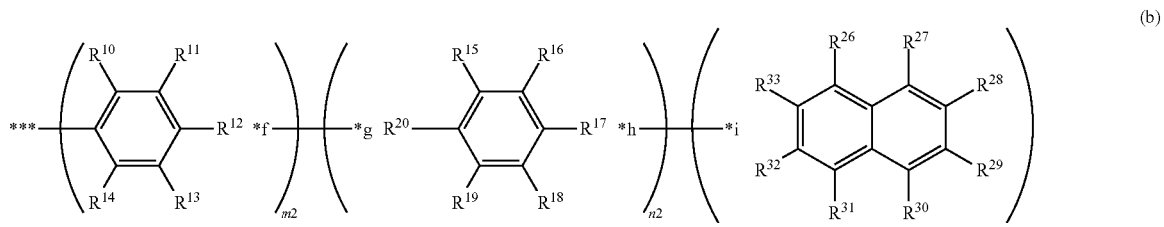
(b)

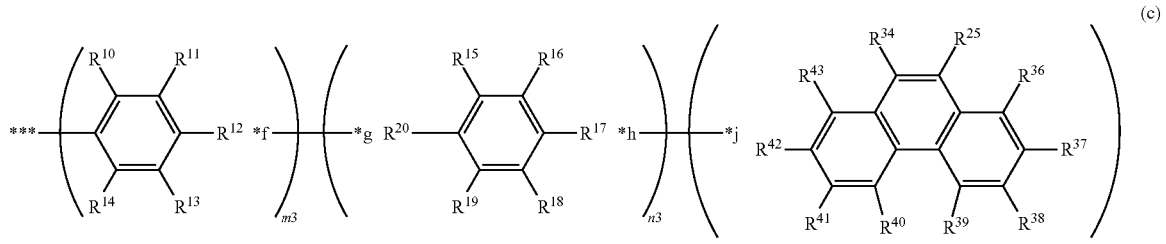
(c)

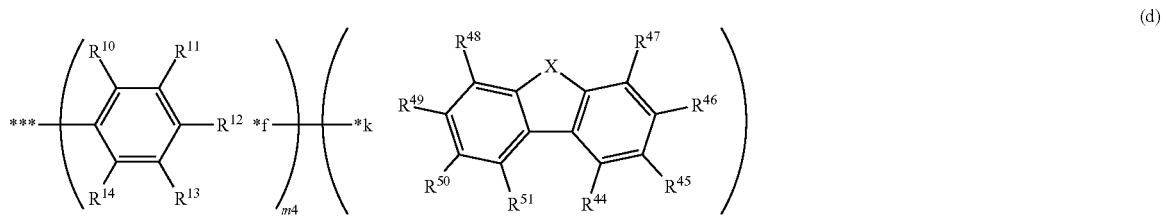
(d)

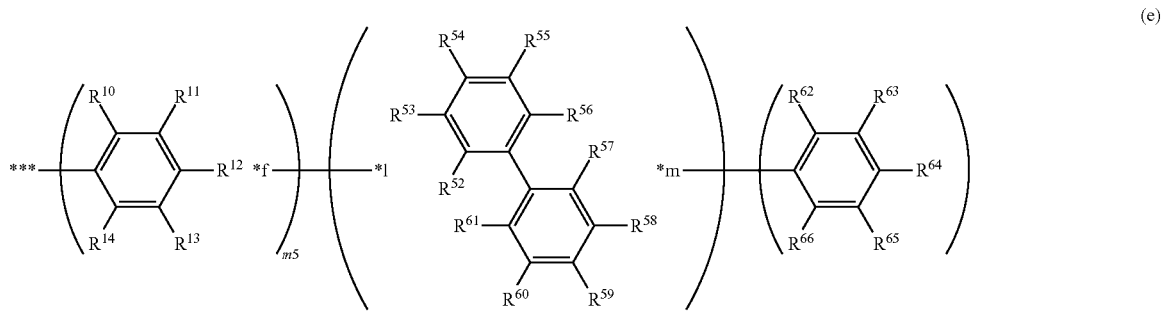
(e)

in the formula (a), $R^{10}$ to $R^{25}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms.

provided that one selected from $R^{10}$ to $R^{14}$ is a single bond bonded to *f, one selected from $R^{15}$ to $R^{20}$ is a single bond bonded to *g, another one selected from $R^{15}$ to $R^{20}$ is a single bond bonded to *h,

*** represents a bonding site to $L^2$ or $L^3$, m1 is 0 or 1, n1 is 0 or 1, when m1 is 0 and n1 is 0, *h is bonded to $L^2$ or $L^3$, when m1 is 0 and n1 is 1, *f is bonded to $L^2$ or $L^3$, when m1 is 1 and n1 is 0, one selected from $R^{10}$ to $R^{14}$ is a single bond bonded to *h, k1 is 1 or 2, and adjacent two selected from $R^{10}$ to $R^{14}$ that are not the single bond are, and adjacent two selected from $R^{15}$ to $R^{20}$ that are not either of the single bonds are, not bonded to each other, thus forming no ring structure;

in the formula (b), $R^{10}$ to $R^{20}$, *f, *g, *h, and *** are the same as described above, $R^{26}$ to $R^{33}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, provided that one selected from $R^{26}$ to $R^{33}$ is a single bond bonded to *i, m2 is 0 or 1, n2 is 0 or 1, when m2 is 0 and n2 is 0, *h is bonded to $L^2$ or $L^3$, when m2 is 0 and n2 is 1, *f is bonded to $L^2$ or $L^3$, when m2 is 1 and n2 is 0, one selected from $R^{10}$ to $R^{14}$ is a single bond bonded to *h, and adjacent two selected from $R^{10}$ to $R^{14}$ that are not the single bond are, and adjacent two selected from $R^{15}$ to $R^{20}$ that are not either of the single bonds are, not bonded to each other, thus forming no ring structure;

in the formula (c), $R^{10}$ to $R^{20}$, *f, *g, *h, and *** are the same as described above, $R^{34}$ to $R^{43}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, provided that one selected from $R^{34}$ to $R^{43}$ is a single bond bonded to *j, m3 is 0 or 1, n3 is 0 or 1, when m3 is 0 and n3 is 0, *h is bonded to $L^2$ or $L^3$, when m3 is 0 and n3 is 1, *f is bonded to $L^2$ or $L^3$, when m3 is 1 and n2 is 0, one selected from $R^{10}$ to $R^{14}$ is a single bond bonded to *h, and adjacent two selected from $R^{10}$ to $R^{14}$ that are not the single bond are, adjacent two selected from $R^{15}$ to $R^{20}$ that are not either of the single bonds are, and $R^{34}$ and $R^{35}$ are, not bonded to each other, thus forming no ring structure;

in the formula (d), $R^{10}$ to $R^{14}$, *f, and *** are the same as described above, $R^{44}$ to $R^{51}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, X is an oxygen atom, a sulfur atom, $CR^aR^b$, or $NR^c$, $R^a$, $R^b$, and $R^c$ are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms, provided that one selected from $R^{44}$ to $R^{51}$ and $R^c$ is a single bond bonded to *k.

m4 is 0 or 1, when m4 is 0, *f is bonded to $L^2$ or L.

combinations of adjacent two selected from $R^{44}$ to $R^{51}$ that are not the single bond may each independently be bonded to each other to form a substituted or unsubstituted ring structure, and $R^a$ and $R^b$ are not crosslinked;

in the formula (e), $R^{10}$ to $R^{14}$, *f, and *** are the same as described above, $R^{52}$ to $R^{66}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, provided that one selected from $R^{52}$ to $R^{56}$ is a single bond bonded to *l, another one selected from $R^{52}$ to $R^{56}$ is a single bond bonded to *m, m5 is 0 or 1, when m5 is 0, *f is bonded to $L^2$ or L adjacent two selected from $R^{10}$ to $R^{14}$ that are not the single bond are, adjacent two selected from $R^{52}$ to $R^{56}$ that are not either of the single bonds are, $R^{52}$ and $R^{61}$ are, and $R^{56}$ and $R^{57}$ are, not bonded to each other, thus forming no ring structure.

In another aspect, the present invention provides a material for organic EL devices, the material containing the compound represented by the formula (1).

In still another aspect, the present invention provides an organic electroluminescence device including an anode, a cathode, and an organic layer disposed between the anode and the cathode, the organic layer including a light emitting layer, at least one layer of the organic layer containing the compound represented by the formula (1).

In still yet another aspect, the present invention provides an electronic instrument including the organic electroluminescence device.

Advantageous Effects of Invention

The organic EL device containing the compound represented by the formula (1) shows an improved device performance.

DESCRIPTION OF EMBODIMENTS

Definitions

Figure 1:
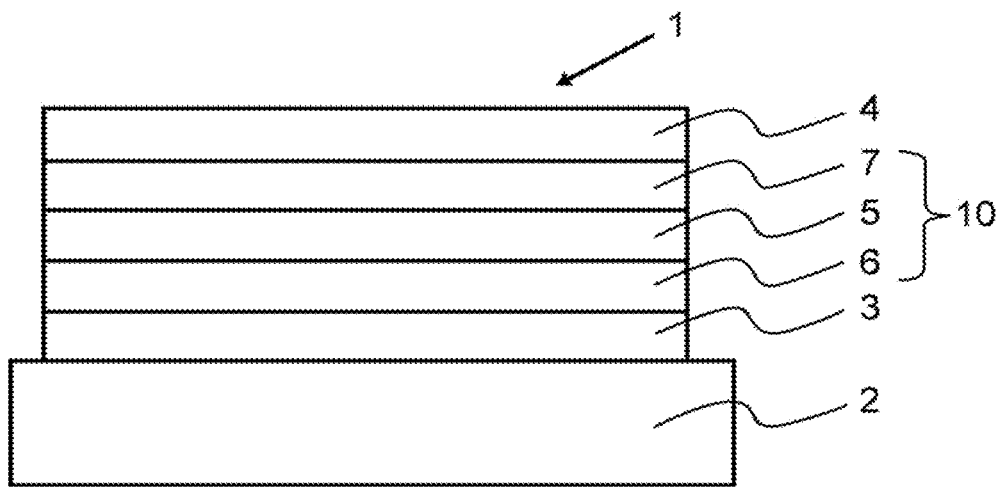
FIG. 1 is a schematic diagram illustrating an example of the layer configuration of the organic EL device according to an aspect of the present invention.

In the description herein, the hydrogen atom encompasses isotopes thereof having different numbers of neutrons, i.e., a light hydrogen atom (protium), a heavy hydrogen atom (deuterium), and tritium.

In the description herein, the bonding site where the symbol, such as "R", or "D" representing a deuterium atom is not shown is assumed to have a hydrogen atom, i.e., a protium atom, a deuterium atom, or a tritium atom, bonded thereto.

In the description herein, the number of ring carbon atoms shows the number of carbon atoms among the atoms constituting the ring itself of a compound having a structure including atoms bonded to form a ring (such as a monocyclic compound, a condensed ring compound, a bridged compound, a carbocyclic compound, and a heterocyclic compound). In the case where the ring is substituted by a substituent, the carbon atom contained in the substituent is not included in the number of ring carbon atoms. The same definition is applied to the "number of ring carbon atoms" described hereinafter unless otherwise indicated. For example, a benzene ring has 6 ring carbon atoms, a naphthalene ring has 10 ring carbon atoms, a pyridine ring has 5 ring carbon atoms, and a furan ring has 4 ring carbon atoms. For example, 9,9-diphenylfluorenyl group has 13 ring carbon atoms, and 9,9'-spirobifluorenyl group has 25 ring carbon atoms.

In the case where a benzene ring has, for example, an alkyl group substituted thereon as a substituent, the number of carbon atoms of the alkyl group is not included in the number of ring carbon atoms of the benzene ring. Accordingly a benzene ring having an alkyl group substituted thereon has 6 ring carbon atoms. In the case where a naphthalene ring has, for example, an alkyl group substituted thereon as a substituent, the number of carbon atoms of the alkyl group is not included in the number of ring carbon atoms of the naphthalene ring. Accordingly a naphthalene ring having an alkyl group substituted thereon has 10 ring carbon atoms.

In the description herein, the number of ring atoms shows the number of atoms constituting the ring itself of a compound having a structure including atoms bonded to form a ring (such as a monocyclic ring, a condensed ring, and a set of rings) (such as a monocyclic compound, a condensed ring compound, a bridged compound, a carbocyclic compound, and a heterocyclic compound). The atom that does not constitute the ring (such as a hydrogen atom terminating the bond of the atom constituting the ring) and, in the case where the ring is substituted by a substituent, the atom contained in the substituent are not included in the number of ring atoms. The same definition is applied to the "number of ring atoms" described hereinafter unless otherwise indicated. For example, a pyridine ring has 6 ring atoms, a quinazoline ring has 10 ring atoms, and a furan ring has 5 ring atoms. For example, the number of hydrogen atoms bonded to a pyridine ring or atoms constituting a substituent is not included in the number of ring atoms of the pyridine ring. Accordingly a pyridine ring having a hydrogen atom or a substituent bonded thereto has 6 ring atoms. For example, the number of hydrogen atoms bonded to carbon atoms of a quinazoline ring or atoms constituting a substituent is not included in the number of ring atoms of the quinazoline ring. Accordingly a quinazoline ring having a hydrogen atom or a substituent bonded thereto has 10 ring atoms.

In the description herein, the expression "having XX to YY carbon atoms" in the expression "substituted or unsubstituted ZZ group having XX to YY carbon atoms" means the number of carbon atoms of the unsubstituted ZZ group, and, in the case where the ZZ group is substituted, the number of carbon atoms of the substituent is not included. Herein, "YY" is larger than "XX", "XX" represents an integer of 1 or more, and "YY" represents an integer of 2 or more.

In the description herein, the expression "having XX to YY atoms" in the expression "substituted or unsubstituted ZZ group having XX to YY atoms" means the number of atoms of the unsubstituted ZZ group, and, in the case where the ZZ group is substituted, the number of atoms of the substituent is not included. Herein, "YY" is larger than "XX", "XX" represents an integer of 1 or more, and "YY" represents an integer of 2 or more.

In the description herein, an unsubstituted ZZ group means the case where the "substituted or unsubstituted ZZ group" is an "unsubstituted ZZ group", and a substituted ZZ group means the case where the "substituted or unsubstituted ZZ group" is a "substituted ZZ group".

In the description herein, the expression "unsubstituted" in the expression "substituted or unsubstituted ZZ group" means that hydrogen atoms in the ZZ group are not substituted by a substituent. The hydrogen atoms in the "unsubstituted ZZ group" each are a protium atom, a deuterium atom, or a tritium atom.

In the description herein, the expression "substituted" in the expression "substituted or unsubstituted ZZ group" means that one or more hydrogen atom in the ZZ group is substituted by a substituent. The expression "substituted" in the expression "BB group substituted by an AA group" similarly means that one or more hydrogen atom in the BB group is substituted by the AA group.

Substituents in Description

The substituents described in the description herein will be explained.

In the description herein, the number of ring carbon atoms of the "unsubstituted aryl group" is 6 to 50, preferably 6 to 30, and more preferably 6 to 18, unless otherwise indicated in the description.

In the description herein, the number of ring atoms of the "unsubstituted heterocyclic group" is 5 to 50, preferably 5 to 30, and more preferably 5 to 18, unless otherwise indicated in the description.

In the description herein, the number of carbon atoms of the "unsubstituted alkyl group" is 1 to 50, preferably 1 to 20, and more preferably 1 to 6, unless otherwise indicated in the description.

In the description herein, the number of carbon atoms of the "unsubstituted alkenyl group" is 2 to 50, preferably 2 to 20, and more preferably 2 to 6, unless otherwise indicated in the description.

In the description herein, the number of carbon atoms of the "unsubstituted alkynyl group" is 2 to 50, preferably 2 to 20, and more preferably 2 to 6, unless otherwise indicated in the description.

In the description herein, the number of ring carbon atoms of the "unsubstituted cycloalkyl group" is 3 to 50, preferably 3 to 20, and more preferably 3 to 6, unless otherwise indicated in the description.

In the description herein, the number of ring carbon atoms of the "unsubstituted arylene group" is 6 to 50, preferably 6 to 30, and more preferably 6 to 18, unless otherwise indicated in the description.

In the description herein, the number of ring atoms of the "unsubstituted divalent heterocyclic group" is 5 to 50, preferably 5 to 30, and more preferably 5 to 18, unless otherwise indicated in the description.

In the description herein, the number of carbon atoms of the "unsubstituted alkylene group" is 1 to 50, preferably 1 to 20, and more preferably 1 to 6, unless otherwise indicated in the description.

Substituted or Unsubstituted Aryl Group

In the description herein, specific examples (set of specific examples G1) of the "substituted or unsubstituted aryl group" include the unsubstituted aryl groups (set of specific examples G1A) and the substituted aryl groups (set of specific examples G1B) shown below. (Herein, the unsubstituted aryl group means the case where the "substituted or unsubstituted aryl group" is an "unsubstituted aryl group", and the substituted aryl group means the case where the "substituted or unsubstituted aryl group" is a "substituted aryl group".) In the description herein, the simple expression "aryl group" encompasses both the "unsubstituted aryl group" and the "substituted aryl group".

The "substituted aryl group" means a group formed by substituting one or more hydrogen atom of the "unsubstituted aryl group" by a substituent. Examples of the "substituted aryl group" include groups formed by one or more hydrogen atom of each of the "unsubstituted aryl groups" in the set of specific examples G1A by a substituent, and the examples of the substituted aryl groups in the set of specific examples G1B. The examples of the "unsubstituted aryl group" and the examples of the "substituted aryl group" enumerated herein are mere examples, and the "substituted aryl group" in the description herein encompasses groups formed by substituting a hydrogen atom bonded to the carbon atom of the aryl group itself of each of the "substituted aryl groups" in the set of specific examples G1B by a substituent, and groups formed by substituting a hydrogen atom of the substituent of each of the "substituted aryl groups" in the set of specific examples G1B by a substituent.

Unsubstituted Aryl Group (Set of Specific Examples G1A):
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
monovalent aryl groups derived by removing one hydrogen atom from each of the ring structures represented by the following general formulae (TEMP-1) to (TEMP-15):

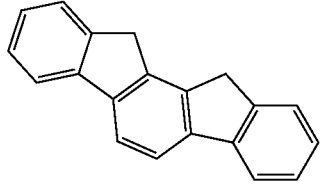

(TEMP-1)

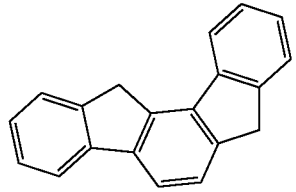

(TEMP-2)

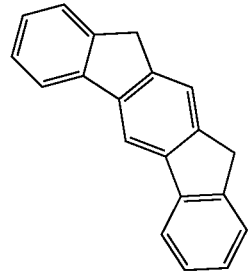

(TEMP-3)

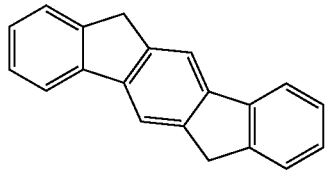

(TEMP-4)

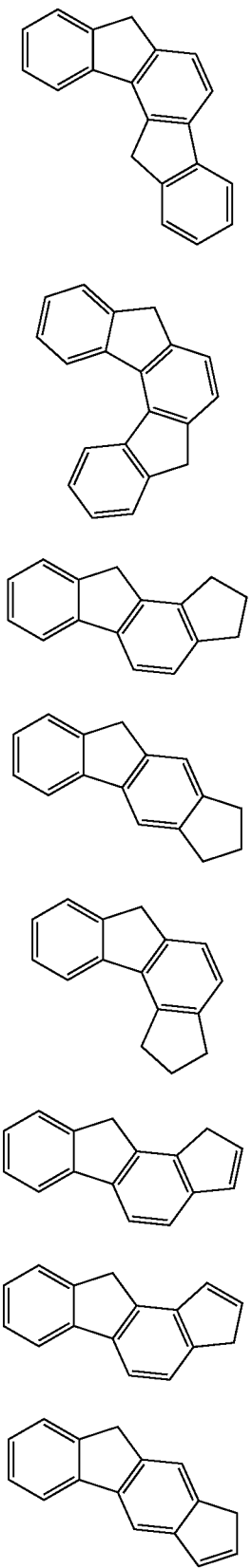

(TEMP-5)
(TEMP-6)
(TEMP-7)
(TEMP-8)
(TEMP-9)
(TEMP-10)
(TEMP-11)
(TEMP-12)

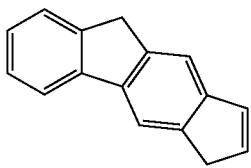

(TEMP-13)

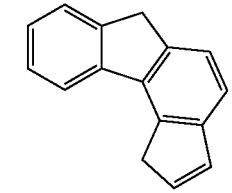

(TEMP-14)

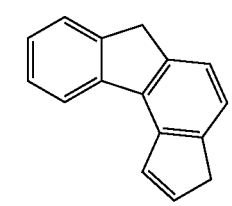

(TEMP-15)

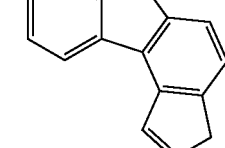

Substituted Aryl Group (Set of Specific Examples G1B):
an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
a o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
groups formed by substituting one or more hydrogen atom of each of monovalent aryl groups derived from the ring structures represented by the general formulae (TEMP-1) to (TEMP-15) by a substituent.

Substituted or Unsubstituted Heterocyclic Group

In the description herein, the "heterocyclic group" means a cyclic group containing at least one hetero atom in the ring atoms. Specific examples of the hetero atom include a nitrogen atom, an oxygen atom, a sulfur atom, a silicon atom, a phosphorus atom, and a boron atom.

In the description herein, the "heterocyclic group" is a monocyclic group or a condensed ring group.

In the description herein, the "heterocyclic group" is an aromatic heterocyclic group or a non-aromatic heterocyclic group.

In the description herein, specific examples (set of specific examples G2) of the "substituted or unsubstituted heterocyclic group" include the unsubstituted heterocyclic groups (set of specific examples G2A) and the substituted heterocyclic groups (set of specific examples G2B) shown below. (Herein, the unsubstituted heterocyclic group means the case where the "substituted or unsubstituted heterocyclic group" is an "unsubstituted heterocyclic group", and the substituted heterocyclic group means the case where the "substituted or unsubstituted heterocyclic group" is a "substituted heterocyclic group".) In the description herein, the simple expression "heterocyclic group" encompasses both the "unsubstituted heterocyclic group" and the "substituted heterocyclic group".

The "substituted heterocyclic group" means a group formed by substituting one or more hydrogen atom of the "unsubstituted heterocyclic group" by a substituent. Specific examples of the "substituted heterocyclic group" include groups formed by substituting a hydrogen atom of each of the "unsubstituted heterocyclic groups" in the set of specific examples G2A by a substituent, and the examples of the substituted heterocyclic groups in the set of specific examples G2B. The examples of the "unsubstituted heterocyclic group" and the examples of the "substituted heterocyclic group" enumerated herein are mere examples, and the "substituted heterocyclic group" in the description herein encompasses groups formed by substituting a hydrogen atom bonded to the ring atom of the heterocyclic group itself of each of the "substituted heterocyclic groups" in the set of specific examples G2B by a substituent, and groups formed by substituting a hydrogen atom of the substituent of each of the "substituted heterocyclic groups" in the set of specific examples G2B by a substituent.

The set of specific examples G2A includes, for example, the unsubstituted heterocyclic group containing a nitrogen atom (set of specific examples G2A1), the unsubstituted heterocyclic group containing an oxygen atom (set of specific examples G2A2), the unsubstituted heterocyclic group containing a sulfur atom (set of specific examples G2A3), and monovalent heterocyclic groups derived by removing one hydrogen atom from each of the ring structures represented by the following general formulae (TEMP-16) to (TEMP-33) (set of specific examples G2A4).

The set of specific examples G2B includes, for example, the substituted heterocyclic groups containing a nitrogen atom (set of specific examples G2B1), the substituted heterocyclic groups containing an oxygen atom (set of specific examples G2B2), the substituted heterocyclic groups containing a sulfur atom (set of specific examples G2B3), and groups formed by substituting one or more hydrogen atom of each of monovalent heterocyclic groups derived from the ring structures represented by the following general formulae (TEMP-16) to (TEMP-33) by a substituent (set of specific examples G2B4).

Unsubstituted Heterocyclic Group Containing Nitrogen Atom (Set of Specific Examples G2A1):
  a pyrrolyl group,
  an imidazolyl group,
  a pyrazolyl group,
  a triazolyl group,
  a tetrazolyl group,
  an oxazolyl group,
  an isoxazolyl group,
  an oxadiazolyl group,
  a thiazolyl group,
  an isothiazolyl group,
  a thiadiazolyl group,
  a pyridyl group,
  a pyridazinyl group,
  a pyrimidinyl group,
  a pyrazinyl group,
  a triazinyl group,
  an indolyl group,
  an isoindolyl group,
  an indolizinyl group,
  a quinolizinyl group,
  a quinolyl group,
  an isoquinolyl group,
  a cinnolinyl group,
  a phthalazinyl group,
  a quinazolinyl group,
  a quinoxalinyl group,
  a benzimidazolyl group,
  an indazolyl group,
  a phenanthrolinyl group,
  a phenanthridinyl group,
  an acridinyl group,
  a phenazinyl group,
  a carbazolyl group,
  a benzocarbazolyl group,
  a morpholino group,
  a phenoxazinyl group,
  a phenothiazinyl group,
  an azacarbazolyl group, and
  a diazacarbazolyl group.

Unsubstituted Heterocyclic Group Containing Oxygen Atom (Set of Specific Examples G2A2):
  a furyl group,
  an oxazolyl group,
  an isoxazolyl group,
  an oxadiazolyl group,
  a xanthenyl group,
  a benzofuranyl group,
  an isobenzofuranyl group,
  a dibenzofuranyl group,
  a naphthobenzofuranyl group,
  a benzoxazolyl group,
  a benzisoxazolyl group,
  a phenoxazinyl group,
  a morpholino group,
  a dinaphthofuranyl group,
  an azadibenzofuranyl group,
  a diazadibenzofuranyl group,
  an azanaphthobenzofuranyl group, and
  a diazanaphthobenzofuranyl group.

Unsubstituted Heterocyclic Group Containing Sulfur Atom (Set of Specific Examples G2A3):
  a thienyl group,
  a thiazolyl group,
  an isothiazolyl group,
  a thiadiazolyl group,
  a benzothiophenyl group (benzothienyl group),
  an isobenzothiophenyl group (isobenzothienyl group),
  a dibenzothiophenyl group (dibenzothienyl group),
  a naphthobenzothiophenyl group (naphthobenzothienyl group),
  a benzothiazolyl group,
  a benzisothiazolyl group,
  a phenothiazinyl group,
  a dinaphthothiophenyl group (dinaphthothienyl group),
  an azadibenzothiophenyl group (azadibenzothienyl group),
  a diazadibenzothiophenyl group (diazadibenzothienyl group),
  an azanaphthobenzothiophenyl group (azanaphthobenzothienyl group), and a diazanaphthobenzothiophenyl group (diazanaphthobenzothienyl group).
Monovalent Heterocyclic Group Derived by Removing One Hydrogen Atom from Ring Structures Represented by General Formulae (TEMP-16) to (TEMP-33) (Set of Specific Examples G2A4)
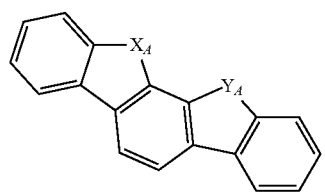
(TEMP-16)
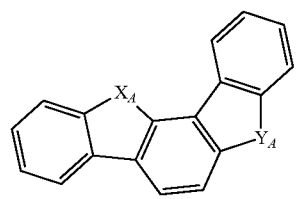
(TEMP-17)
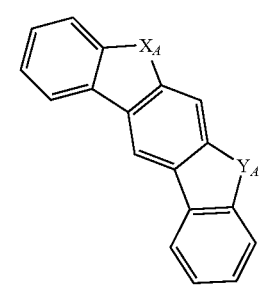
(TEMP-18)
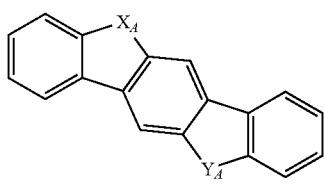
(TEMP-19)
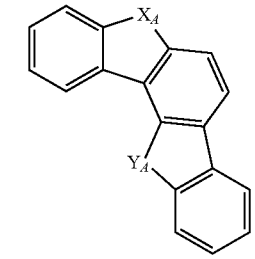
(TEMP-20)
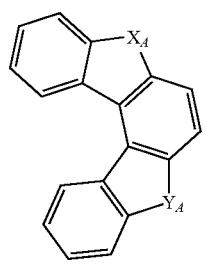
(TEMP-21)
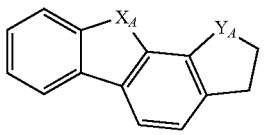
(TEMP-22)
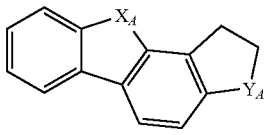
(TEMP-23)
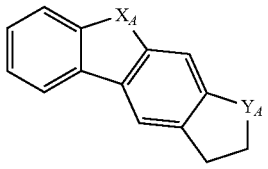
(TEMP-24)
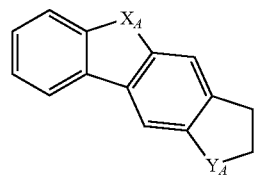
(TEMP-25)
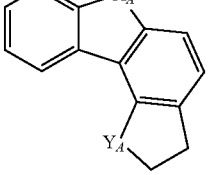
(TEMP-26)
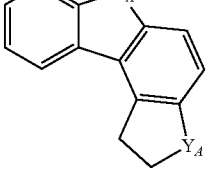
(TEMP-27)
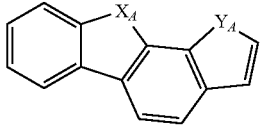
(TEMP-28)
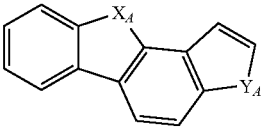
(TEMP-29)
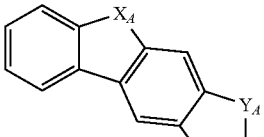
(TEMP-30)

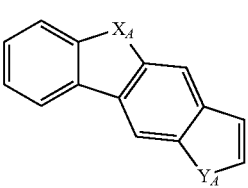
(TEMP-31)

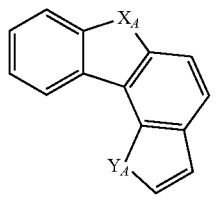
(TEMP-32)

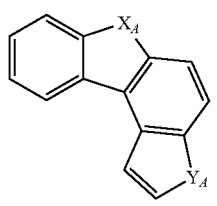
(TEMP-33)

In the general formulae (TEMP-16) to (TEMP-33), $X_A$ and $Y_A$ each independently represent an oxygen atom, a sulfur atom, NH, or $CH_2$, provided that at least one of $X_A$ and $Y_A$ represents an oxygen atom, a sulfur atom, or NH.

In the general formulae (TEMP-16) to (TEMP-33), in the case where at least one of $X_A$ and $Y_A$ represents NH or $CH_2$, the monovalent heterocyclic groups derived from the ring structures represented by the general formulae (TEMP-16) to (TEMP-33) include monovalent groups formed by removing one hydrogen atom from the NH or $CH_2$.

Substituted Heterocyclic Group Containing Nitrogen Atom (Set of Specific Examples G2B1):
  a (9-phenyl)carbazolyl group,
  a (9-biphenylyl)carbazolyl group,
  a (9-phenyl)phenylcarbazolyl group,
  a (9-naphthyl)carbazolyl group,
  a diphenylcarbazol-9-yl group,
  a phenylcarbazol-9-yl group,
  a methylbenzimidazolyl group,
  an ethylbenzimidazolyl group,
  a phenyltriazinyl group,
  a biphenyltriazinyl group,
  a diphenyltriazinyl group,
  a phenylquinazolinyl group, and
  a biphenylquinazolinyl group.

Substituted Heterocyclic Group Containing Oxygen Atom (Set of Specific Examples G2B2):
  a phenyldibenzofuranyl group,
  a methyldibenzofuranyl group,
  a t-butyldibenzofuranyl group, and
  a monovalent residual group of spiro[9H-xanthene-9,9'-[9H]fluorene].

Substituted Heterocyclic Group Containing Sulfur Atom (Set of Specific Examples G2B3):
  a phenyldibenzothiophenyl group,
  a methyldibenzothiophenyl group,
  a t-butyldibenzothiophenyl group, and
  a monovalent residual group of spiro[9H-thioxanthene-9, 9'-[9H]fluorene].

Group Formed by Substituting One or More Hydrogen Atom of Monovalent Heterocyclic Group Derived from Ring Structures Represented by General Formulae (TEMP-16) to (TEMP-33) by Substituent (Set of Specific Examples G2B4)

The "one or more hydrogen atom of the monovalent heterocyclic group" means one or more hydrogen atom selected from the hydrogen atom bonded to the ring carbon atom of the monovalent heterocyclic group, the hydrogen atom bonded to the nitrogen atom in the case where at least one of $X_A$ and $Y_A$ represents NH, and the hydrogen atom of the methylene group in the case where one of $X_A$ and $Y_A$ represents $CH_2$.

Substituted or Unsubstituted Alkyl Group

In the description herein, specific examples (set of specific examples G3) of the "substituted or unsubstituted alkyl group" include the unsubstituted alkyl groups (set of specific examples G3A) and the substituted alkyl groups (set of specific examples G3B) shown below. (Herein, the unsubstituted alkyl group means the case where the "substituted or unsubstituted alkyl group" is an "unsubstituted alkyl group", and the substituted alkyl group means the case where the "substituted or unsubstituted alkyl group" is a "substituted alkyl group".) In the description herein, the simple expression "alkyl group" encompasses both the "unsubstituted alkyl group" and the "substituted alkyl group".

The "substituted alkyl group" means a group formed by substituting one or more hydrogen atom of the "unsubstituted alkyl group" by a substituent. Specific examples of the "substituted alkyl group" include groups formed by substituting one or more hydrogen atom of each of the "unsubstituted alkyl groups" (set of specific examples G3A) by a substituent, and the examples of the substituted alkyl groups (set of specific examples G3B). In the description herein, the alkyl group in the "unsubstituted alkyl group" means a chain-like alkyl group. Accordingly the "unsubstituted alkyl group" encompasses an "unsubstituted linear alkyl group" and an "unsubstituted branched alkyl group". The examples of the "unsubstituted alkyl group" and the examples of the "substituted alkyl group" enumerated herein are mere examples, and the "substituted alkyl group" in the description herein encompasses groups formed by substituting a hydrogen atom of the alkyl group itself of each of the "substituted alkyl groups" in the set of specific examples G3B by a substituent, and groups formed by substituting a hydrogen atom of the substituent of each of the "substituted alkyl groups" in the set of specific examples G3B by a substituent.

Unsubstituted Alkyl Group (Set of Specific Examples G3A):
  a methyl group,
  an ethyl group,
  a n-propyl group,
  an isopropyl group,
  a n-butyl group,
  an isobutyl group,
  a s-butyl group, and
  a t-butyl group.

Substituted Alkyl Group (Set of Specific Examples G3B):
  a heptafluoropropyl group (including isomers),
  a pentafluoroethyl group,
  a 2,2,2-trifluoroethyl group, and
  a trifluoromethyl group.

Substituted or Unsubstituted Alkenyl Group

In the description herein, specific examples (set of specific examples G4) of the "substituted or unsubstituted alkenyl group" include the unsubstituted alkenyl groups (set of specific examples G4A) and the substituted alkenyl groups (set of specific examples G4B) shown below. (Herein, the unsubstituted alkenyl group means the case where the "substituted or unsubstituted alkenyl group" is an "unsubstituted alkenyl group", and the substituted alkenyl group means the case where the "substituted or unsubstituted alkenyl group" is a "substituted alkenyl group".) In the description herein, the simple expression "alkenyl group" encompasses both the "unsubstituted alkenyl group" and the "substituted alkenyl group".

The "substituted alkenyl group" means a group formed by substituting one or more hydrogen atom of the "unsubstituted alkenyl group" by a substituent. Specific examples of the "substituted alkenyl group" include the "unsubstituted alkenyl groups" (set of specific examples G4A) that each have a substituent, and the examples of the substituted alkenyl groups (set of specific examples G4B). The examples of the "unsubstituted alkenyl group" and the examples of the "substituted alkenyl group" enumerated herein are mere examples, and the "substituted alkenyl group" in the description herein encompasses groups formed by substituting a hydrogen atom of the alkenyl group itself of each of the "substituted alkenyl groups" in the set of specific examples G4B by a substituent, and groups formed by substituting a hydrogen atom of the substituent of each of the "substituted alkenyl groups" in the set of specific examples G4B by a substituent.

Unsubstituted Alkenyl Group (Set of Specific Examples G4A):
- a vinyl group,
- an allyl group,
- a 1-butenyl group,
- a 2-butenyl group, and
- a 3-butenyl group.

Substituted Alkenyl Group (Set of Specific Examples G4B):
- a 1,3-butanedienyl group,
- a 1-methylvinyl group,
- a 1-methylallyl group,
- a 1,1-dimethylallyl group,
- a 2-methylallyl group, and
- a 1,2-dimethylallyl group.

Substituted or Unsubstituted Alkynyl Group

In the description herein, specific examples (set of specific examples G5) of the "substituted or unsubstituted alkynyl group" include the unsubstituted alkynyl group (set of specific examples G5A) shown below. (Herein, the unsubstituted alkynyl group means the case where the "substituted or unsubstituted alkynyl group" is an "unsubstituted alkynyl group".) In the description herein, the simple expression "alkynyl group" encompasses both the "unsubstituted alkynyl group" and the "substituted alkynyl group".

The "substituted alkynyl group" means a group formed by substituting one or more hydrogen atom of the "unsubstituted alkynyl group" by a substituent. Specific examples of the "substituted alkenyl group" include groups formed by substituting one or more hydrogen atom of the "unsubstituted alkynyl group" (set of specific examples G5A) by a substituent.

Unsubstituted Alkynyl Group (Set of Specific Examples G5A):
- an ethynyl group.

Substituted or Unsubstituted Cycloalkyl Group

In the description herein, specific examples (set of specific examples G6) of the "substituted or unsubstituted cycloalkyl group" include the unsubstituted cycloalkyl groups (set of specific examples G6A) and the substituted cycloalkyl group (set of specific examples G6B) shown below. (Herein, the unsubstituted cycloalkyl group means the case where the "substituted or unsubstituted cycloalkyl group" is an "unsubstituted cycloalkyl group", and the substituted cycloalkyl group means the case where the "substituted or unsubstituted cycloalkyl group" is a "substituted cycloalkyl group".) In the description herein, the simple expression "cycloalkyl group" encompasses both the "unsubstituted cycloalkyl group" and the "substituted cycloalkyl group".

The "substituted cycloalkyl group" means a group formed by substituting one or more hydrogen atom of the "unsubstituted cycloalkyl group" by a substituent. Specific examples of the "substituted cycloalkyl group" include groups formed by substituting one or more hydrogen atom of each of the "unsubstituted cycloalkyl groups" (set of specific examples G6A) by a substituent, and the example of the substituted cycloalkyl group (set of specific examples G6B). The examples of the "unsubstituted cycloalkyl group" and the examples of the "substituted cycloalkyl group" enumerated herein are mere examples, and the "substituted cycloalkyl group" in the description herein encompasses groups formed by substituting one or more hydrogen atom bonded to the carbon atoms of the cycloalkyl group itself of the "substituted cycloalkyl group" in the set of specific examples G6B by a substituent, and groups formed by substituting a hydrogen atom of the substituent of the "substituted cycloalkyl group" in the set of specific examples G6B by a substituent.

Unsubstituted Cycloalkyl Group (Set of Specific Examples G6A):
- a cyclopropyl group,
- a cyclobutyl group,
- a cyclopentyl group,
- a cyclohexyl group,
- a 1-adamantyl group,
- a 2-adamantyl group,
- a 1-norbornyl group, and
- a 2-norbornyl group.

Substituted Cycloalkyl Group (Set of Specific Examples G6B):
- a 4-methylcyclohexyl group.

Group Represented by —Si($R_{901}$)($R_{902}$)($R_{903}$)

In the description herein, specific examples (set of specific examples G7) of the group represented by —Si($R_{901}$)($R_{902}$)($R_{903}$) include:
- —Si(G1)(G1)(G1),
- —Si(G1)(G2)(G2),
- —Si(G1)(G1)(G2),
- —Si(G2)(G2)(G2),
- —Si(G3)(G3)(G3), and
- —Si(G6)(G6)(G6).

Herein,
G1 represents the "substituted or unsubstituted aryl group" described in the set of specific examples G1,
G2 represents the "substituted or unsubstituted heterocyclic group" described in the set of specific examples G2,
G3 represents the "substituted or unsubstituted alkyl group" described in the set of specific examples G3, and
G6 represents the "substituted or unsubstituted cycloalkyl group" described in the set of specific examples G6.

Plural groups represented by G1 in —Si(G1)(G1)(G1) are the same as or different from each other.

Plural groups represented by G2 in —Si(G1)(G2)(G2) are the same as or different from each other.

Plural groups represented by G1 in —Si(G1)(G1)(G2) are the same as or different from each other.

Plural groups represented by G2 in —Si(G2)(G2)(G2) are the same as or different from each other.

Plural groups represented by G3 in —Si(G3)(G3)(G3) are the same as or different from each other.

Plural groups represented by G6 in —Si(G6)(G6)(G6) are the same as or different from each other.

Group Represented by —O—($R_{904}$)

In the description herein, specific examples (set of specific examples G8) of the group represented by —O—($R_{904}$) include:
- —O(G1),
- —O(G2),
- —O(G3), and
- —O(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group Represented by —S—($R_{905}$)

In the description herein, specific examples (set of specific examples G9) of the group represented by —S—($R_{905}$) include:
- —S(G1),
- —S(G2),
- —S(G3), and
- —S(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group Represented by —N($R_{906}$)($R_{907}$) In the description herein, specific examples (set of specific examples G10) of the group represented by —N($R_{906}$)($R_{907}$) include:
- —N(G1)(G1),
- —N(G2)(G2),
- —N(G1)(G2),
- —N(G3)(G3), and
- —N(G6)(G6).

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —N(G1)(G1) are the same as or different from each other.

Plural groups represented by G2 in —N(G2)(G2) are the same as or different from each other.

Plural groups represented by G3 in —N(G3)(G3) are the same as or different from each other.

Plural groups represented by G6 in —N(G6)(G6) are the same as or different from each other.

Halogen Atom

In the description herein, specific examples (set of specific examples G11) of the "halogen atom" include a fluorine atom, a chlorine atom, a bromine atom, and an iodine atom.

Substituted or Unsubstituted Fluoroalkyl Group

In the description herein, the "substituted or unsubstituted fluoroalkyl group" means a group formed by substituting at least one hydrogen atom bonded to the carbon atom constituting the alkyl group in the "substituted or unsubstituted alkyl group" by a fluorine atom, and encompasses a group formed by substituting all the hydrogen atoms bonded to the carbon atoms constituting the alkyl group in the "substituted or unsubstituted alkyl group" by fluorine atoms (i.e., a perfluoroalkyl group). The number of carbon atoms of the "unsubstituted fluoroalkyl group" is 1 to 50, preferably 1 to 30, and more preferably 1 to 18, unless otherwise indicated in the description. The "substituted fluoroalkyl group" means a group formed by substituting one or more hydrogen atom of the "fluoroalkyl group" by a substituent. In the description herein, the "substituted fluoroalkyl group" encompasses a group formed by substituting one or more hydrogen atom bonded to the carbon atom of the alkyl chain in the "substituted fluoroalkyl group" by a substituent, and a group formed by substituting one or more hydrogen atom of the substituent in the "substituted fluoroalkyl group" by a substituent. Specific examples of the "unsubstituted fluoroalkyl group" include examples of groups formed by substituting one or more hydrogen atom in each of the "alkyl group" (set of specific examples G3) by a fluorine atom.

Substituted or Unsubstituted Haloalkyl Group

In the description herein, the "substituted or unsubstituted haloalkyl group" means a group formed by substituting at least one hydrogen atom bonded to the carbon atom constituting the alkyl group in the "substituted or unsubstituted alkyl group" by a halogen atom, and encompasses a group formed by substituting all the hydrogen atoms bonded to the carbon atoms constituting the alkyl group in the "substituted or unsubstituted alkyl group" by halogen atoms. The number of carbon atoms of the "unsubstituted haloalkyl group" is 1 to 50, preferably 1 to 30, and more preferably 1 to 18, unless otherwise indicated in the description. The "substituted haloalkyl group" means a group formed by substituting one or more hydrogen atom of the "haloalkyl group" by a substituent. In the description herein, the "substituted haloalkyl group" encompasses a group formed by substituting one or more hydrogen atom bonded to the carbon atom of the alkyl chain in the "substituted haloalkyl group" by a substituent, and a group formed by substituting one or more hydrogen atom of the substituent in the "substituted haloalkyl group" by a substituent. Specific examples of the "unsubstituted haloalkyl group" include examples of groups formed by substituting one or more hydrogen atom in each of the "alkyl group" (set of specific examples G3) by a halogen atom. A haloalkyl group may be referred to as a halogenated alkyl group in some cases.

Substituted or Unsubstituted Alkoxy Group

In the description herein, specific examples of the "substituted or unsubstituted alkoxy group" include a group represented by —O(G3), wherein G3 represents the "substituted or unsubstituted alkyl group" described in the set of specific examples G3. The number of carbon atoms of the "unsubstituted alkoxy group" is 1 to 50, preferably 1 to 30, and more preferably 1 to 18, unless otherwise indicated in the description.

Substituted or Unsubstituted Alkylthio Group

In the description herein, specific examples of the "substituted or unsubstituted alkylthio group" include a group represented by —S(G3), wherein G3 represents the "substituted or unsubstituted alkyl group" described in the set of specific examples G3. The number of carbon atoms of the "unsubstituted alkylthio group" is 1 to 50, preferably 1 to 30, and more preferably 1 to 18, unless otherwise indicated in the description.

Substituted or Unsubstituted Aryloxy Group

In the description herein, specific examples of the "substituted or unsubstituted aryloxy group" include a group represented by —O(G1), wherein G1 represents the "substituted or unsubstituted aryl group" described in the set of specific examples G1. The number of ring carbon atoms of the "unsubstituted aryloxy group" is 6 to 50, preferably 6 to 30, and more preferably 6 to 18, unless otherwise indicated in the description.

Substituted or Unsubstituted Arylthio Group

In the description herein, specific examples of the "substituted or unsubstituted arylthio group" include a group represented by —S(G1), wherein G1 represents the "substituted or unsubstituted aryl group" described in the set of specific examples G1. The number of ring carbon atoms of the "unsubstituted arylthio group" is 6 to 50, preferably 6 to 30, and more preferably 6 to 18, unless otherwise indicated in the description.

Substituted or Unsubstituted Trialkylsilyl Group

In the description herein, specific examples of the "trialkylsilyl group" include a group represented by —Si(G3)(G3)(G3), wherein G3 represents the "substituted or unsubstituted alkyl group" described in the set of specific examples G3. Plural groups represented by G3 in —Si(G3)(G3)(G3) are the same as or different from each other. The number of carbon atoms of each of alkyl groups of the "substituted or unsubstituted trialkylsilyl group" is 1 to 50, preferably 1 to 20, and more preferably 1 to 6, unless otherwise indicated in the description.

Substituted or Unsubstituted Aralkyl Group

In the description herein, specific examples of the "substituted or unsubstituted aralkyl group" include a group represented by -(G3)-(G1), wherein G3 represents the "substituted or unsubstituted alkyl group" described in the set of specific examples G3, and G1 represents the "substituted or unsubstituted aryl group" described in the set of specific examples G1. Accordingly, the "aralkyl group" is a group formed by substituting a hydrogen atom of an "alkyl group" by an "aryl group" as a substituent, and is one embodiment of the "substituted alkyl group". The "unsubstituted aralkyl group" is an "unsubstituted alkyl group" that is substituted by an "unsubstituted aryl group", and the number of carbon atoms of the "unsubstituted aralkyl group" is 7 to 50, preferably 7 to 30, and more preferably 7 to 18, unless otherwise indicated in the description.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

In the description herein, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, a 9,9-diphenylfluorenyl group, and the like, unless otherwise indicated in the description.

In the description herein, the substituted or unsubstituted heterocyclic group is preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (e.g., a 1-carbazolyl, group, a 2-carbazolyl, group, a 3-carbazolyl, group, a 4-carbazolyl, group, or a 9-carbazolyl, group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (e.g., a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like, unless otherwise indicated in the description.

In the description herein, the carbazolyl group is specifically any one of the following groups unless otherwise indicated in the description.

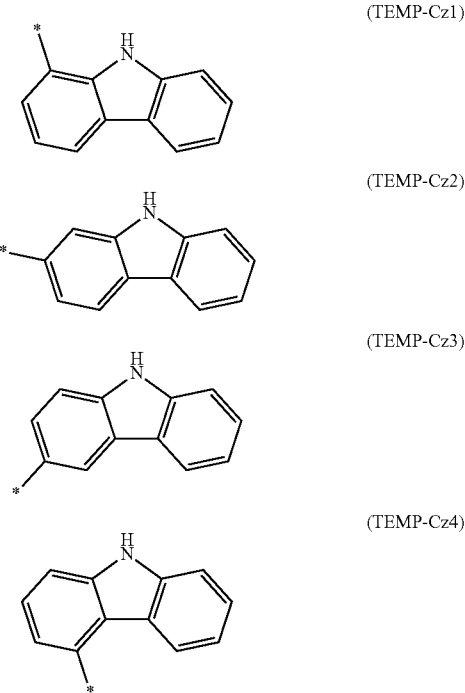

(TEMP-Cz5)

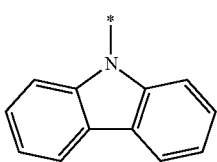

In the description herein, the (9-phenyl)carbazolyl group is specifically any one of the following groups unless otherwise indicated in the description.

(TEMP-Cz6)

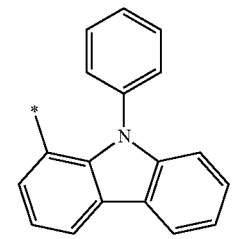

(TEMP-Cz7)

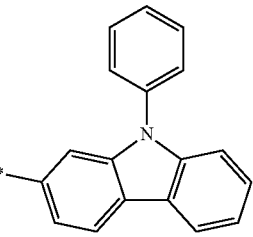

(TEMP-Cz8)

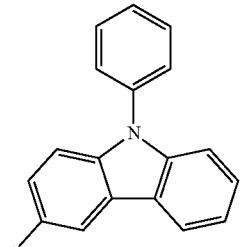

(TEMP-Cz9)

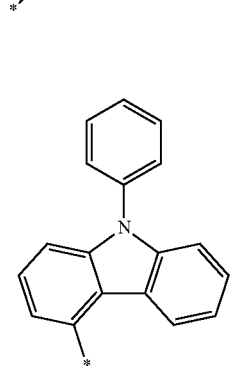

In the general formulae (TEMP-Cz1) to (TEMP-Cz9), * represents a bonding site.

In the description herein, the dibenzofuranyl group and the dibenzothiophenyl group are specifically any one of the following groups unless otherwise indicated in the description.

(TEMP-34)

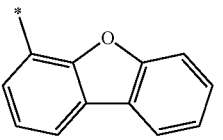

(TEMP-35)

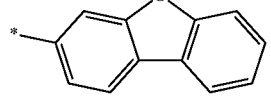

(TEMP-36)

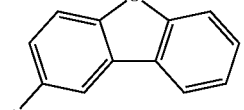

(TEMP-37)

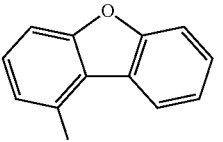

(TEMP-38)

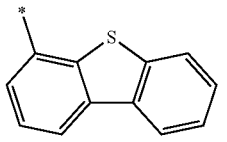

(TEMP-39)

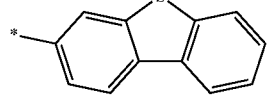

(TEMP-40)

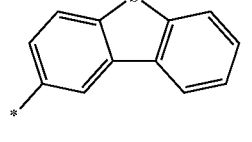

(TEMP-41)

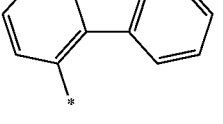

In the general formulae (TEMP-34) to (TEMP-41), * represents a bonding site.

In the description herein, the substituted or unsubstituted alkyl group is preferably a methyl group, an ethyl group, a propyl group, an isopropyl group, a n-butyl group, an isobutyl group, a t-butyl group, or the like unless otherwise indicated in the description.

Substituted or Unsubstituted Arylene Group

In the description herein, the "substituted or unsubstituted arylene group" is a divalent group derived by removing one hydrogen atom on the aryl ring from the "substituted or unsubstituted aryl group" described above unless otherwise indicated in the description. Specific examples (set of specific examples G12) of the "substituted or unsubstituted arylene group" include divalent groups derived by removing one hydrogen atom on the aryl ring from the "substituted or unsubstituted aryl groups" described in the set of specific examples G1.

Substituted or Unsubstituted Divalent Heterocyclic Group

In the description herein, the "substituted or unsubstituted divalent heterocyclic group" is a divalent group derived by removing one hydrogen atom on the heterocyclic ring from the "substituted or unsubstituted heterocyclic group" described above unless otherwise indicated in the description. Specific examples (set of specific examples G13) of the "substituted or unsubstituted divalent heterocyclic group" include divalent groups derived by removing one hydrogen atom on the heterocyclic ring from the "substituted or unsubstituted heterocyclic groups" described in the set of specific examples G2.

Substituted or Unsubstituted Alkylene Group

In the description herein, the "substituted or unsubstituted alkylene group" is a divalent group derived by removing one hydrogen atom on the alkyl chain from the "substituted or unsubstituted alkyl group" described above unless otherwise indicated in the description. Specific examples (set of specific examples G14) of the "substituted or unsubstituted alkylene group" include divalent groups derived by removing one hydrogen atom on the alkyl chain from the "substituted or unsubstituted alkyl groups" described in the set of specific examples G3.

In the description herein, the substituted or unsubstituted arylene group is preferably any one of the groups represented by the following general formulae (TEMP-42) to (TEMP-68) unless otherwise indicated in the description.

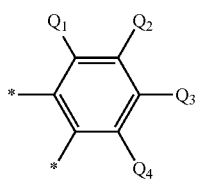

(TEMP-42)

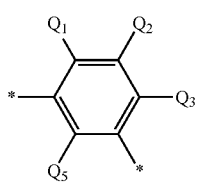

(TEMP-43)

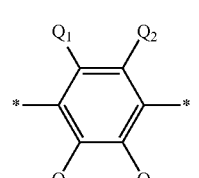

(TEMP-44)

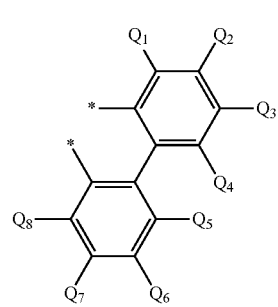

(TEMP-45)

-continued

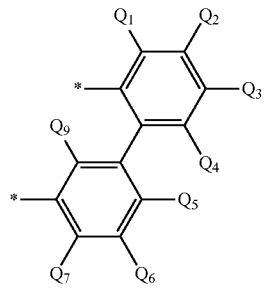

(TEMP-46)

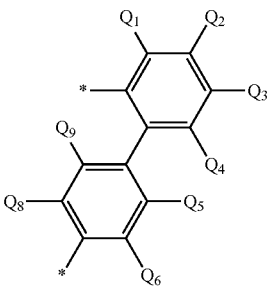

(TEMP-47)

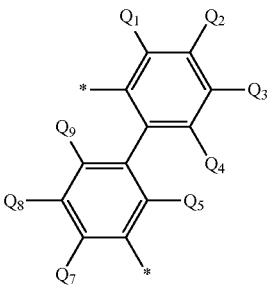

(TEMP-48)

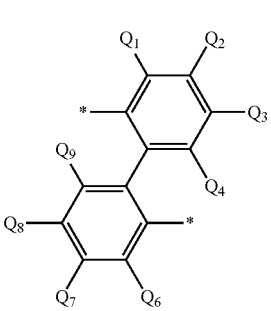

(TEMP-49)

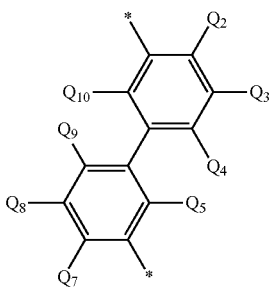

(TEMP-50)

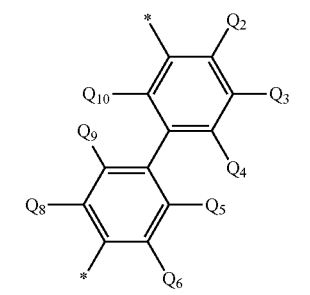
(TEMP-51)

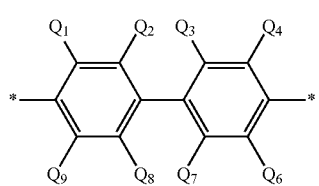
(TEMP-52)

In the general formulae (TEMP-42) to (TEMP-52), $Q_1$ to $Q_{10}$ each independently represent a hydrogen atom or a substituent.

In the general formulae (TEMP-42) to (TEMP-52), * represents a bonding site.

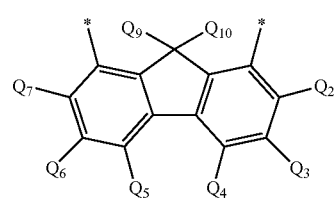
(TEMP-53)

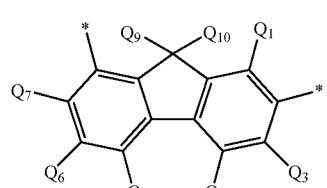
(TEMP-54)

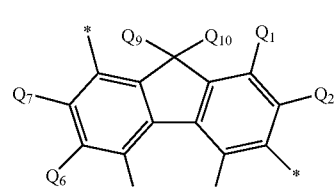
(TEMP-55)

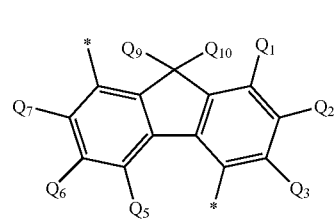
(TEMP-56)

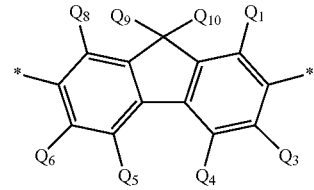
(TEMP-57)

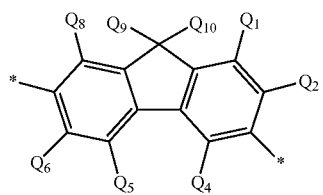
(TEMP-58)

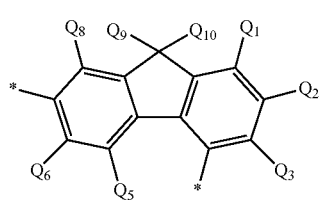
(TEMP-59)

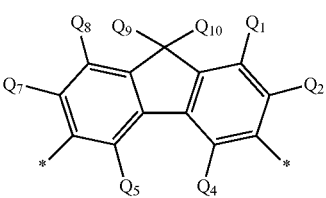
(TEMP-60)

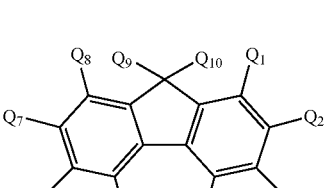
(TEMP-61)

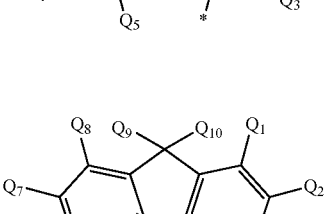
(TEMP-62)

In the general formulae (TEMP-53) to (TEMP-62), $Q_1$ to $Q_{10}$ each independently represent a hydrogen atom or a substituent.

The formulae $Q_9$ and $Q_{10}$ may be bonded to each other to form a ring via a single bond.

In the general formulae (TEMP-53) to (TEMP-62), * represents a bonding site.

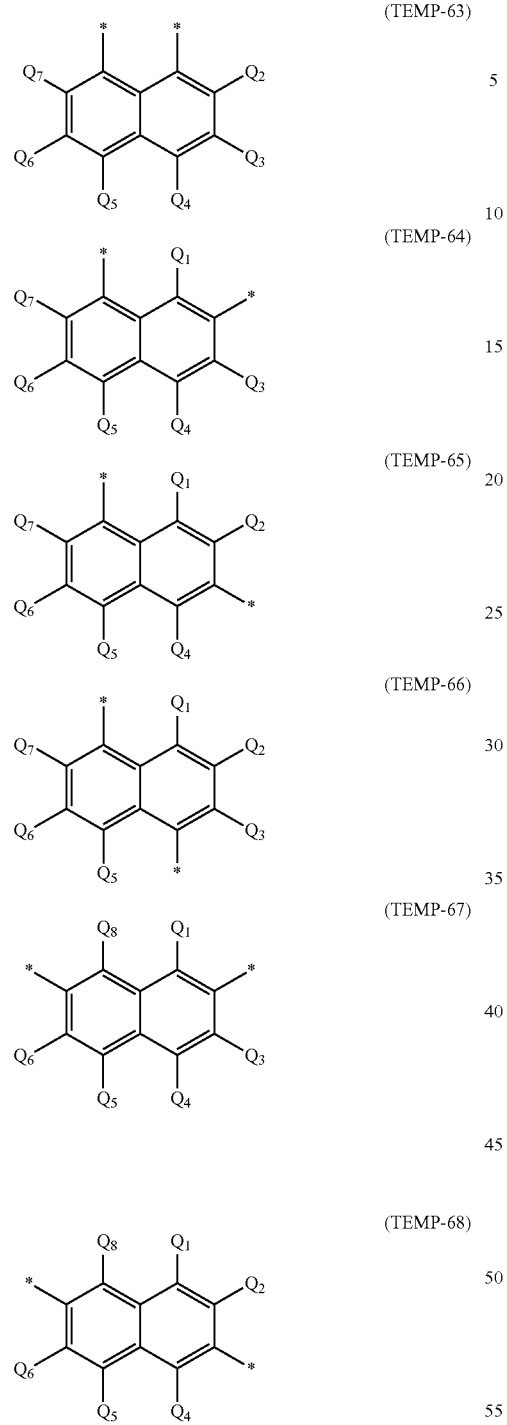

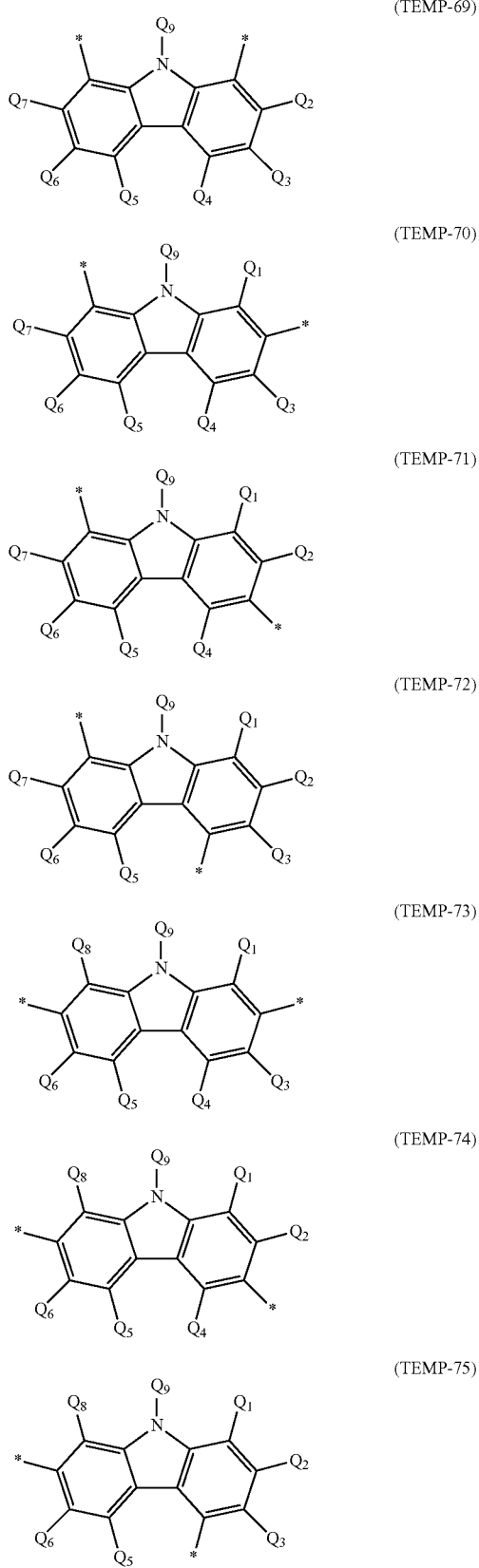

In the general formulae (TEMP-63) to (TEMP-68), $Q_1$ to $Q_8$ each independently represent a hydrogen atom or a substituent.

In the general formulae (TEMP-63) to (TEMP-68), * represents a bonding site.

In the description herein, the substituted or unsubstituted divalent heterocyclic group is preferably the groups represented by the following general formulae (TEMP-69) to (TEMP-102) unless otherwise indicated in the description.

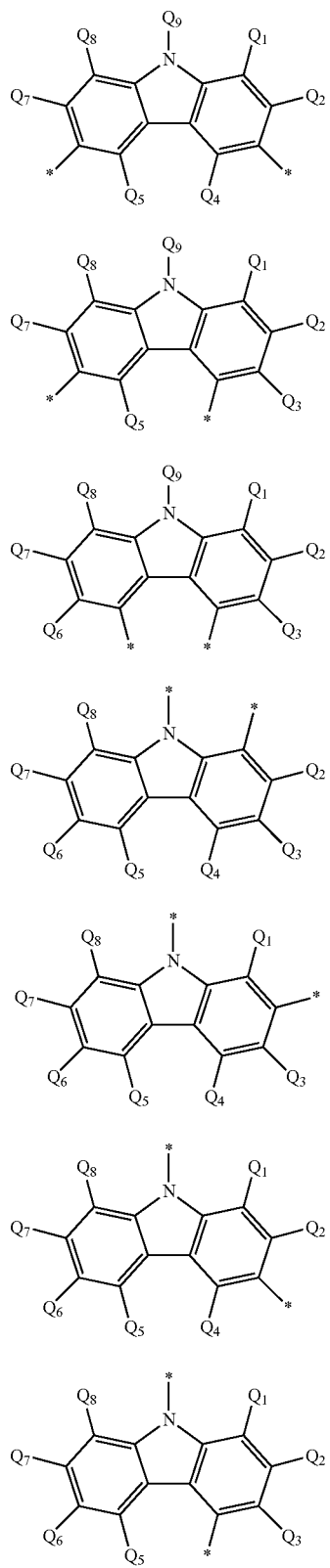
In the general formulae (TEMP-69) to (TEMP-82), $Q_1$ to $Q_9$ each independently represent a hydrogen atom or a substituent.

(TEMP-91)
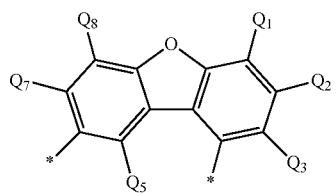

(TEMP-92)
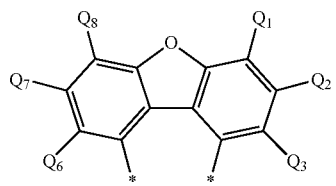

(TEMP-93)
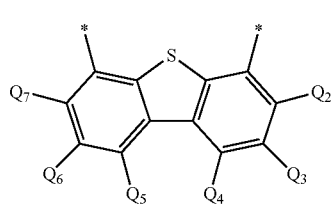

(TEMP-94)
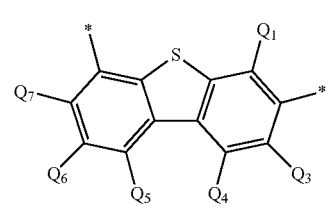

(TEMP-95)
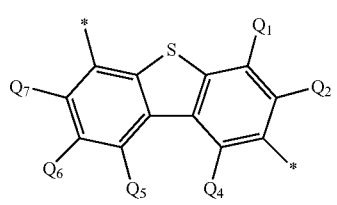

(TEMP-96)
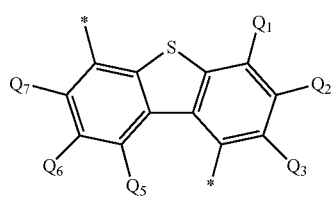

(TEMP-97)
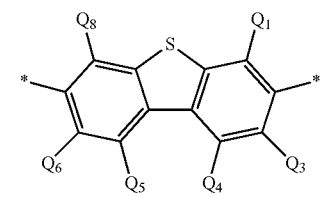

(TEMP-98)
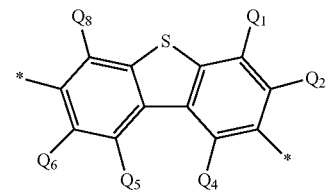

(TEMP-99)
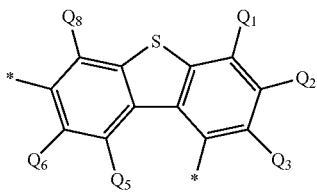

(TEMP-100)
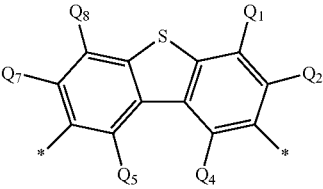

(TEMP-101)
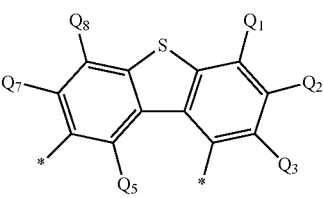

(TEMP-102)
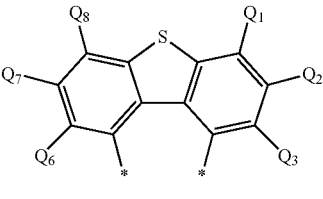

In the general formulae (TEMP-83) to (TEMP-102), $Q_1$ to $Q_8$ each independently represent a hydrogen atom or a substituent.

The above are the explanation of the "substituents in the description herein".

Case Forming Ring by Bonding

In the description herein, the case where "one or more combinations of combinations each including adjacent two or more each are bonded to each other to form a substituted or unsubstituted monocyclic ring, or each are bonded to each other to form a substituted or unsubstituted condensed ring, or each are not bonded to each other" means a case where "one or more combinations of combinations each including adjacent two or more each are bonded to each other to form a substituted or unsubstituted monocyclic ring", a case where "one or more combinations of combinations each including adjacent two or more each are bonded to each other to form a substituted or unsubstituted condensed ring", and a case where "one or more combinations of combinations each including adjacent two or more each are not bonded to each other".

In the description herein, the case where "one or more combinations of combinations each including adjacent two or more each are bonded to each other to form a substituted or unsubstituted monocyclic ring" and the case where "one or more combinations of combinations each including adjacent two or more each are bonded to each other to form a substituted or unsubstituted condensed ring" (which may be hereinafter collectively referred to as a "case forming a ring by bonding") will be explained below. The cases will be explained for the anthracene compound represented by the following general formula (TEMP-103) having an anthracene core skeleton as an example.

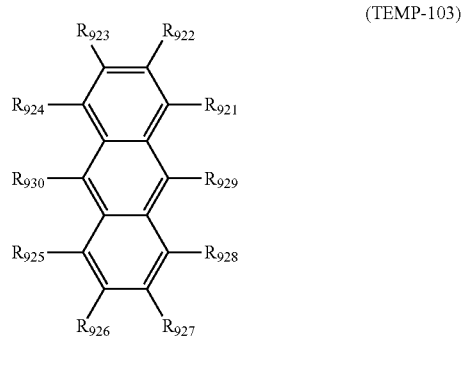

(TEMP-103)

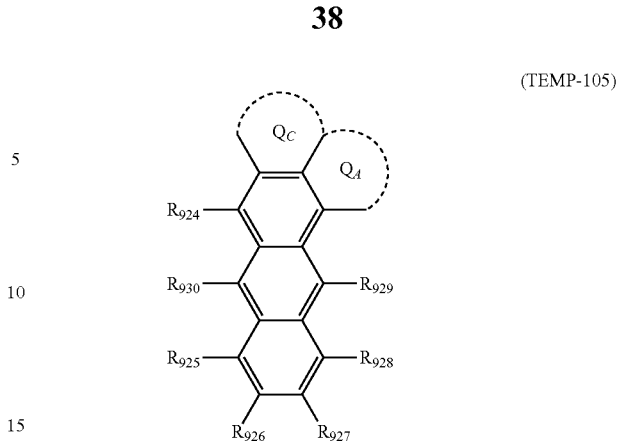

(TEMP-105)

For example, in the case where "one or more combinations of combinations each including adjacent two or more each are bonded to each other to form a ring" among $R_{921}$ to $R_{930}$, the combinations each including adjacent two as one combination include a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, and a combination of $R_{929}$ and $R_{921}$.

The "one or more combinations" mean that two or more combinations each including adjacent two or more may form rings simultaneously. For example, in the case where $R_{921}$ and $R_{922}$ are bonded to each other to form a ring $Q_A$, and simultaneously $R_{925}$ and $R_{926}$ are bonded to each other to form a ring $Q_B$, the anthracene compound represented by the general formula (TEMP-103) is represented by the following general formula (TEMP-104).

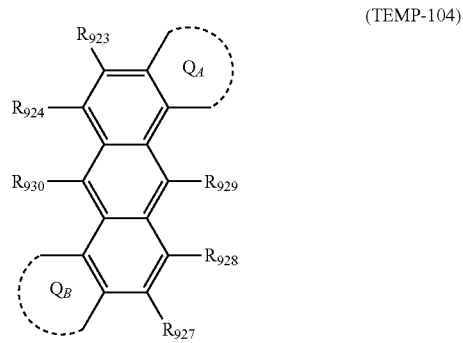

(TEMP-104)

The case where the "combination including adjacent two or more forms rings" encompasses not only the case where adjacent two included in the combination are bonded as in the aforementioned example, but also the case where adjacent three or more included in the combination are bonded. For example, this case means that $R_{921}$ and $R_{922}$ are bonded to each other to form a ring $Q_A$, $R_{922}$ and $R_{923}$ are bonded to each other to form a ring $Q_C$, and adjacent three ($R_{921}$, $R_{922}$, and $R_{923}$) included in the combination are bonded to each other to form rings, which are condensed to the anthracene core skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

The formed "monocyclic ring" or "condensed ring" may be a saturated ring or an unsaturated ring in terms of structure of the formed ring itself. In the case where the "one combination including adjacent two" forms a "monocyclic ring" or a "condensed ring", the "monocyclic ring" or the "condensed ring" may form a saturated ring or an unsaturated ring. For example, the ring $Q_A$ and the ring $Q_B$ formed in the general formula (TEMP-104) each are a "monocyclic ring" or a "condensed ring". The ring $Q_A$ and the ring $Q_C$ formed in the general formula (TEMP-105) each are a "condensed ring". The ring $Q_A$ and the ring $Q_C$ in the general formula (TEMP-105) form a condensed ring through condensation of the ring $Q_A$ and the ring $Q_C$. In the case where the ring $Q_A$ in the general formula (TMEP-104) is a benzene ring, the ring $Q_A$ is a monocyclic ring. In the case where the ring $Q_A$ in the general formula (TMEP-104) is a naphthalene ring, the ring $Q_A$ is a condensed ring.

The "unsaturated ring" means an aromatic hydrocarbon ring or an aromatic heterocyclic ring. The "saturated ring" means an aliphatic hydrocarbon ring or a non-aromatic heterocyclic ring.

Specific examples of the aromatic hydrocarbon ring include the structures formed by terminating the groups exemplified as the specific examples in the set of specific examples G1 with a hydrogen atom.

Specific examples of the aromatic heterocyclic ring include the structures formed by terminating the aromatic heterocyclic groups exemplified as the specific examples in the set of specific examples G2 with a hydrogen atom.

Specific examples of the aliphatic hydrocarbon ring include the structures formed by terminating the groups exemplified as the specific examples in the set of specific examples G6 with a hydrogen atom.

The expression "to form a ring" means that the ring is formed only with the plural atoms of the core structure or with the plural atoms of the core structure and one or more arbitrary element. For example, the ring $Q_A$ formed by bonding $R_{921}$ and $R_{922}$ each other shown in the general formula (TEMP-104) means a ring formed with the carbon atom of the anthracene skeleton bonded to $R_{921}$, the carbon atom of the anthracene skeleton bonded to $R_{922}$, and one or more arbitrary element. As a specific example, in the case where the ring $Q_A$ is formed with $R_{921}$ and $R_{922}$, and in the case where a monocyclic unsaturated ring is formed with the carbon atom of the anthracene skeleton bonded to $R_{921}$, the carbon atom of the anthracene skeleton bonded to $R_{922}$, and four carbon atoms, the ring formed with $R_{921}$ and $R_{922}$ is a benzene ring.

Herein, the "arbitrary element" is preferably at least one kind of an element selected from the group consisting of a carbon element, a nitrogen element, an oxygen element, and a sulfur element, unless otherwise indicated in the description. For the arbitrary element (for example, for a carbon element or a nitrogen element), a bond that does not form a ring may be terminated with a hydrogen atom or the like, and may be substituted by an "arbitrary substituent" described later. In the case where an arbitrary element other than a carbon element is contained, the formed ring is a heterocyclic ring.

The number of the "one or more arbitrary element" constituting the monocyclic ring or the condensed ring is preferably 2 or more and 15 or less, more preferably 3 or more and 12 or less, and further preferably 3 or more and 5 or less, unless otherwise indicated in the description.

What is preferred between the "monocyclic ring" and the "condensed ring" is the "monocyclic ring" unless otherwise indicated in the description.

What is preferred between the "saturated ring" and the "unsaturated ring" is the "unsaturated ring" unless otherwise indicated in the description.

The "monocyclic ring" is preferably a benzene ring unless otherwise indicated in the description.

The "unsaturated ring" is preferably a benzene ring unless otherwise indicated in the description.

In the case where the "one or more combinations of combinations each including adjacent two or more" each are "bonded to each other to form a substituted or unsubstituted monocyclic ring", or each are "bonded to each other to form a substituted or unsubstituted condensed ring", it is preferred that the one or more combinations of combinations each including adjacent two or more each are bonded to each other to form a substituted or unsubstituted "unsaturated ring" containing the plural atoms of the core skeleton and 1 or more and 15 or less at least one kind of an element selected from the group consisting of a carbon element, a nitrogen element, an oxygen element, and a sulfur element, unless otherwise indicated in the description.

In the case where the "monocyclic ring" or the "condensed ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

In the case where the "saturated ring" or the "unsaturated ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

The above are the explanation of the case where "one or more combinations of combinations each including adjacent two or more" each are "bonded to each other to form a substituted or unsubstituted monocyclic ring", and the case where "one or more combinations of combinations each including adjacent two or more" each are "bonded to each other to form a substituted or unsubstituted condensed ring" (i.e., the "case forming a ring by bonding").

Substituent for "Substituted or Unsubstituted"

In one embodiment in the description herein, the substituent for the case of "substituted or unsubstituted" (which may be hereinafter referred to as an "arbitrary substituent") is, for example, a group selected from the group consisting of an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
an unsubstituted aryl group having 6 to 50 ring carbon atoms, and
an unsubstituted heterocyclic group having 5 to 50 ring atoms,
wherein $R_{901}$ to $R_{907}$ each independently represent
a hydrogen atom,
a substituted or unsubstituted alkyl group having 1 to 50 carbon atoms
a substituted or unsubstituted cycloalkyl group having 3 to 50 ring carbon atoms,
a substituted or unsubstituted aryl group having 6 to 50 ring carbon atoms, or
a substituted or unsubstituted heterocyclic group having 5 to 50 ring atoms.

In the case where two or more groups each represented by $R_{901}$ exist, the two or more groups each represented by $R_{901}$ are the same as or different from each other,
in the case where two or more groups each represented by $R_{902}$ exist, the two or more groups each represented by $R_{902}$ are the same as or different from each other,
in the case where two or more groups each represented by $R_{903}$ exist, the two or more groups each represented by $R_{903}$ are the same as or different from each other,
in the case where two or more groups each represented by $R_{904}$ exist, the two or more groups each represented by $R_{904}$ are the same as or different from each other,
in the case where two or more groups each represented by $R_{905}$ exist, the two or more groups each represented by $R_{905}$ are the same as or different from each other,
in the case where two or more groups each represented by $R_{906}$ exist, the two or more groups each represented by $R_{906}$ are the same as or different from each other, and
in the case where two or more groups each represented by $R_{907}$ exist, the two or more groups each represented by $R_{907}$ are the same as or different from each other.

In one embodiment, the substituent for the case of "substituted or unsubstituted" may be a group selected from the group consisting of
an alkyl group having 1 to 50 carbon atoms,
an aryl group having 6 to 50 ring carbon atoms, and
a heterocyclic group having 5 to 50 ring atoms.

In one embodiment, the substituent for the case of "substituted or unsubstituted" may be a group selected from the group consisting of
an alkyl group having 1 to 18 carbon atoms,
an aryl group having 6 to 18 ring carbon atoms, and
a heterocyclic group having 5 to 18 ring atoms.

The specific examples of the groups for the arbitrary substituent described above are the specific examples of the substituent described in the section "Substituents in Description" described above.

In the description herein, the arbitrary adjacent substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring, unless otherwise indicated.

In the description herein, the arbitrary substituent may further have a substituent unless otherwise indicated in the description. The definition of the substituent that the arbitrary substituent further has may be the same as the arbitrary substituent.

In the description herein, a numerical range shown by "AA to BB" means a range including the numerical value AA as the former of "AA to BB" as the lower limit value and the numerical value BB as the latter of "AA to BB" as the upper limit value.

The compound of the present invention will be described below.

The compound of the present invention is represented by the following formula (1). Hereinafter, the compound of the present invention represented by the formula (1) or each formula mentioned later is sometimes simply referred to as "the inventive compound".

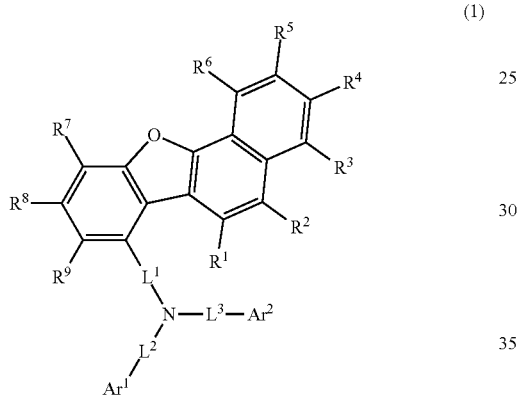

(1)

Signs in the formula (1) and each formula mentioned later will be described below. The same signs have the same meanings in the following formulae unless otherwise specified.

In the Formula (1), $R^1$ to $R^9$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, or a substituted or unsubstituted heterocyclic group having 5 to 50 ring atoms.

$R^1$ to $R^9$ are preferably each independently a hydrogen atom, a substituted or unsubstituted alkyl group having 1 to 50 carbon atoms, a substituted or unsubstituted cycloalkyl group having 3 to 50 ring carbon atoms, more preferably each independently a hydrogen atom, a substituted or unsubstituted alkyl group having 1 to 50 carbon atoms, or a substituted or unsubstituted cycloalkyl group having 3 to 50 carbon atoms, and further preferably a hydrogen atom.

Details of the halogen atom are as described above in the section "Substituents in Description", and preferred is a fluorine atom.

Details of the substituted or unsubstituted alkyl group having 1 to 50 carbon atoms are as described above in the section "Substituents in Description".

The unsubstituted alkyl group is preferably a methyl group, an ethyl group, an n-propyl group, an isopropyl group, or a t-butyl group, and more preferably a methyl group, an isopropyl group, or a t-butyl group, Details of the substituted or unsubstituted cycloalkyl group having 3 to 50 ring carbon atoms are as described above in the section "Substituents in Description".

The unsubstituted cycloalkyl group is preferably a cyclopropyl group, a cyclobutyl group, a cyclopentyl group, a cyclohexyl group, or an adamantyl group.

In an embodiment of the present invention, all of $R^1$ to $R^9$ are preferably a hydrogen atom.

Adjacent two selected from $R^1$ to $R^9$ are not bonded to each other, thus forming no ring structure.

$L^1$ is a substituted or unsubstituted arylene group having 6 to 30 ring carbon atoms or a substituted or unsubstituted divalent heterocyclic group having 5 to 30 ring atoms. $L^1$ is preferably a substituted or unsubstituted arylene group having 6 to 30 ring carbon atoms.

Details of the substituted or unsubstituted arylene group having 6 to 30 ring carbon atoms are as described above in the section "Substituents in Description".

The unsubstituted arylene group having 6 to 30 ring carbon atoms is preferably a phenylene group, a biphenylene group, a terphenylene group, or a naphthylene group.

Details of the substituted or unsubstituted divalent heterocyclic group having 5 to 30 ring atoms are as described above in the section "Substituents in Description".

In an embodiment of the present invention, $L^1$ is preferably a substituted or unsubstituted phenylene group, a substituted or unsubstituted biphenylene group, or a substituted or unsubstituted naphthylene group, and more preferably a substituted or unsubstituted phenylene group.

$L^2$ and $L^3$ are each independently a single bond, a substituted or unsubstituted divalent heterocyclic group having 5 to 30 ring atoms, or a group represented by any of the following formulae (i) to (iii).

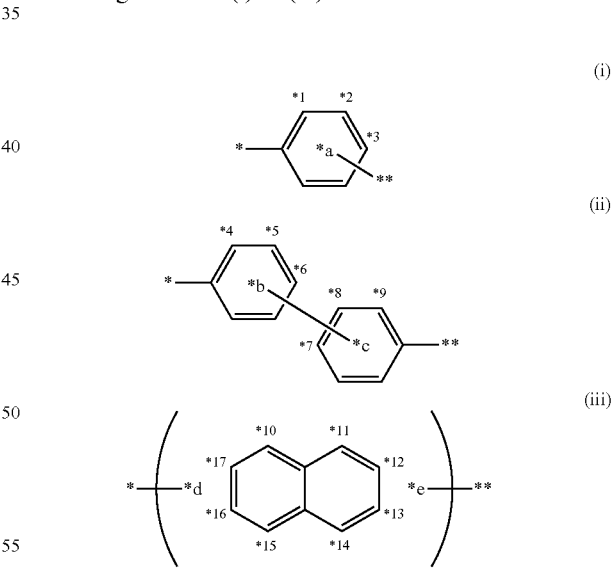

In the formulae (i) to (iii),

*a is bonded to one selected from the carbon atoms *1 to *3,

*b is bonded to one selected from the carbon atoms *4 to *6,

*c is bonded to one selected from the carbon atoms *7 to *9,

*d is bonded to one selected from the carbon atoms *10 to *17, *e is bonded to another one selected from the carbon atoms *10 to *17, \* represents a bonding site to the central nitrogen atom, and \*\* represents a bonding site to $Ar^1$ or $Ar^2$.

In an embodiment of the present invention, $L^2$ and $L^3$ are preferably each independently a single bond or a group represented by the formula (i) or (ii).

Details of the substituted or unsubstituted divalent heterocyclic group having 5 to 30 ring atoms represented by $L^2$ and La are as described above in the section "Substituents in Description".

In an embodiment of the present invention, \*a is preferably bonded to the carbon atom \*3.

In another embodiment of the present invention, \*b is preferably bonded to the carbon atom \*6.

In still another embodiment of the present invention, \*c is preferably bonded to the carbon atom \*7.

$Ar^1$ and $Ar^2$ are each independently a group represented by any of the following formulae (a) to (e).

In the Formula (a), $R^{10}$ to $R^{25}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms.

Provided that one selected from $R^{10}$ to $R^{14}$ is a single bond bonded to \*f, one selected from $R^{15}$ to $R^{20}$ is a single bond bonded to \*g, another one selected from $R^{15}$ to $R^{20}$ is a single bond bonded to \*h, \*\*\* represents a bonding site to $L^2$ or $L^3$, m1 is 0 or 1, n1 is 0 or 1, when m1 is 0 and n1 is 0, \*h is bonded to $L^2$ or $L^3$,

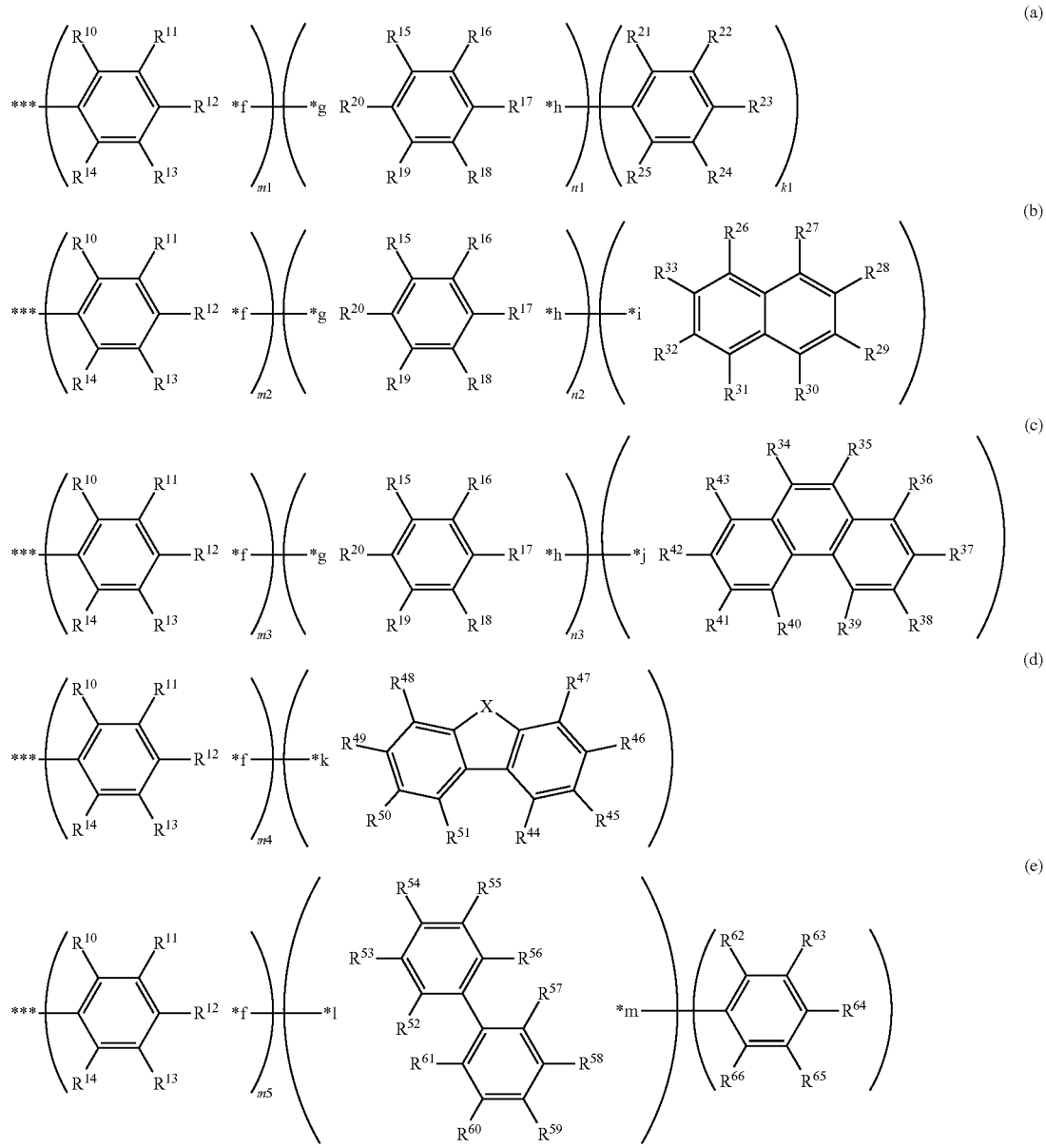

when m1 is 0 and n1 is 1, *f is bonded to $L^2$ or $L^3$,
when m1 is 1 and n1 is 0, one selected from $R^{10}$ to $R^{14}$ is a single bond bonded to *h, and
k1 is 1 or 2.

Adjacent two selected from $R^{10}$ to $R^{14}$ that are not the single bond are, and adjacent two selected from $R^{15}$ to $R^{20}$ that are not either of the single bonds are, not bonded to each other, thus forming no ring structure.

When $Ar^1$ is a group represented by the formula (a) in which m1 is 0, n1 is 0, and $L^2$ is a single bond, *h is bonded to the central nitrogen atom.

When $Ar^2$ is a group represented by the formula (a) in which m1 is 0, n1 is 0, and $L^3$ is a single bond, *h is bonded to the central nitrogen atom.

When $Ar^1$ is a group represented by the formula (a) in which m1 is 0, n1 is 1, and $L^2$ is a single bond, *f is bonded to the central nitrogen atom.

When $Ar^2$ is a group represented by the formula (a) in which m1 is 0, n1 is 1, and La is a single bond, *f is bonded to the central nitrogen atom.

When $Ar^1$ is a group represented by the formula (a) in which m1 is 1, n1 is 1, and $L^2$ is a single bond, *** represents a bonding site to the central nitrogen atom.

When $Ar^2$ is a group represented by the formula (a) in which m1 is 1, n1 is 1, and La is a single bond, *** represents a bonding site to the central nitrogen atom.

k1 is preferably 1.

In an embodiment of the present invention, it is preferred that m1 is 0, n1 is 0, and k1 is 1, in another embodiment, it is preferred that m1 is 0, n1 is 1, and k1 is 1, or that m1 is 1, n1 is 0, and k1 is 1. In still another embodiment, it is preferred that m1 is 1, n1 is 1, and k1 is 1. In still yet another embodiment, it is preferred that m1 is 1, n1 is 1, and k1 is 2.

In an embodiment of the present invention, at least one of $Ar^1$ and $Ar^2$ is preferably a group represented by the formula (a).

In the formula (b),
$R^{10}$ to $R^{20}$, *f, *g, *h, and *** are the same as described above,
$R^{26}$ to $R^{33}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms.

Provided that, one selected from $R^{26}$ to $R^{33}$ is a single bond bonded to *i.

m2 is 0 or 1, n2 is 0 or 1,
when m2 is 0 and n2 is 0, *h is bonded to $L^2$ or $L^3$,
when m2 is 0 and n2 is 1, *f is bonded to $L^2$ or $L^3$, and
when m2 is 1 and n2 is 0, one selected from $R^{10}$ to $R^{14}$ is a single bond bonded to *h.

Adjacent two selected from $R^{10}$ to $R^{14}$ that are not the single bond are, and adjacent two selected from $R^{15}$ to $R^{20}$ that are not either of the single bonds are, not bonded to each other, thus forming no ring structure.

When $Ar^1$ is a group represented by the formula (b) in which m2 is 0, n2 is 0, and $L^2$ is a single bond, *h is bonded to the central nitrogen atom.

When $Ar^2$ is a group represented by the formula (b) in which m2 is 0, n2 is 0, and La is a single bond, *h is bonded to the central nitrogen atom.

When $Ar^1$ is a group represented by the formula (b) in which m2 is 0, n2 is 1, and $L^2$ is a single bond, *f is bonded to the central nitrogen atom.

When $Ar^2$ is a group represented by the formula (b) in which m2 is 0, n2 is 1, and $L^3$ is a single bond, *f is bonded to the central nitrogen atom.

When $Ar^1$ is a group represented by the formula (b) in which m2 is 1, n2 is 1, and $L^2$ is a single bond, *** represents a bonding site to the central nitrogen atom.

When $Ar^2$ is a group represented by the formula (b) in which m2 is 1, n2 is 1, and $L^3$ is a single bond, *** represents a bonding site to the central nitrogen atom.

In an embodiment of the present invention, it is preferred that m2 is 0 and n2 is 0, in another embodiment, it is preferred that m2 is 0 and n2 is 1, or that m2 is 1 and n2 is 0. In still another embodiment, it is preferred that m2 is 1 and n2 is 1.

In the Formula (c),
$R^{10}$ to $R^{20}$, *f, *g, *h, and *** are the same as described above,
$R^{34}$ to $R^{43}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms.

Provided that, one selected from $R^{34}$ to $R^{43}$ is a single bond bonded to *j.

m3 is 0 or 1, n3 is 0 or 1,
when m3 is 0 and n3 is 0, *h is bonded to $L^2$ or $L^3$,
when m3 is 0 and n3 is 1, *f is bonded to $L^2$ or $L^3$, and
when m3 is 1 and n2 is 0, one selected from $R^{10}$ to $R^{14}$ is a single bond bonded to *h.

Adjacent two selected from $R^{10}$ to $R^{14}$ that are not the single bond are, adjacent two selected from $R^{15}$ to $R^{20}$ that are not either of the single bonds are, and $R^{34}$ and $R^{35}$ are, not bonded to each other, thus forming no ring structure.

In an embodiment of the present invention, $R^{34}$ or $R^{37}$ is preferably a single bond bonded to *j.

When $Ar^1$ is a group represented by the formula (c) in which m3 is 0, n3 is 0, and $L^2$ is a single bond, *h is bonded to the central nitrogen atom.

When $Ar^2$ is a group represented by the formula (c) in which m3 is 0, n3 is 0, and $L^3$ is a single bond, *h is bonded to the central nitrogen atom.

When $Ar^1$ is a group represented by the formula (c) in which m3 is 0, n3 is 1, and $L^2$ is a single bond, *f is bonded to the central nitrogen atom.

When $Ar^2$ is a group represented by the formula (c) in which m3 is 0, n3 is 1, and $L^3$ is a single bond, *f is bonded to the central nitrogen atom.

When $Ar^1$ is a group represented by the formula (c) in which m3 is 1, n3 is 1, and $L^2$ is a single bond, *** represents a bonding site to the central nitrogen atom.

When $Ar^2$ is a group represented by the formula (c) in which m3 is 1, n3 is 1, and L is a single bond, *** represents a bonding site to the central nitrogen atom.

In an embodiment of the present invention, it is preferred that m3 is 0 and n3 is 0, and in another embodiment, it is preferred that m3 is 0 and n3 is 1, or that m3 is 1 and n3 is 0. In still another embodiment, it is preferred that m3 is 1 and n3 is 1.

In the Formula (d),
$R^{10}$ to $R^{14}$, *f, and *** are the same as described above, $R^{44}$ to $R^{51}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms.

X is an oxygen atom, a sulfur atom, $CR^aR^b$, or $NR^c$, $R^a$, $R^b$, and $R^c$ are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

Provided that, one selected from $R^{44}$ to $R^{51}$ and $R^c$ is a single bond bonded to *k.

m4 is 0 or 1, and when m4 is 0, *f is bonded to $L^2$ or L.

combinations of adjacent two selected from $R^{44}$ to $R^{51}$ that are not the single bond may each independently be bonded to each other to form a substituted or unsubstituted ring structure.

$R^a$ and $R^b$ are not crosslinked.

In an embodiment of the present invention, X is preferably an oxygen atom, $CR^aR^b$, or $NR^c$, and more preferably an oxygen atom.

Details of the substituted or unsubstituted alkyl group having 1 to 50 carbon atoms represented by $R^a$, $R^b$, and $R^c$ are as described above for $R^1$ to $R^9$.

Details of the substituted or unsubstituted aryl group having 6 to 50 ring carbon atoms represented by $R^a$, $R^b$, and $R^c$ are as described above in the section "Substituents in Description".

The unsubstituted aryl groups having 5 to 50 ring carbon atoms represented by $R^a$, $R^b$, and $R^c$ are preferably each independently selected from a phenyl group, a biphenyl group, and a naphthyl group.

Details of the substituted or unsubstituted heterocyclic group having 5 to 50 carbon atoms represented by $R^a$, $R^b$, and $R^c$ are as described above for $R^1$ to $R^9$.

When $Ar^1$ is a group represented by the formula (d) in which m4 is 0 and $L^2$ is a single bond, *f is bonded to the central nitrogen atom.

When $Ar^2$ is a group represented by the formula (d) in which m4 is 0 and $L^3$ is a single bond, *f is bonded to the central nitrogen atom.

When $Ar^1$ is a group represented by the formula (d) in which m4 is 1 and $L^2$ is a single bond, *** represents a bonding site to the central nitrogen atom.

When $Ar^2$ is a group represented by the formula (d) in which m4 is 1 and L is a single bond, *** represents a bonding site to the central nitrogen atom.

In an embodiment of the present invention, m4 is preferably 0, and in another embodiment, m4 is preferably 1.

In an embodiment of the present invention, combinations of adjacent two selected from $R^{44}$ to $R^{51}$ that are not the single bond are each independently not bonded to each other to form a substituted or unsubstituted ring structure.

In the formula (e), $R^{10}$ to $R^{14}$, *f, and *** are the same as described above, $R^{52}$ to $R^{66}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms.

Provided that, one selected from $R^{52}$ to $R^{56}$ is a single bond bonded to *l, another one selected from $R^{52}$ to $R^{56}$ is a single bond bonded to *m, m5 is 0 or 1, and when m5 is 0, *f is bonded to $L^2$ or L.

Adjacent two selected from $R^{10}$ to $R^{14}$ that are not the single bond are, adjacent two selected from $R^{52}$ to $R^{56}$ that are not either of the single bonds are, $R^{52}$ and $R^{61}$ are, and $R^{56}$ and $R^{57}$ are, not bonded to each other, thus forming no ring structure.

In an embodiment of the present invention, it is preferred that $R^{53}$ is a single bond bonded to *l and $R^{56}$ is a single bond bonded to *m.

When $Ar^1$ is a group represented by the formula (e) in which m5 is 0 and $L^2$ is a single bond, *f is bonded to the central nitrogen atom.

When $Ar^2$ is a group represented by the formula (e) in which m5 is 0 and $L^3$ is a single bond, *f is bonded to the central nitrogen atom.

When $Ar^1$ is a group represented by the formula (e) in which m5 is 1 and $L^2$ is a single bond, *** represents a bonding site to the central nitrogen atom.

When $Ar^2$ is a group represented by the formula (e) in which m5 is 1 and $L^3$ is a single bond, *** represents a bonding site to the central nitrogen atom.

In an embodiment of the present invention, m5 is preferably 0, and in another embodiment, m5 is preferably 1.

Details of the substituted or unsubstituted aryl group having 6 to 50 ring carbon atoms represented by $R^{10}$ to $R^{66}$ are as described above in the section "Substituents in Description".

The unsubstituted aryl group having 5 to 50 ring carbon atoms represented by $R^{10}$ to $R^{66}$ are preferably each independently selected from a phenyl group, a biphenyl group, and a naphthyl group.

Details of each group other than the aryl group represented by $R^{10}$ to $R^{66}$ are the same as the details of the corresponding group described for $R^1$ to $R^9$.

$Ar^1$ and $Ar^2$ are preferably each independently a group represented by any of the following formulae (a-1) to (e-1).

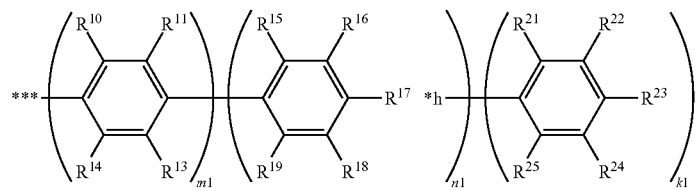

(a-1)

-continued (b-1), (c-1), (d-1), (e-1) [chemical structures]

In the formulae (a-1) to (e-1), $R^{10}$, $R^{11}$, $R^{13}$, $R^{14}$, $R^{15}$ to $R^{19}$, $R^{21}$ to $R^{66}$, X, *i, *j, *k, *l, *m, m1, n1, k1, m2, n2, m3, n3, m4, and m5 are as defined in the formula (1).

In an embodiment of the present invention, in the formula (a), all of $R^{10}$ to $R^{14}$ that are not the single bond bonded to *f may be a hydrogen atom, in the formula (a), all of $R^{15}$ to $R^{20}$ that are not the single bond bonded to *g nor the single bond bonded to *h may be a hydrogen atom, and all of $R^{21}$ to $R^{25}$ may be a hydrogen atom, in the formula (b), all of $R^{10}$ to $R^{14}$ that are not the single bond bonded to *f may be a hydrogen atom, in the formula (b), all of $R^{15}$ to $R^{20}$ that are not the single bond bonded to *g nor the single bond bonded to *h may be a hydrogen atom, and all of $R^{26}$ to $R^{33}$ that are not the single bond bonded to *i may be a hydrogen atom, in the formula (c), all of $R^{10}$ to $R^{14}$ that are not the single bond bonded to *f may be a hydrogen atom, in the formula (c), all of $R^{15}$ to $R^{20}$ that are not the single bond bonded to *g nor the single bond bonded to *h may be a hydrogen atom, and all of $R^{34}$ to $R^{43}$ that are not the single bond bonded to *j may be a hydrogen atom, in the formula (d), all of $R^{10}$ to $R^{14}$ that are not the single bond bonded to *f may be a hydrogen atom, and all of $R^{44}$ to $R^{51}$ that are not the single bond bonded to *k may be a hydrogen atom, and in the formula (e), all of $R^{10}$ to $R^{14}$ that are not the single bond bonded to *f may be a hydrogen atom, all of $R^{52}$ to $R^{56}$ that are not the single bond bonded to *l nor the single bond bonded to *m may be a hydrogen atom, all of $R^{57}$ to $R^{61}$ may be a hydrogen atom, and all of $R^{62}$ to $R^{66}$ may be a hydrogen atom.

As described above, a "hydrogen atom" as used herein includes a light hydrogen atom, a deuterium atom, and a tritium atom. Thus, the inventive compound may contain a naturally-derived deuterium atom.

A deuterium atom may also be intentionally introduced in the inventive compound by using a deuterated compound in a part or all of raw material compounds. Thus, in an embodiment of the present invention, the inventive compound contains at least one deuterium atom. Specifically, the inventive compound may be a compound represented by formula (1), at least one of the hydrogen atoms contained in the compound being a deuterium atom.

At least one hydrogen atom selected from the following hydrogen atoms may be a deuterium atom:

a hydrogen atom represented by any of $R^1$ to $R^9$; a hydrogen atom of a substituted or unsubstituted alkyl group, a cycloalkyl group, a halogen atom, a cyano group, a nitro group, or a heterocyclic group represented by any of $R^1$ to $R^9$;

a hydrogen atom represented by any of $R^{10}$ to $R^{25}$; a hydrogen atom of a substituted or unsubstituted alkyl group, a substituted or unsubstituted cycloalkyl group, a halogen atom, a cyano group, a nitro group, a substituted or unsubstituted aryl group constituted only of 6-membered rings, or a substituted or unsubstituted heterocyclic group represented by any of $R^{10}$ to $R^{25}$;

a hydrogen atom represented by any of $R^{26}$ to $R^{33}$; a hydrogen atom of a substituted or unsubstituted alkyl group, a substituted or unsubstituted cycloalkyl group, a halogen atom, a cyano group, a nitro group, a substituted or unsubstituted aryl group constituted only of 6-membered rings, or a substituted or unsubstituted a heterocyclic group represented by any of $R^{26}$ to $R^{33}$;

a hydrogen atom represented by any of $R^{34}$ to $R^{43}$; a hydrogen atom of a substituted or unsubstituted alkyl group, a substituted or unsubstituted cycloalkyl group, a halogen atom, a cyano group, a nitro group, a substituted or unsubstituted aryl group constituted only of 6-membered rings, or a substituted or unsubstituted heterocyclic group represented by any of $R^{34}$ to $R^{43}$;

a hydrogen atom represented by any of $R^{44}$ to $R^{51}$; a hydrogen atom of a substituted or unsubstituted alkyl group, a substituted or unsubstituted cycloalkyl group, a halogen atom, a cyano group, a nitro group, a substituted or unsubstituted aryl group constituted only of 6-membered rings, or a substituted or unsubstituted heterocyclic group represented by any of $R^{44}$ to $R^{51}$;

a hydrogen atom represented by any of $R^a$, $R^b$, and $R^c$; a hydrogen atom of a substituted or unsubstituted alkyl group, a substituted or unsubstituted aryl group, or a substituted or unsubstituted heterocyclic group represented by any of $R^a$, $R^b$, and $R^c$;

a hydrogen atom of a substituted or unsubstituted arylene group or a substituted or unsubstituted divalent heterocyclic group represented by $L^1$; and a hydrogen atom of a substituted or unsubstituted divalent heterocyclic group represented by either of $L^2$ and $L^3$; a hydrogen atom of a group represented by the any of the formulae (i) to (iii) represented by either of $L^2$ and $L^3$.

The deuteration ratio of the inventive compound depends on the deuteration ratio of the raw material compound used. Even when a raw material having a predetermined deuteration ratio is used, light hydrogen isomers may be contained at a certain naturally-derived ratio. Thus, the embodiments of the deuteration ratio of the inventive compound shown below are a ratio obtained by taking a minor amount of naturally-derived isomers into account based on a ratio obtained by simply counting the number of deuterium atoms shown by the chemical formula.

The deuteration ratio of the inventive compound is preferably 1% or more, more preferably 3% or more, further preferably 5% or more, furthermore preferably 10% or more, and still furthermore preferably 50% or more.

The inventive compound may be a mixture containing a deuterated compound and a non-deuterated compound or a mixture of two or more compounds having different deuteration ratios. The deuteration ratio of such a mixture is preferably 1% or more, more preferably 3% or more, further preferably 5% or more, further preferably 10% or more, furthermore preferably 50% or more, and less than 100%.

The ratio of the number of the deuterium atoms based on the number of all the hydrogen atoms in the inventive compound is preferably 1% or more, more preferably 3% or more, further preferably 5% or more, further preferably 10% or more, and 100% or less.

Details of the substituent (arbitrary substituent) in the "substituted or unsubstituted" included in the definition of each formula as mentioned above are as described in the section "Substituent for "Substituted or Unsubstituted"".

Here, said arbitrary substituent in the definition of each formula according to the formula (1) does not include an aryl group, a heterocyclic group, and the substituent in which $R_{901}$ to $R_{907}$ are a heterocyclic group among the substituents described in the section "Substituent for "Substituted or Unsubstituted"".

The inventive compound can be easily produced by a person skilled in the art with reference to synthetic examples described below and known synthetic methods.

Specific examples of the inventive compound will be shown below, but were not limited to the exemplified compounds.

In the following specific examples, D represents a deuterium atom.

[Chem. 29]

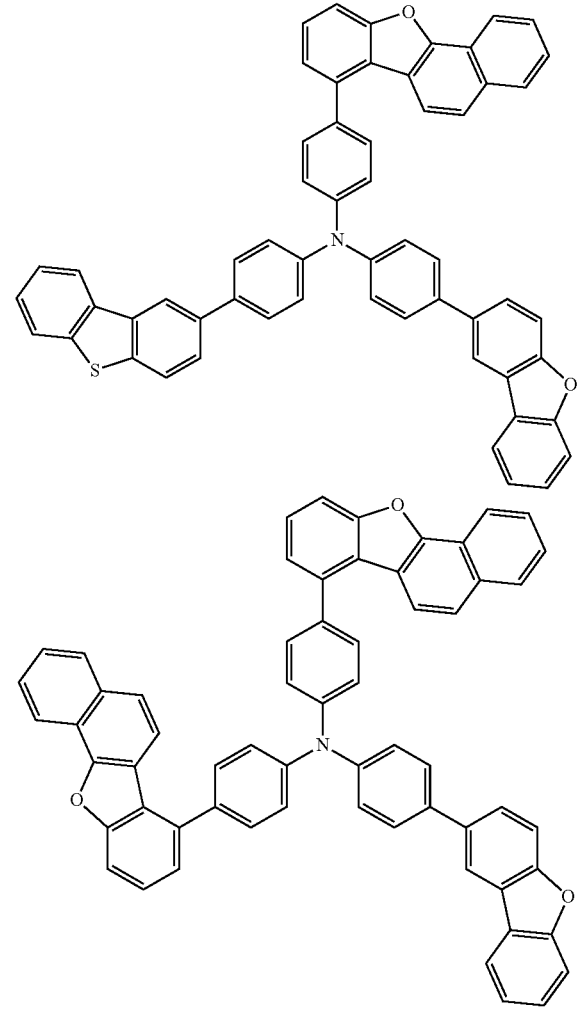

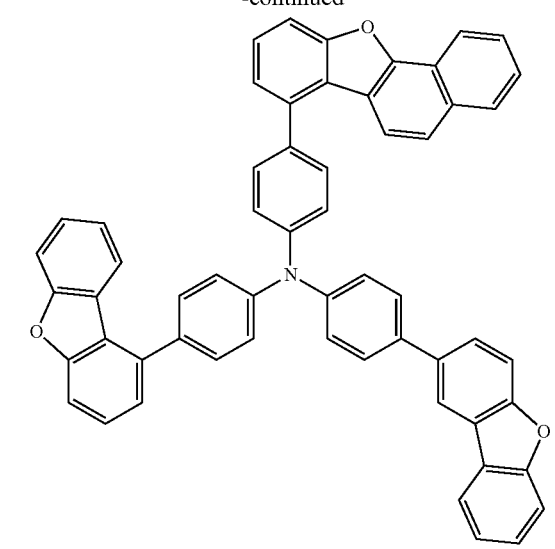
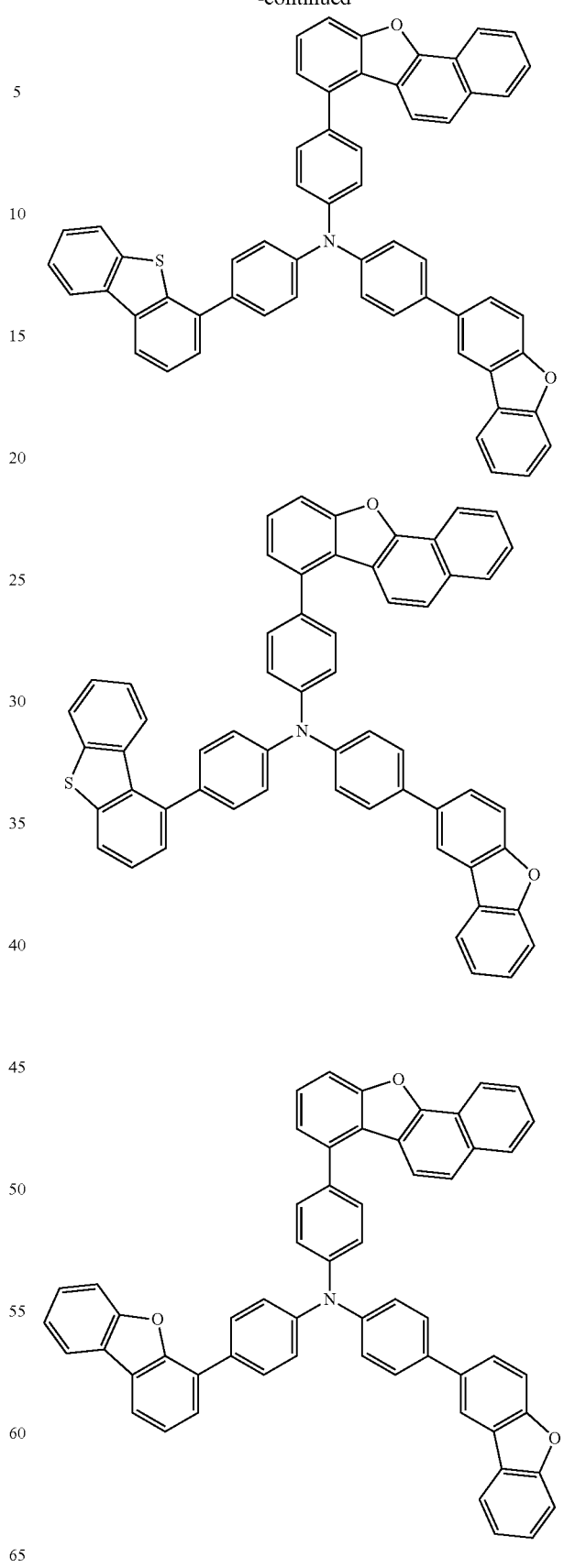

[Chem. 30]
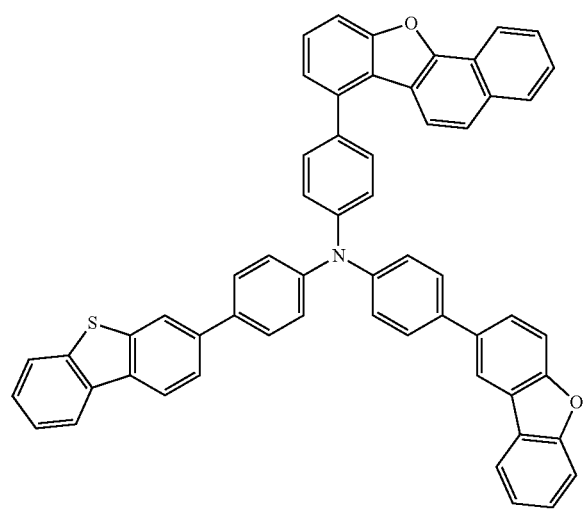
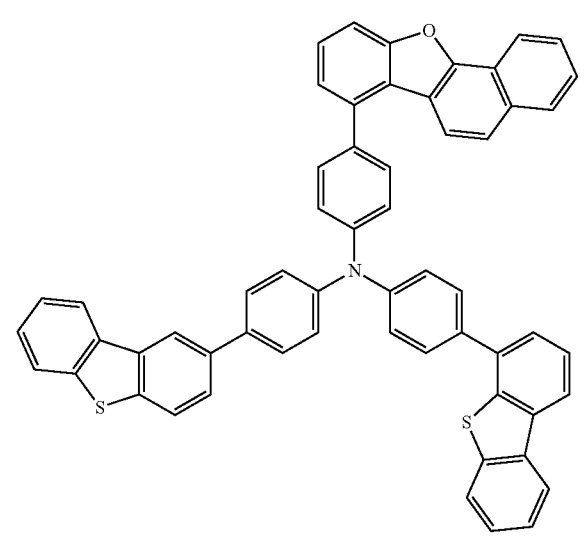
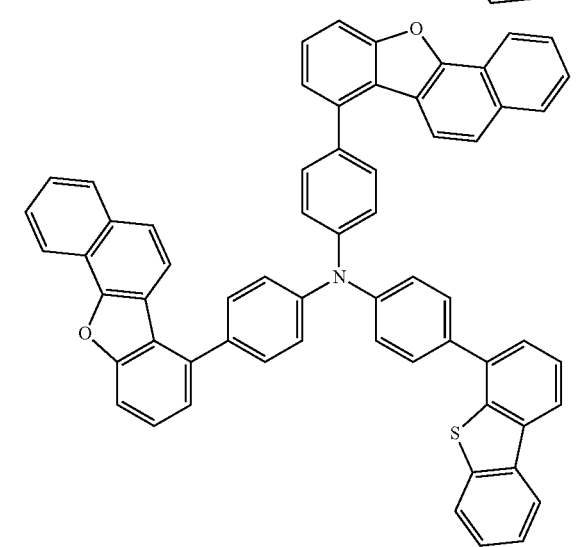
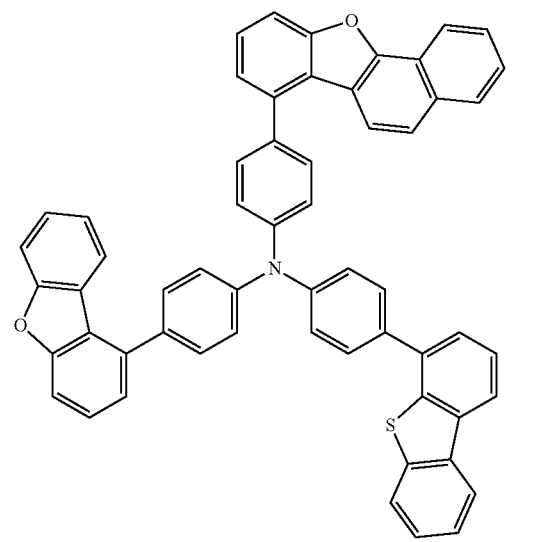
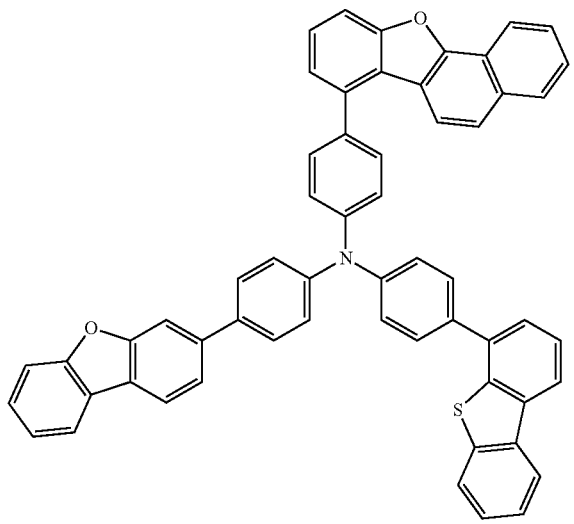
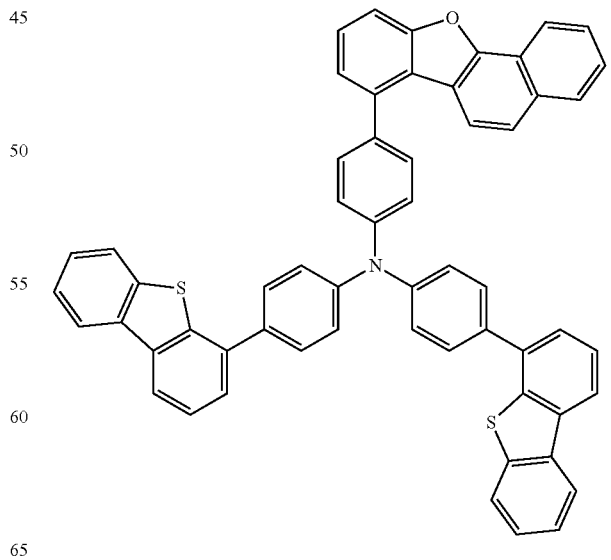

57
-continued
58
-continued
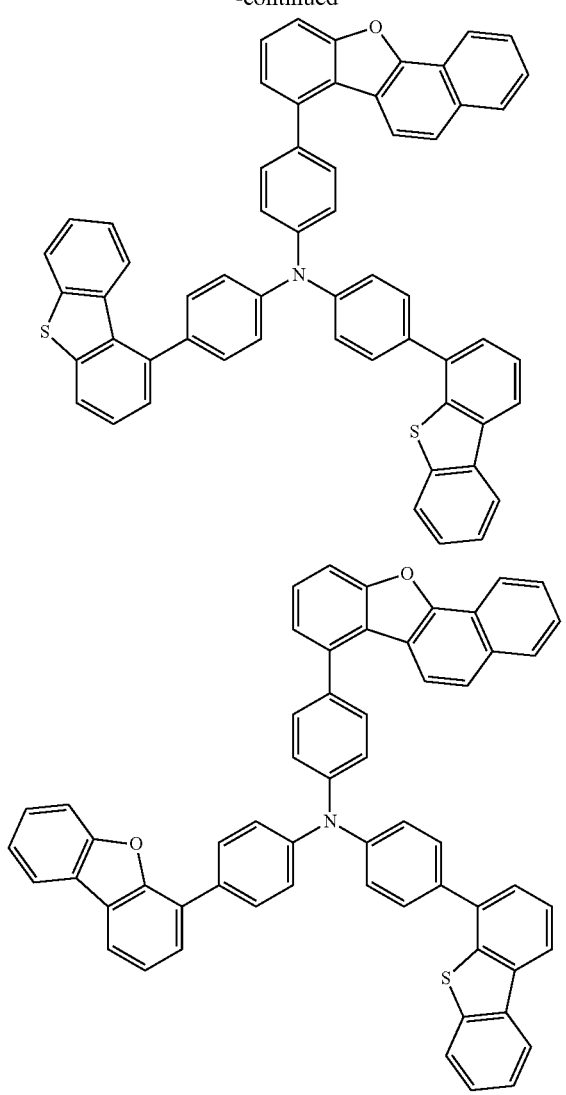
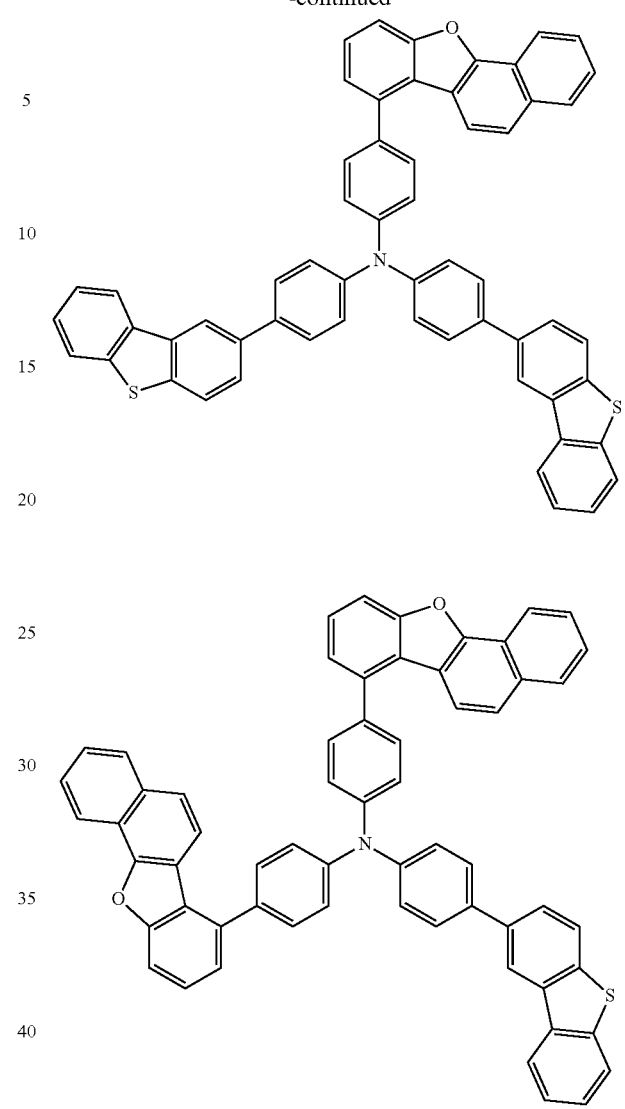
[Chem. 31]
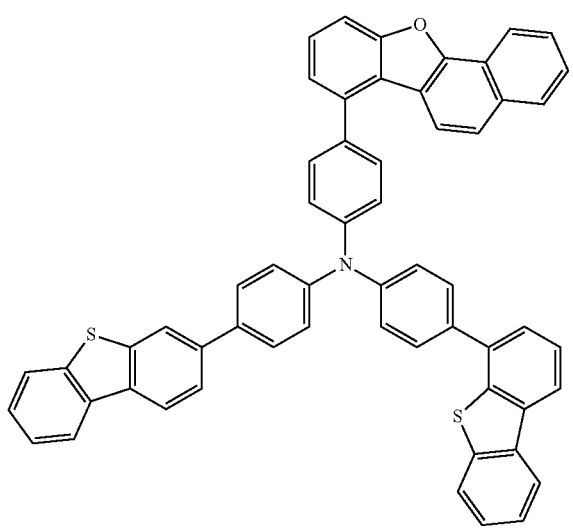
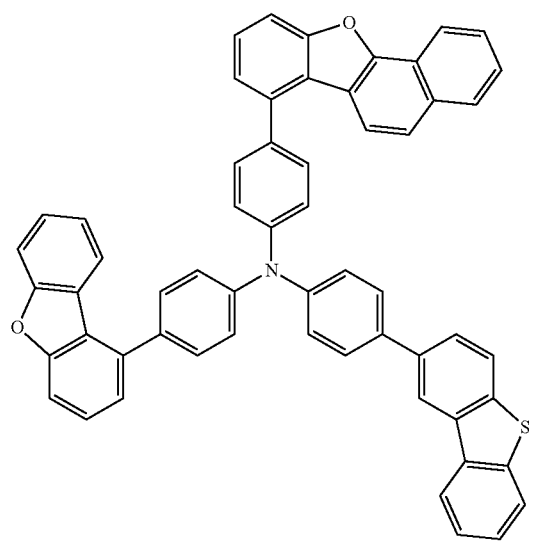

59
-continued
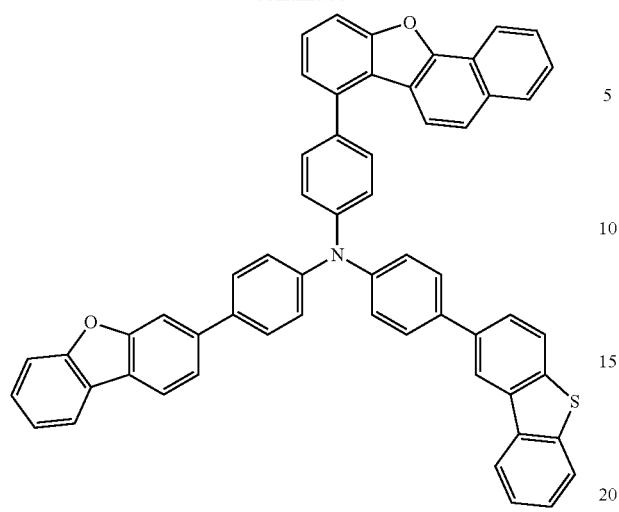
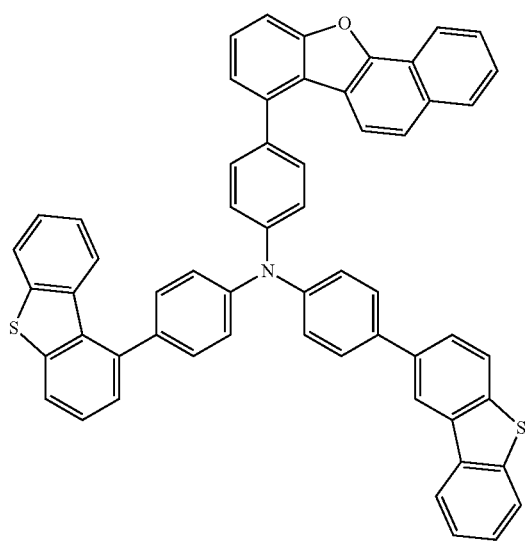
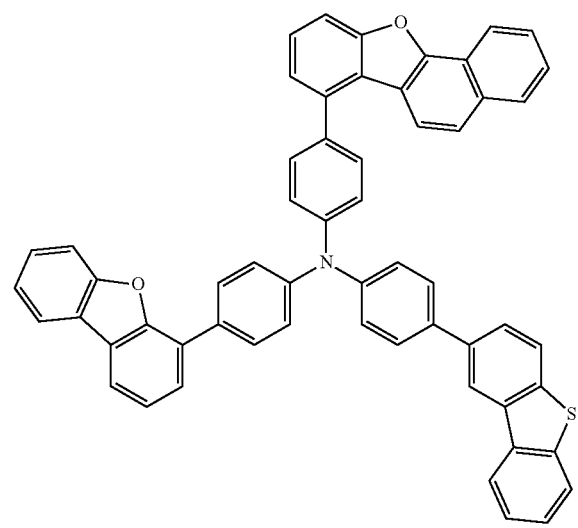
60
-continued
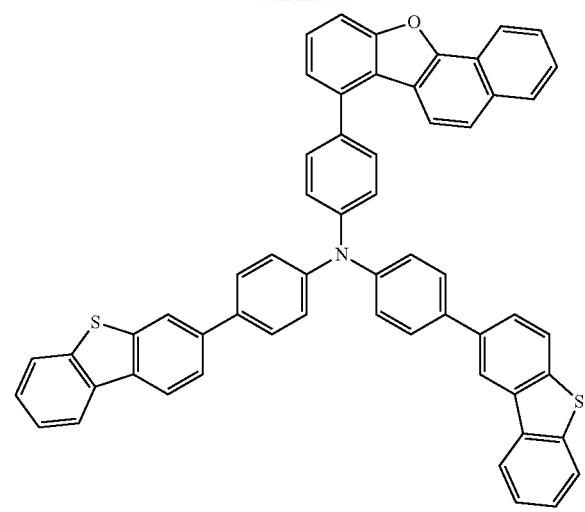
[Chem. 32]
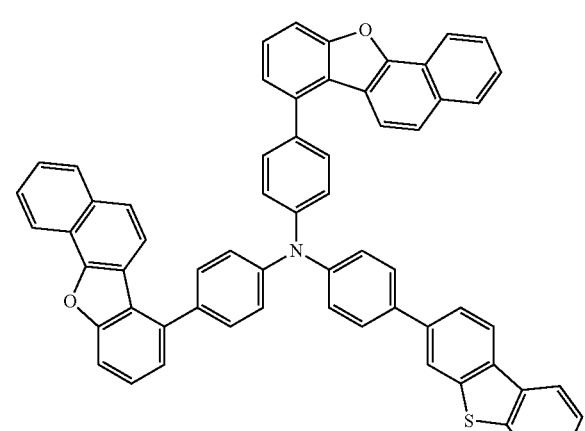
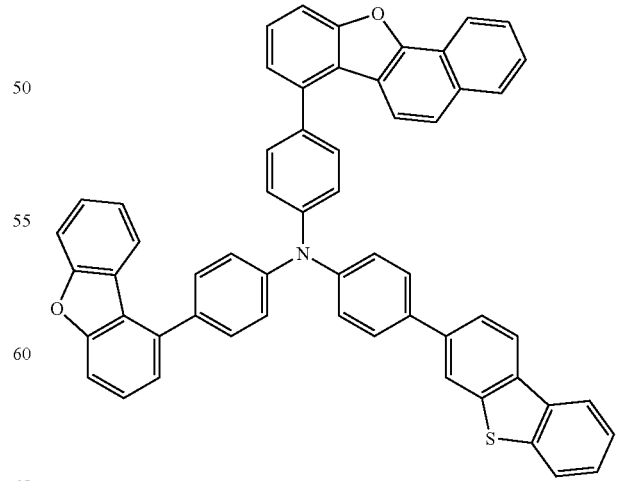

-continued
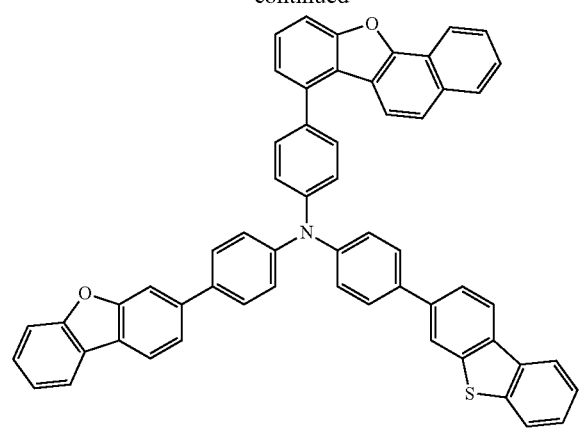
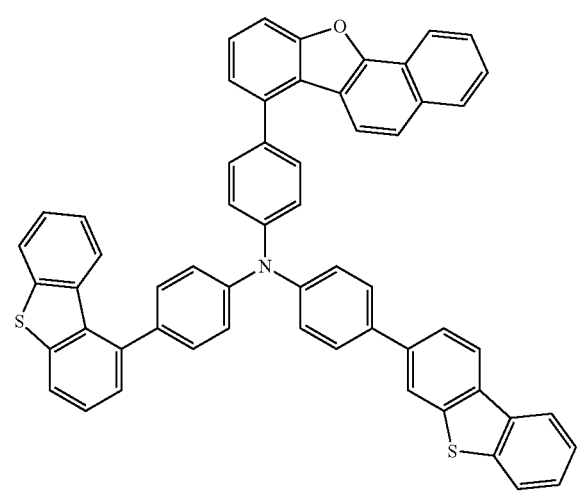
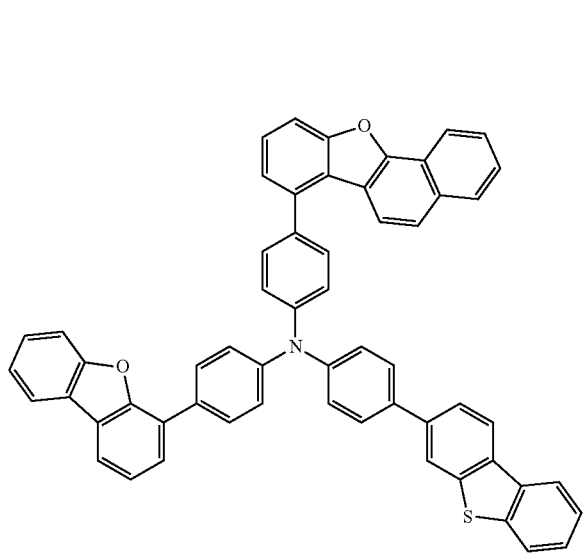
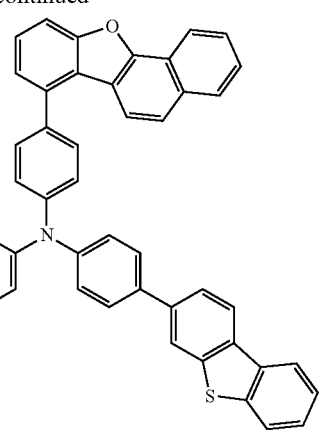
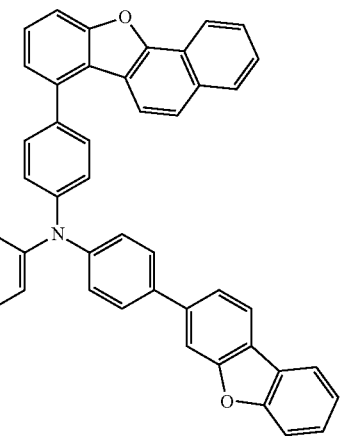
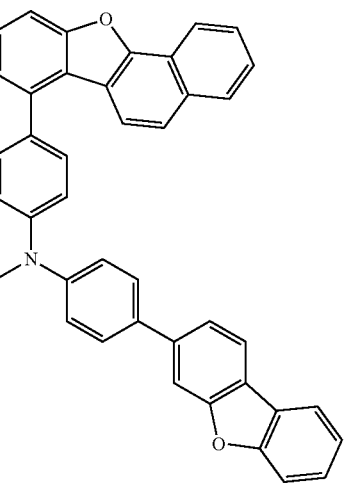

[Chem. 33]
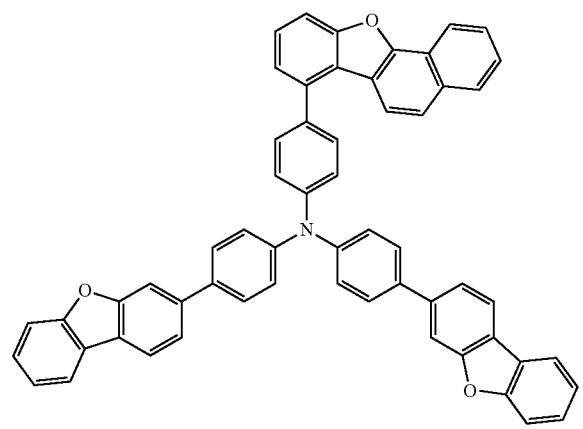
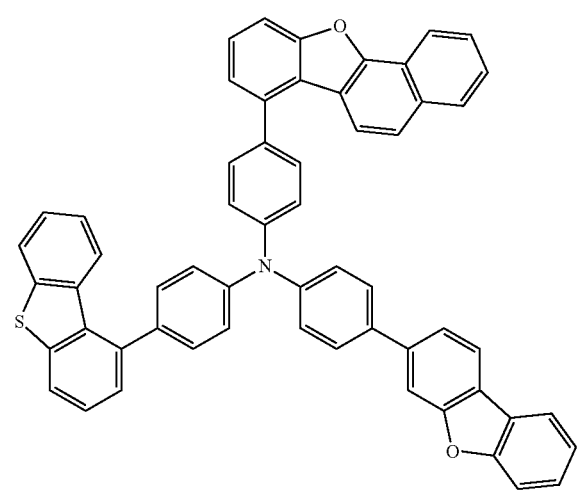
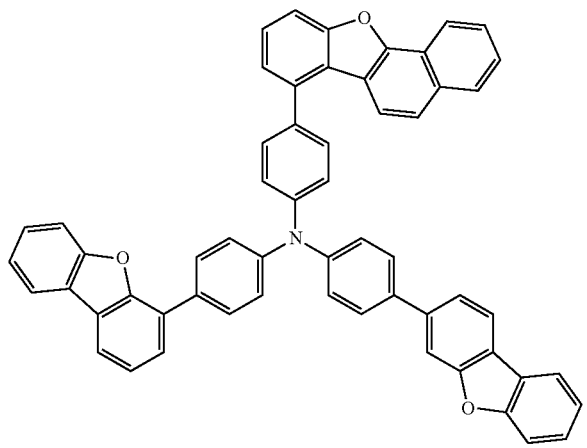
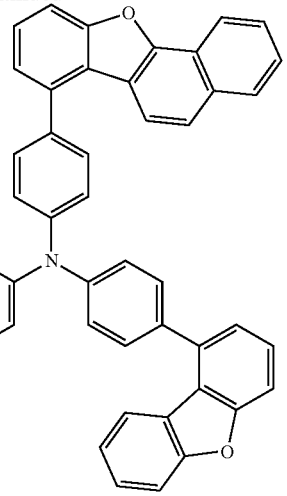
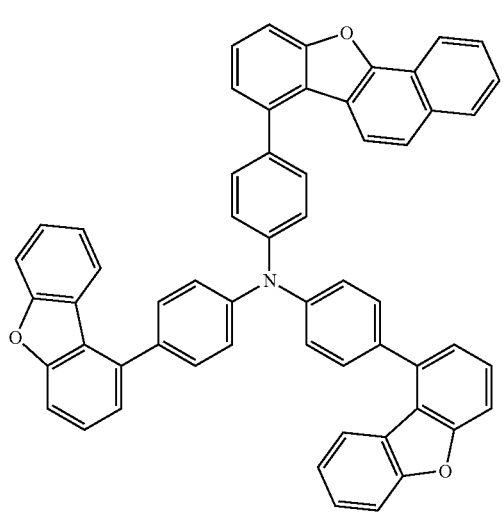
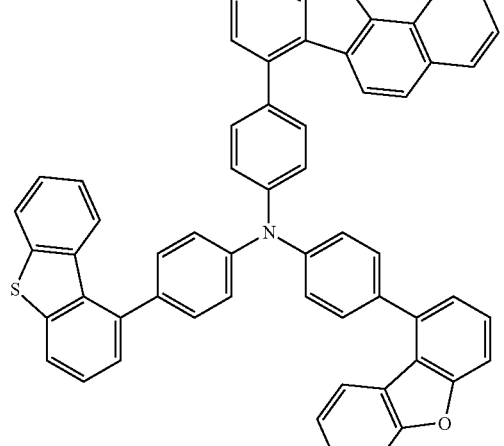

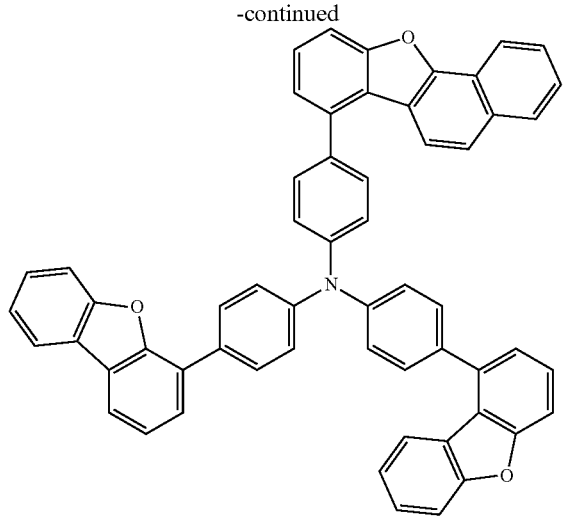
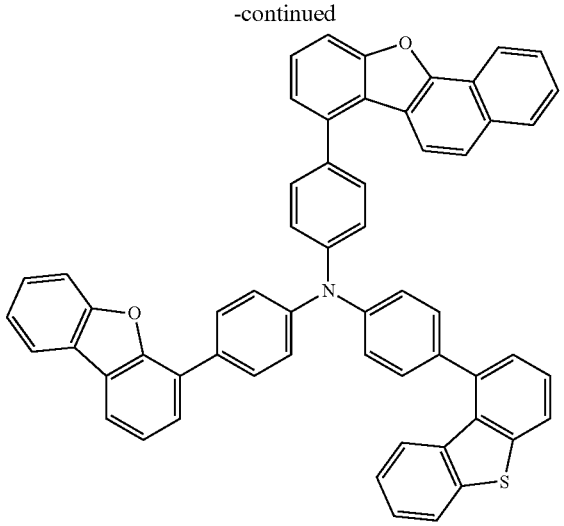
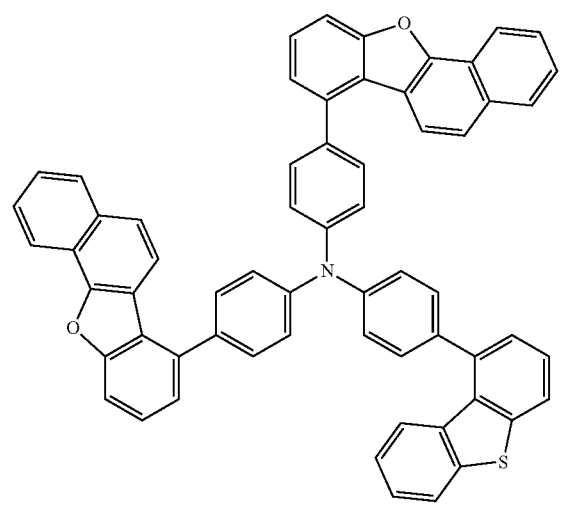
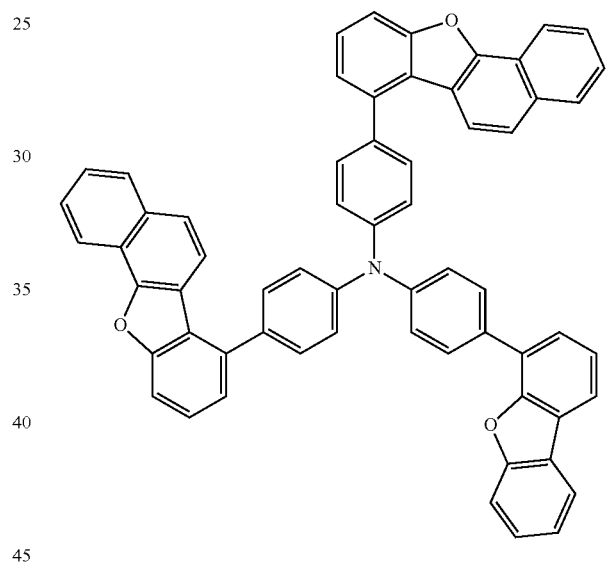
[Chem. 34]
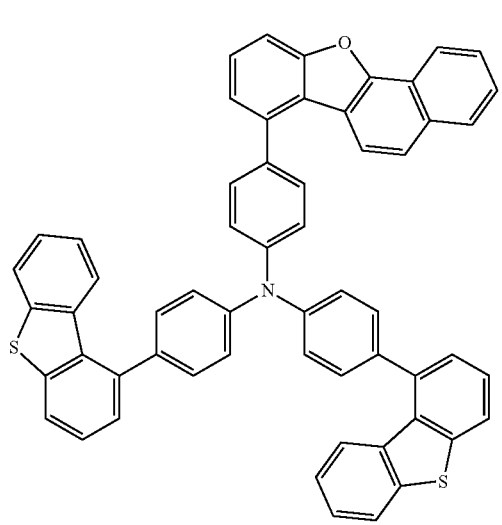
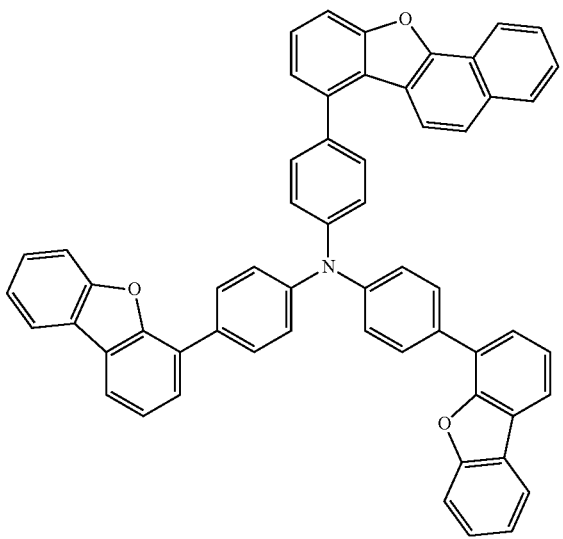

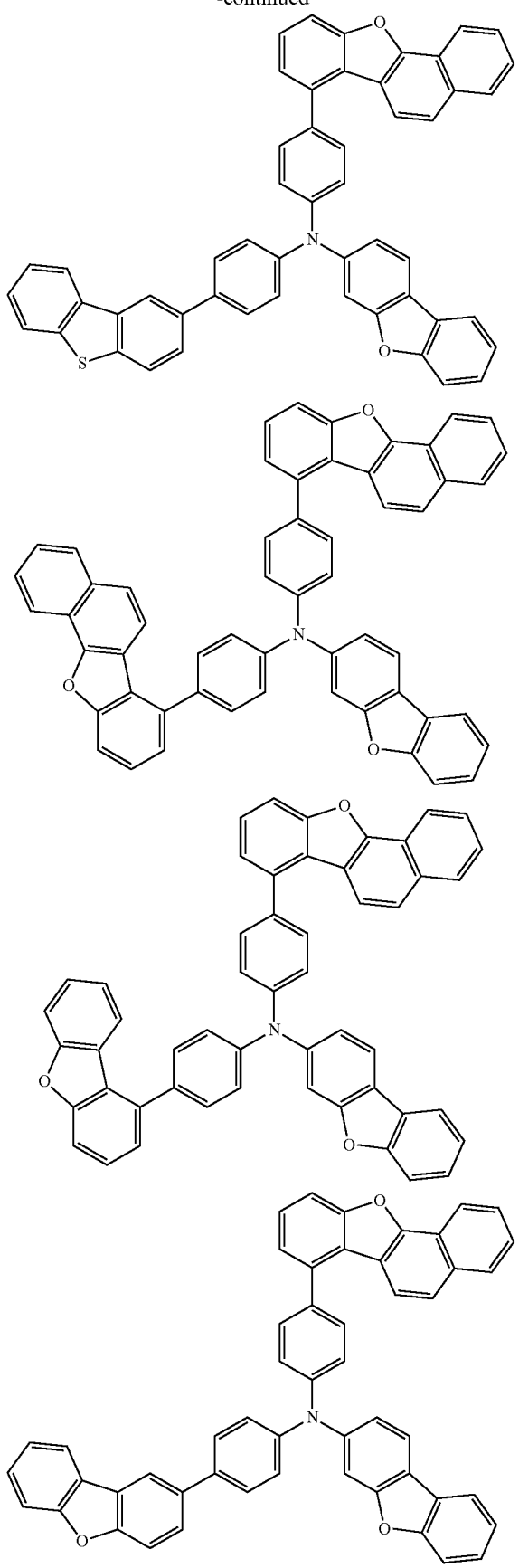
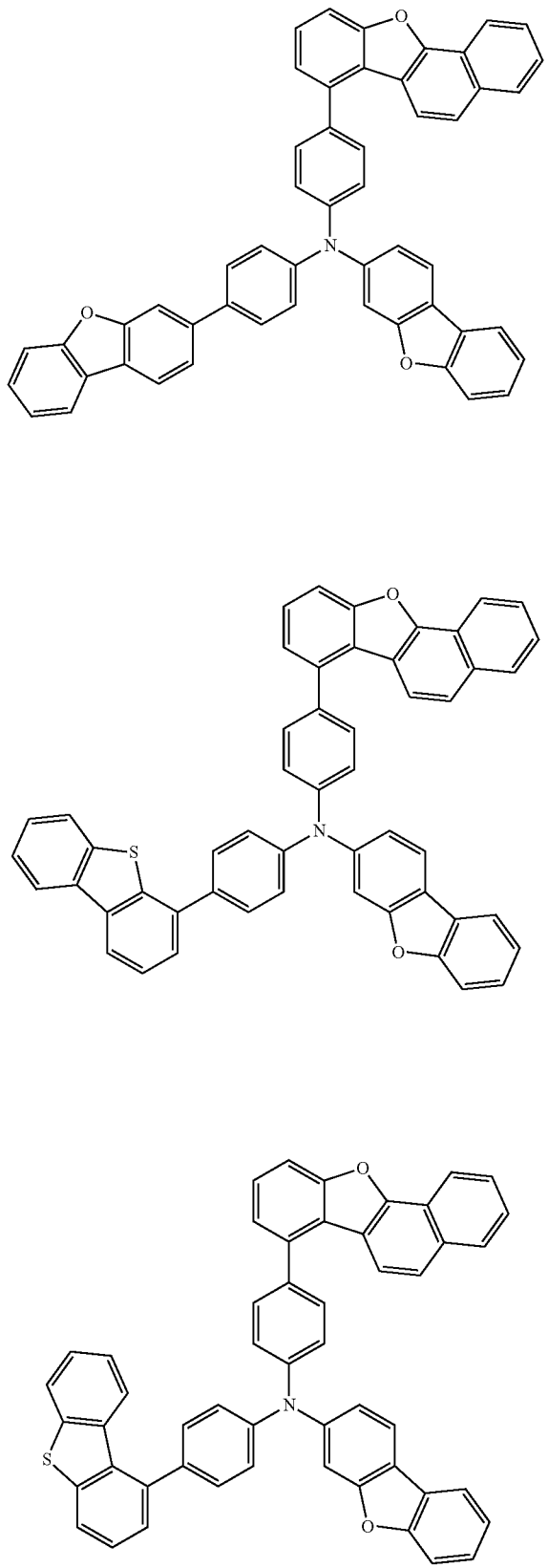

69
-continued
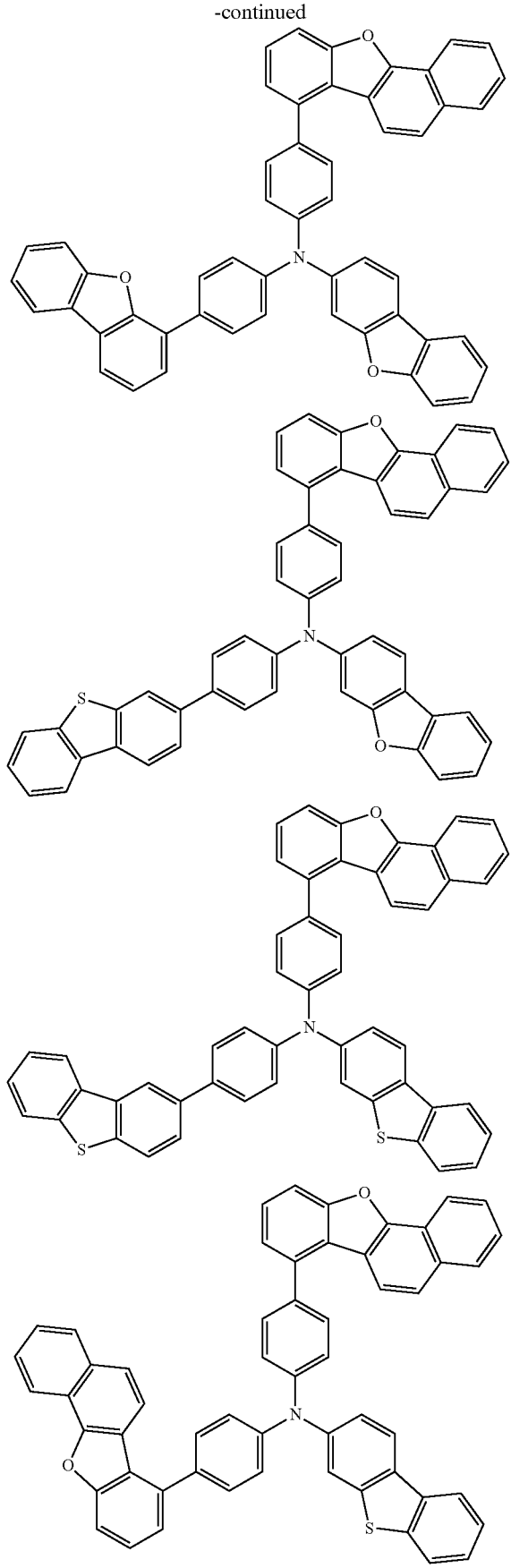
[Chem. 36]
70
-continued
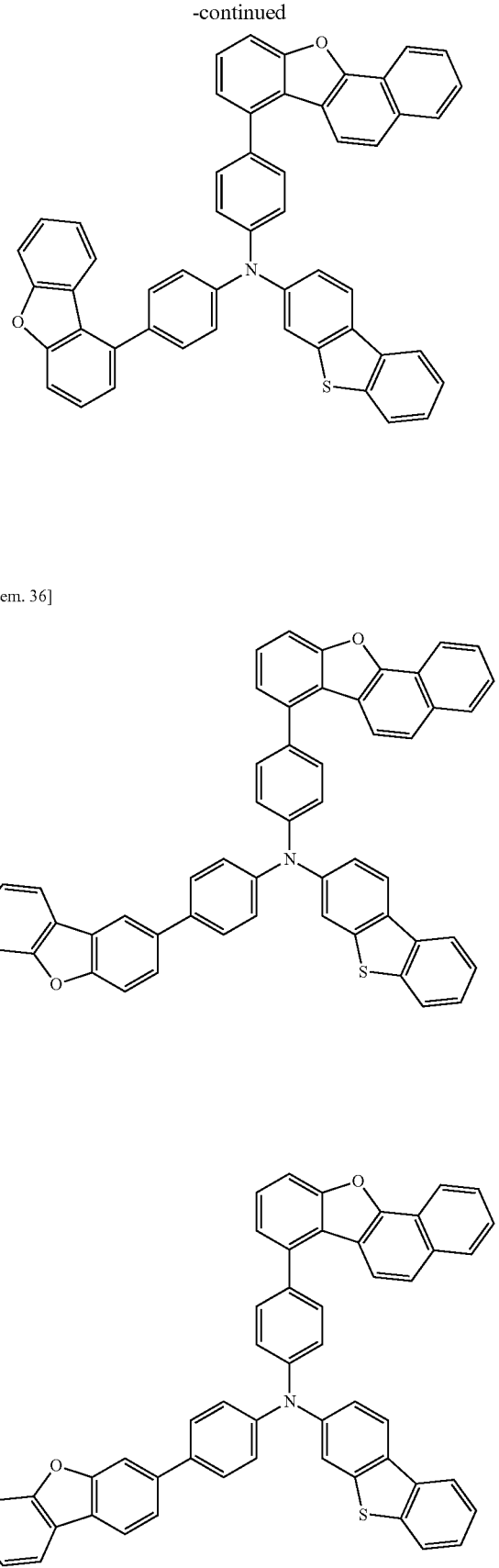

71
-continued
72
-continued
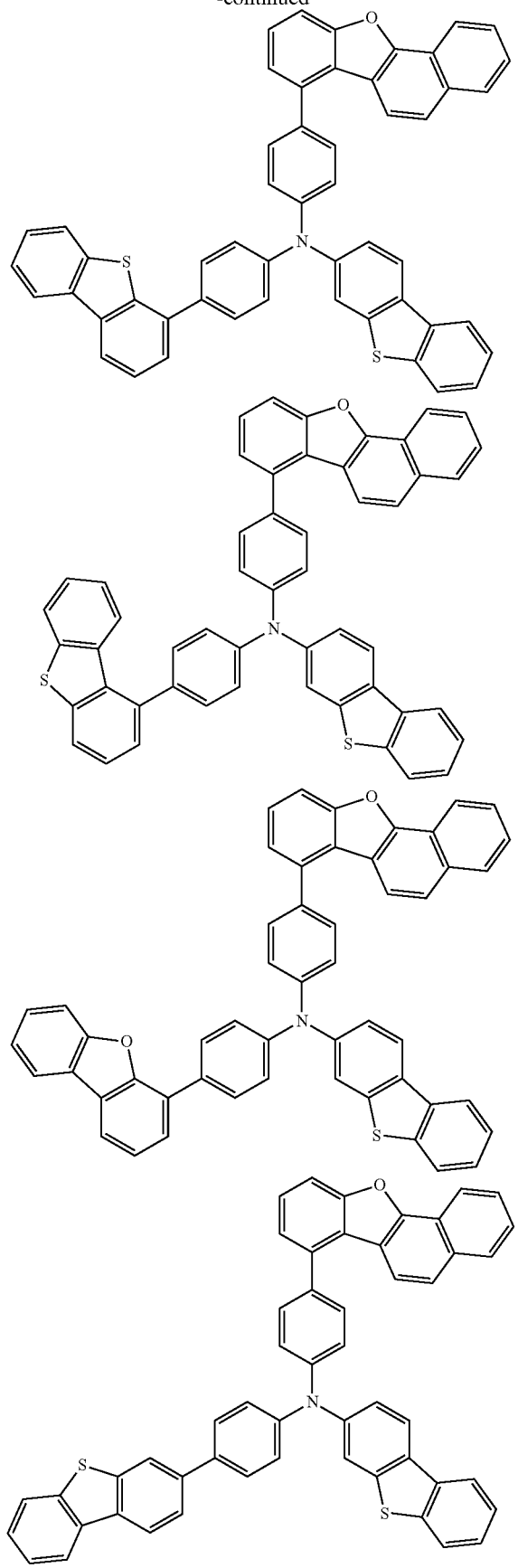
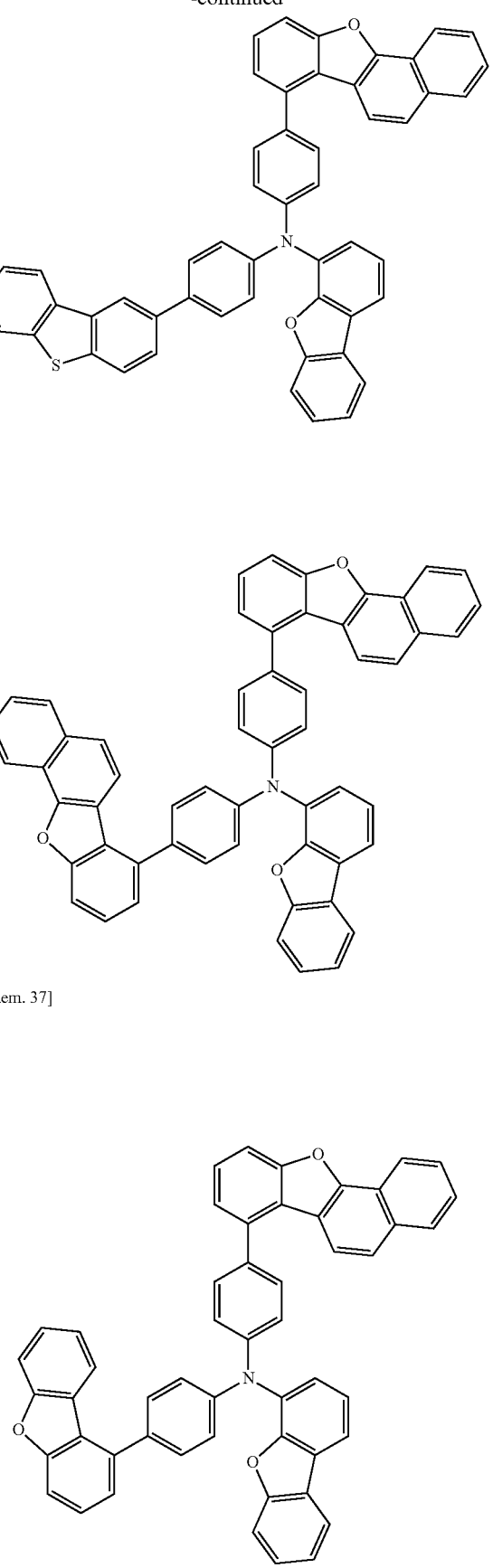
[Chem. 37]

73
-continued
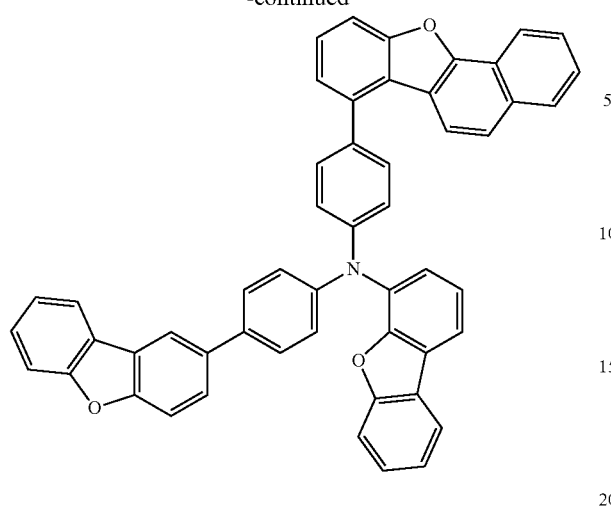
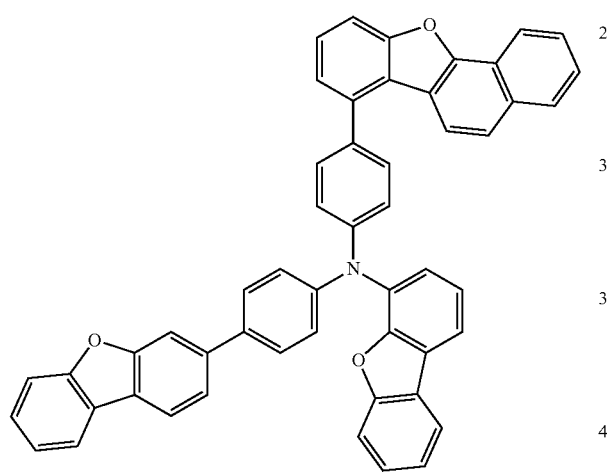
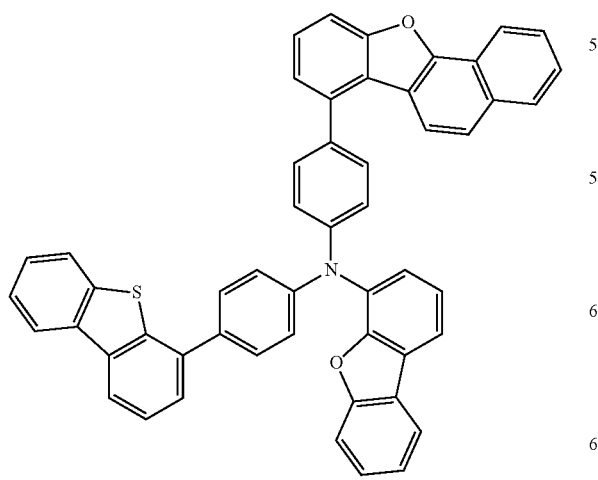
74
-continued
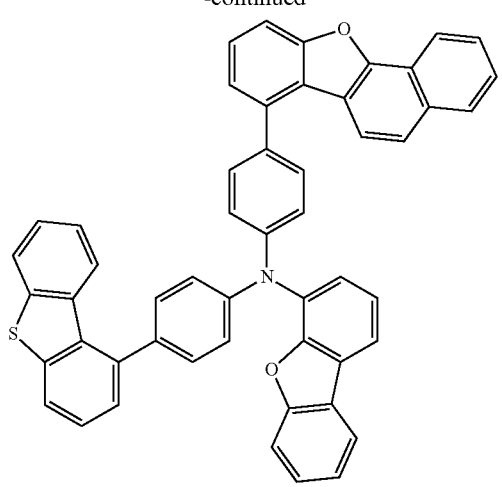
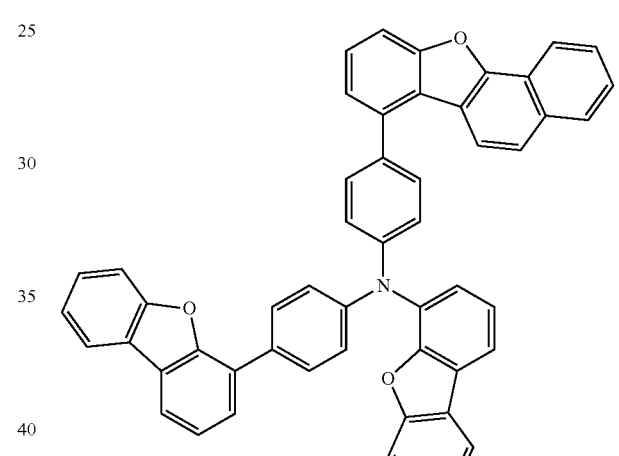
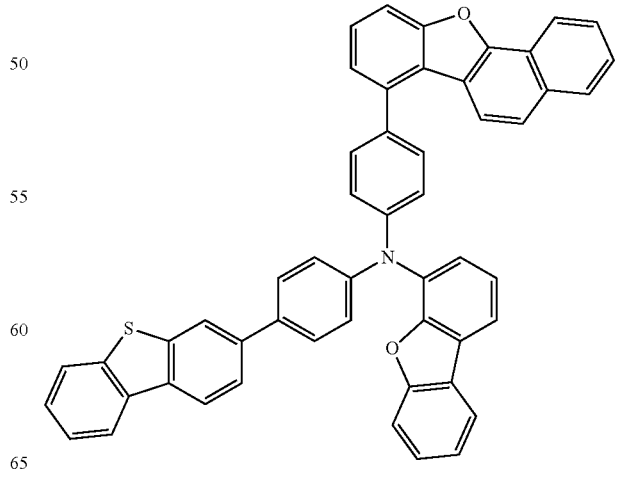

75
-continued
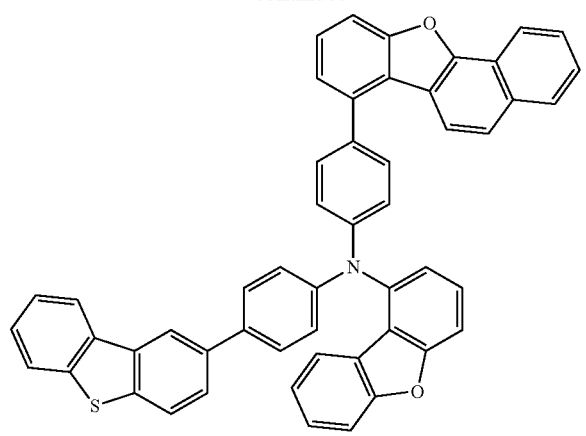
[Chem. 38]
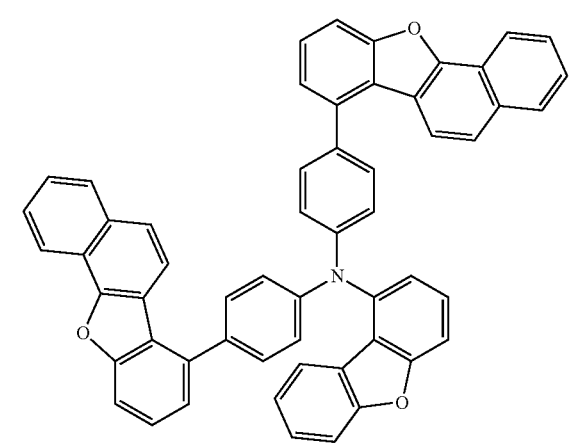
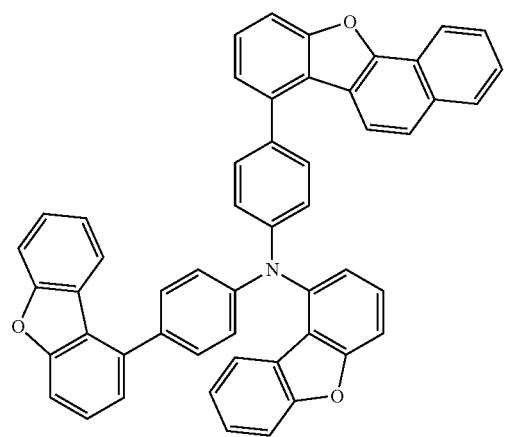
76
-continued
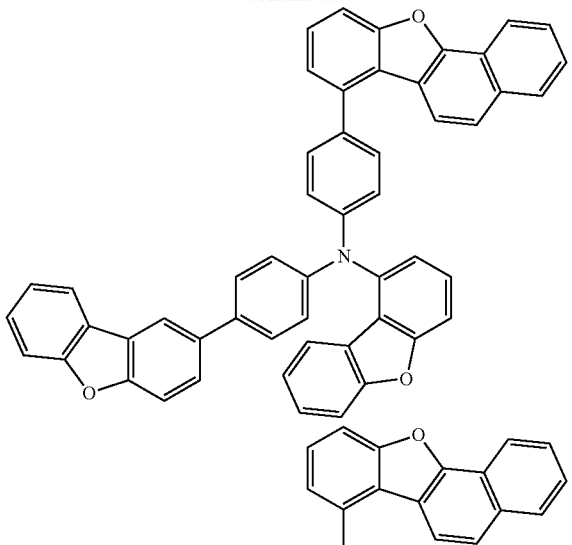

77
-continued
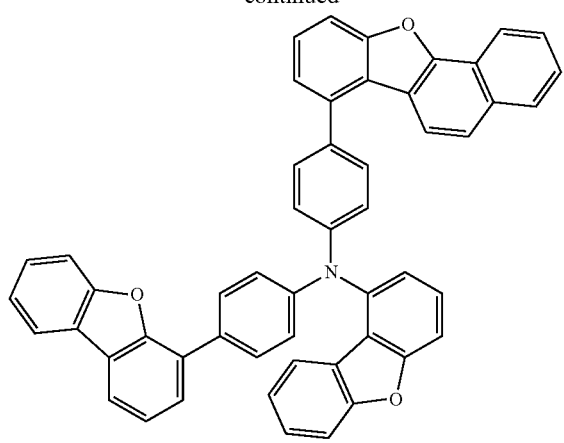
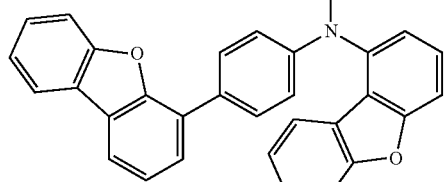
[Chem. 39]

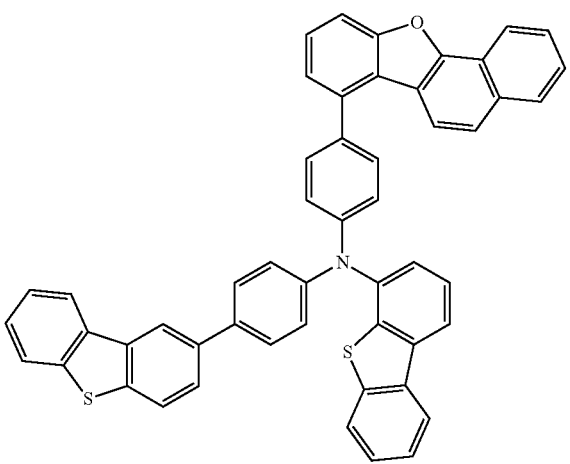
78
-continued

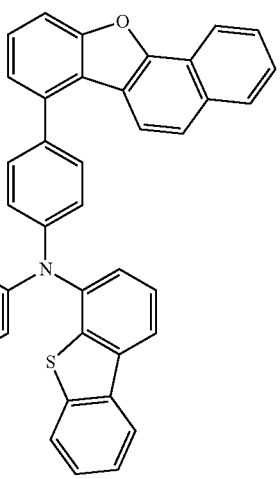
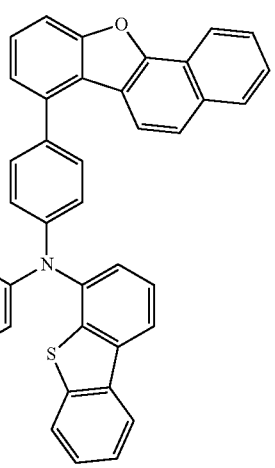

79
-continued
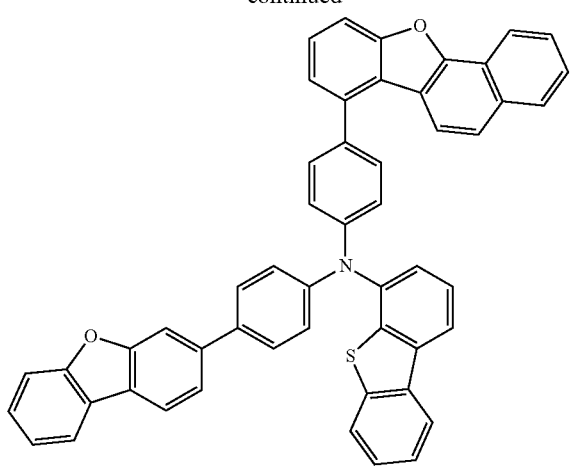
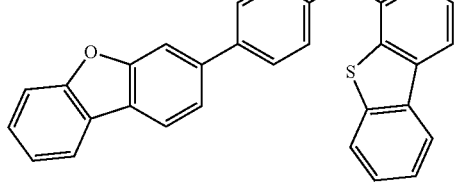
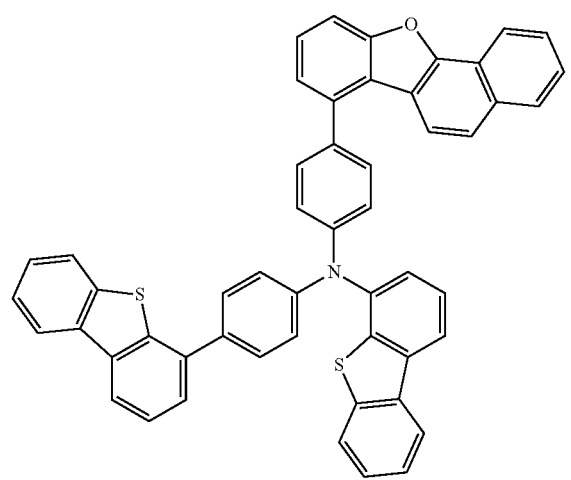
80
-continued
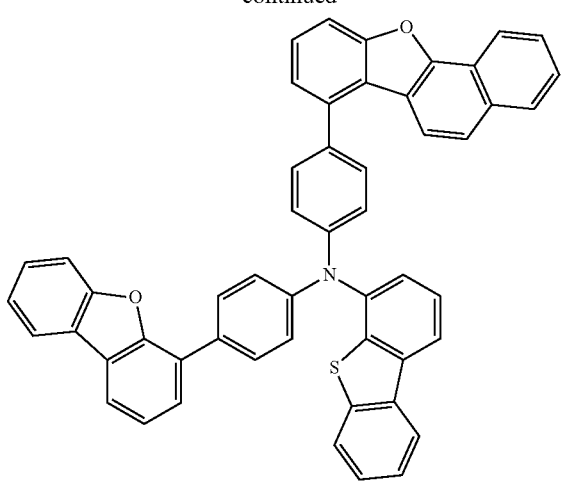
[Chem. 40]
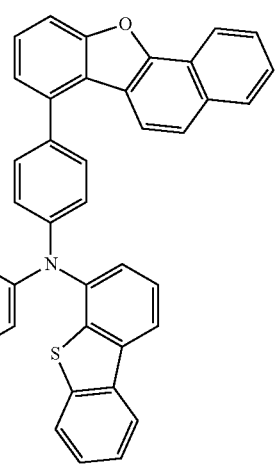
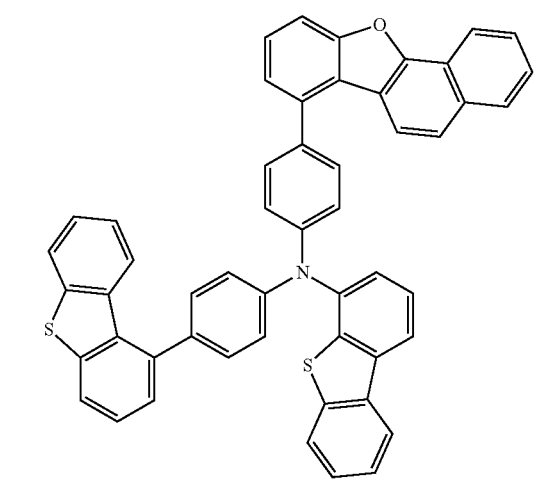
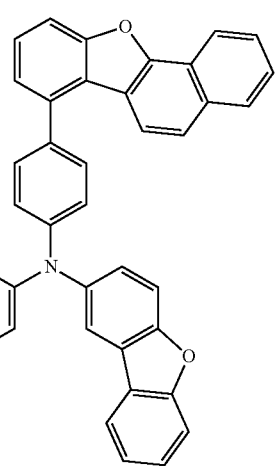

81
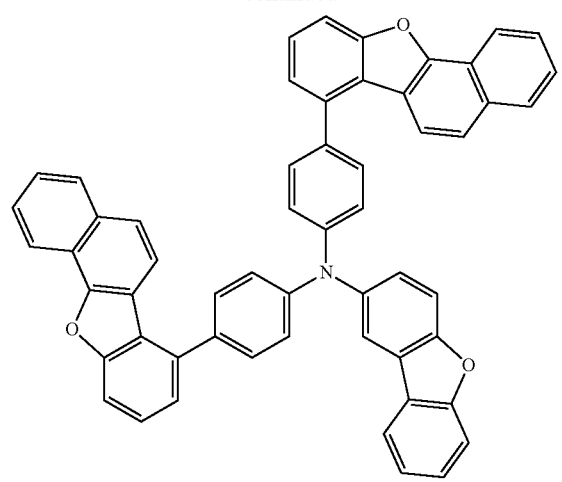
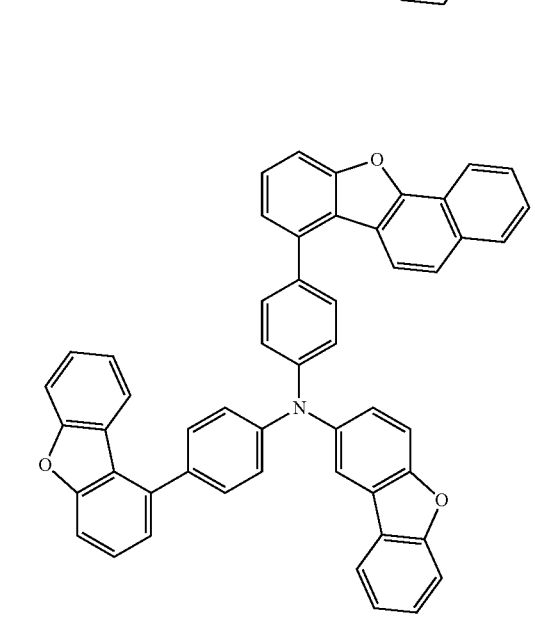
82
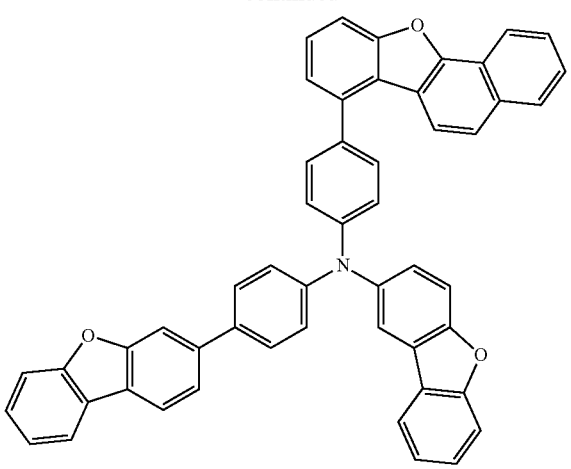
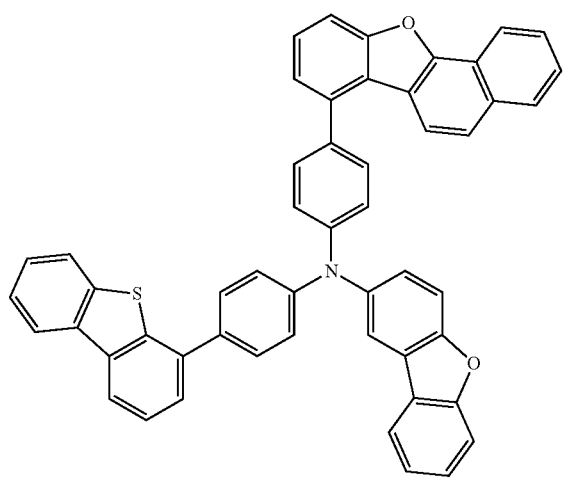
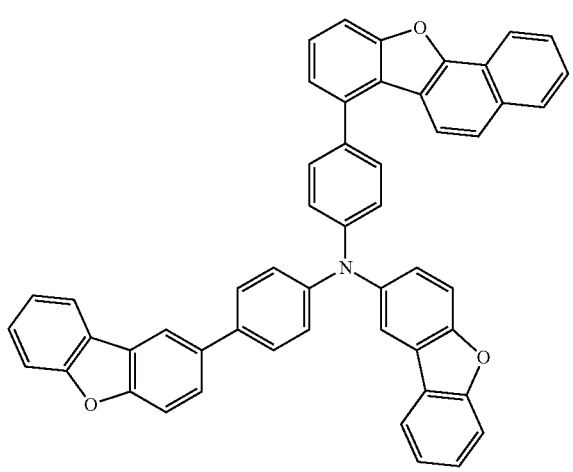
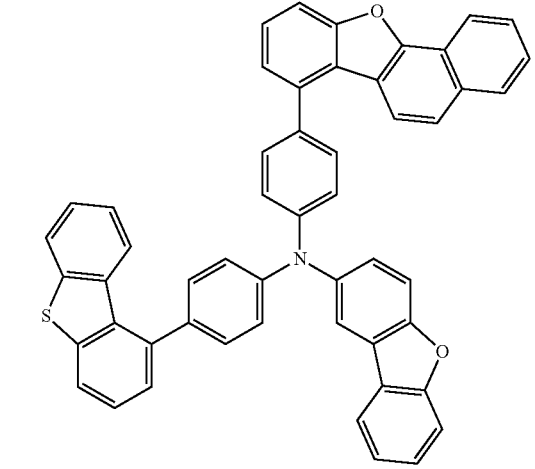

83
-continued
[Chem. 41]
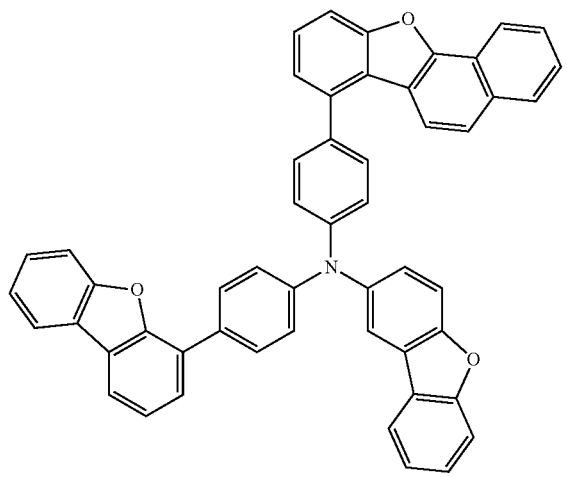
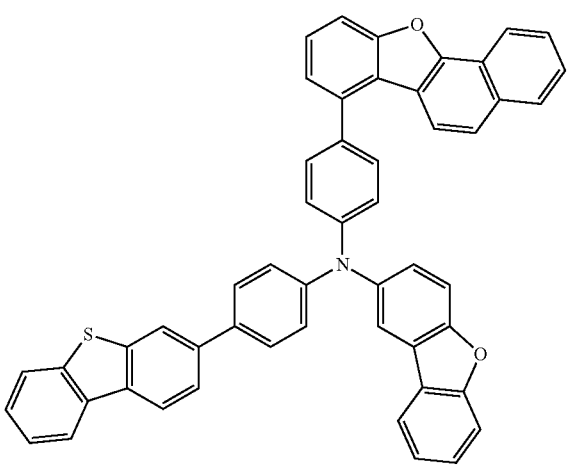
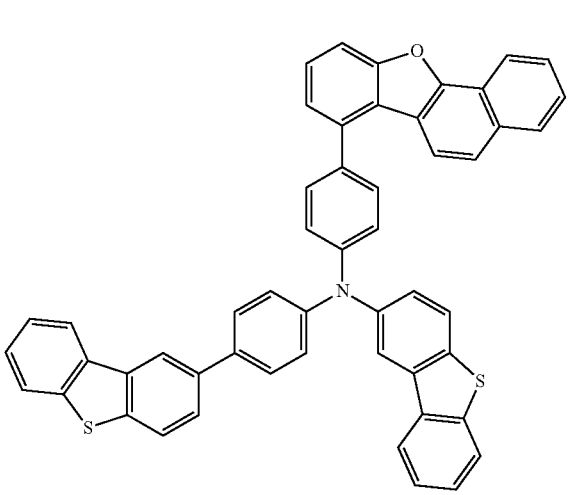
84
-continued
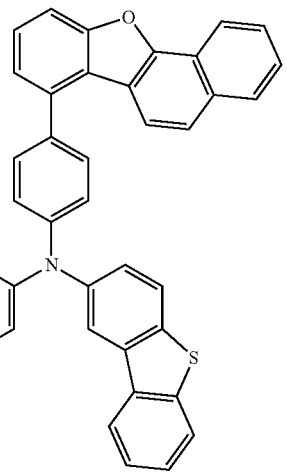
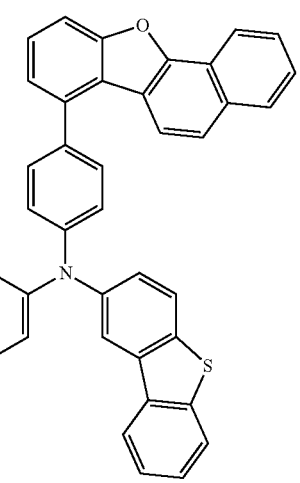
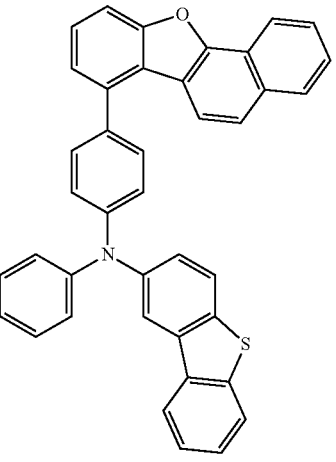

85
-continued
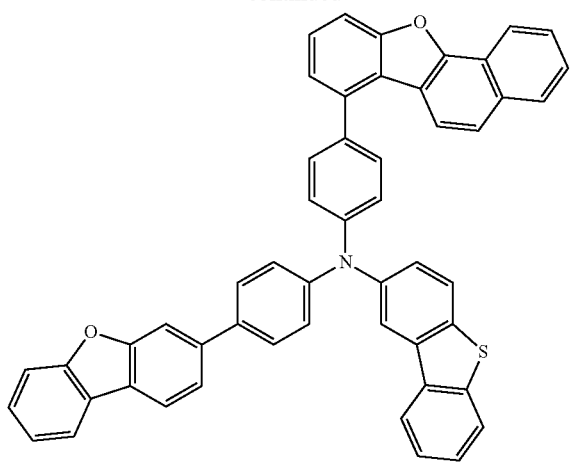
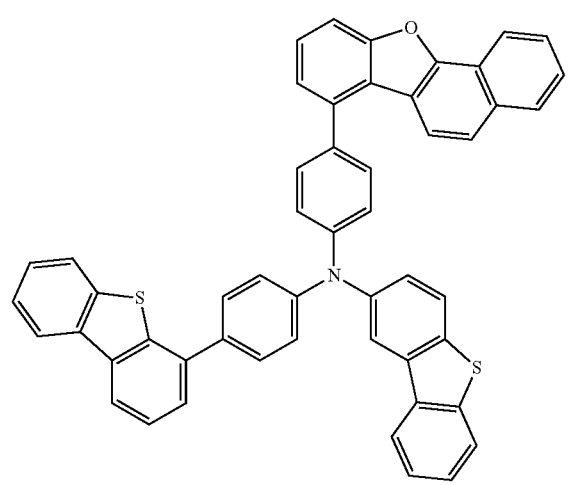
[Chem. 42]
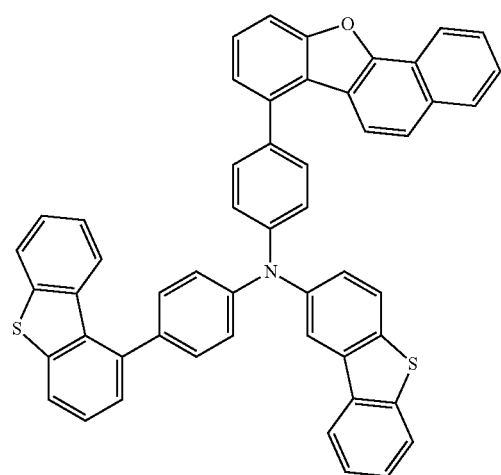
86
-continued
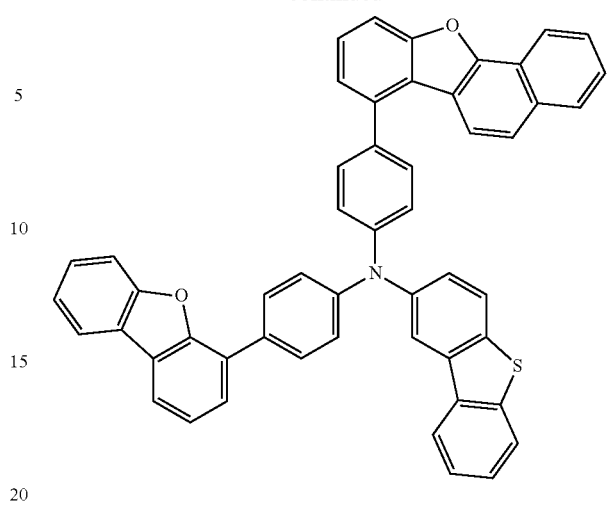
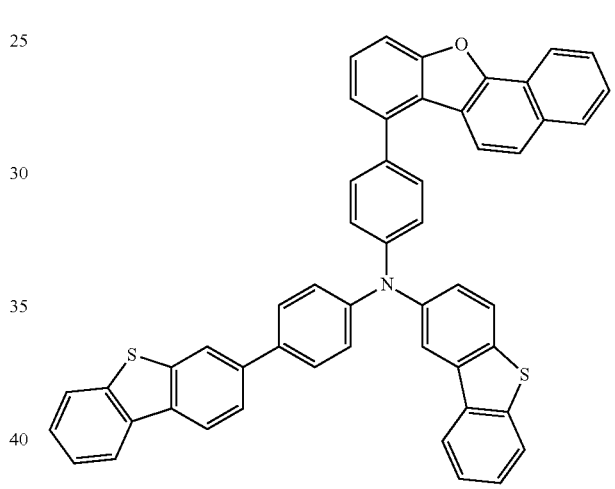
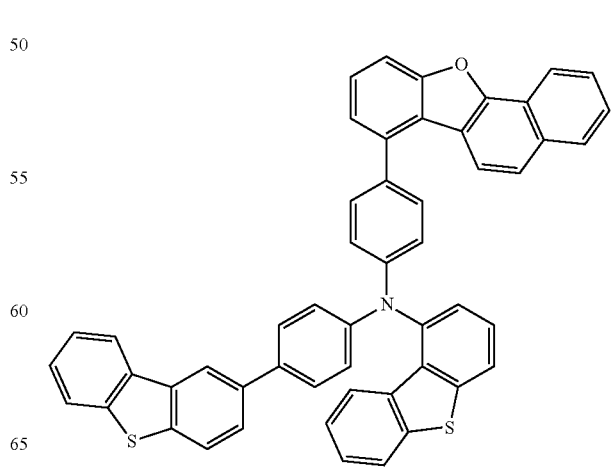

87
-continued
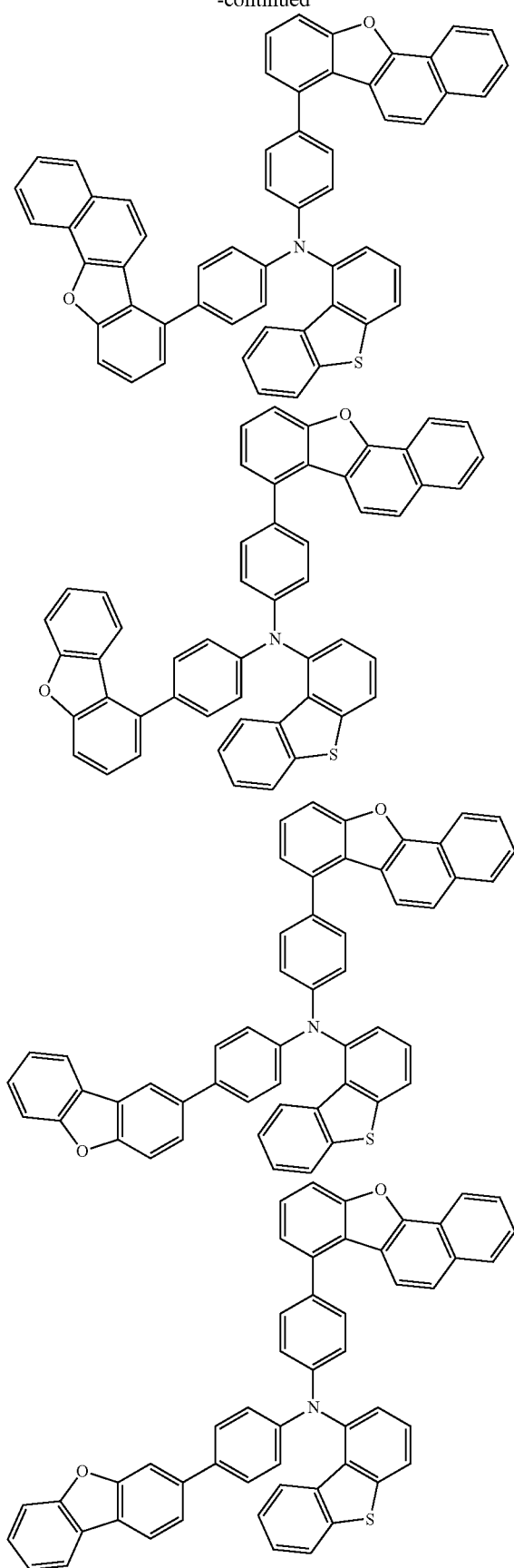
88
-continued
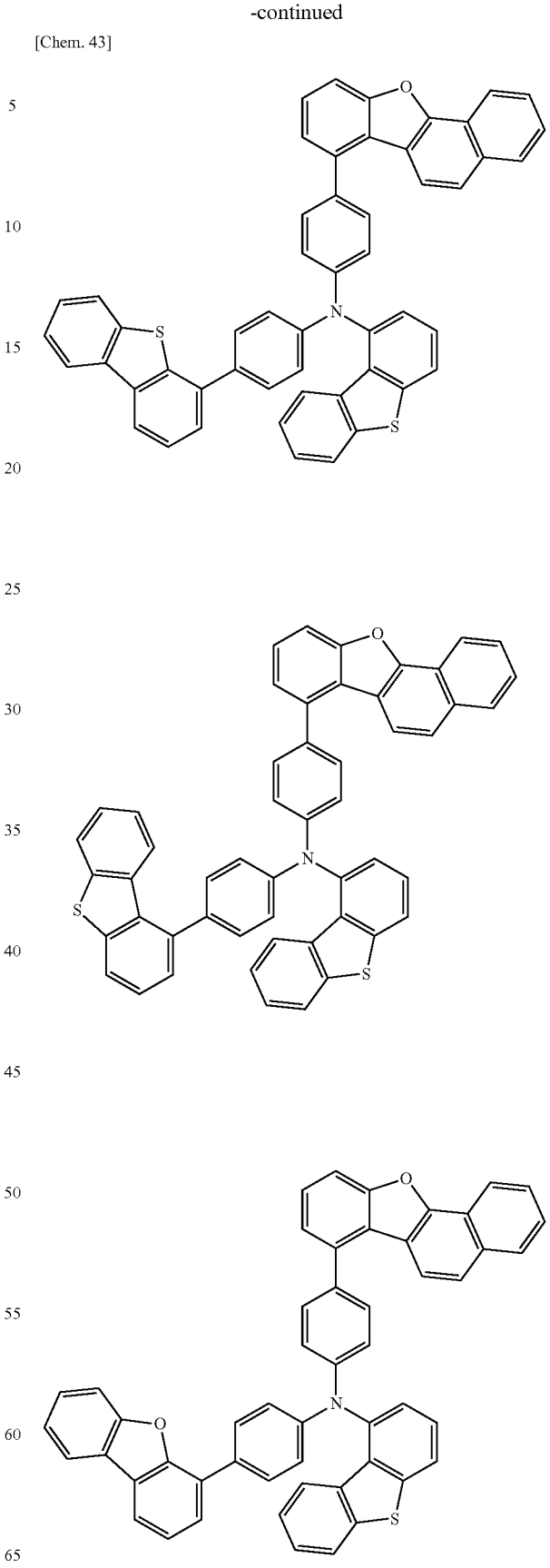
[Chem. 43]

89
-continued
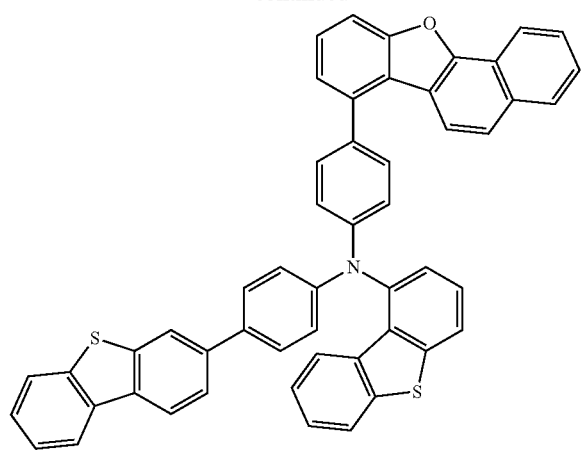
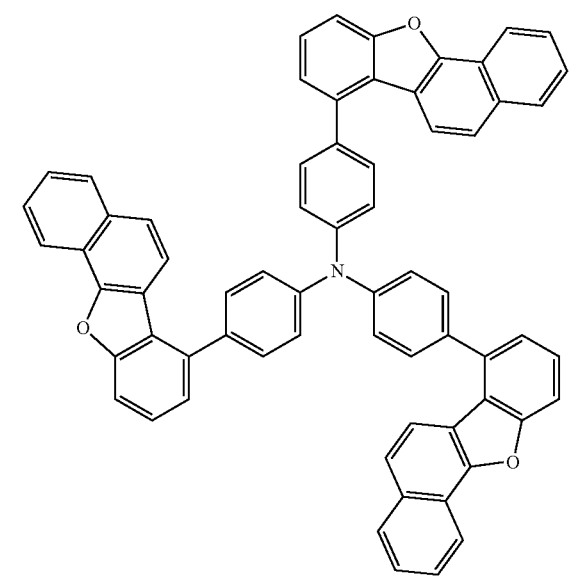
[Chem. 44]
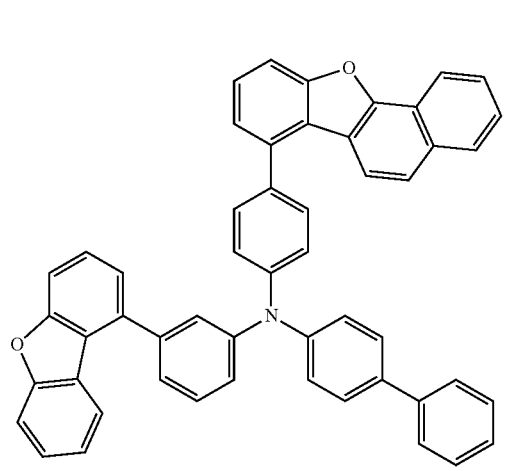
90
-continued
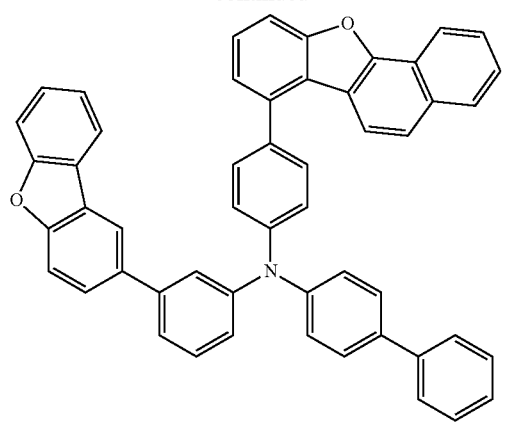
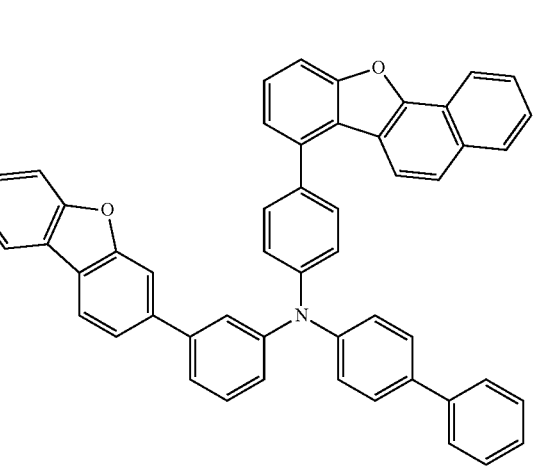
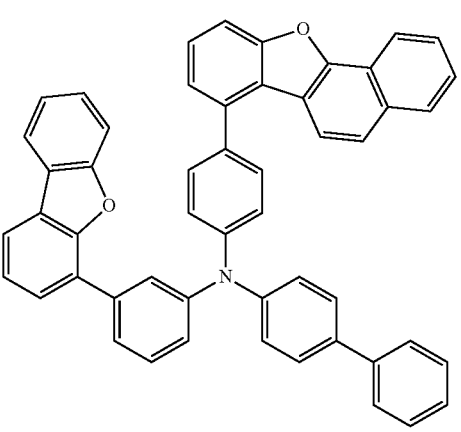

91
-continued
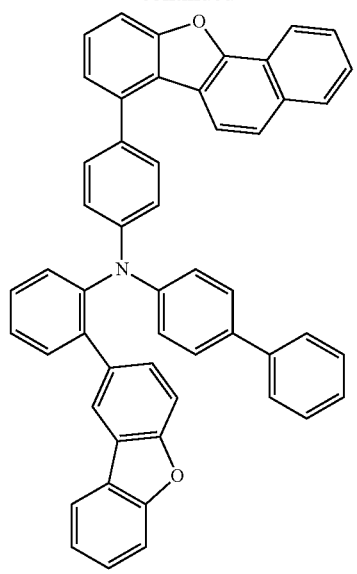
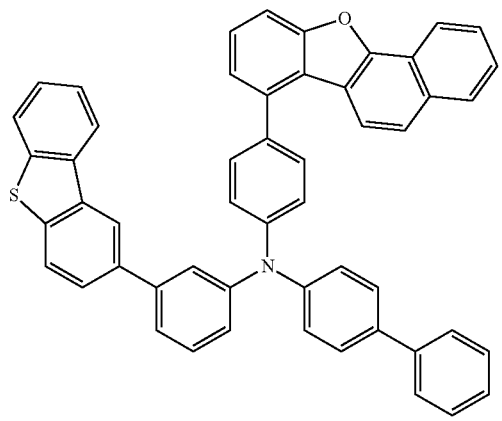
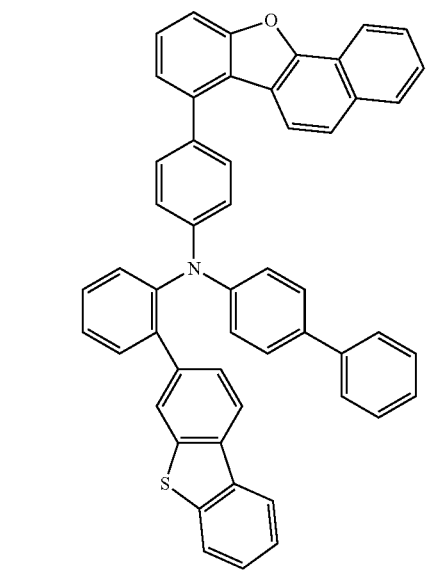
92
-continued
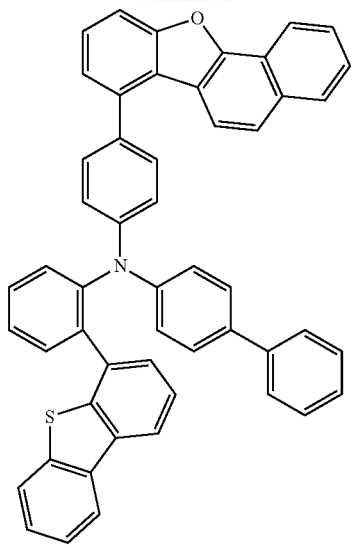
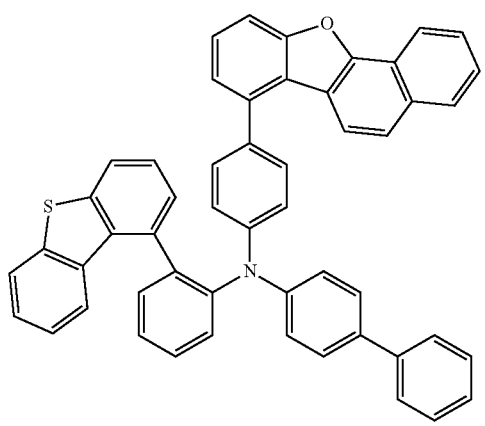
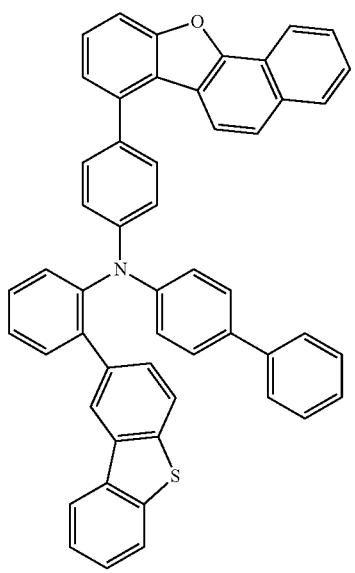

93
-continued
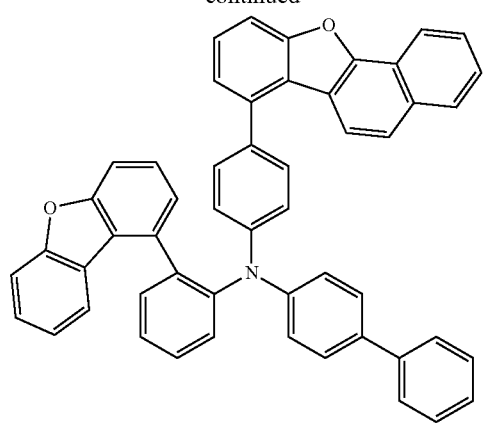
[Chem. 45]
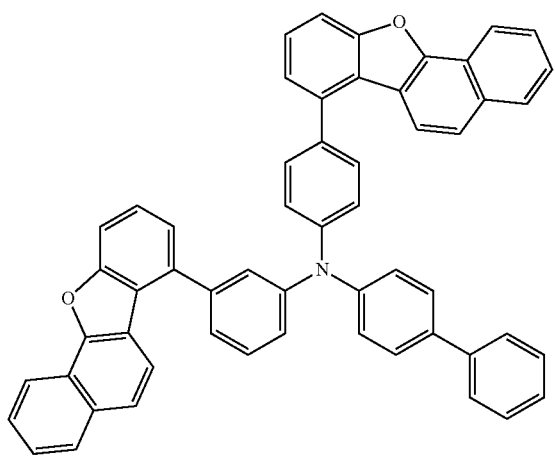
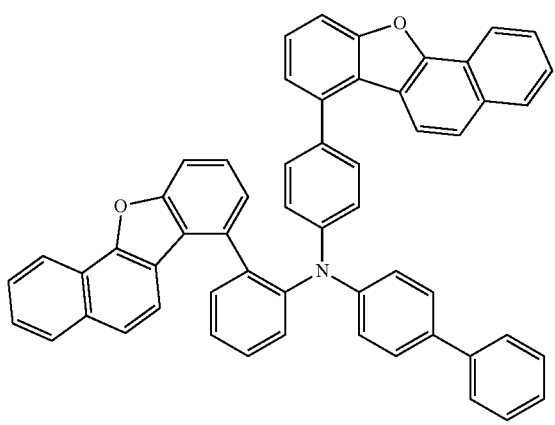
94
-continued
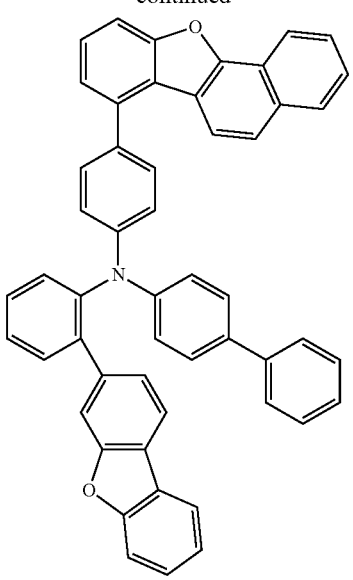
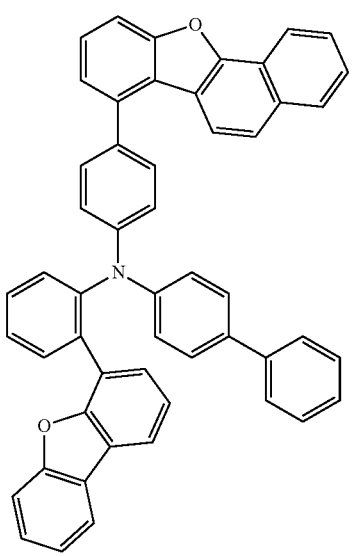
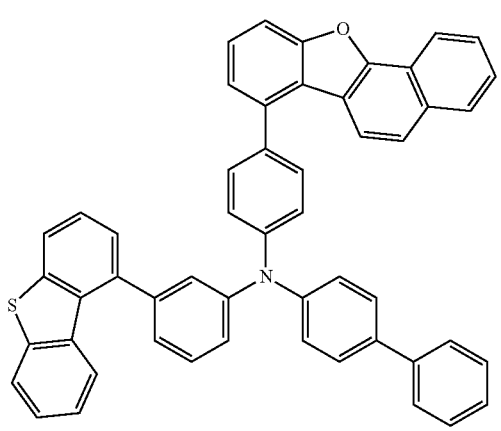

95
-continued
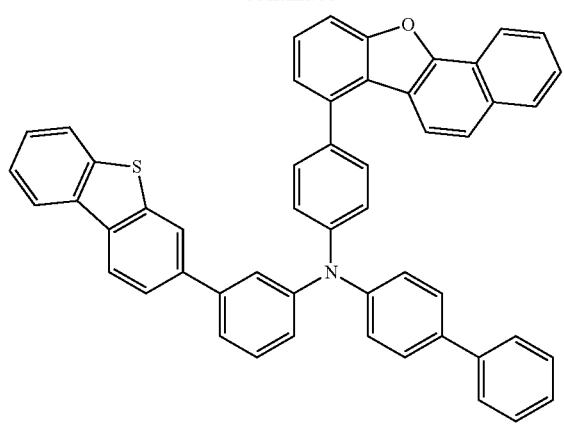
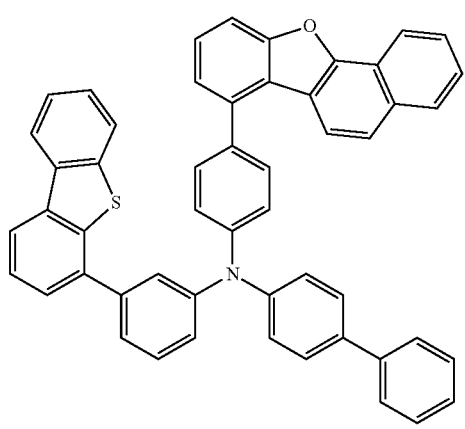
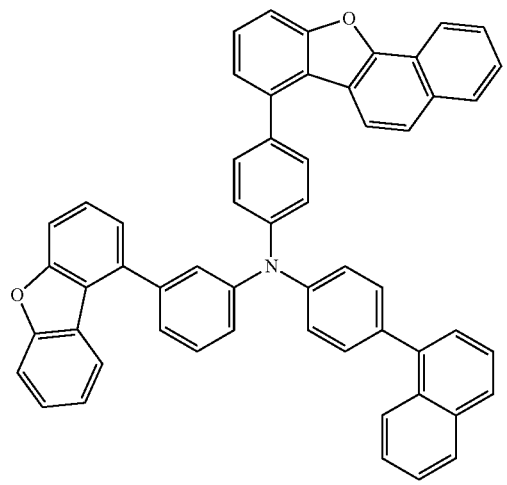
96
-continued
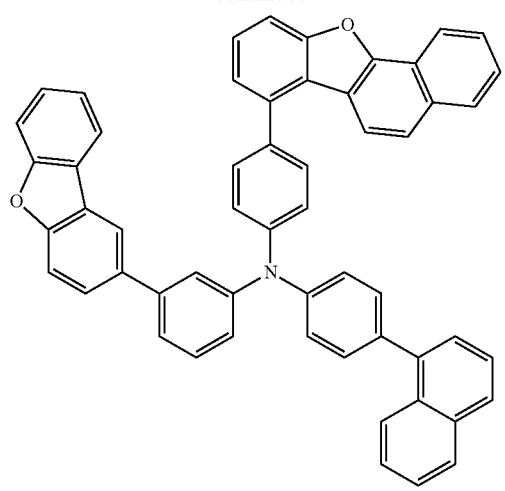
[Chem. 46]
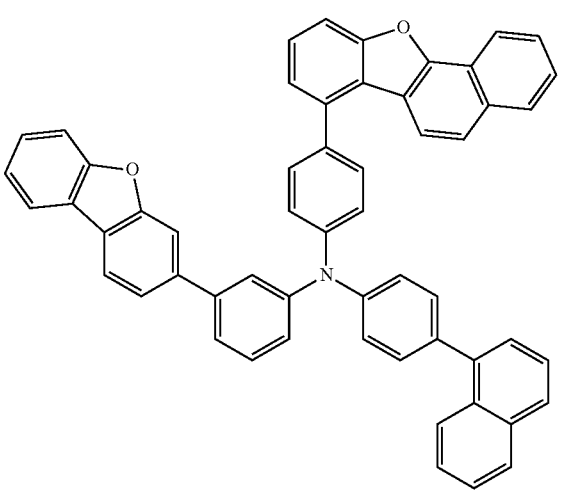
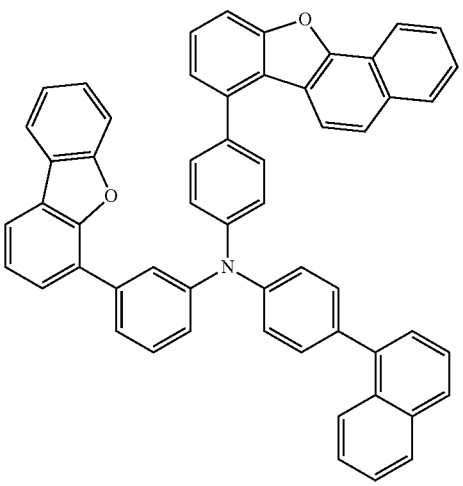

97
-continued
98
-continued
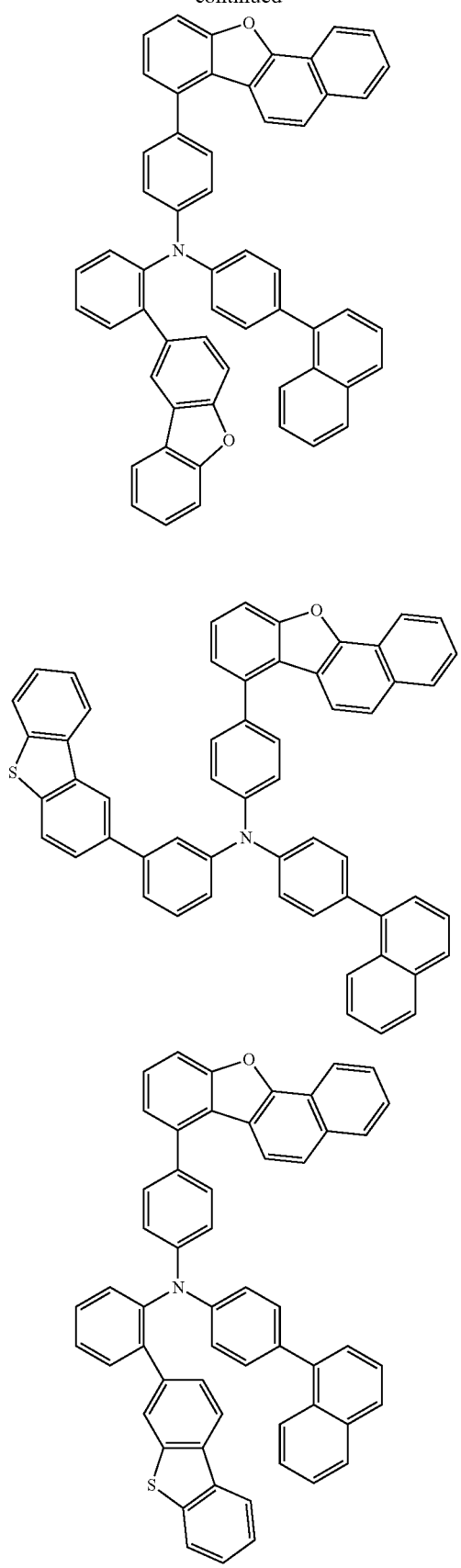
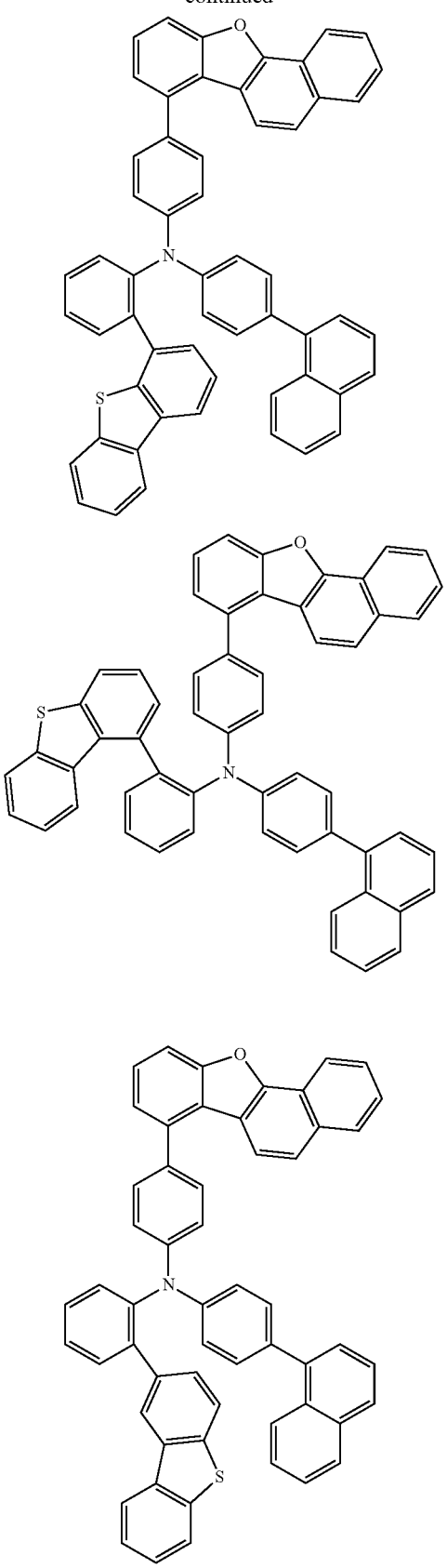

[Chem. 47]
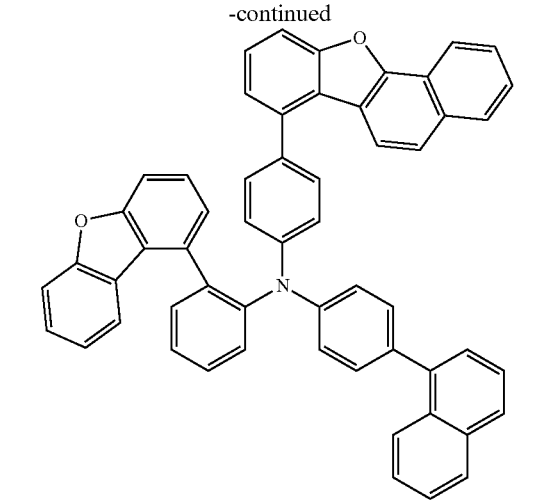
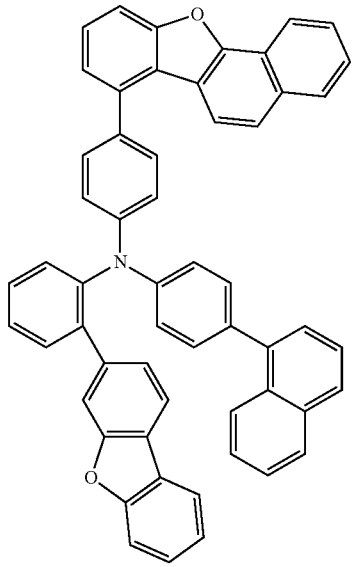
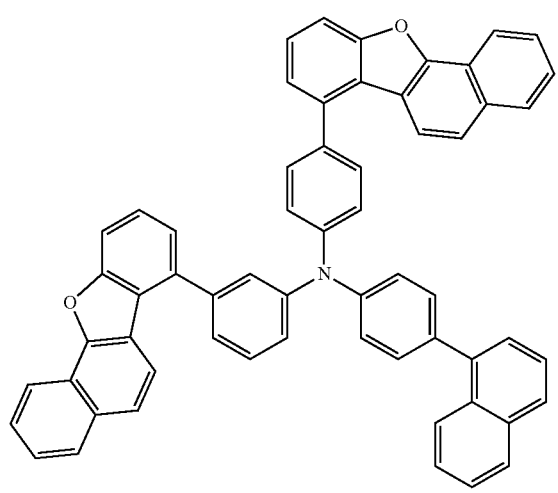
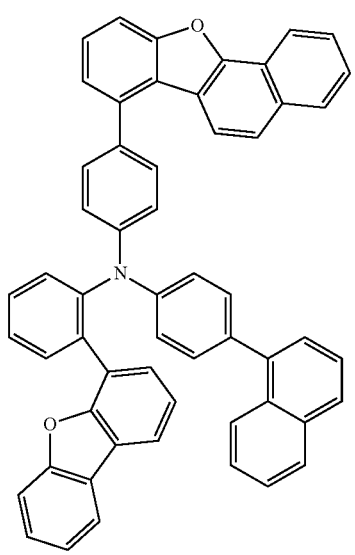
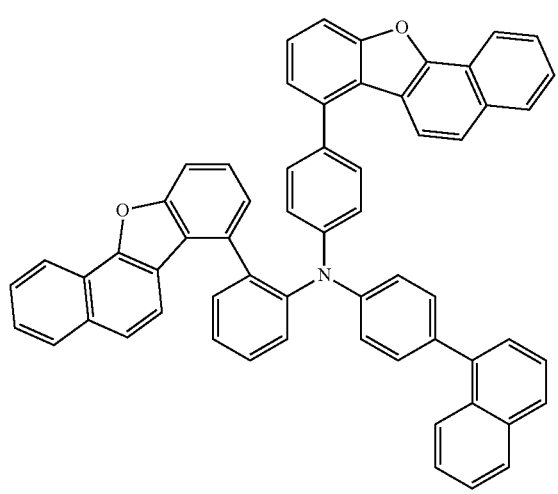
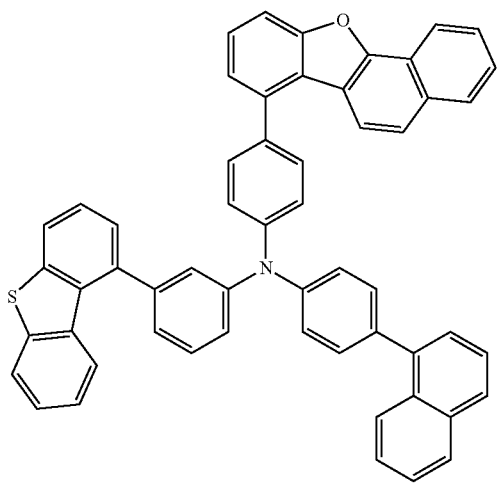

101
-continued
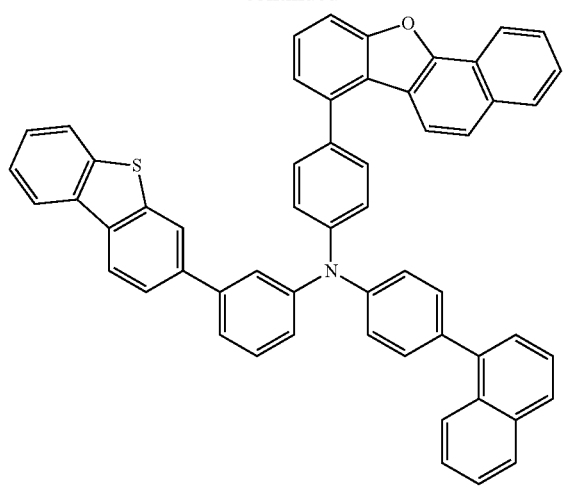
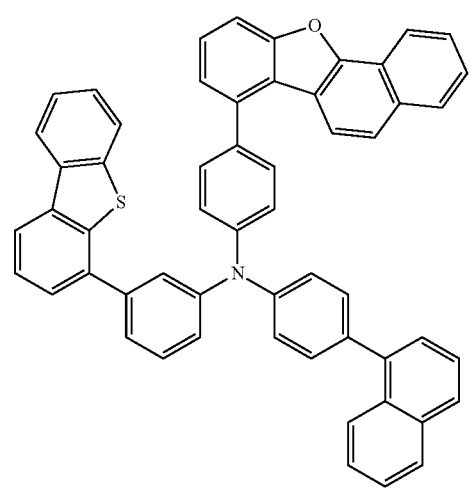
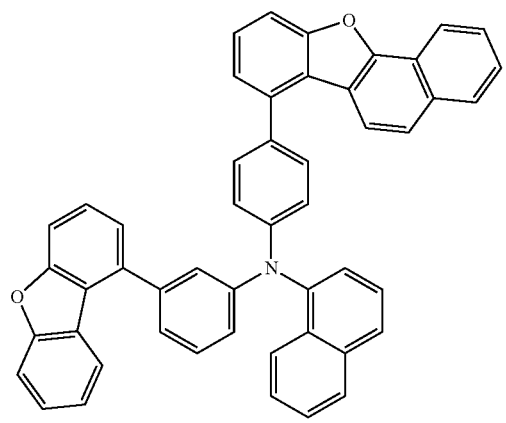
102
-continued
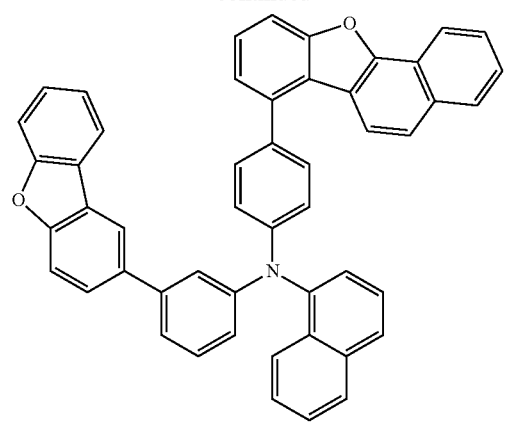
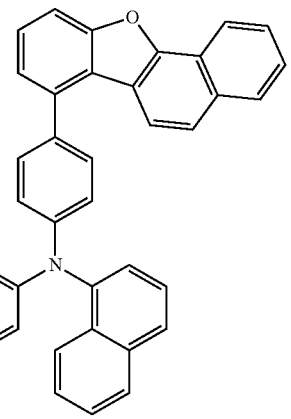
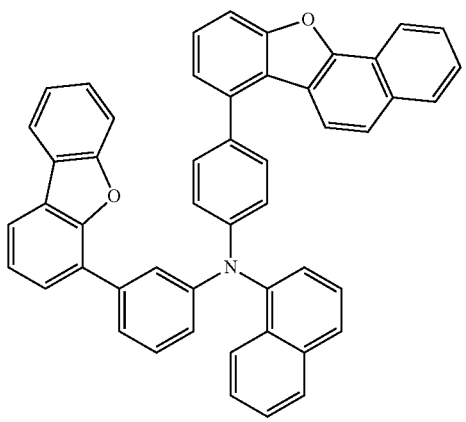

103
-continued
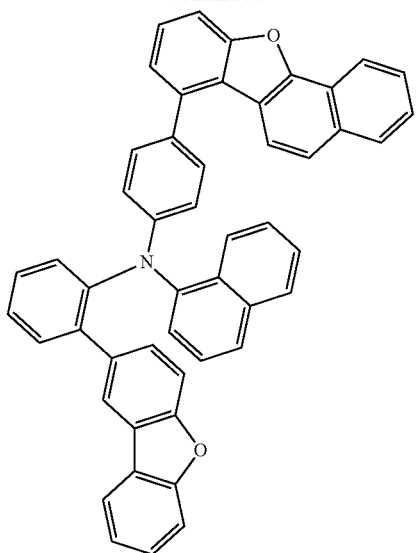
[Chem. 48]
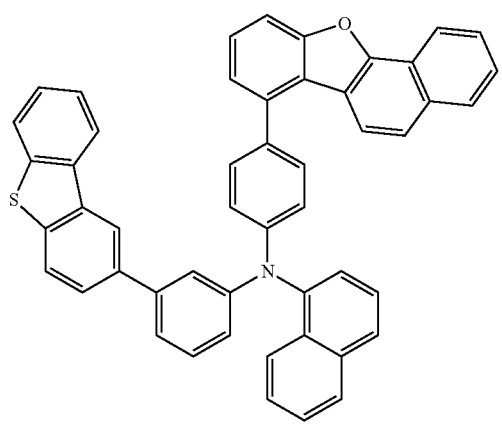
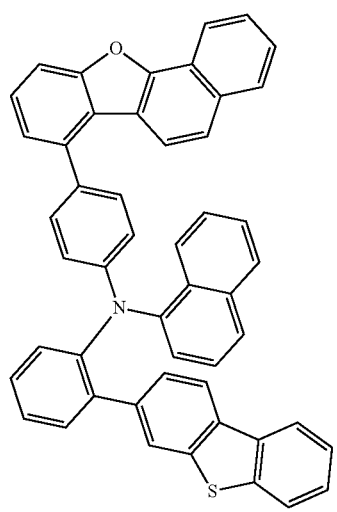
104
-continued
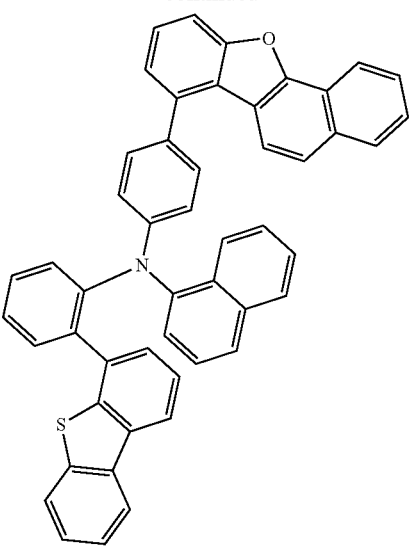
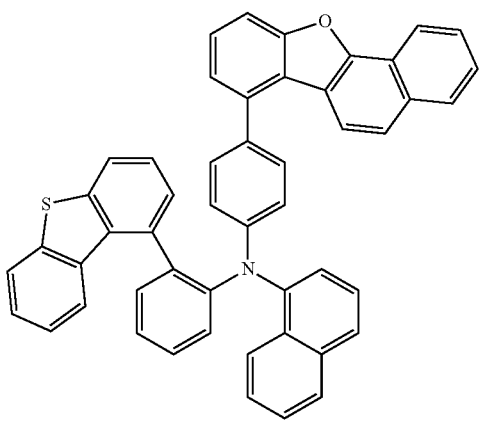
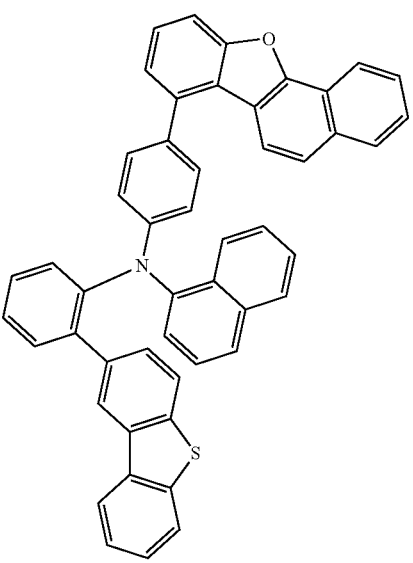

105
-continued
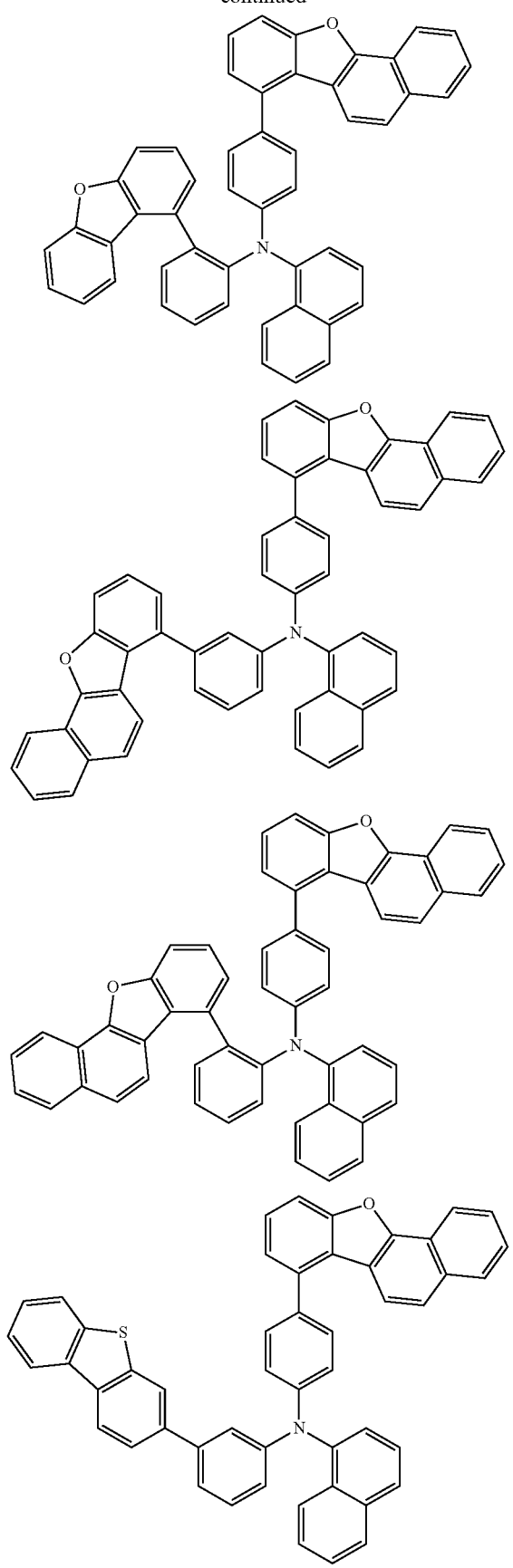
106
-continued
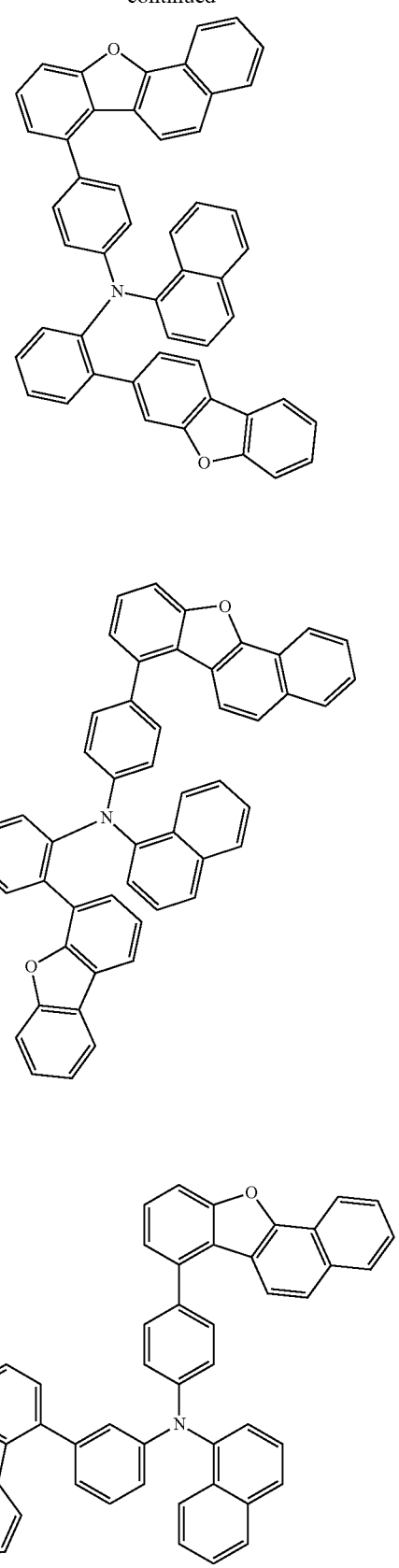

107
-continued
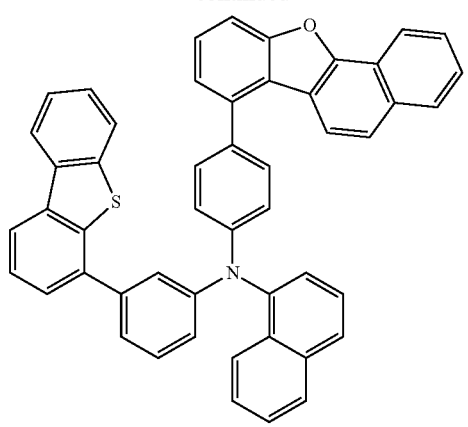
[Chem. 49]
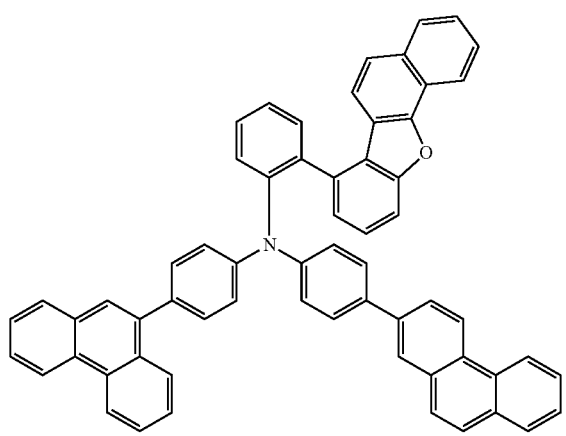
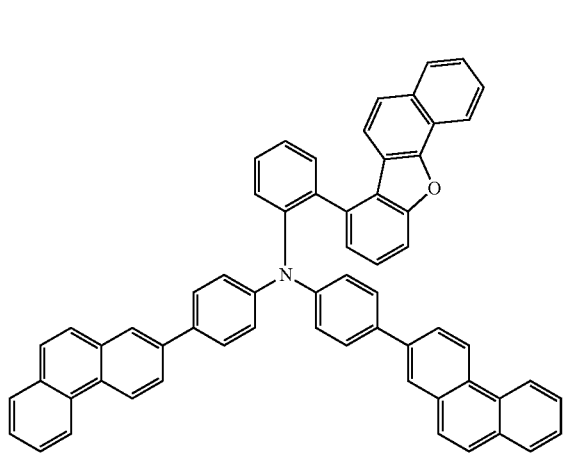
108
-continued
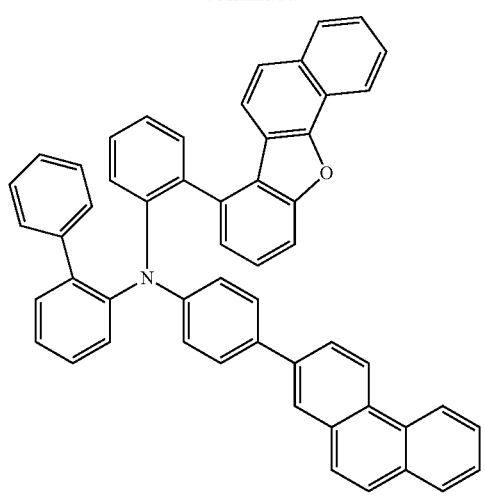
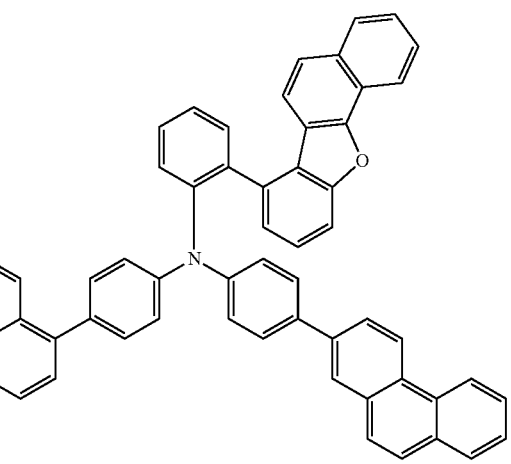
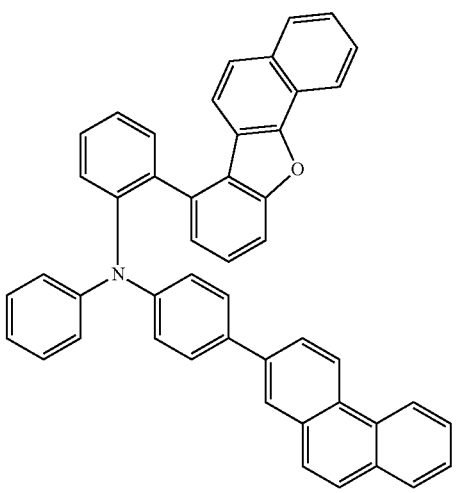

-continued
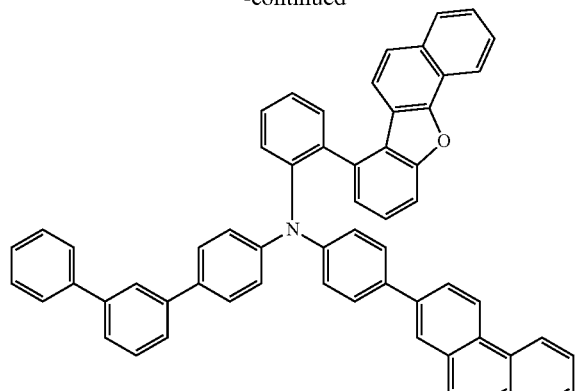
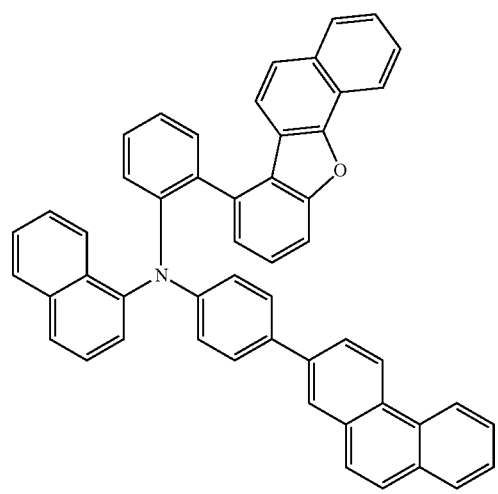
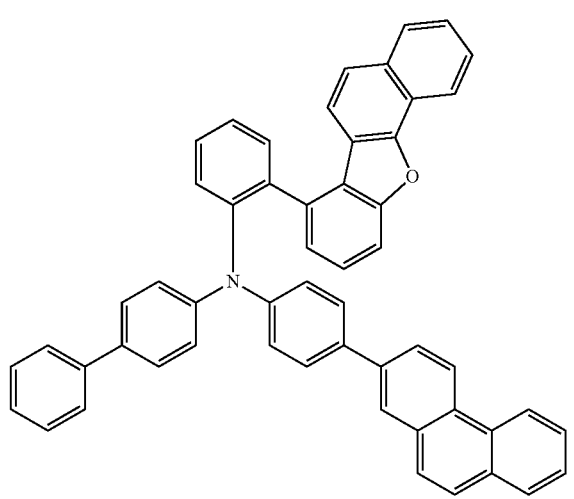
-continued
[Chem. 50]
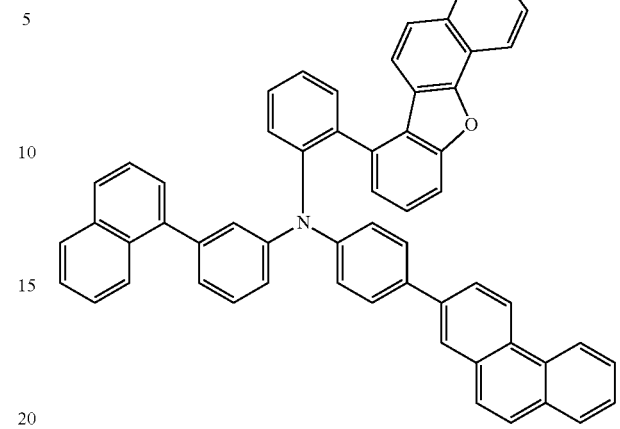

111
-continued
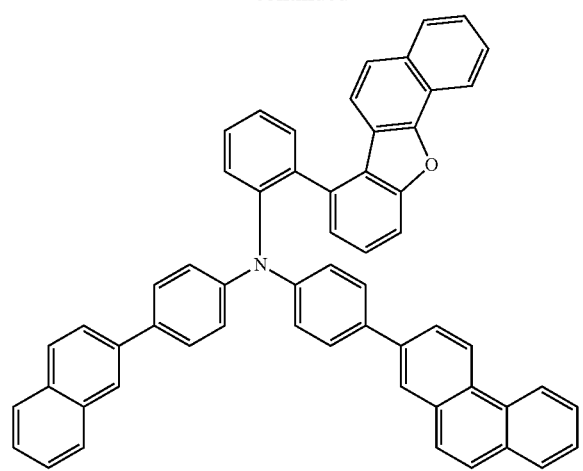
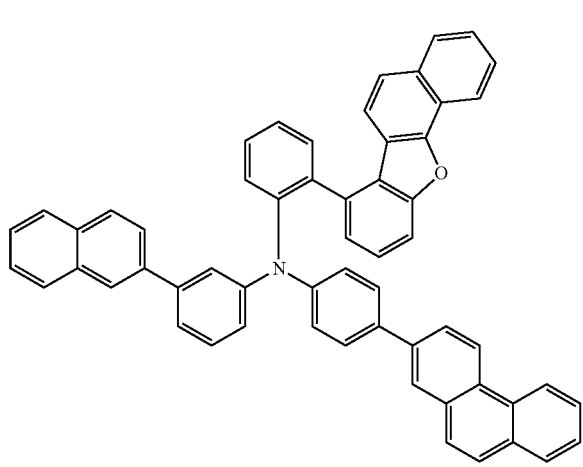
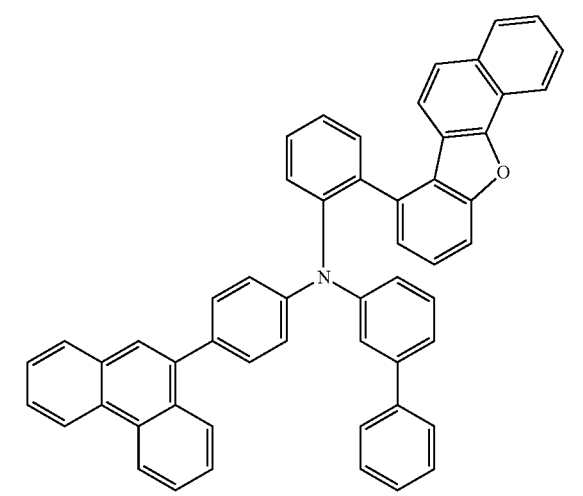
112
-continued
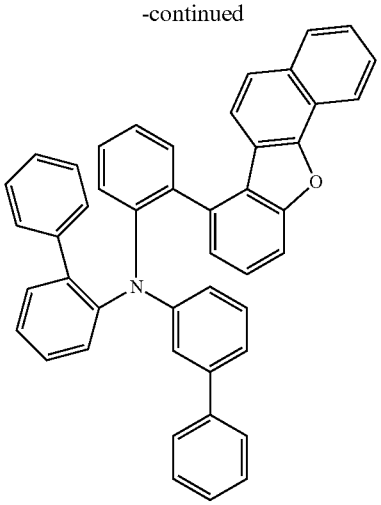
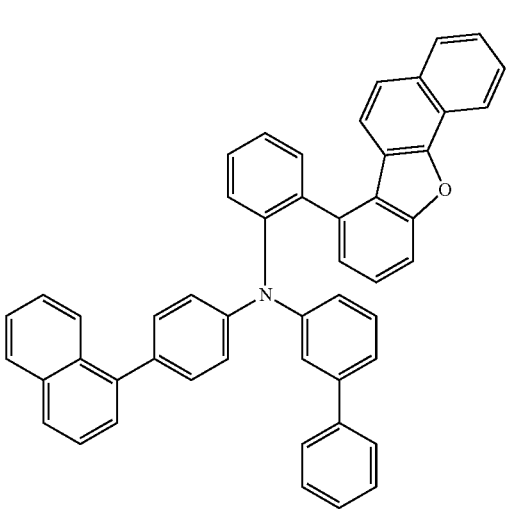
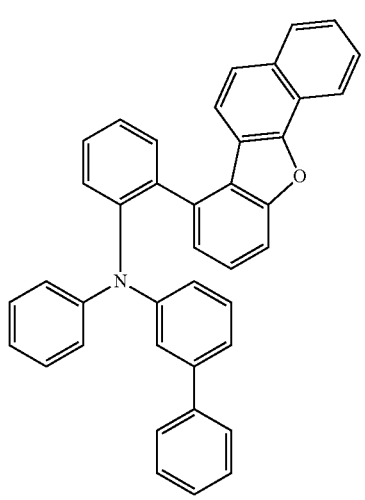

[Chem. 51]
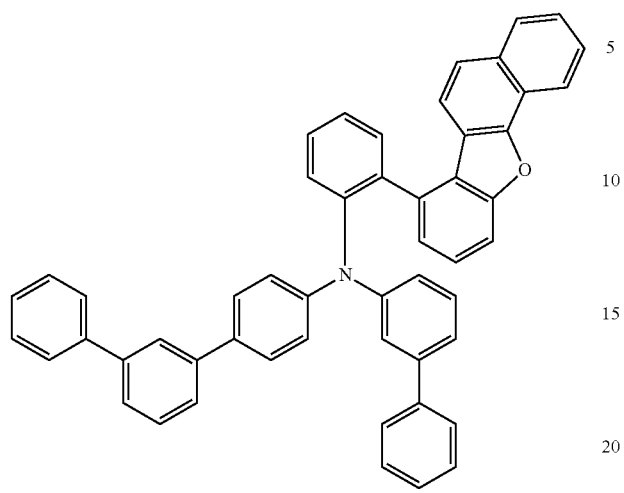
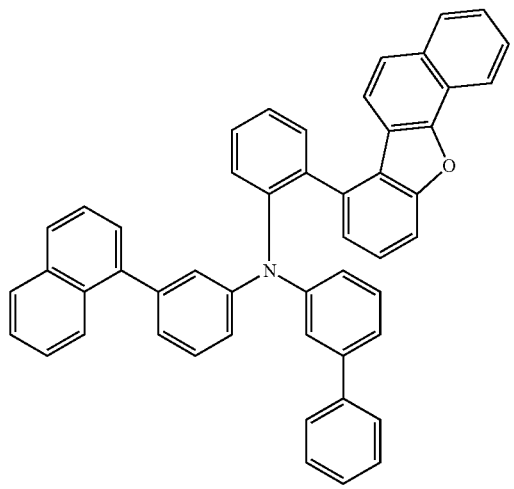
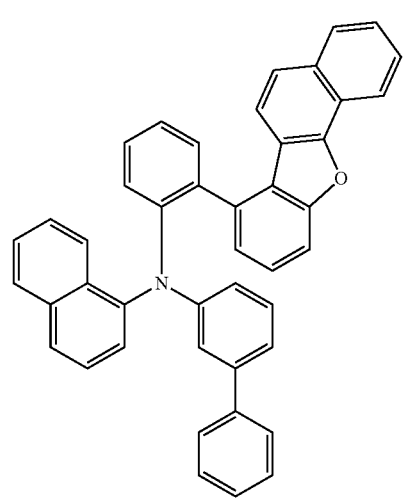
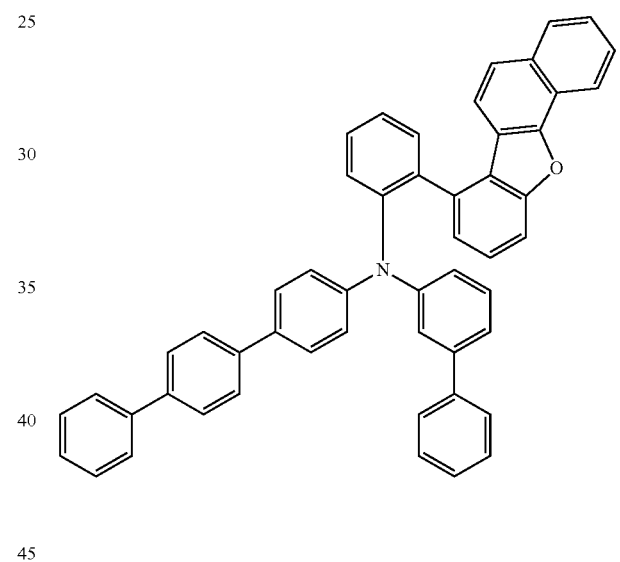
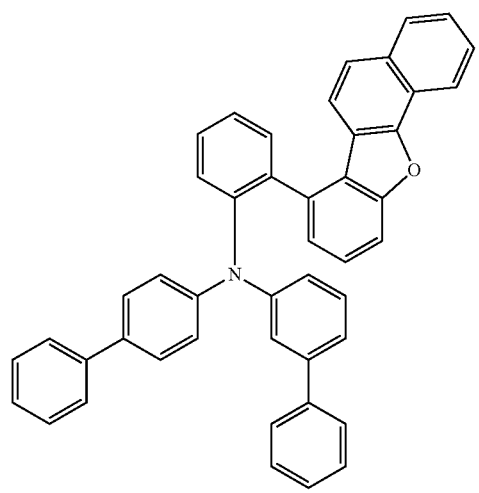
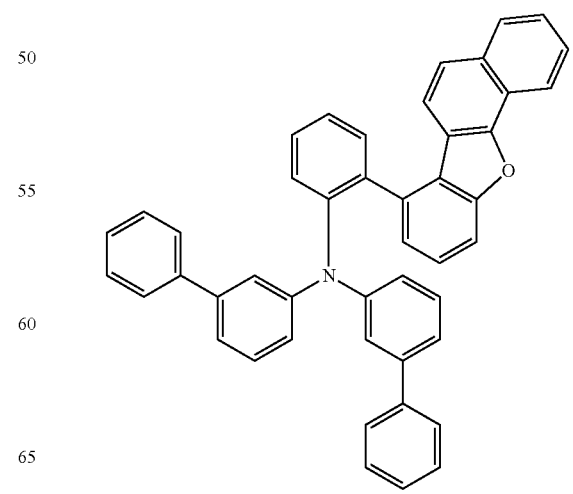

115
-continued
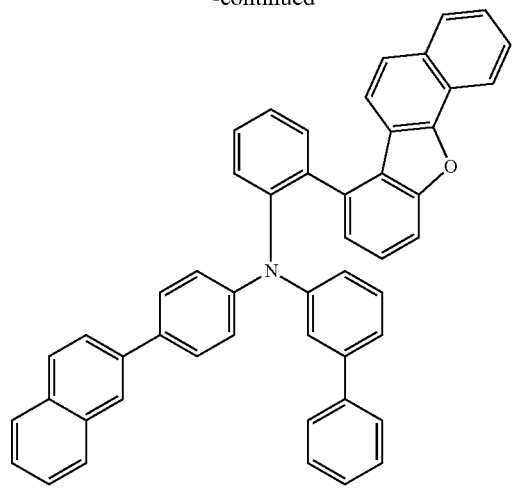
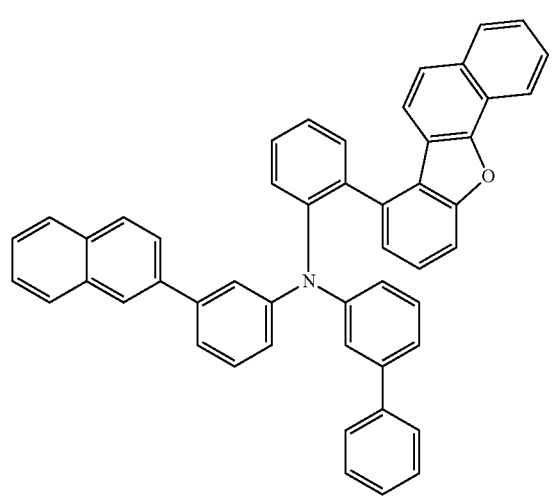
[Chem. 52]
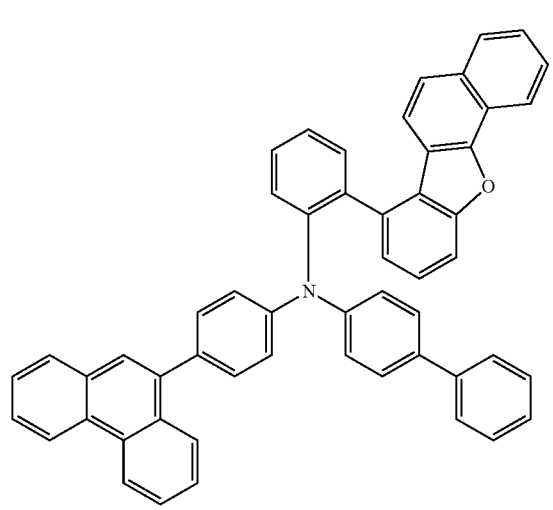
116
-continued
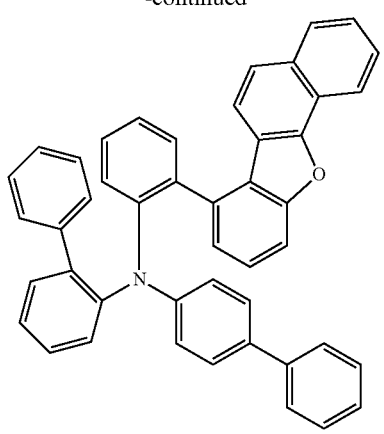
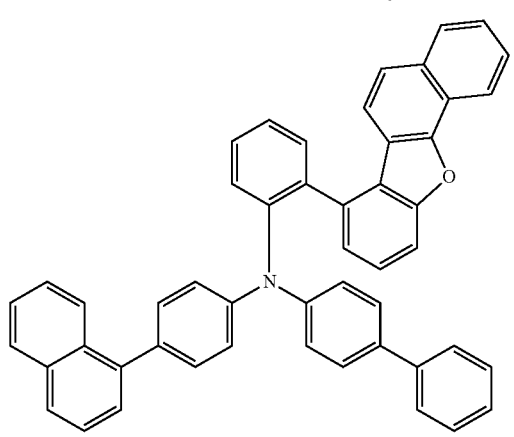
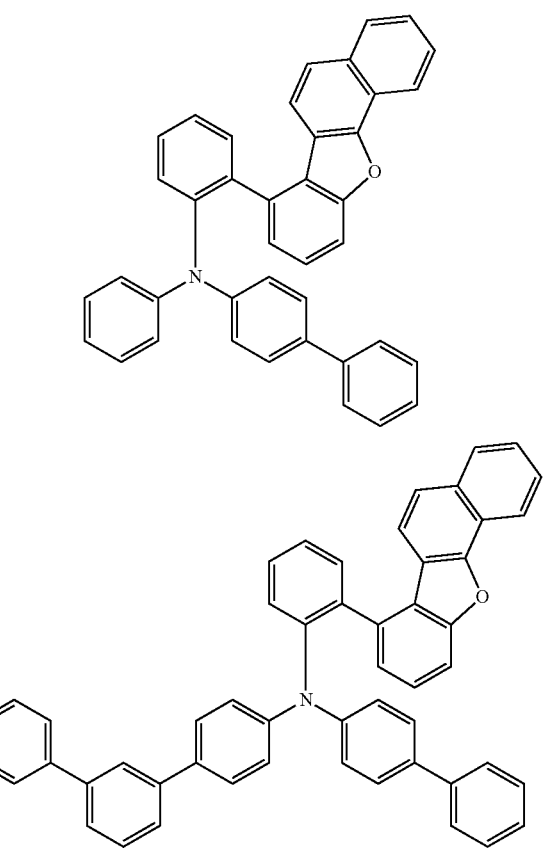

[Chem. 53]
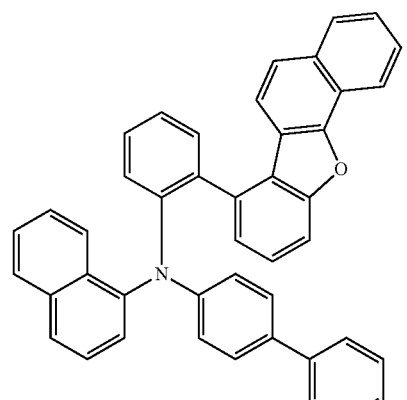
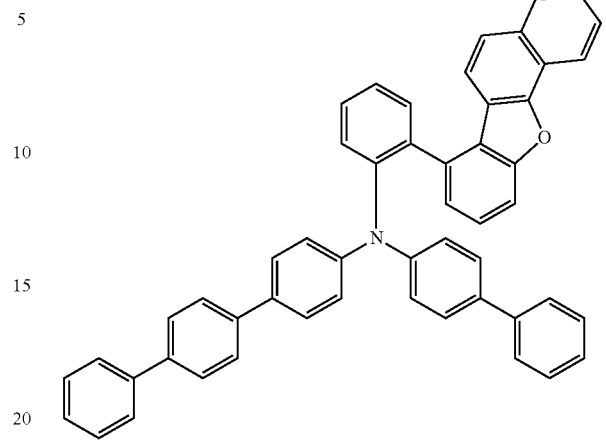
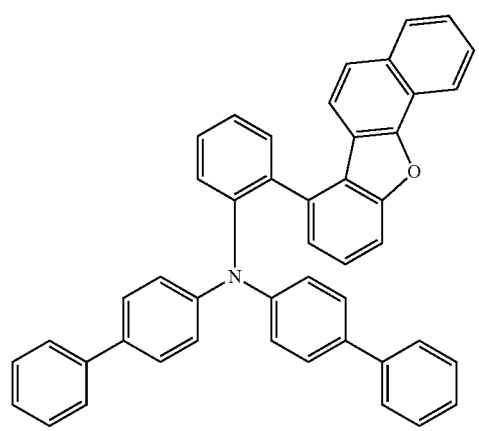
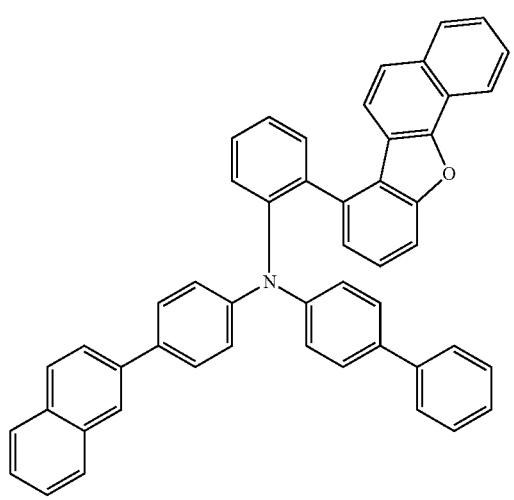
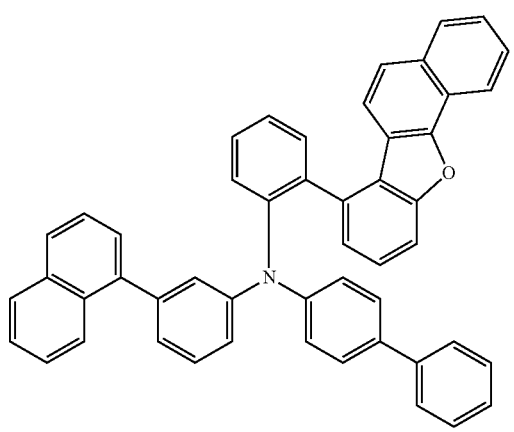

119
-continued
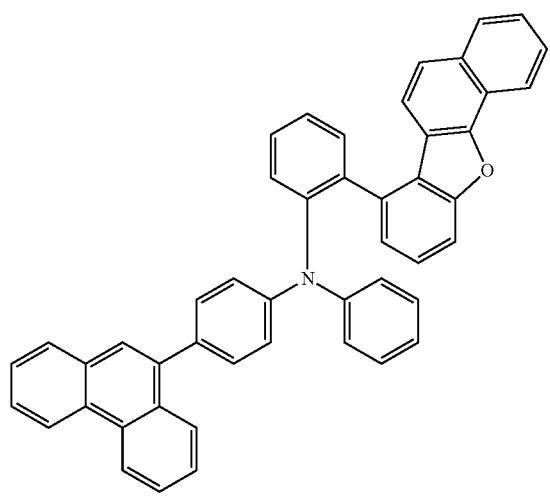
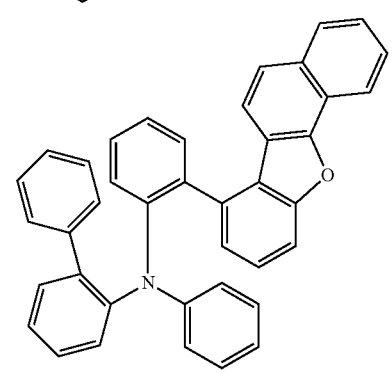
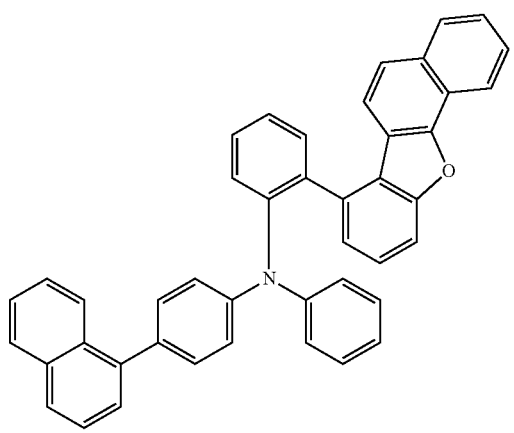
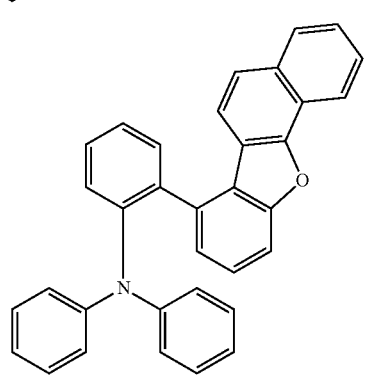
120
-continued
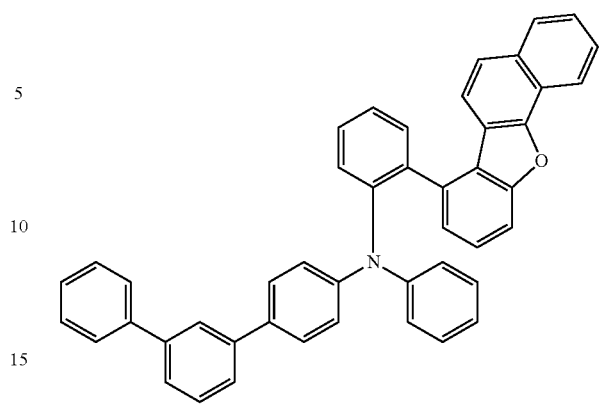
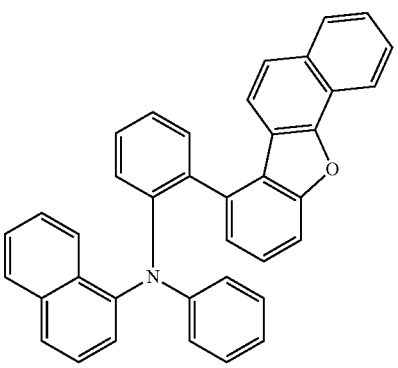
[Chem. 54]
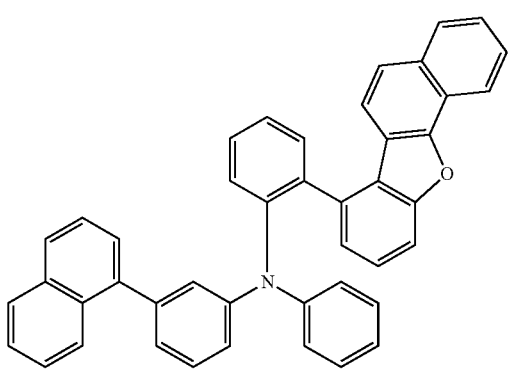
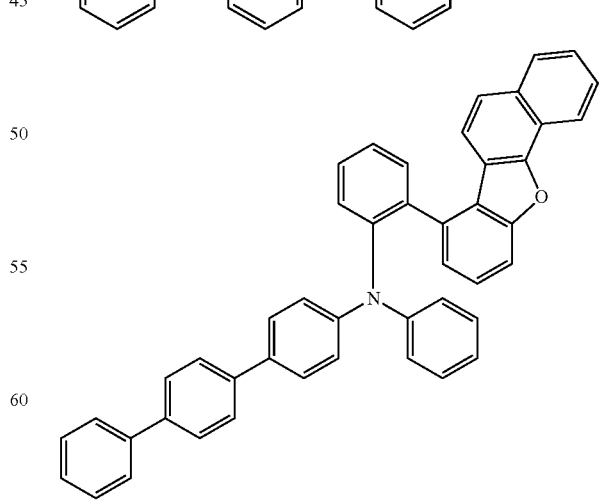

121
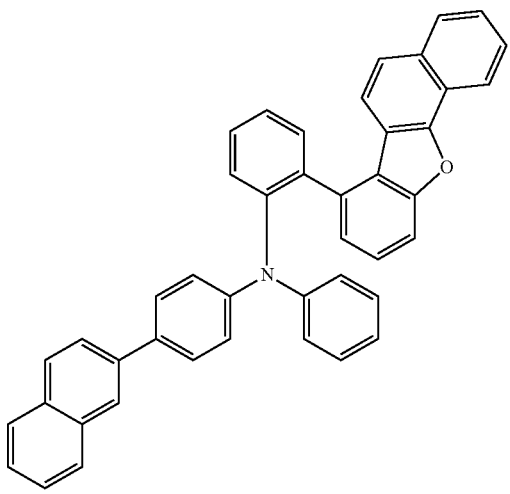
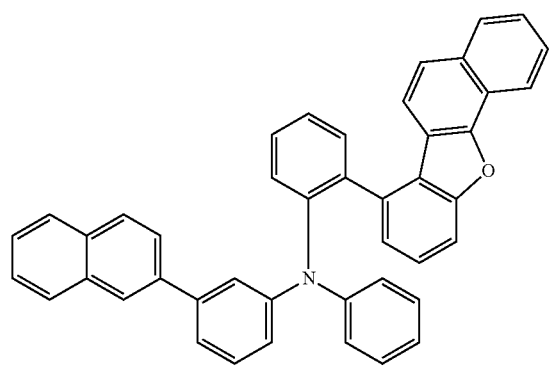
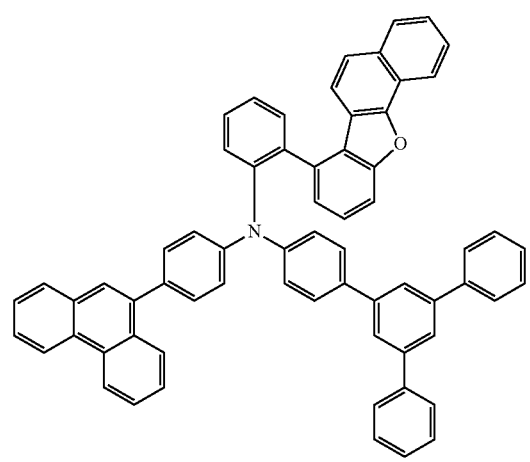
122
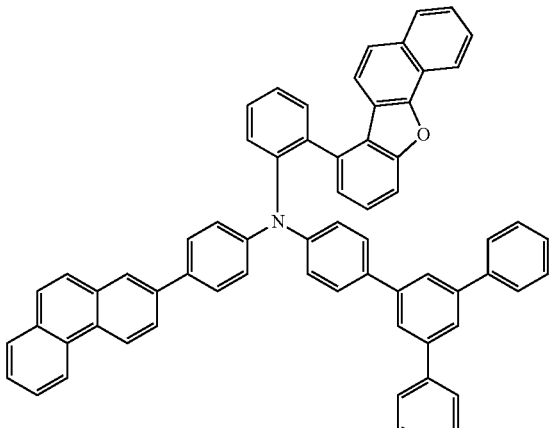
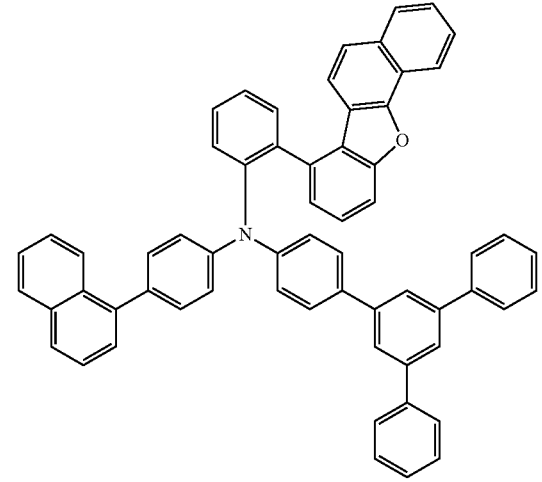

123
-continued
[Chem. 55]
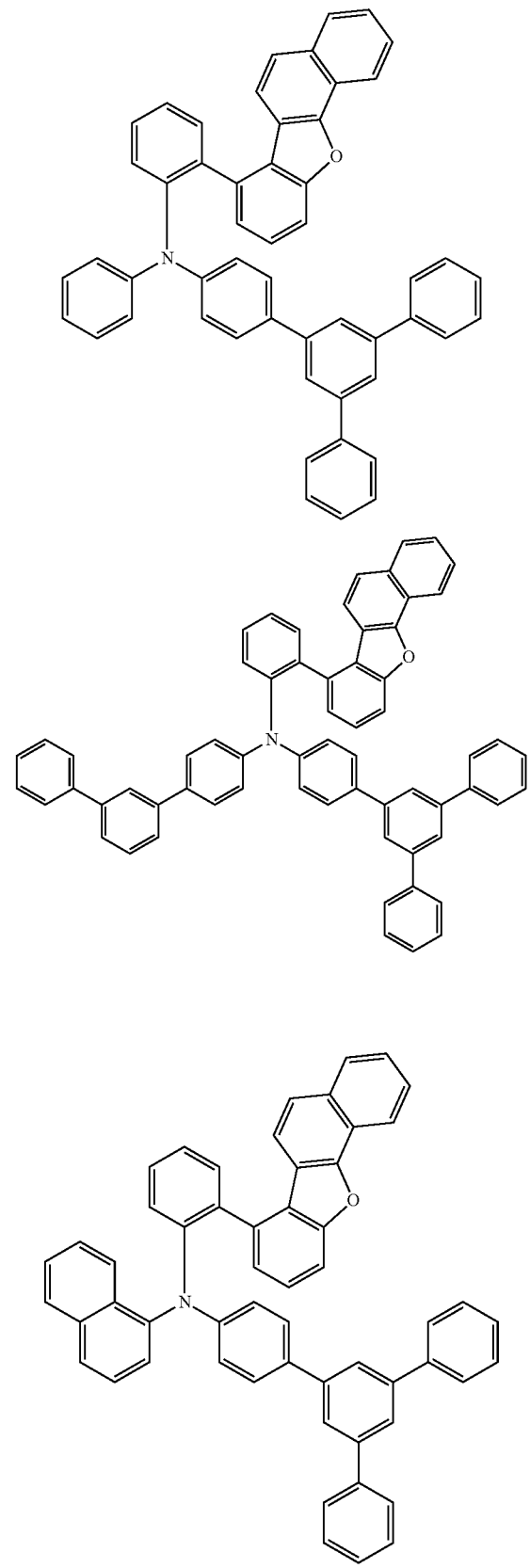
124
-continued
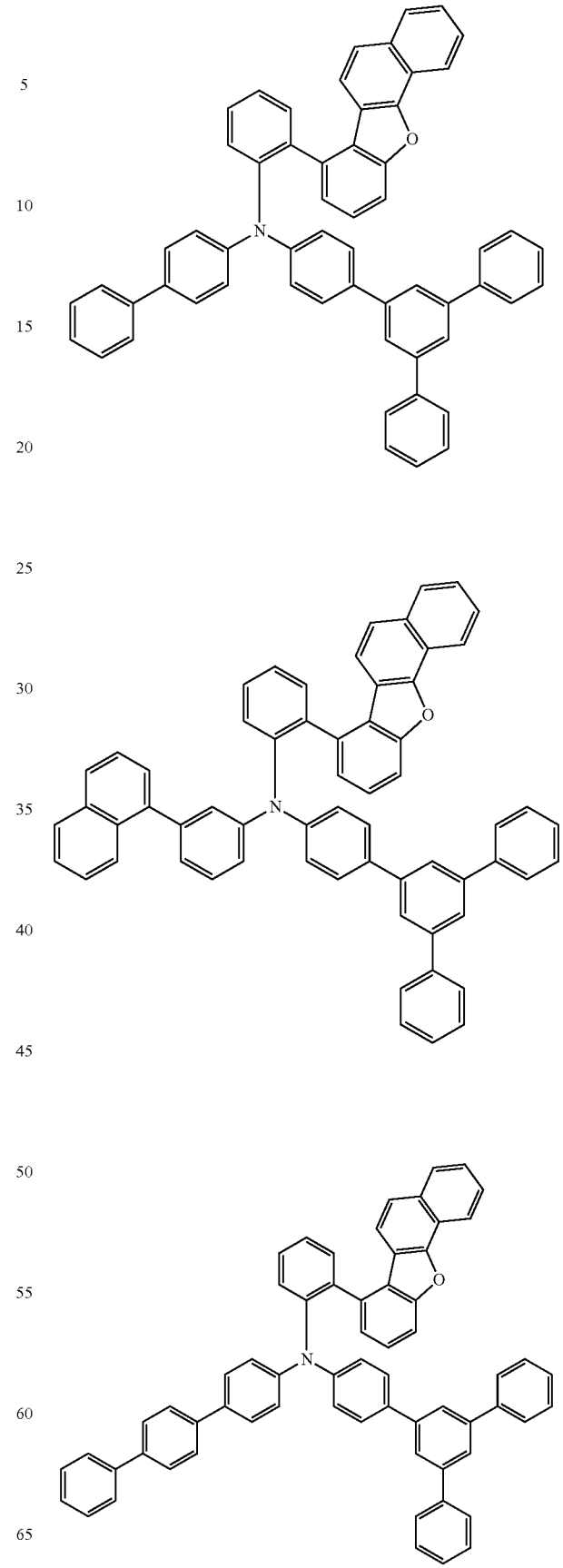

125
-continued
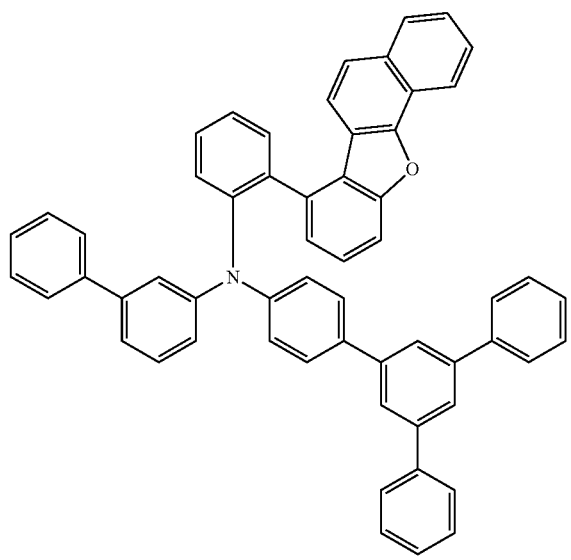
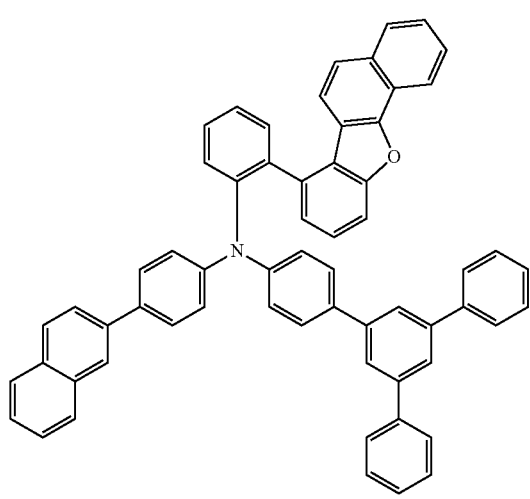
[Chem. 56]
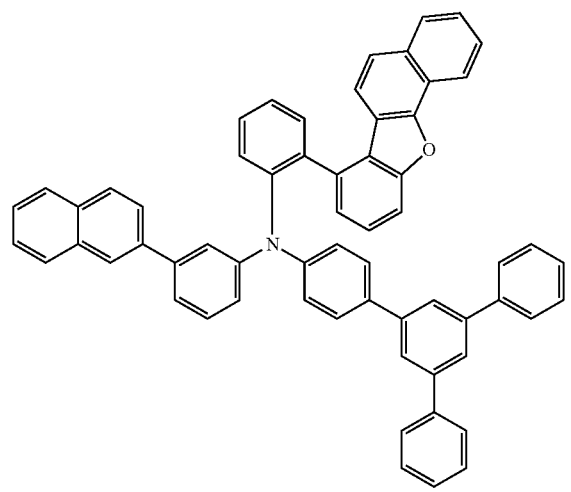
126
-continued
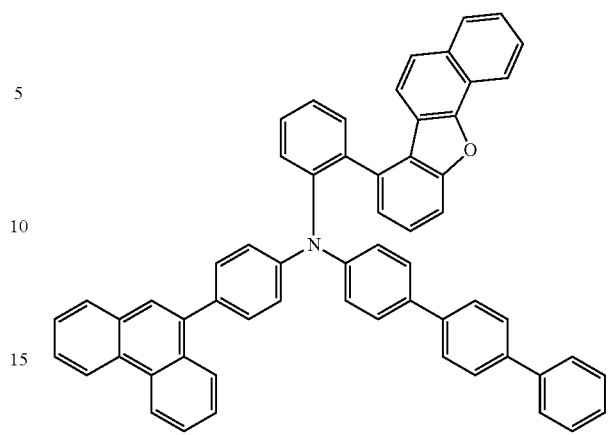
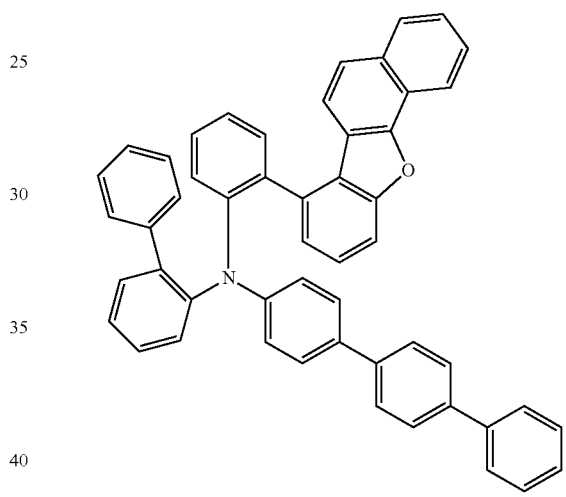
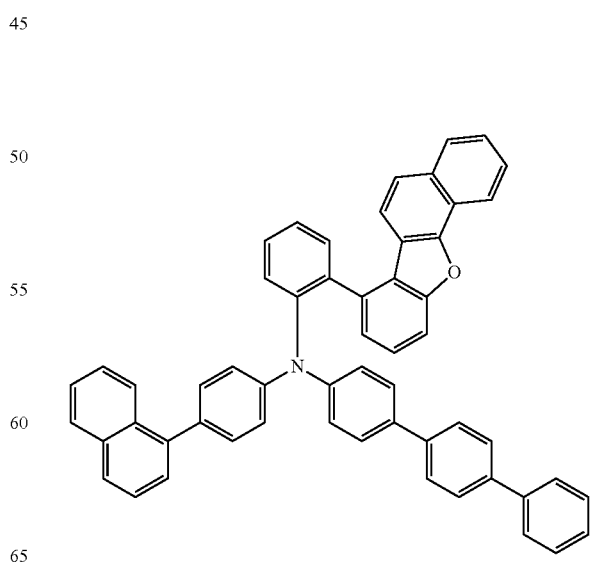

127
-continued
128
-continued
[Chem. 57]
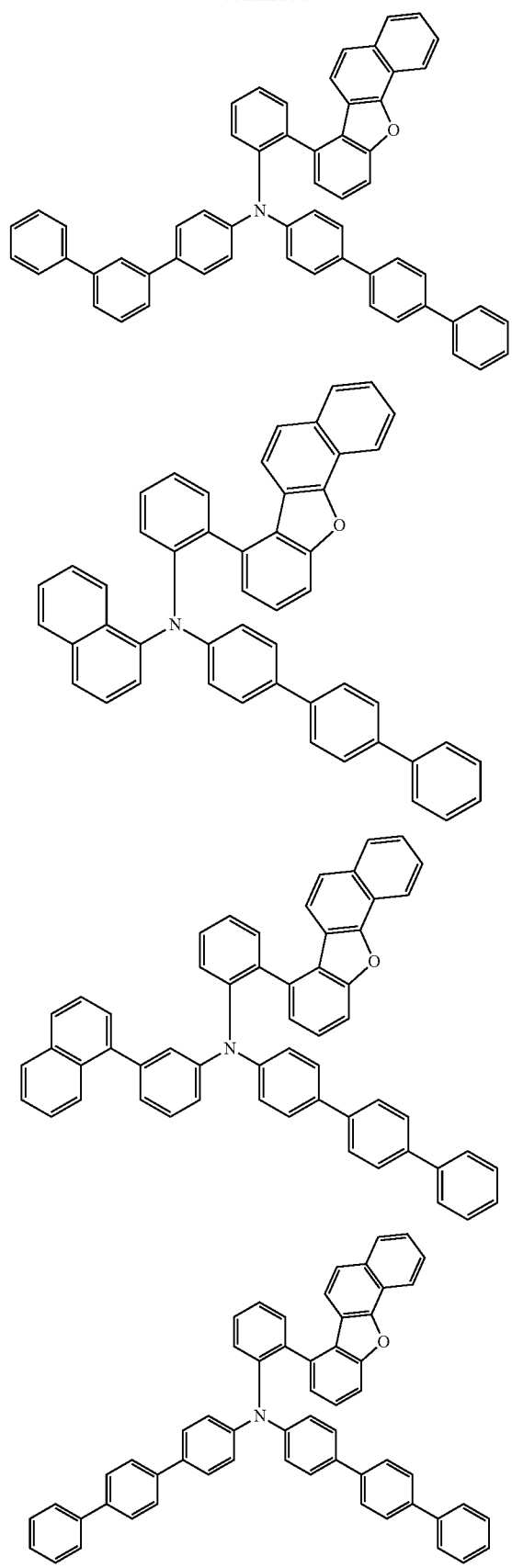
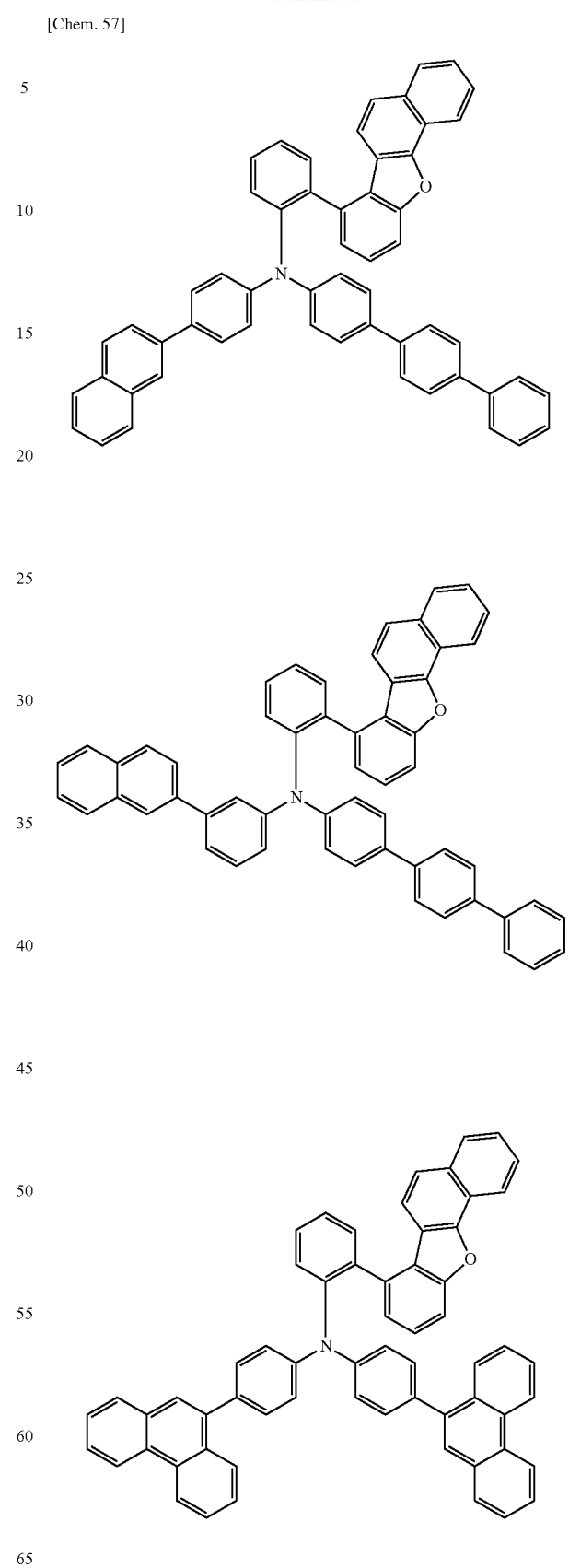

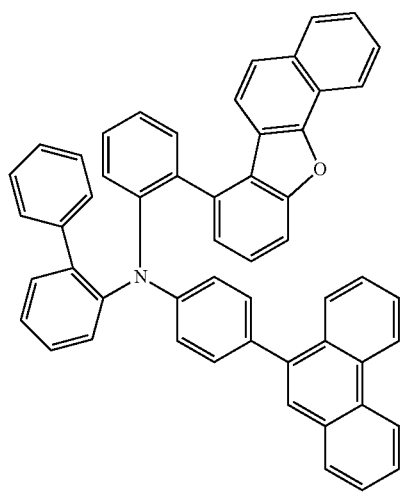
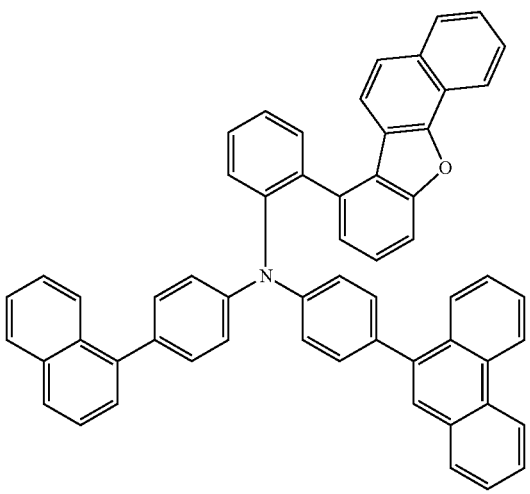
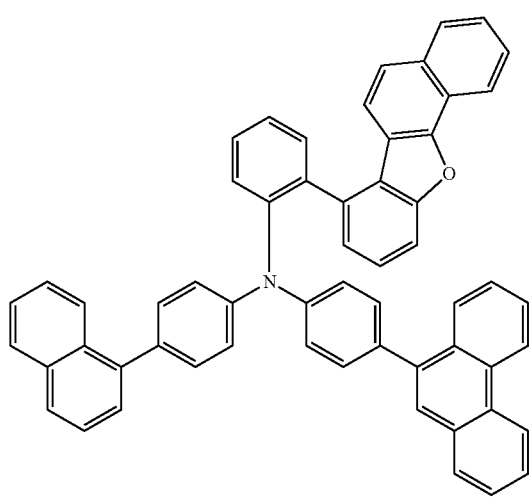
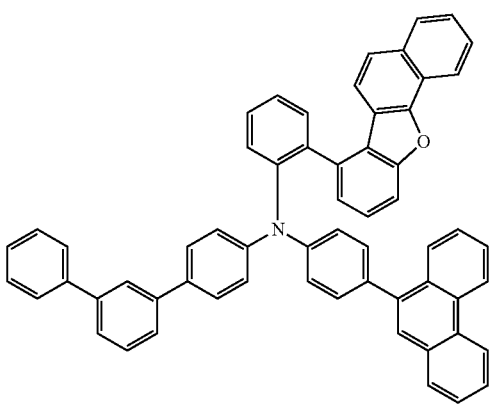
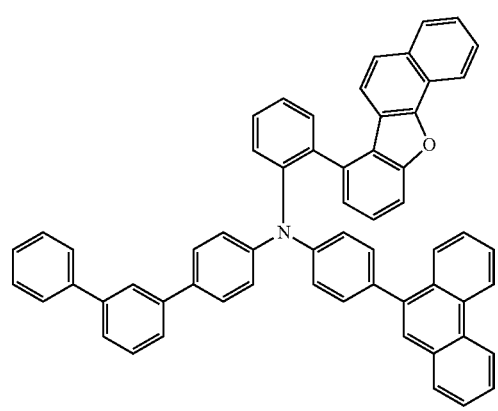
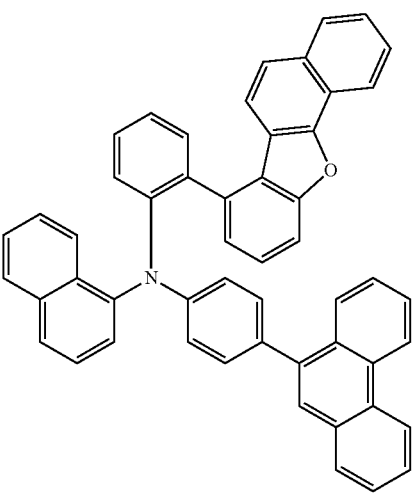

131
-continued
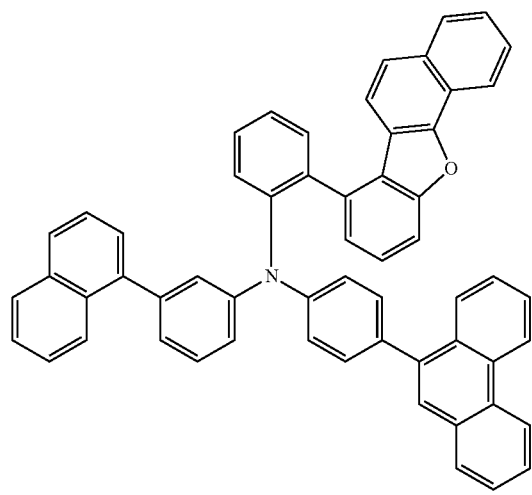
[Chem. 58]
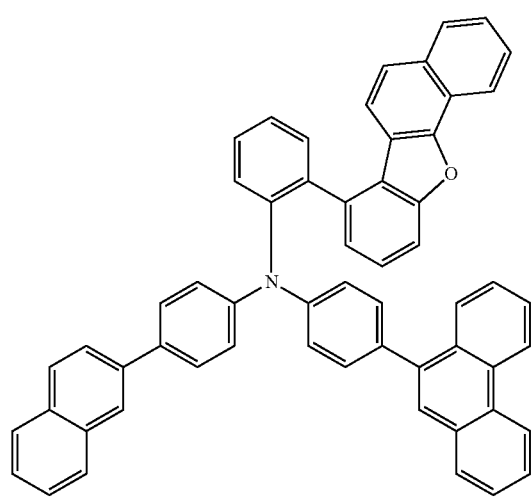
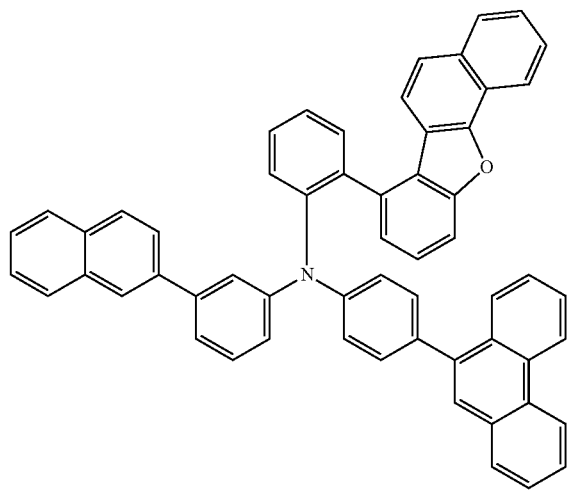
132
-continued
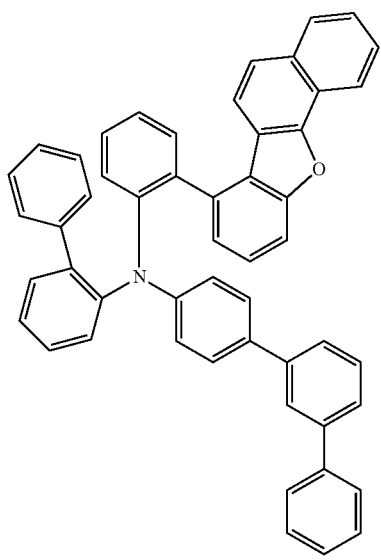
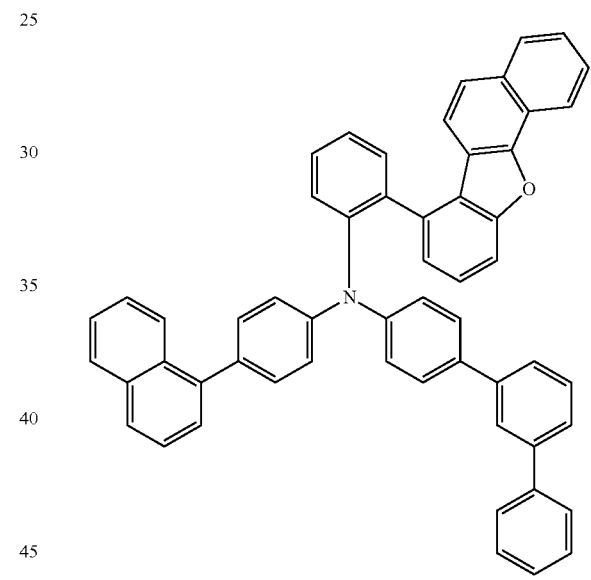
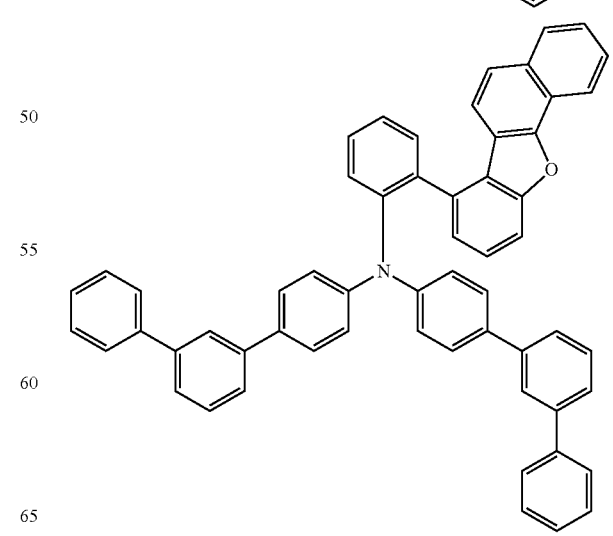

133
-continued
[Chem. 59]
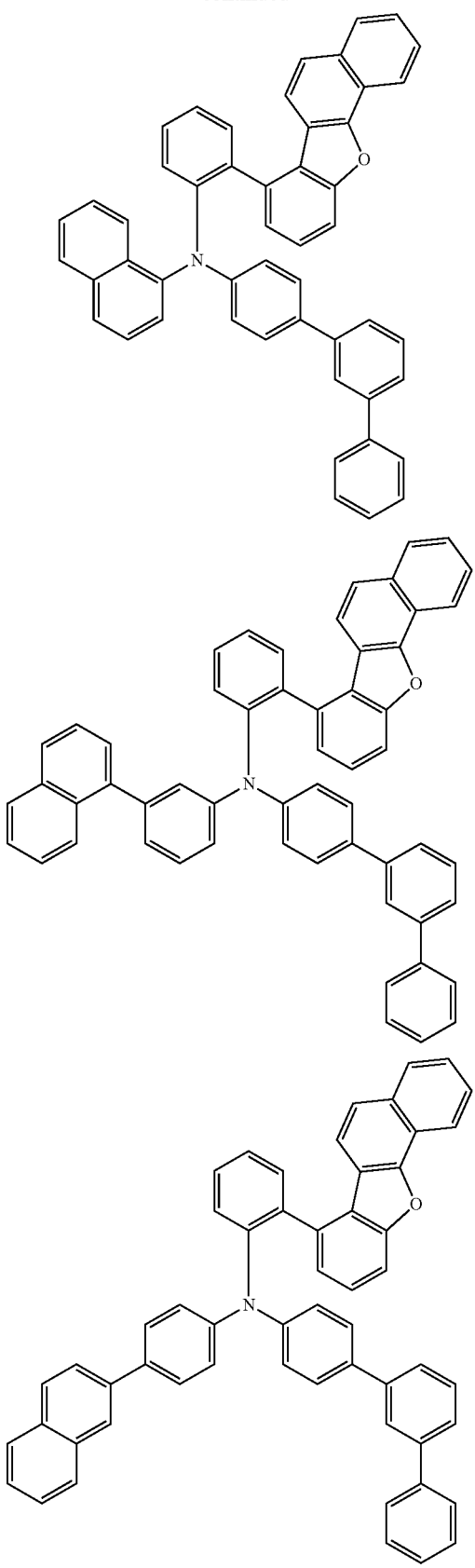
134
-continued
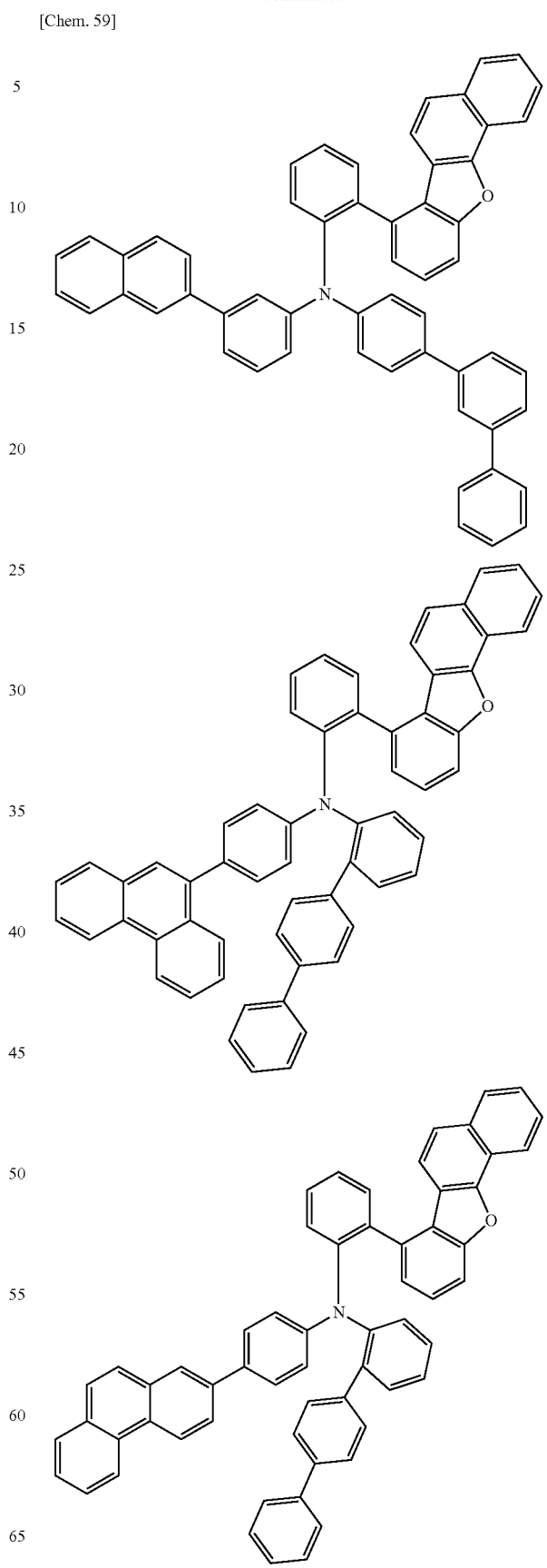

135
-continued
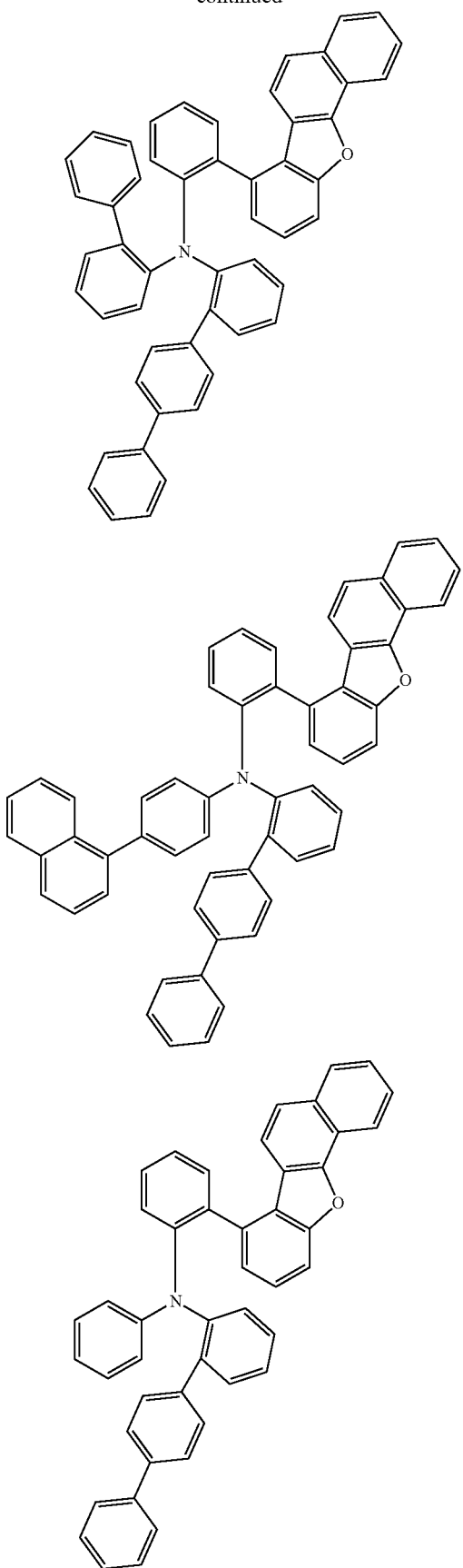
136
-continued
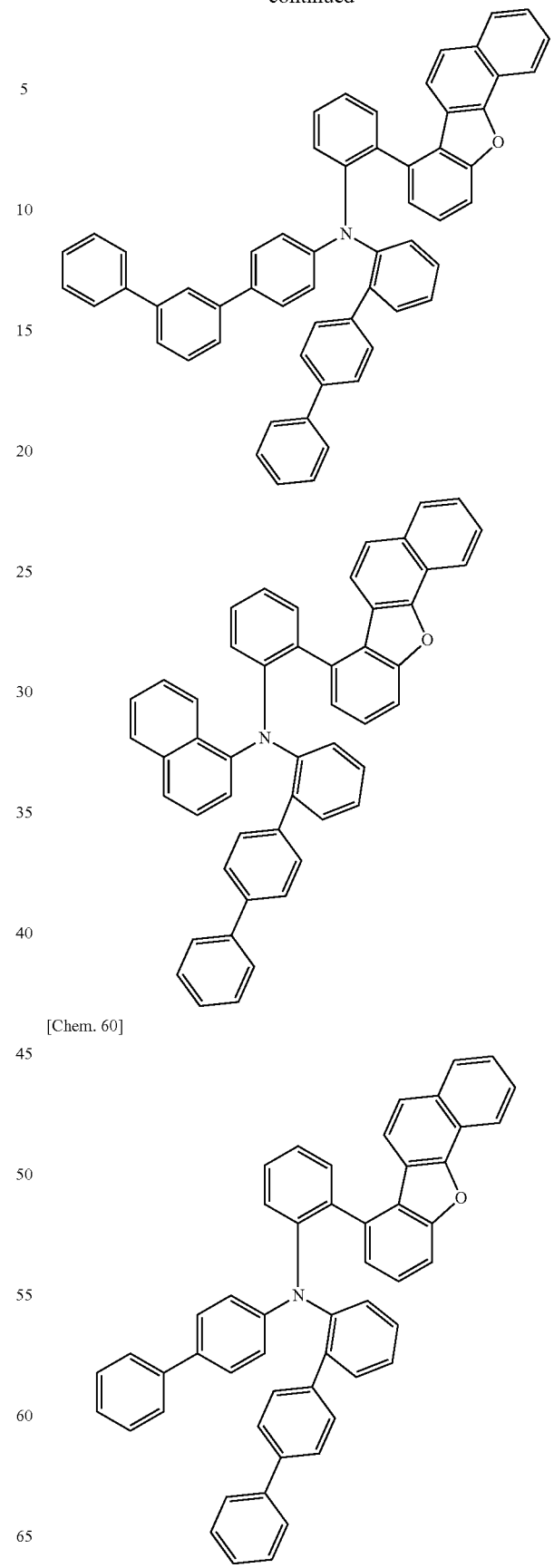
[Chem. 60]

137
-continued
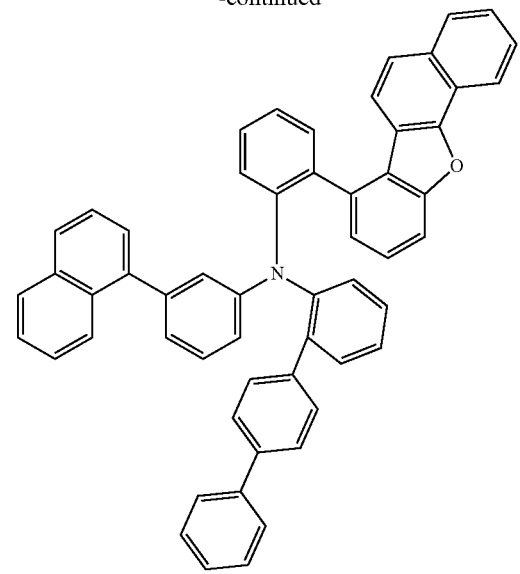
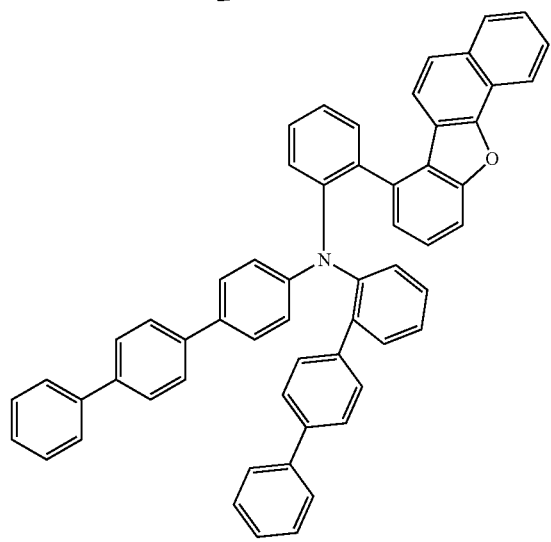
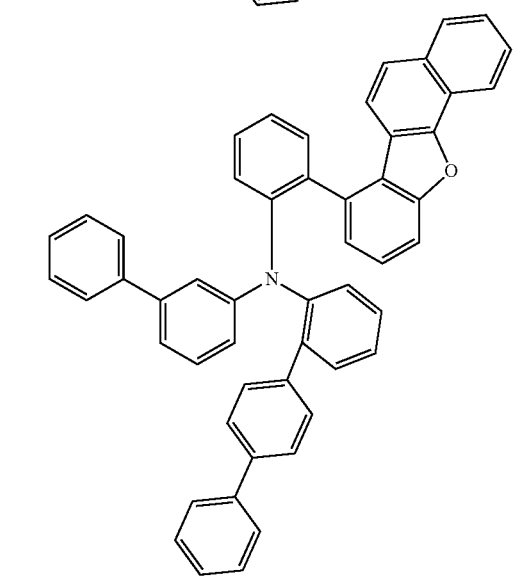
138
-continued
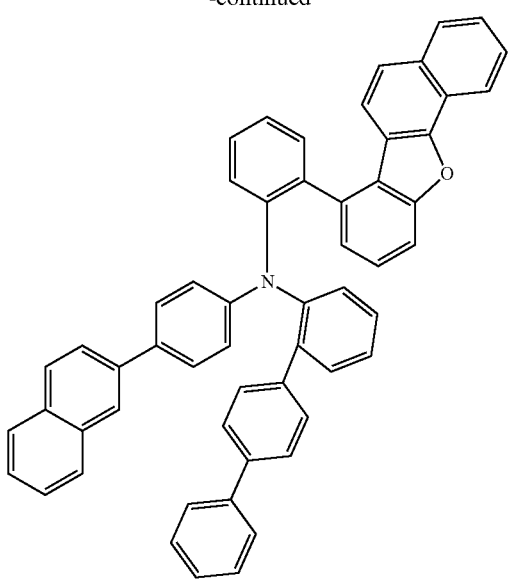
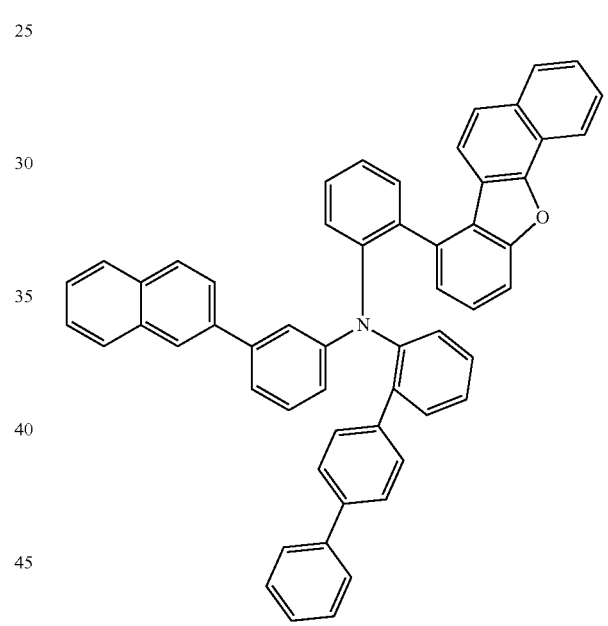
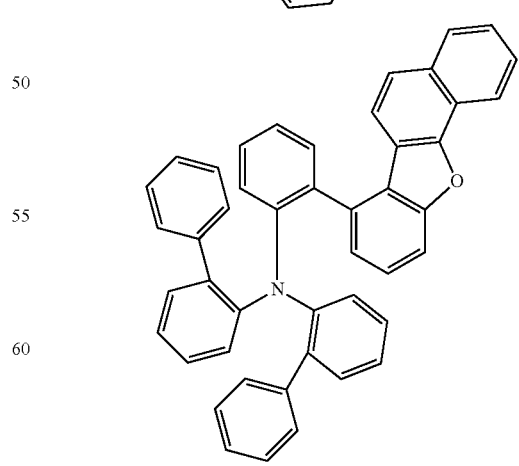

139
-continued
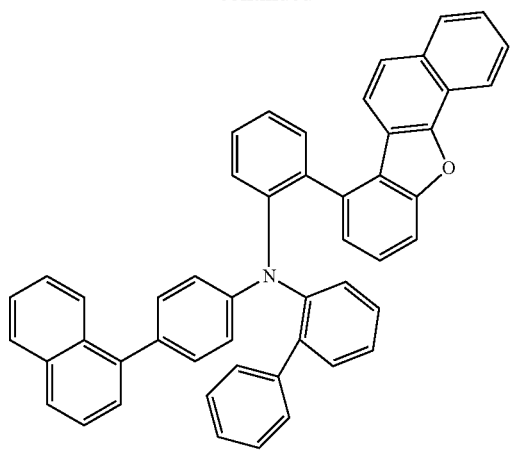
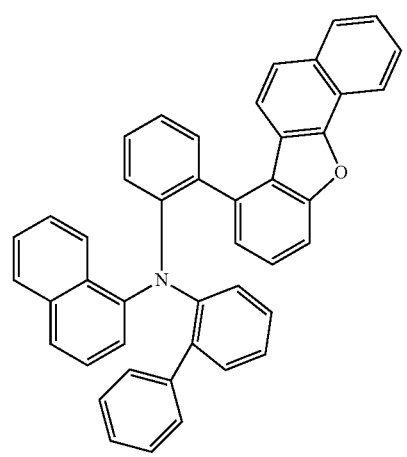
[Chem. 61]
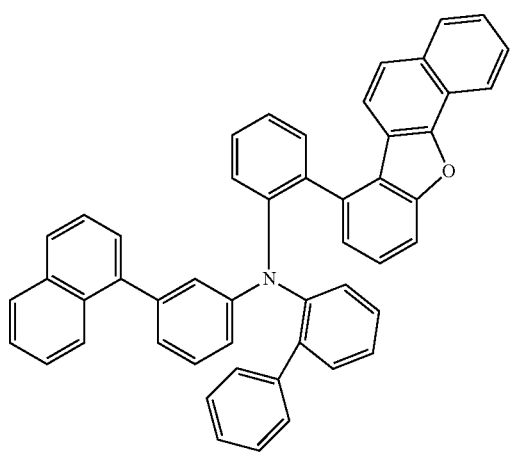
140
-continued
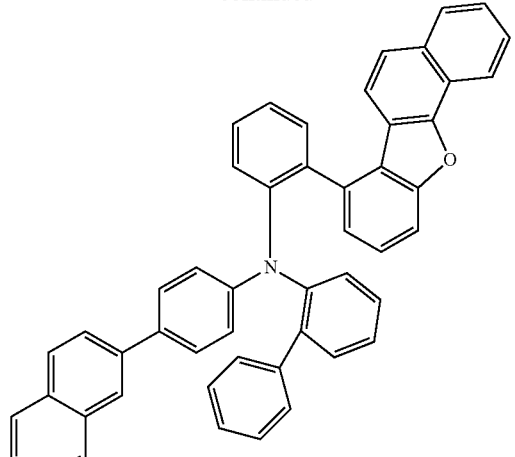
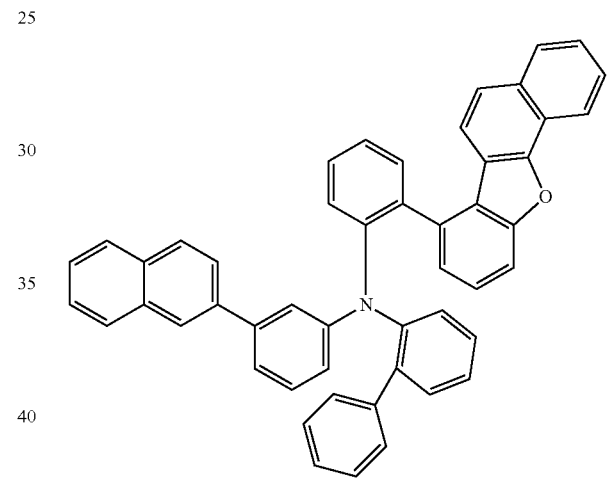
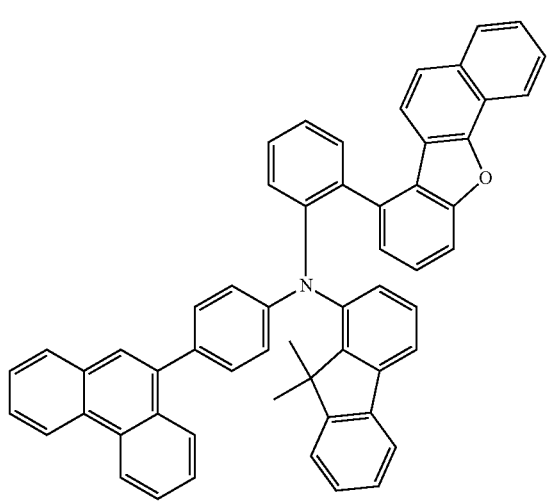

141
-continued
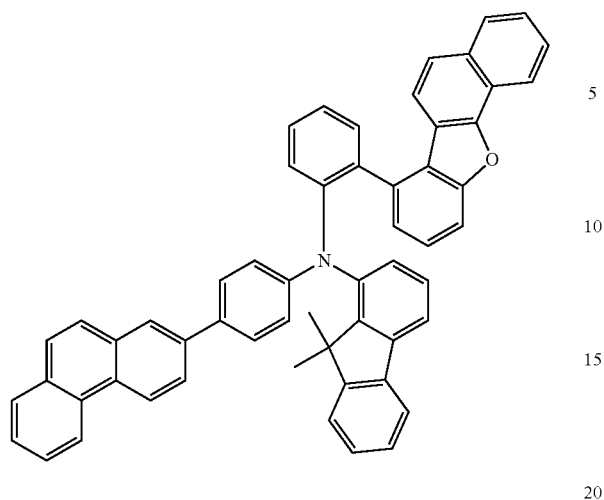
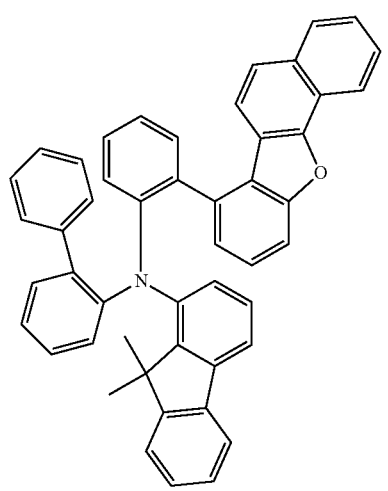
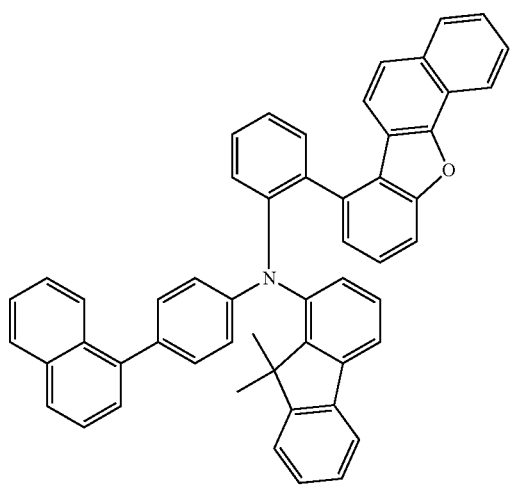
142
-continued
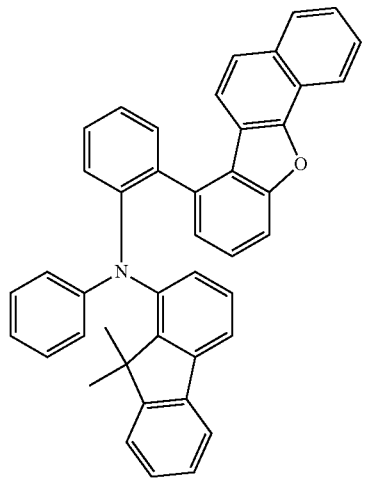
[Chem. 62]
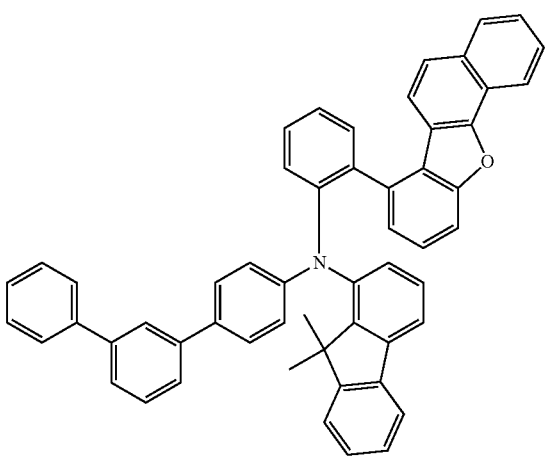
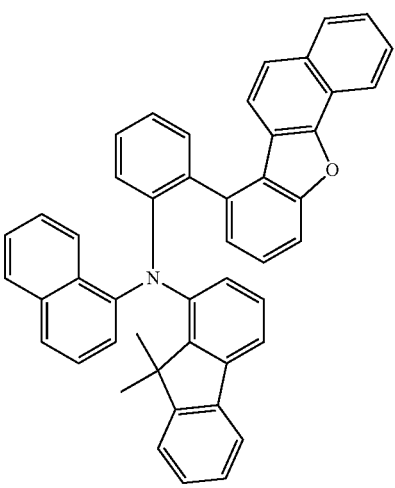

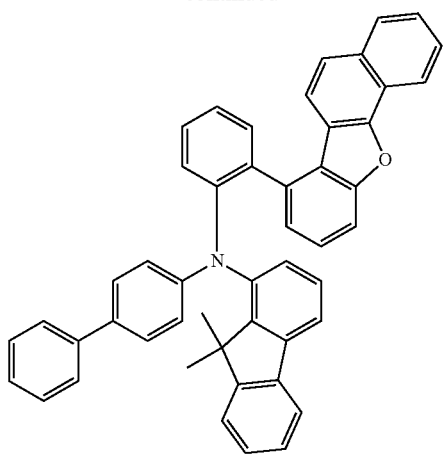
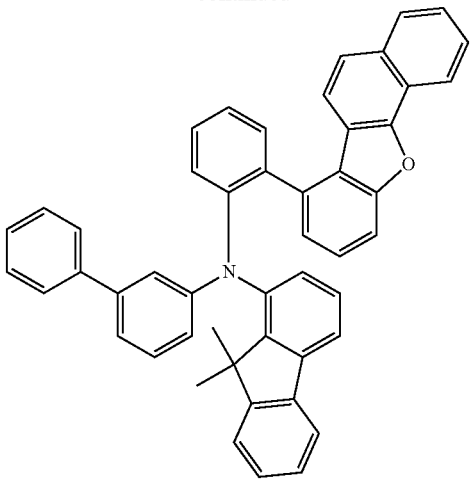
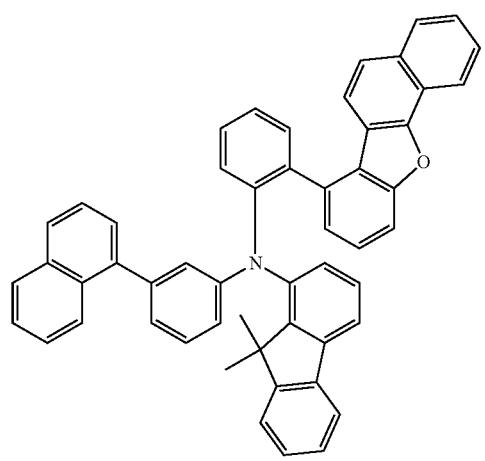
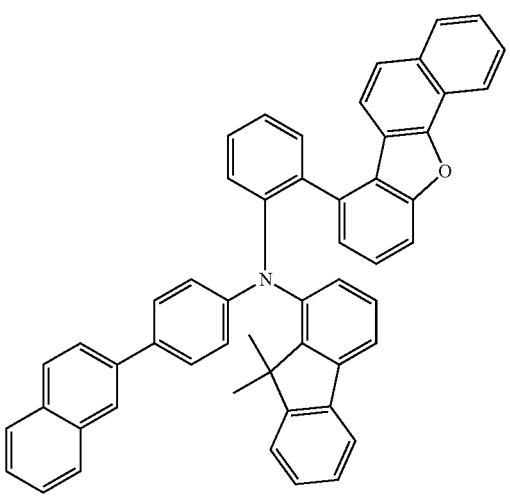
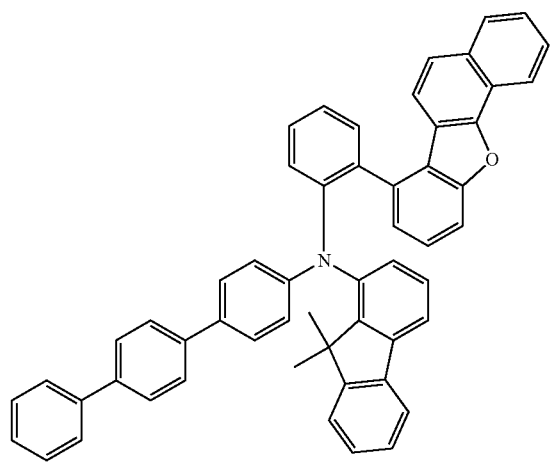
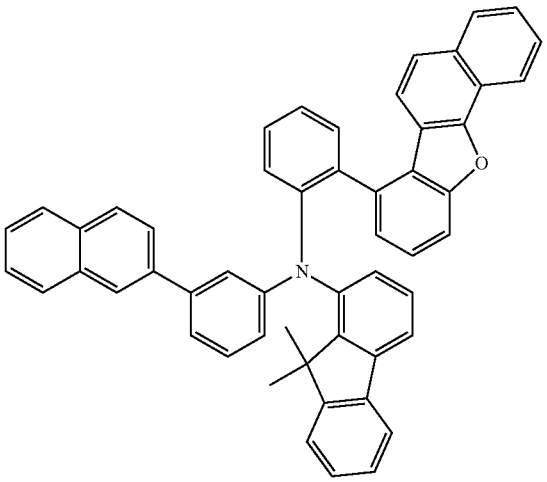

-continued
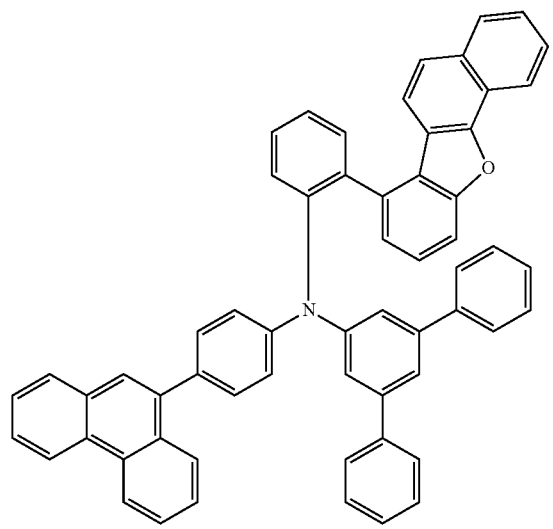
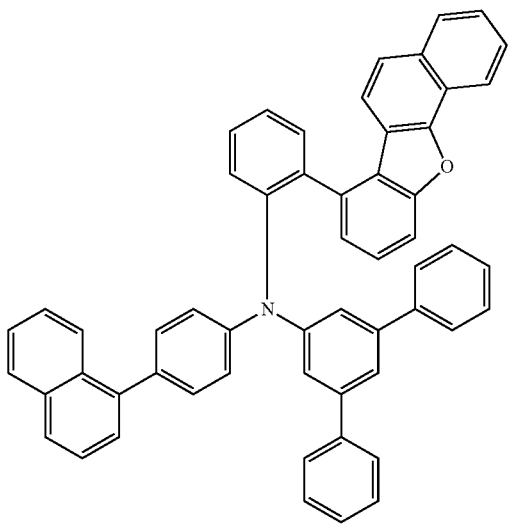
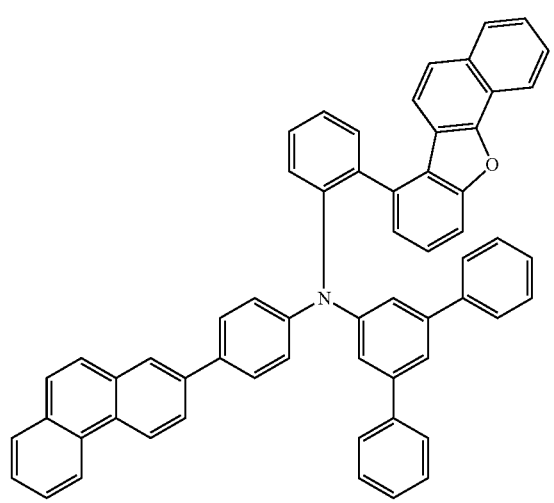
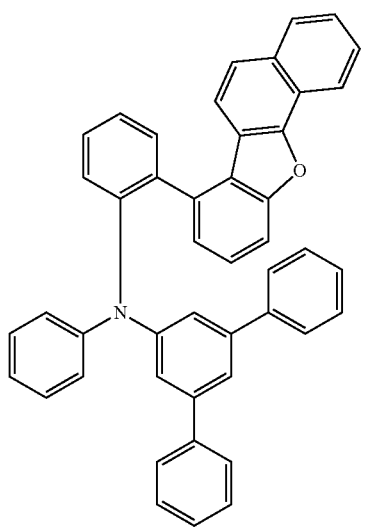
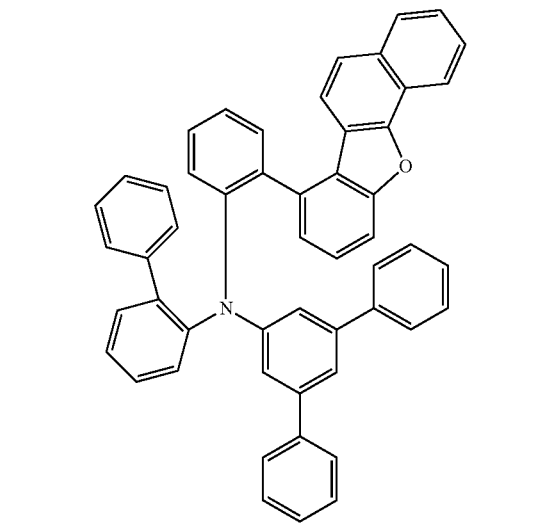
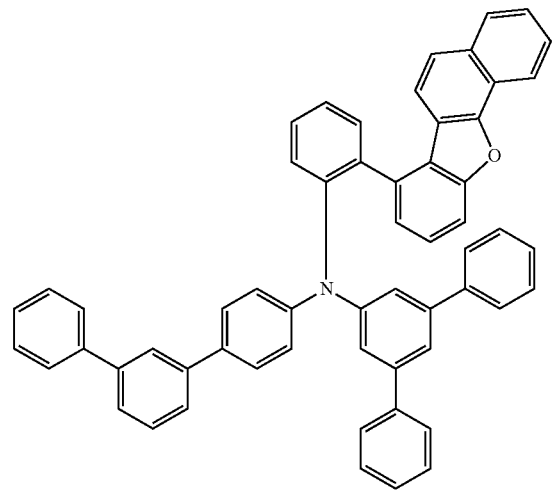

147
-continued
[Chem. 64]
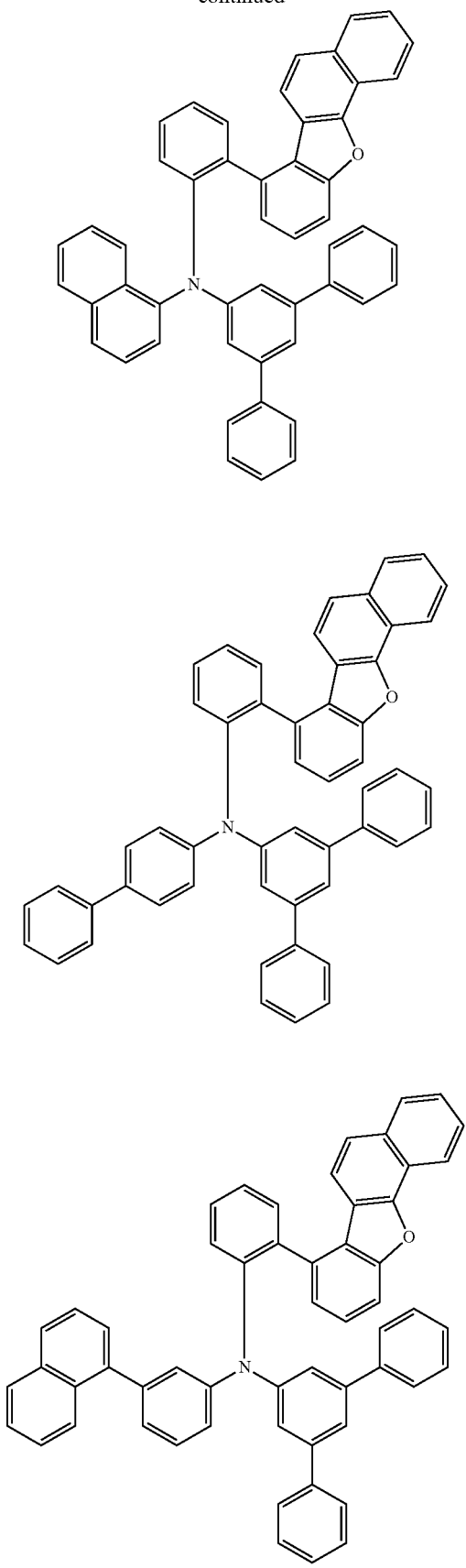
148
-continued
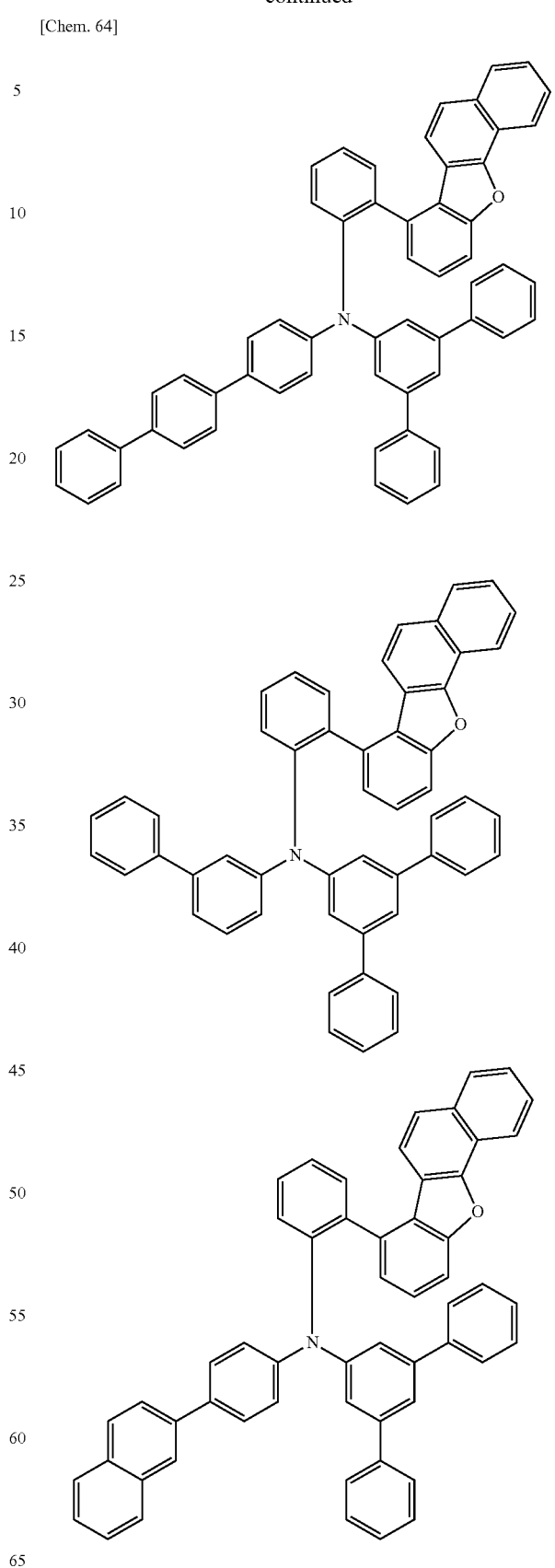

149
-continued
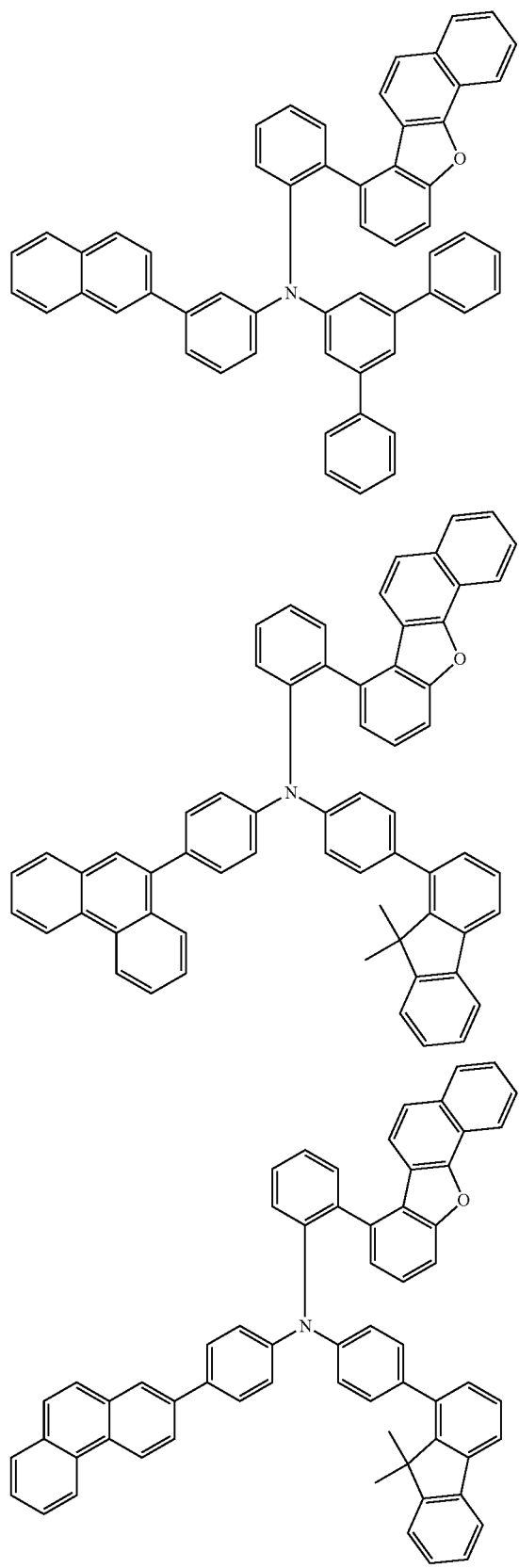
150
-continued
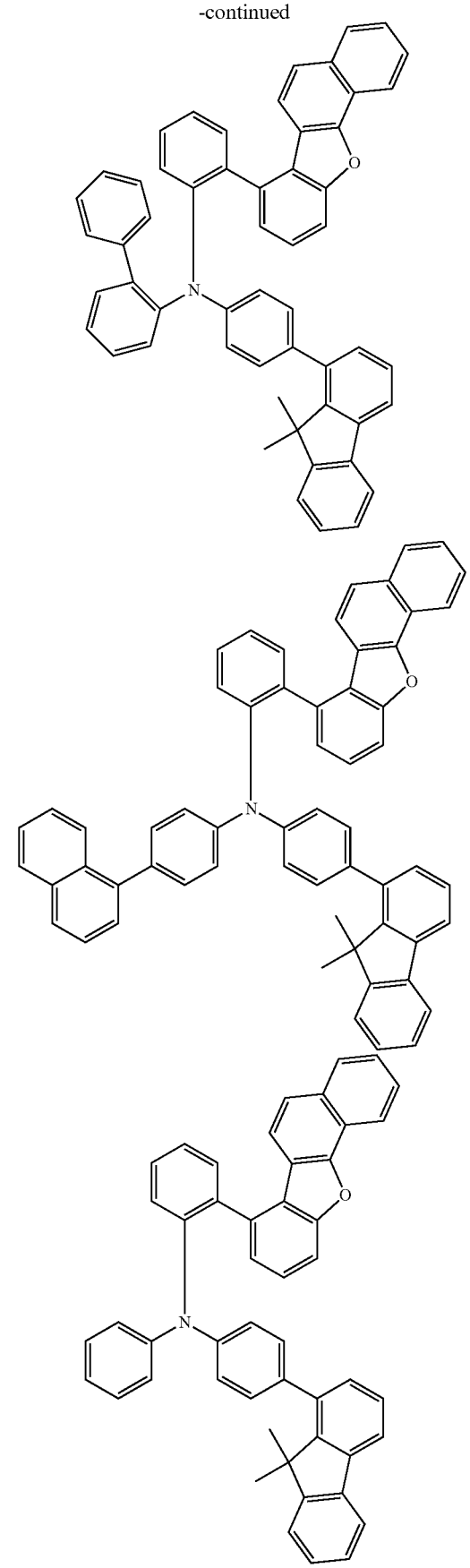

151
-continued
[Chem. 65]
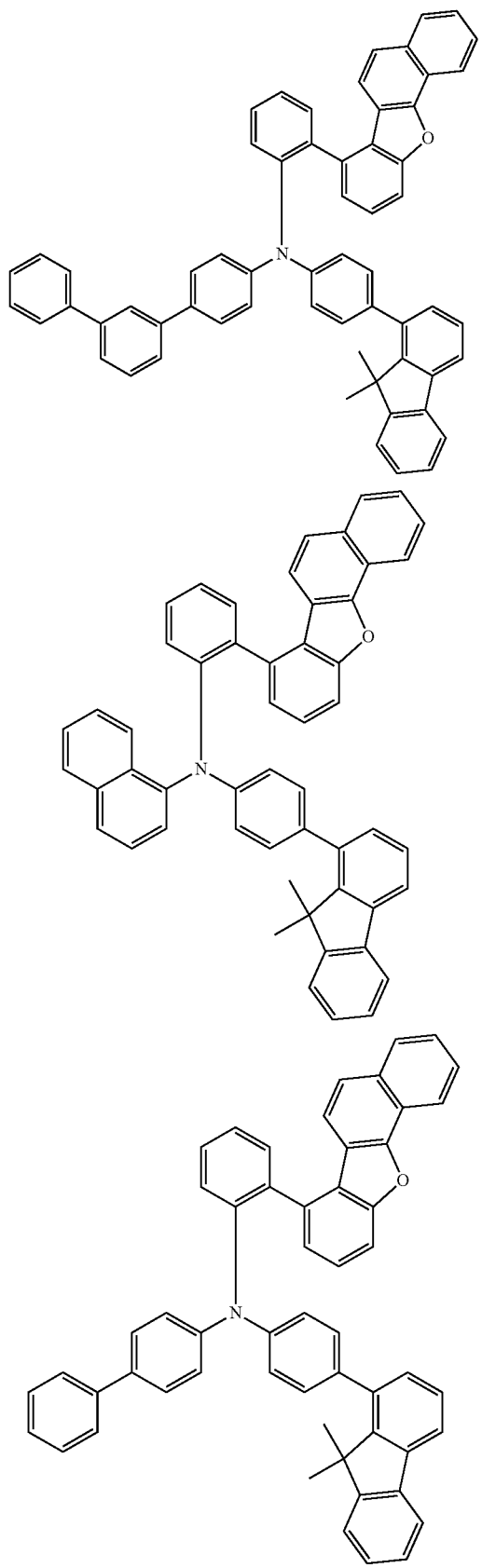
152
-continued
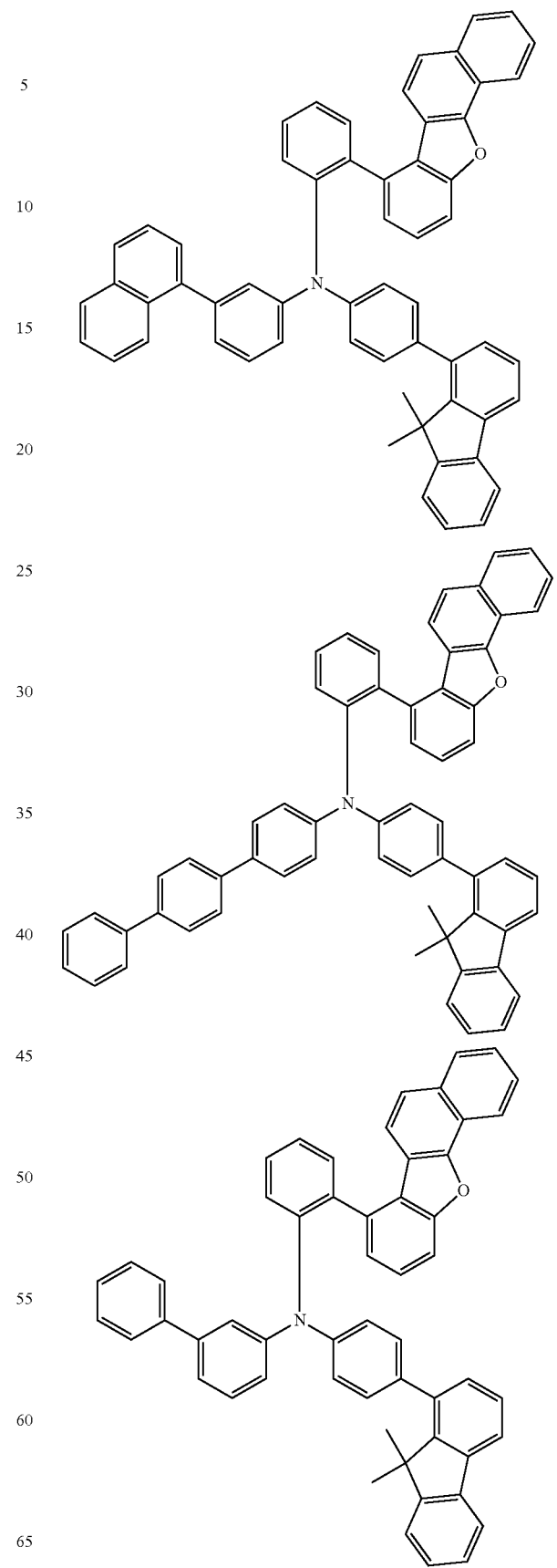

153
-continued
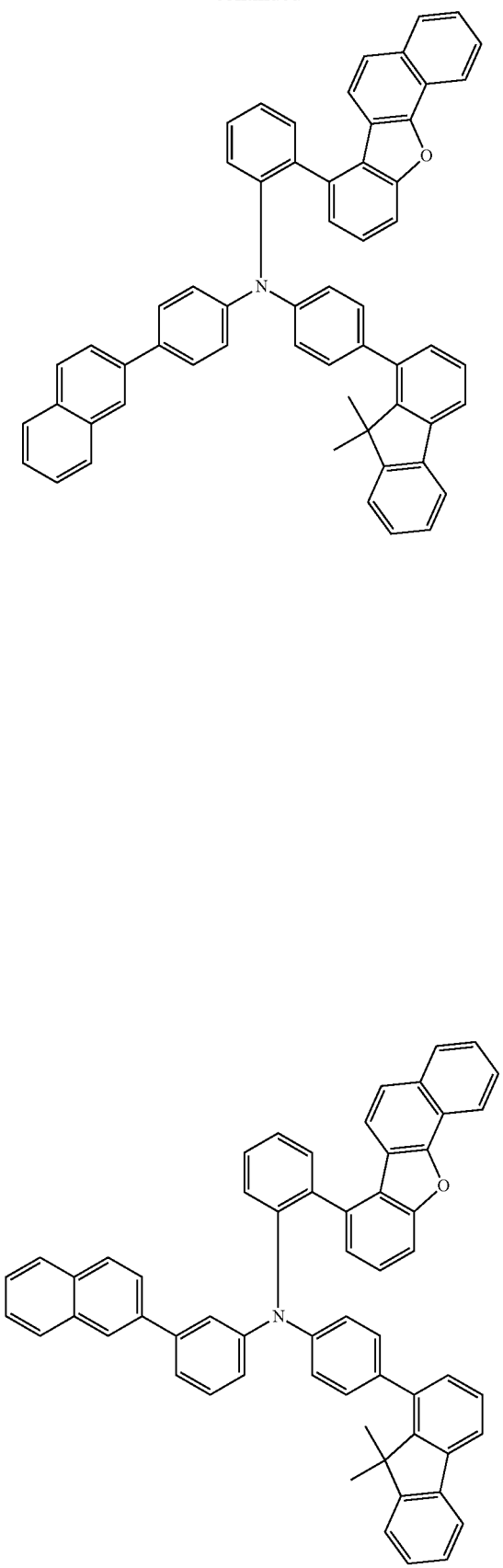
154
-continued
[Chem. 66]
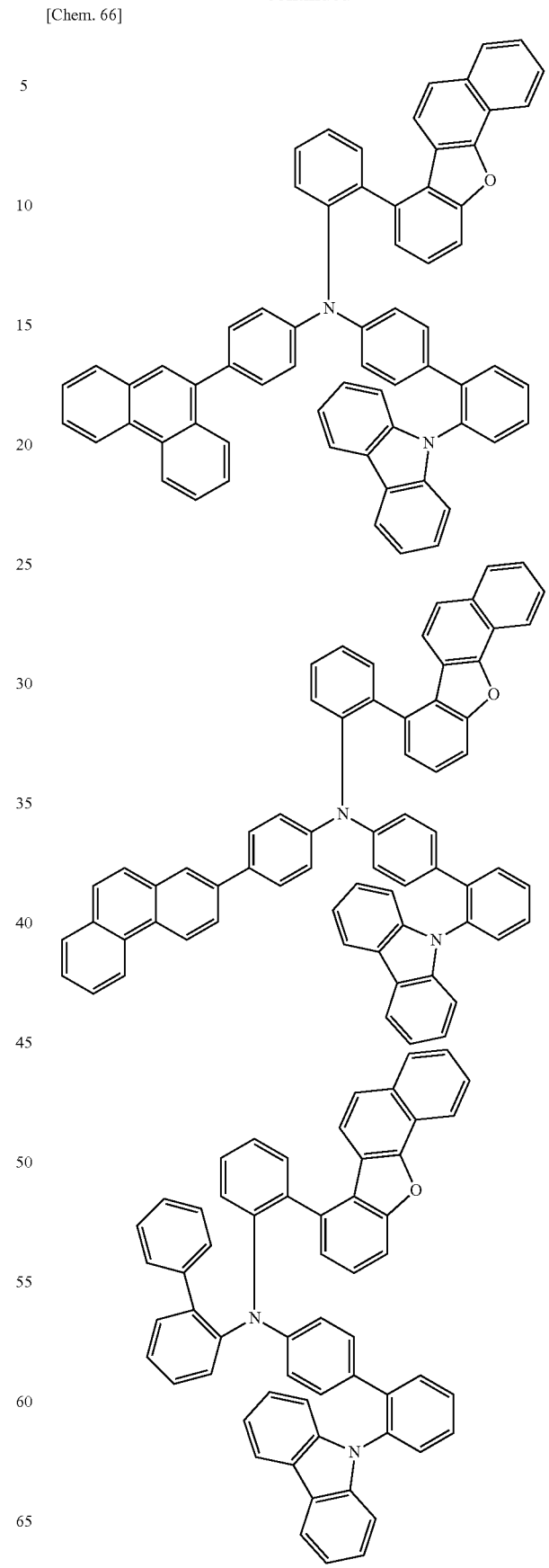

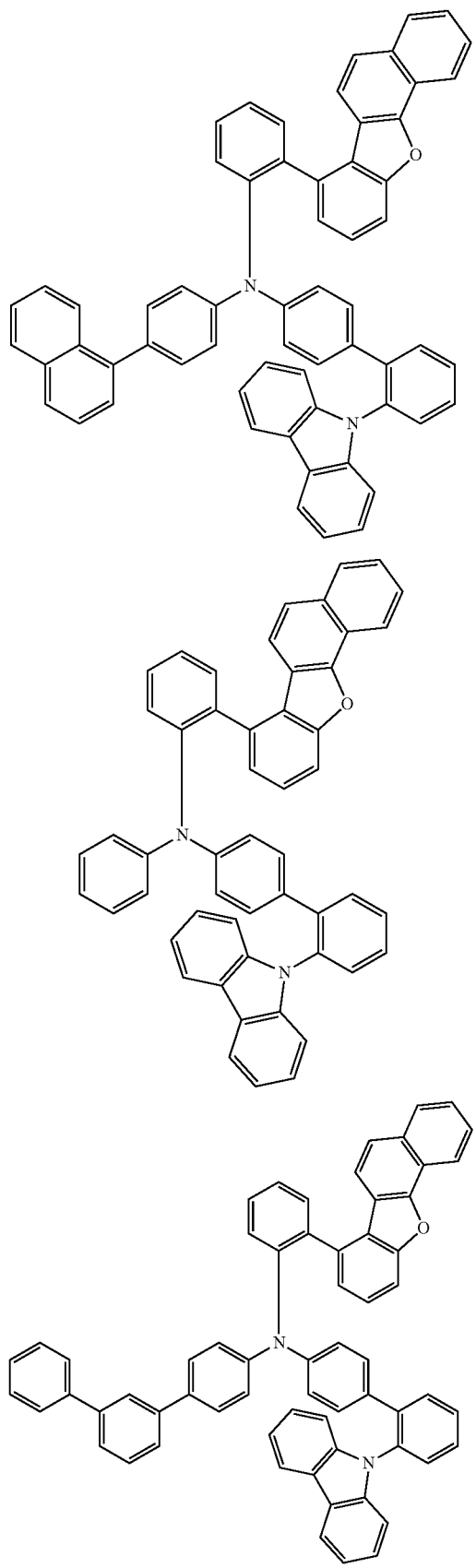
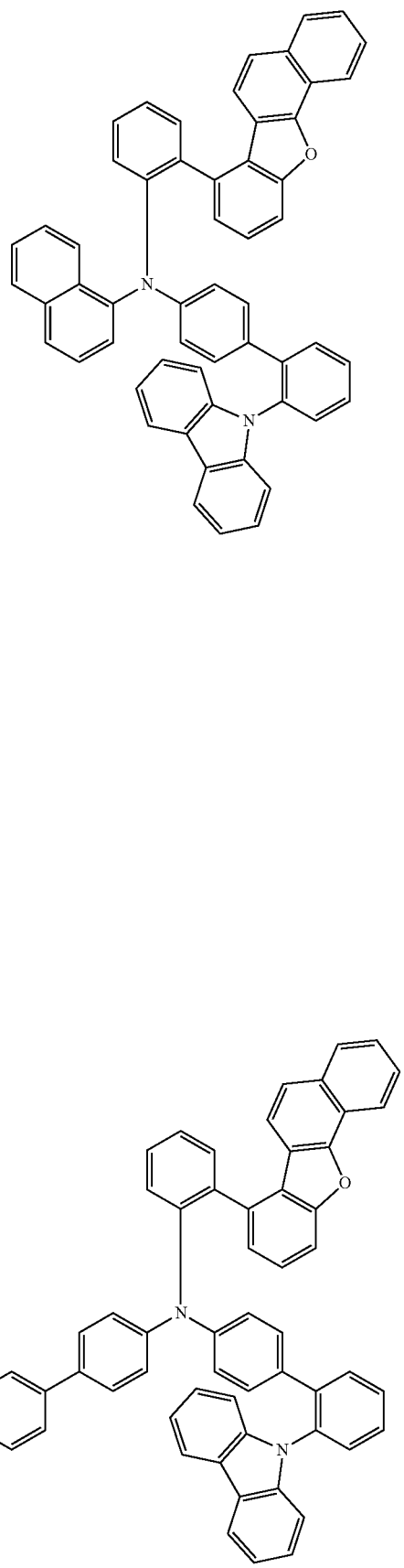

157
-continued
158
-continued
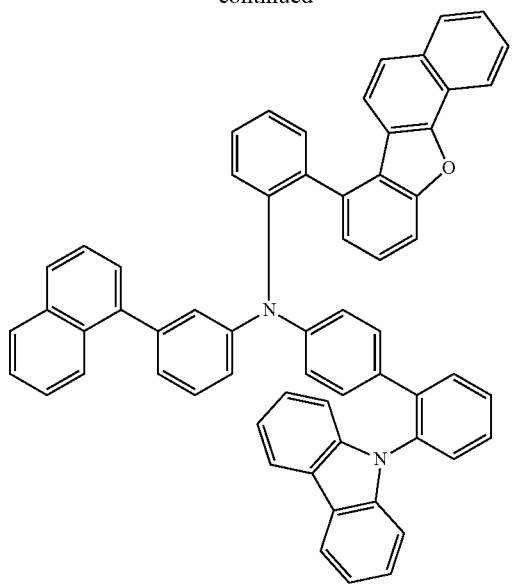
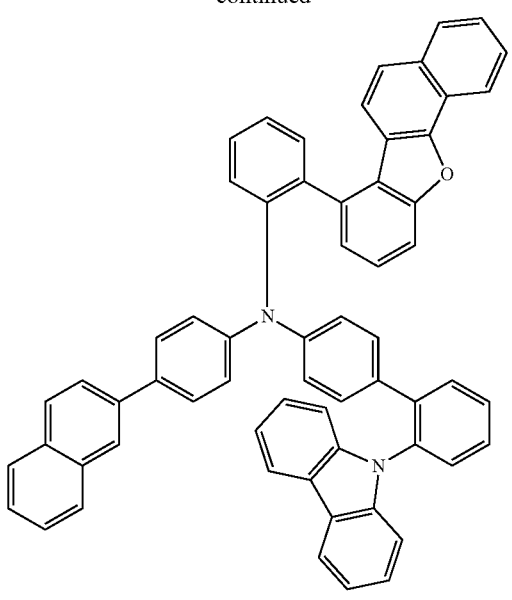
[Chem. 67]
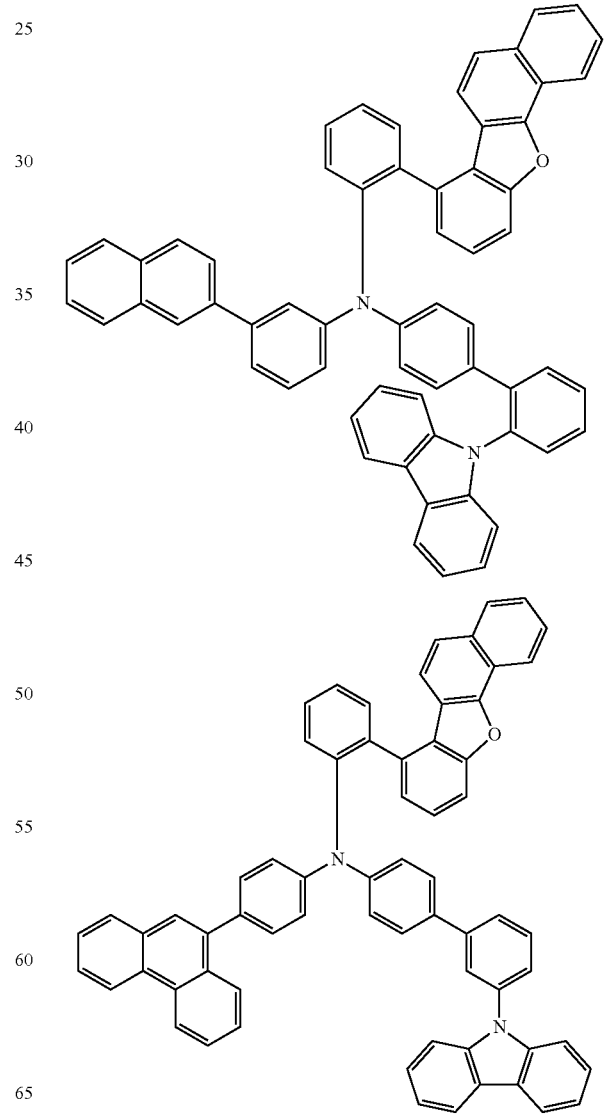

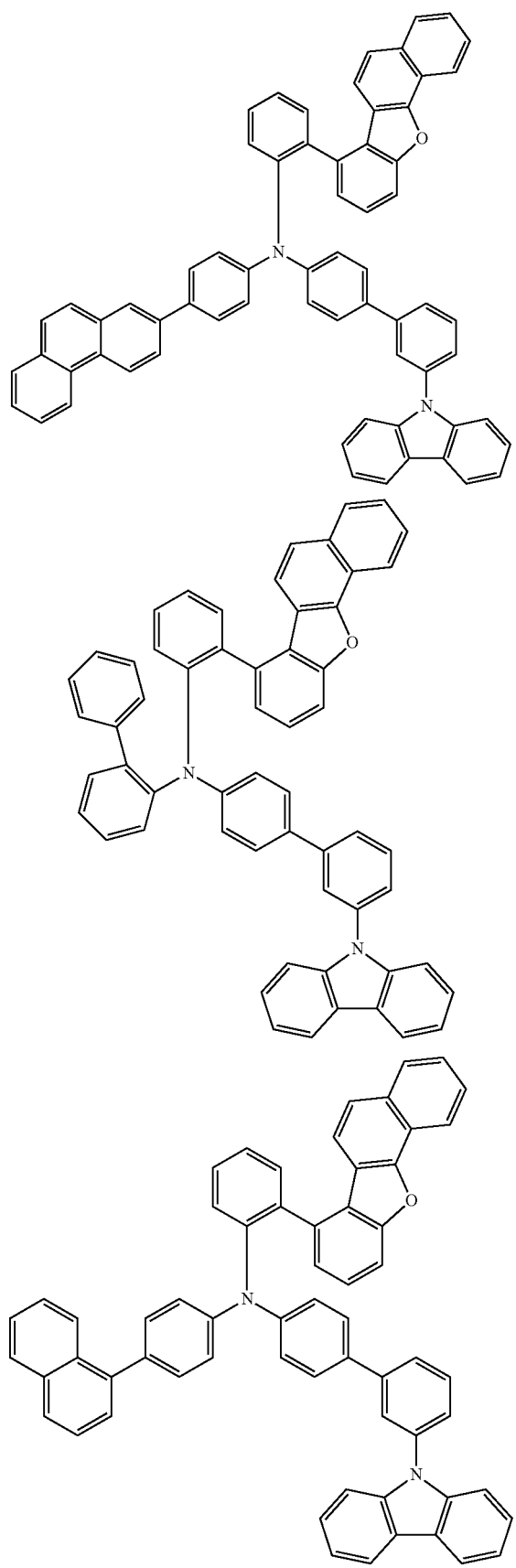
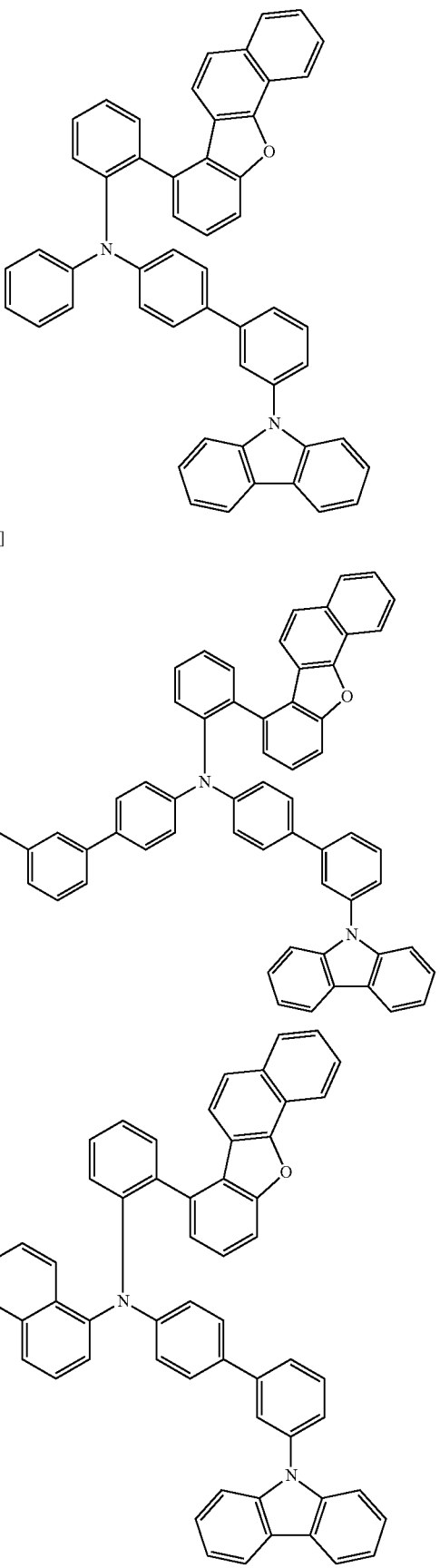

161
-continued
162
-continued
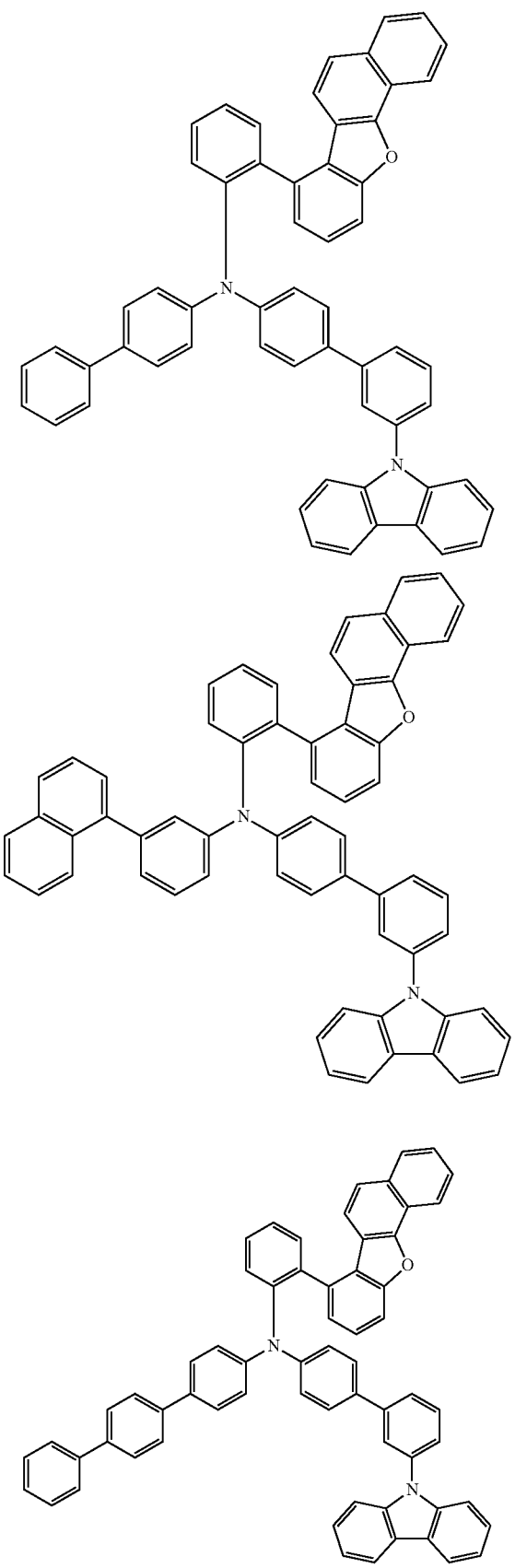
[Chem. 69]
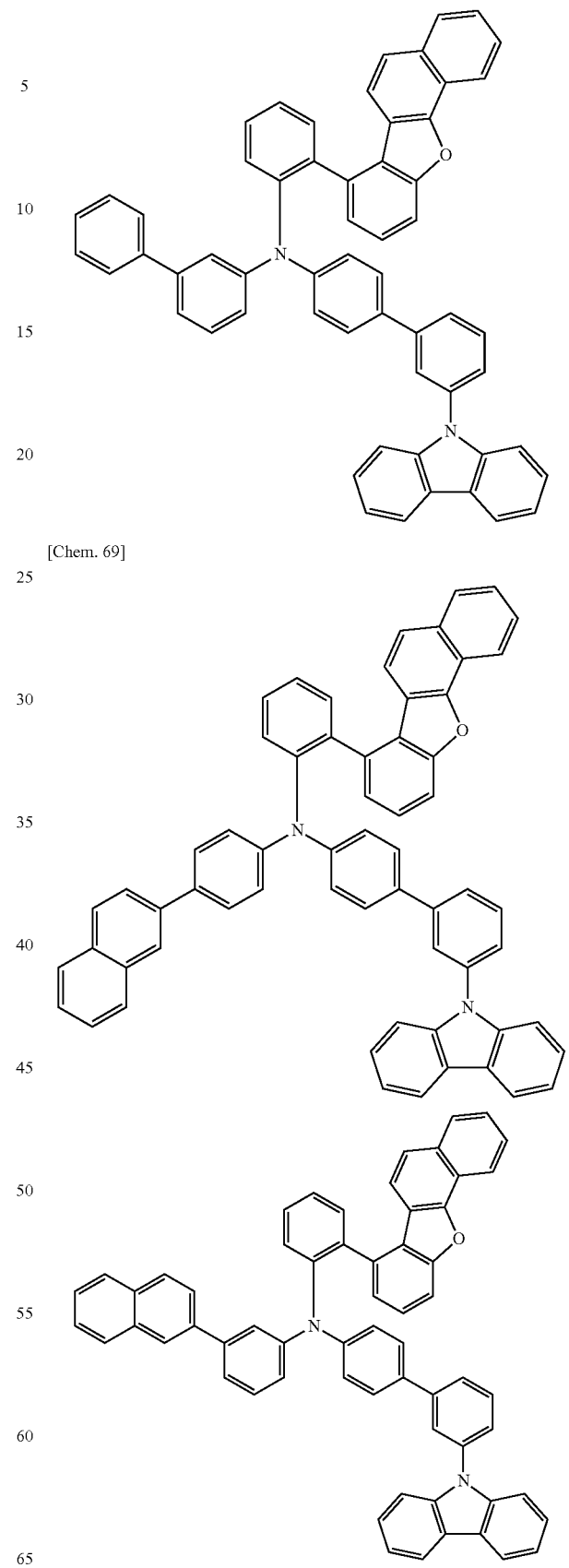

163
-continued
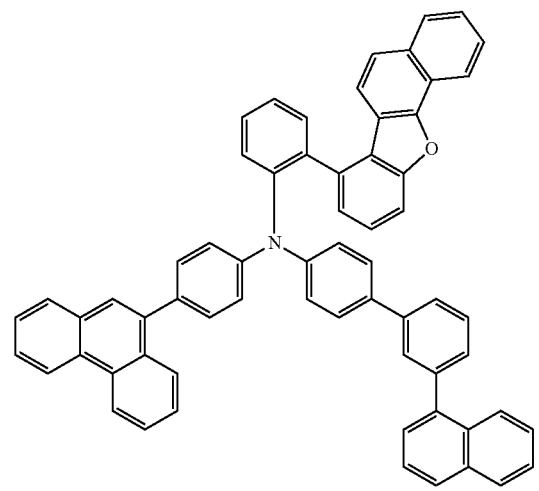
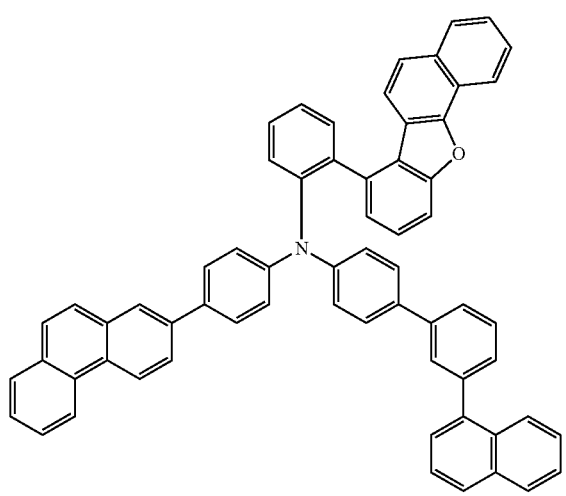
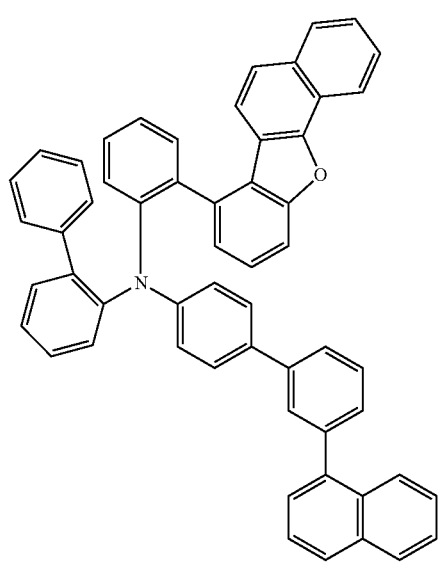
164
-continued
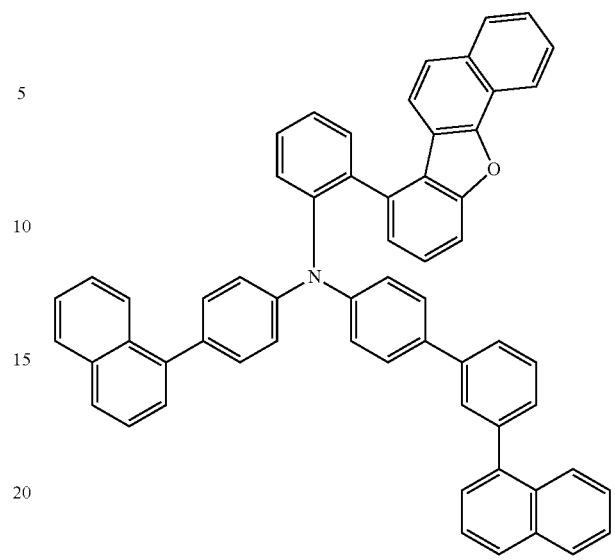
[Chem. 70]
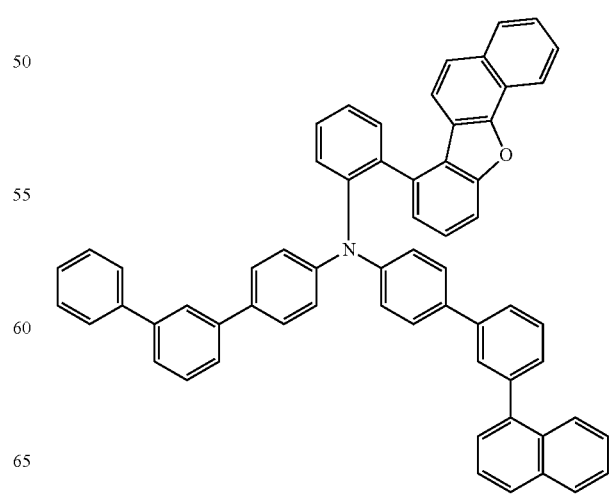

165
-continued
166
-continued
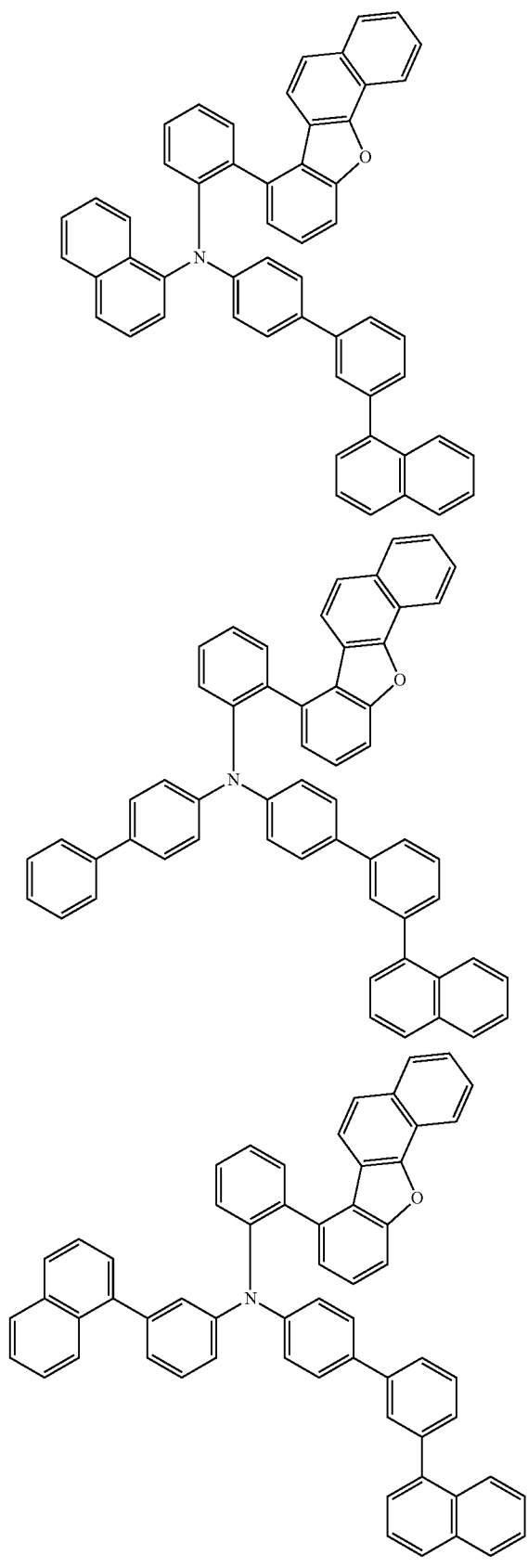

167
-continued
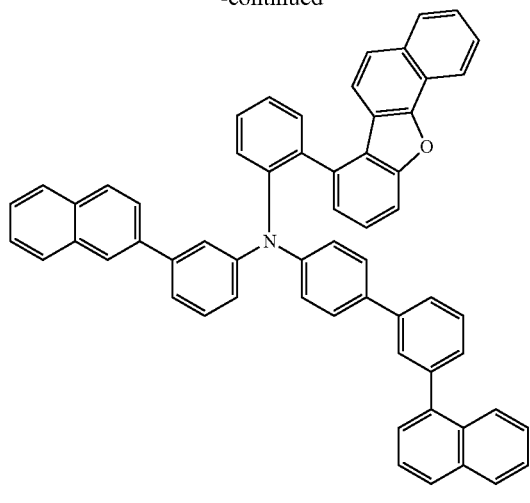
[Chem. 71]
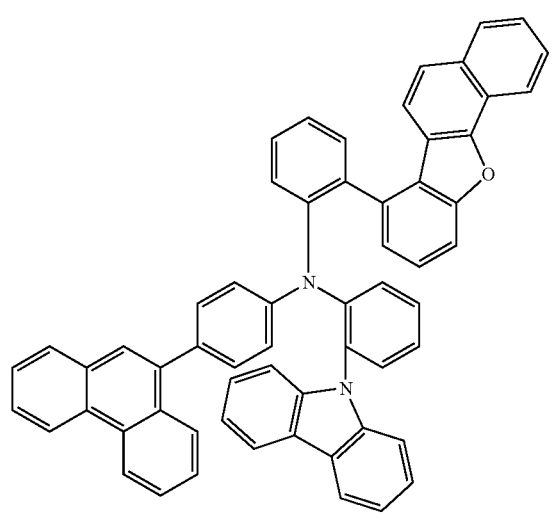
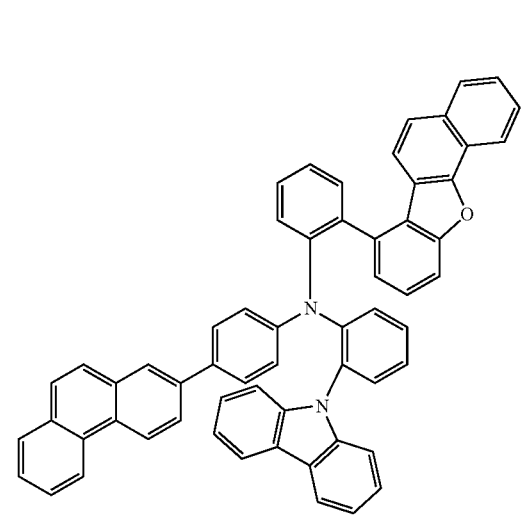
168
-continued
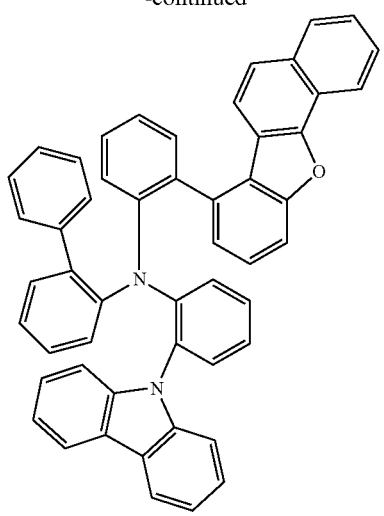
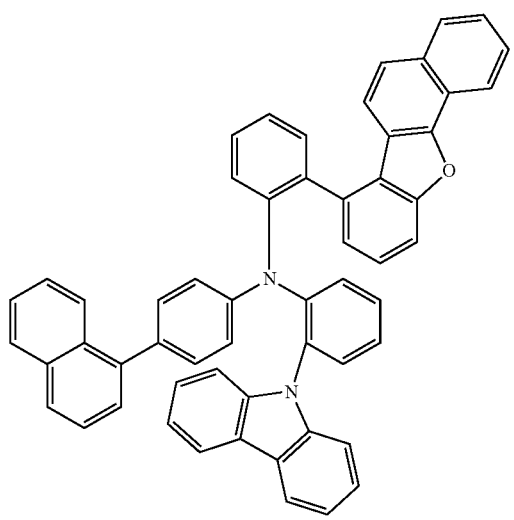
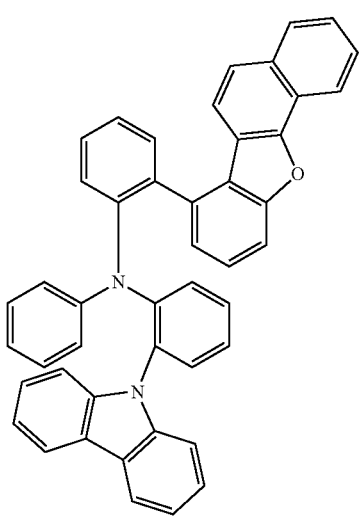

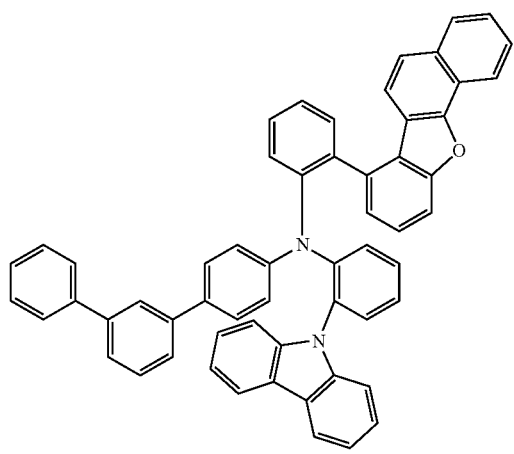
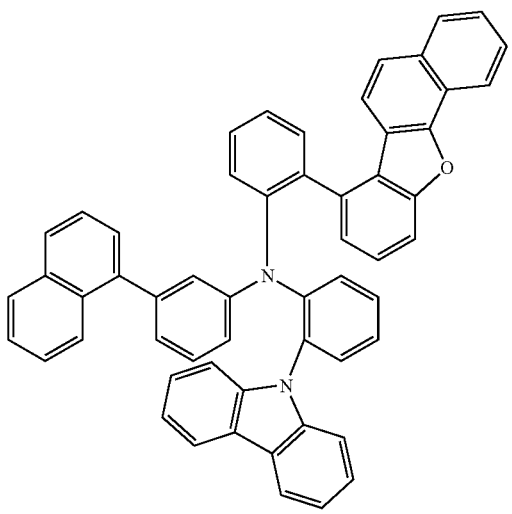
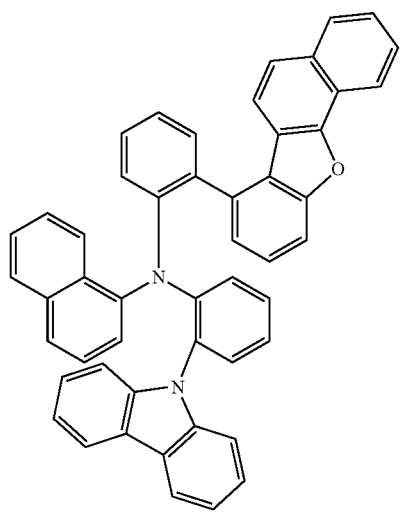
[Chem. 72]
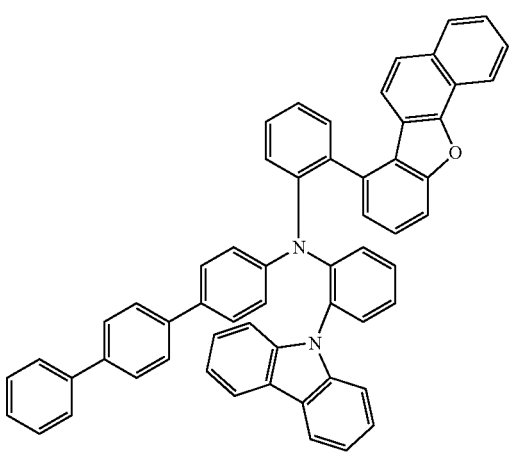
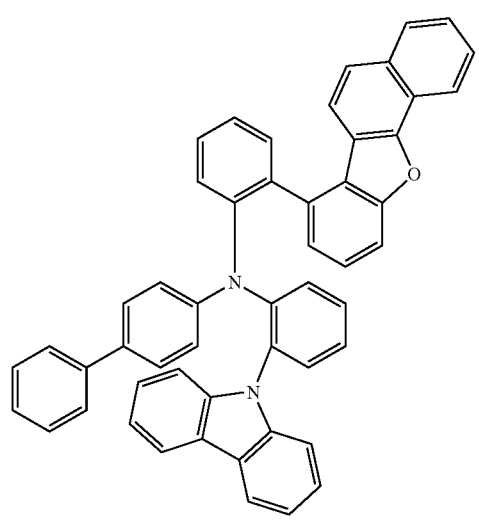
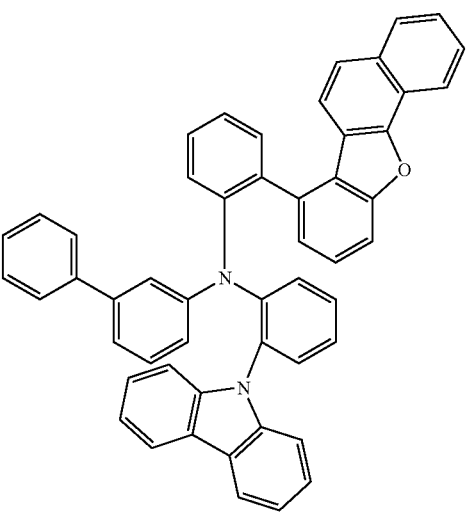

171
-continued
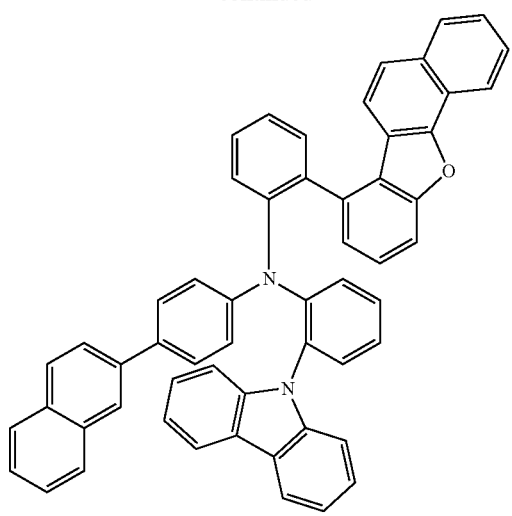
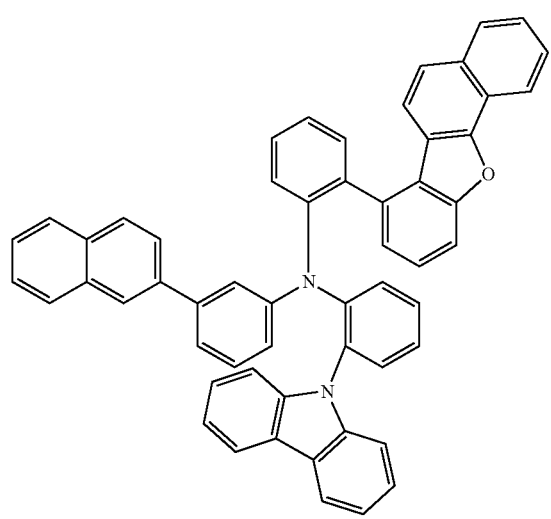
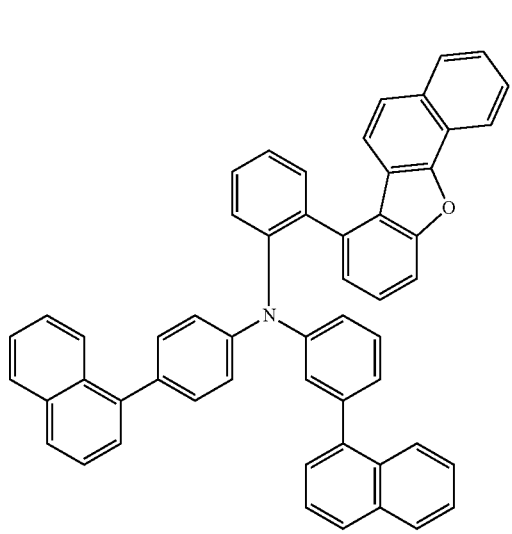
172
-continued
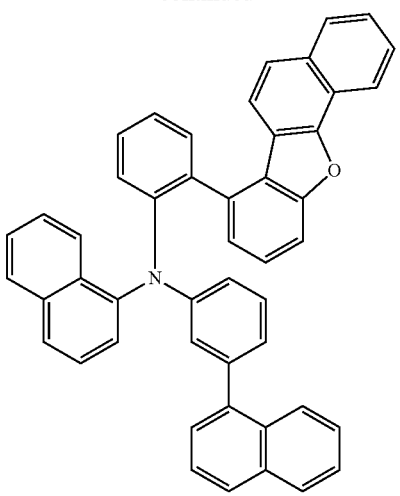
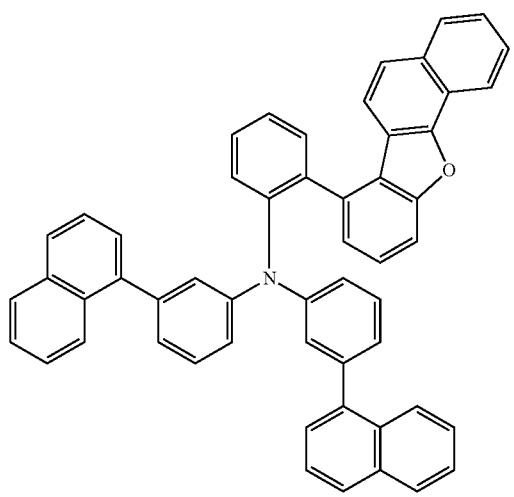
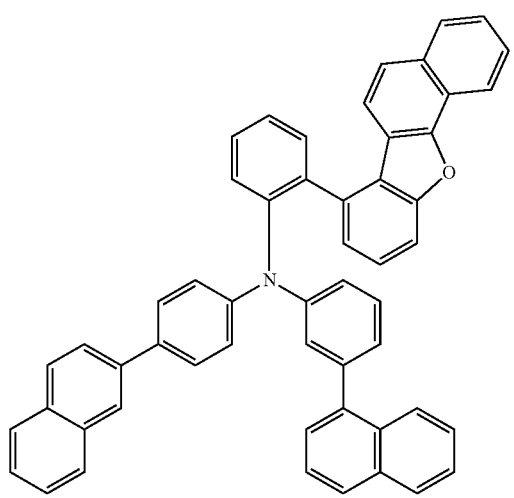

173
-continued
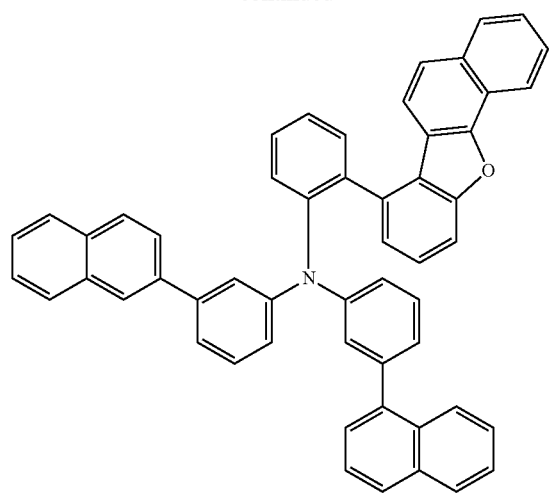
[Chem. 73]
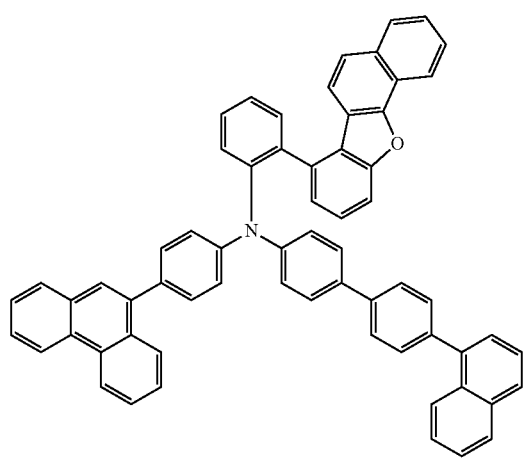
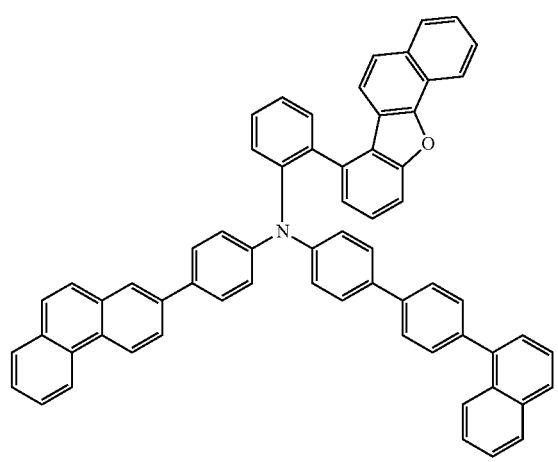
174
-continued
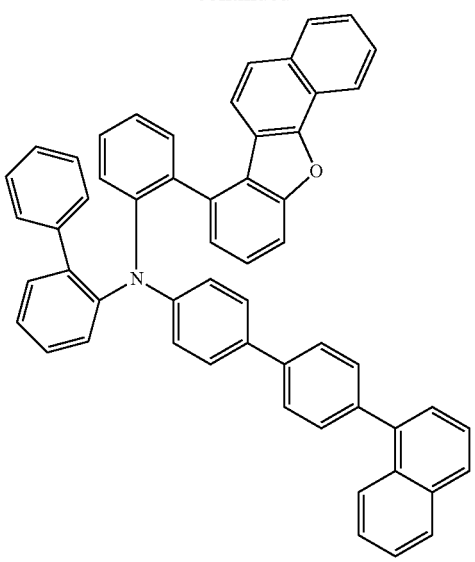
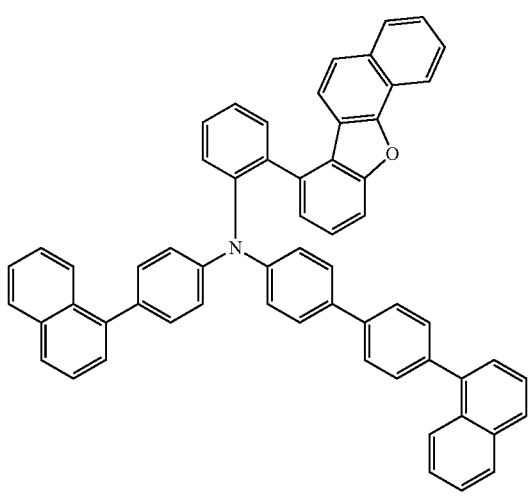

175
-continued
176
-continued
[Chem. 74]
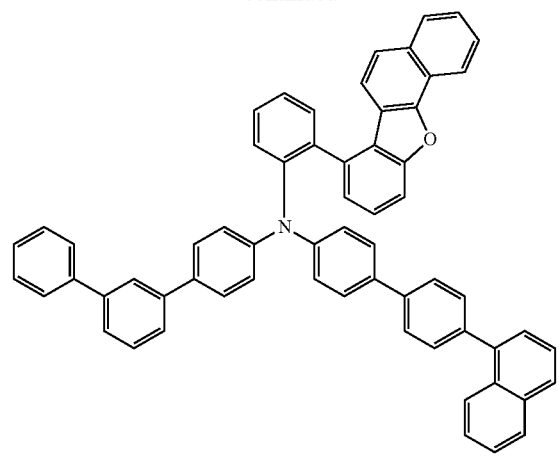
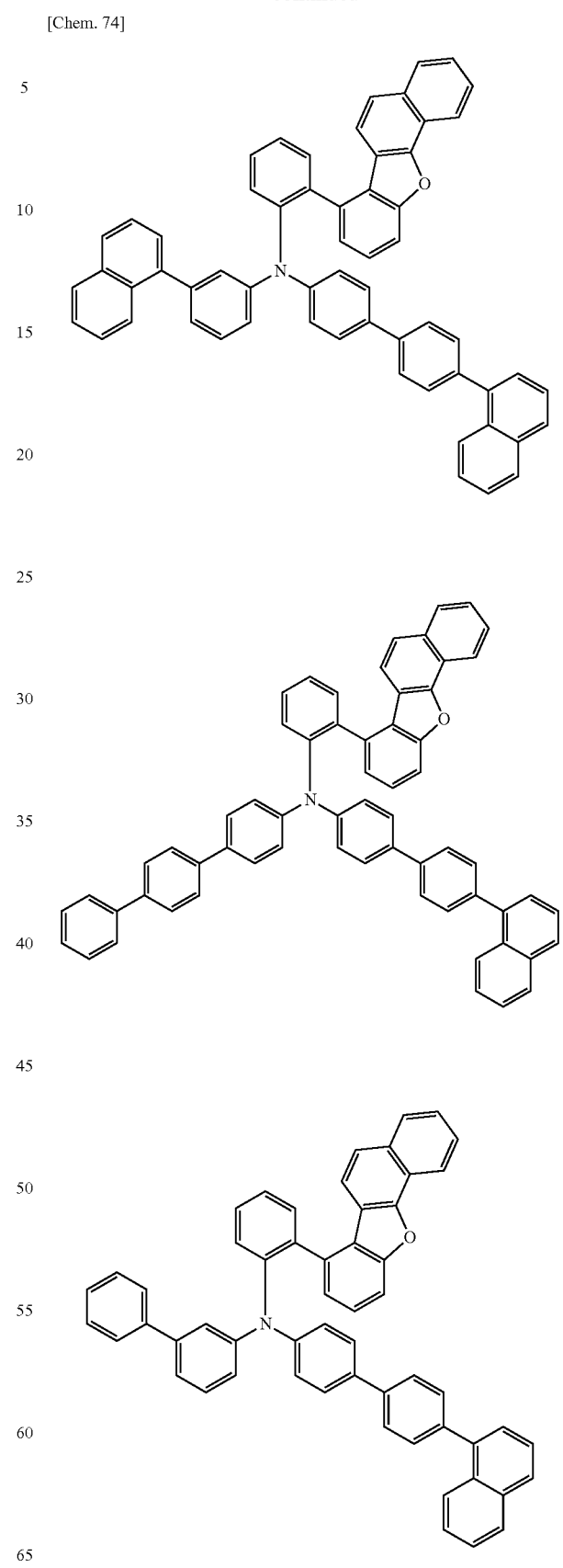

177
-continued
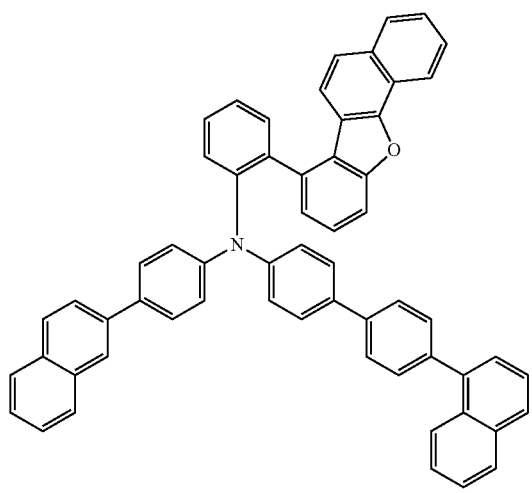
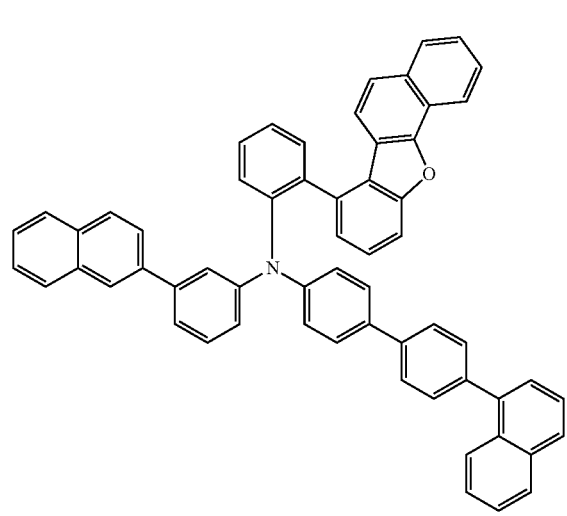
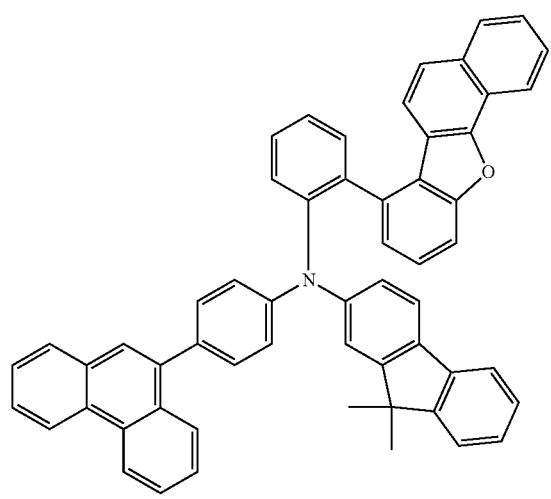
178
-continued
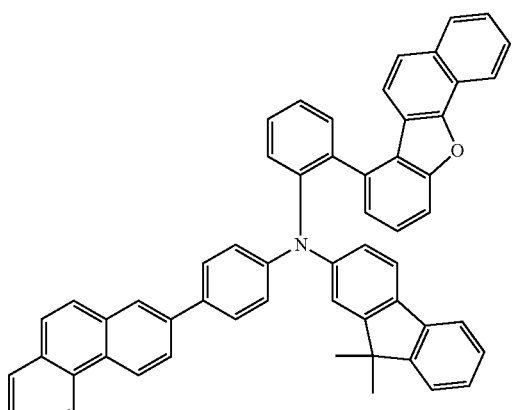
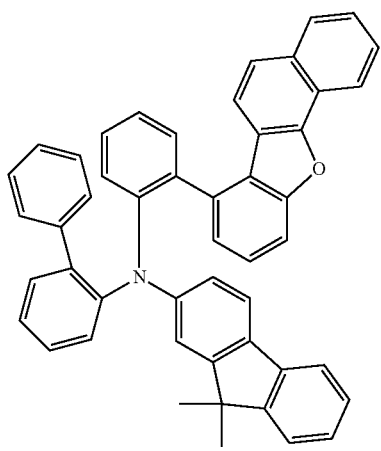
[Chem. 75]
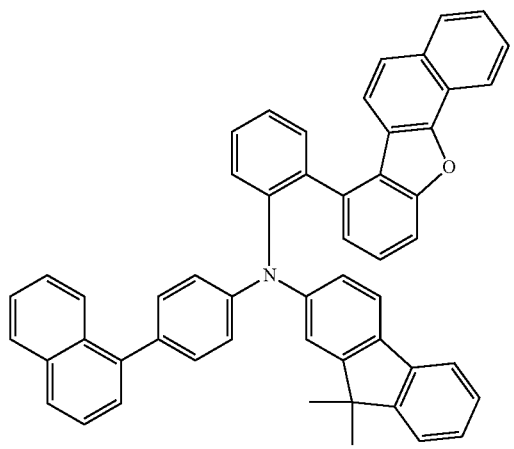

179
-continued
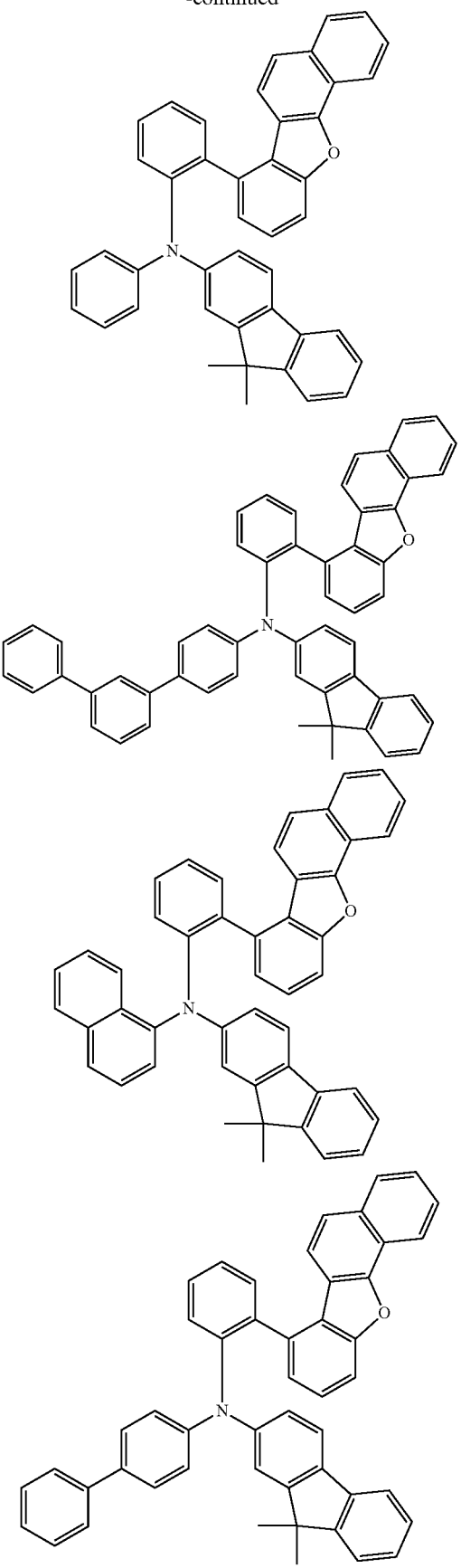
180
-continued
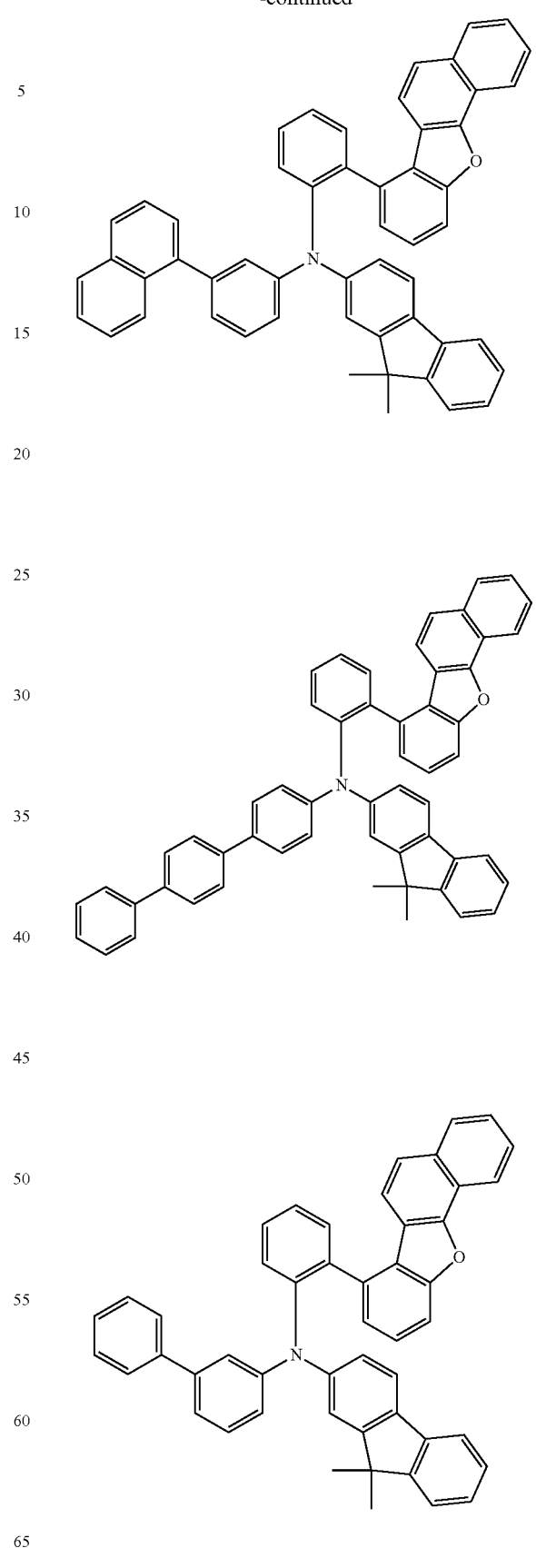

[Chem. 76]
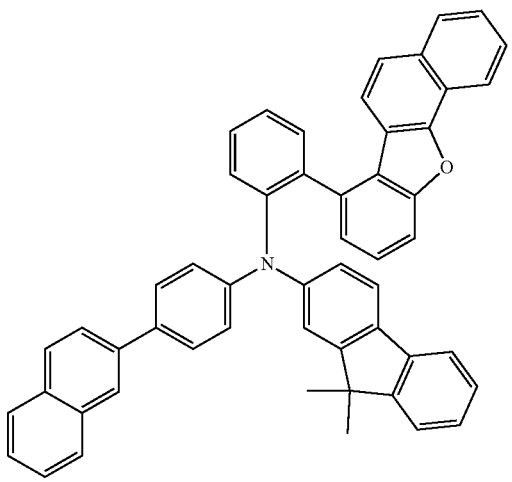
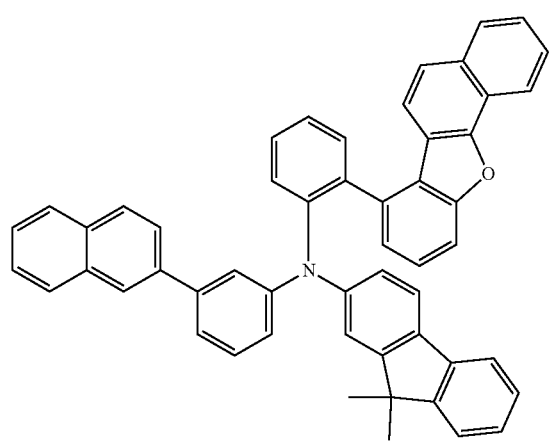
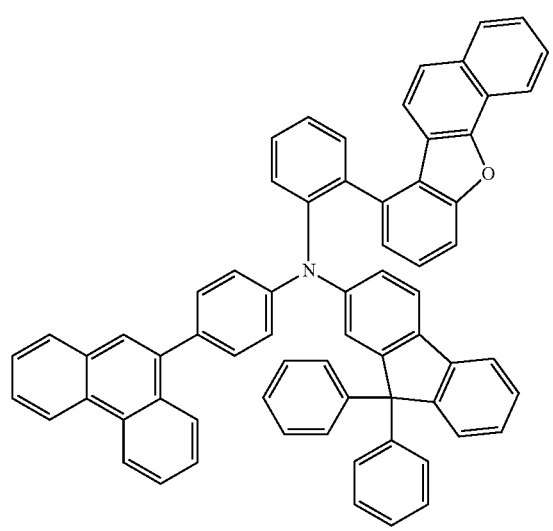
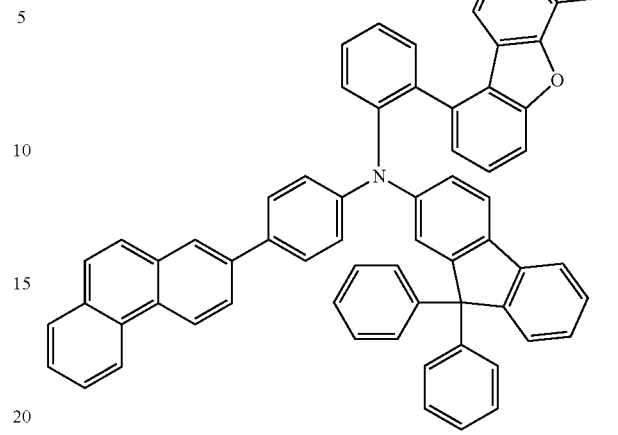
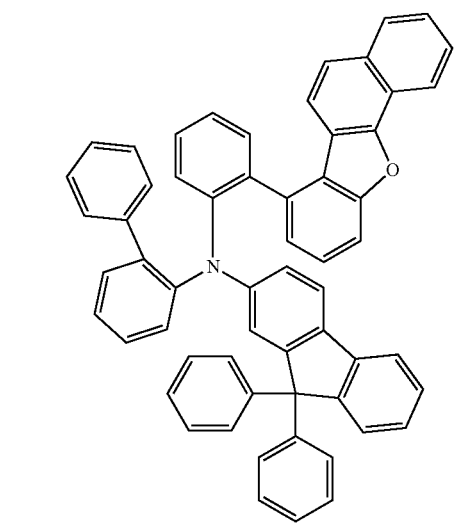
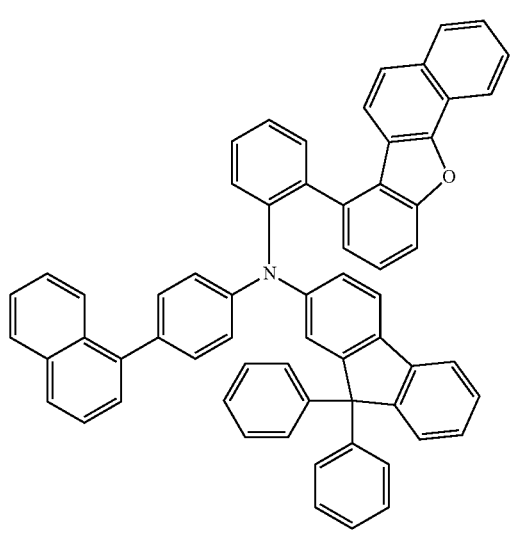

[Chem. 77]
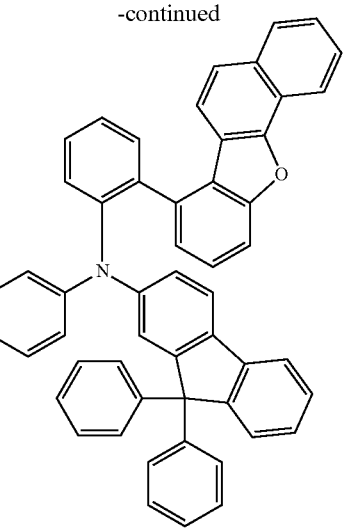
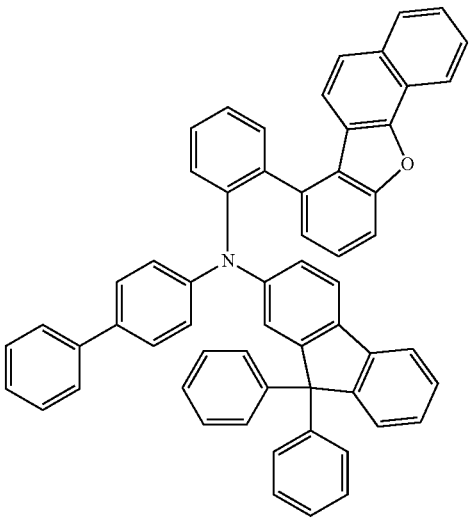
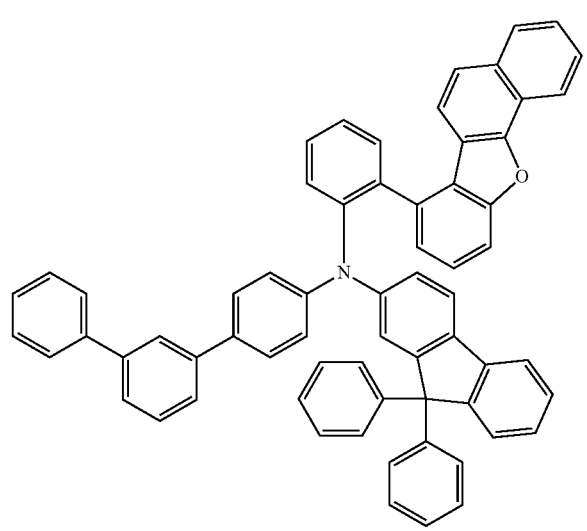
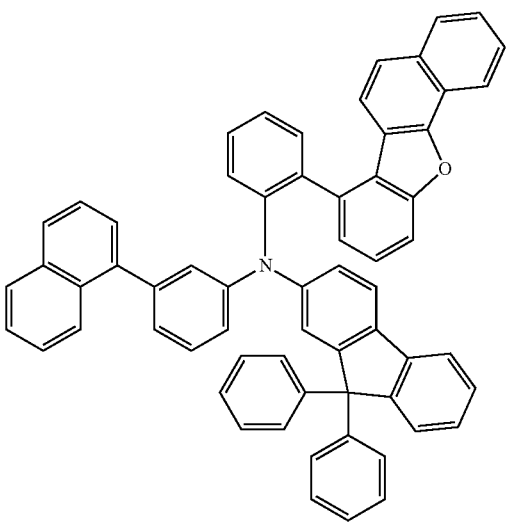
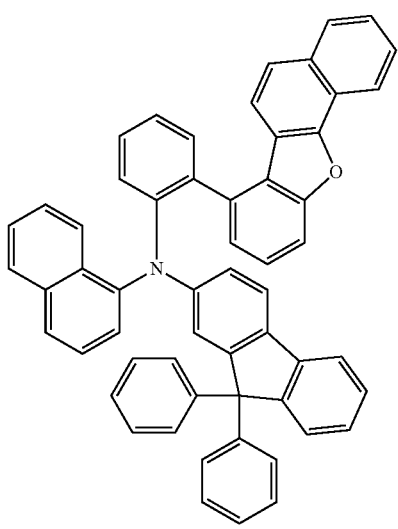
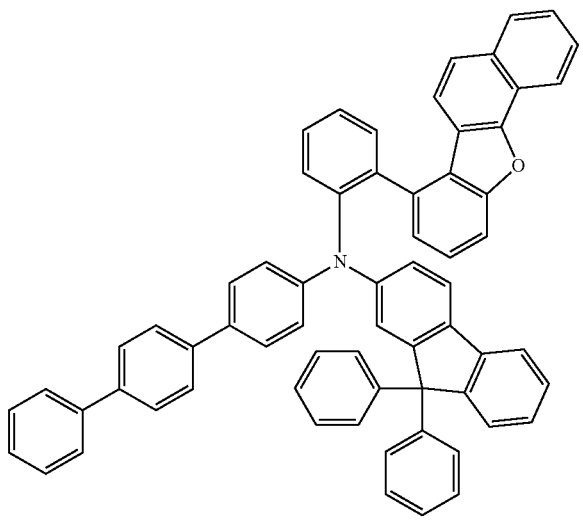

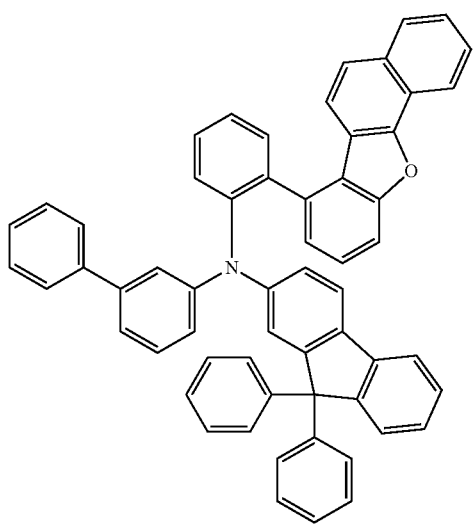
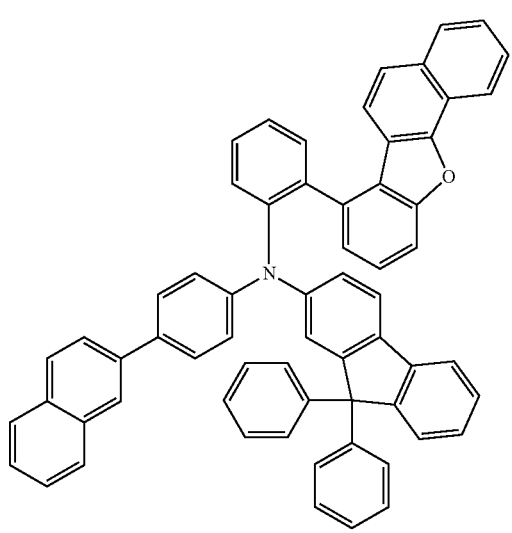
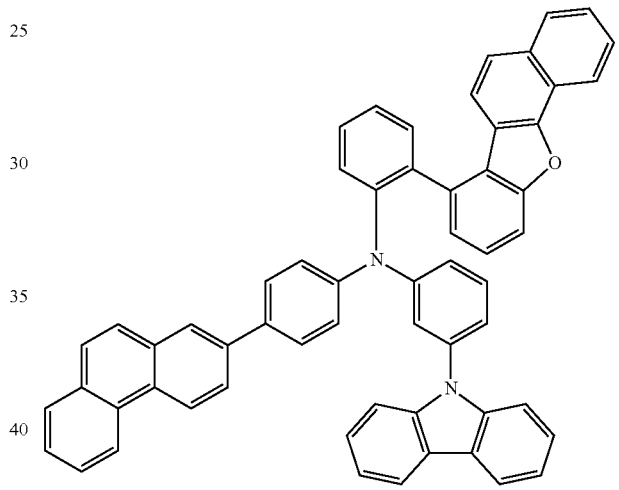
[Chem. 78]
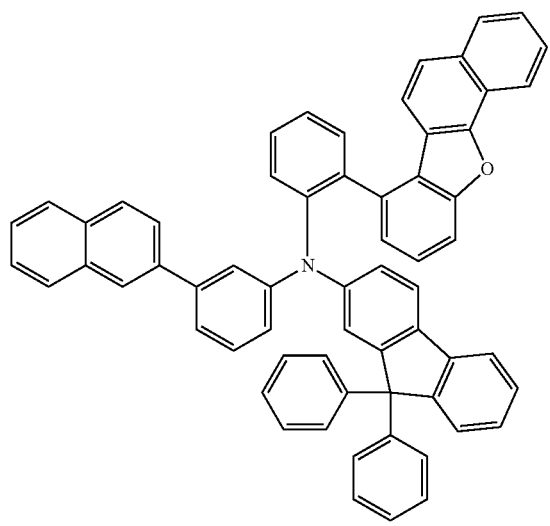
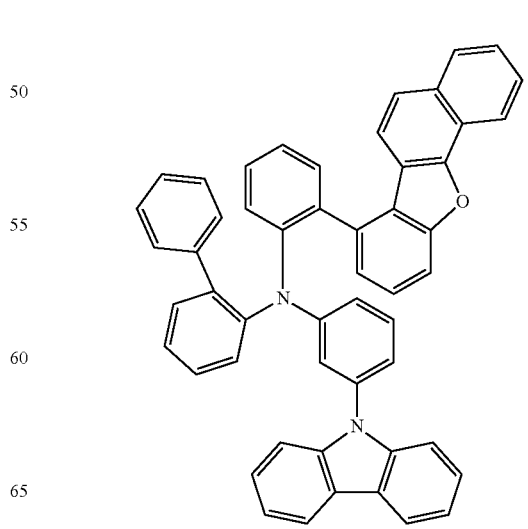

187
-continued
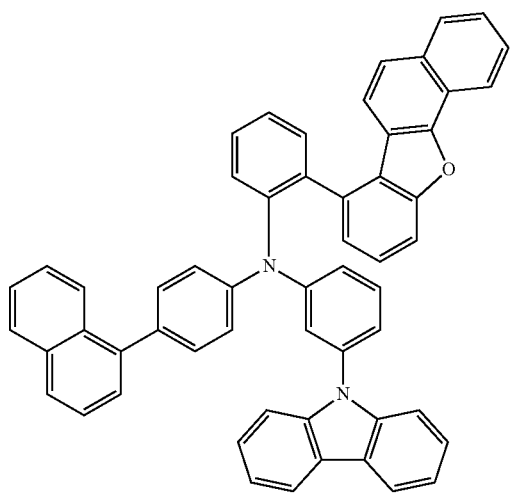
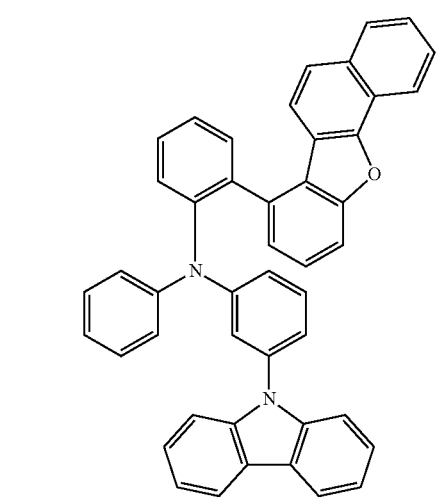
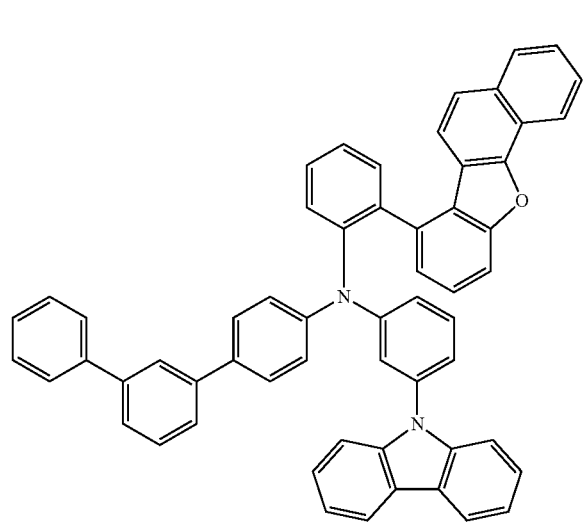
188
-continued
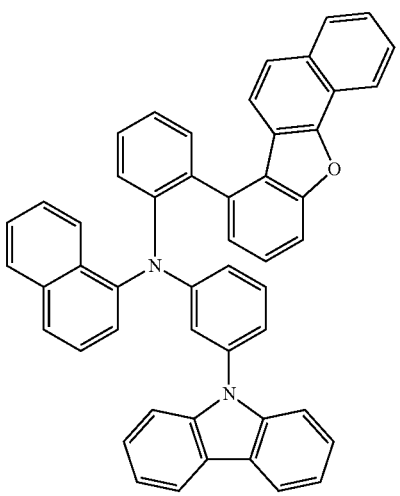
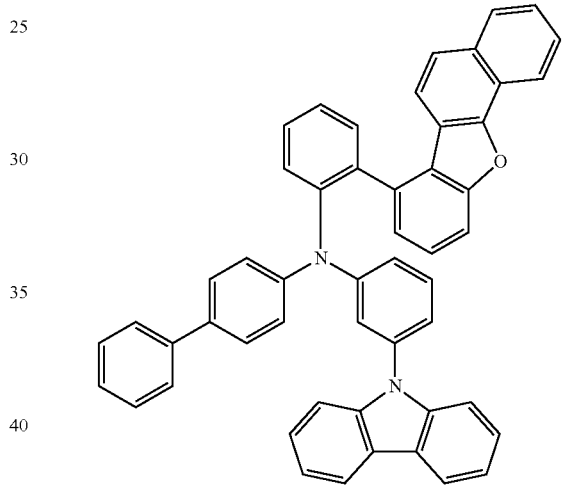
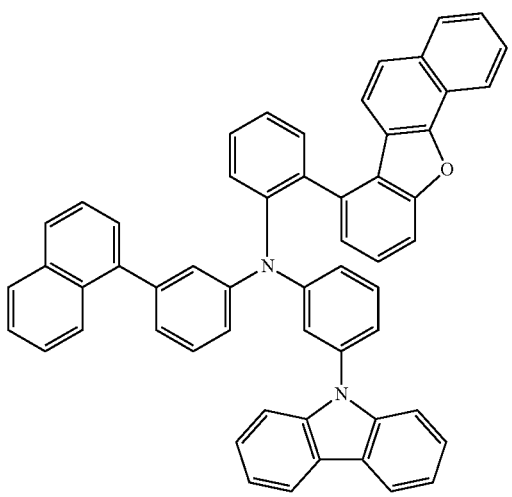

189
-continued
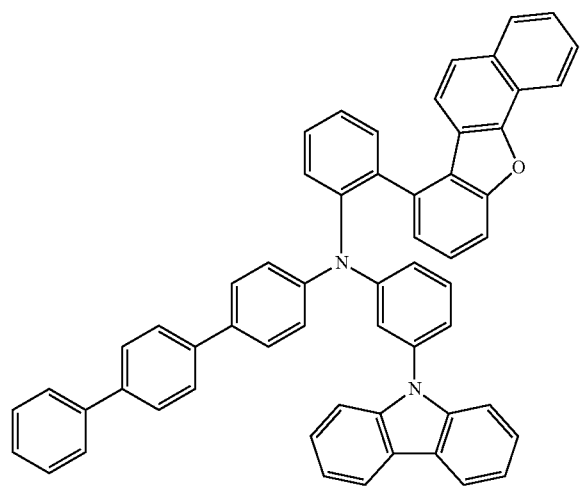
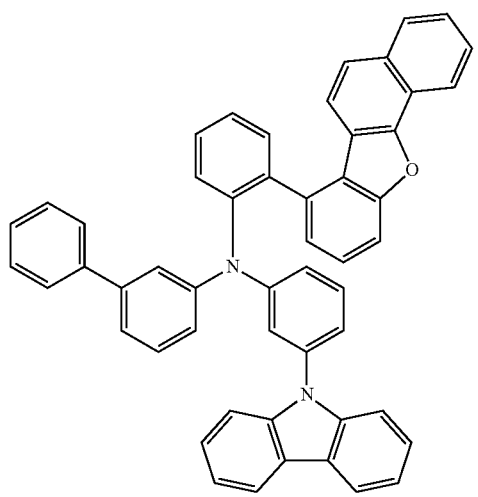
[Chem. 79]
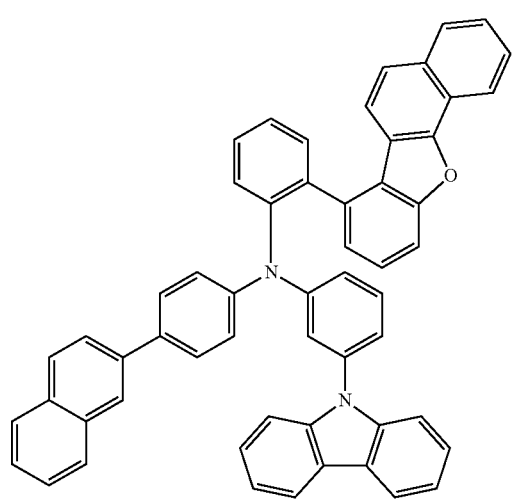
190
-continued
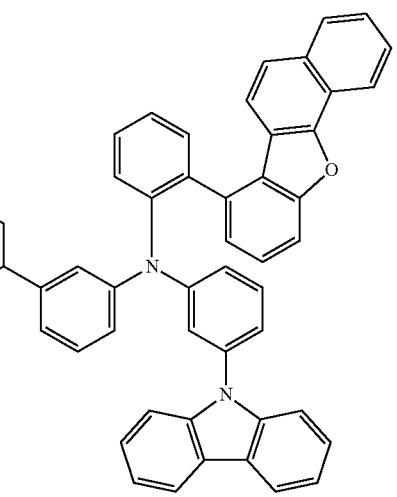
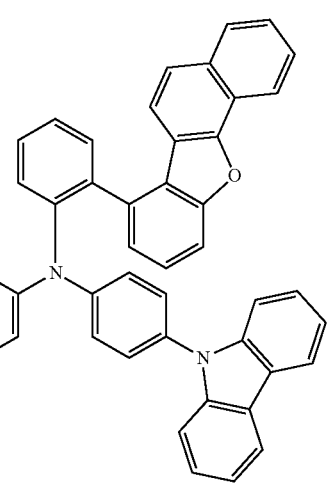
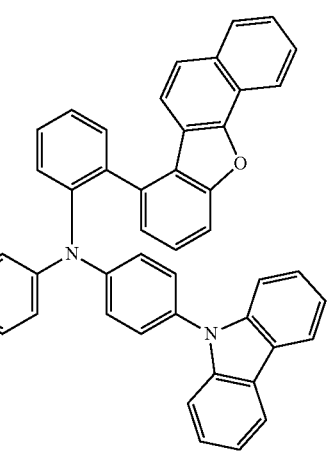

191
-continued
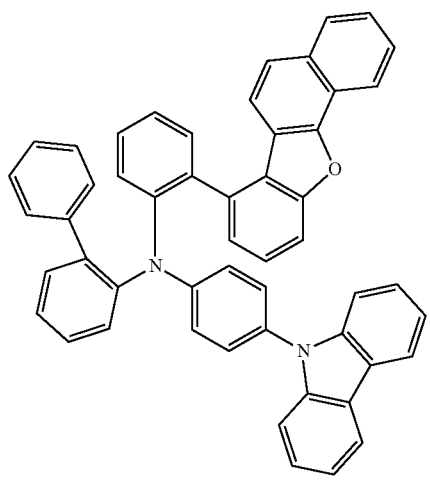
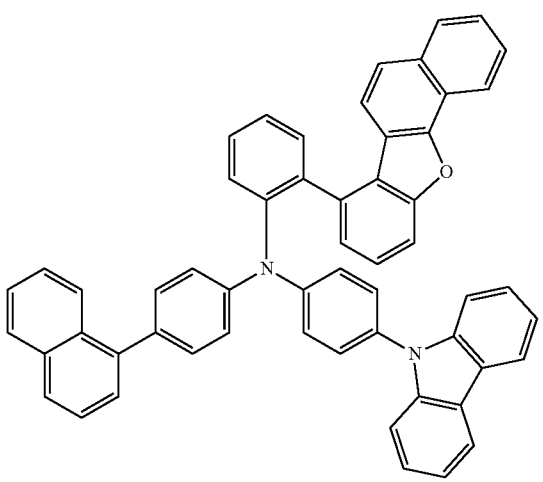
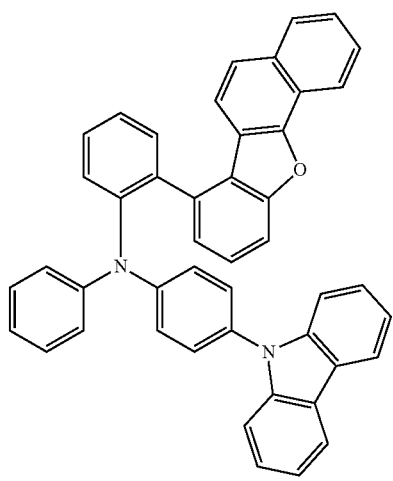
192
-continued
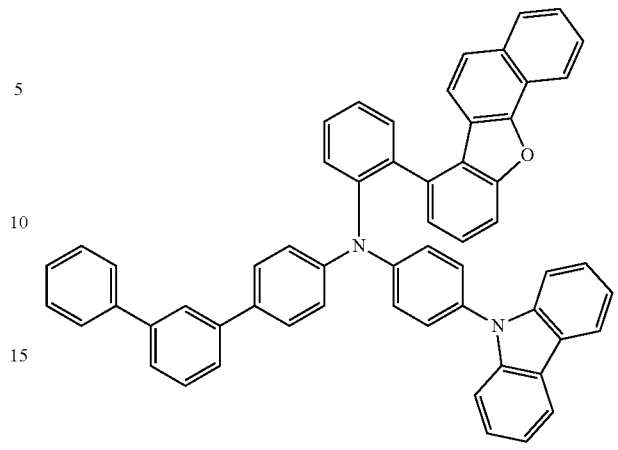
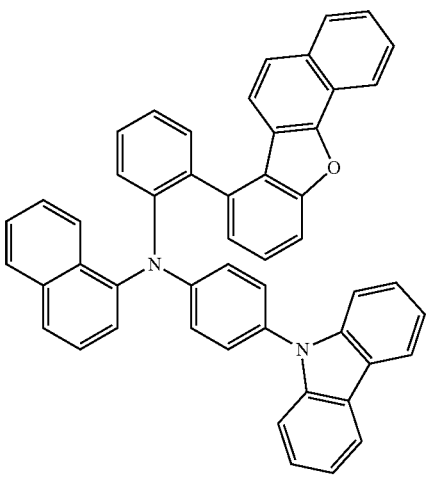
[Chem. 80]
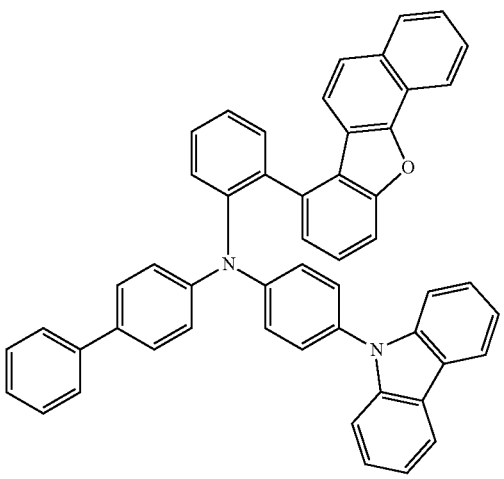

193
-continued
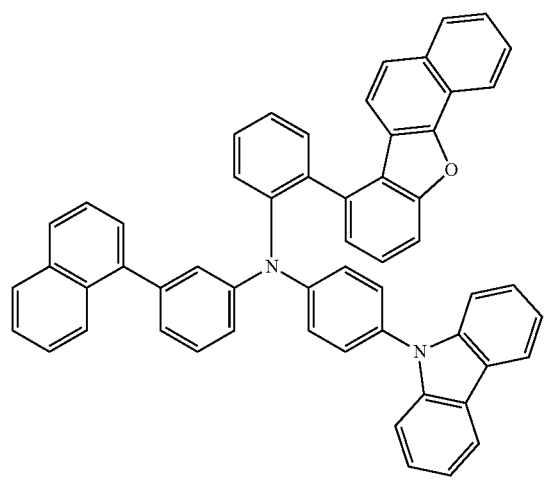
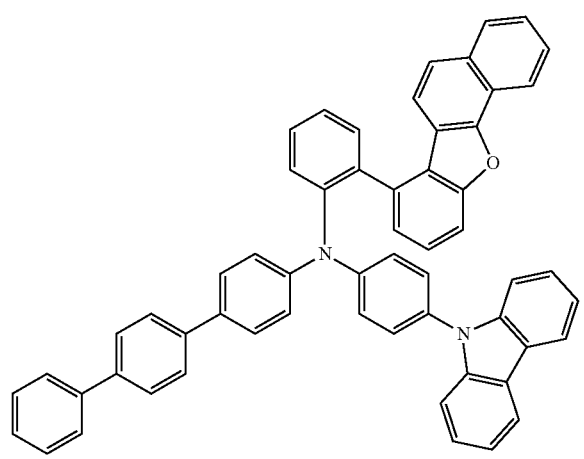
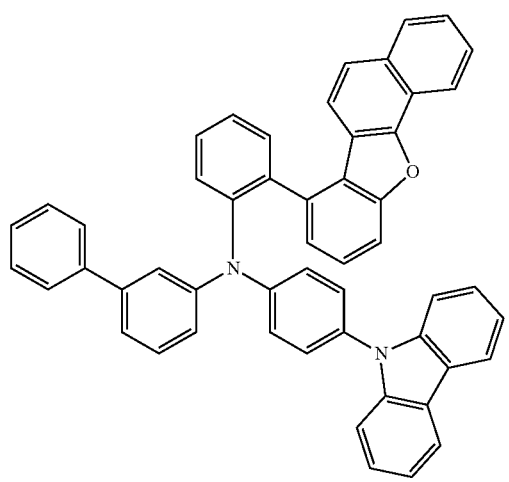
194
-continued
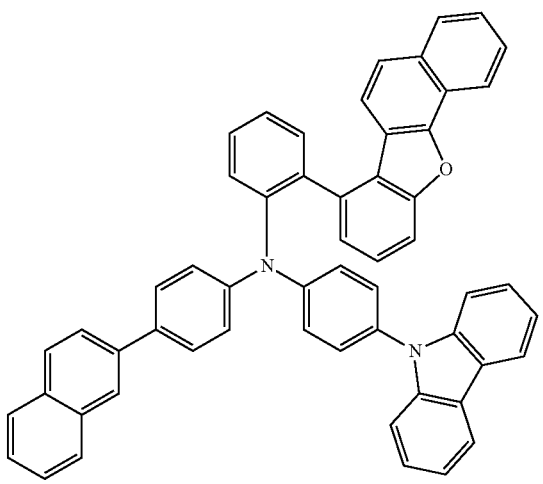
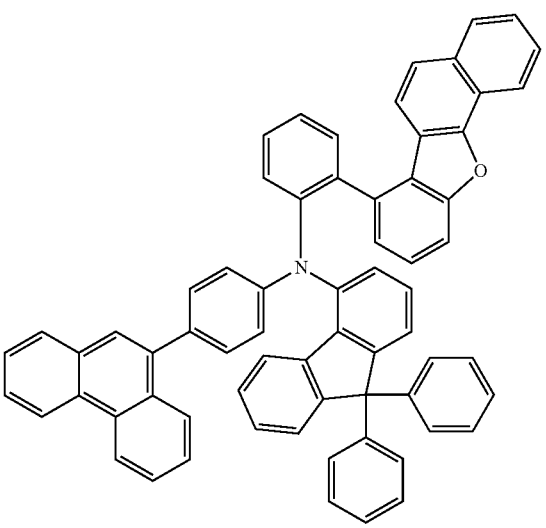

195
-continued
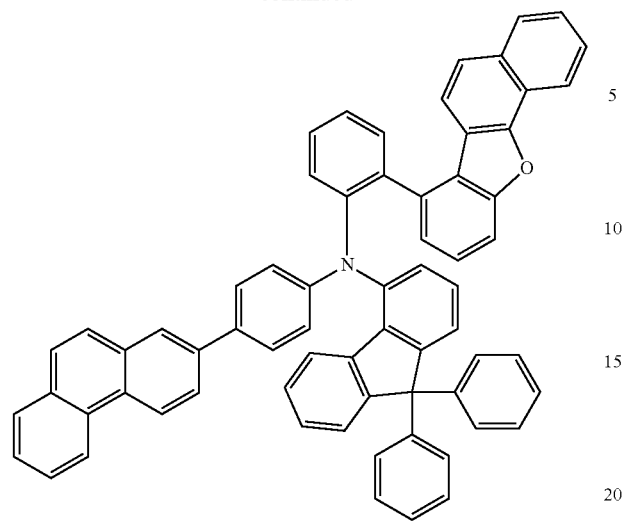
[Chem. 81]
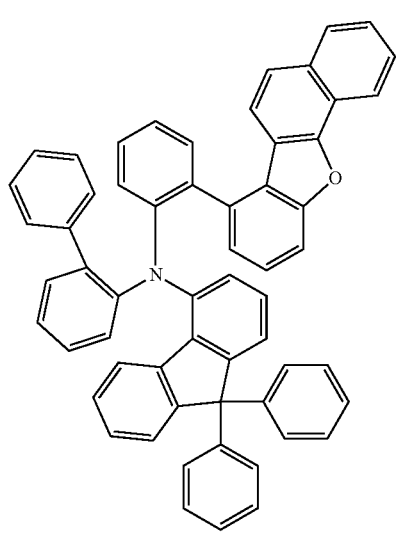
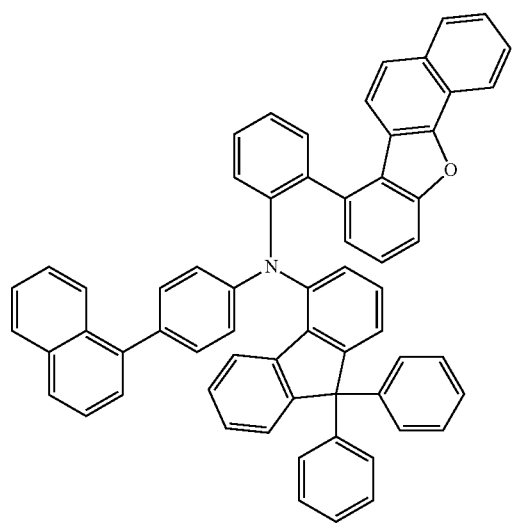
196
-continued
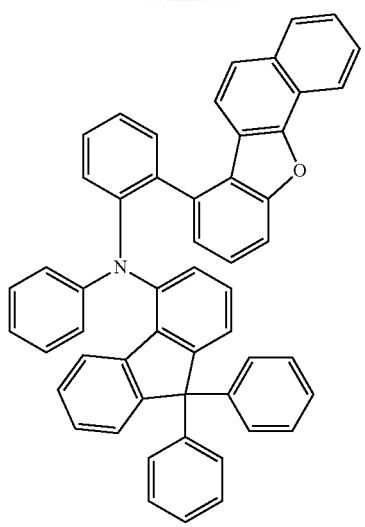
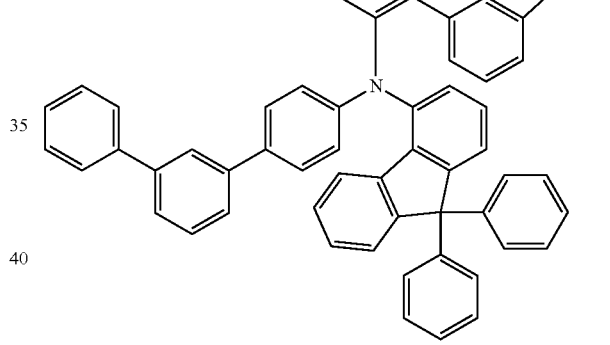
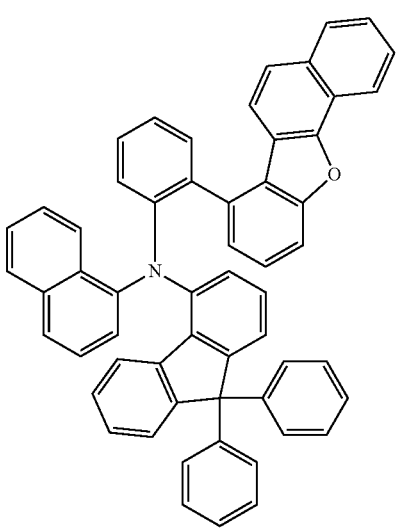

197
-continued
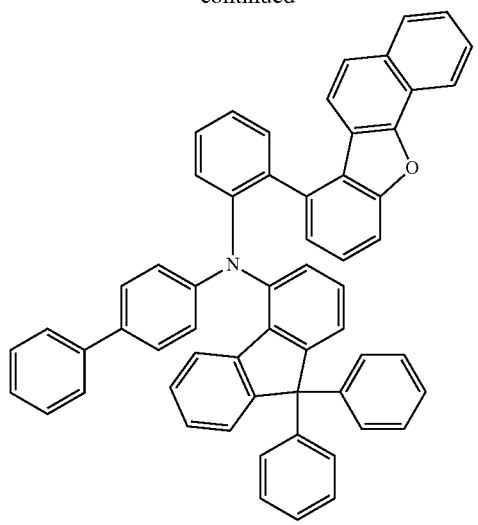
198
-continued
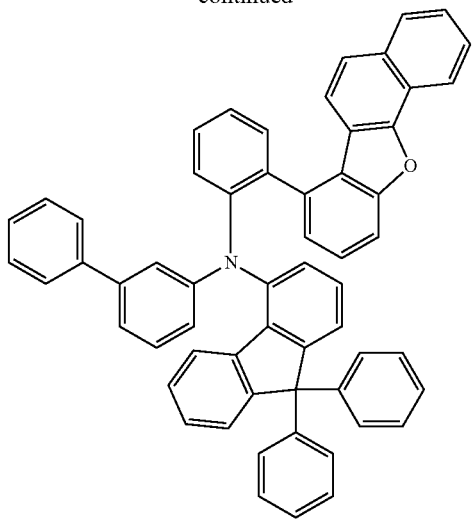
[Chem. 82]
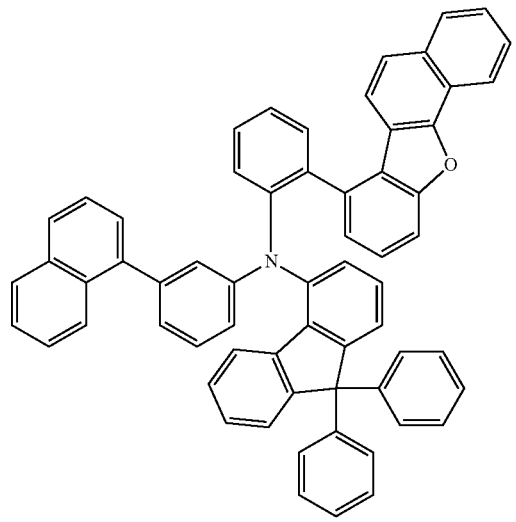
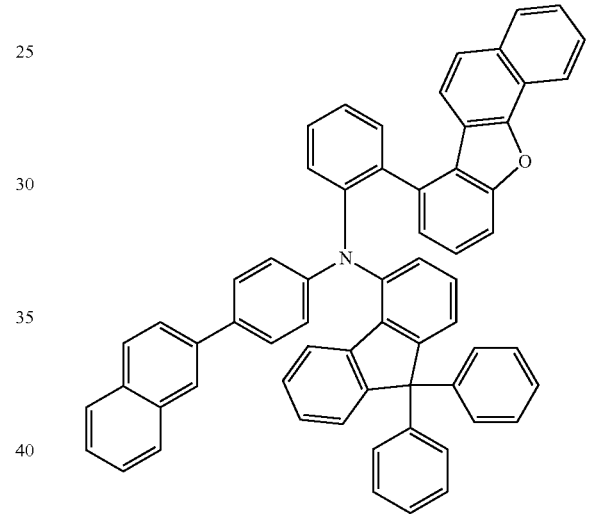
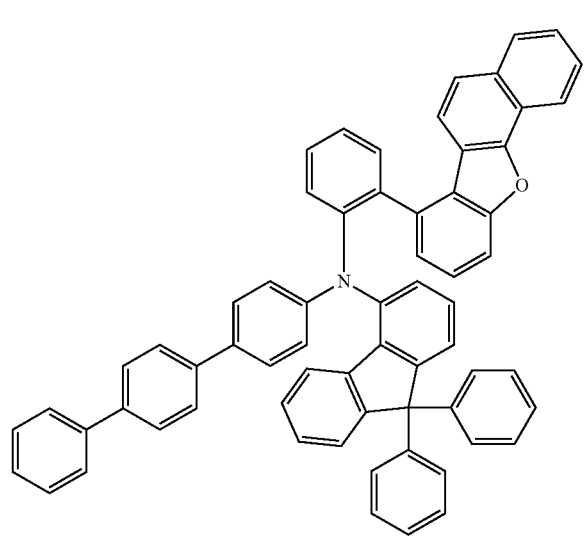

199
-continued
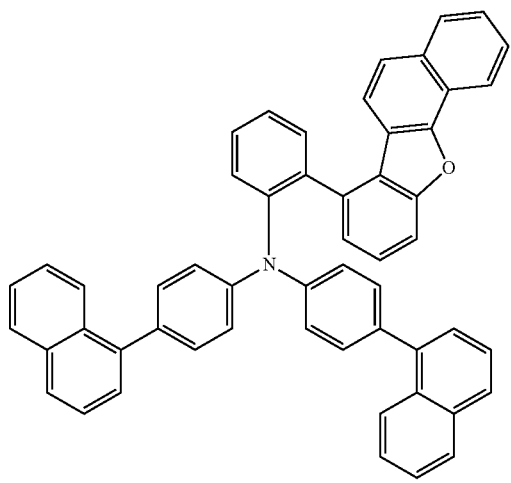
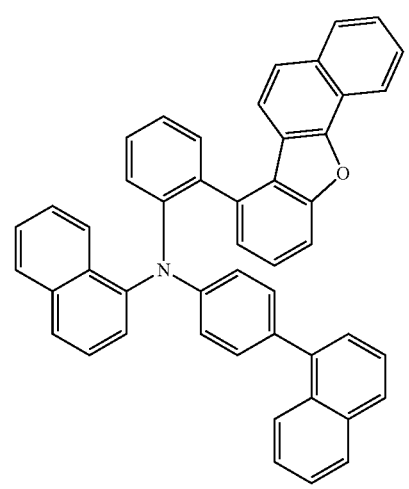
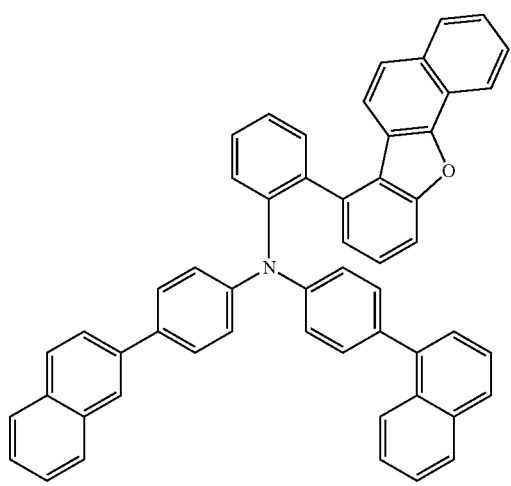
200
-continued
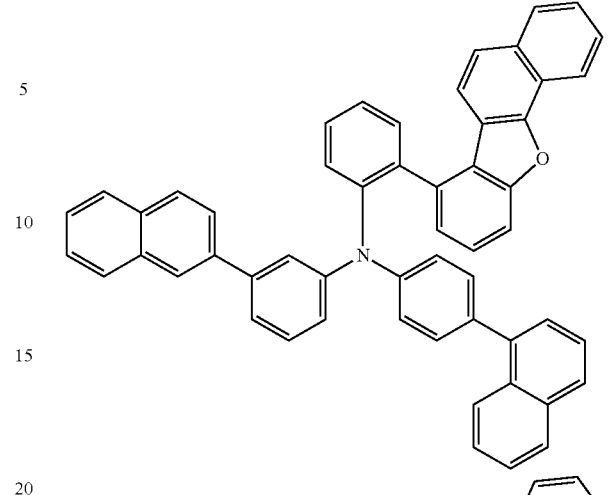
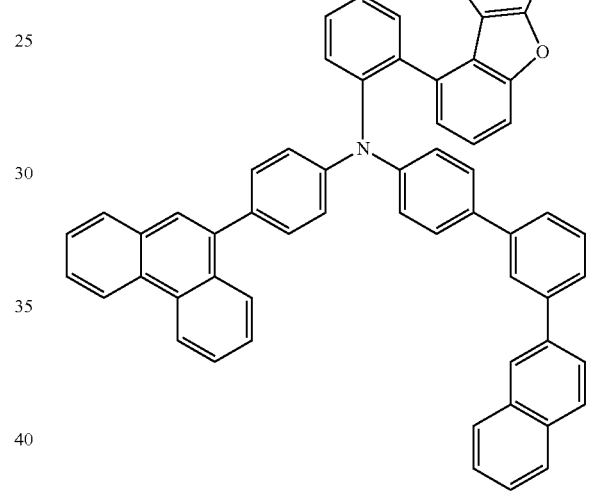
[Chem. 83]
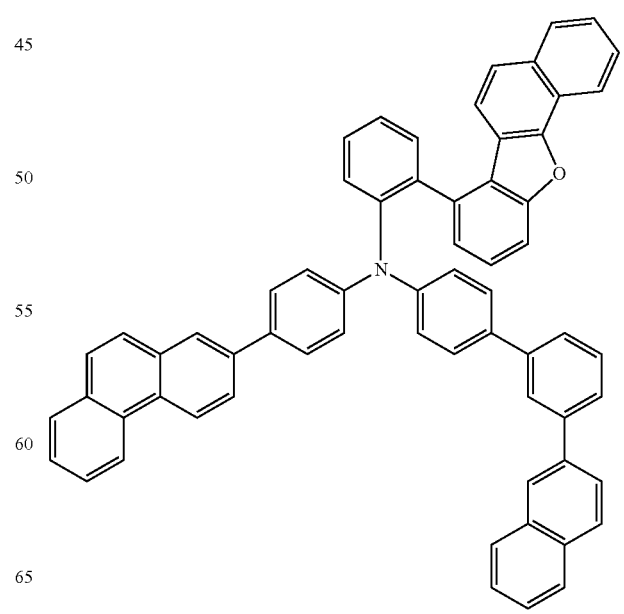

201
-continued
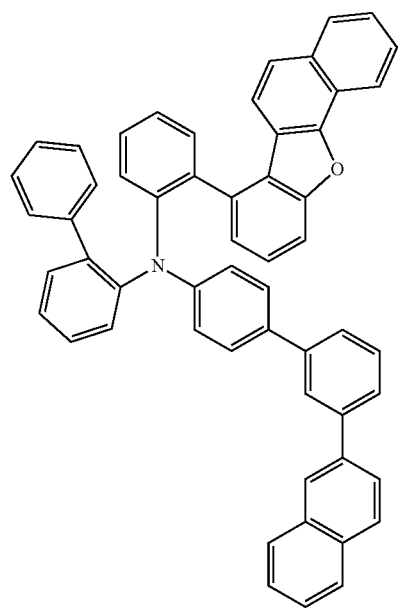
202
-continued
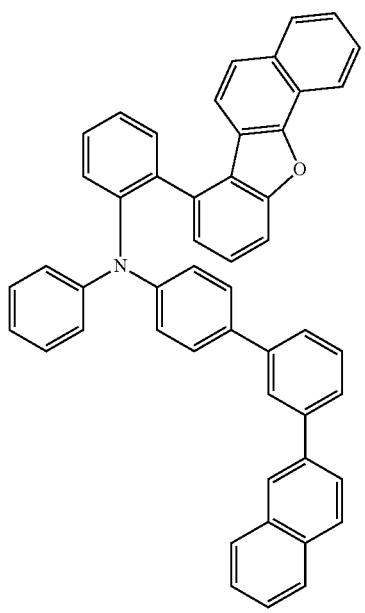
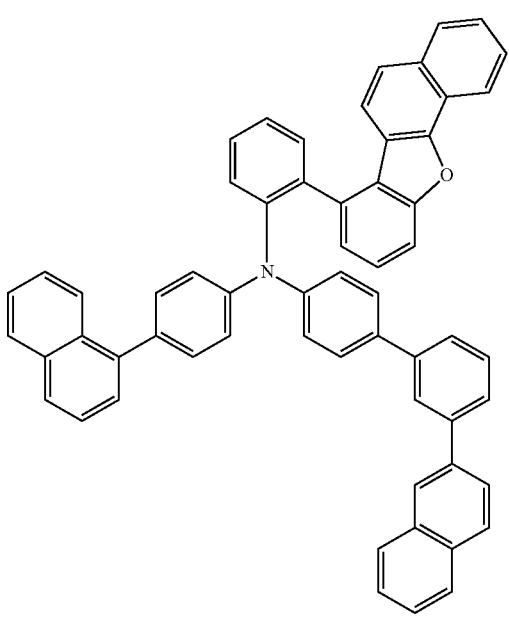
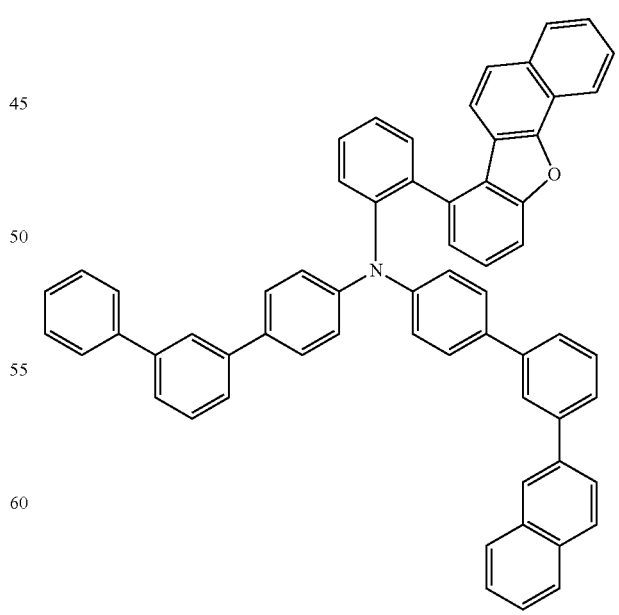

203
-continued
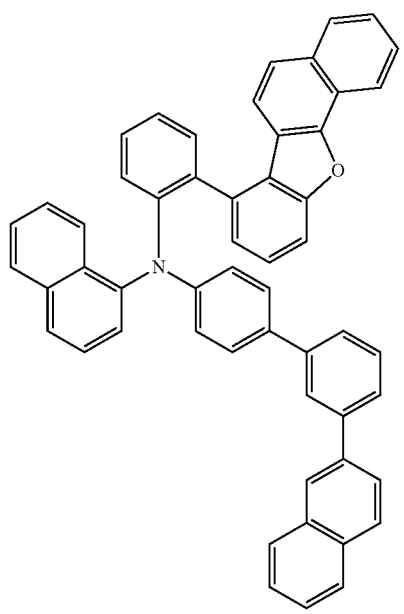
204
-continued
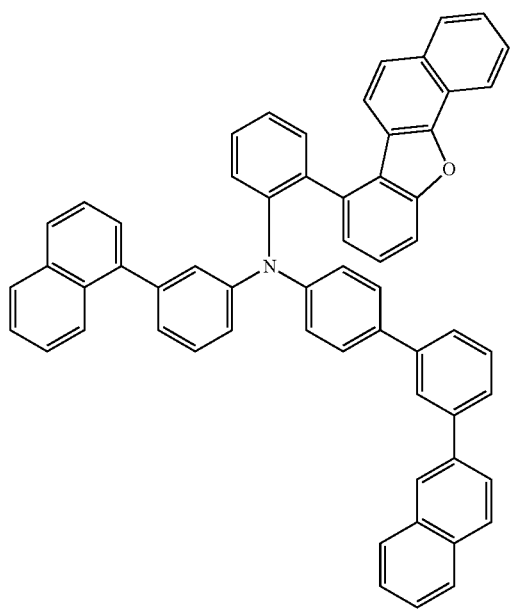
[Chem. 84]
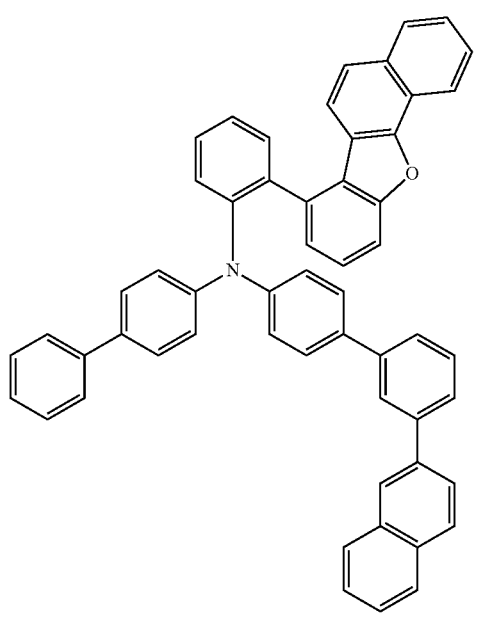
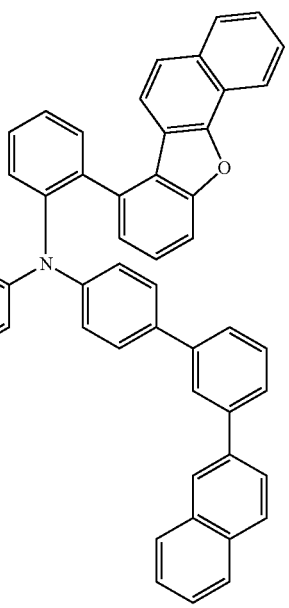

205
-continued
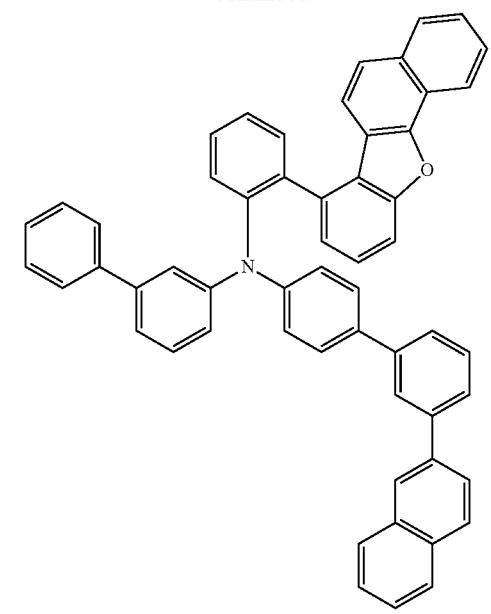
206
-continued
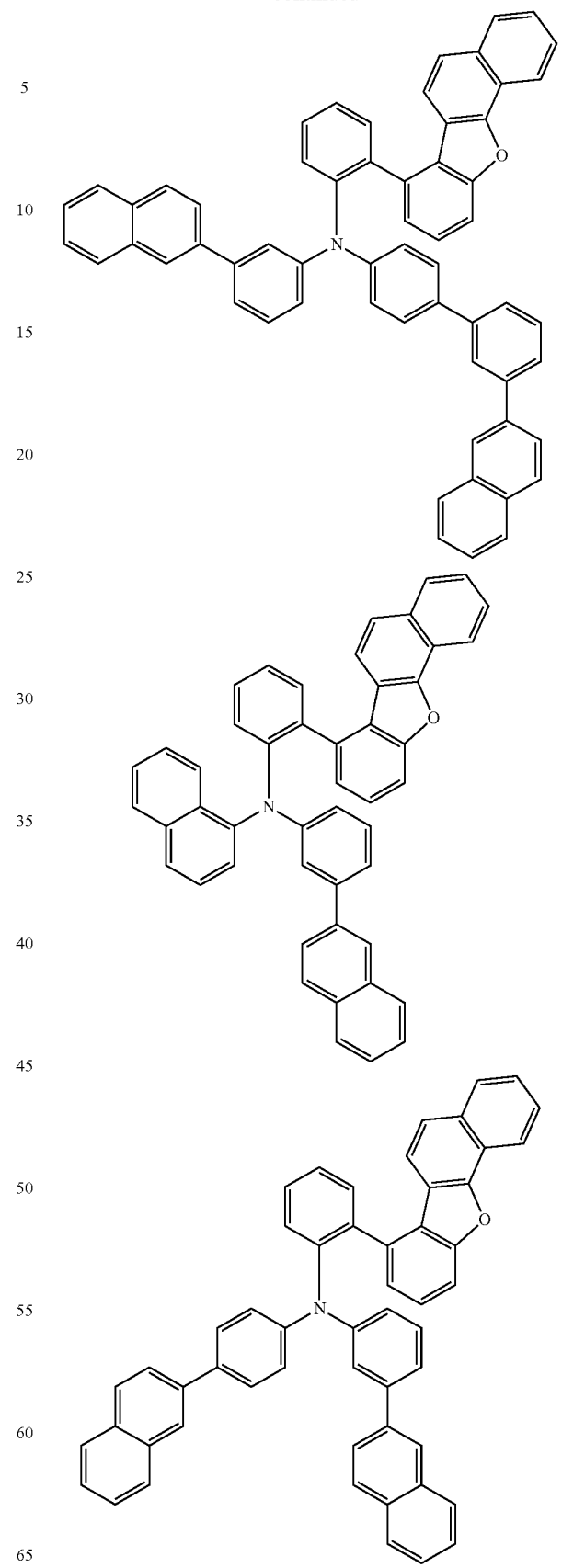

207
-continued
[Chem. 85]
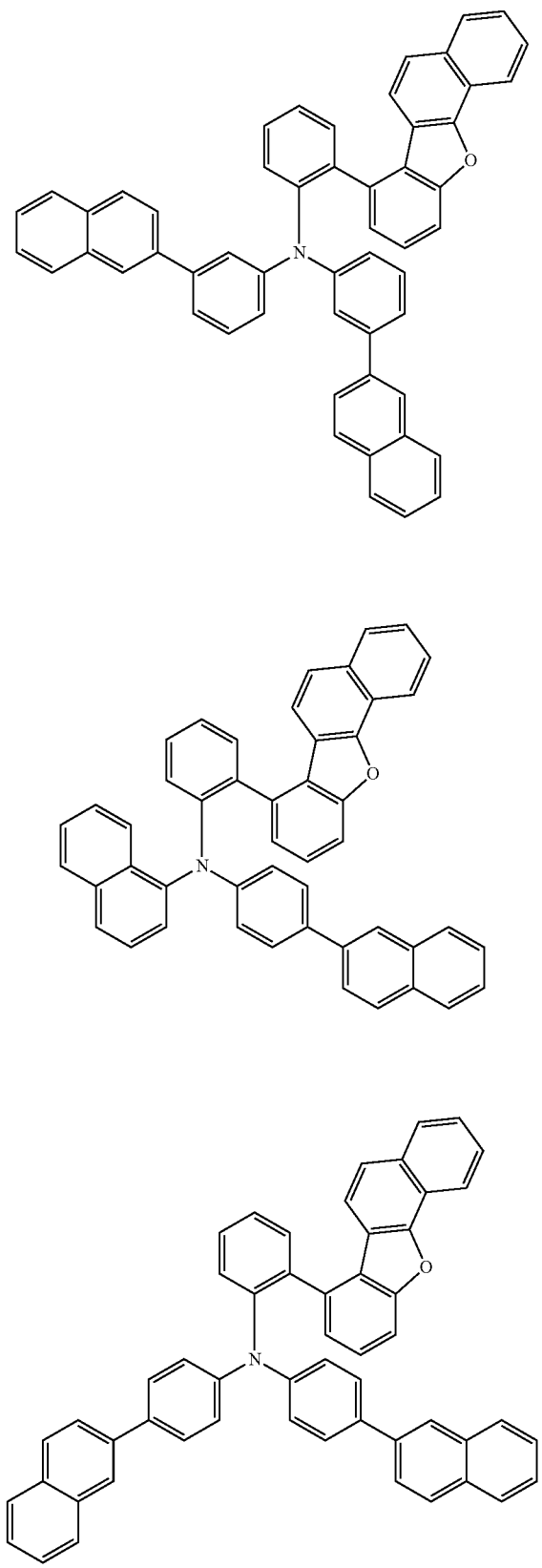
208
-continued
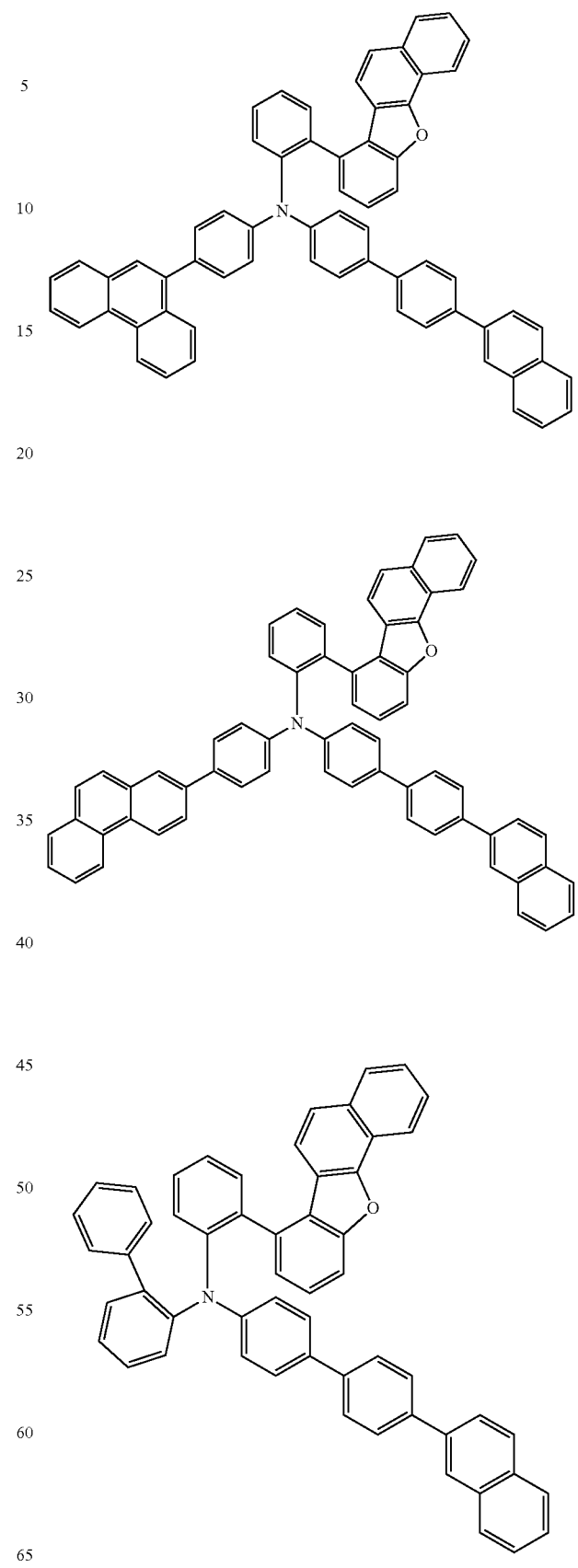

209
-continued
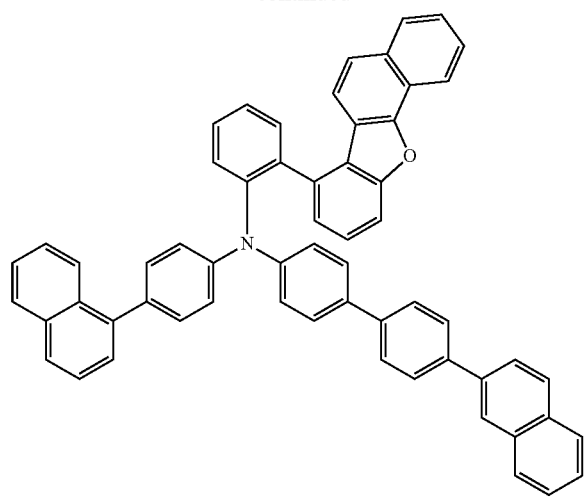
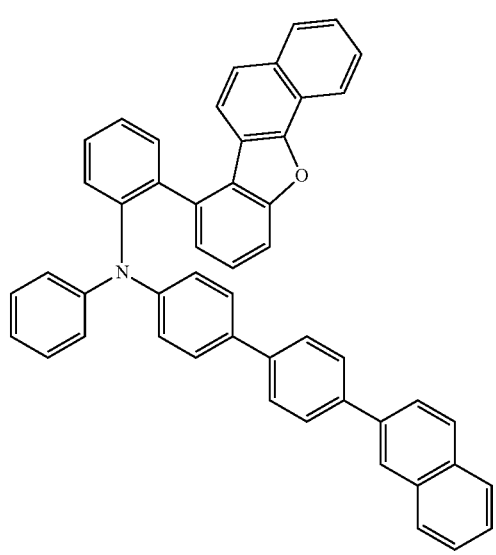
[Chem. 86]
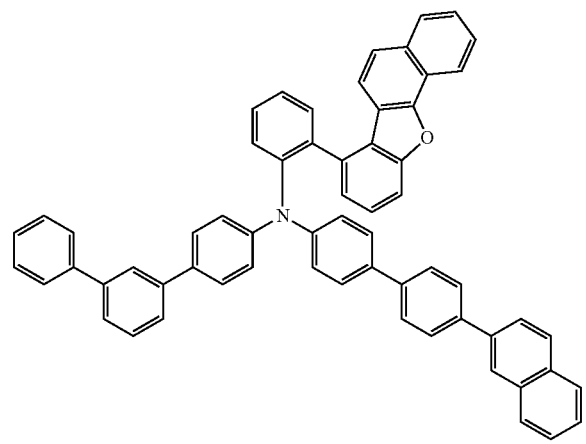
210
-continued
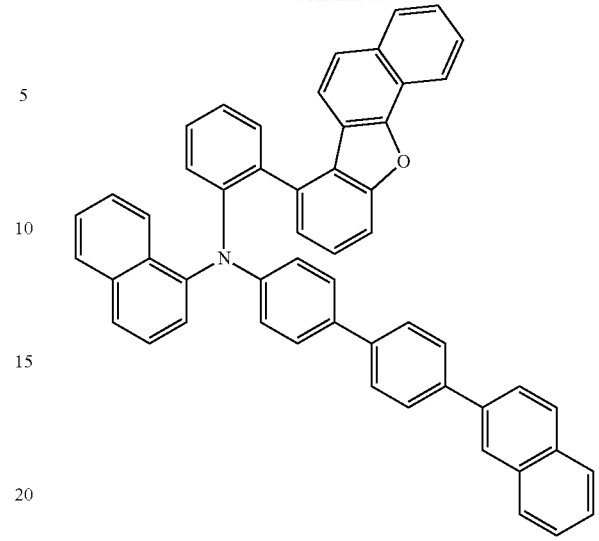
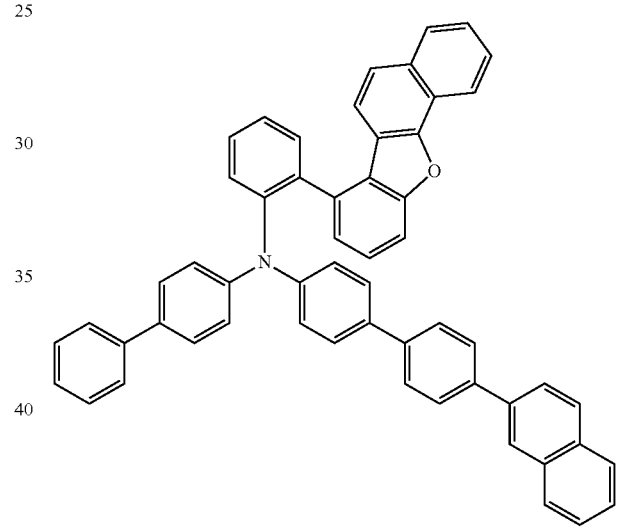
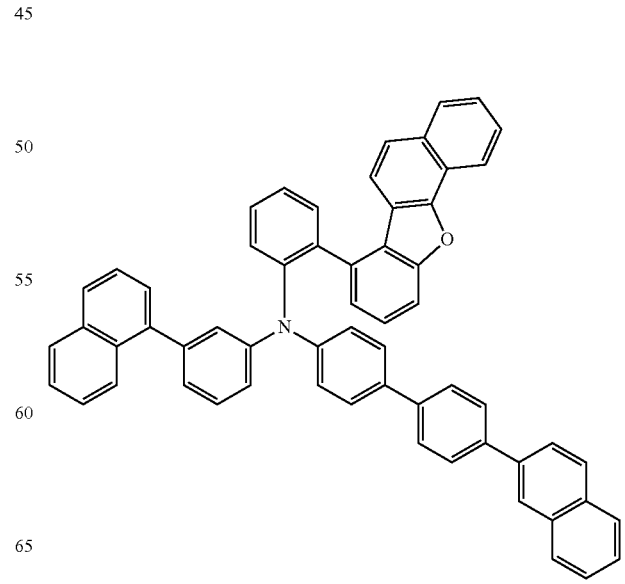

211
-continued
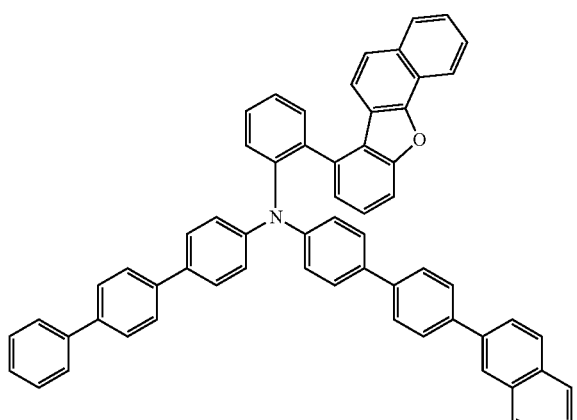
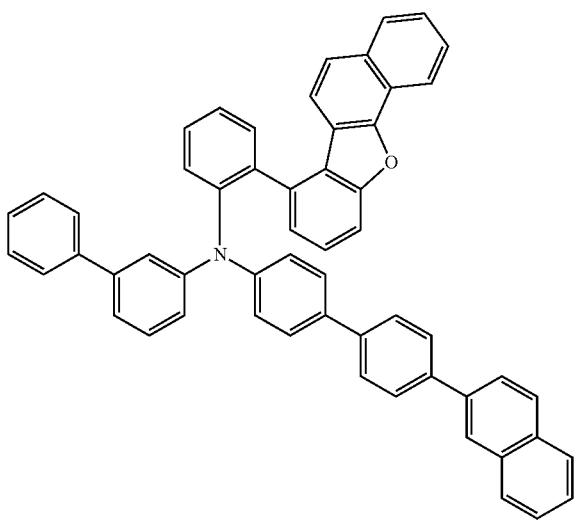
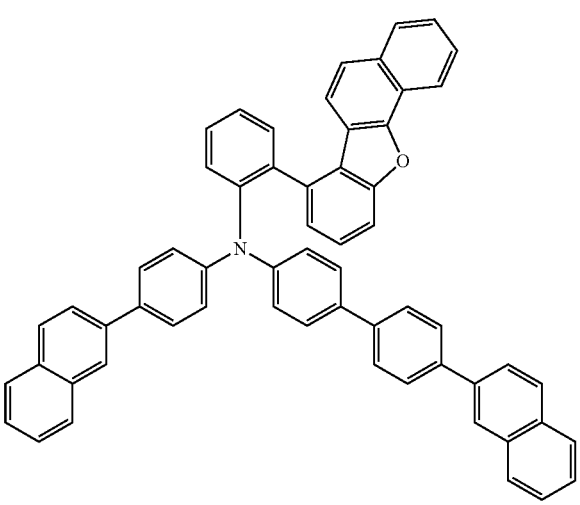
212
-continued
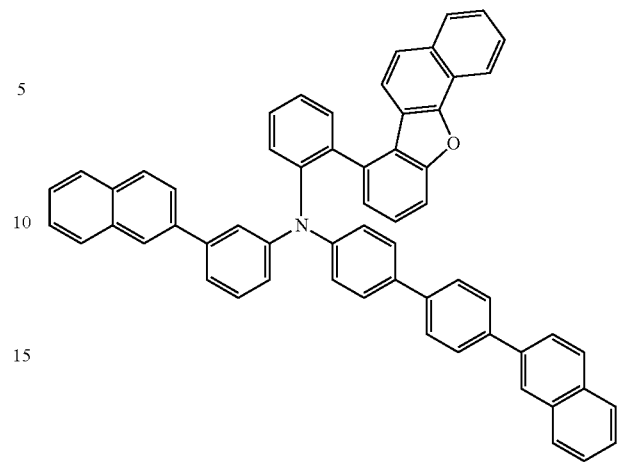
[Chem. 87]
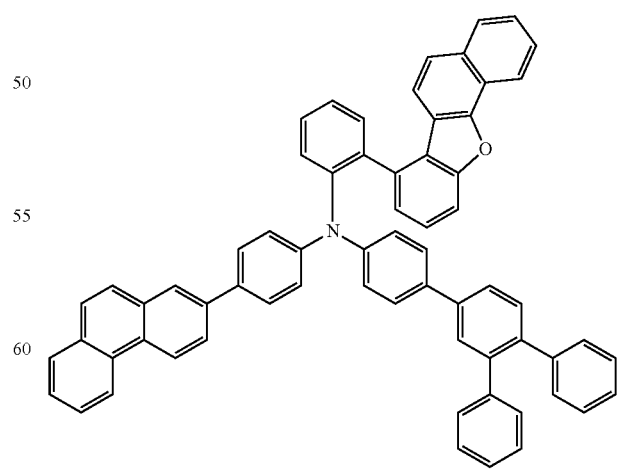

213
-continued
214
-continued
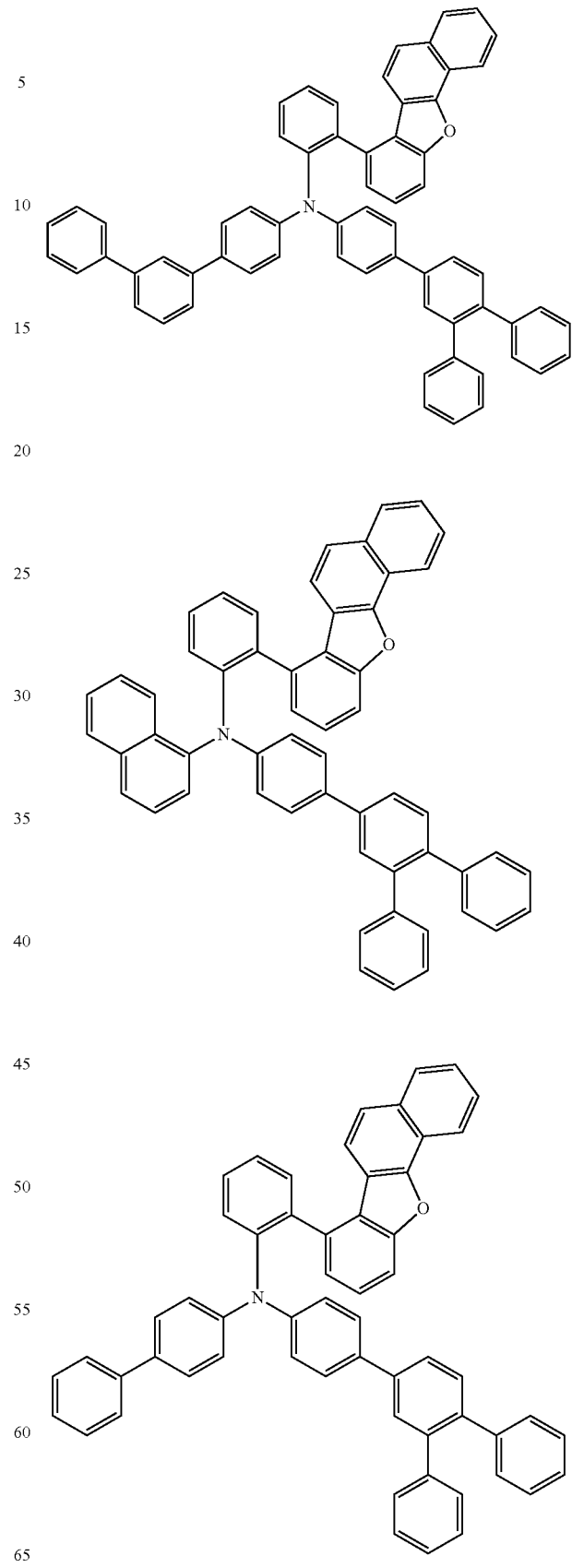

215
-continued
[Chem. 88]
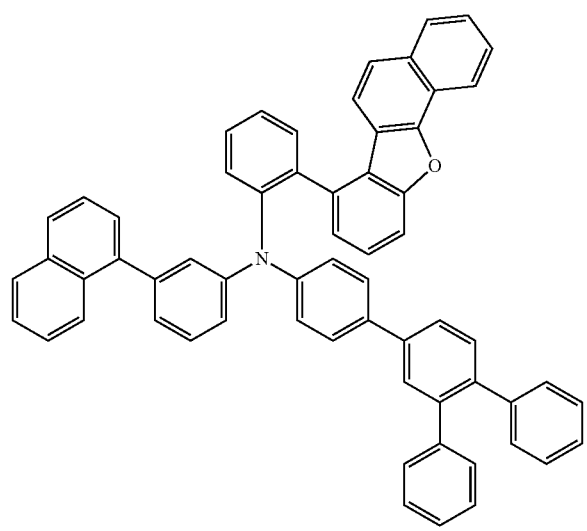
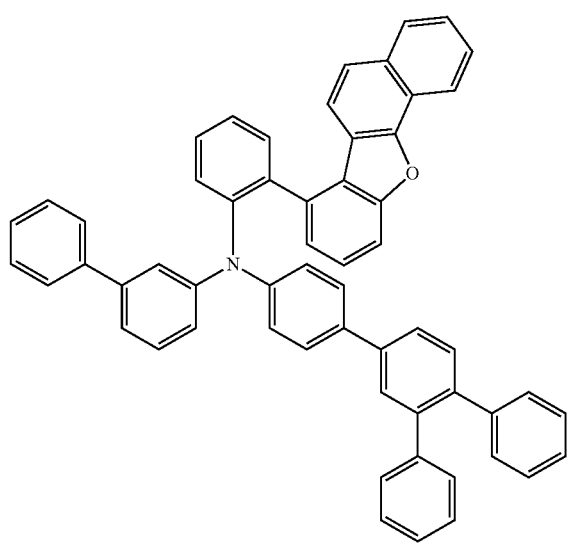
216
-continued
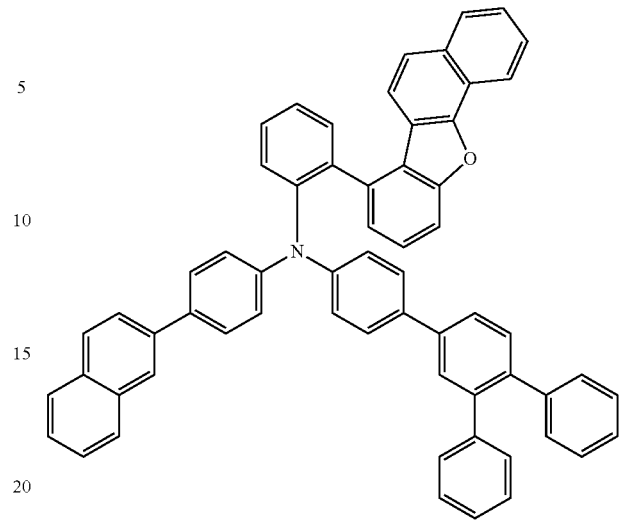
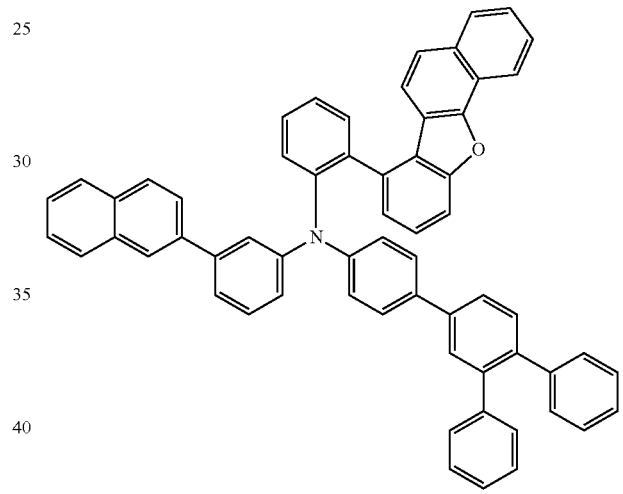
[Chem. 89]
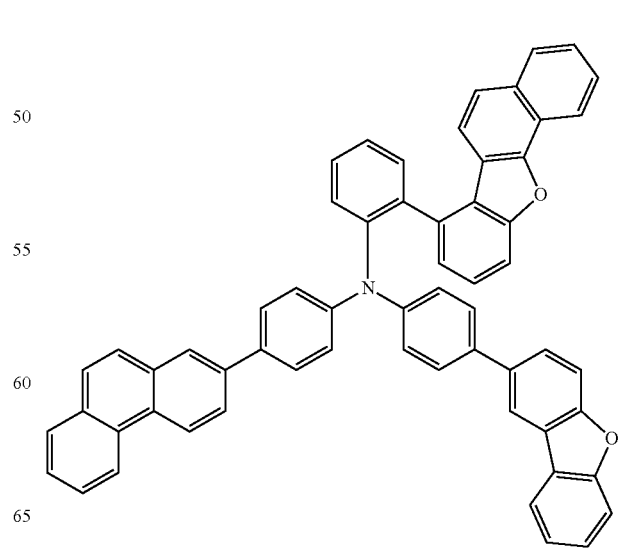

217
-continued
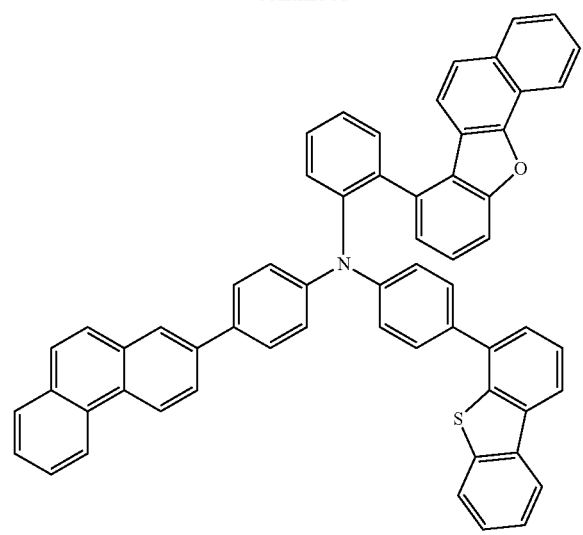
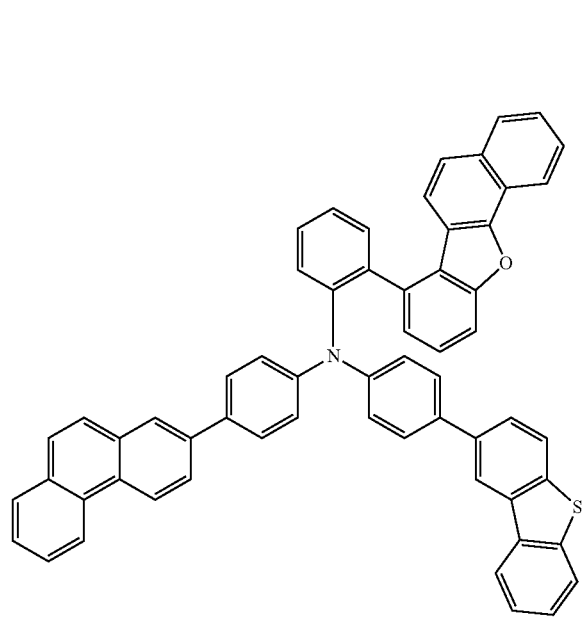
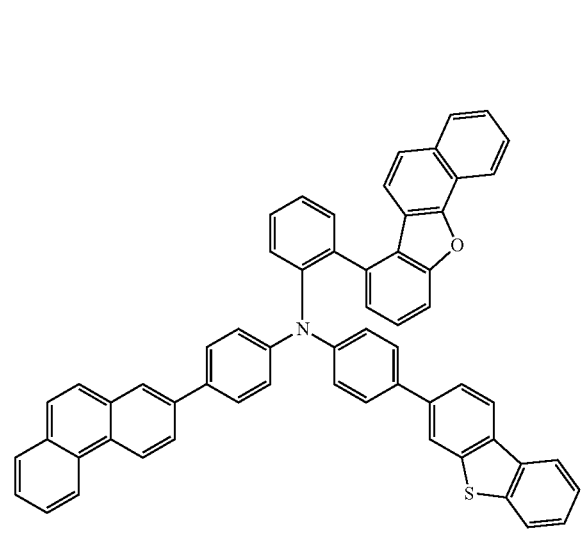
218
-continued
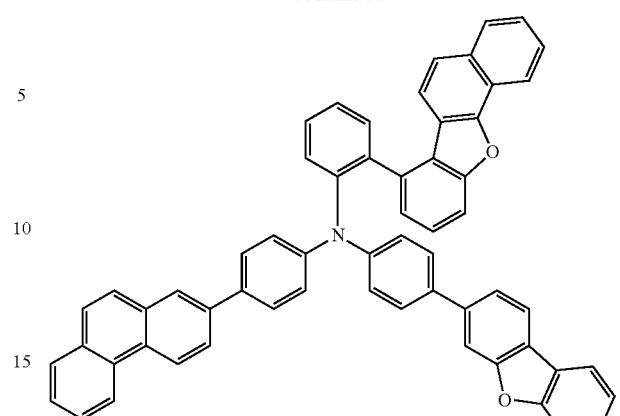
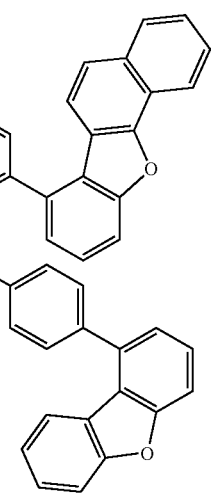
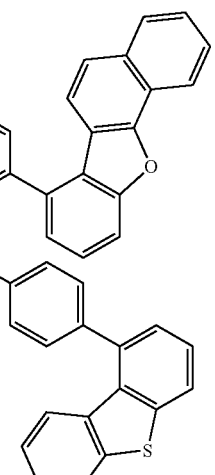

219
-continued
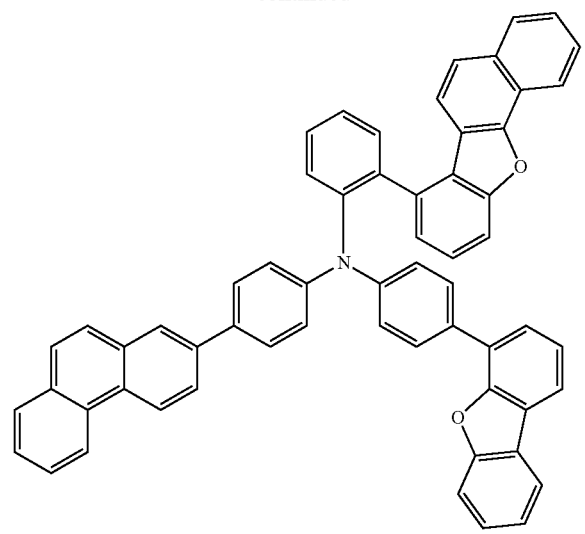
[Chem. 90]
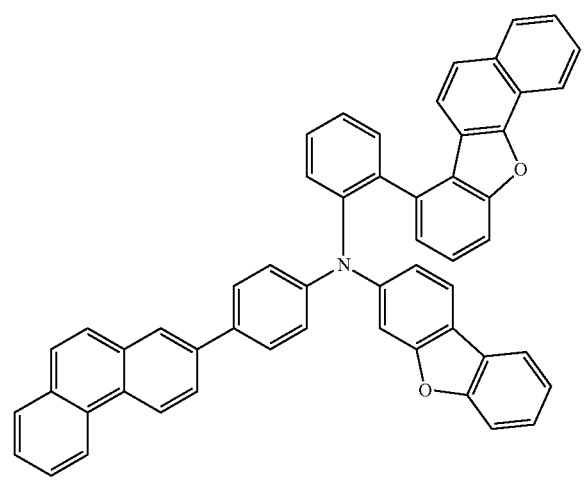
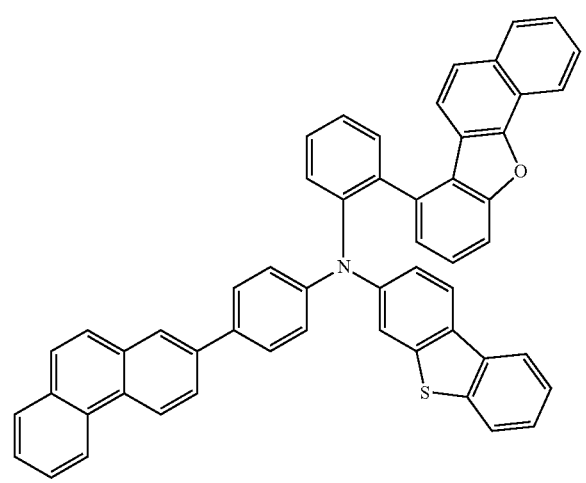
220
-continued
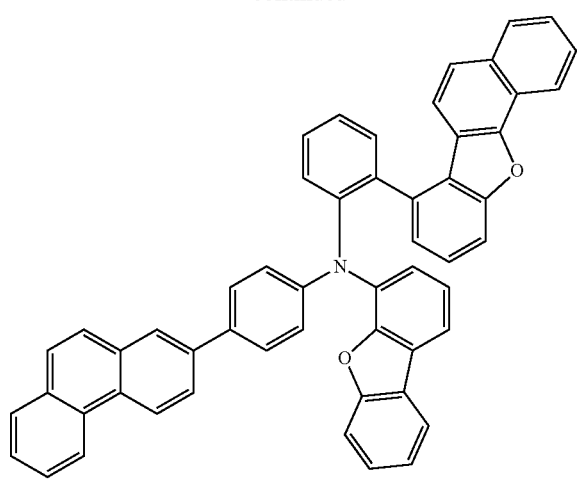
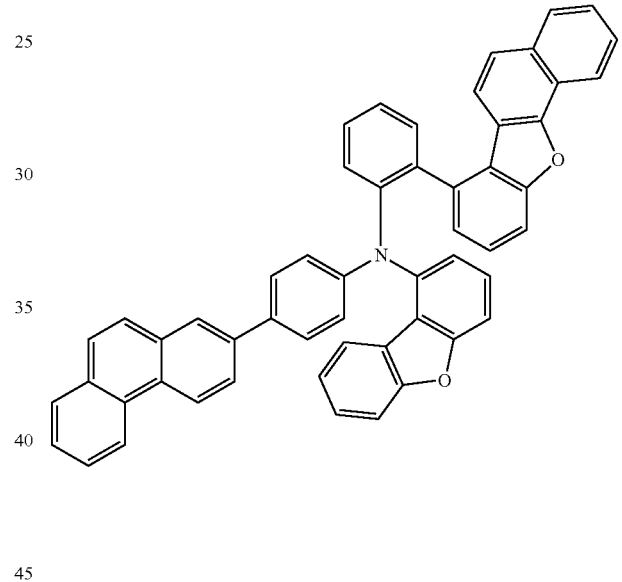
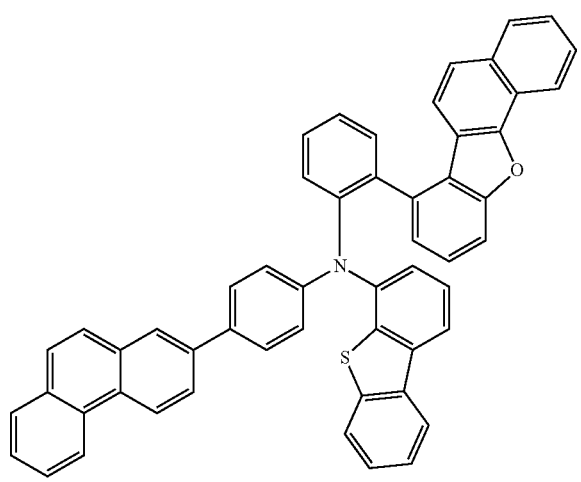

221
-continued
222
-continued
[Chem. 91]
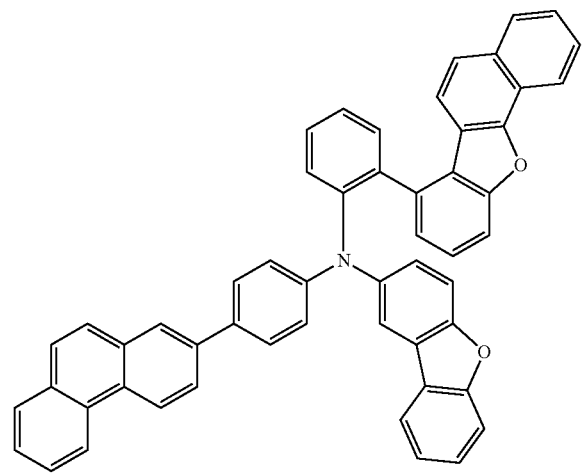
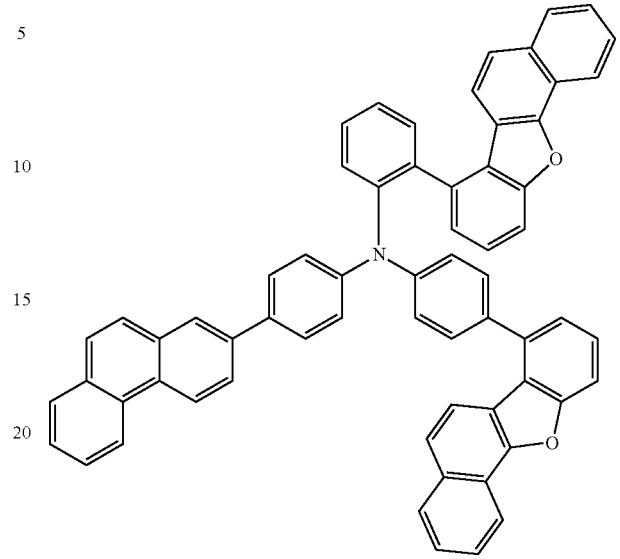
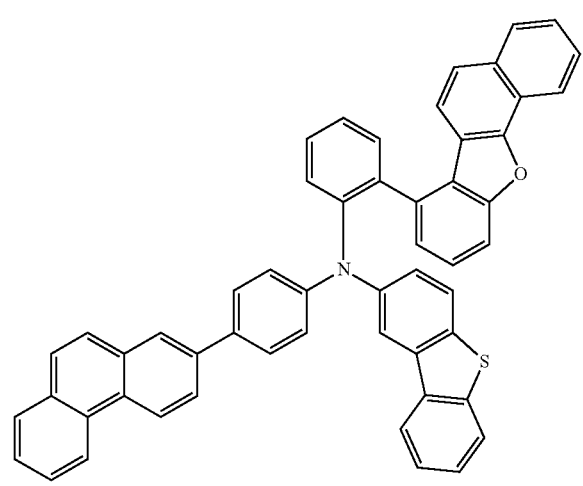
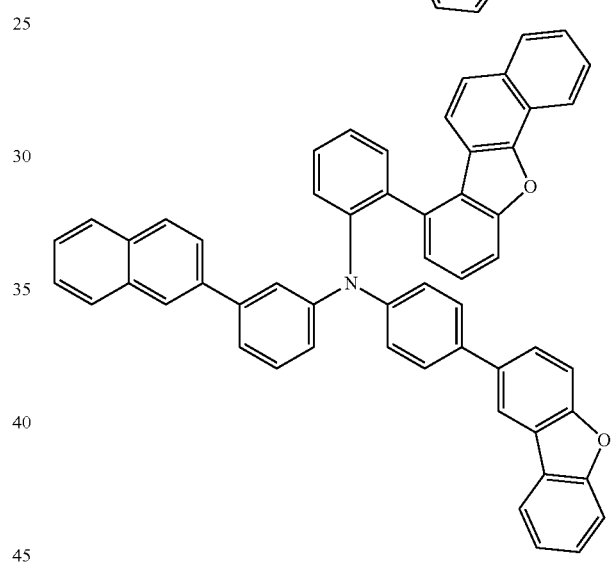
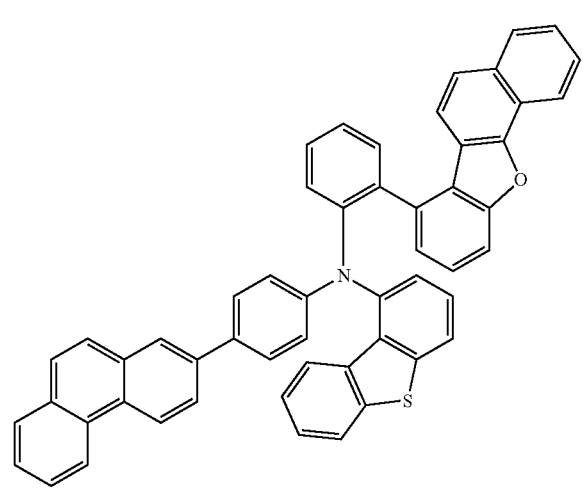
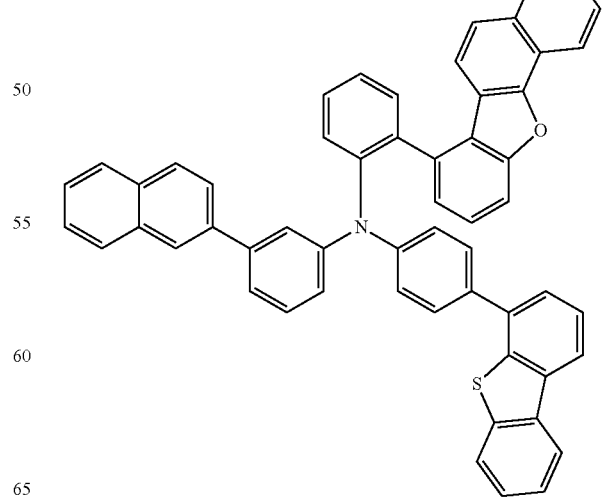

223
-continued
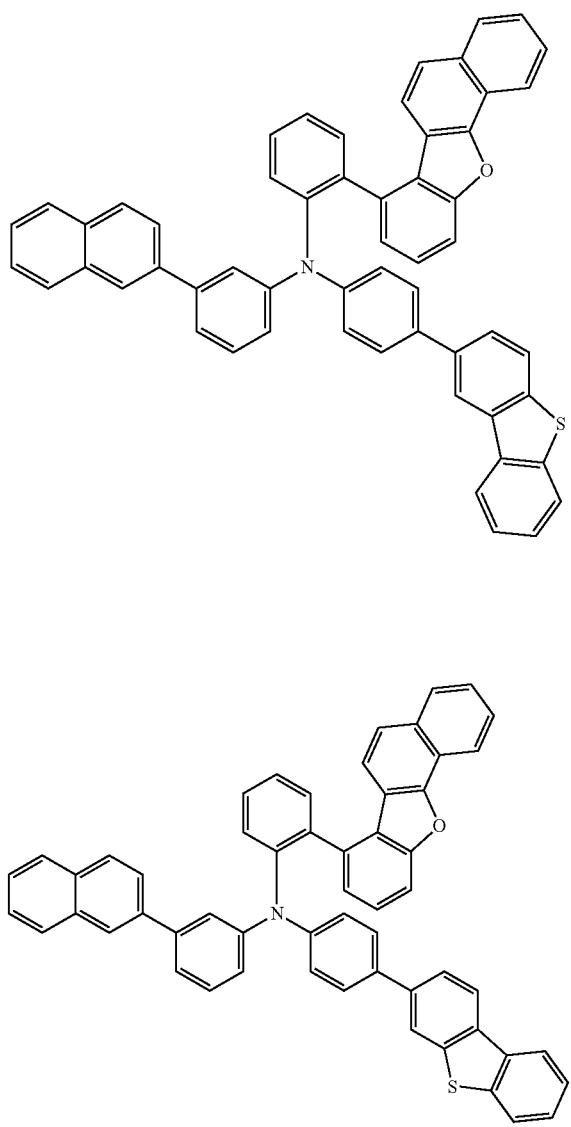
224
-continued
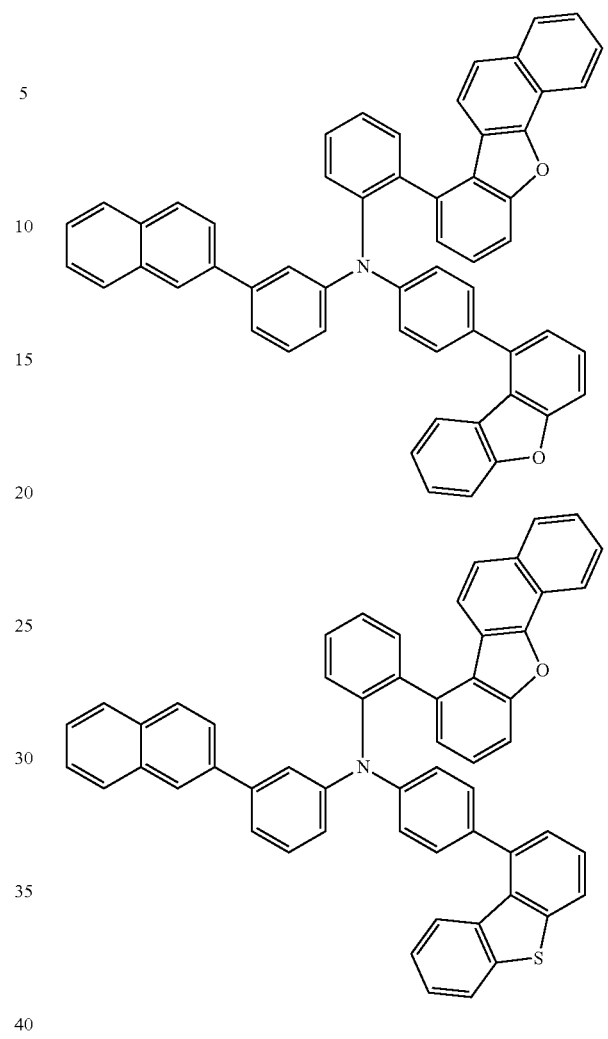
[Chem. 92]
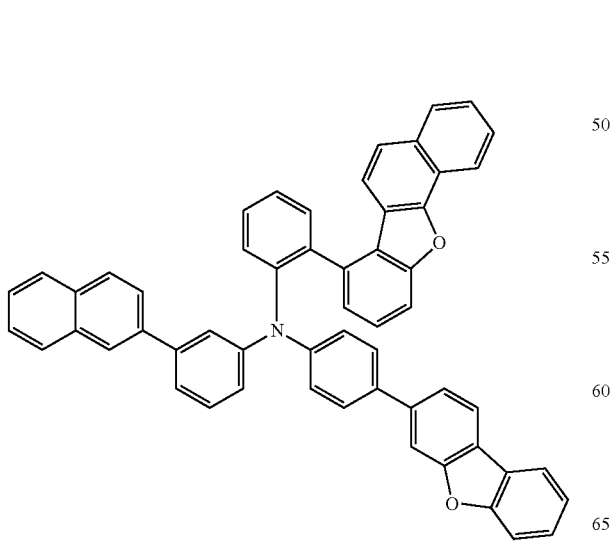
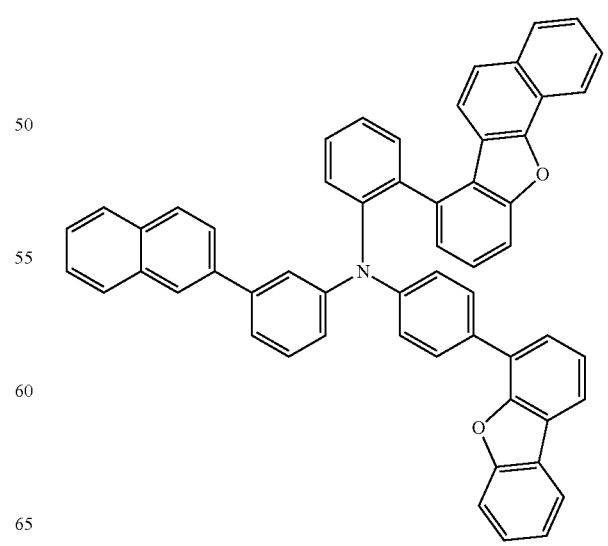

225
-continued
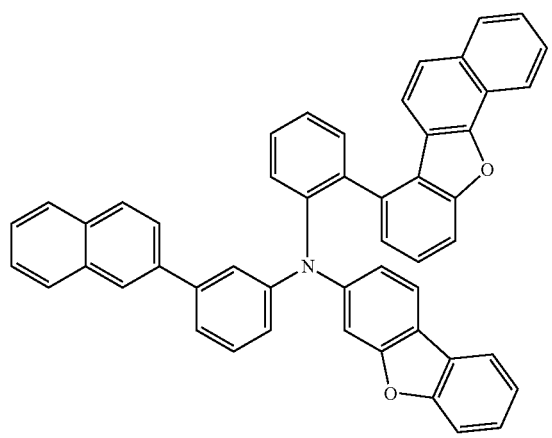
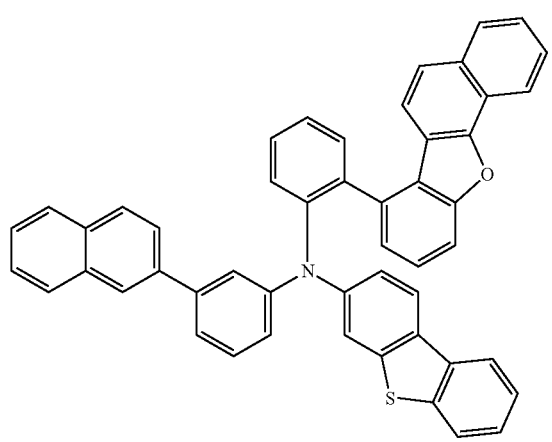
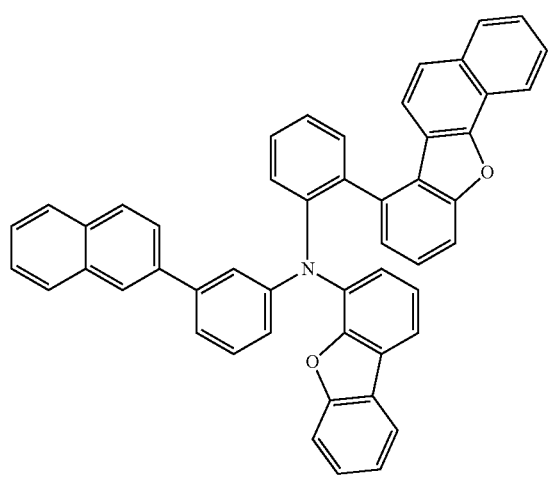
226
-continued
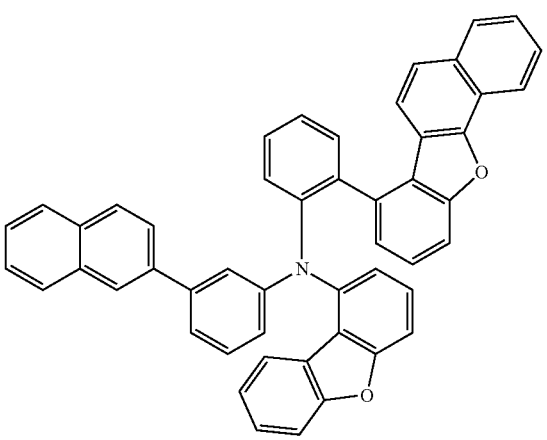
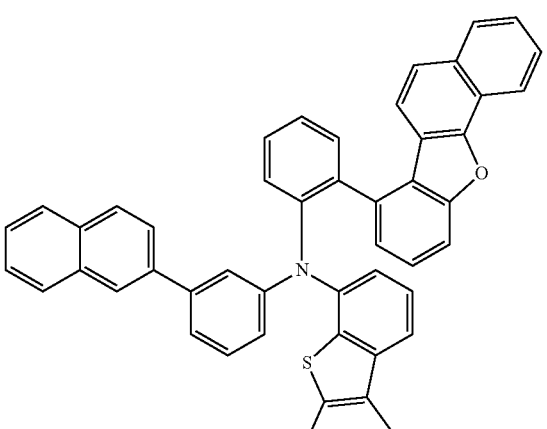
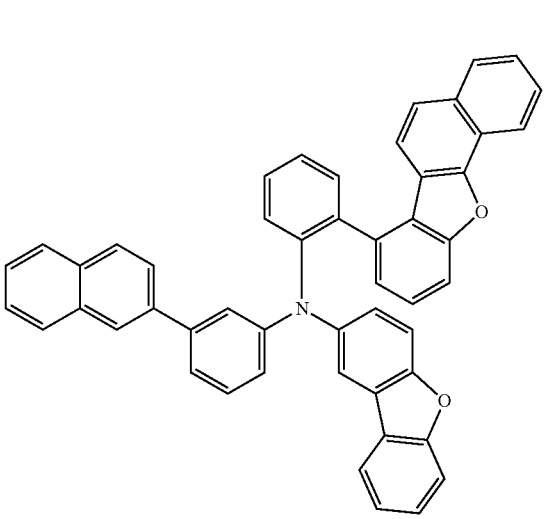

227
-continued
228
-continued
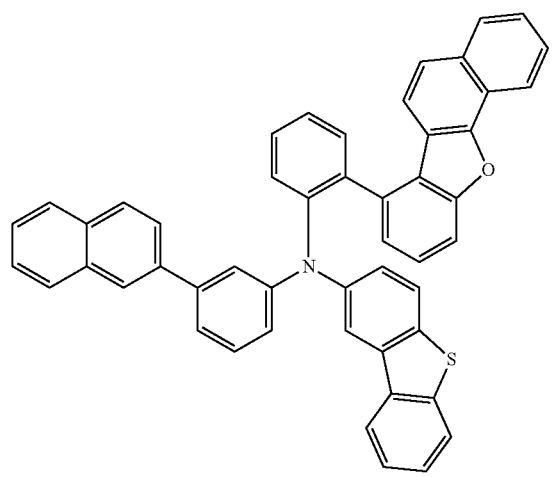
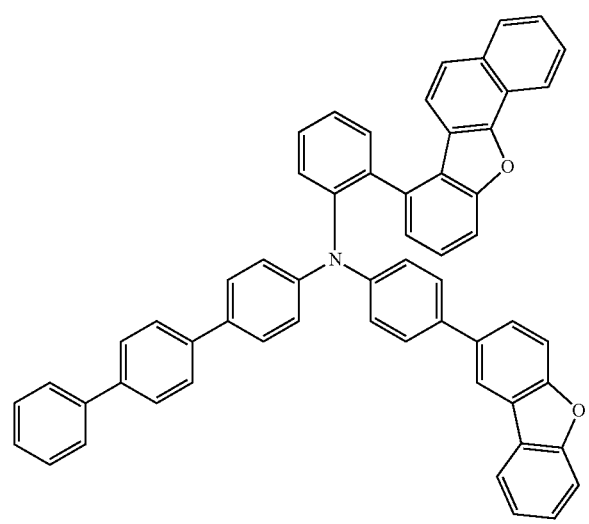
[Chem. 93]

229
-continued
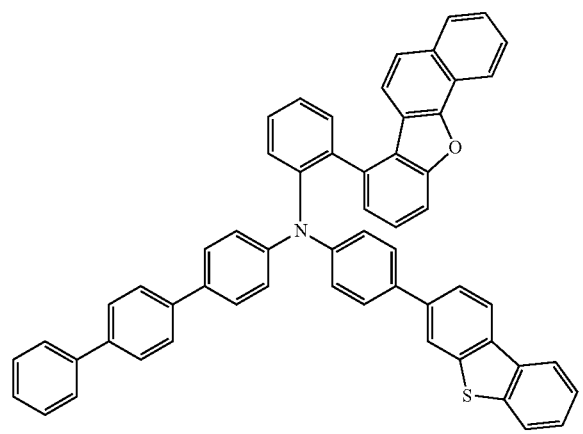
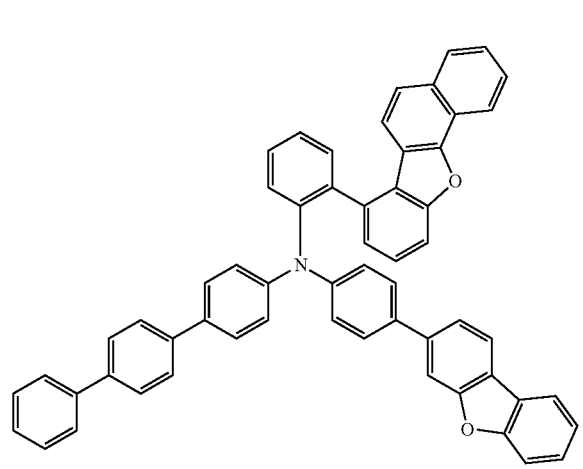
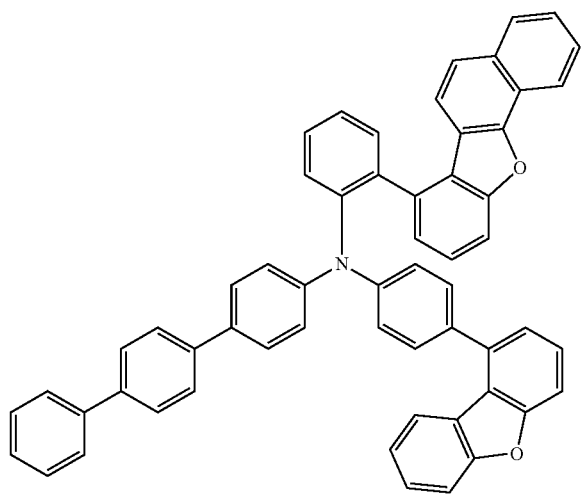
230
-continued
[Chem. 94]
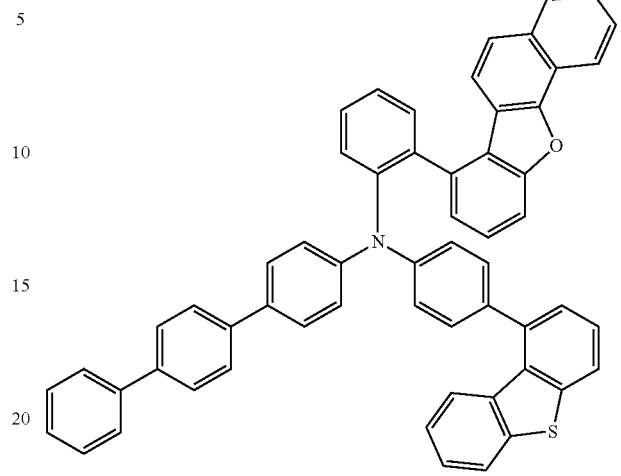
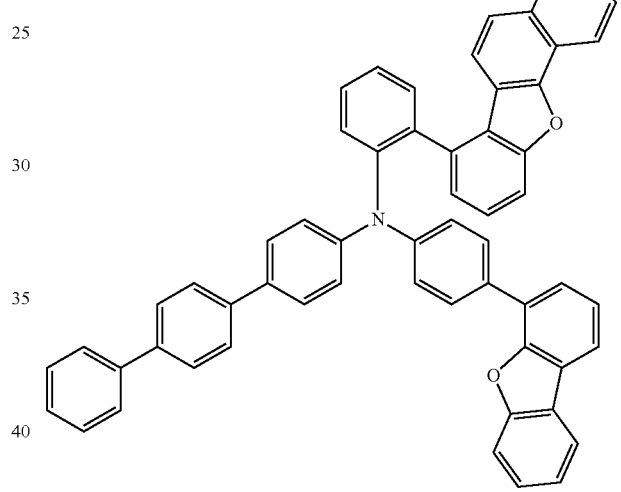
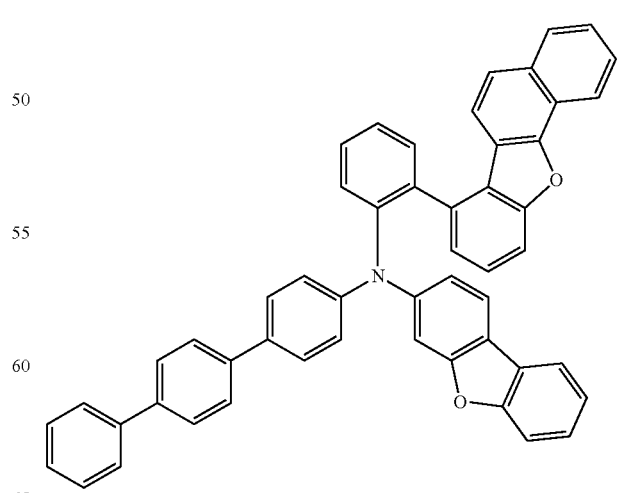

231
-continued
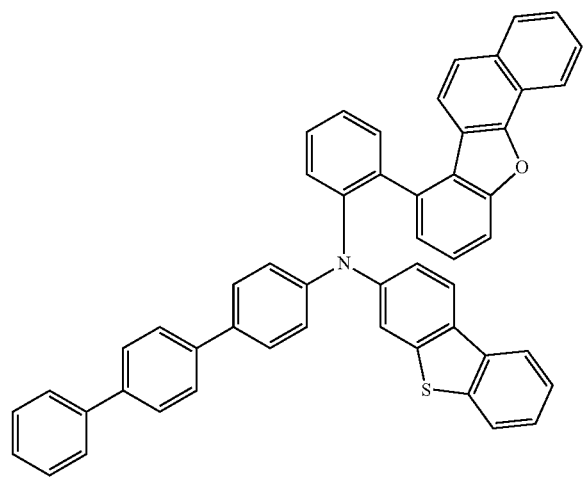
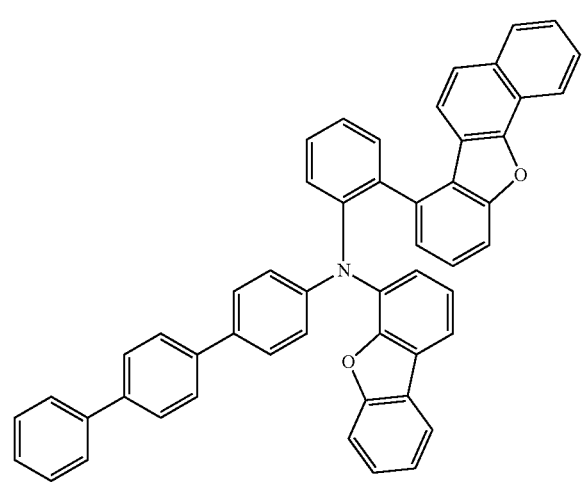
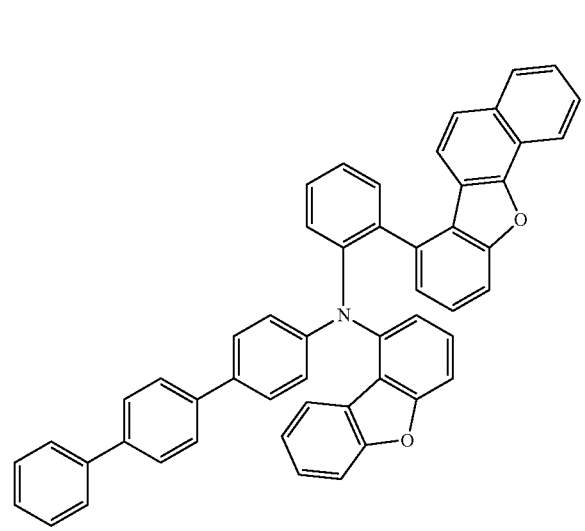
232
-continued
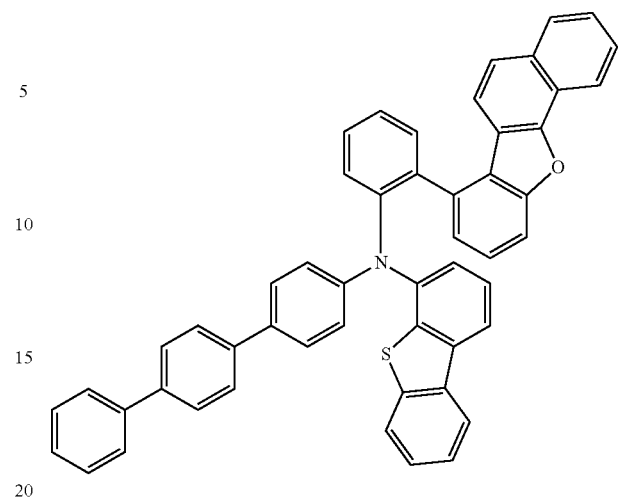
[Chem. 95]
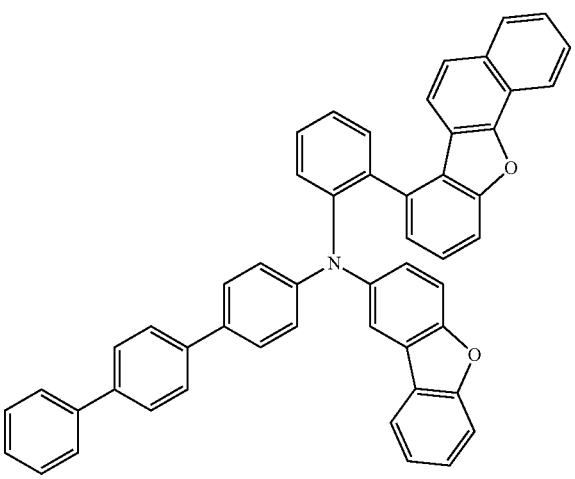
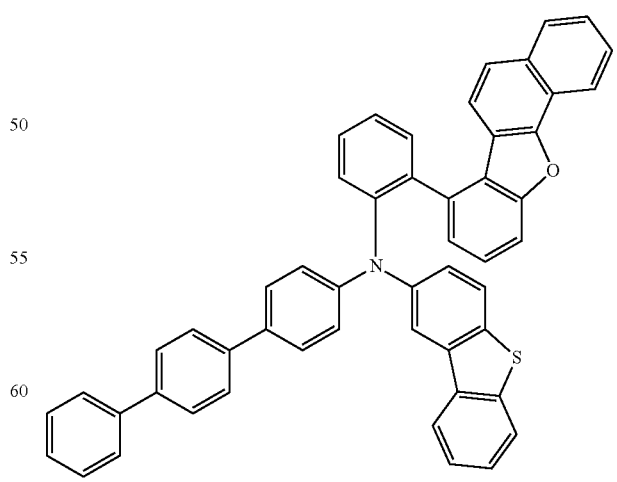

233
-continued
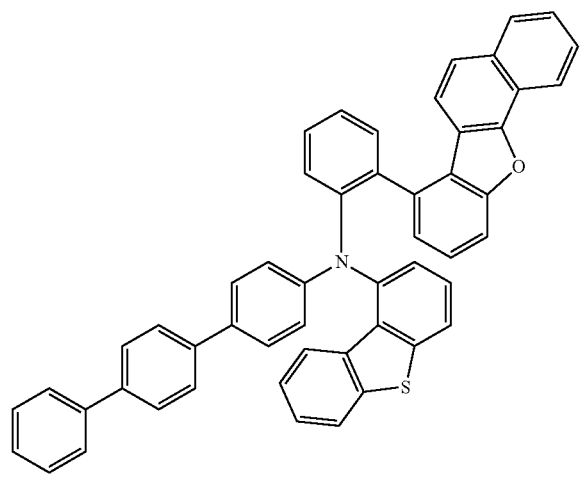
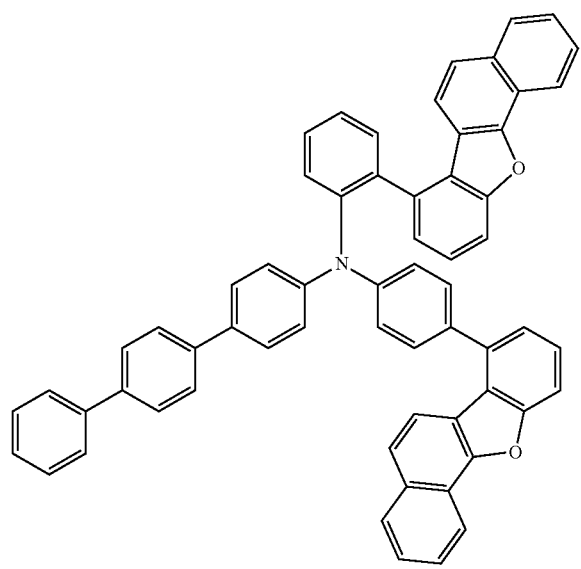
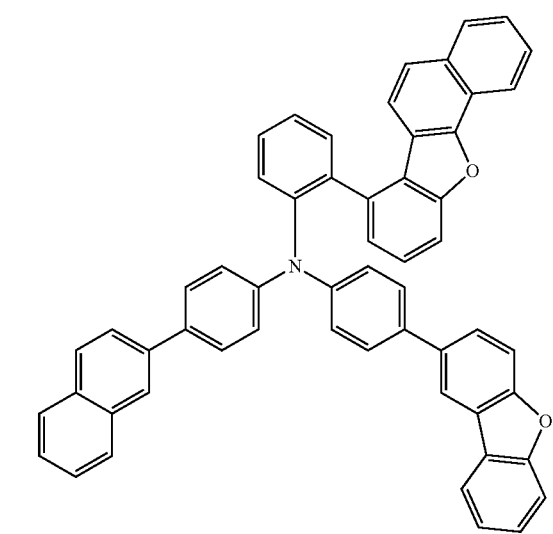
234
-continued
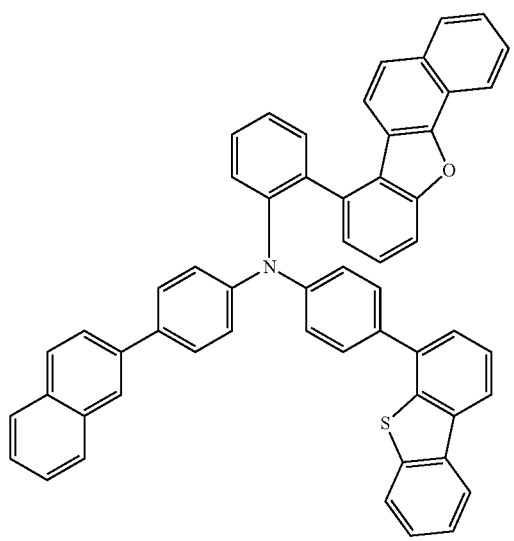
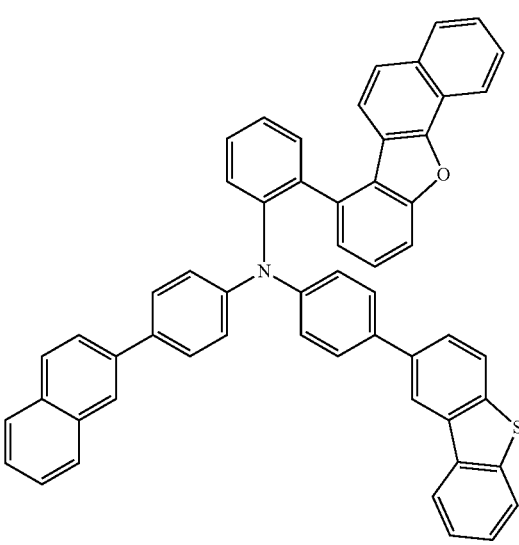
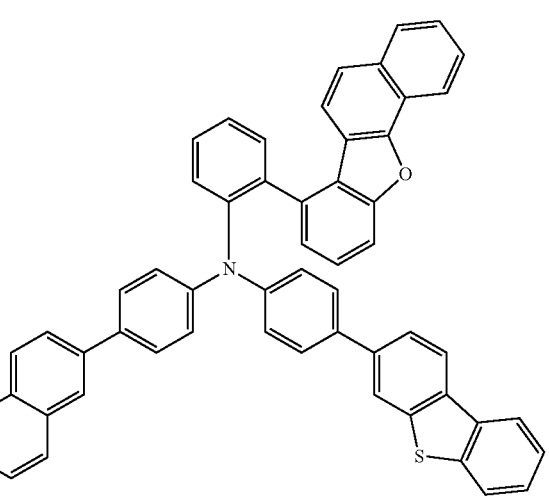

235
-continued
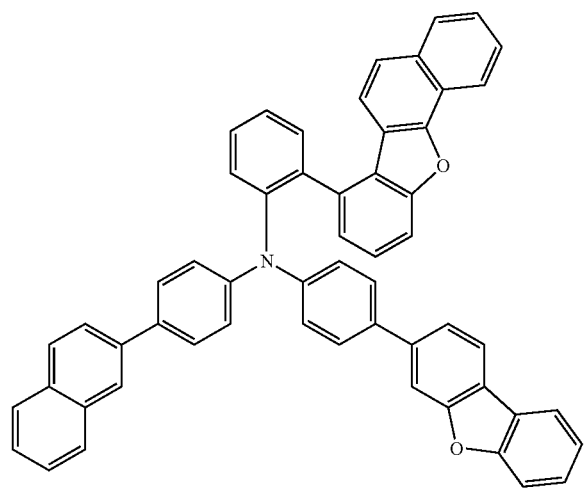
[Chem. 96]
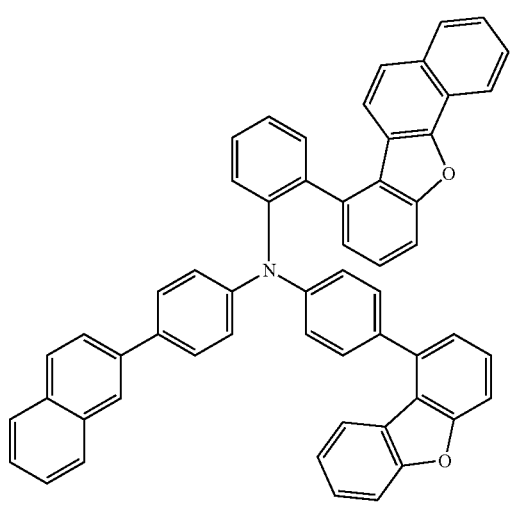
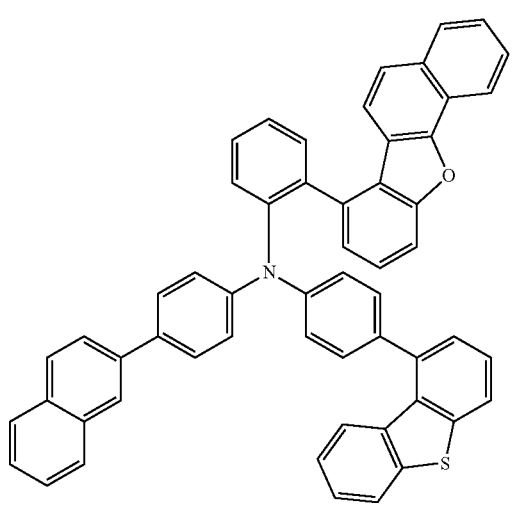
236
-continued
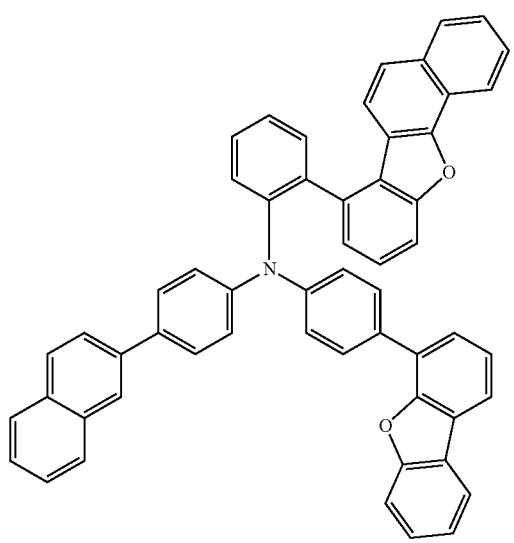
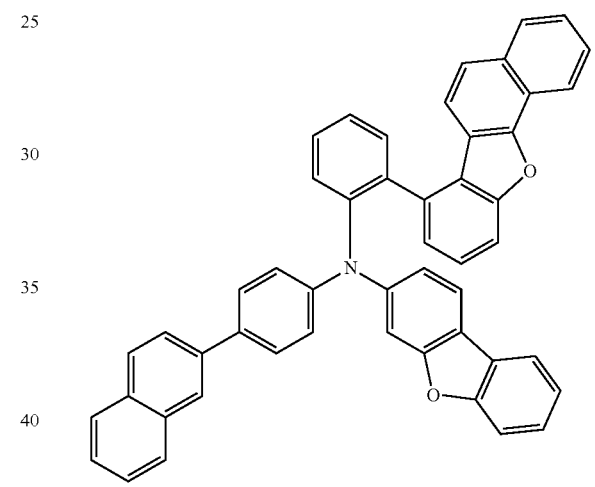
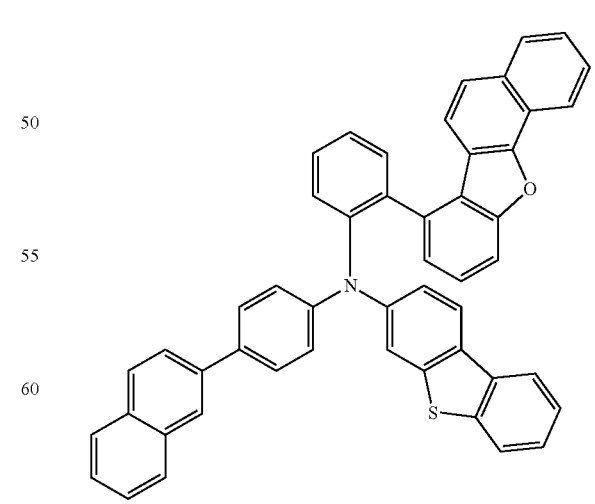

237
-continued
[Chem. 97]
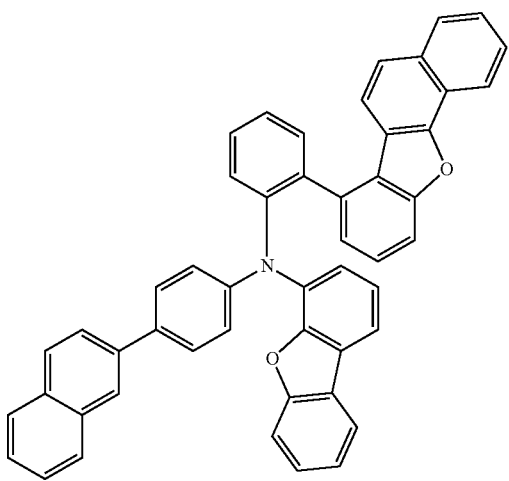
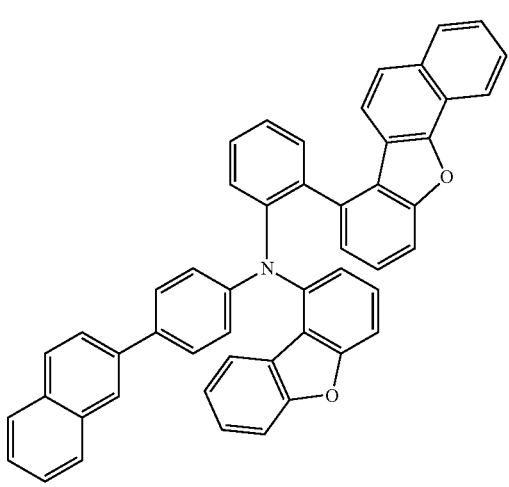
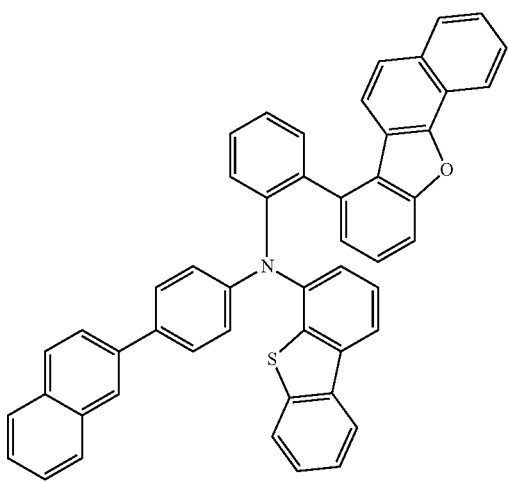
238
-continued
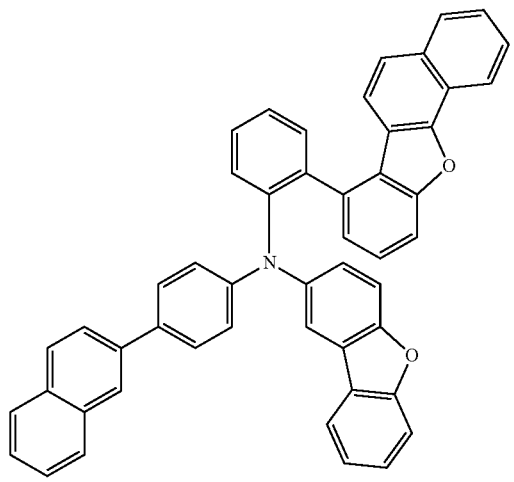
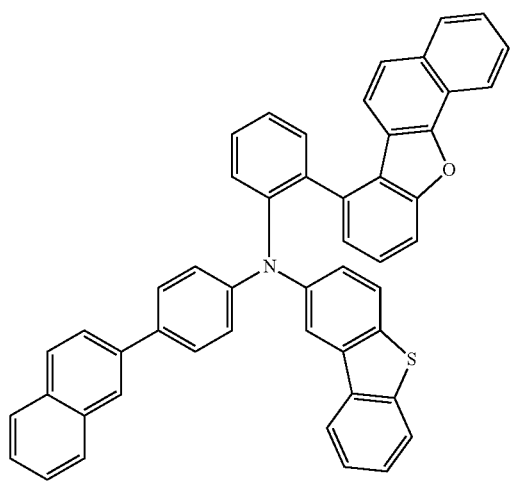
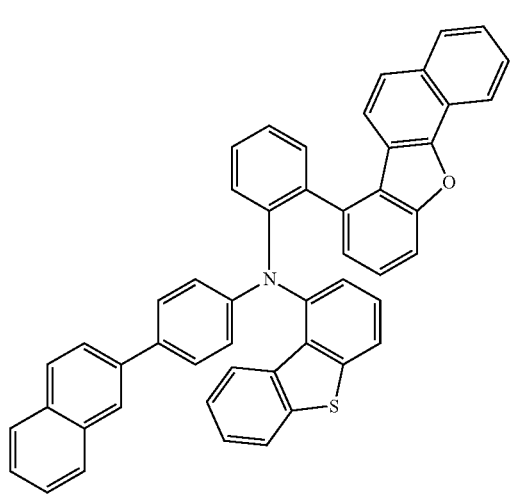

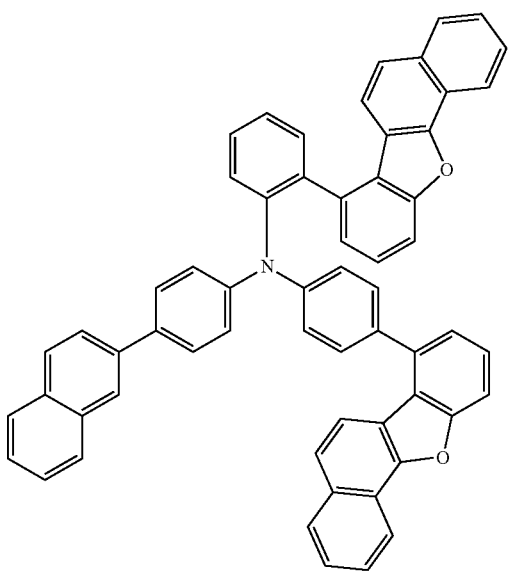
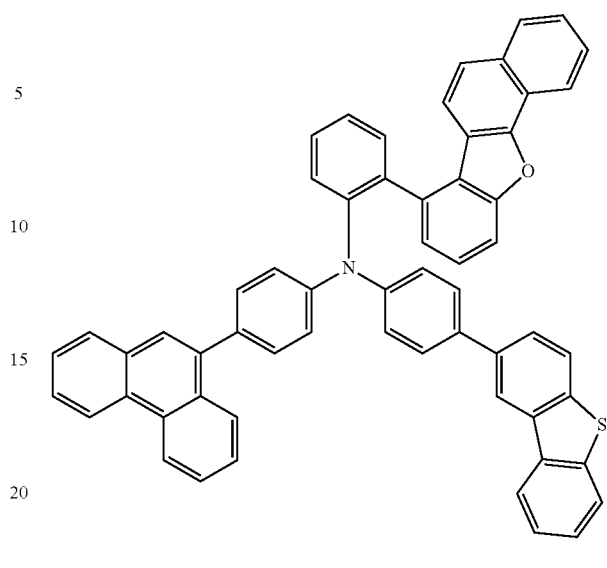
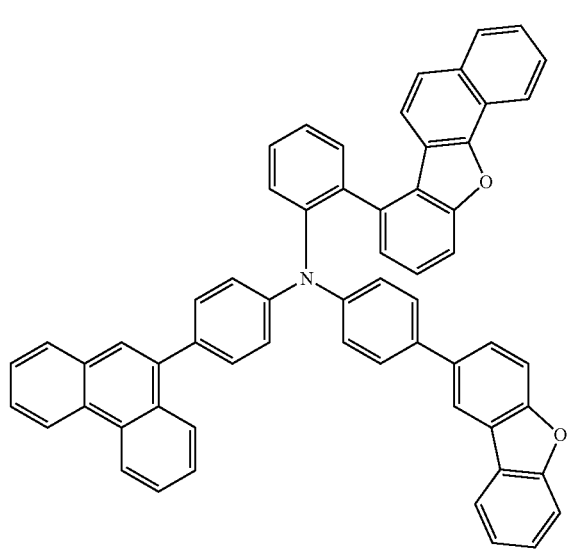
[Chem. 98]
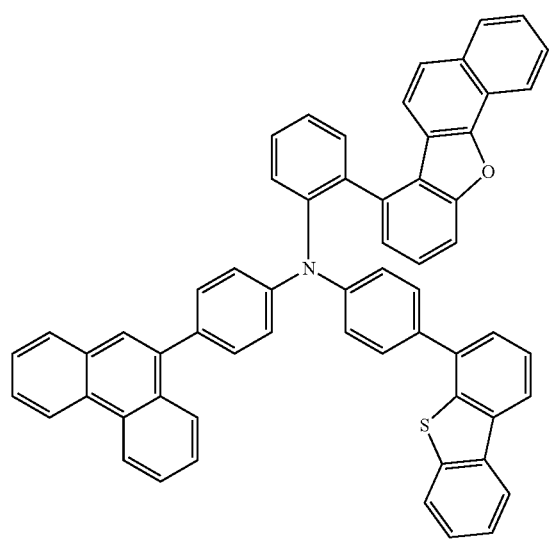
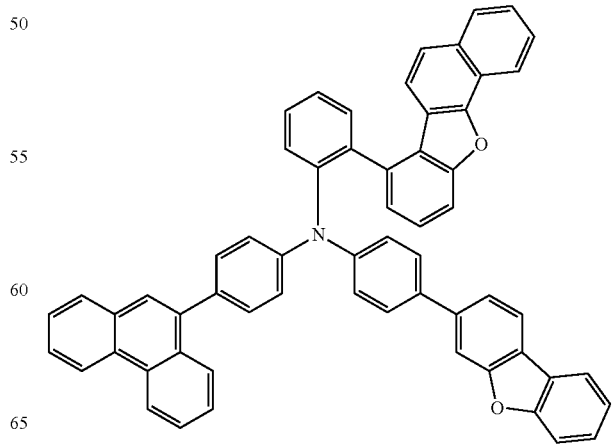

241
-continued
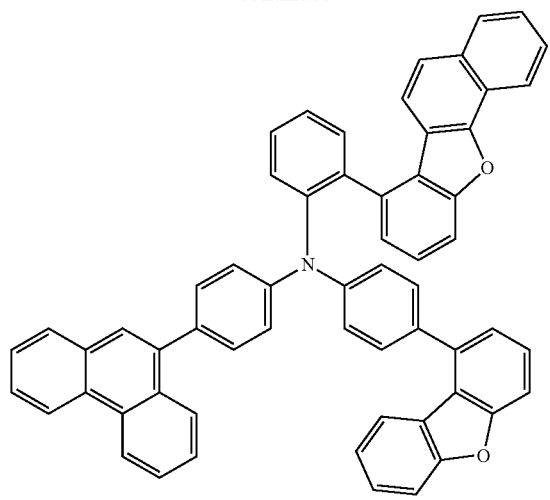
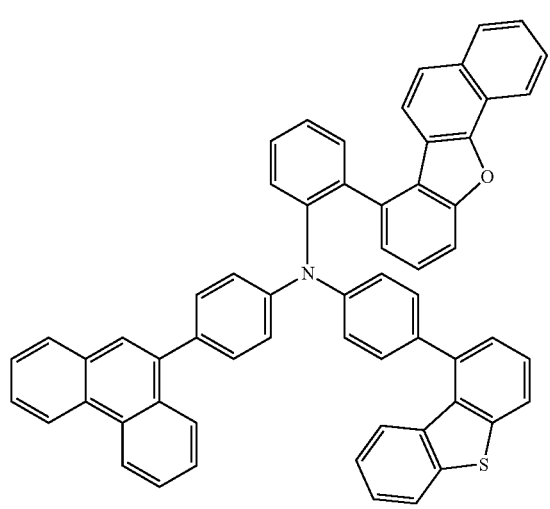
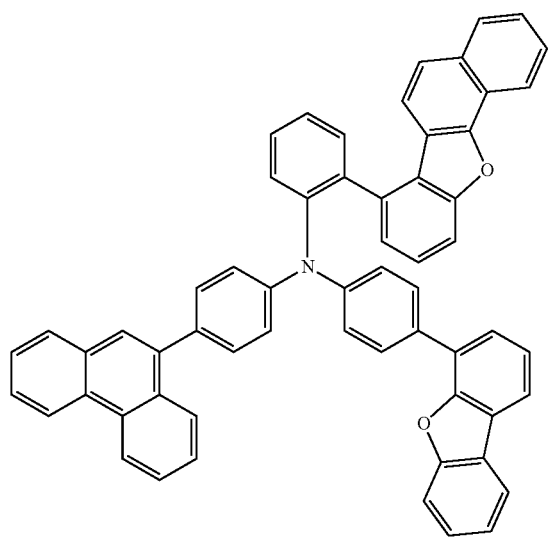
242
-continued
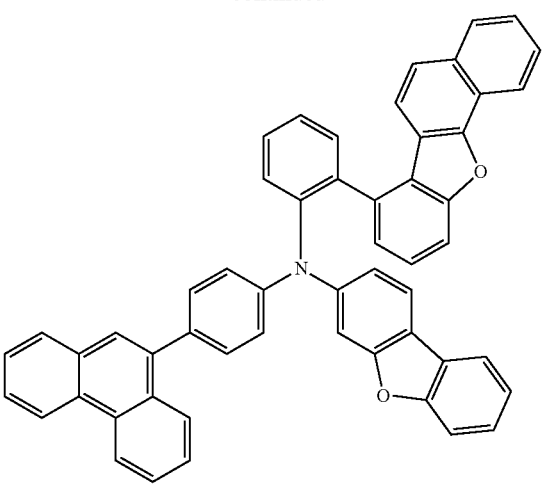
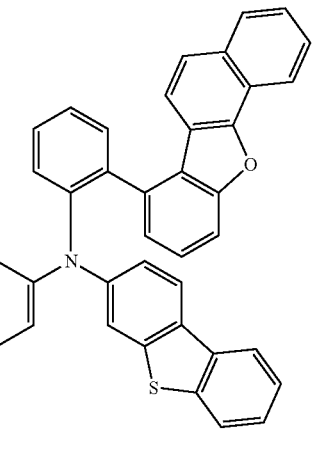
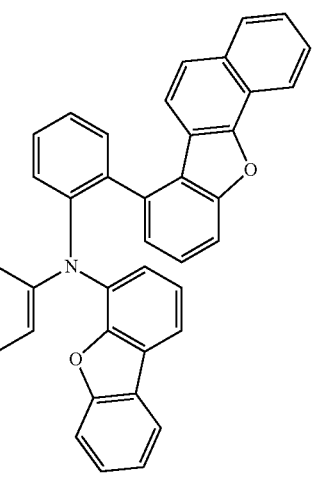

243
-continued
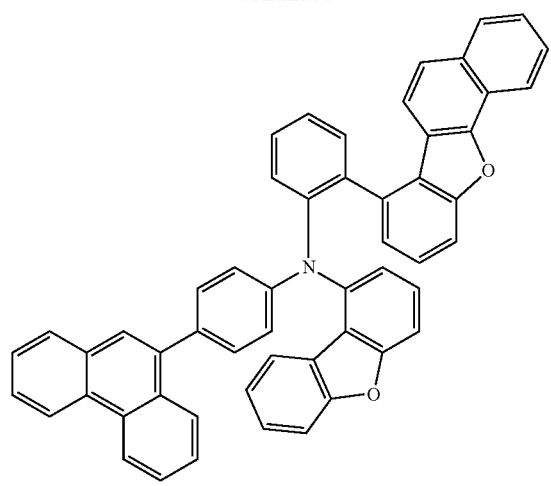
[Chem. 99]
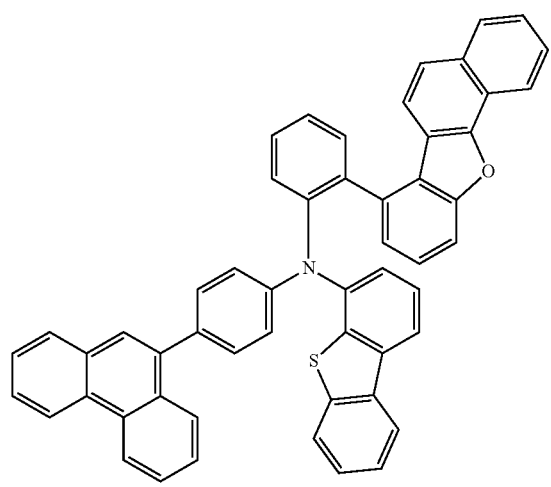
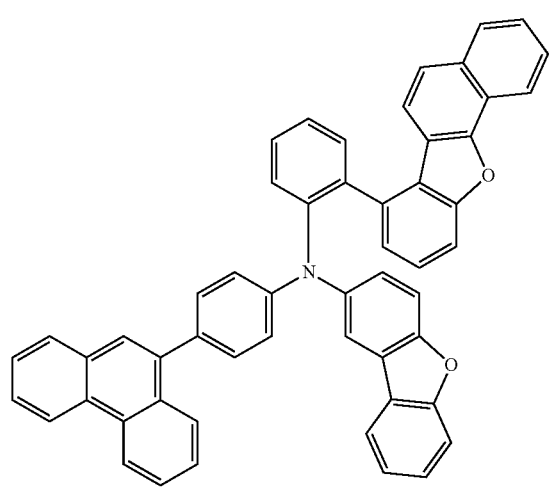
244
-continued
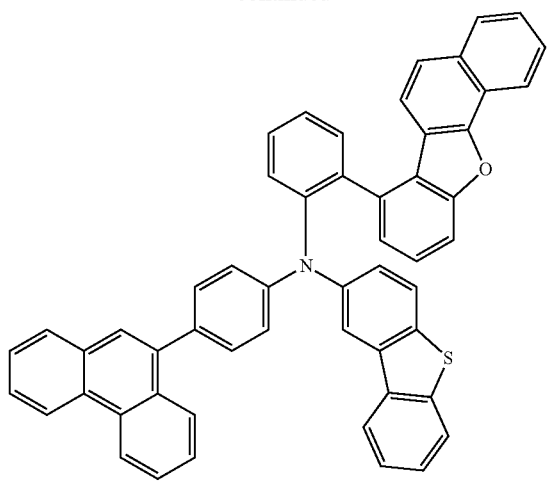
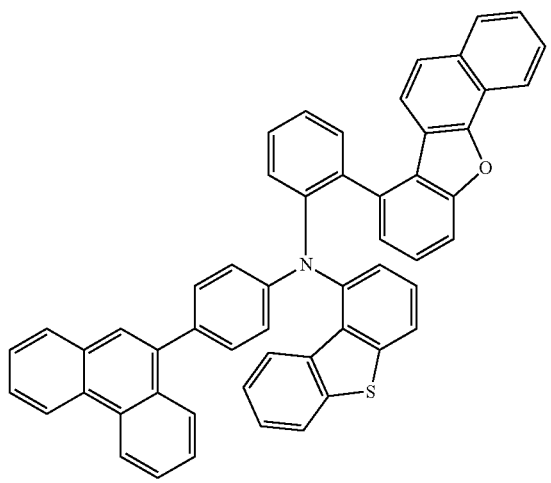
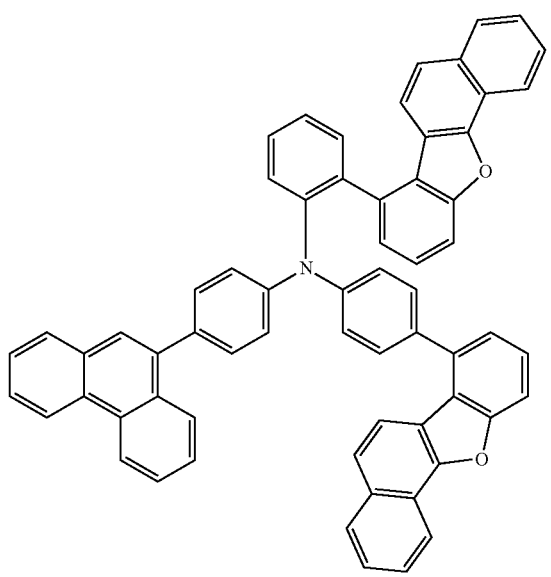

245
-continued
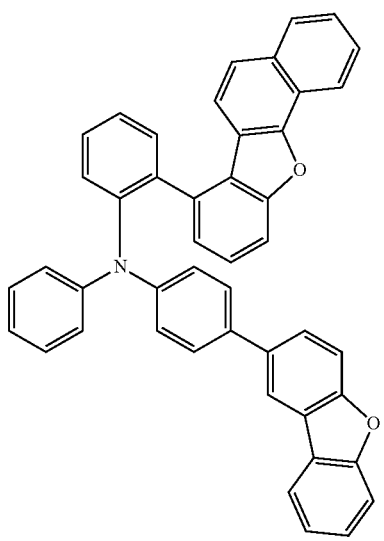
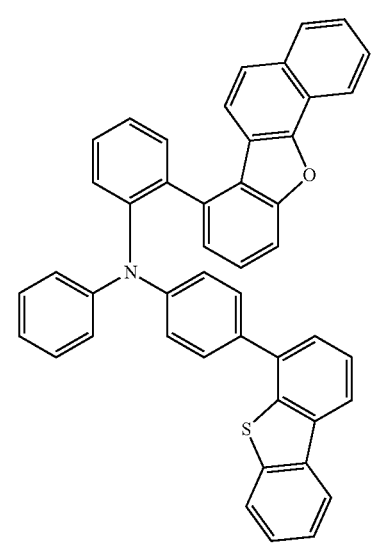
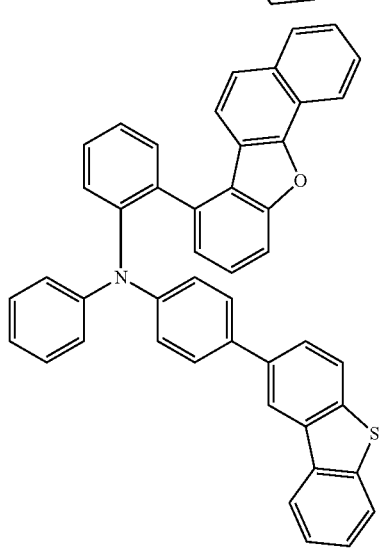
246
-continued
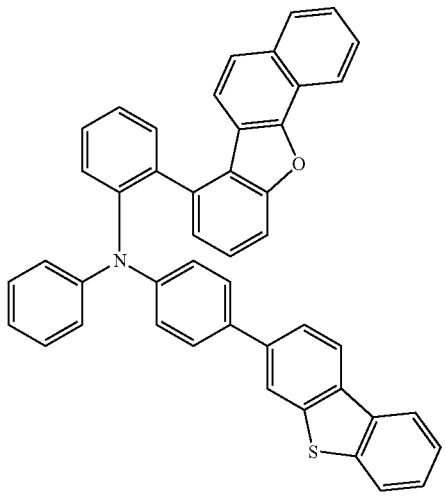
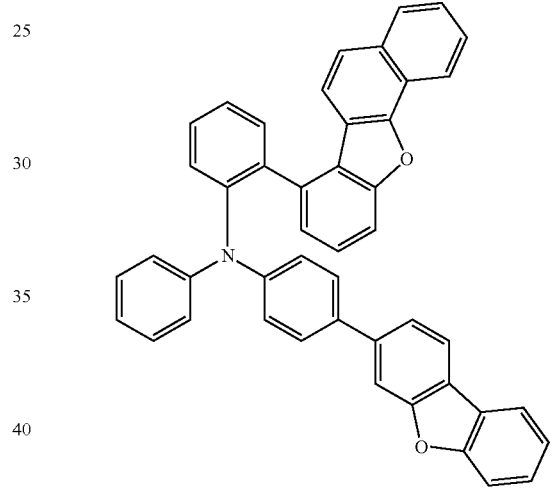
[Chem. 100]
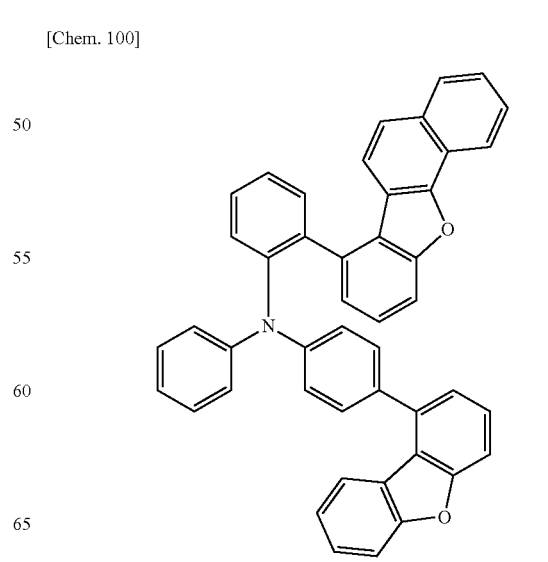

247
-continued
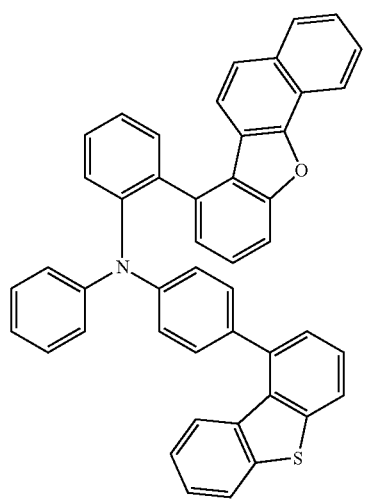
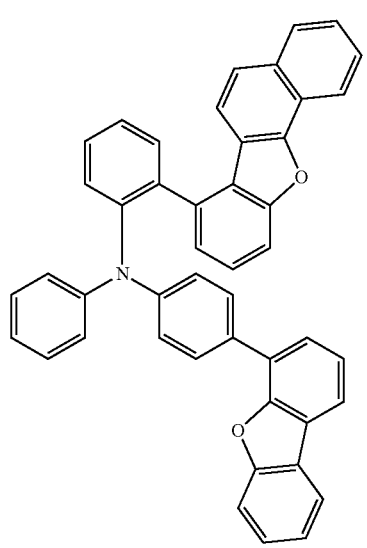
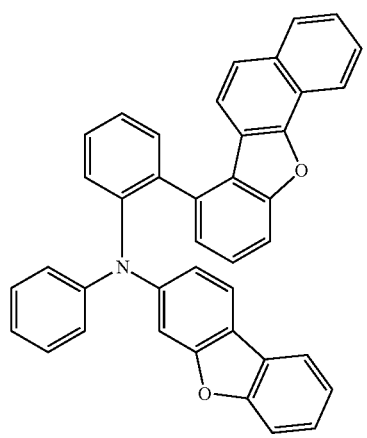
248
-continued
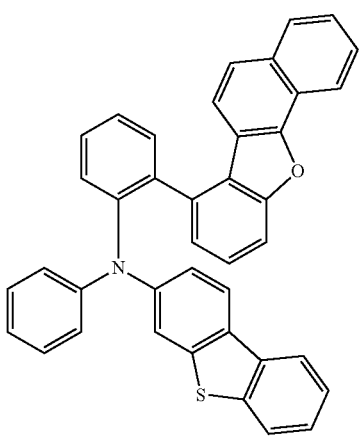
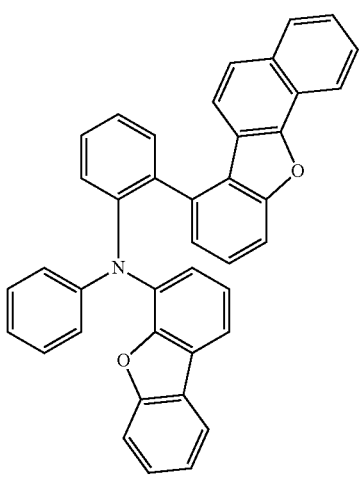
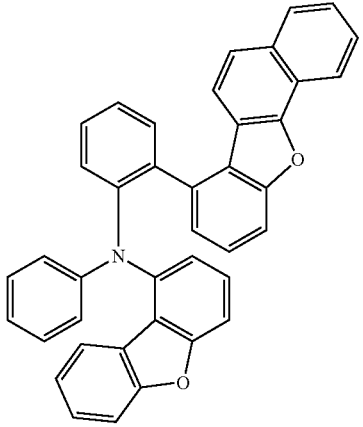

249
-continued
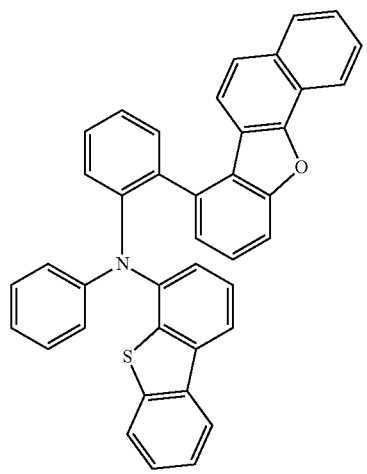
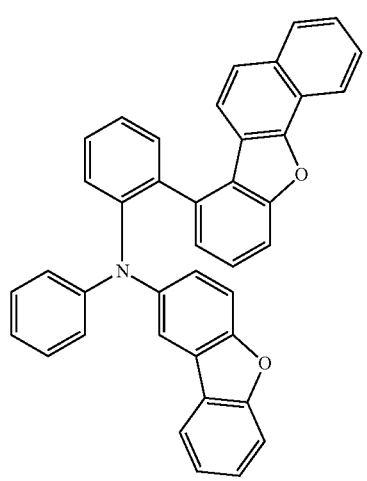
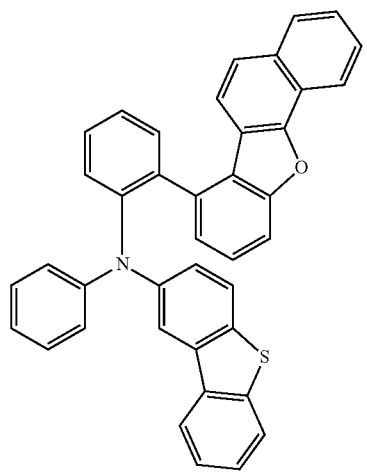
250
-continued
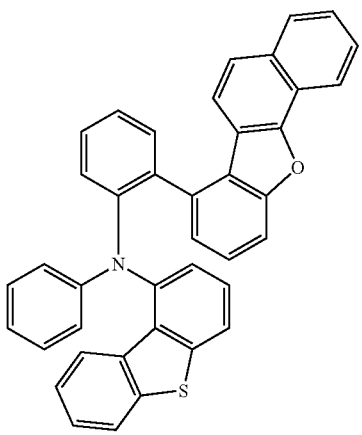
[Chem. 101]
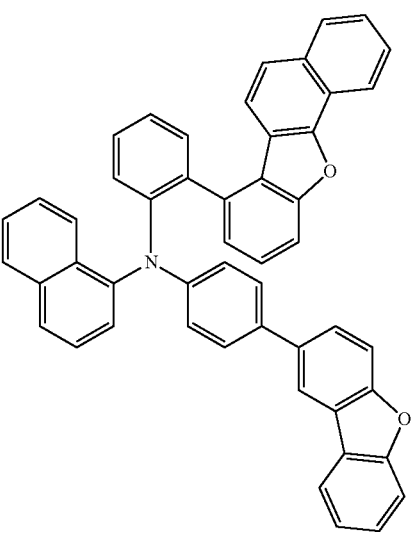

-continued
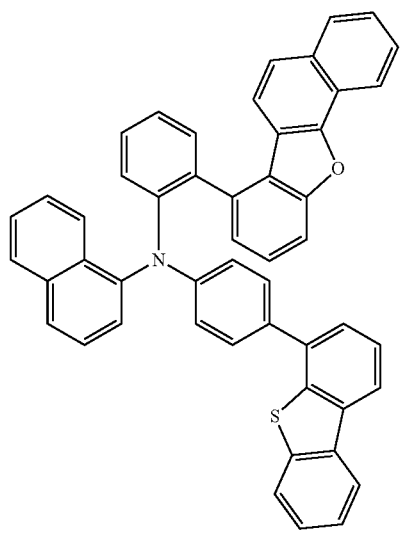
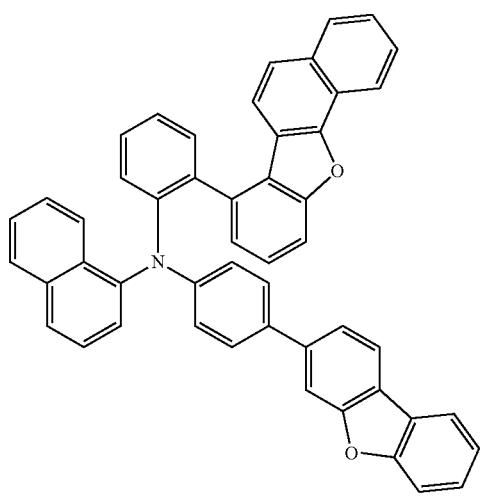
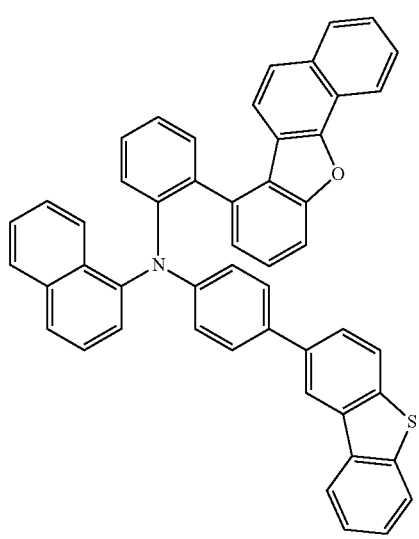
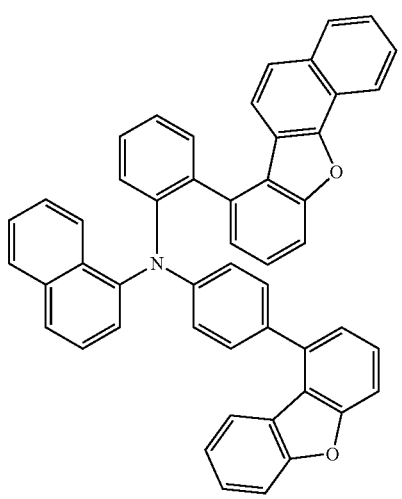
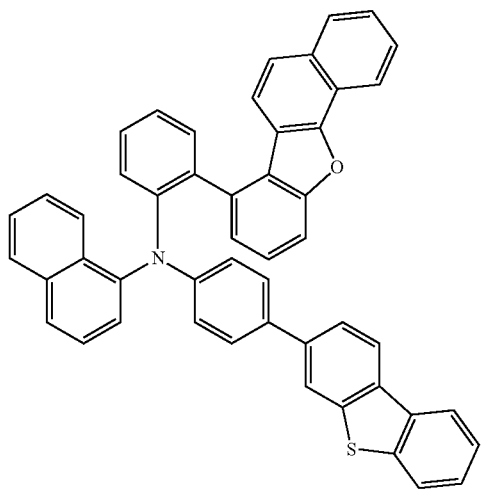
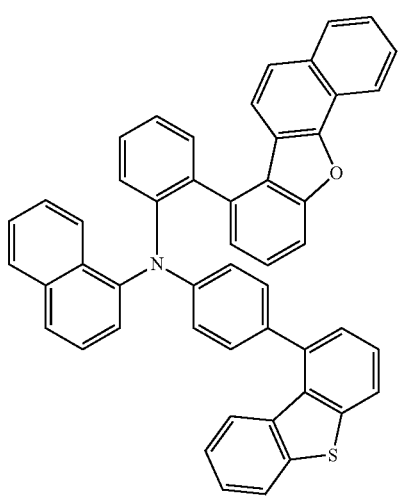

253
-continued
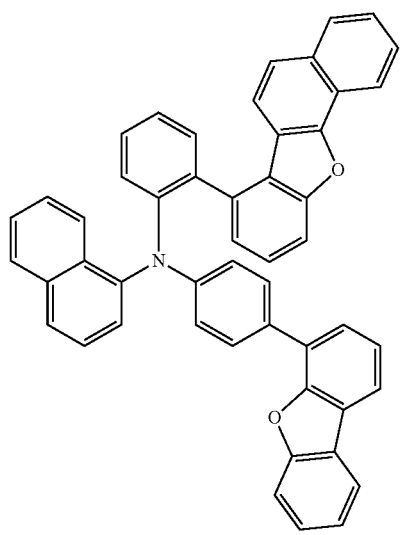
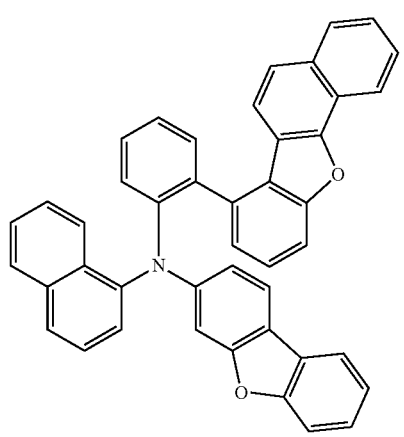
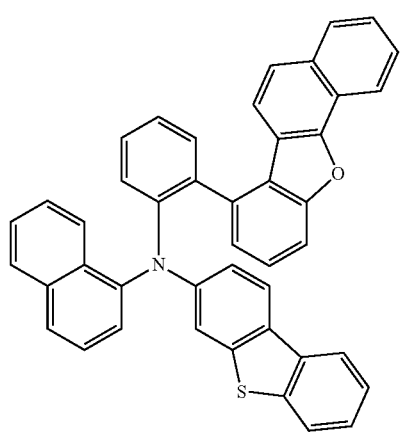
254
-continued
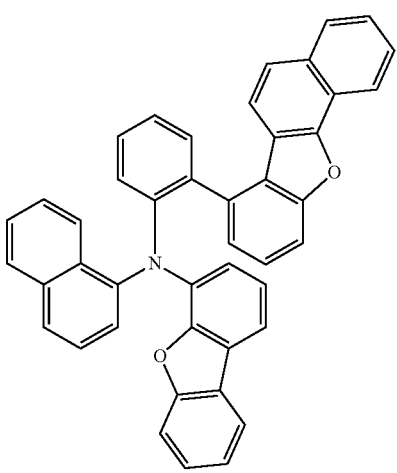
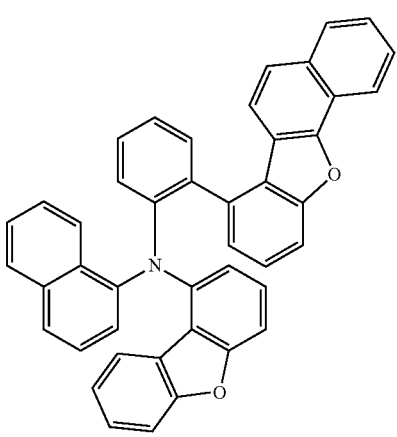
[Chem. 102]
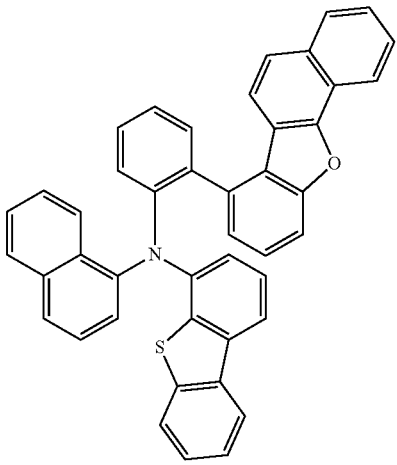

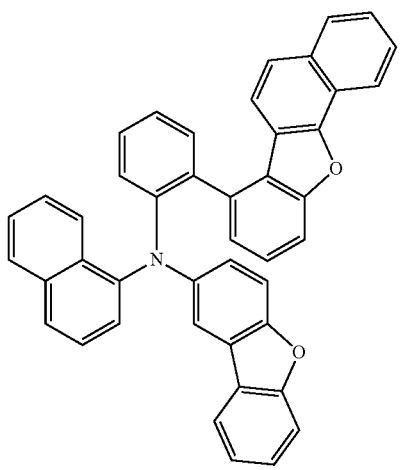
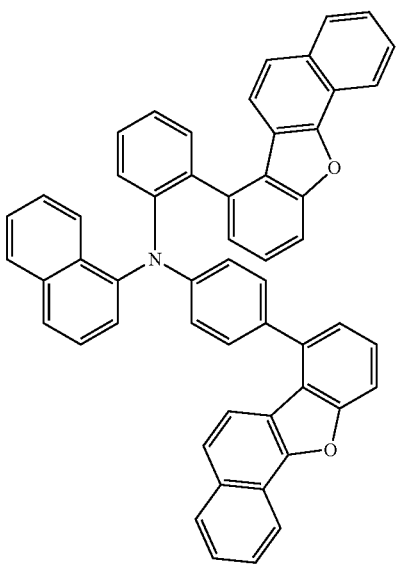
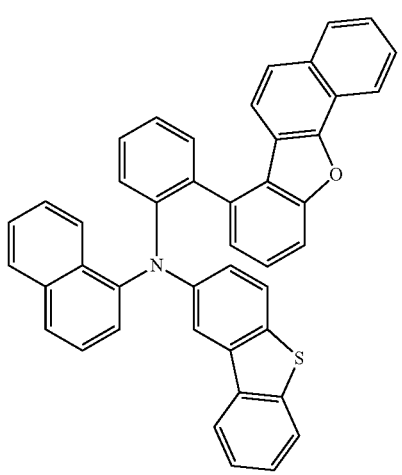
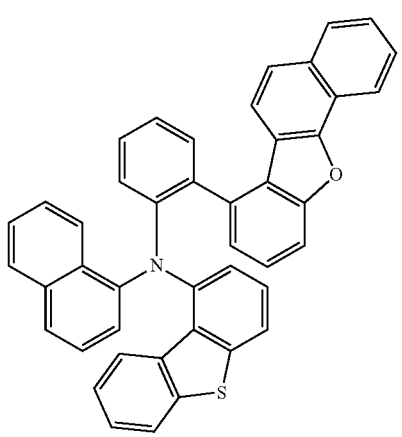

257
-continued
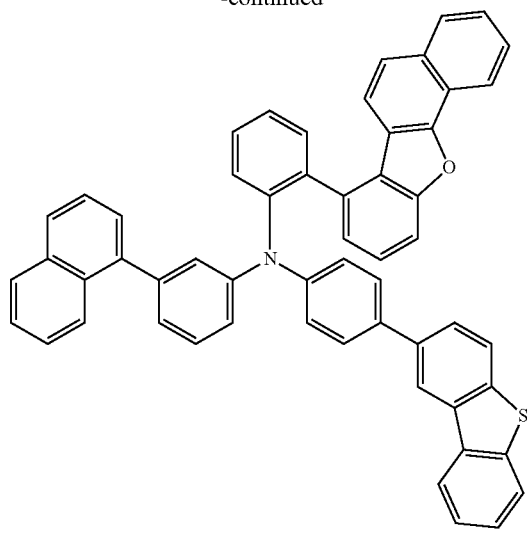
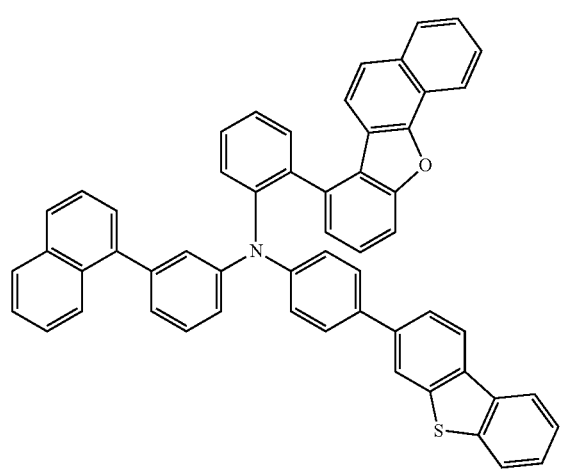
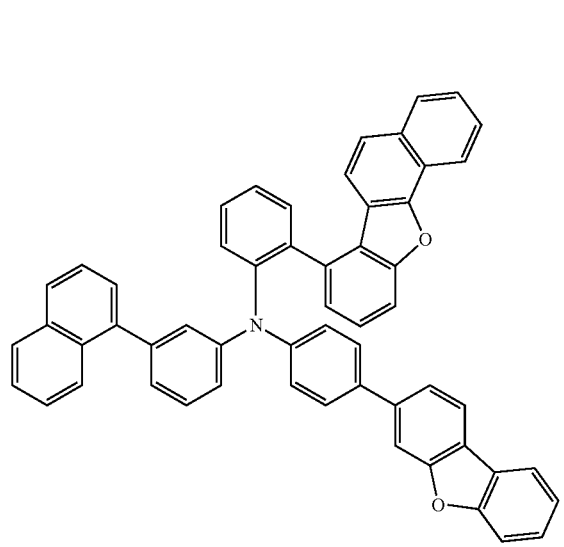
258
-continued
[Chem. 103]
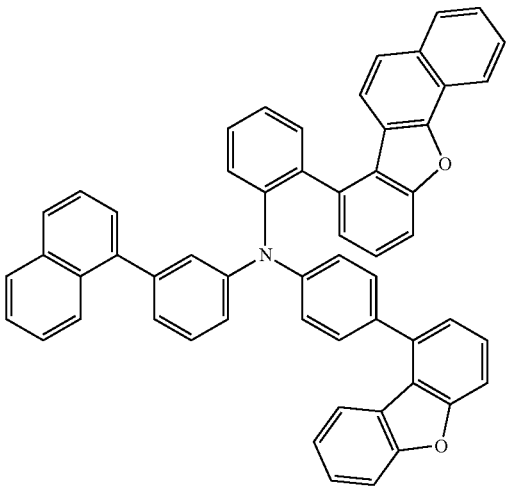
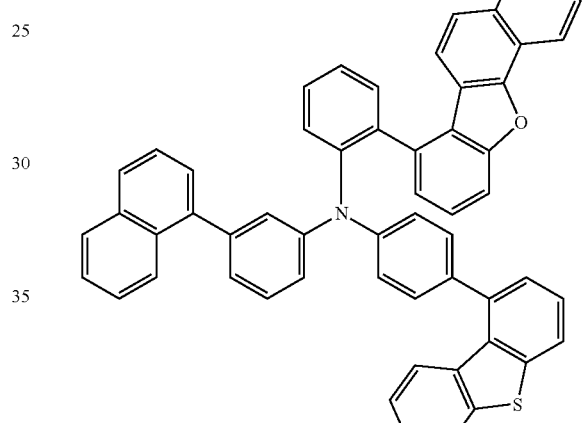
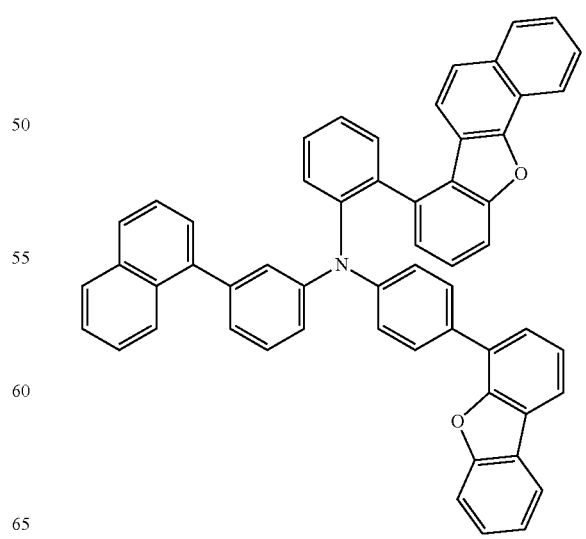

259
-continued
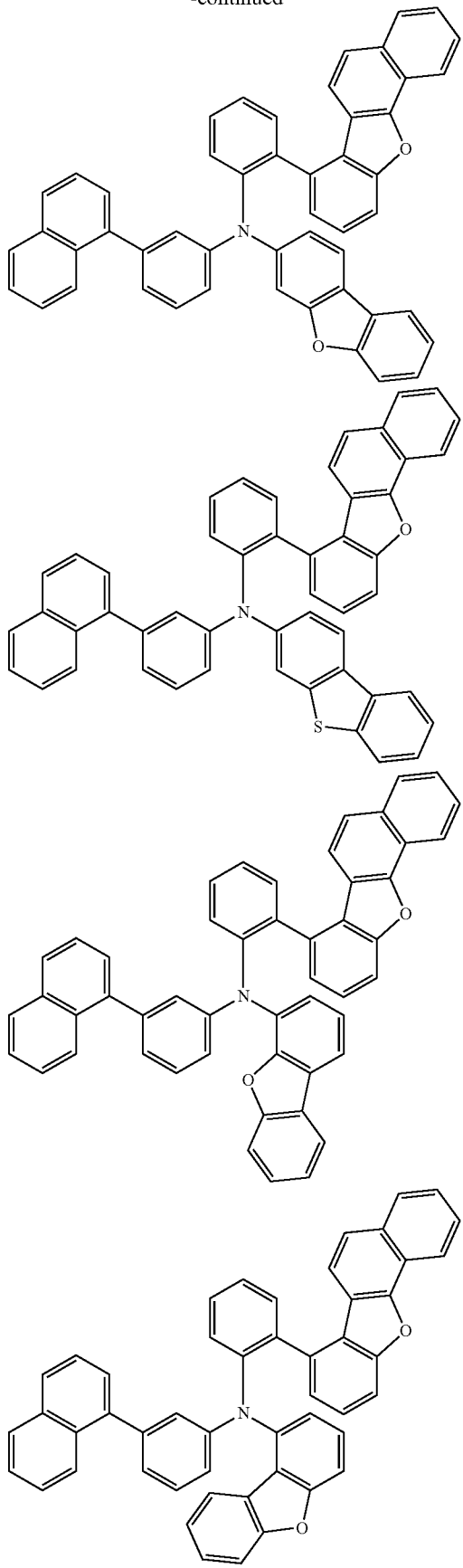
260
-continued
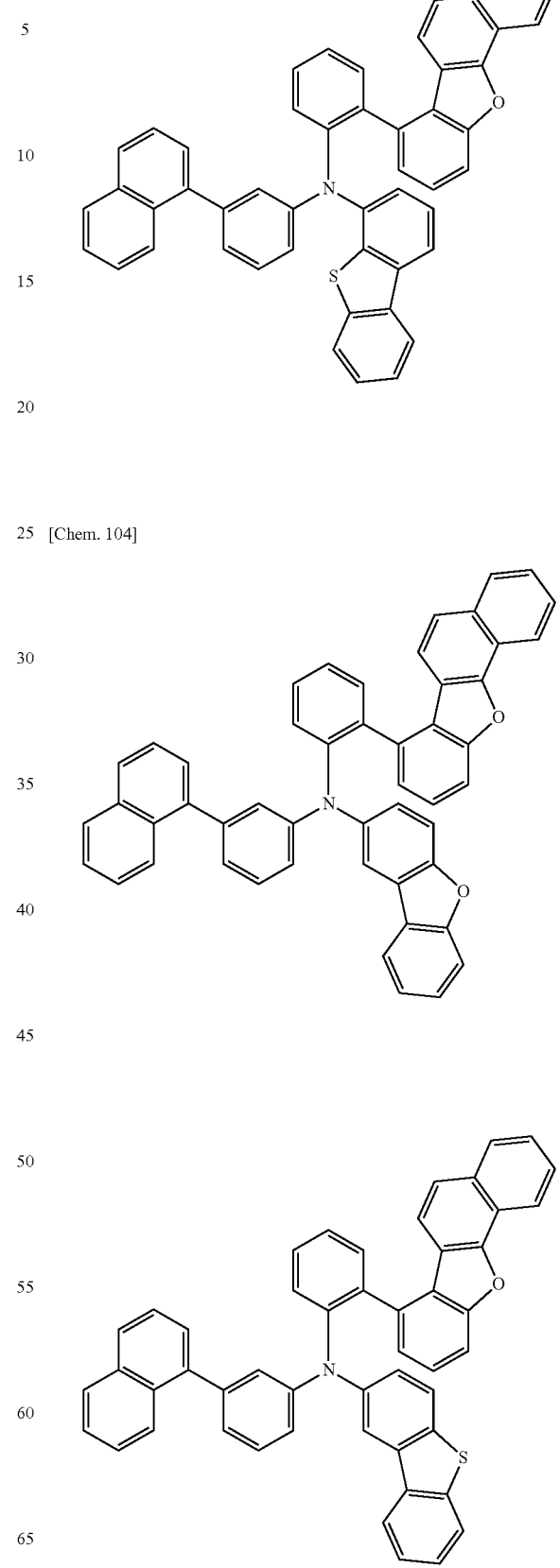
[Chem. 104]

261
-continued
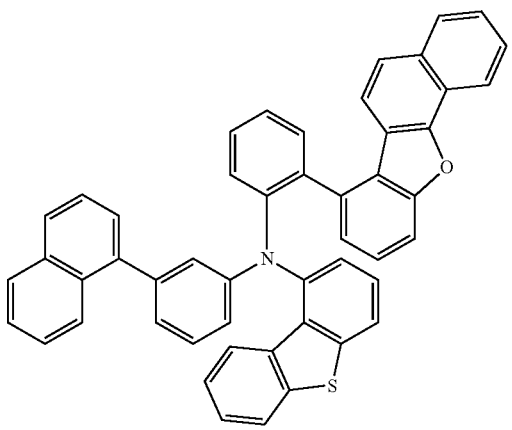
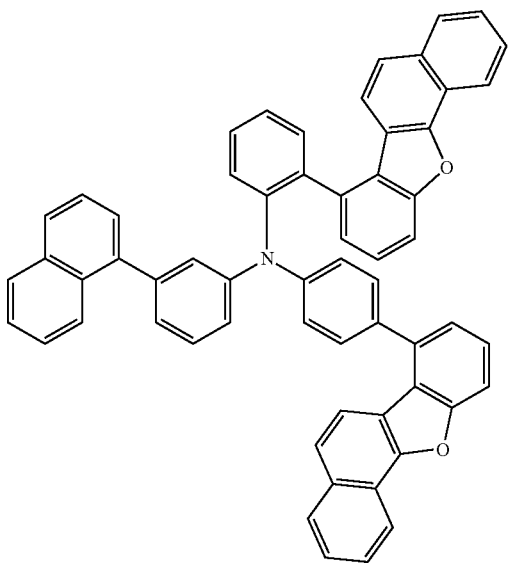
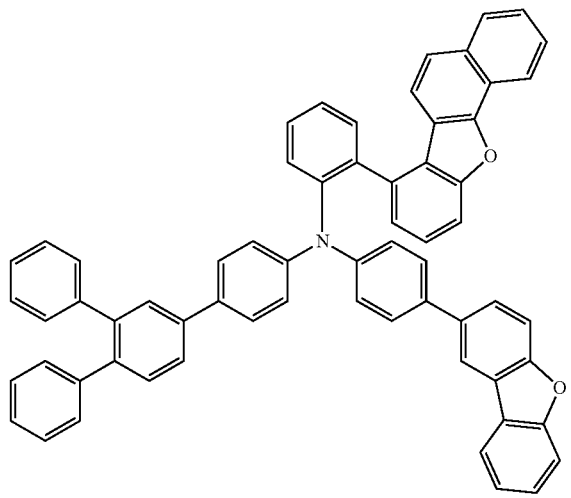
262
-continued
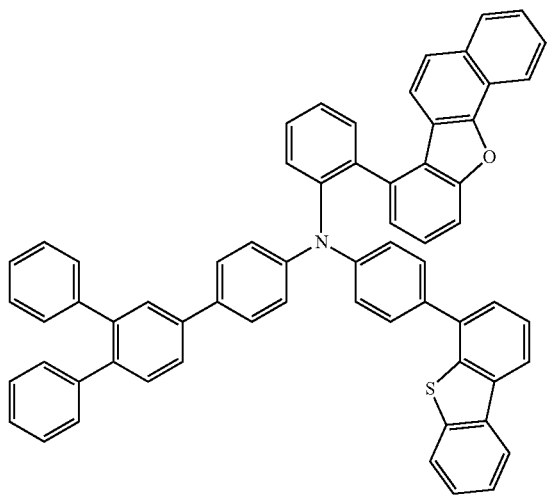
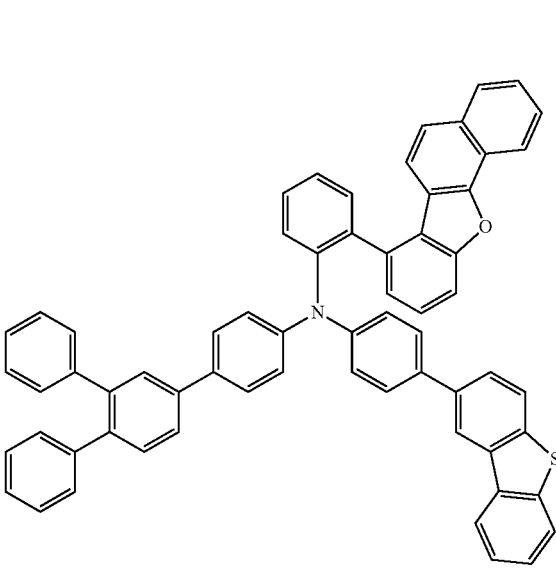
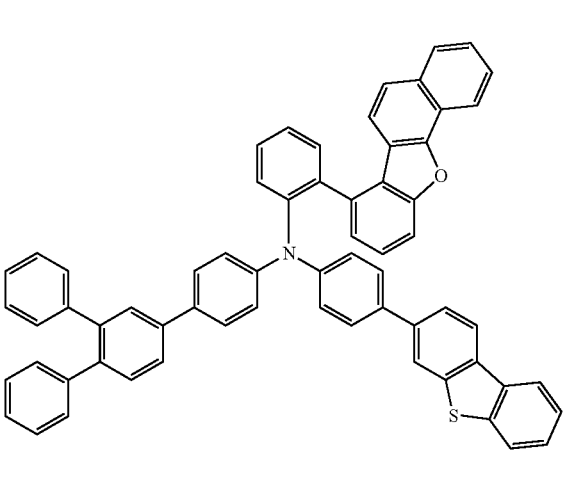

263
-continued
[Chem. 105]
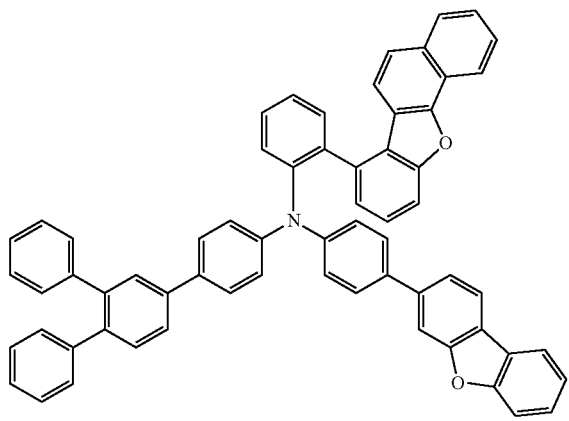
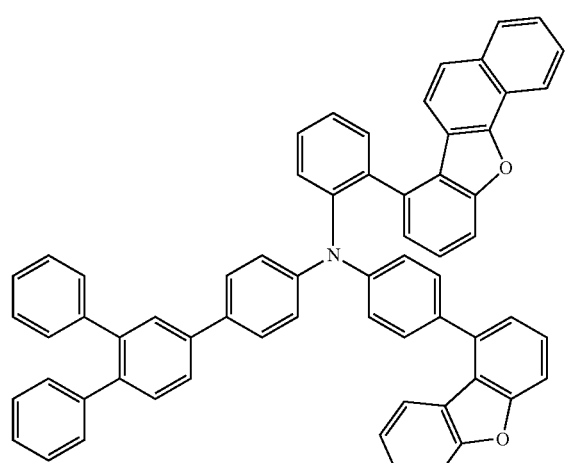
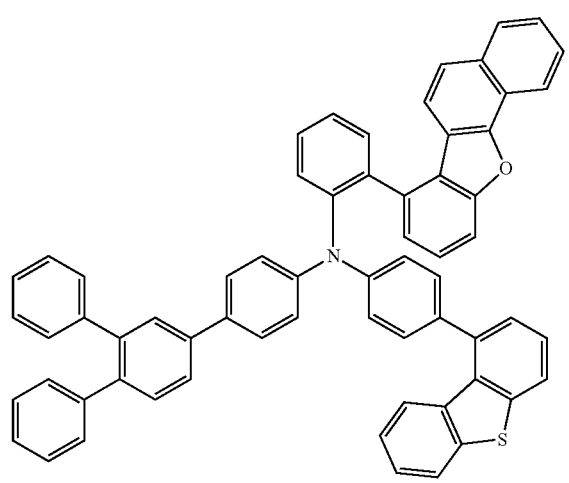
264
-continued
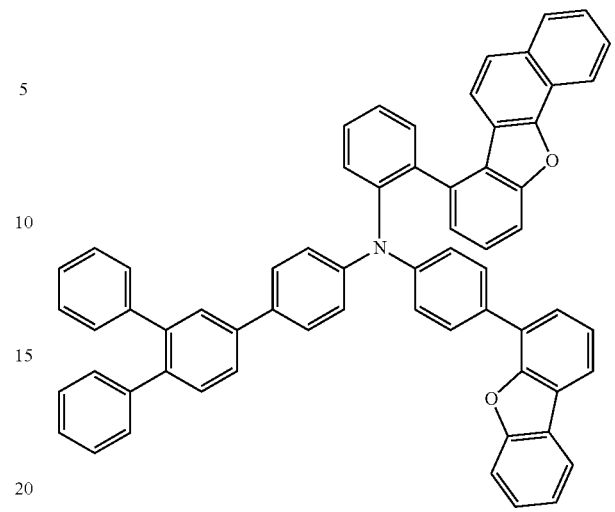
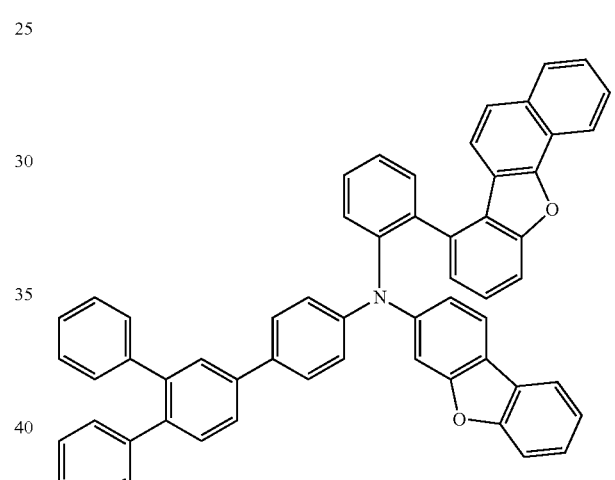
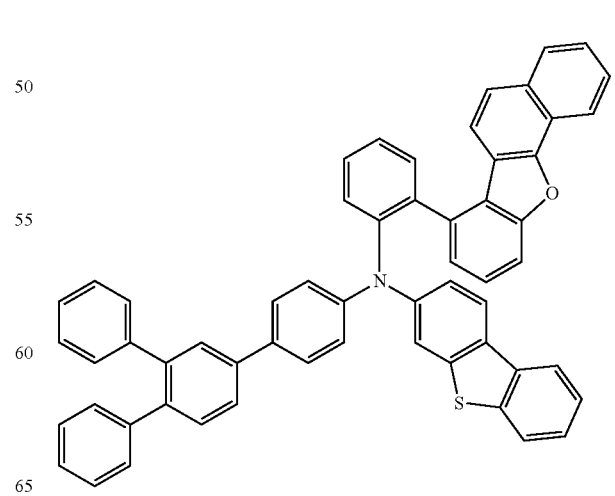

265
-continued
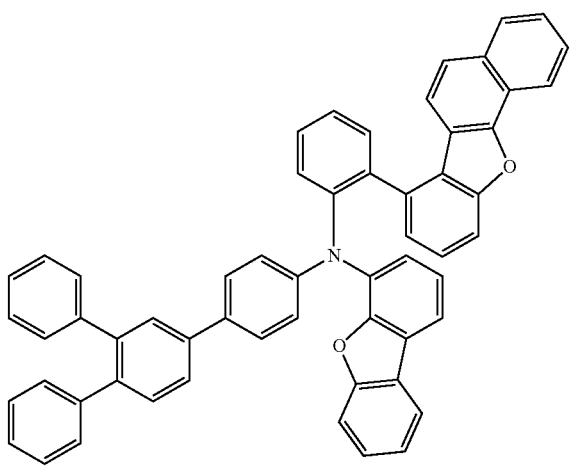
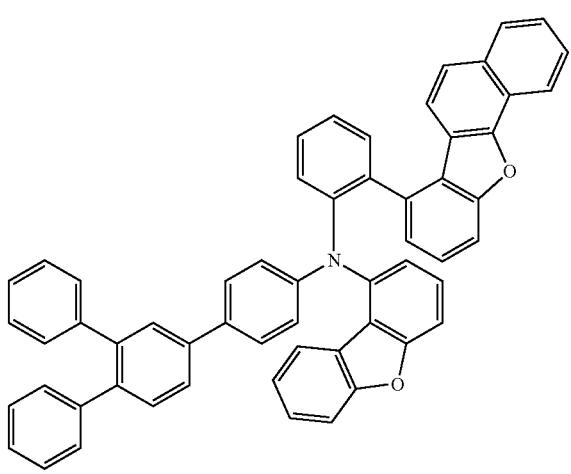
[Chem. 106]
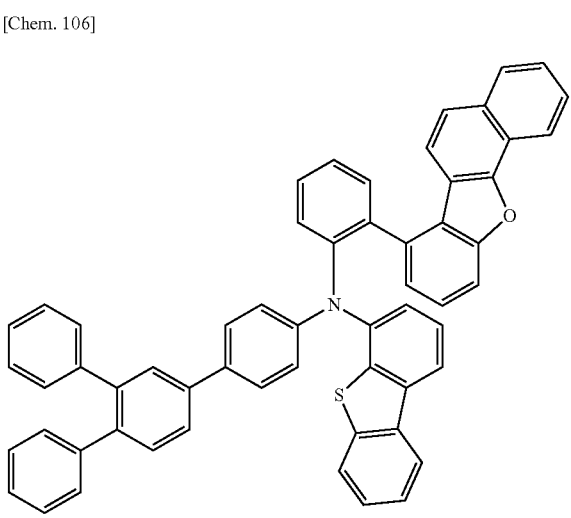
266
-continued
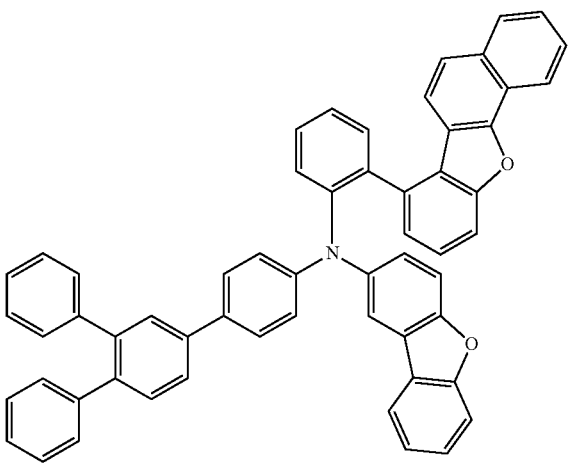
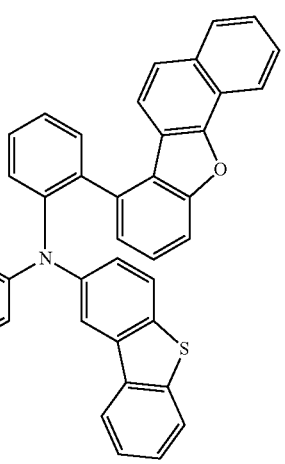
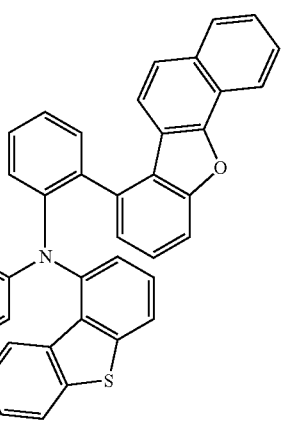

267
-continued
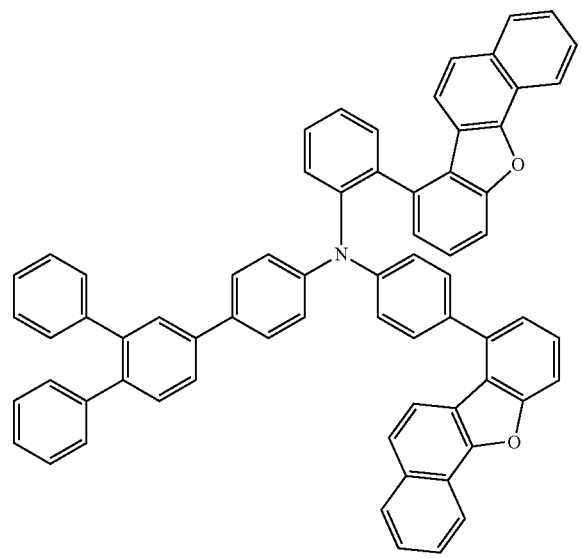
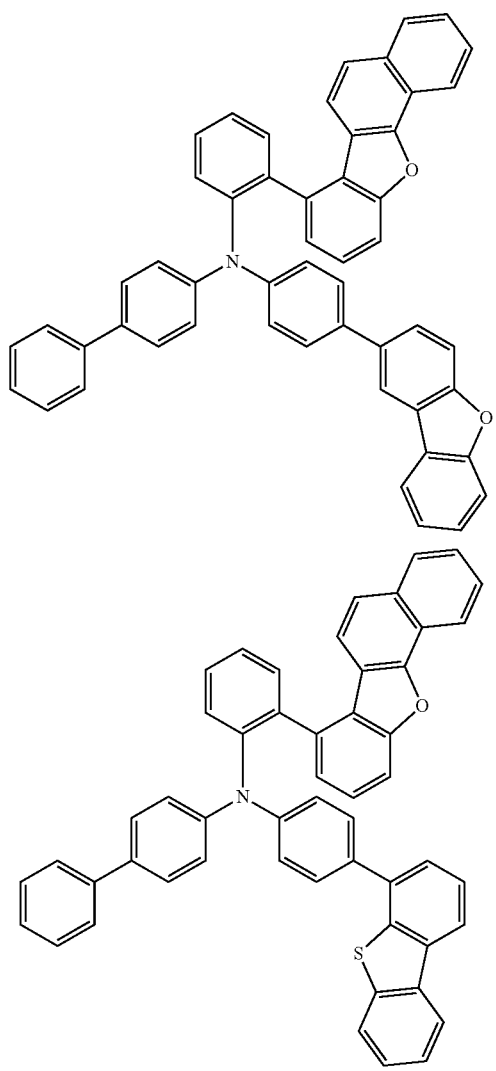
268
-continued
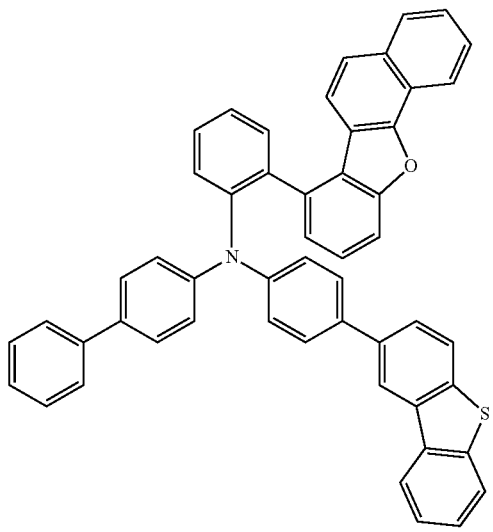
[Chem. 107]

269
-continued
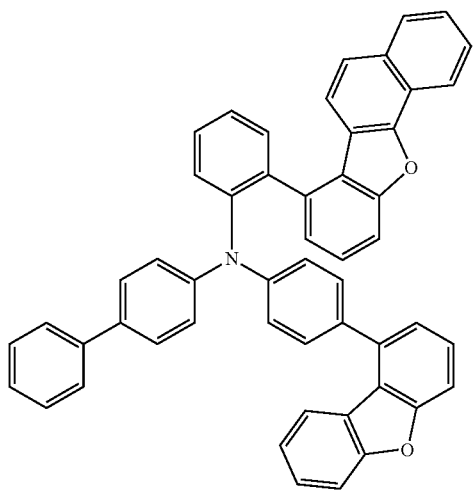
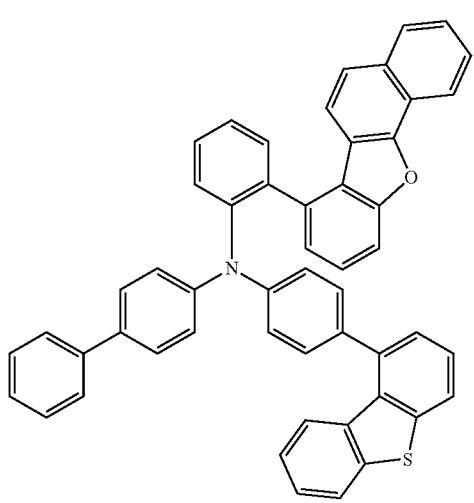
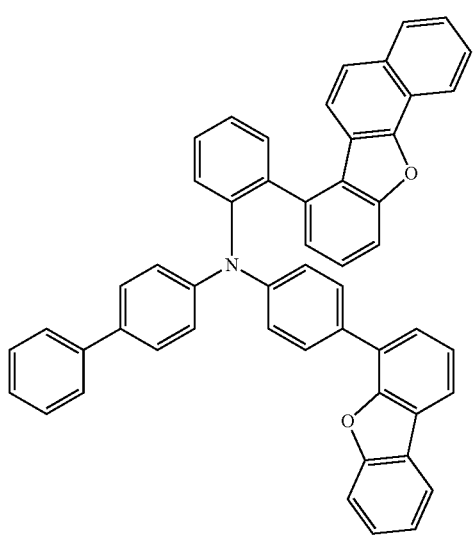
270
-continued
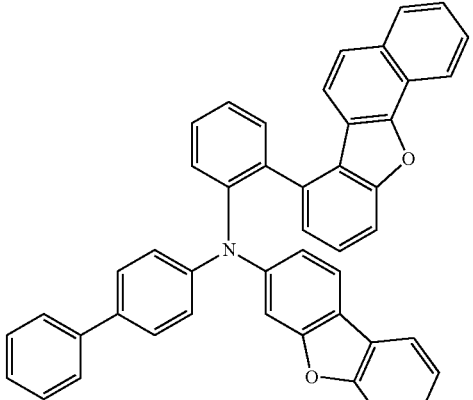
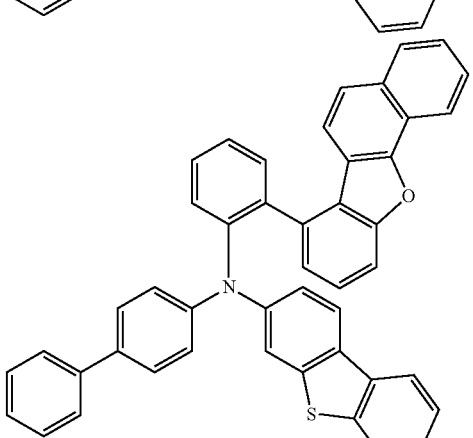
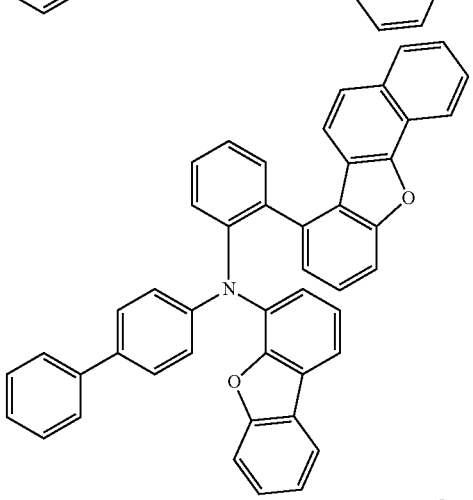
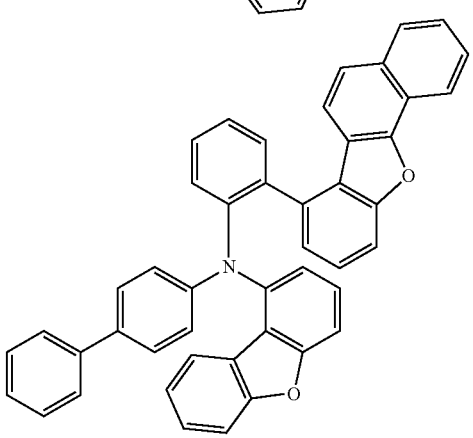

271
-continued
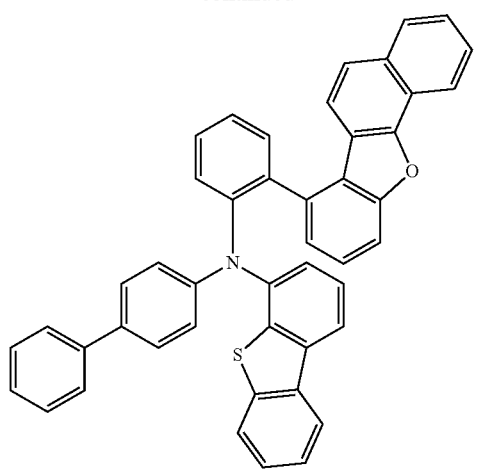
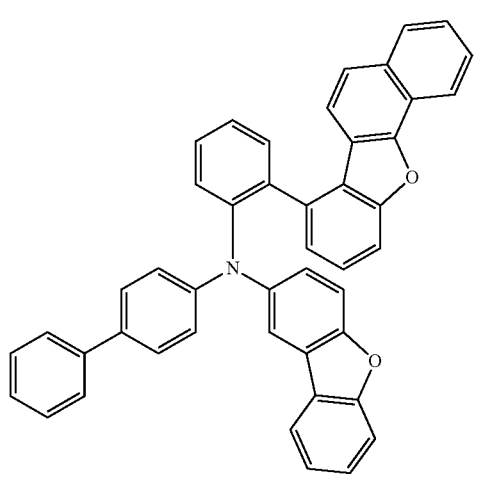
[Chem. 108]
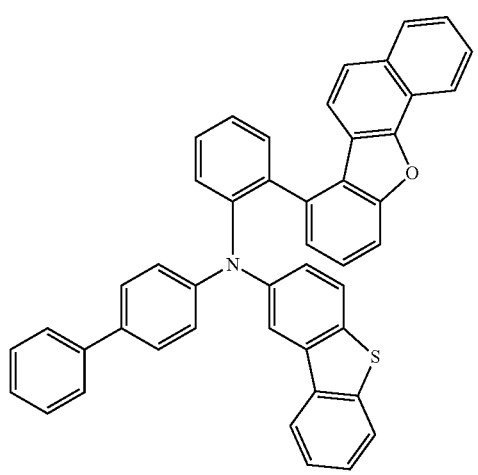
272
-continued
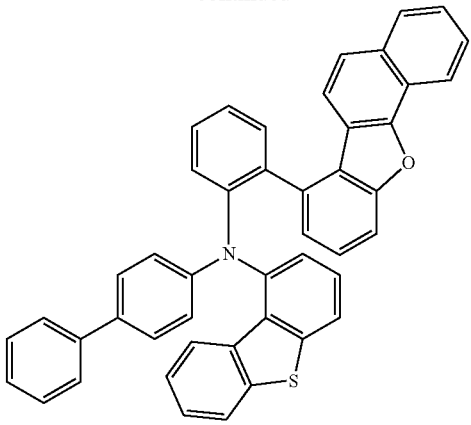
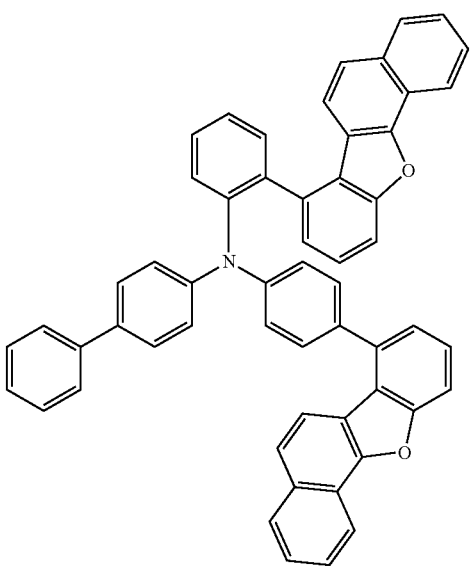
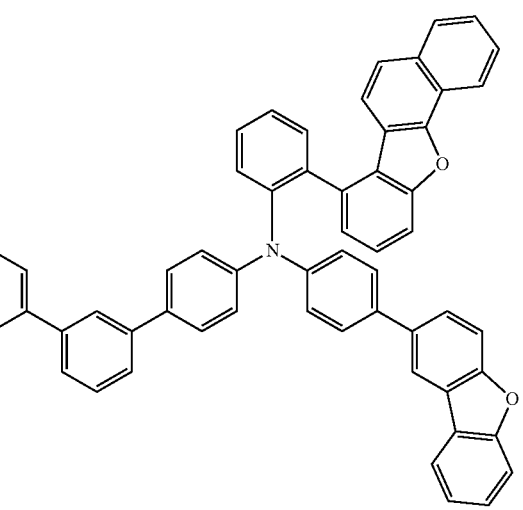

273
-continued
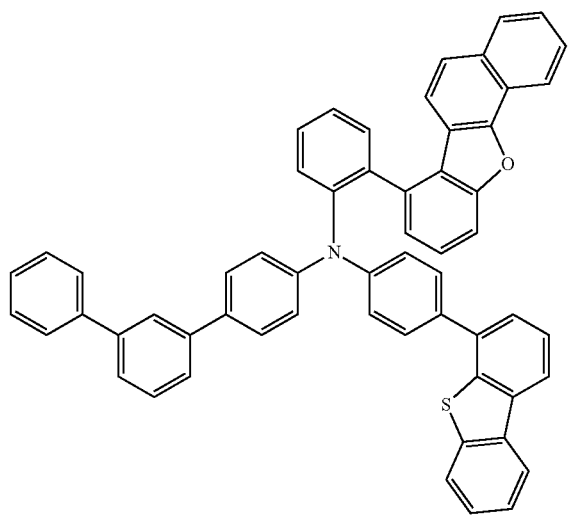
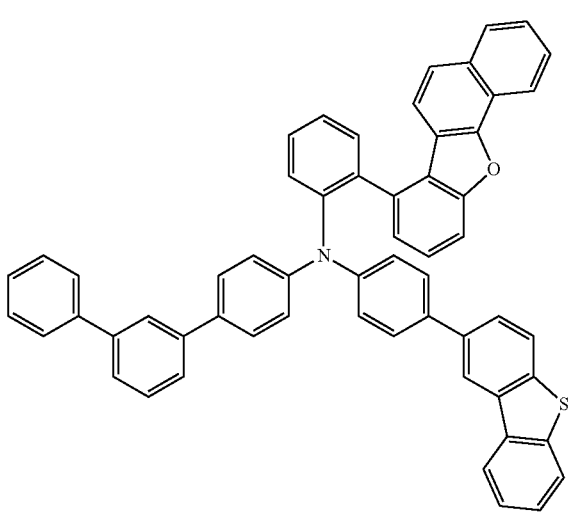
274
-continued
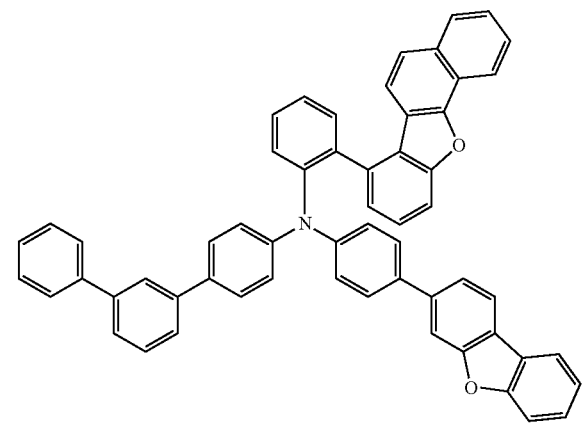
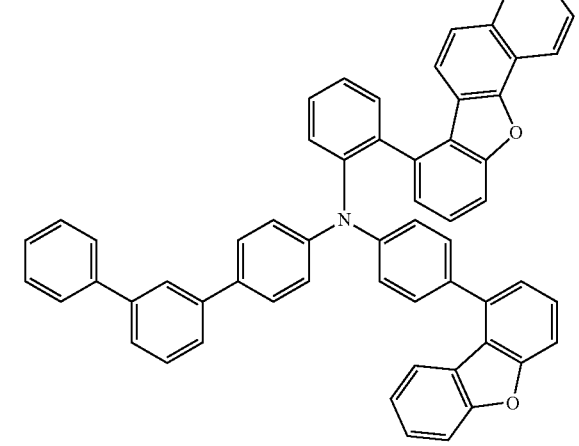
[Chem. 109]
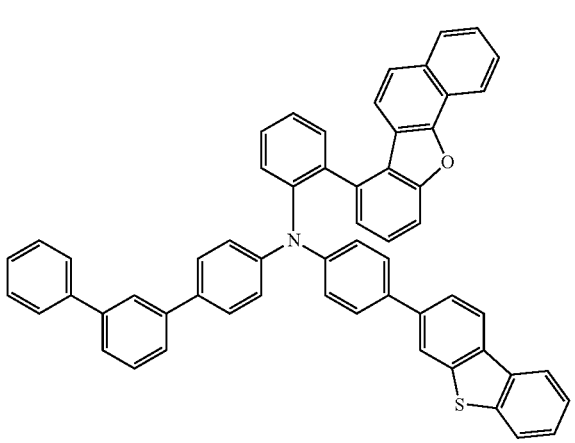
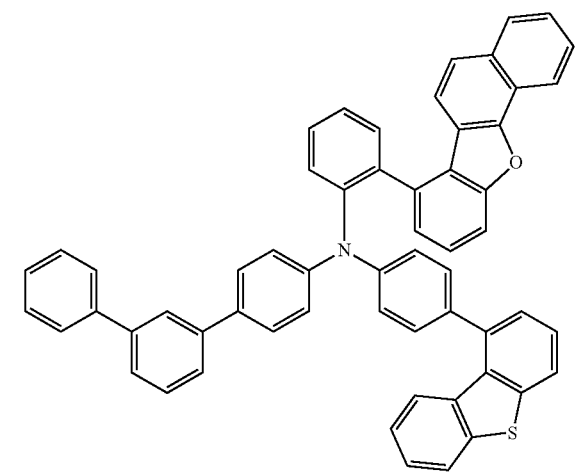

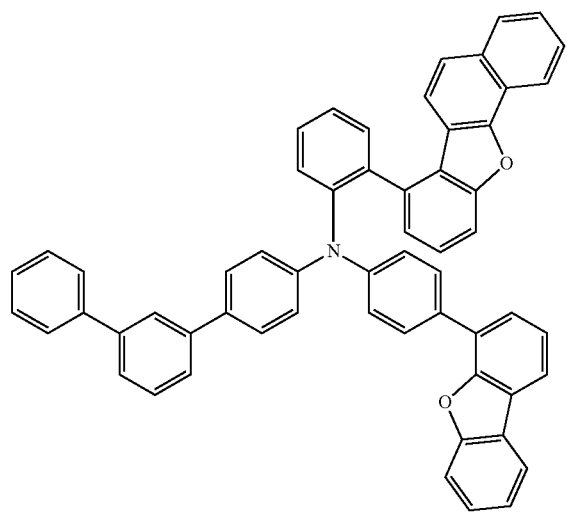
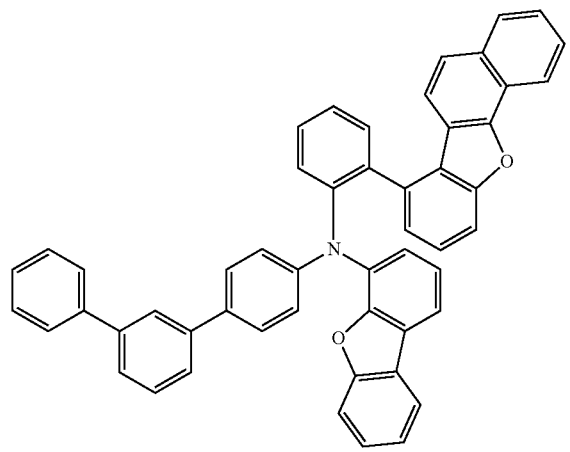
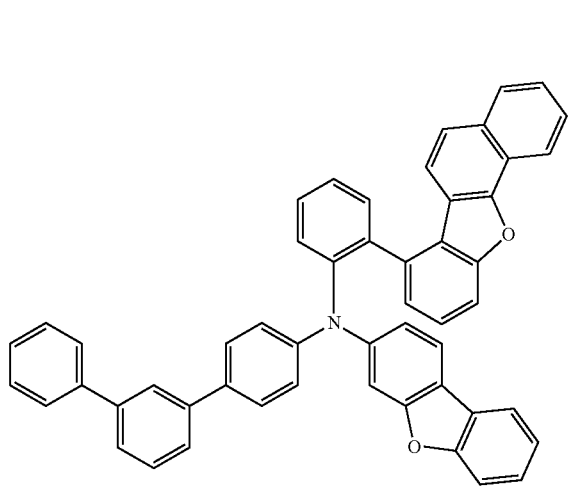
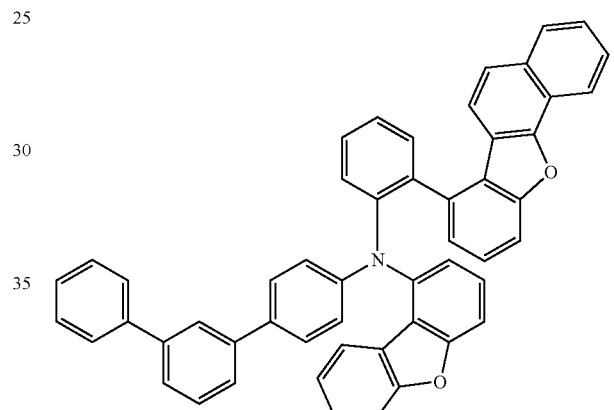
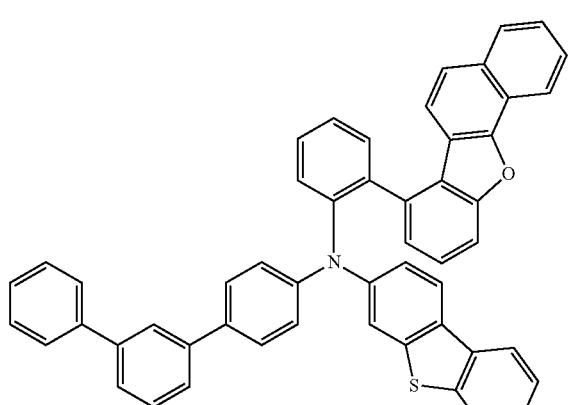
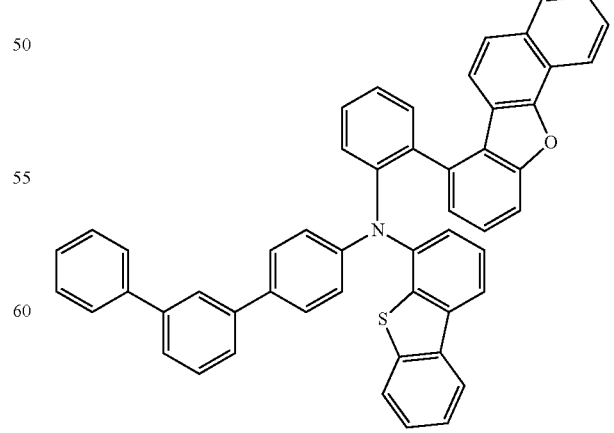

277
-continued
278
-continued
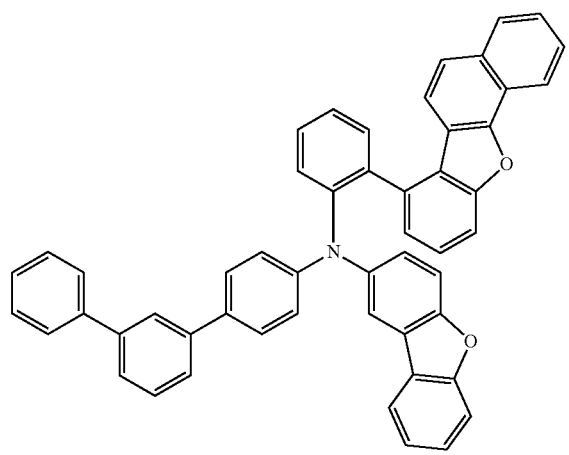
[Chem. 110]
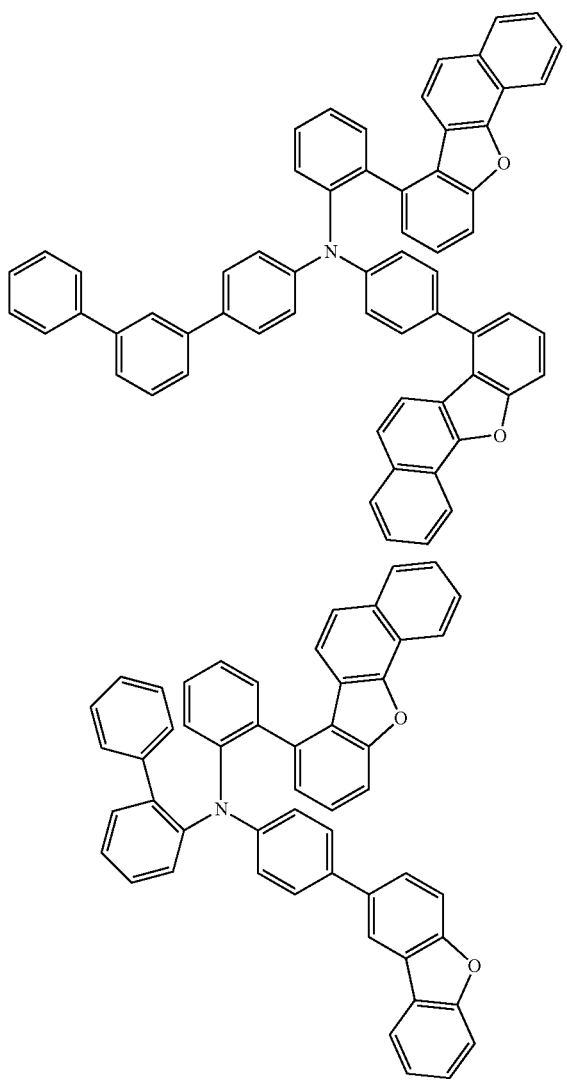
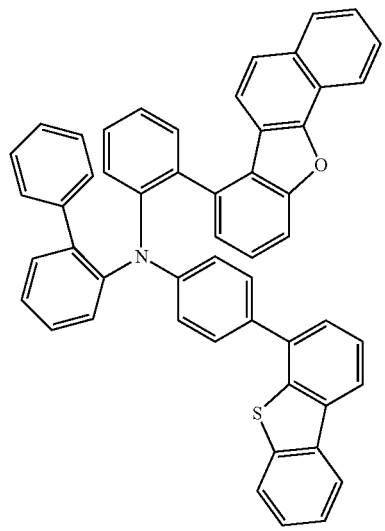

279
-continued
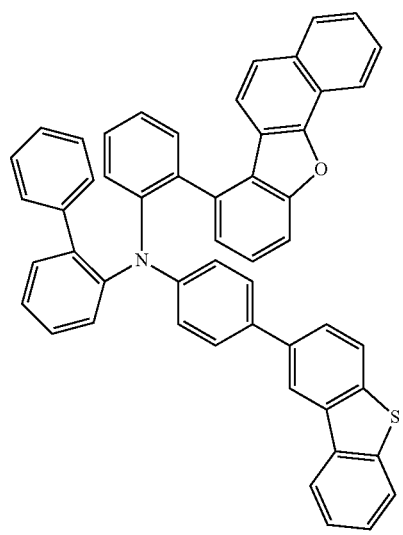
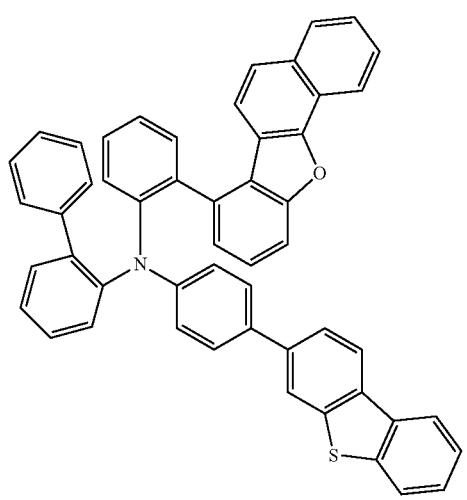
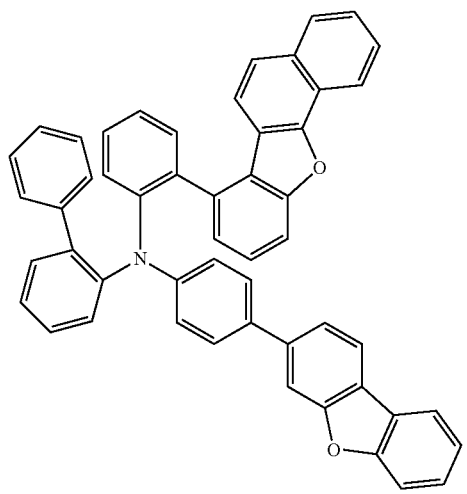
280
-continued
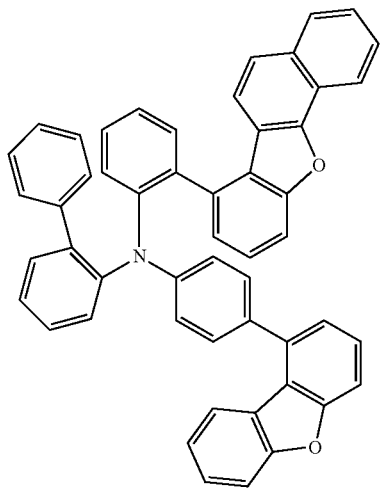
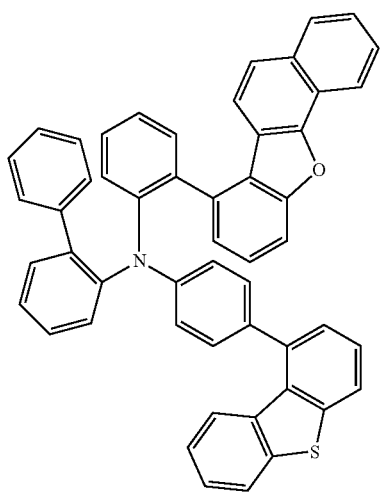
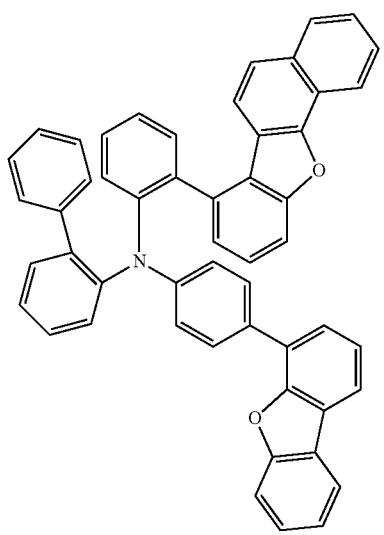

[Chem. 111]
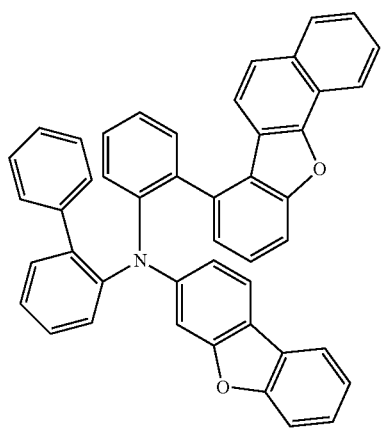
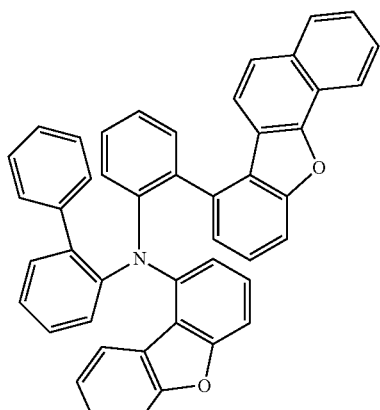
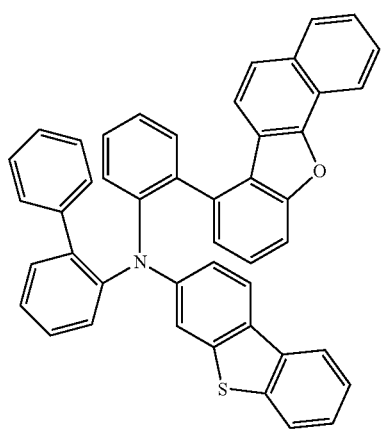
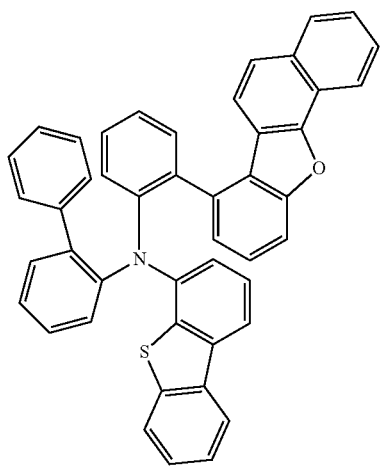
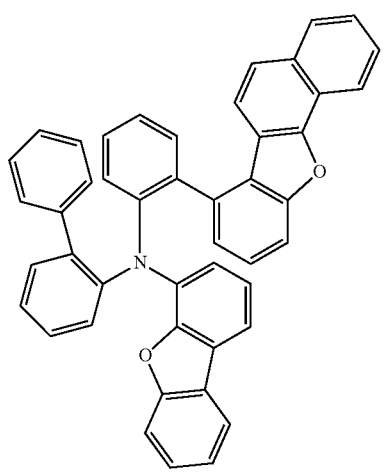
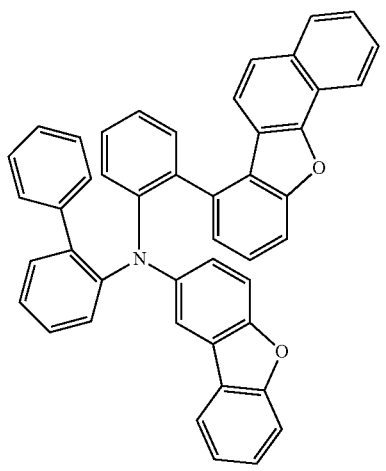

283
-continued
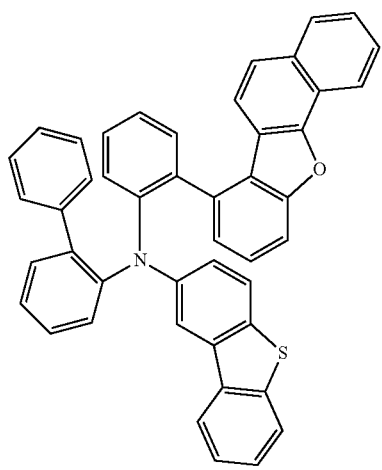
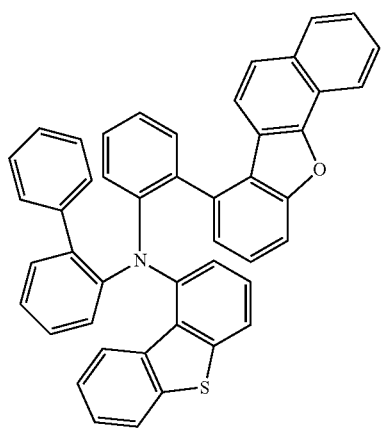
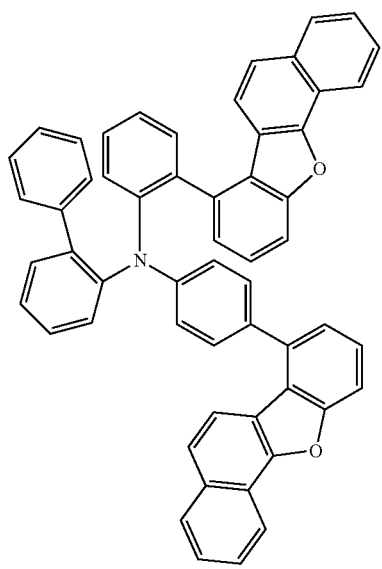
284
-continued
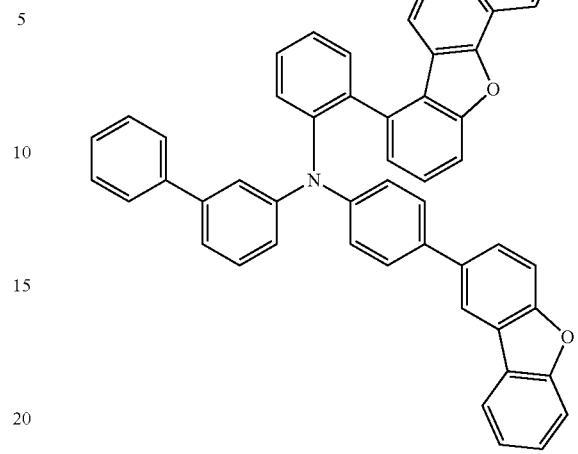
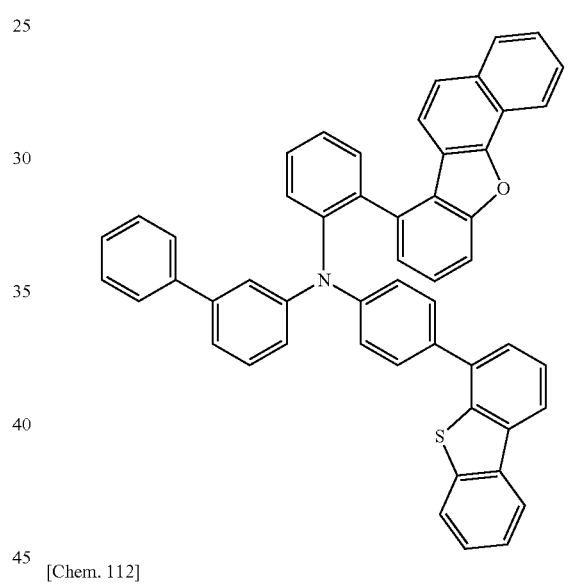
[Chem. 112]
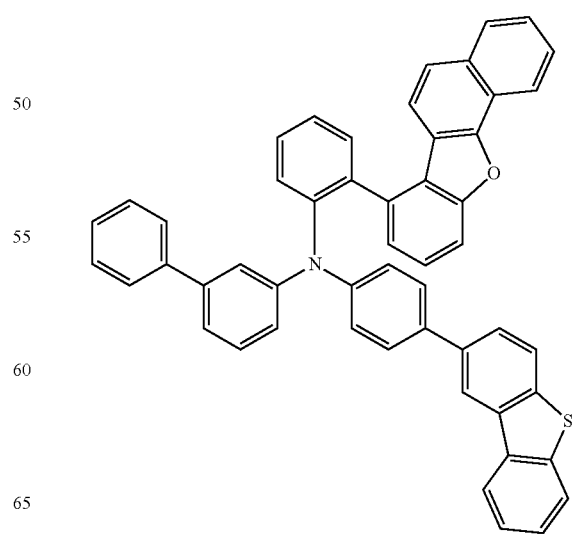

285
-continued
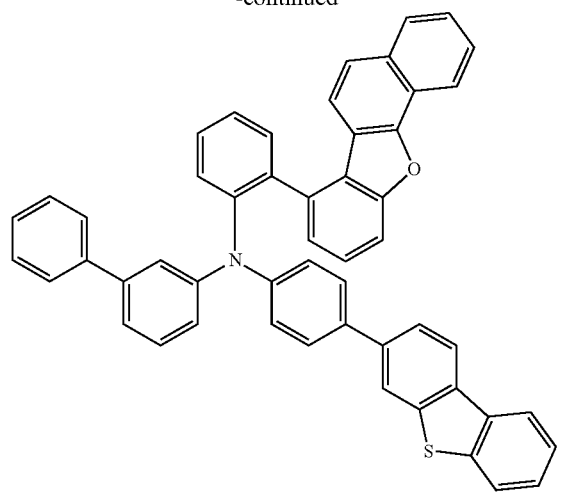
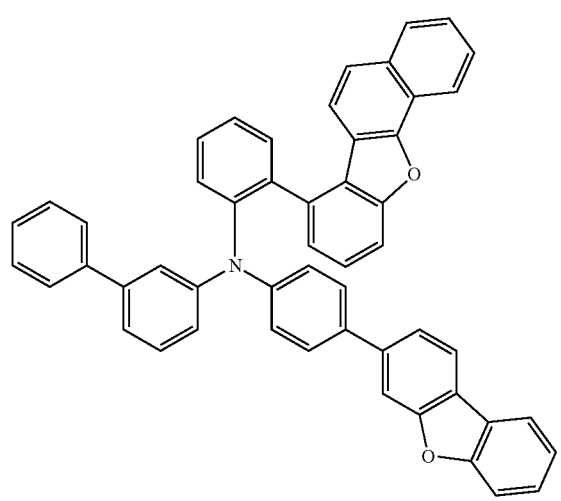
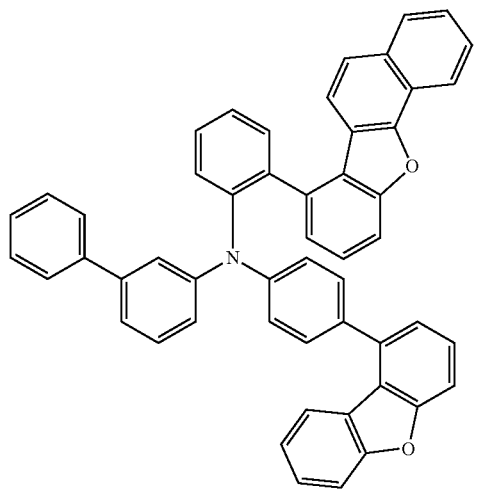
286
-continued
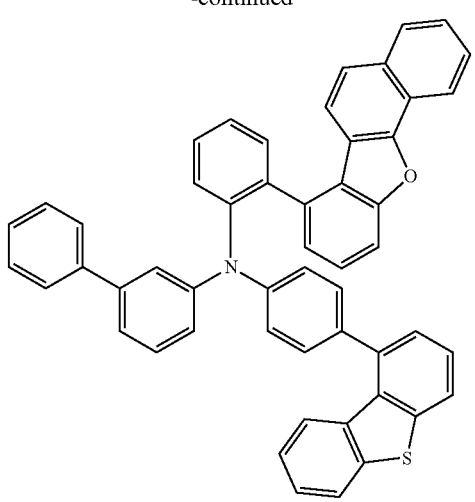
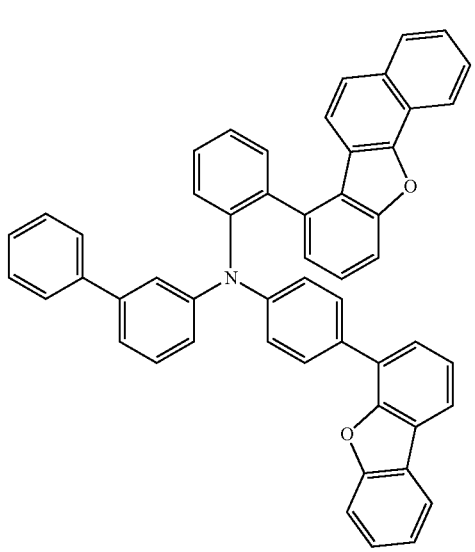
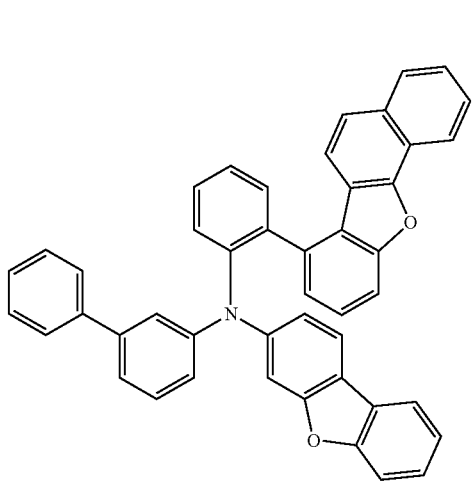

287
288
[Chem. 113]
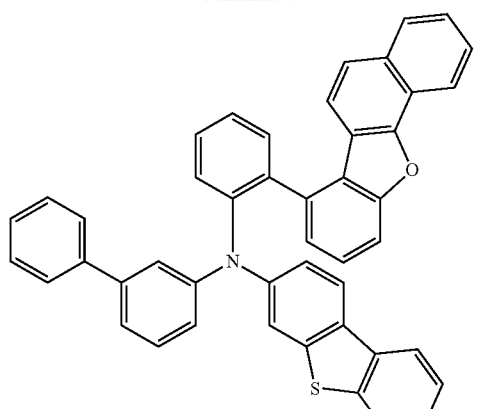
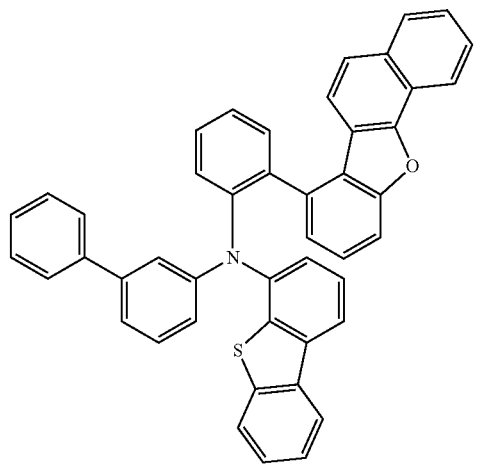
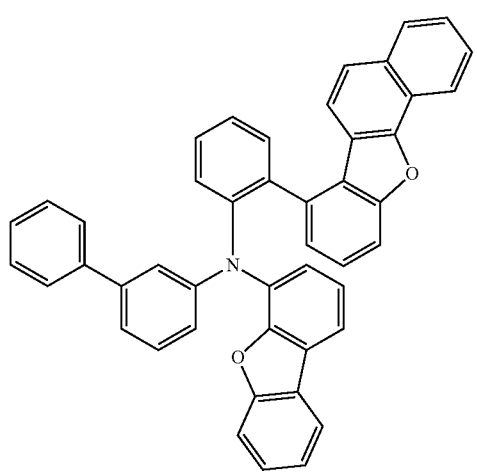
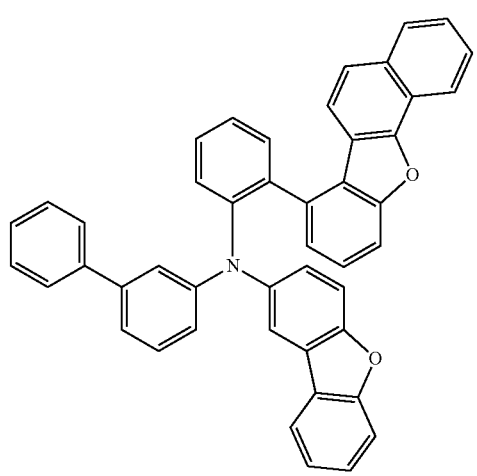
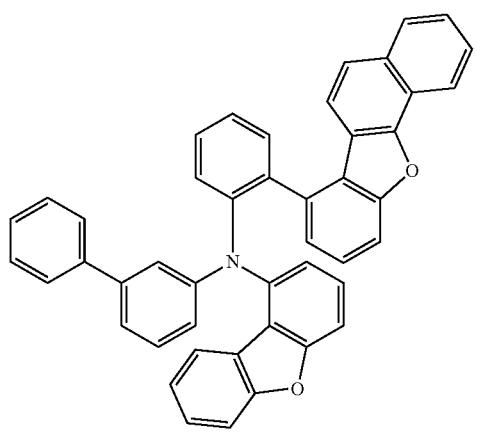
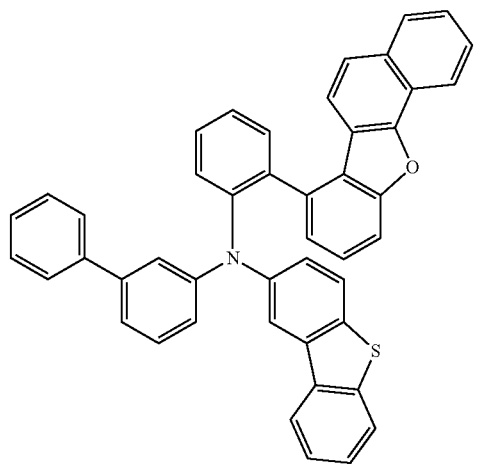

289
-continued
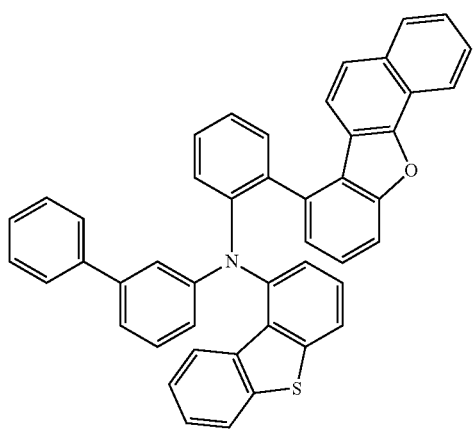
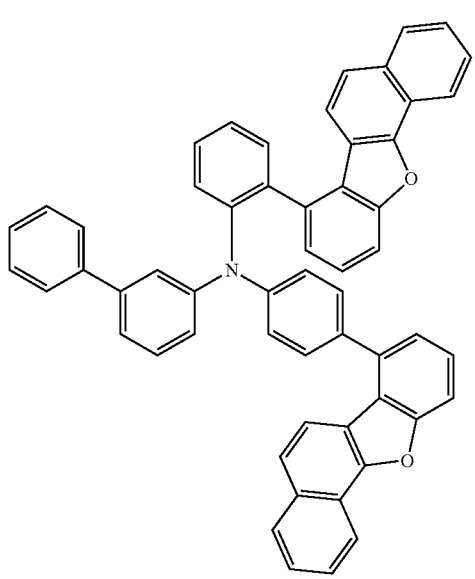
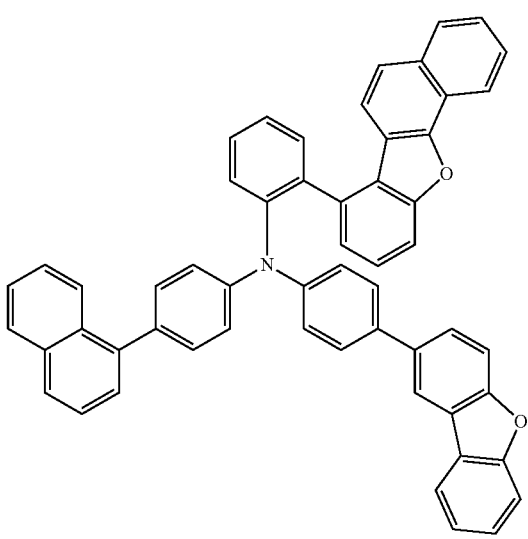
290
-continued
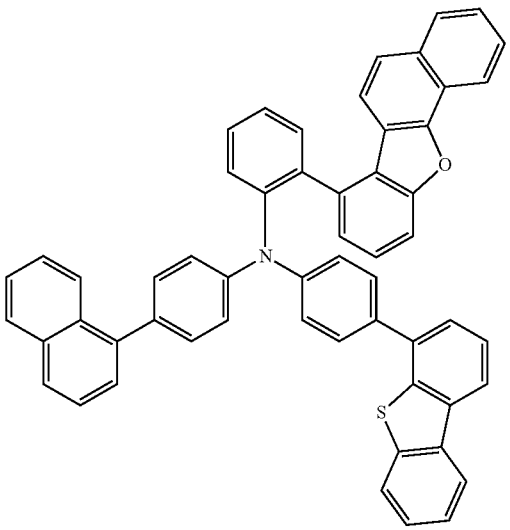

[Chem. 114]
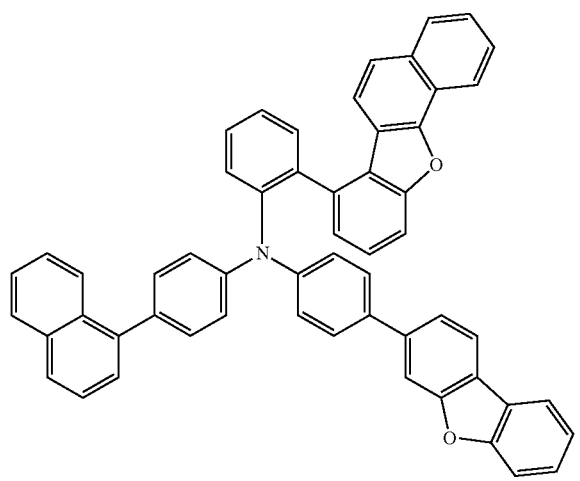
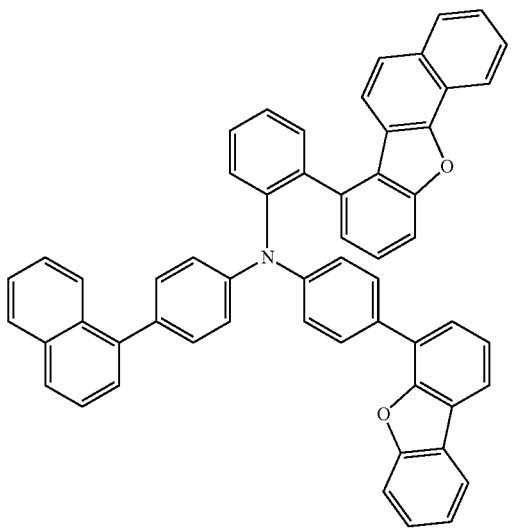
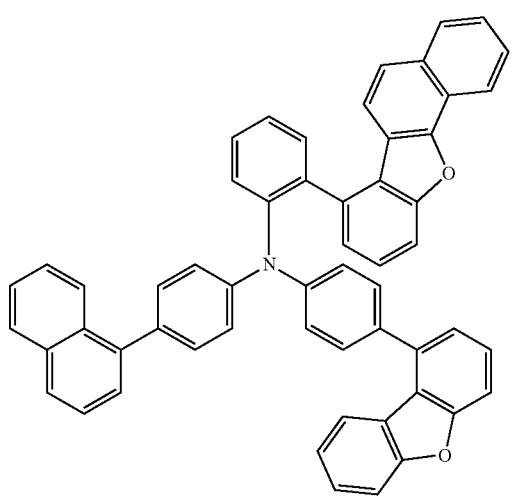
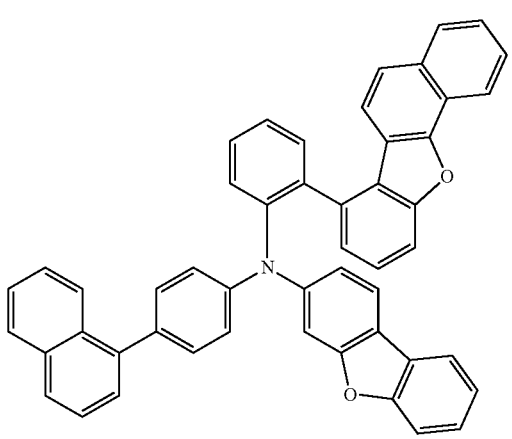
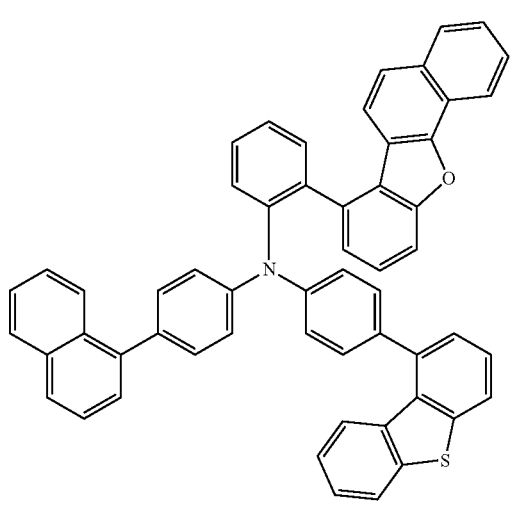
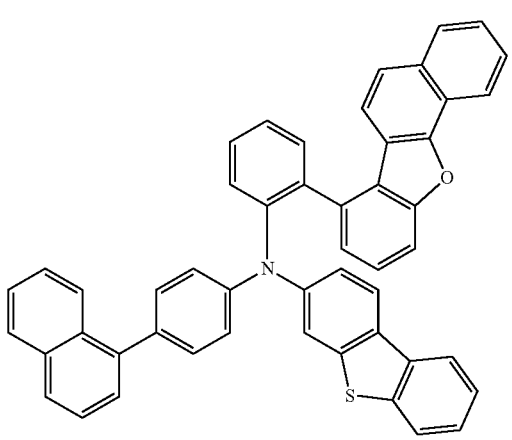

293
-continued
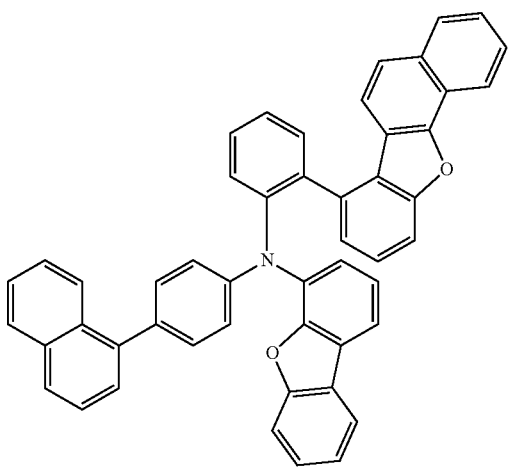
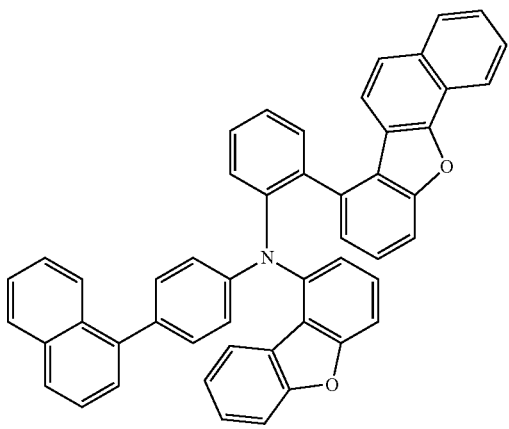
[Chem. 115]
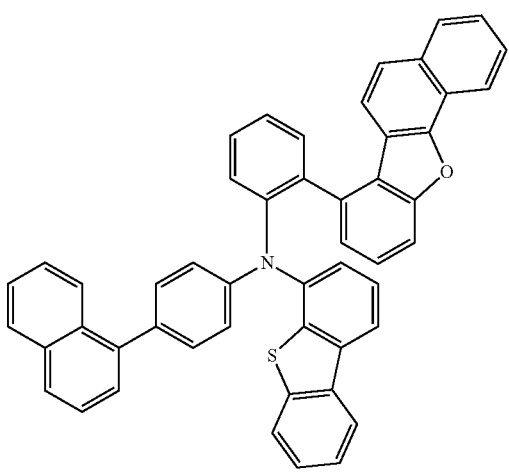
294
-continued
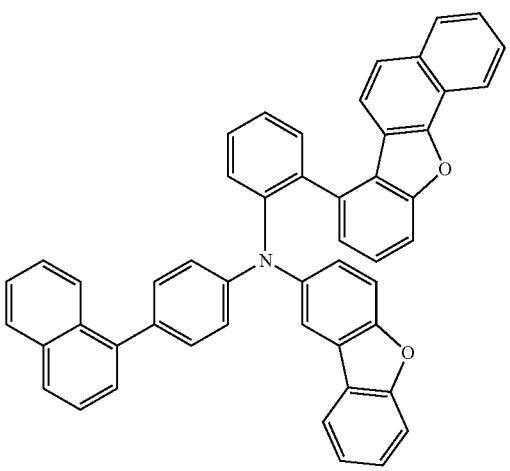
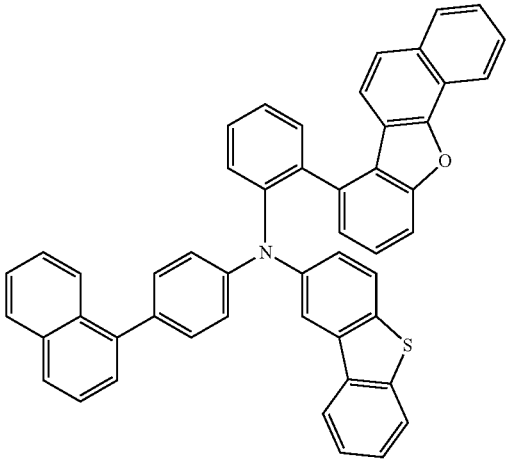
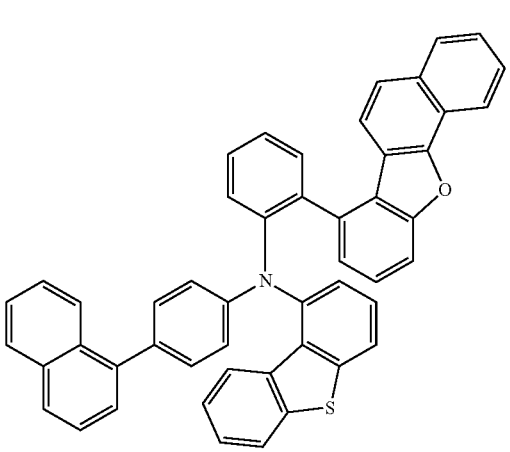

295
-continued
296
-continued
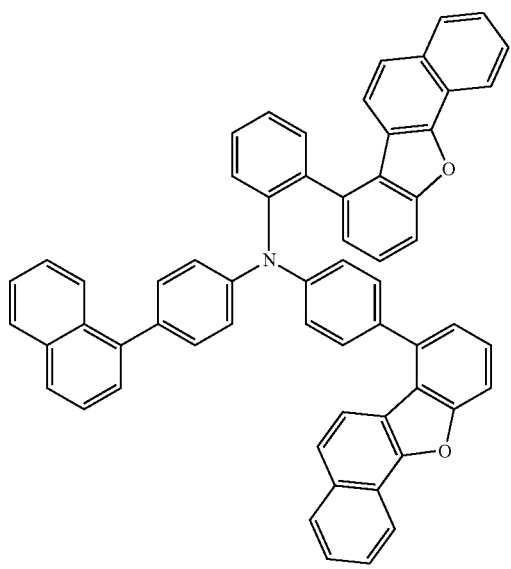
[Chem. 116]
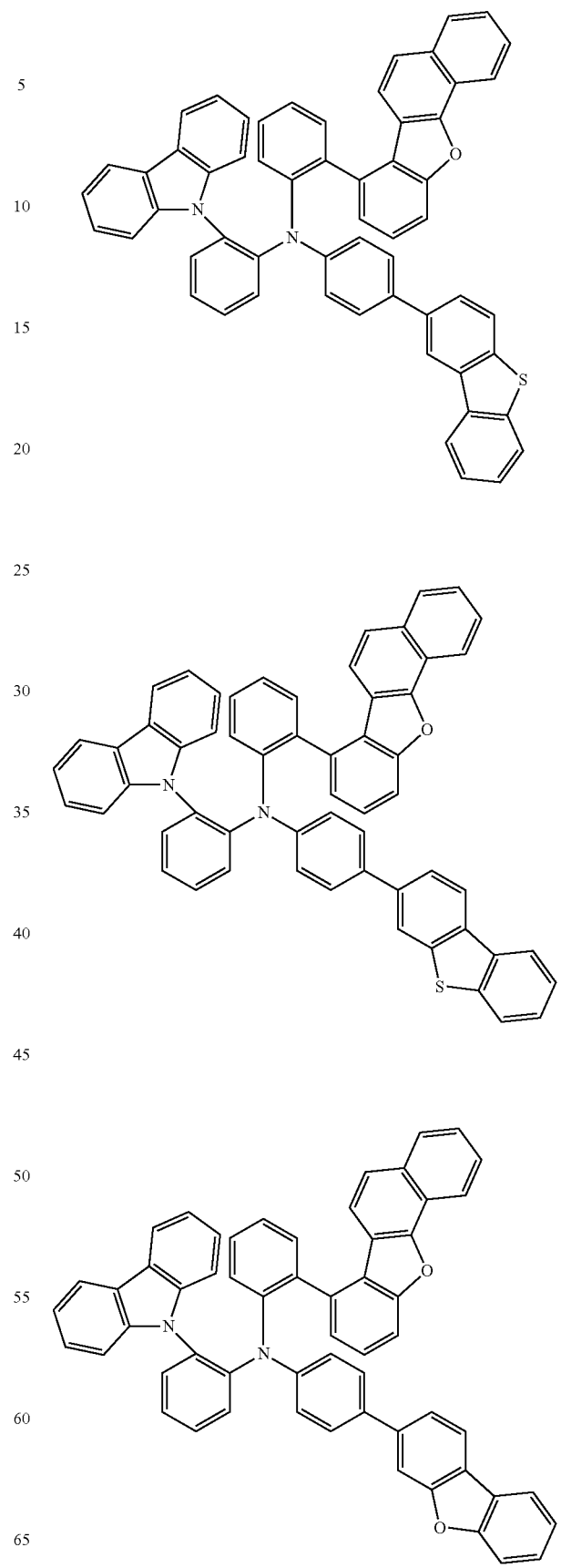

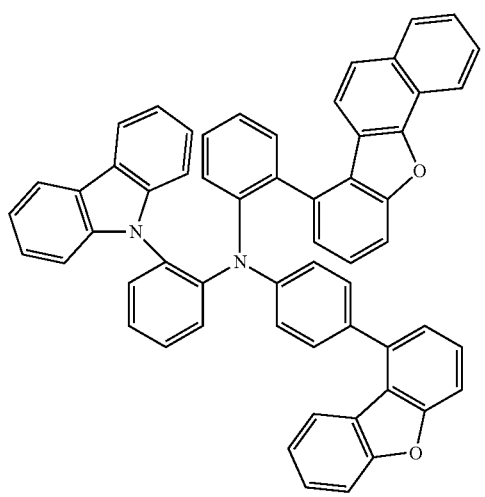
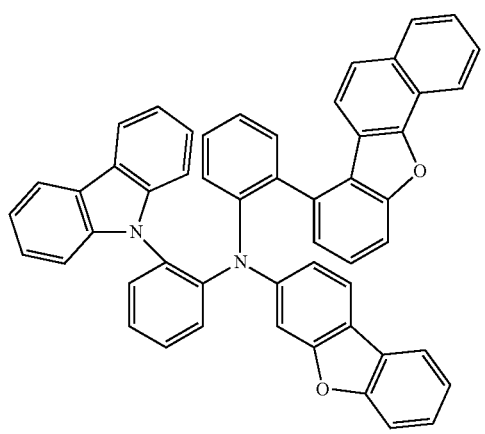
[Chem. 117]
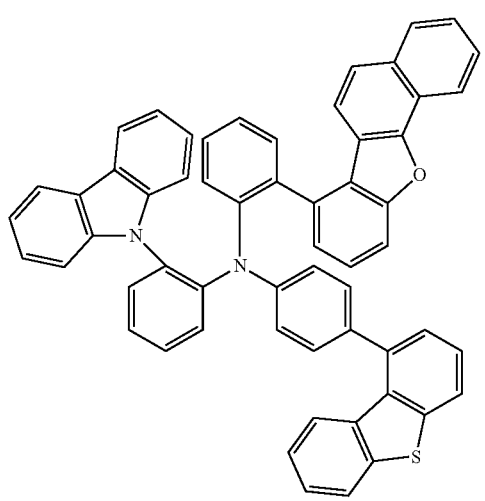
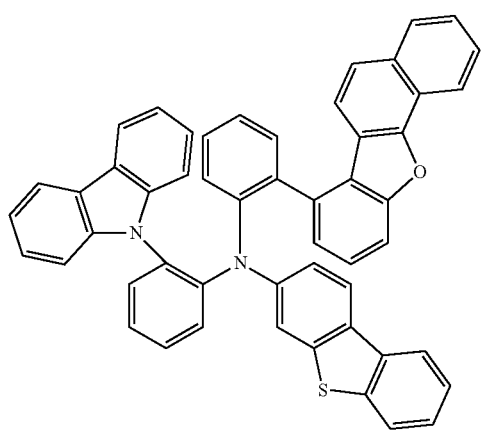
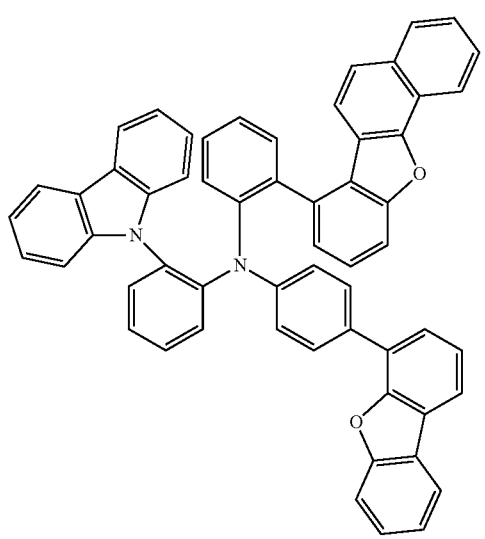
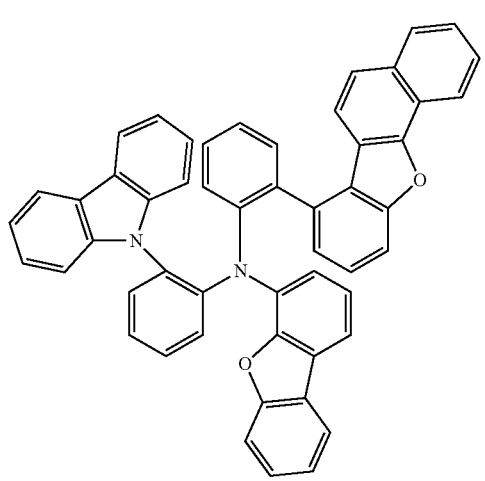

299
-continued
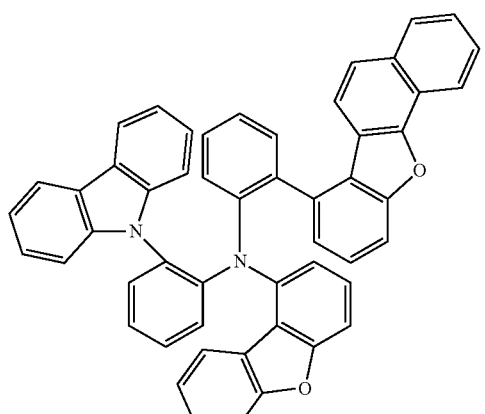
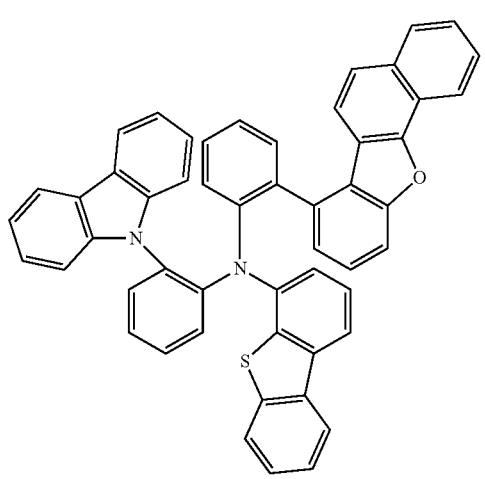
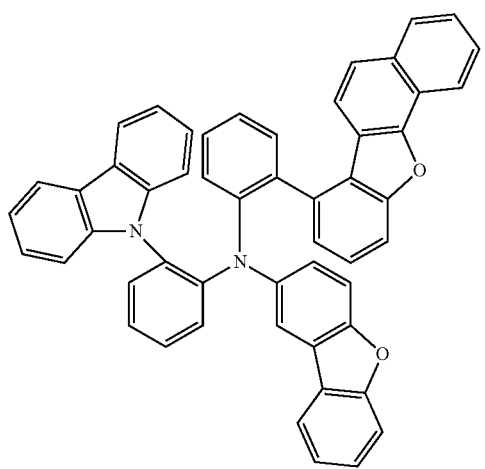
300
-continued
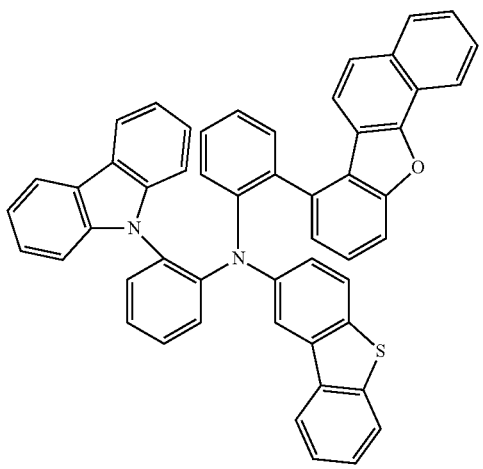
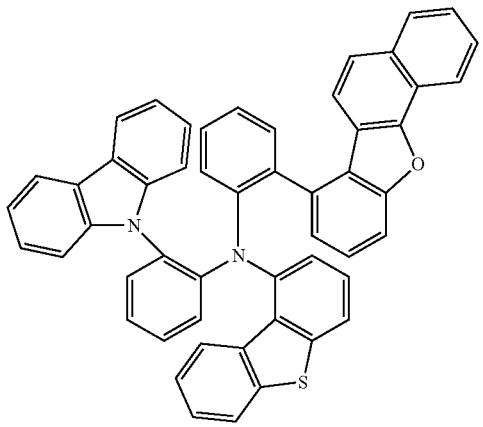
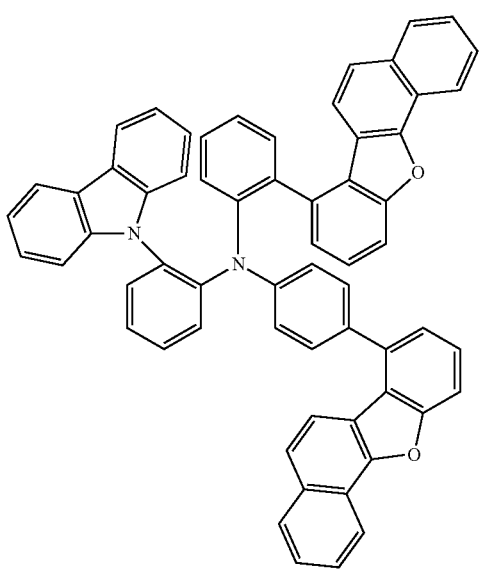

301
-continued
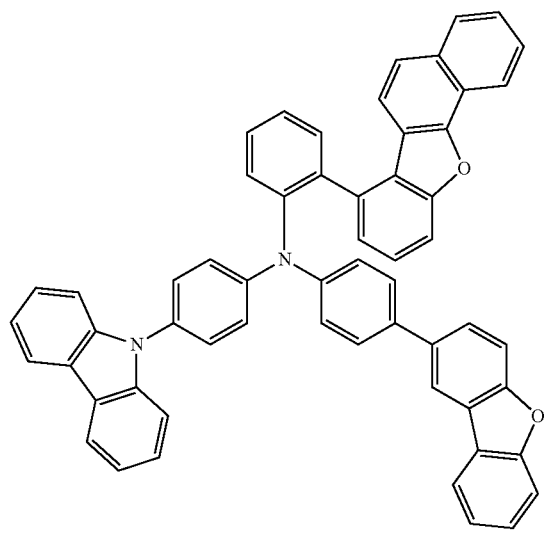
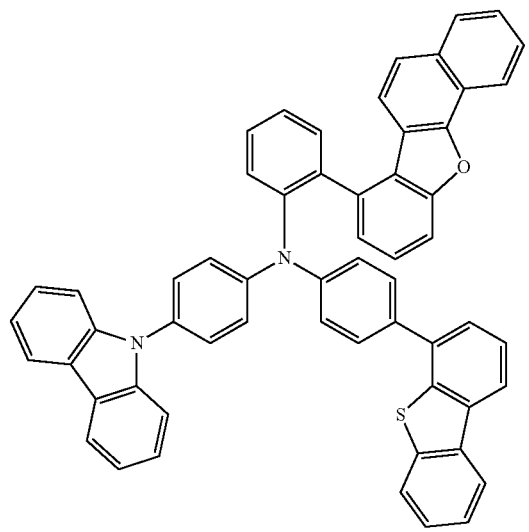
[Chem. 118]
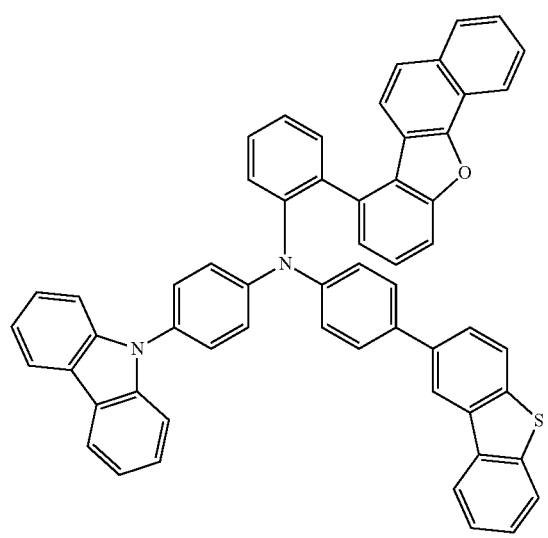
302
-continued
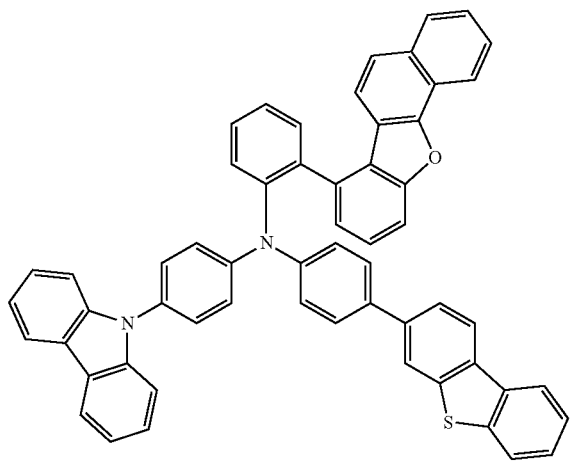
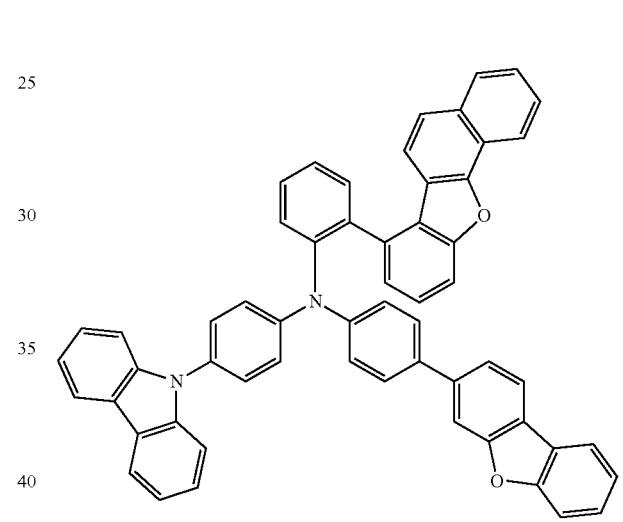
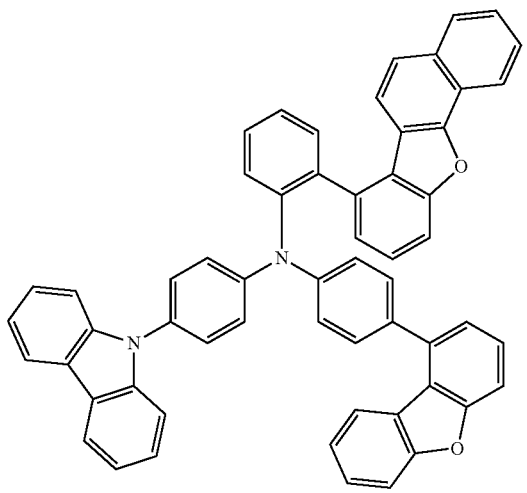

303
-continued
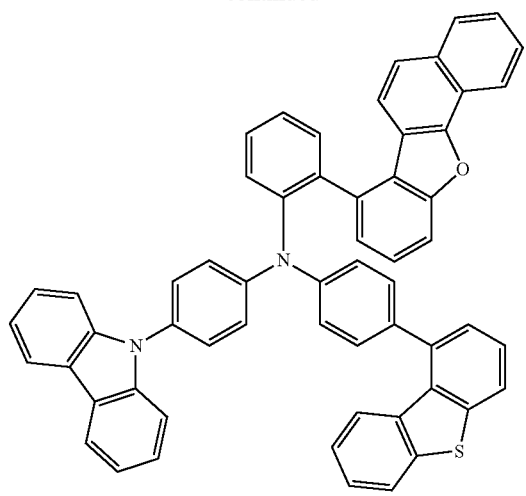
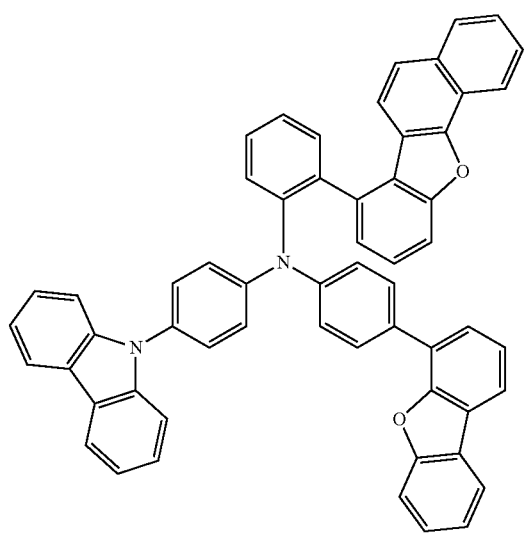
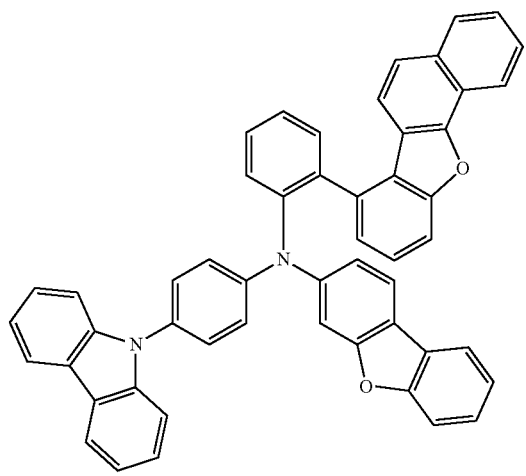
304
-continued
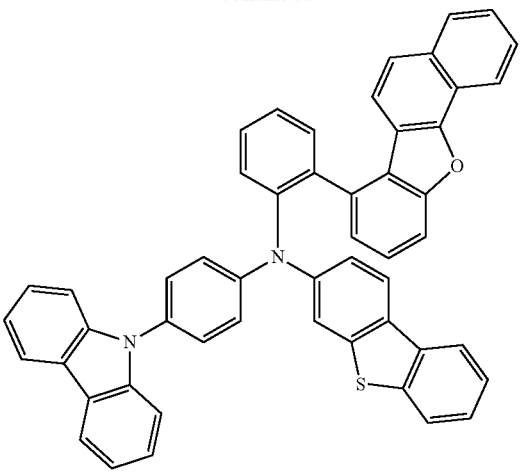
[Chem. 119]
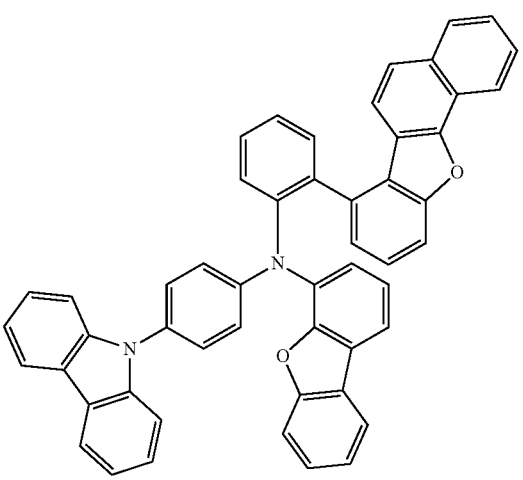
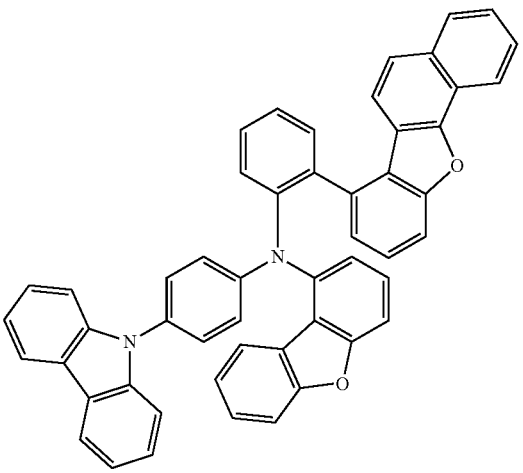

305
-continued
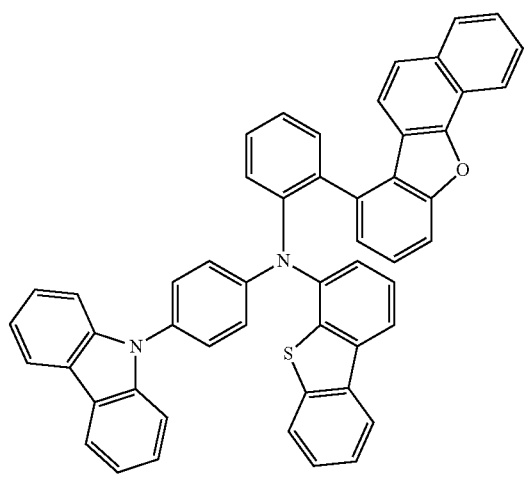
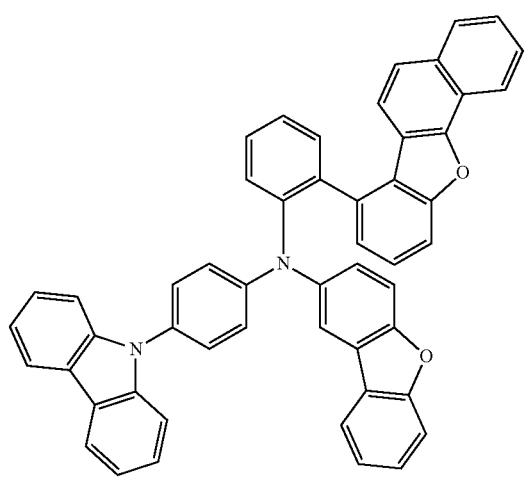
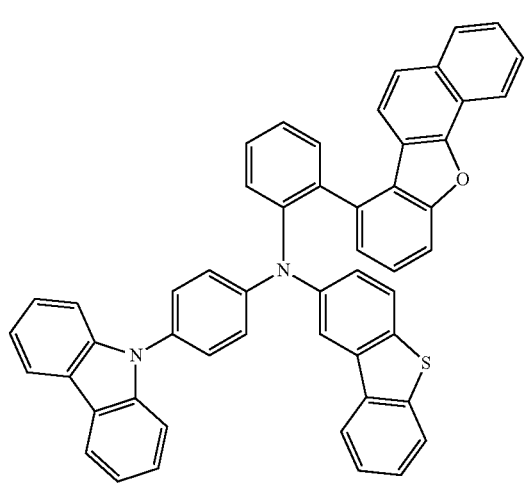
306
-continued
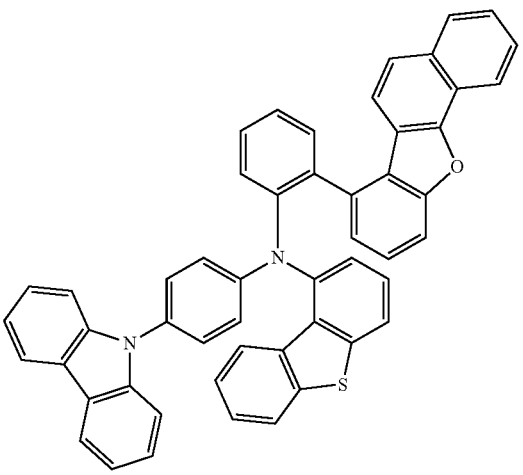
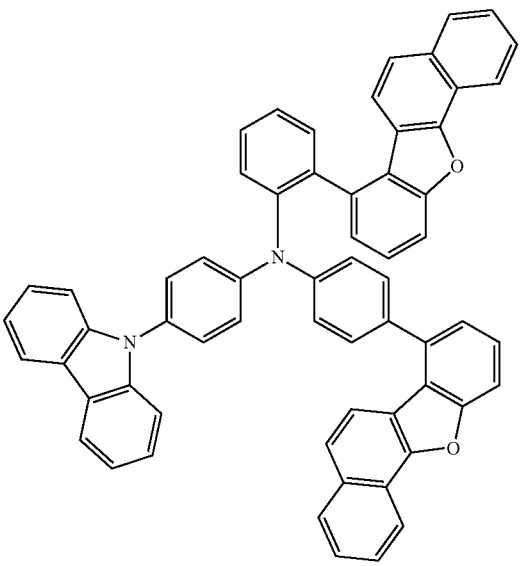
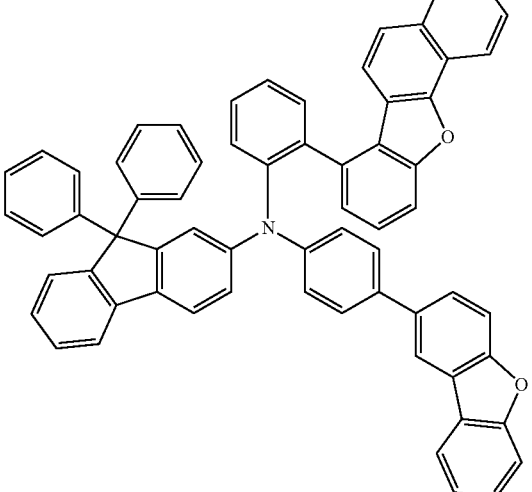

[Chem. 120]
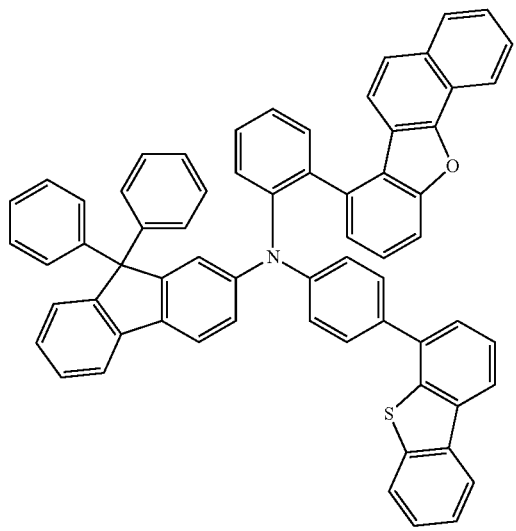
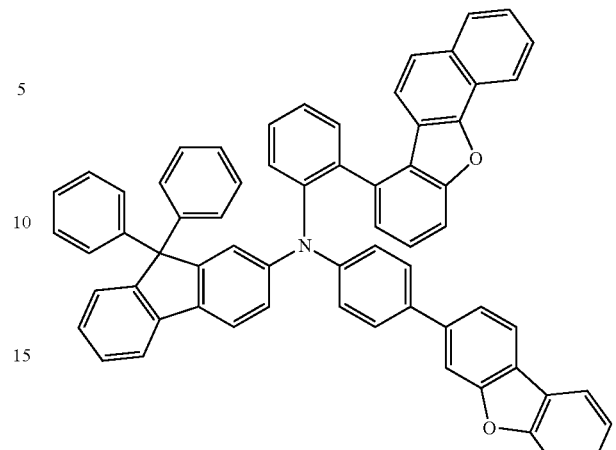
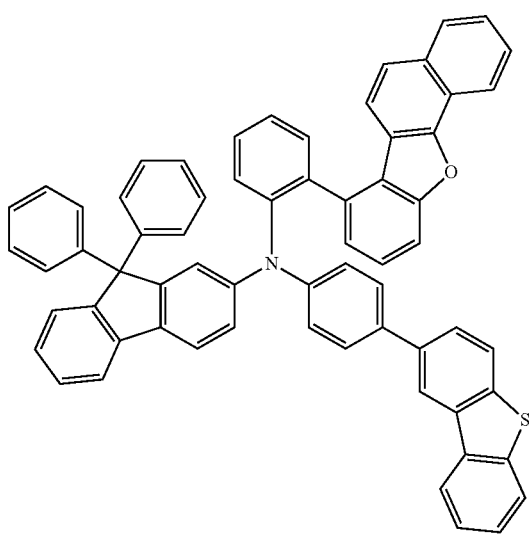
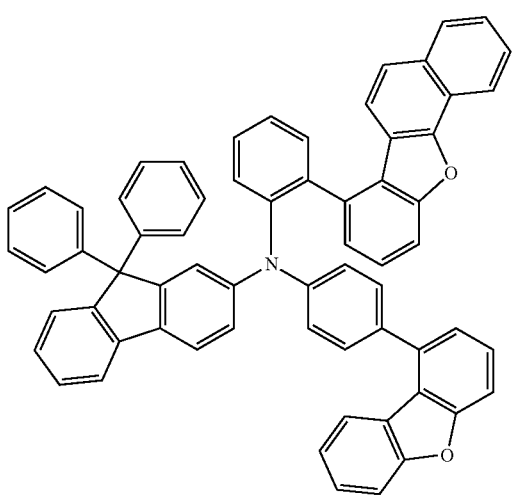
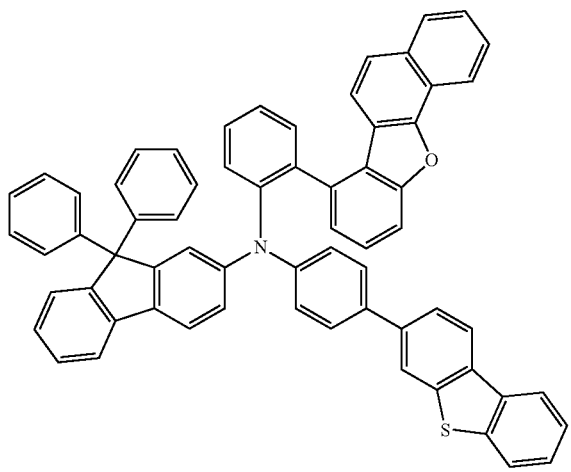
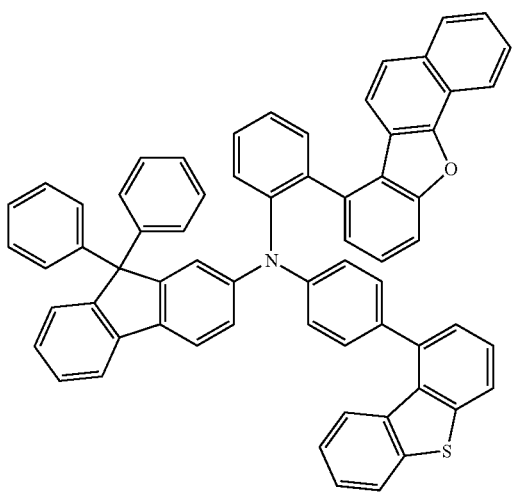

309
-continued
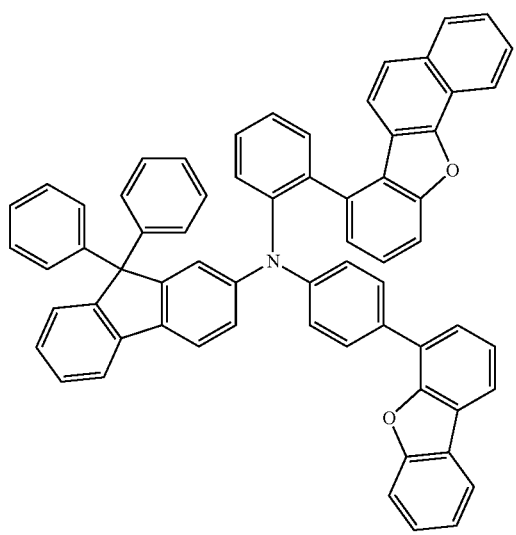
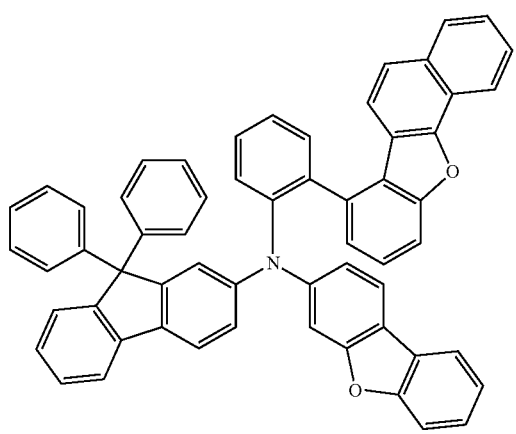
[Chem. 121]
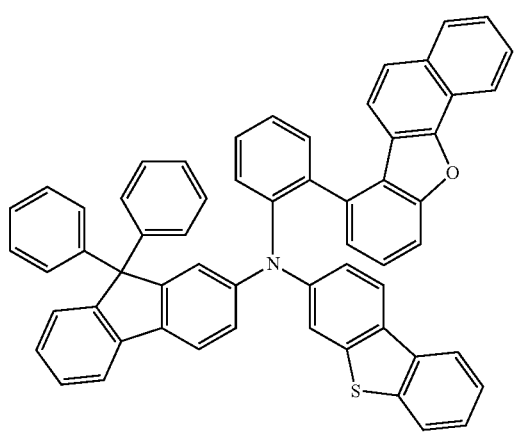
310
-continued
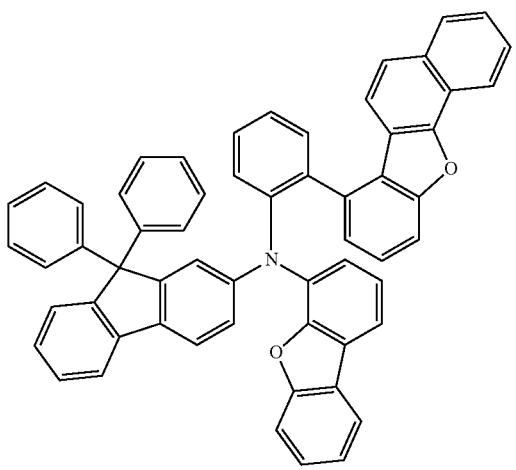
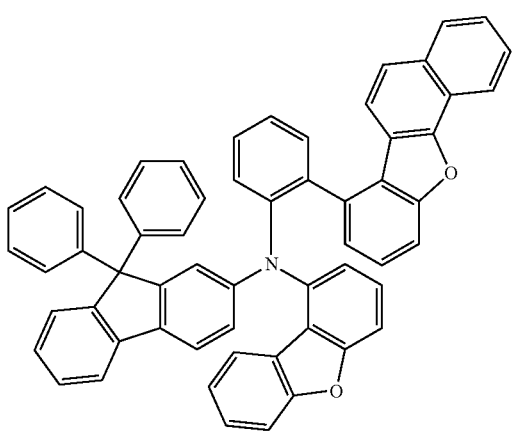
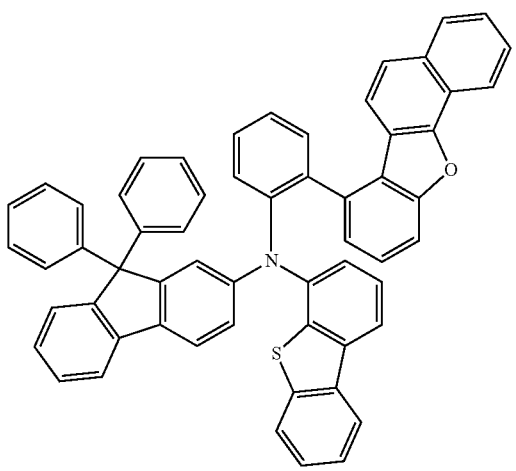

311
-continued
312
-continued
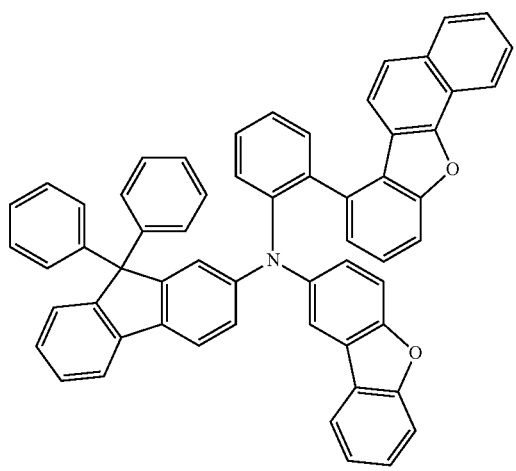
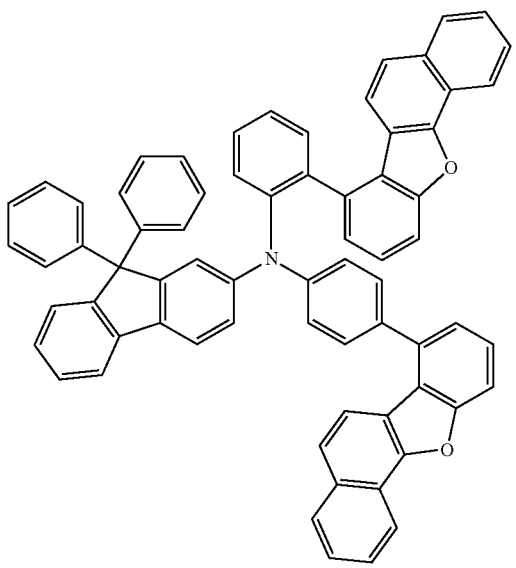
[Chem. 122]
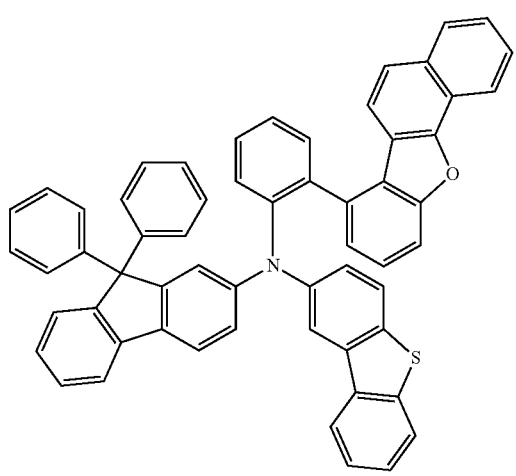
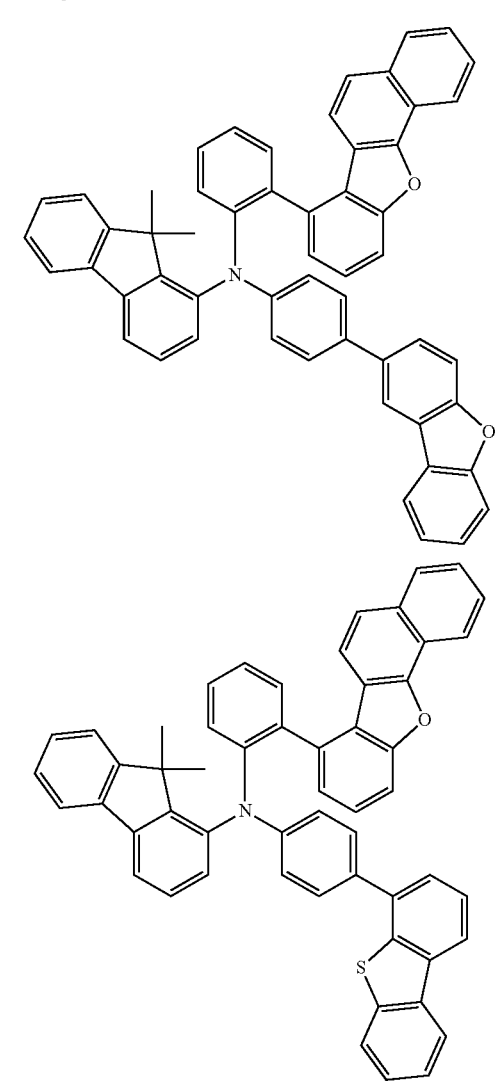

313
-continued
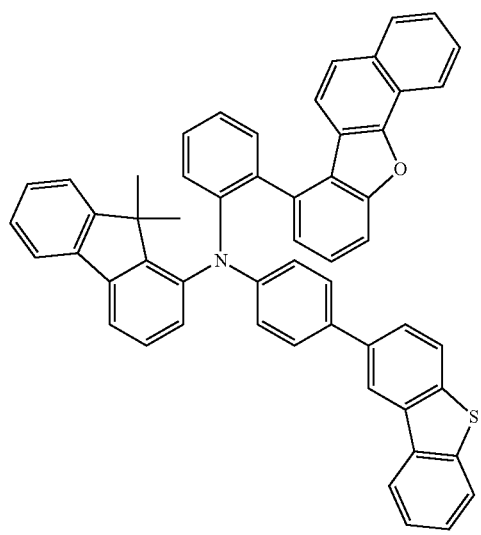
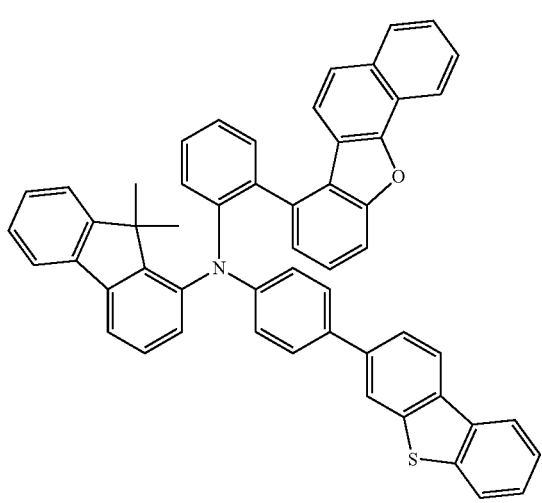
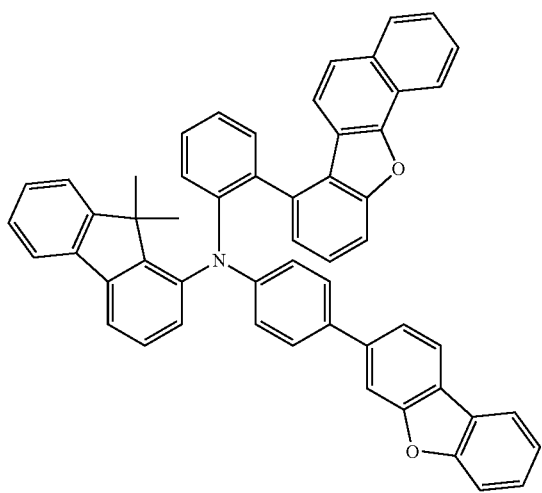
314
-continued
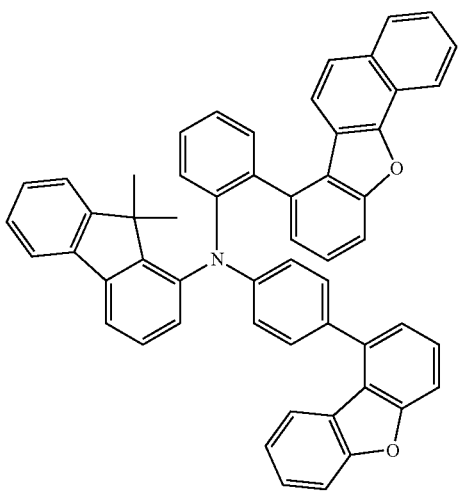
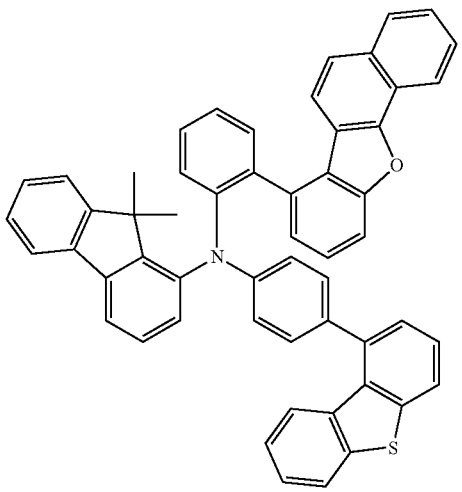
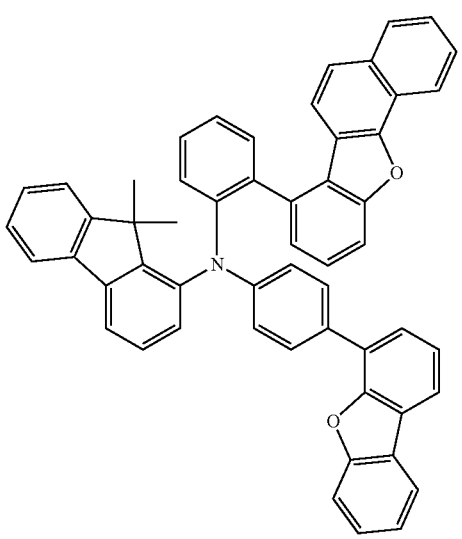

315
-continued
316
-continued
[Chem. 123]
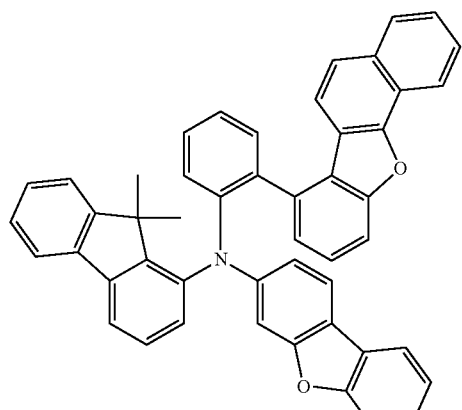
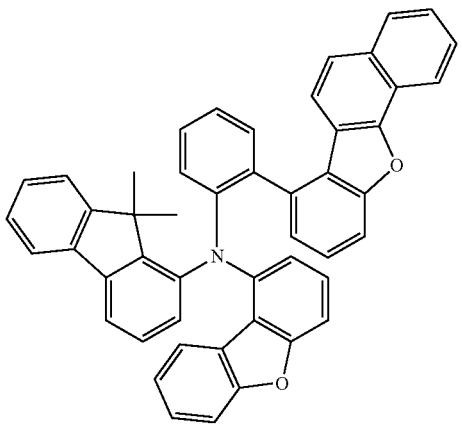
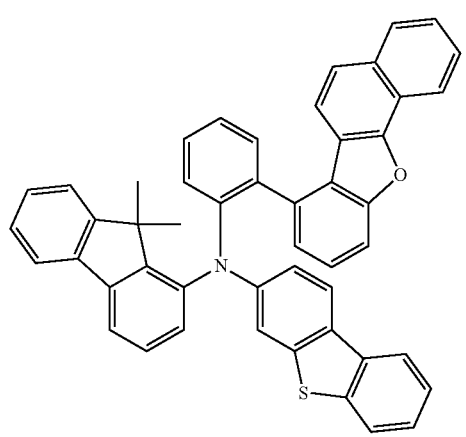
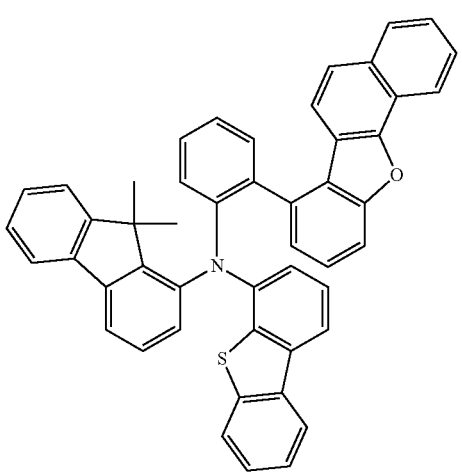
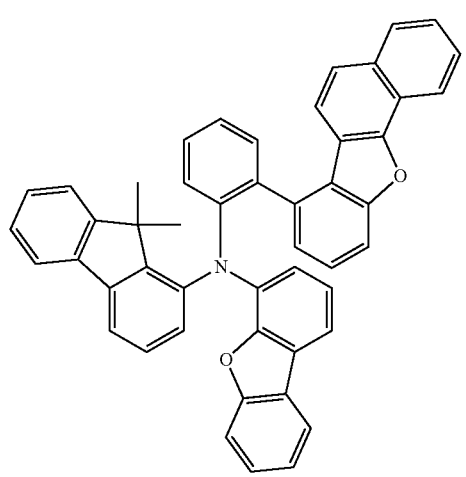
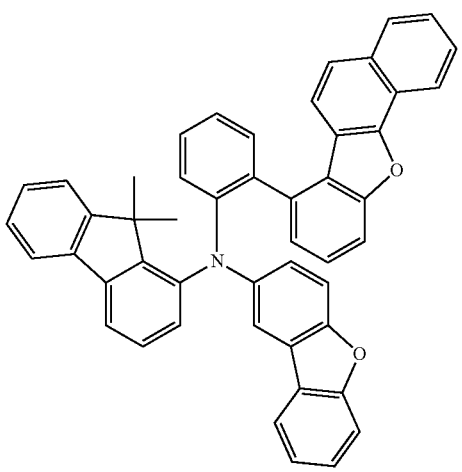

317
-continued
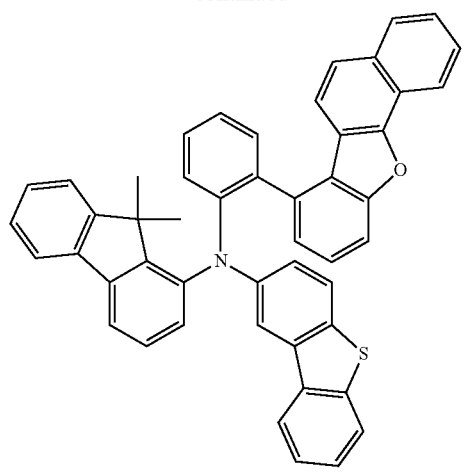
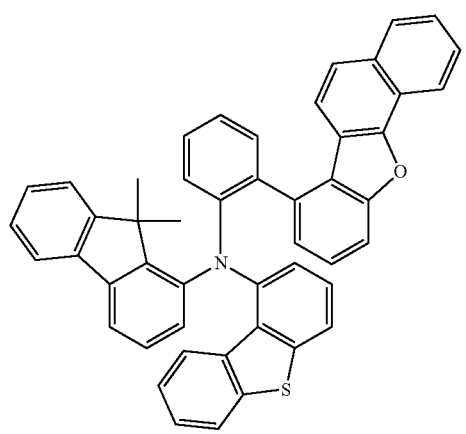
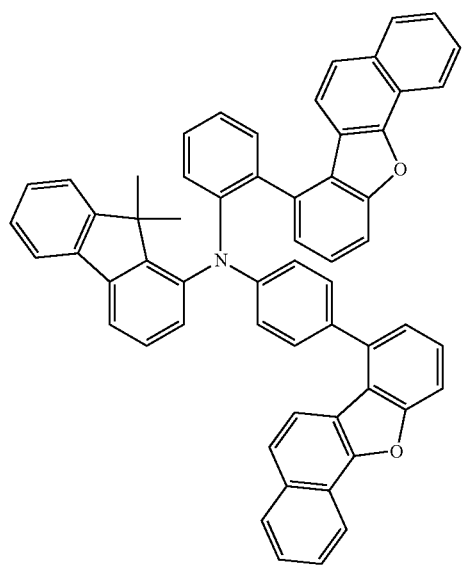
318
-continued
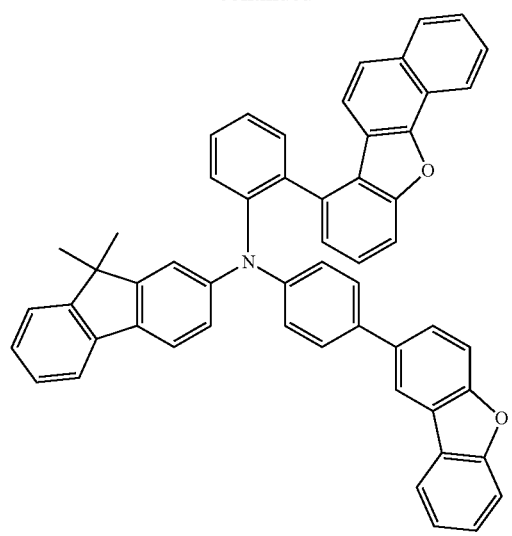
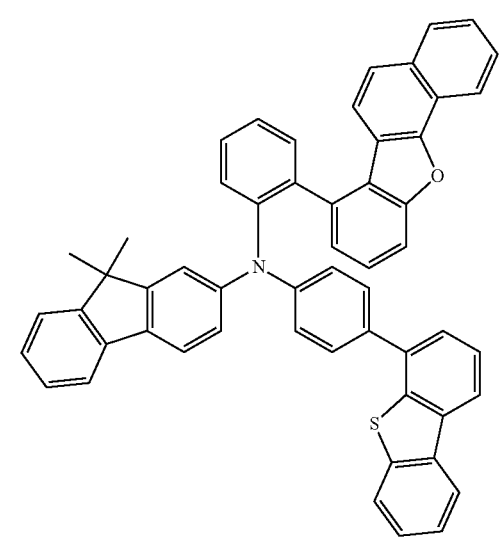
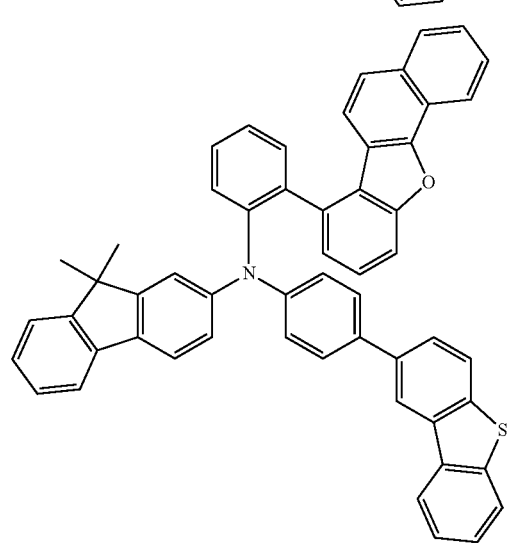

319
-continued
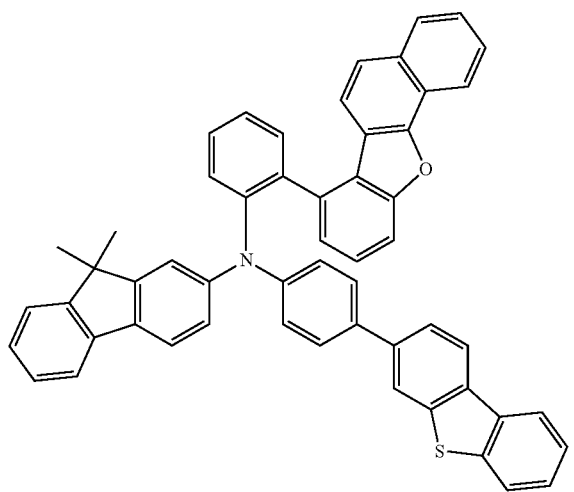
[Chem. 124]
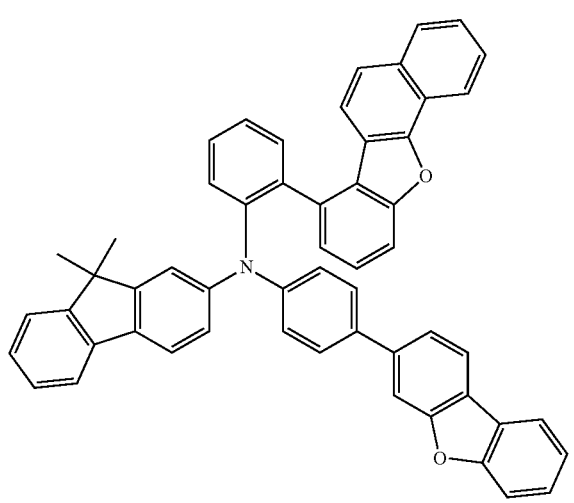
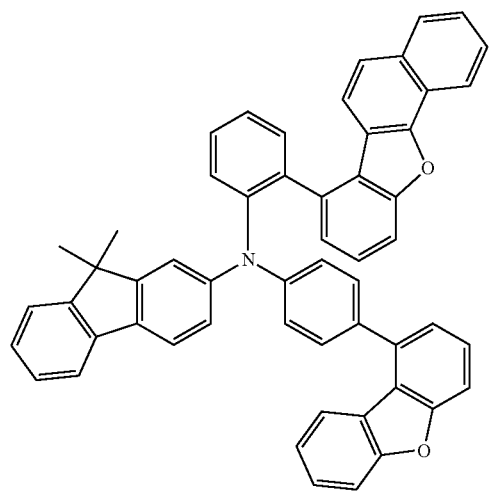
320
-continued
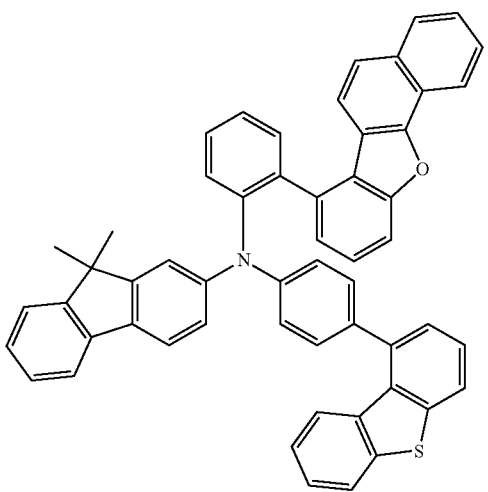
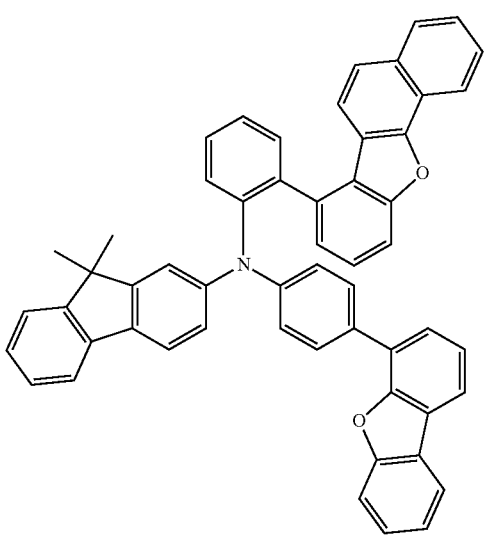
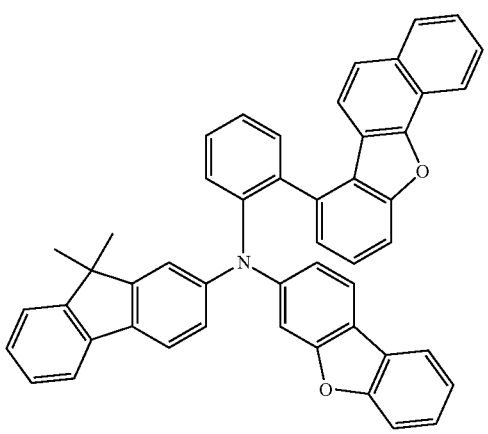

-continued
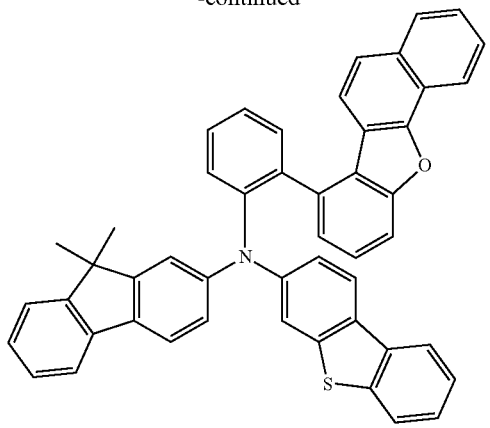
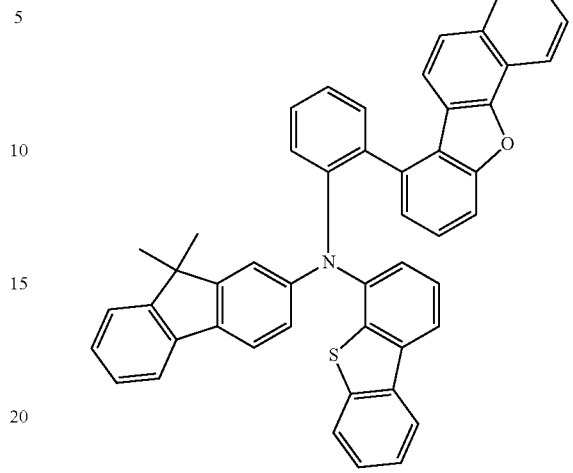
[Chem. 125]
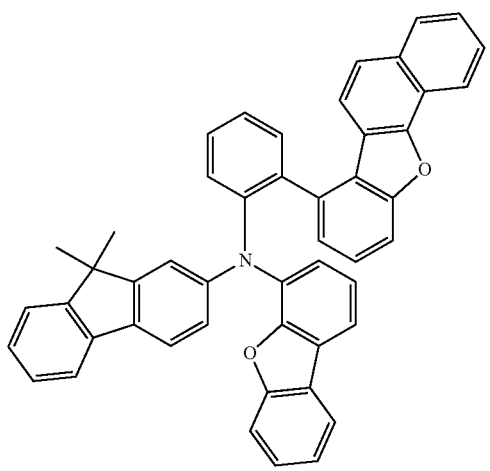
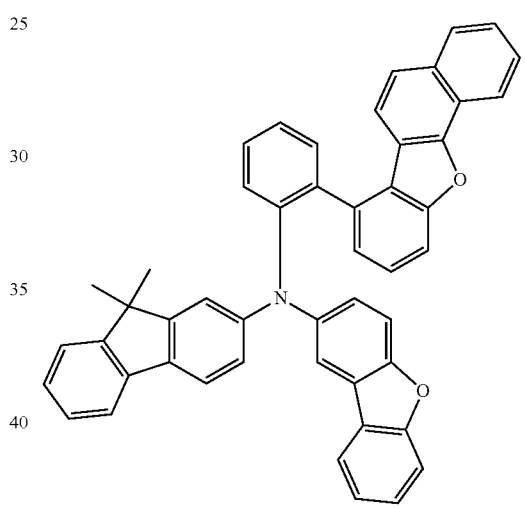
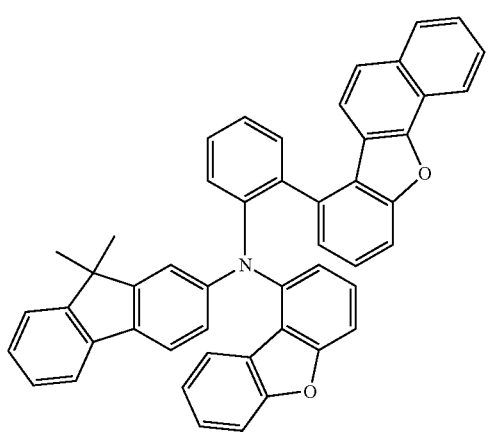
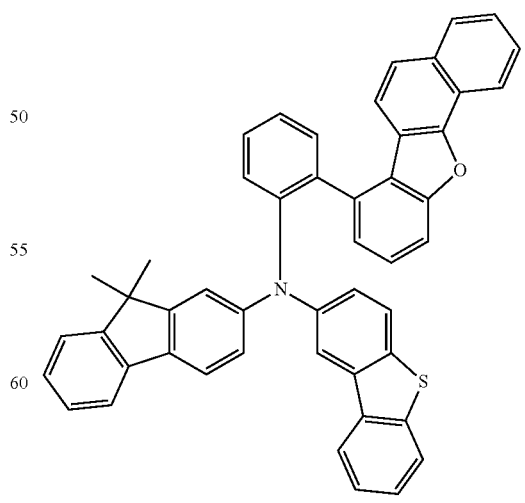

323
-continued
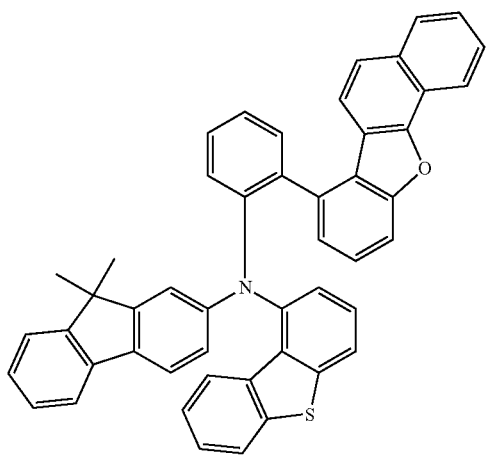
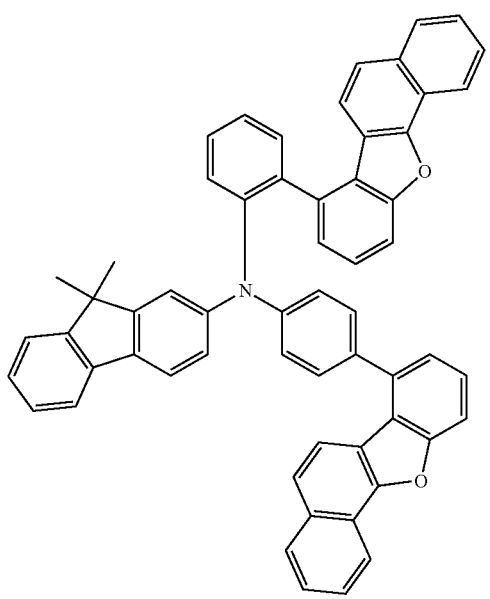
324
-continued
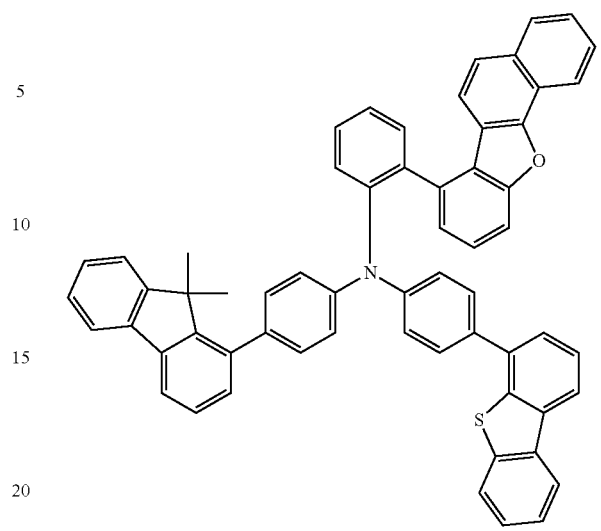
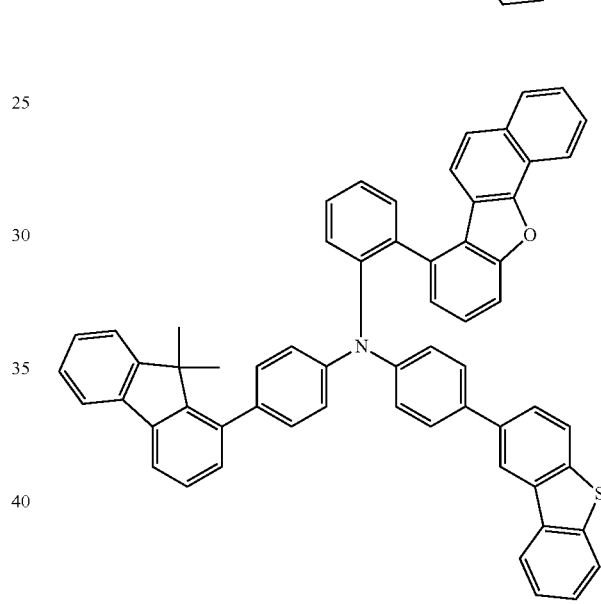
[Chem. 126]
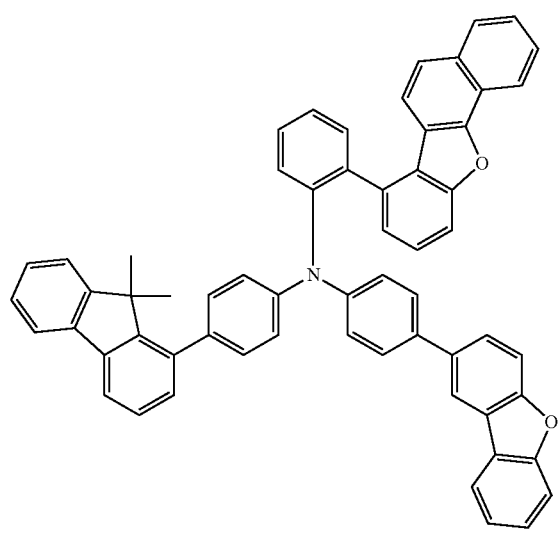
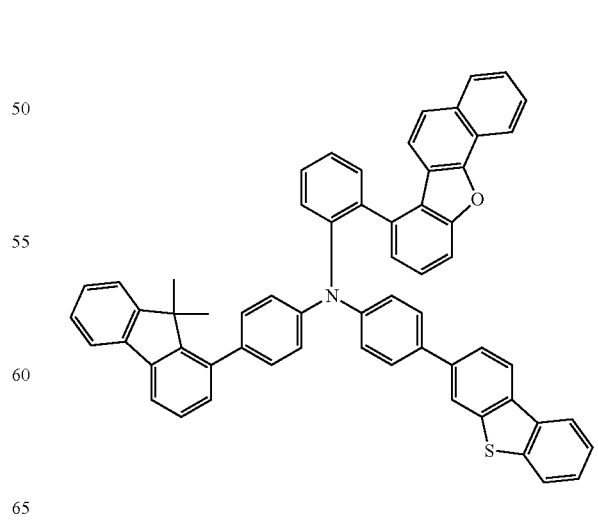

325
-continued
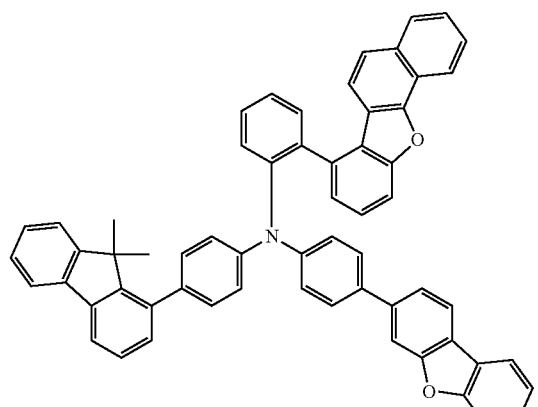
326
-continued
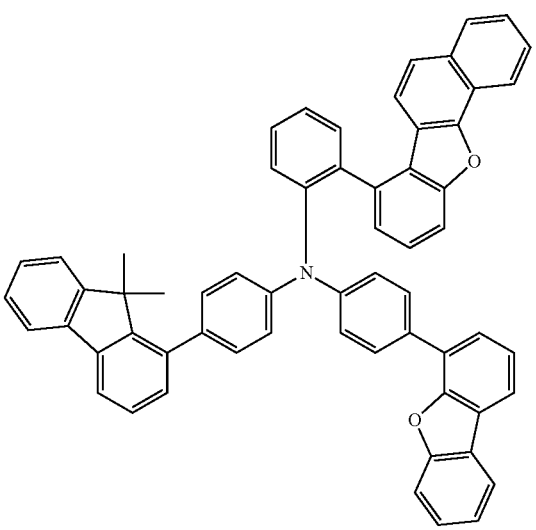
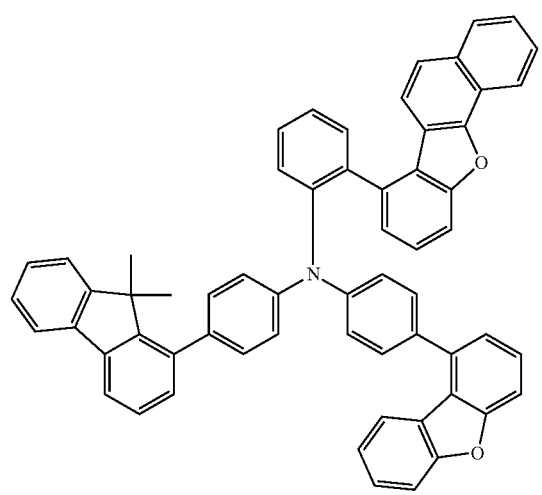
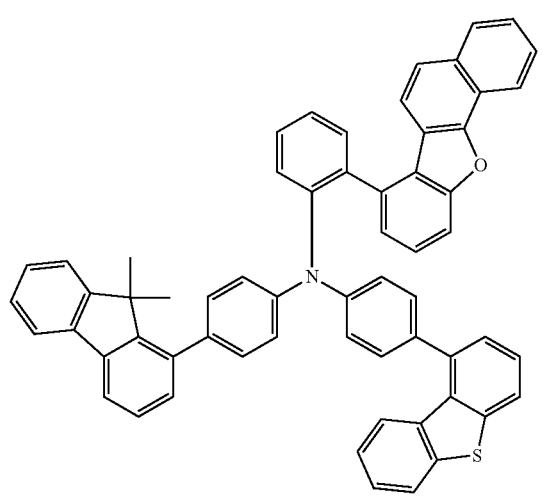
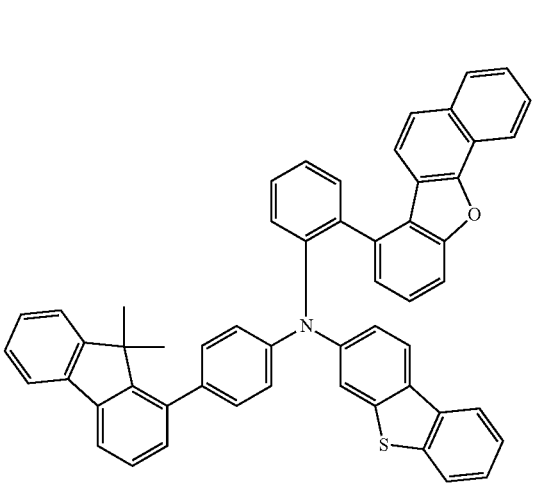

327
-continued
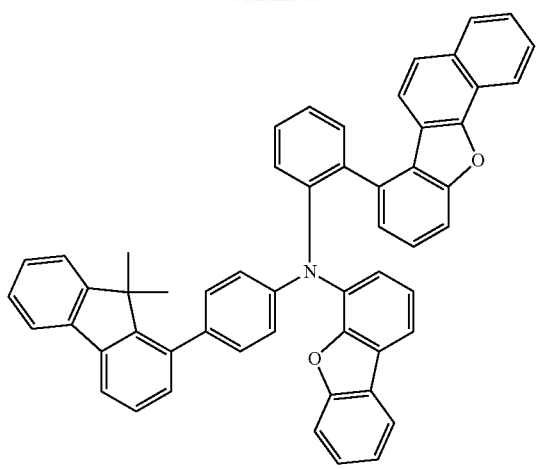
328
-continued
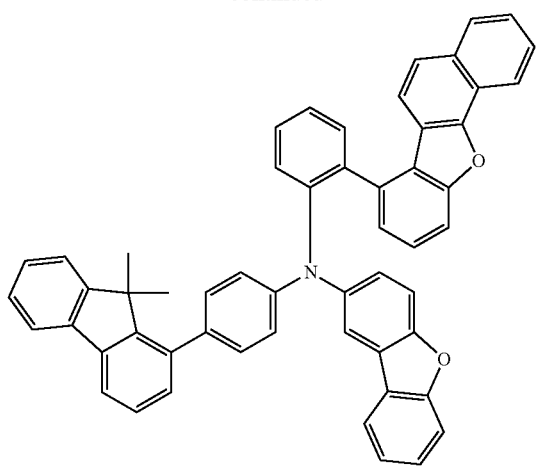
[Chem.127]
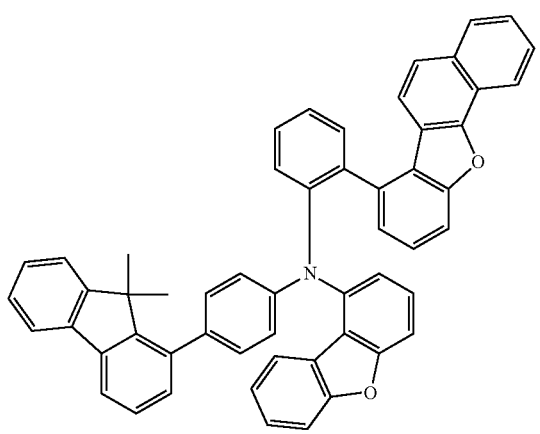
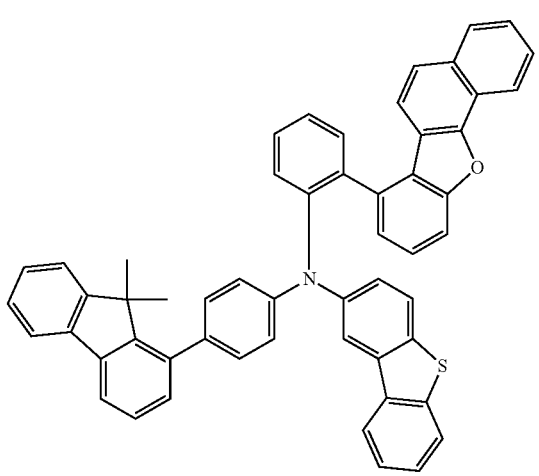
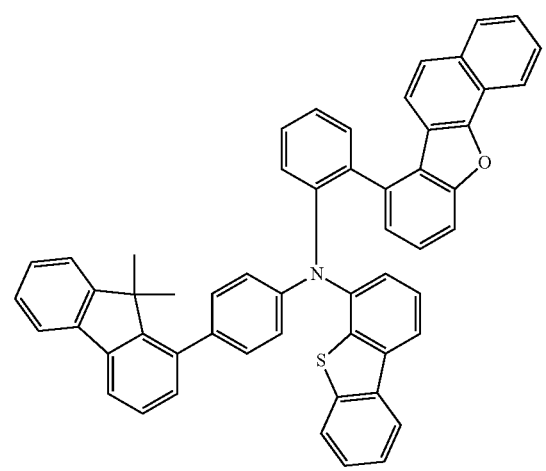
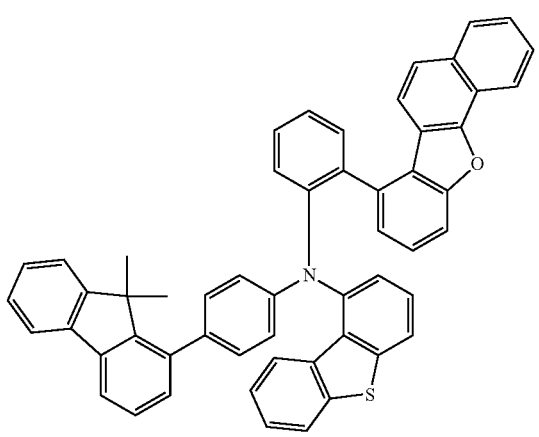

329
-continued
330
-continued
[Chem. 128]
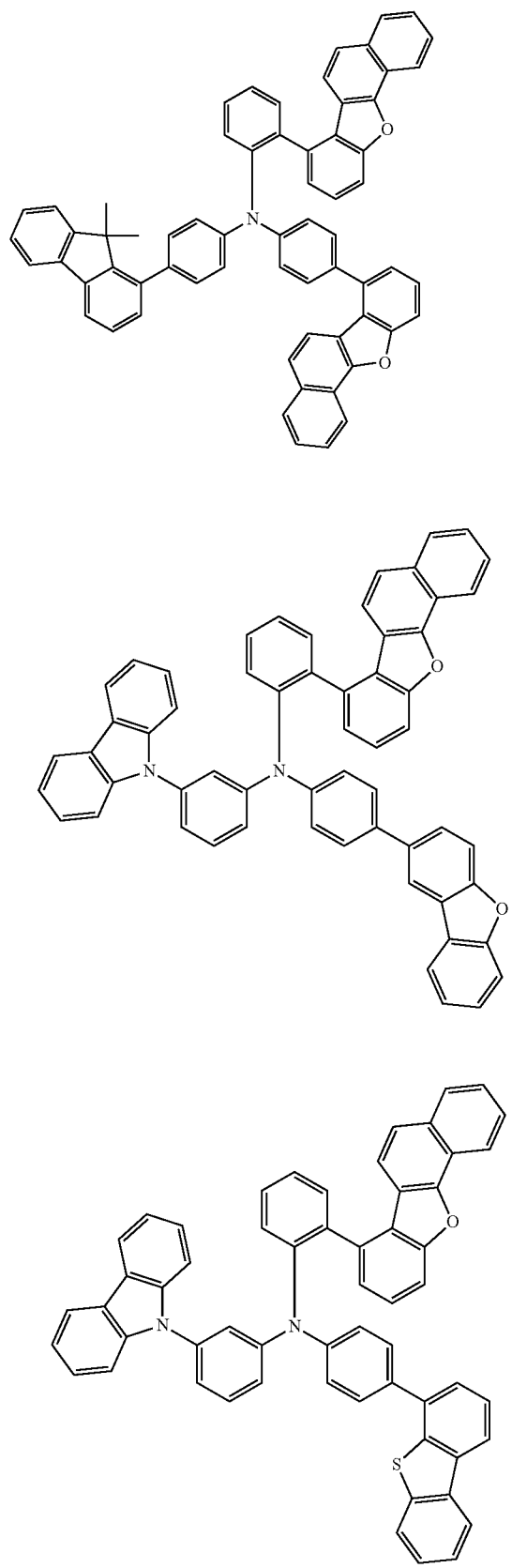
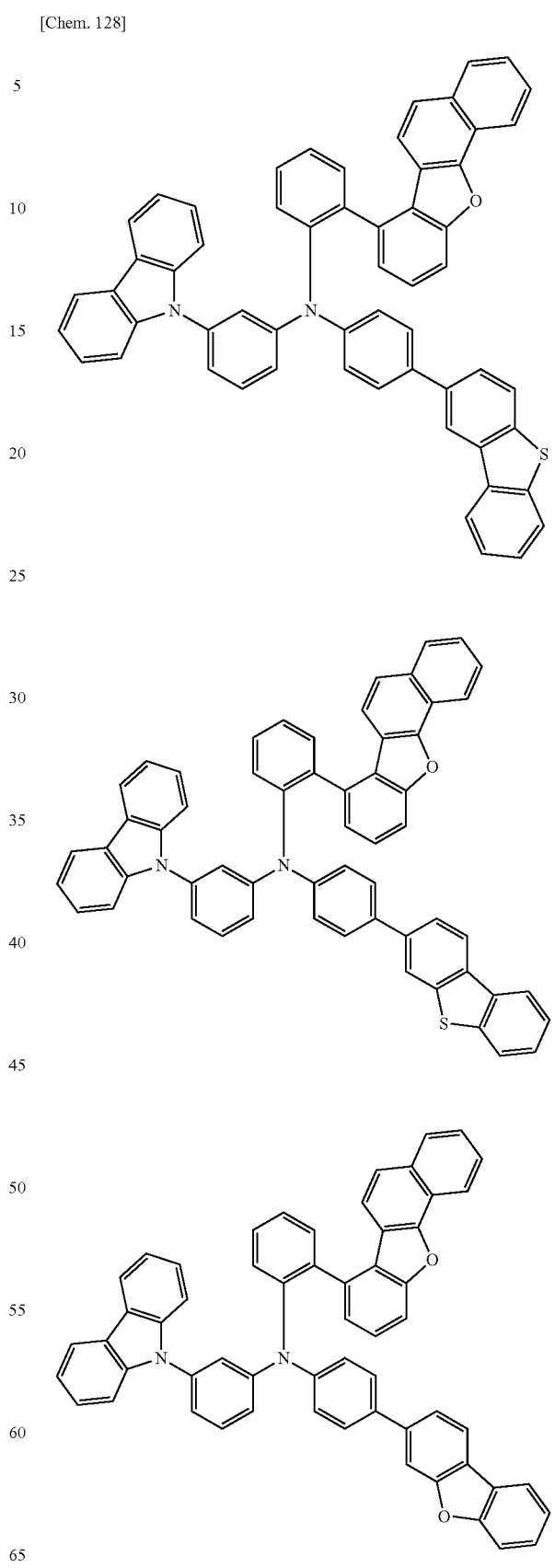

331
-continued
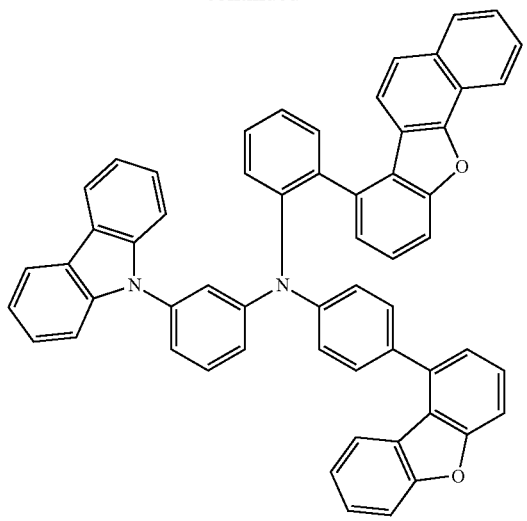
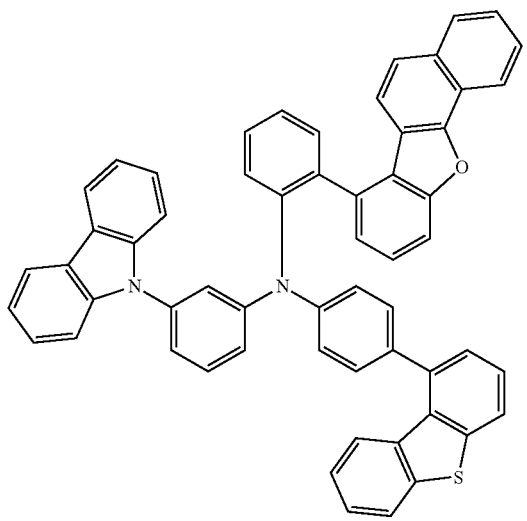
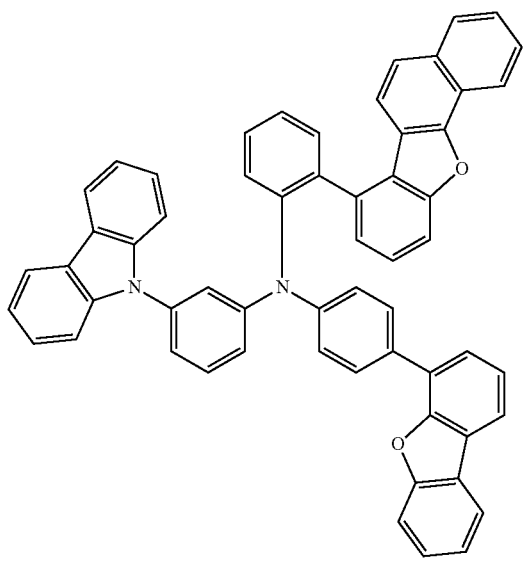
332
-continued
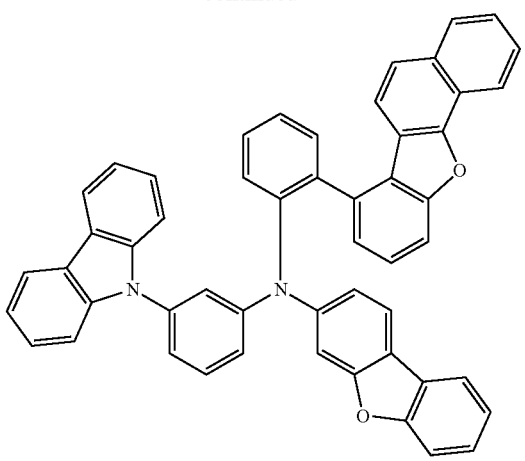
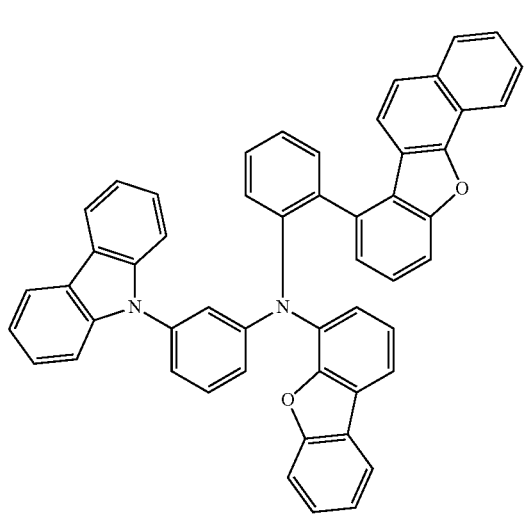
[Chem. 129]

333
-continued
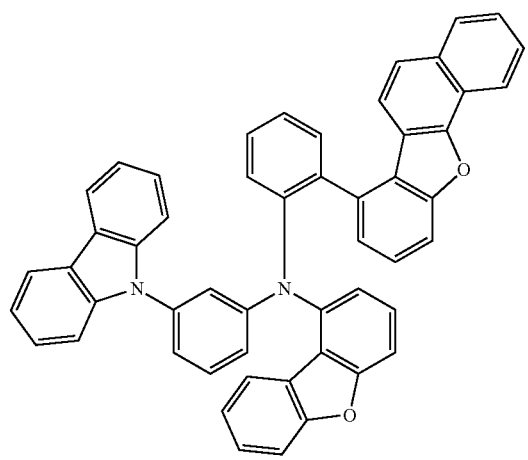
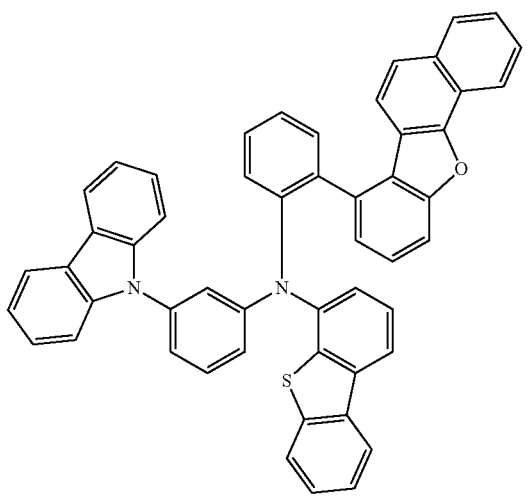
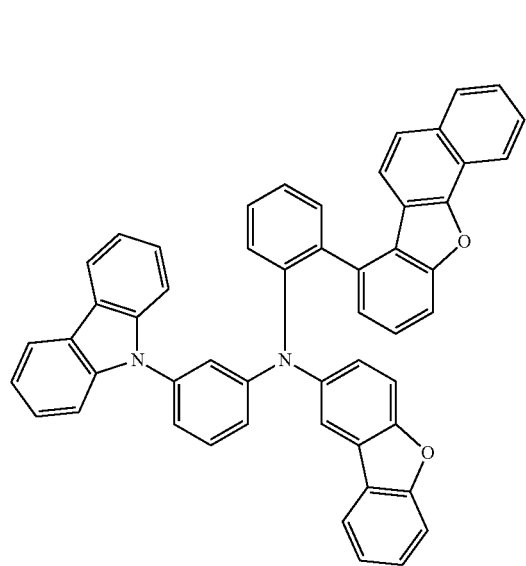
334
-continued
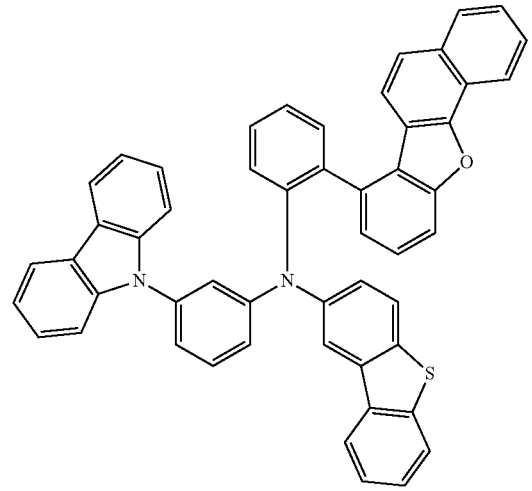
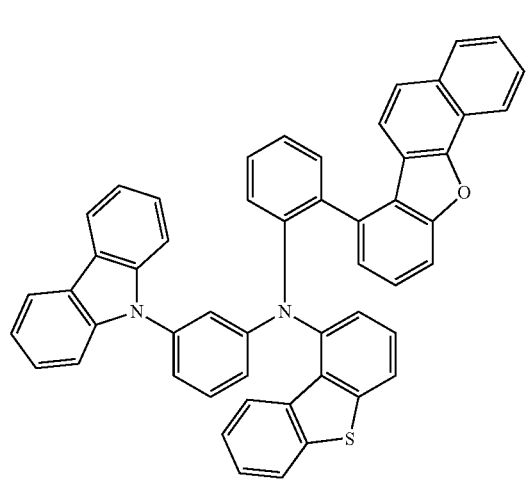
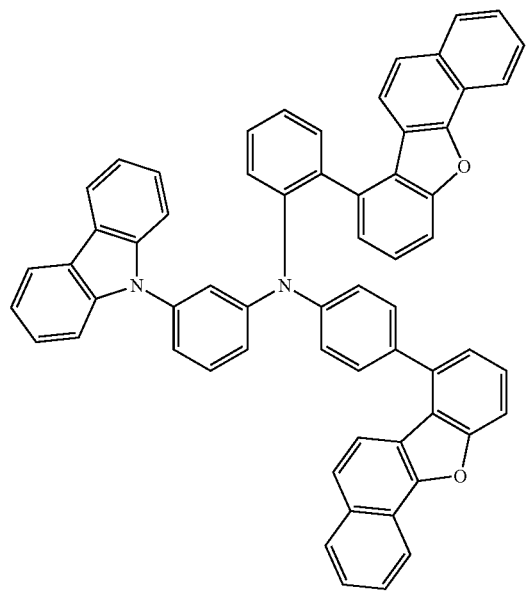

335
-continued
336
-continued
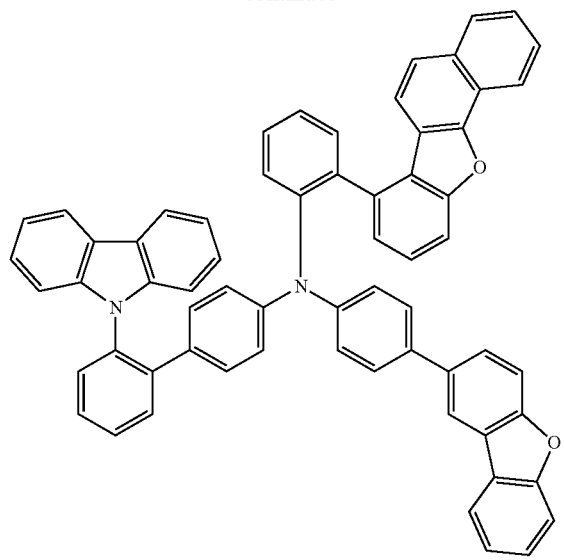
[Chem. 130]
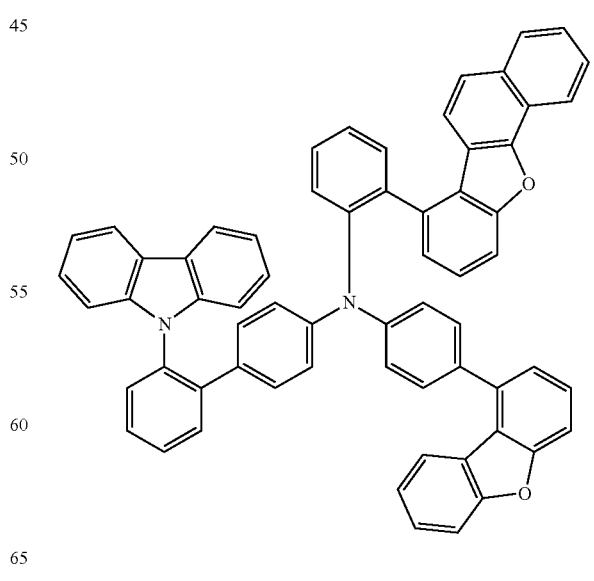

337
-continued
338
-continued
[Chem. 131]
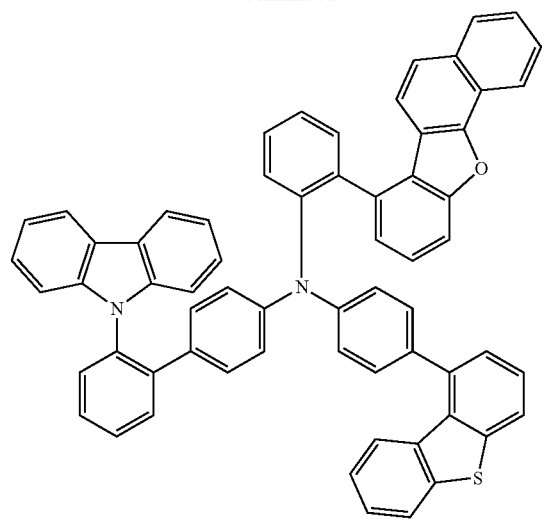
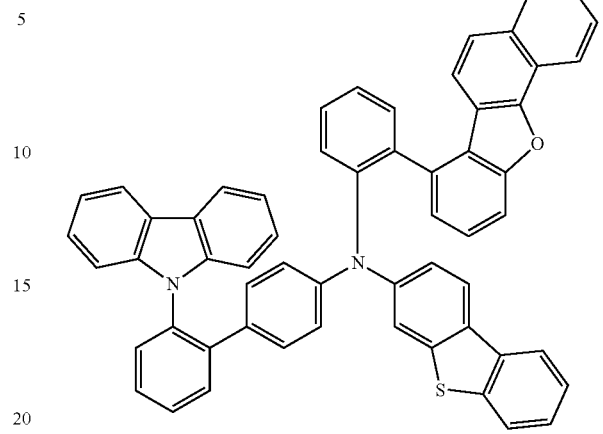
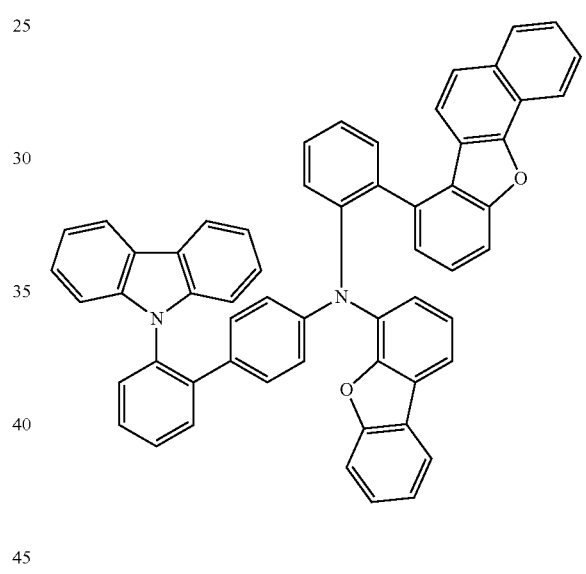
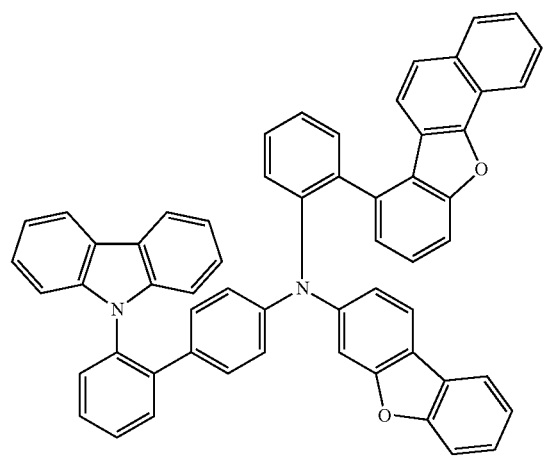
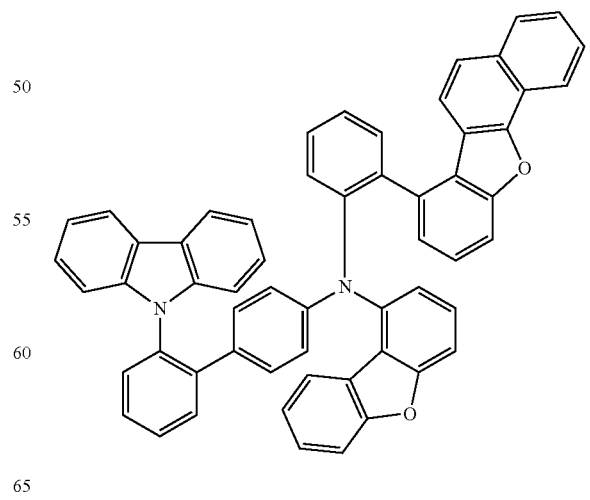

339
-continued
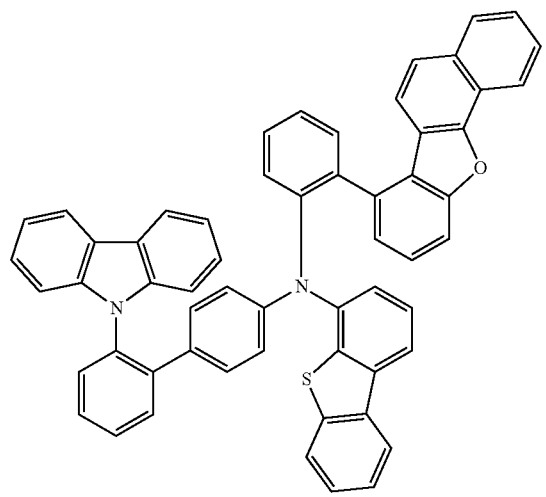
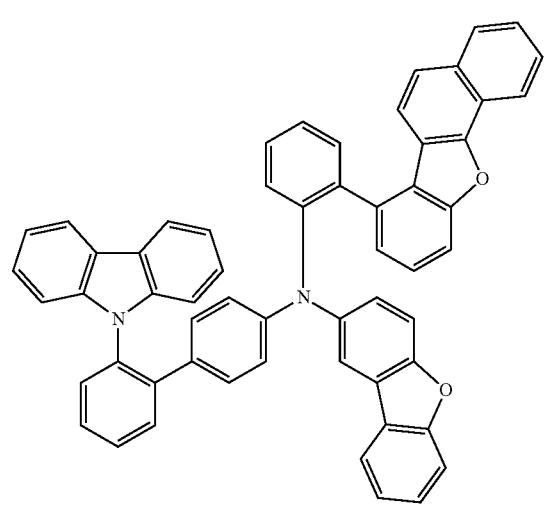
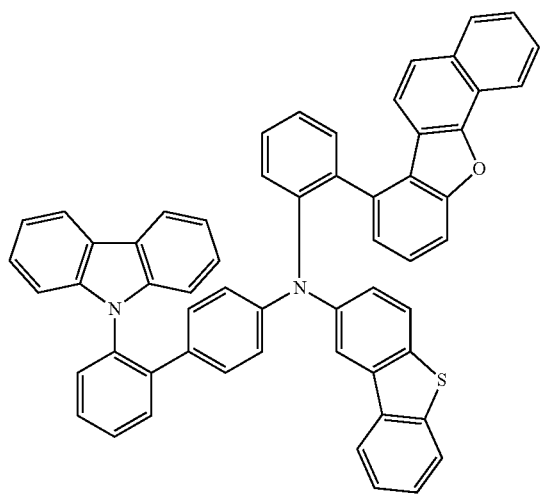
340
-continued
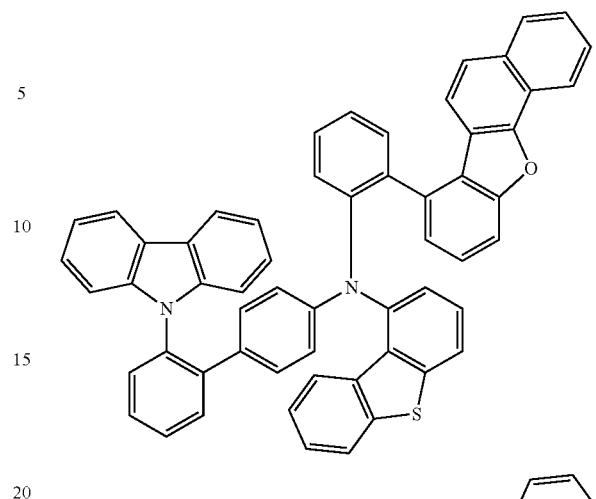
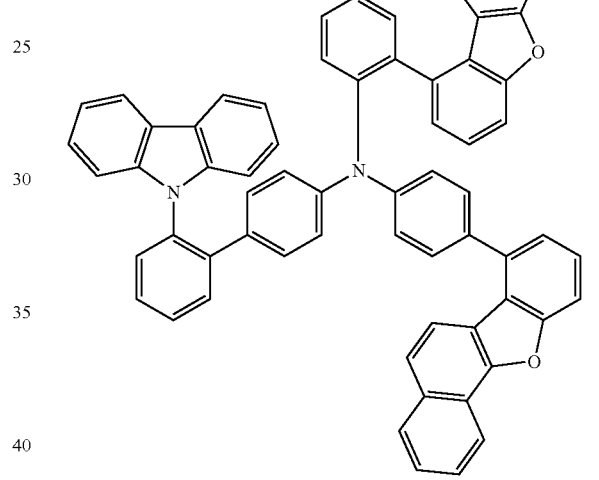
[Chem. 132]
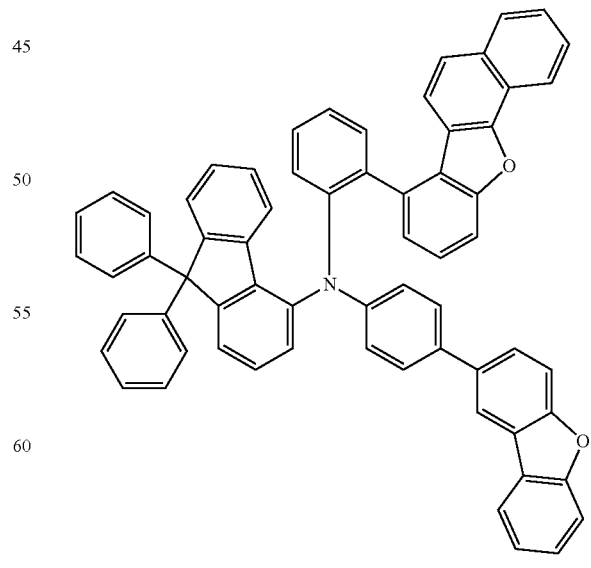

341
-continued
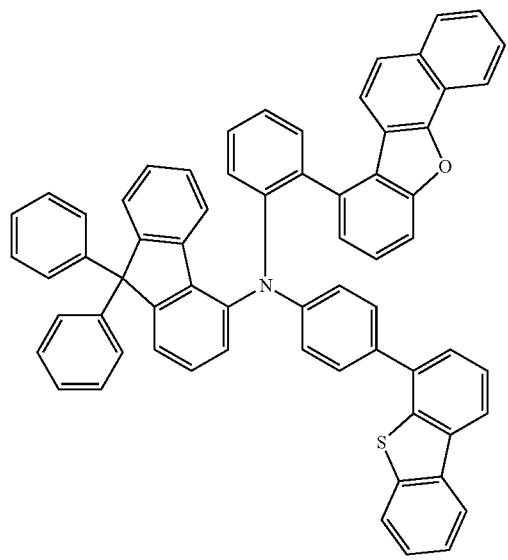
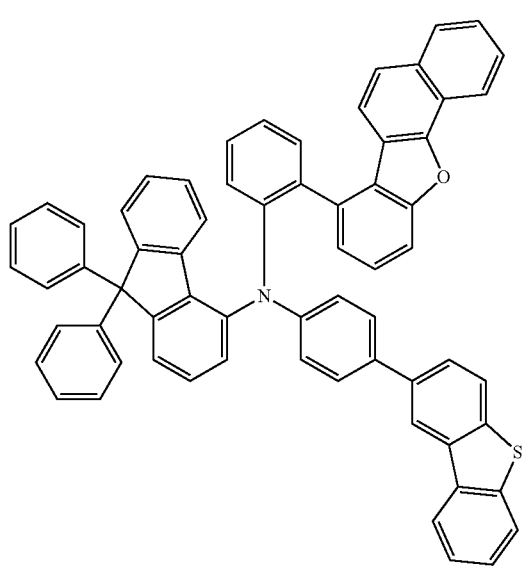
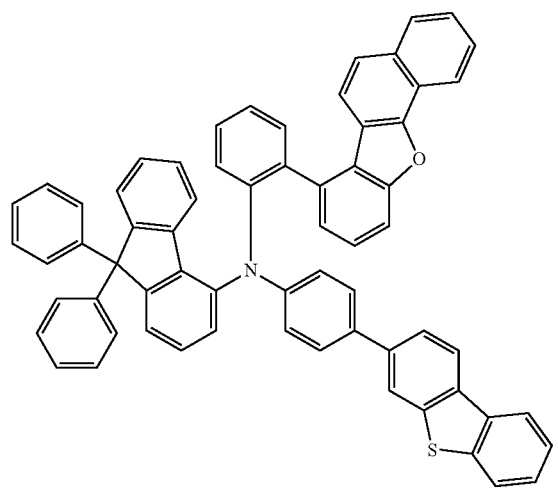
342
-continued
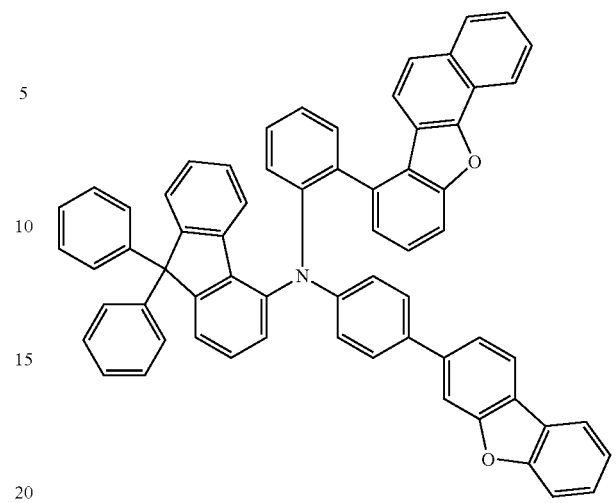
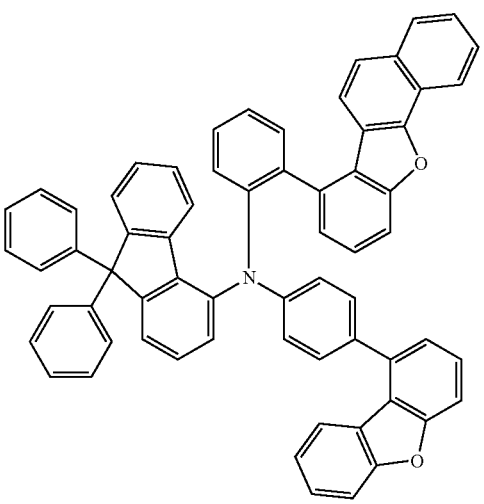
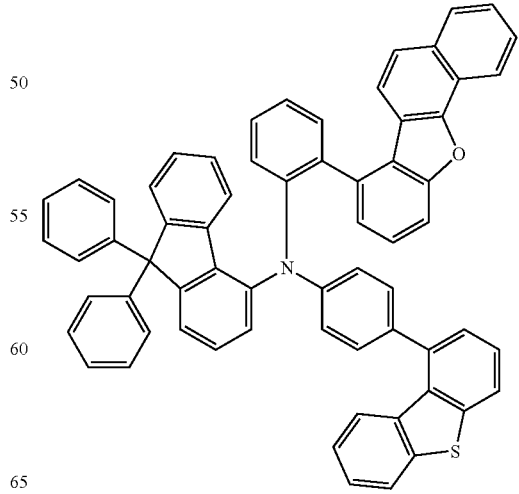

343
-continued
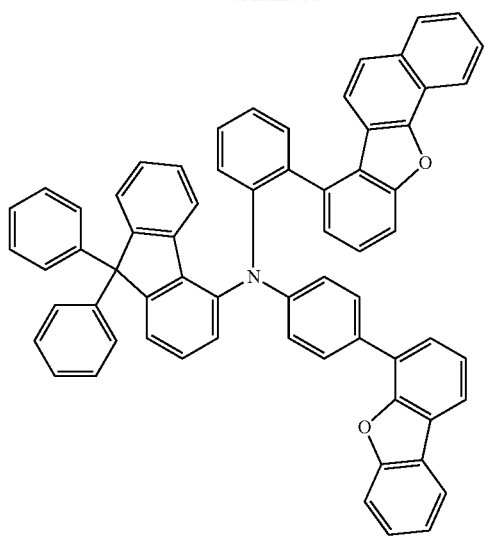
[Chem. 133]
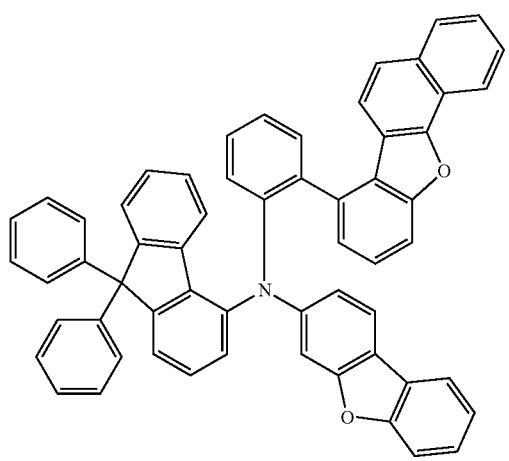
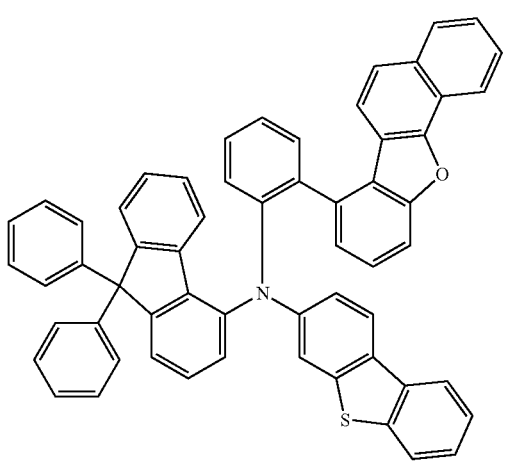
344
-continued
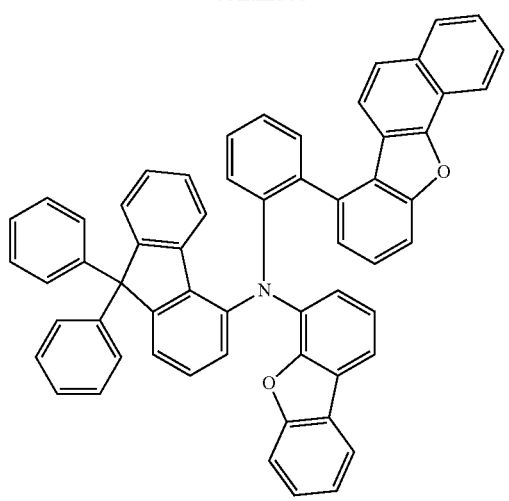
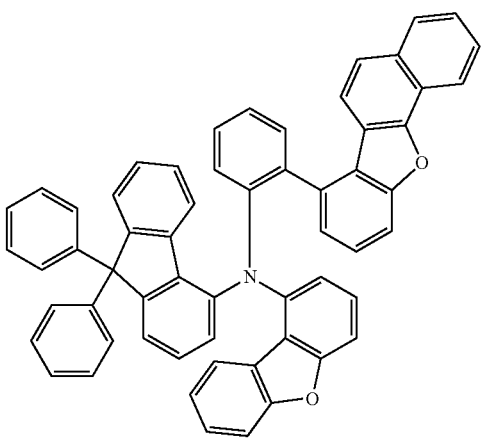
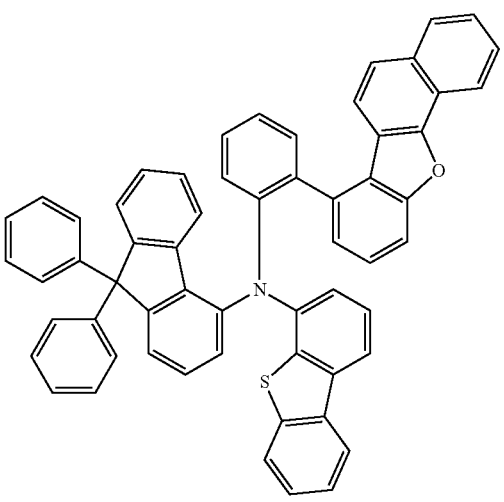

345
-continued
346
-continued
[Chem. 134]
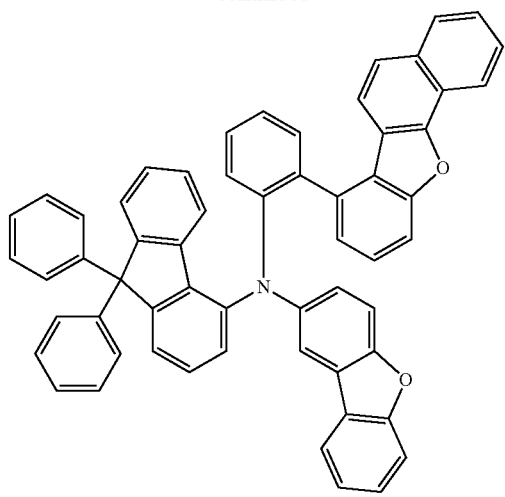
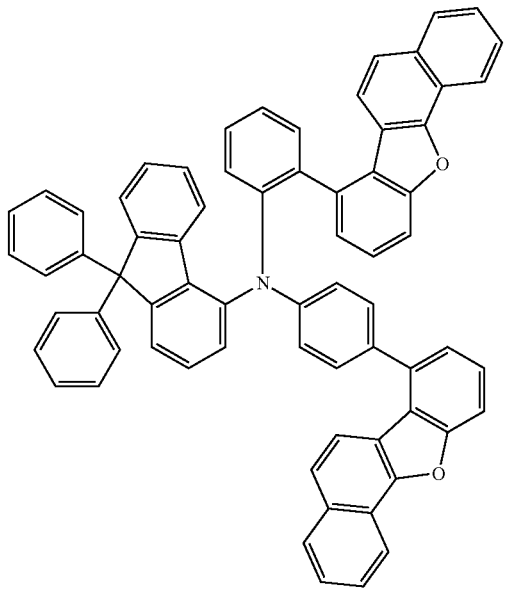
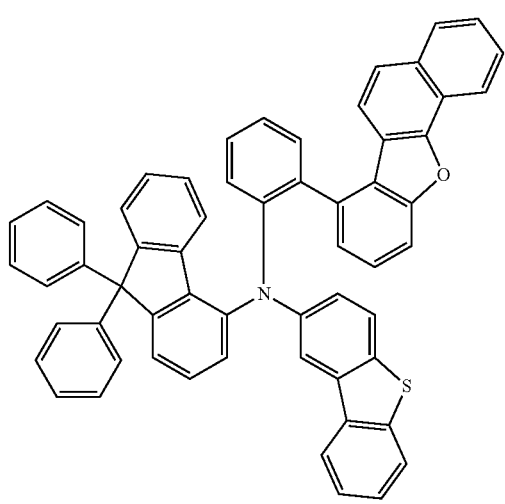
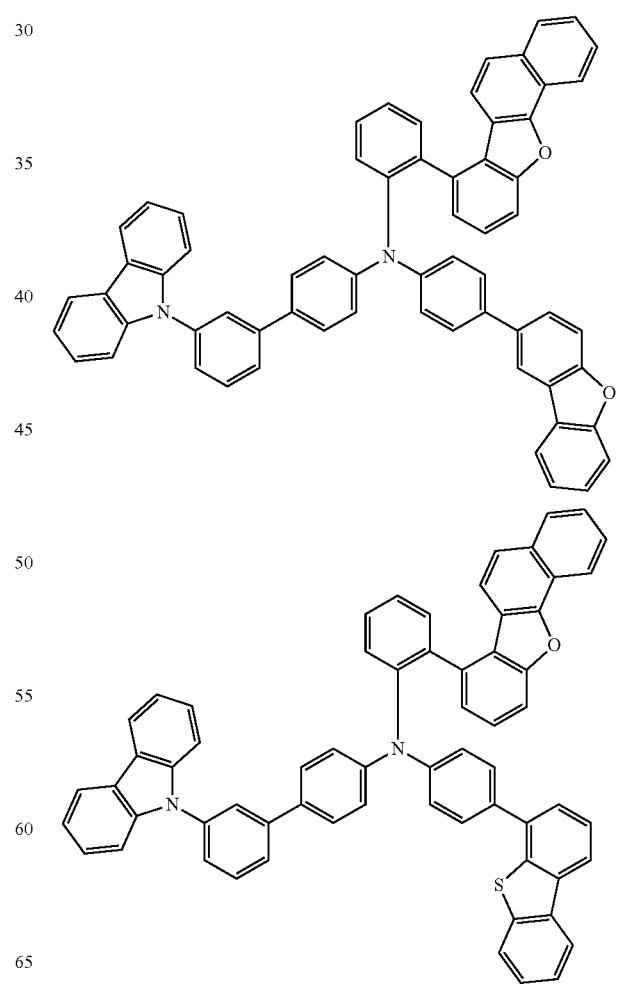
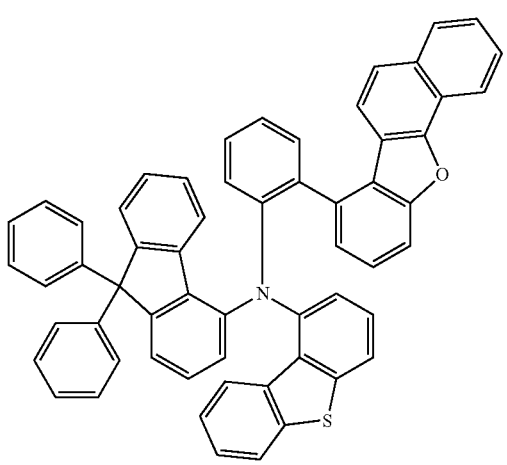

347
-continued
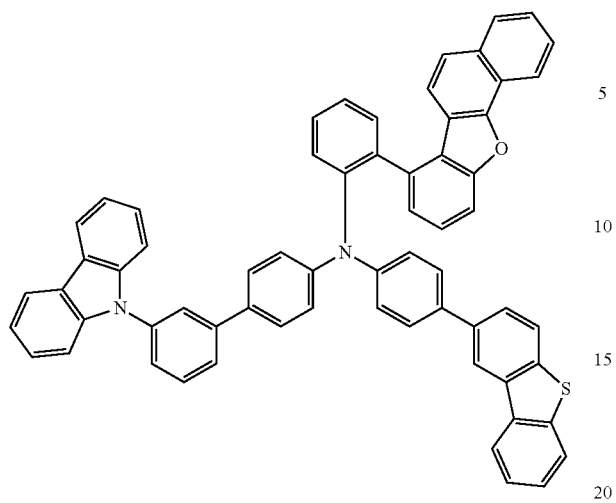
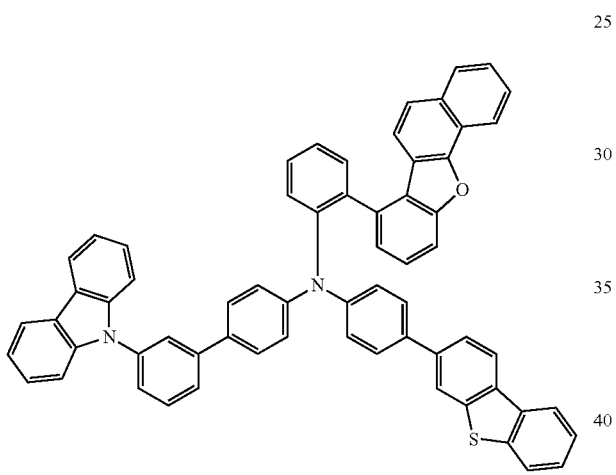
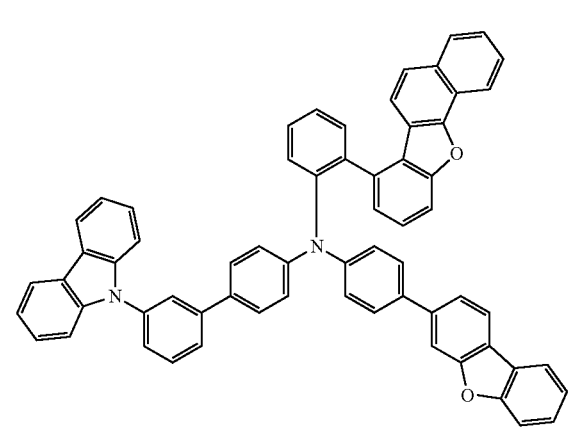
348
-continued
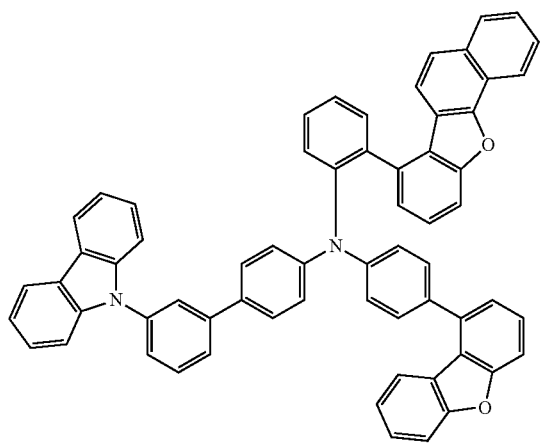
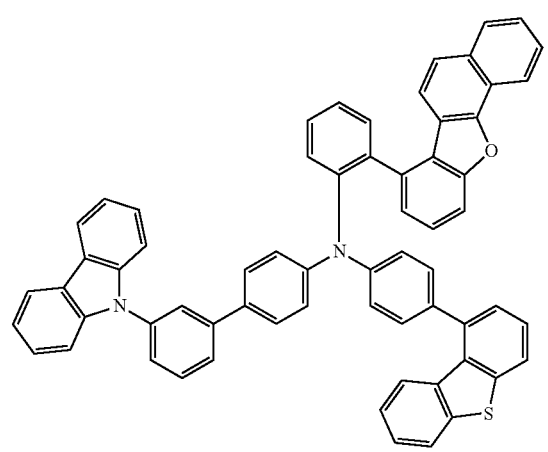
[Chem. 135]
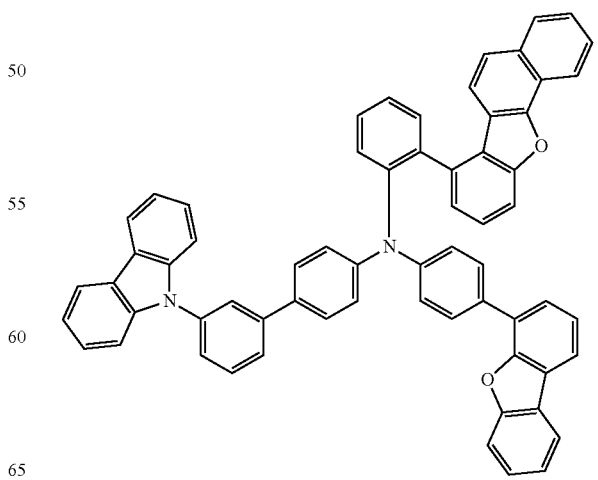

349
-continued
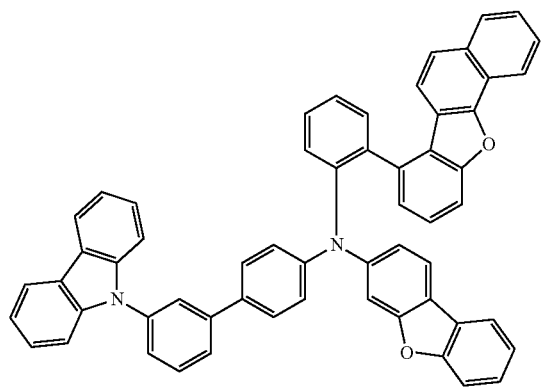
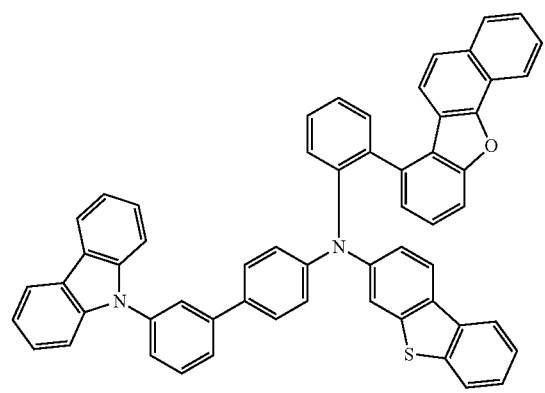
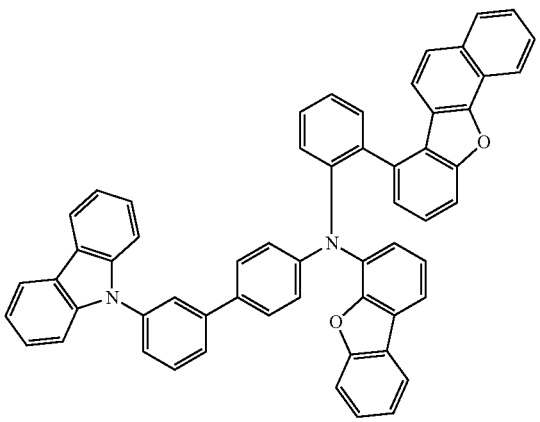
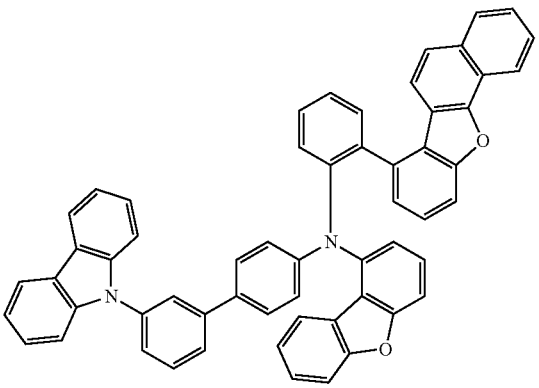
350
-continued
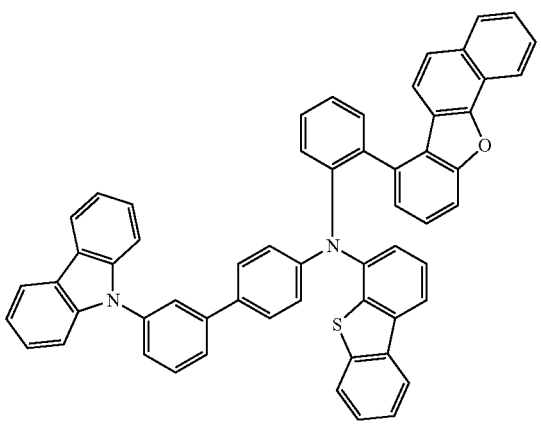
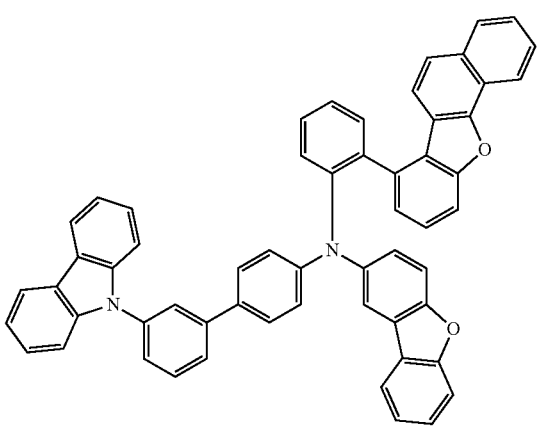
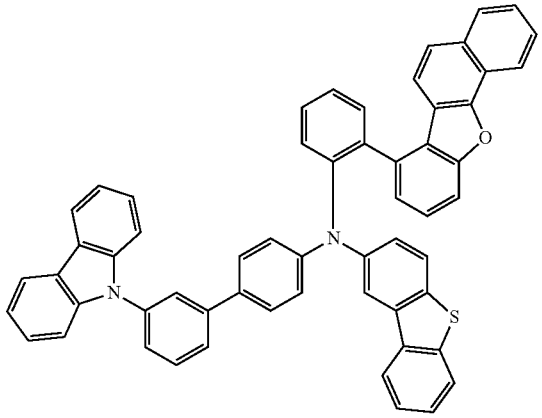
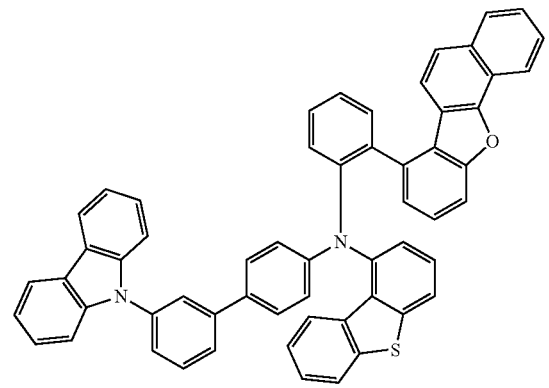

351
-continued
352
-continued
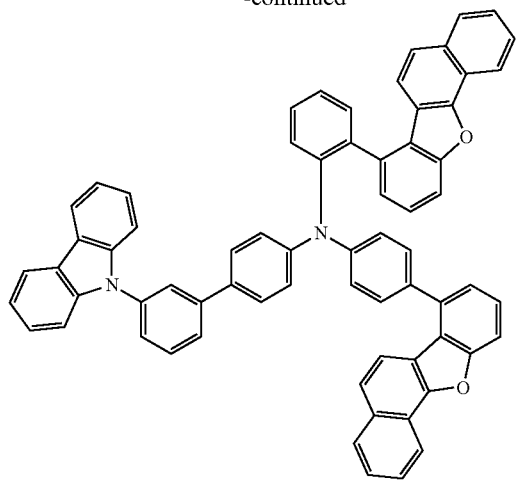
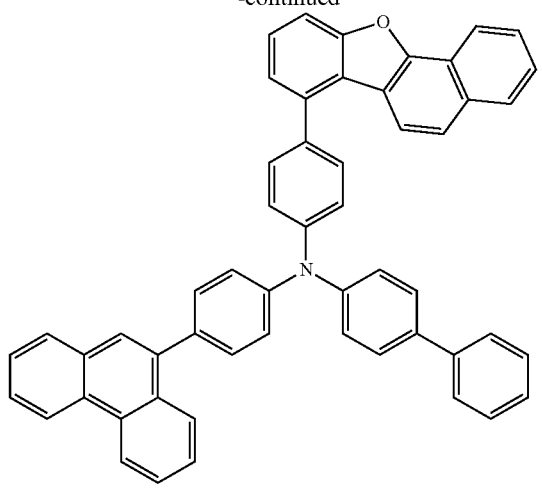
[Chem. 136]
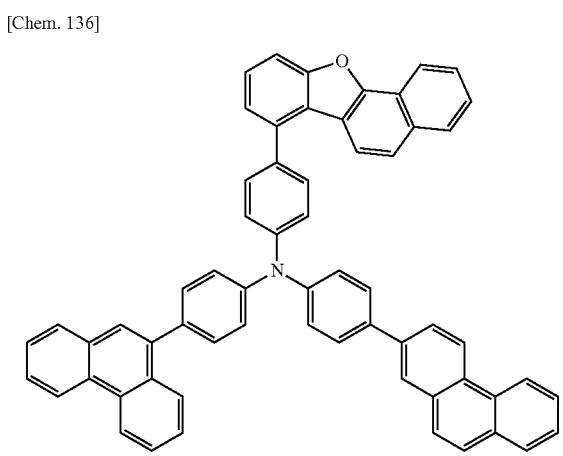
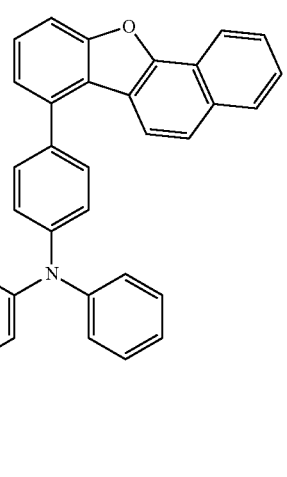
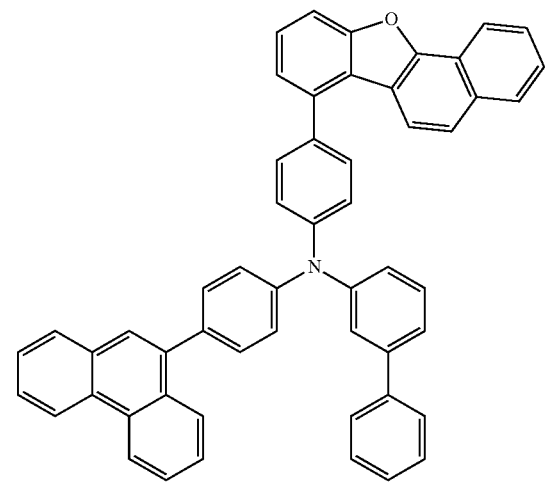
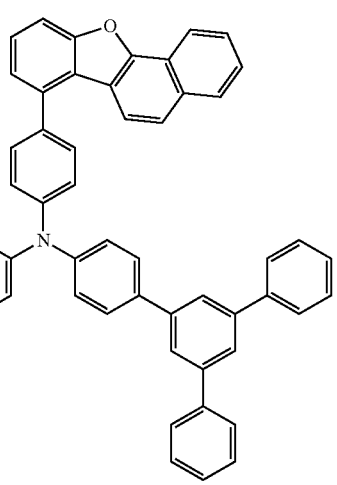

353
-continued
354
-continued
[Chem. 137]
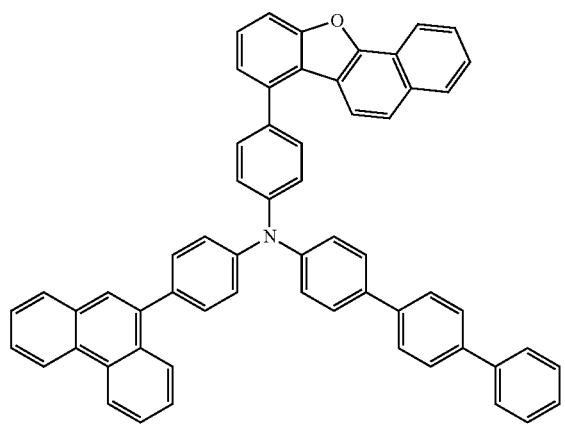
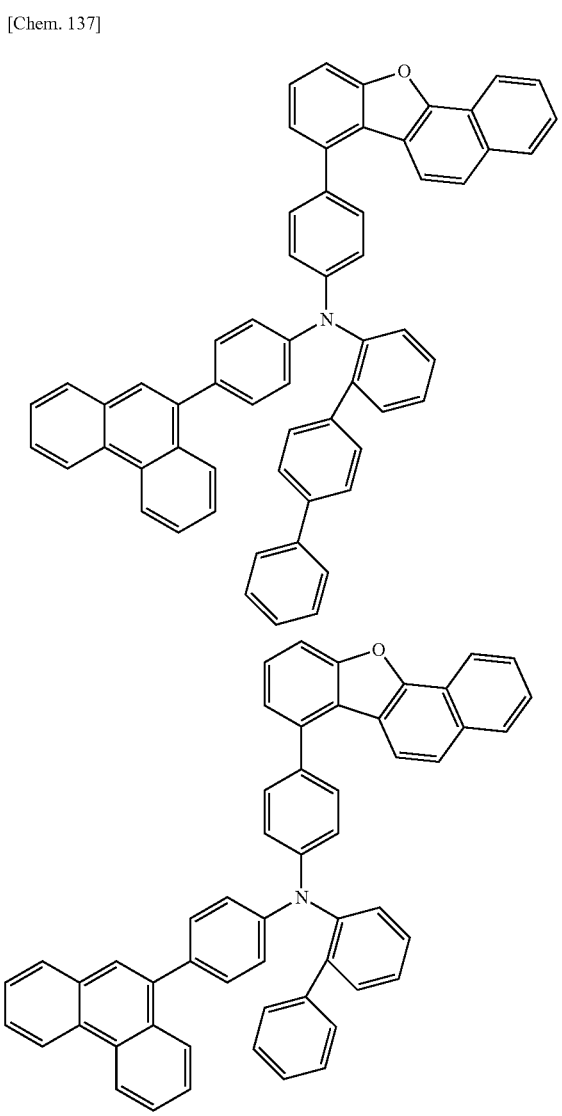
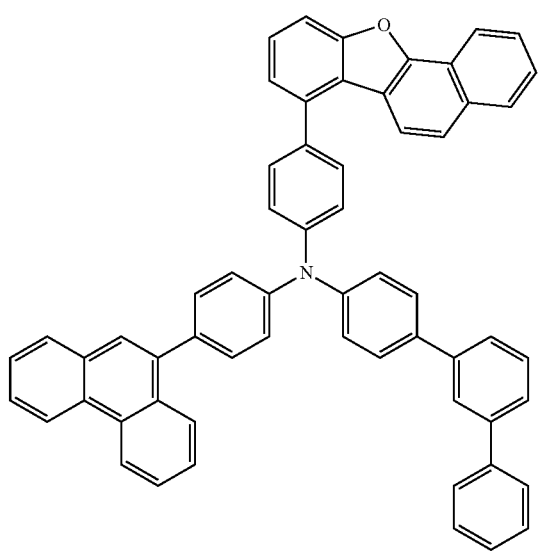
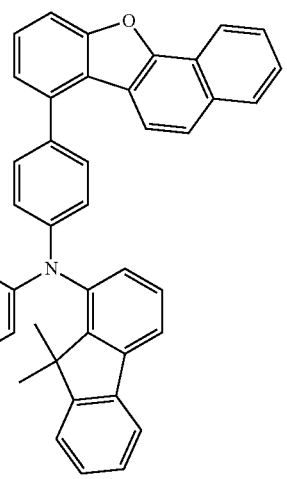

355
-continued
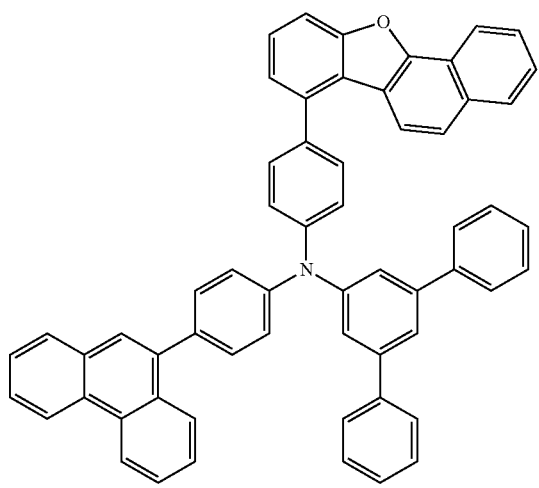
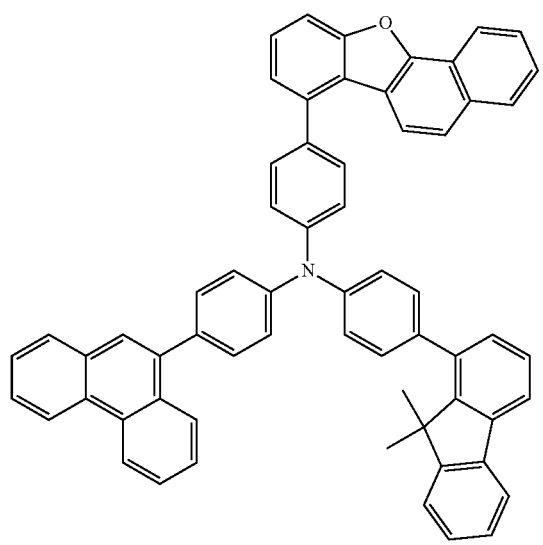
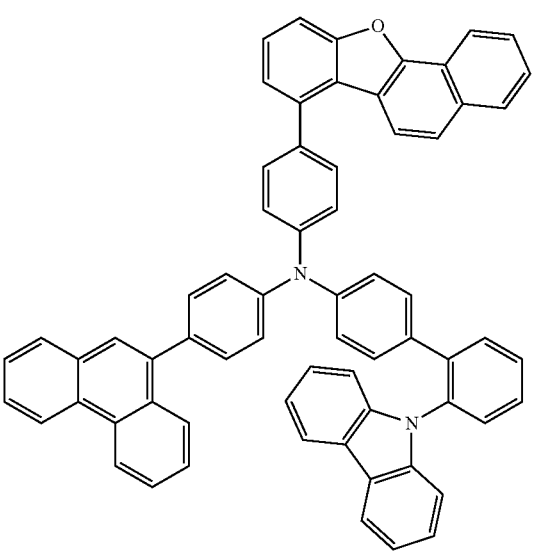
356
-continued
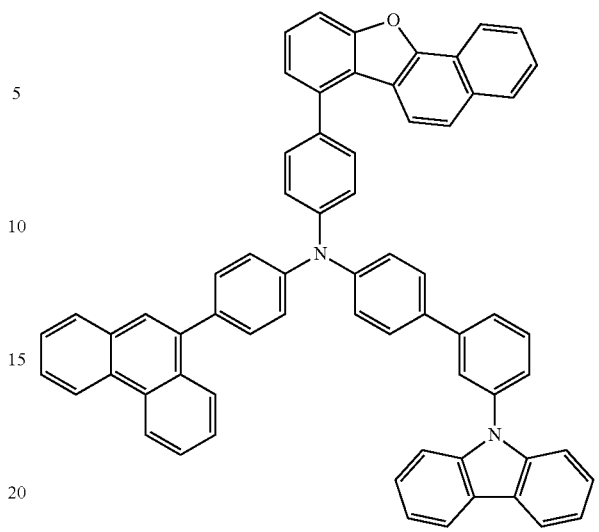
[Chem. 138]
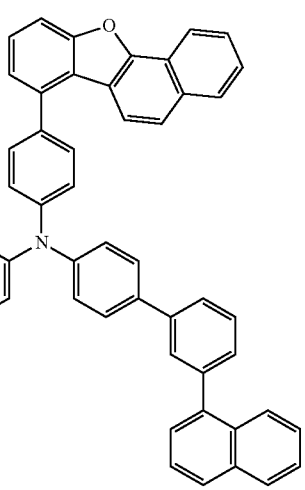

357
-continued
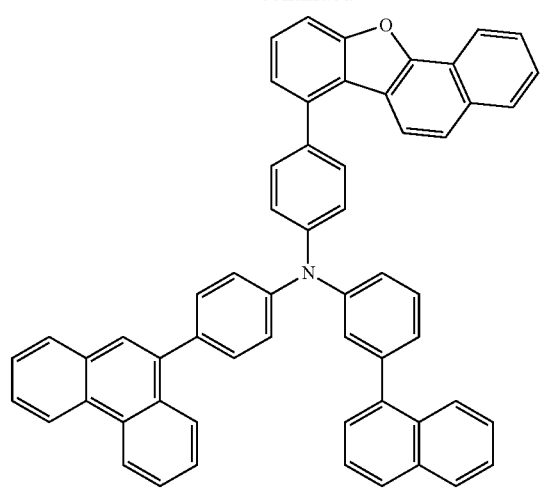
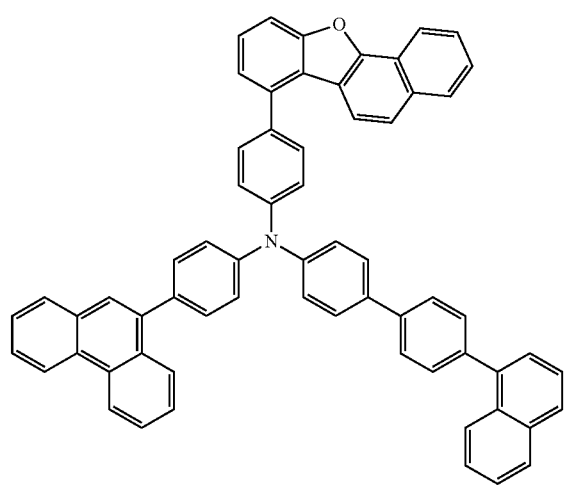
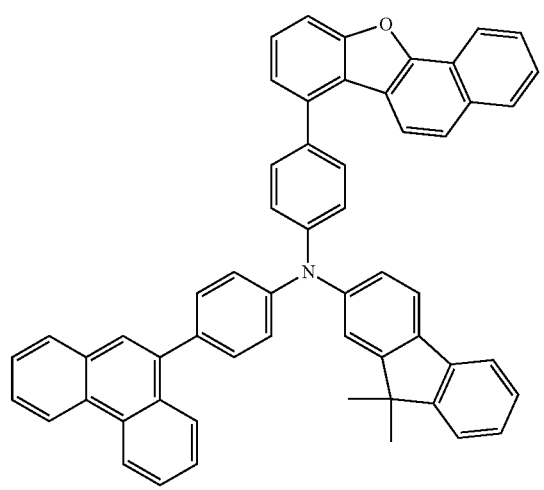
358
-continued
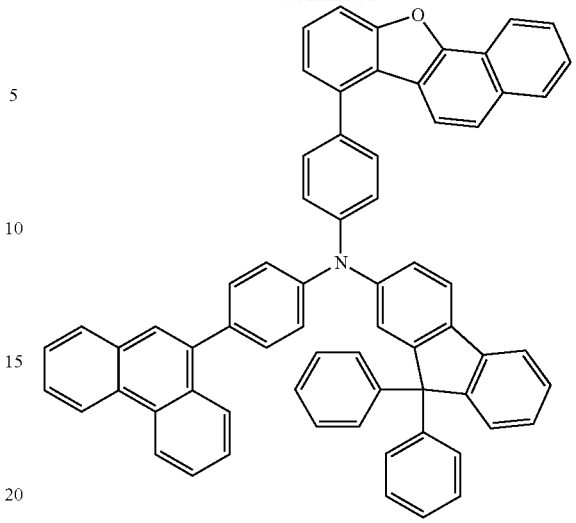
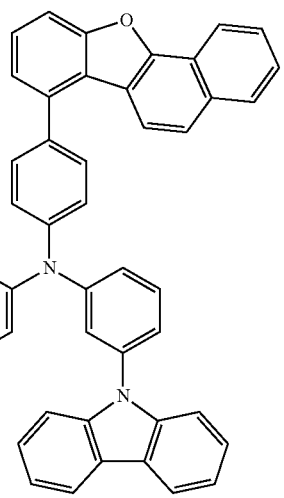
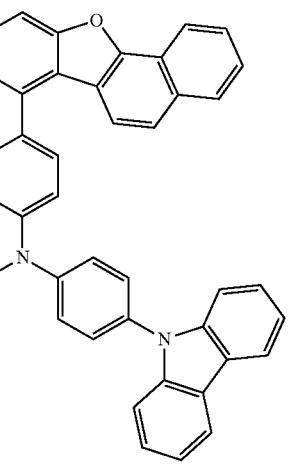

359
-continued
360
-continued
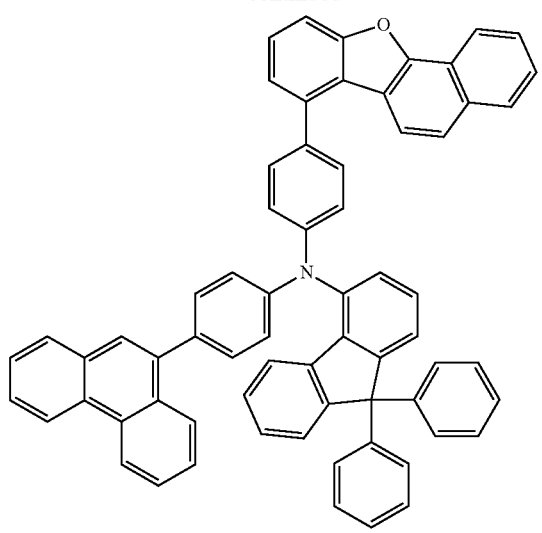
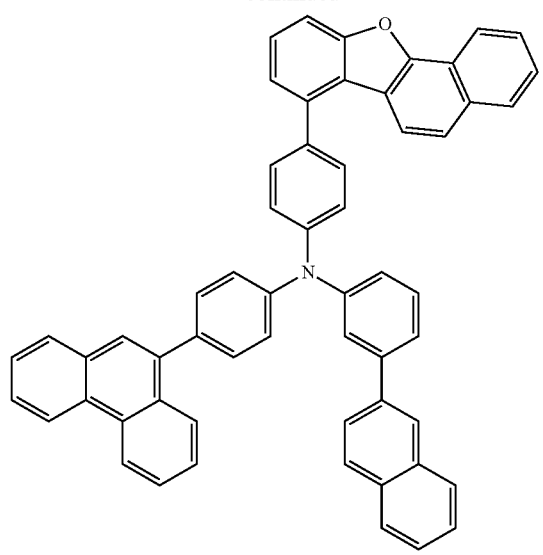
[Chem. 139]
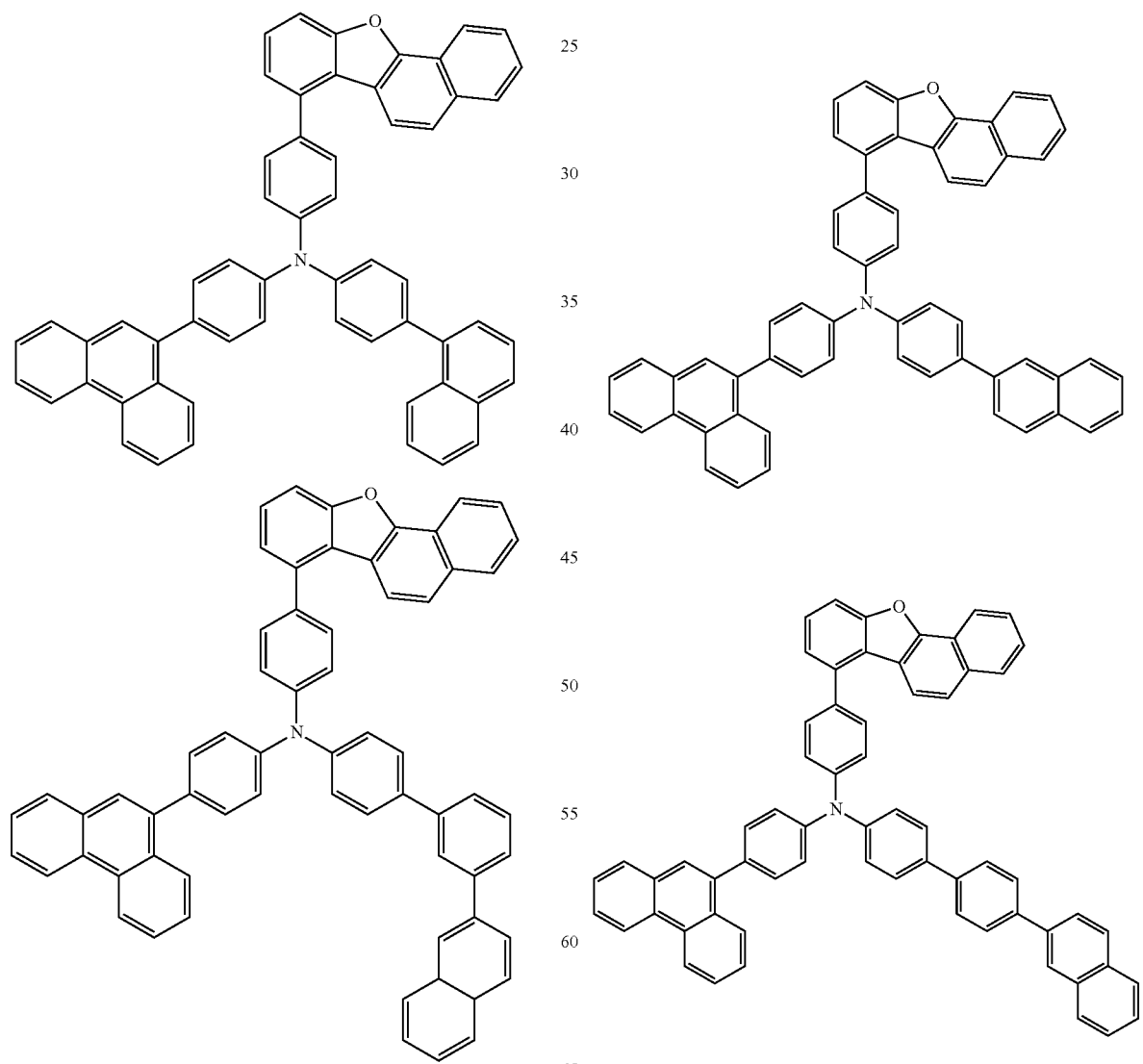

361 -continued
362 -continued
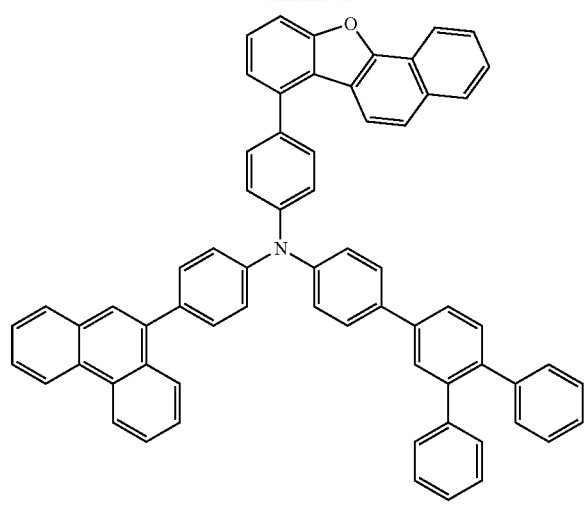
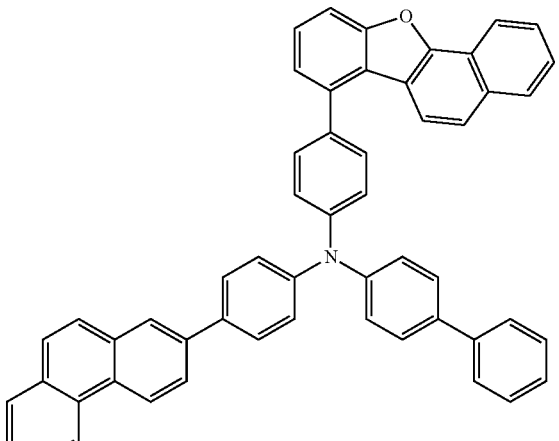
[Chem. 140]
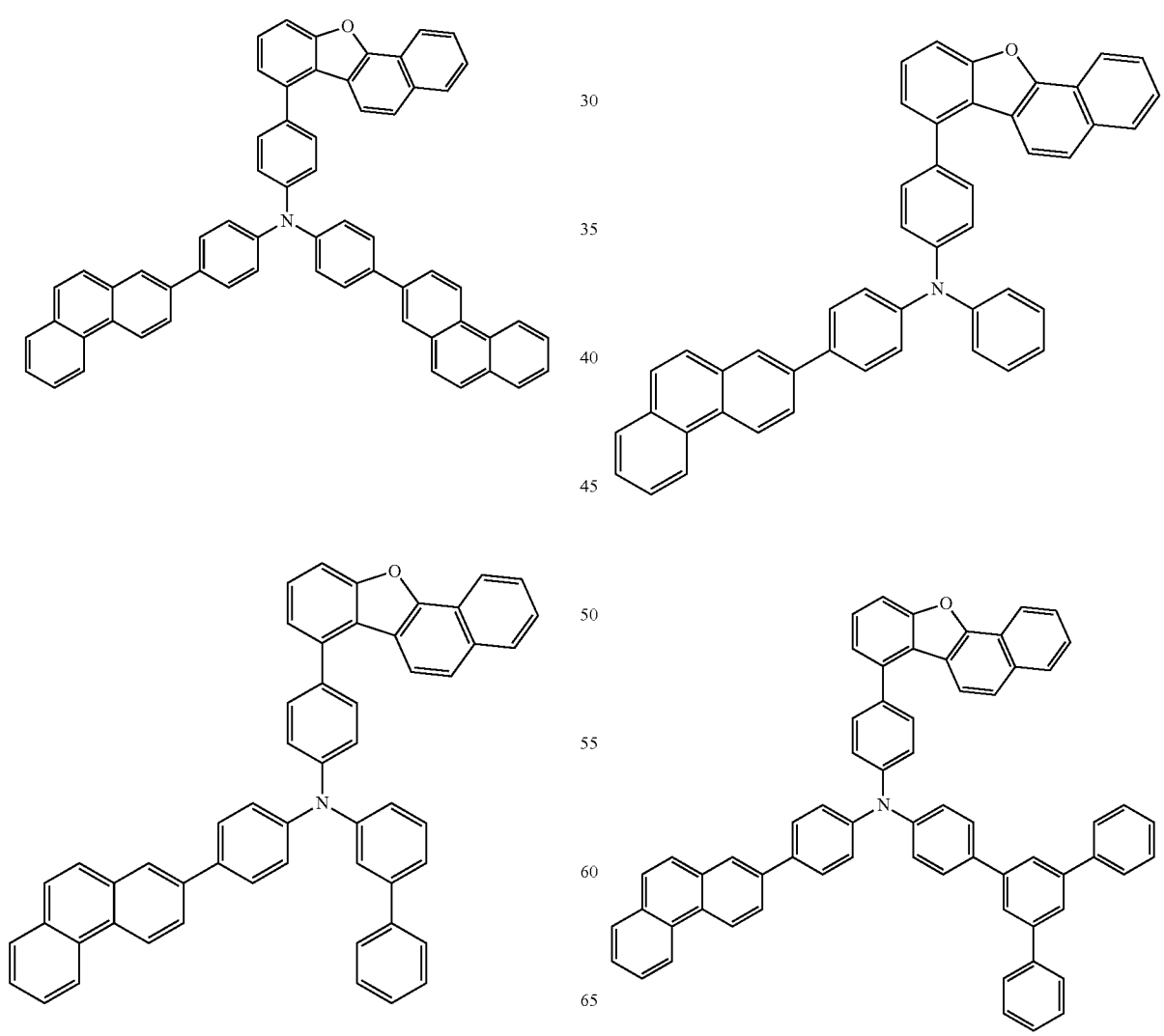

363
-continued
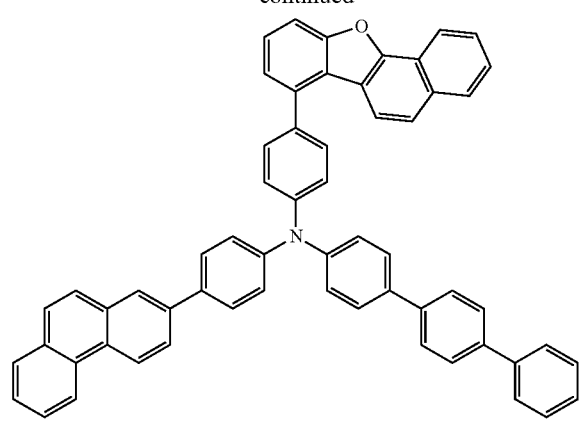
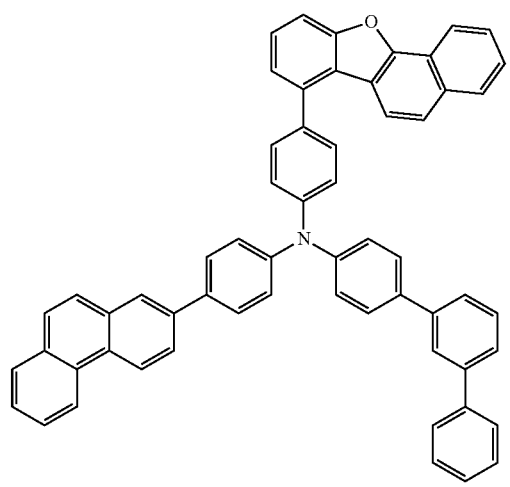
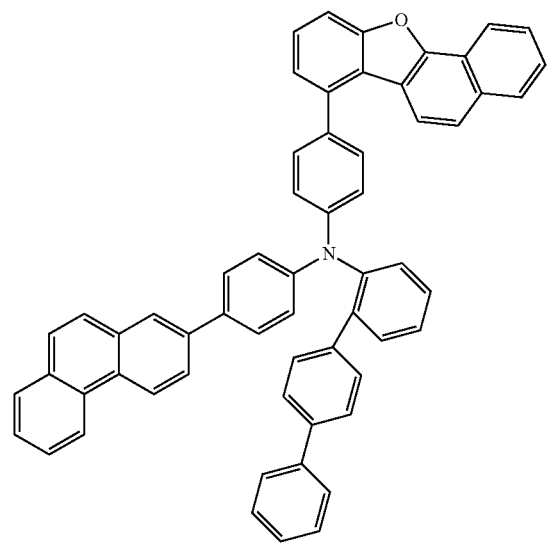
364
-continued
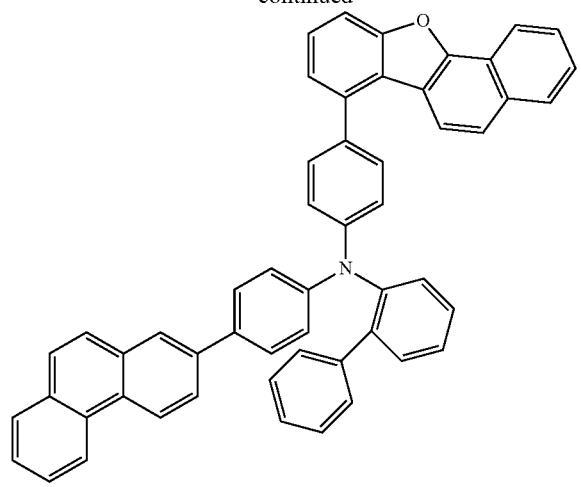
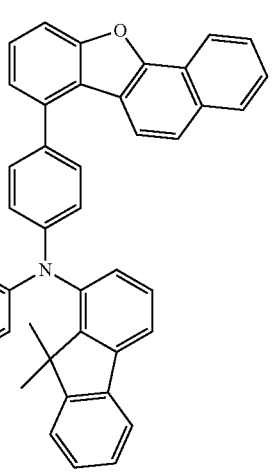
[Chem. 141]
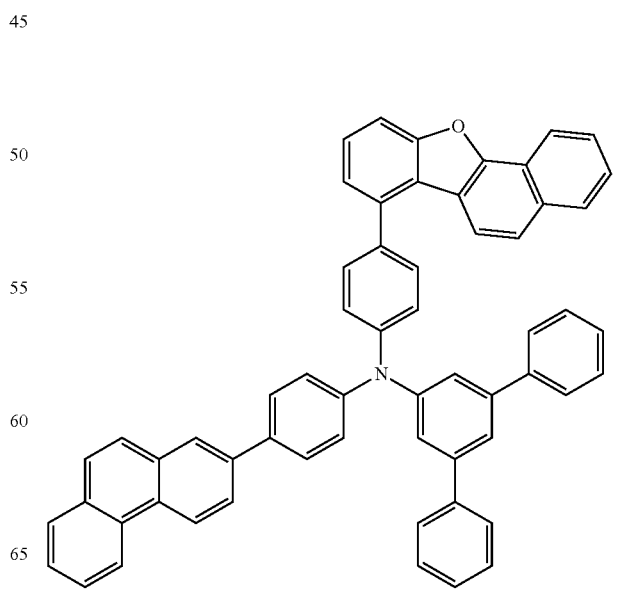

365
-continued
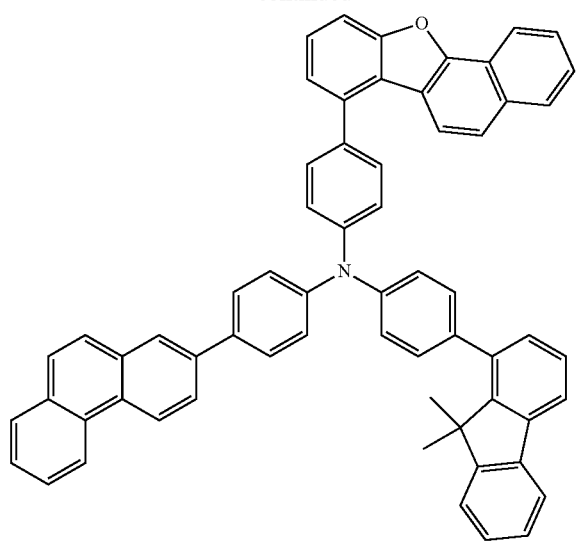
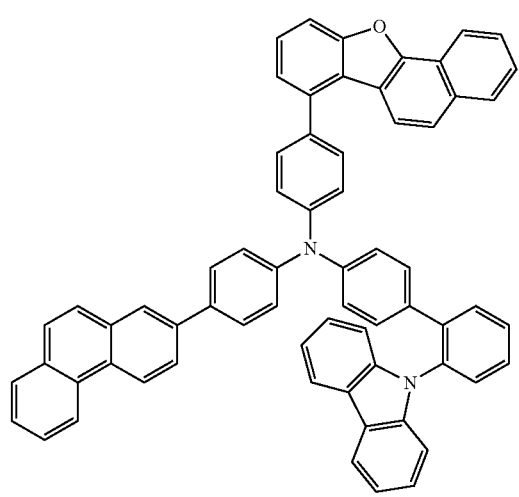

366
-continued
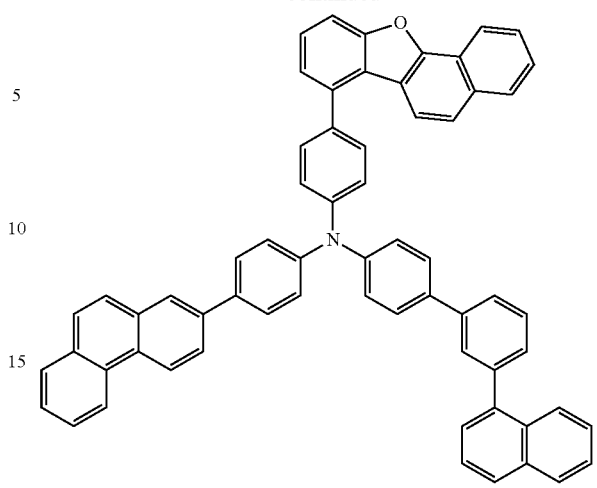
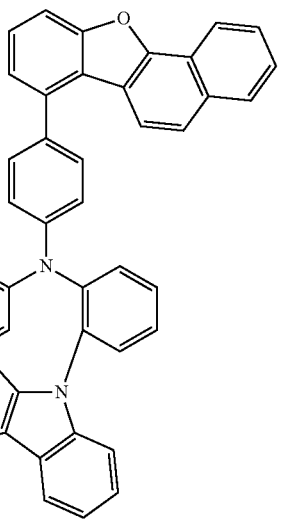
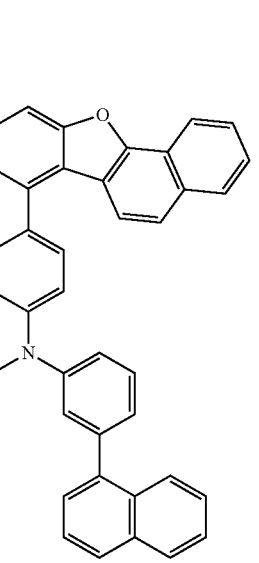

367
-continued
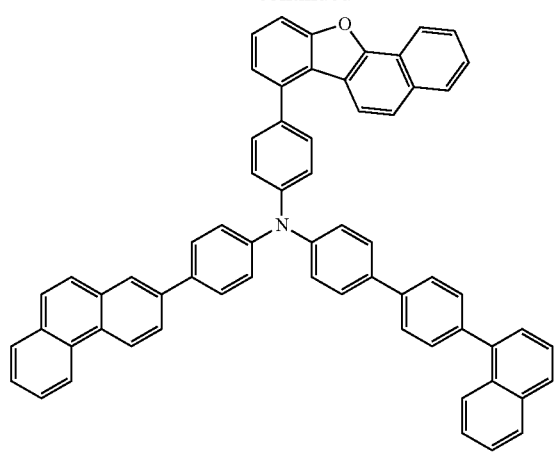
[Chem. 142]
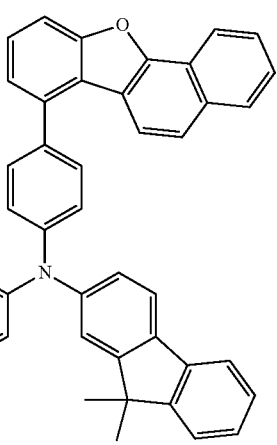
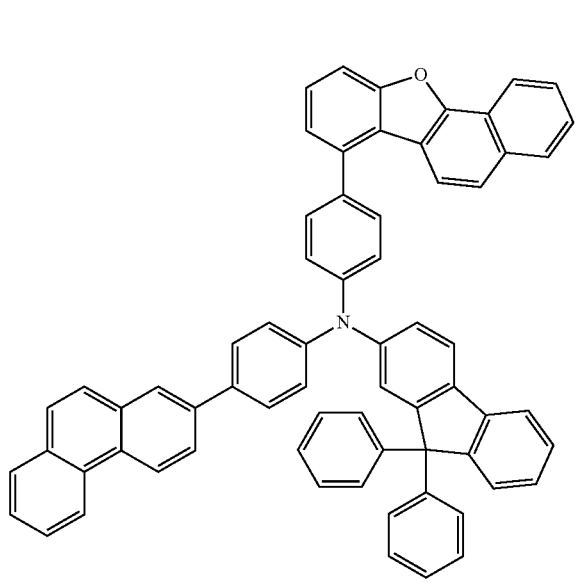
368
-continued
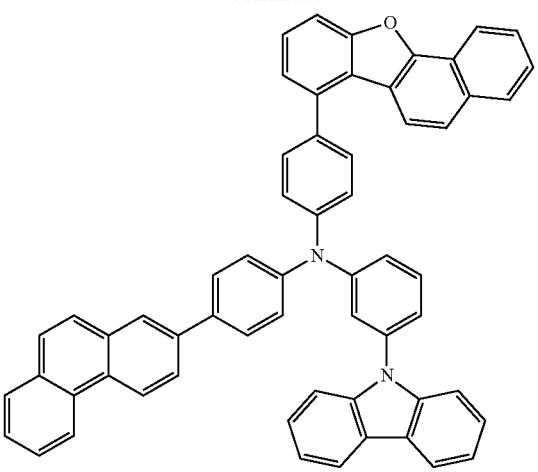
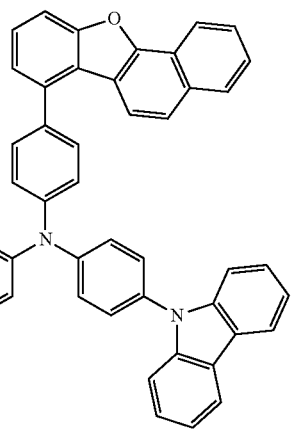
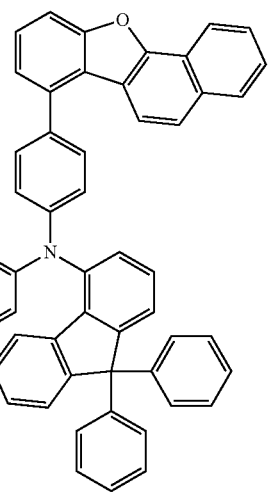

369
-continued
370
-continued
[Chem. 143]
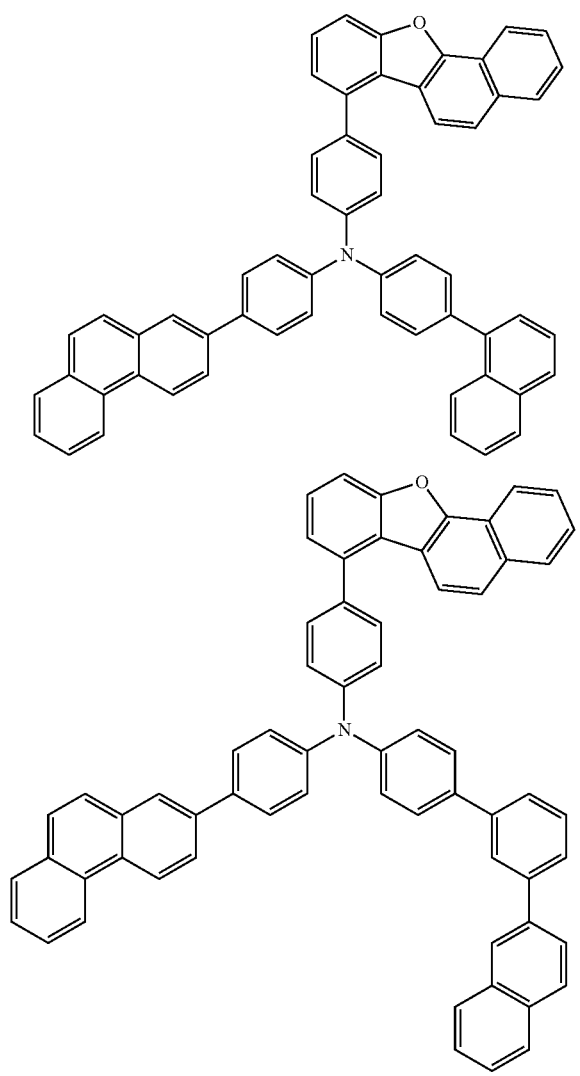
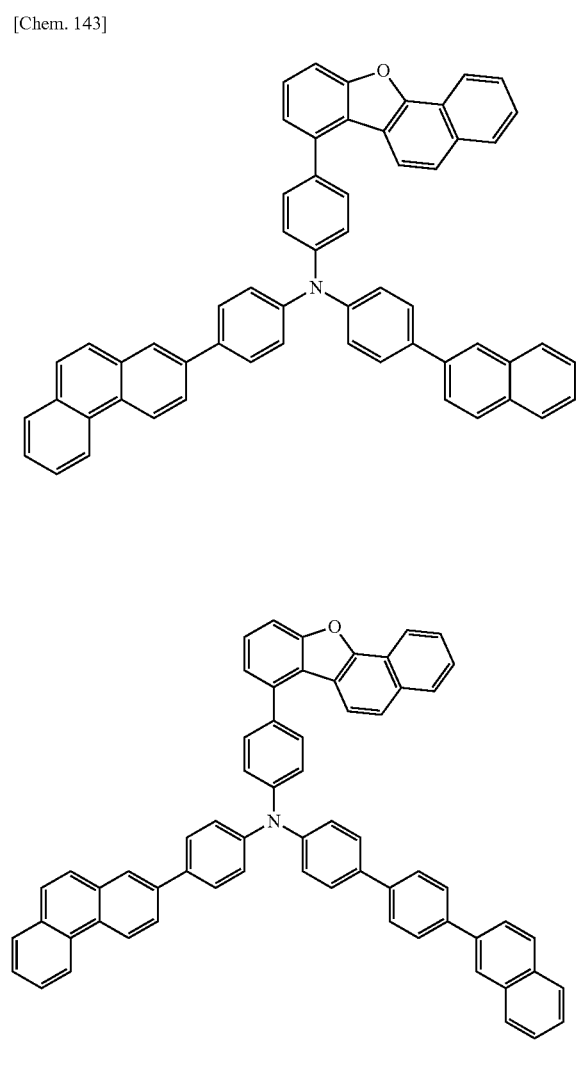
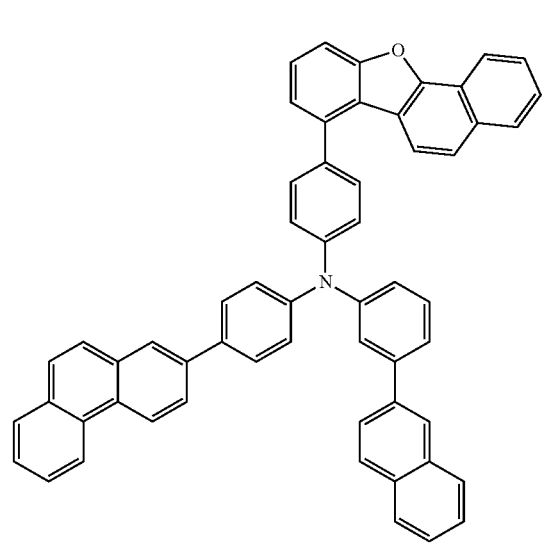

371
-continued
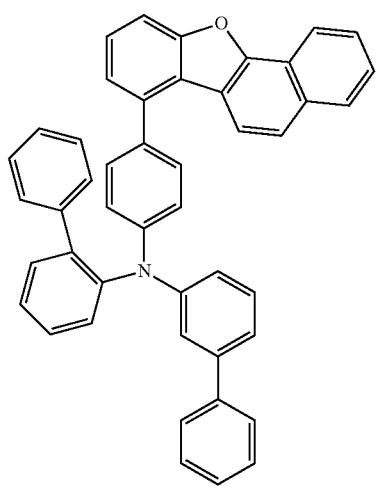
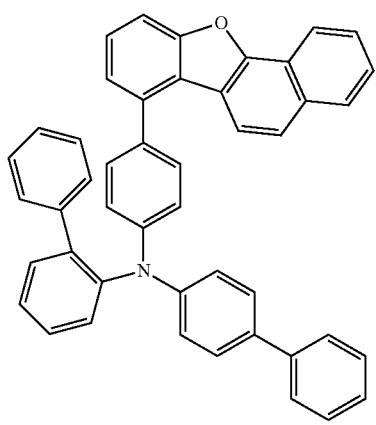
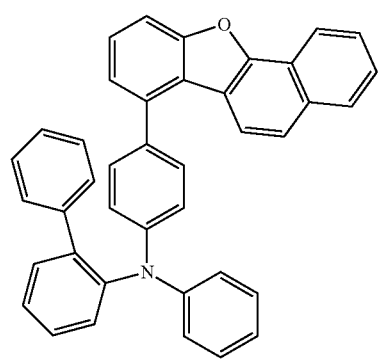
372
-continued
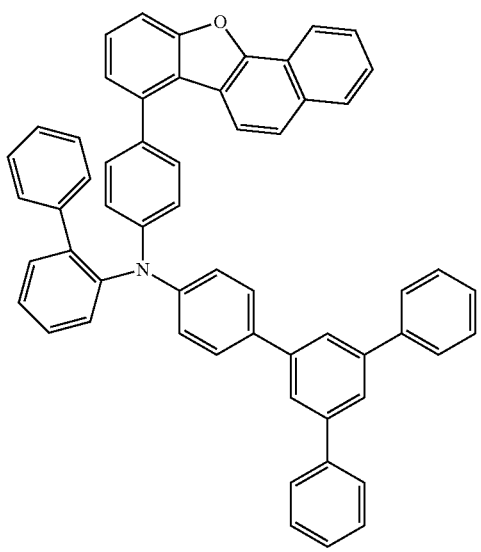
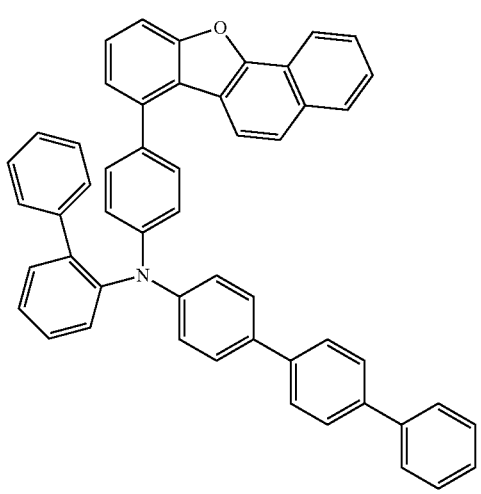
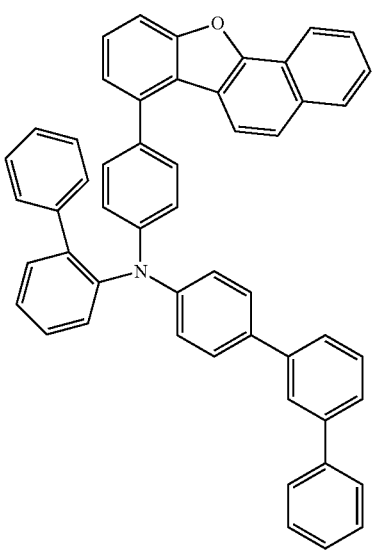

373
-continued
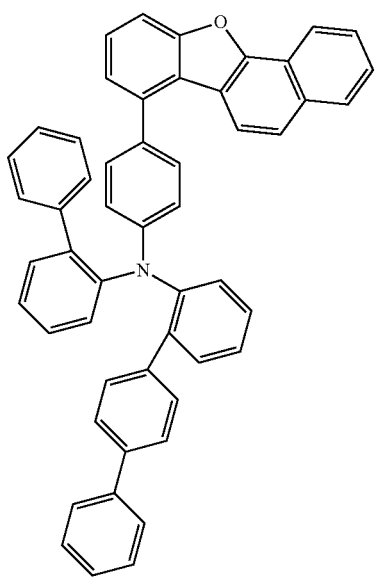
[Chem. 144]
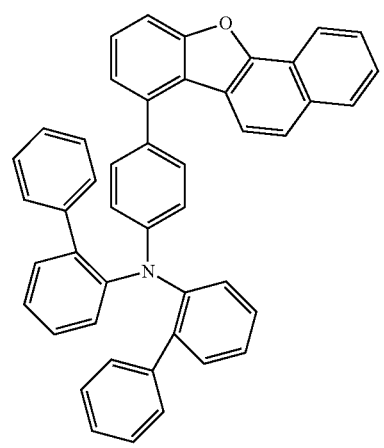
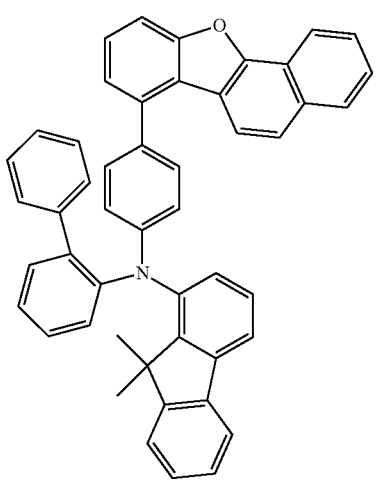
374
-continued
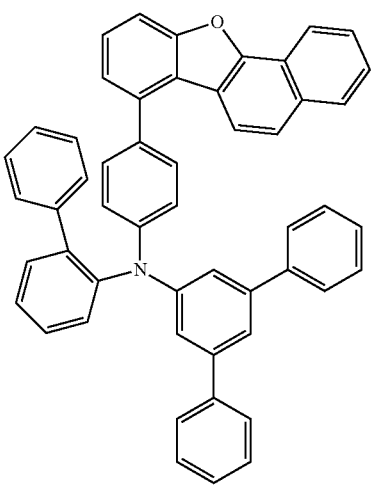
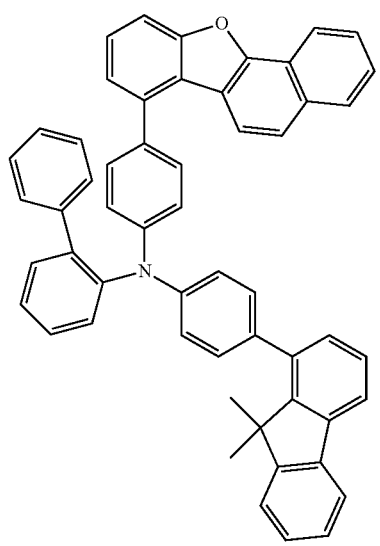
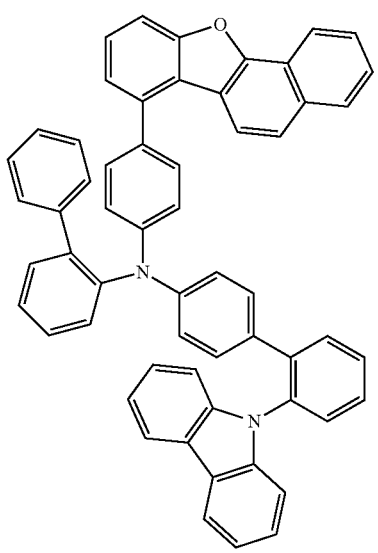

-continued
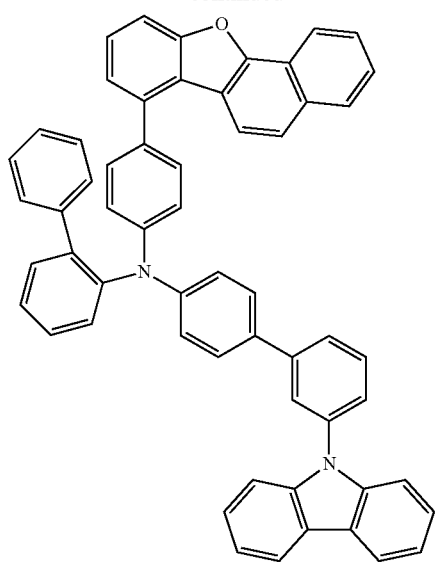
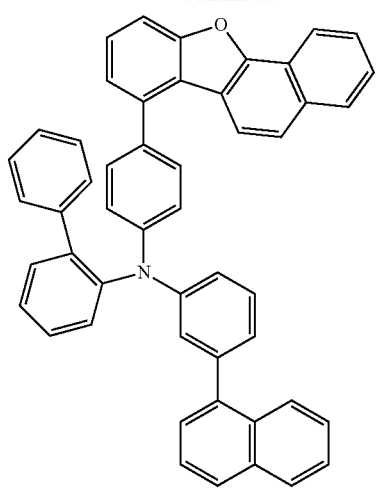
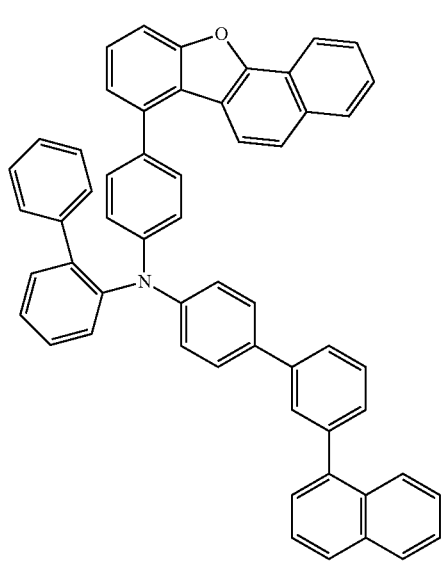
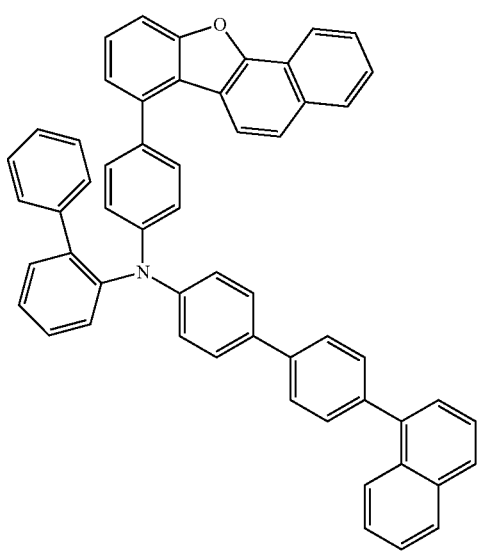
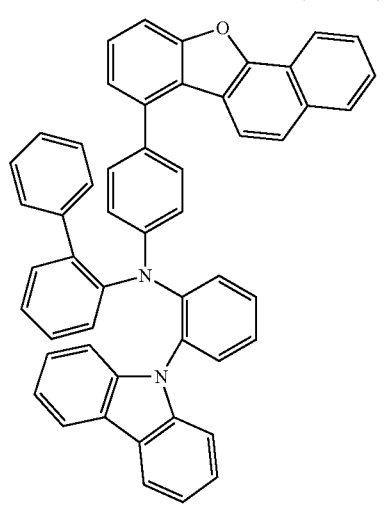
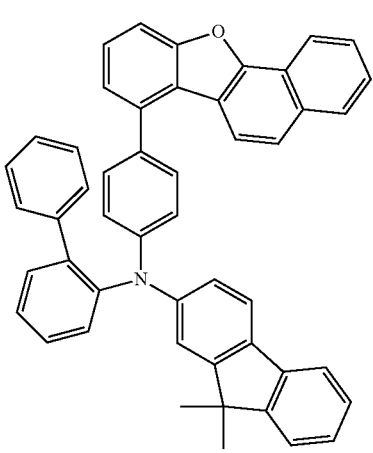

377
-continued
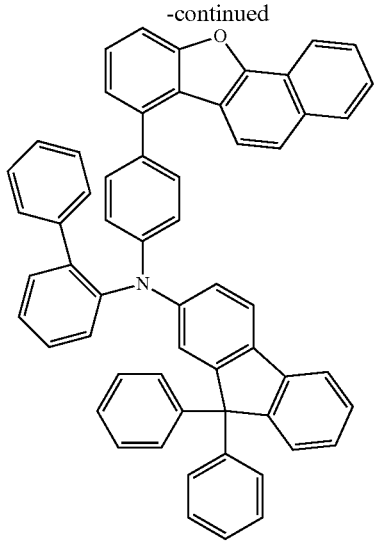
[Chem. 145]
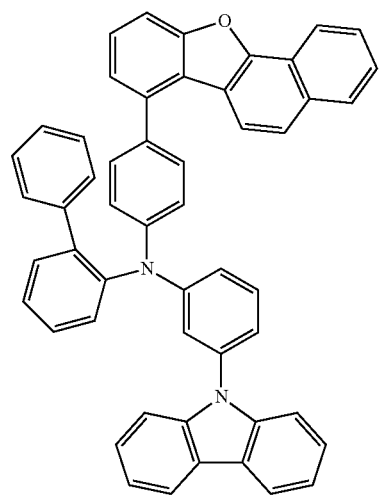
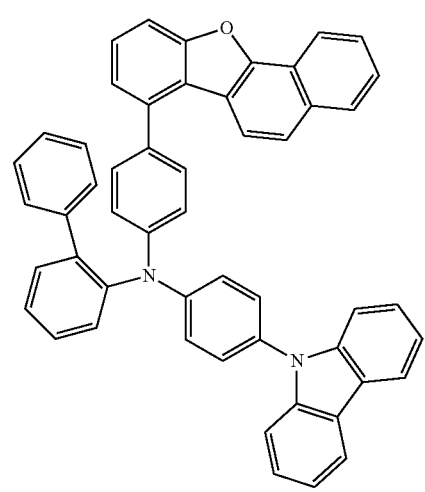
378
-continued
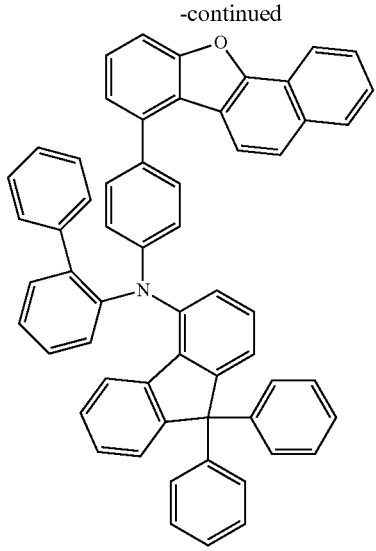
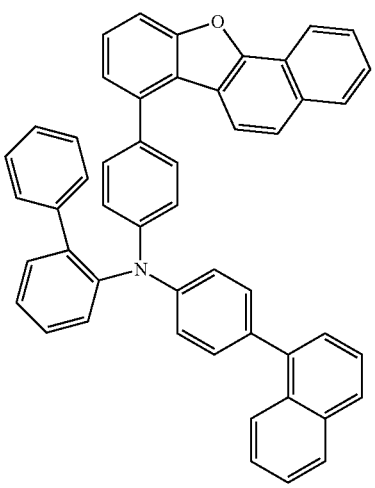
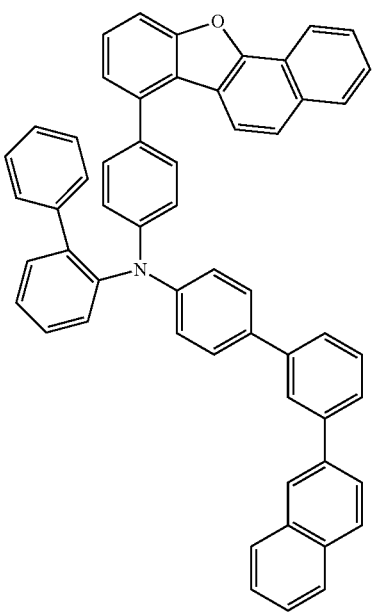

379
-continued
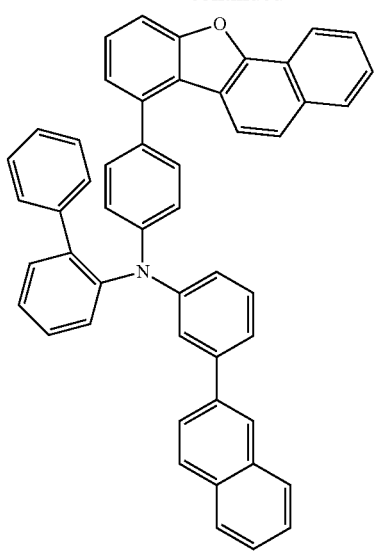
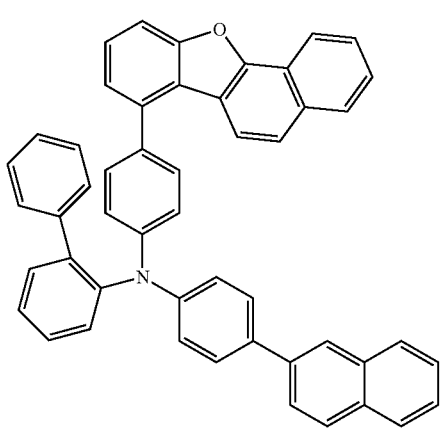
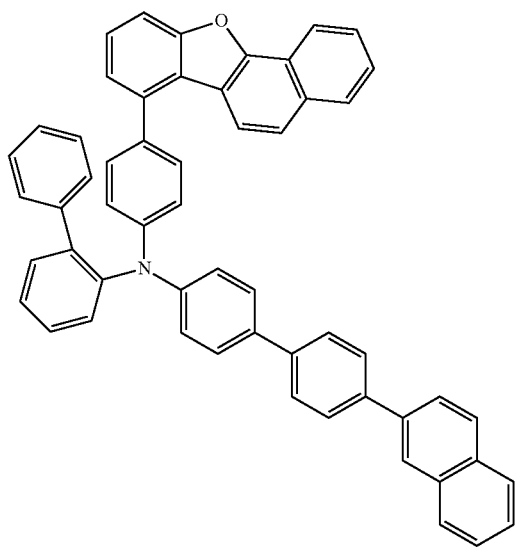
380
-continued
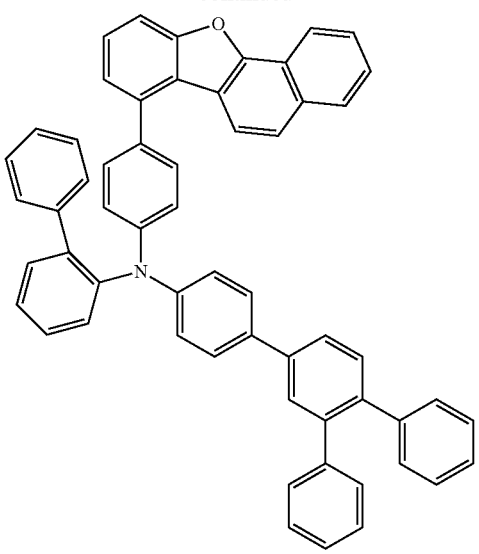
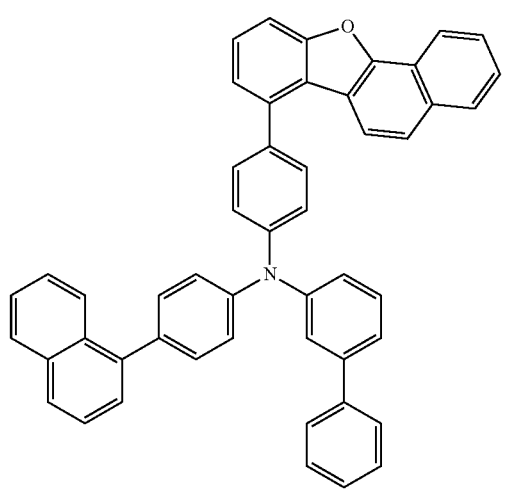
[Chem. 146]
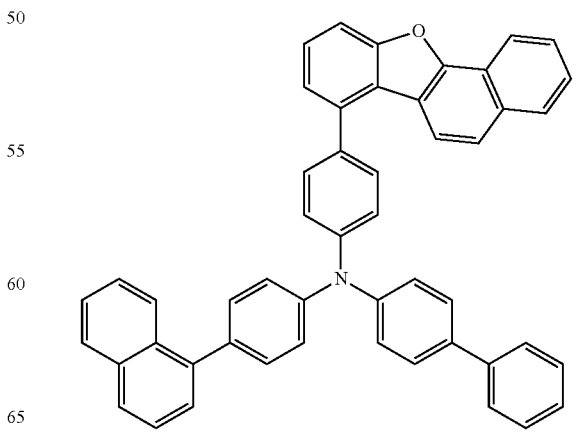

381
-continued
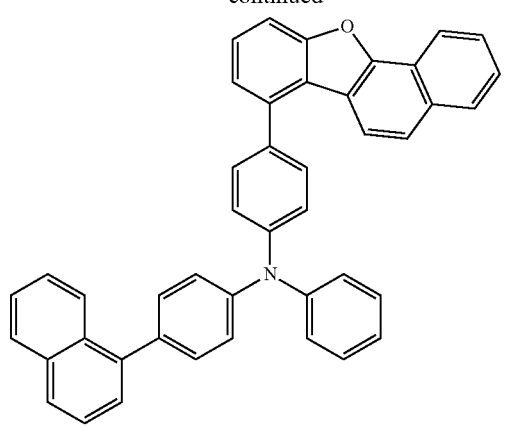
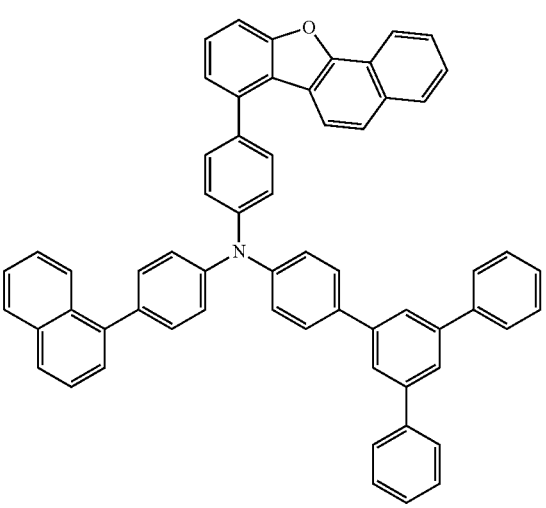
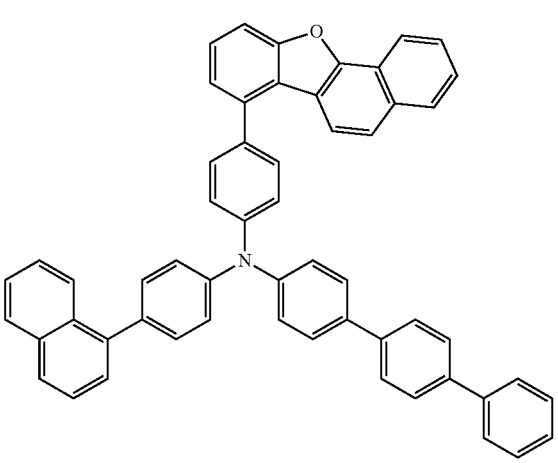
382
-continued
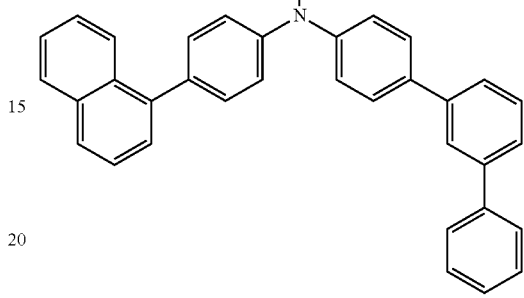
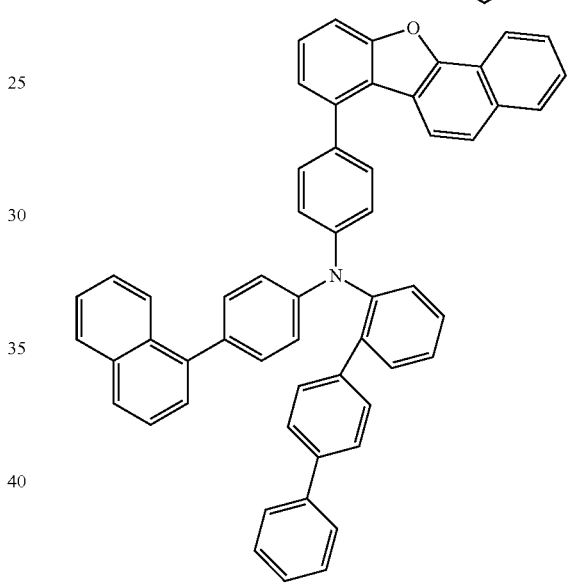
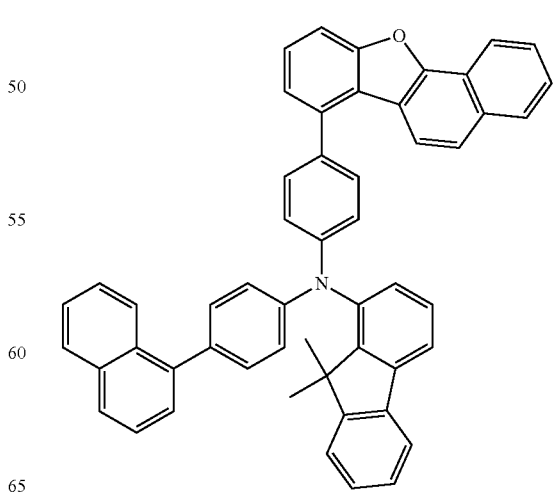

383
-continued
384
-continued
[Chem. 147]
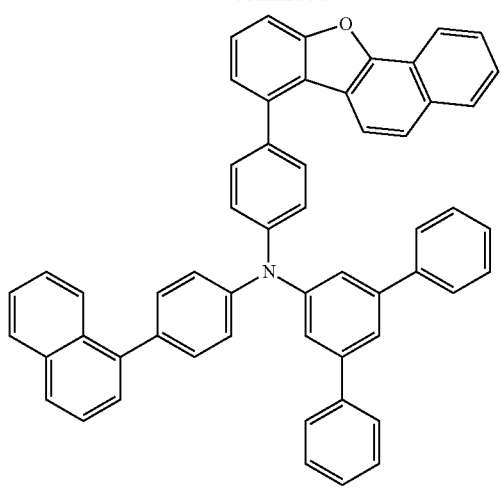
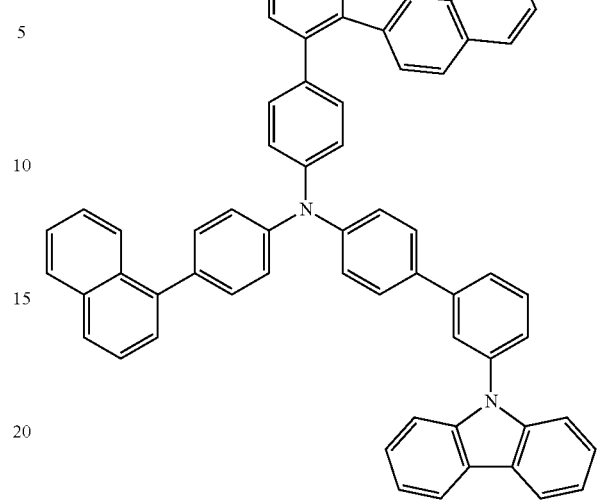

385
-continued
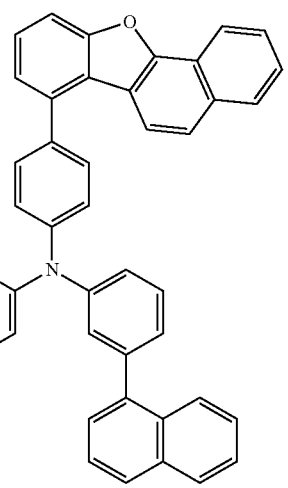
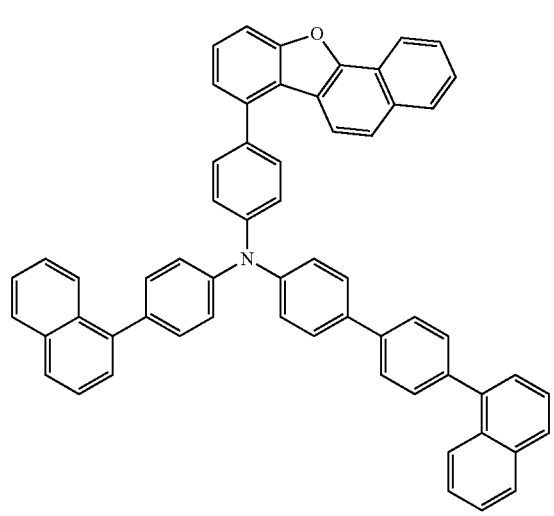
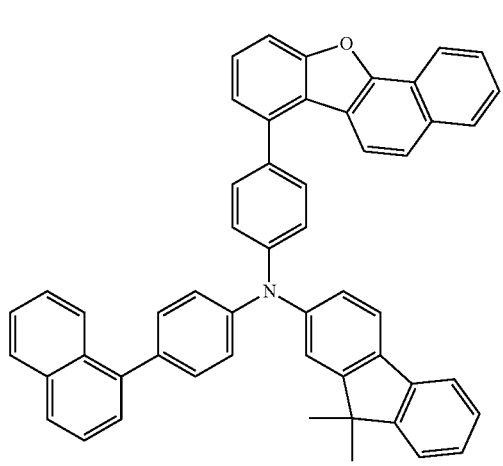
386
-continued
[Chem. 148]
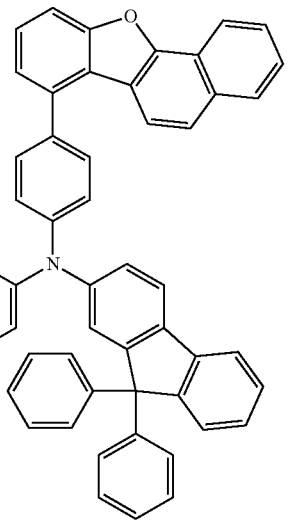
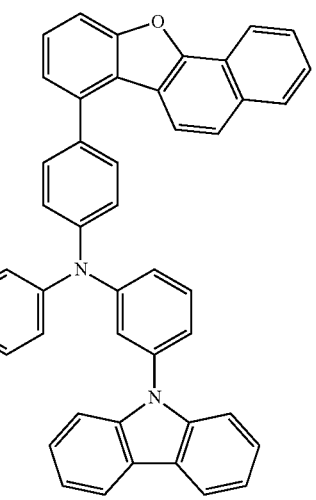
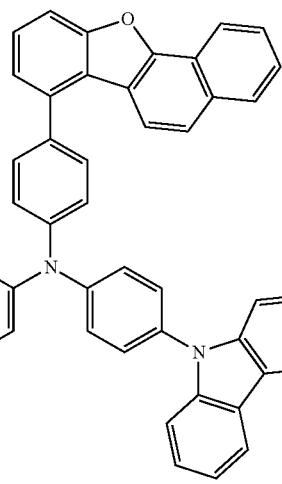

387
-continued
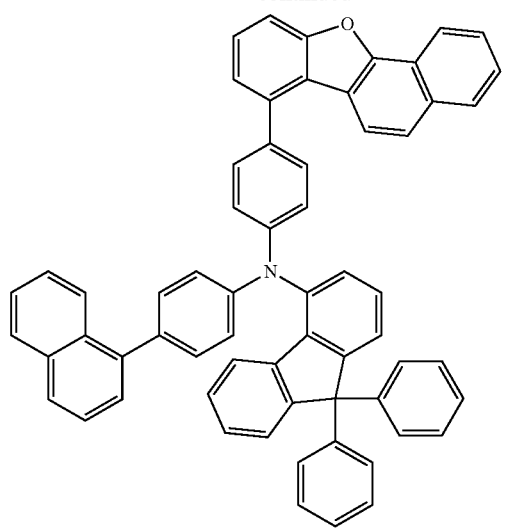
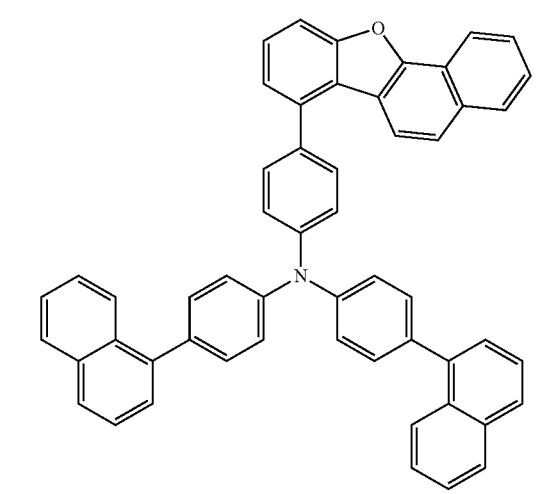
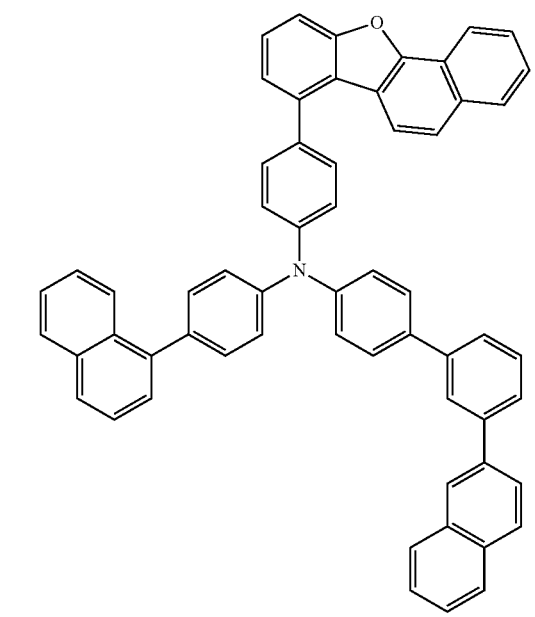
388
-continued
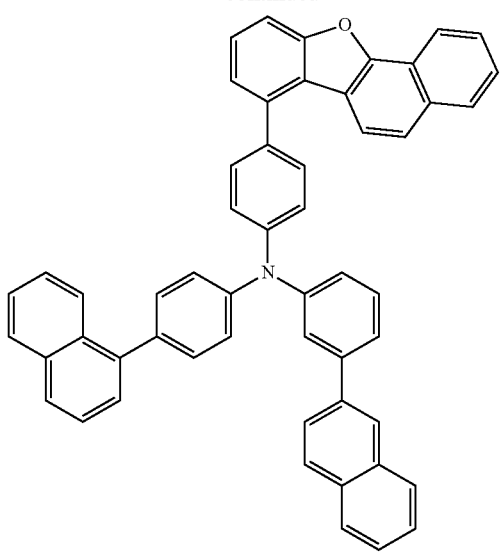
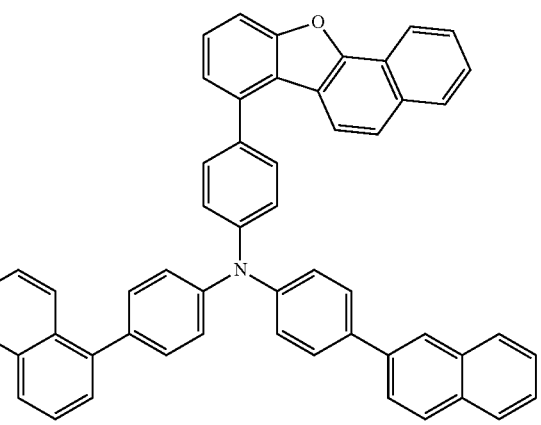
[Chem. 149]
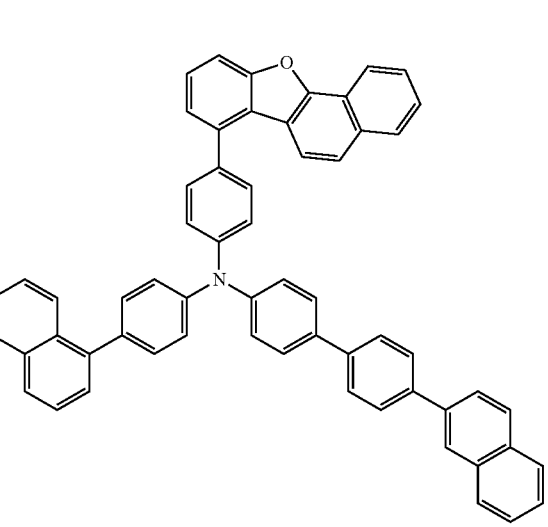

389
-continued
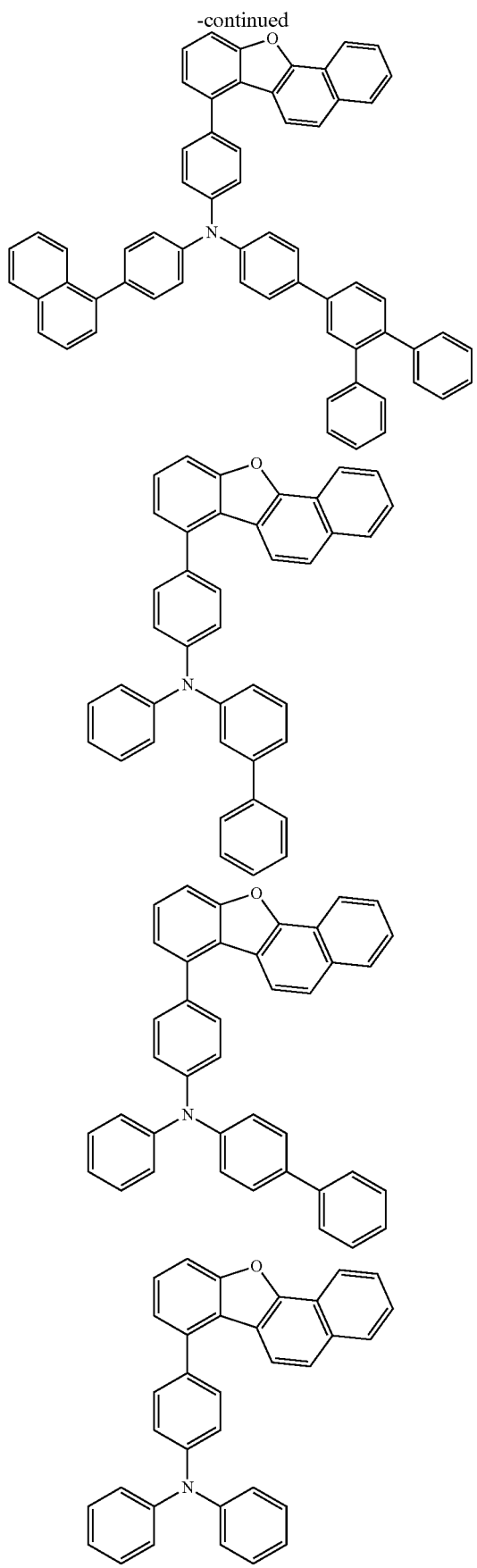
390
-continued
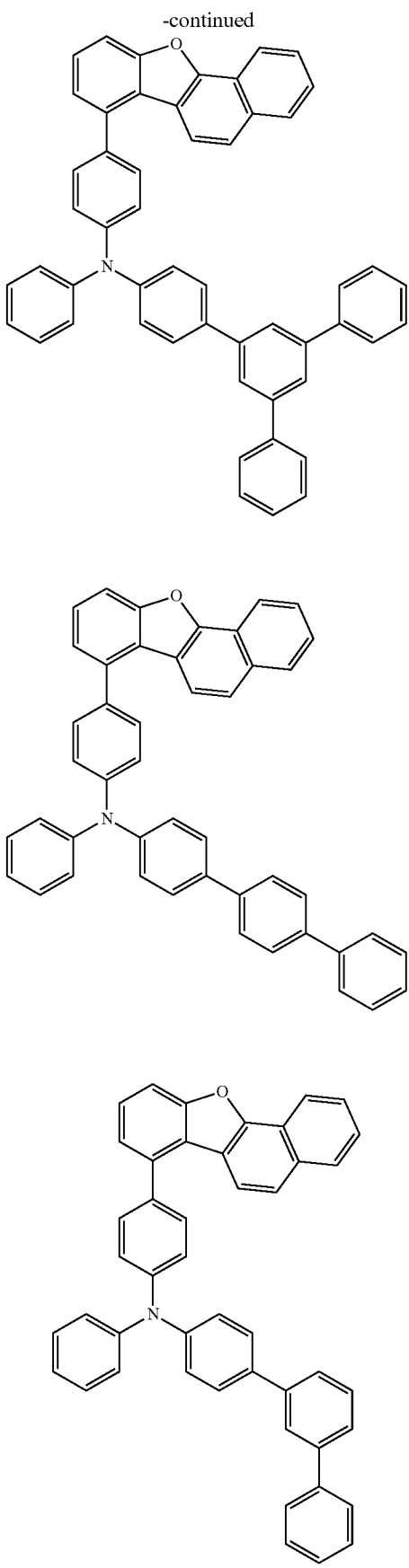

391
-continued
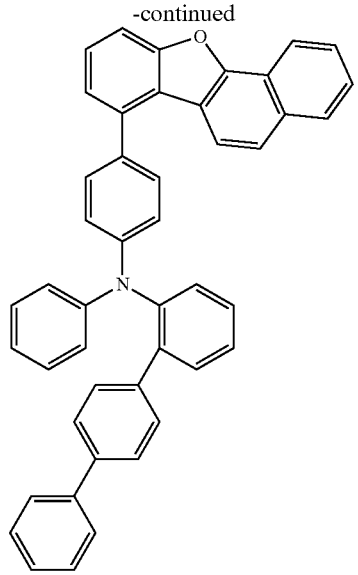
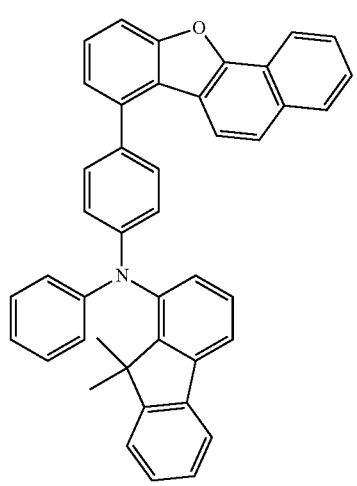
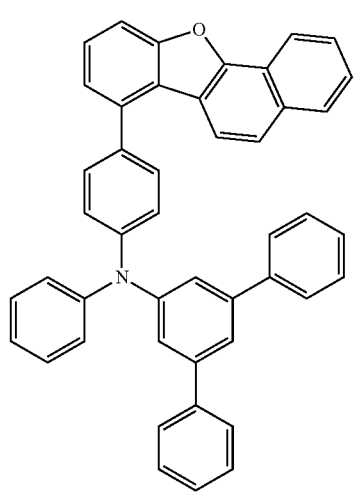
392
-continued
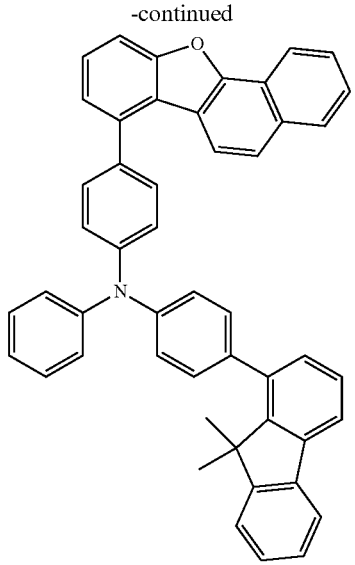
[Chem. 150]
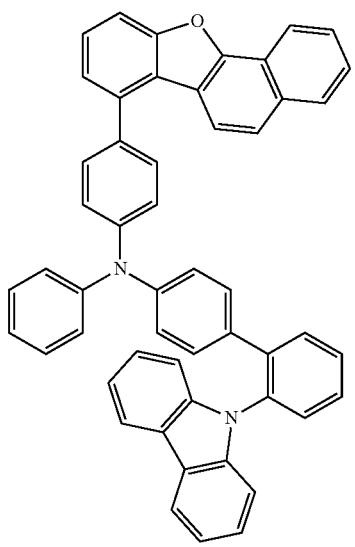
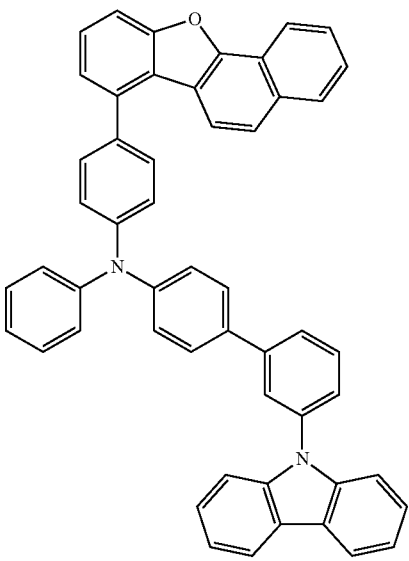

393
-continued
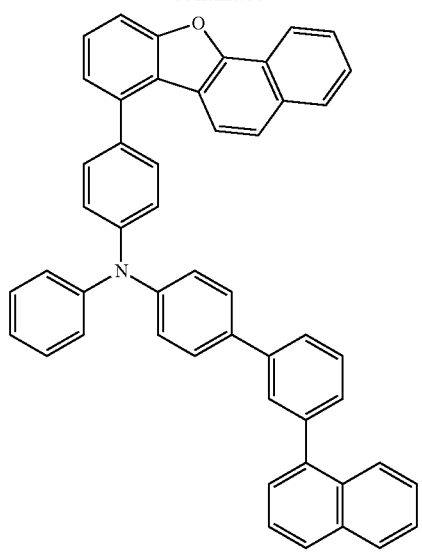
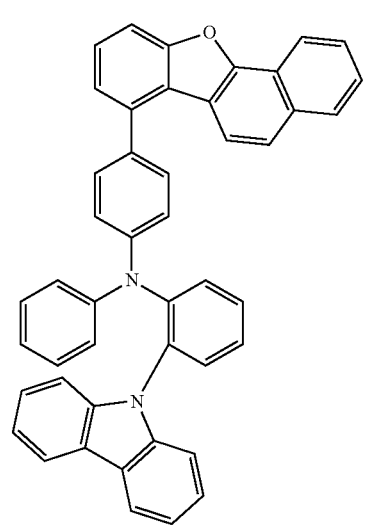
394
-continued
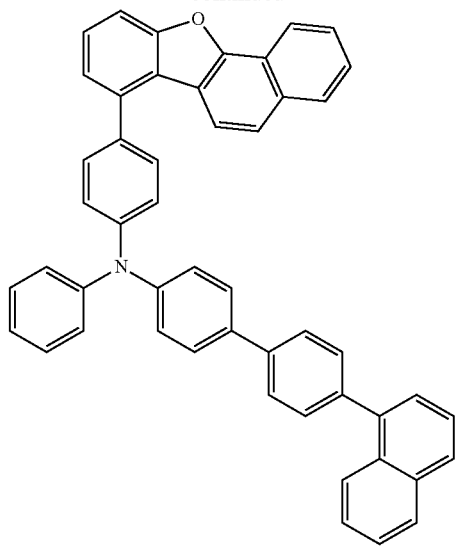
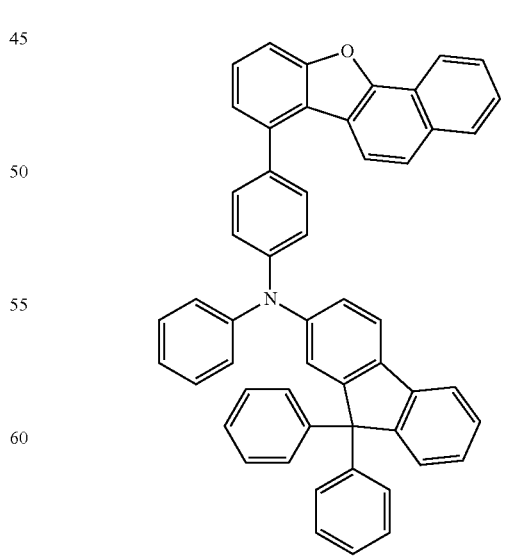

395
-continued
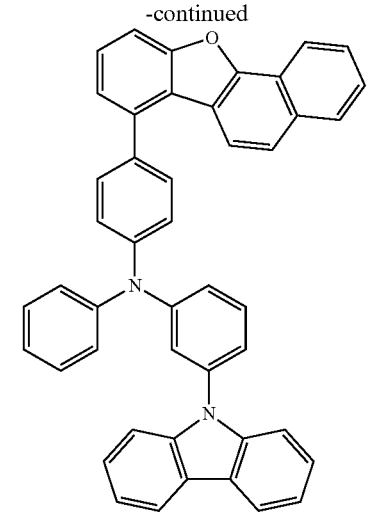
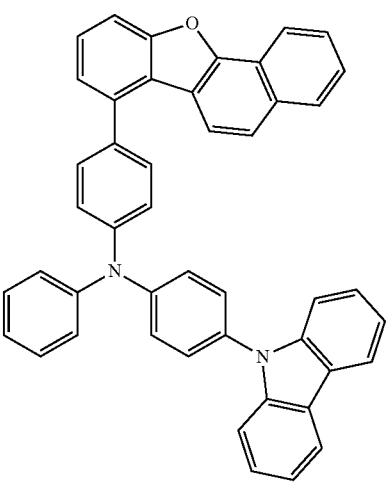
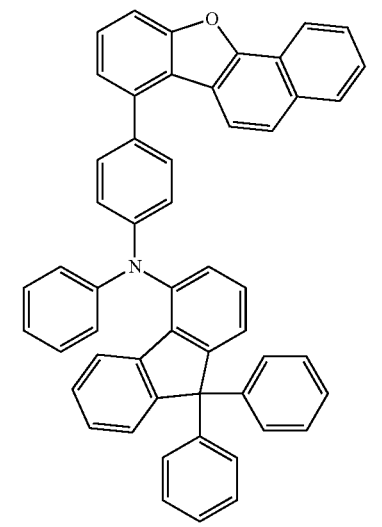
396
-continued
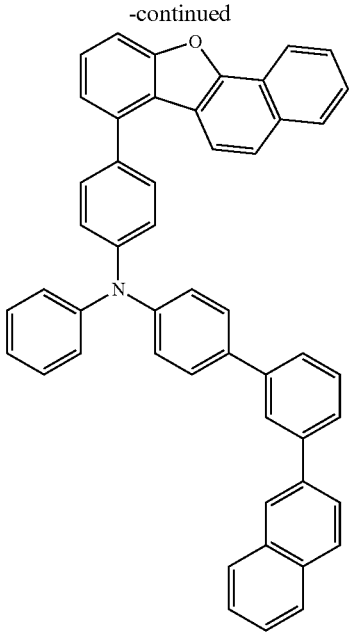
[Chem. 151]
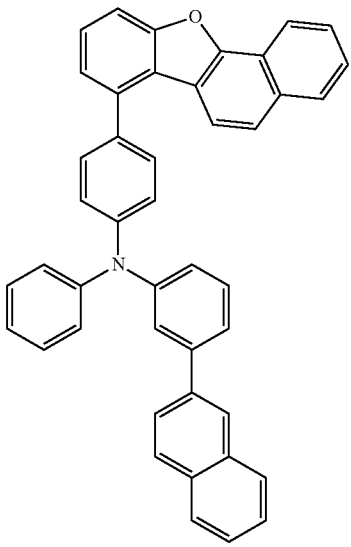
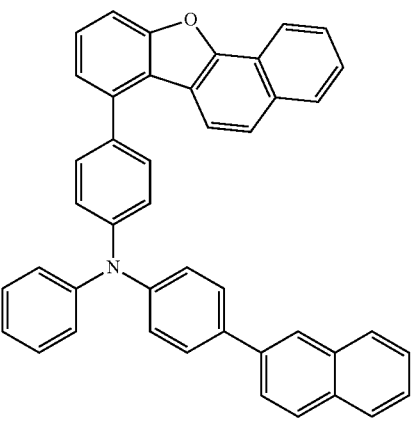

-continued
397
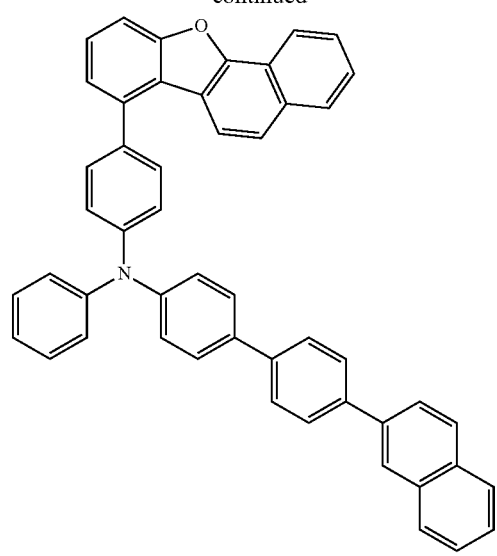
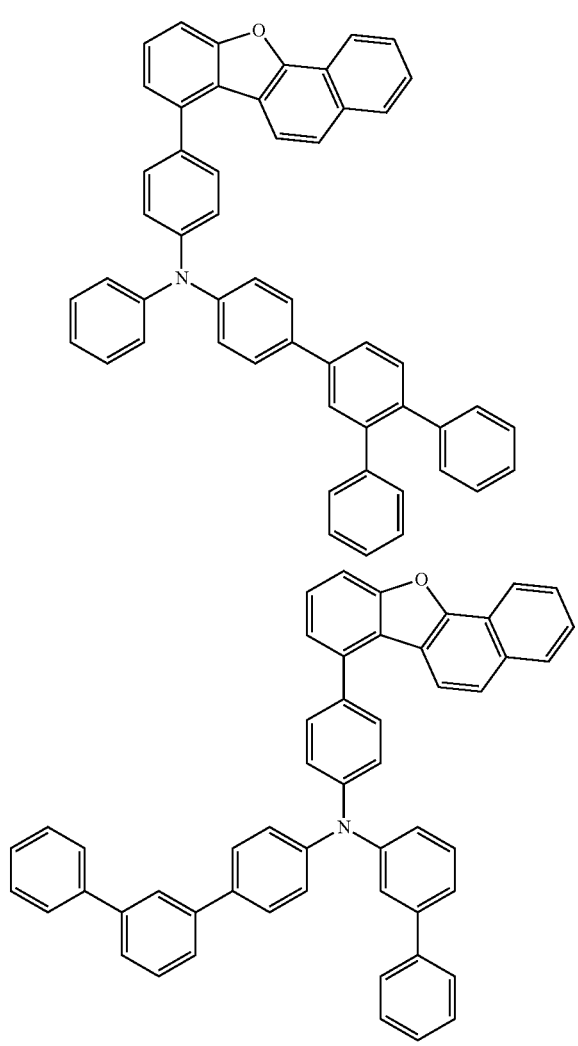
398
-continued
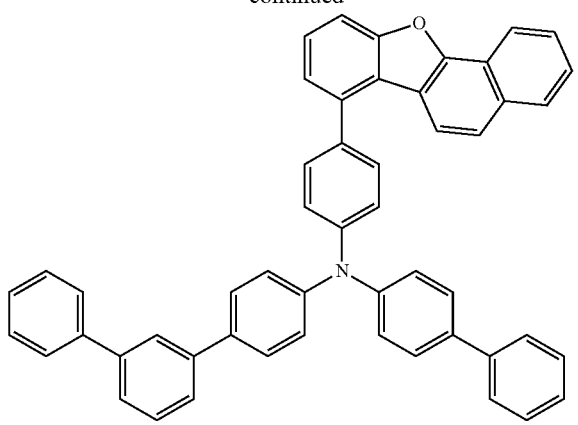
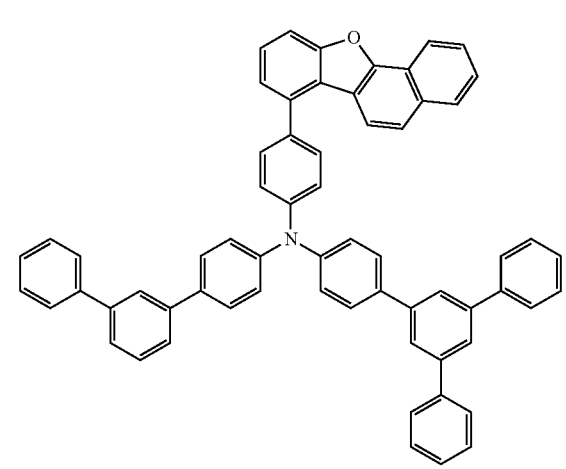
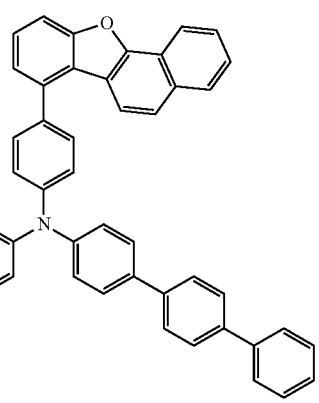

399
-continued
400
-continued
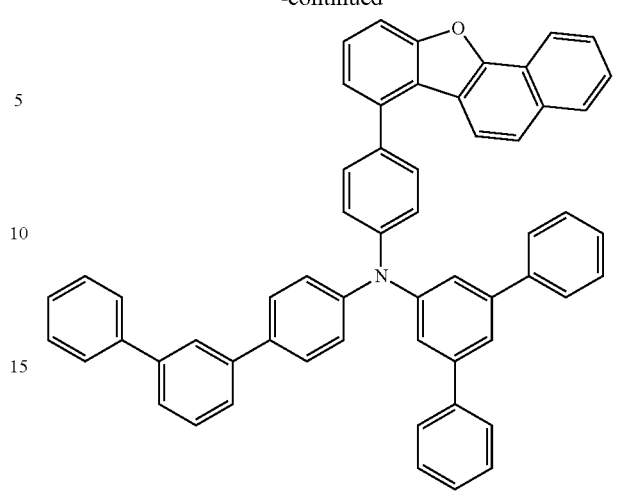
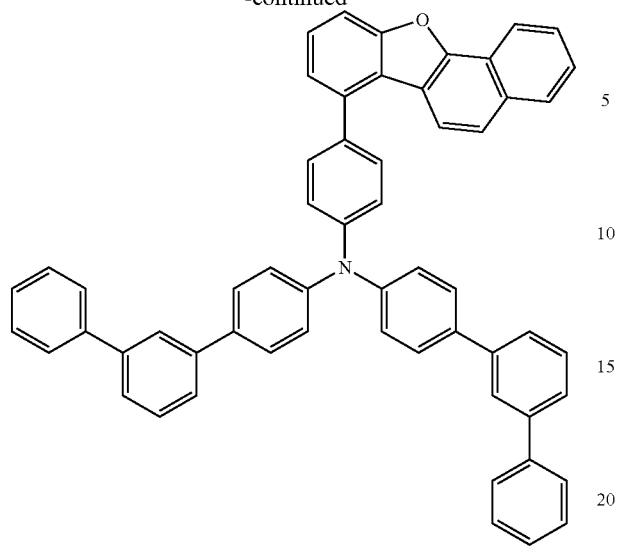
[Chem. 152]
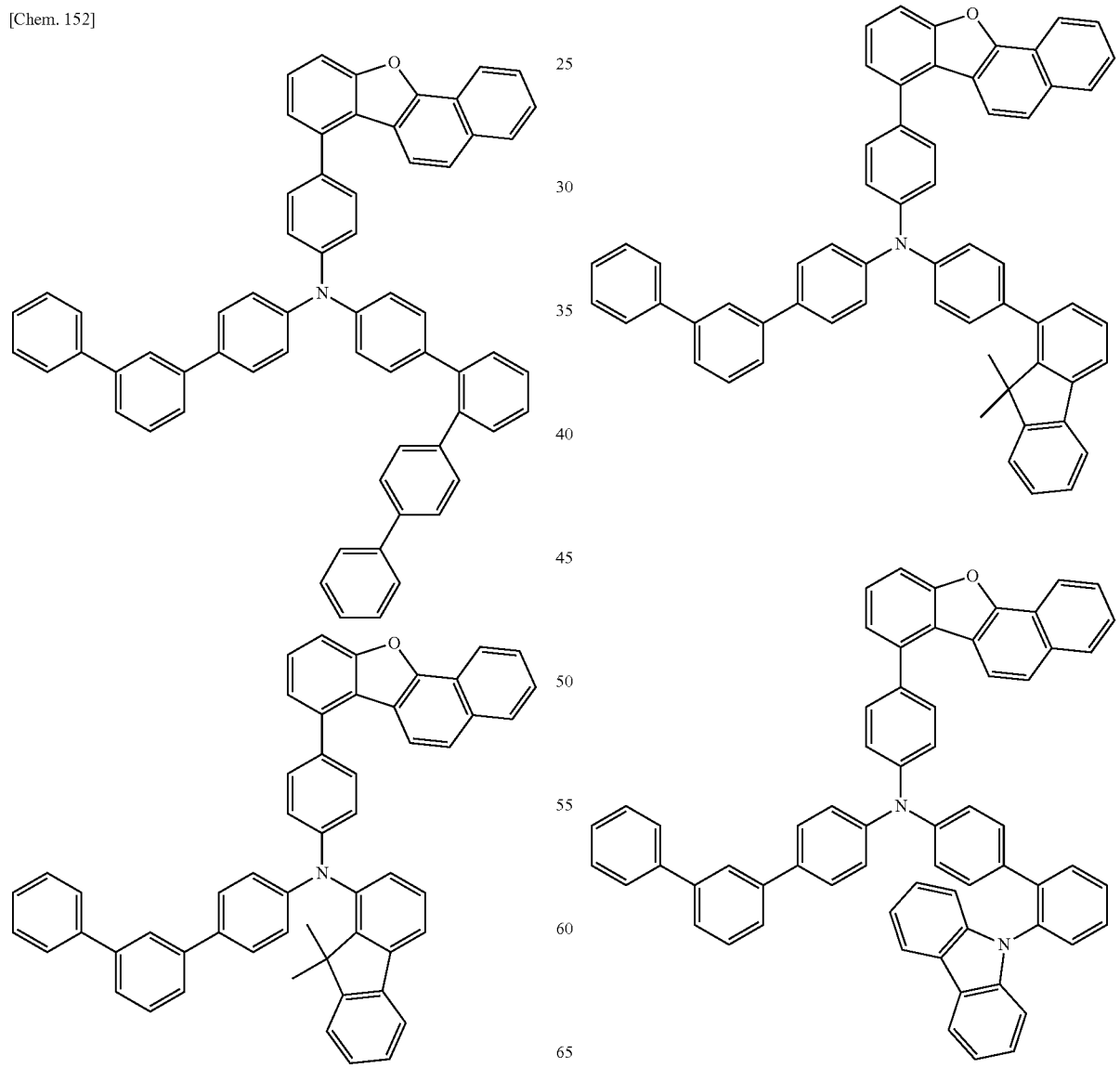

401
-continued
402
-continued
[Chem. 153]
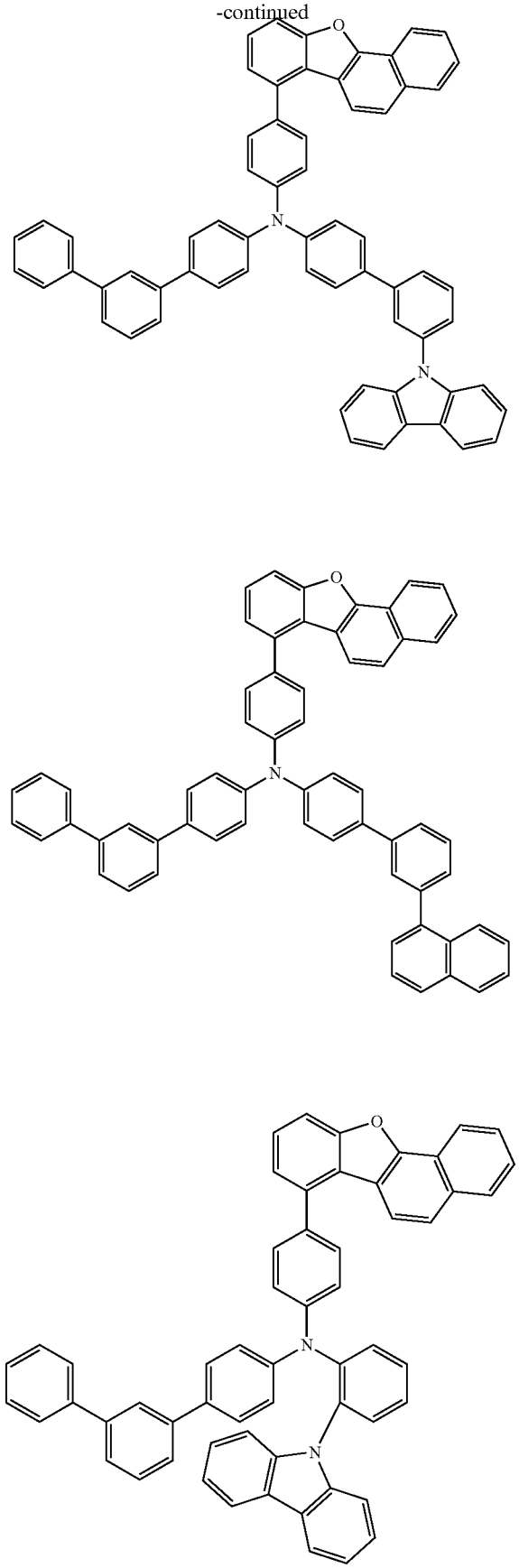
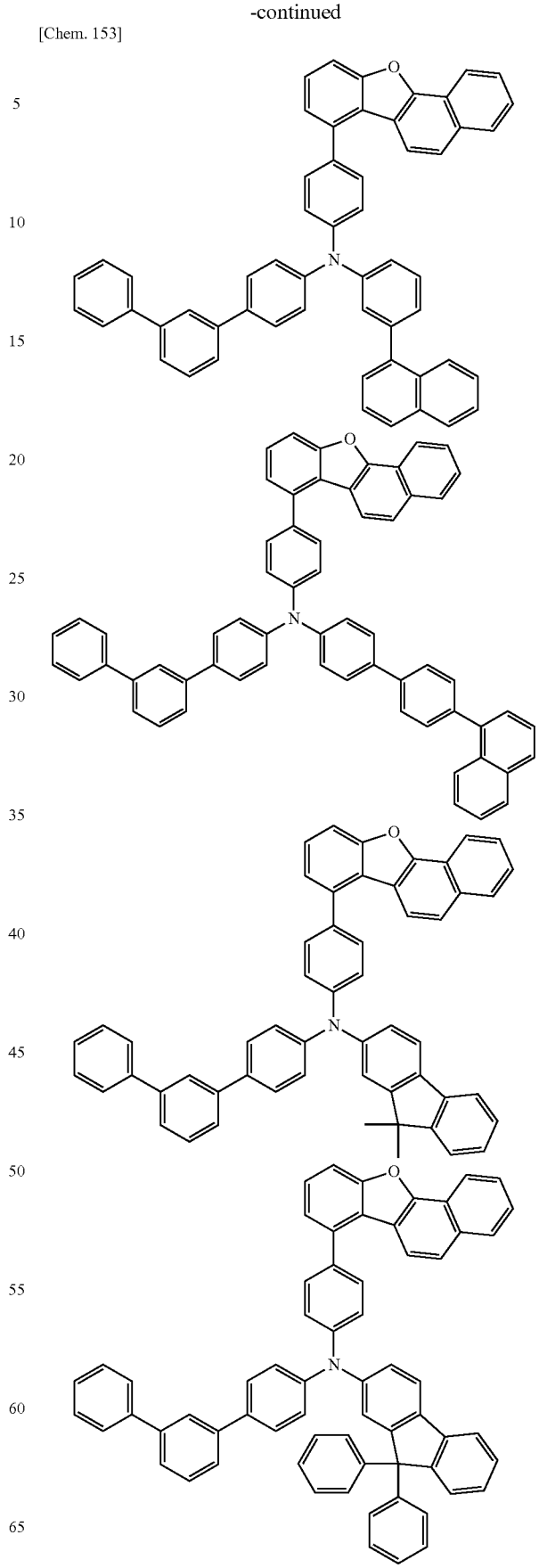

403
-continued
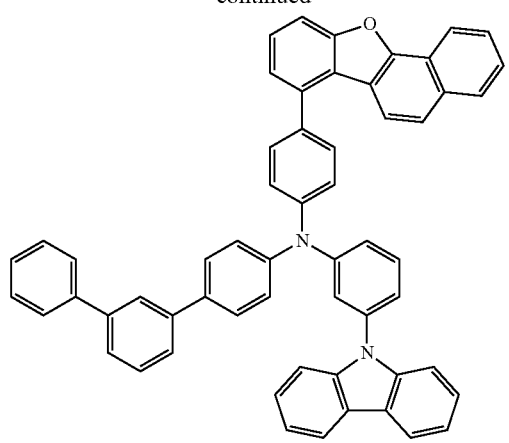
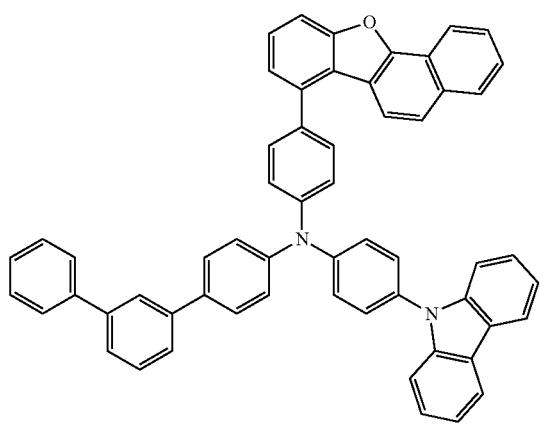
404
-continued
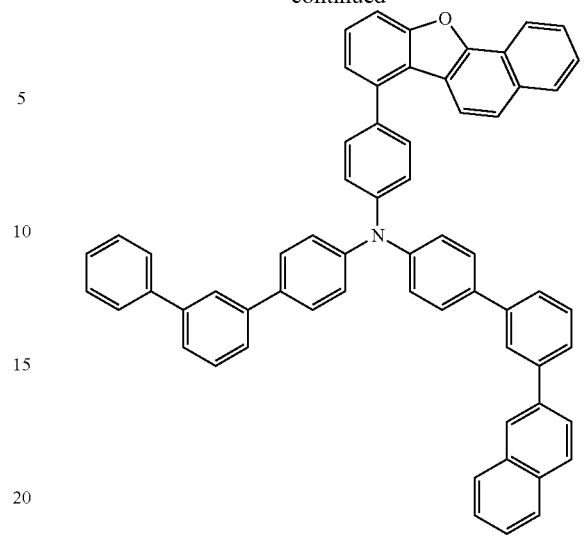
[Chem. 154]
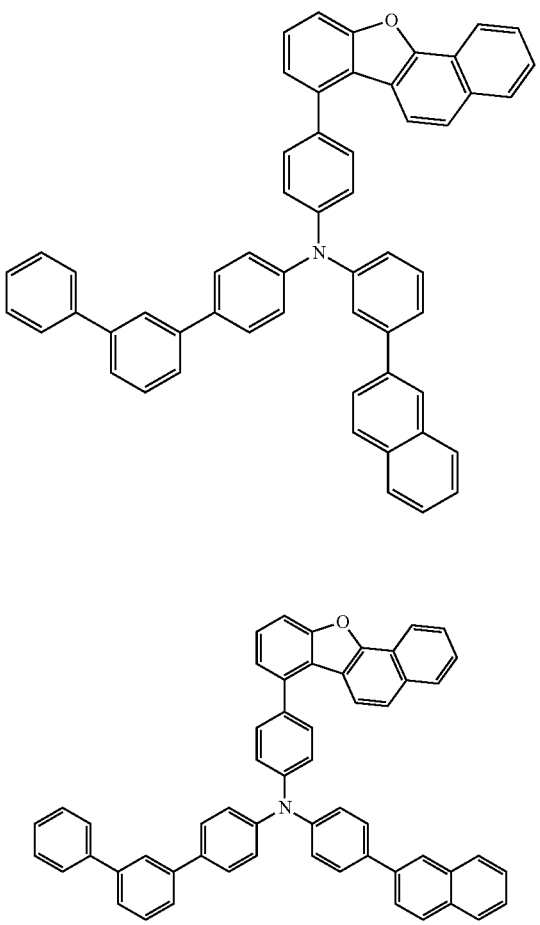

405
-continued
406
-continued
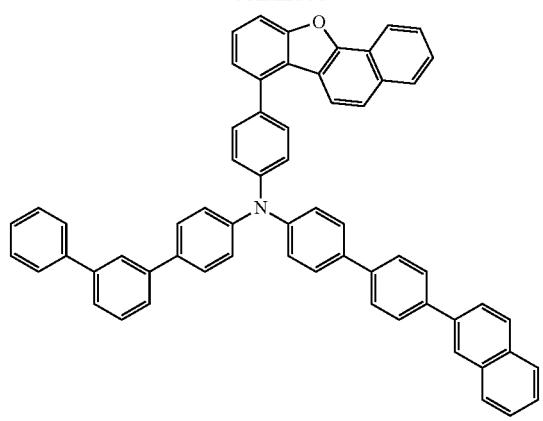
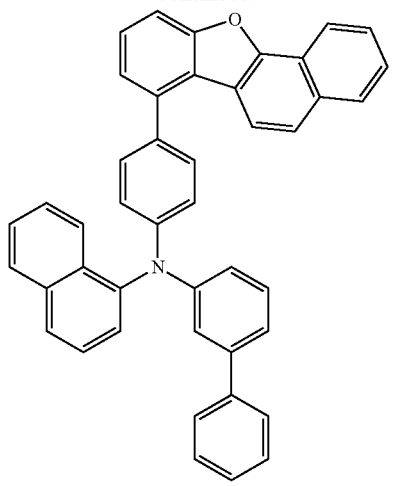
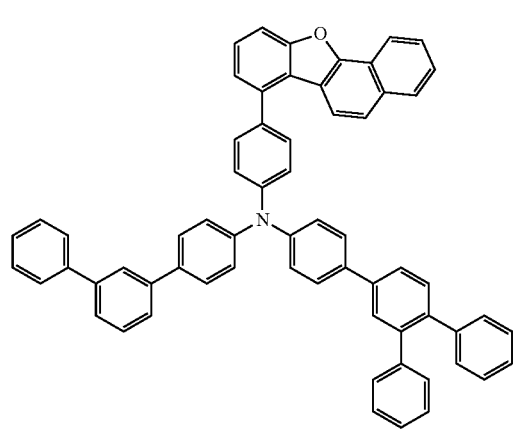
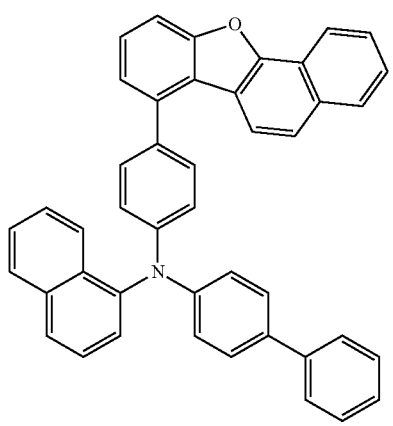
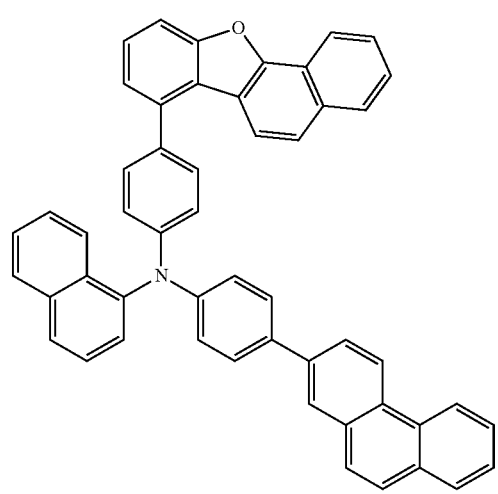
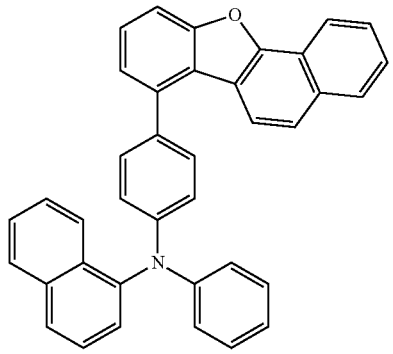

407
-continued
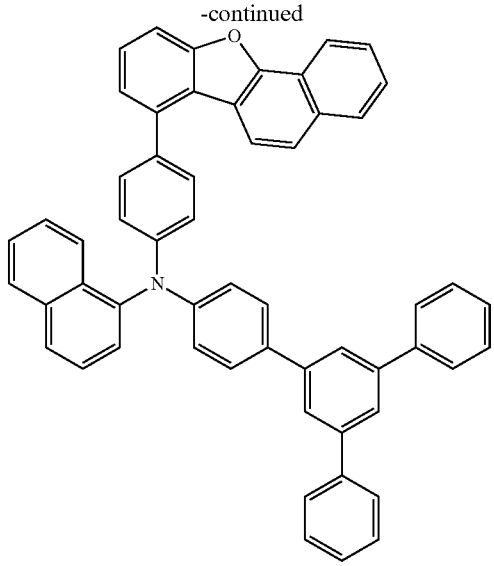
408
-continued
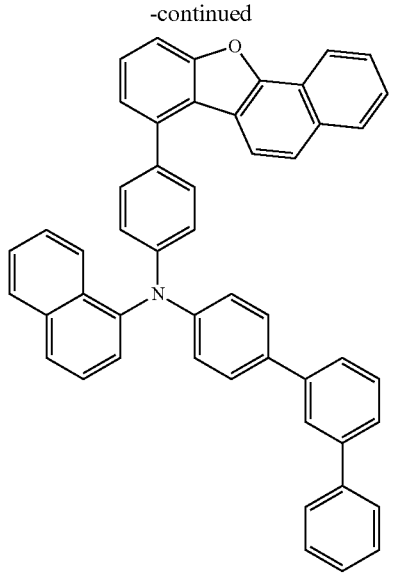
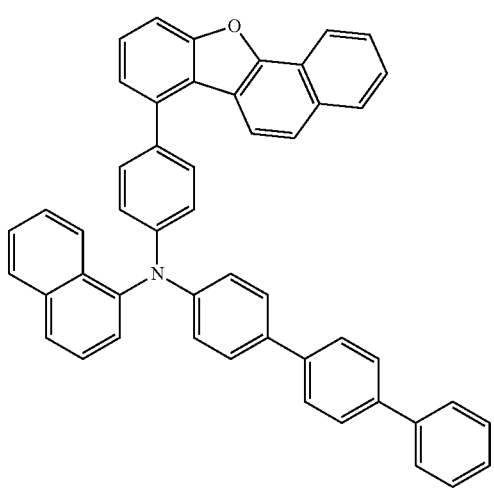
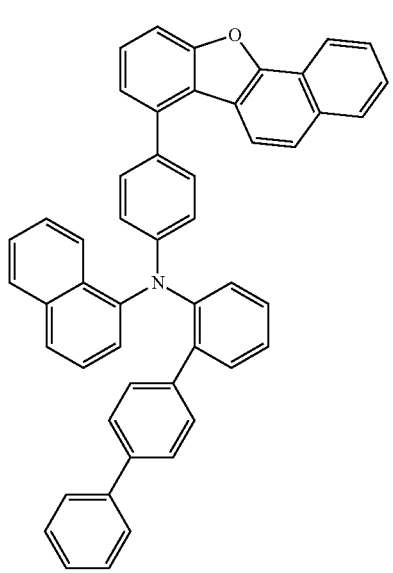
[Chem. 155]
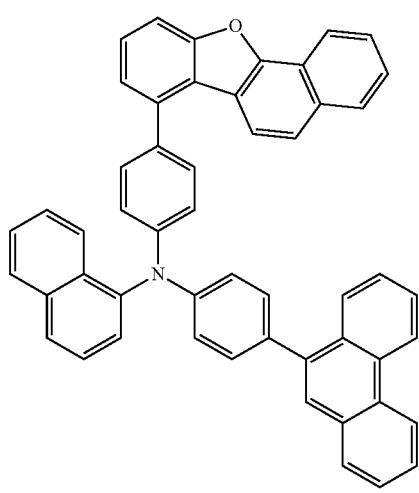
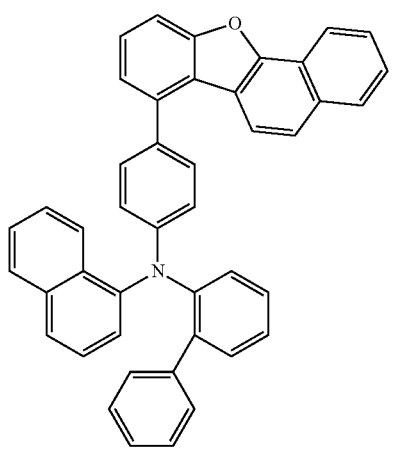

409
-continued
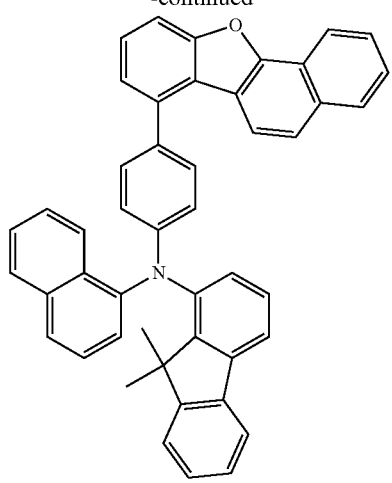
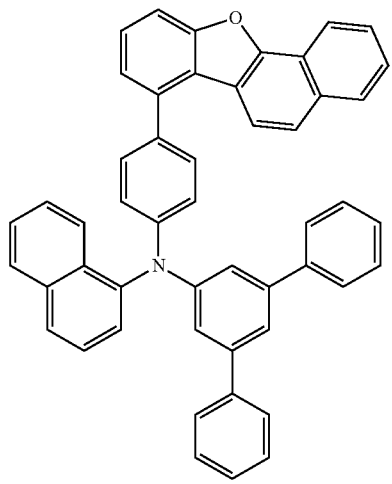
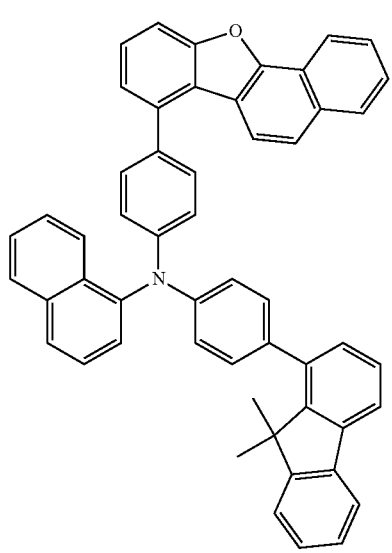
410
-continued
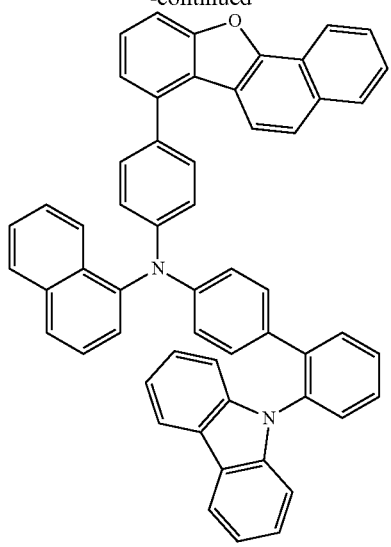
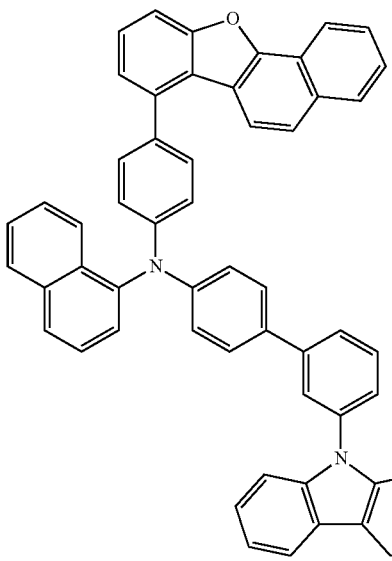

411
-continued
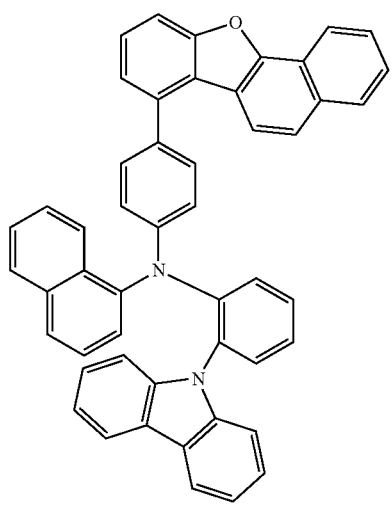
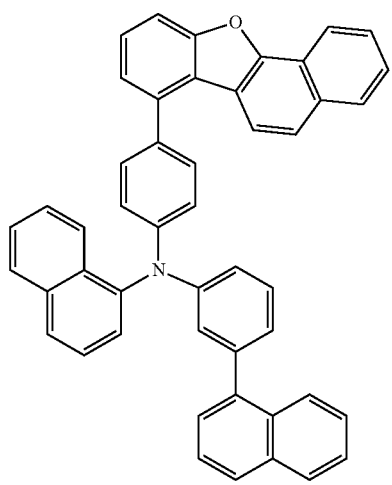
[Chem. 156]
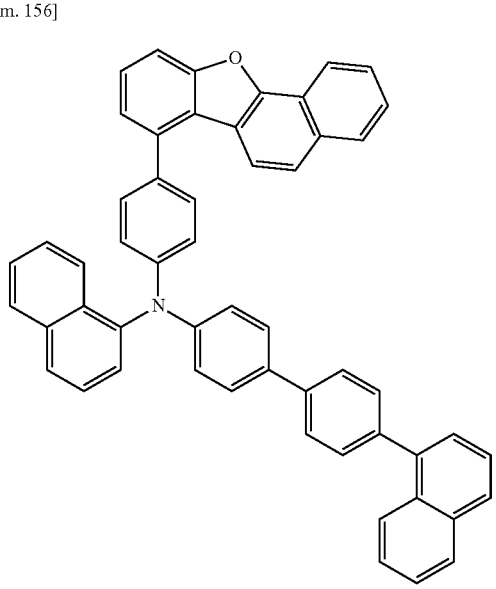
412
-continued
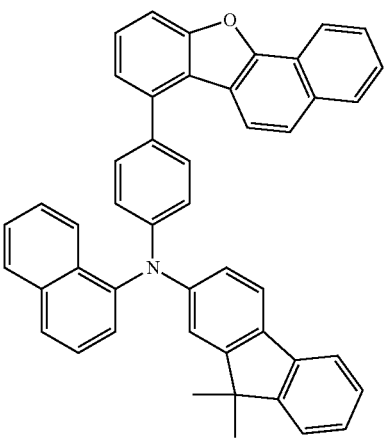
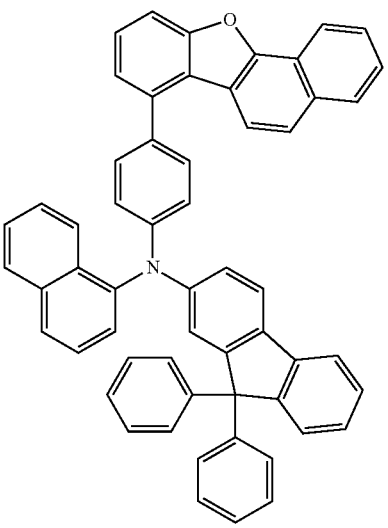
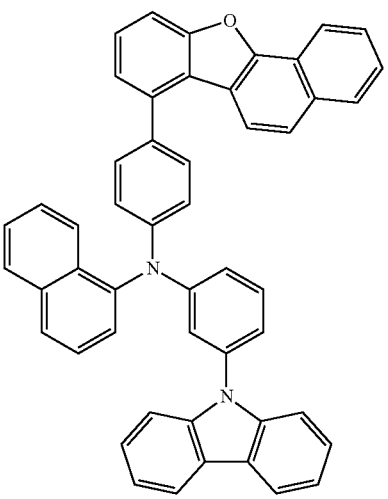

413
-continued
414
-continued
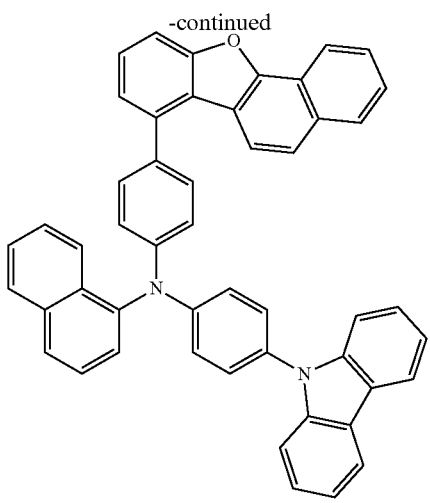
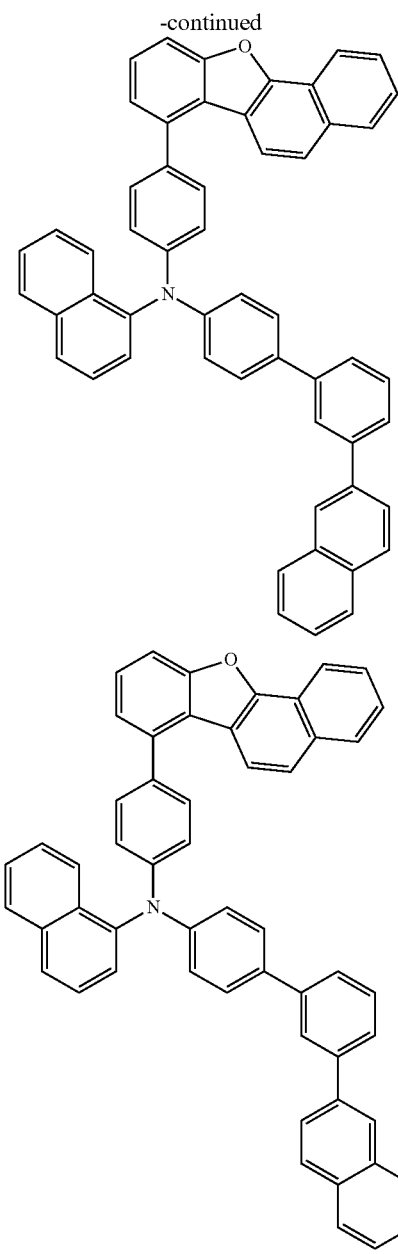
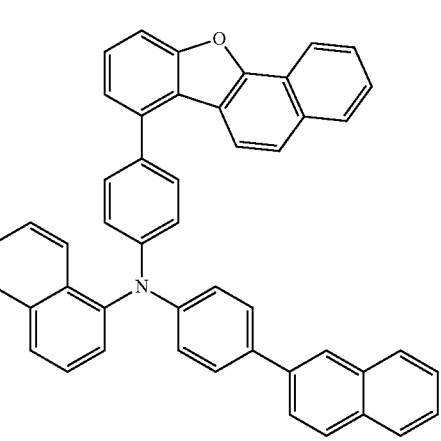

415
-continued
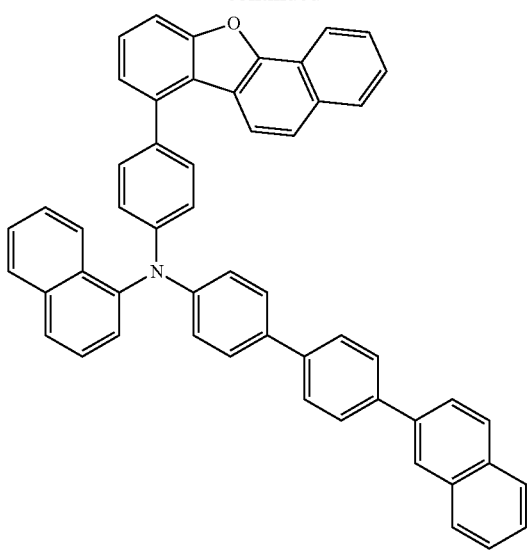
[Chem. 157]
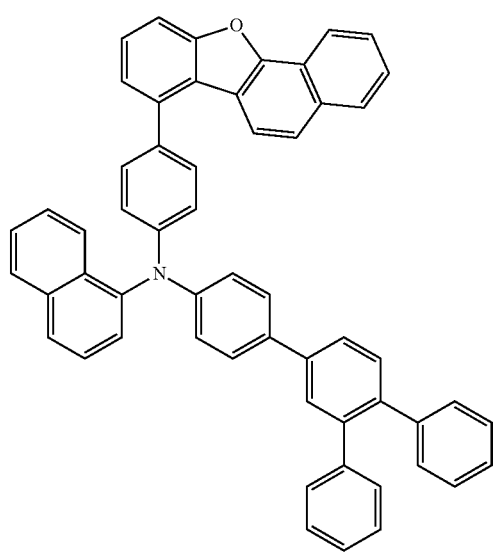
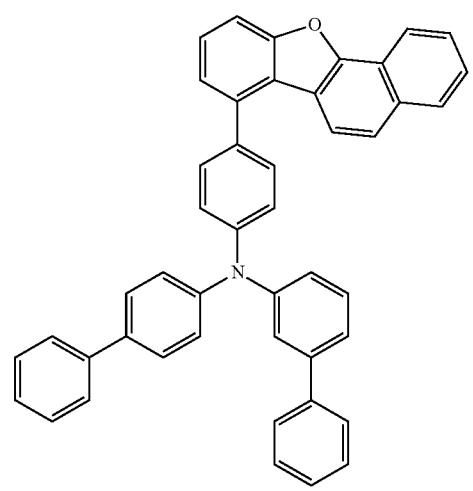
416
-continued
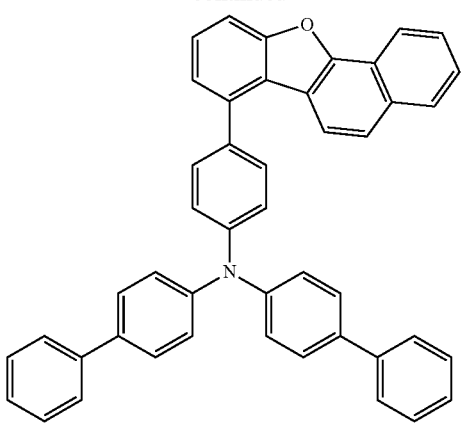
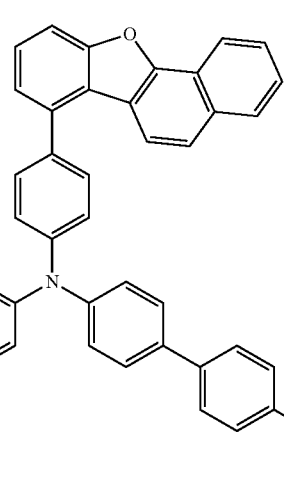

417
-continued
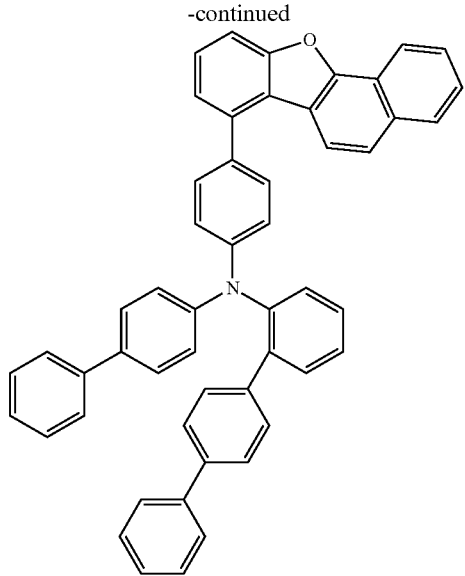
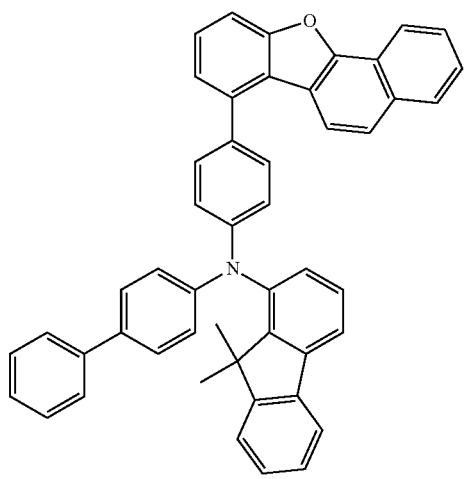
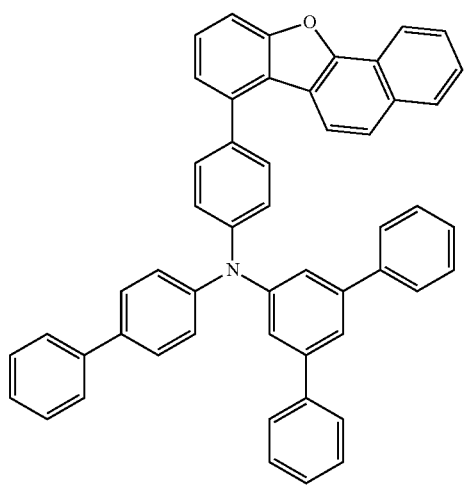
418
-continued
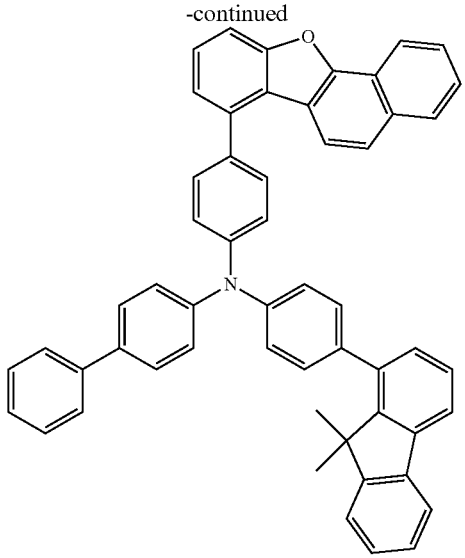
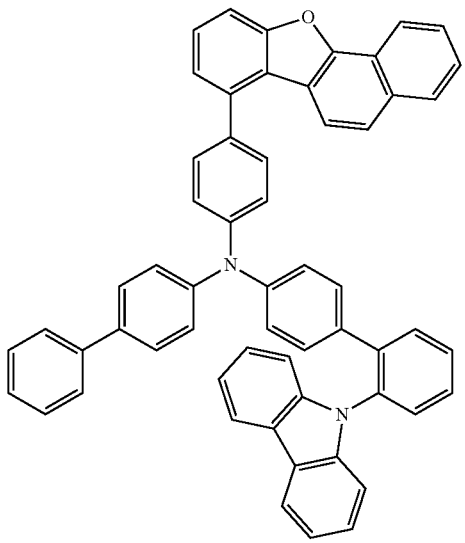
[Chem. 158]
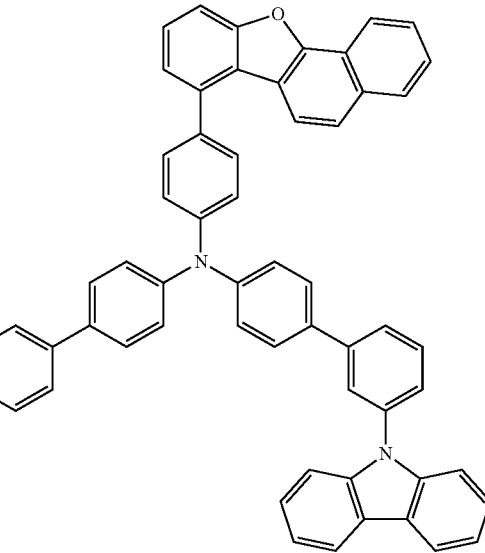

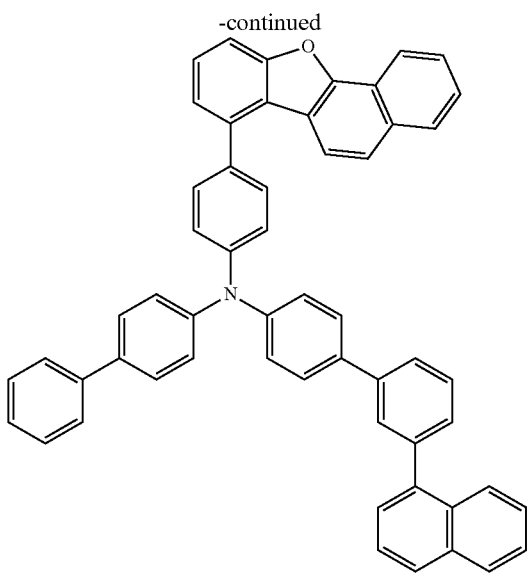
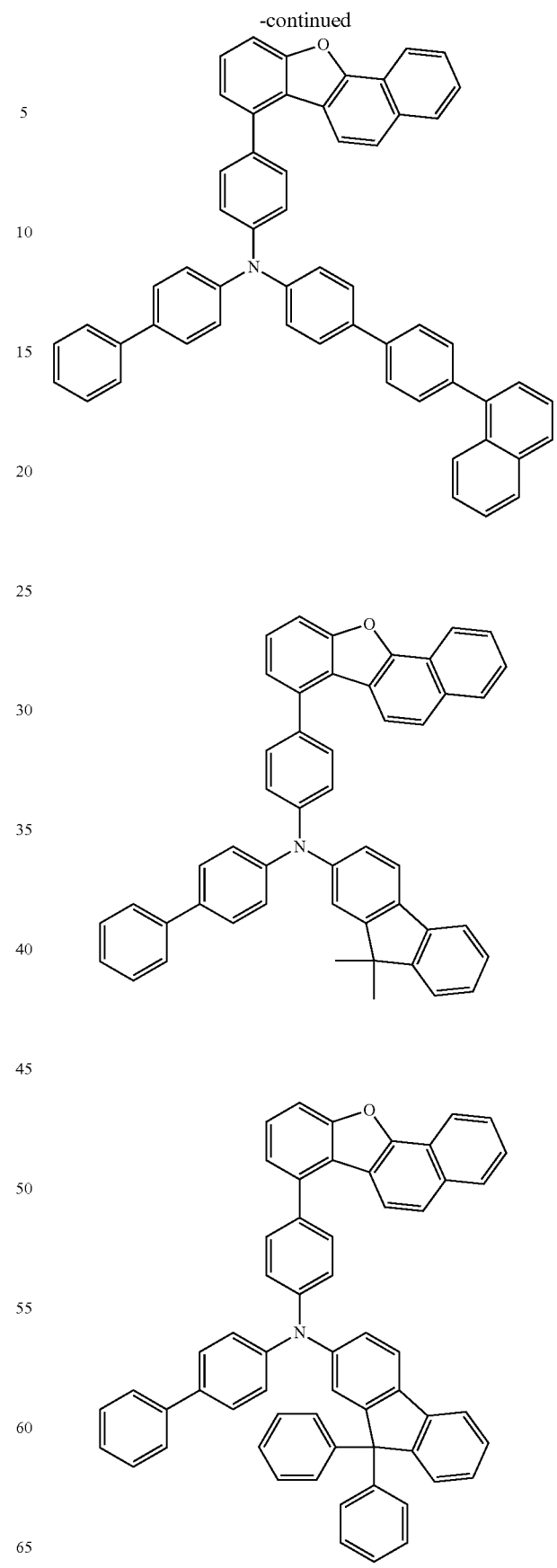

421
-continued
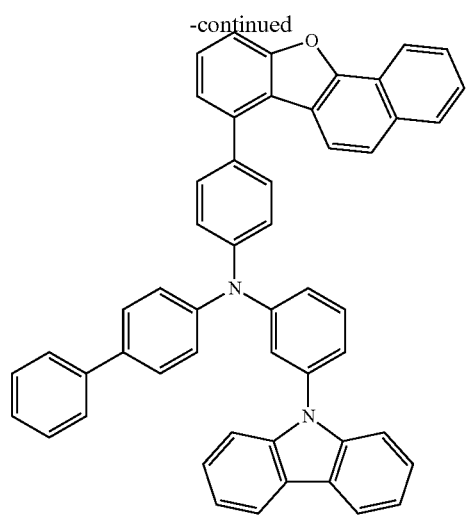
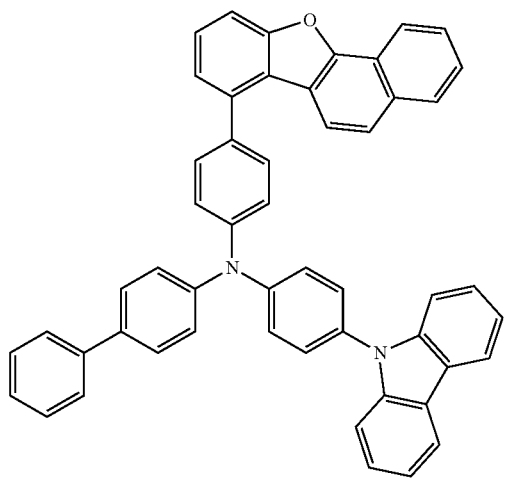
[Chem. 159]
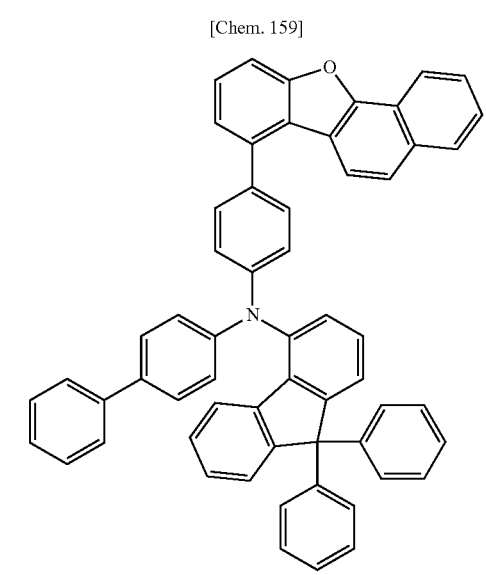
422
-continued
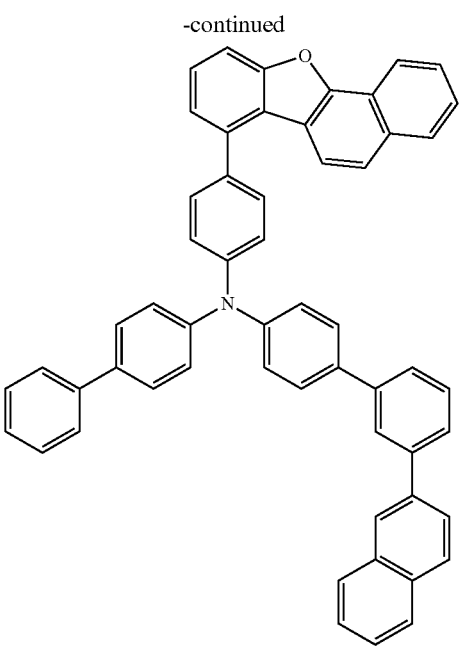
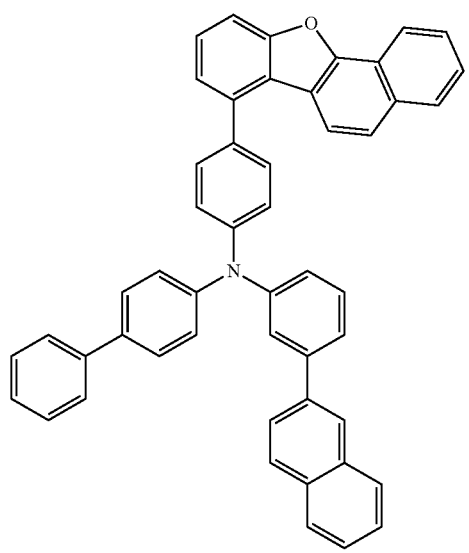
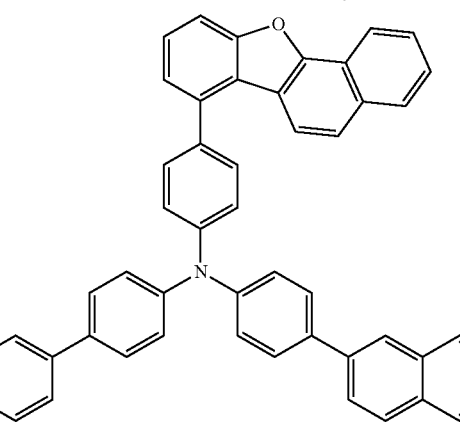

423
-continued
424
-continued
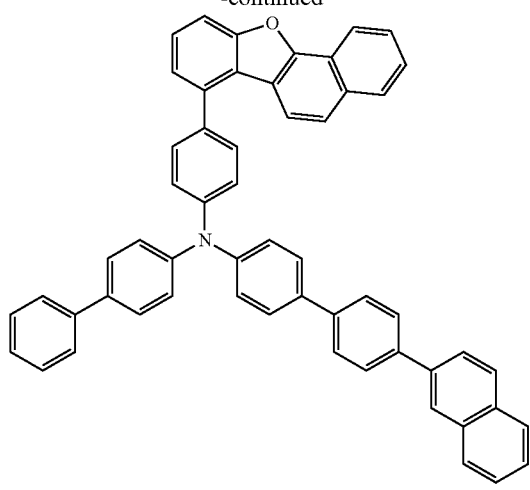
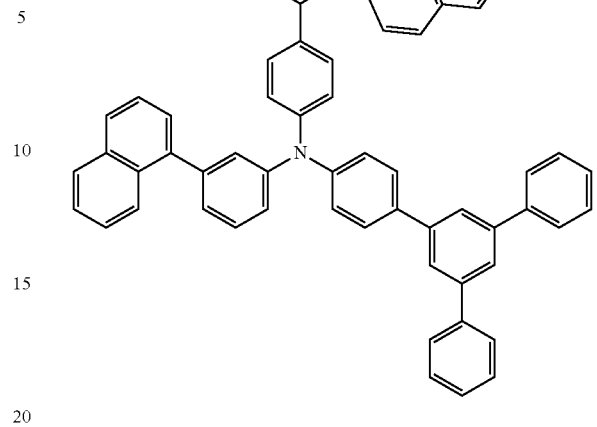
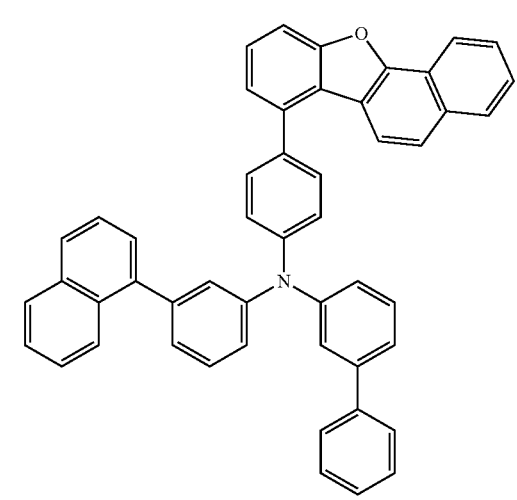
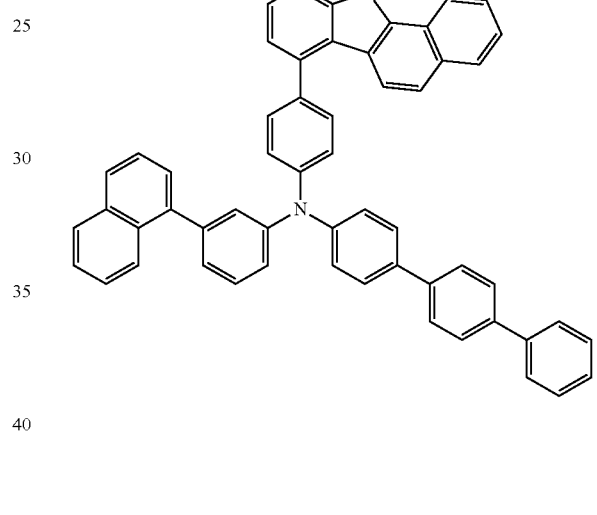
[Chem. 160]
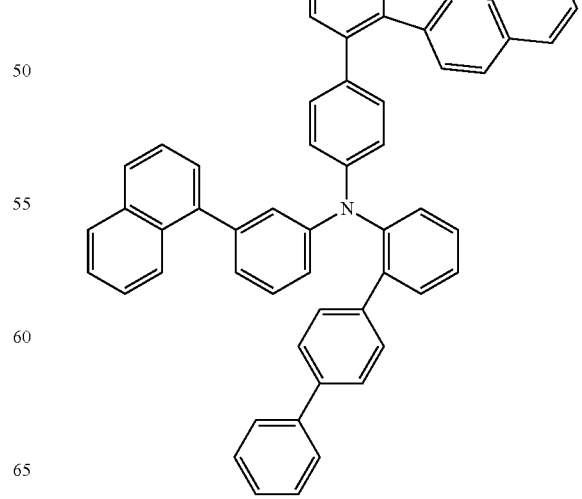

425
-continued
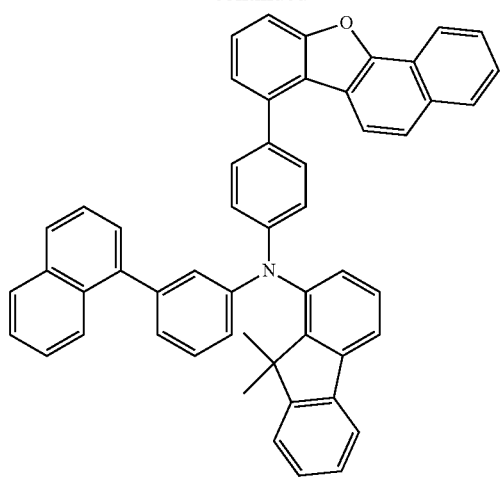
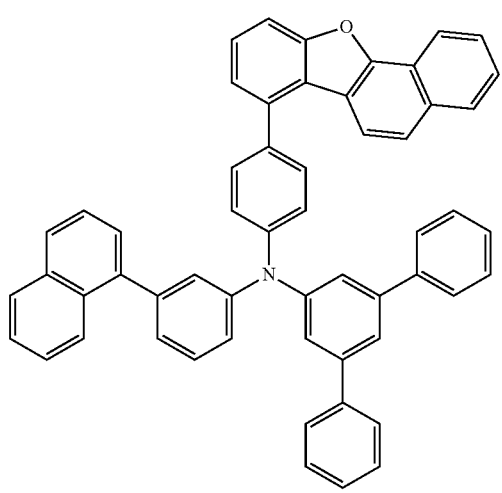
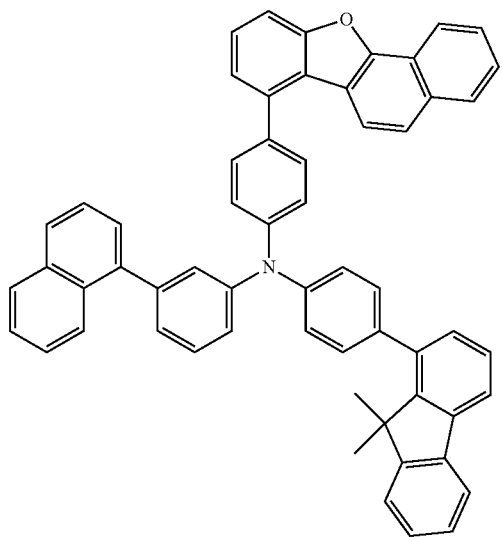
426
-continued
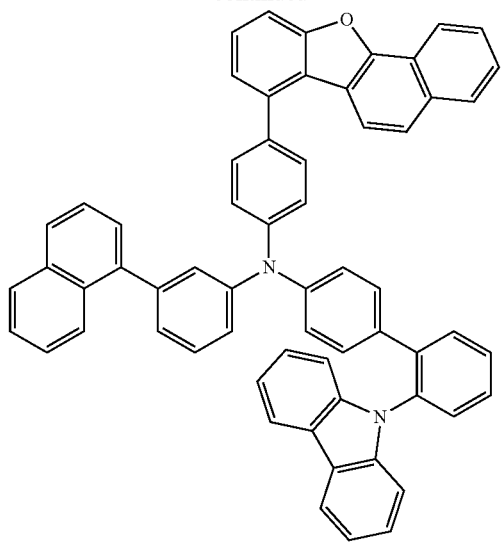
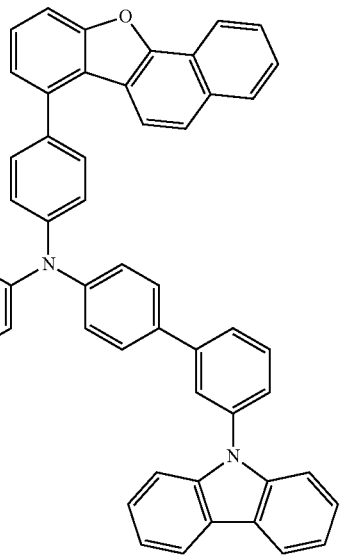

427
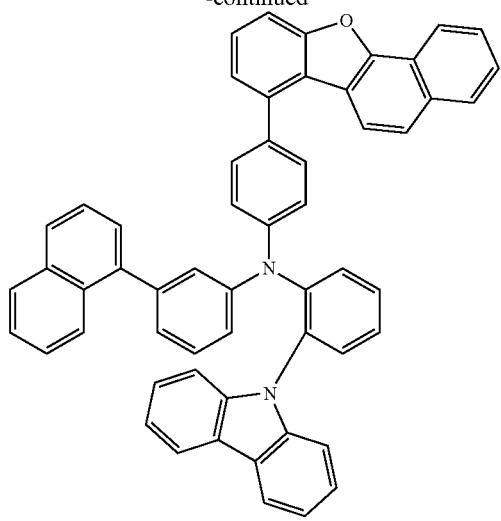
428
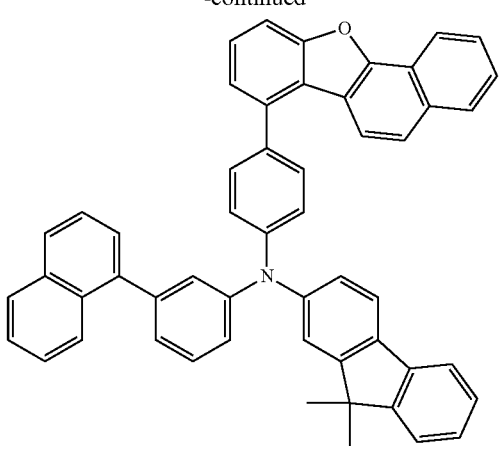
[Chem. 161]
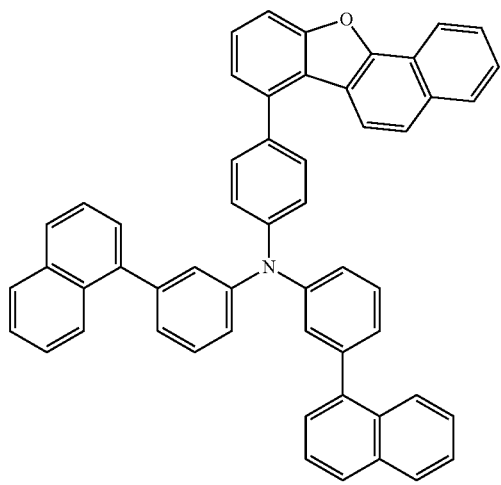
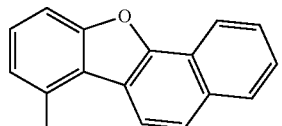

429
-continued
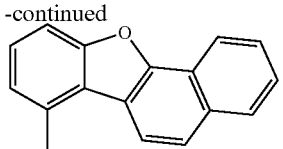
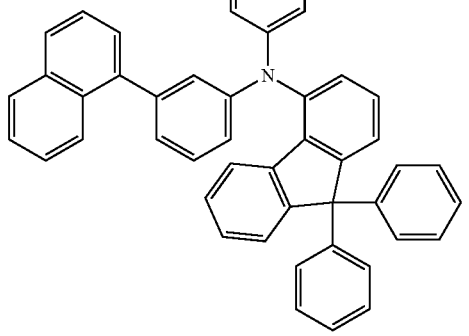
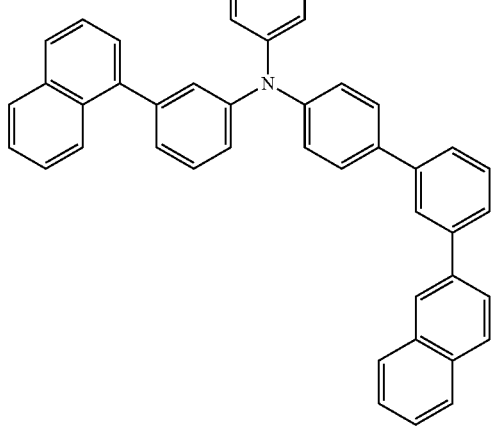
430
-continued
[Chem. 162]
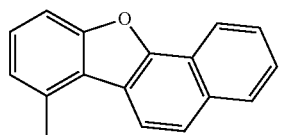
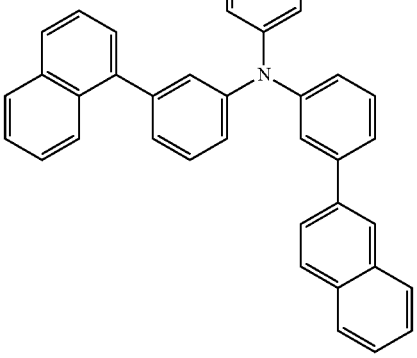
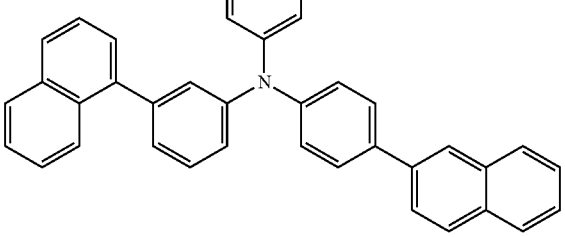
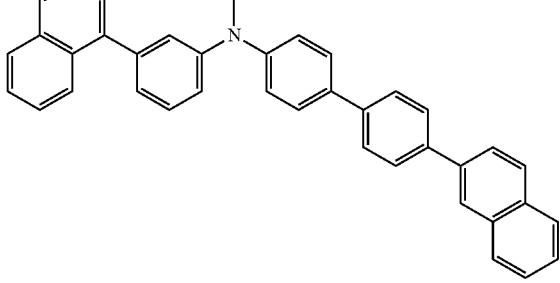

431
-continued
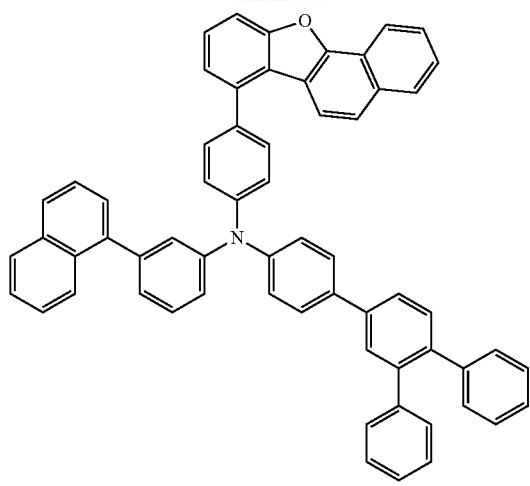
432
-continued
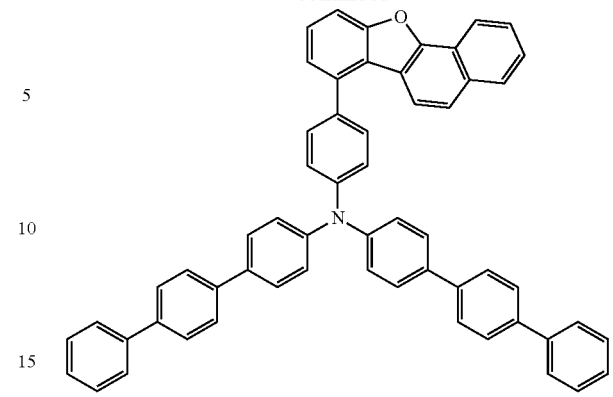
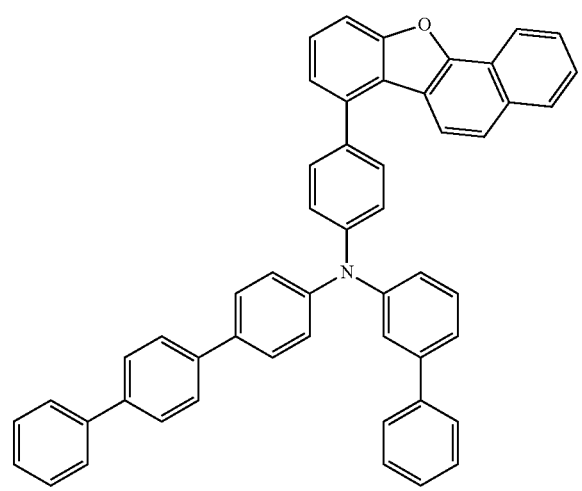
[Chem. 163]
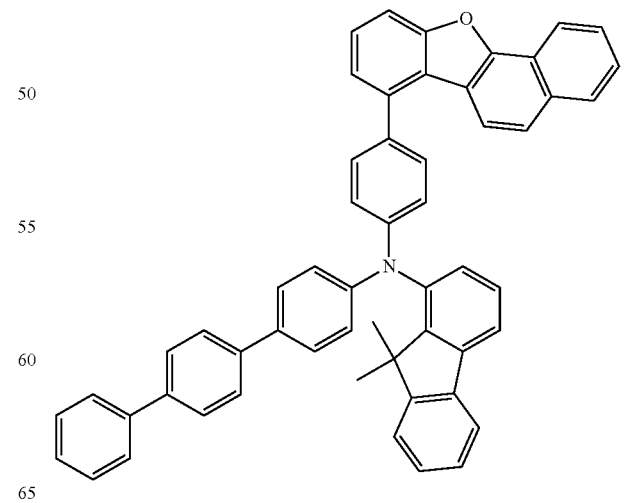

433
-continued
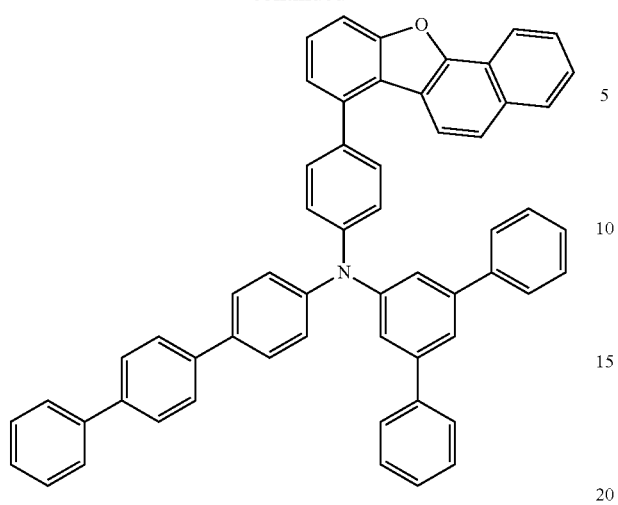
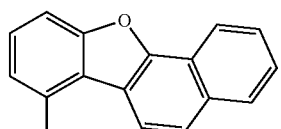
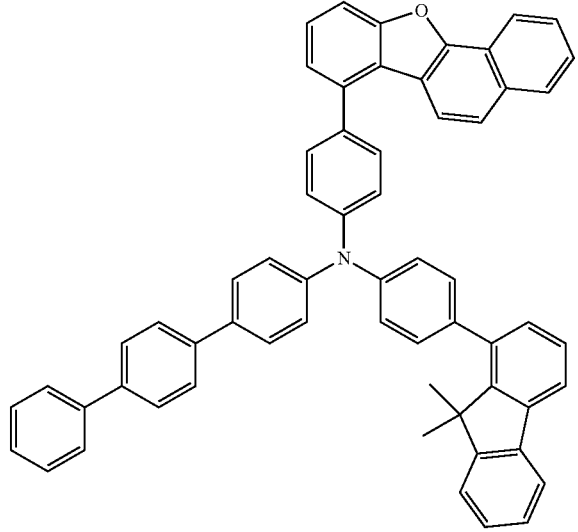
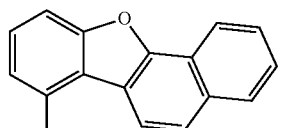
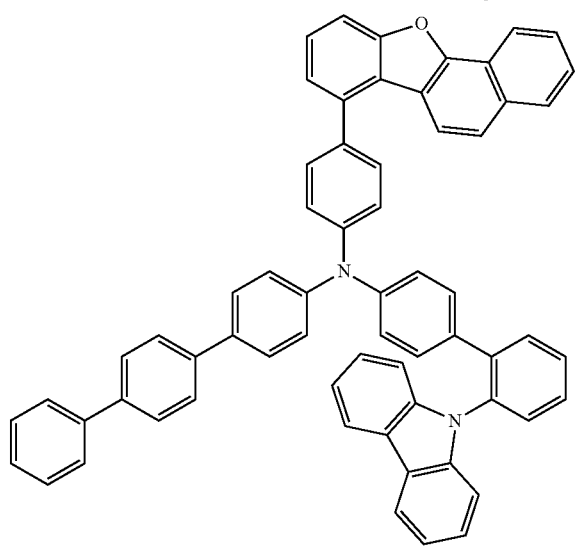
434
-continued
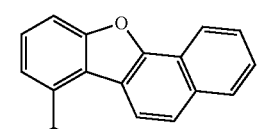
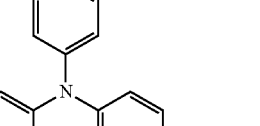
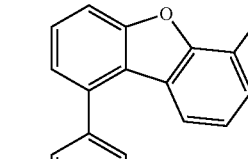

435
-continued
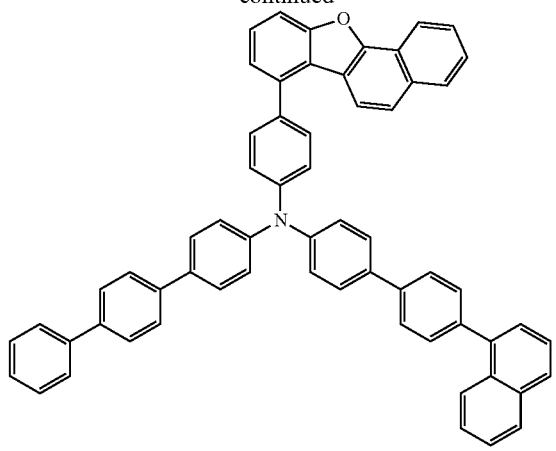
[Chem. 164]
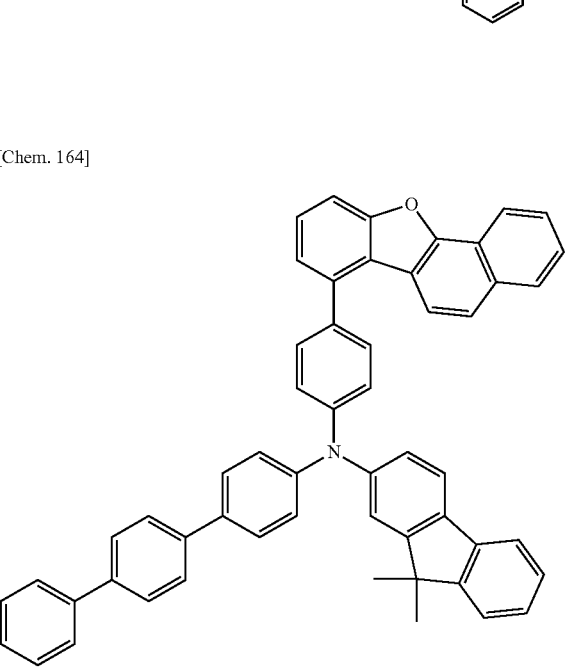
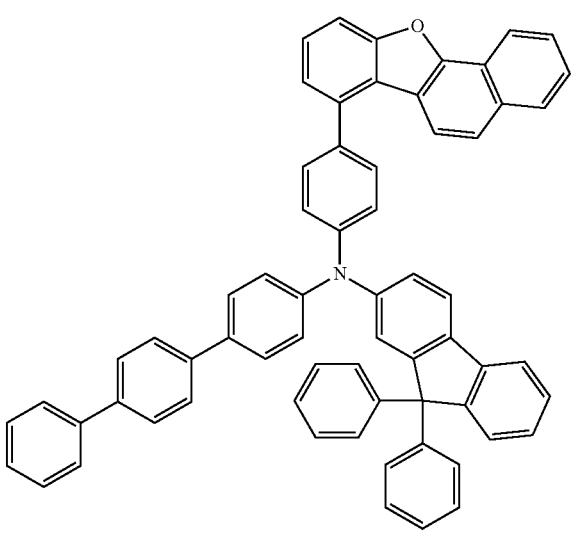
436
-continued
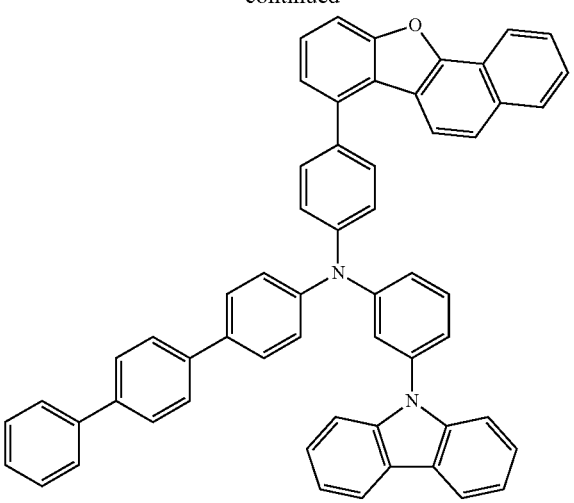
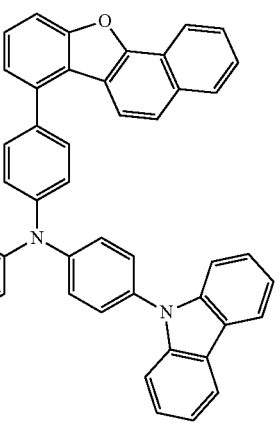
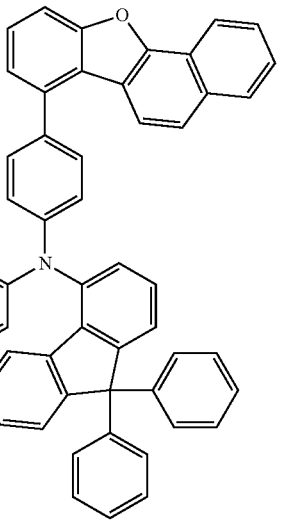

437
-continued
438
-continued
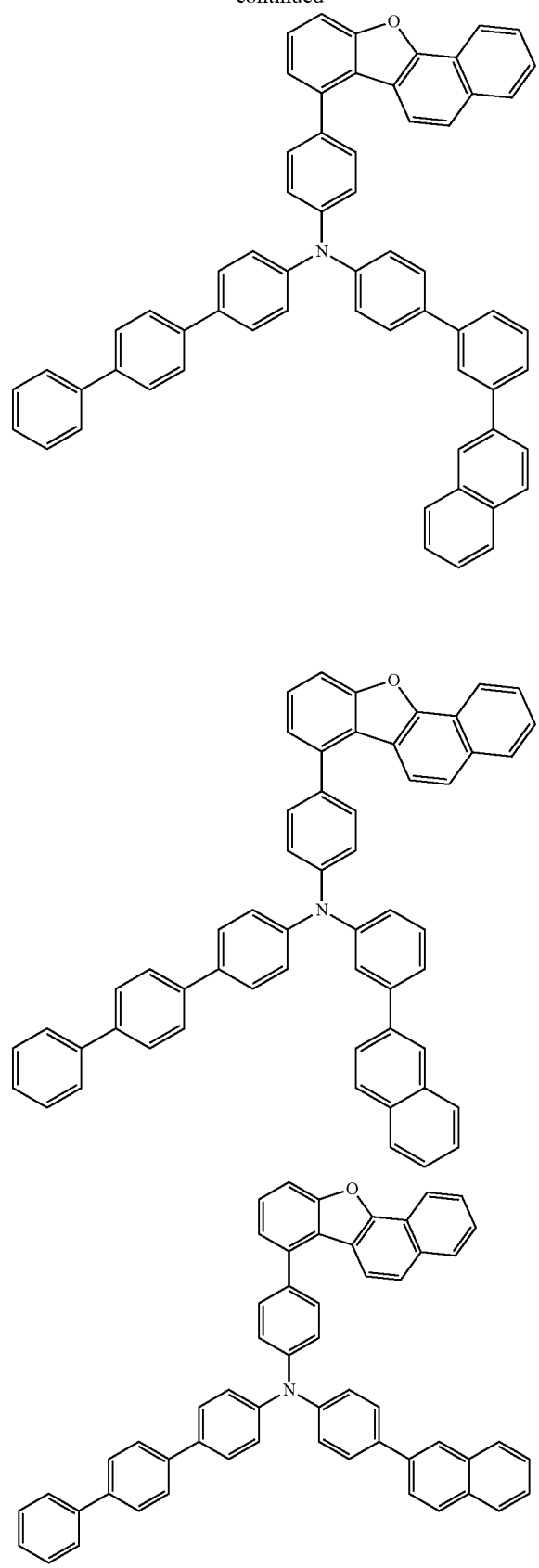
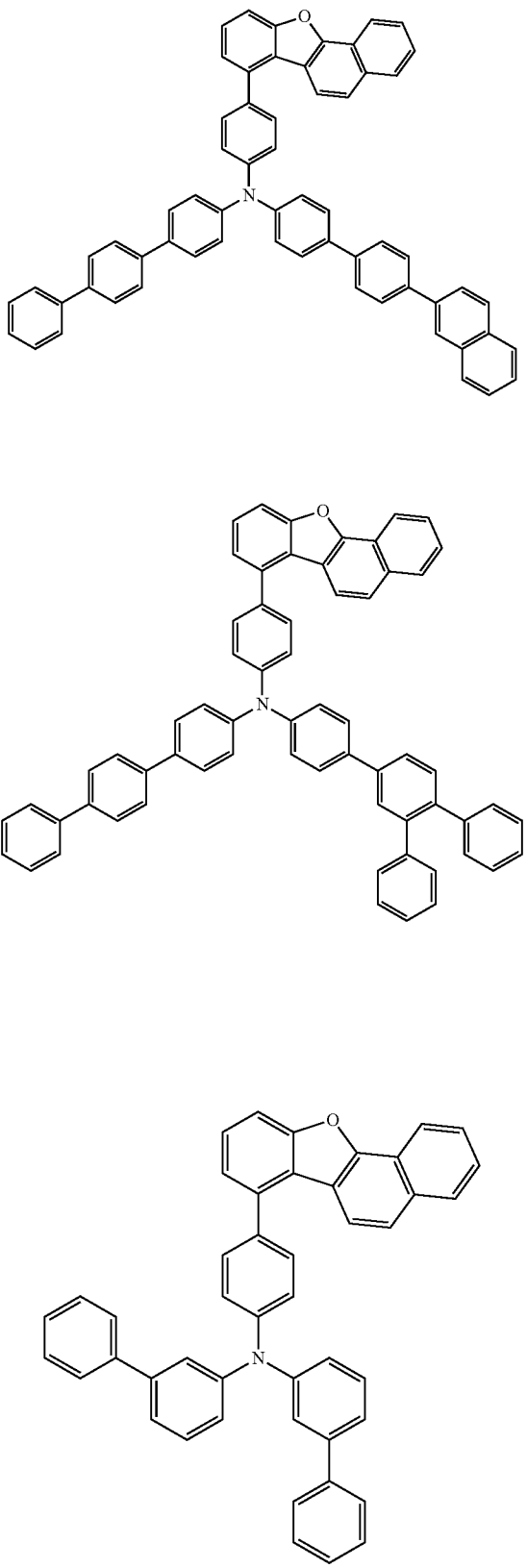

439
-continued
440
-continued
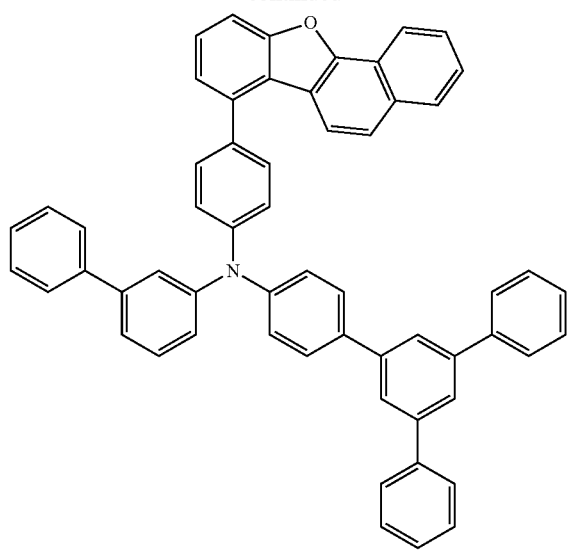
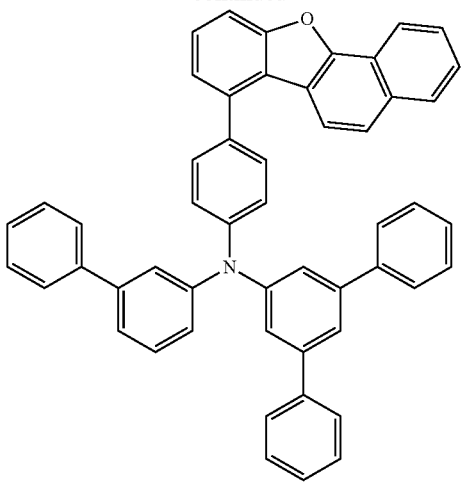
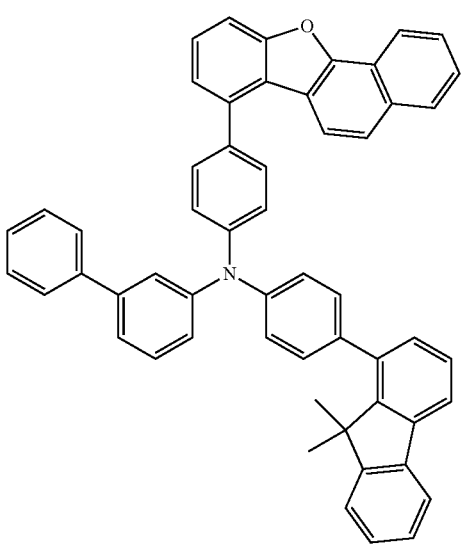
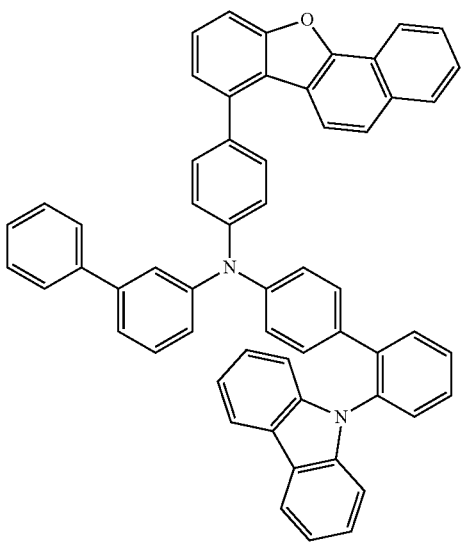

441
-continued
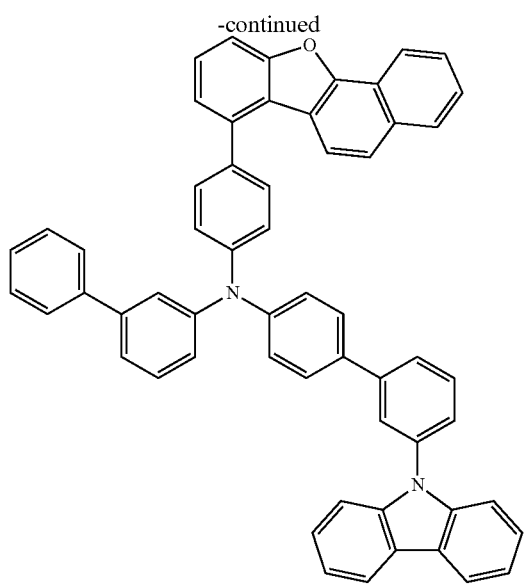
442
-continued
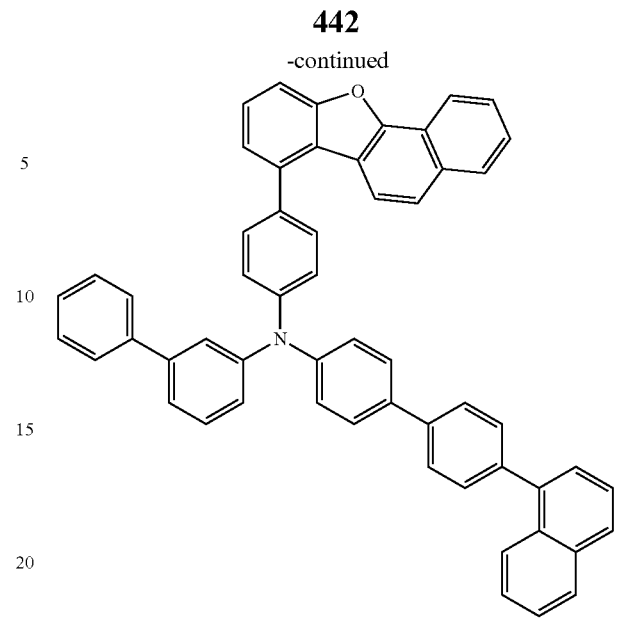
[Chem. 166]
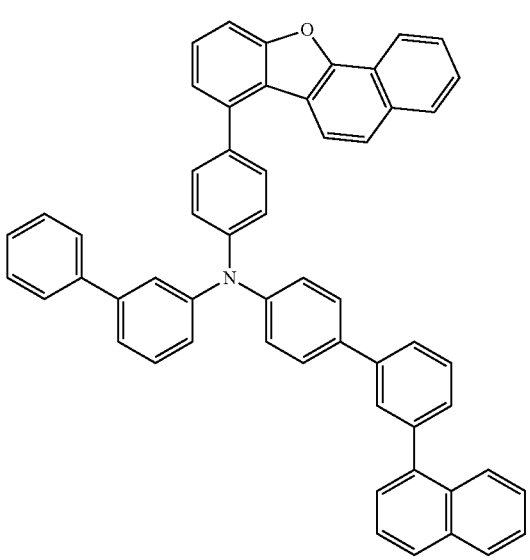
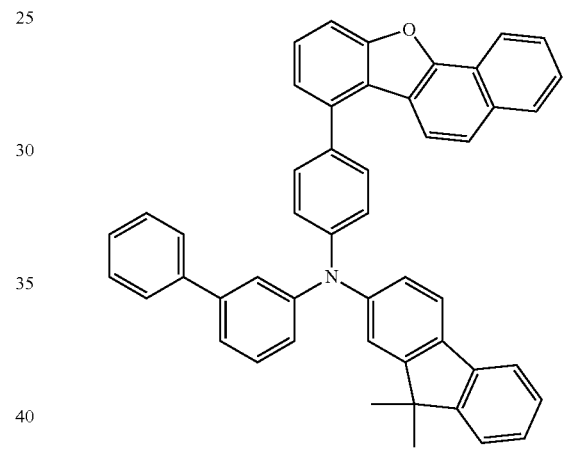
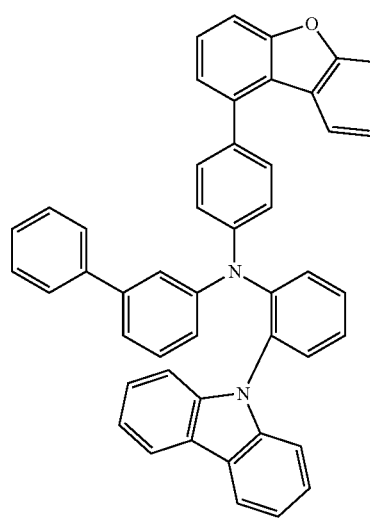

443
-continued
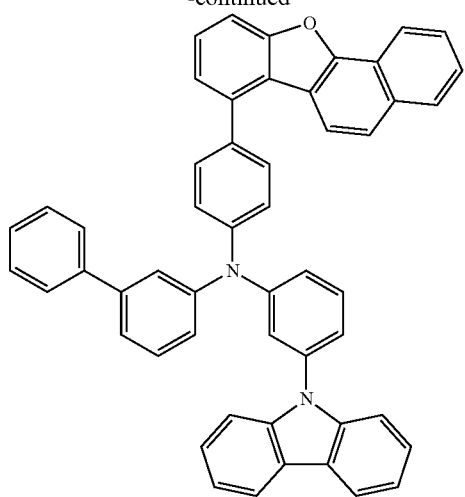
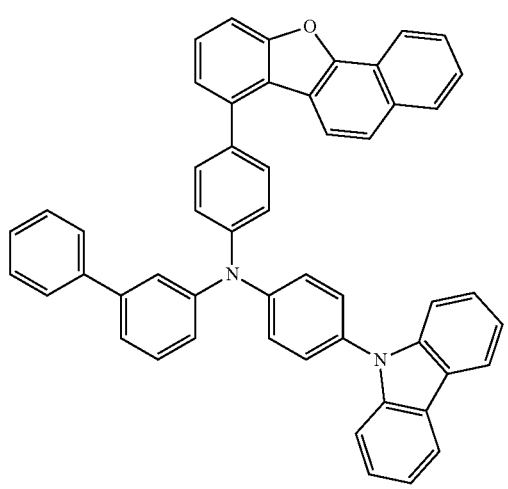
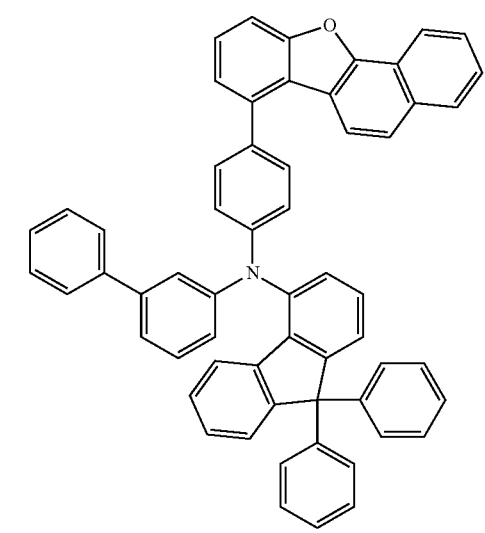
444
-continued
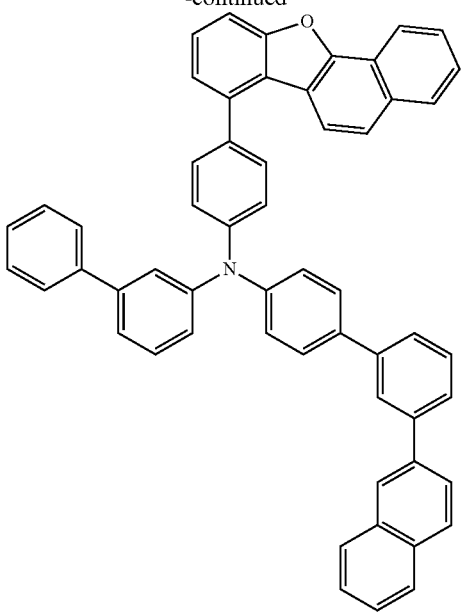
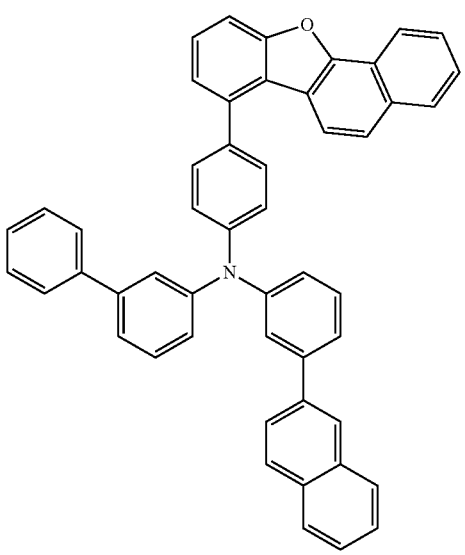
[Chem. 167]

445
-continued
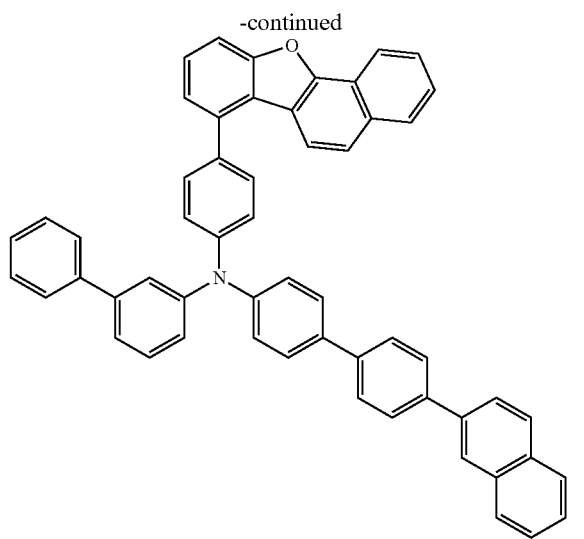
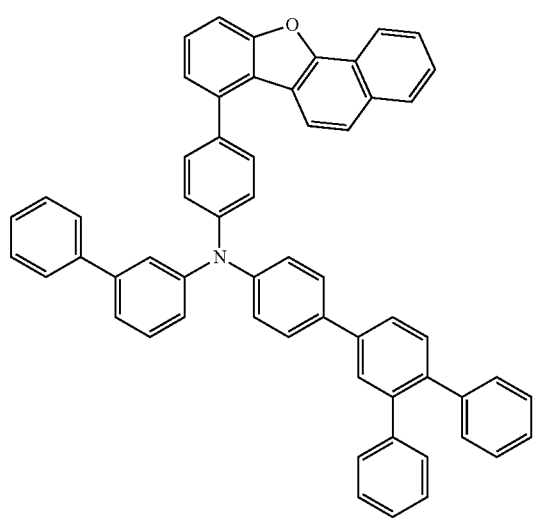
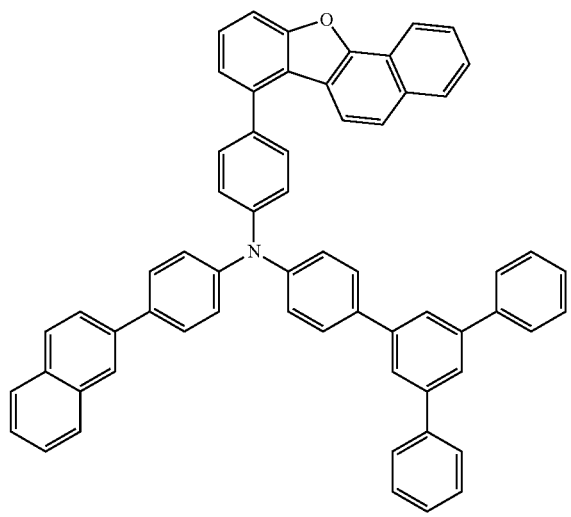
446
-continued
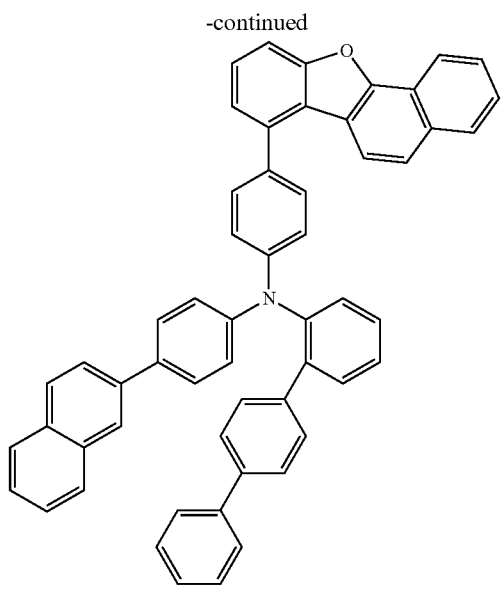
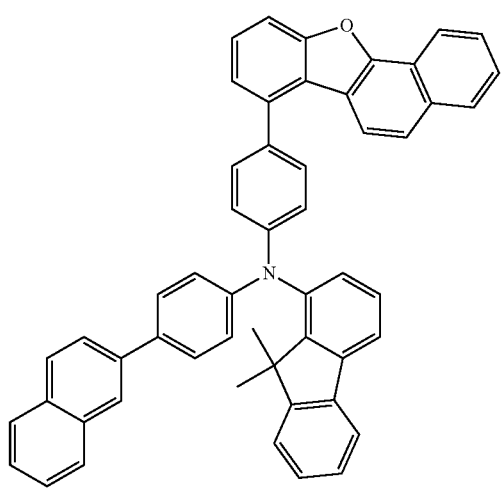
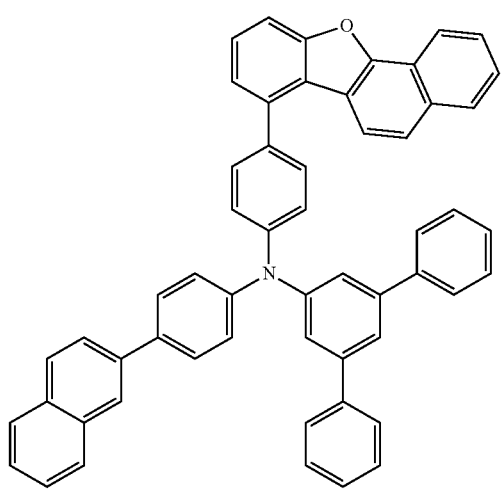

447
-continued
448
-continued
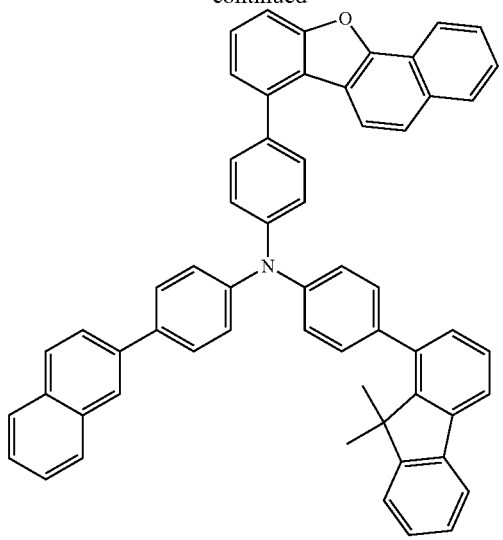
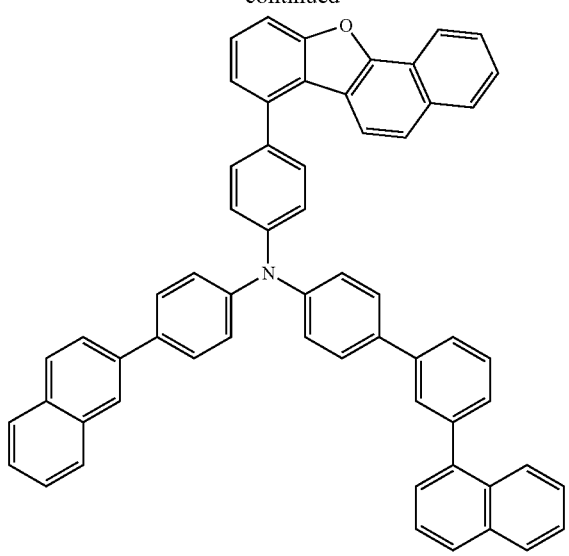
[Chem. 168]
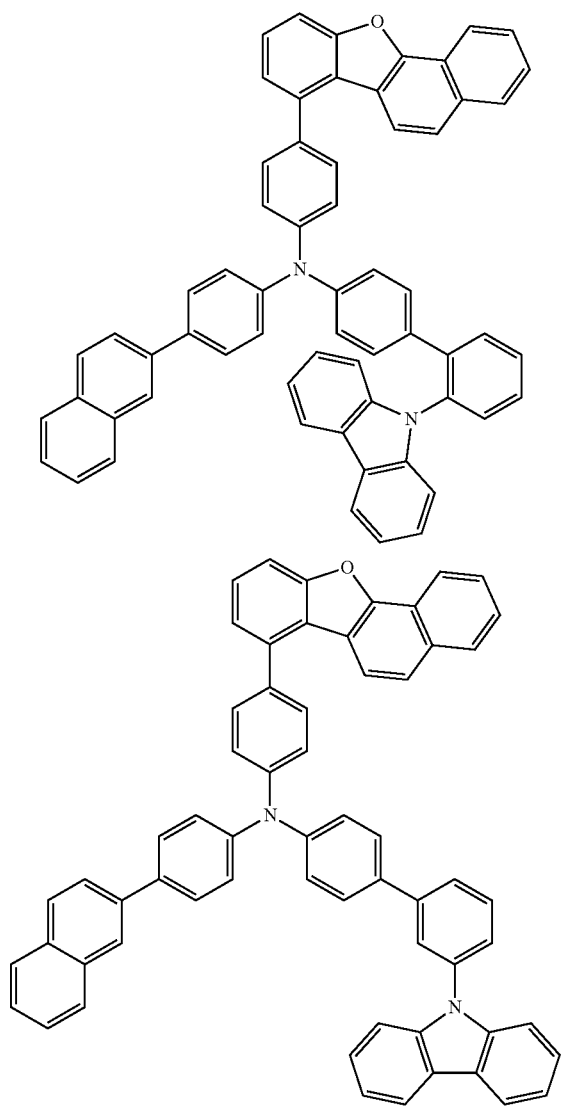
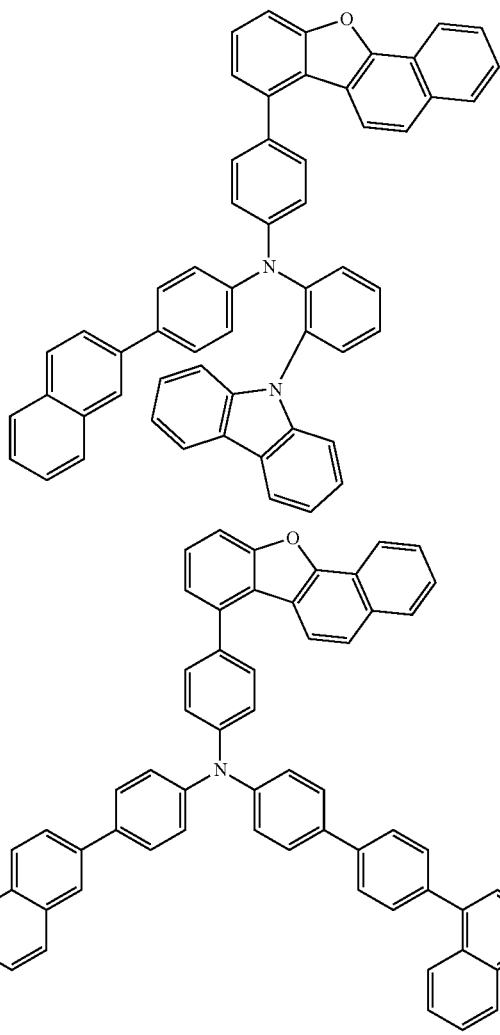

449
-continued
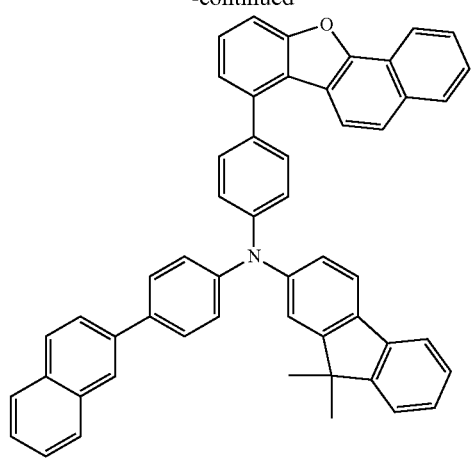
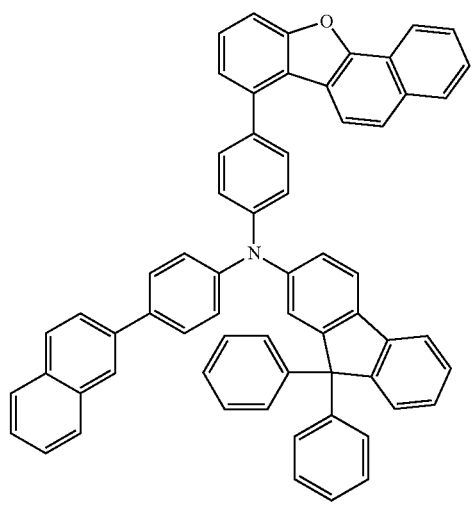
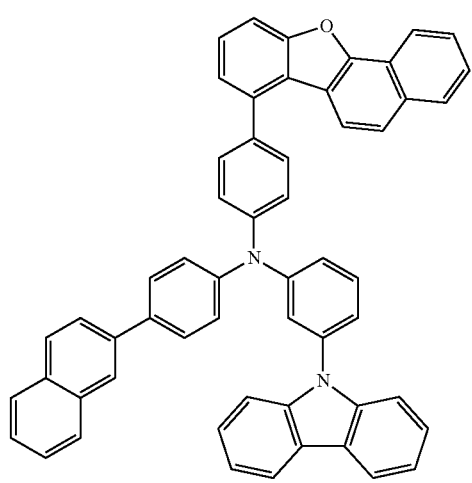
450
-continued
[Chem. 169]
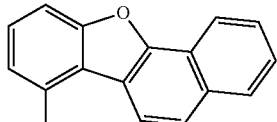
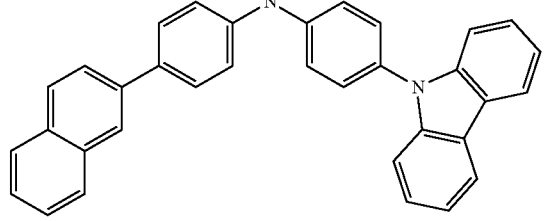
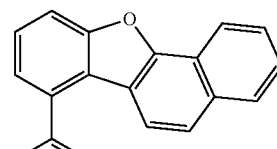
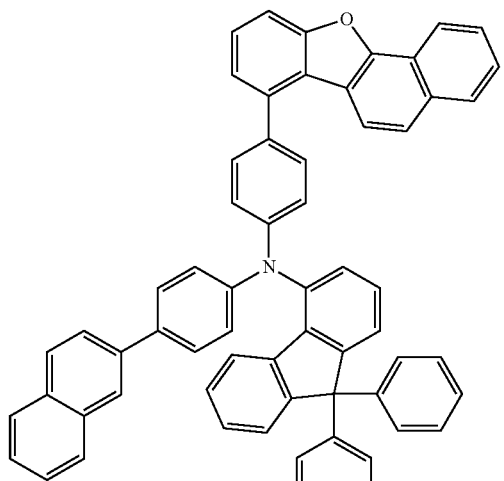
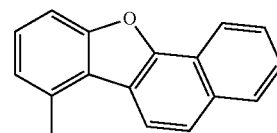
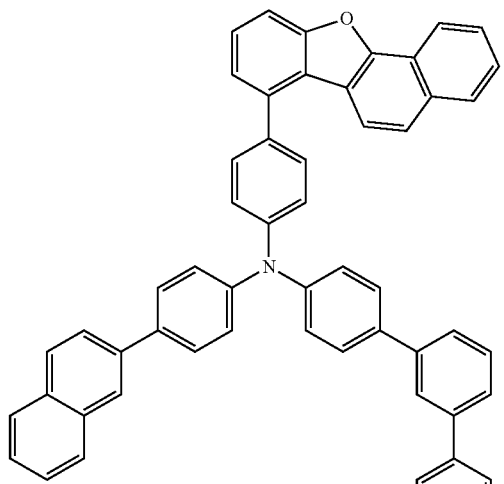

451
-continued
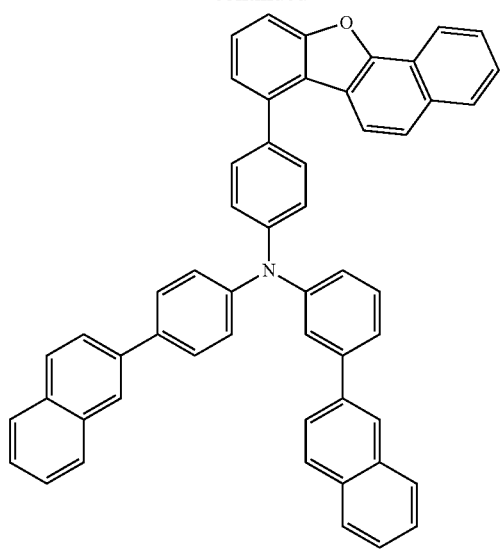
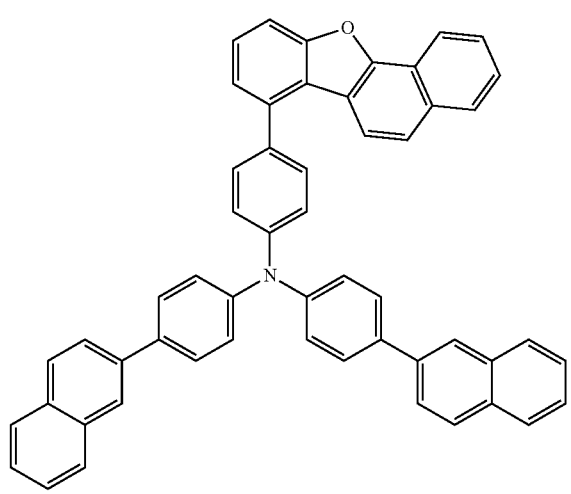
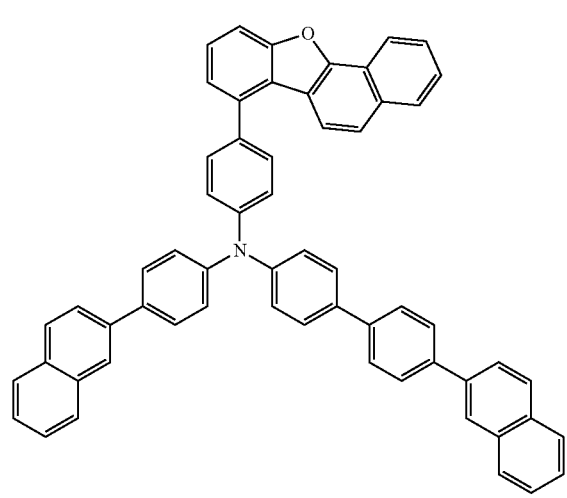
452
-continued
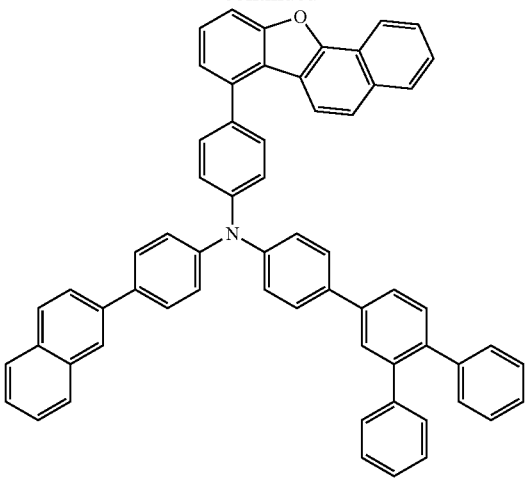
[Chem. 170]
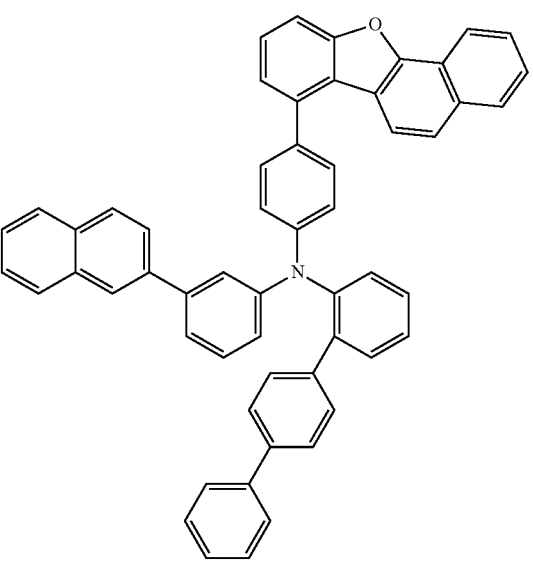

| 453 -continued | 454 -continued |
|---|---|
| 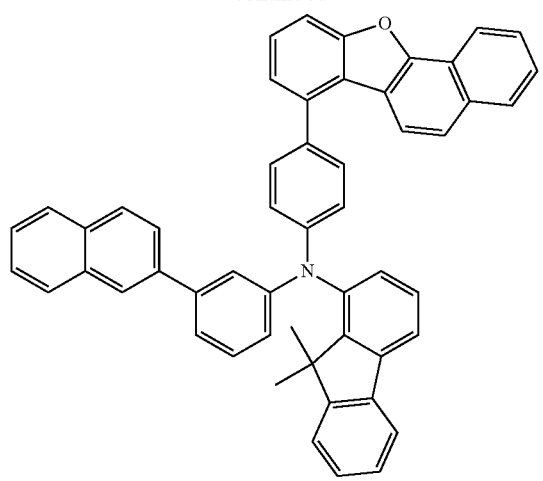 | 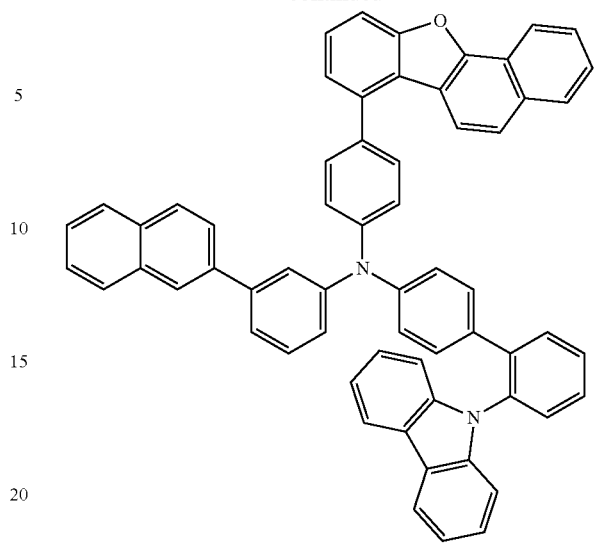 |
| 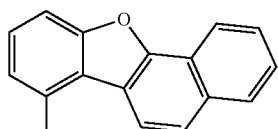 | 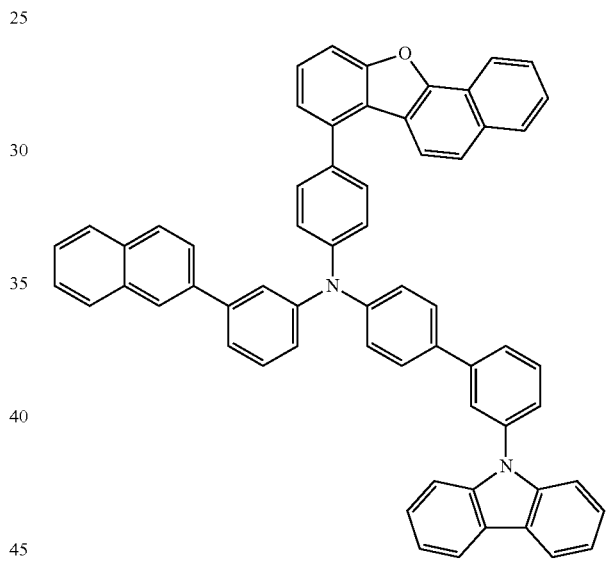 |
| 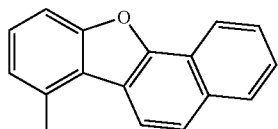 | 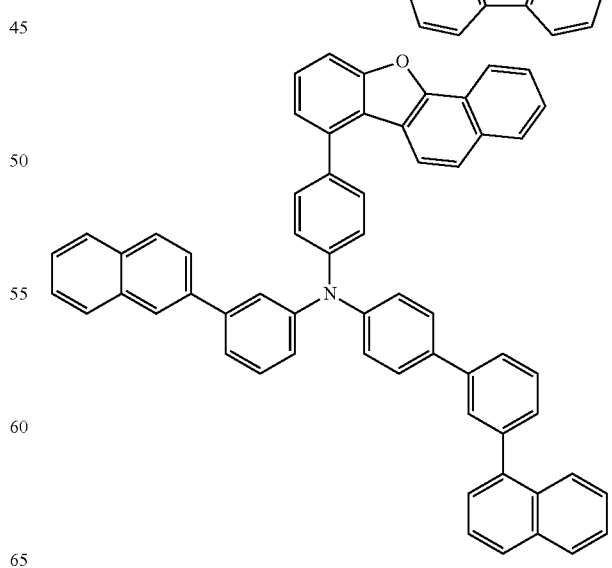 |

455
-continued
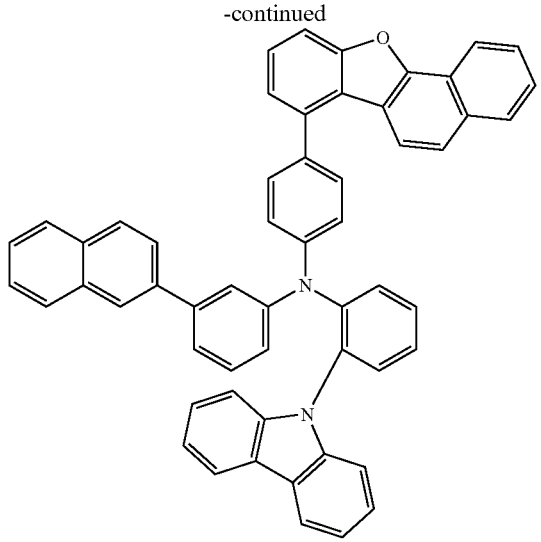
[Chem. 171]
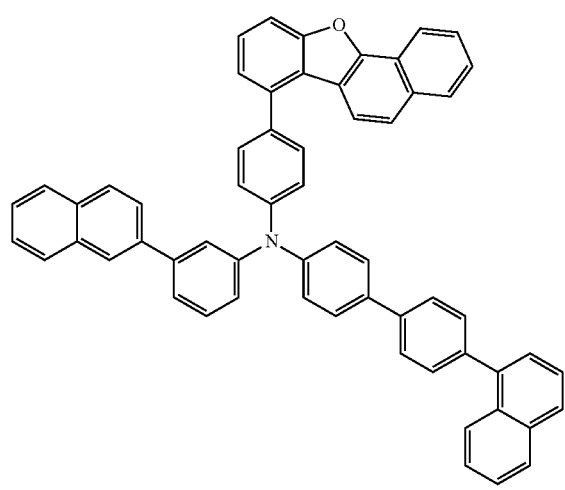
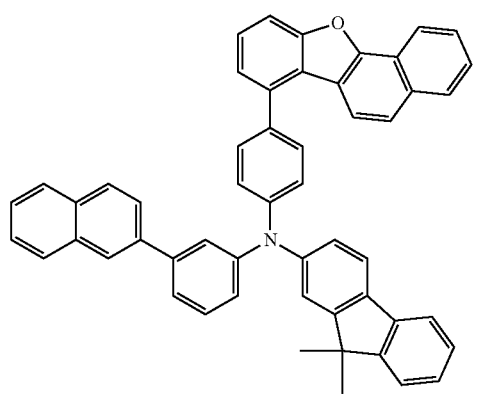
456
-continued
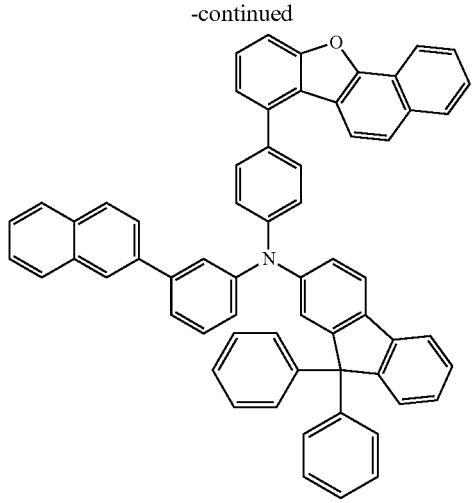
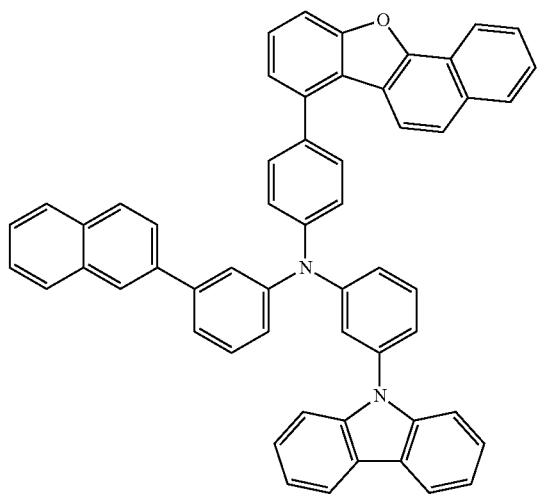
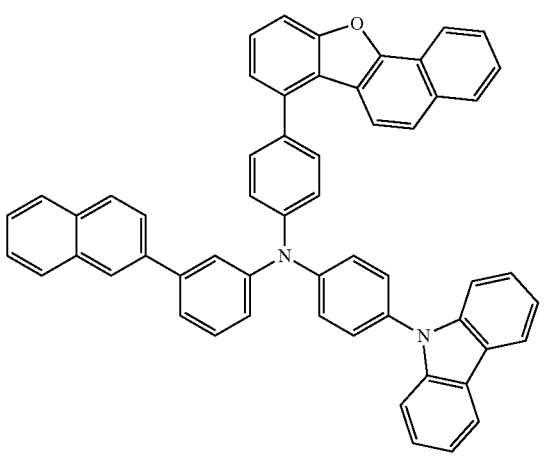

457
-continued
458
-continued
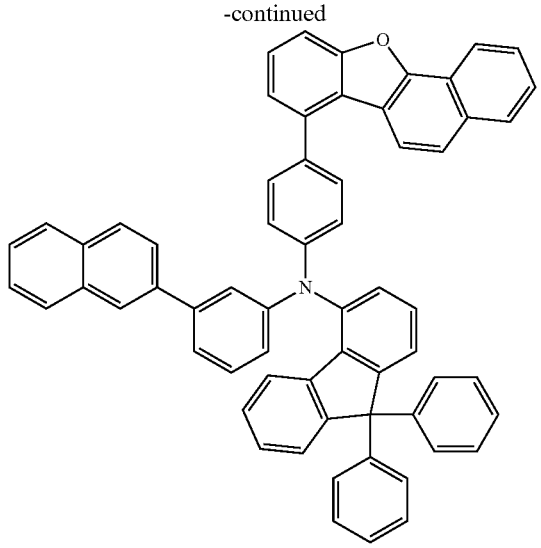
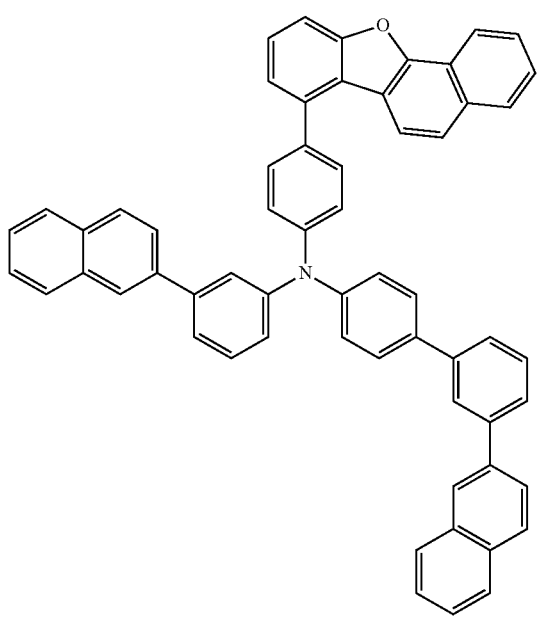
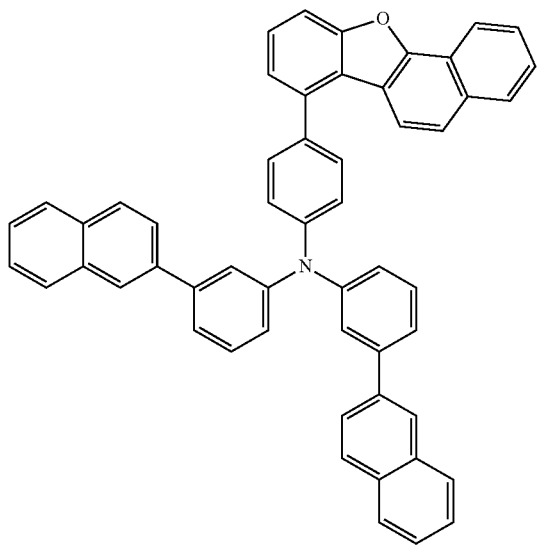
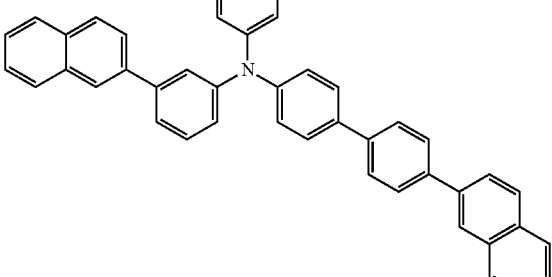
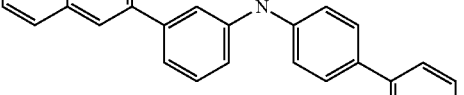
[Chem. 172]

459
-continued
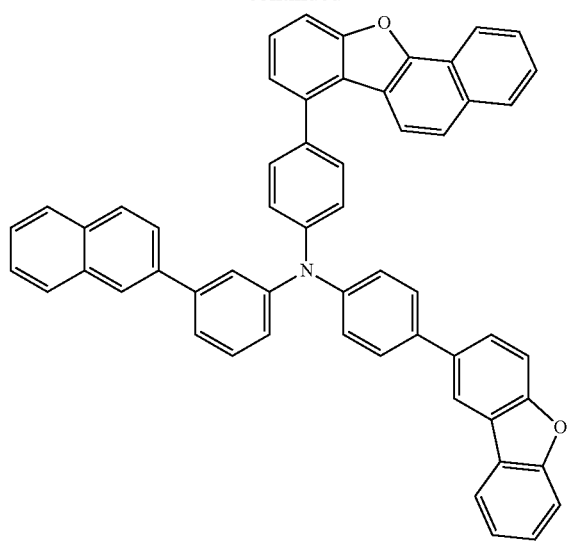
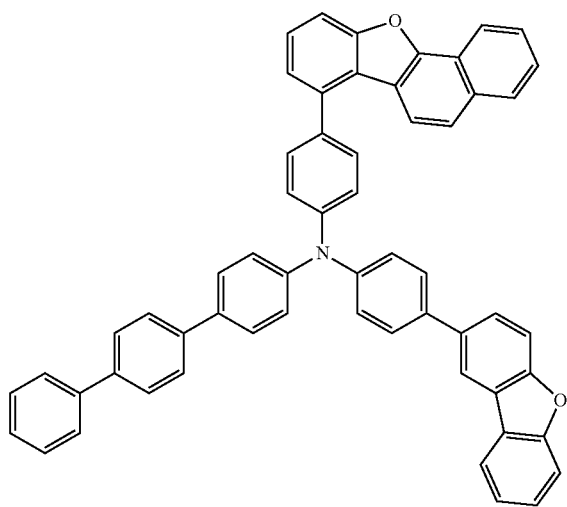
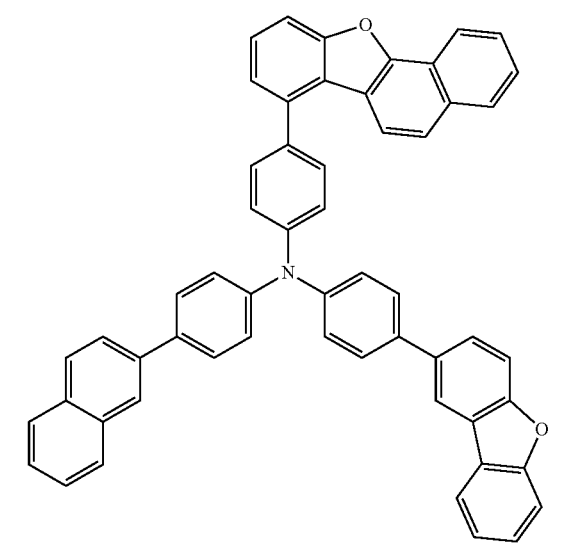
460
-continued
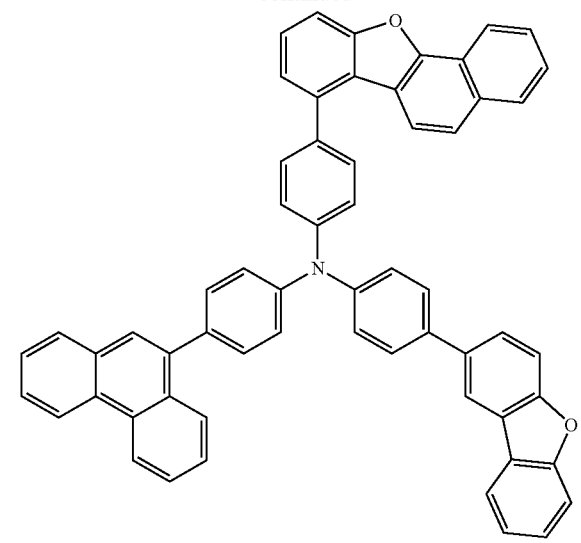
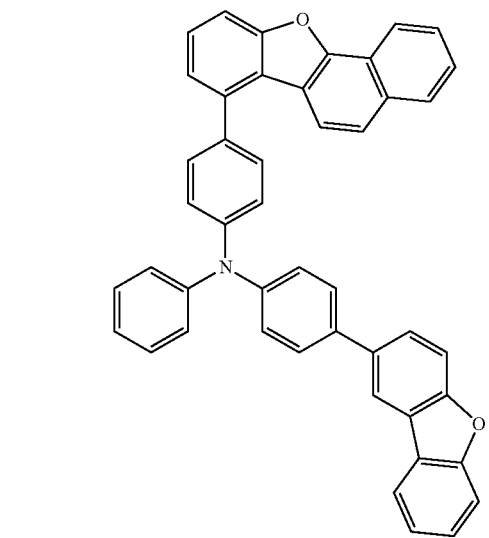
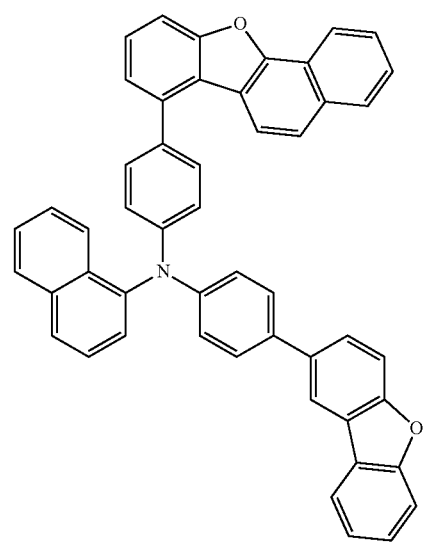

461
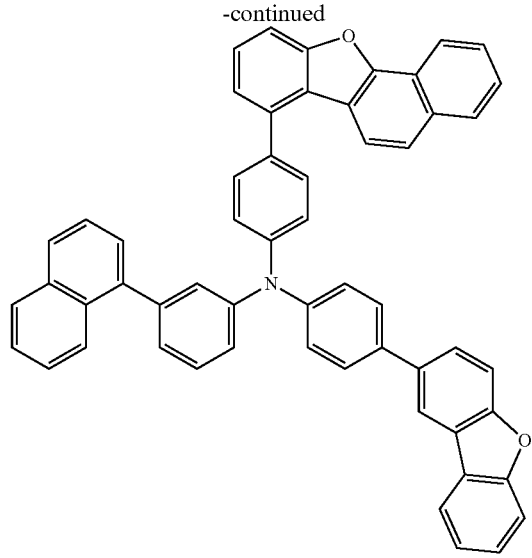
462
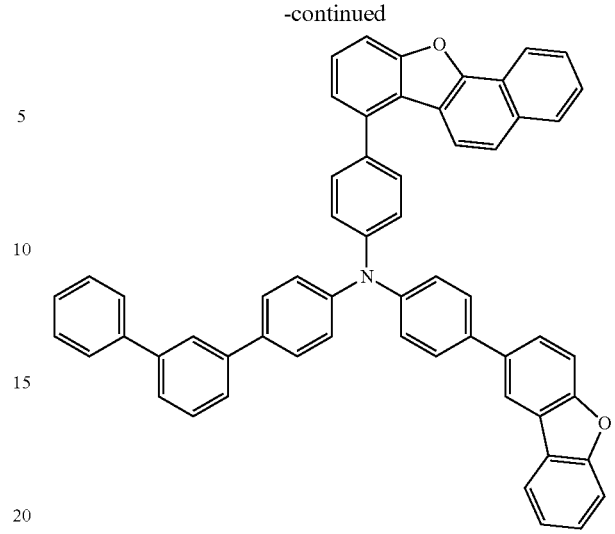
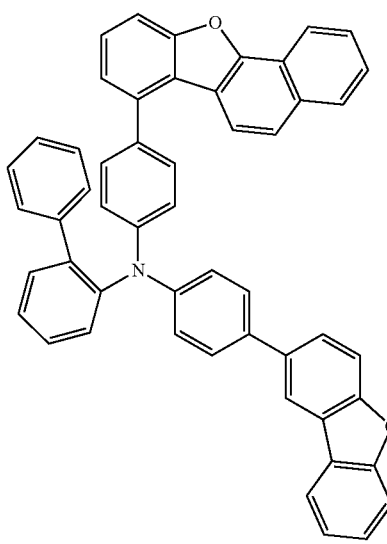
[Chem. 173]
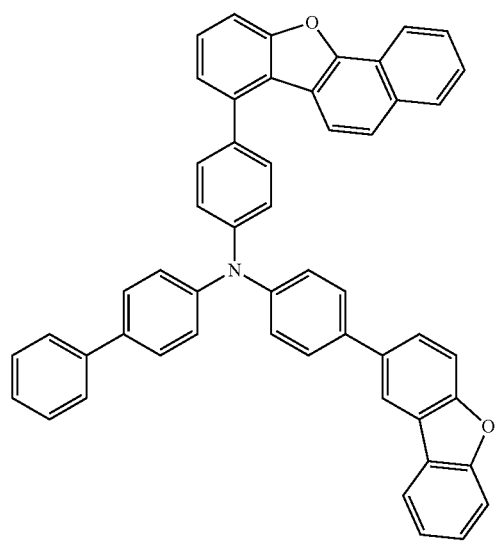
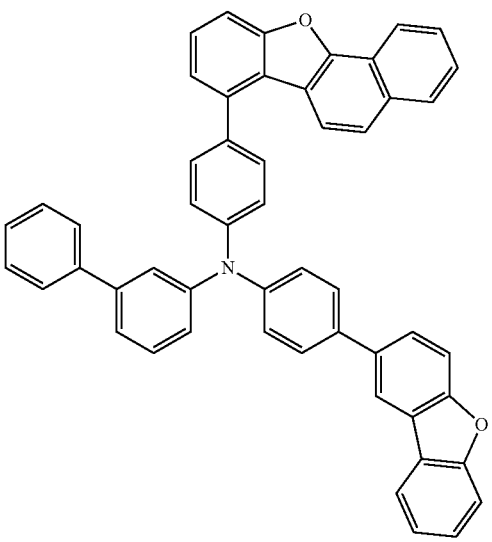

463
-continued
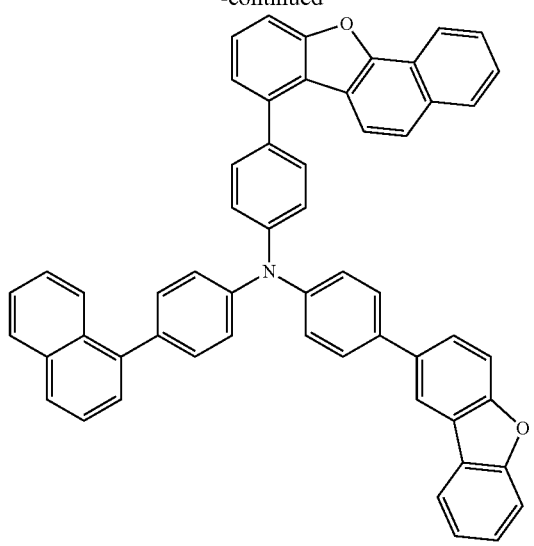
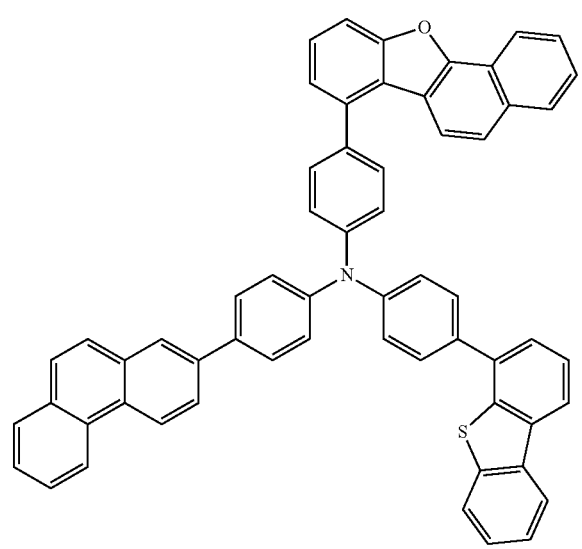
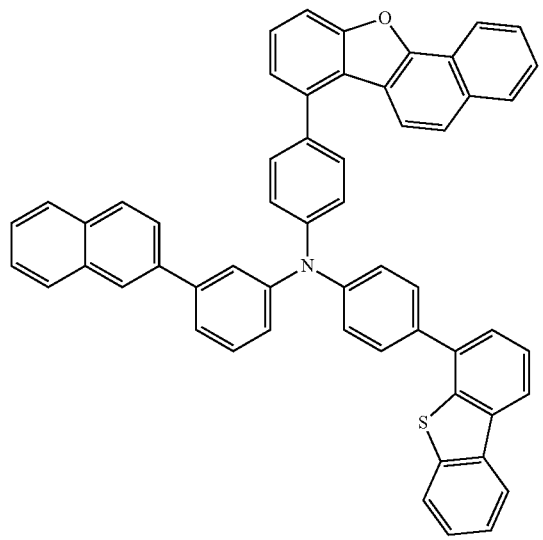
464
-continued
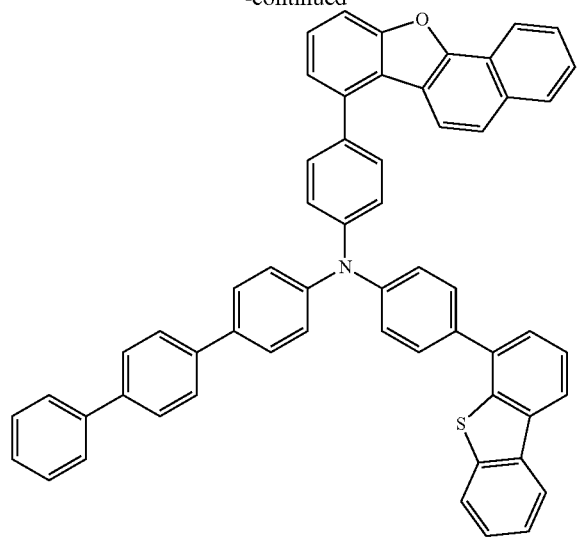
[Chem. 174]
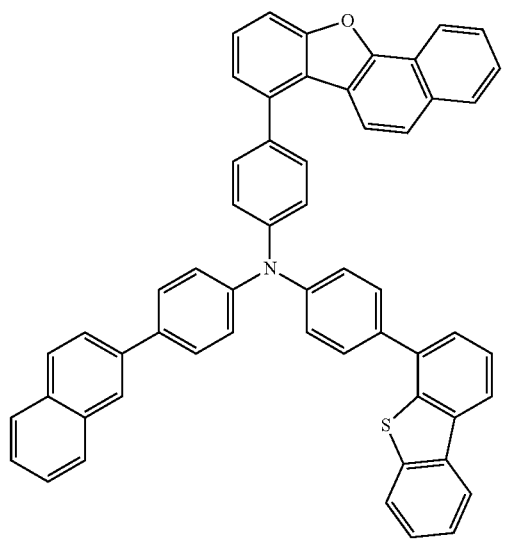
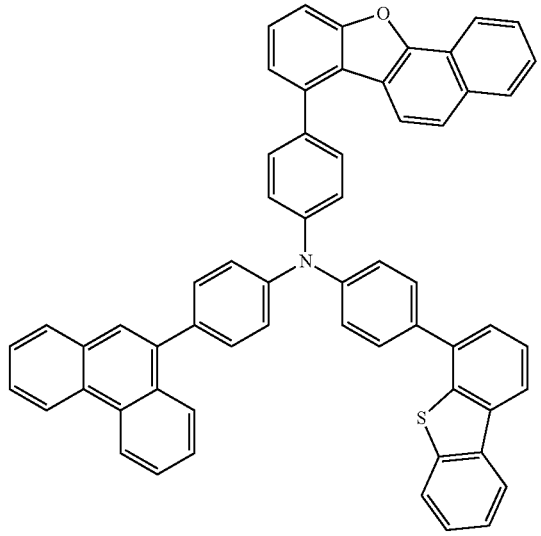

465
-continued
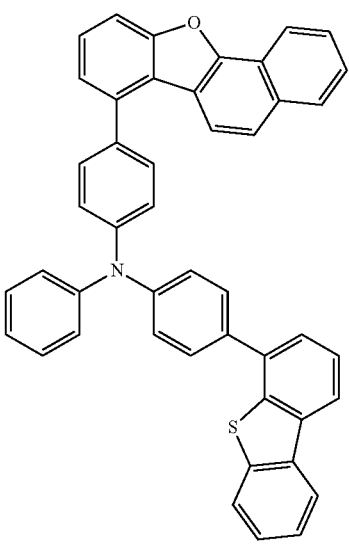
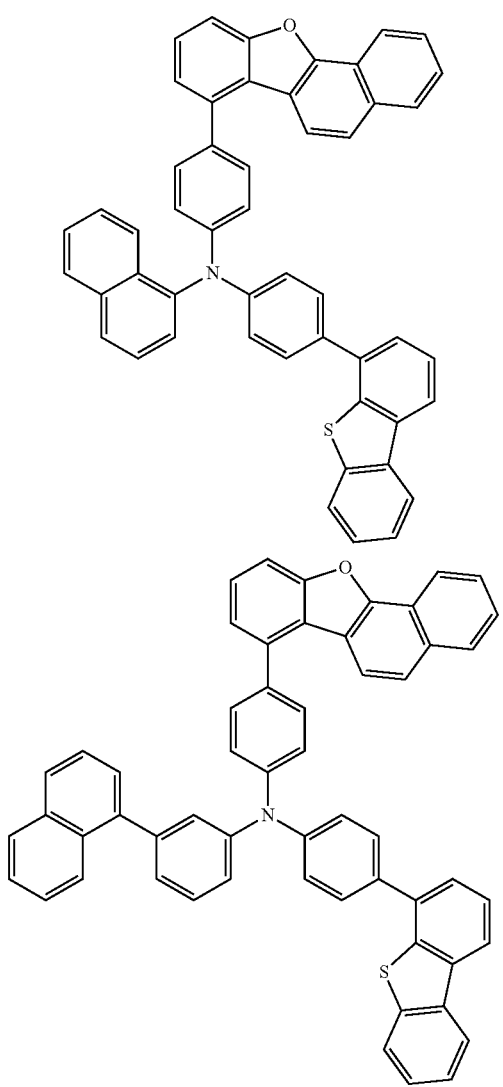
466
-continued
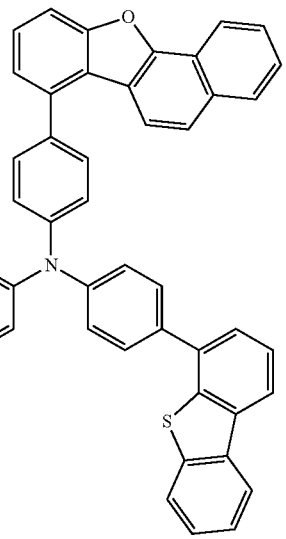
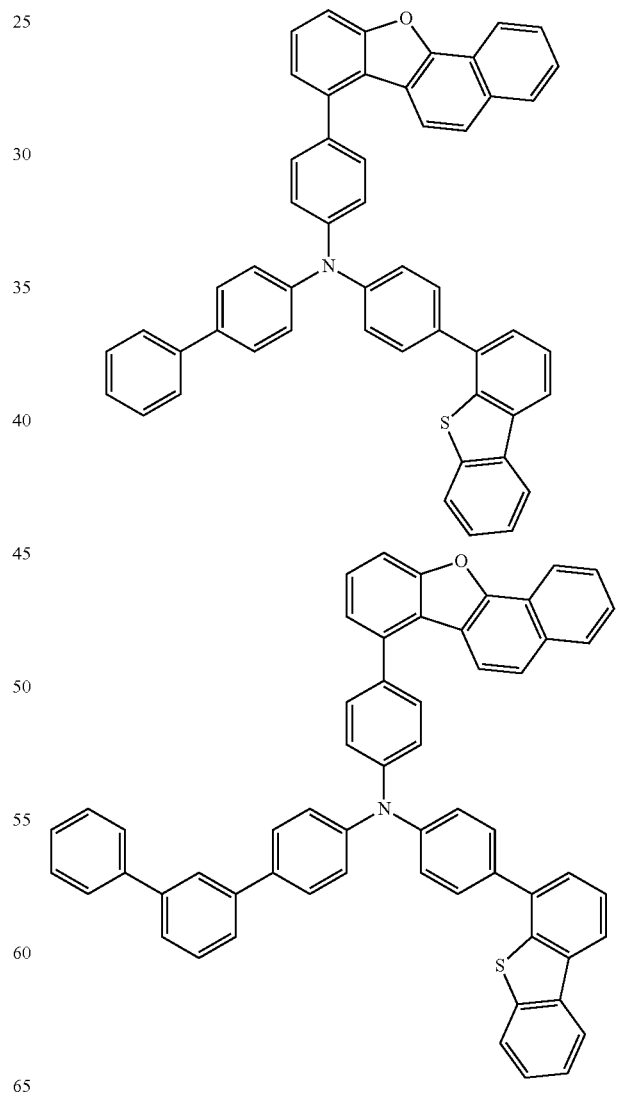

467
-continued
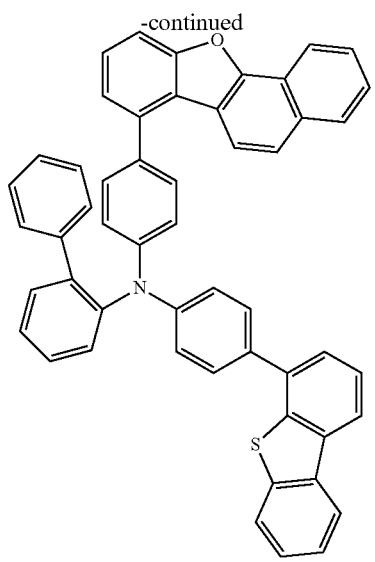
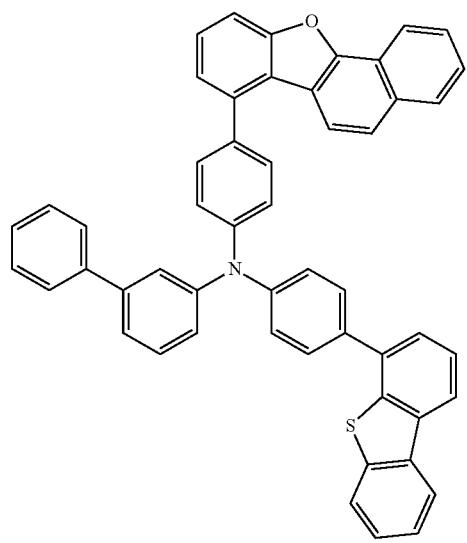
[Chem. 175]
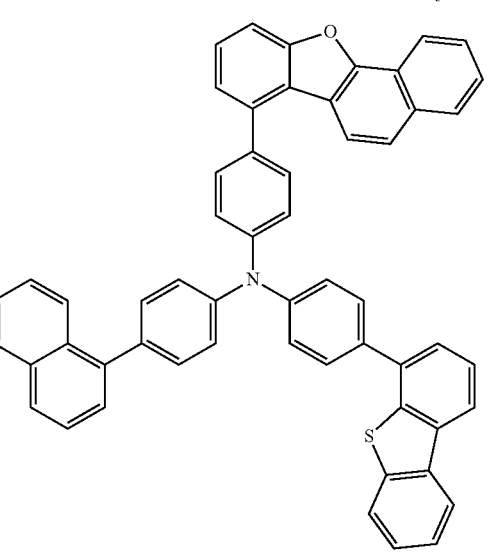
468
-continued
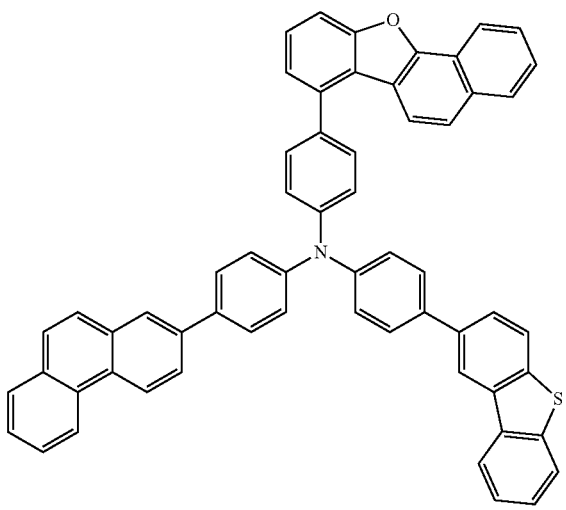
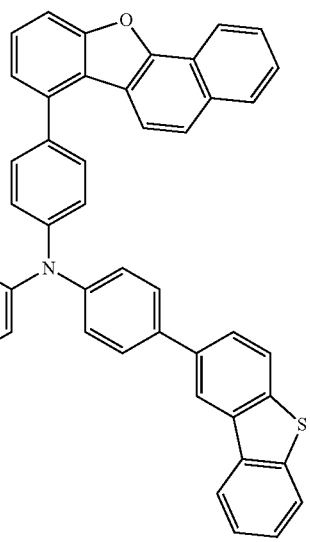
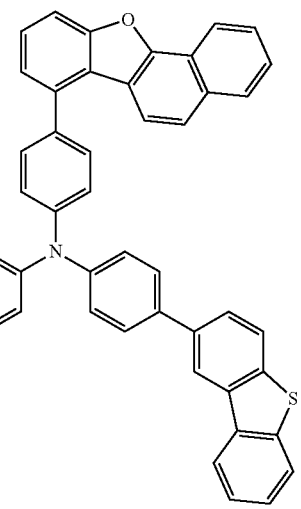

469
-continued
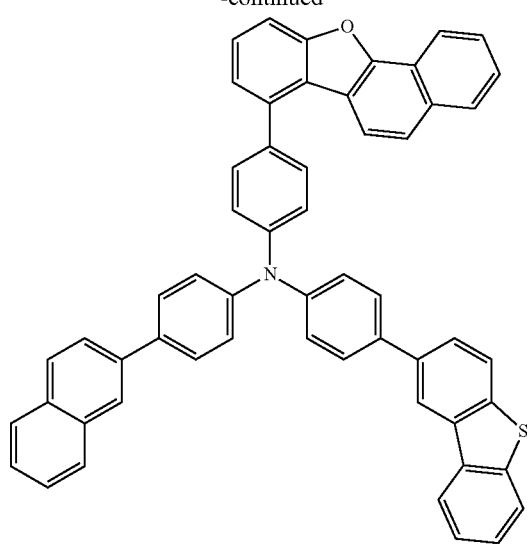
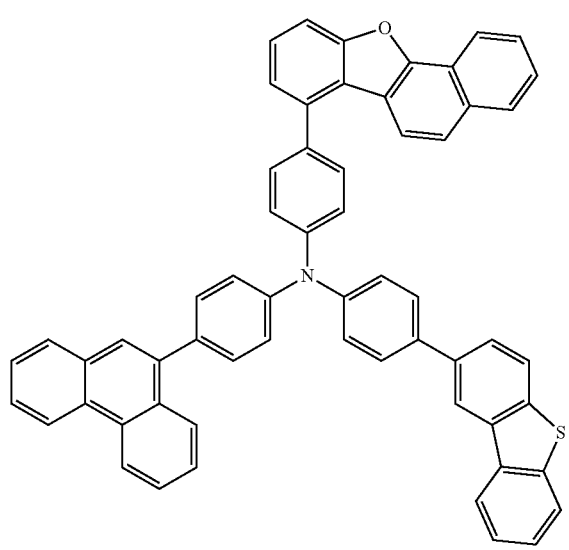
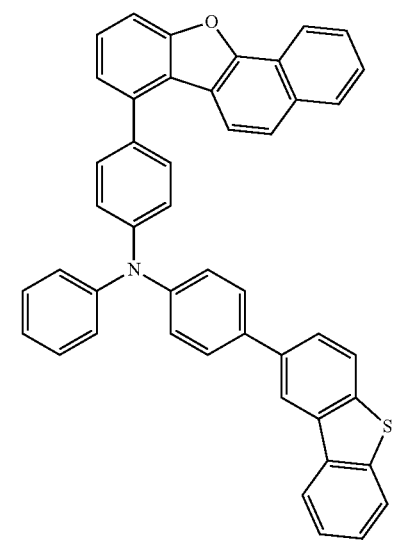
470
-continued
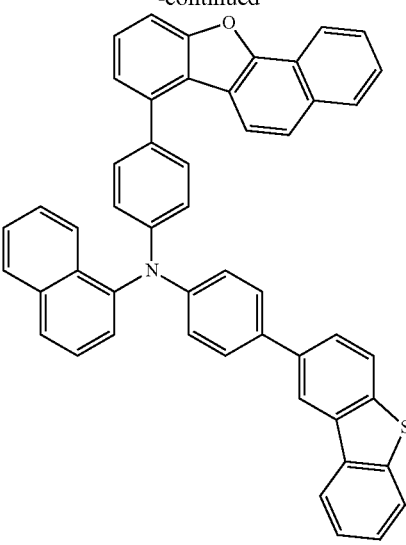
[Chem. 176]
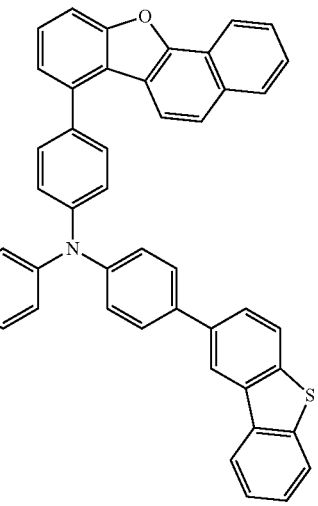

| 471 -continued | 472 -continued |
|---|---|
| 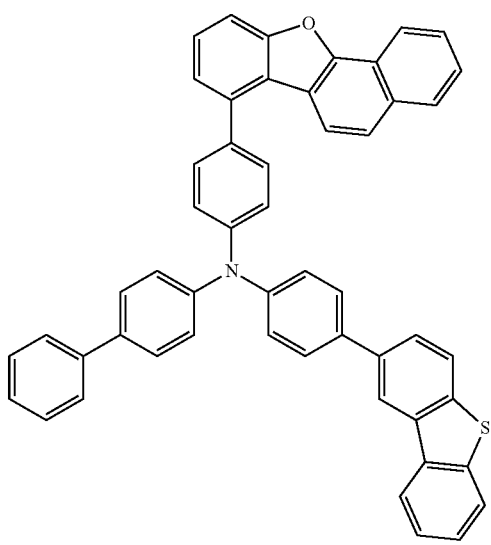 | 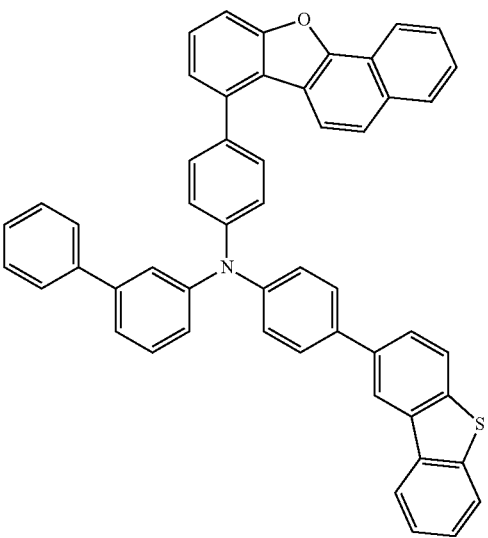 |
| 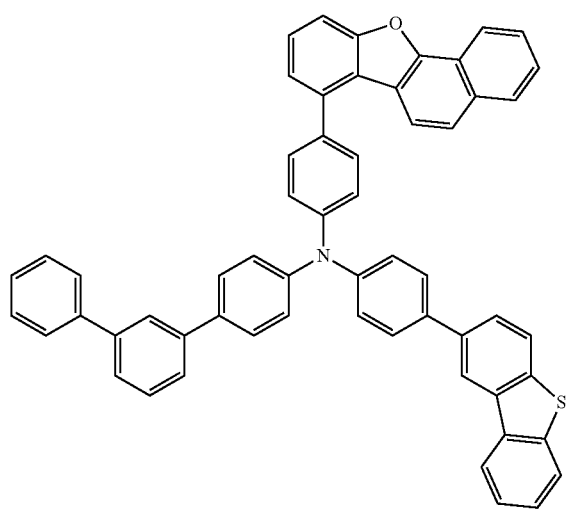 | 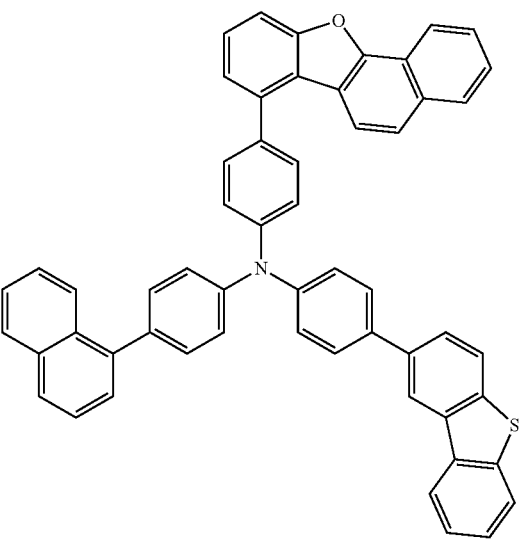 |
| 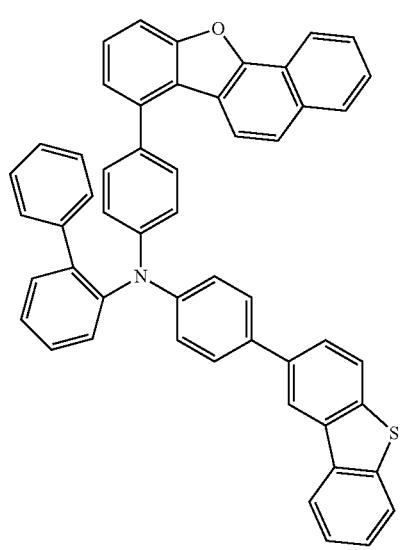 | 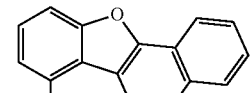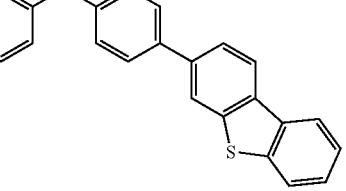 |

473
-continued
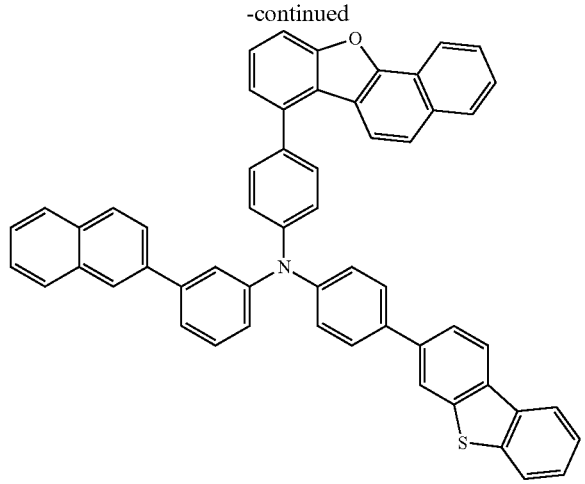
474
-continued
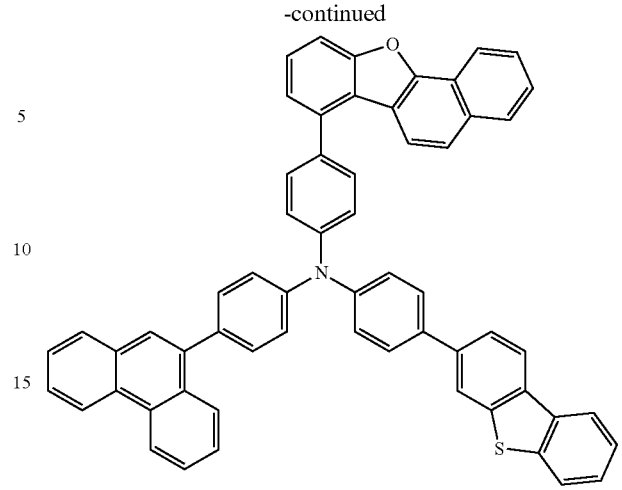
[Chem. 177]
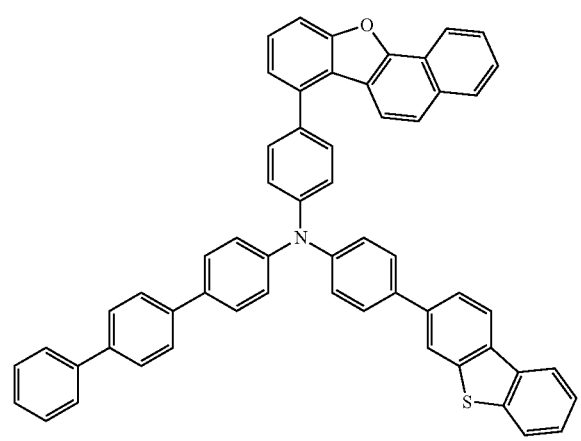
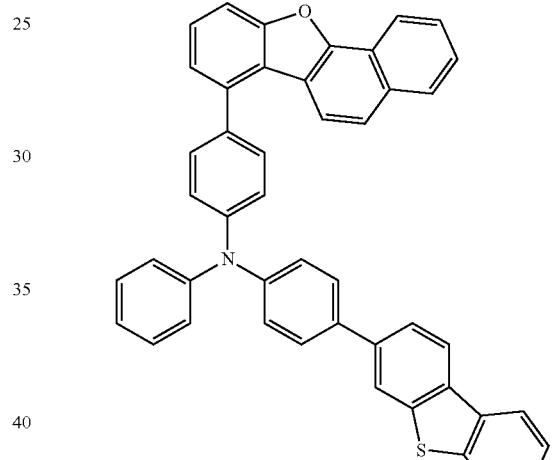
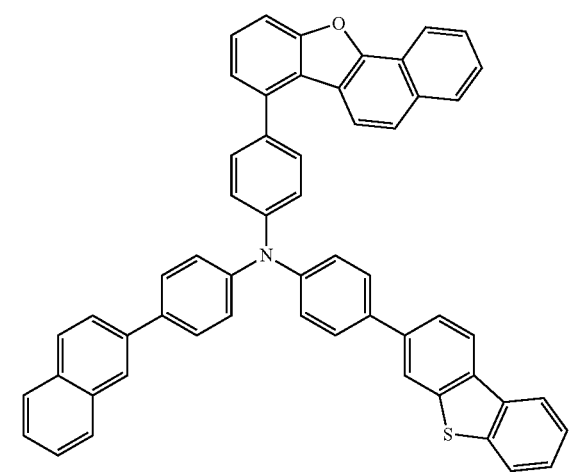
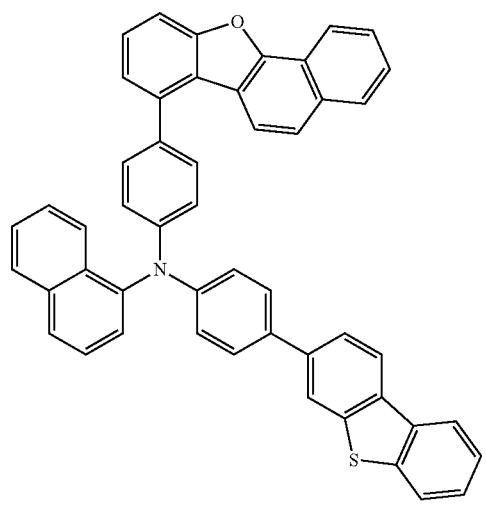

475
-continued
476
-continued
[Chem. 178]
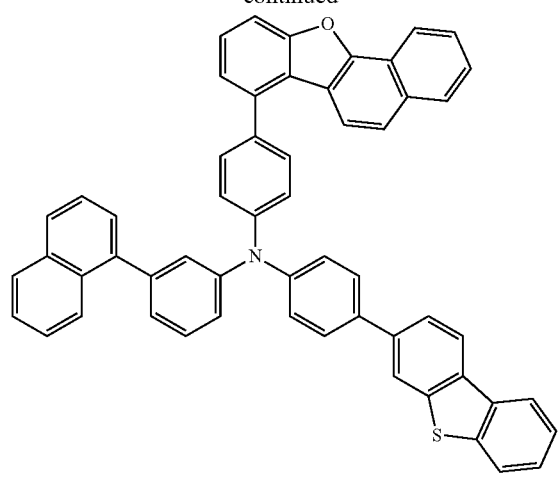
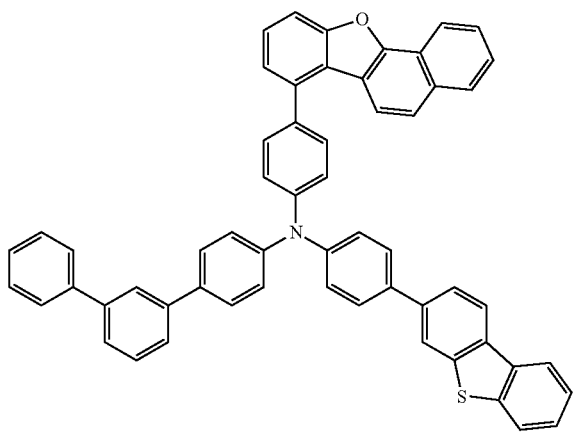
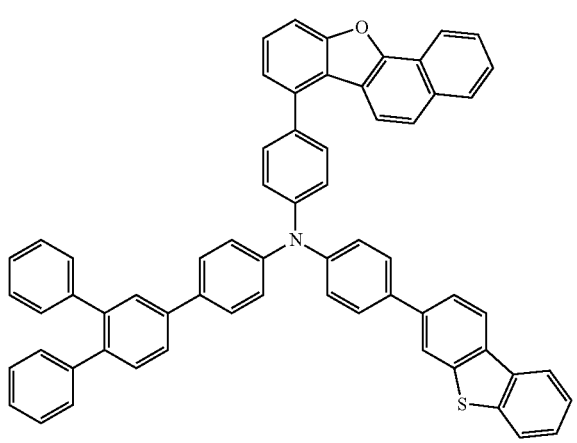
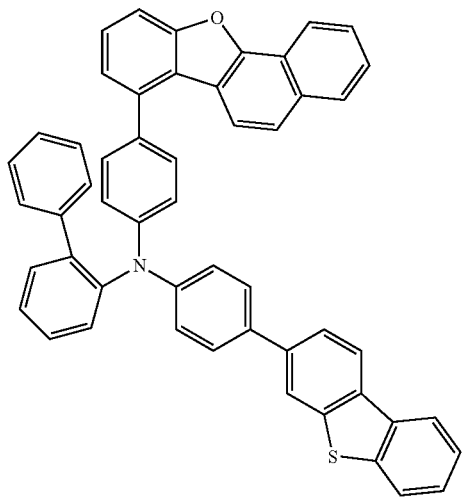
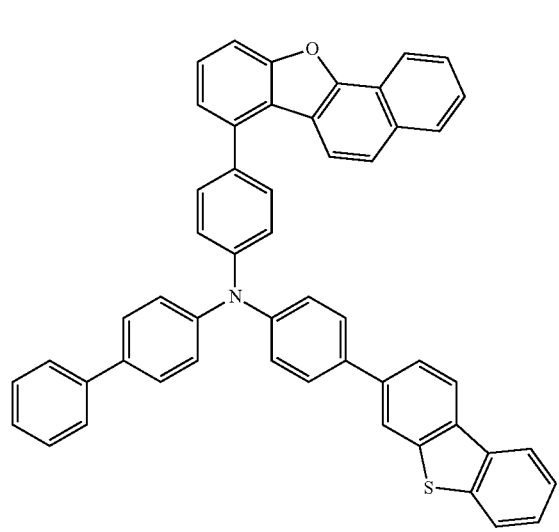
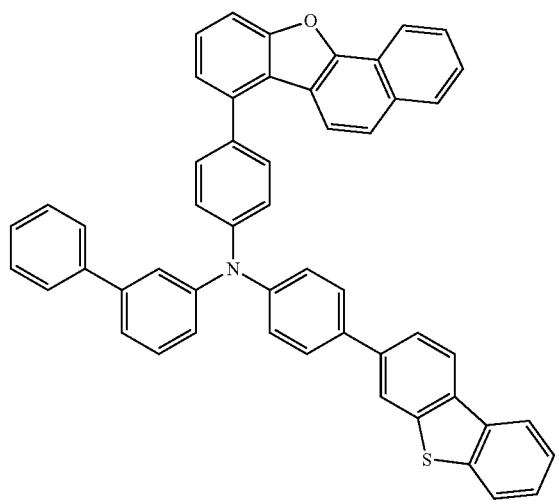

477

478

-continued

-continued

[Chem. 179]

479
-continued
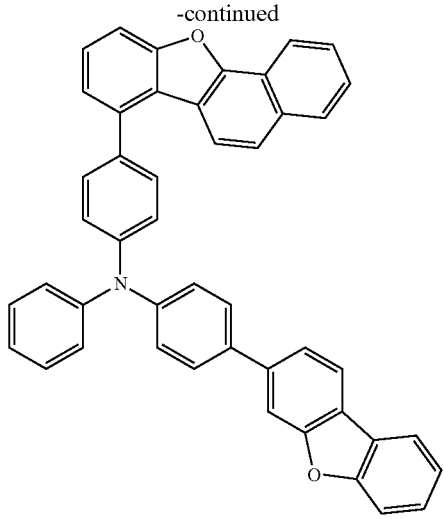
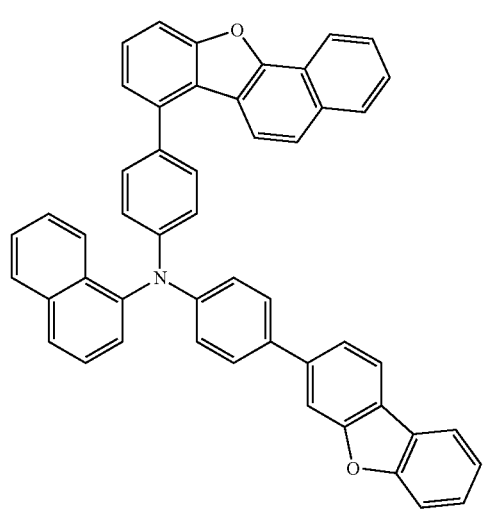
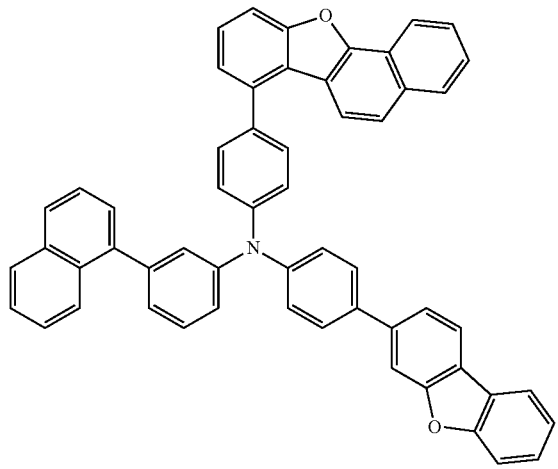
480
-continued
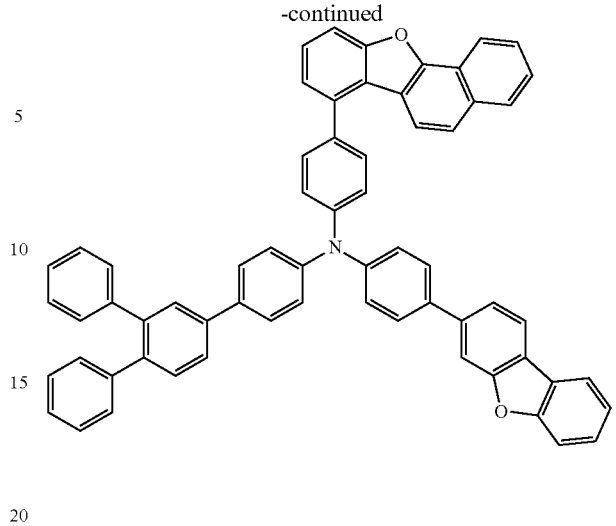
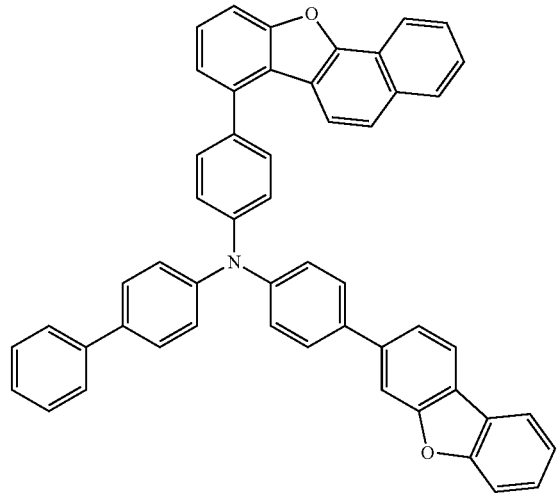
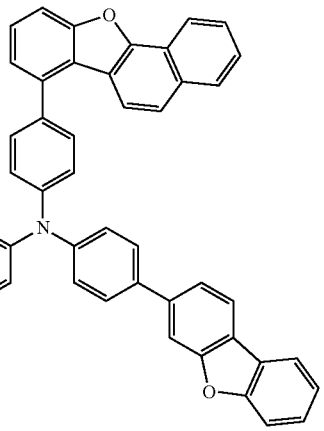

481
-continued
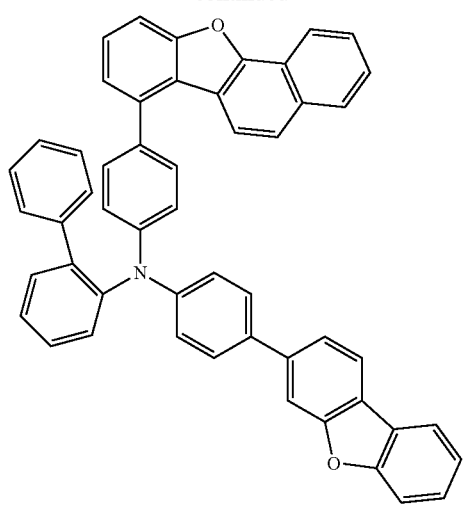
[Chem. 180]
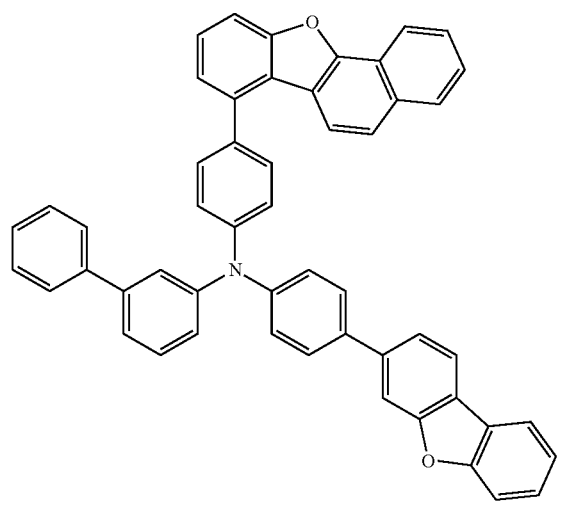
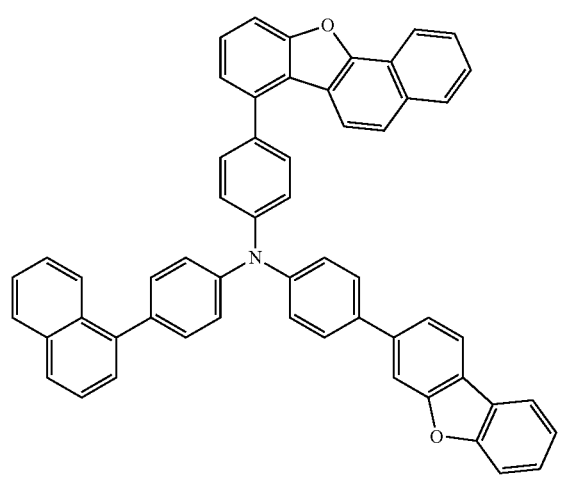
482
-continued
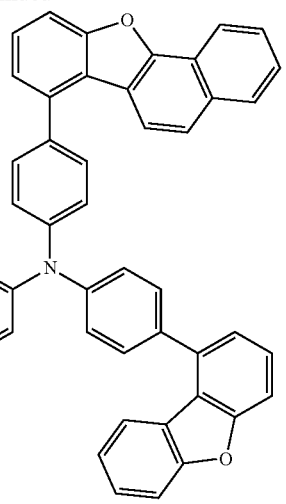
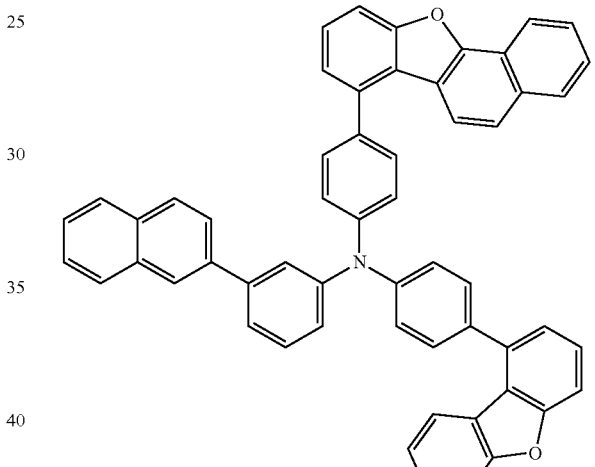
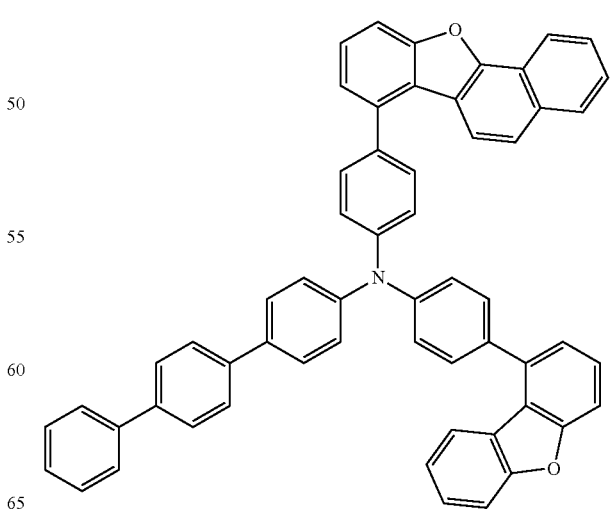

483
-continued
484
-continued
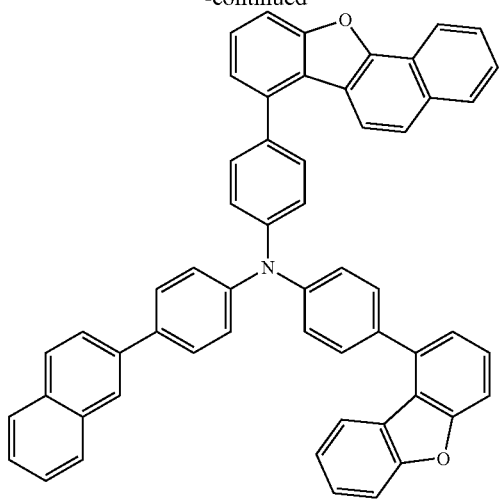
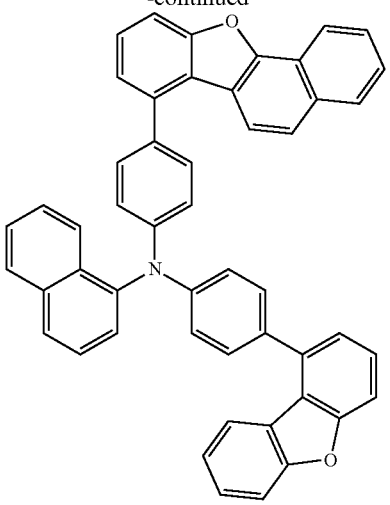
[Chem. 181]
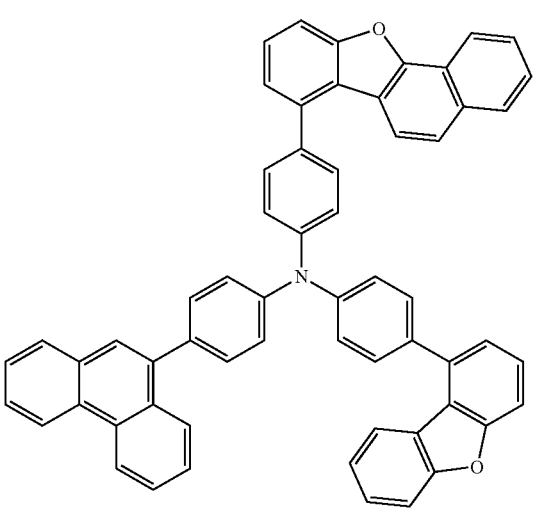
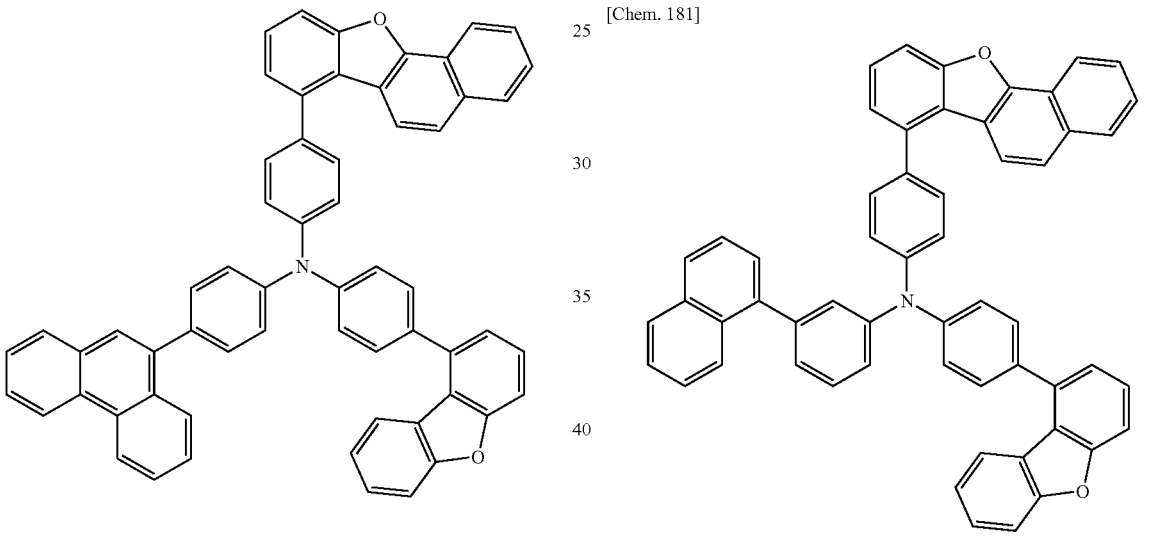
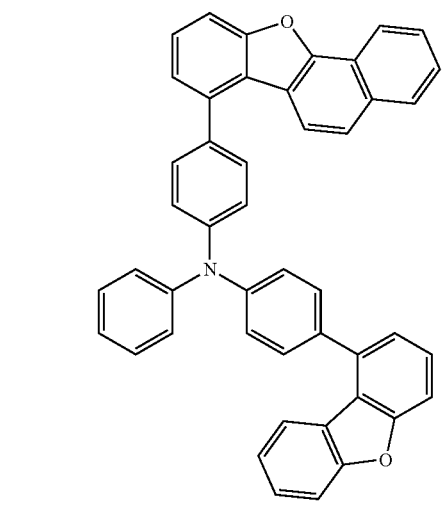
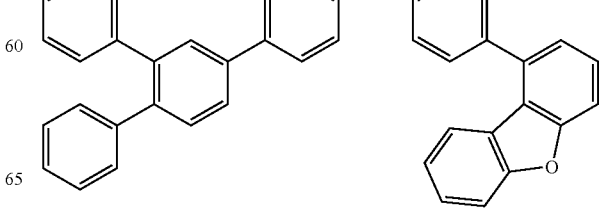

485
-continued
486
-continued
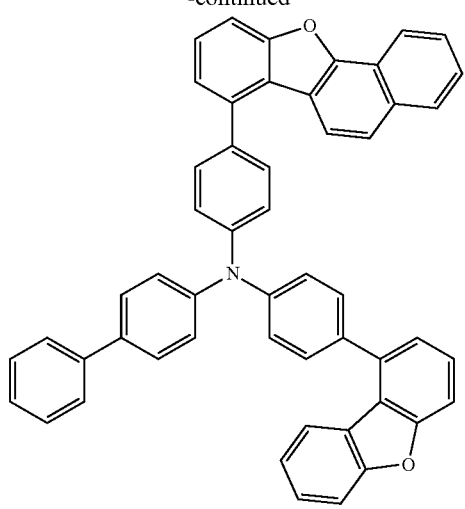
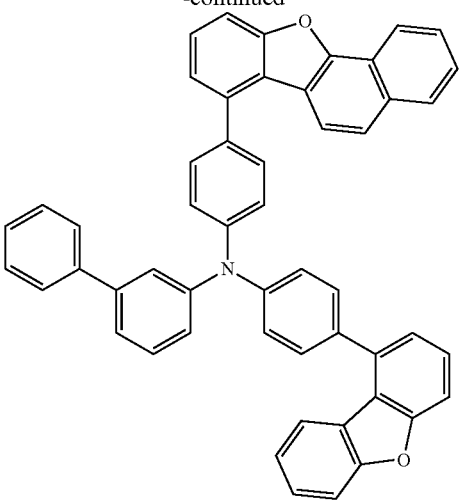
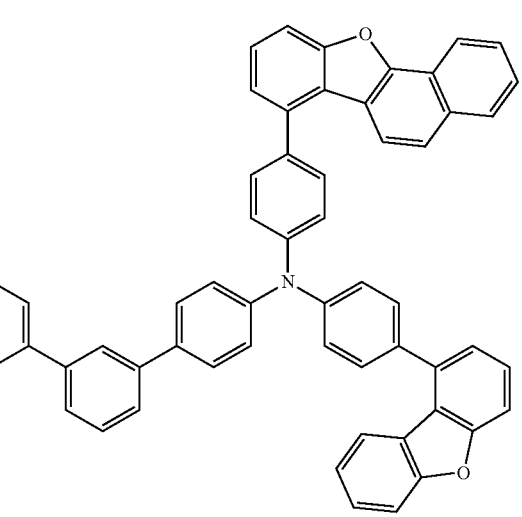
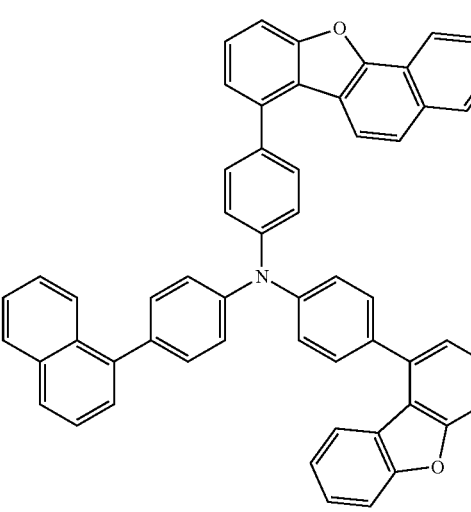
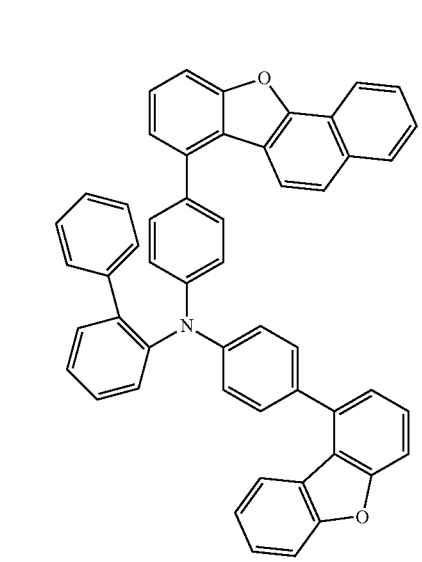
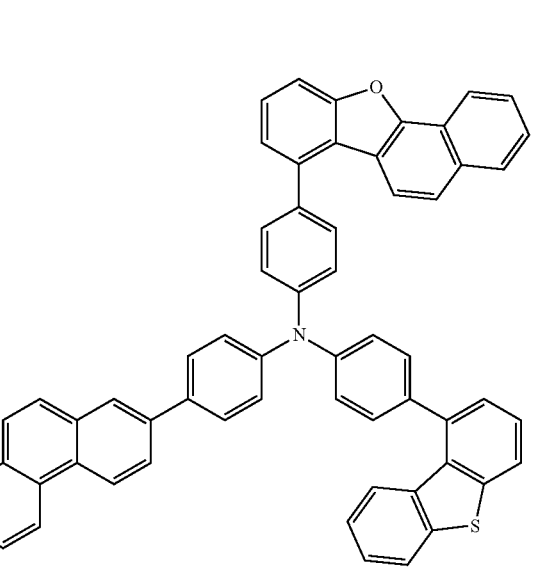

487
-continued
488
-continued
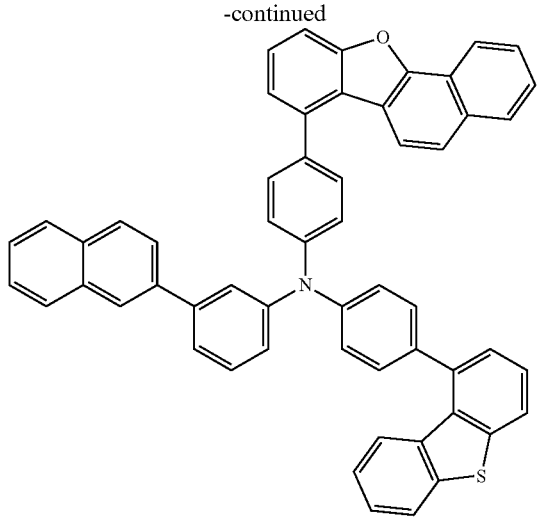
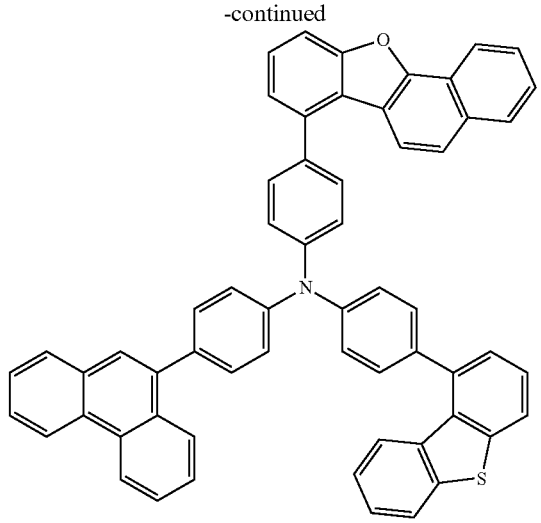
[Chem. 182]
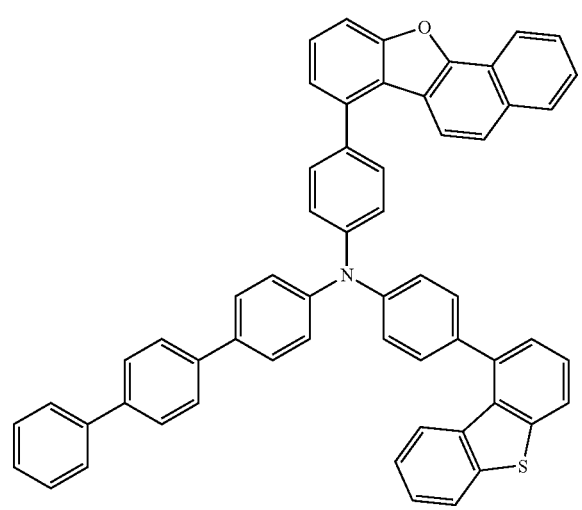
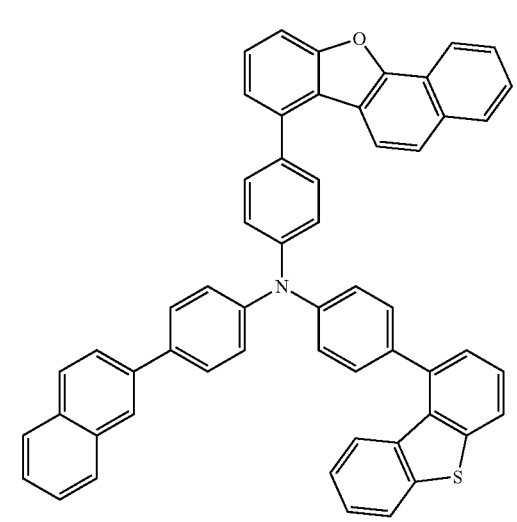
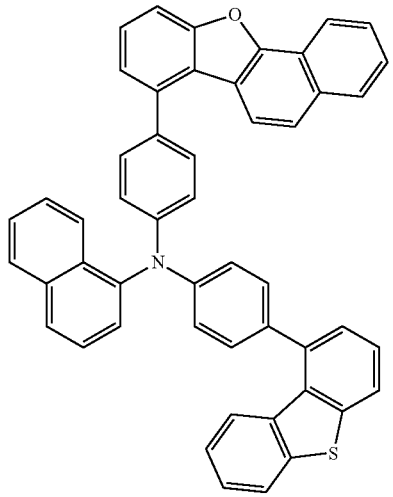

489
-continued
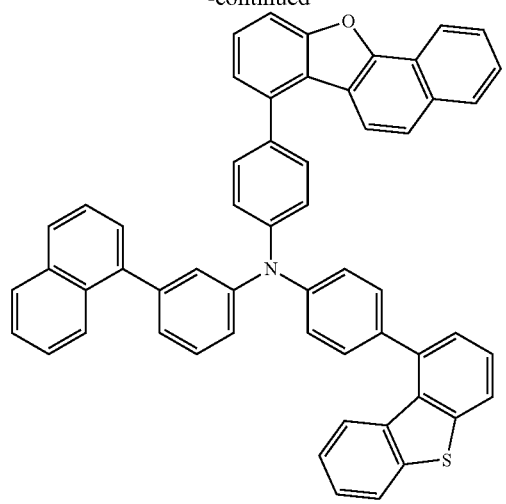
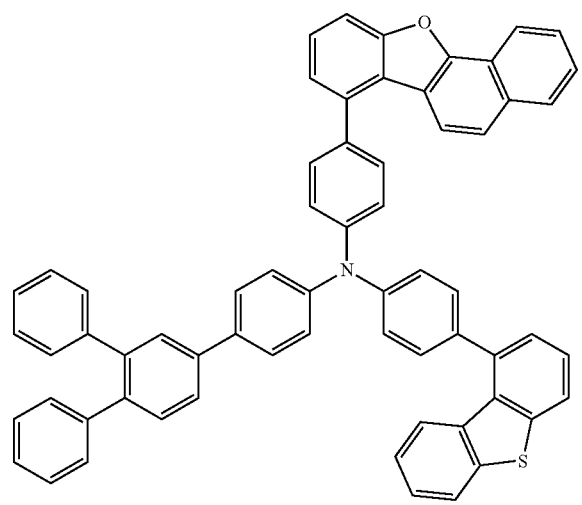
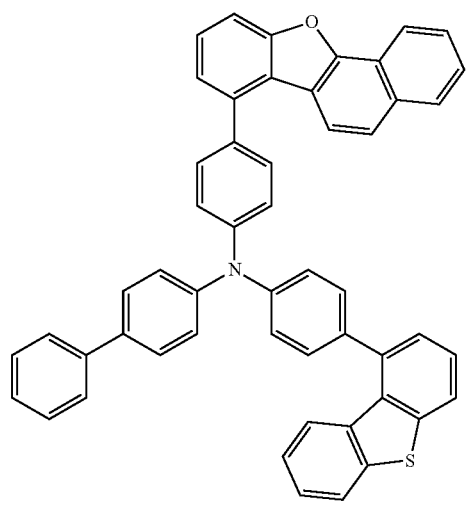
490
-continued
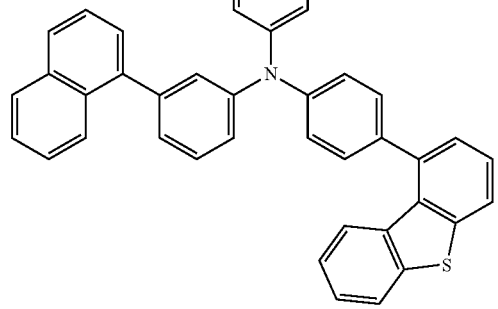
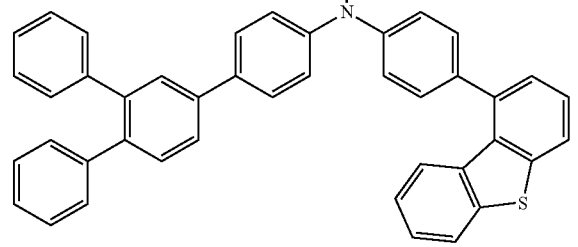
[Chem. 183]
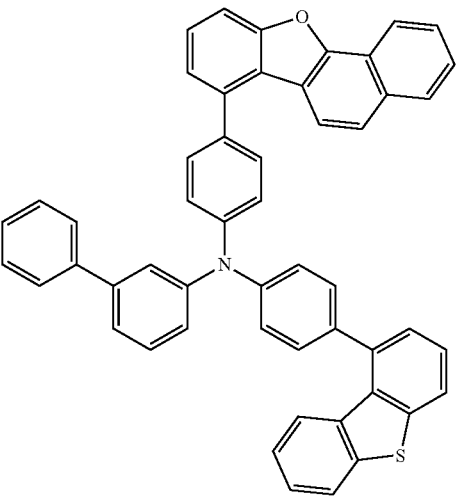

491
-continued
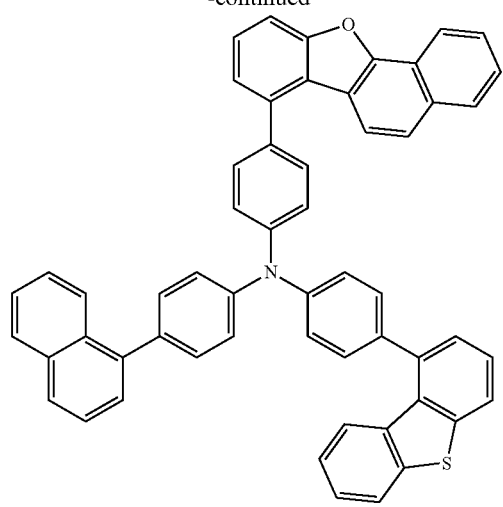
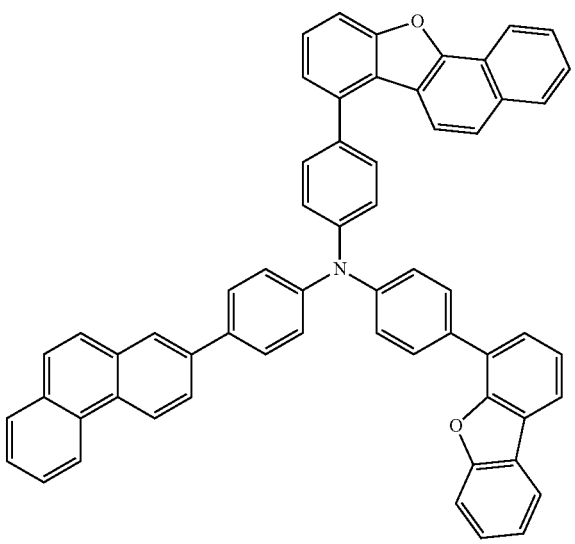
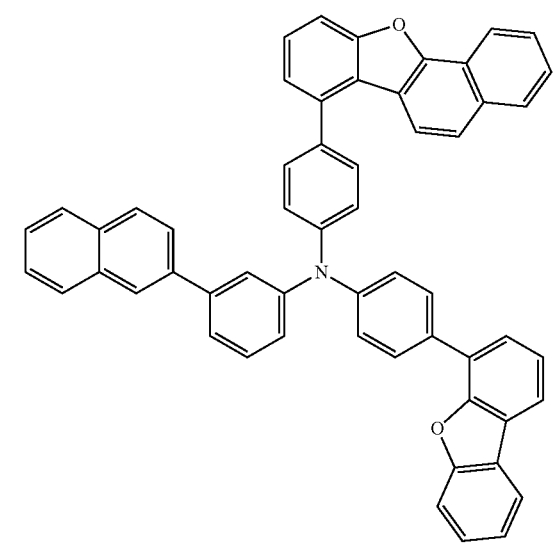
492
-continued
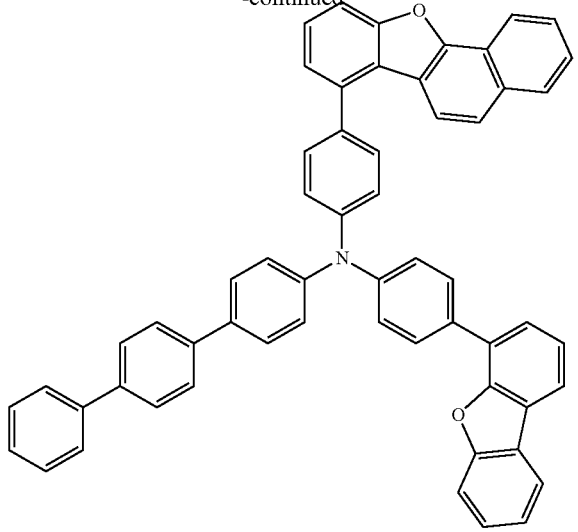
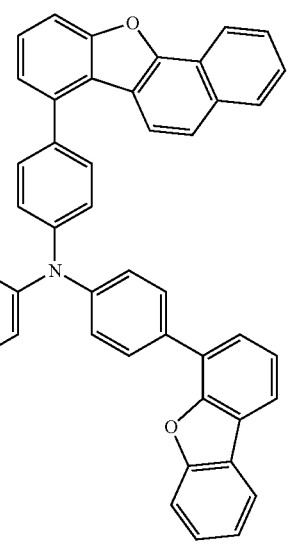

493
-continued
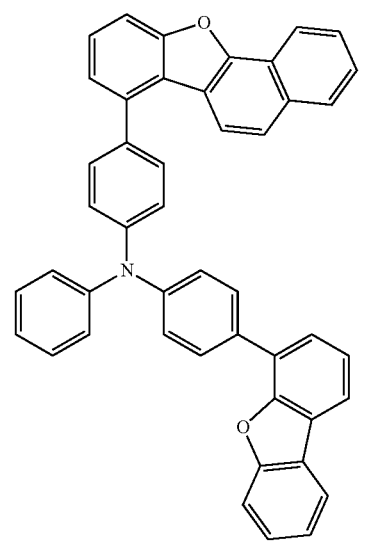
[Chem. 184]
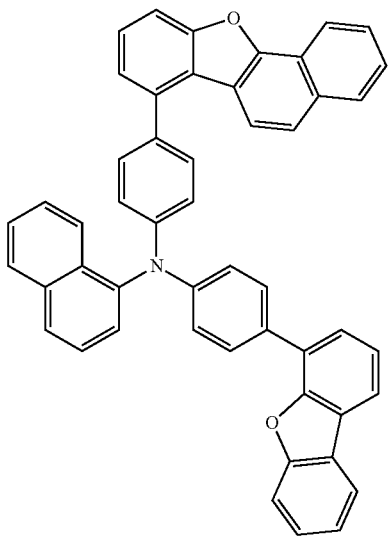
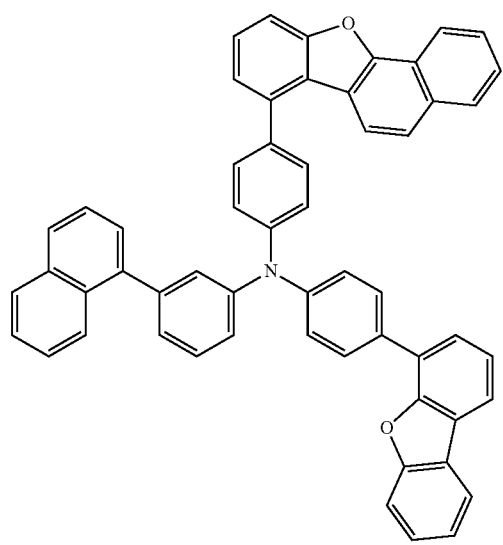
494
-continued
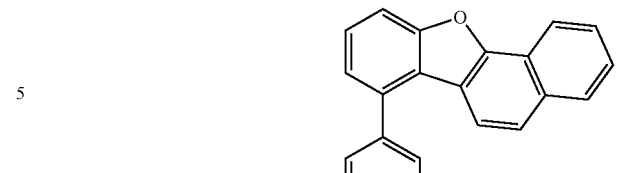
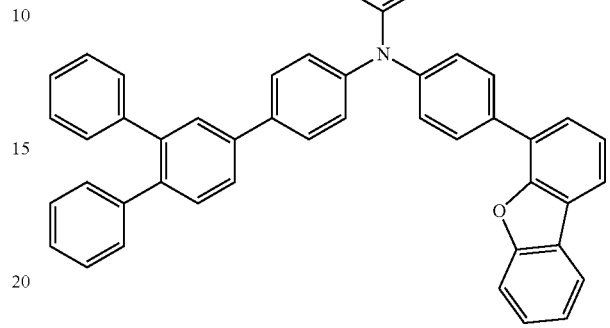
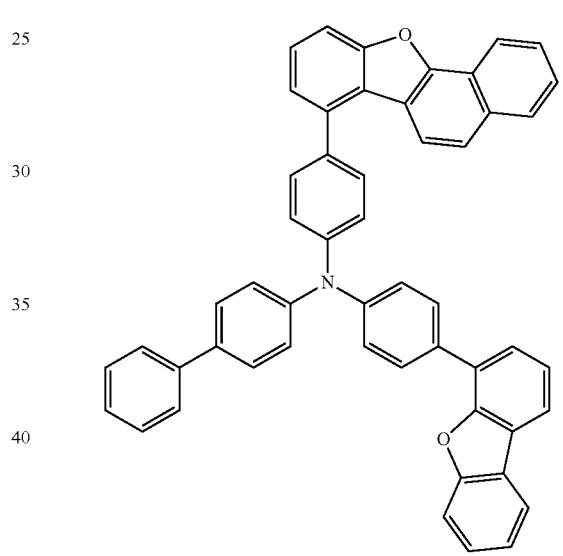
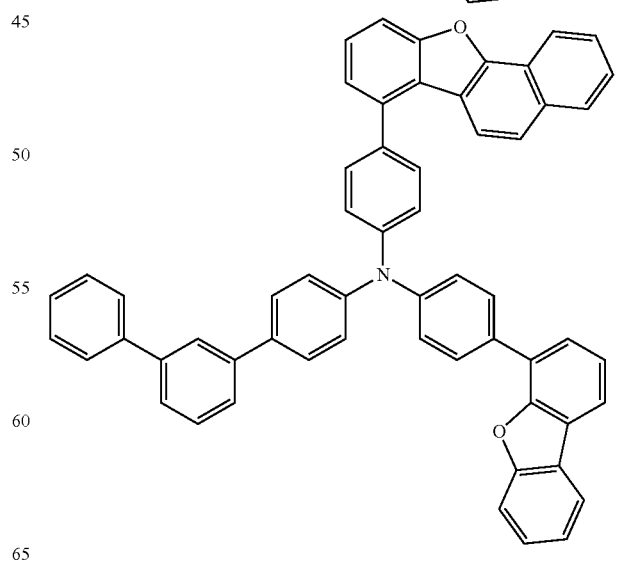

-continued
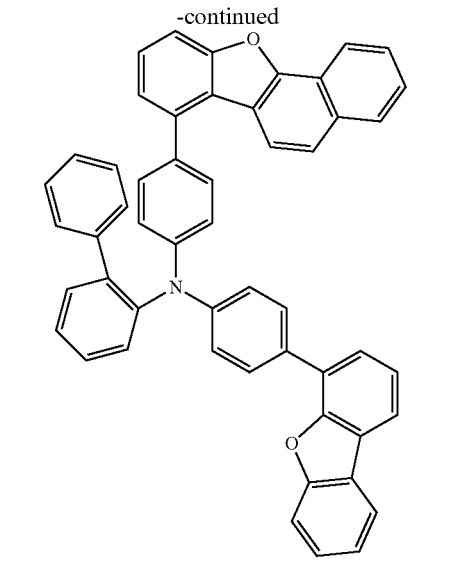
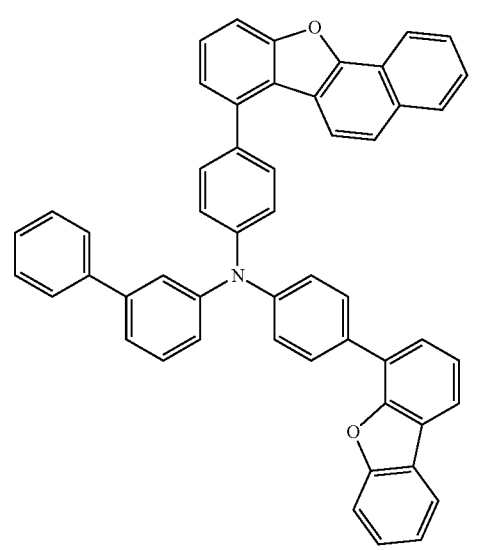
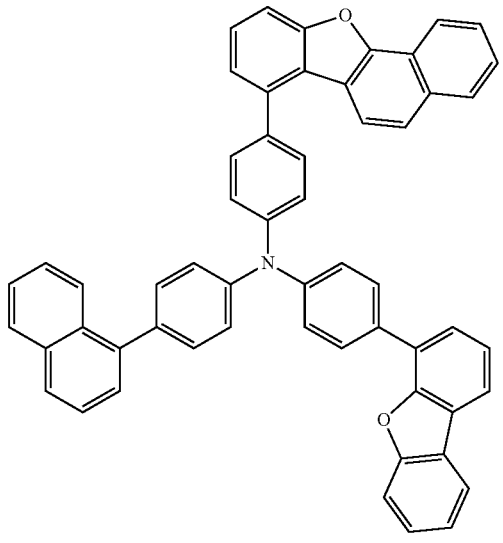
-continued
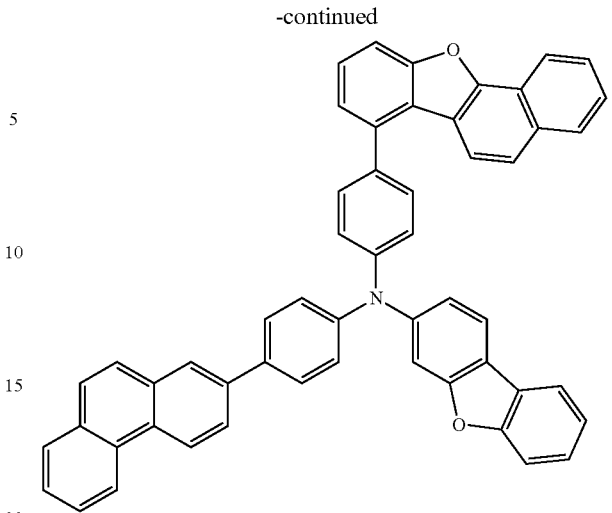
[Chem. 185]
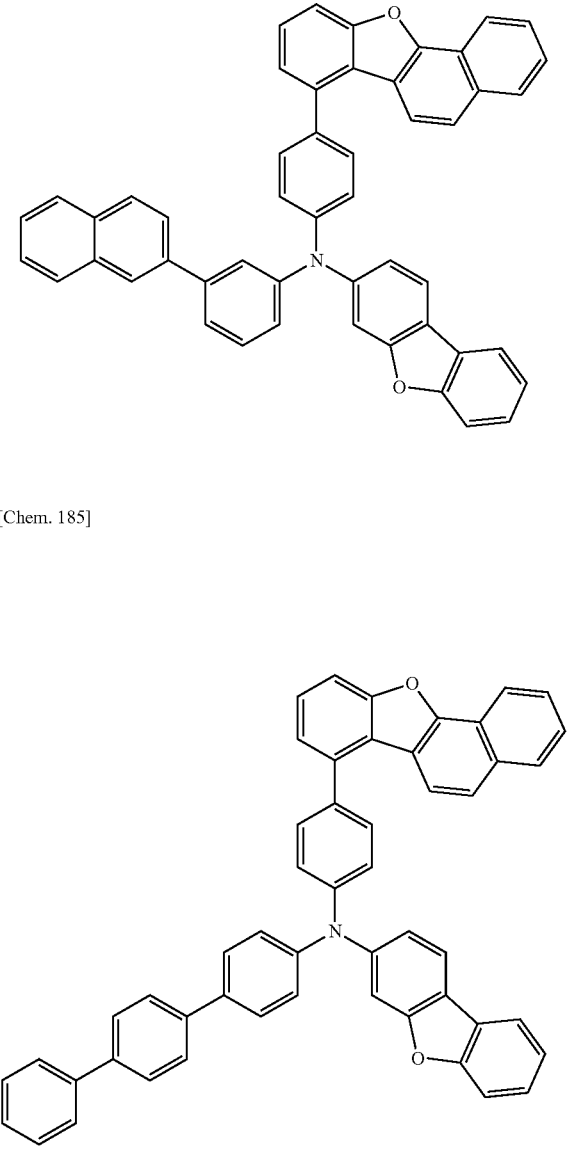

497
-continued
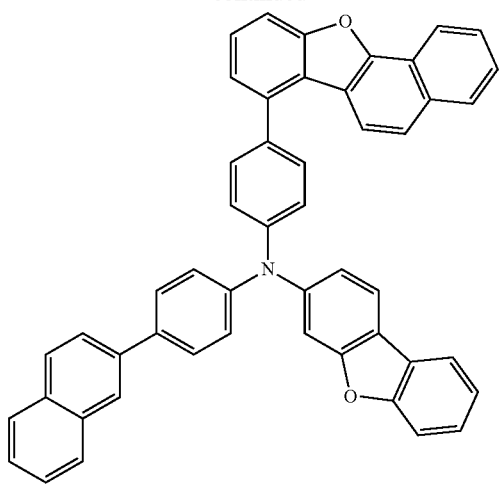
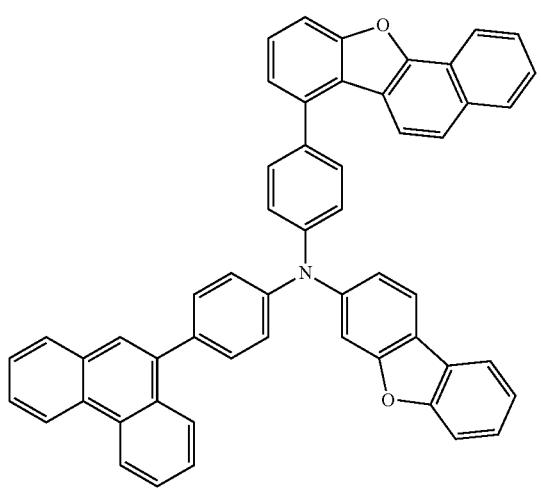
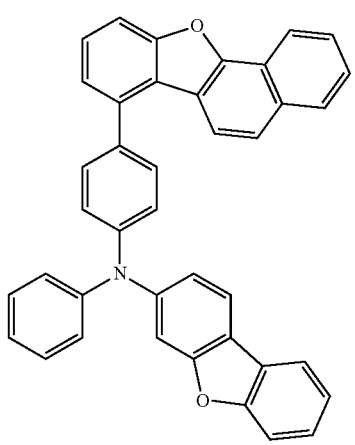
498
-continued
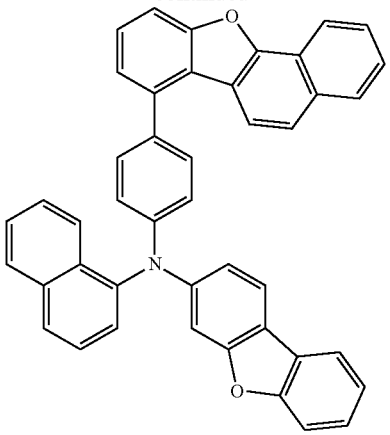
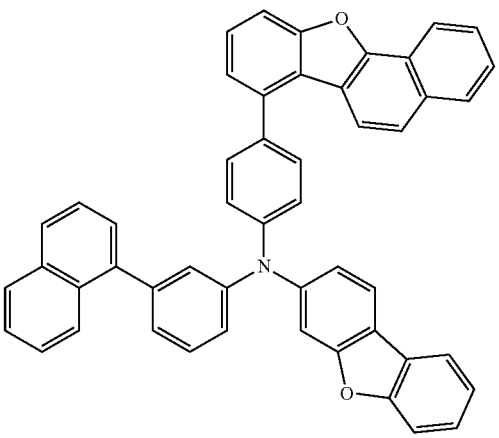
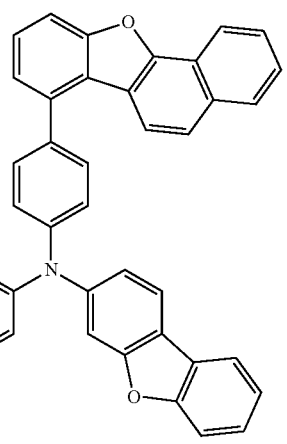

499
-continued
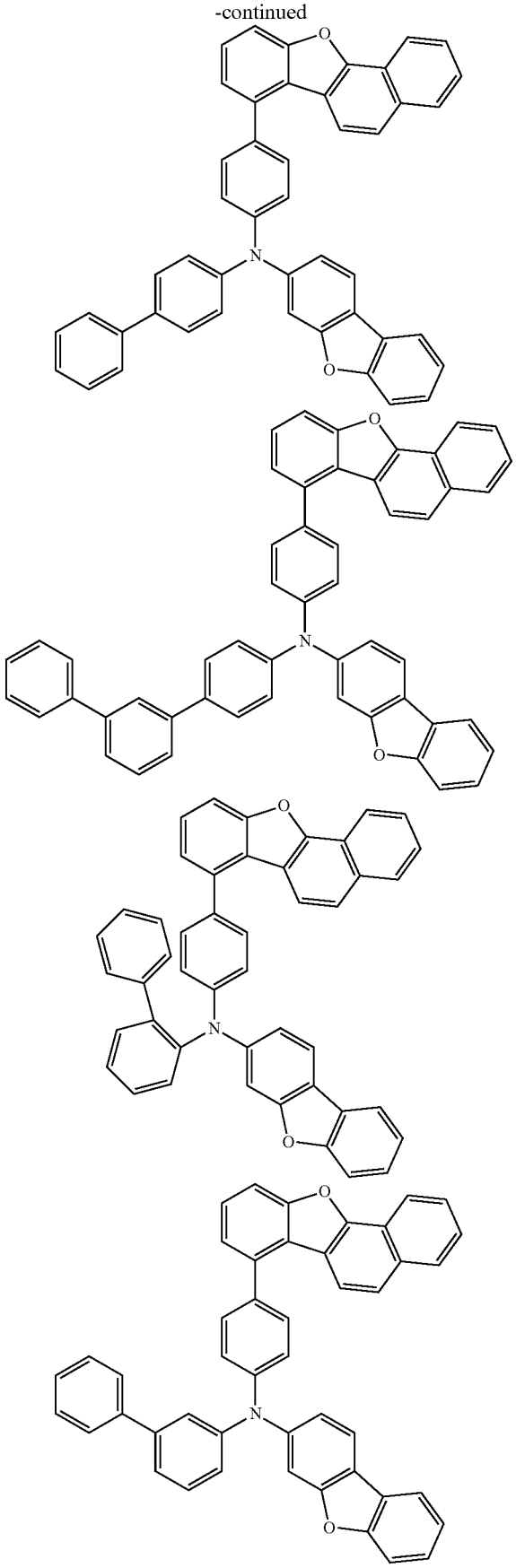
500
-continued
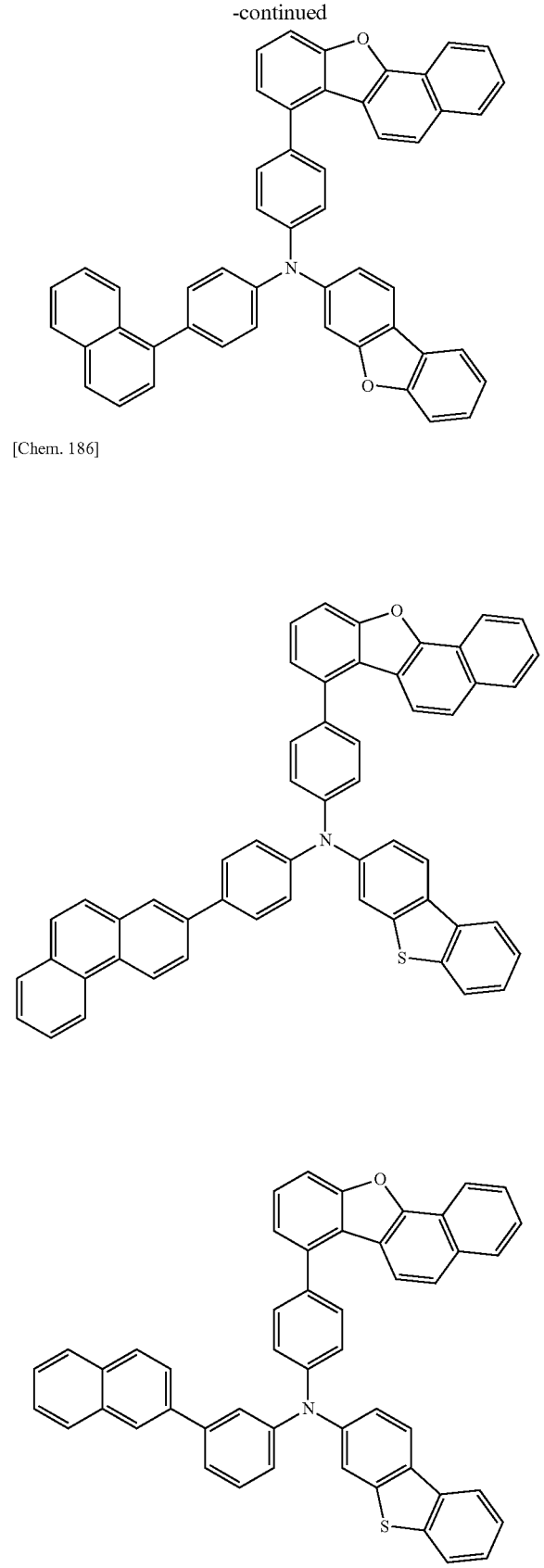
[Chem. 186]

501
-continued
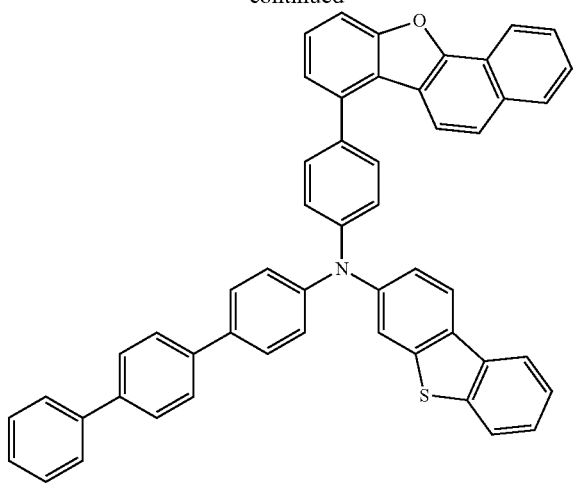
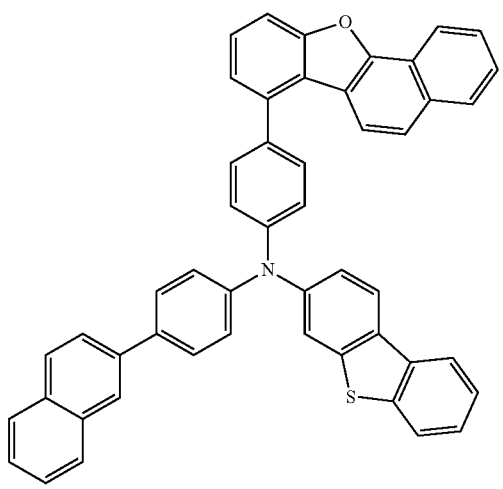
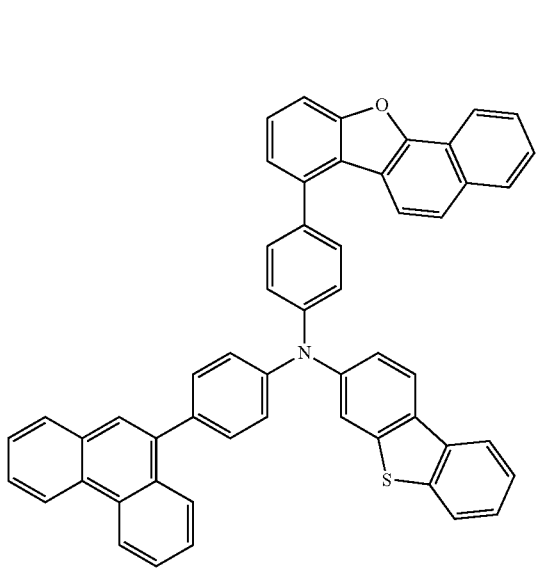
502
-continued
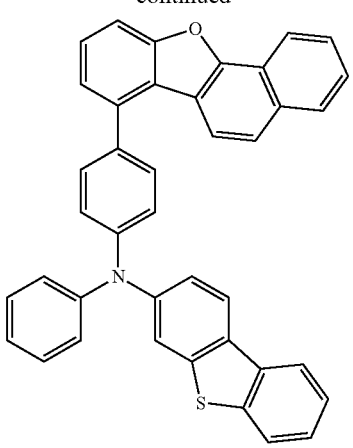
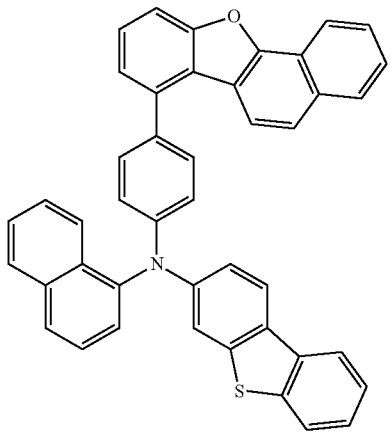
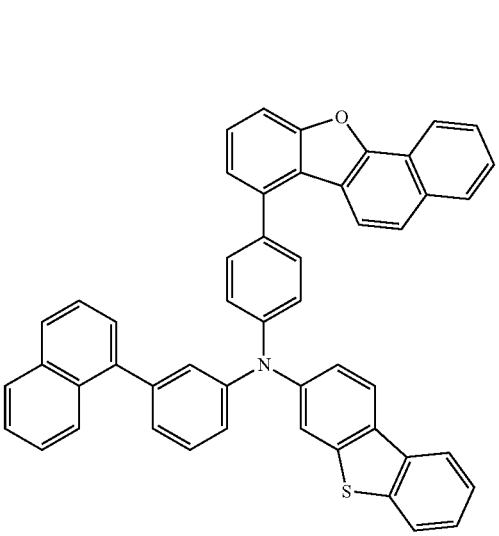

503
-continued
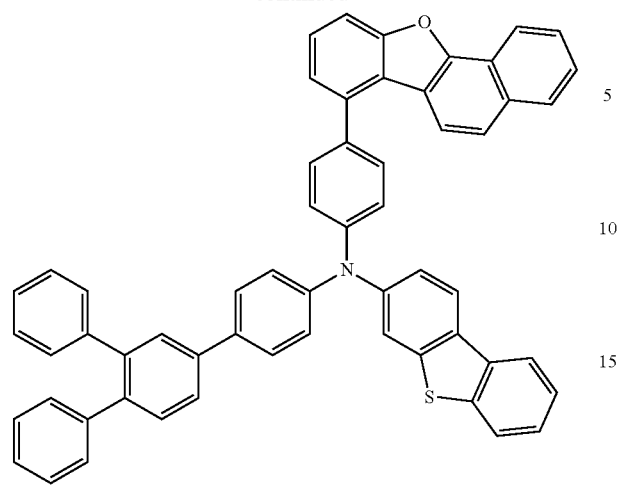
[Chem. 187]
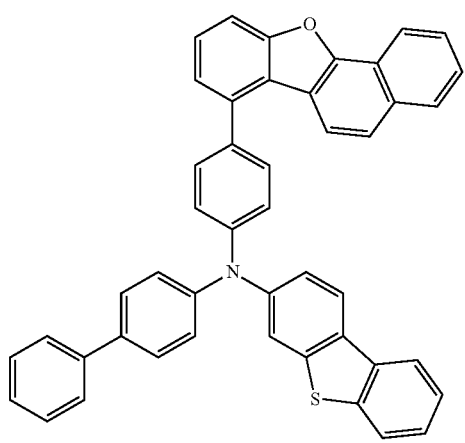
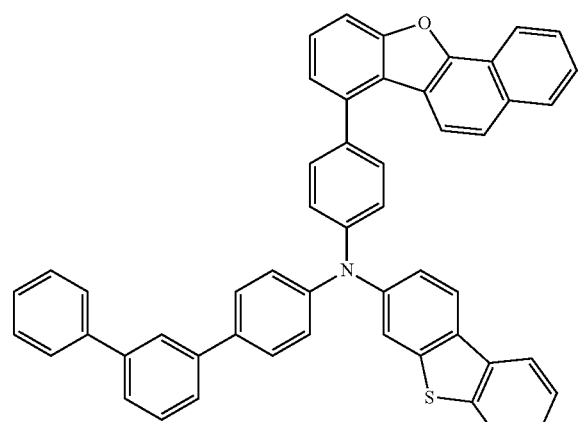
504
-continued
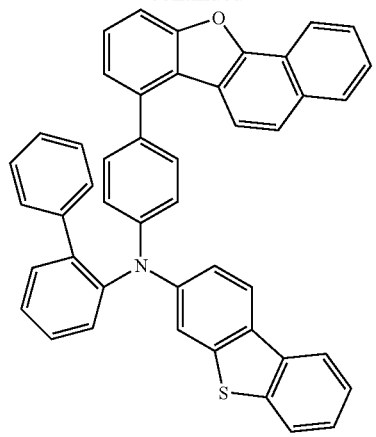
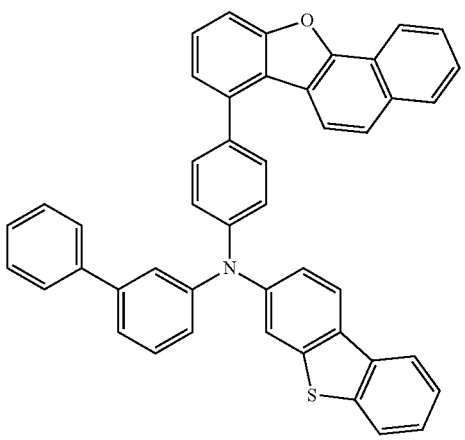
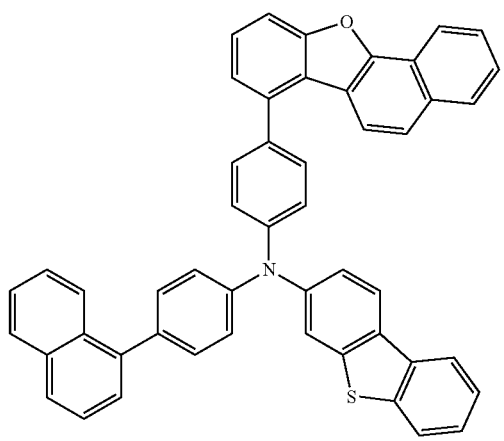

505
-continued
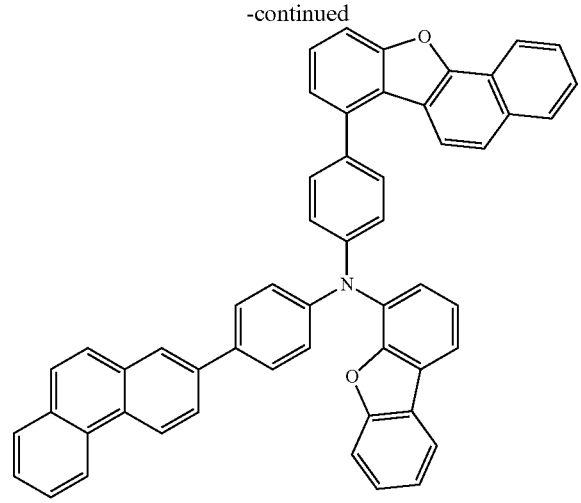
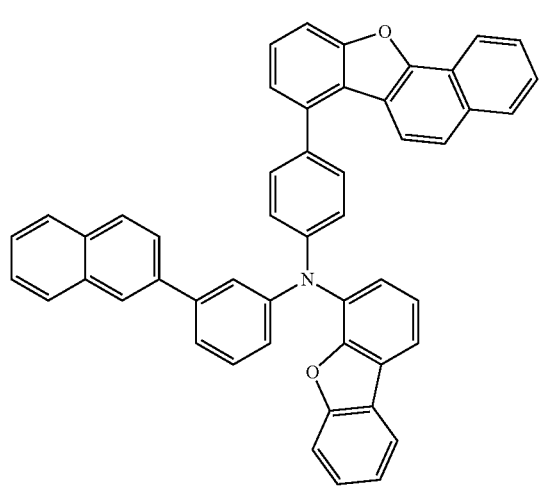
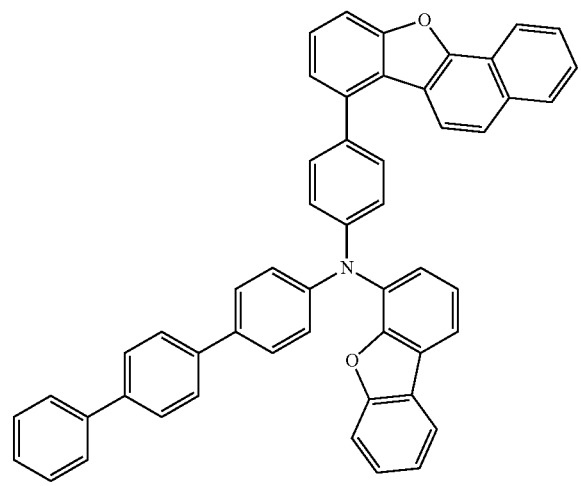
506
-continued
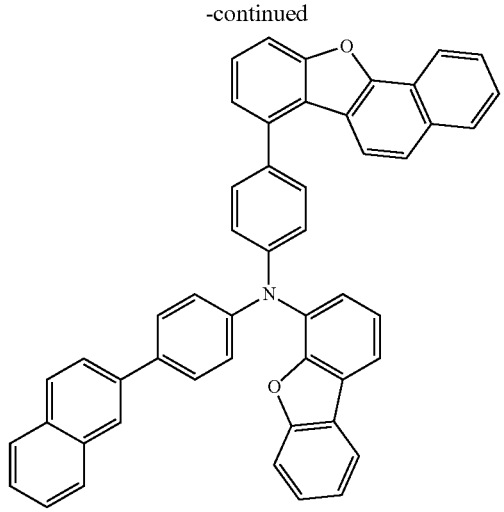
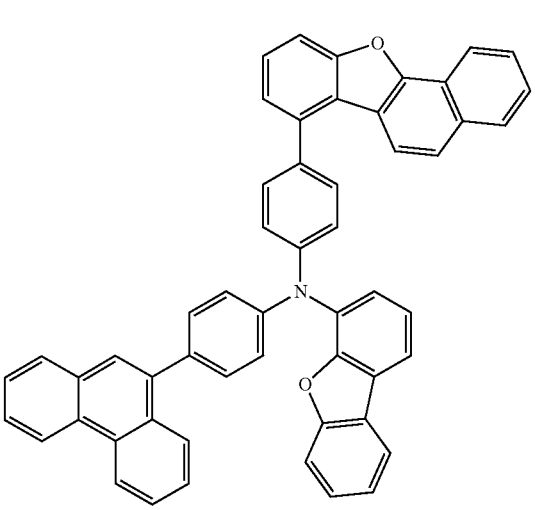
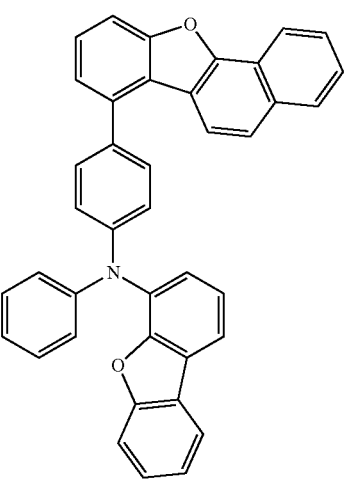

507
-continued
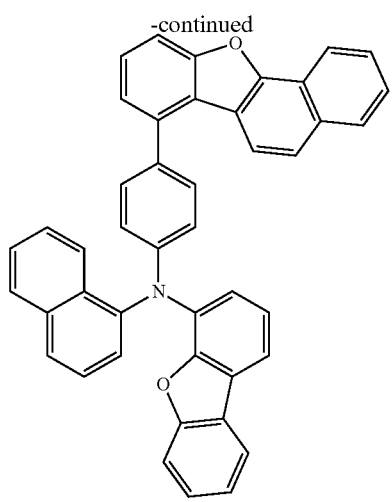
508
-continued
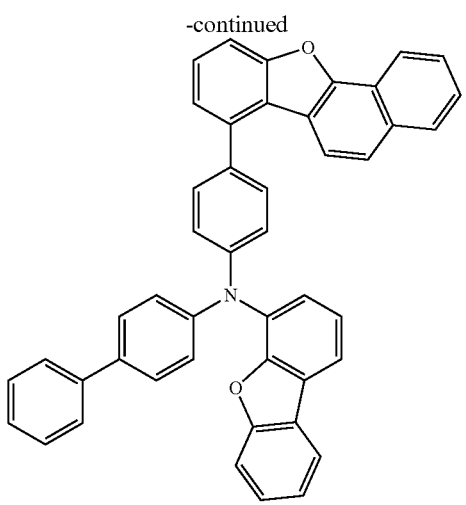
[Chem. 188]
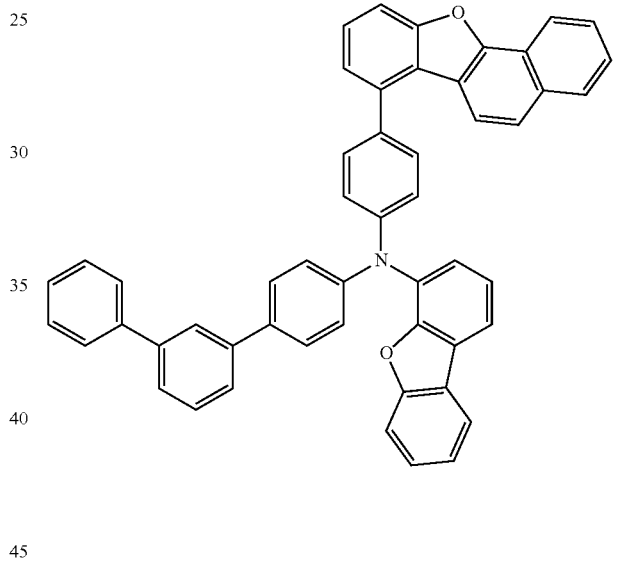
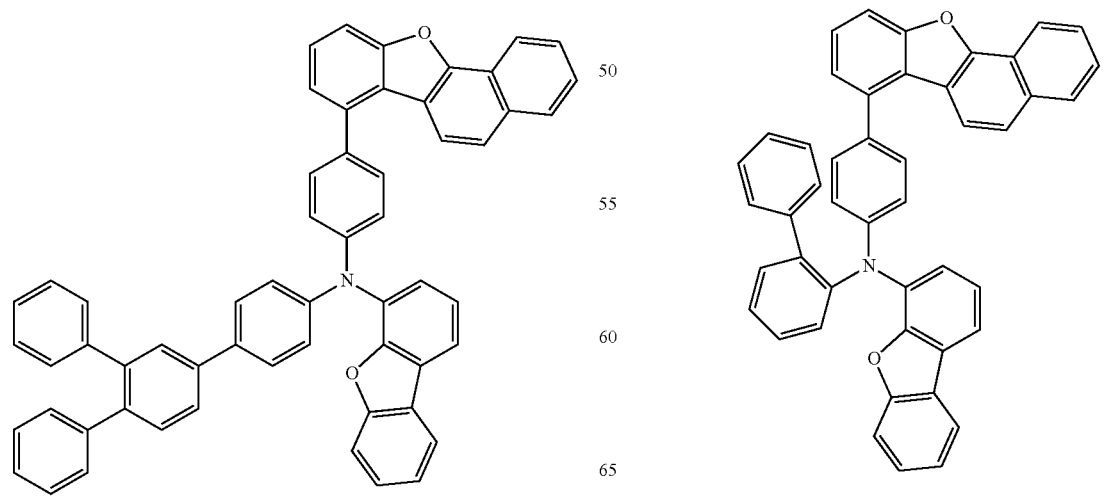

509
-continued
510
-continued
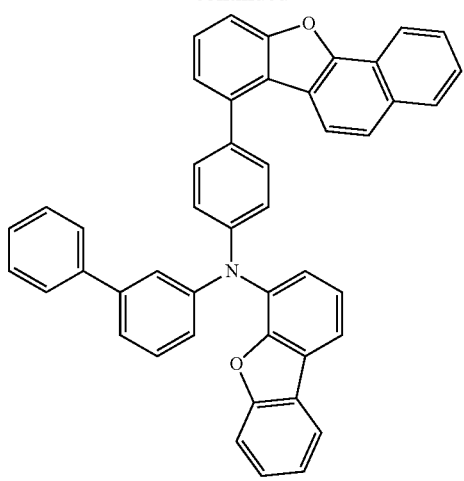
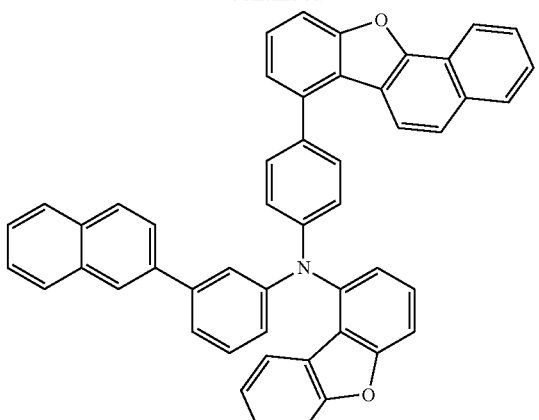
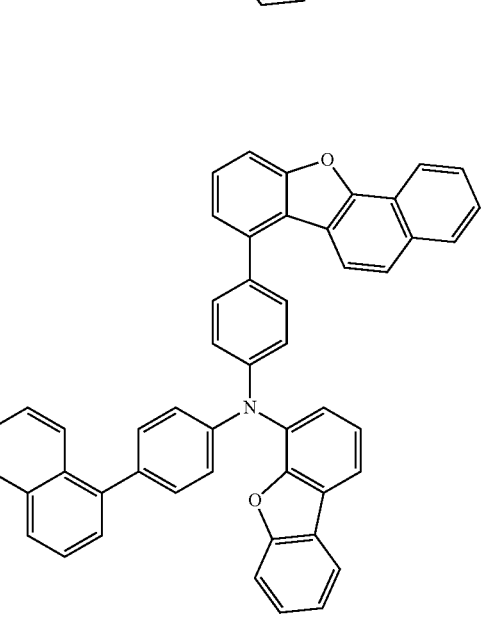
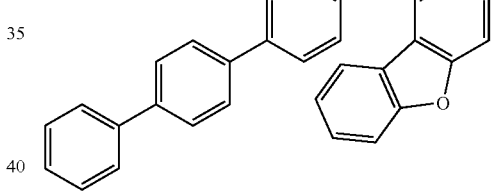
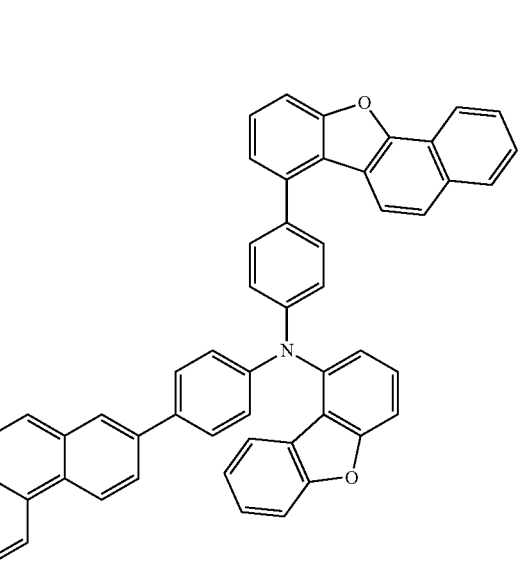
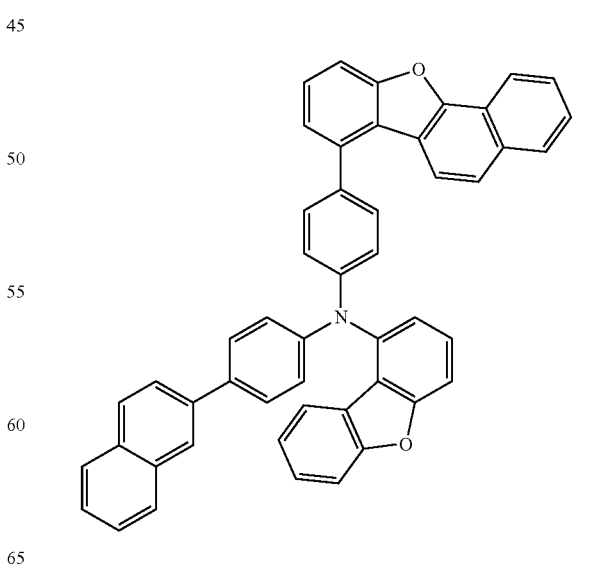

511
-continued
[Chem. 189]
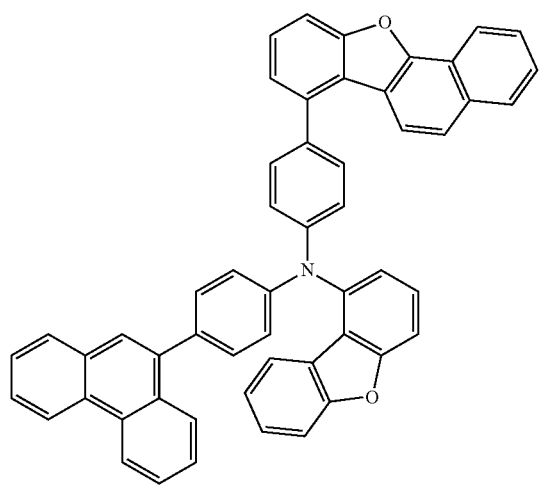
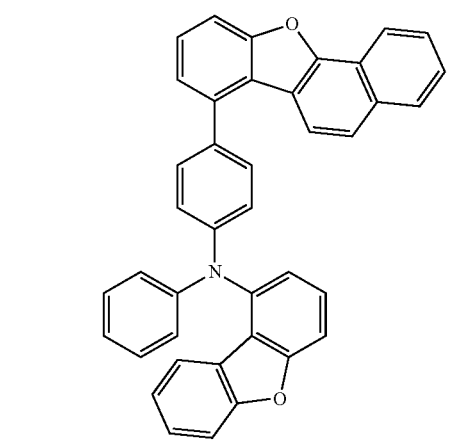
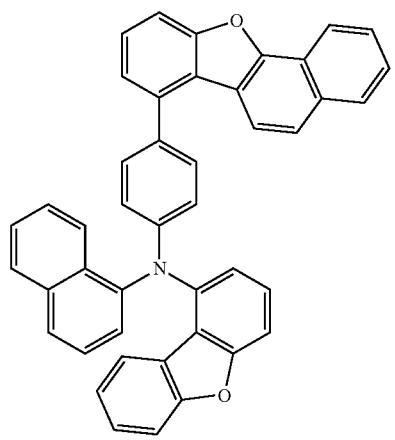
512
-continued
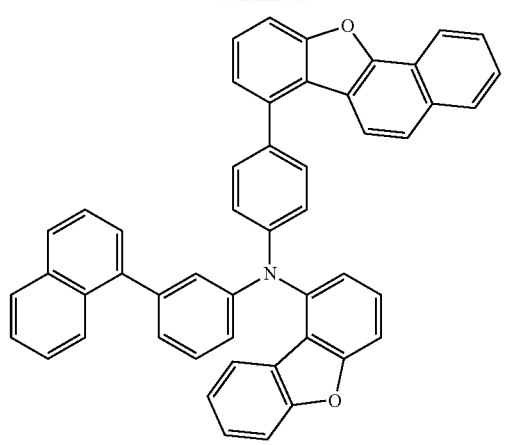
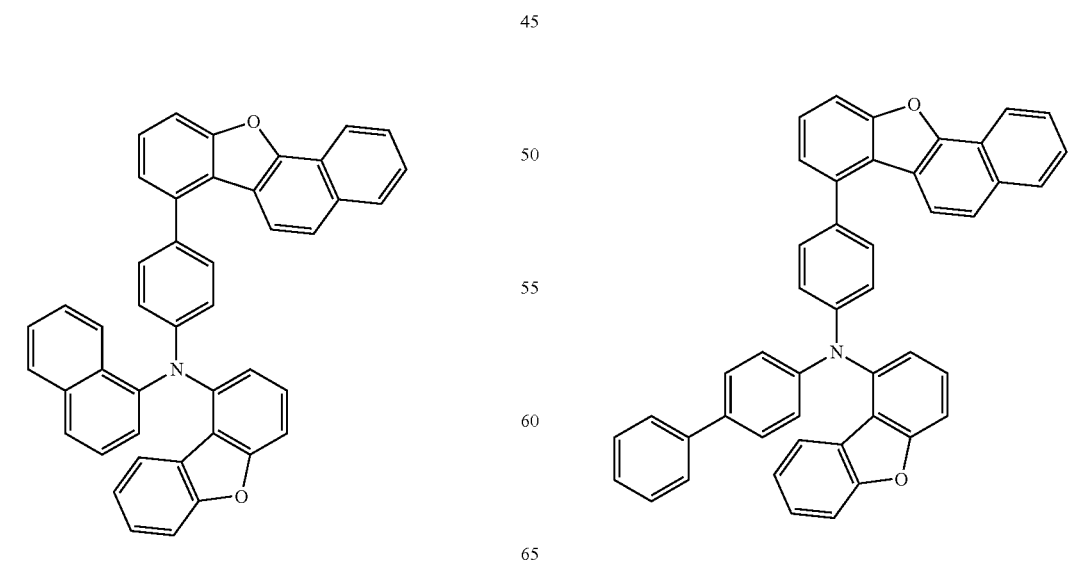

513
-continued
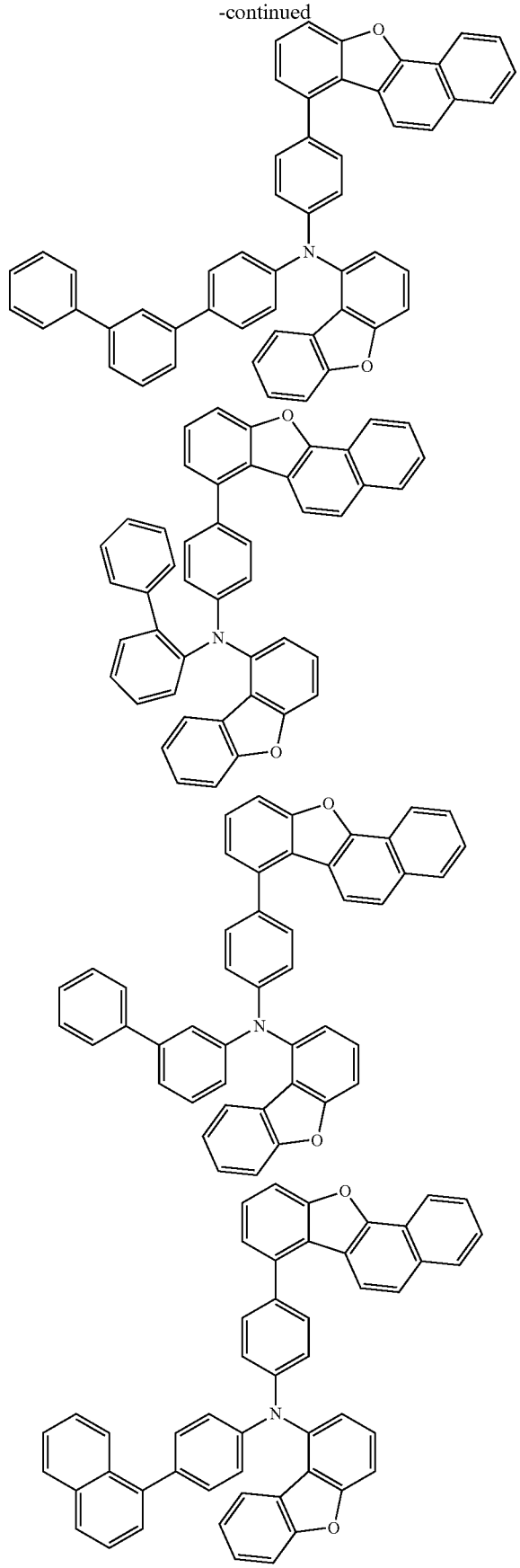
514
-continued
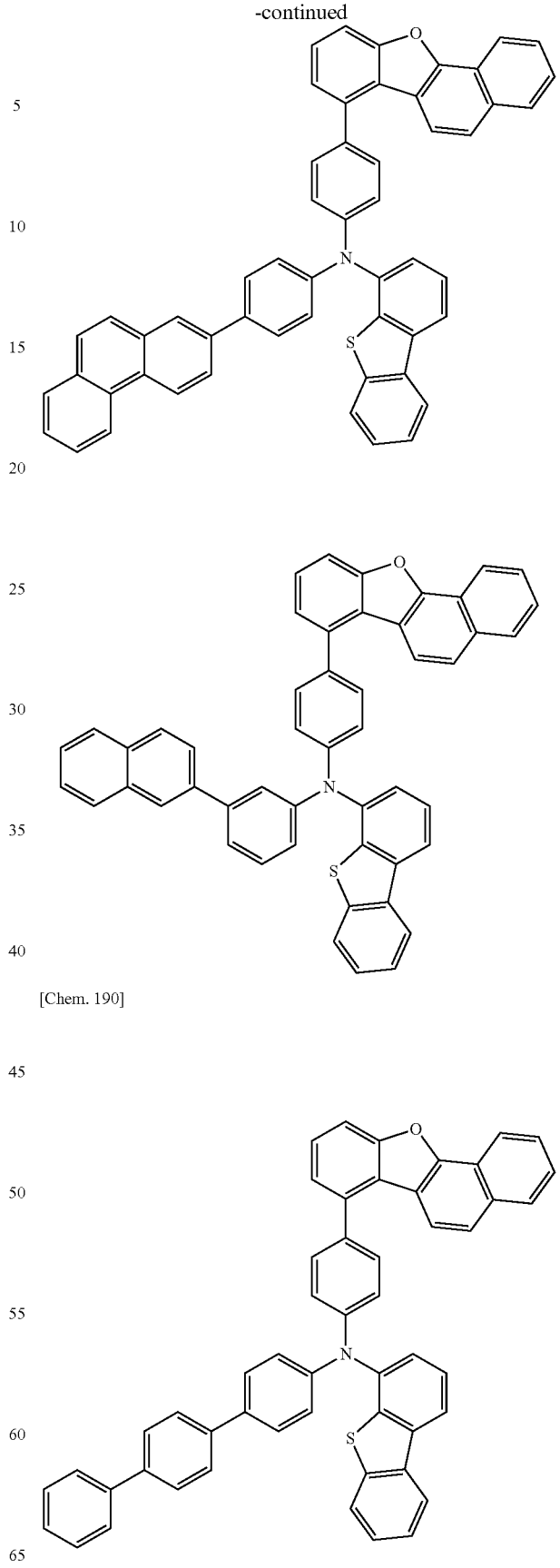
[Chem. 190]

515
-continued
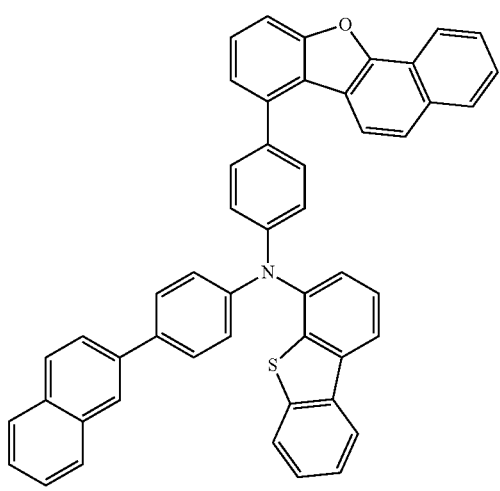
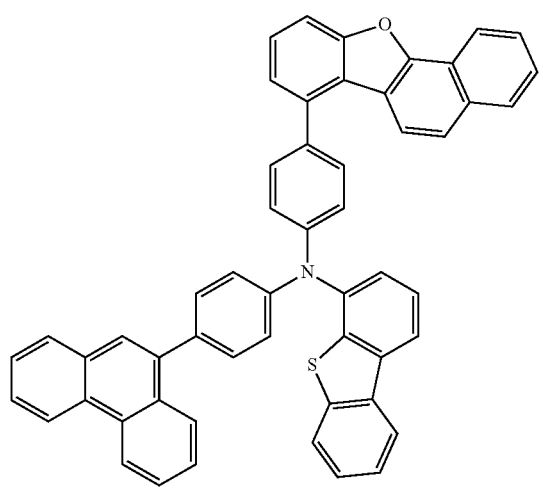
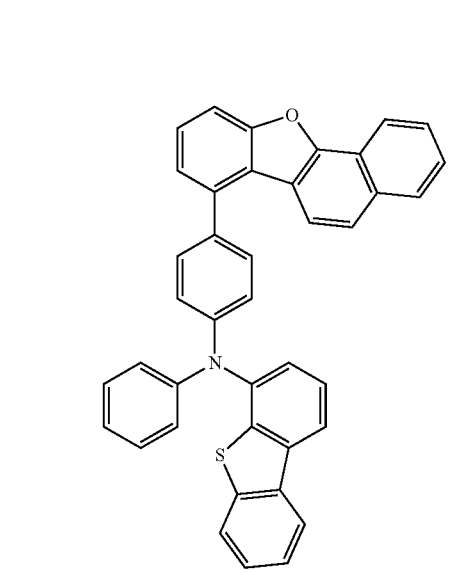
516
-continued
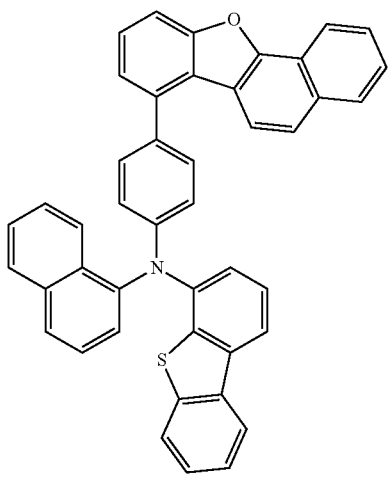
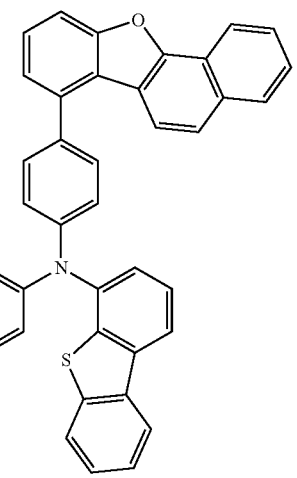

517
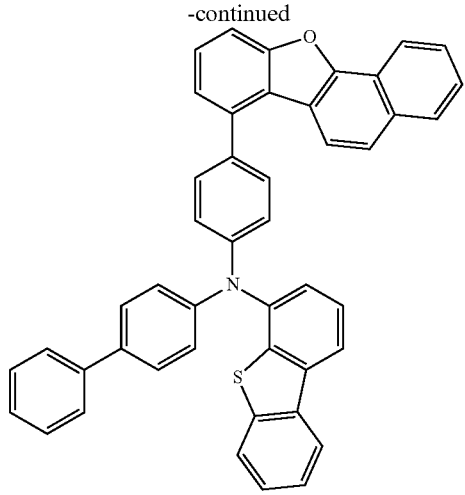
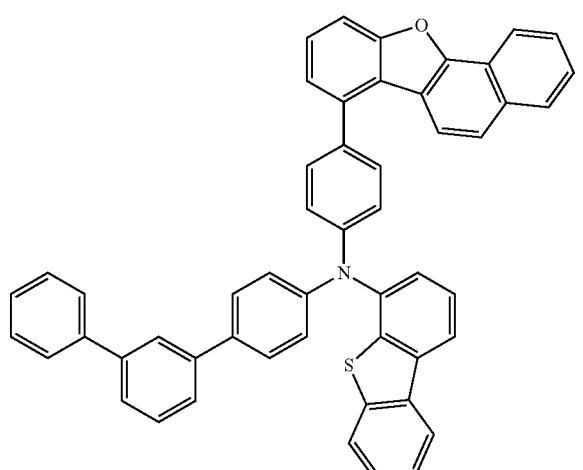
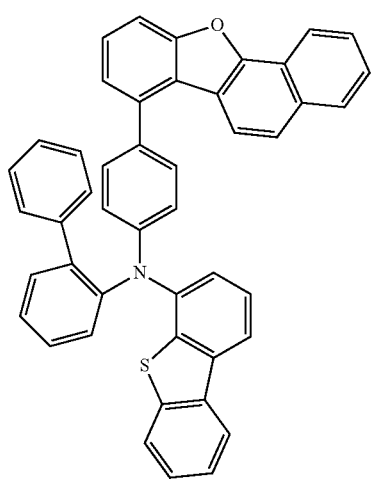
518
[Chem. 191]
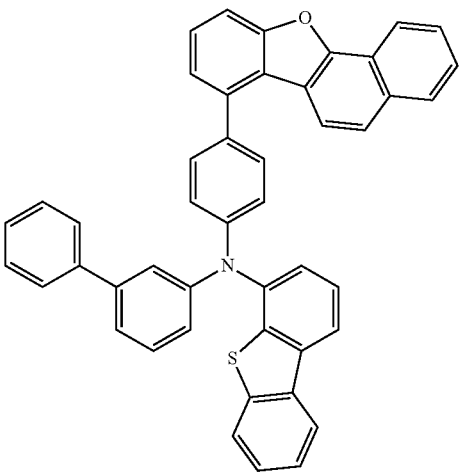
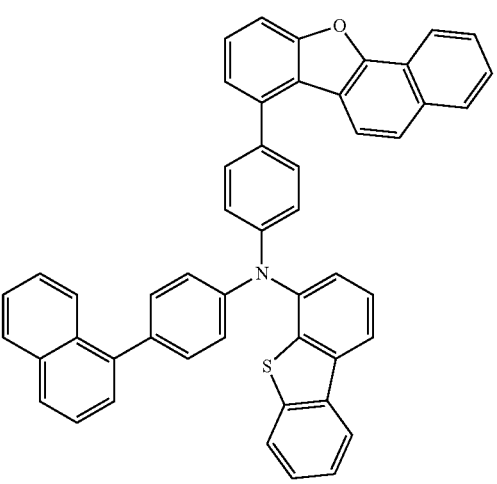
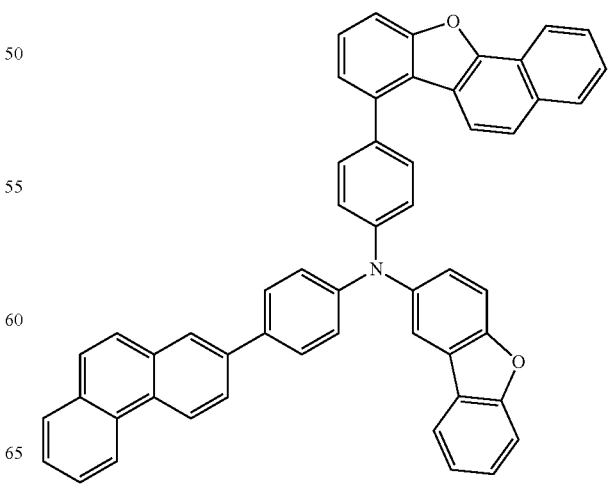

519
-continued
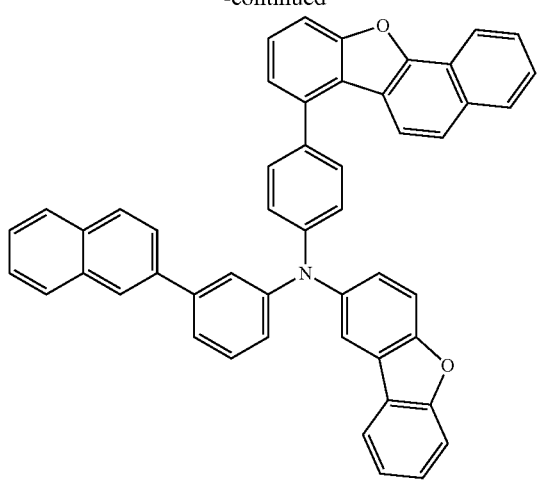
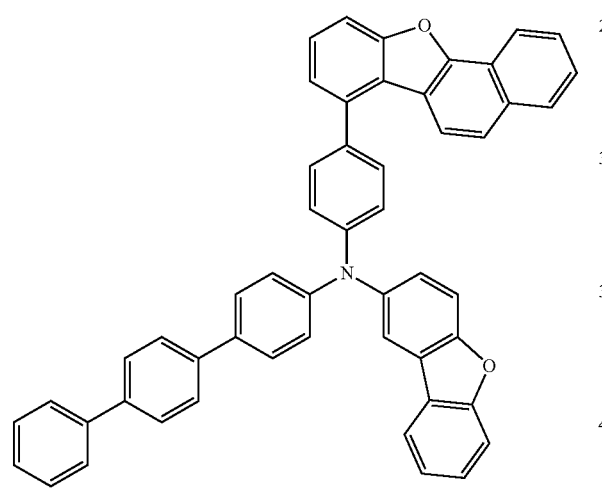
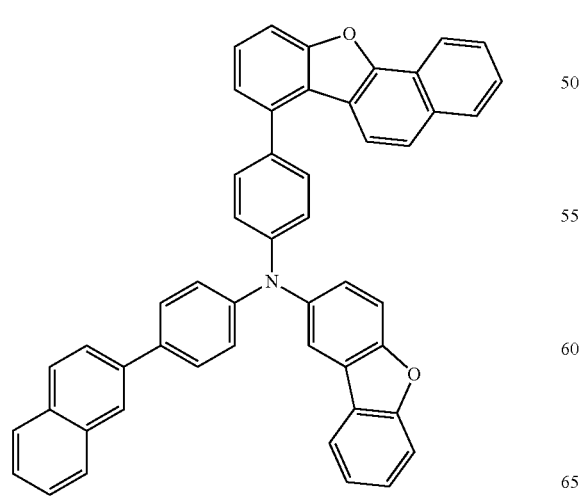
520
-continued
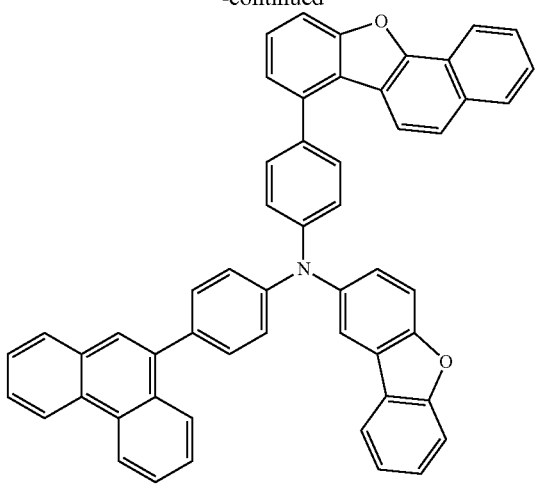
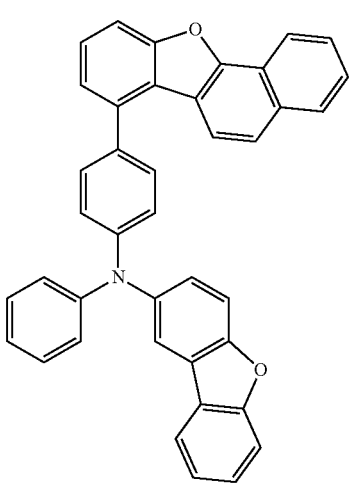
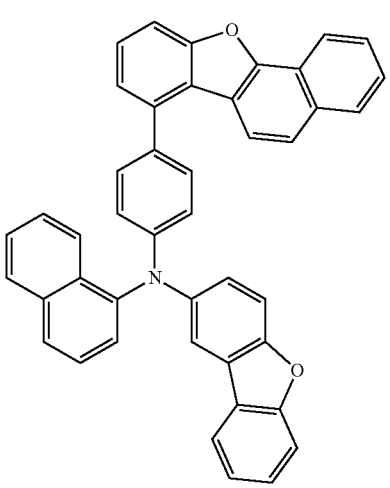

521
-continued
[Chem. 192]
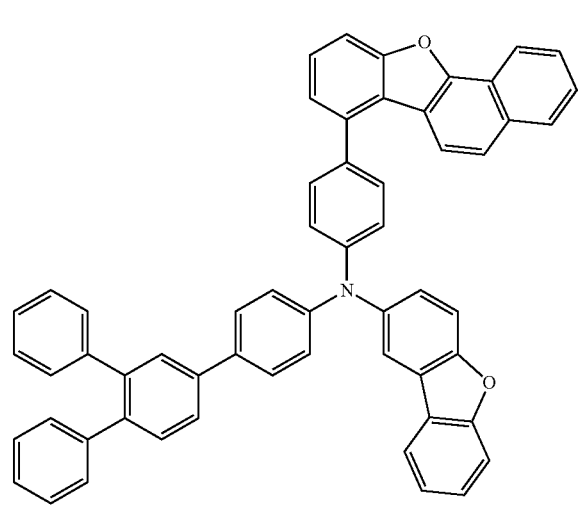
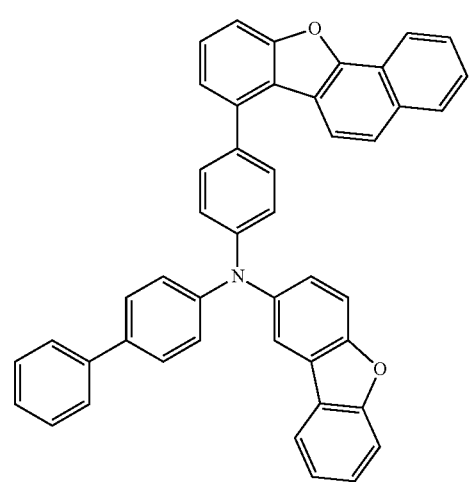
522
-continued
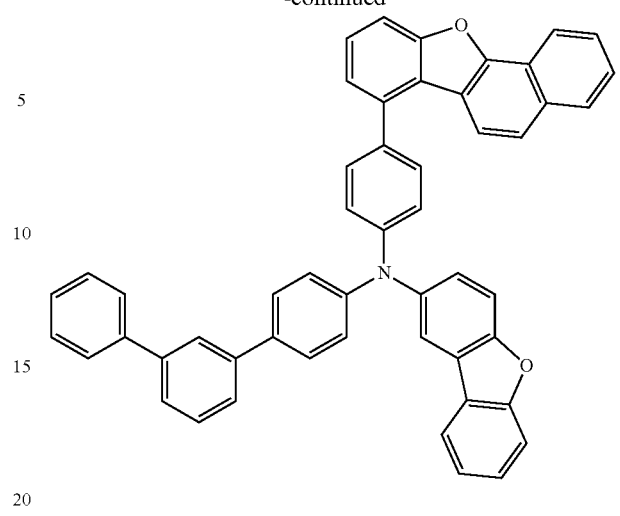
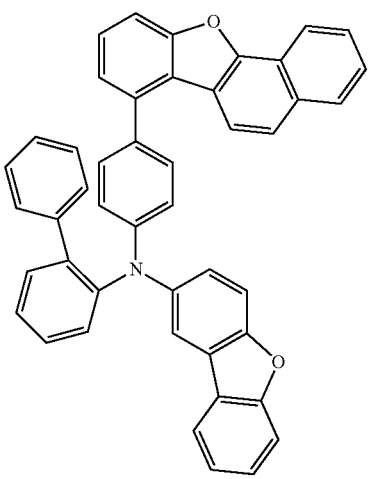
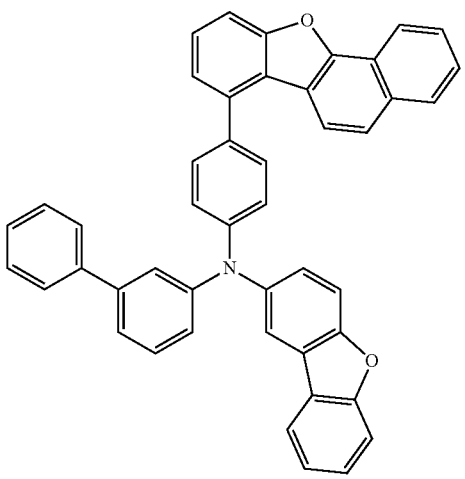

523
-continued
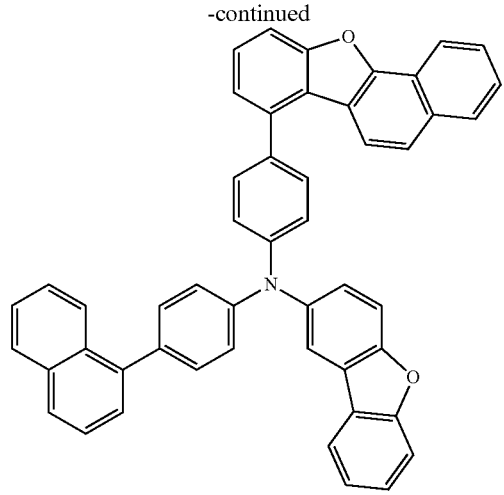
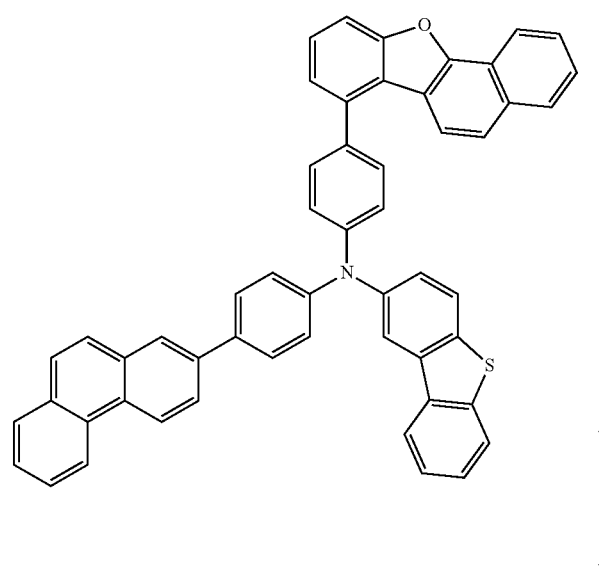
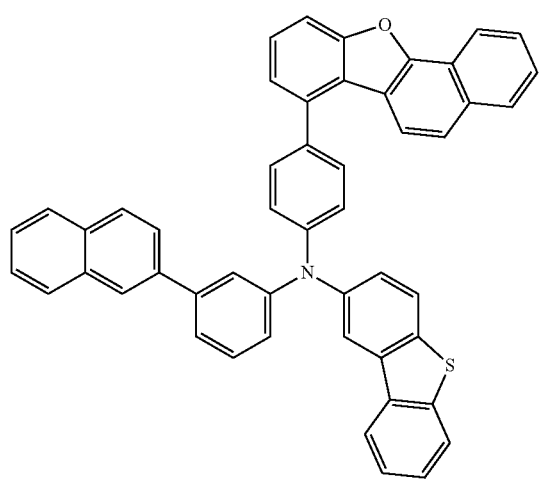
524
-continued
[Chem. 193]
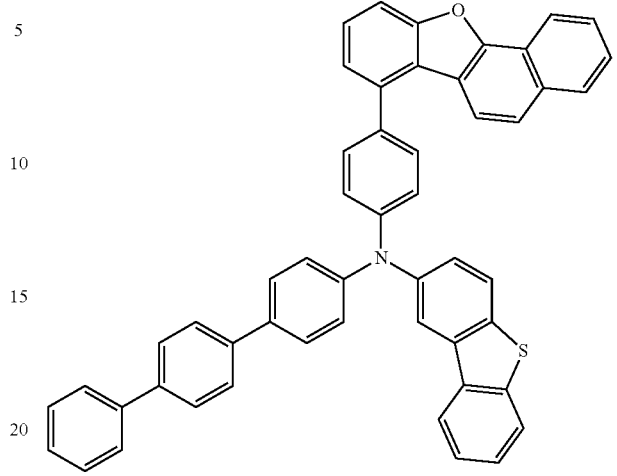
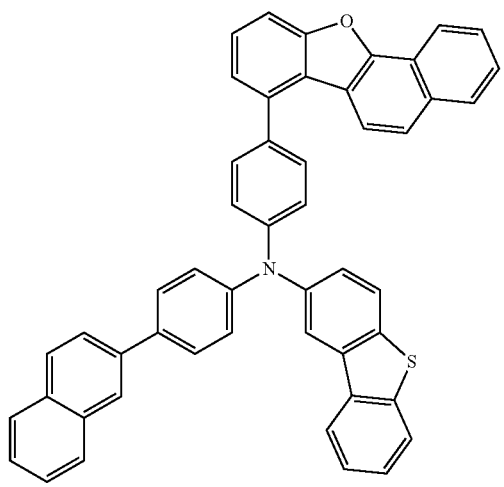
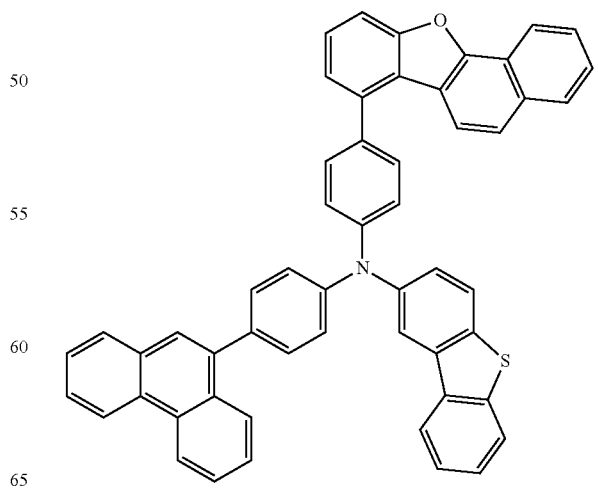

525
-continued
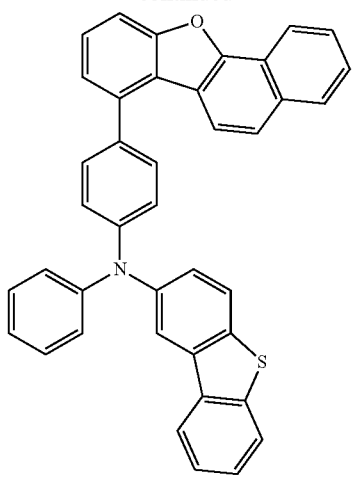
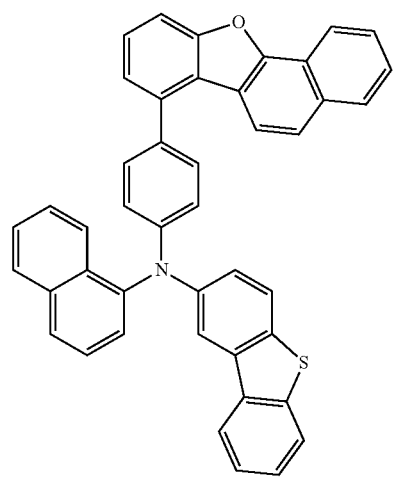
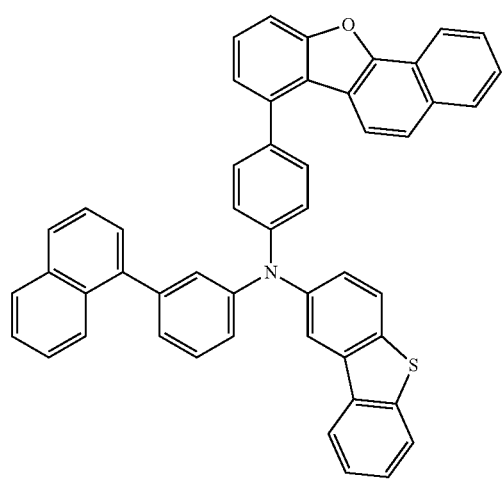
526
-continued
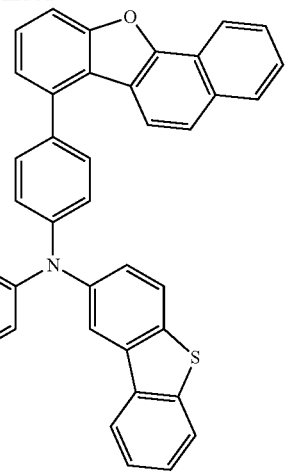
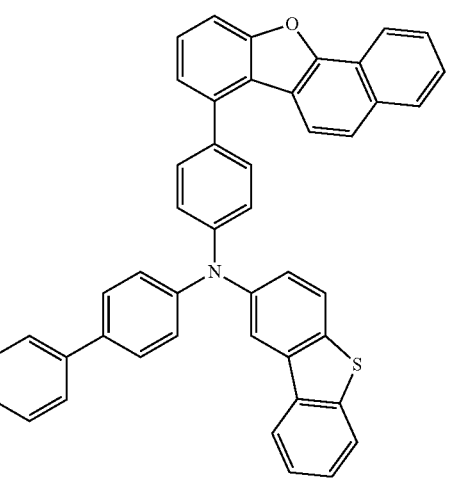
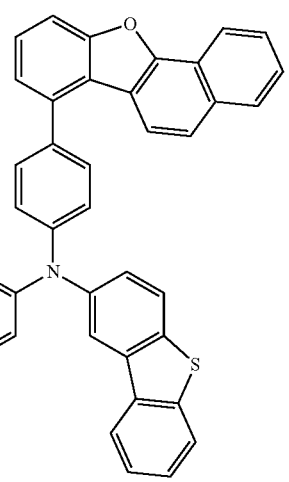

527
-continued
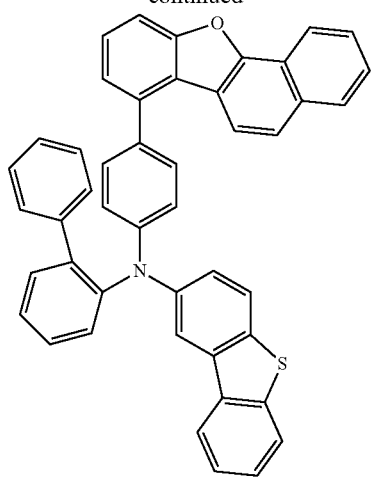
[Chem. 194]
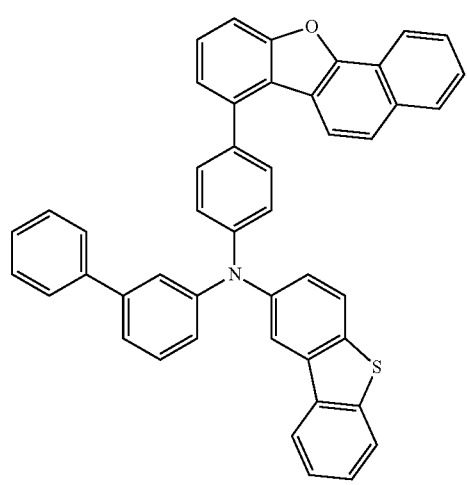
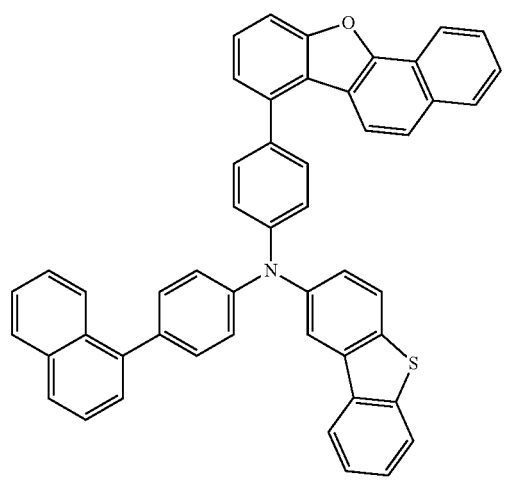
528
-continued
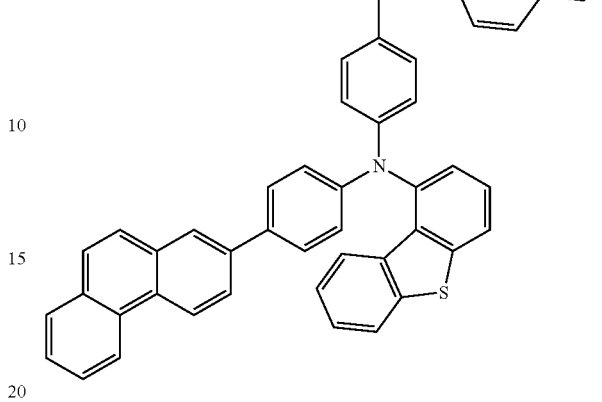
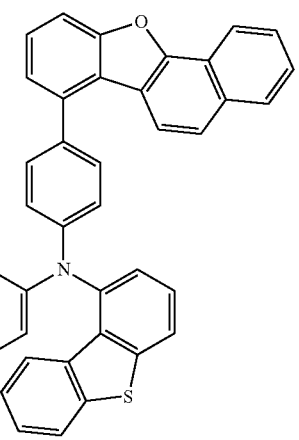
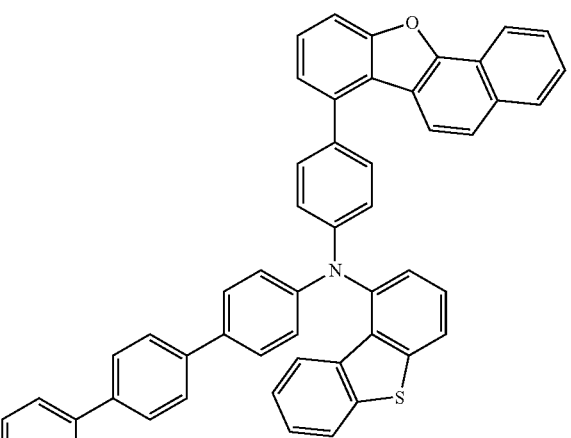

-continued
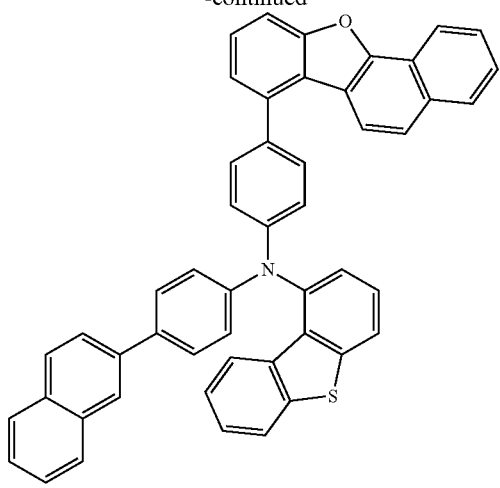
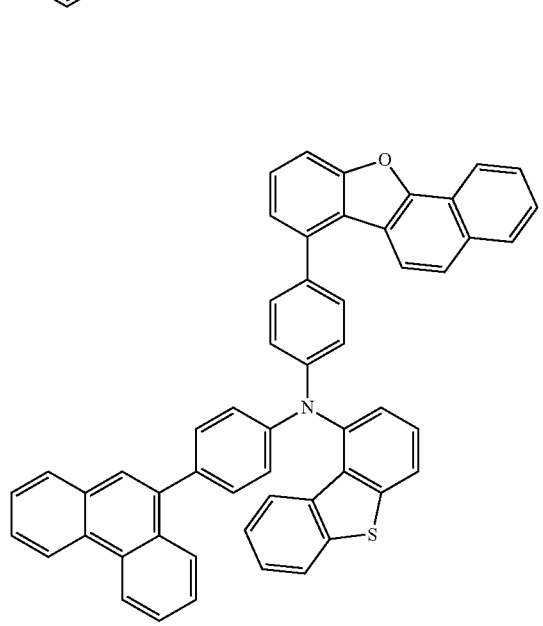
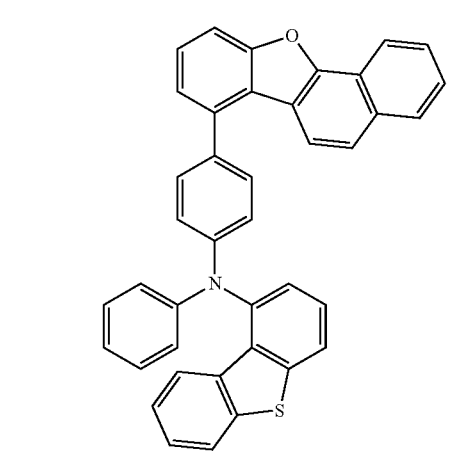
-continued
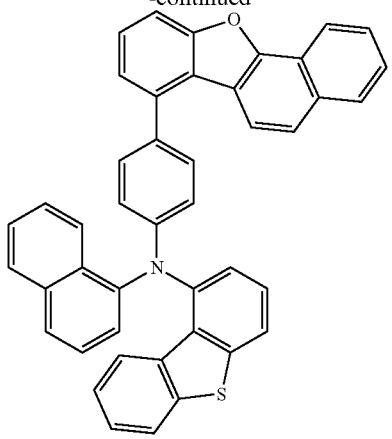
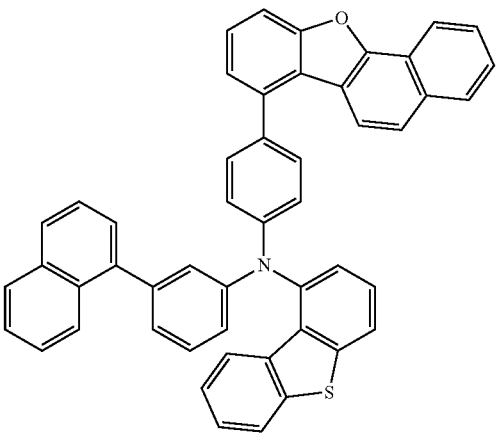
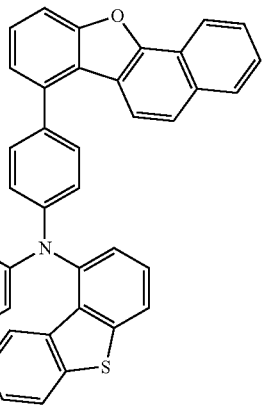

531
-continued
[Chem. 195]
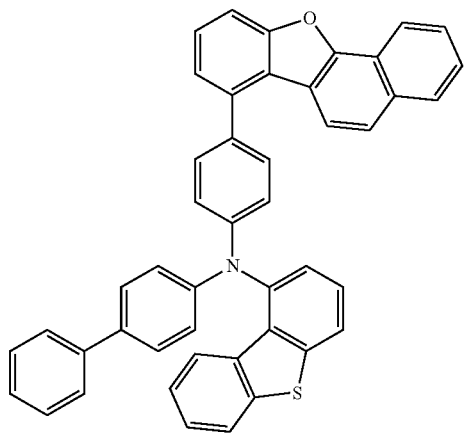
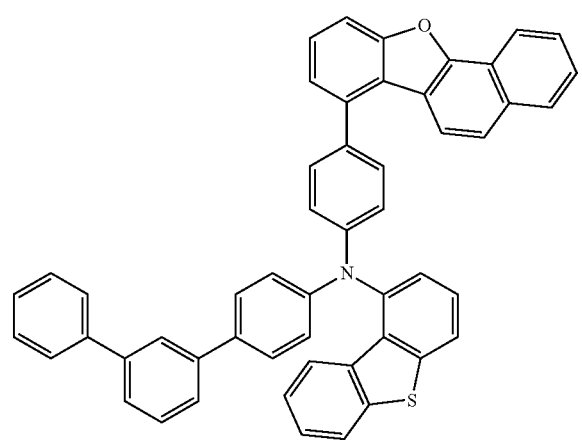
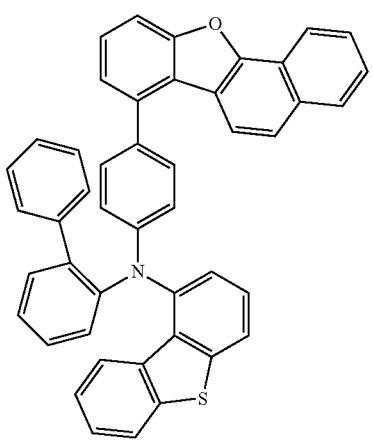
532
-continued
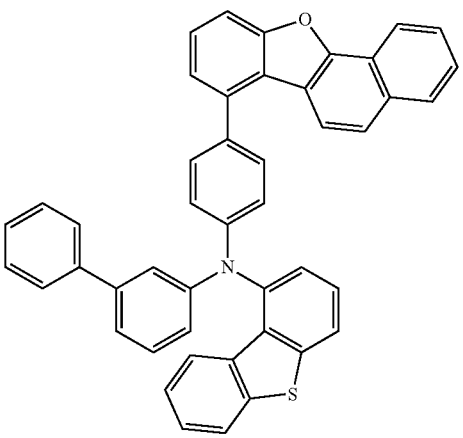
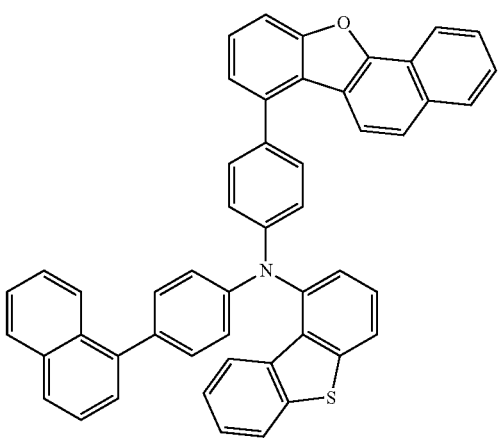
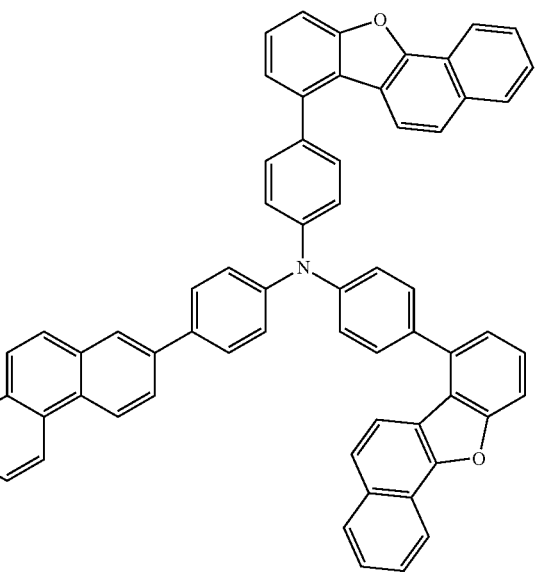

533
-continued
534
-continued
[Chem. 196]
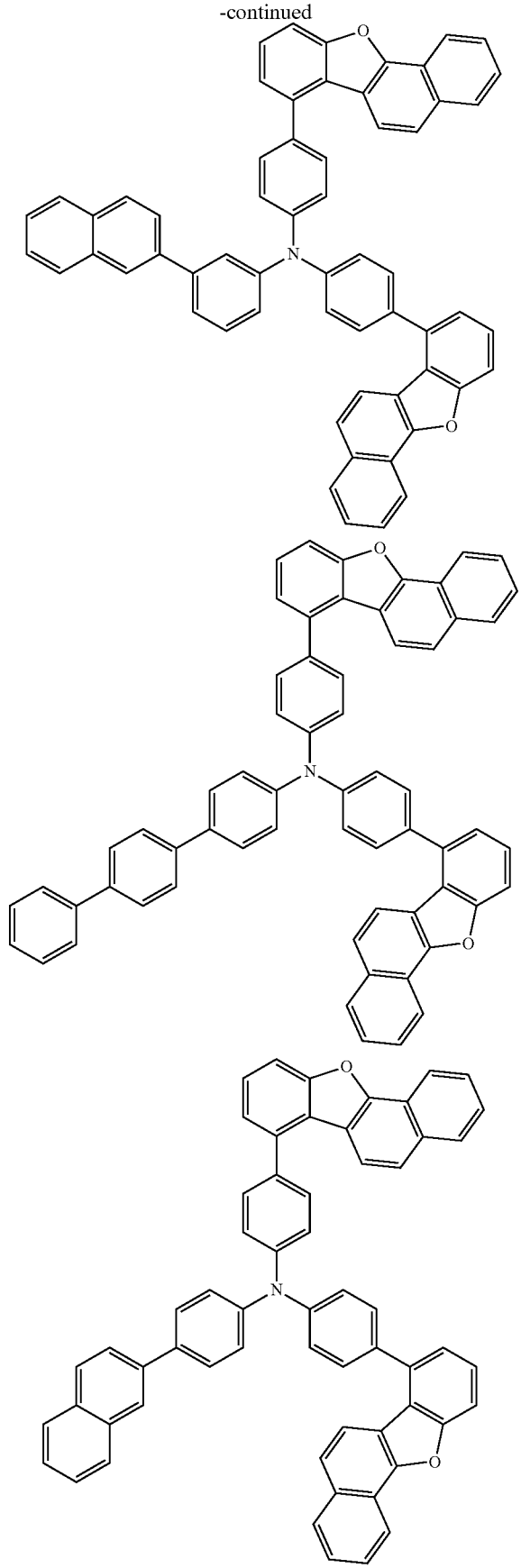
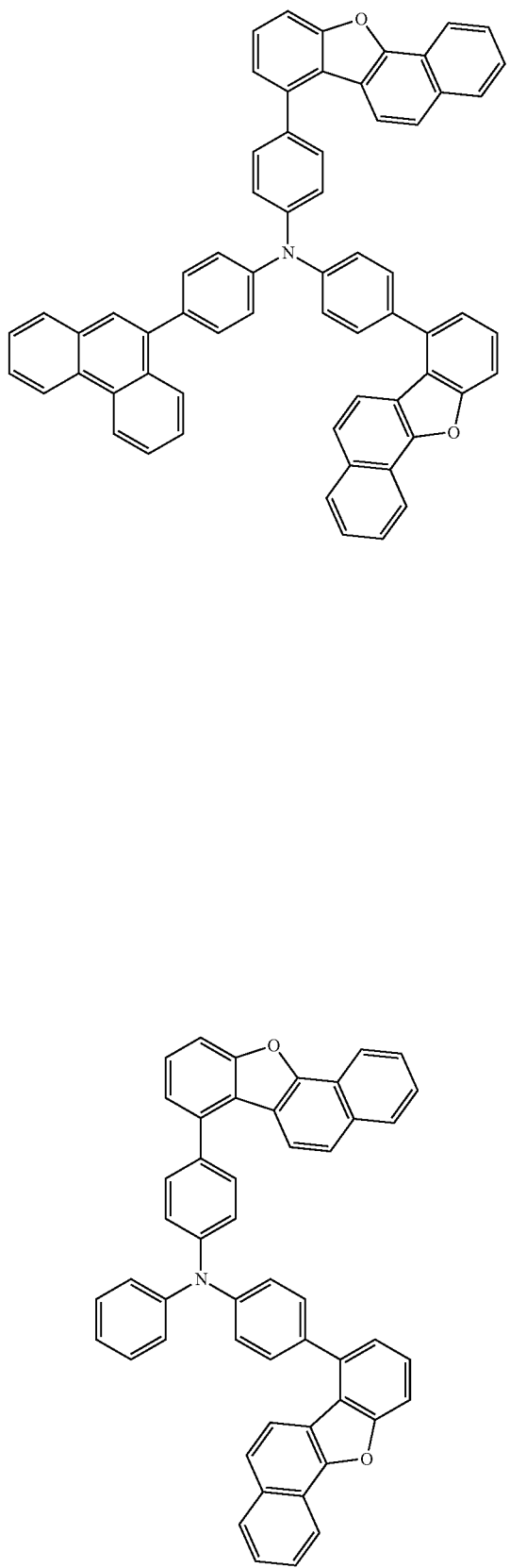

535
-continued
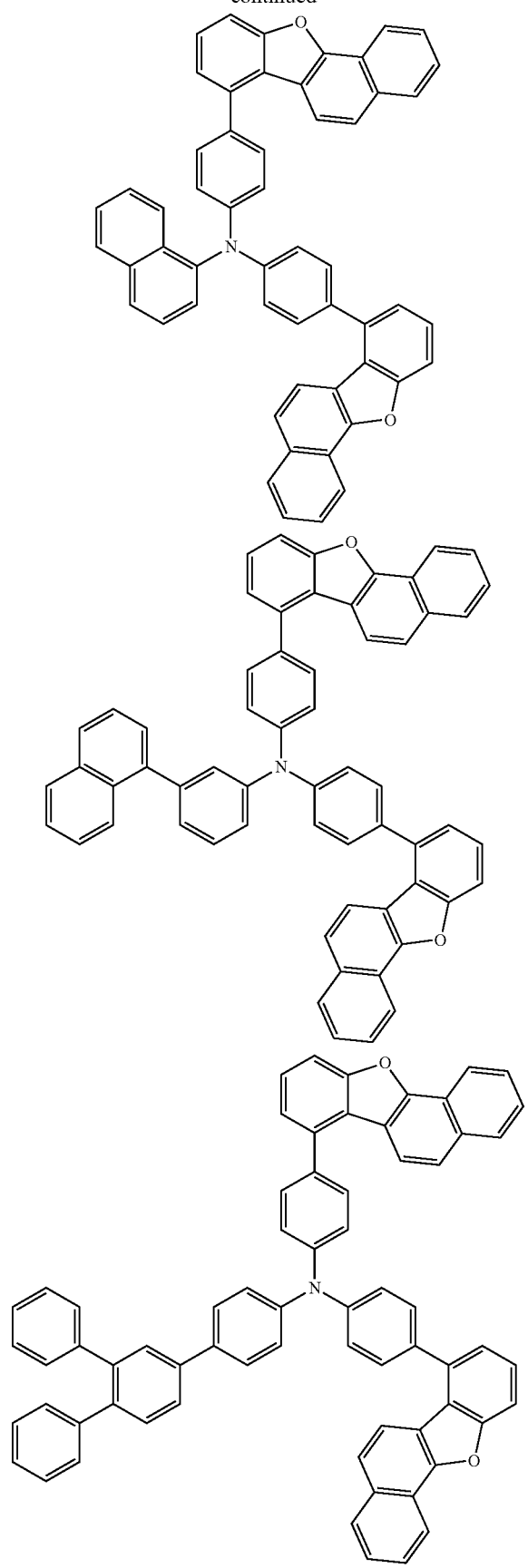
536
-continued
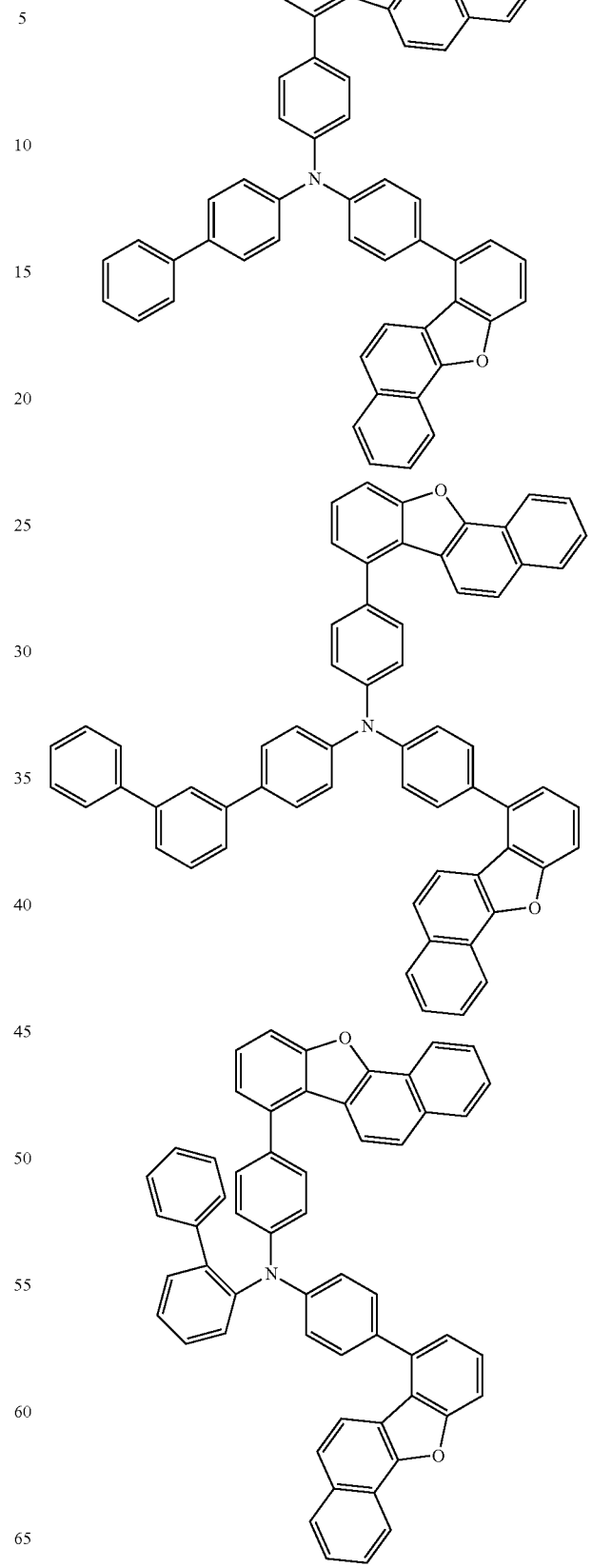

-continued
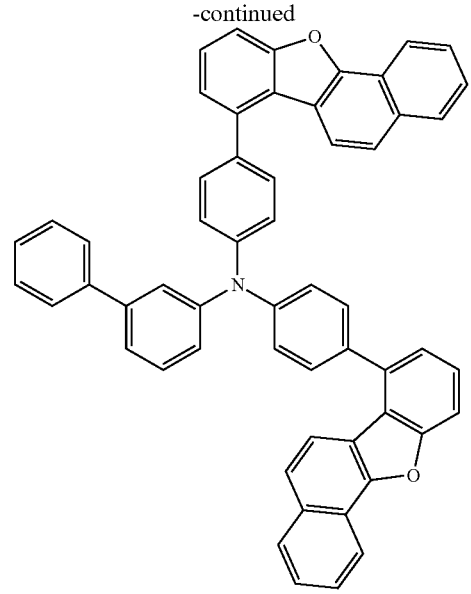
[Chem. 197]
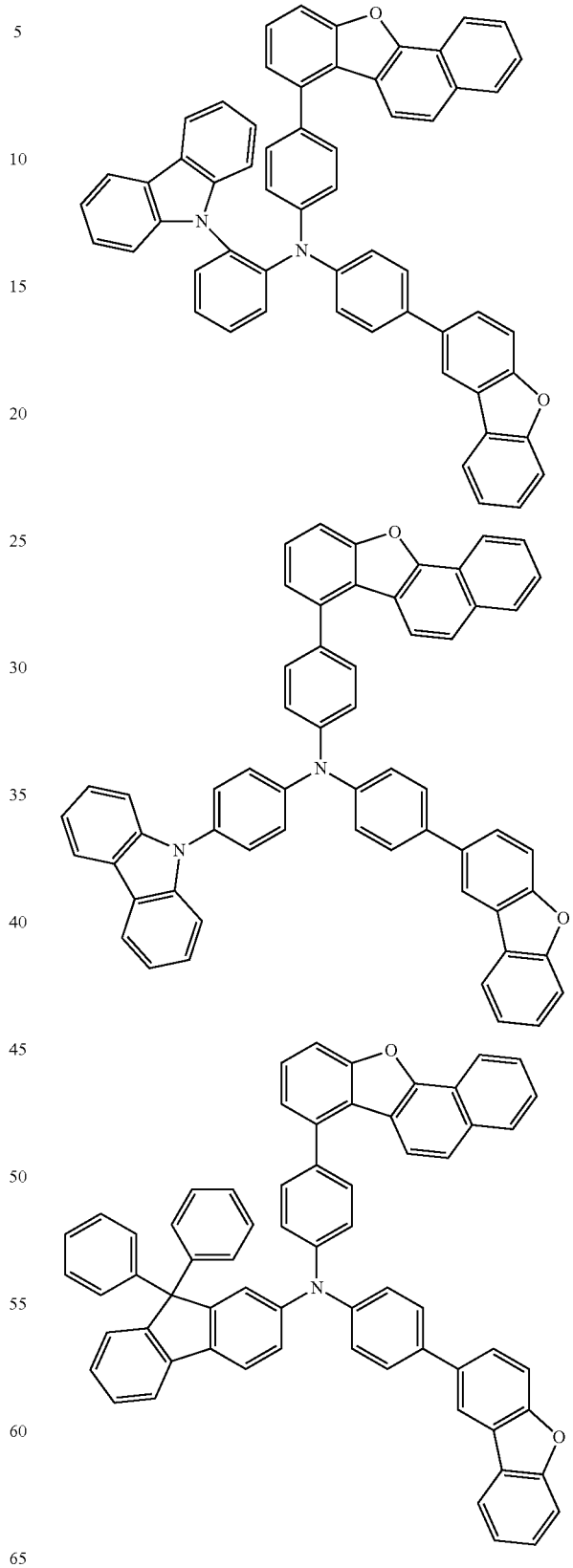

539
-continued
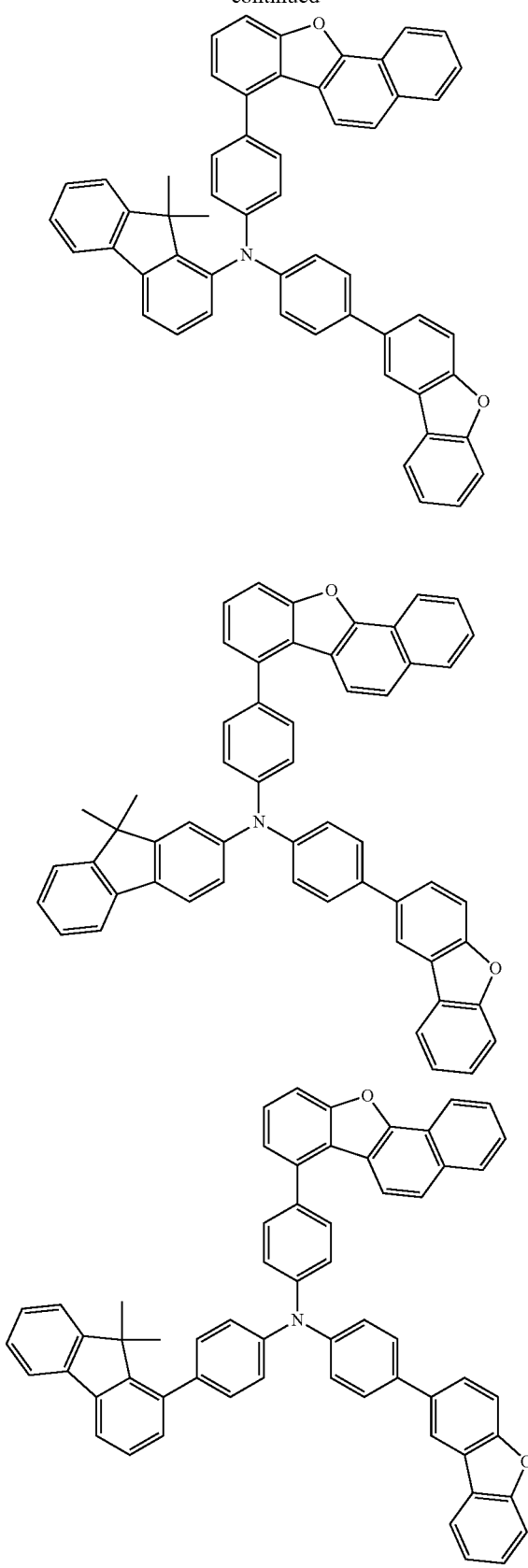
540
-continued
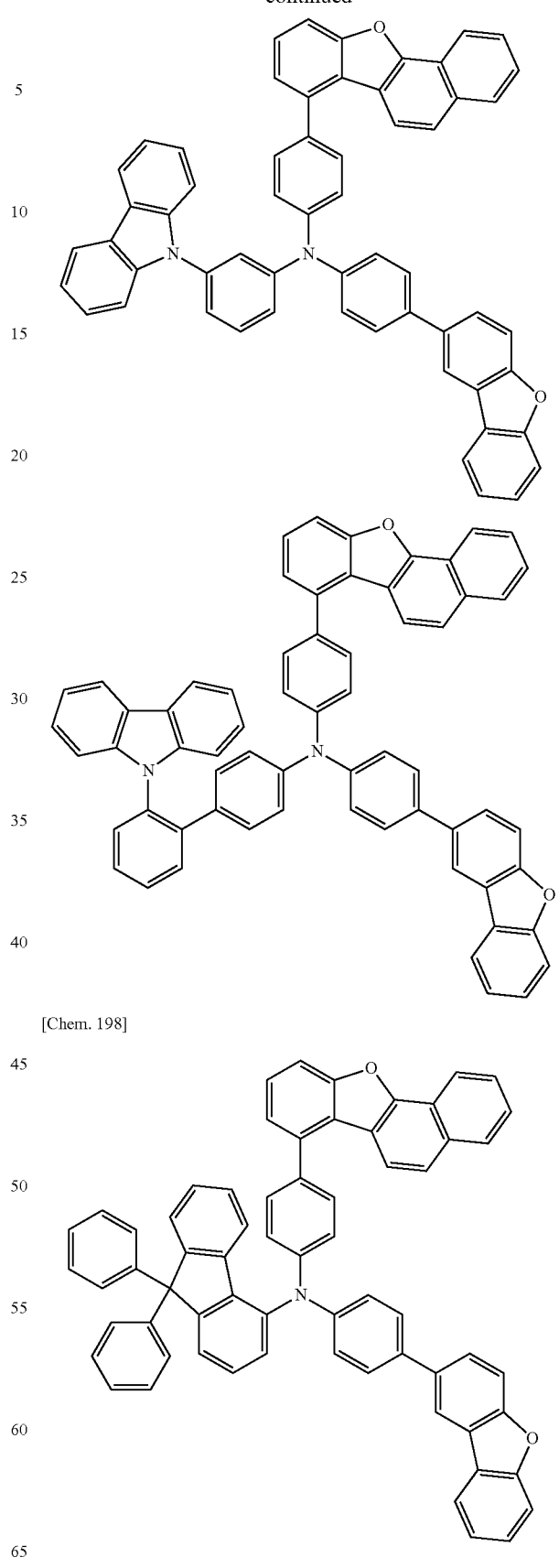
[Chem. 198]

541
-continued
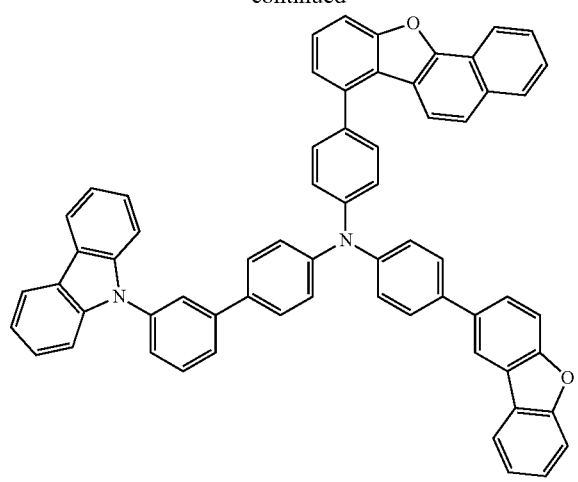
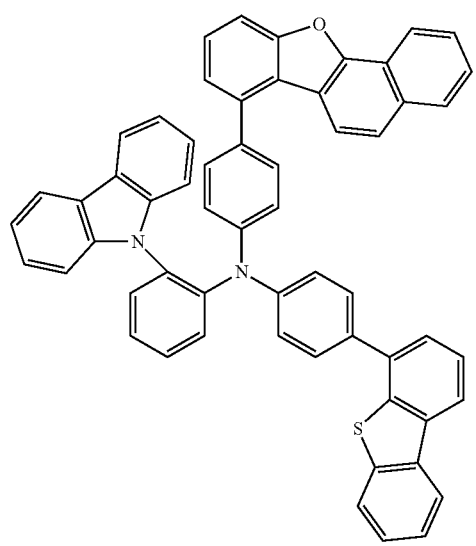
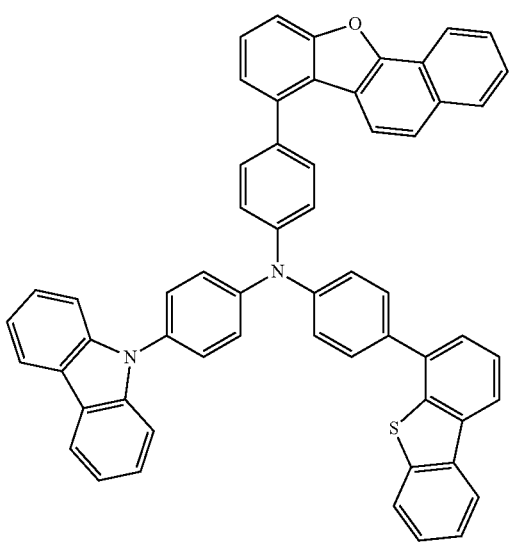
542
-continued
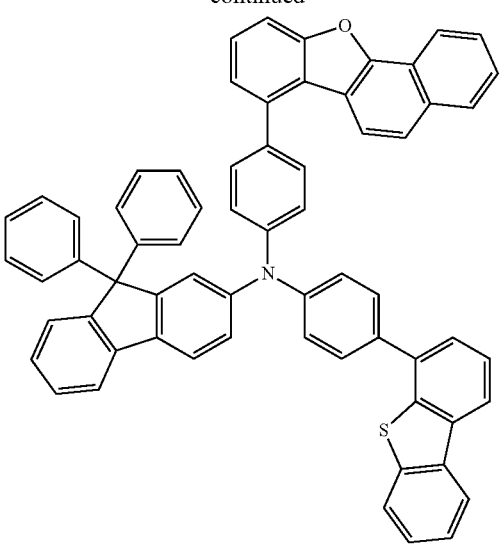
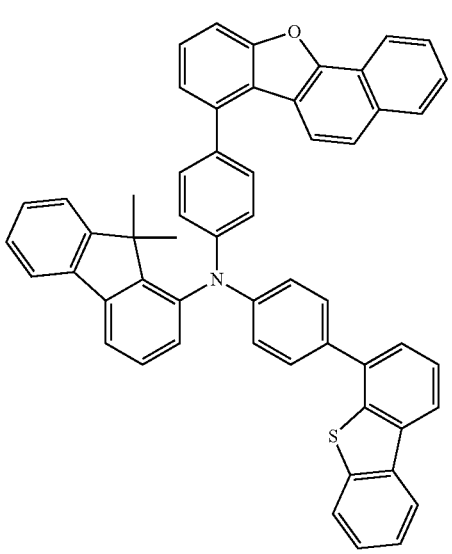
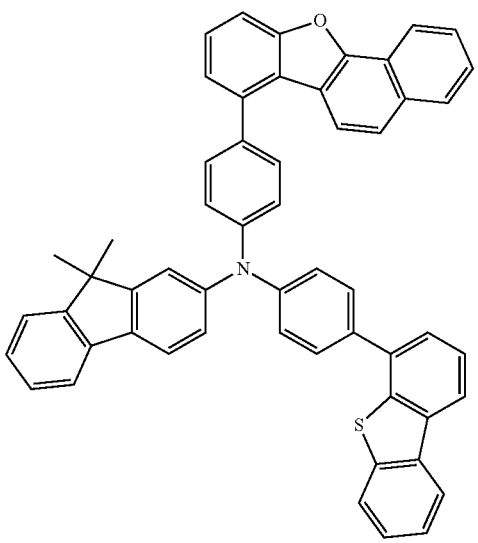

543
-continued
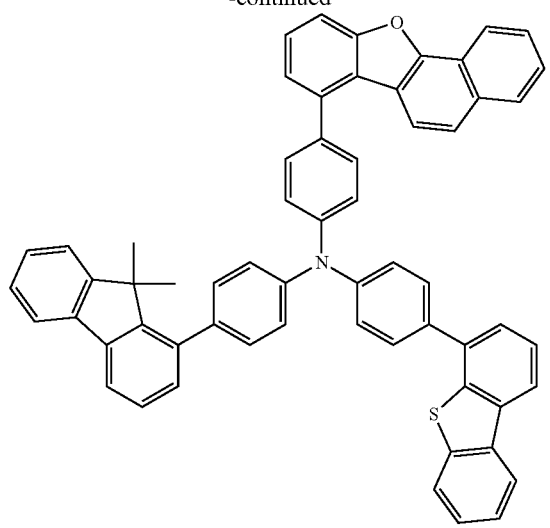
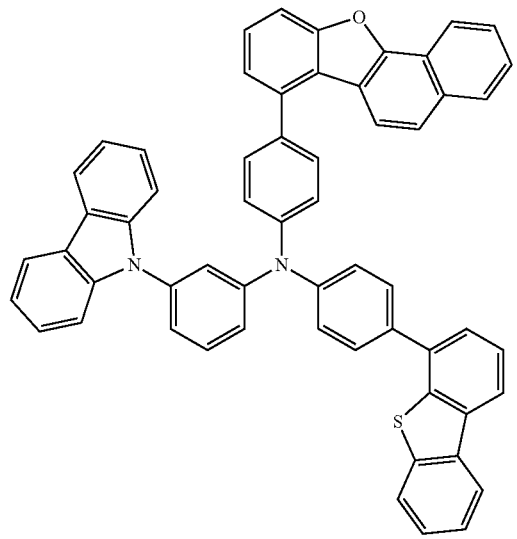
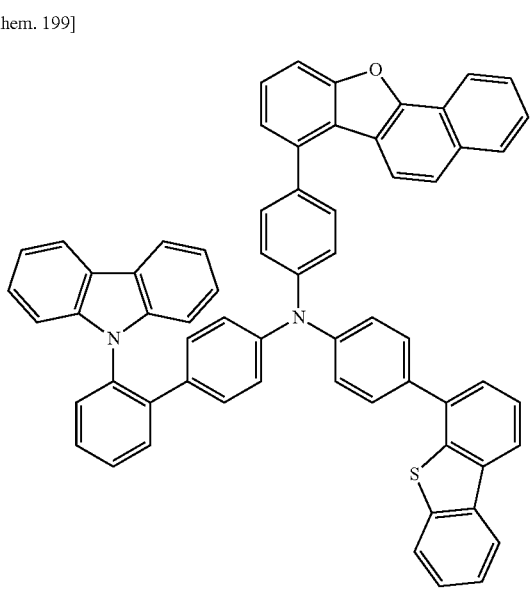
544
-continued
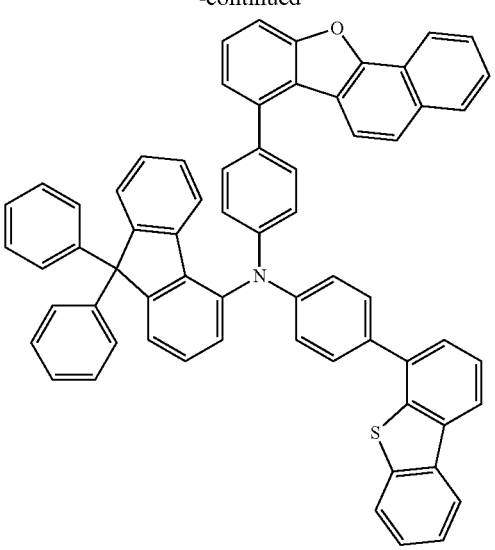
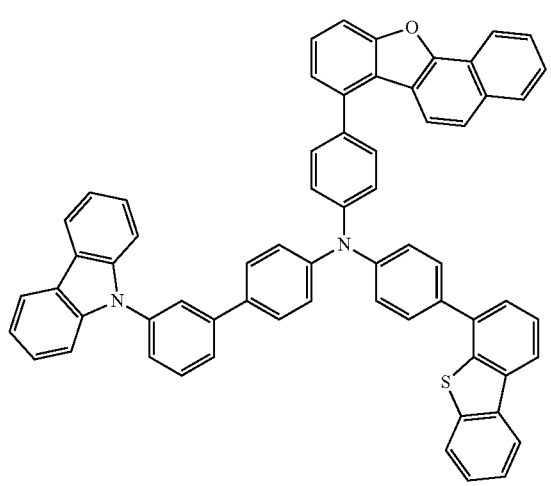
[Chem. 199]
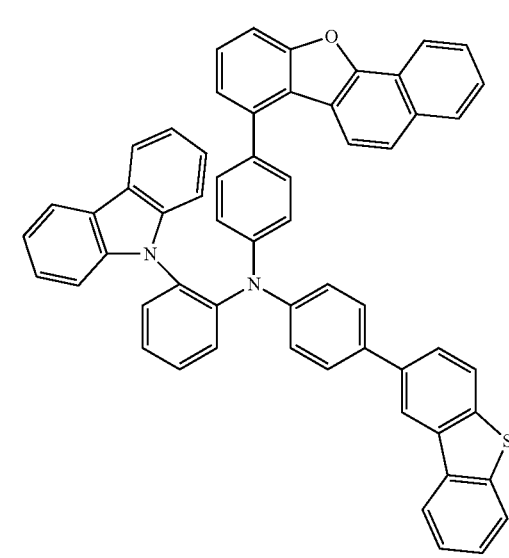

545
-continued
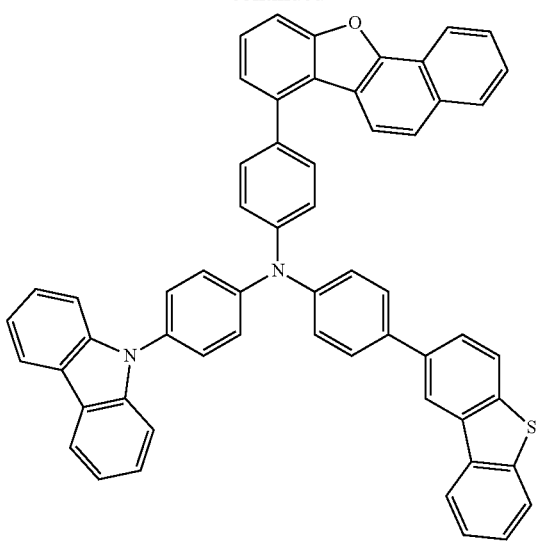
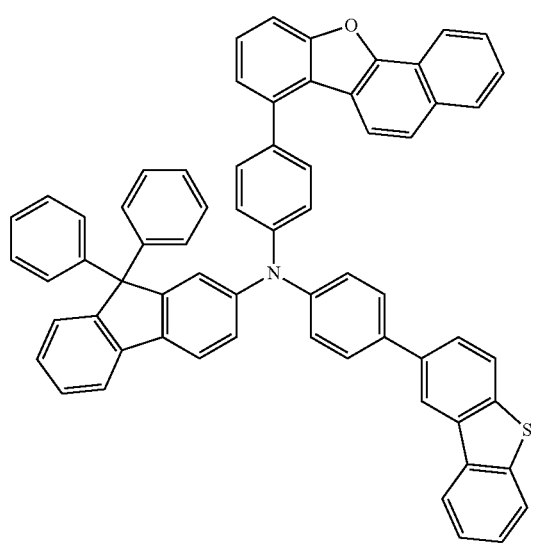
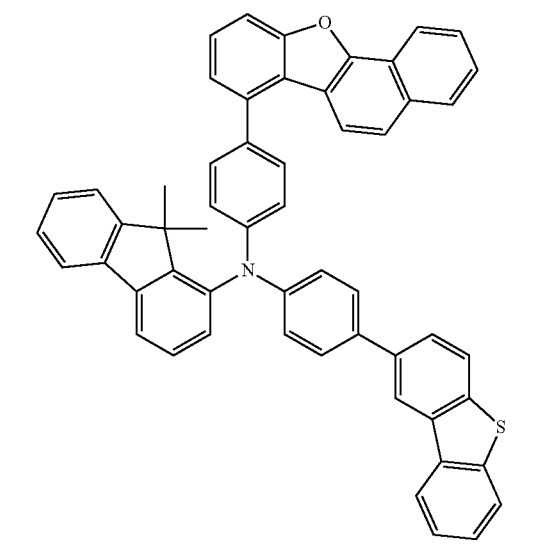
546
-continued
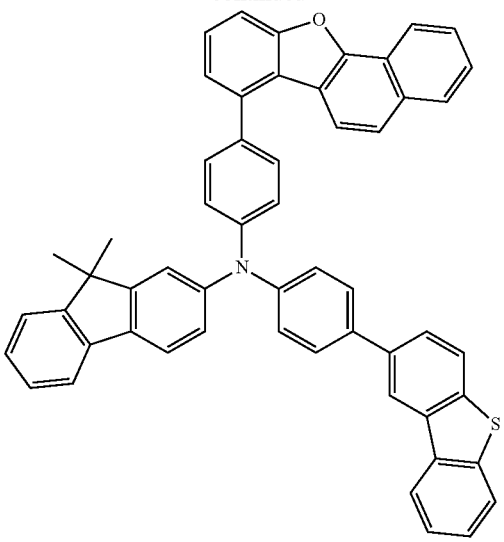
[Chem. 200]
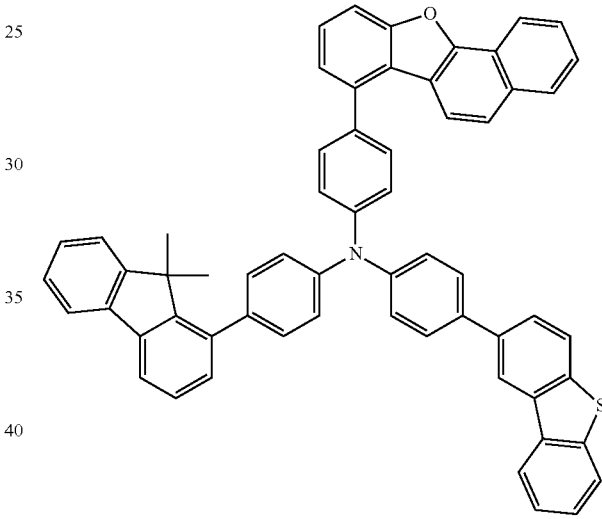
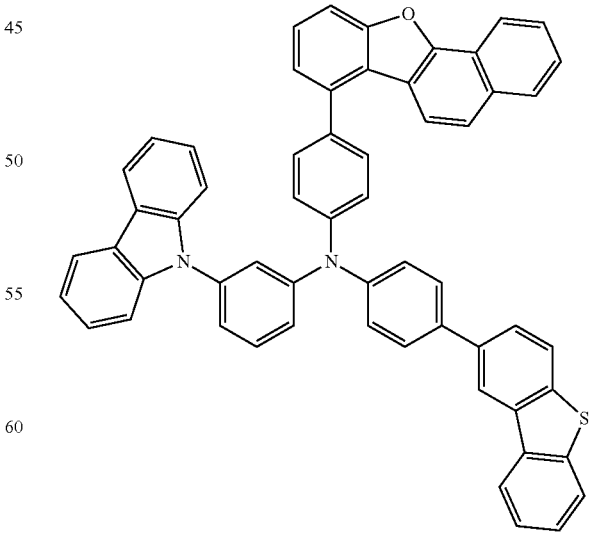

547
-continued
548
-continued
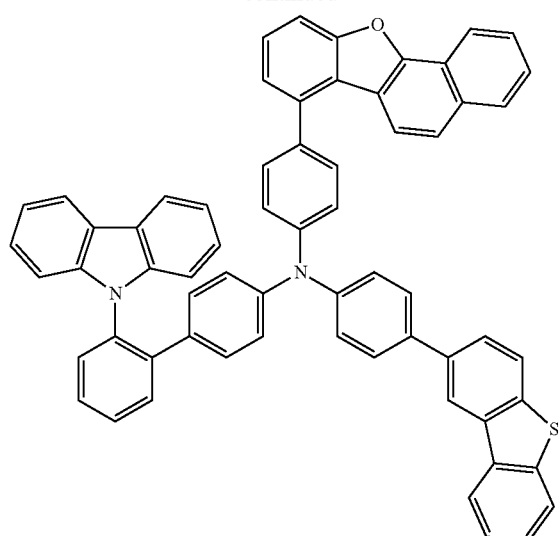
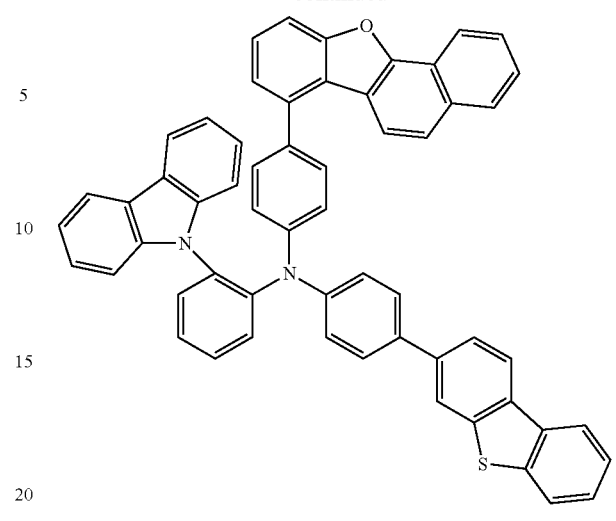
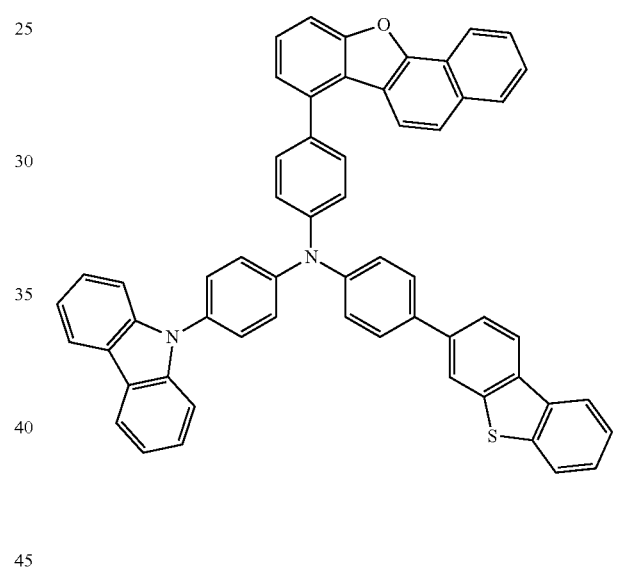
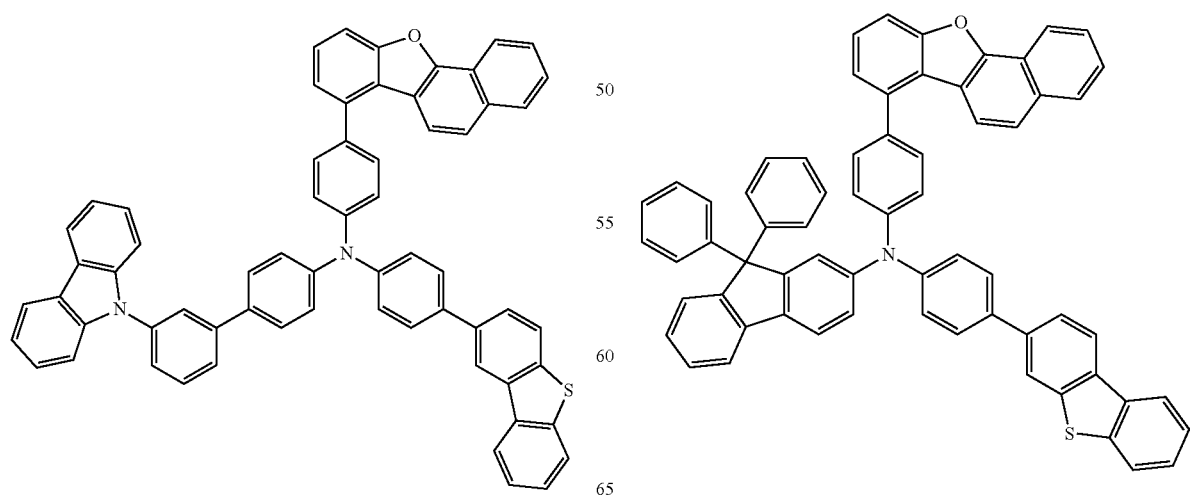

549
-continued
[Chem. 201]
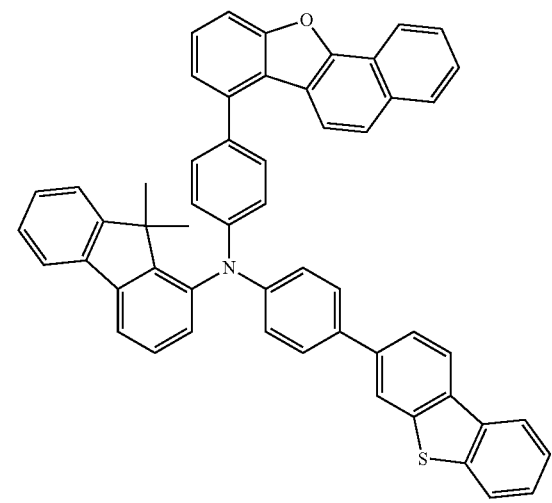
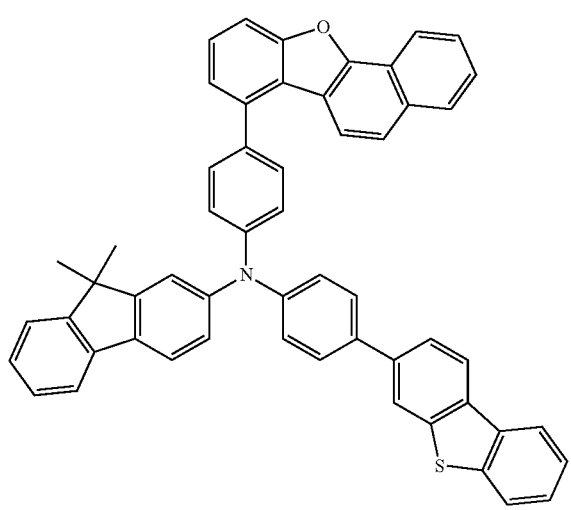
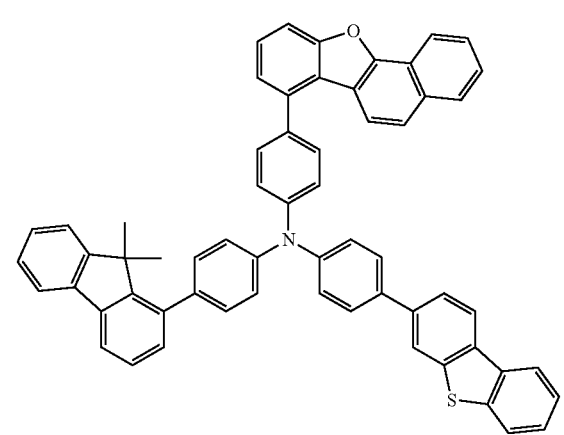
550
-continued
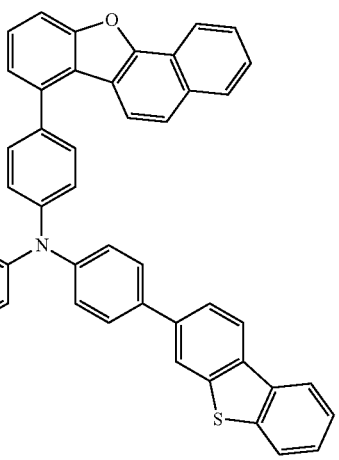
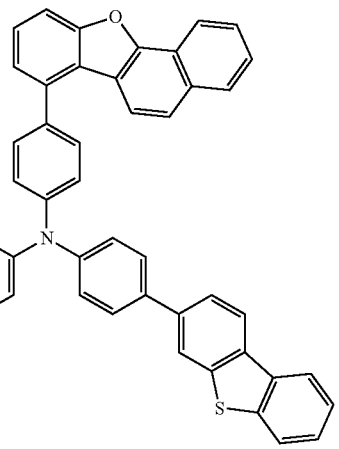
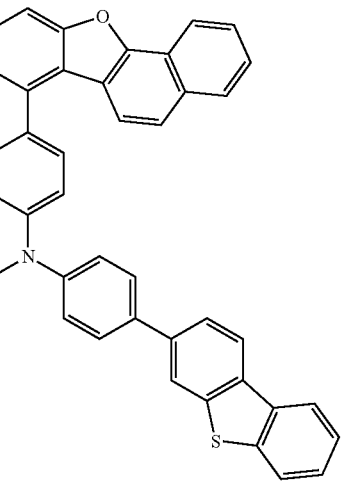

551
-continued
552
-continued
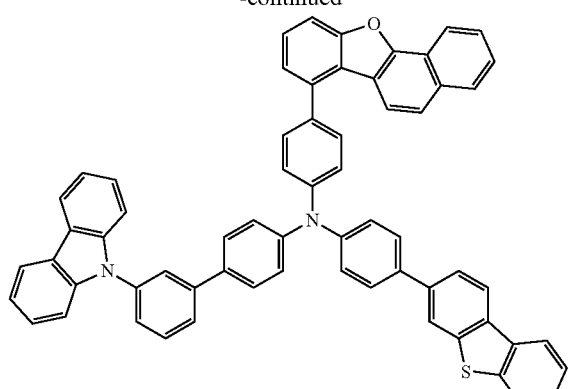
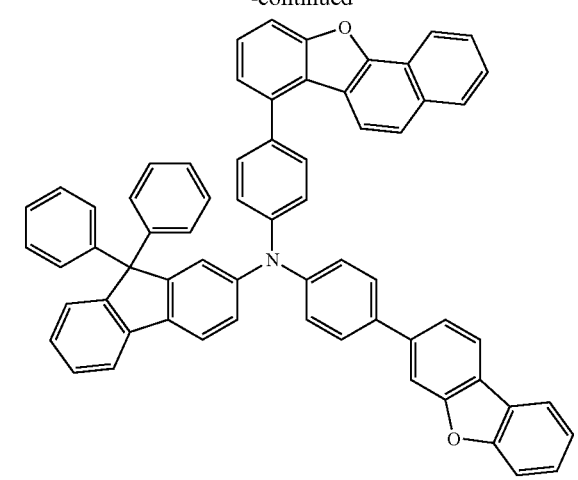
[Chem. 202]
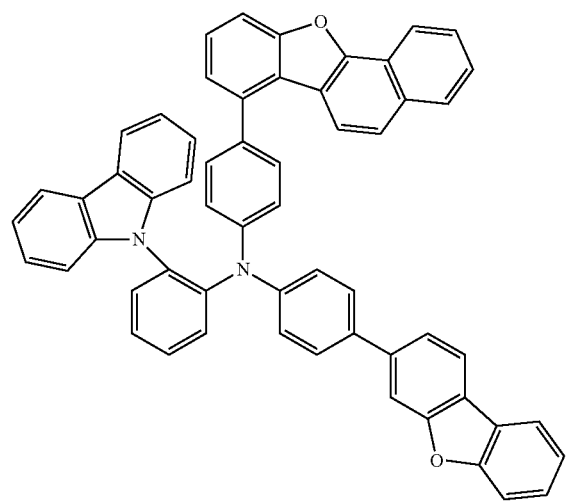
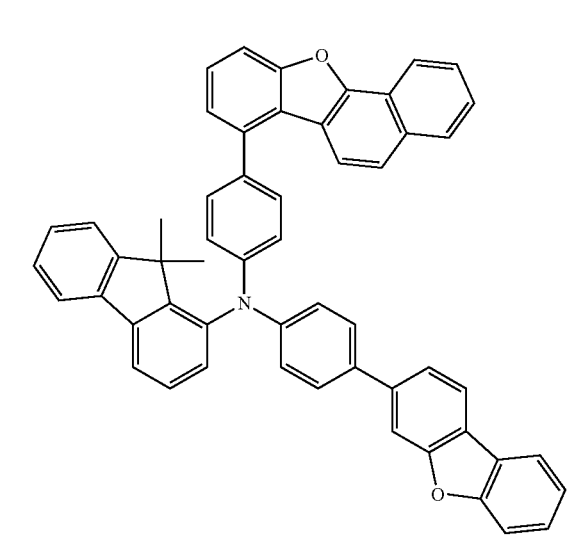
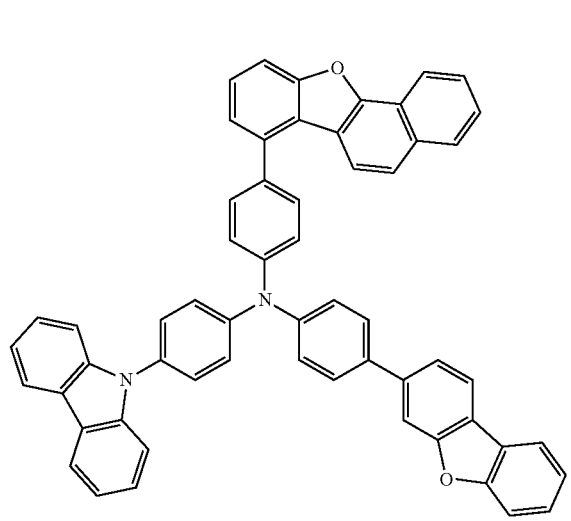
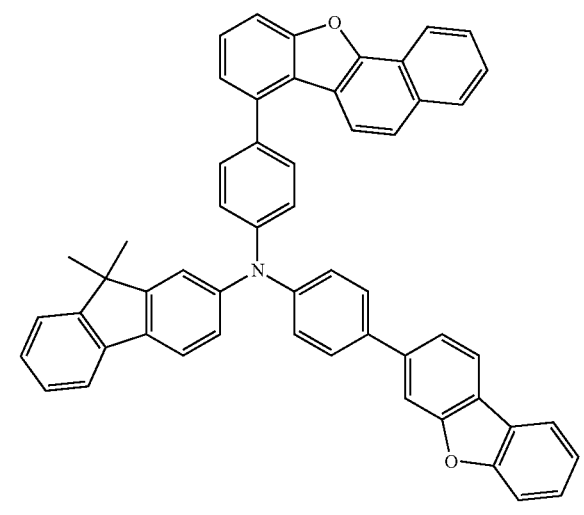

553
-continued
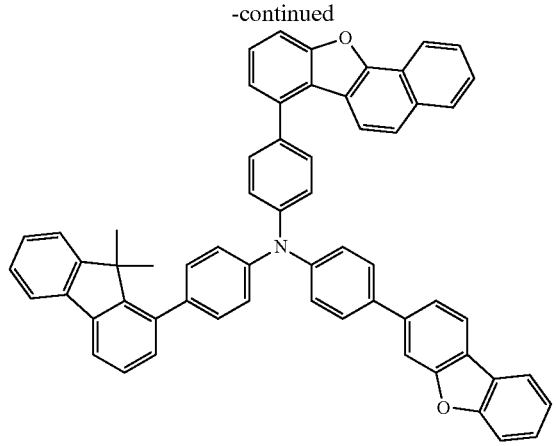
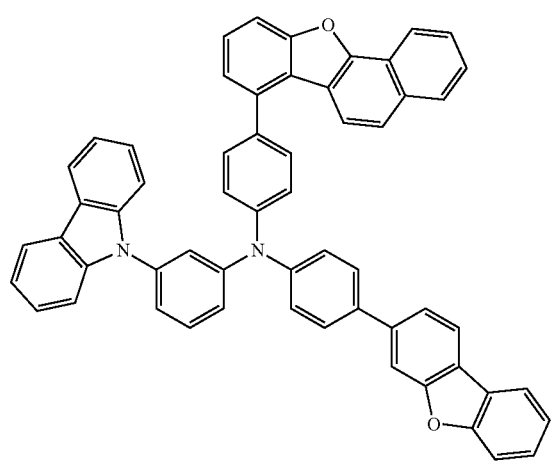
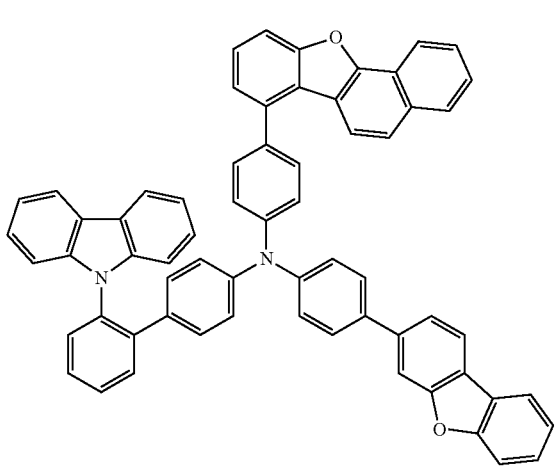
554
-continued
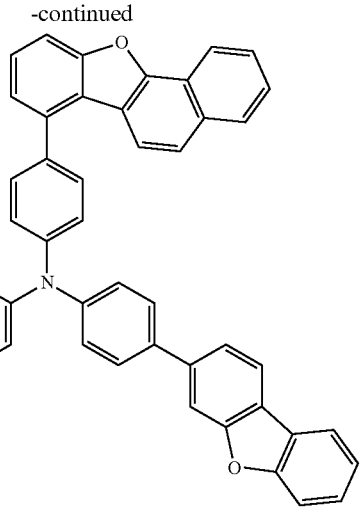
[Chem. 203]
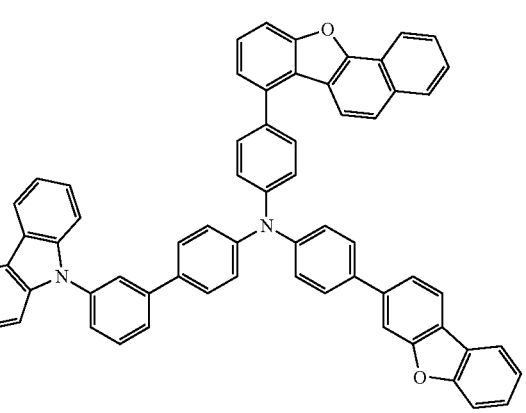
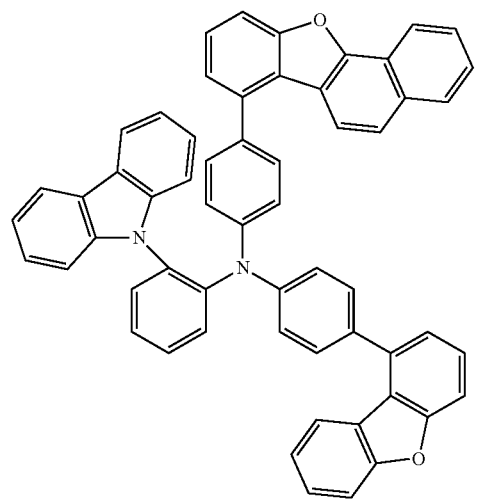

555
-continued
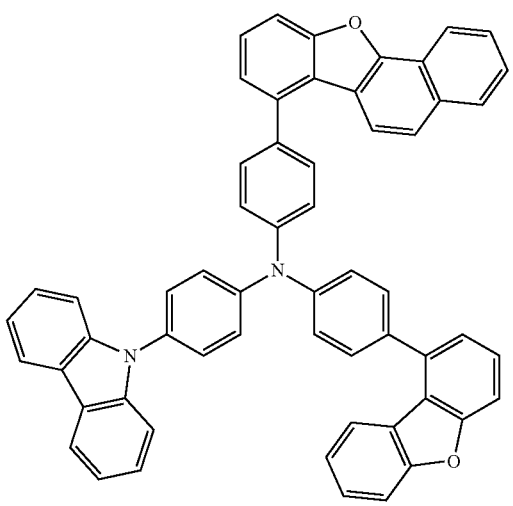
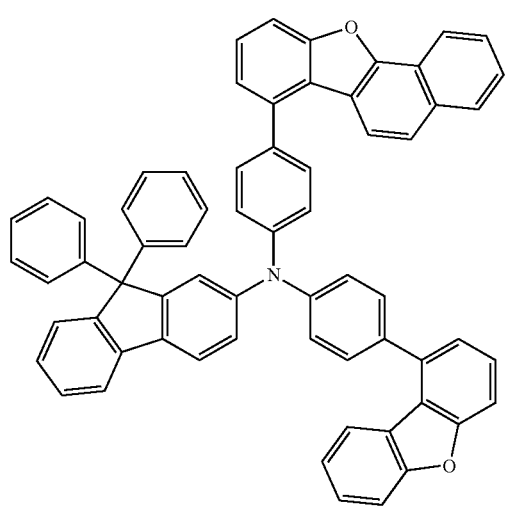
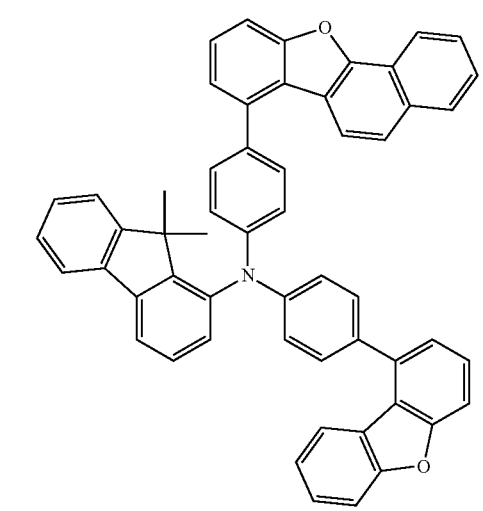
556
-continued
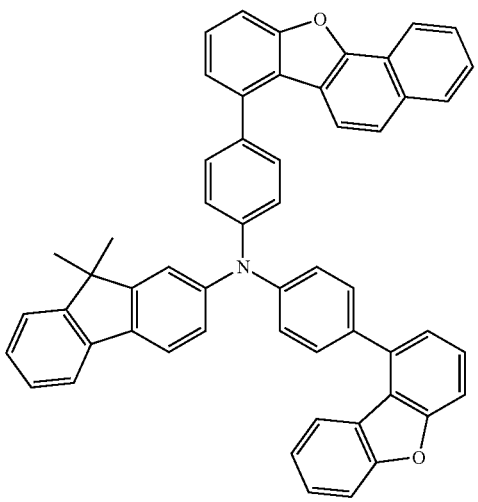
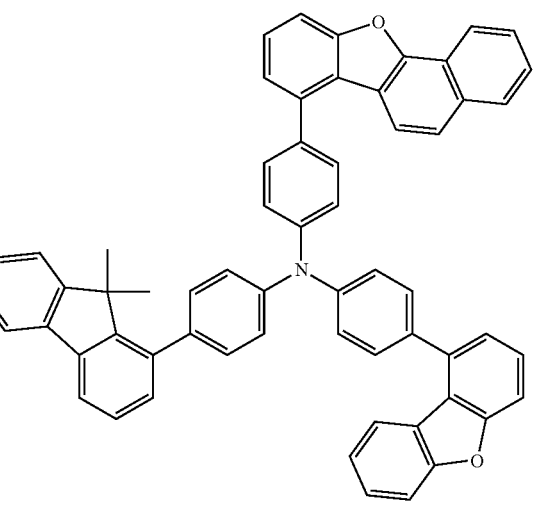
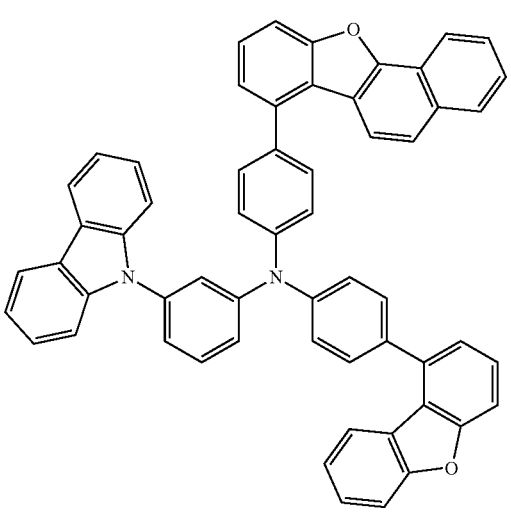

557
-continued
[Chem. 204]
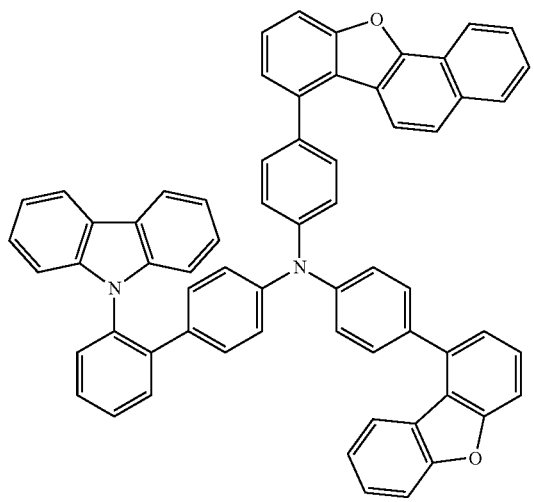
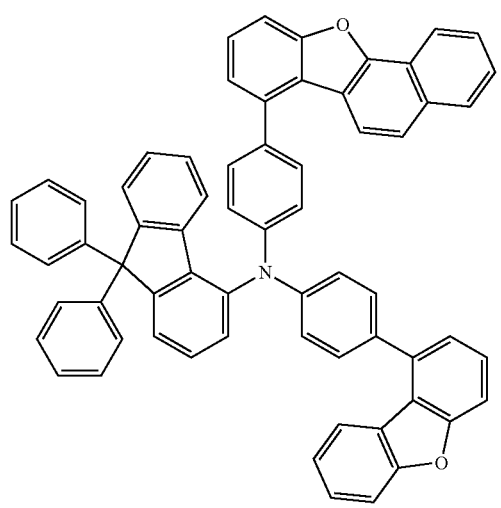
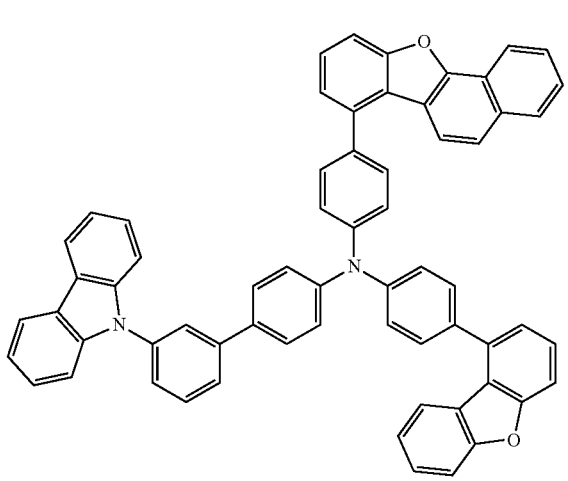
558
-continued
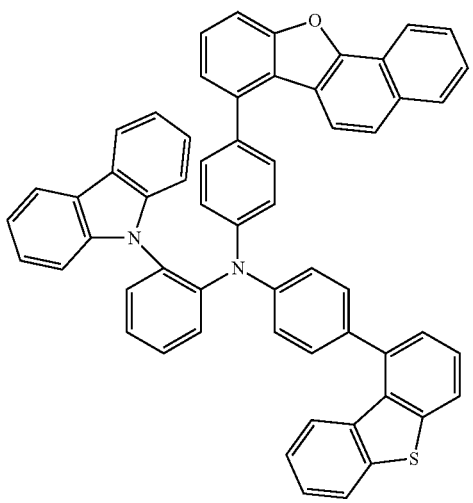
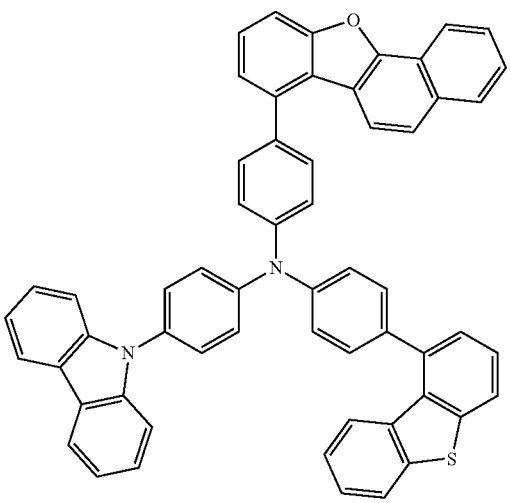
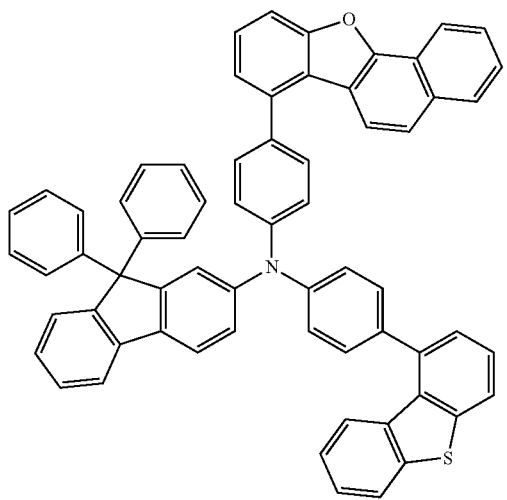

559
-continued
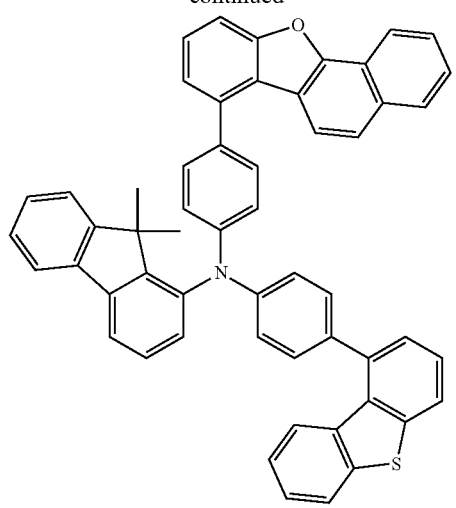
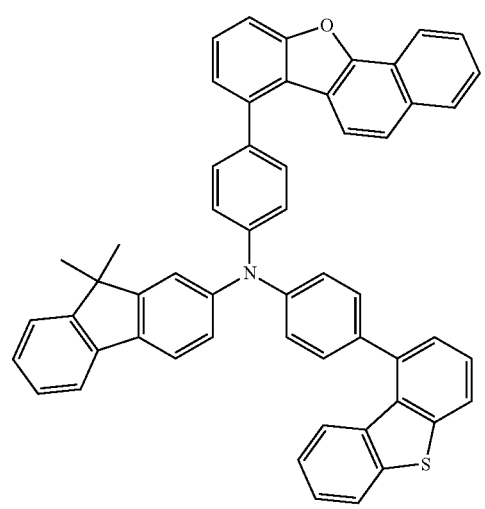
[Chem. 205]
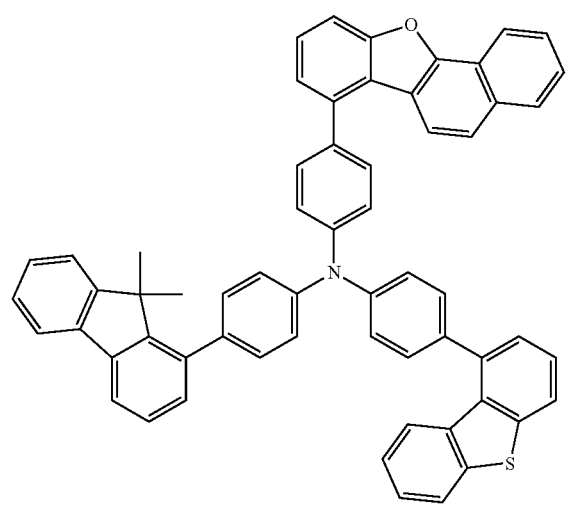
560
-continued
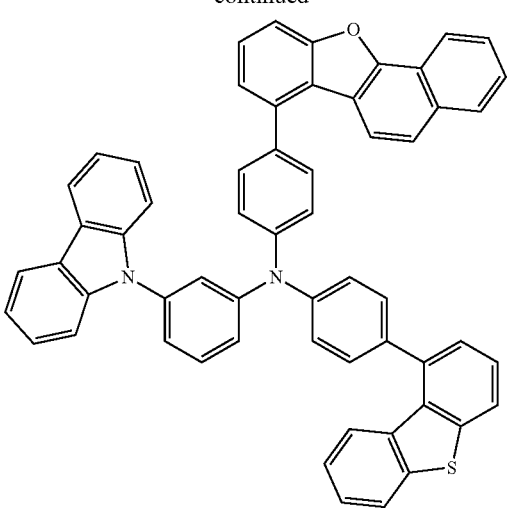
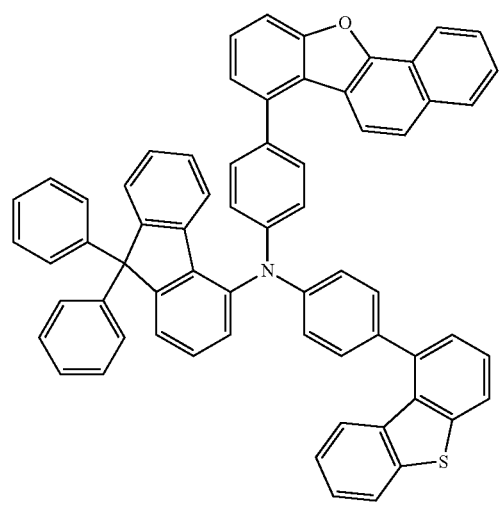

561
-continued
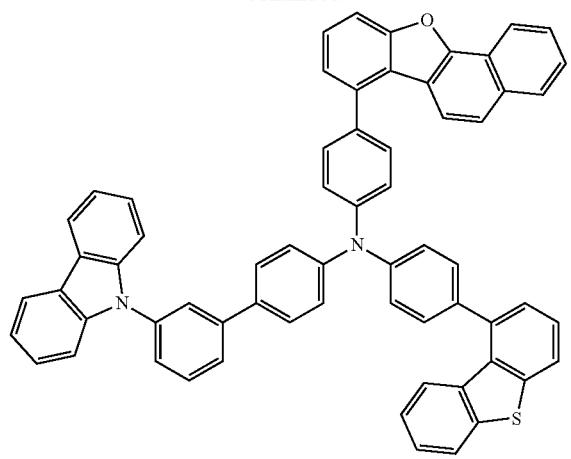
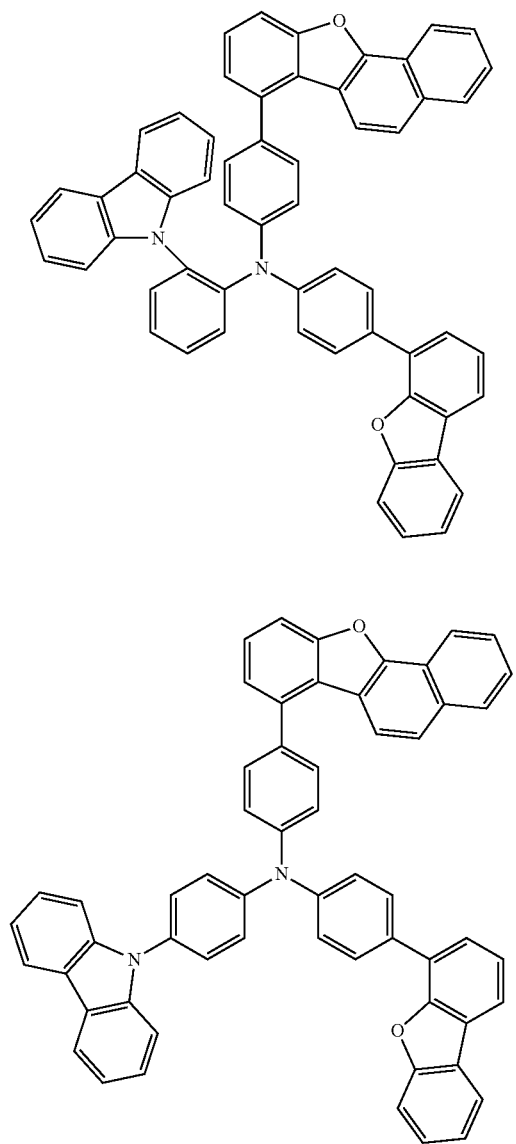
562
-continued
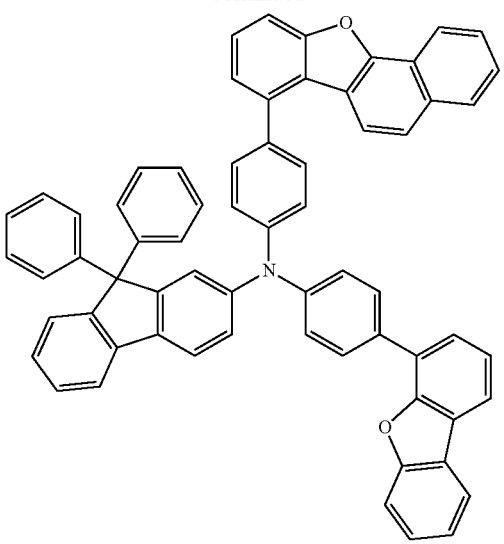
[Chem. 206]
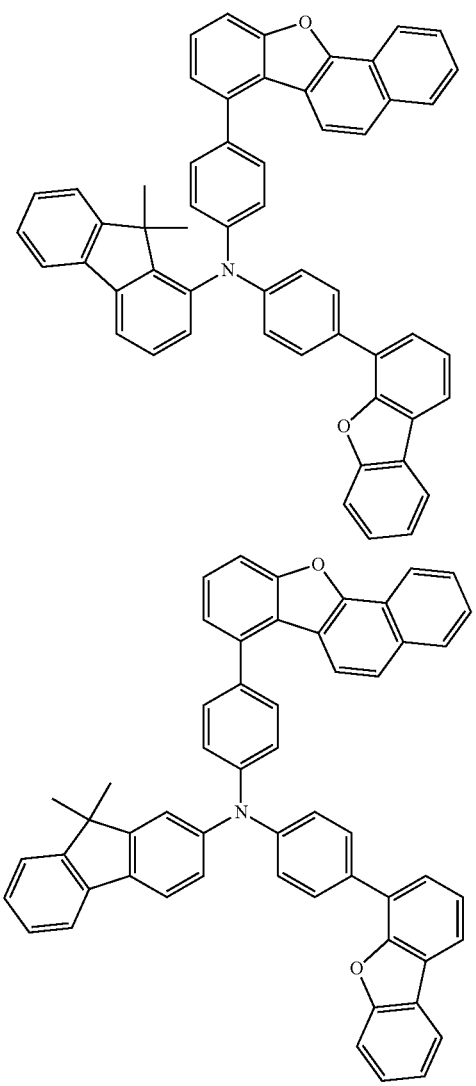

563
-continued
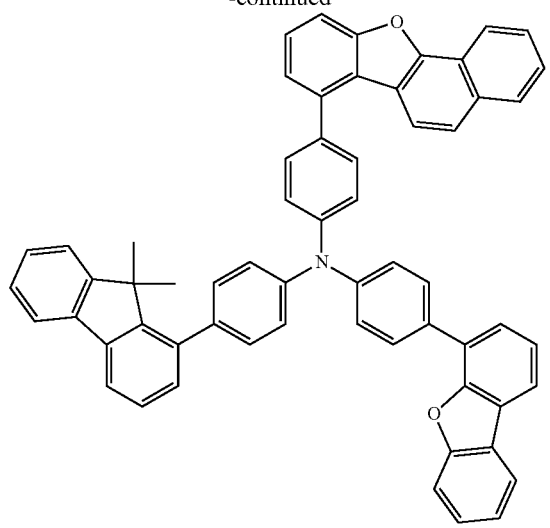
564
-continued
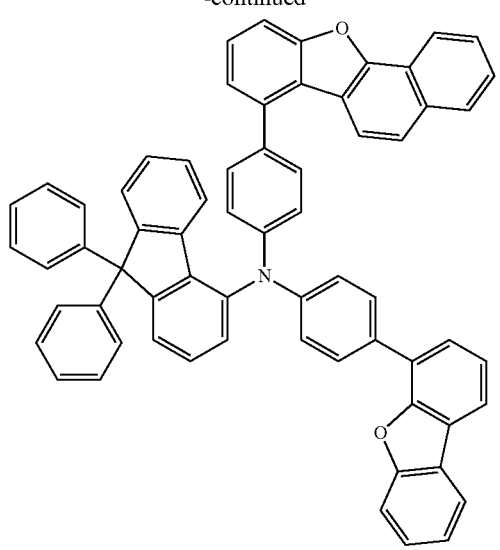
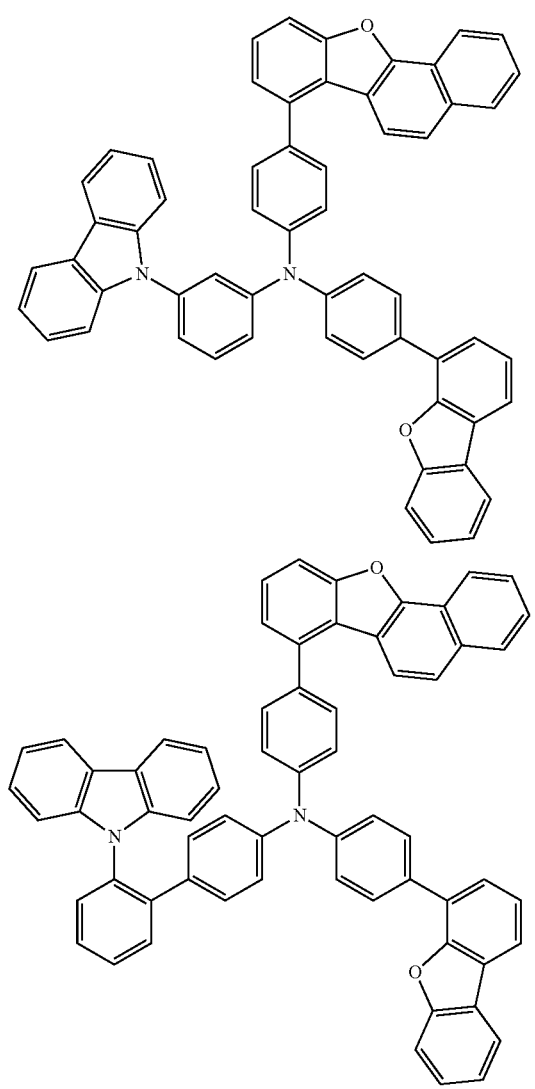

565
-continued
[Chem. 207]
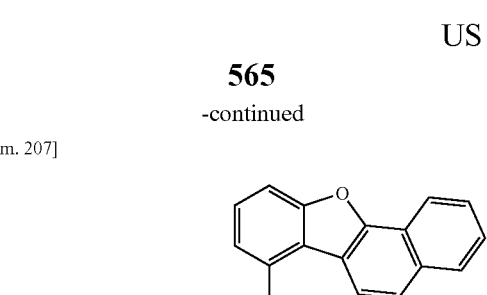
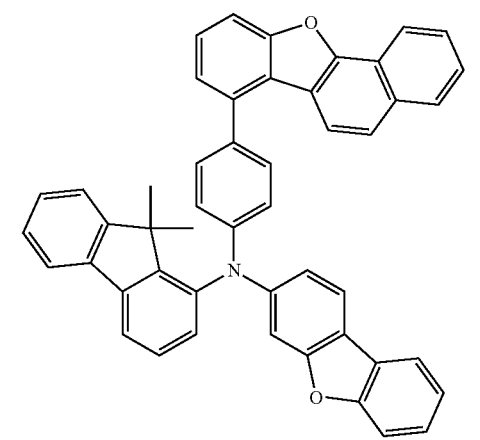
566
-continued
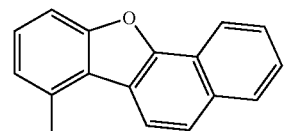
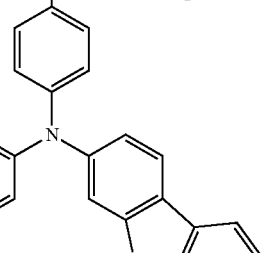
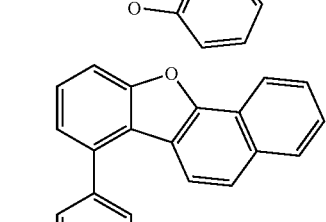
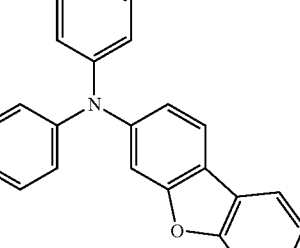
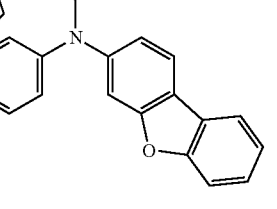

567
-continued
568
-continued
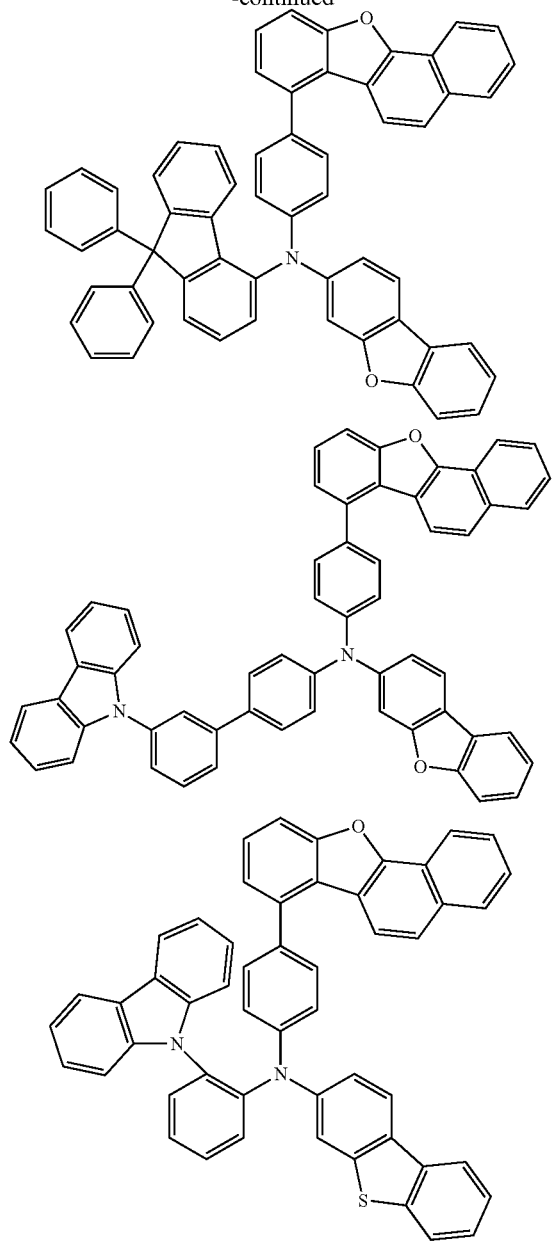
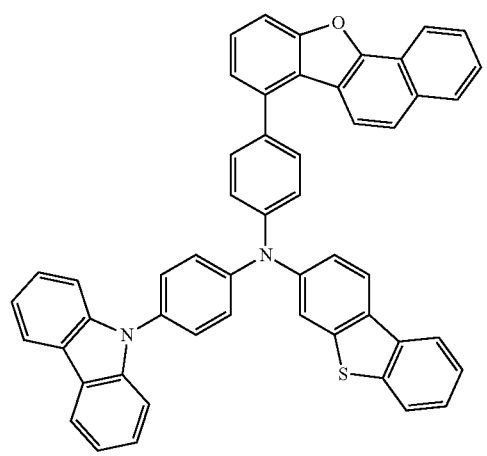
[Chem. 208]
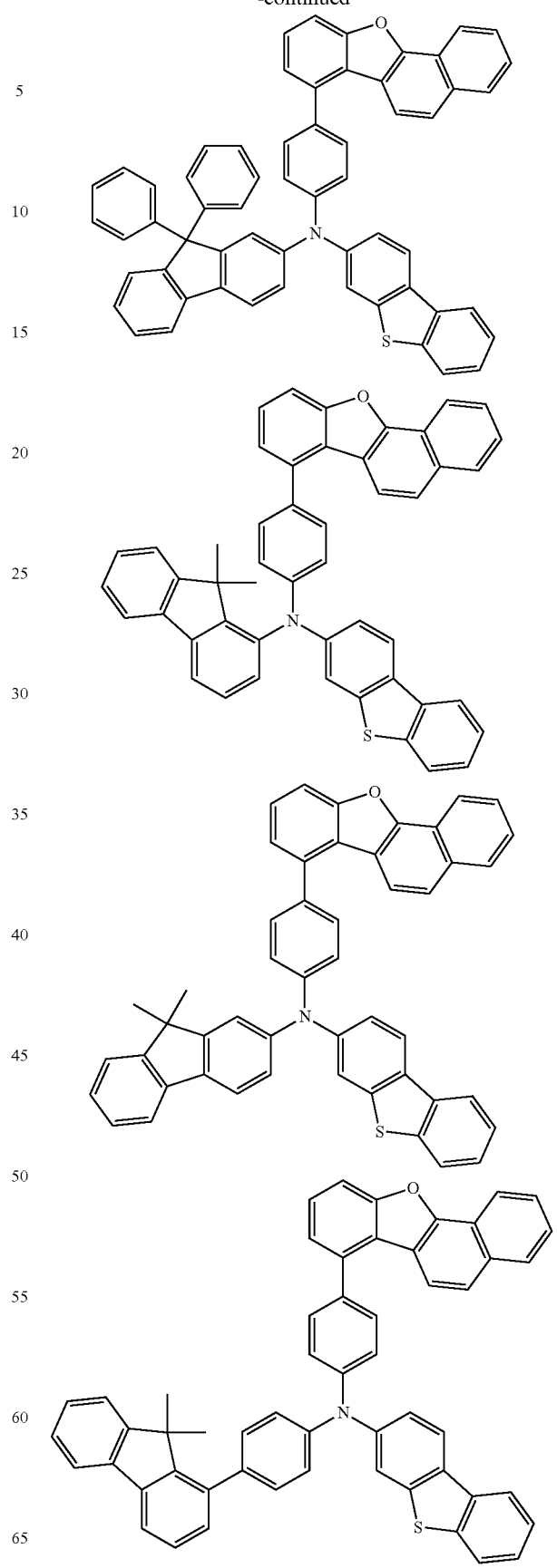

569
-continued
570
-continued
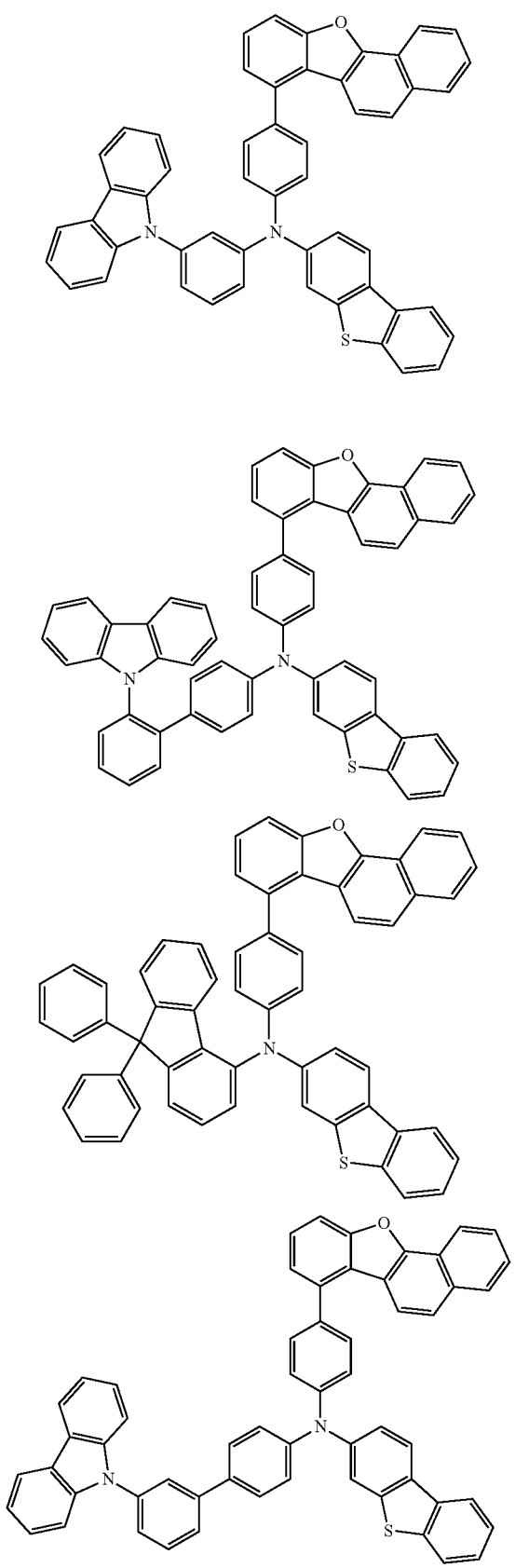
[Chem. 209]

571
-continued
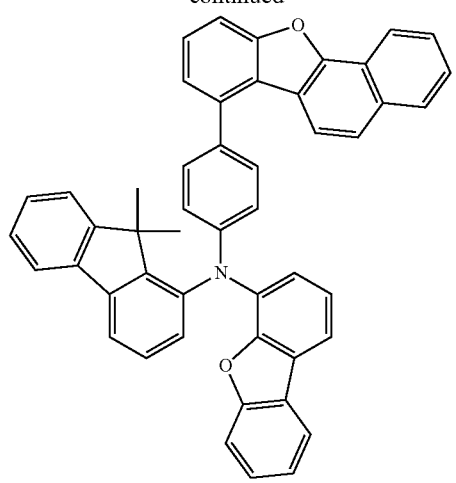
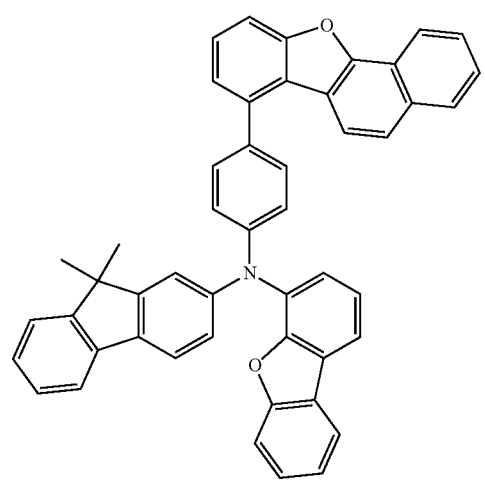
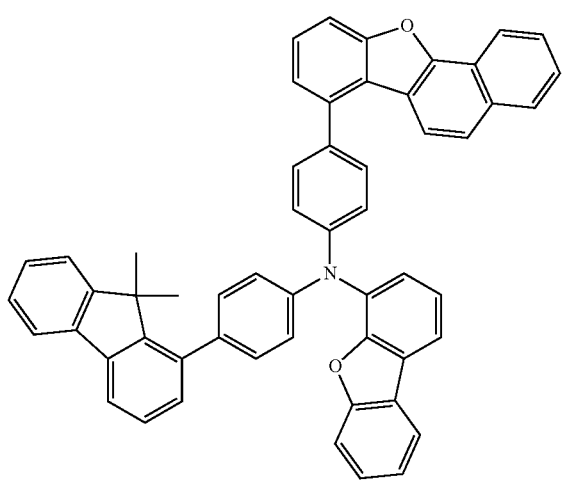
572
-continued
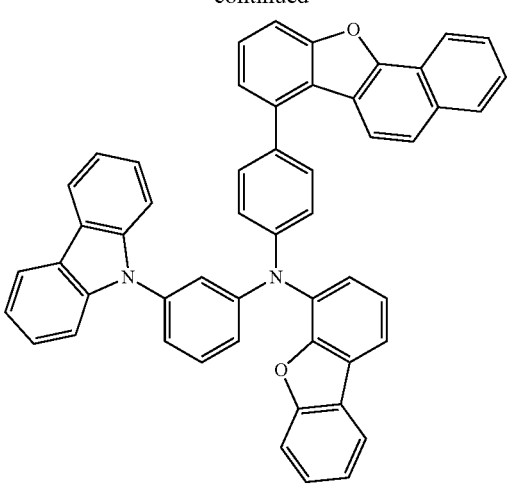
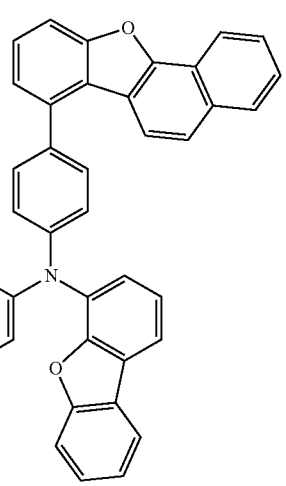
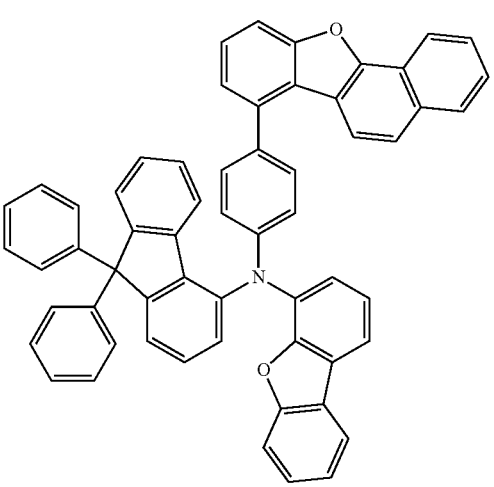

573
-continued
[Chem. 210]
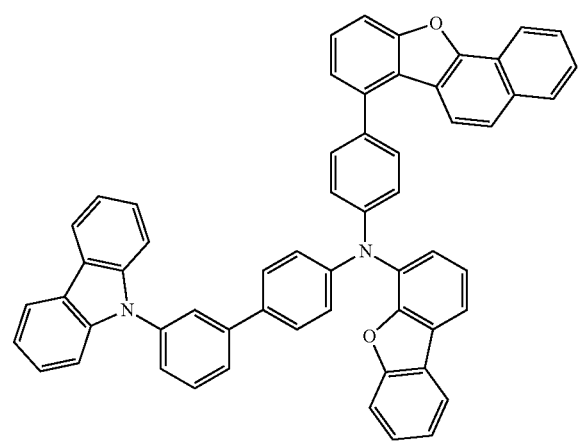
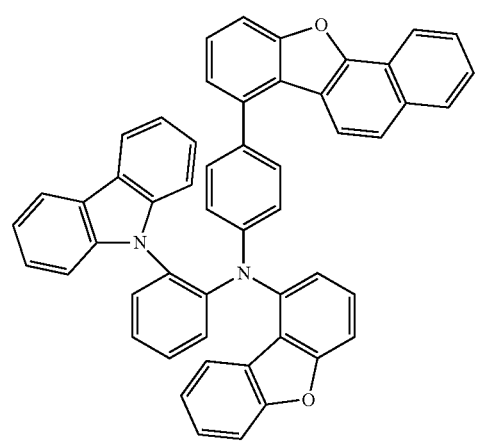
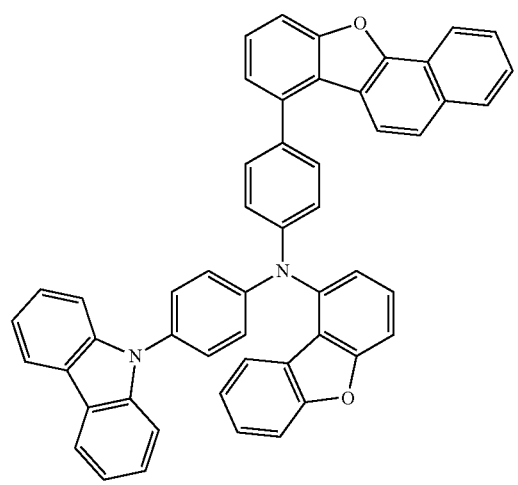
574
-continued
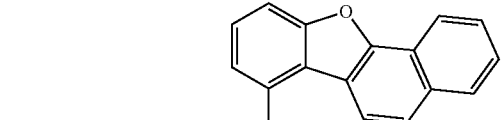
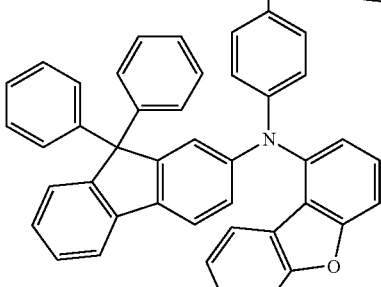
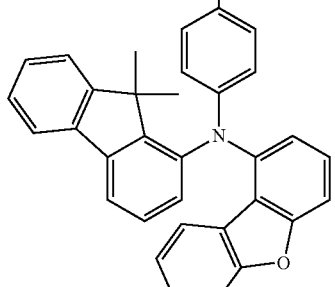
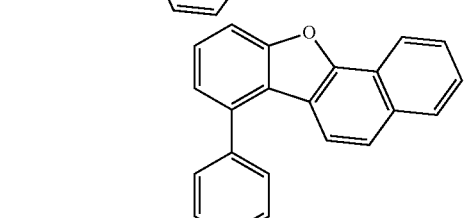
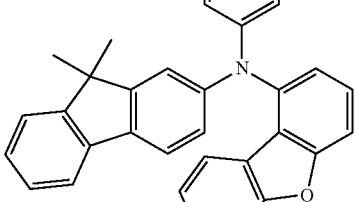
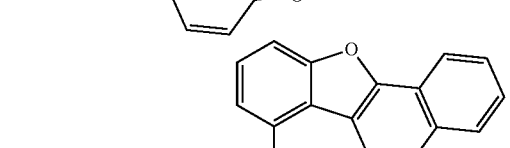
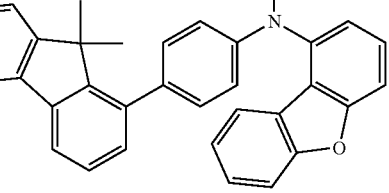

575
-continued
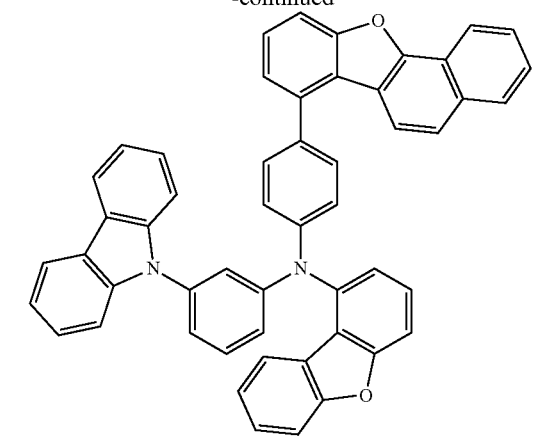
[Chem. 211]
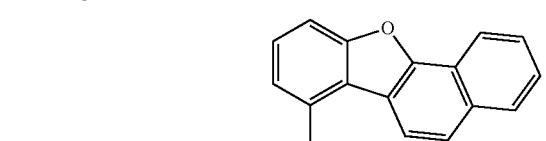
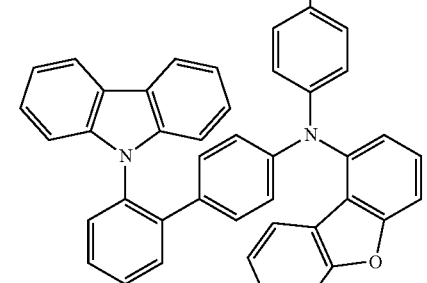
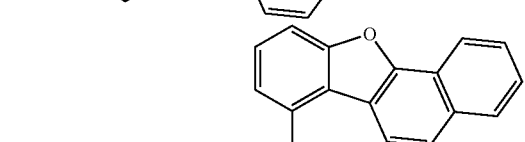
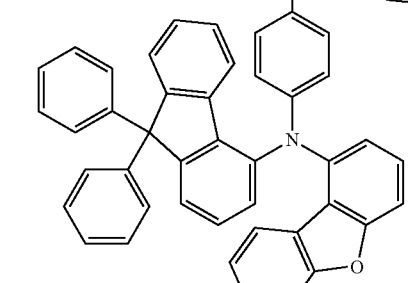
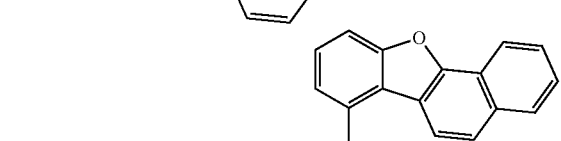
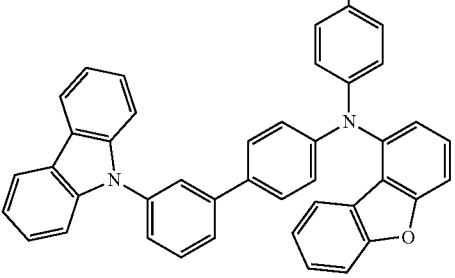
576
-continued
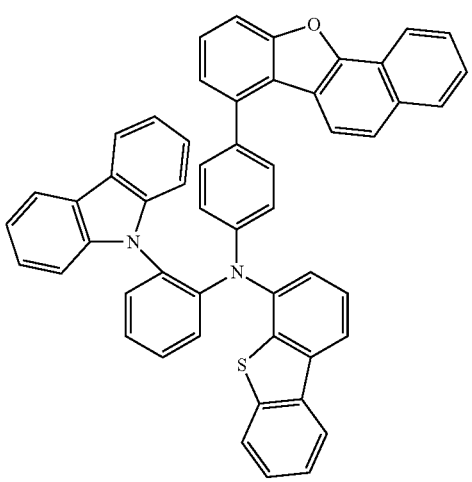
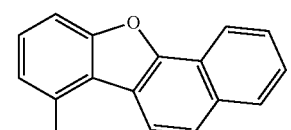
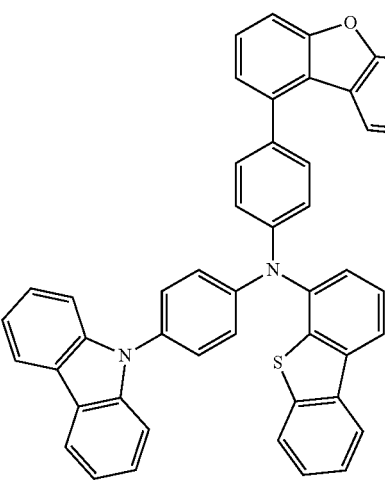
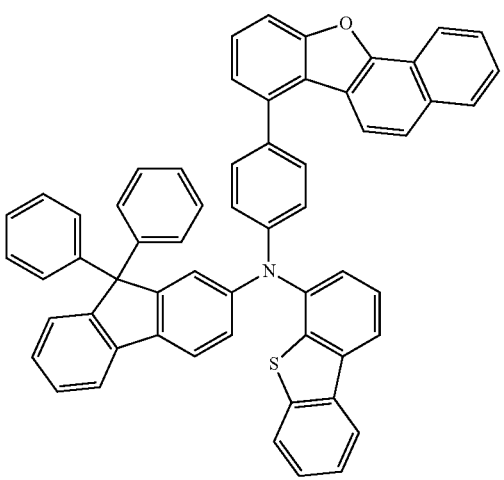

577
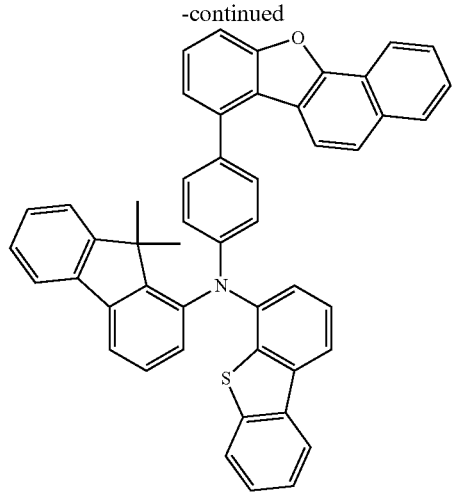
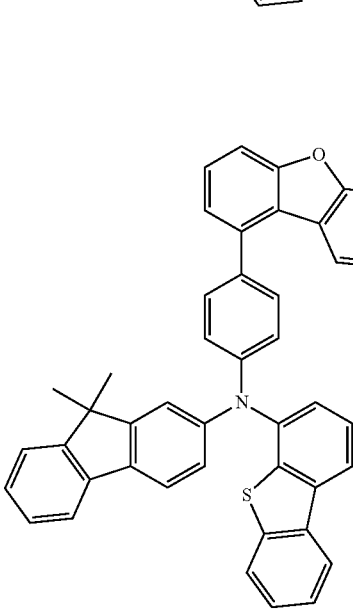
[Chem. 212]
578
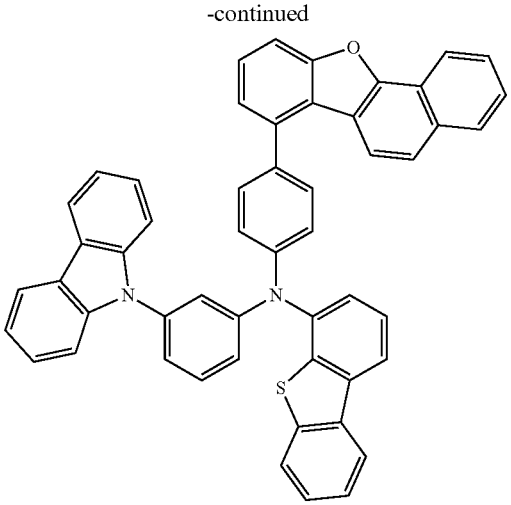
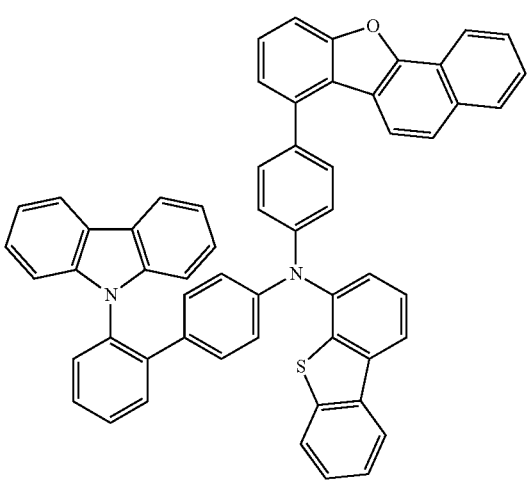
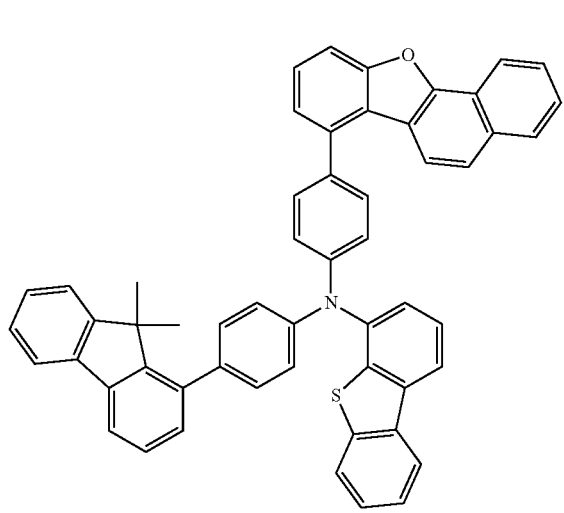
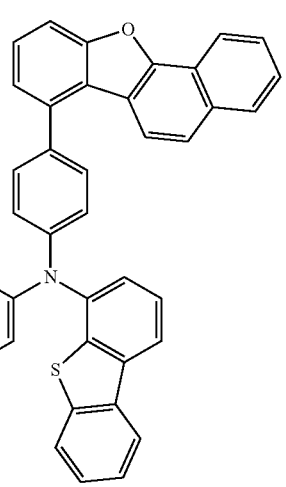

579
-continued
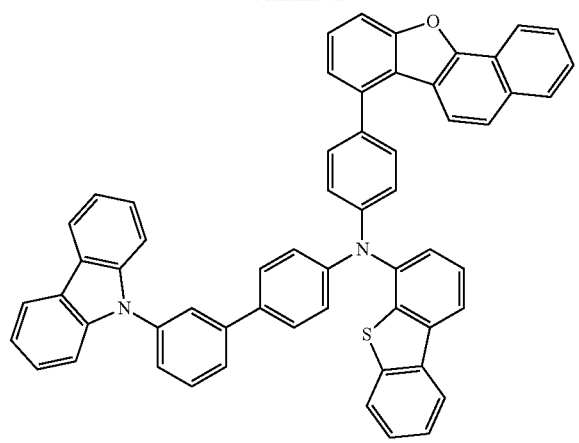
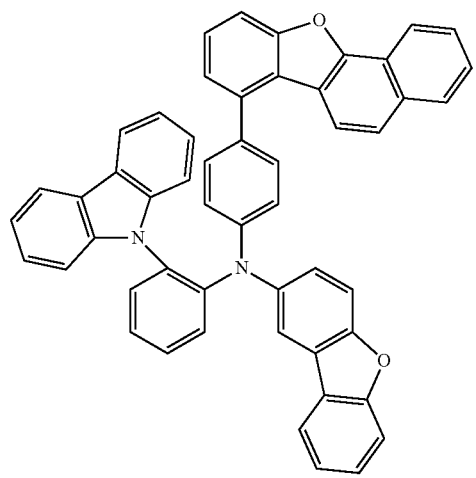
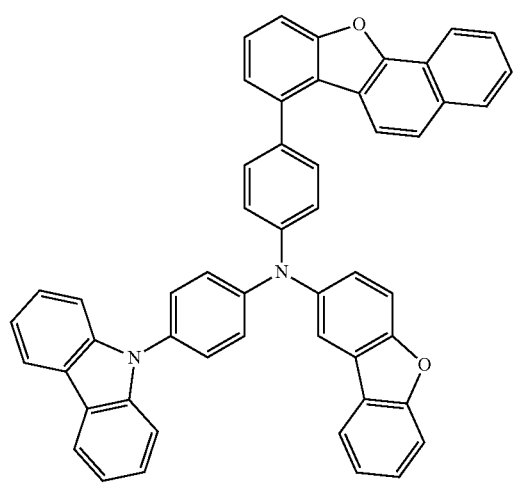
580
-continued
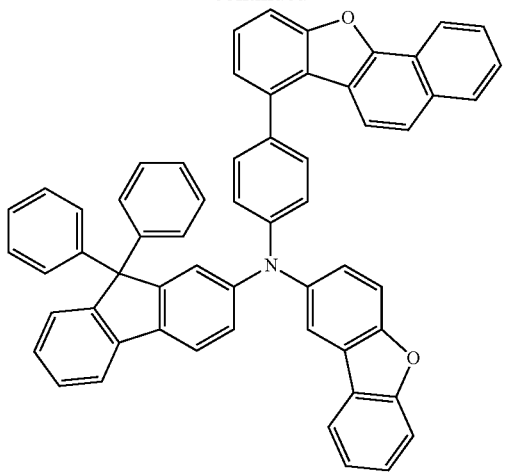
[Chem. 213]
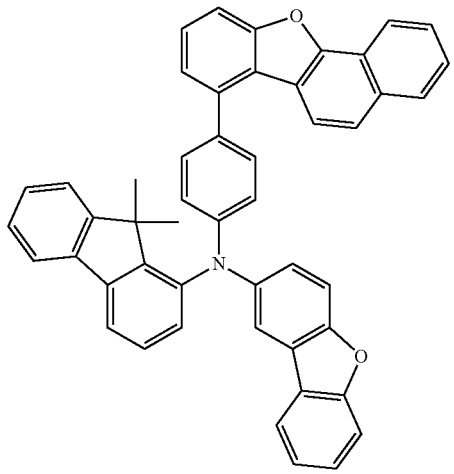
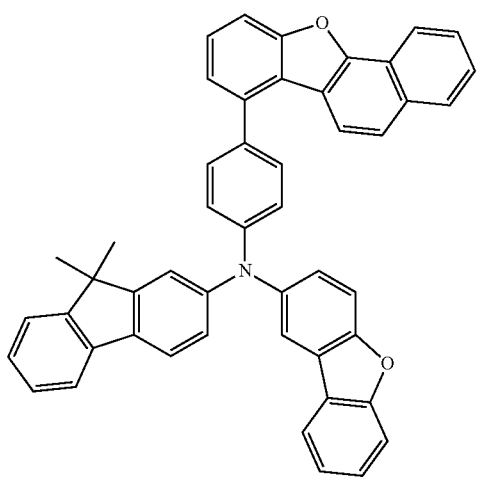

581
-continued
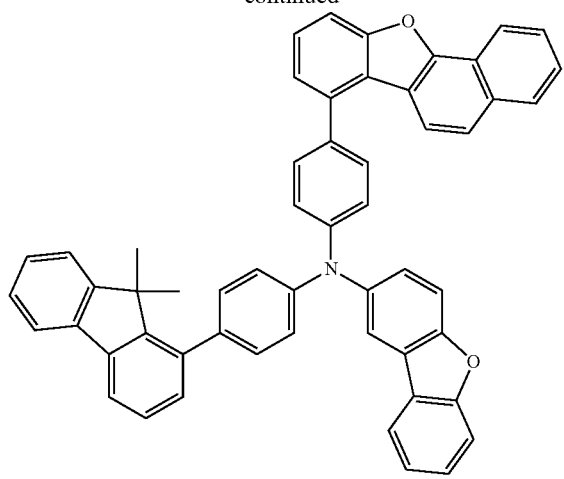
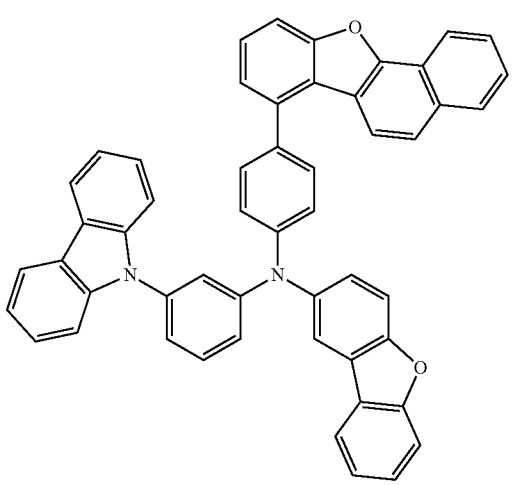
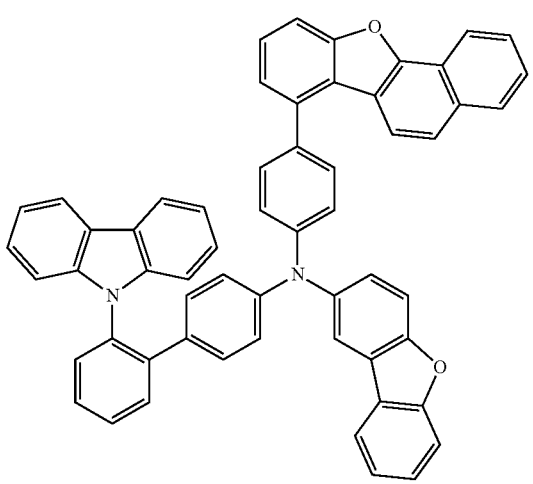
582
-continued
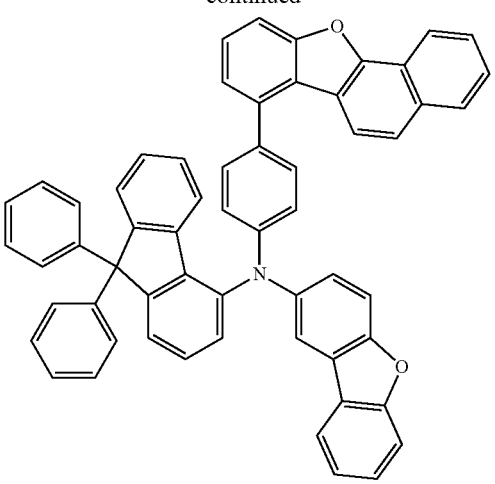
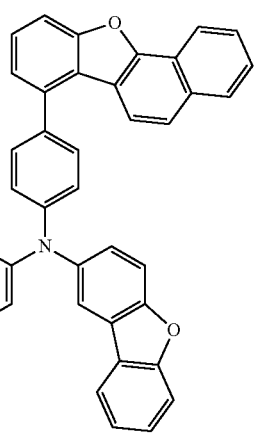
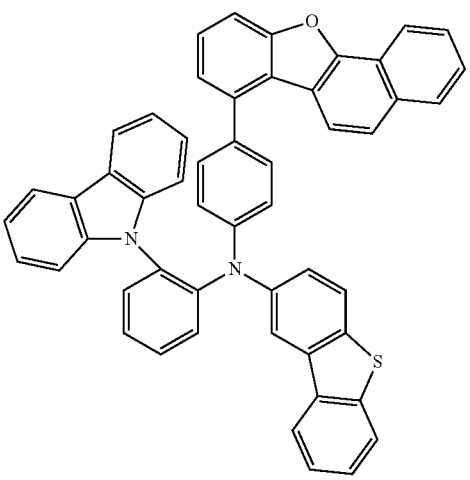

583
-continued
[Chem. 214]
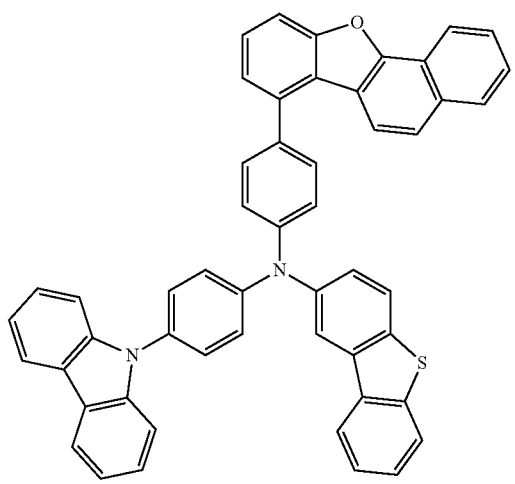
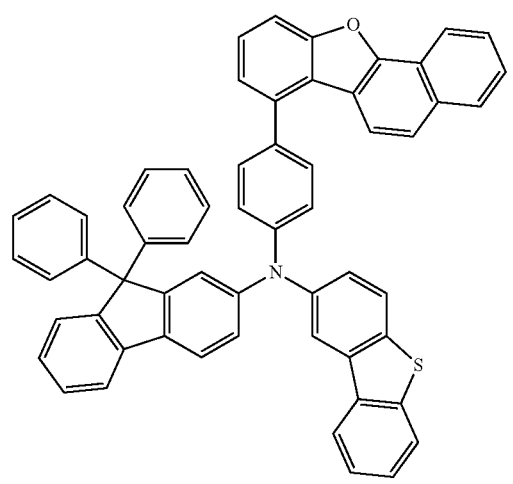
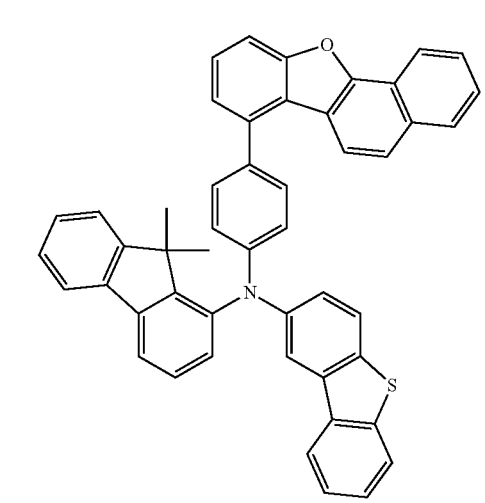
584
-continued
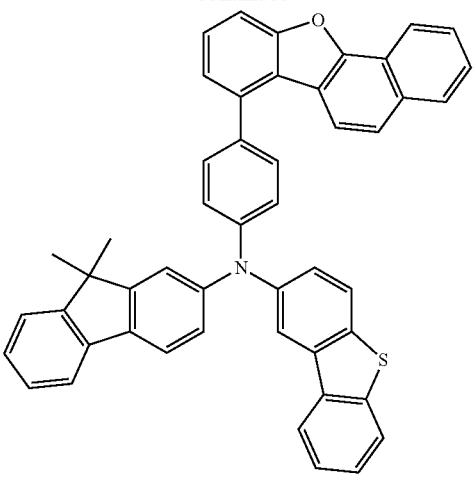
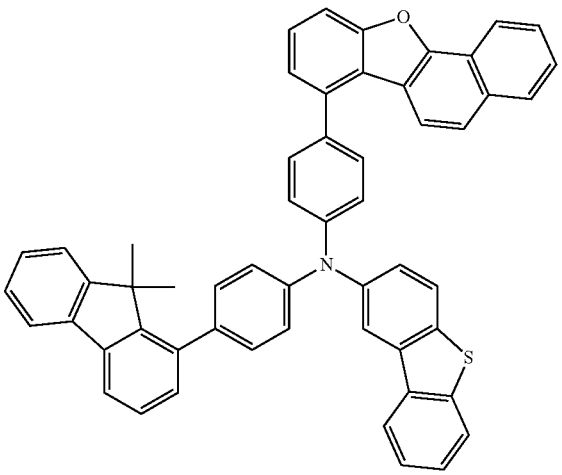
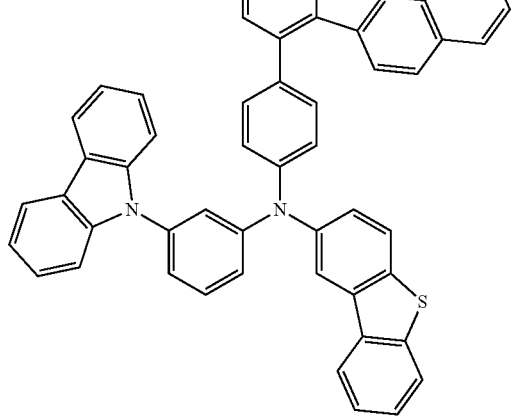

585
-continued
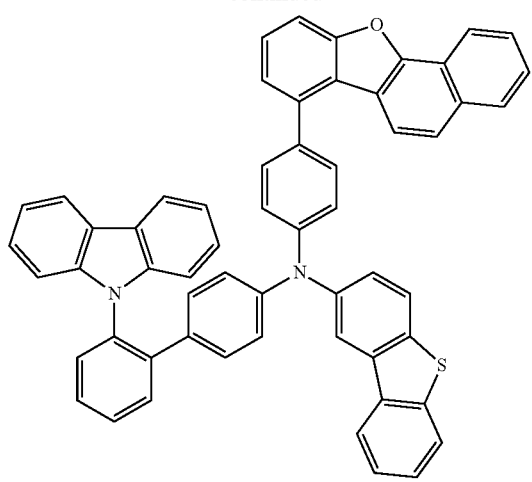
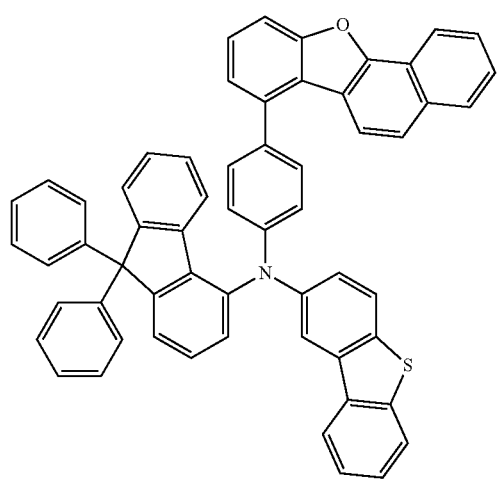
[Chem. 215]
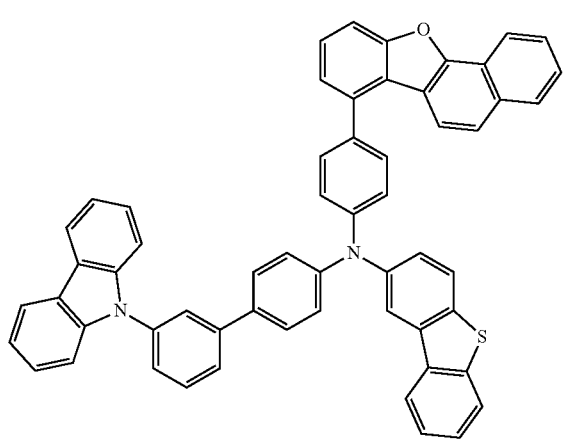
586
-continued
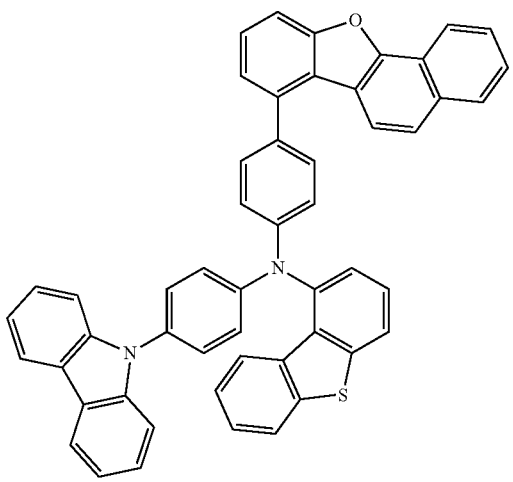
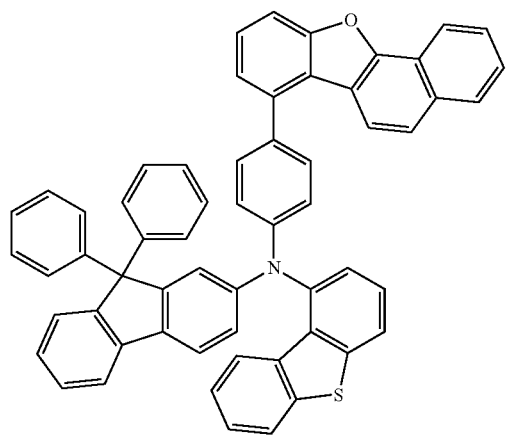

587
-continued
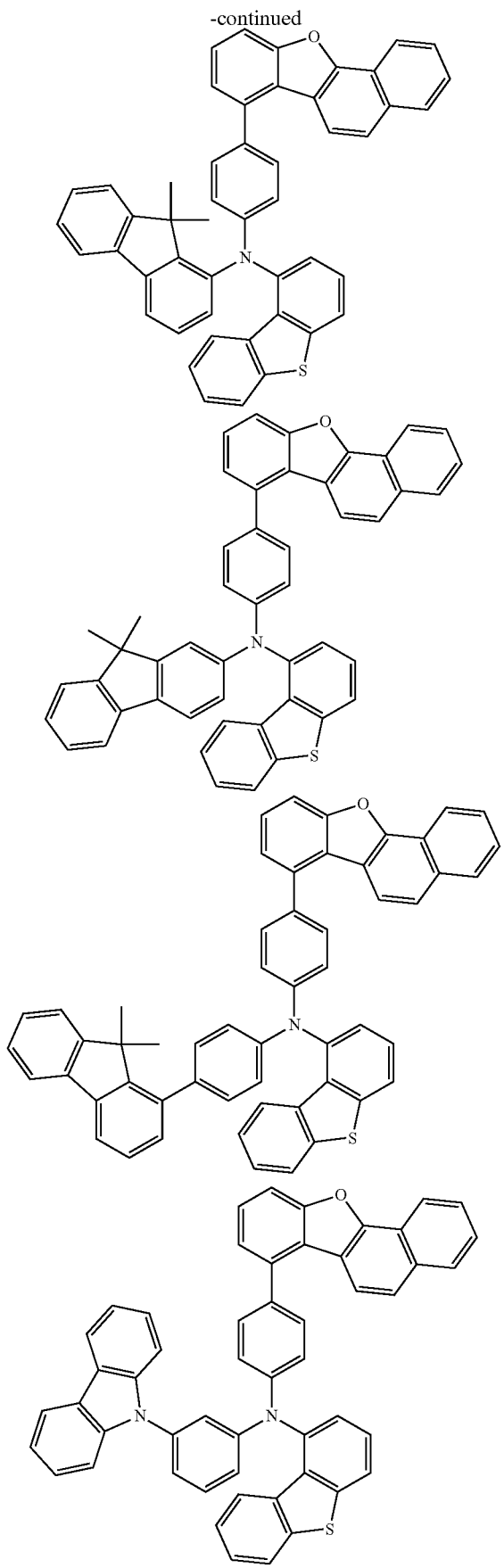
588
-continued
[Chem. 216]
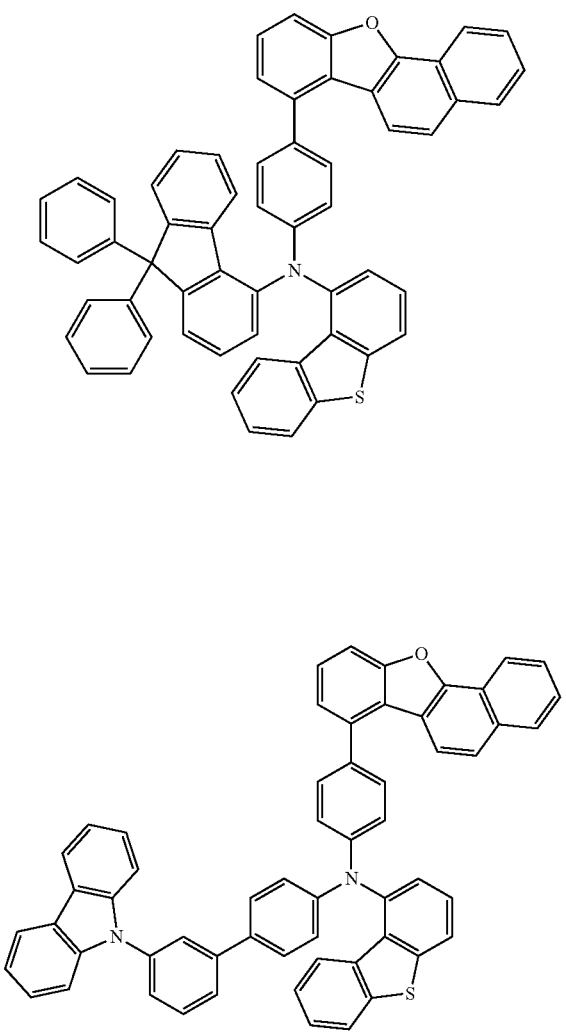

589
-continued
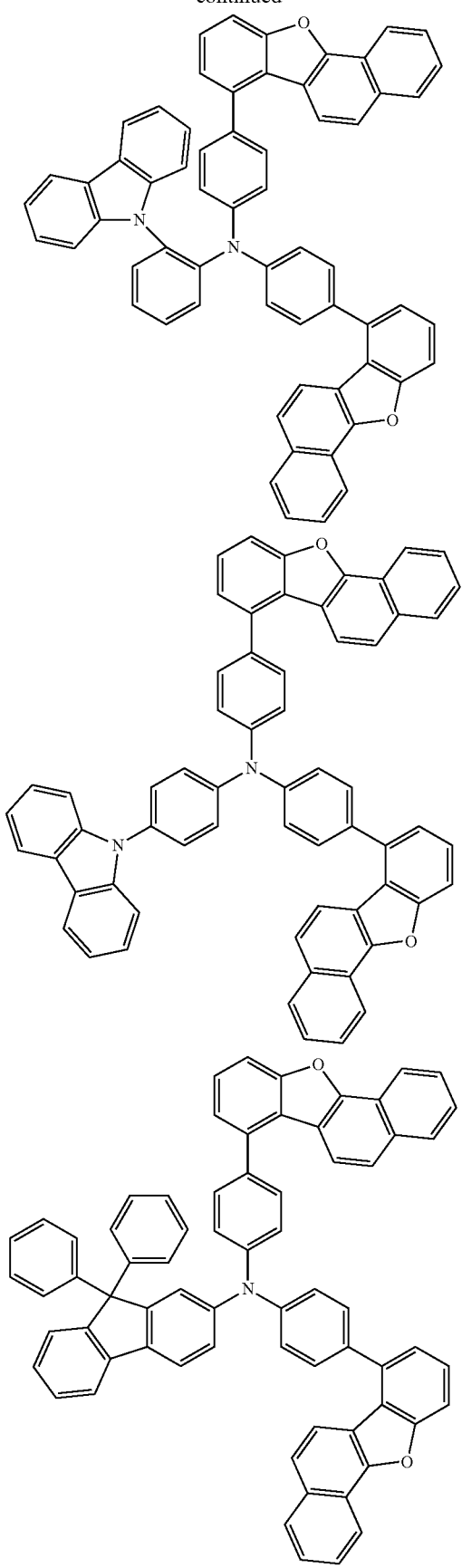
590
-continued
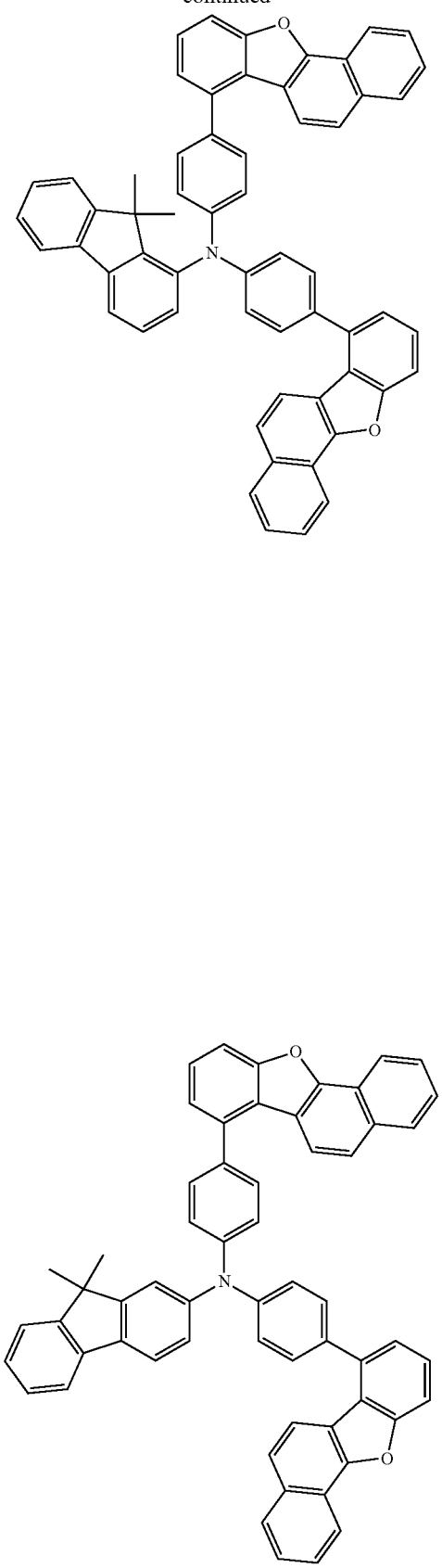

591
-continued
[Chem. 217]
592
-continued
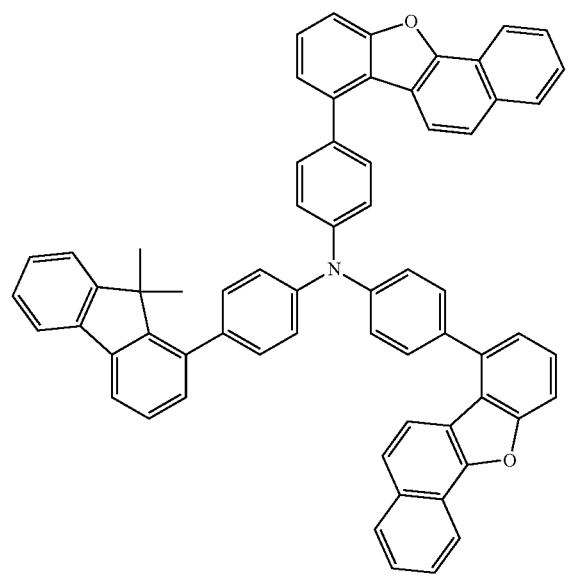
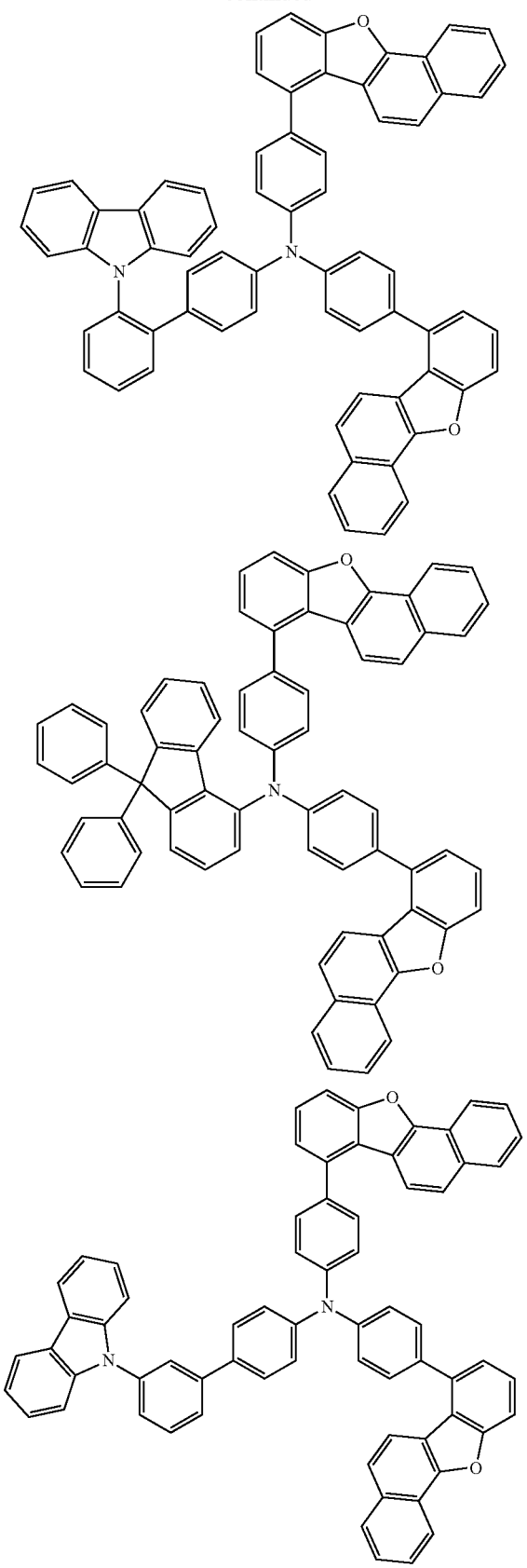

593
-continued
[Chem. 218]
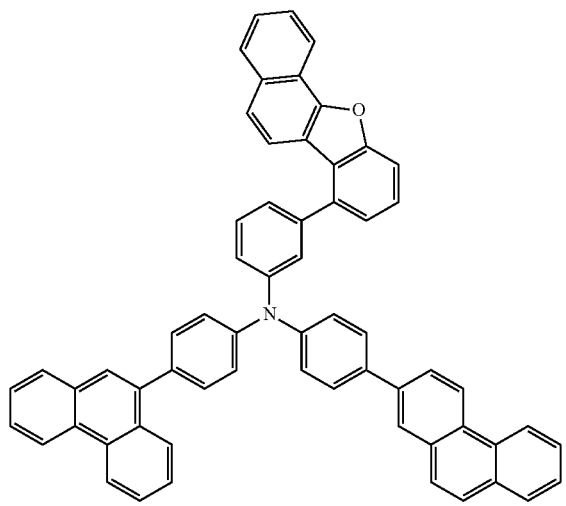
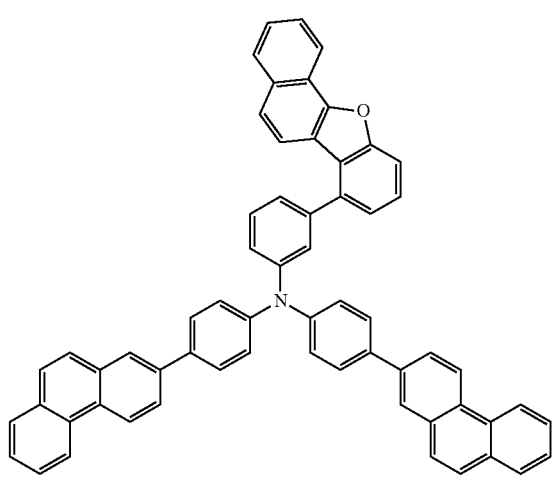
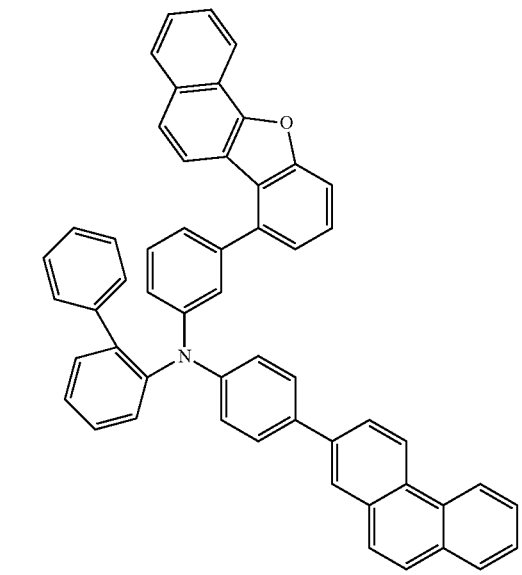
594
-continued
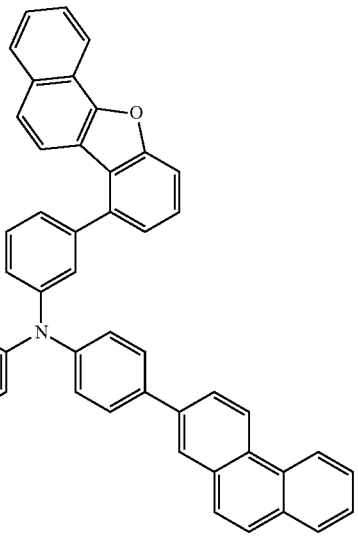
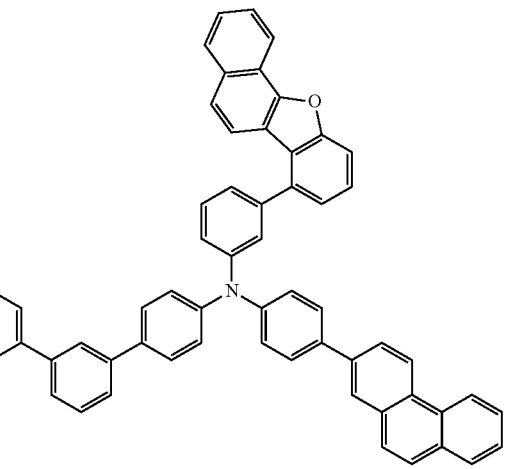

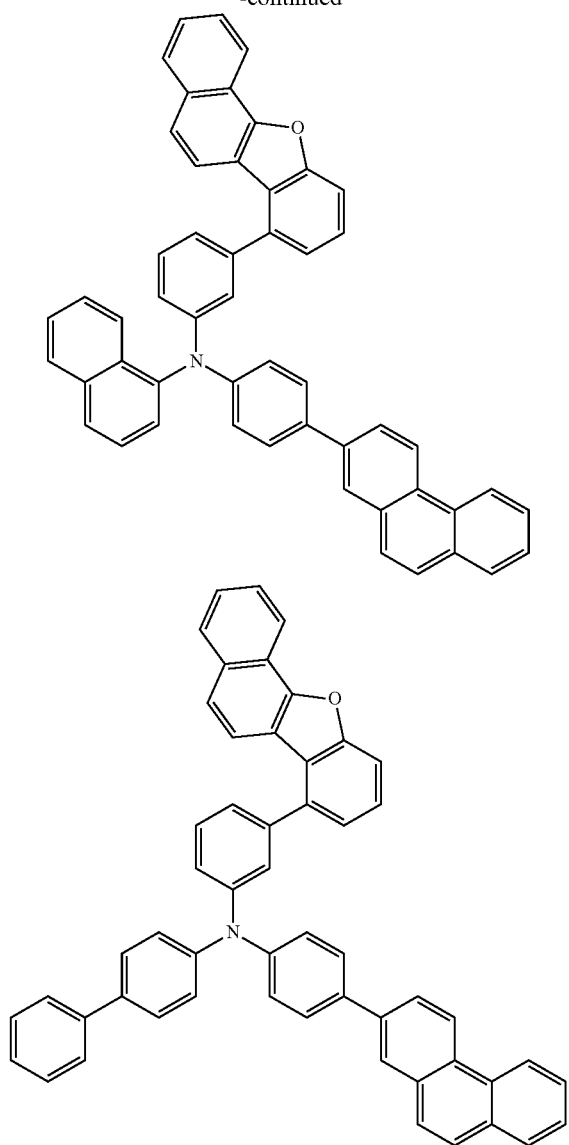
[Chem. 219]
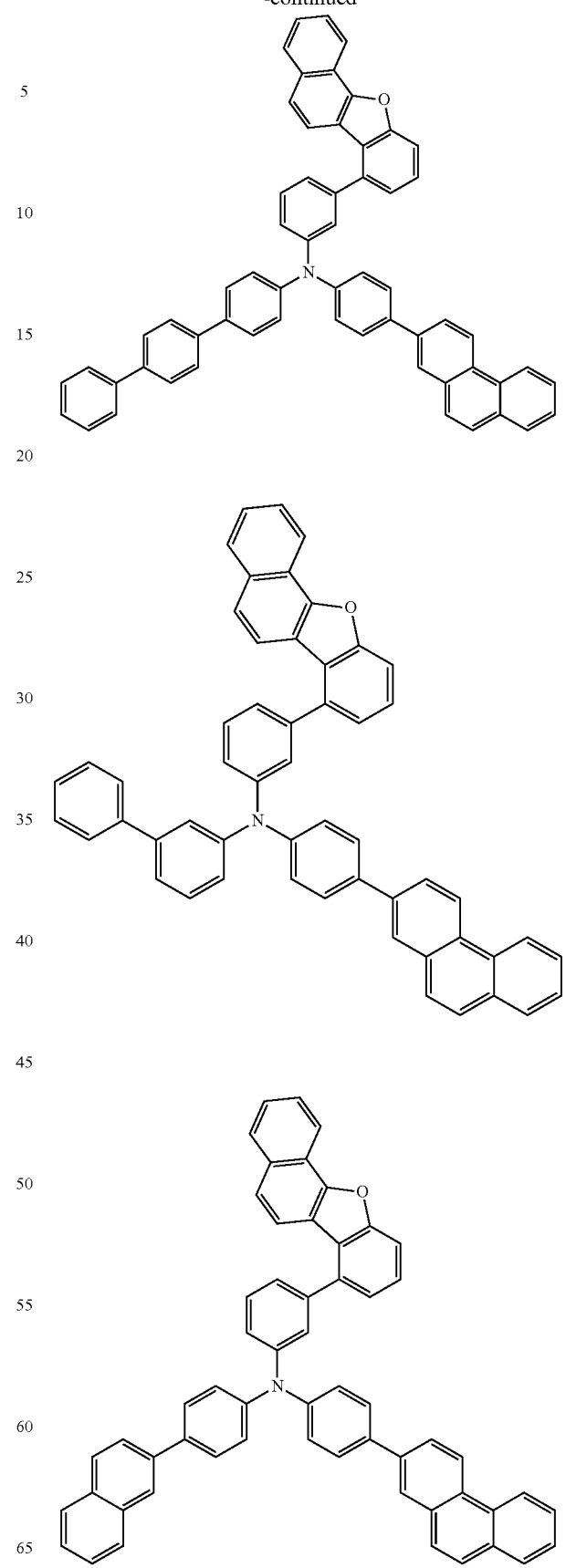

597
-continued
598
-continued
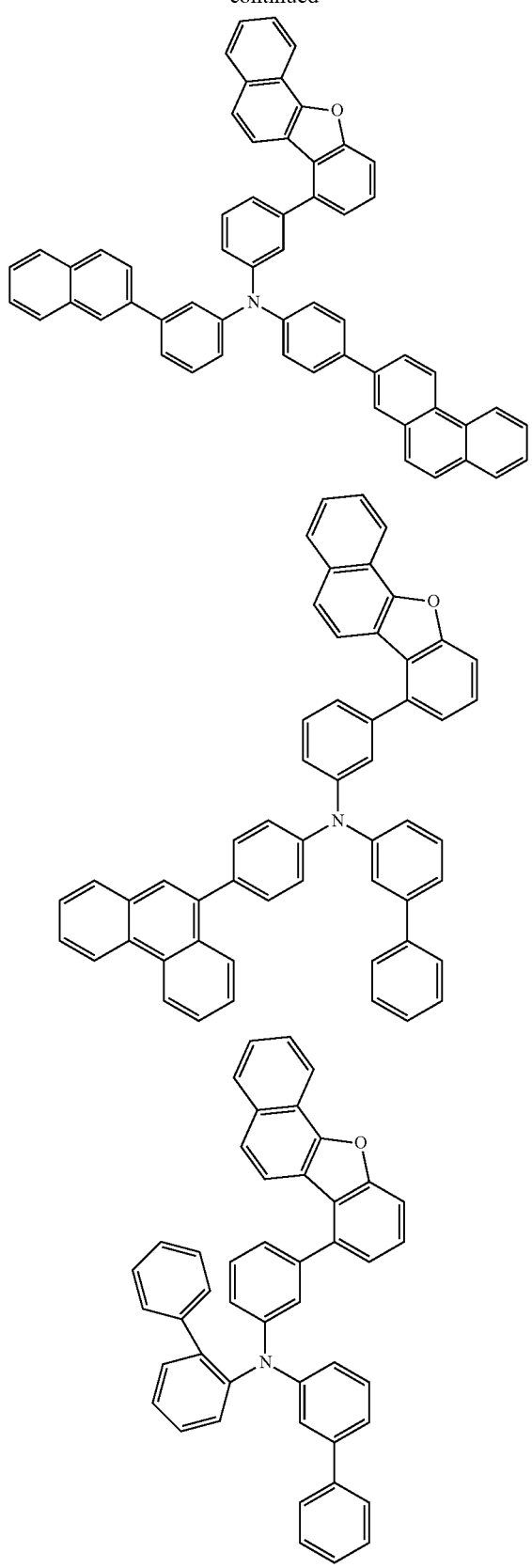
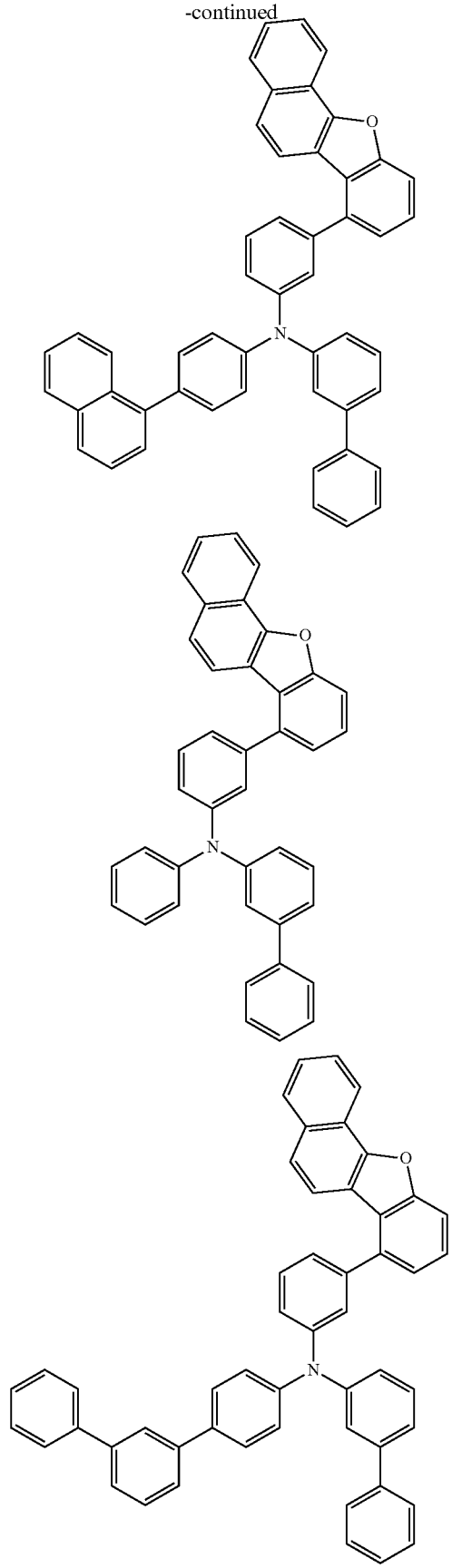

[Chem. 220]
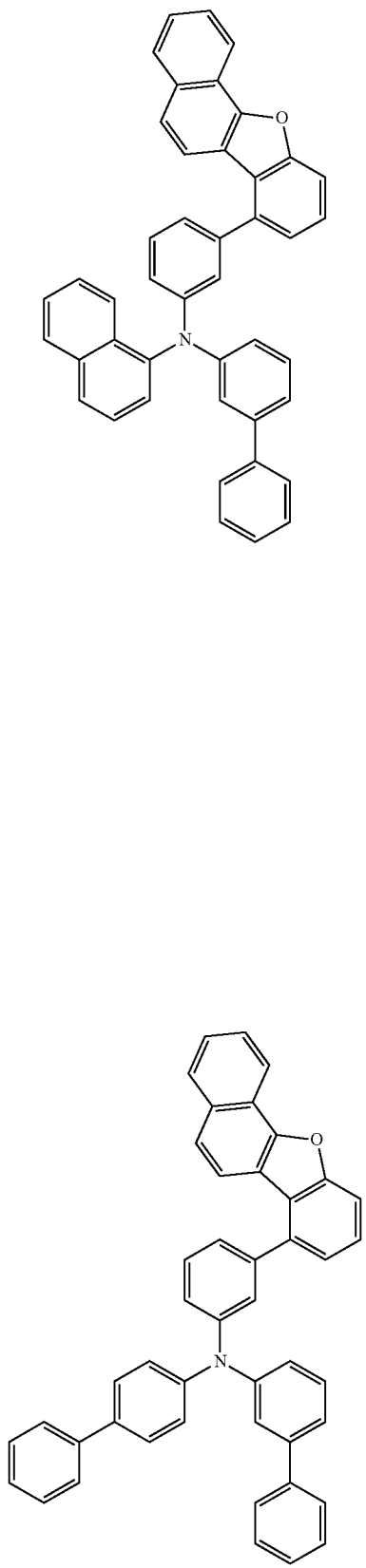
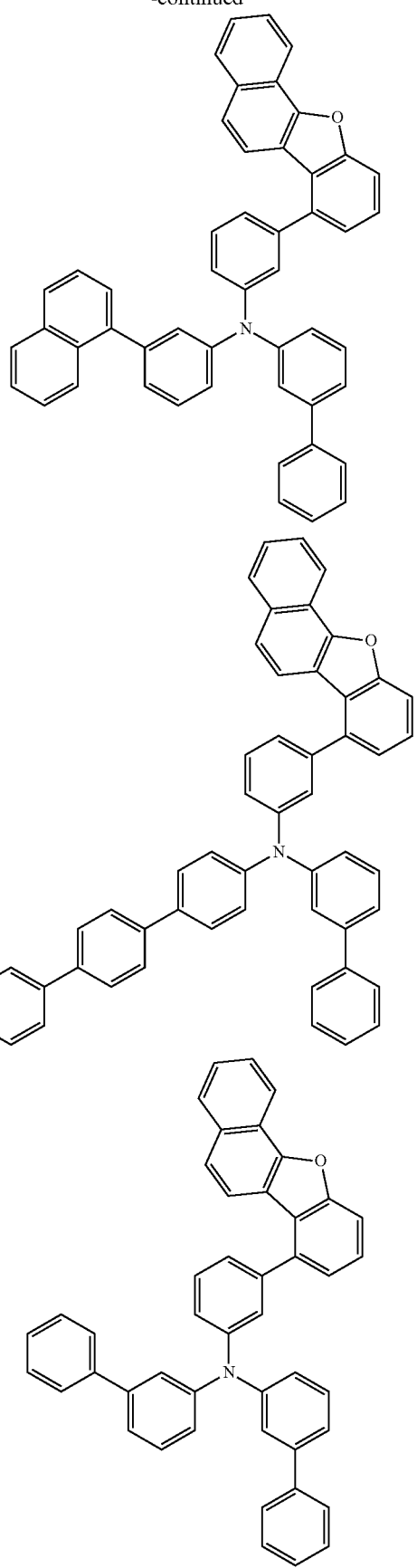

601 -continued
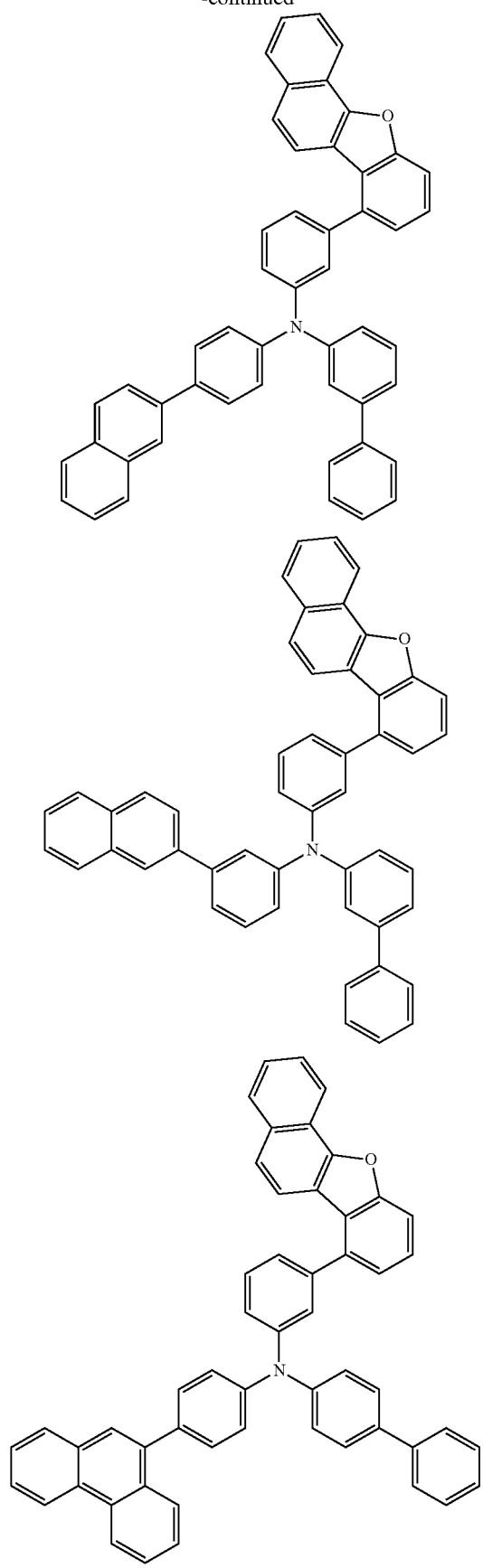
602 -continued
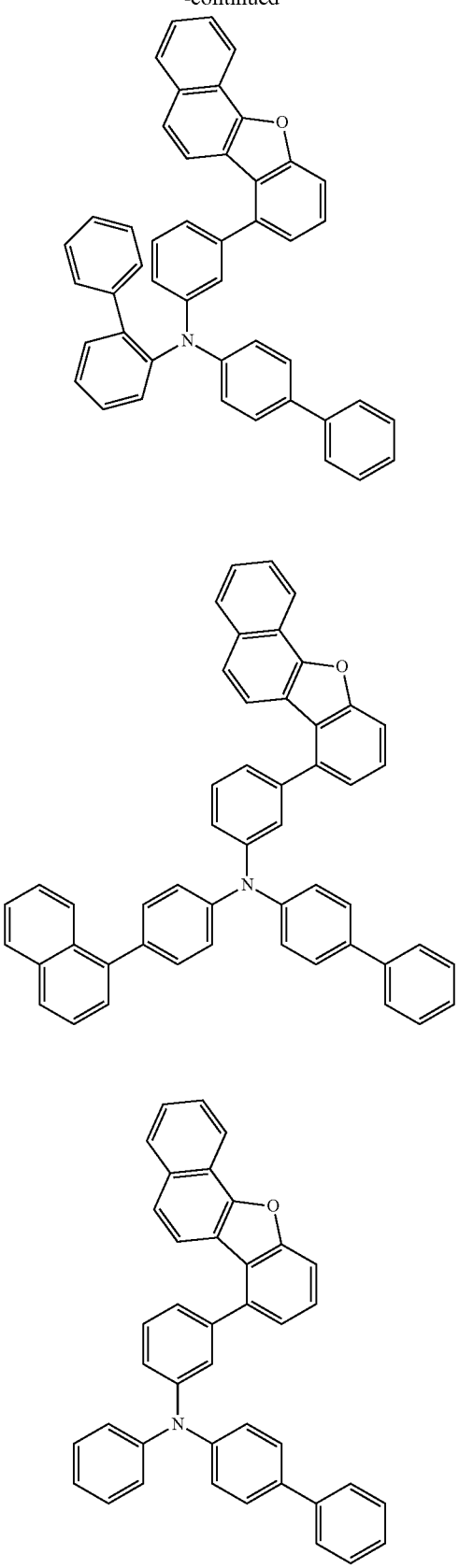

603
-continued
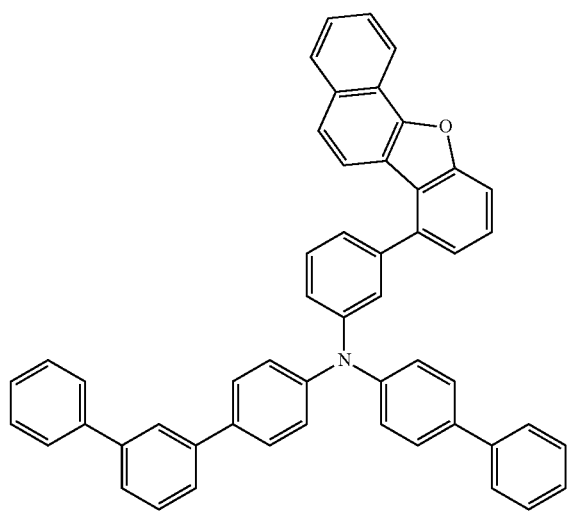
[Chem. 221]
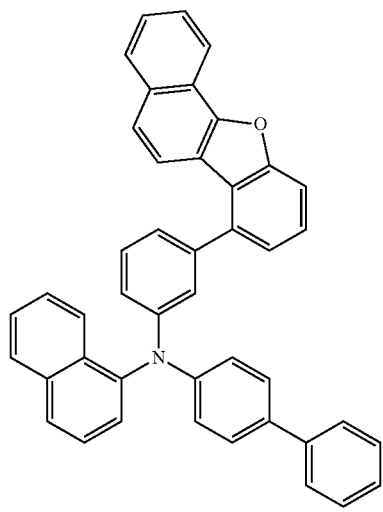
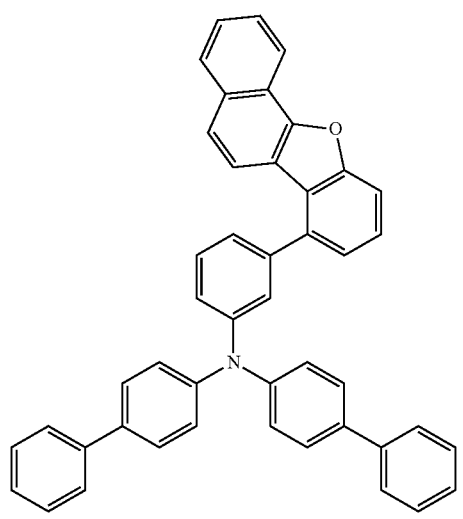
604
-continued
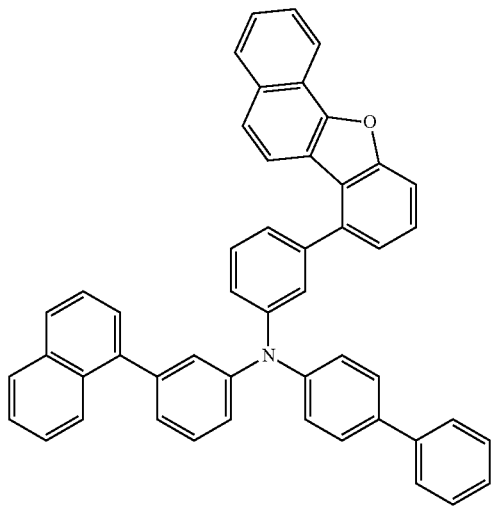
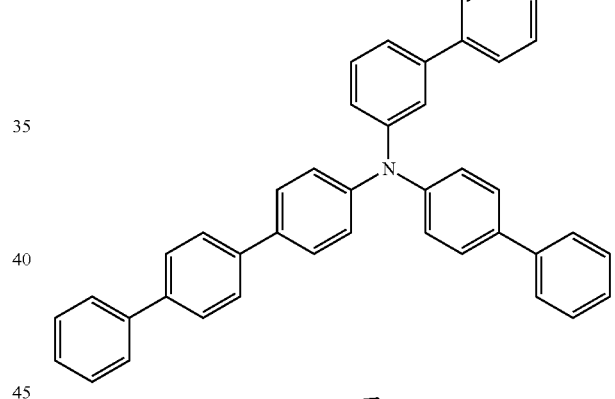
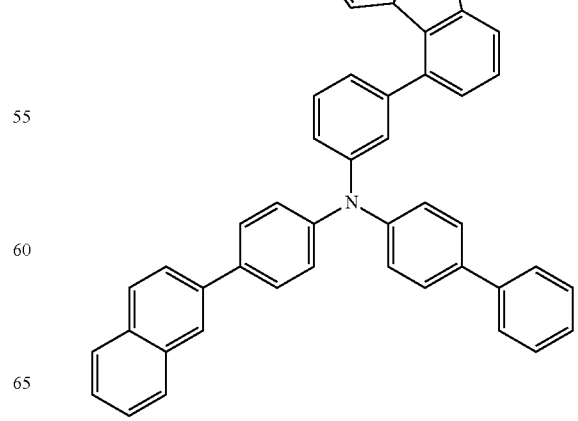

| 605 | 606 |
|---|---|
| 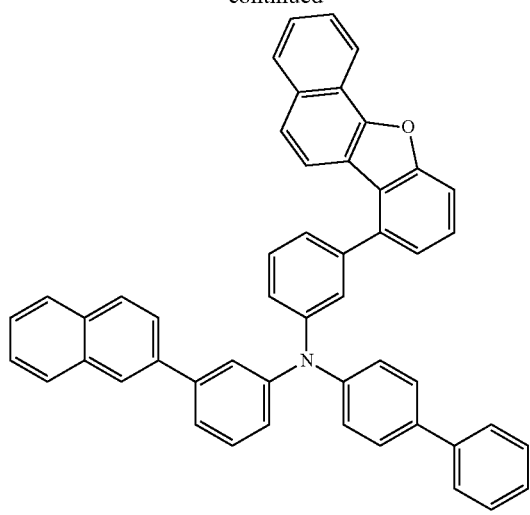 | 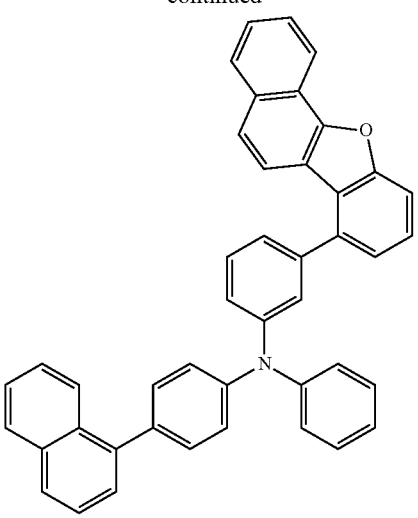 |
| 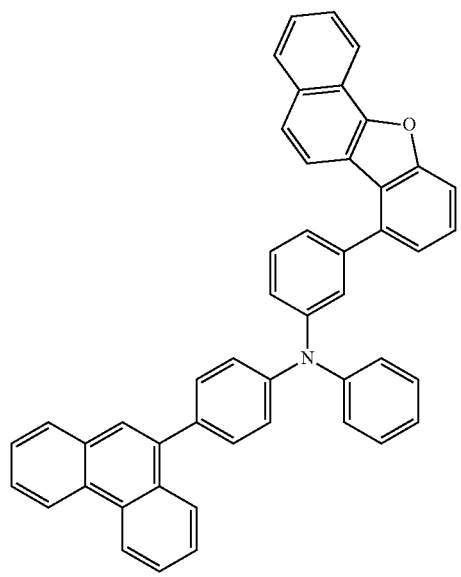 | 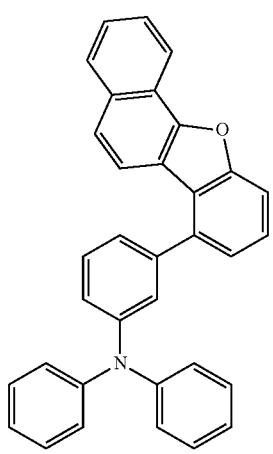 |
| 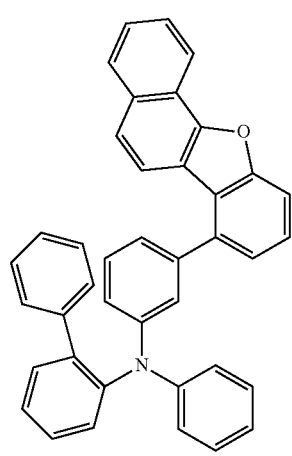 | 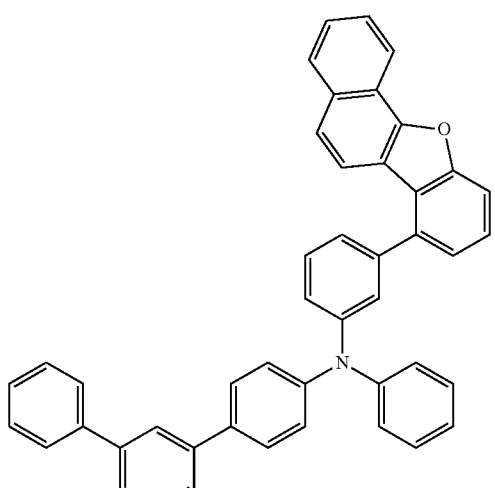 |

607
-continued
[Chem. 222]
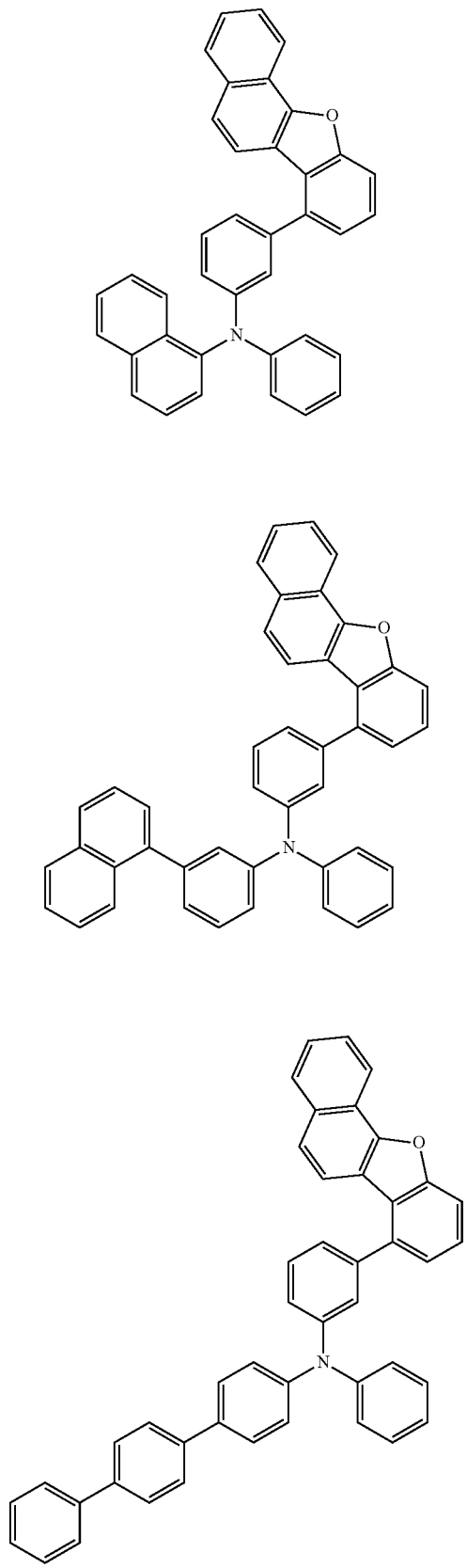
608
-continued
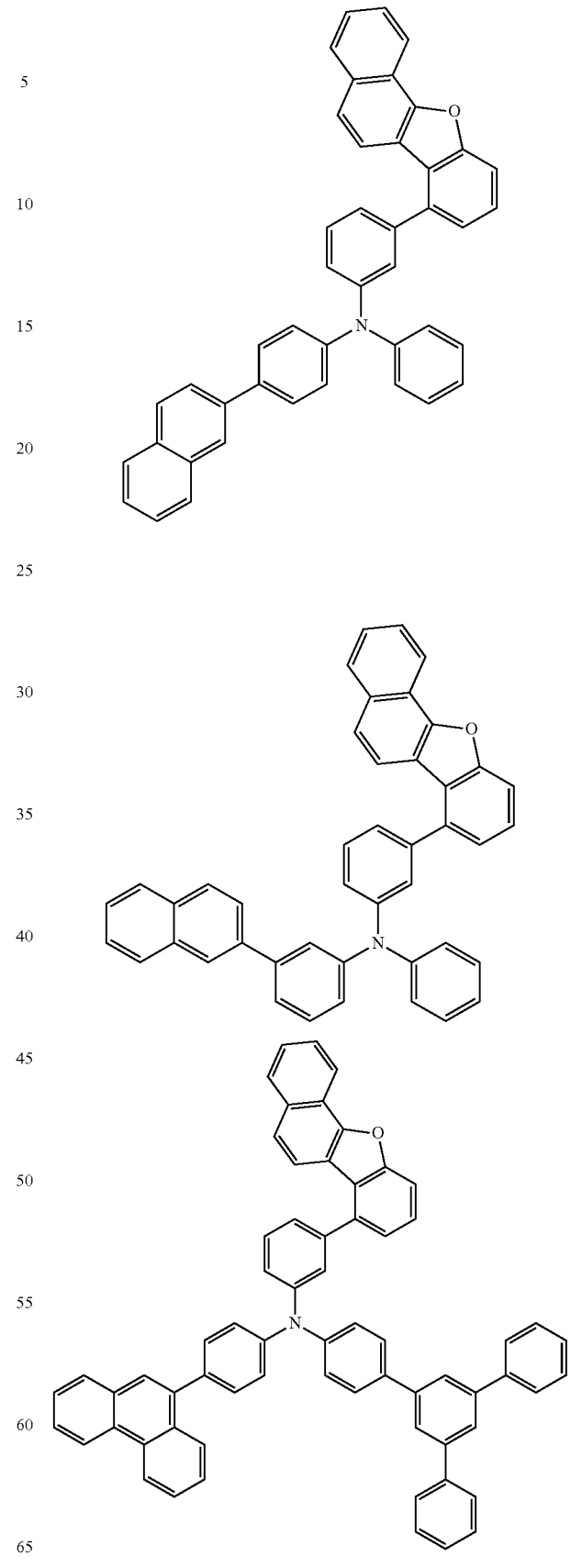

609
-continued
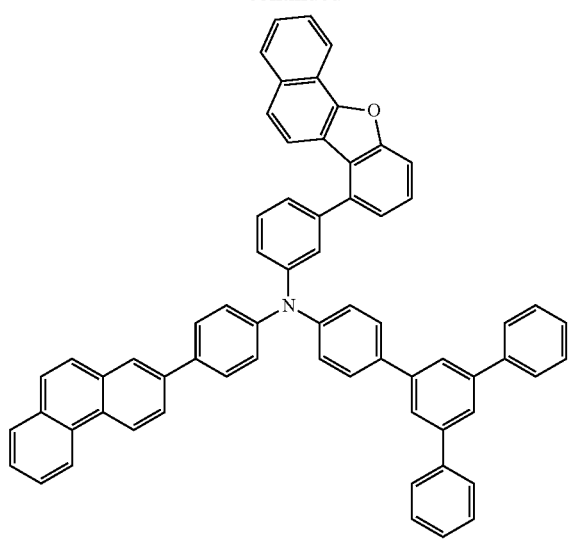
610
-continued
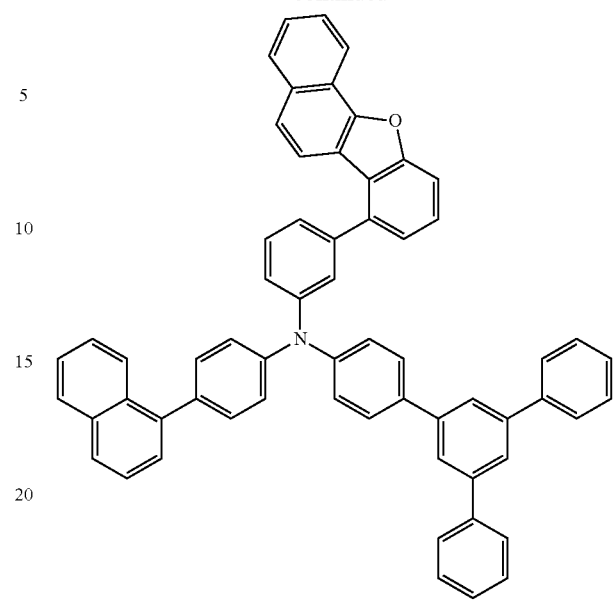
[Chem. 223]
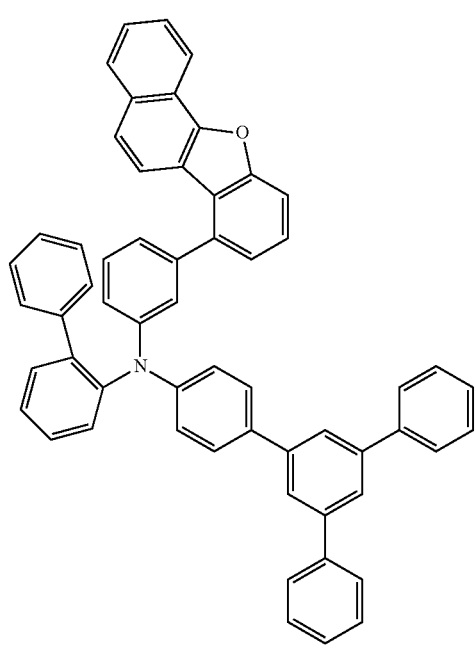
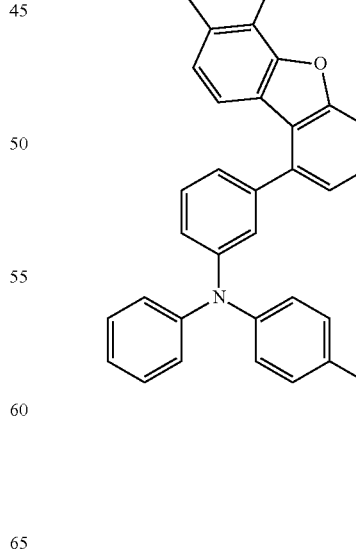

611
-continued
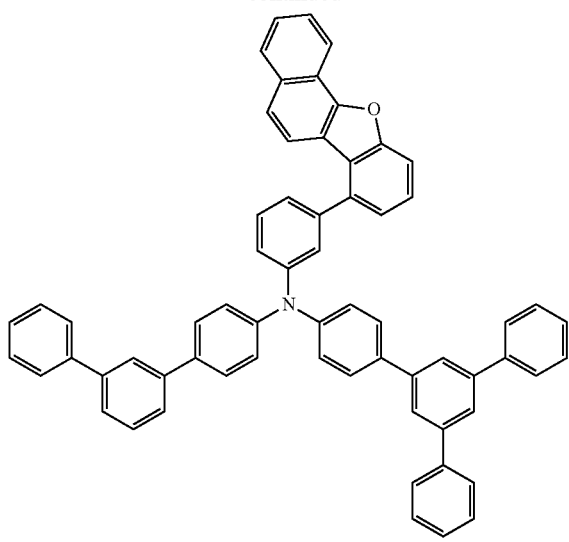
612
-continued
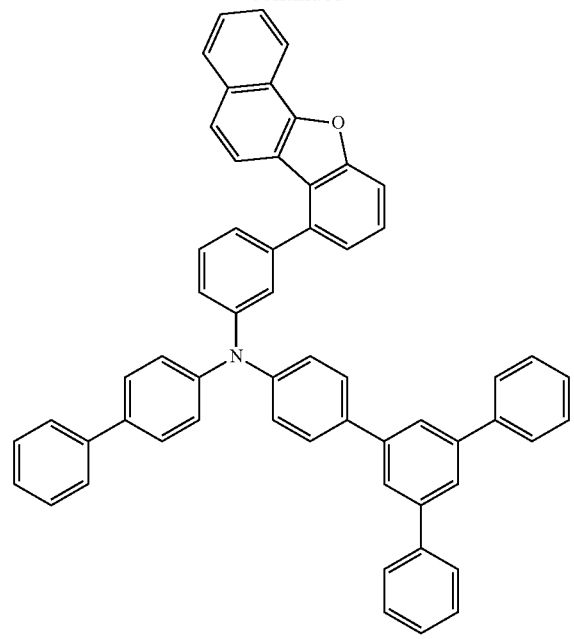
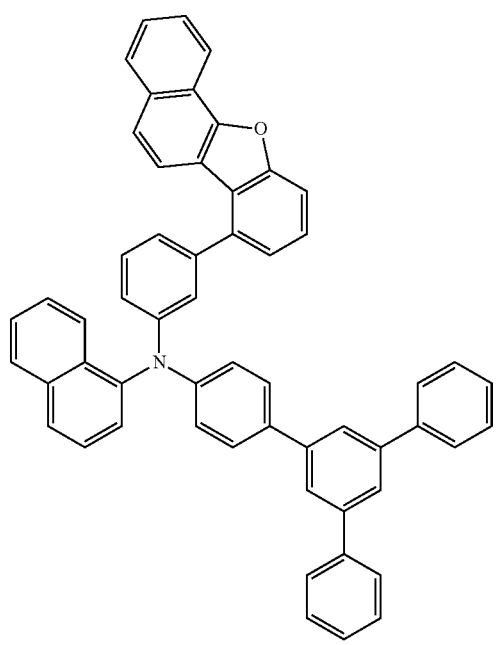
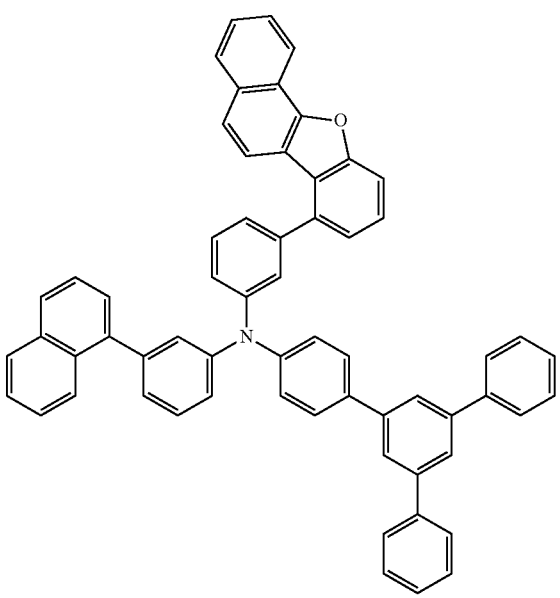

613
-continued
614
-continued
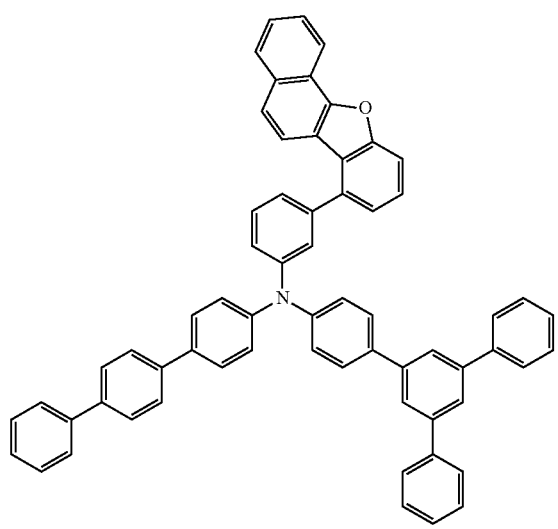
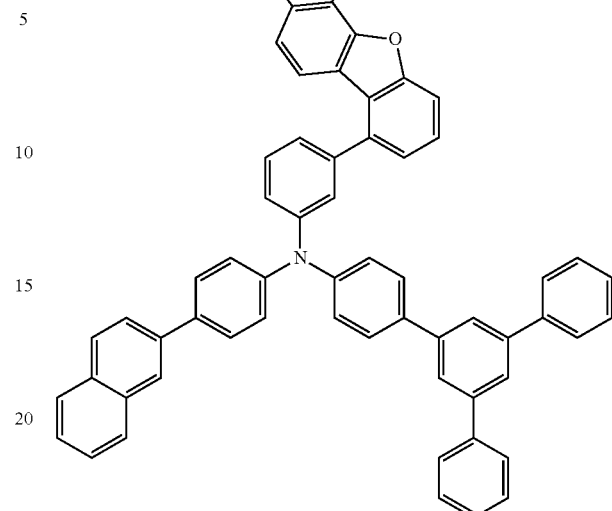
[Chem. 224]
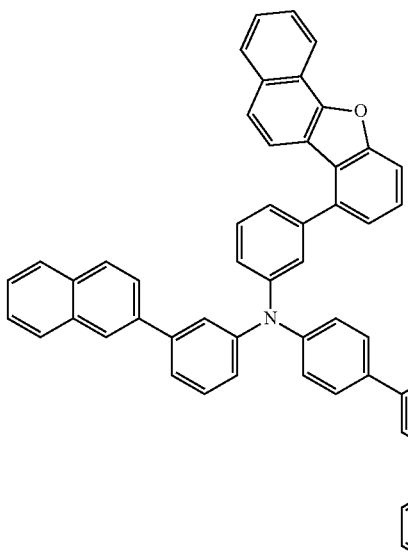
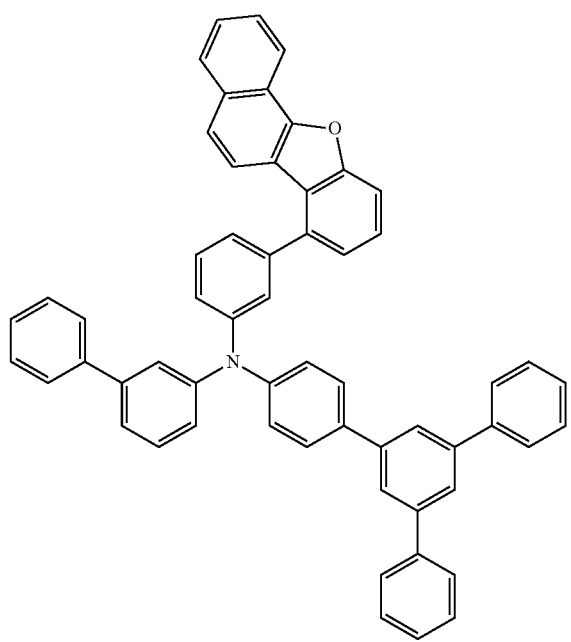
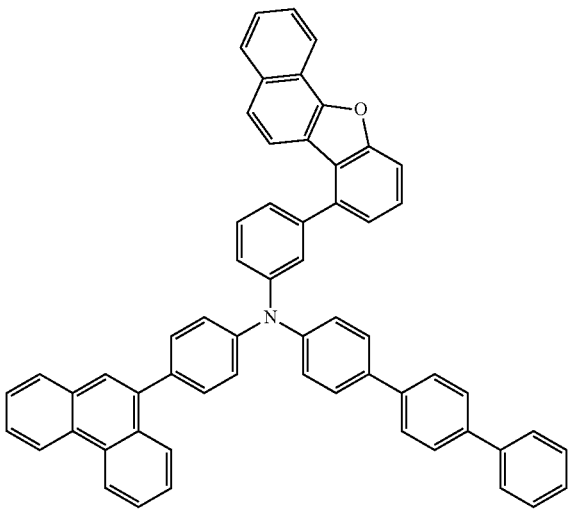

615
-continued
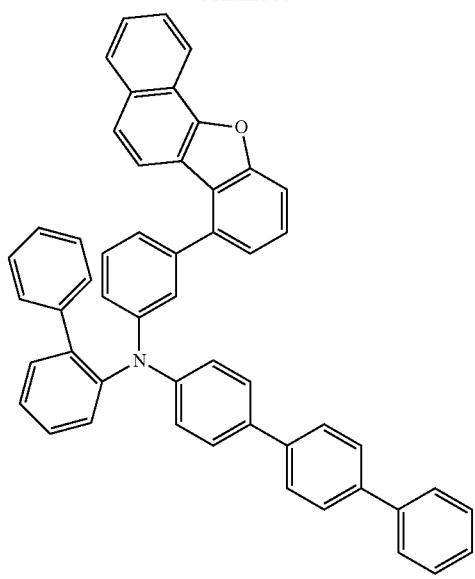
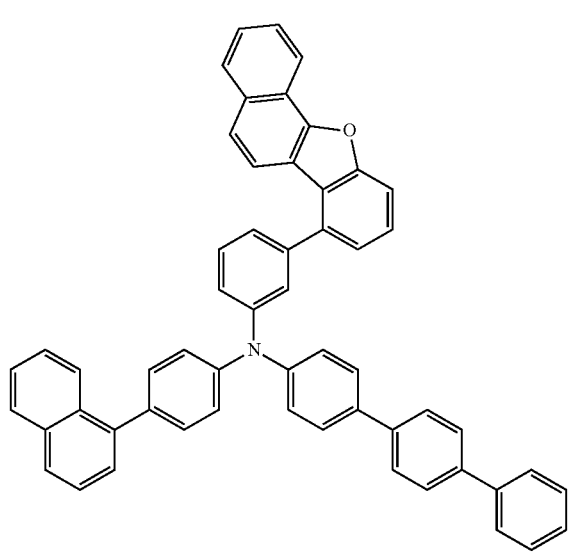
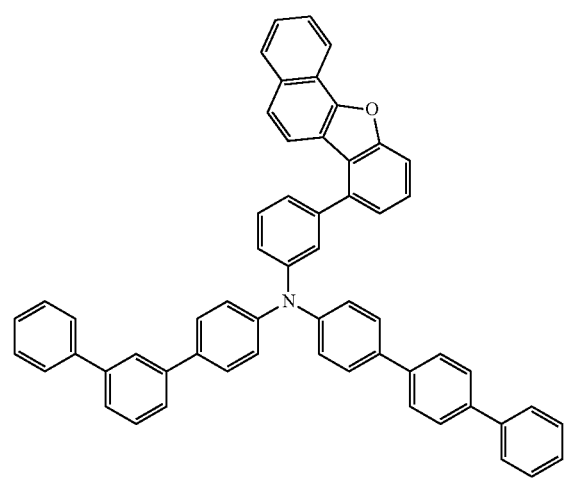
616
-continued
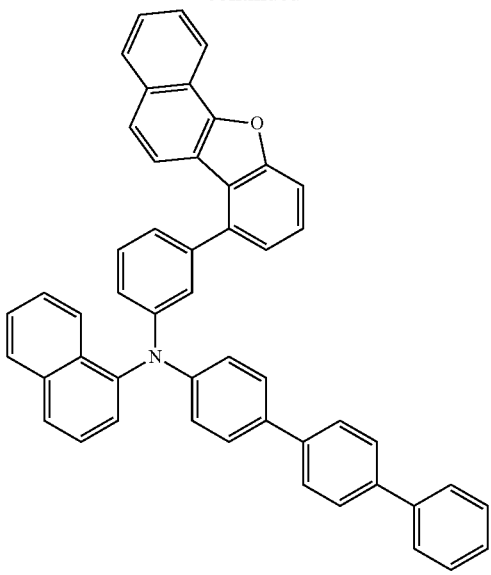
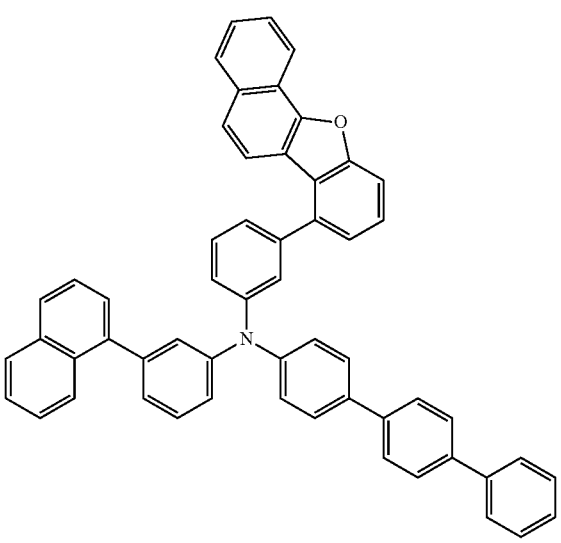
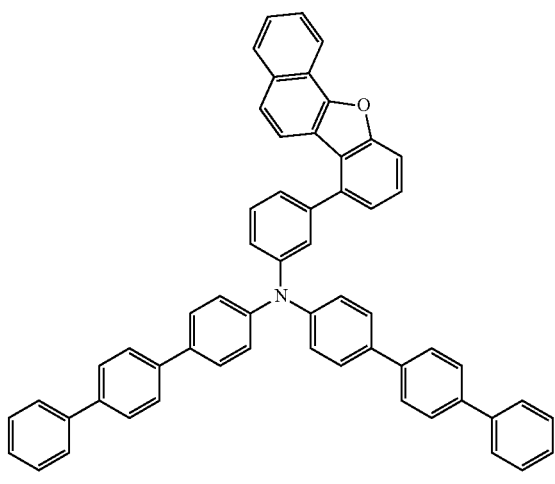

617
-continued
[Chem. 225]
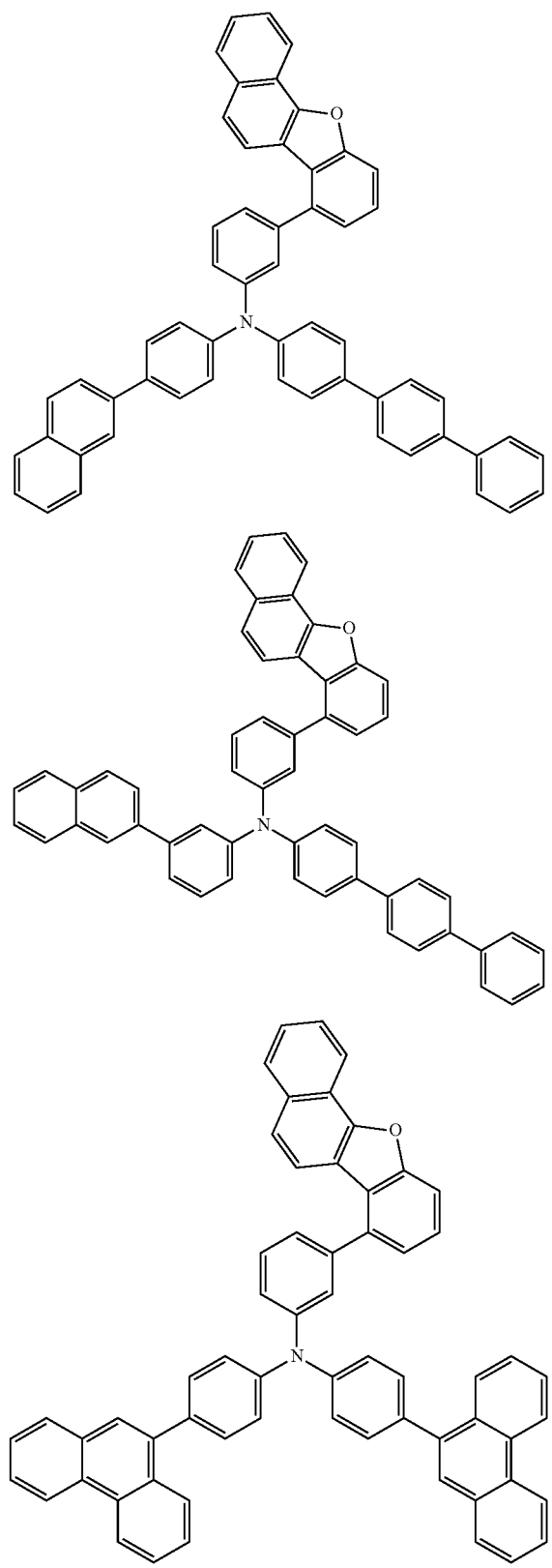
618
-continued
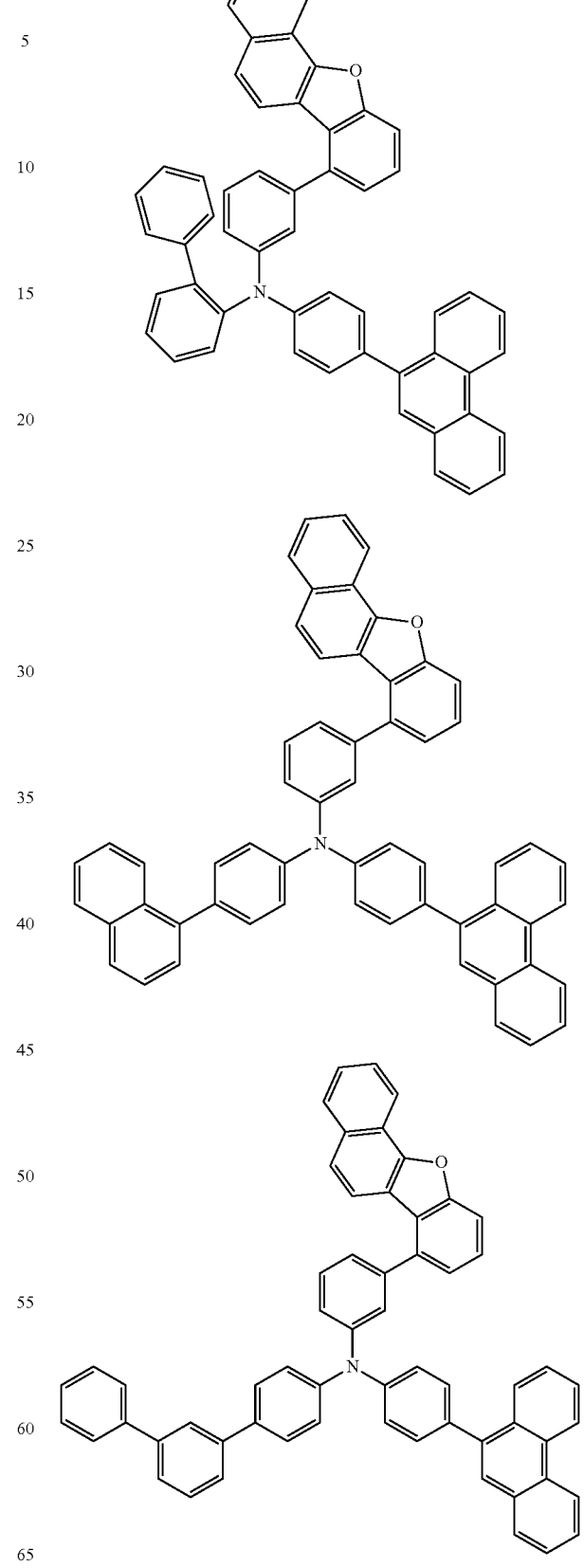

619
-continued
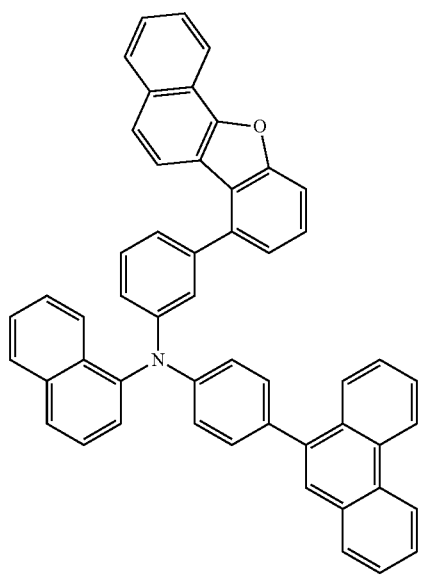
620
-continued
[Chem. 226]
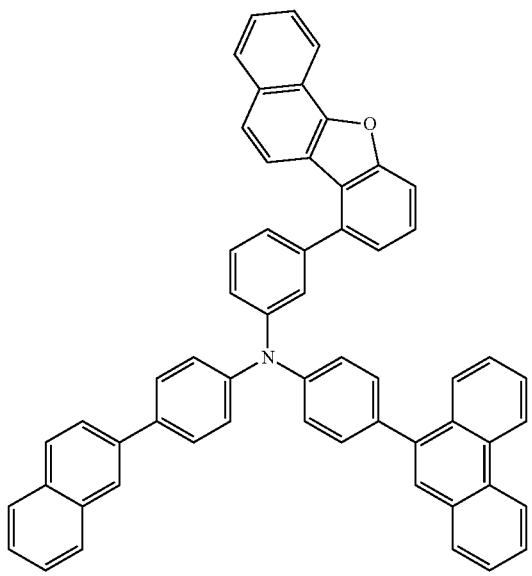
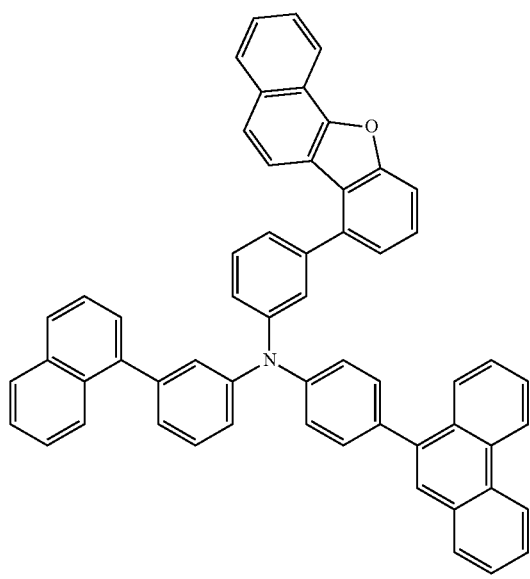
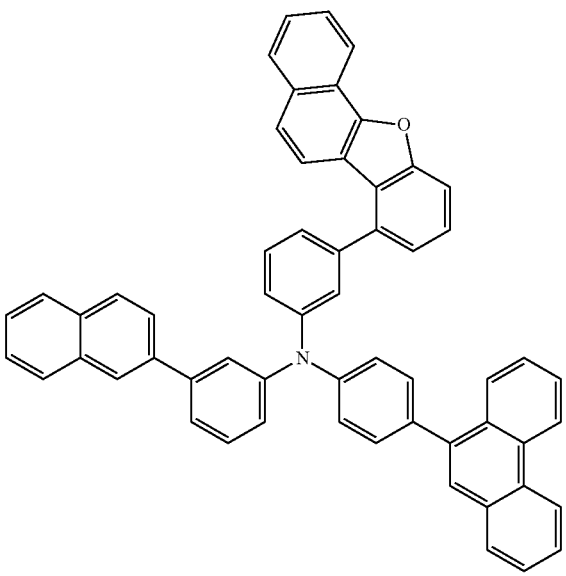

621
-continued
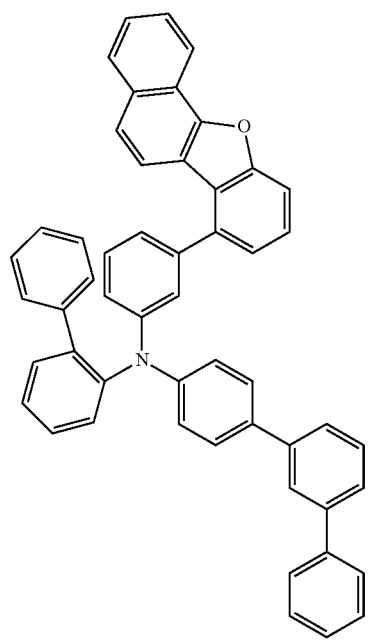
622
-continued
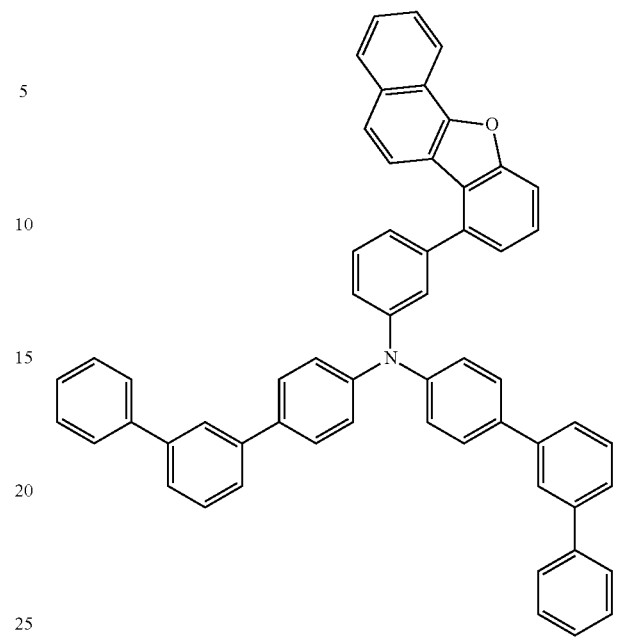
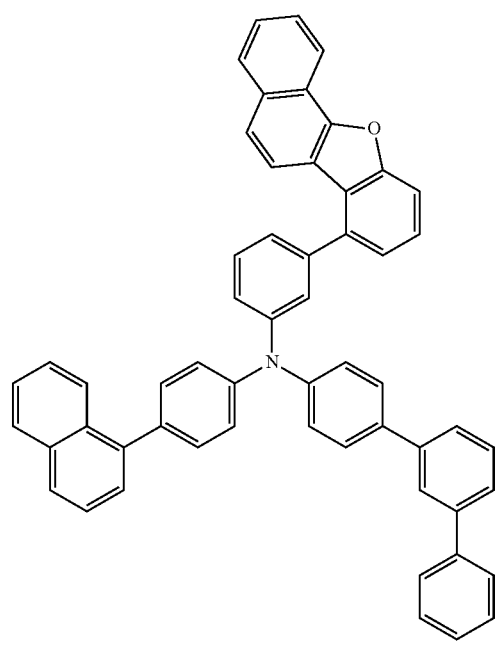
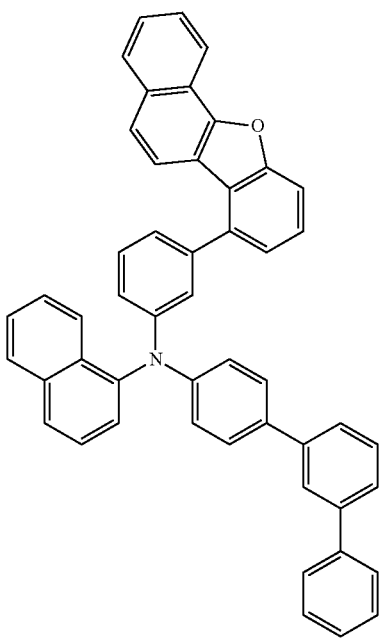

623
-continued
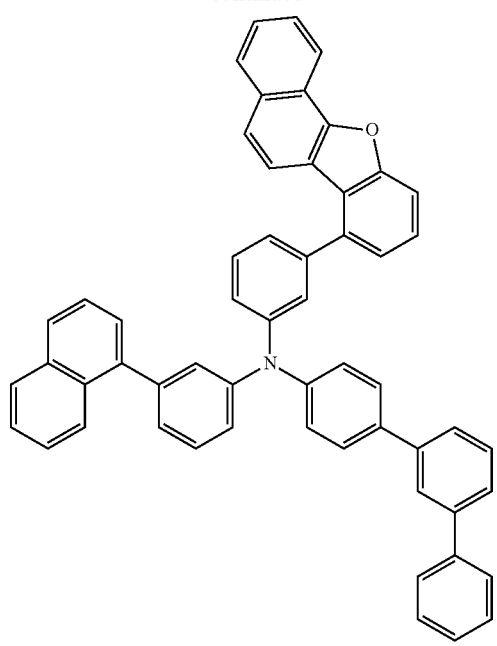
624
-continued
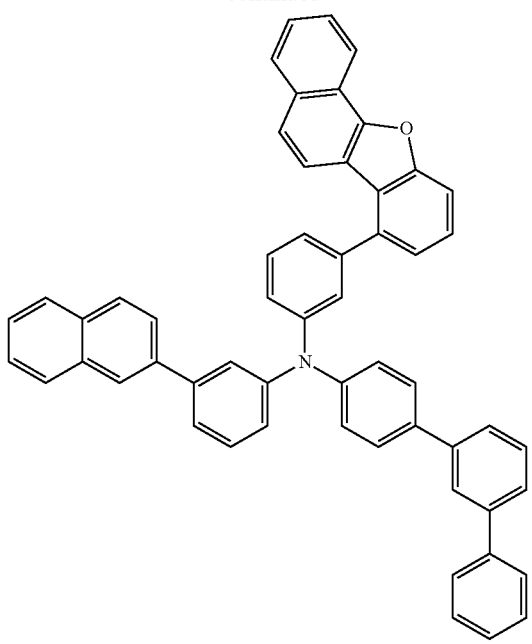
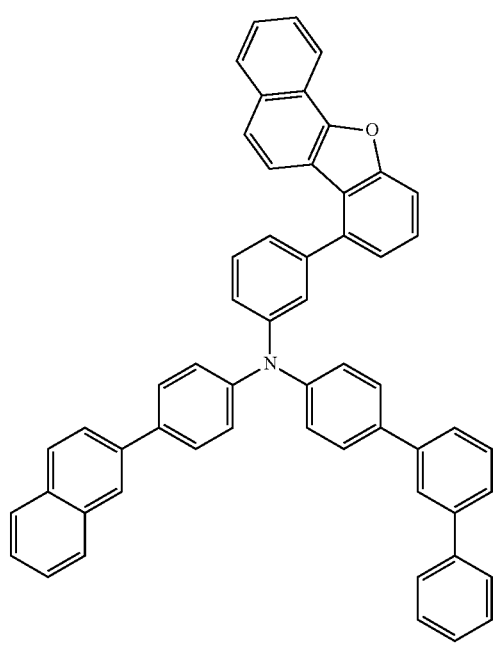

625
-continued
[Chem. 227]
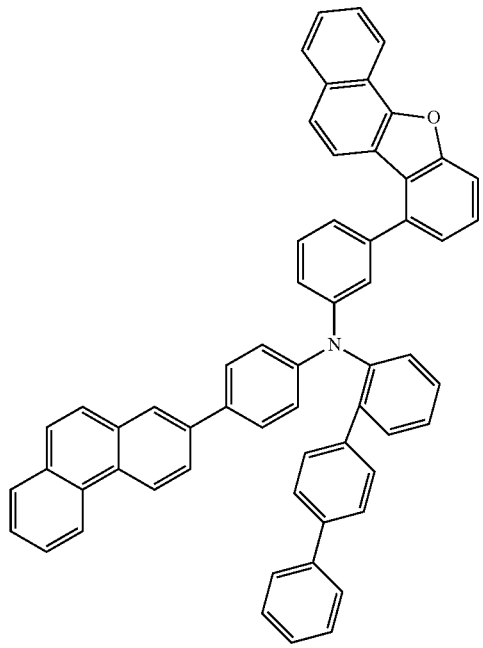
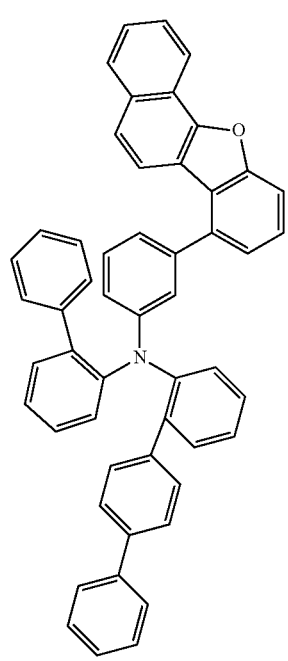
626
-continued
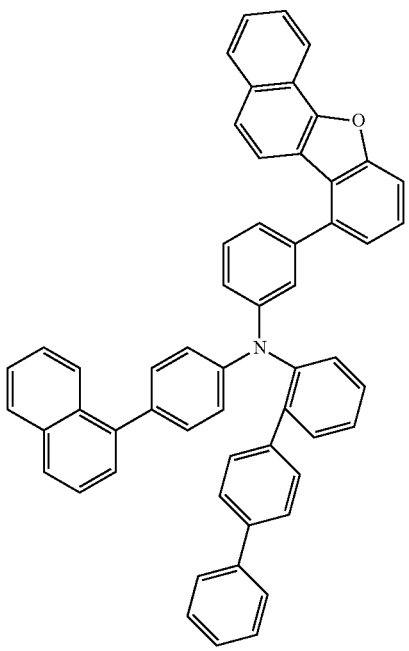
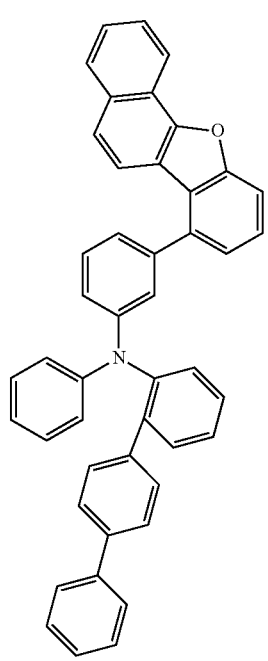

627
-continued
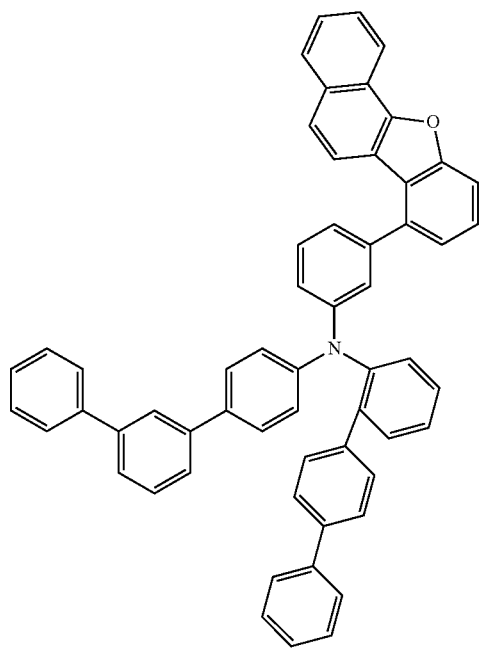
628
-continued
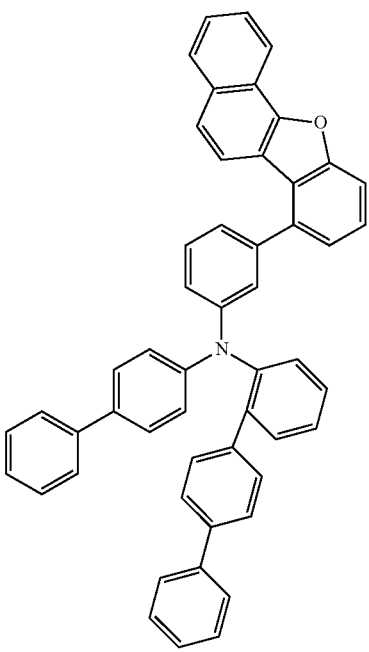
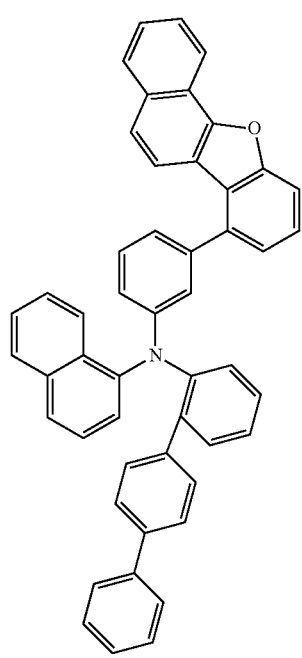
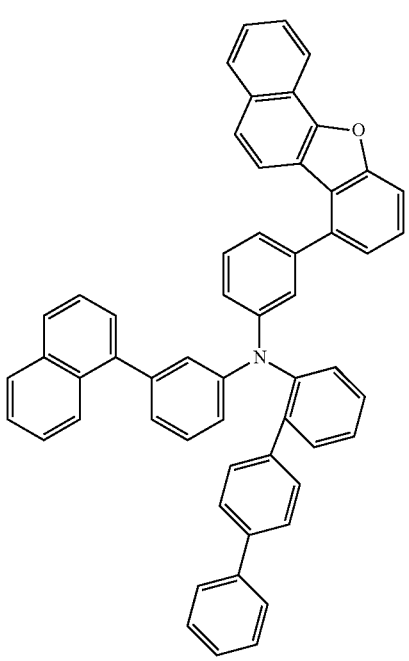

629
-continued
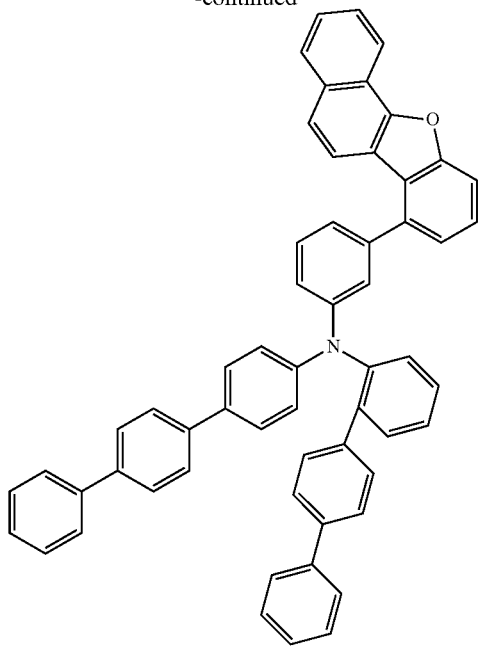
630
-continued
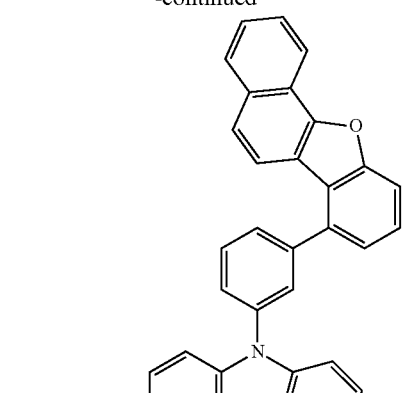
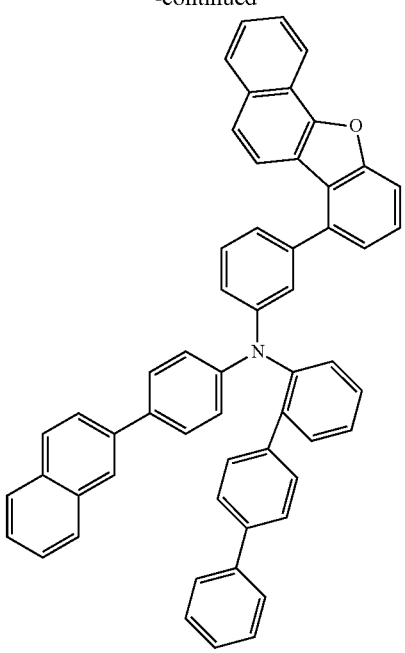
[Chem. 228]
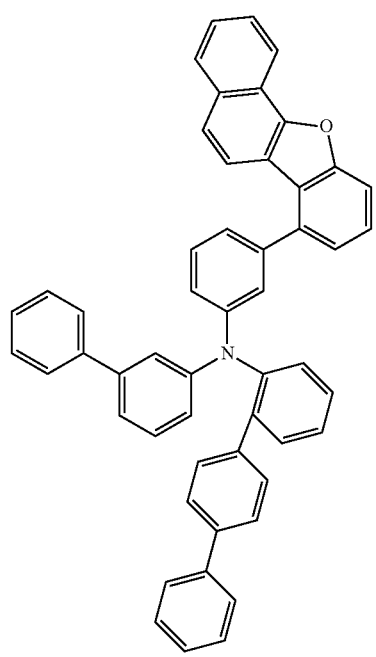
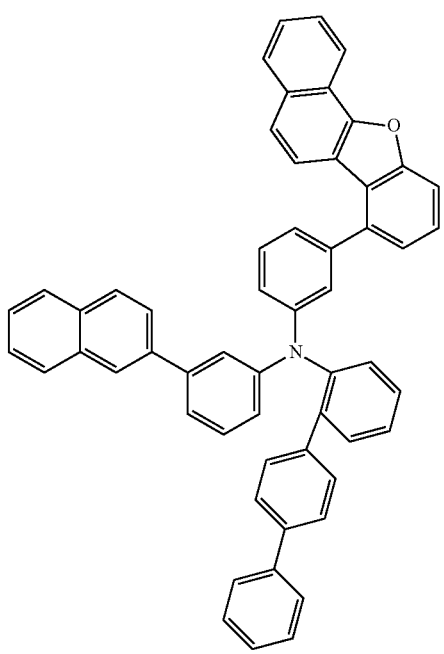

631
-continued
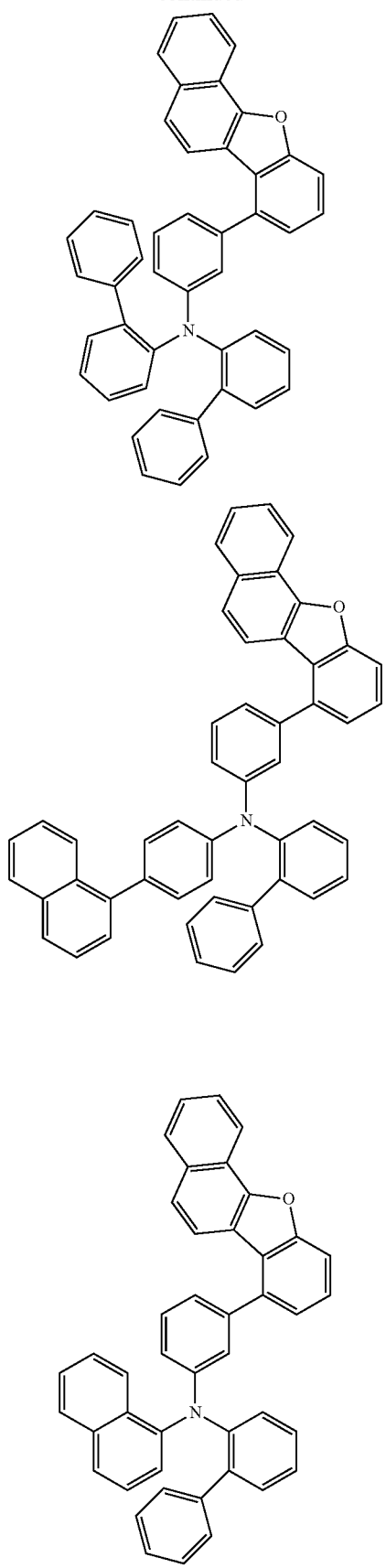
632
-continued
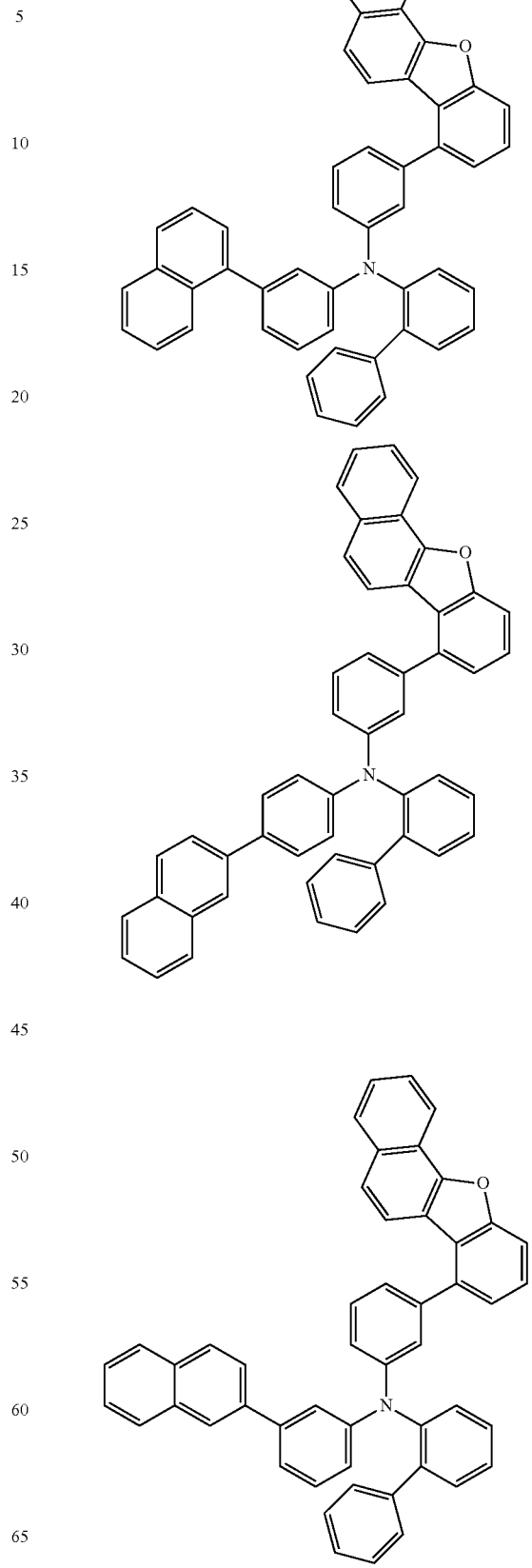

633
-continued
634
-continued
[Chem. 229]
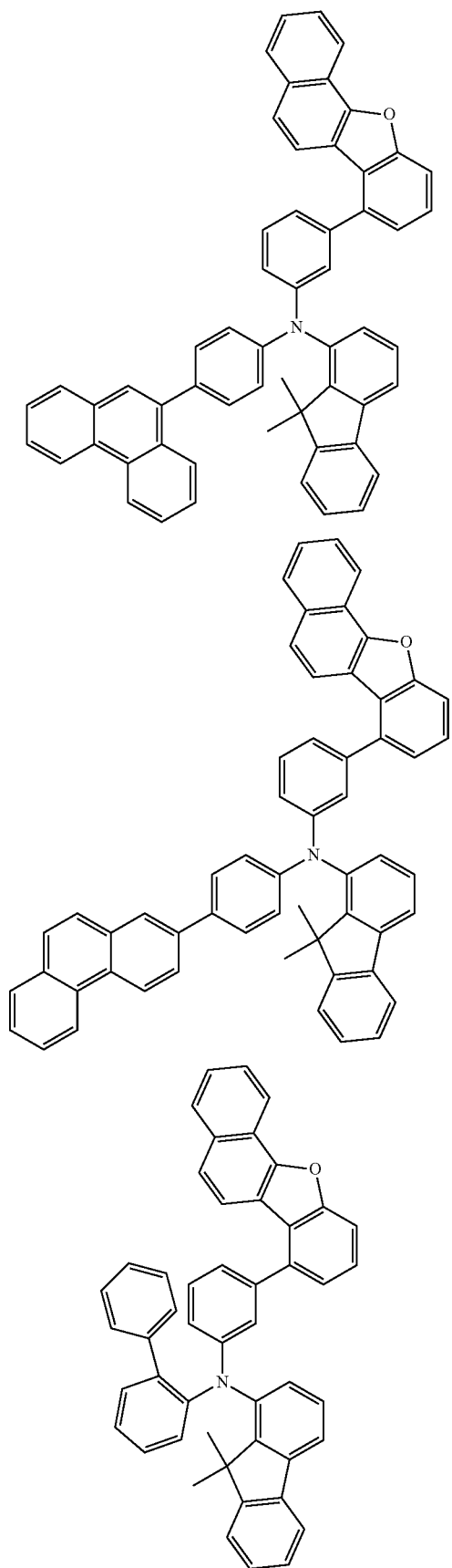

635
-continued
636
-continued
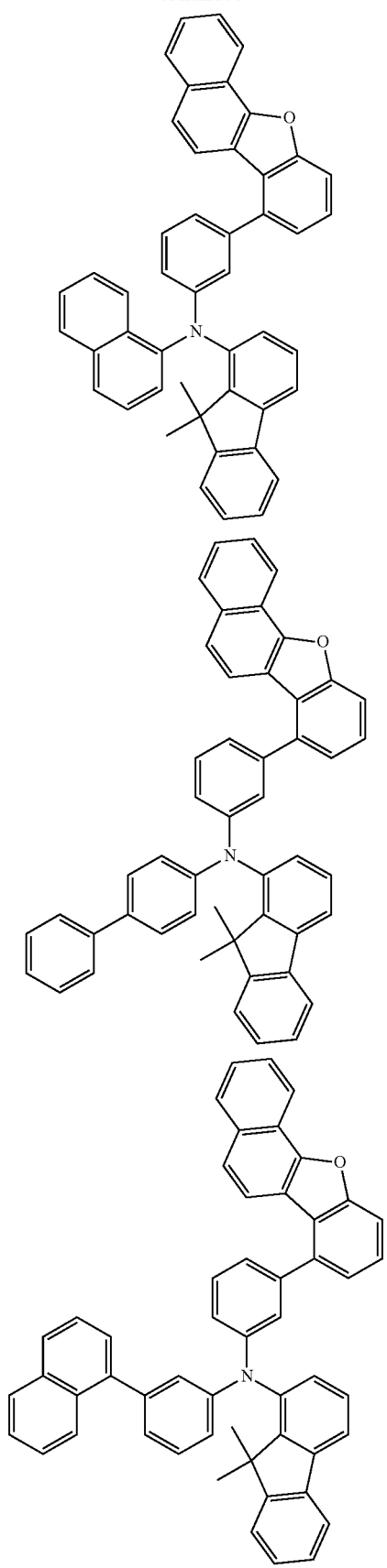
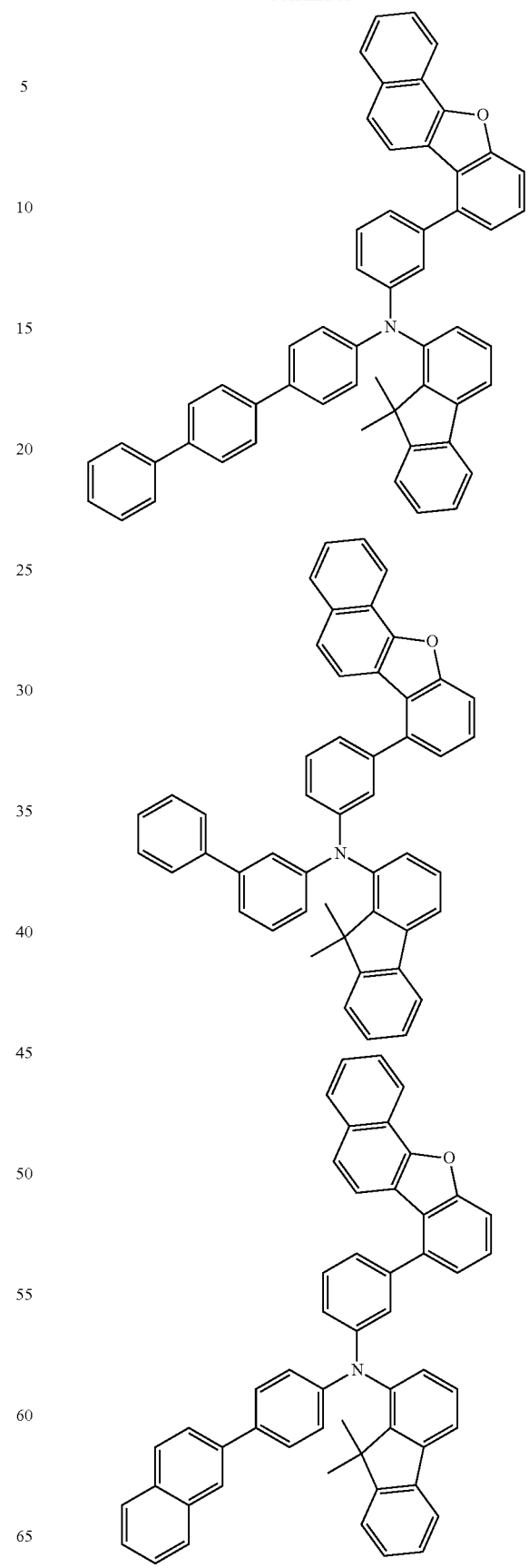

637
-continued
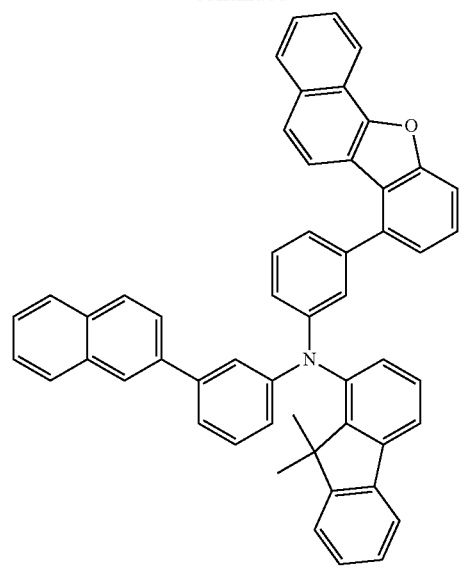
[Chem. 230]
638
-continued
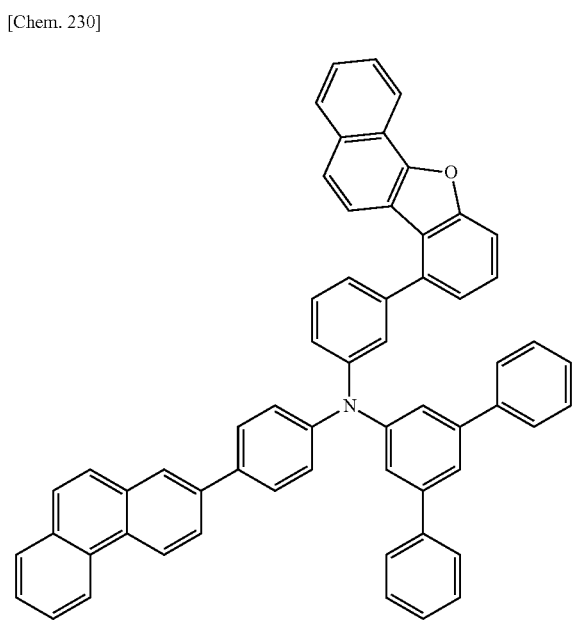
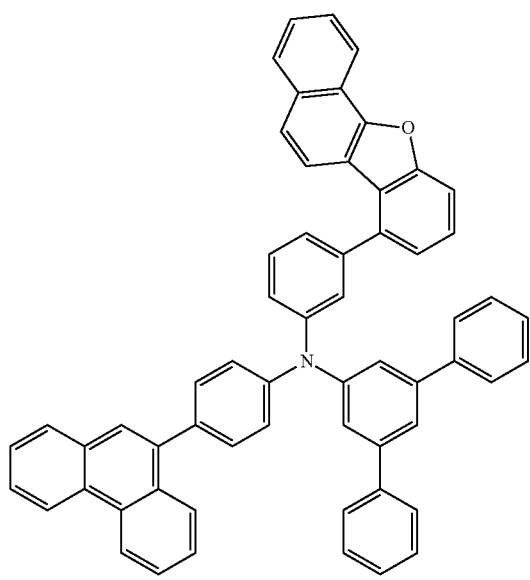
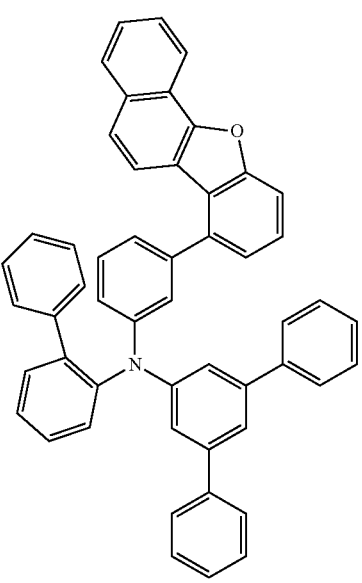

639
-continued
640
-continued
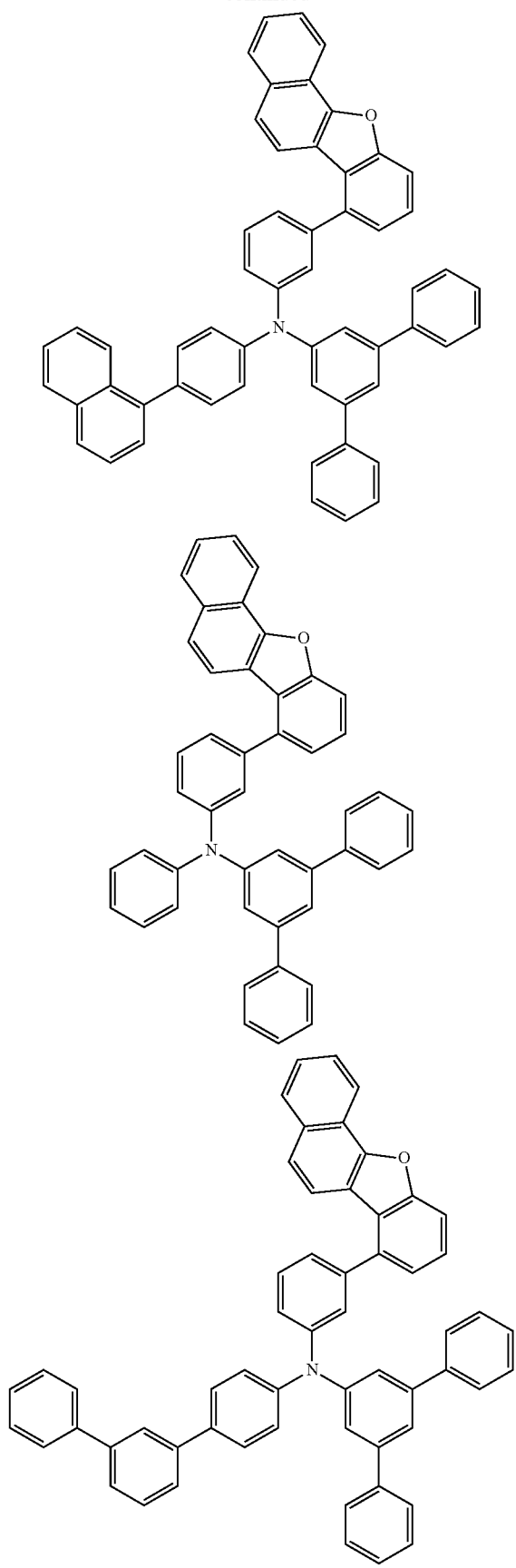
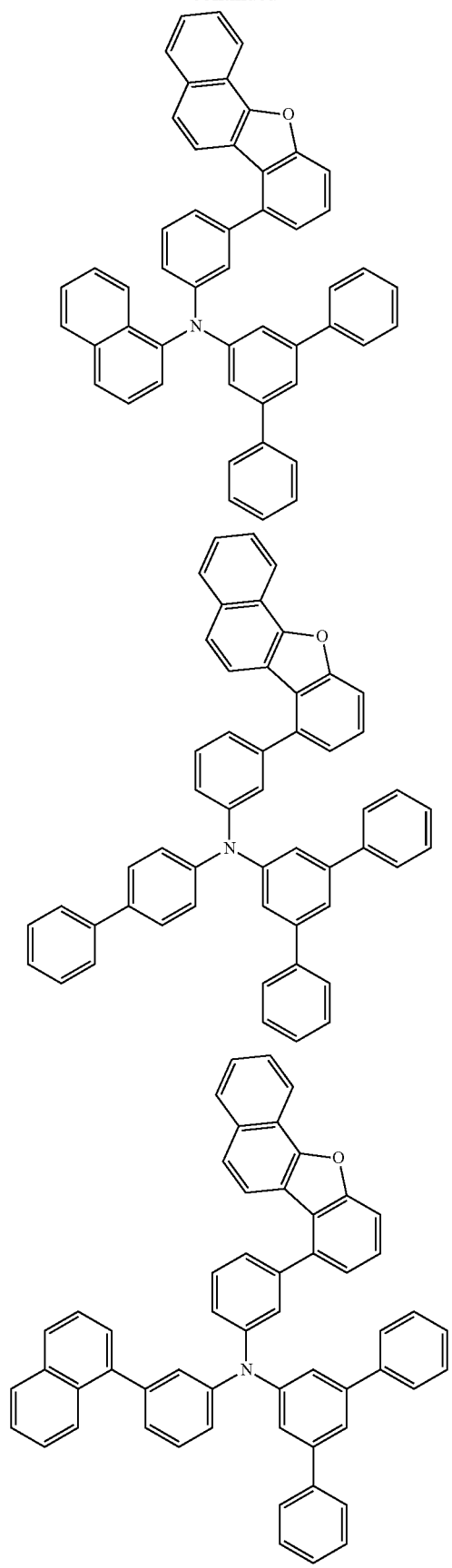

641
-continued
642
-continued
[Chem. 231]
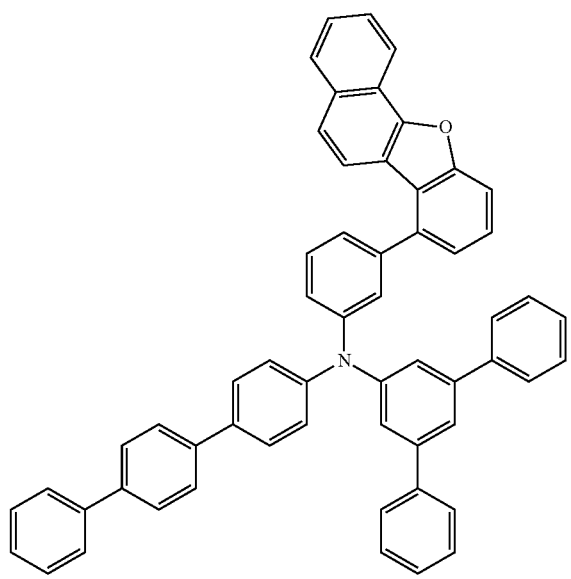
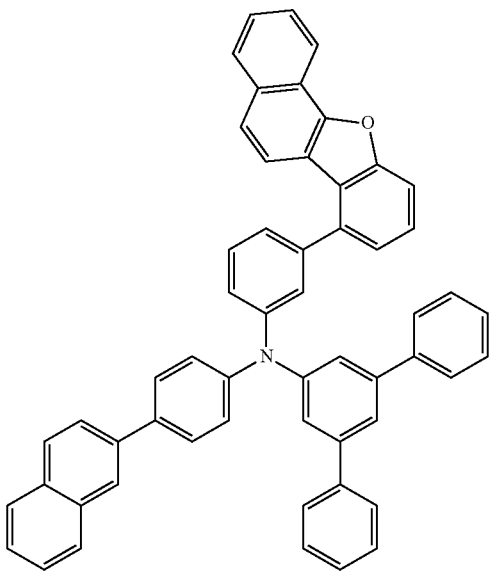
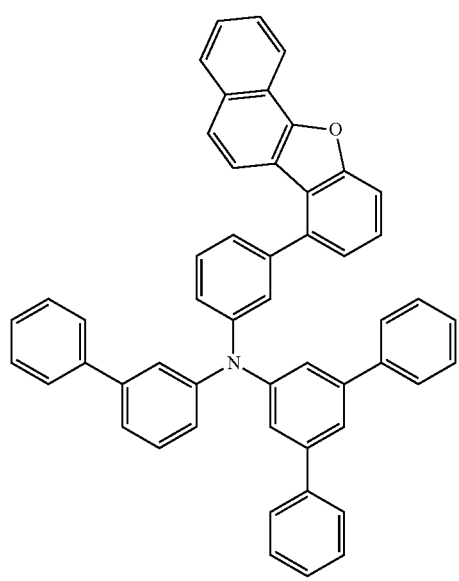
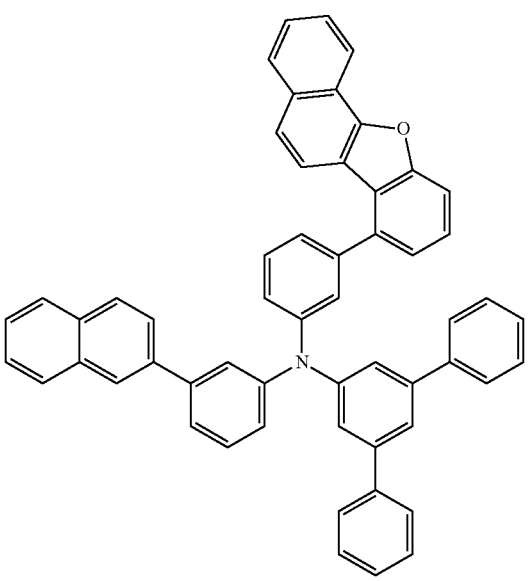

643
-continued
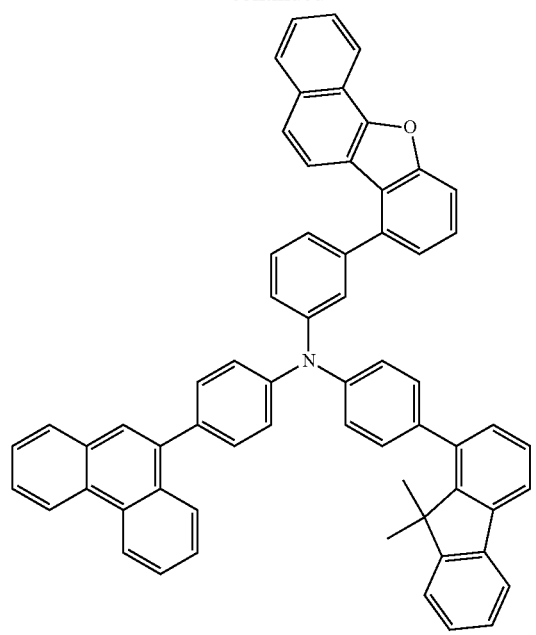
644
-continued
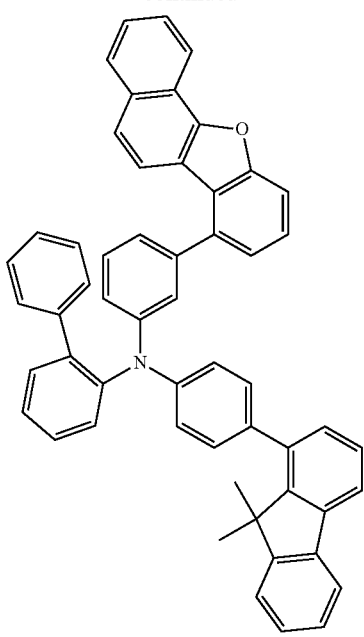
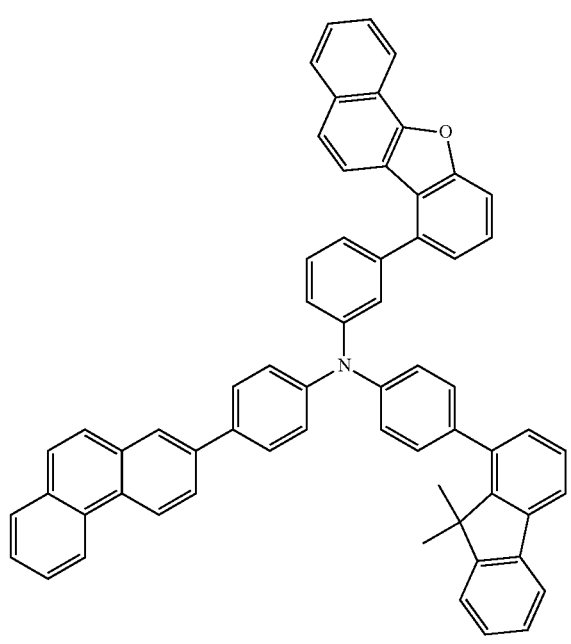
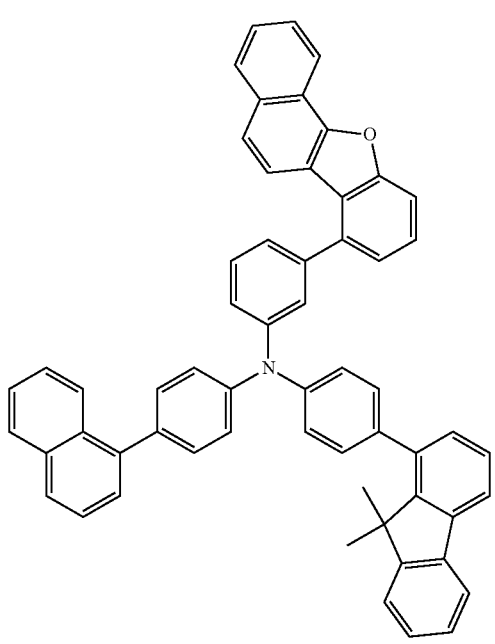

645
-continued
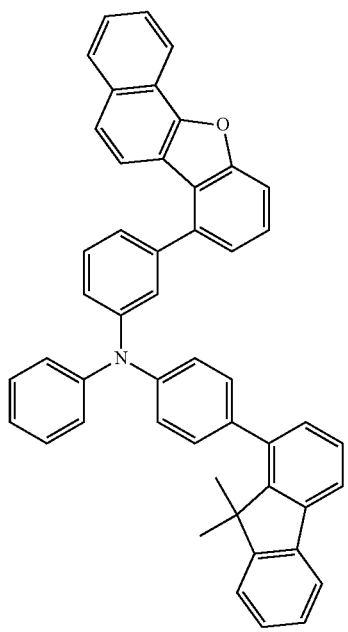
646
-continued
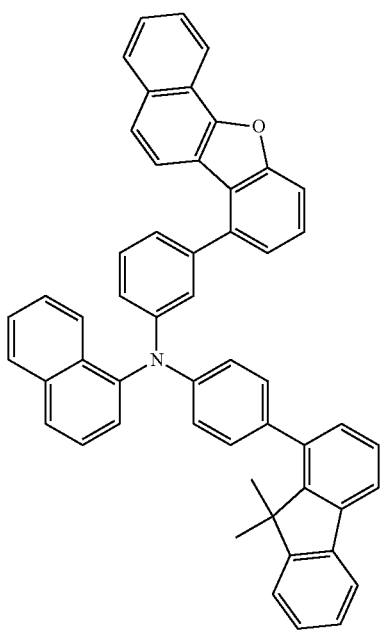

647
-continued
[Chem. 232]
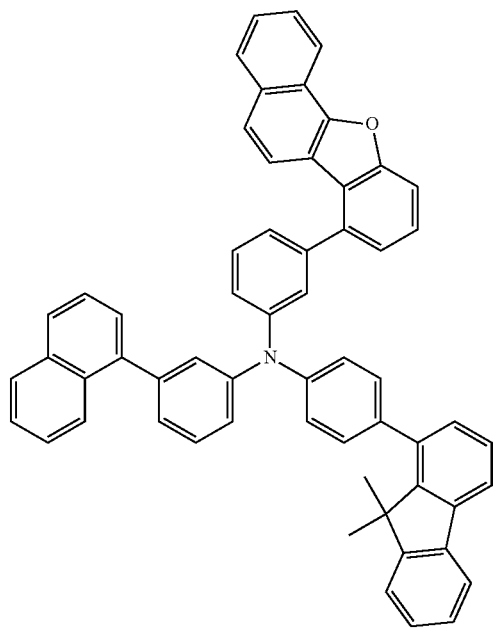
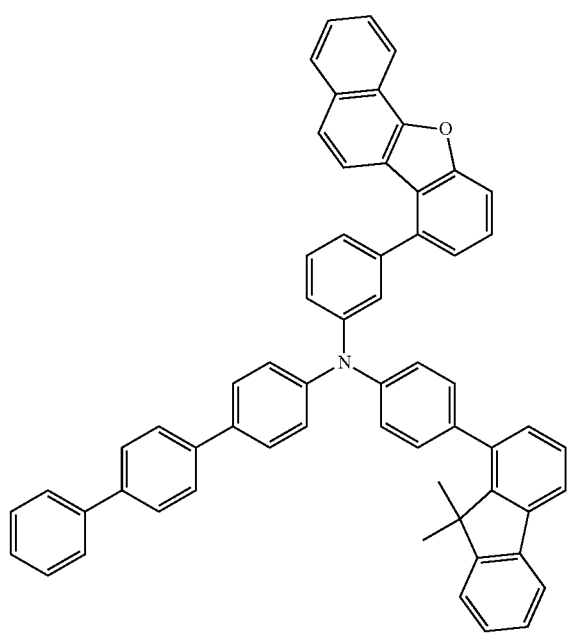
648
-continued
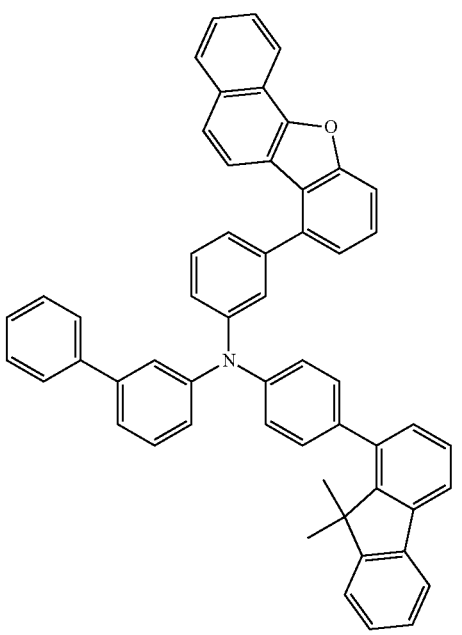
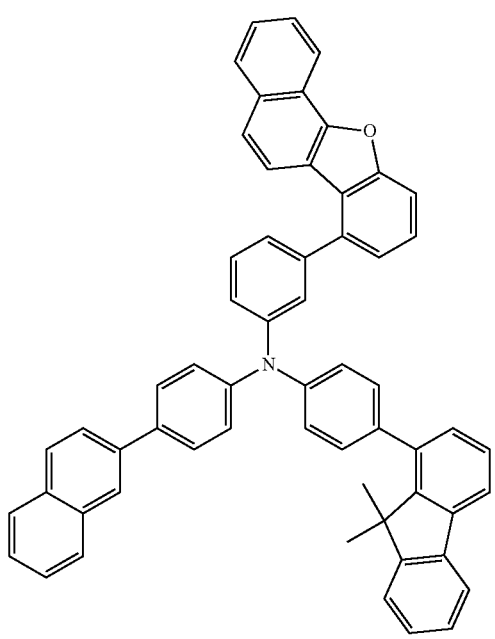

649
-continued
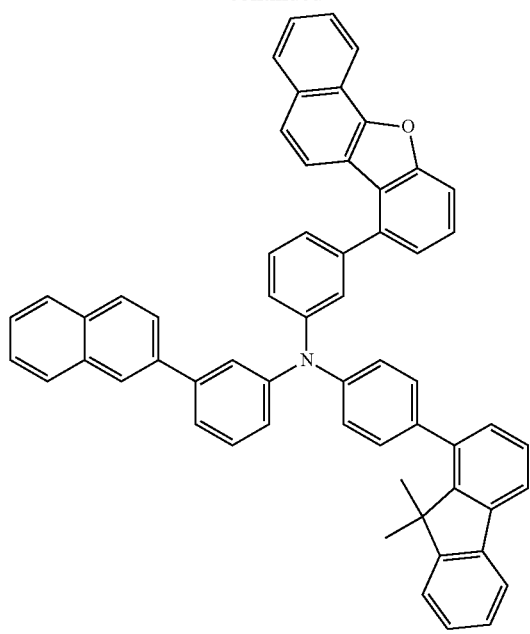
[Chem. 233]
650
-continued
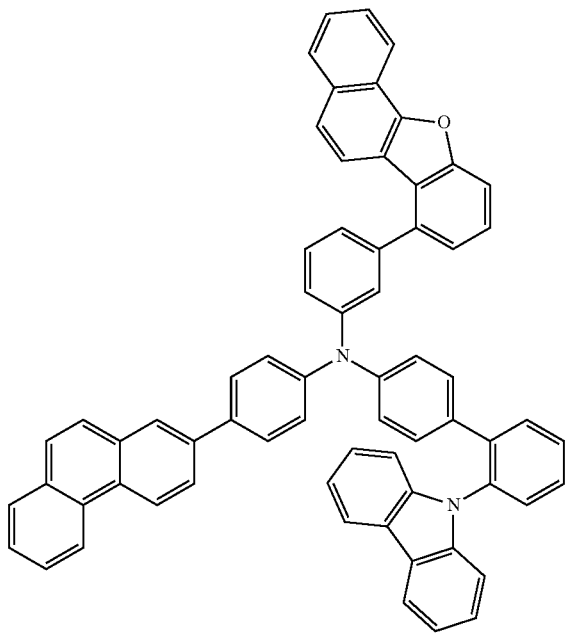
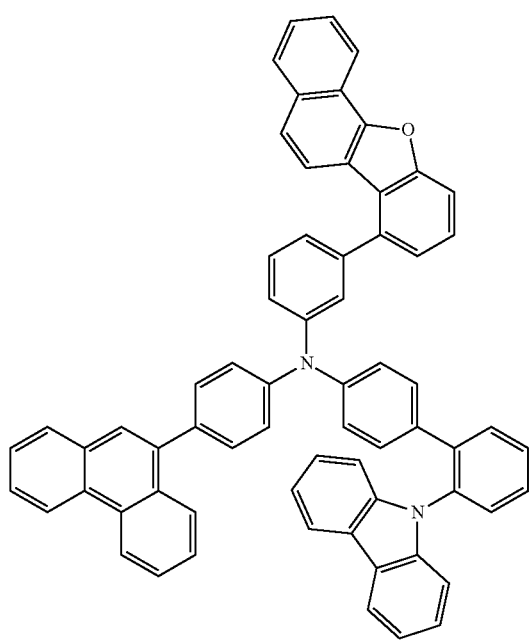
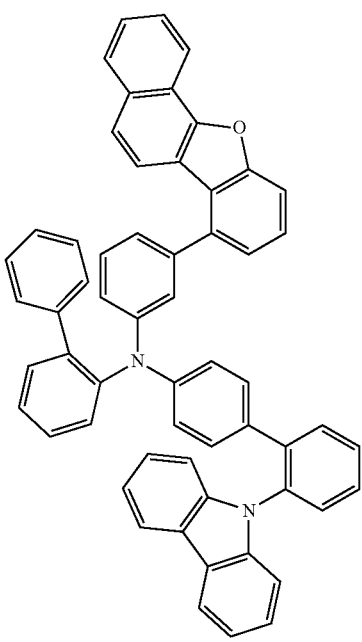

651
-continued
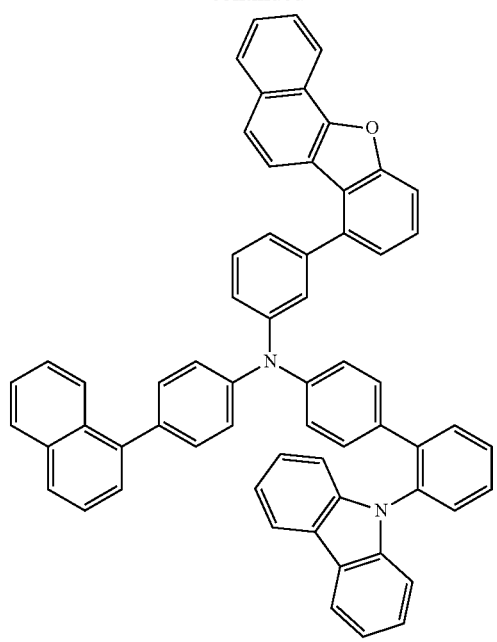
652
-continued
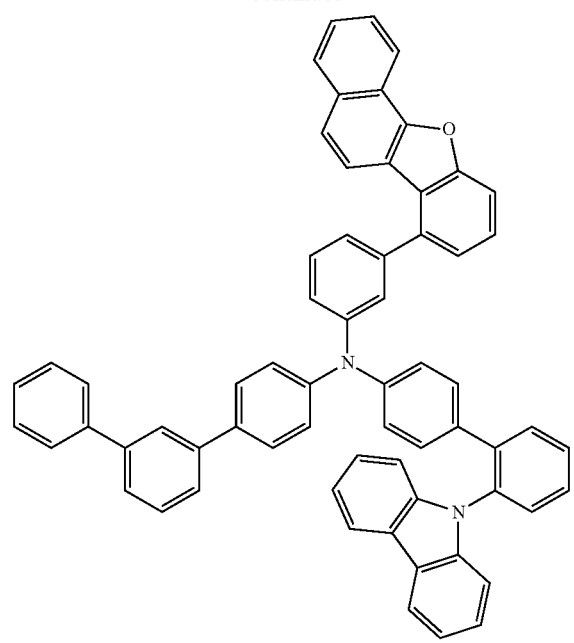
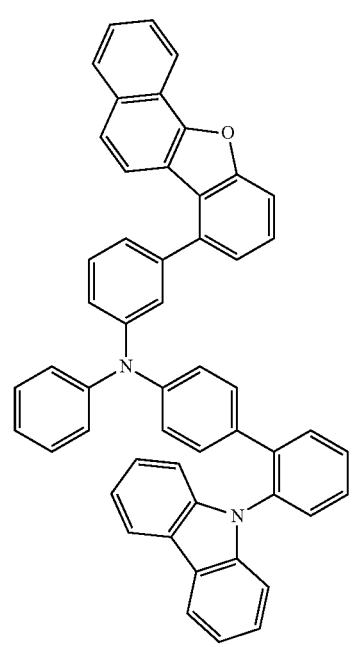
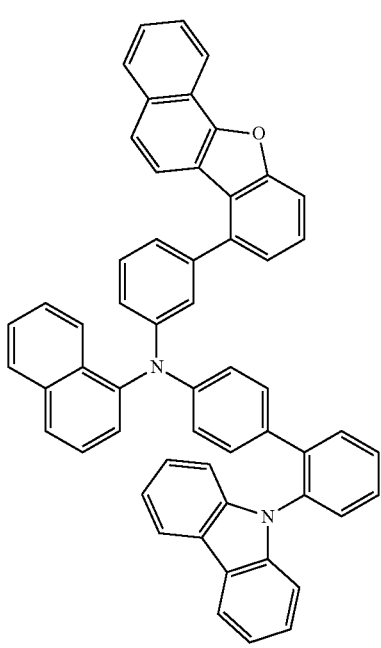

653
-continued
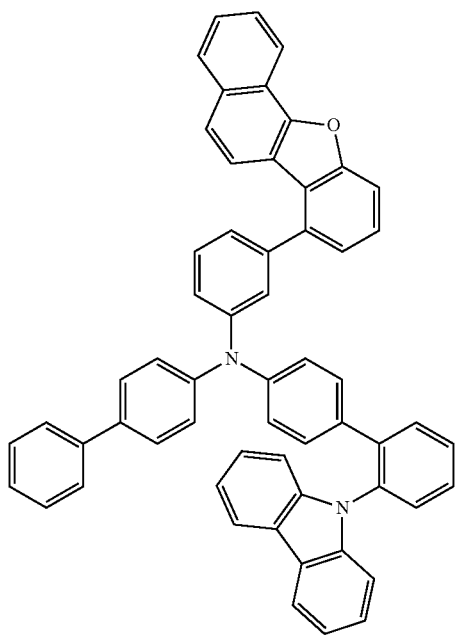
654
-continued
[Chem. 234]
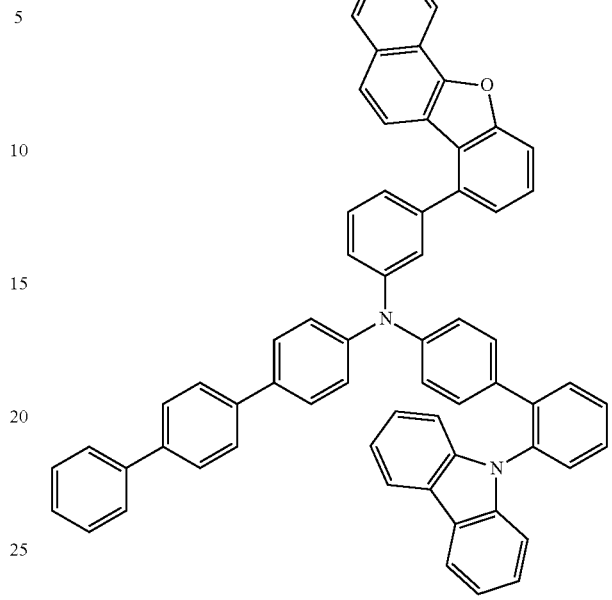
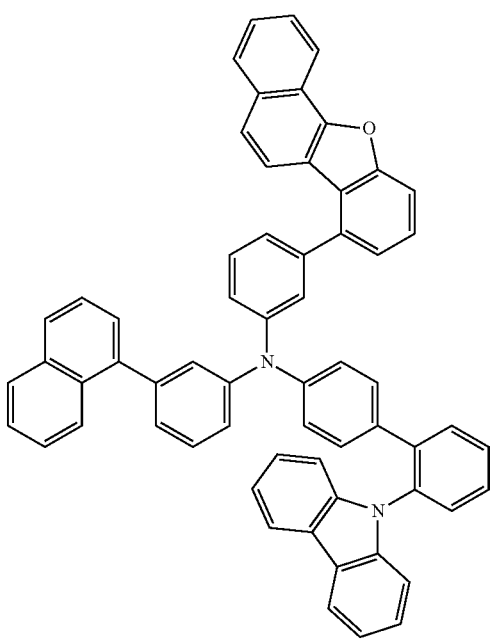
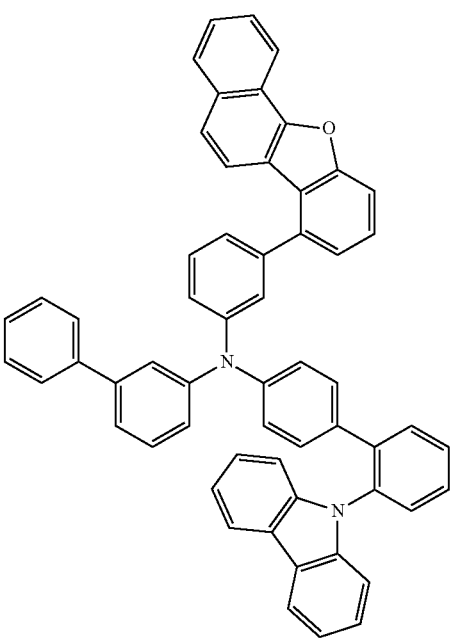

655
-continued
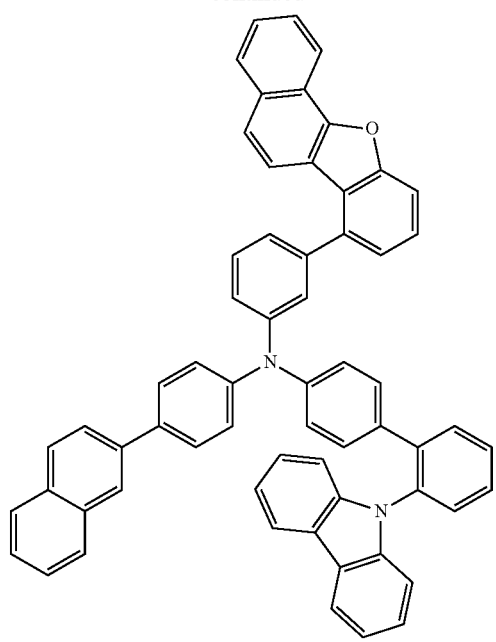
656
-continued
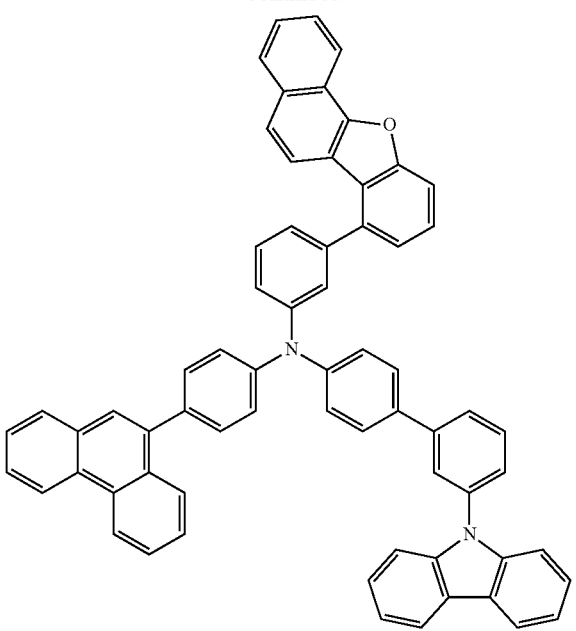
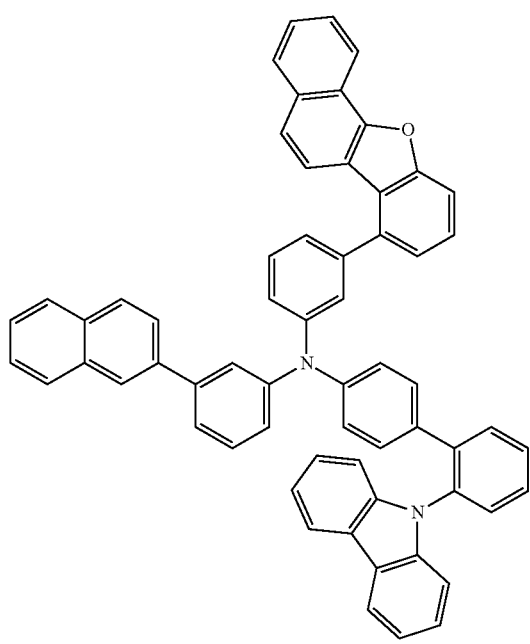
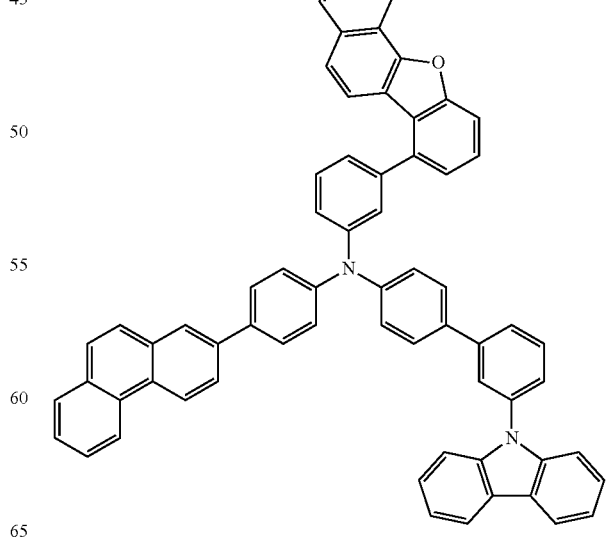

657
-continued
[Chem. 235]
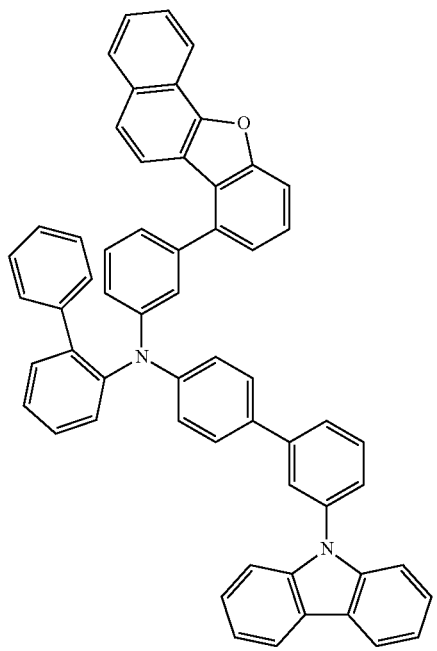
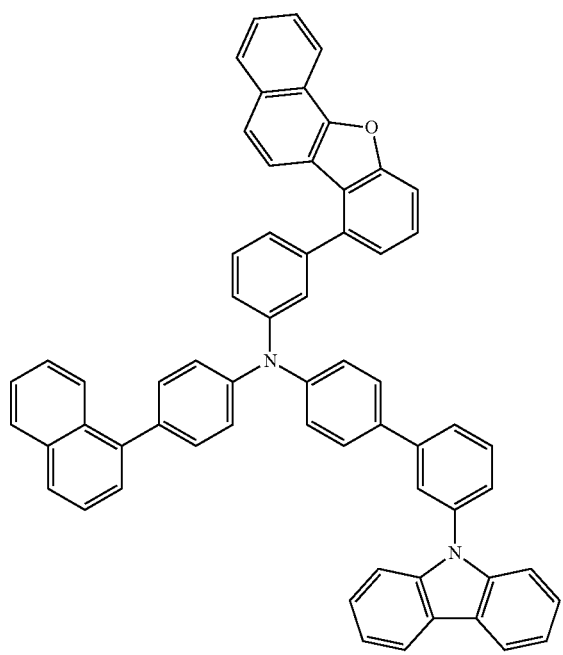
658
-continued
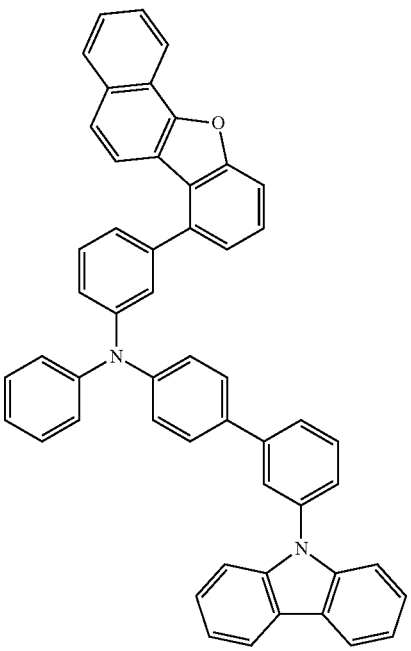
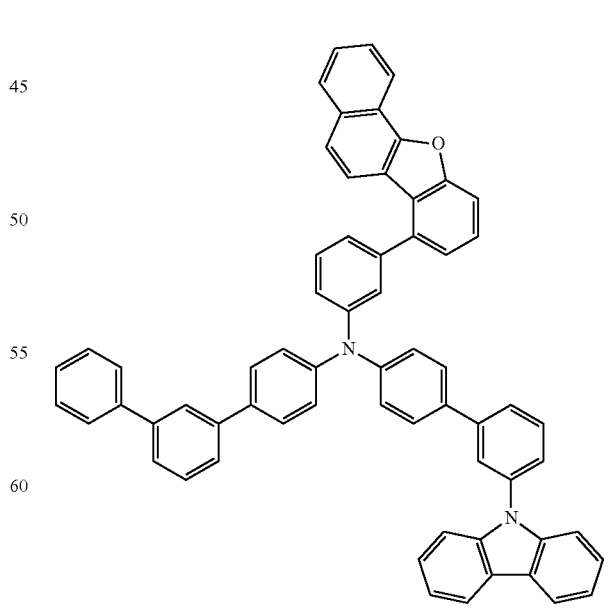

659
-continued
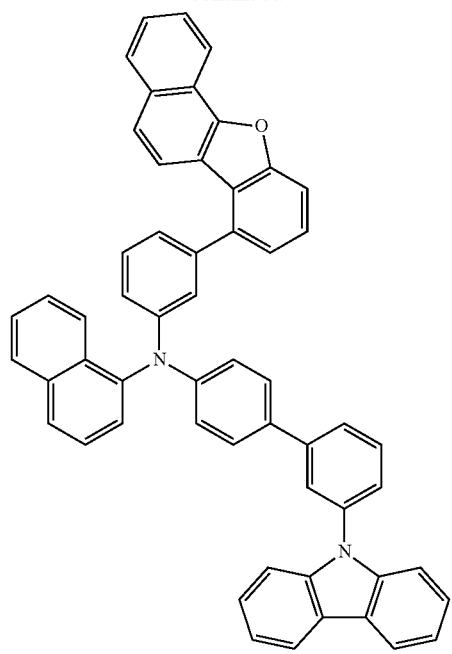
660
-continued
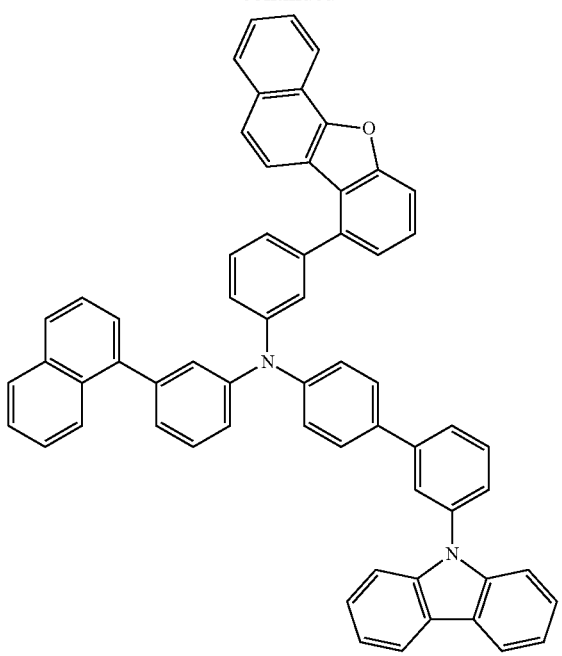
[Chem. 236]
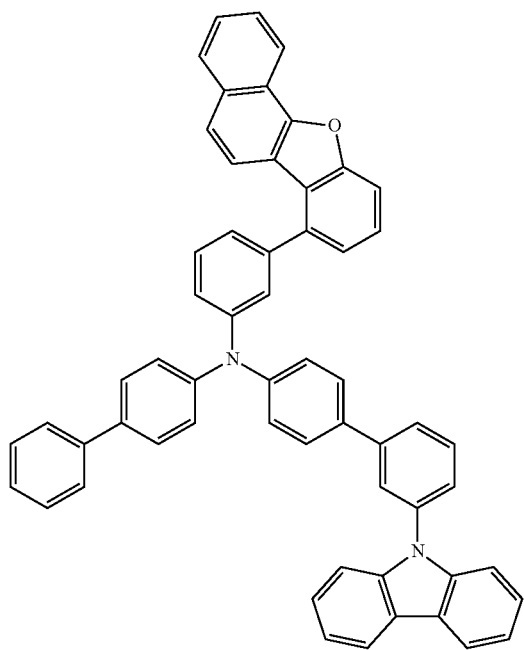
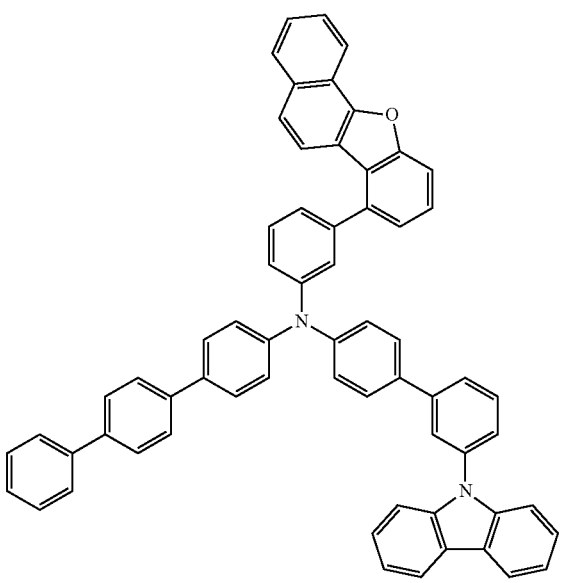

661
-continued
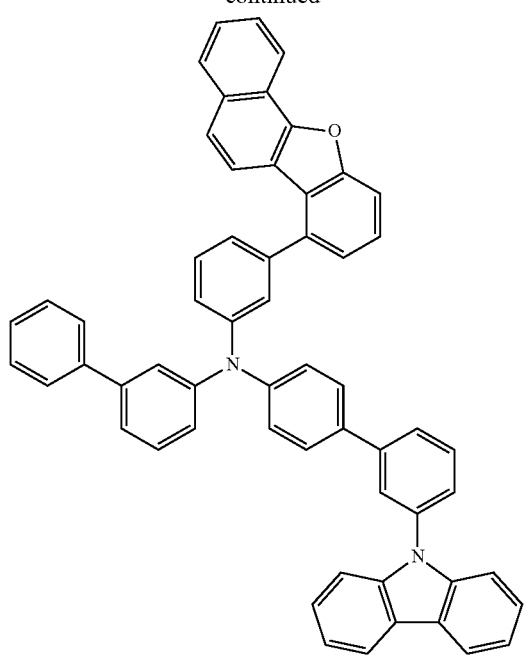
662
-continued
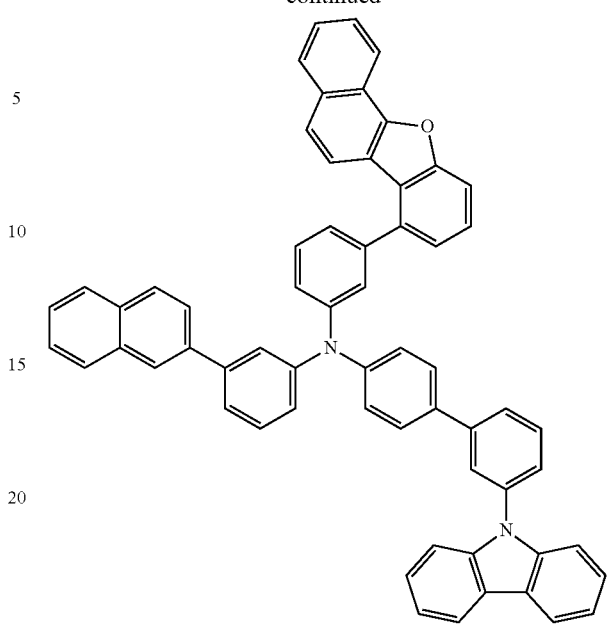
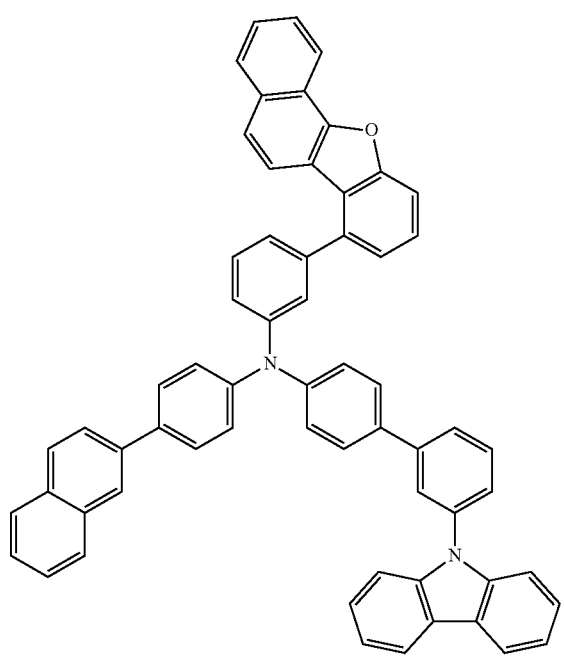
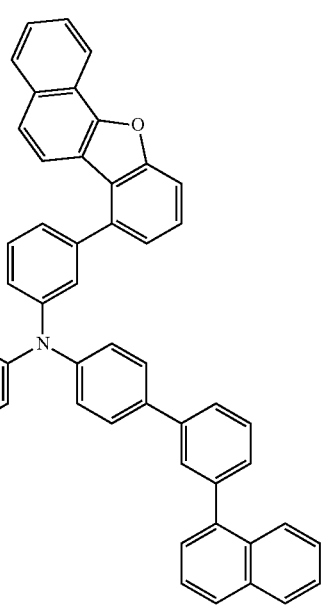

663
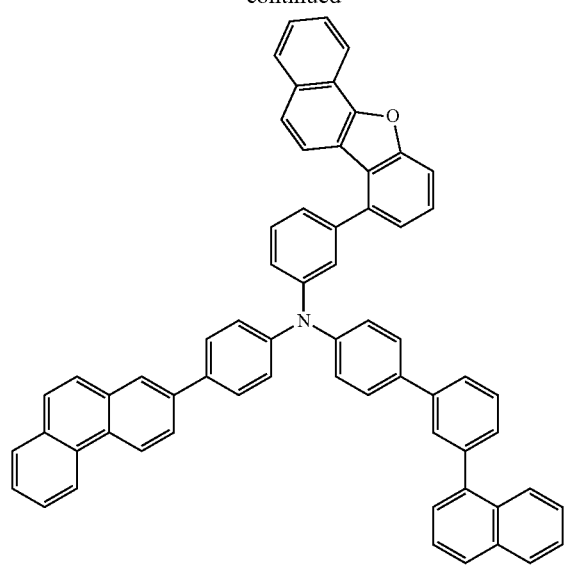
664
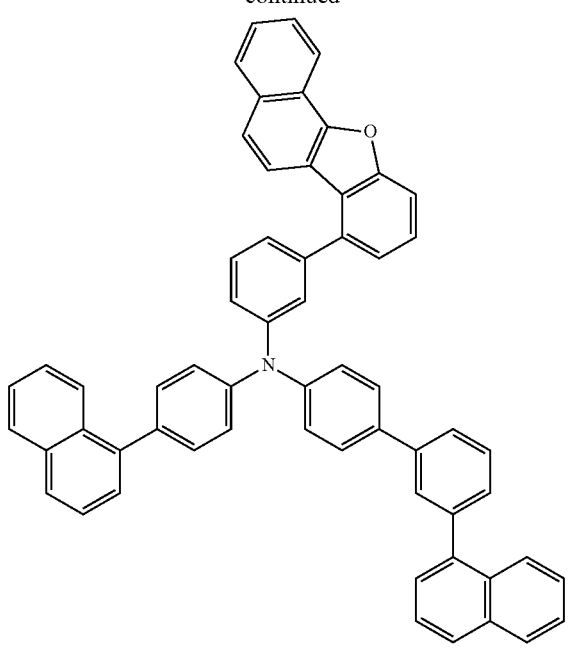
[Chem. 237]
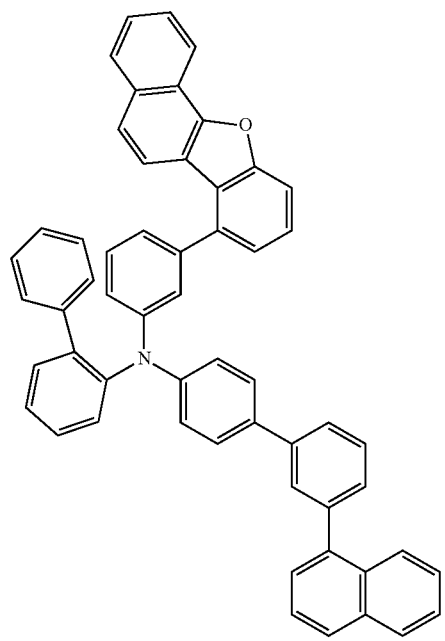
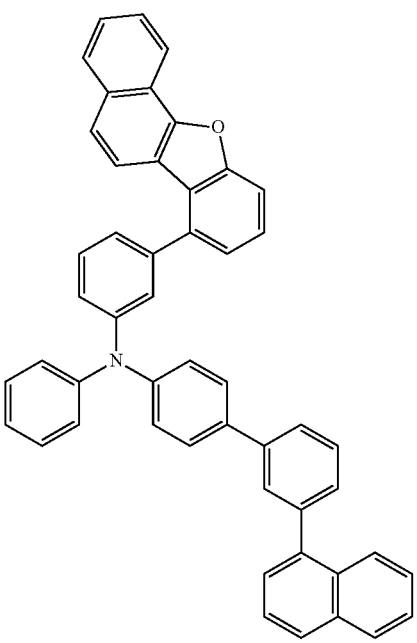

665
-continued
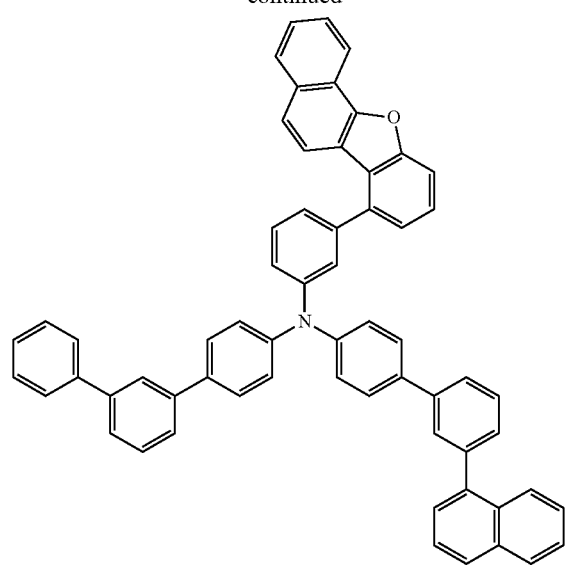
666
-continued
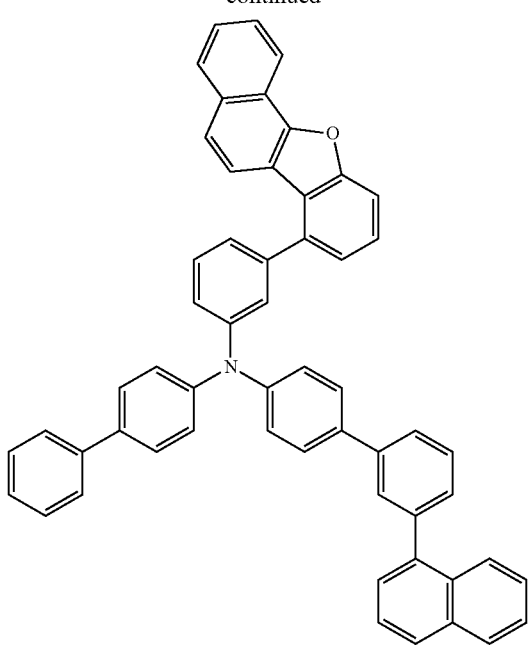
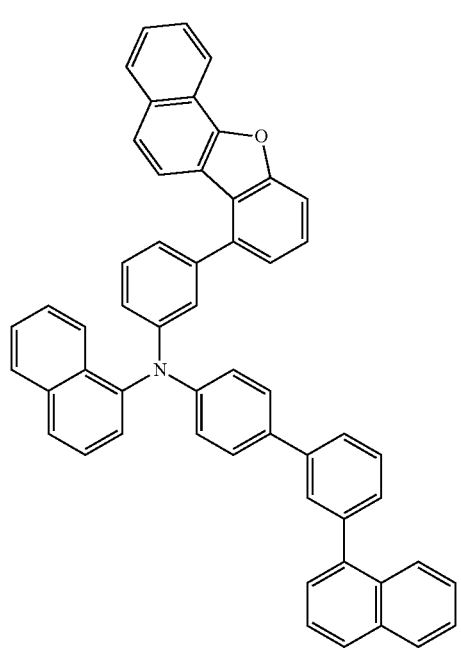
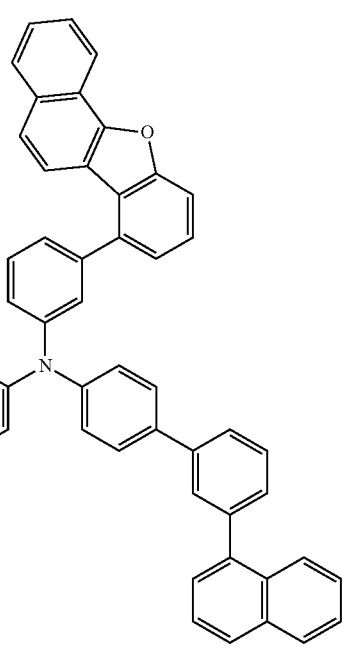

667
-continued
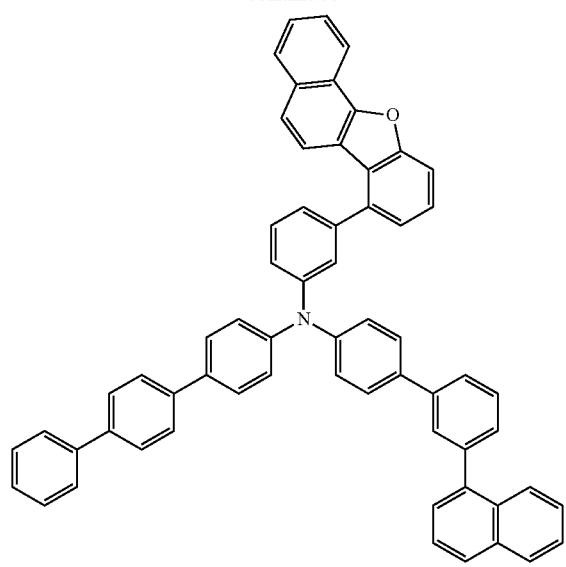
668
-continued
[Chem. 238]
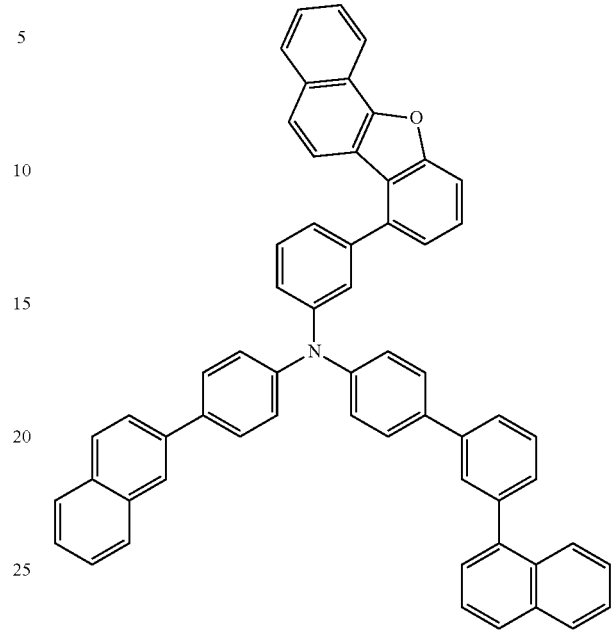
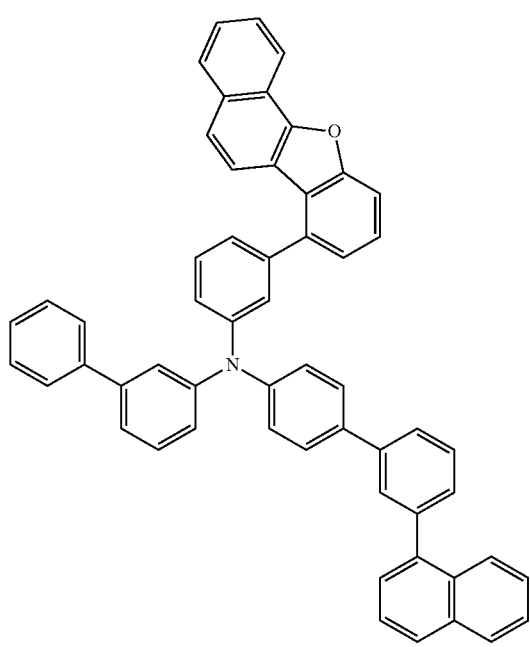
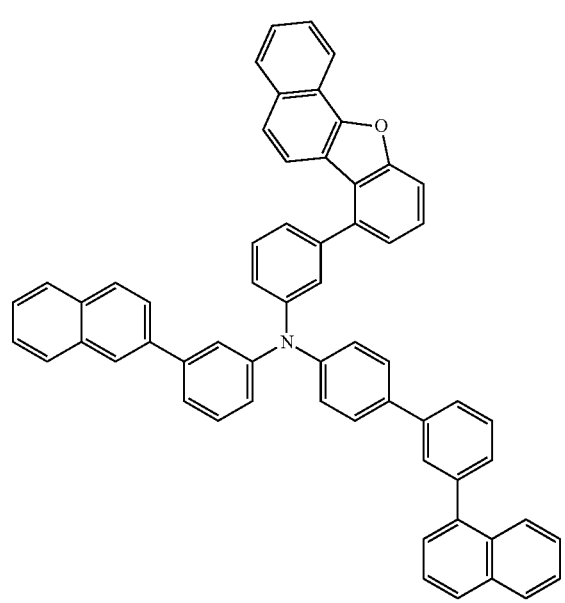

669
-continued
670
-continued
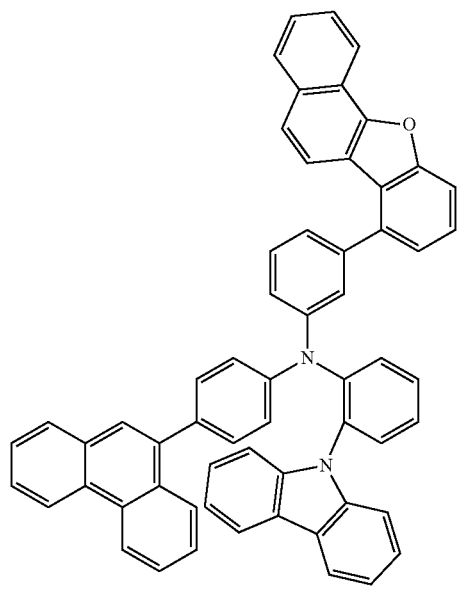
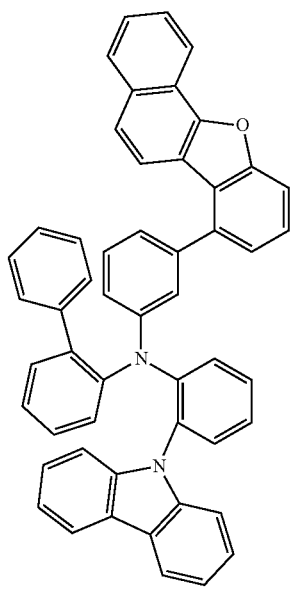

671
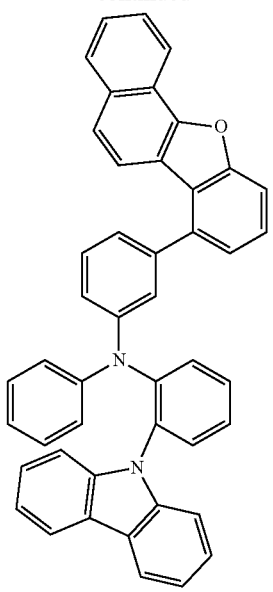
672
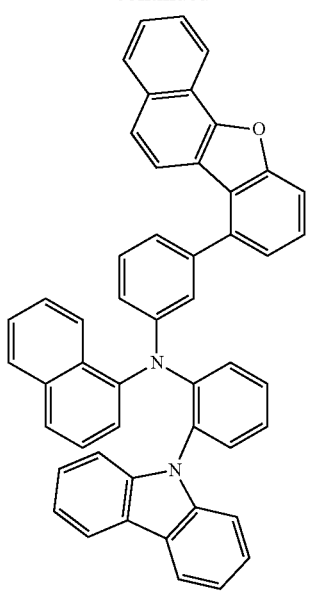
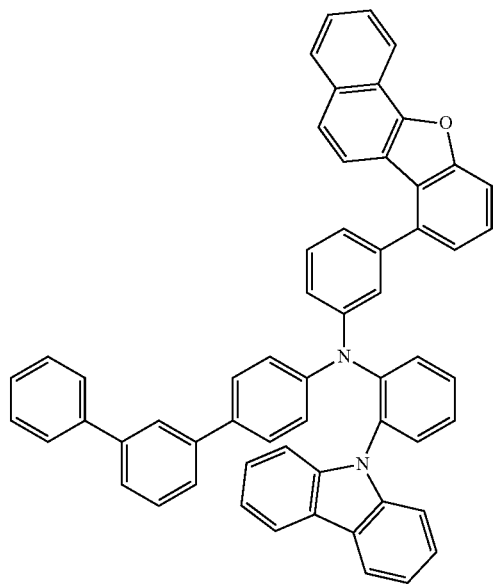
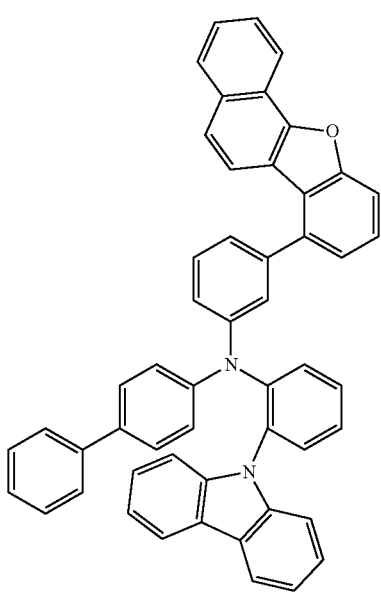

673
-continued
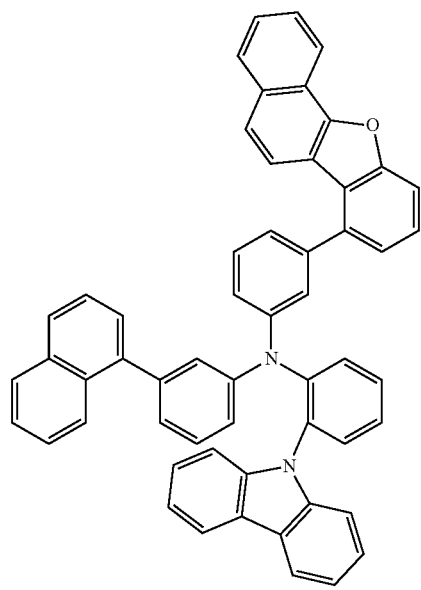
674
-continued
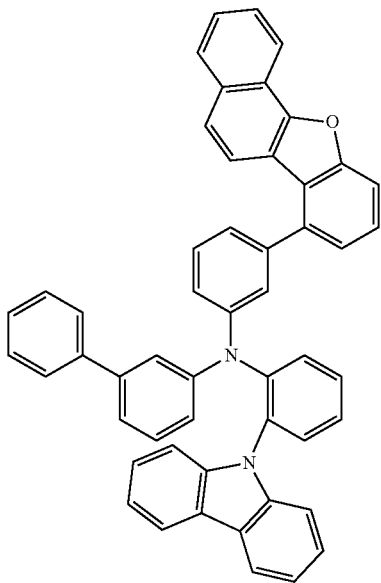
[Chem. 239]
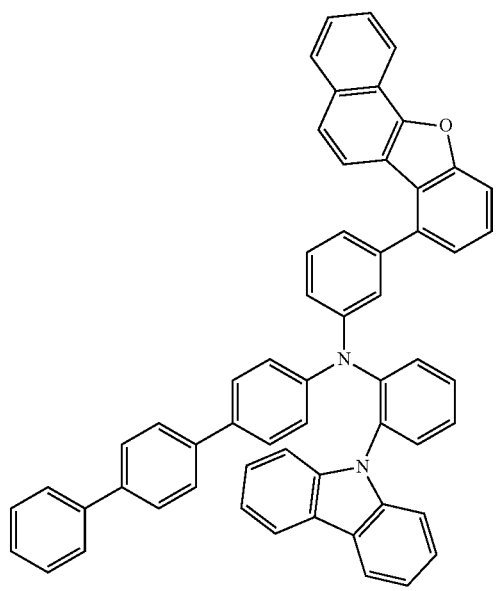
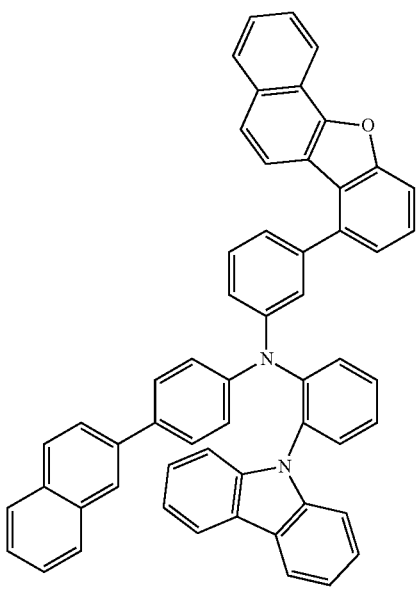

675
-continued
676
-continued
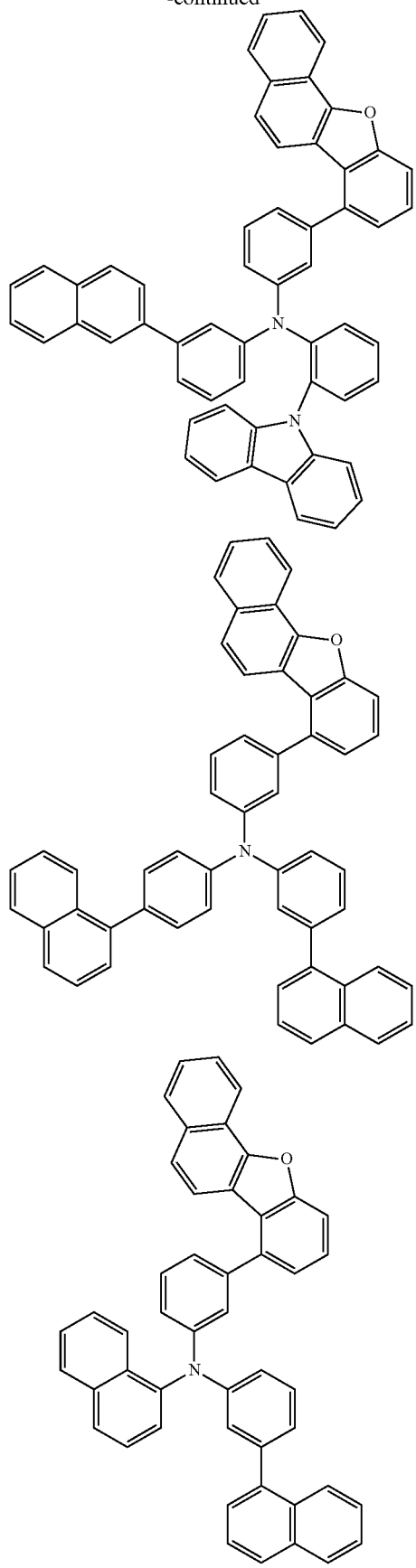
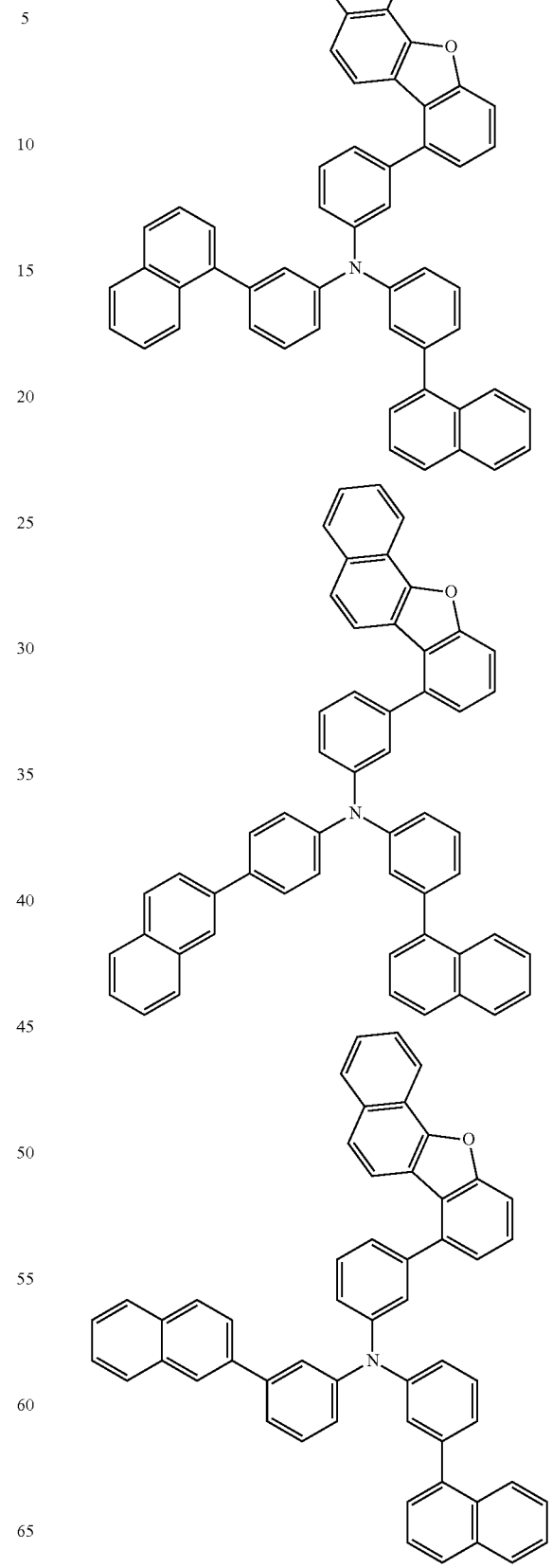

677
-continued
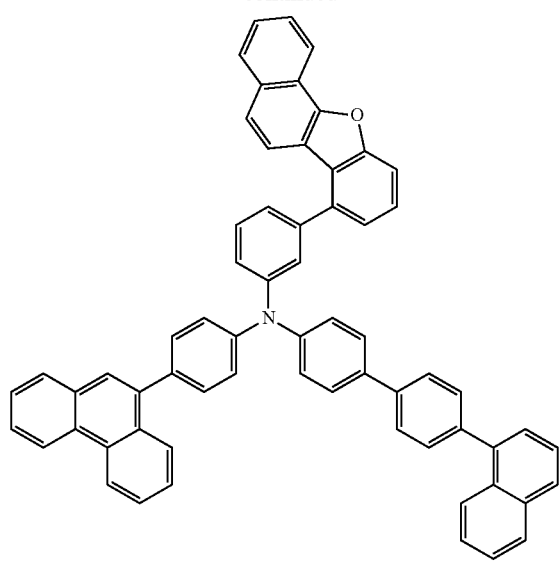
[Chem. 240]
678
-continued
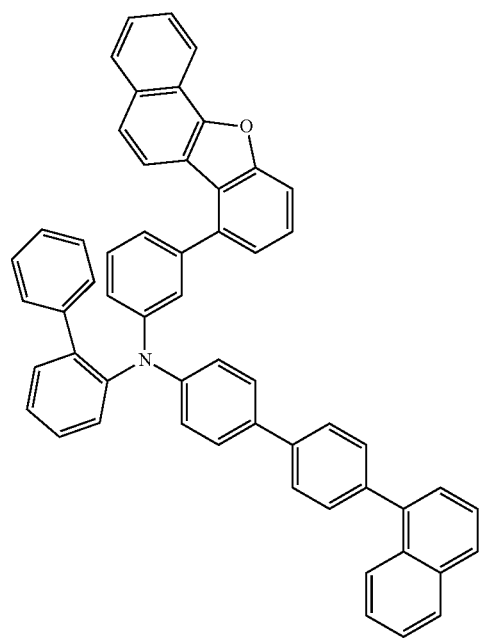
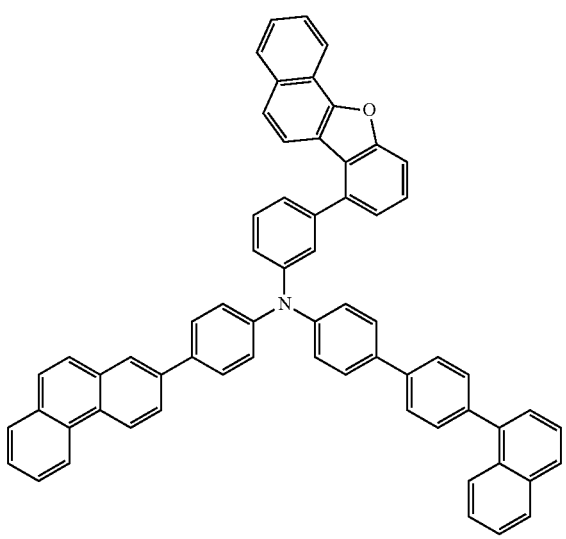
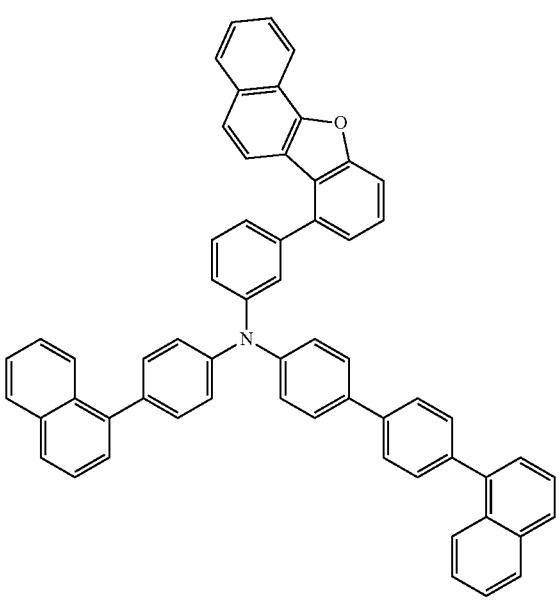

679
-continued
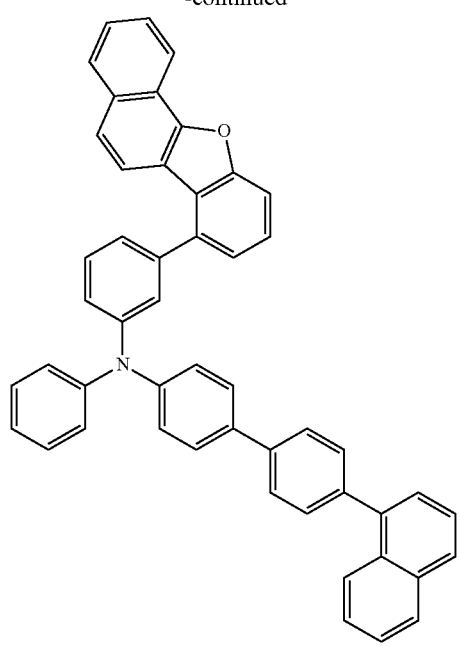
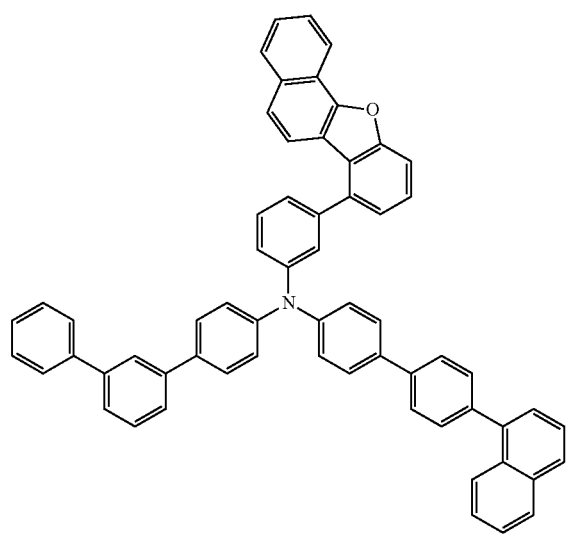
680
-continued
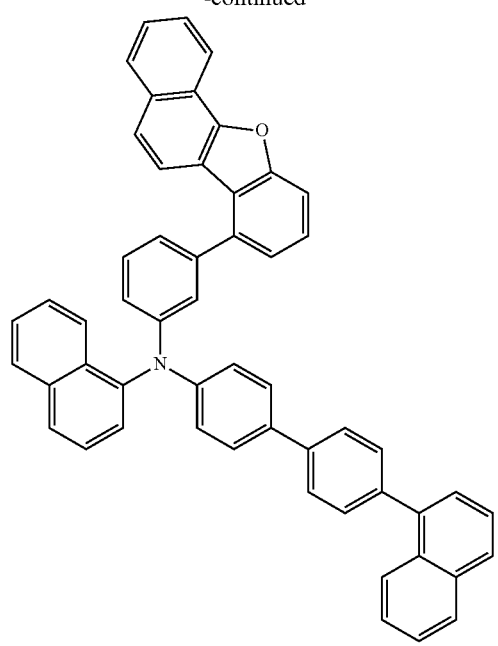
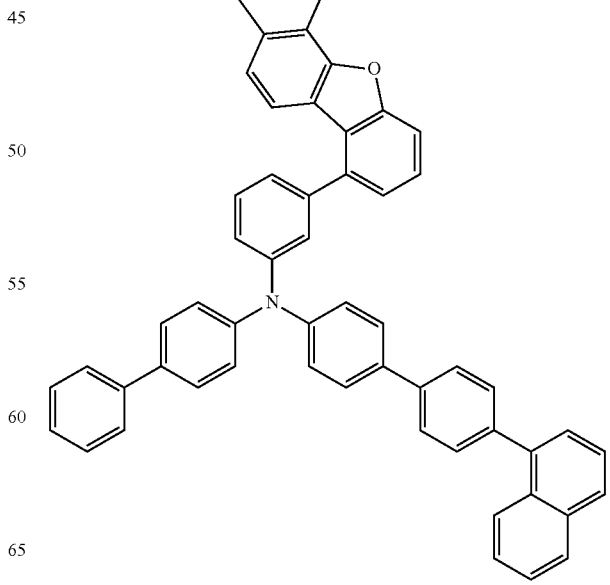

681
-continued
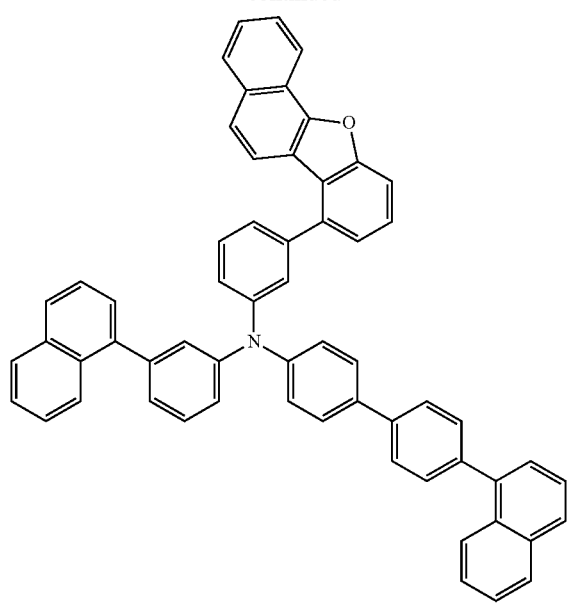
[Chem. 241]
682
-continued
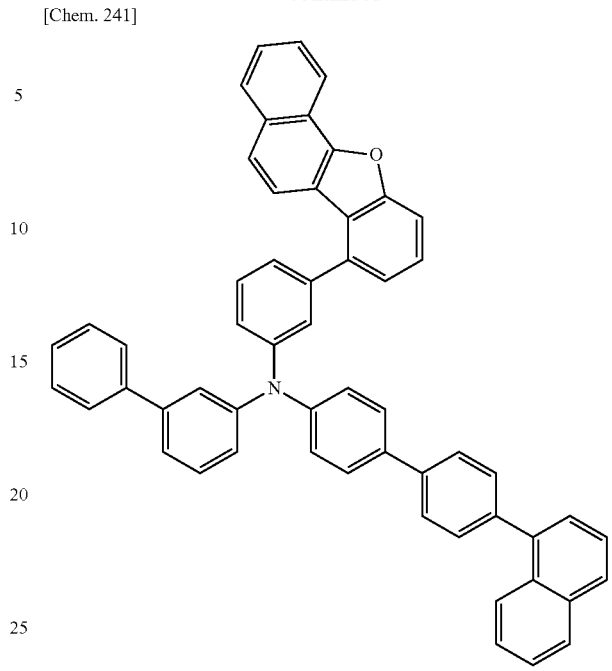
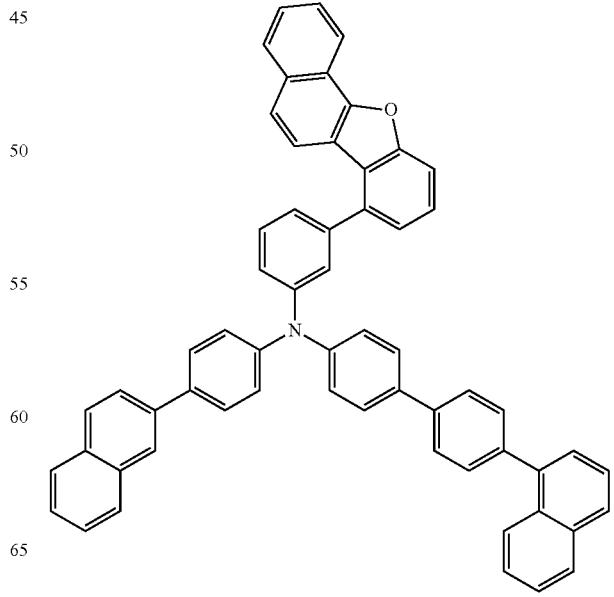

683
-continued
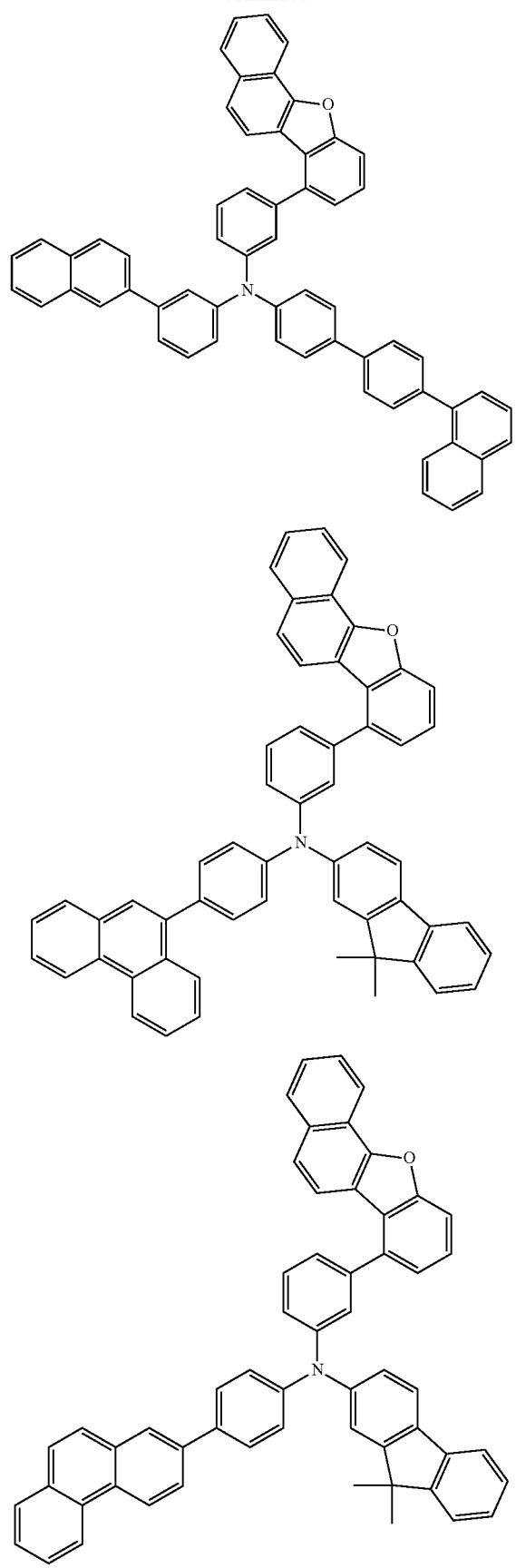
684
-continued
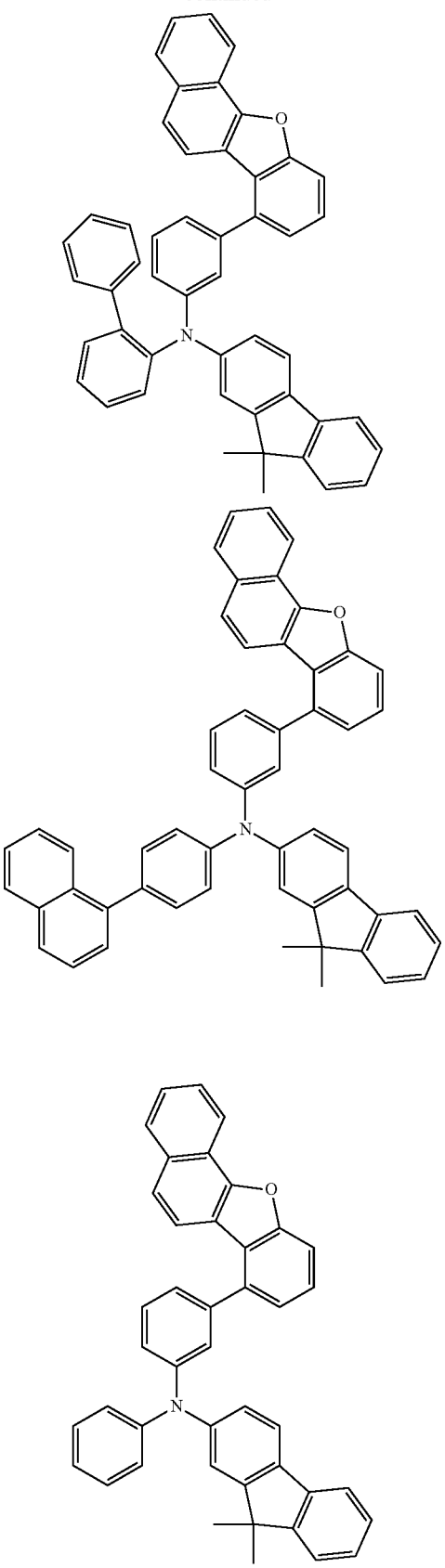

-continued
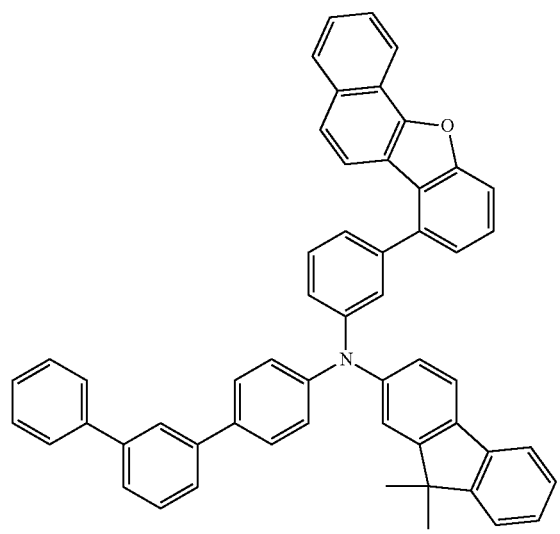
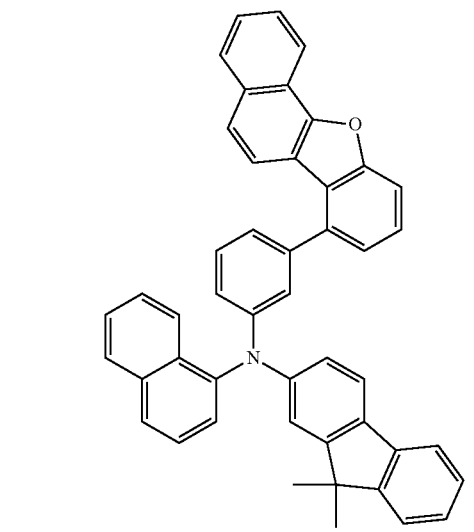
[Chem. 242]
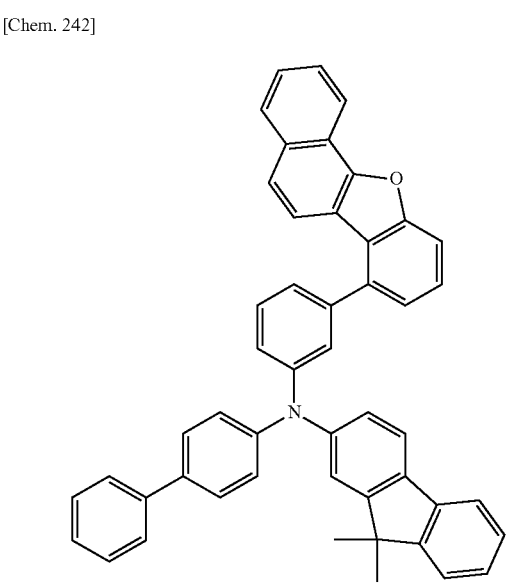
-continued
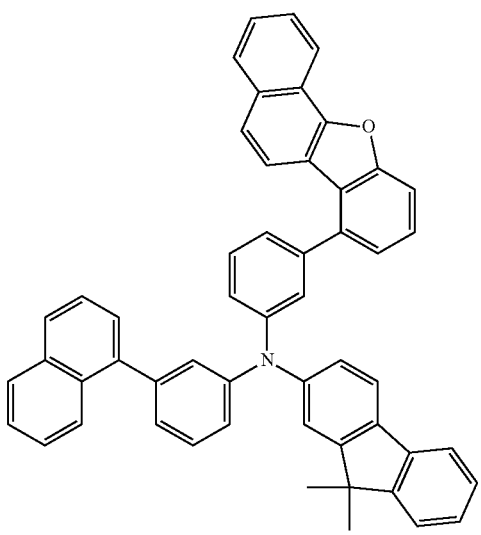
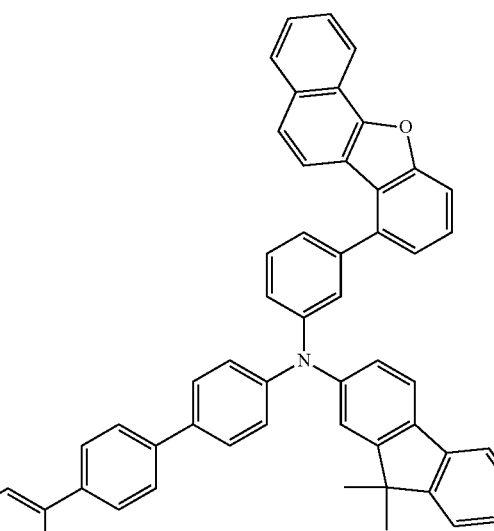
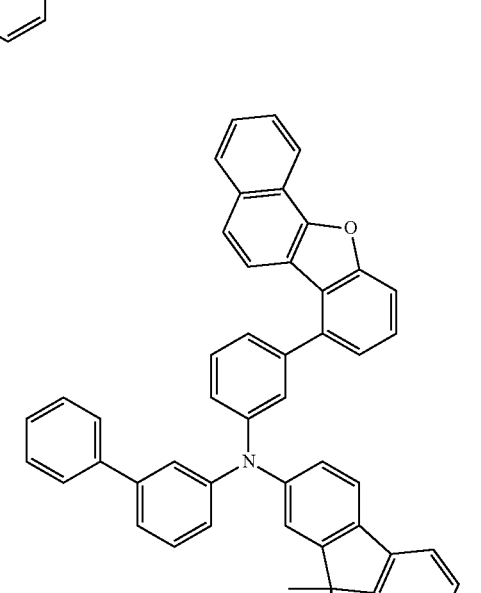

687
-continued
688
-continued
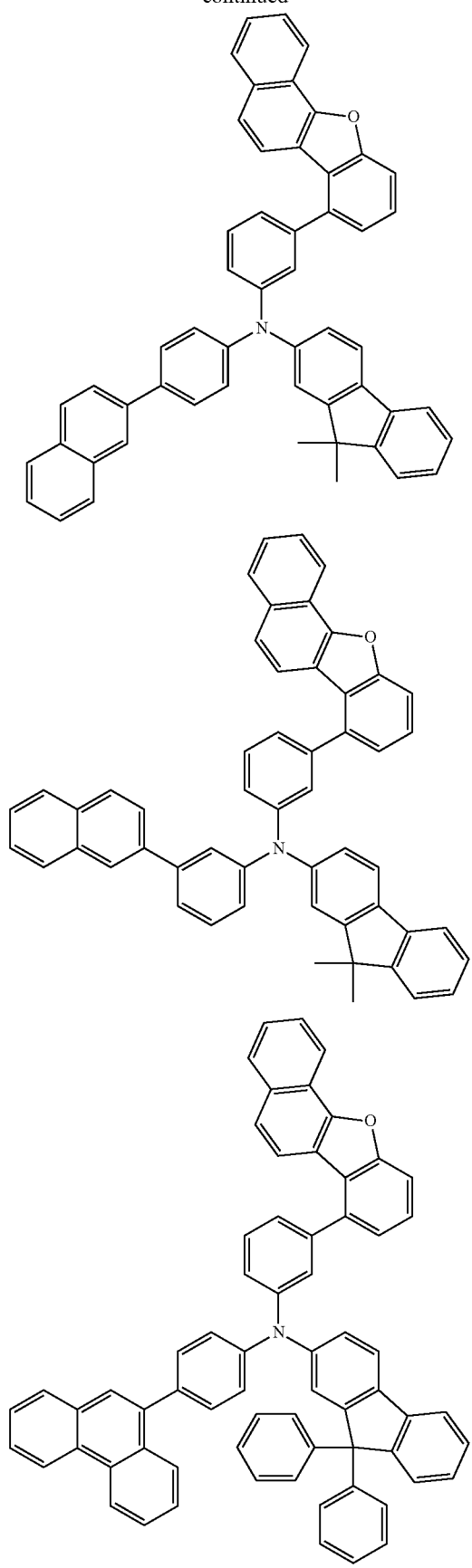
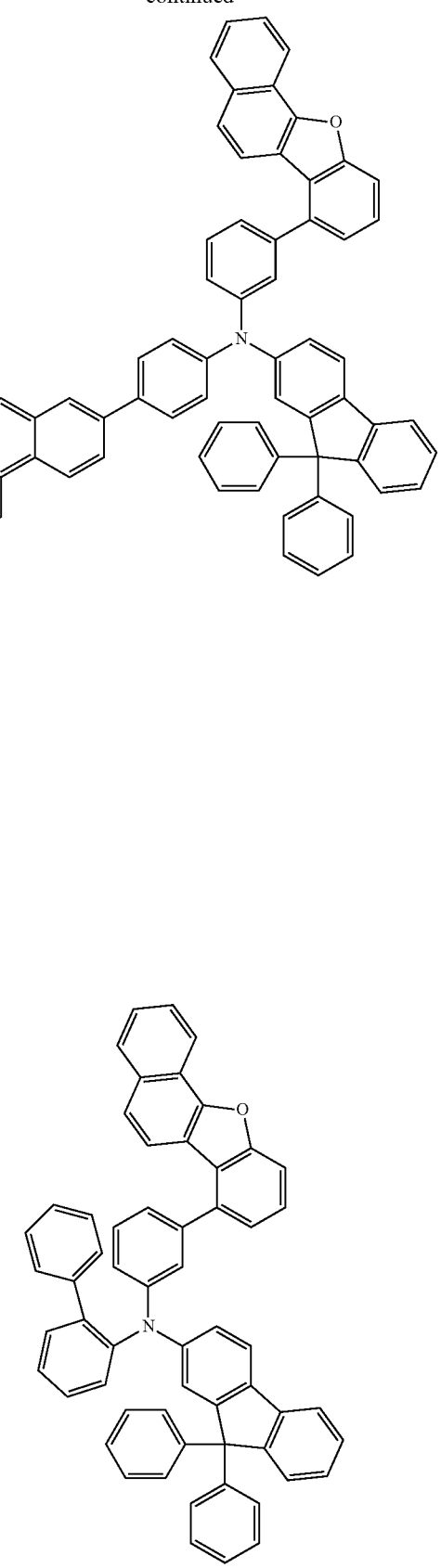

689
[Chem. 243]
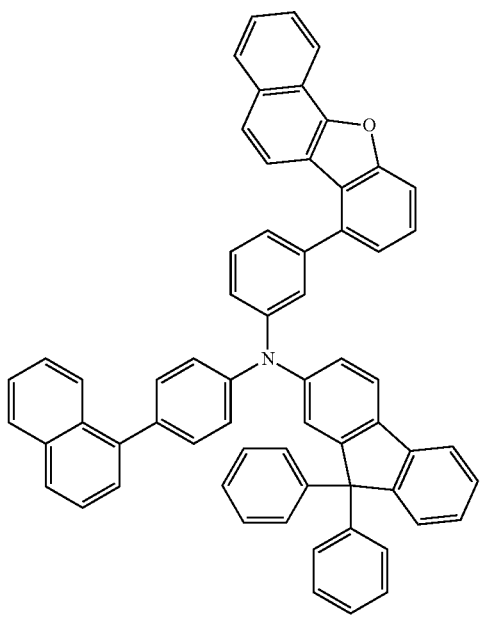
690
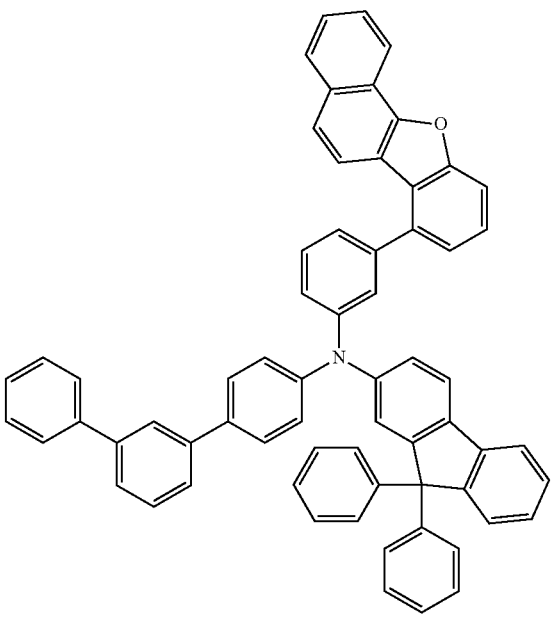
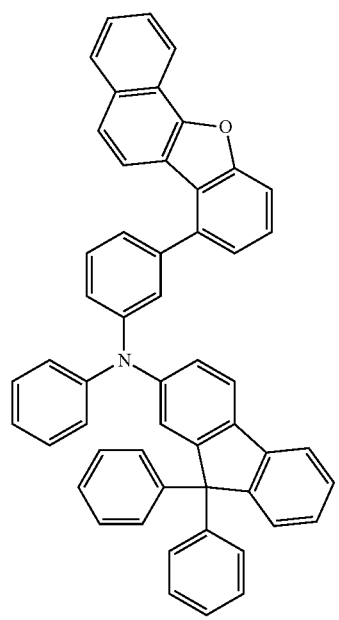

691
-continued
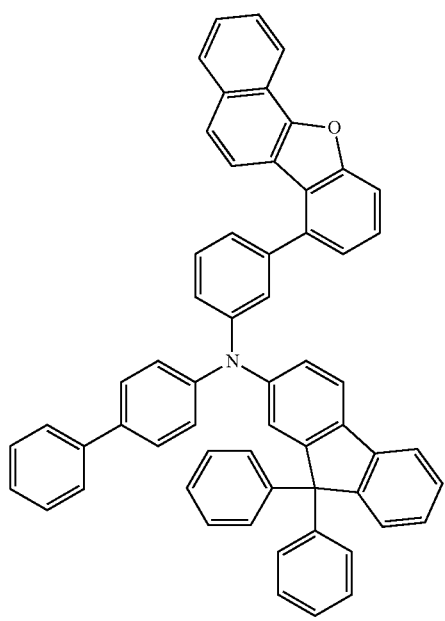
692
-continued
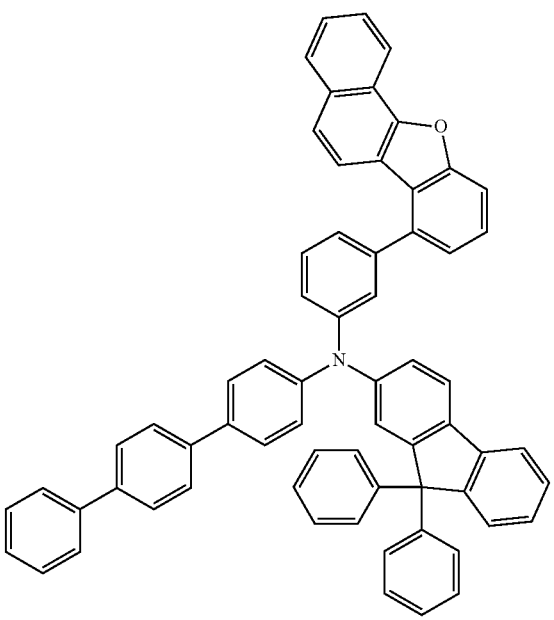
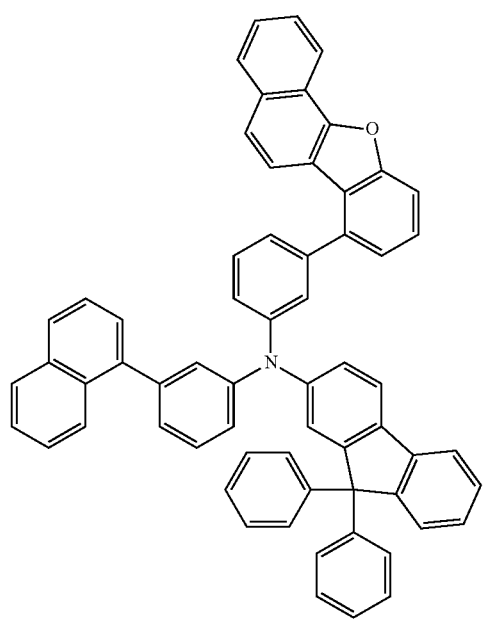
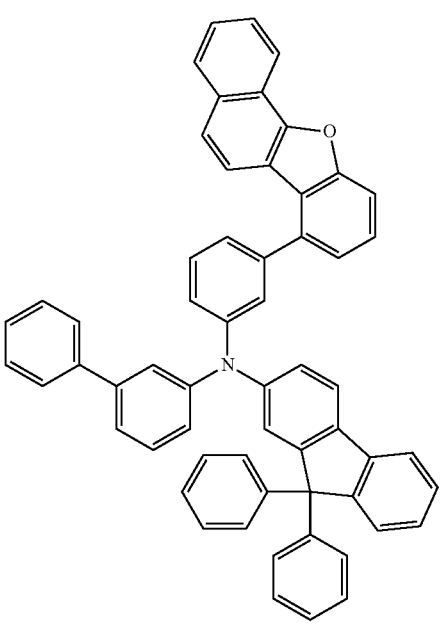

[Chem. 254]
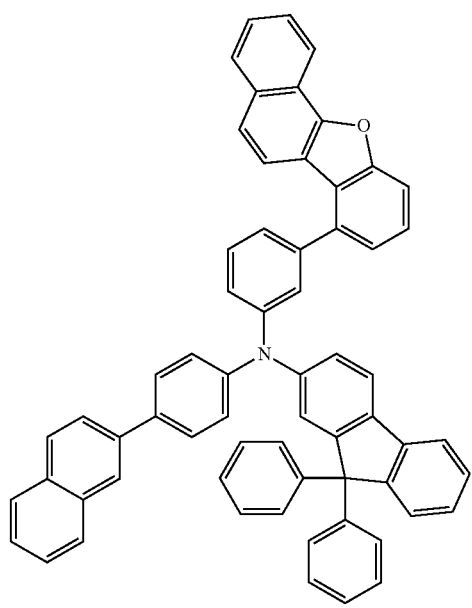
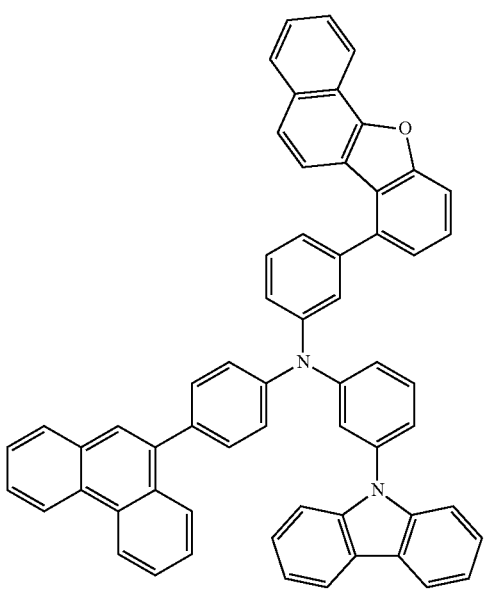
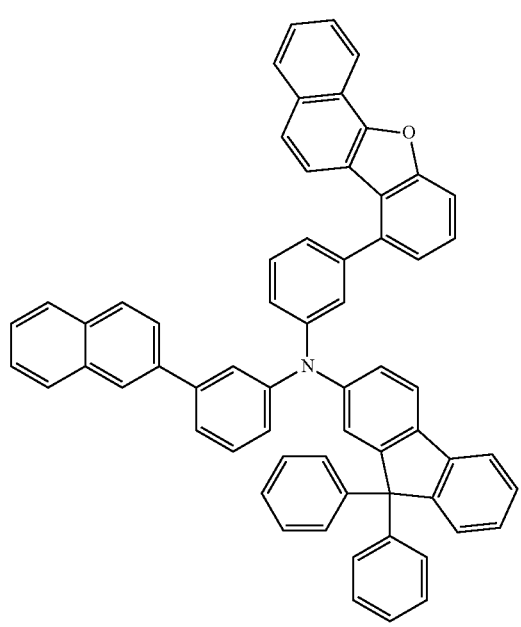
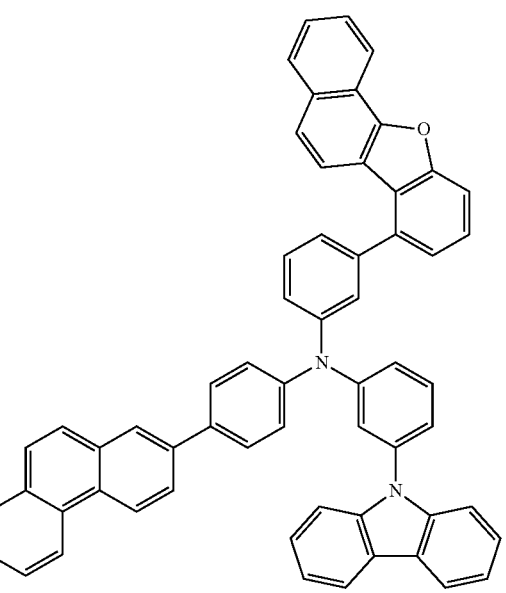

695
-continued
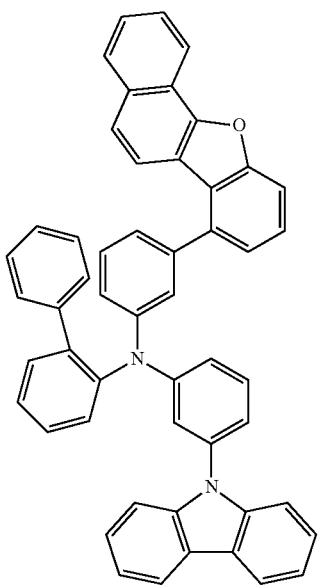
696
-continued
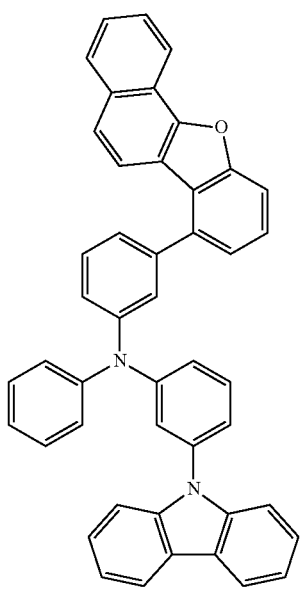
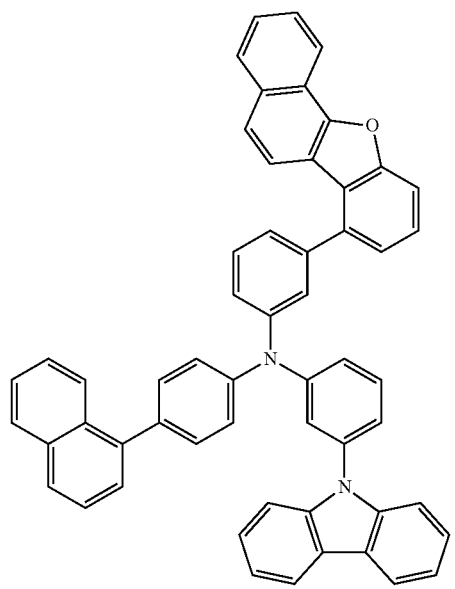
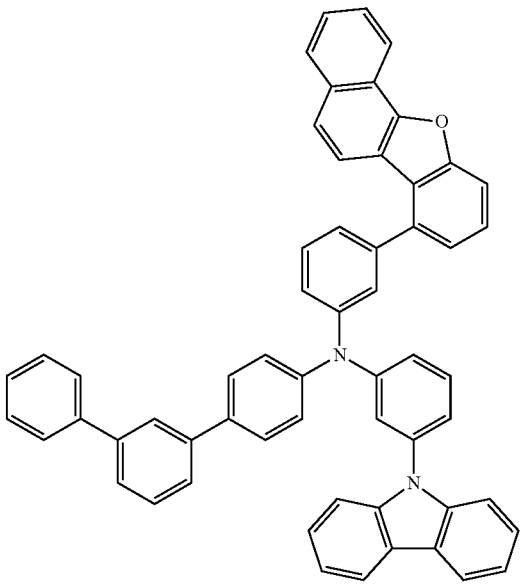

697
-continued
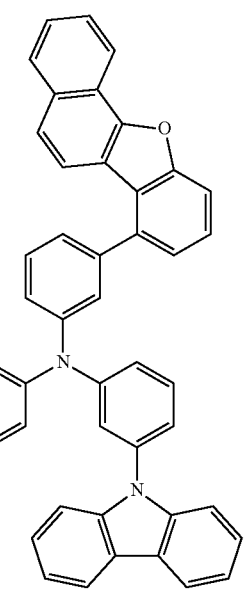
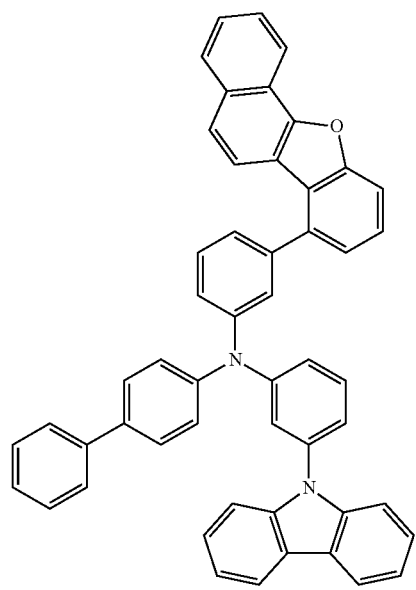
698
-continued
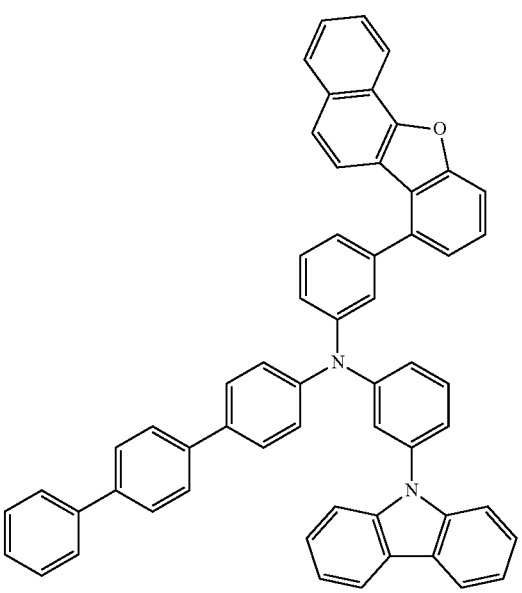
[Chem. 245]

| 699 | 700 |
|---|---|
| -continued | -continued |
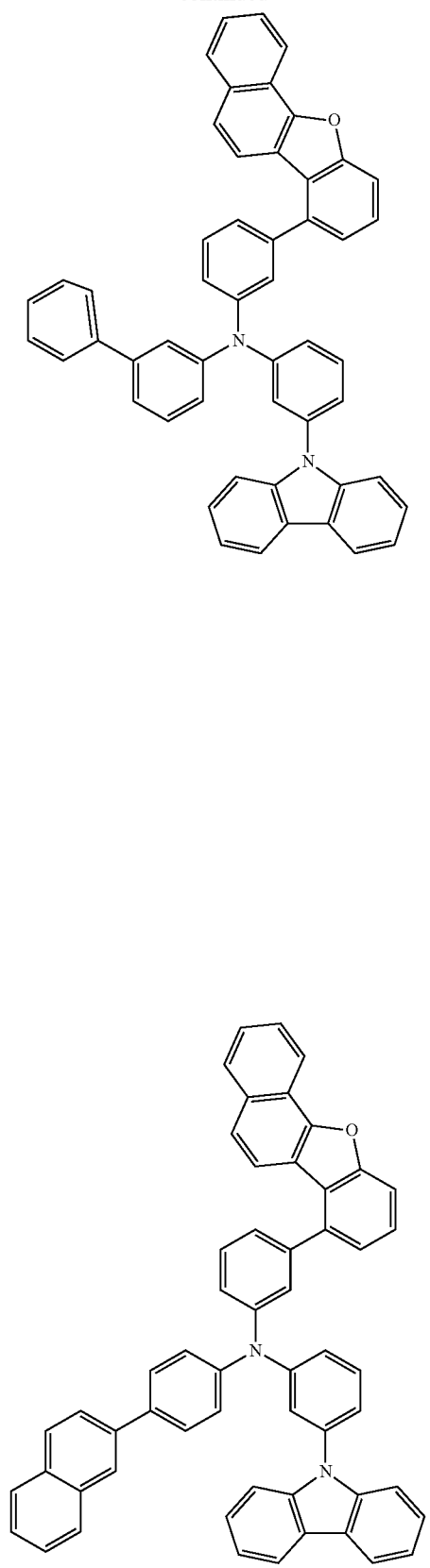
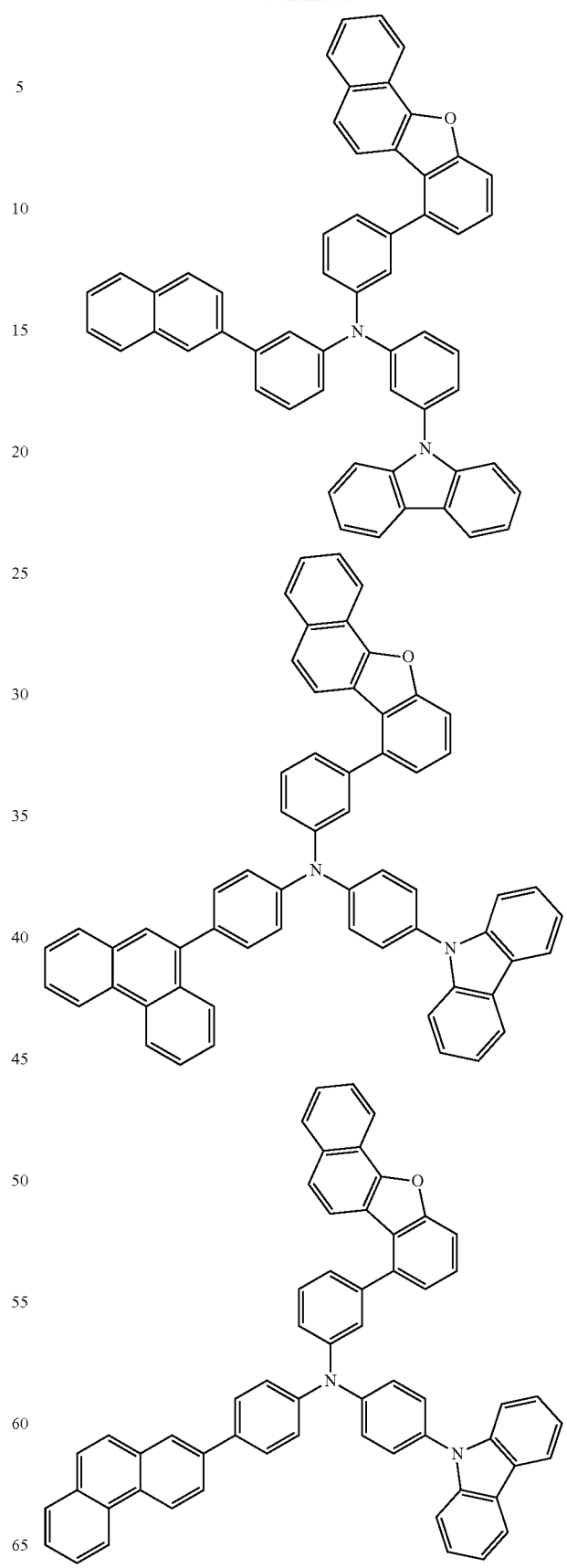

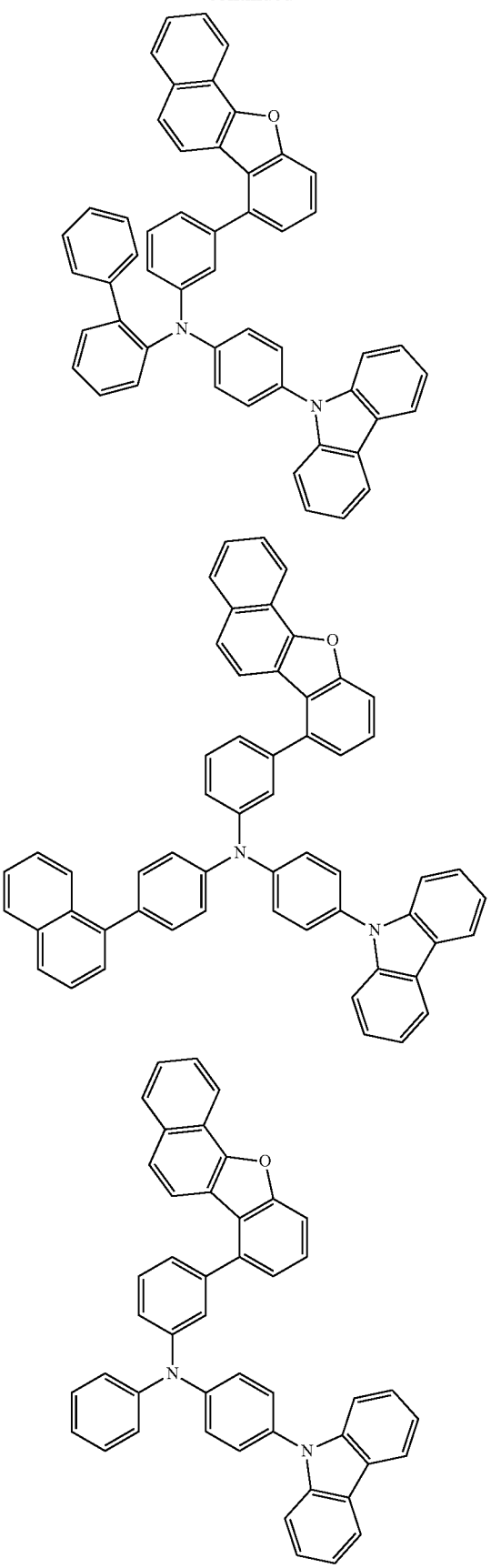

703
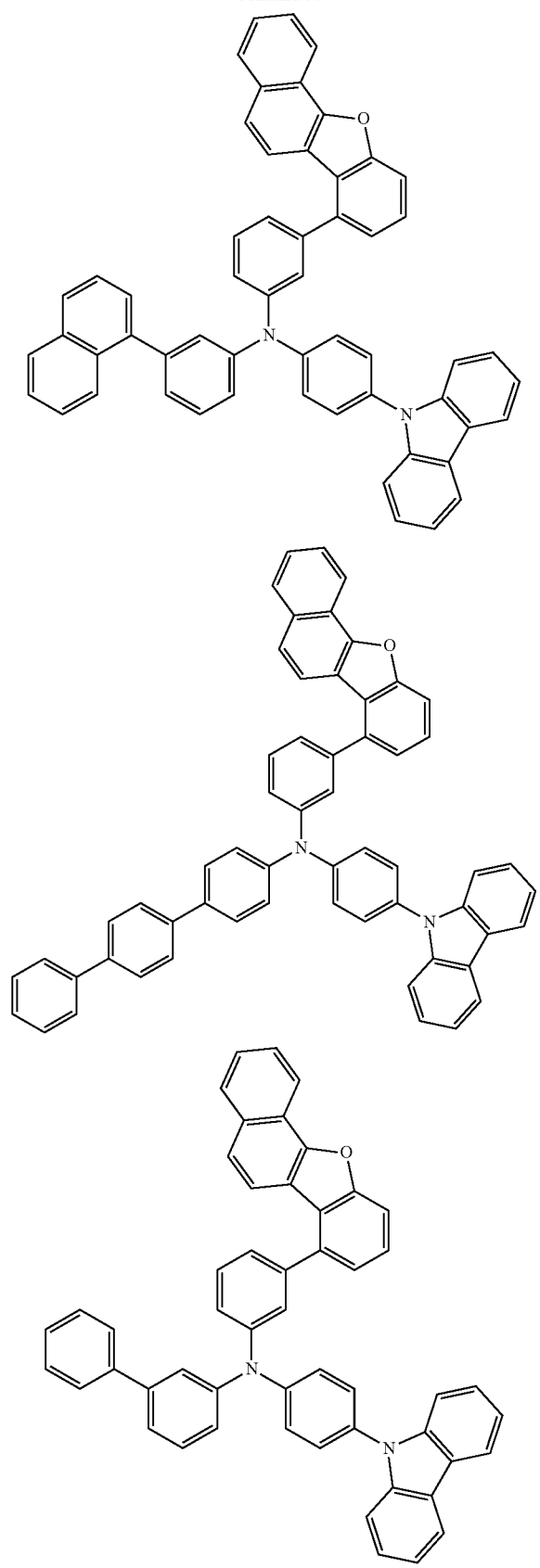
704
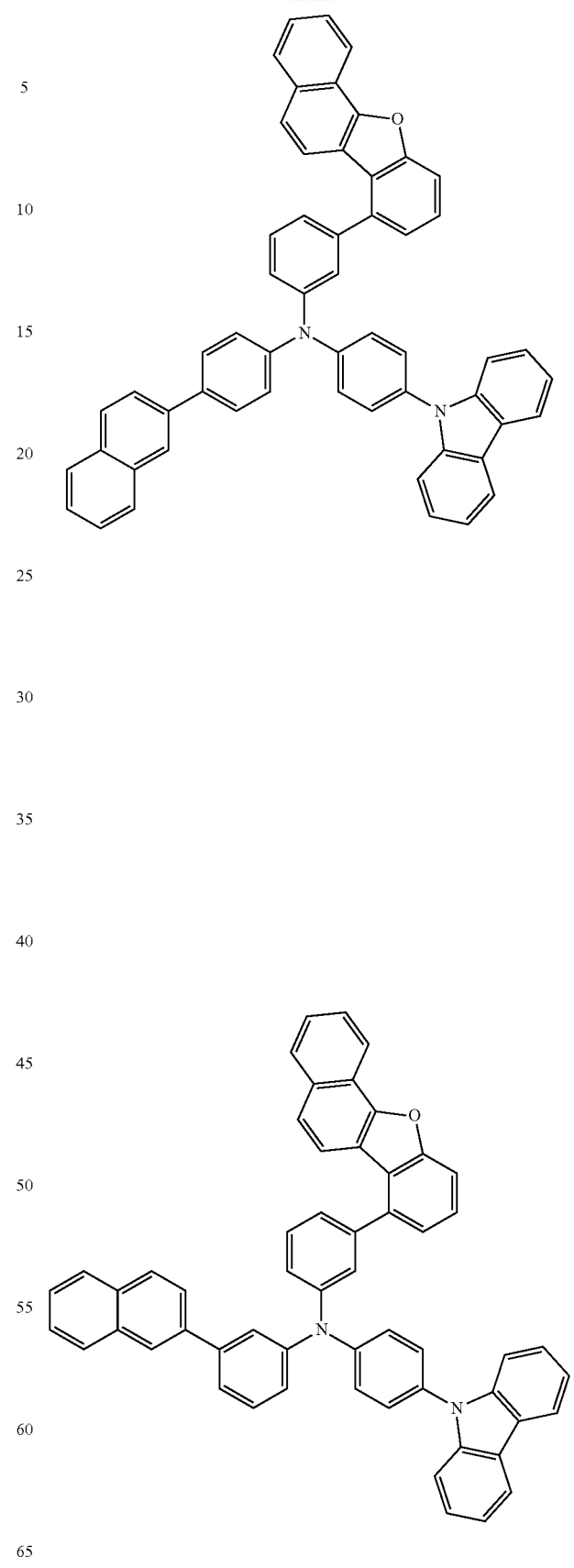

705
-continued
[Chem. 247]
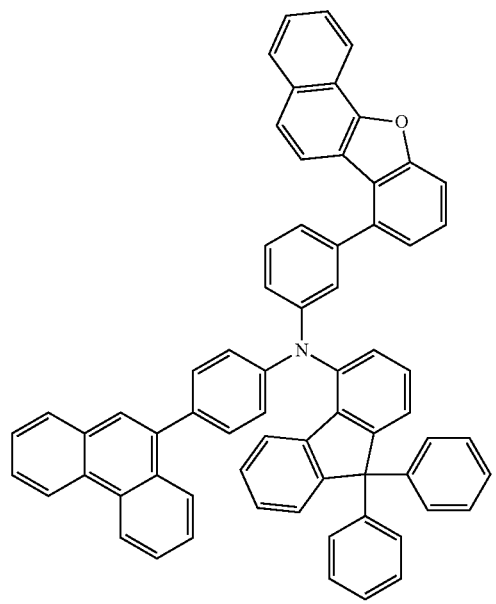
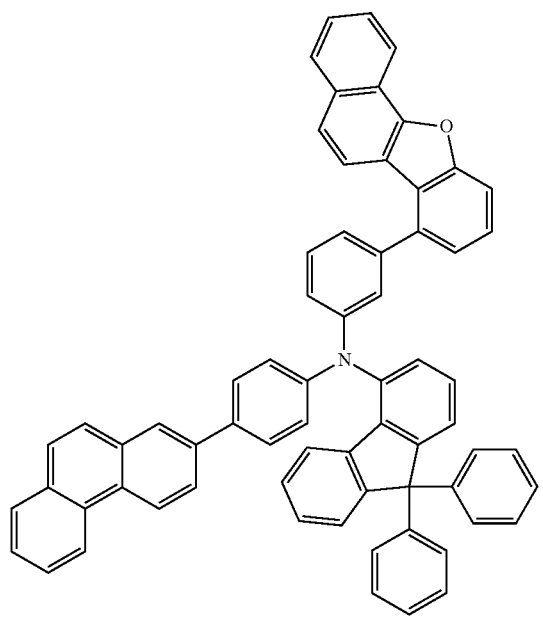
706
-continued
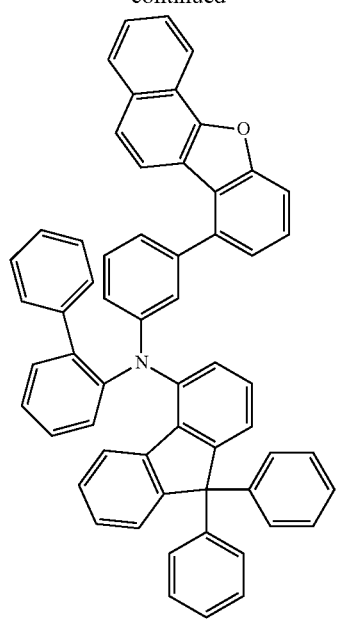
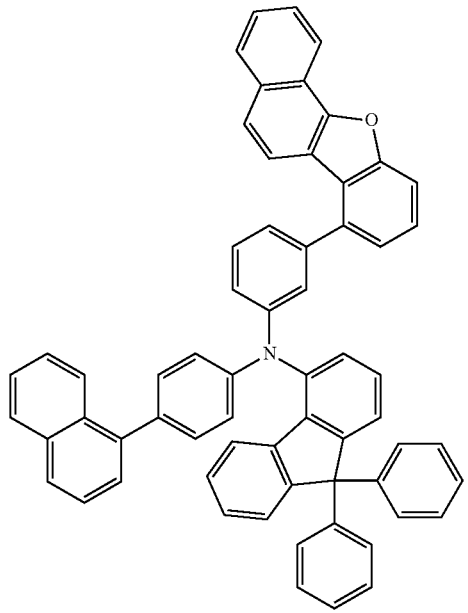

707
-continued
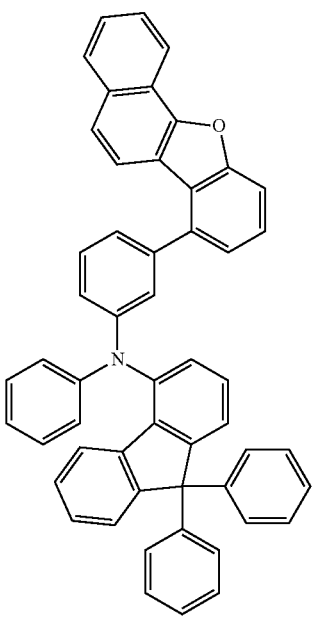
708
-continued
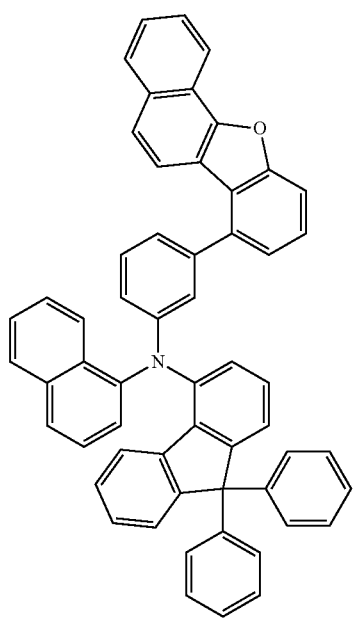
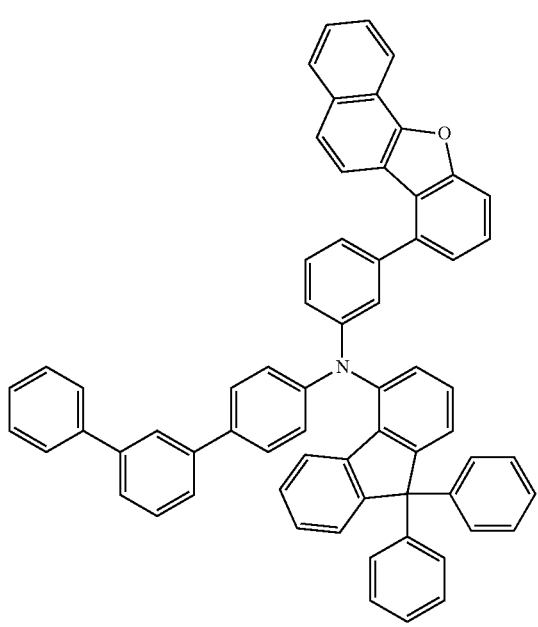
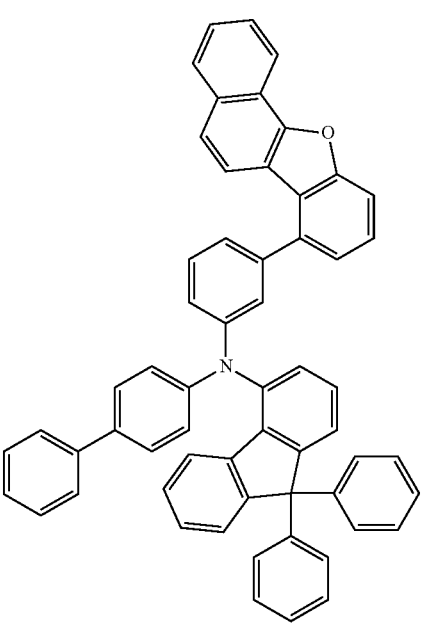

709
-continued
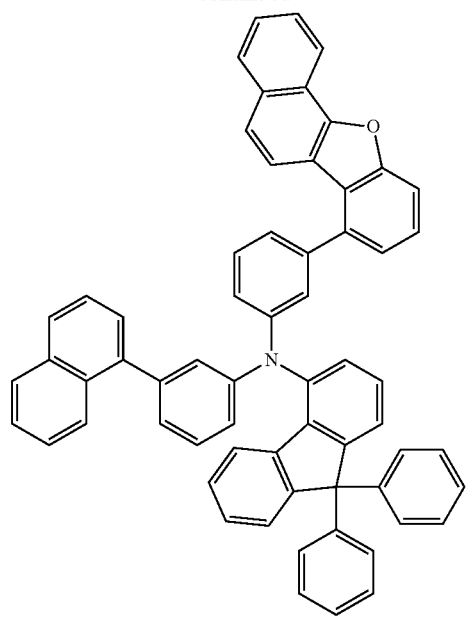
710
-continued
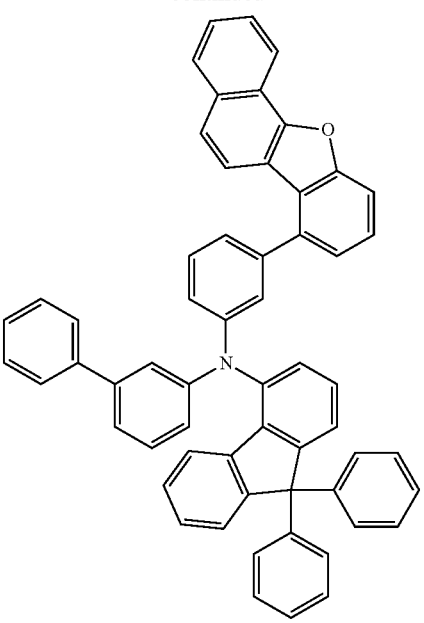
[Chem. 248]
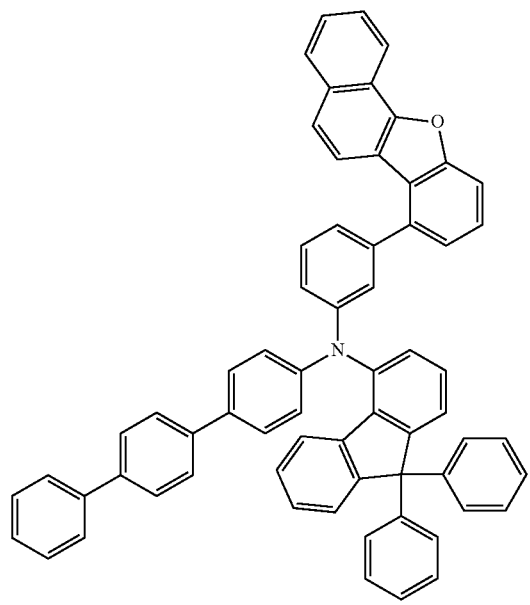
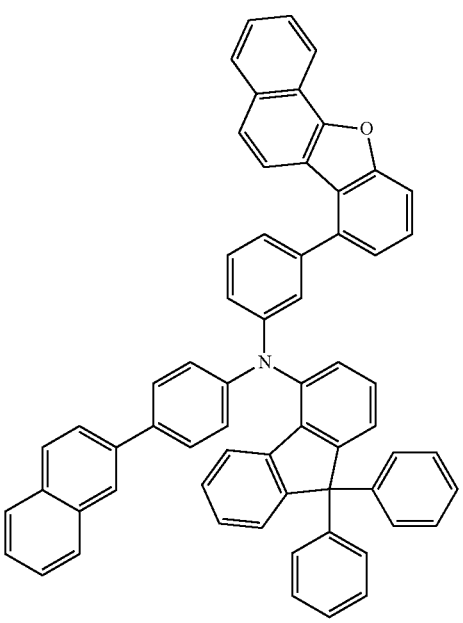

711
-continued
712
-continued
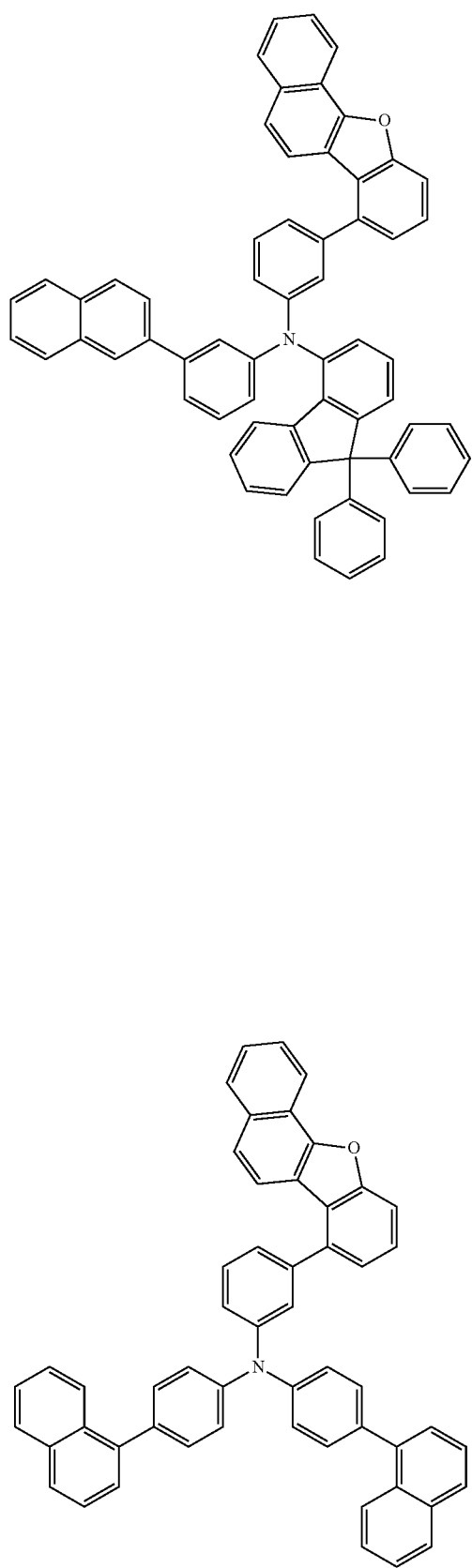
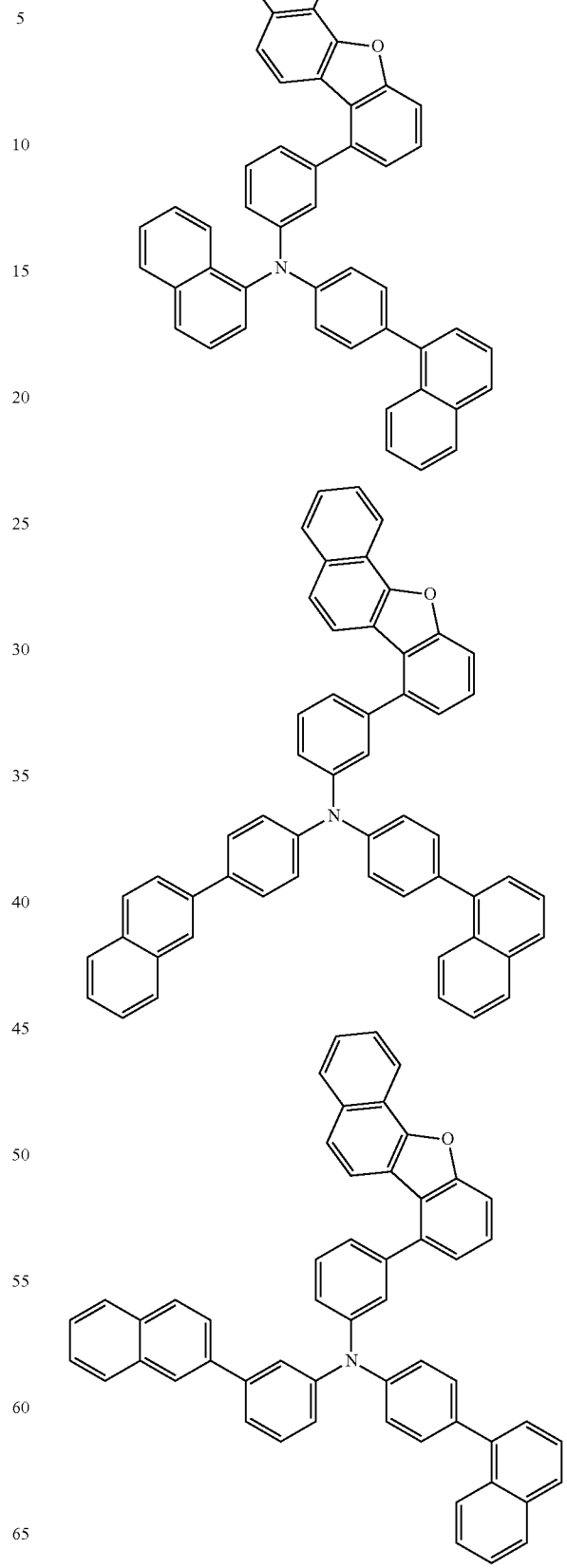

713
-continued
[Chem. 249]
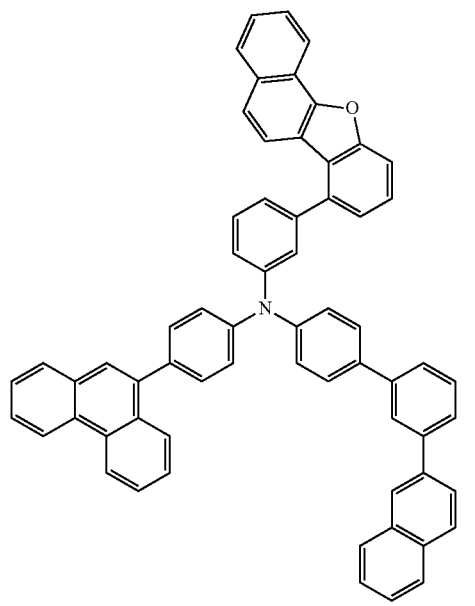
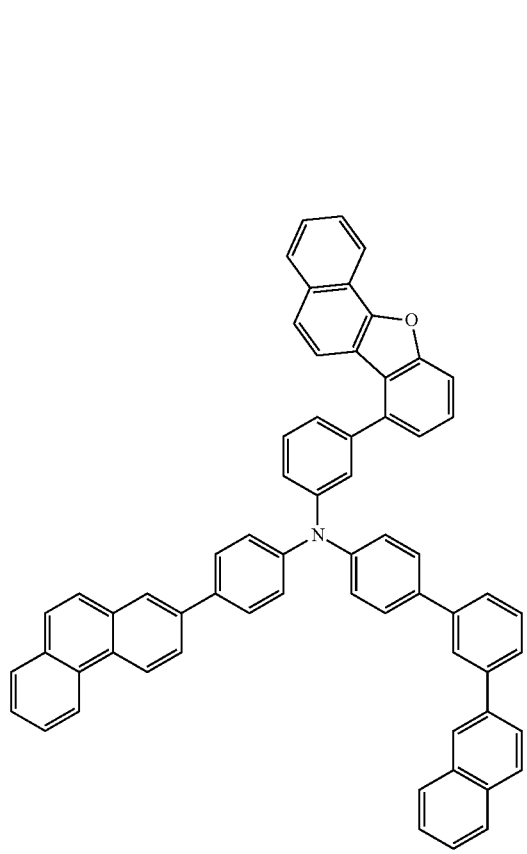
714
-continued
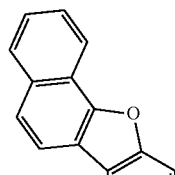
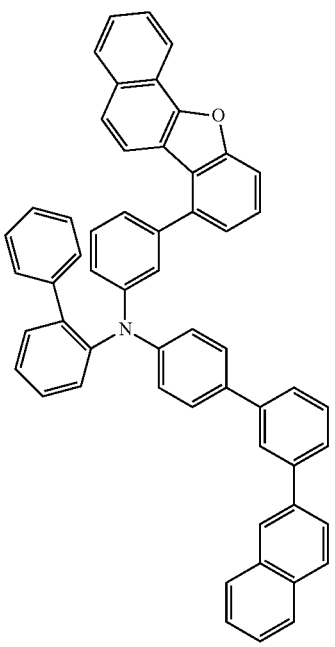
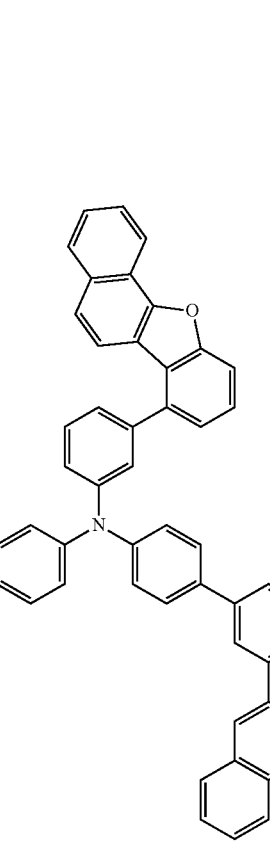

715
-continued
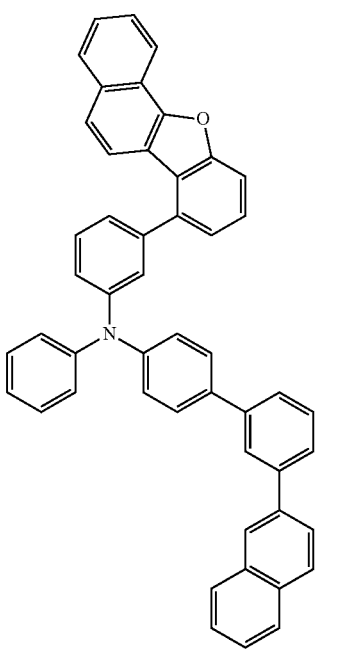 [SMILES: c1ccc(N(c2ccc(-c3cccc(-c4ccc5ccccc5c4)c3)cc2)c2cccc(-c3cccc4oc5c6ccccc6ccc5c34)c2)cc1]
716
-continued
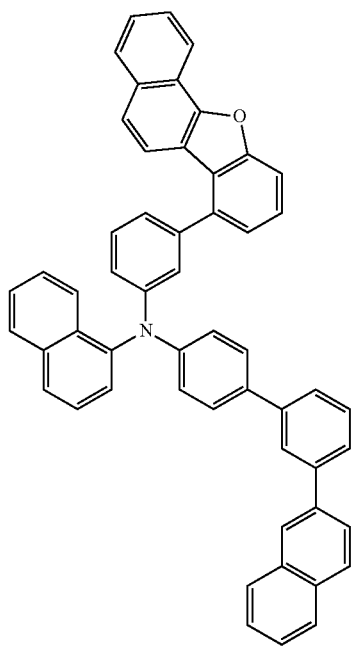
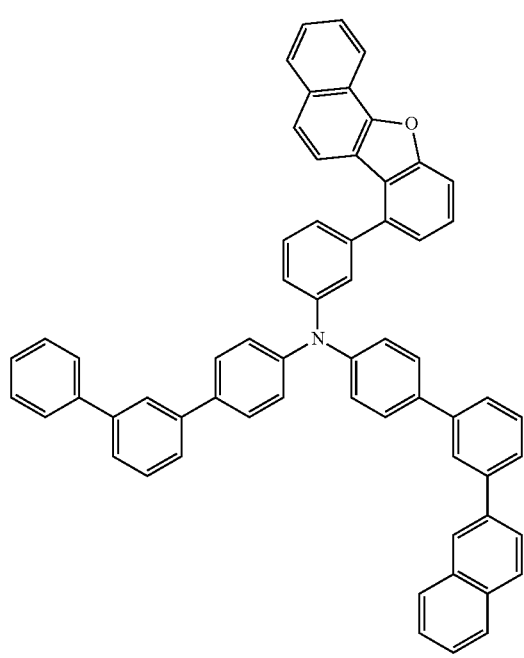
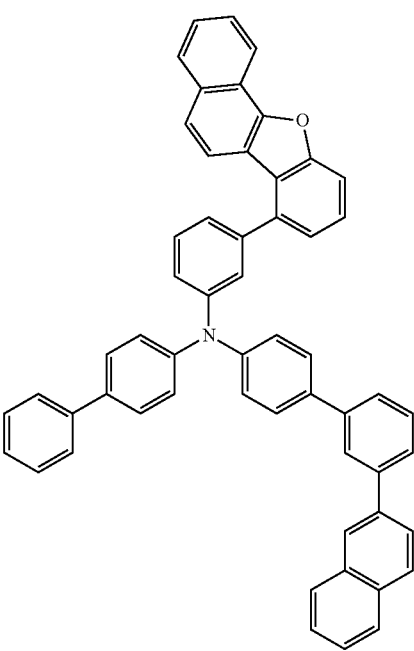 [SMILES: c1ccc(-c2ccc(N(c3ccc(-c4cccc(-c5ccc6ccccc6c5)c4)cc3)c3cccc(-c4cccc5oc6c7ccccc7ccc6c45)c3)cc2)cc1]

717
-continued
[Chem. 250]
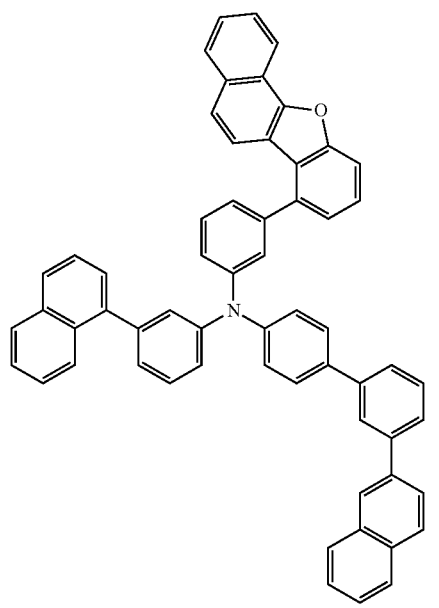
718
-continued
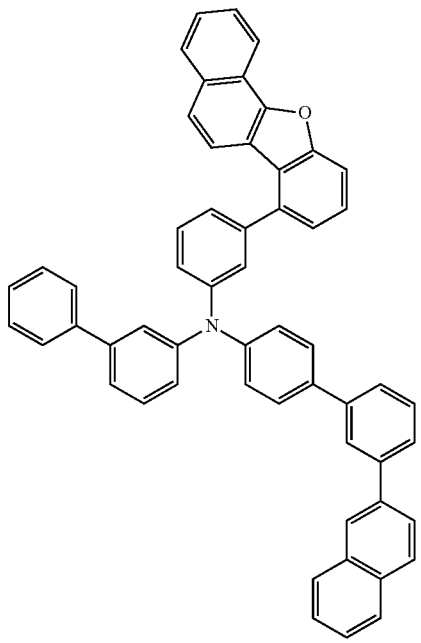
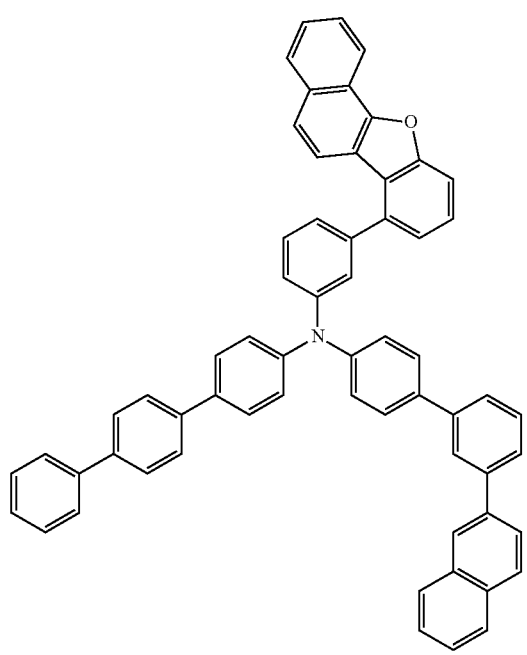
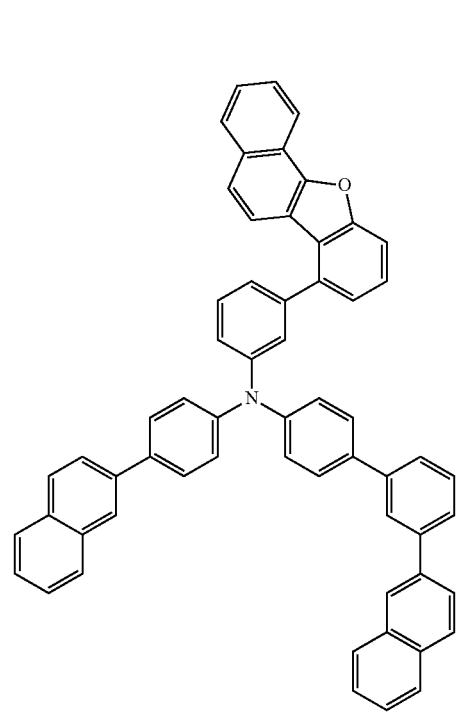

719
-continued
720
-continued
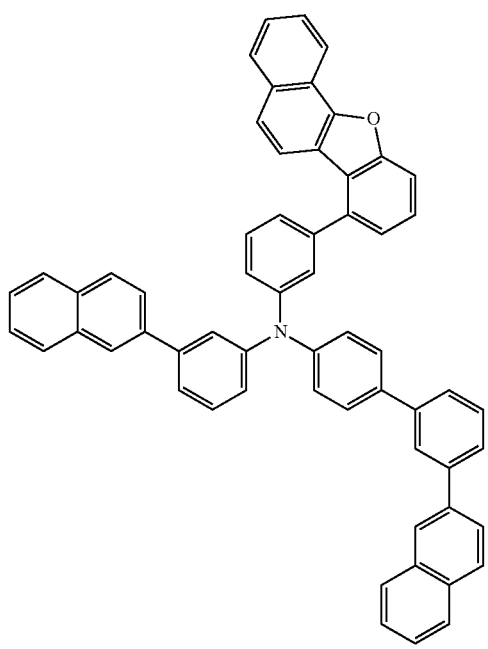
[Chem. 251]
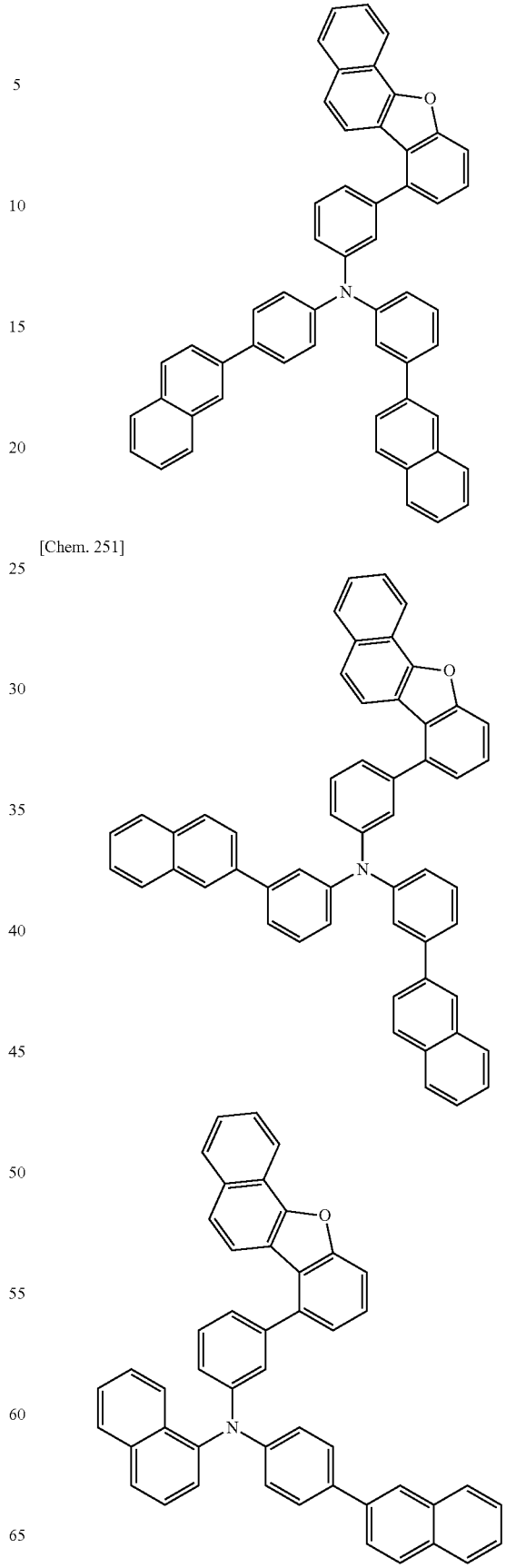

721
-continued
722
-continued
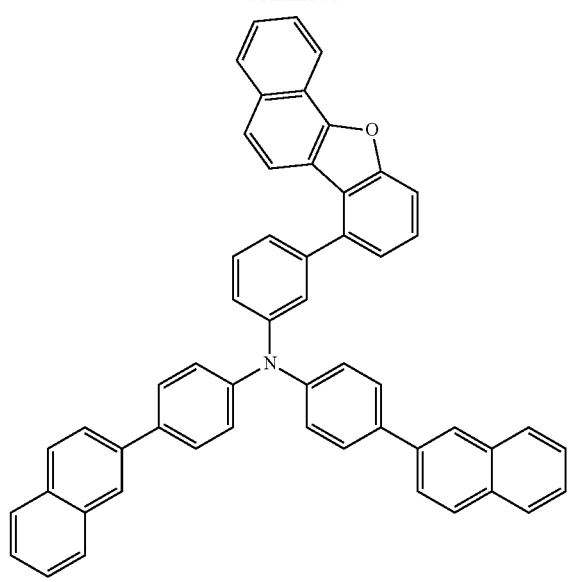
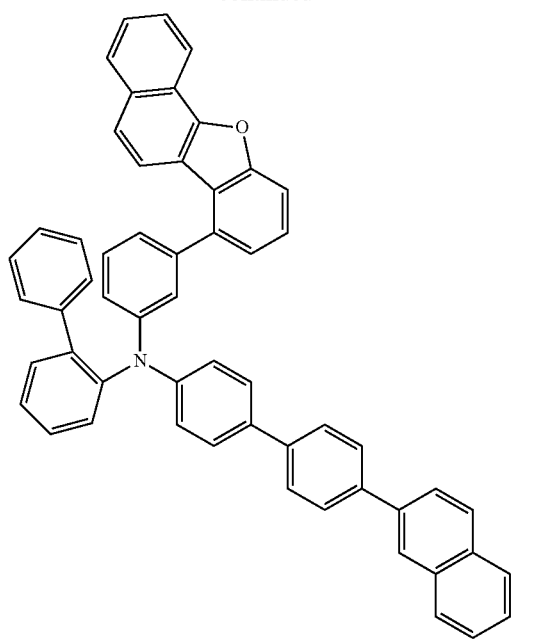
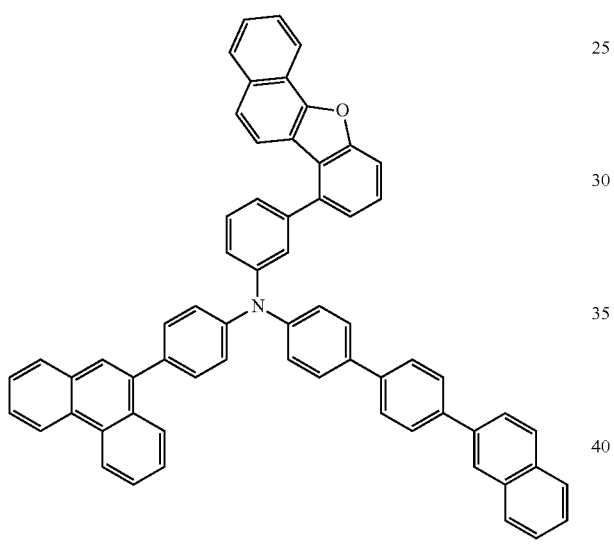
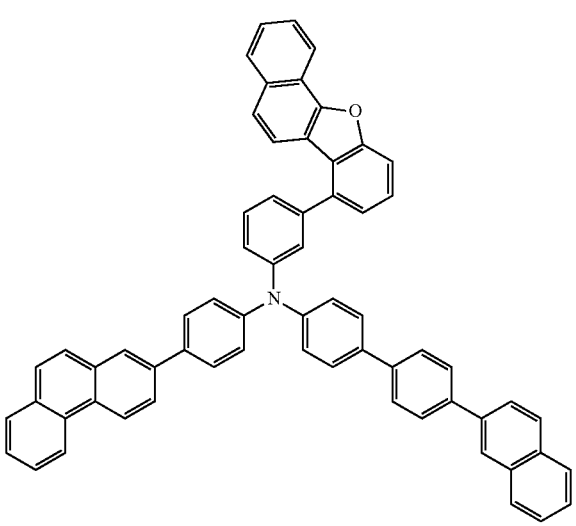
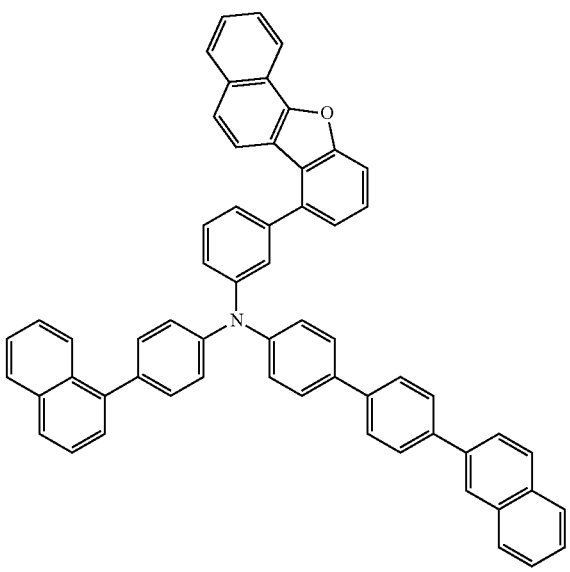

723
-continued
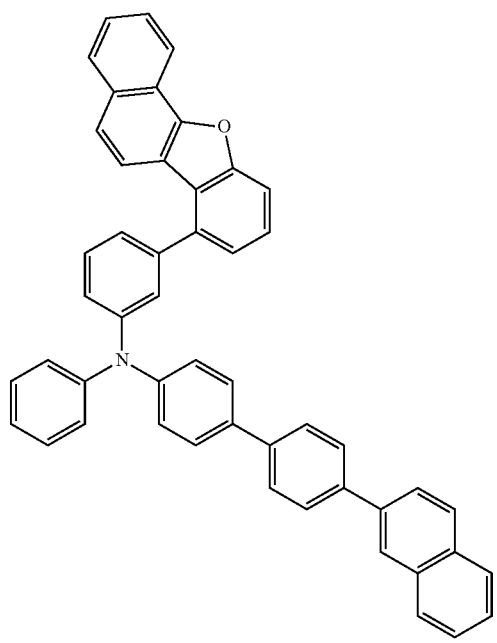
724
-continued
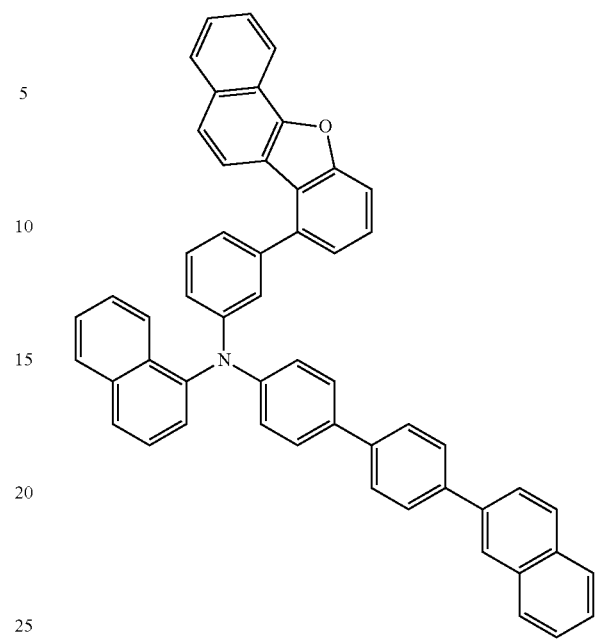
[Chem. 252]
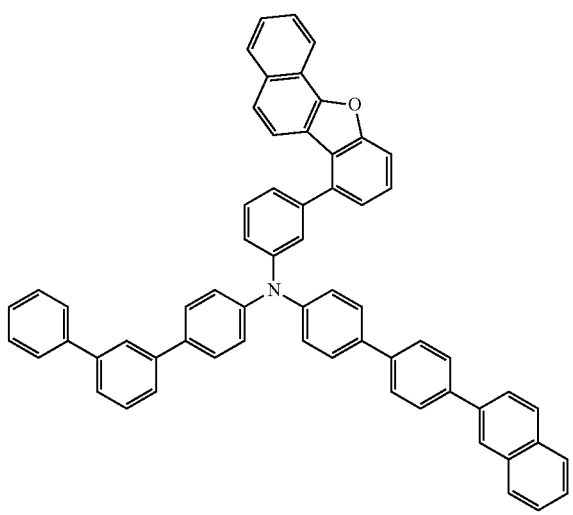
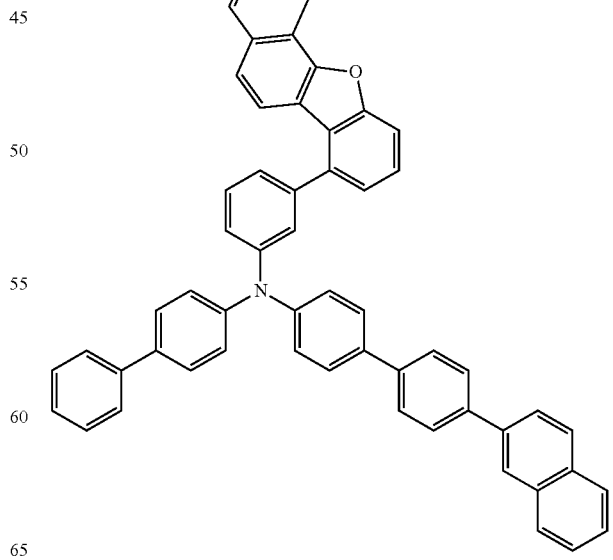

725
-continued
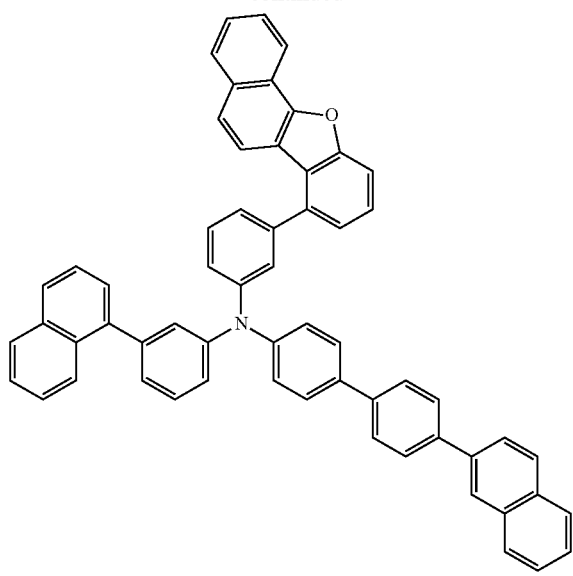
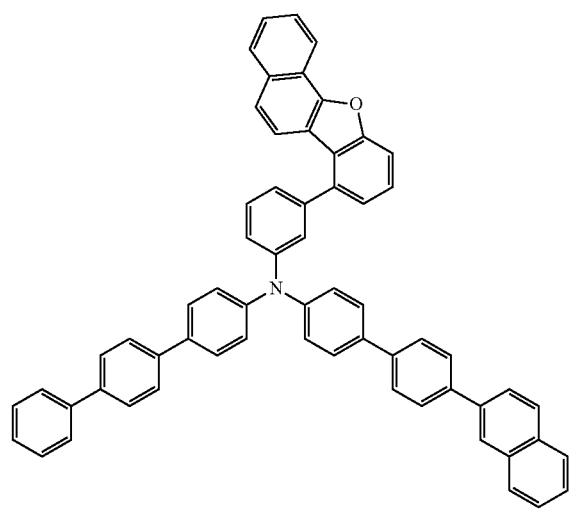
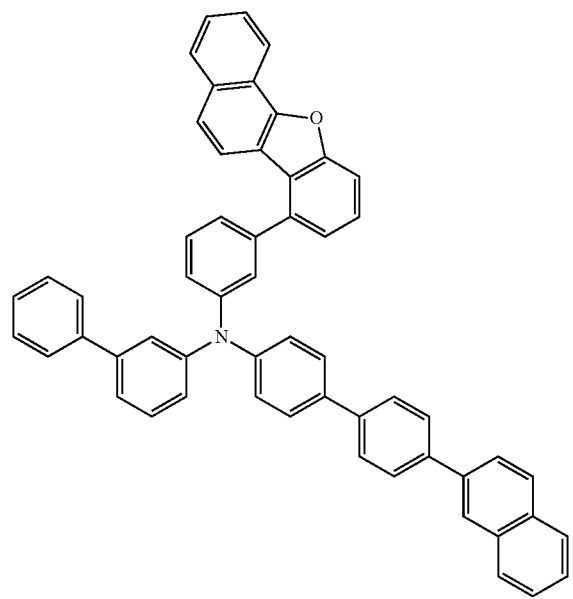
726
-continued
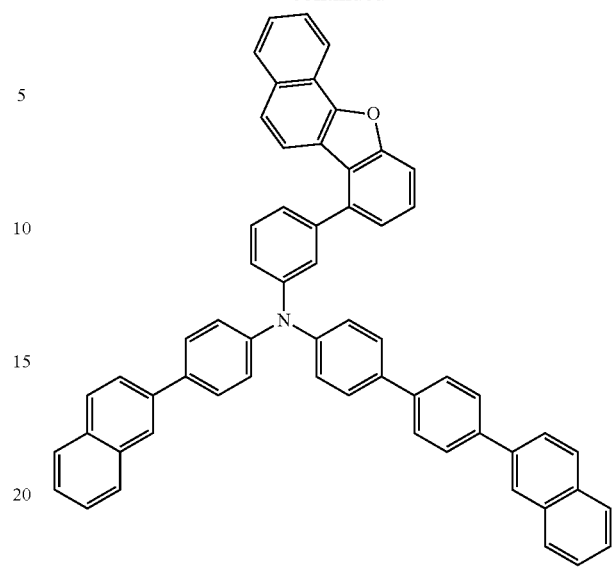
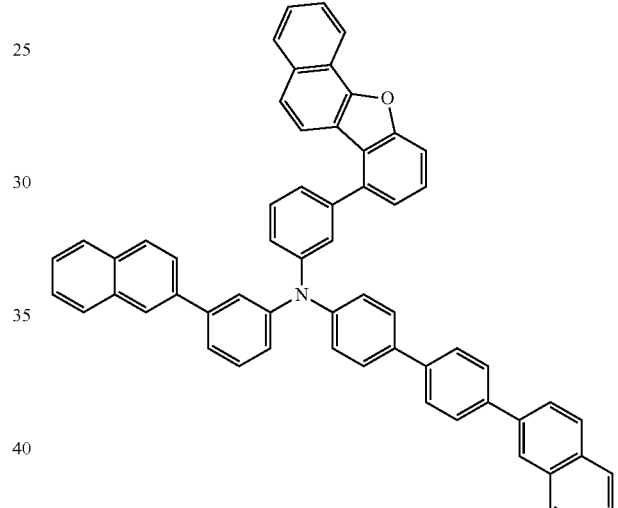
[Chem. 253]
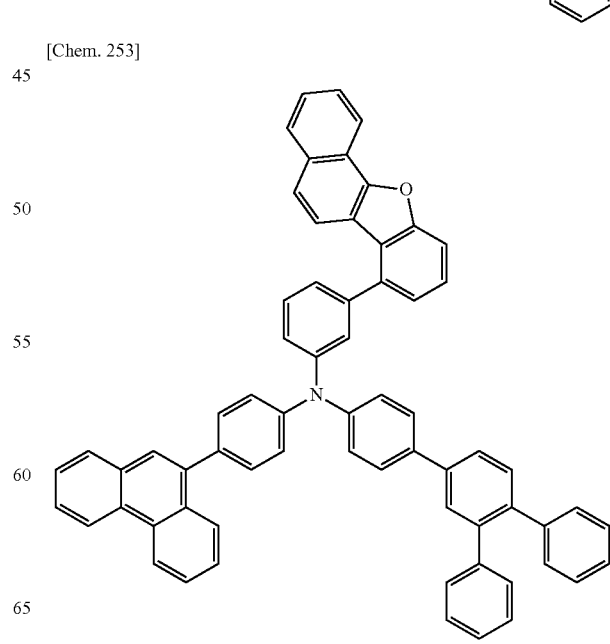

727
-continued
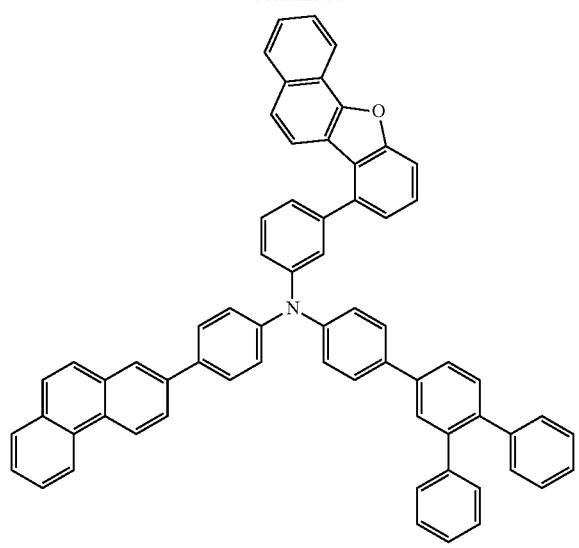
728
-continued
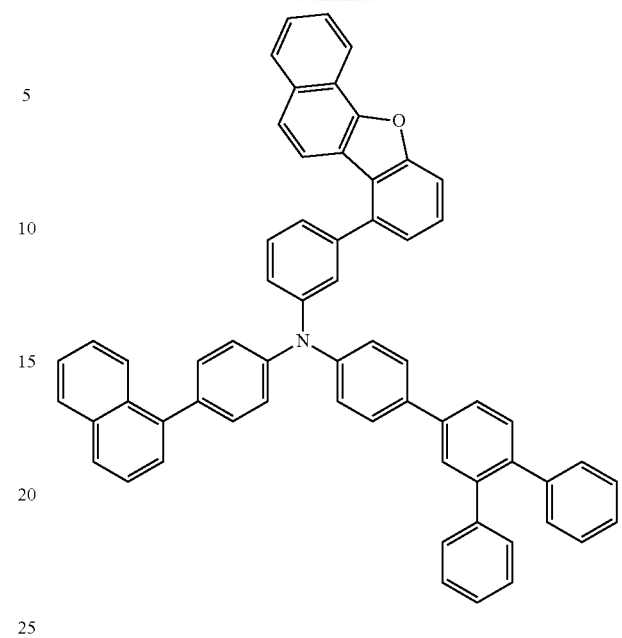
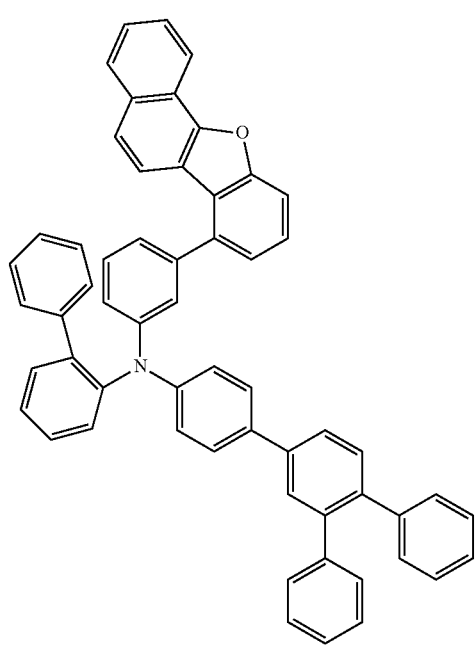
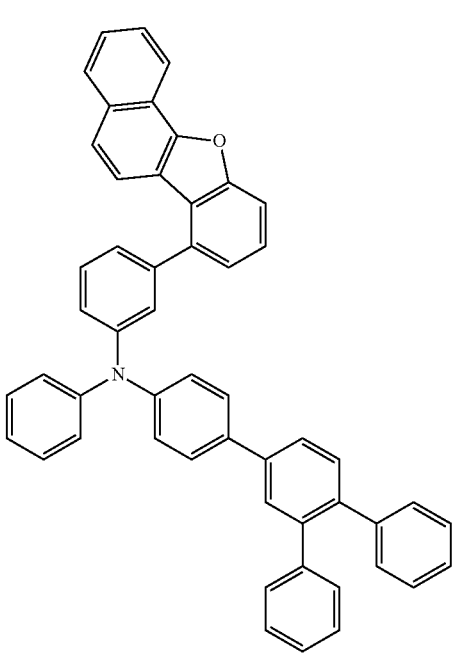

729
-continued
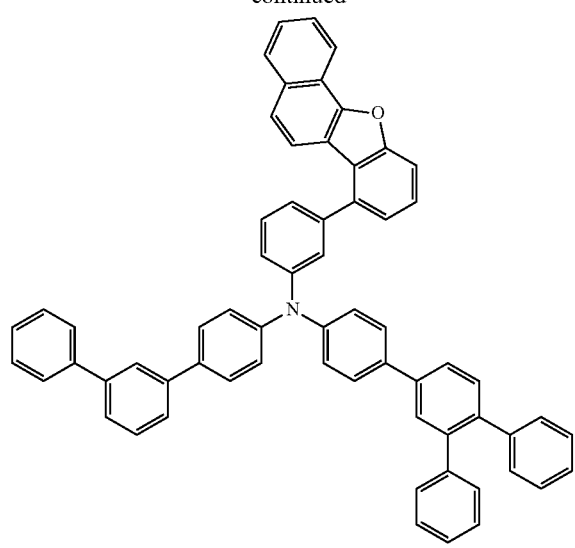
730
-continued
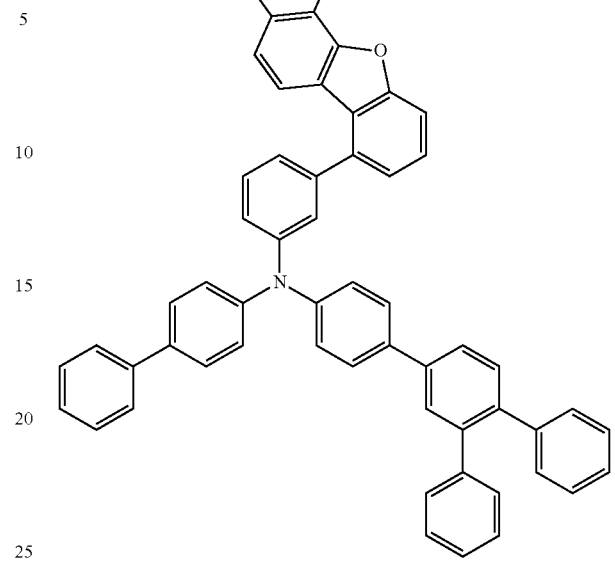
[Chem. 254]
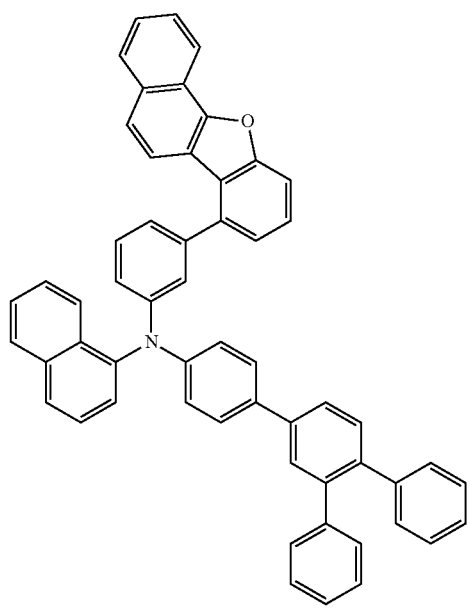
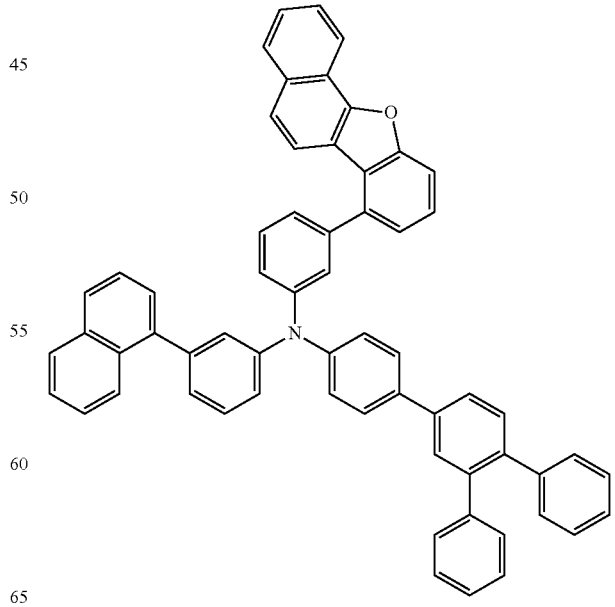

731 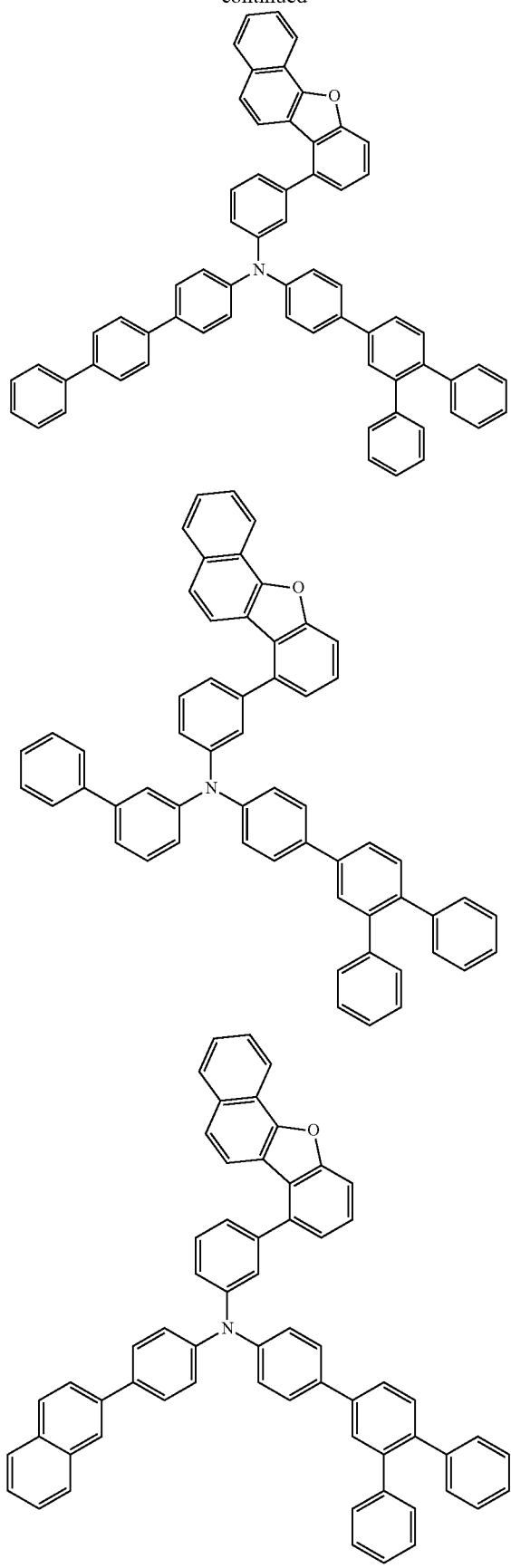
732 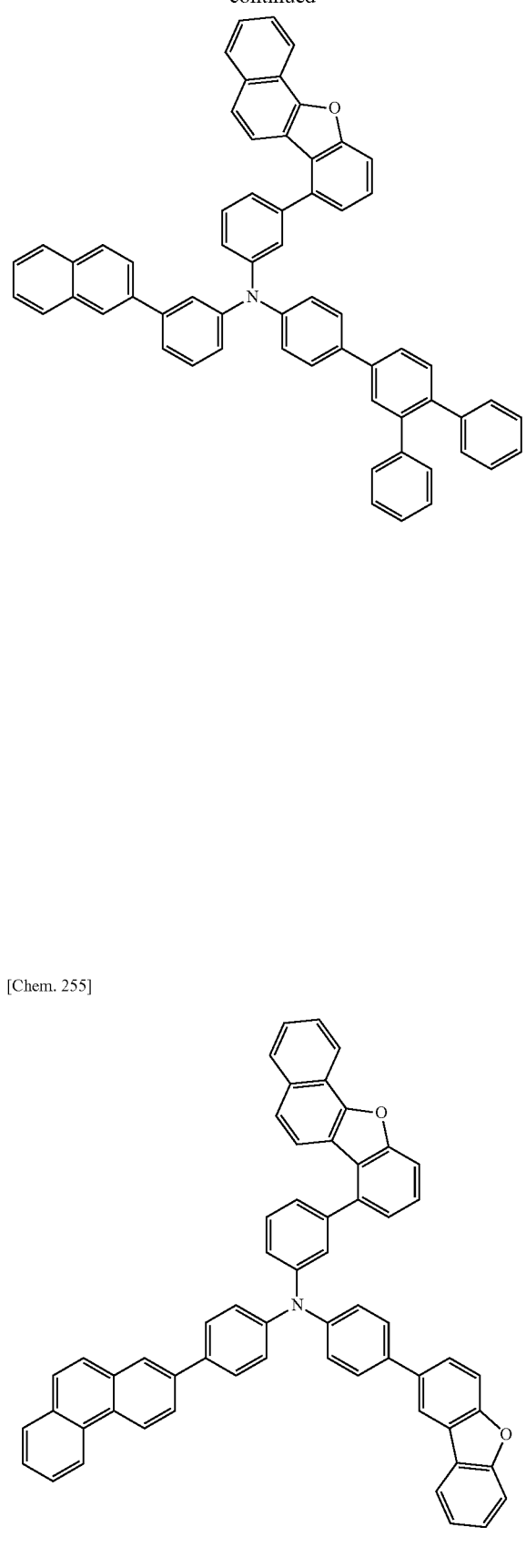
[Chem. 255]

733
-continued
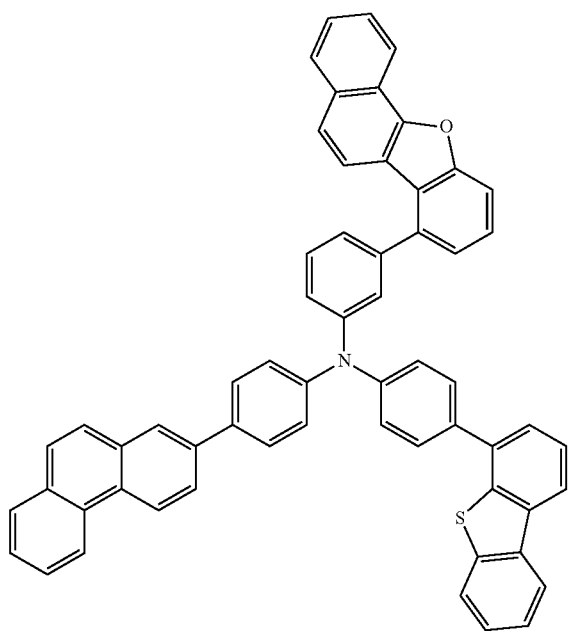
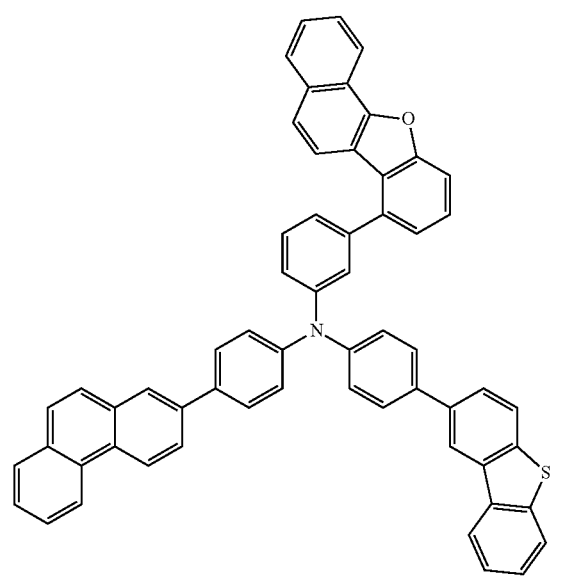
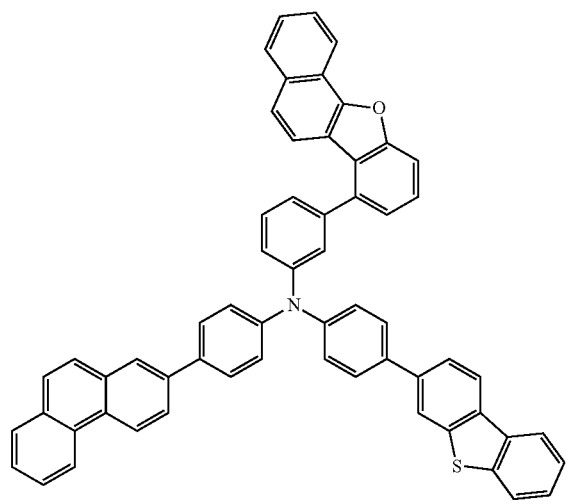
734
-continued
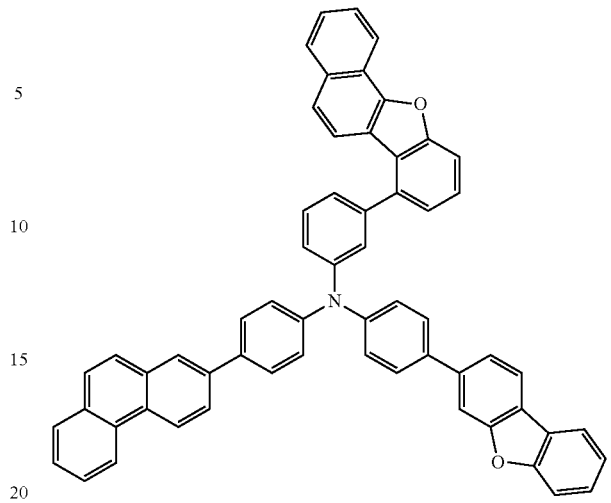
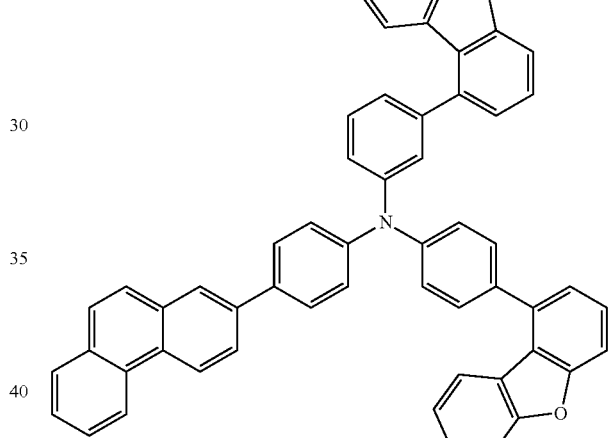
[Chem. 256]
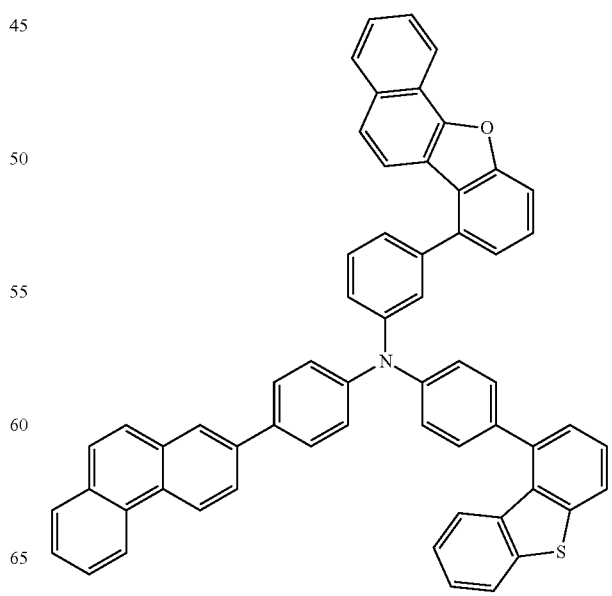

735
-continued
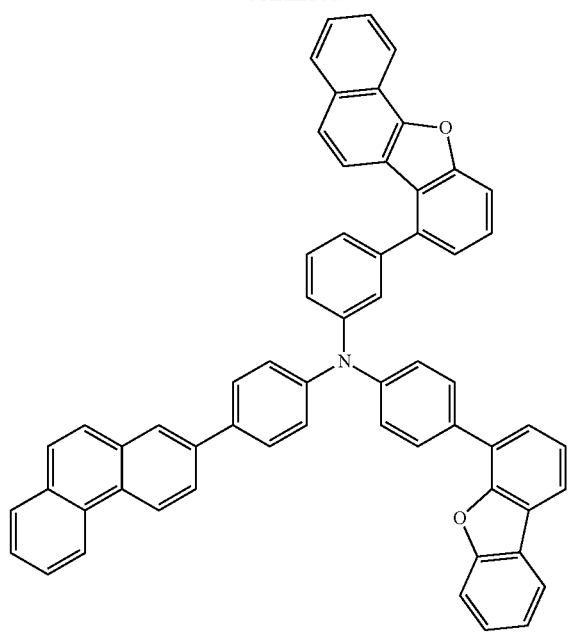
736
-continued
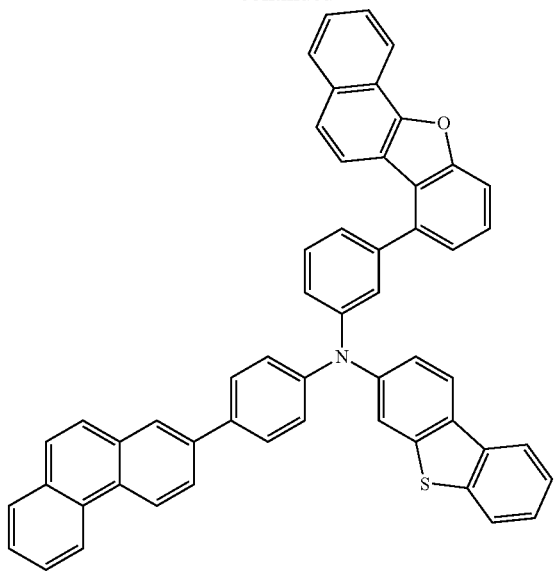
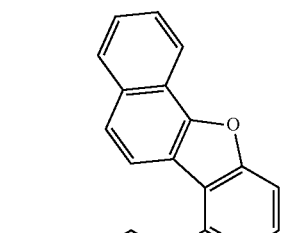
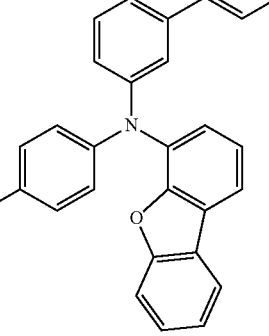
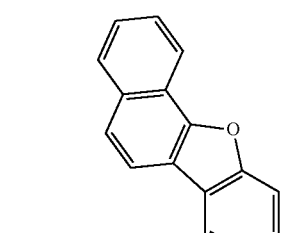
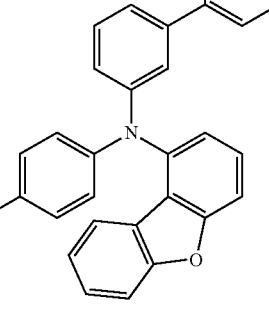

737
-continued
738
-continued
[Chem. 257]
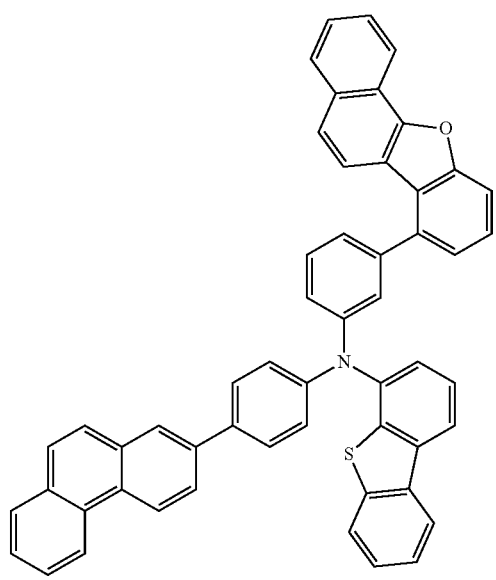
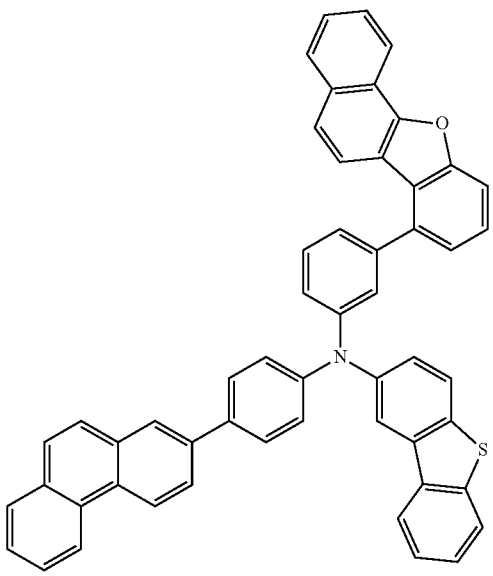

739
-continued
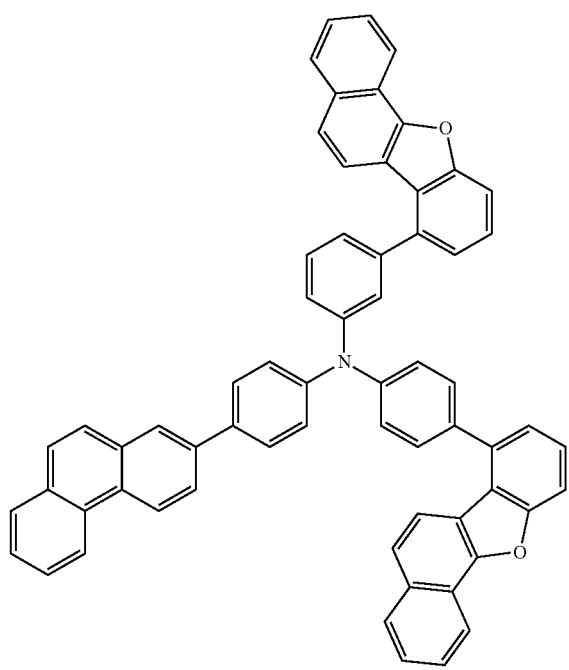
740
-continued
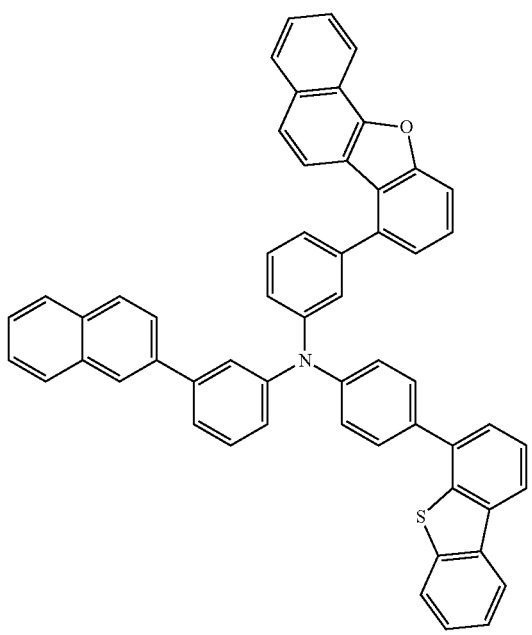
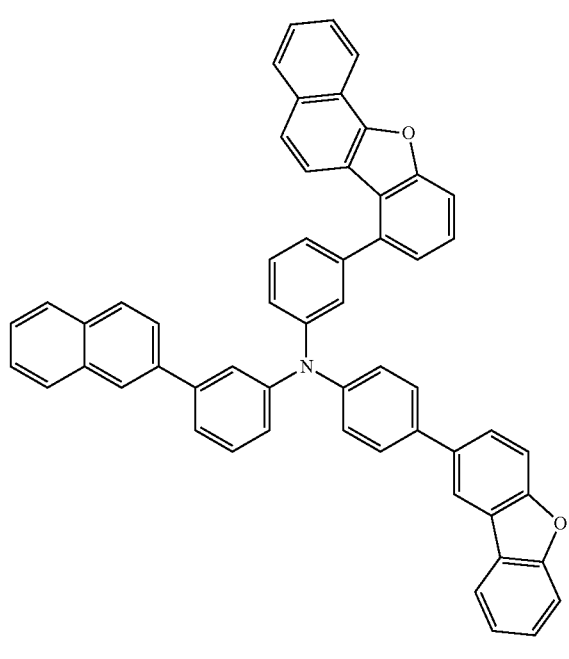

741
-continued
[Chem. 258]
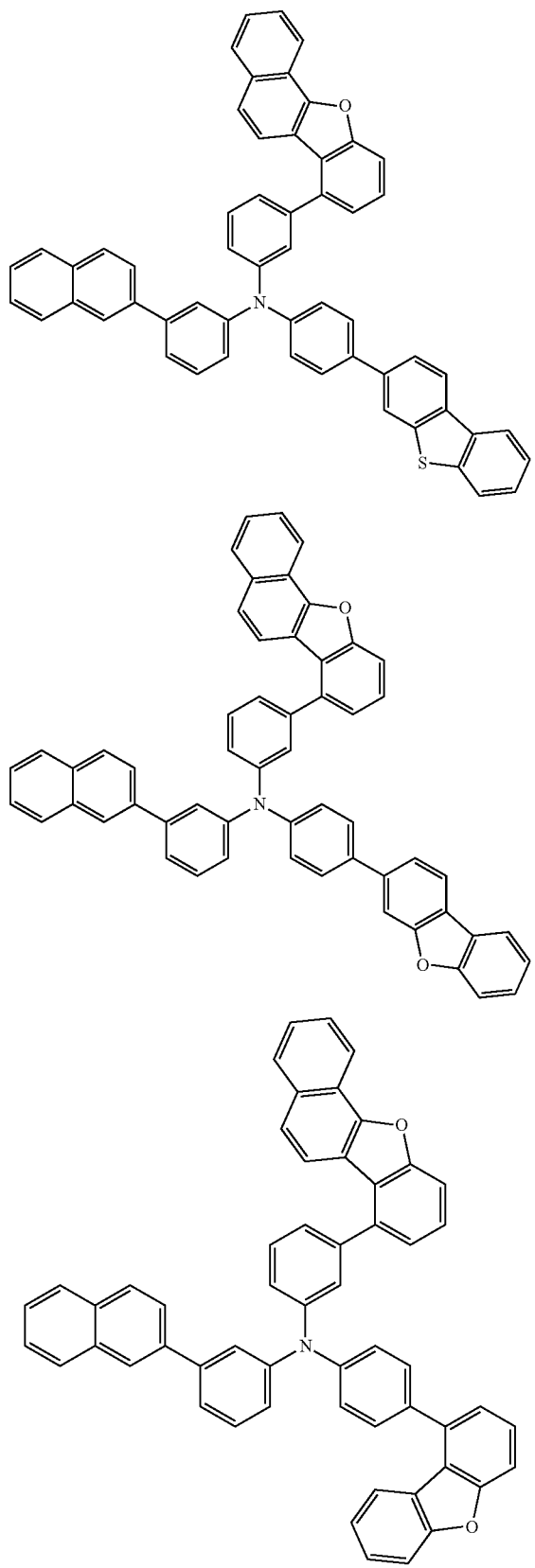
742
-continued
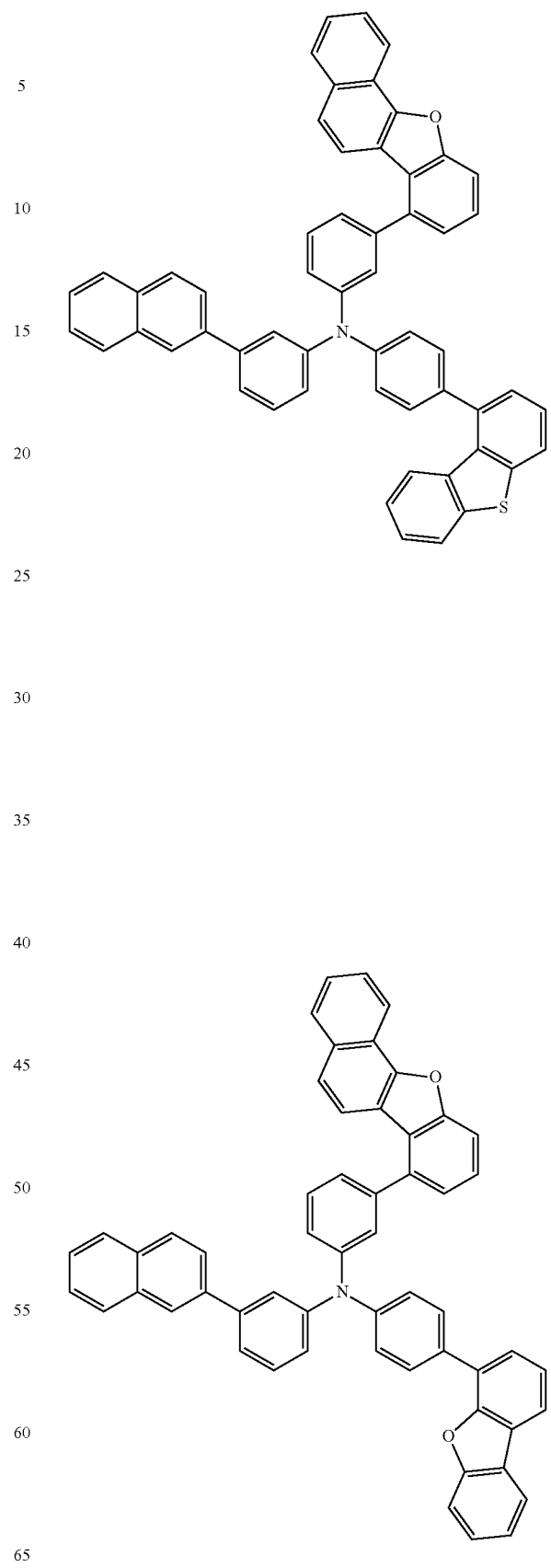

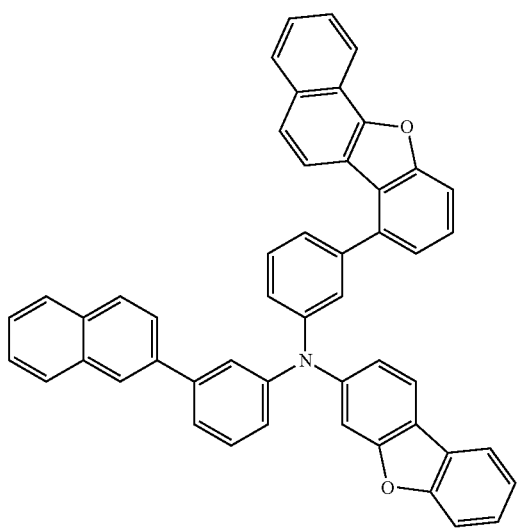
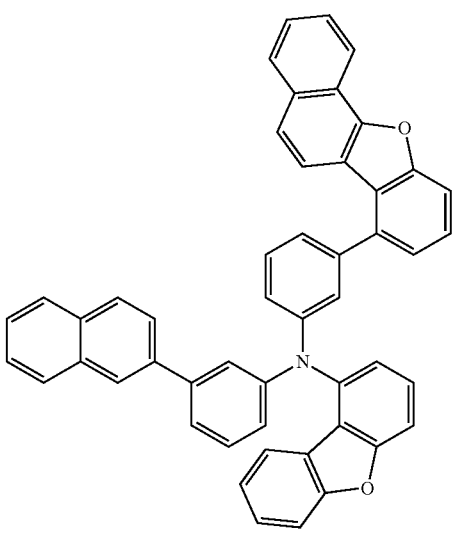 [SMILES: c1cc(-c2ccc3ccccc3c2)cc(N(c2cccc(-c3cccc4oc5c6ccccc6ccc5c34)c2)c2cccc3oc4ccccc4c23)c1]
[Chem. 259]
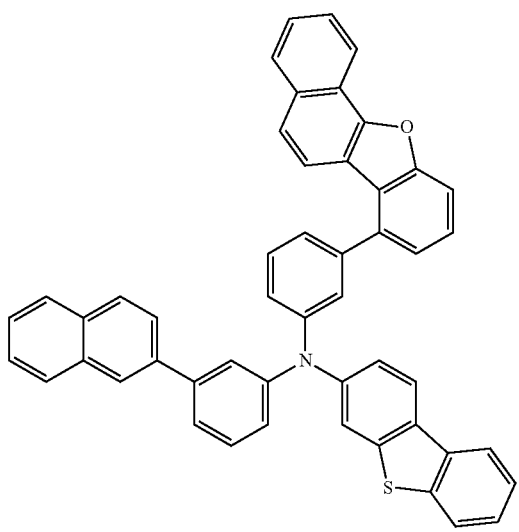
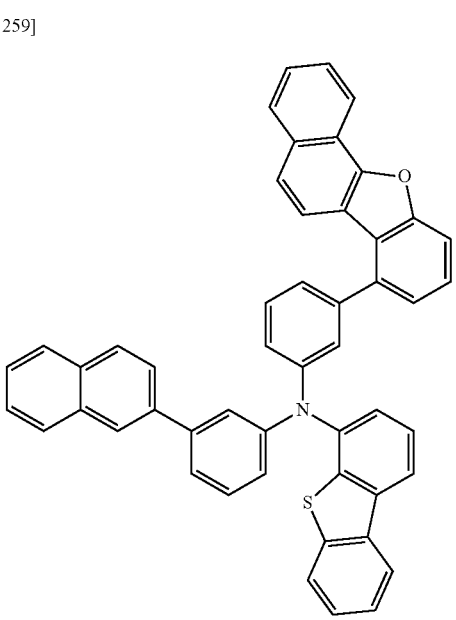
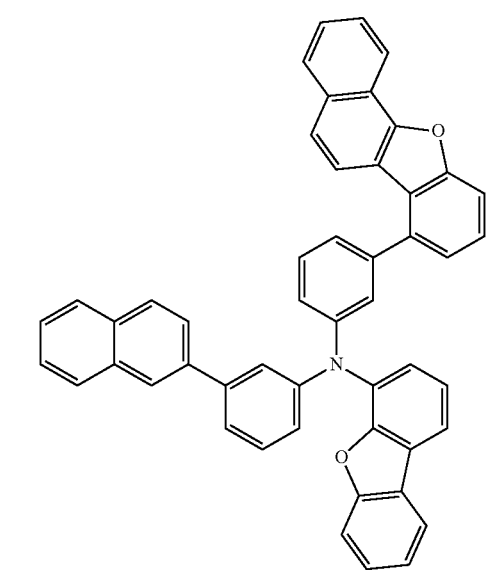
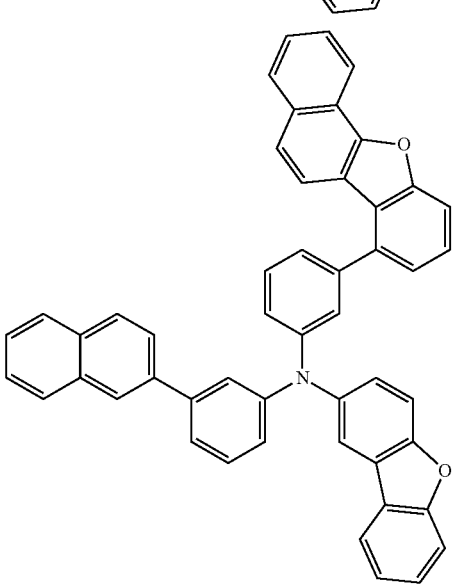

745
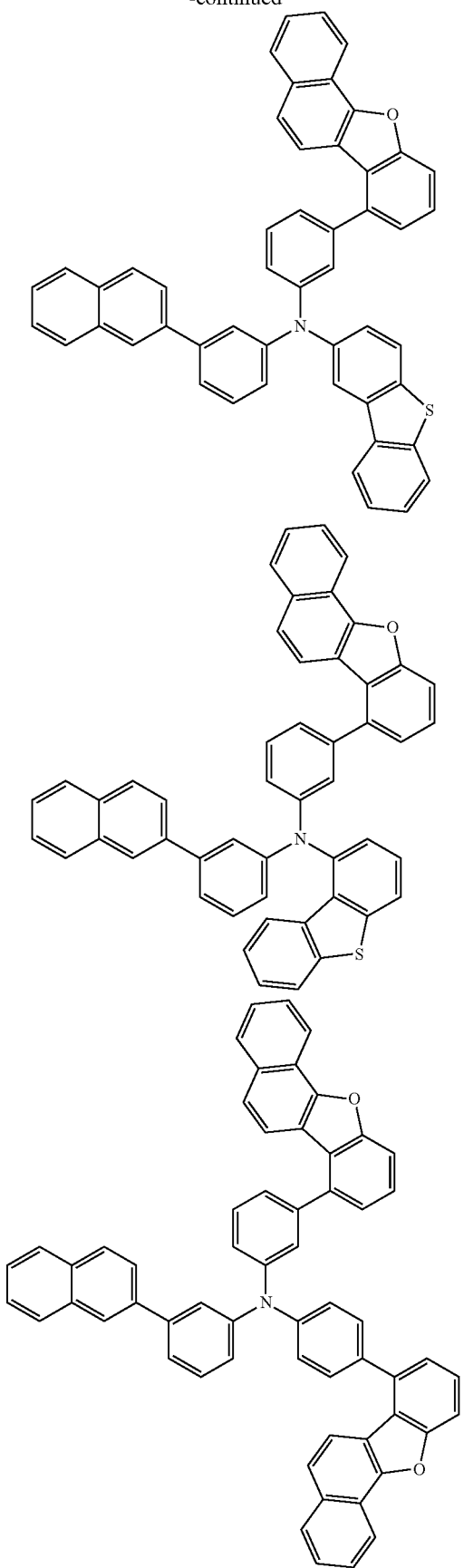
746
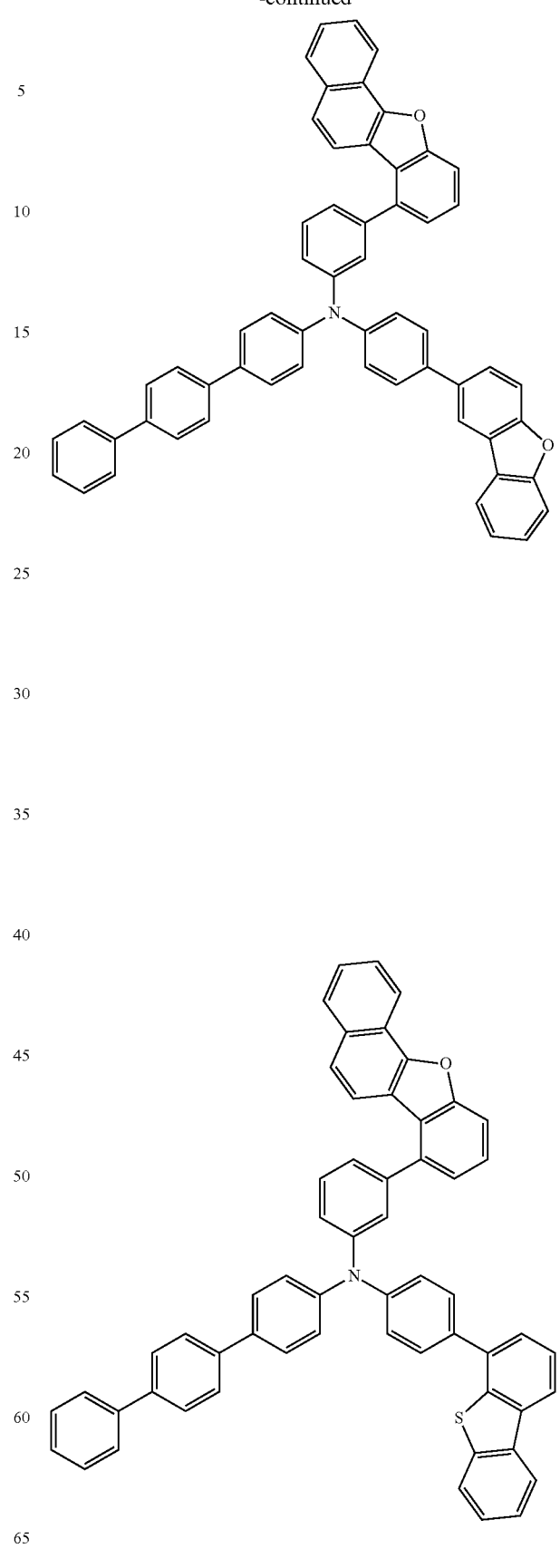

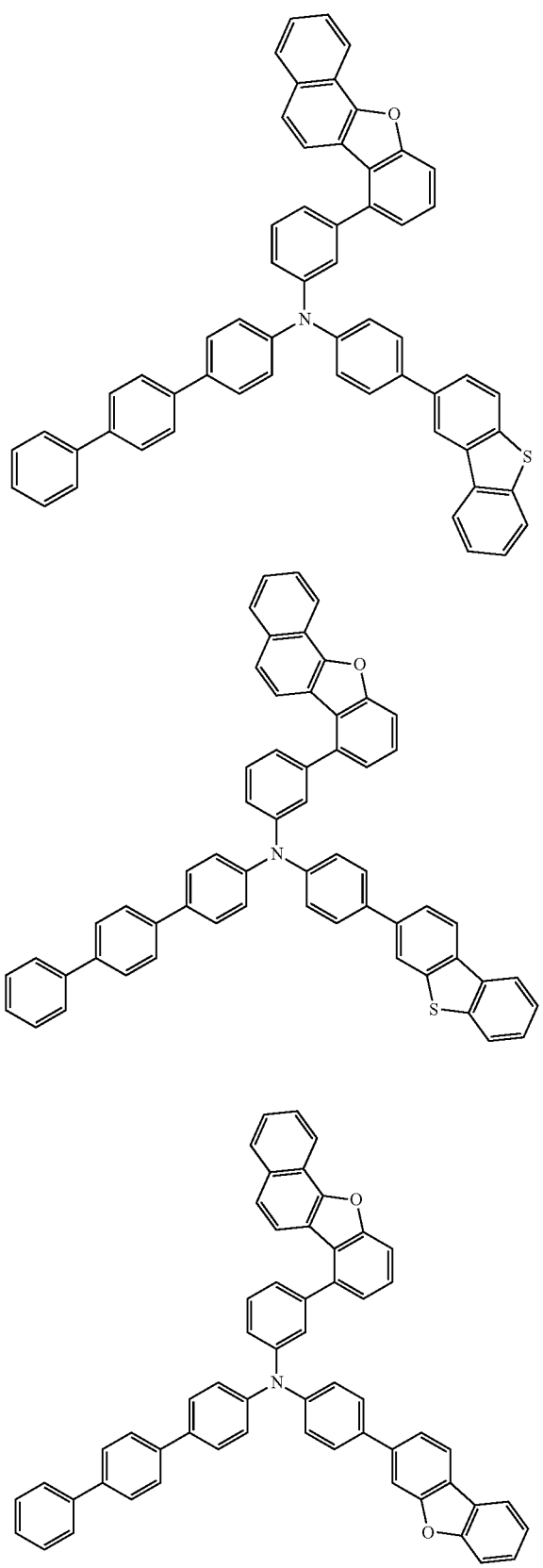
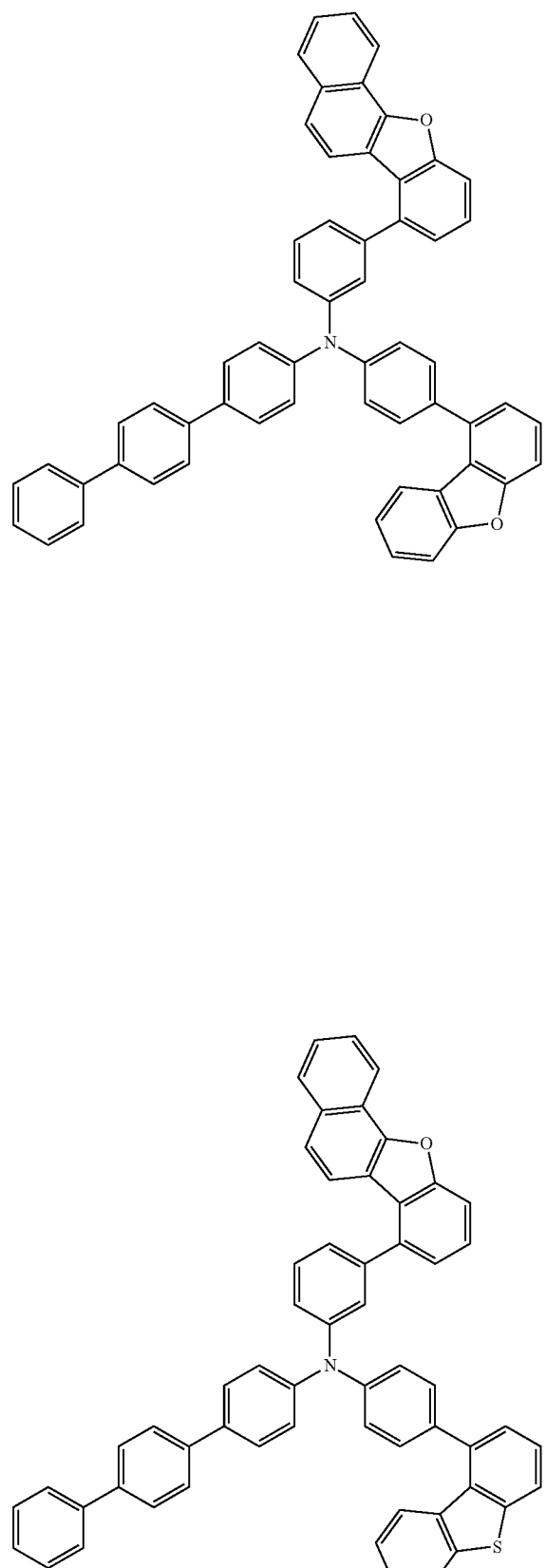

749
-continued
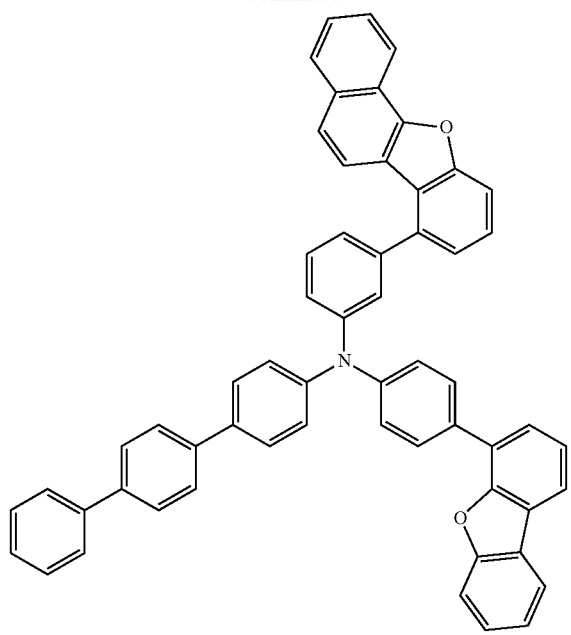
750
-continued
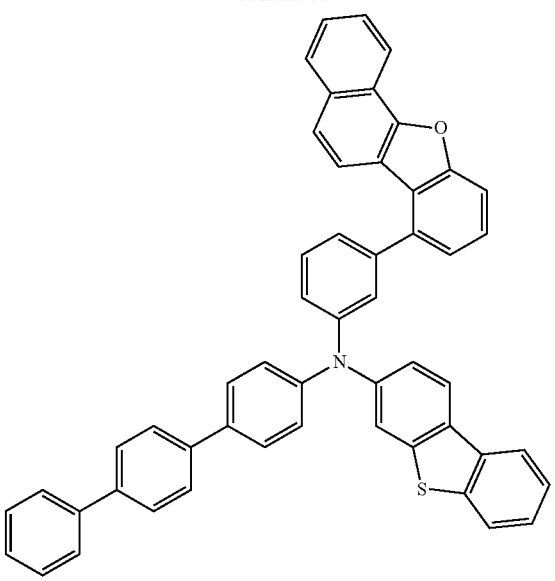
[Chem. 261]
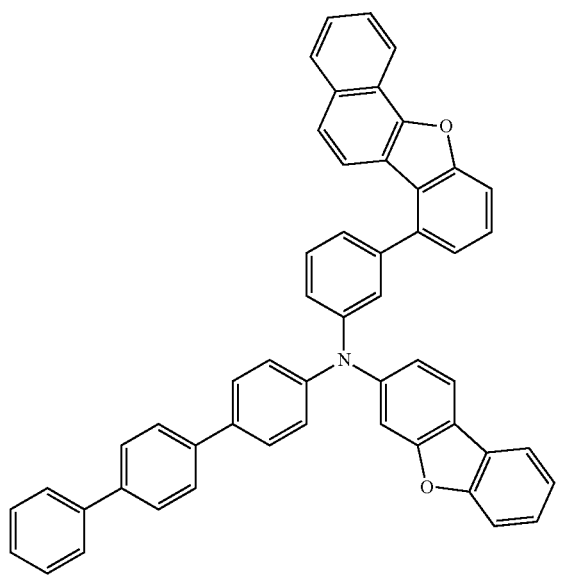
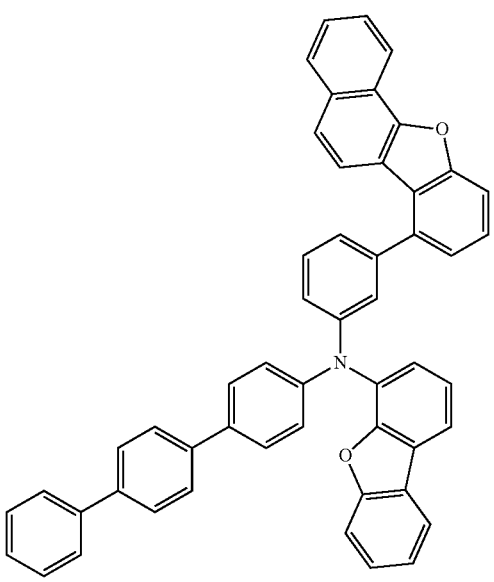

751
-continued
752
-continued
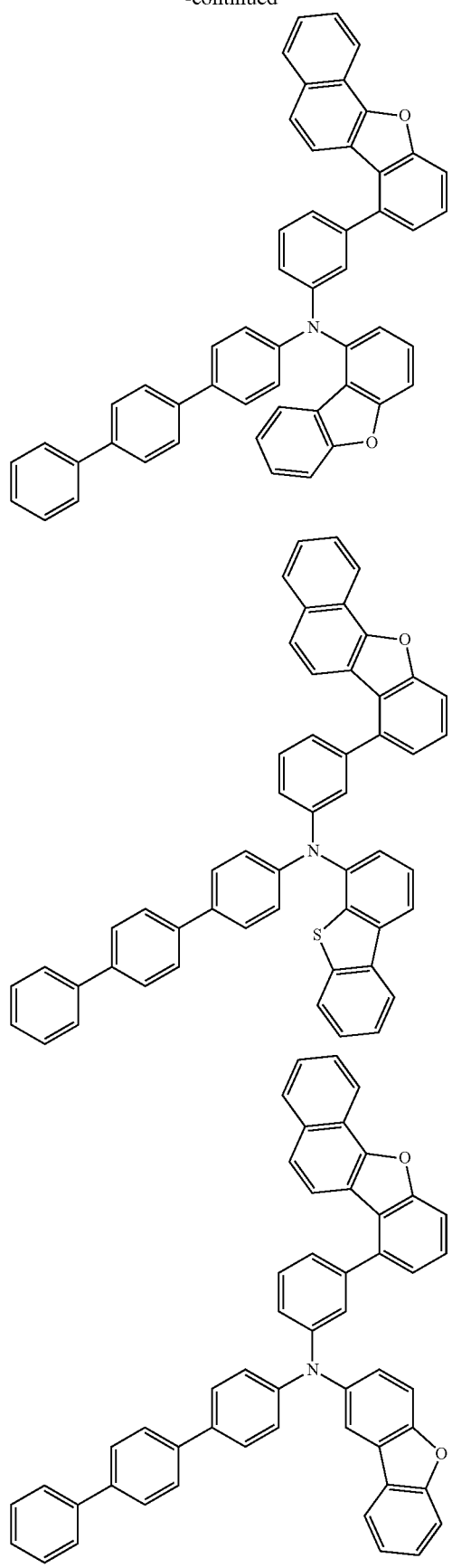
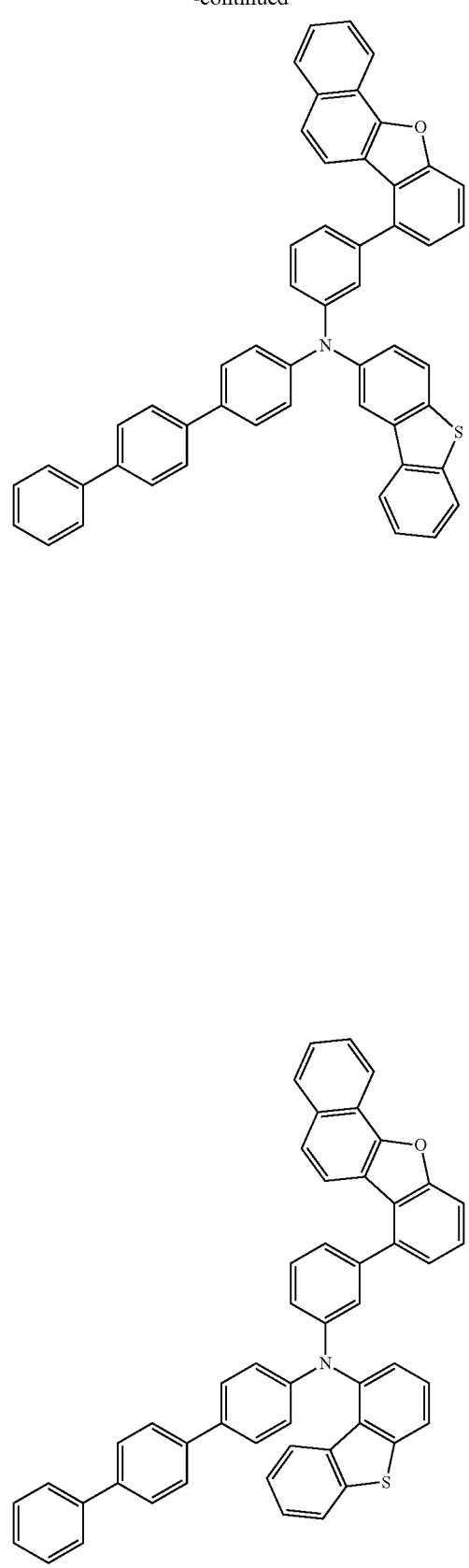

753
-continued
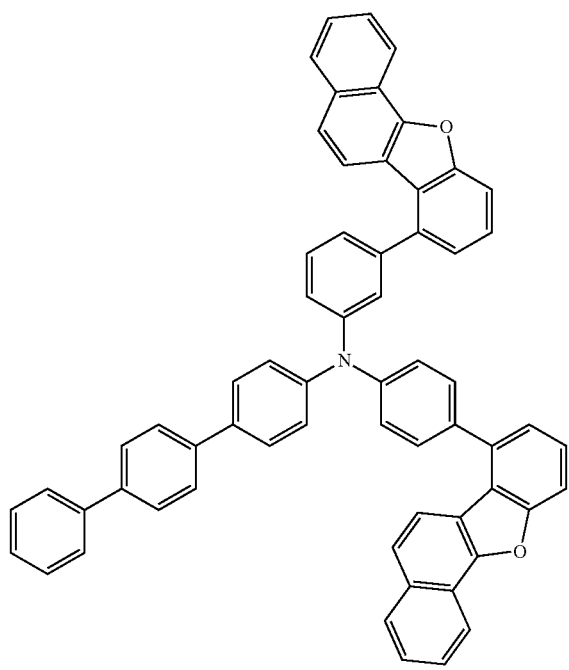
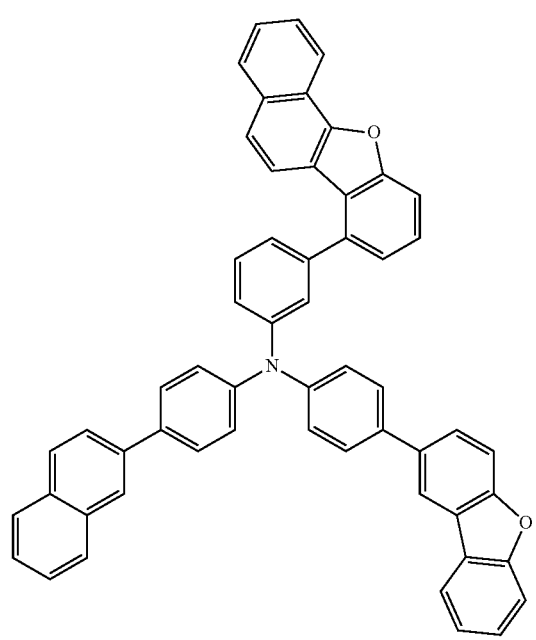
754
-continued
[Chem. 262]
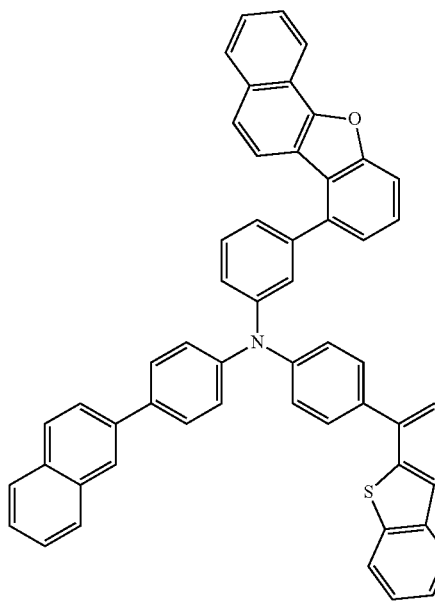
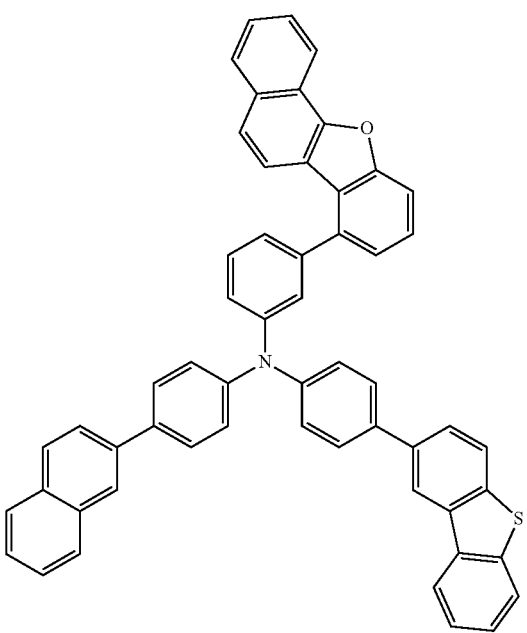

755
-continued
756
-continued
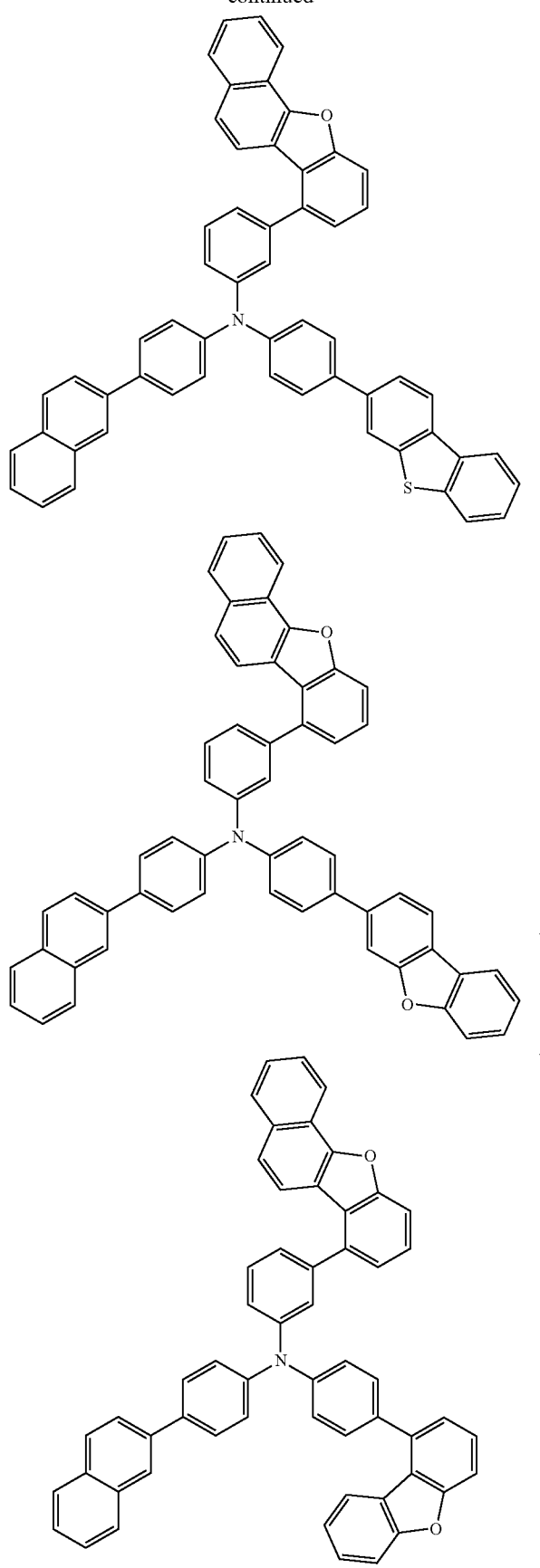
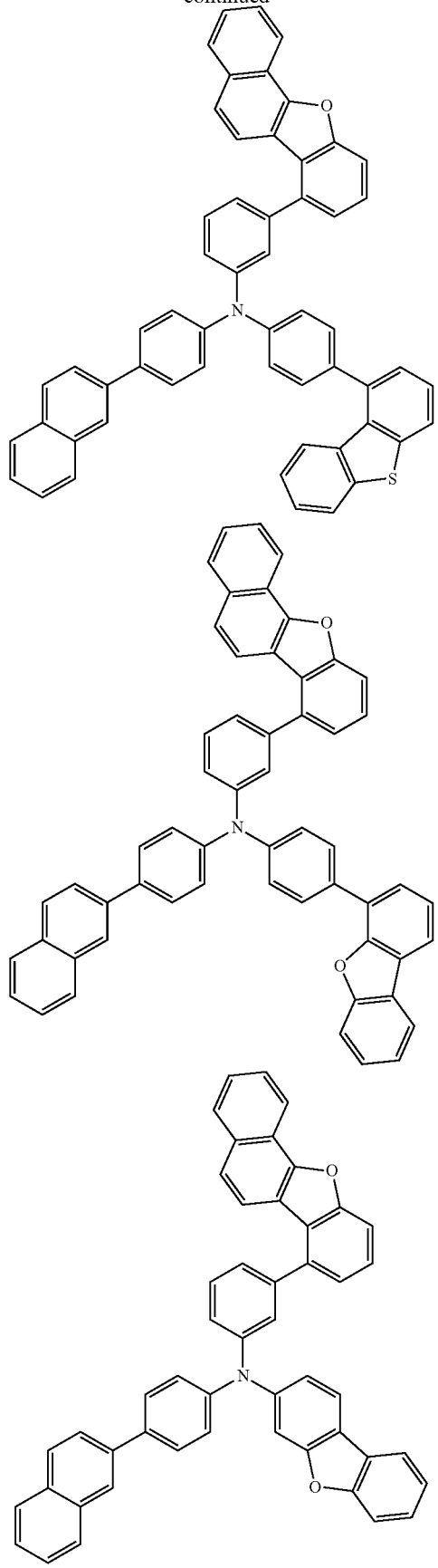

757
-continued
[Chem. 263]
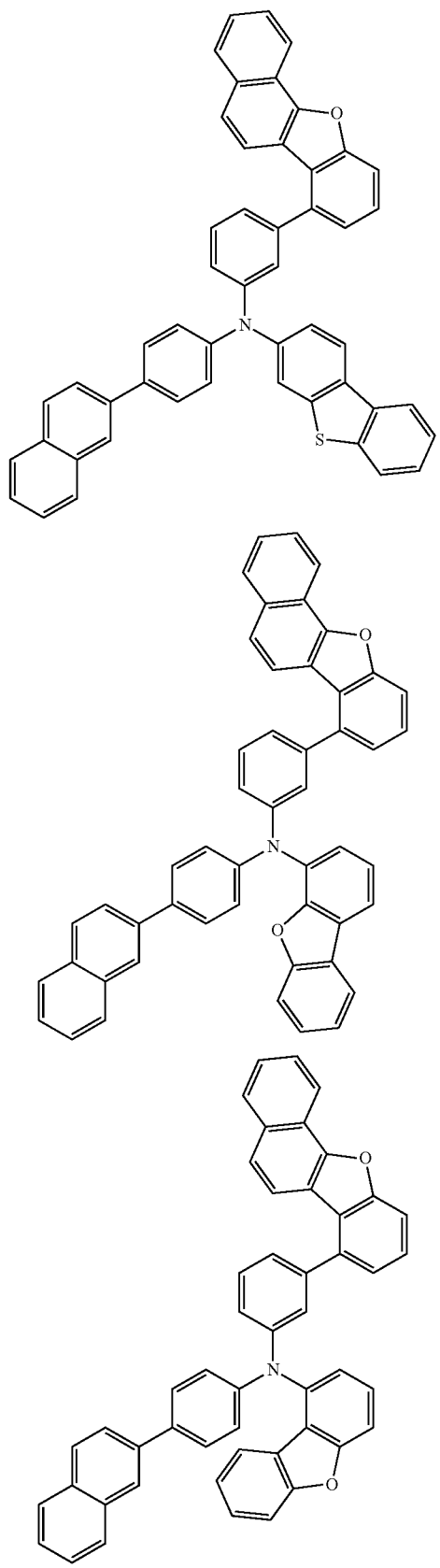
758
-continued
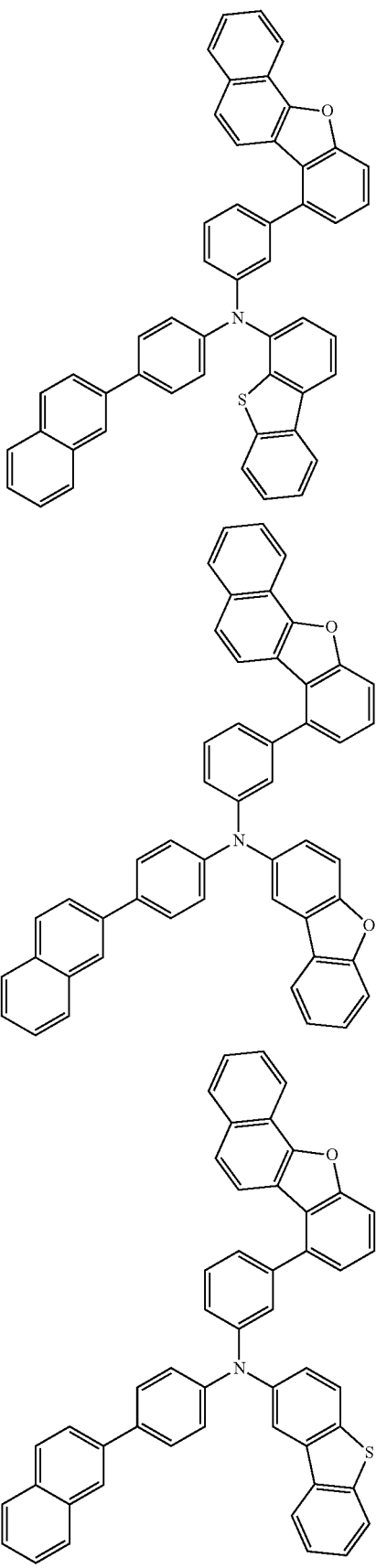

759
-continued
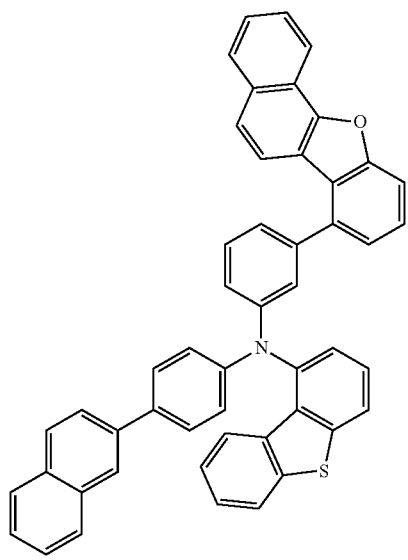 [SMILES: c1cc(-c2cccc3oc4c5ccccc5ccc4c23)cc(N(c2ccc(-c3ccc4ccccc4c3)cc2)c2cccc3oc4ccccc4c23)c1]
760
-continued
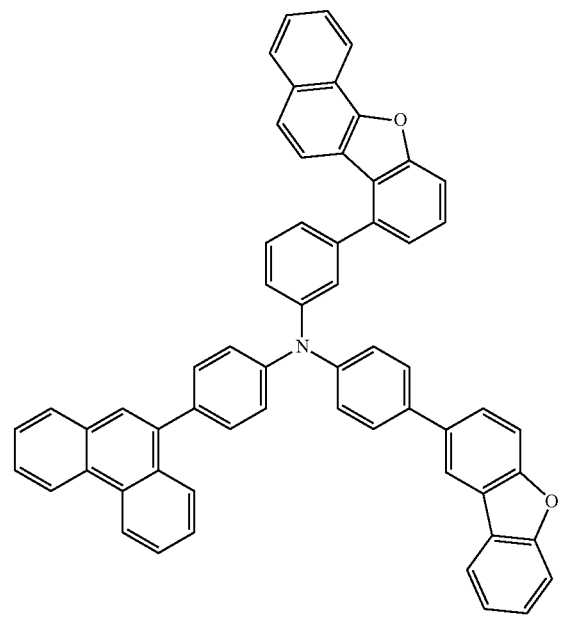
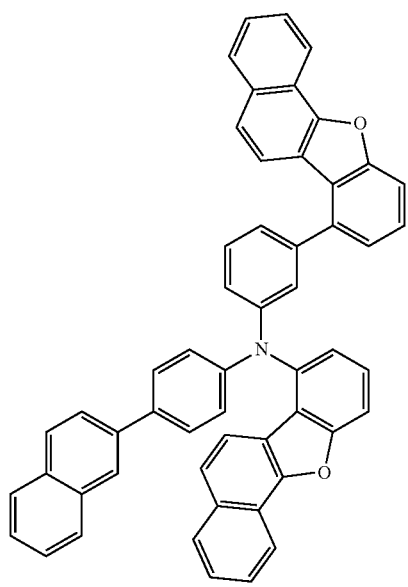
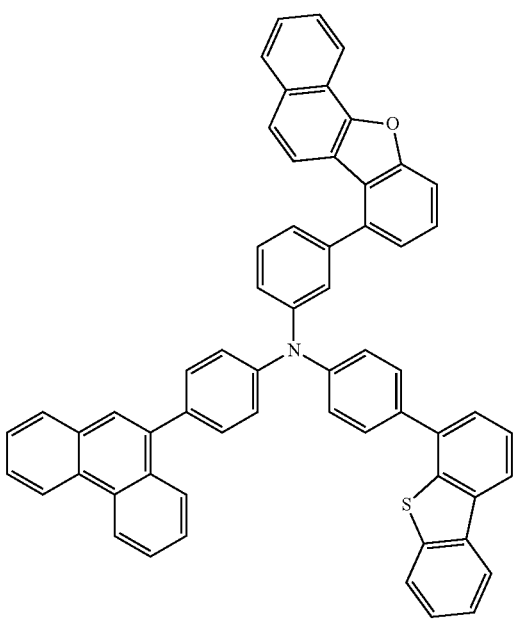

761
-continued
[Chem. 264]
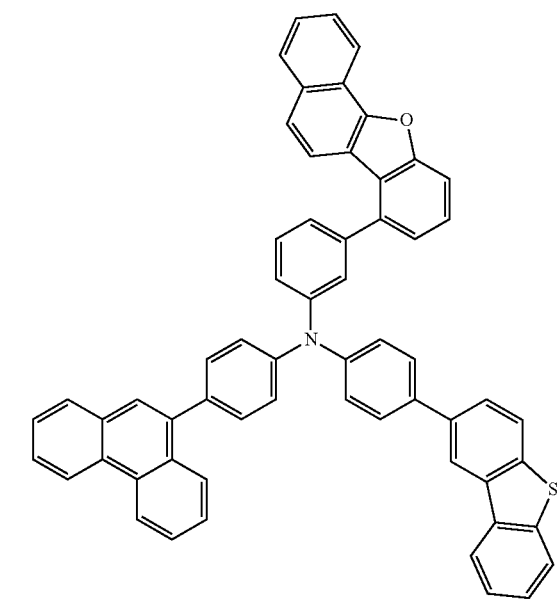
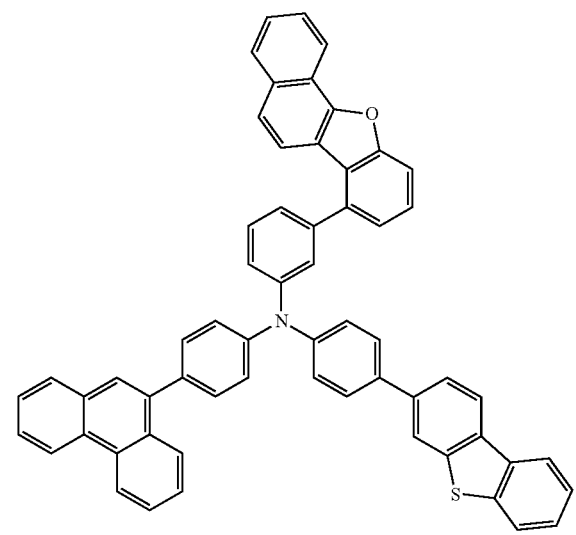
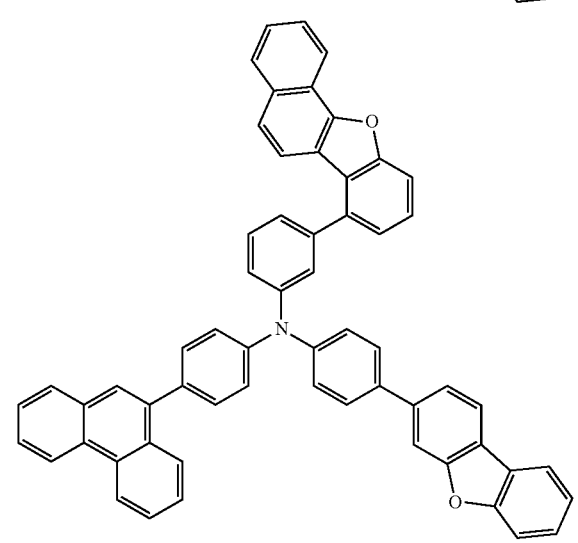
762
-continued
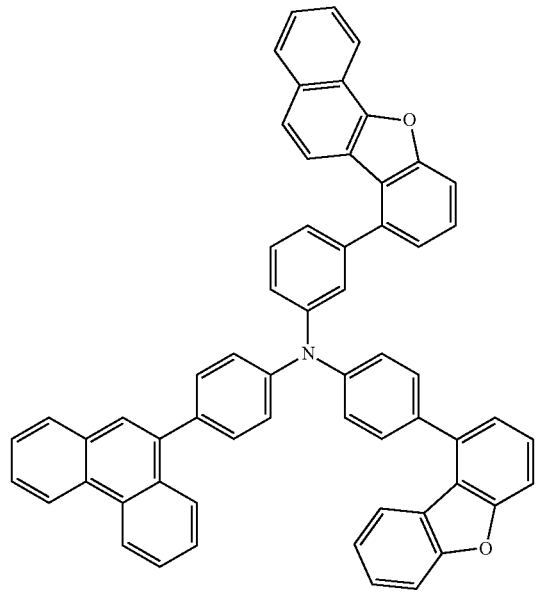
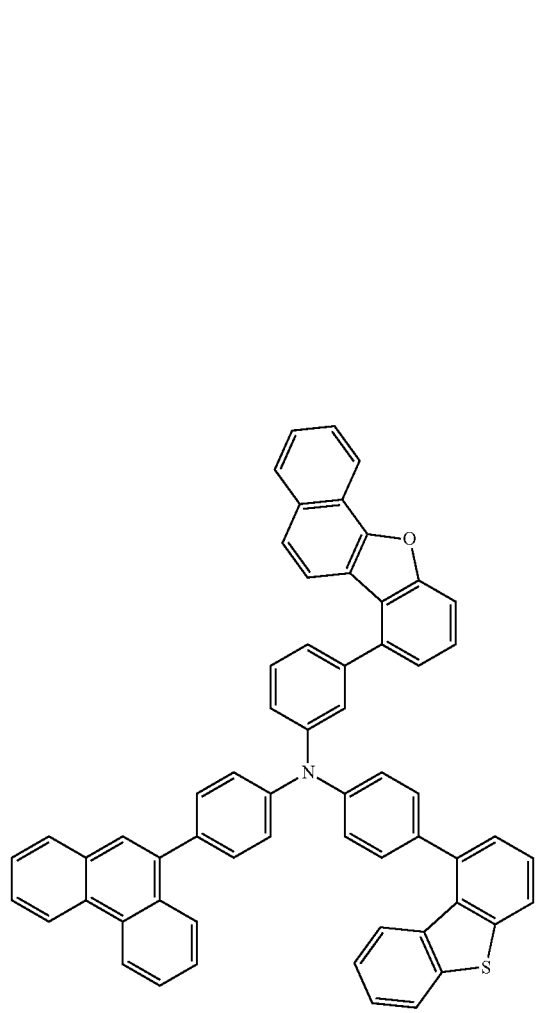

763
-continued
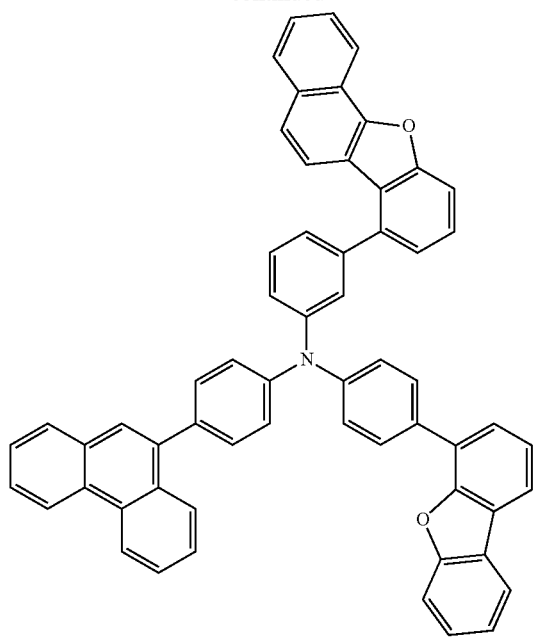
764
-continued
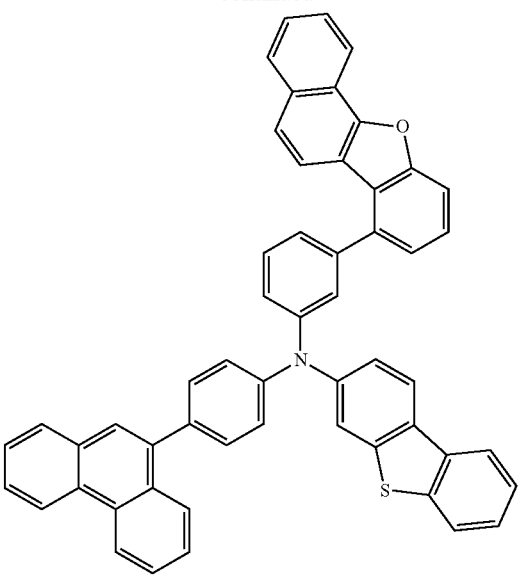
[Chem. 265]
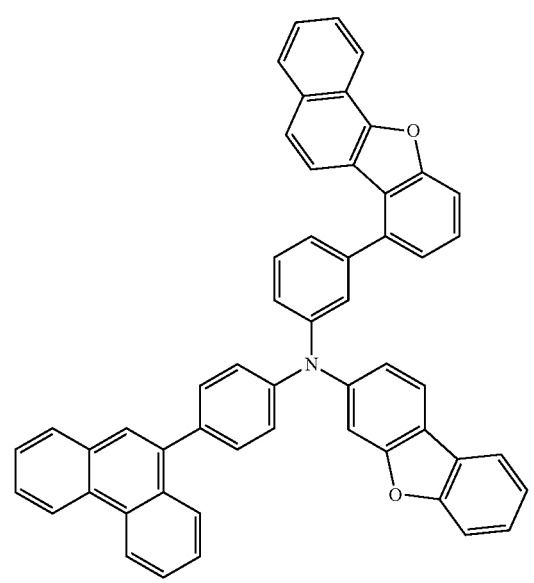
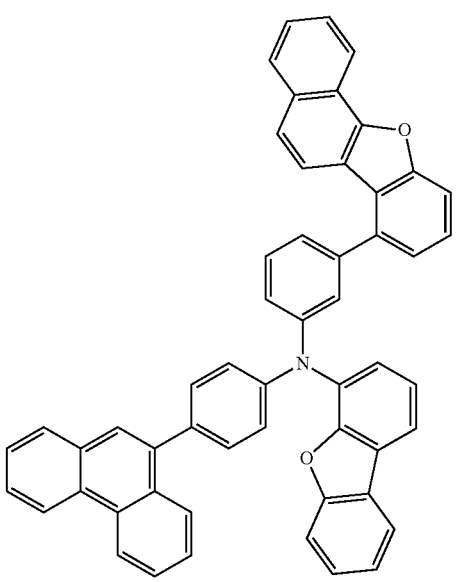

765
-continued
766
-continued
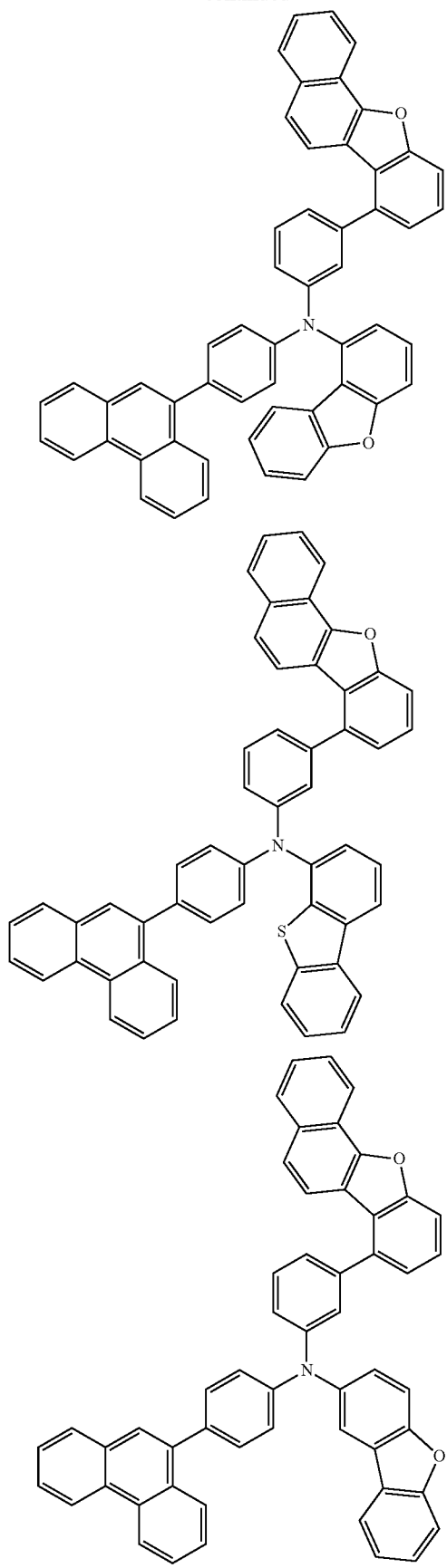

767
-continued
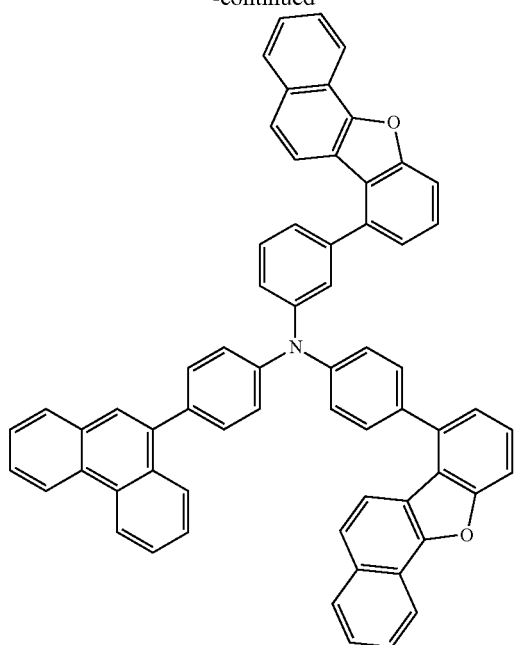
768
-continued
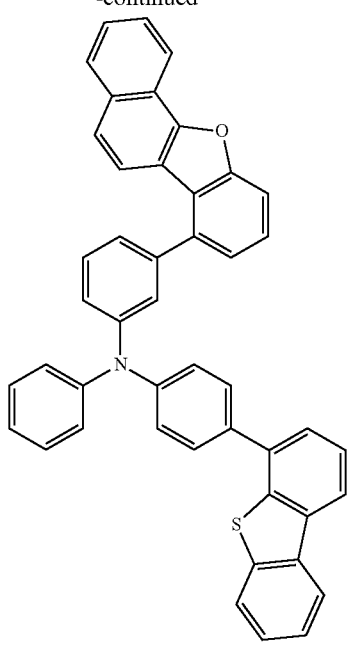
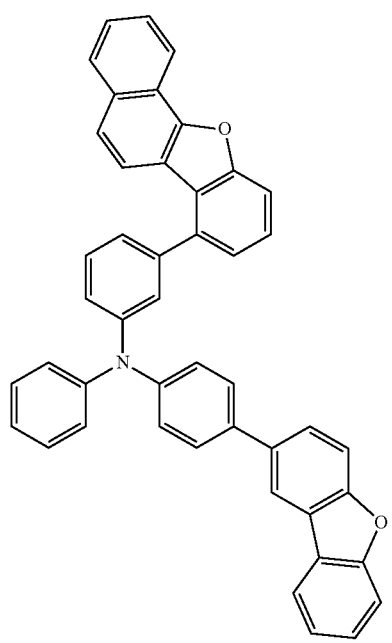
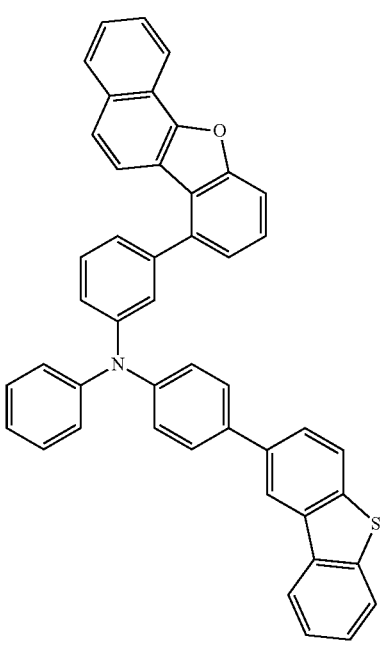

769
-continued
770
-continued
[Chem. 266]
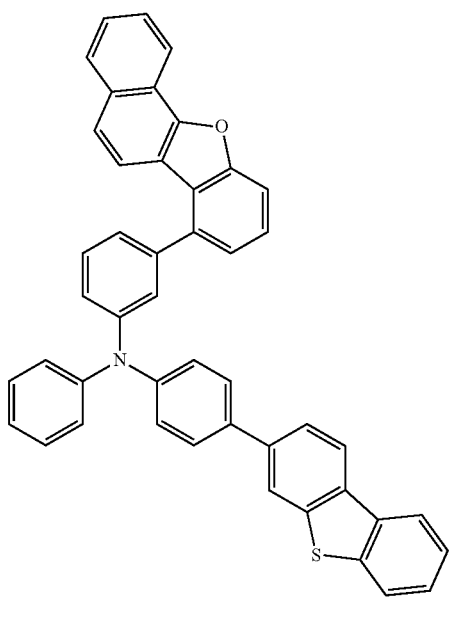
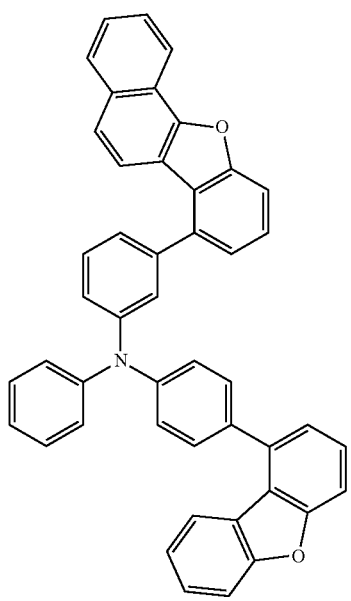
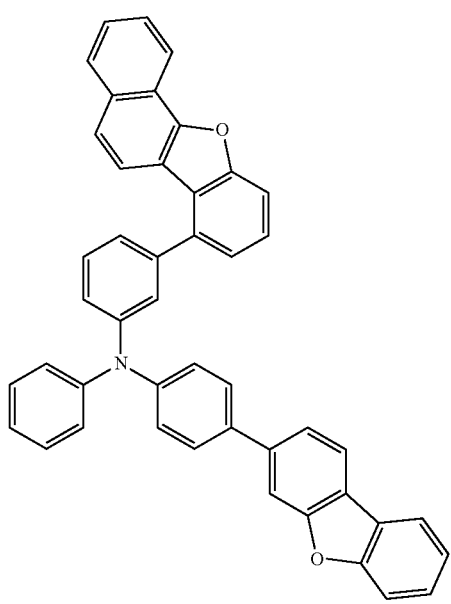
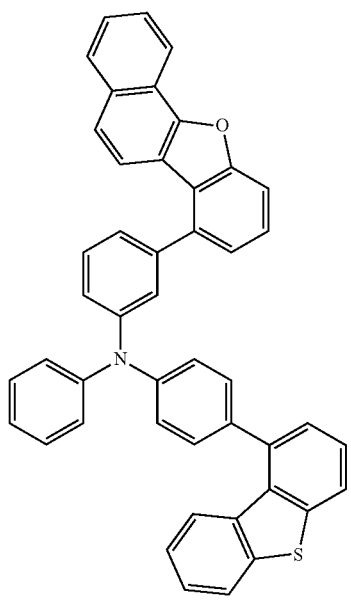

771
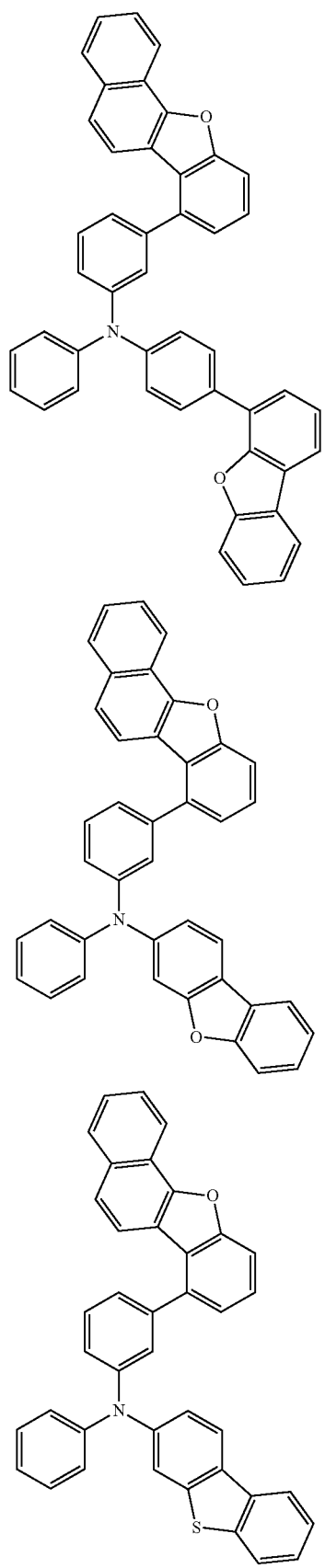
772
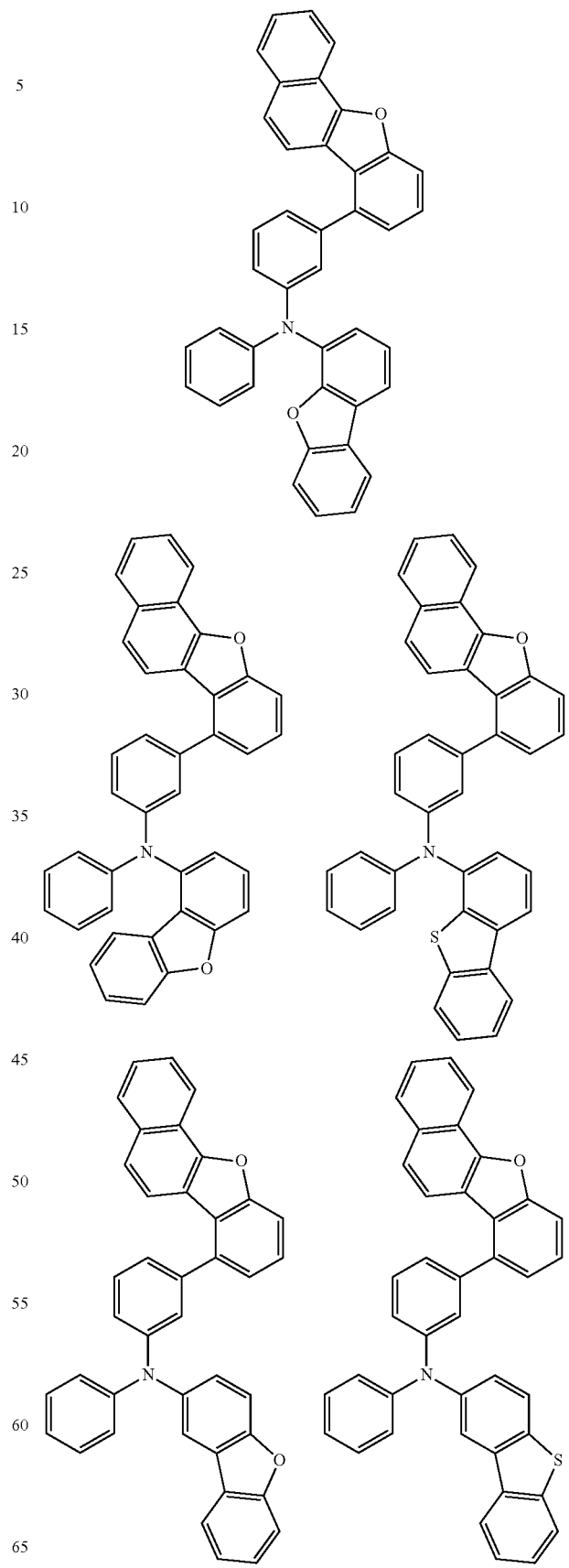

773
-continued
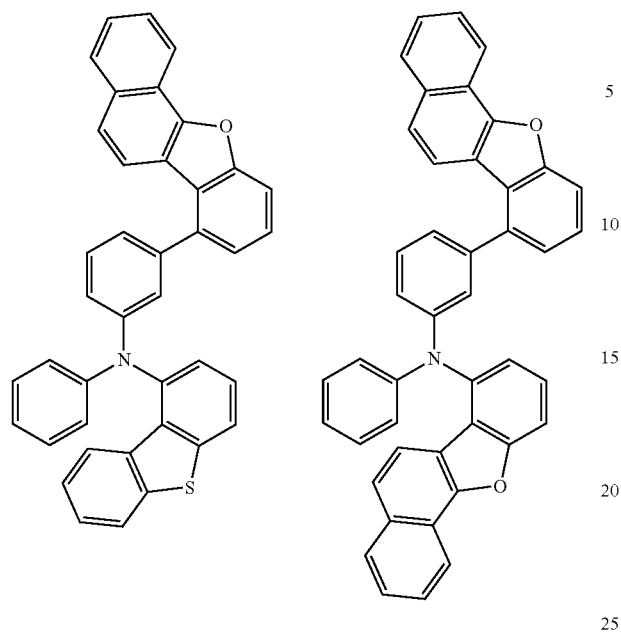
774
-continued
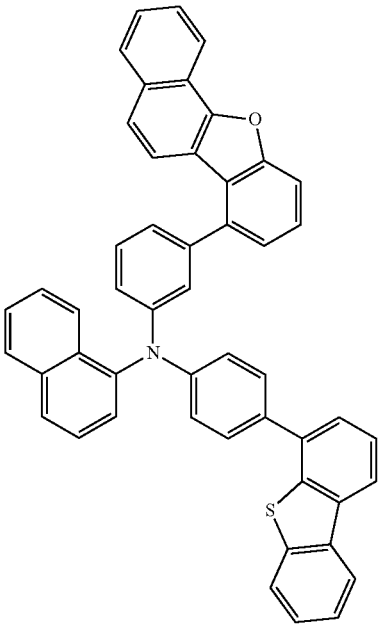
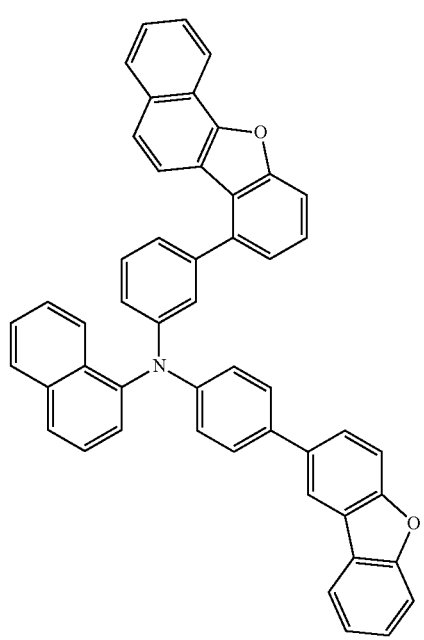
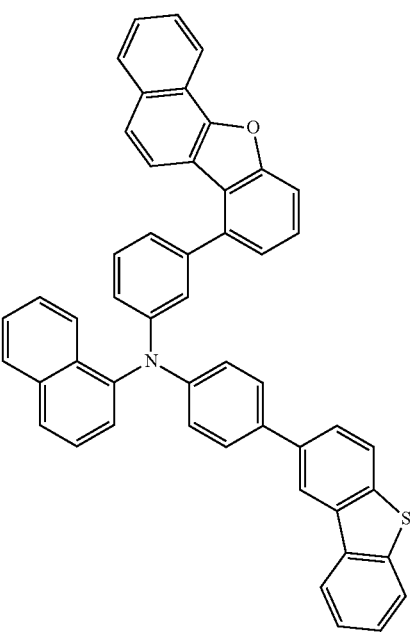 [SMILES: c1cc(-c2cccc3oc4c5ccccc5ccc4c23)cc(N(c2ccc(-c3ccc4sc5ccccc5c4c3)cc2)c2cccc3ccccc23)c1]

775
-continued
[Chem. 267]
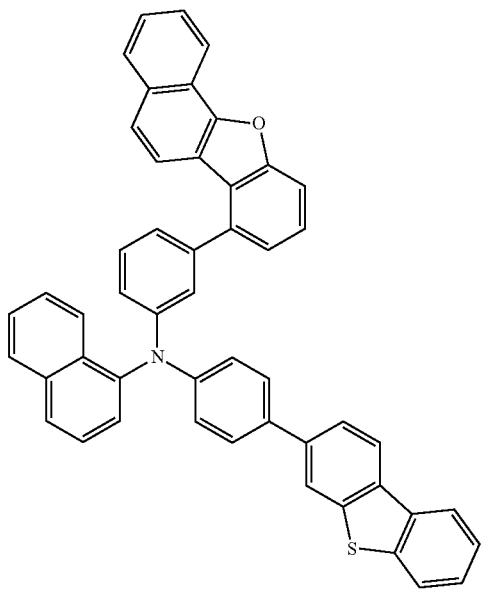
776
-continued
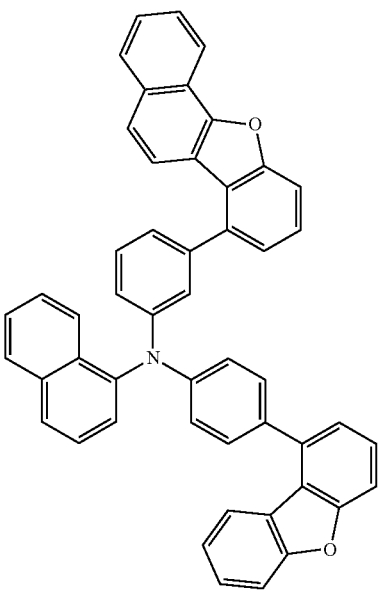 [SMILES: c1cc(-c2cccc3oc4c5ccccc5ccc4c23)cc(N(c2ccc(-c3cccc4oc5ccccc5c34)cc2)c2cccc3ccccc23)c1]
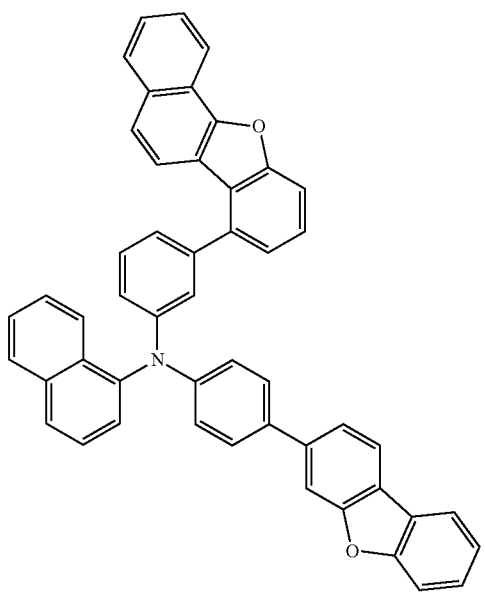
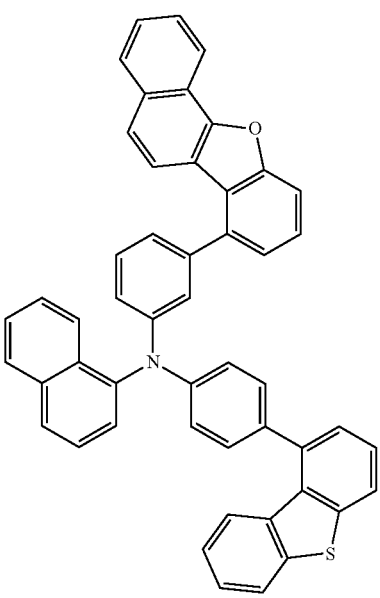

777
-continued
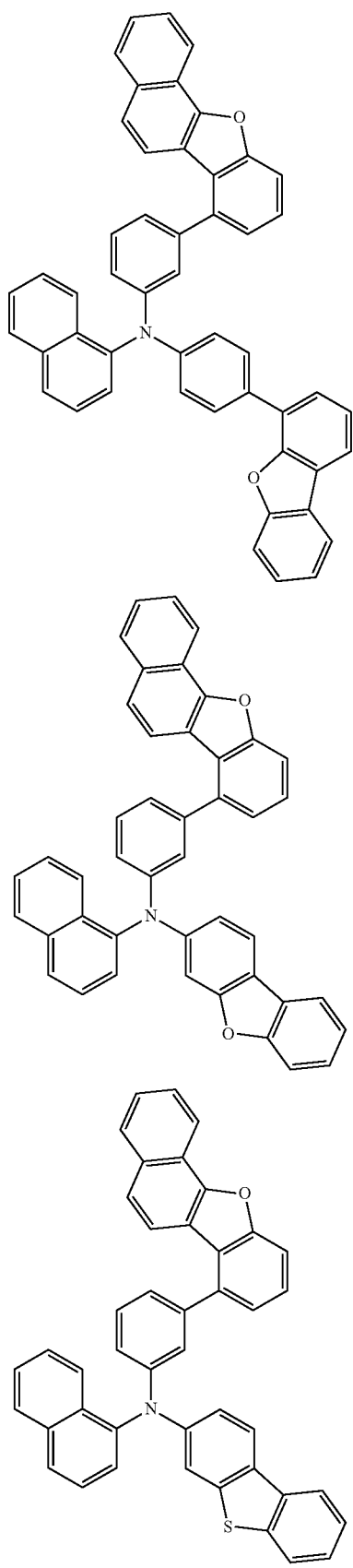
778
-continued
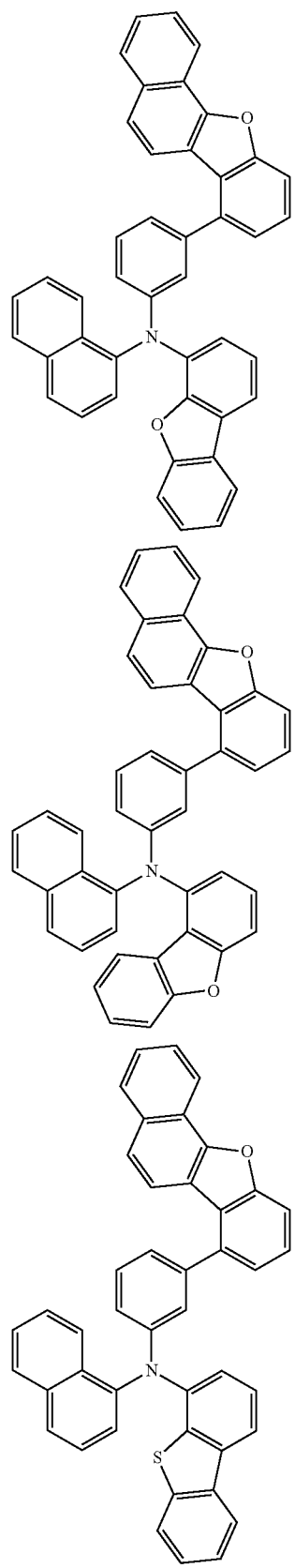

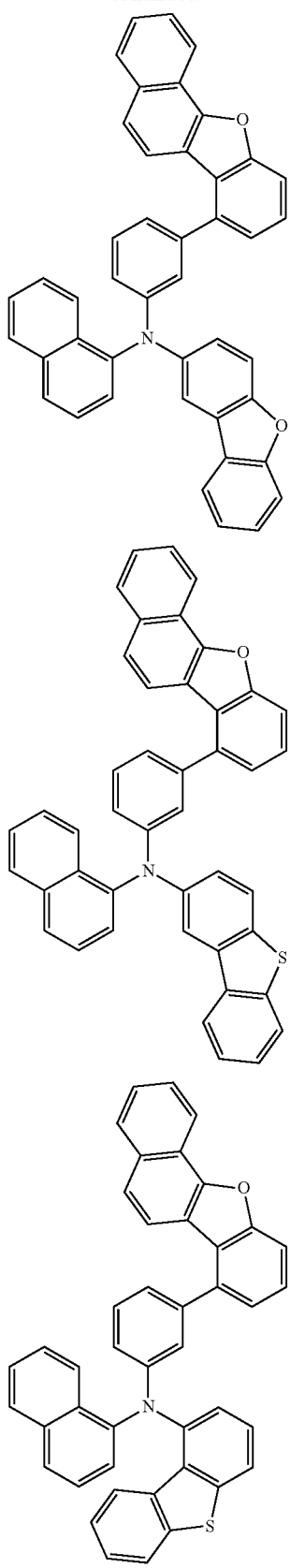
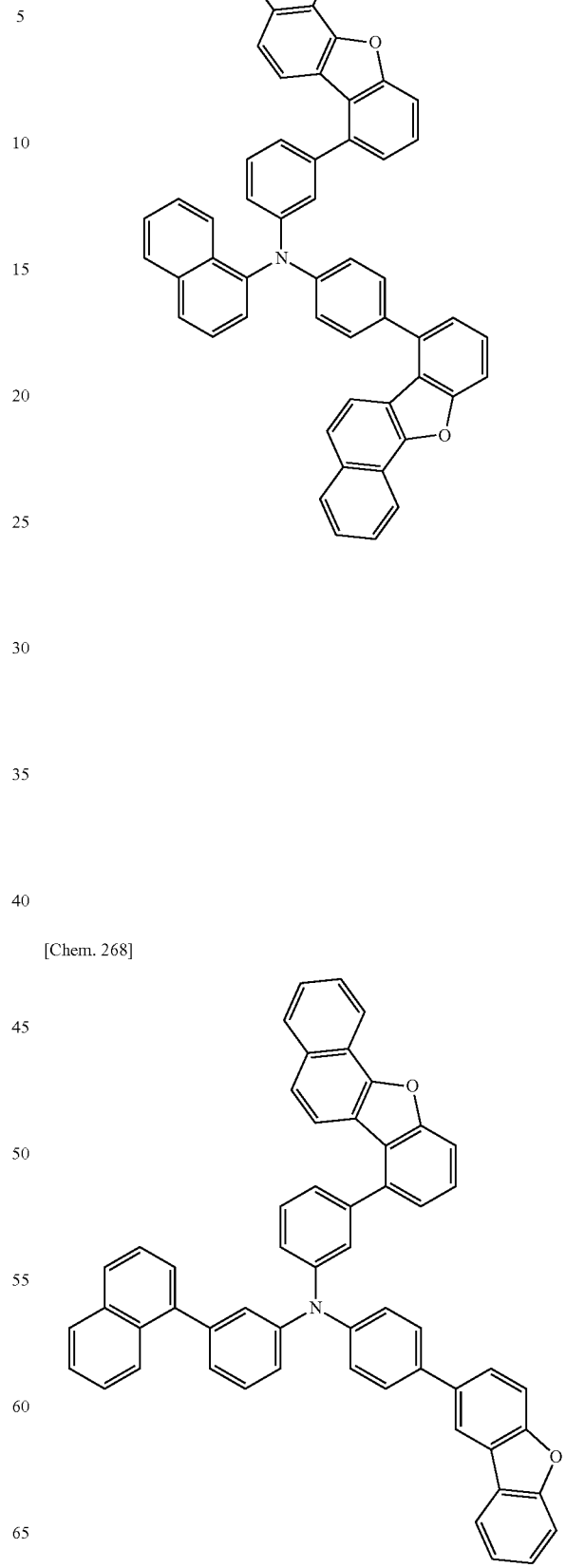
[Chem. 268]

781
-continued
782
-continued
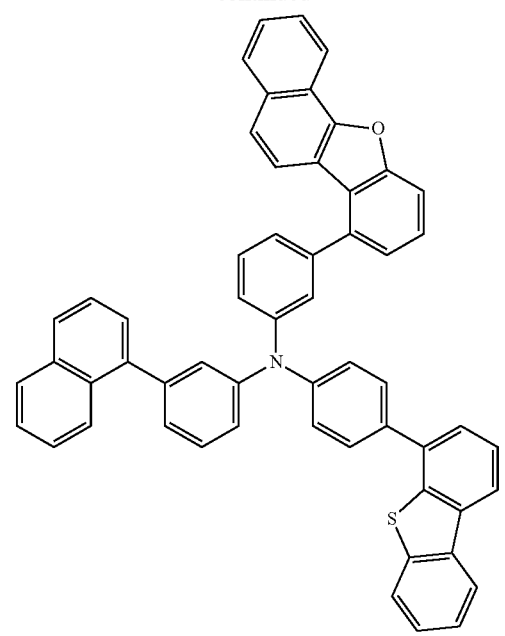
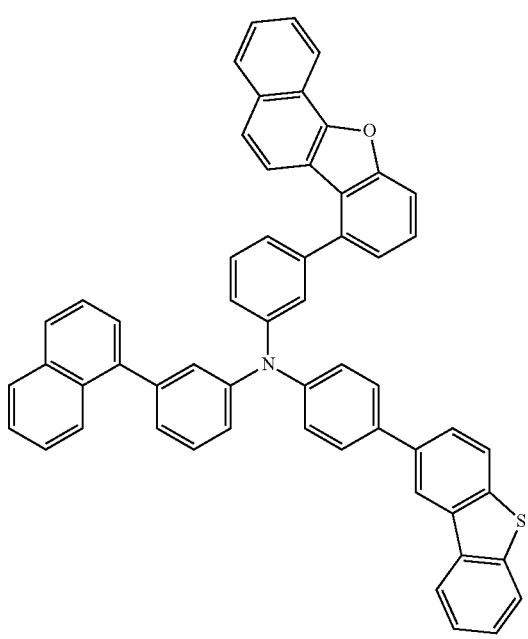
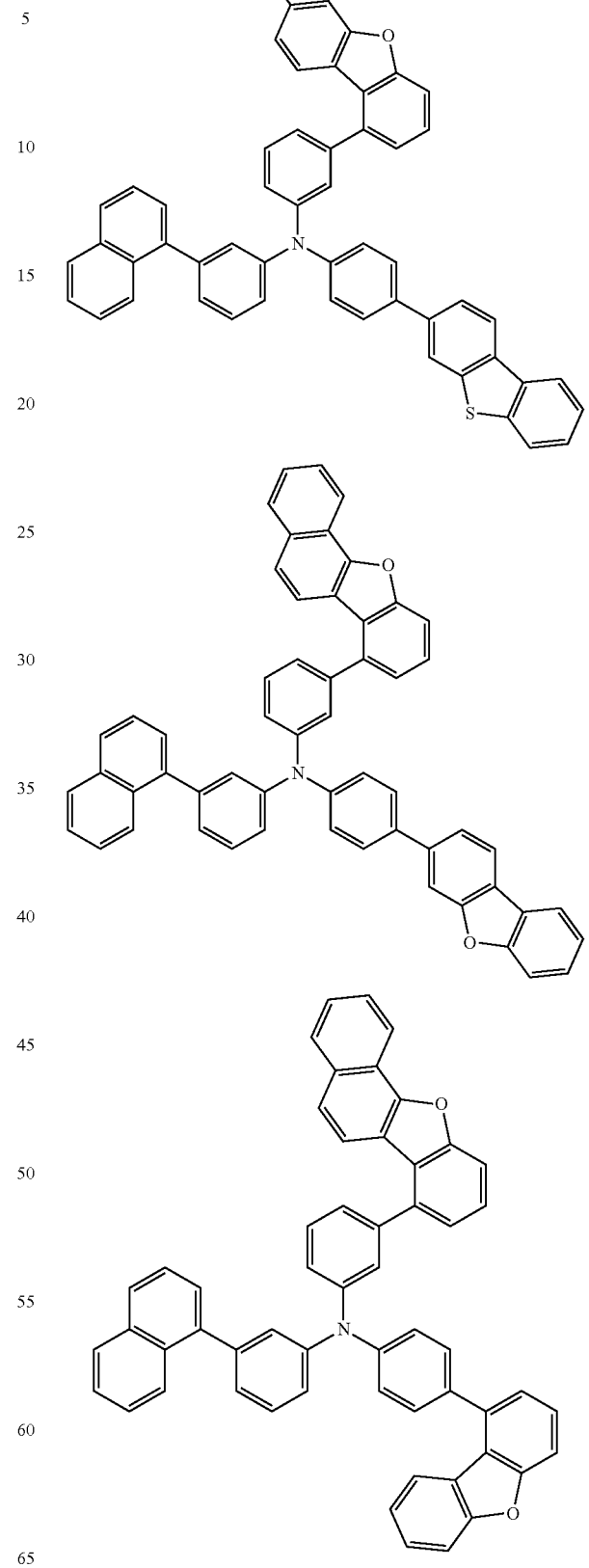

[Chem. 269]
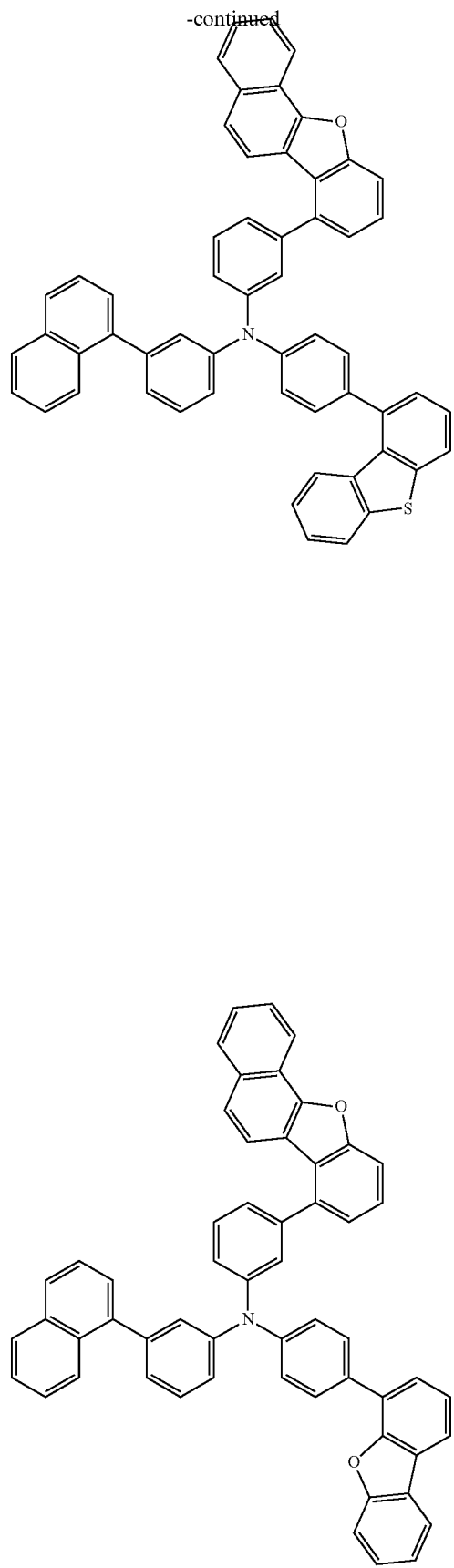
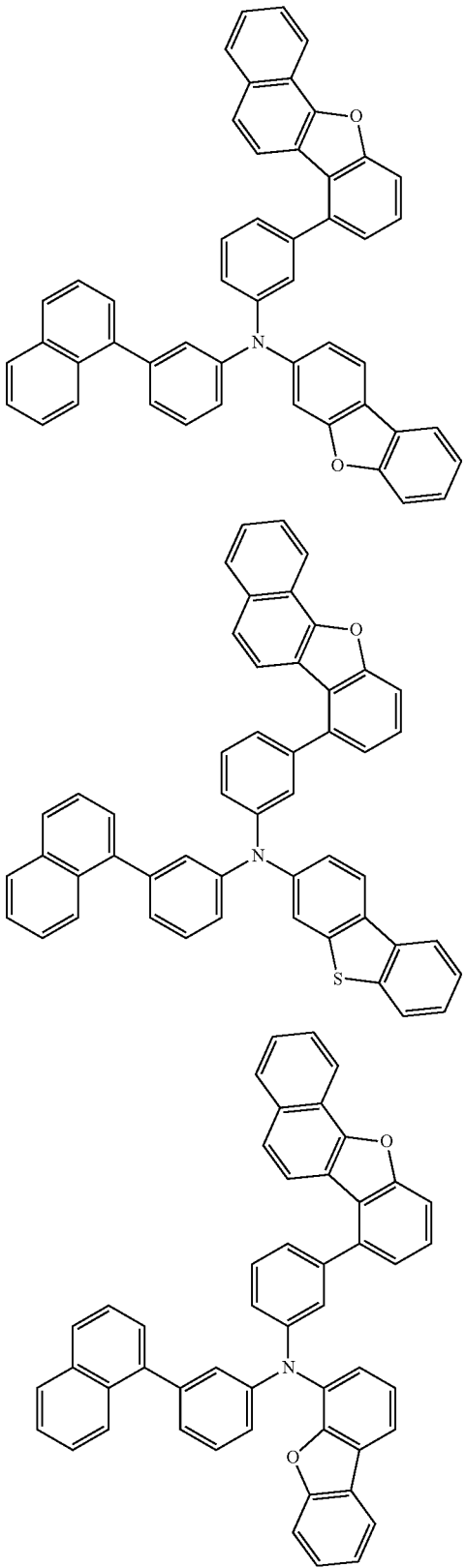

785
-continued
786
-continued
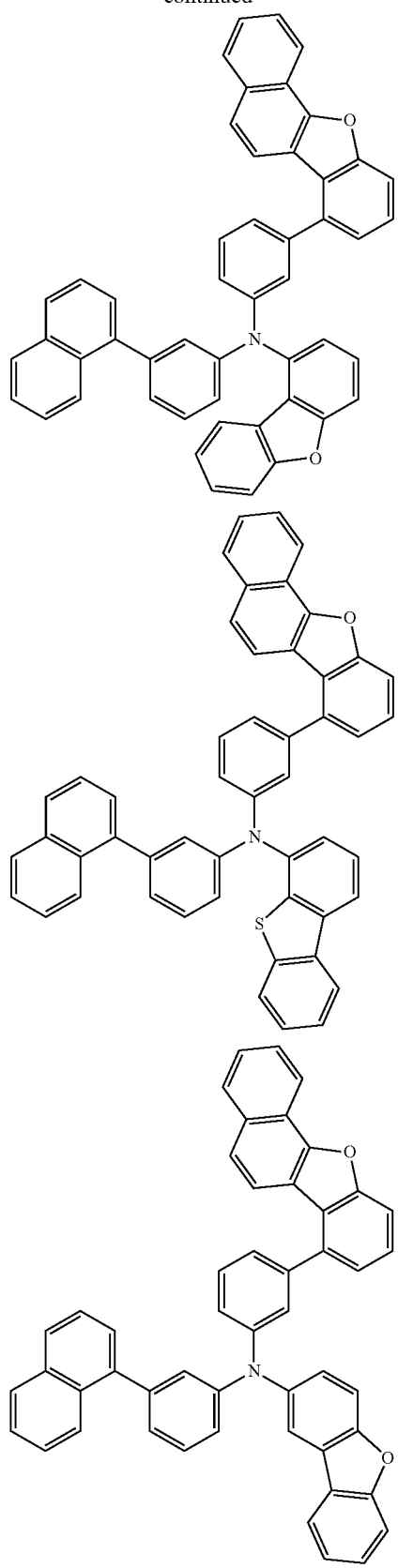

787
-continued
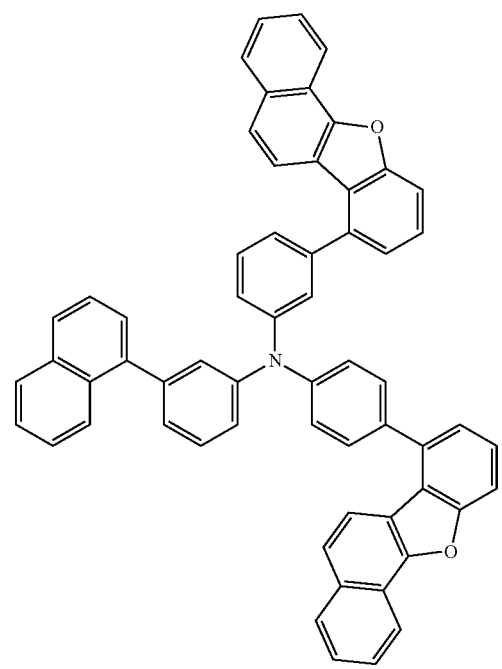
788
-continued
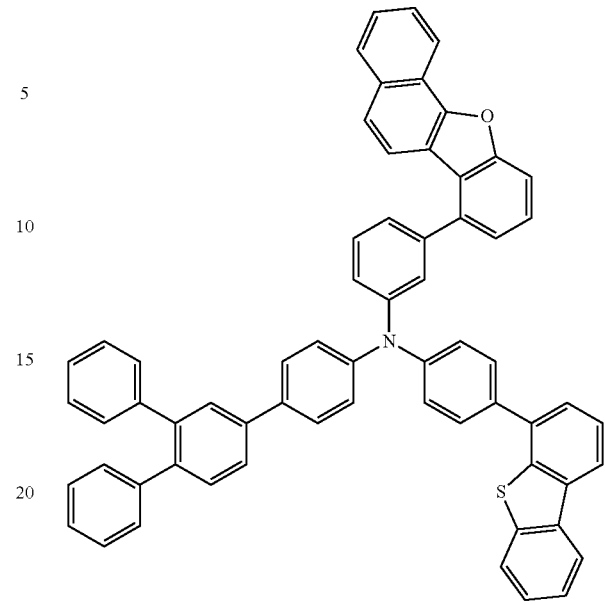
[Chem. 270]
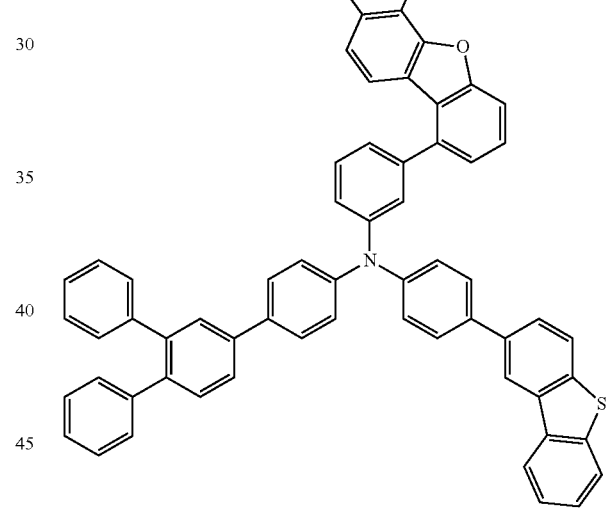
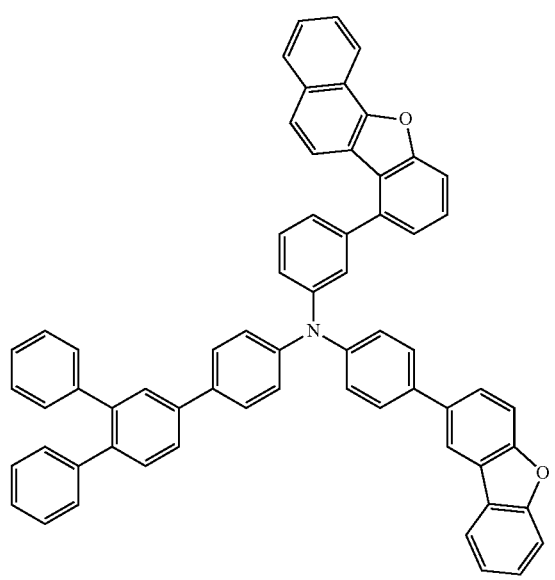
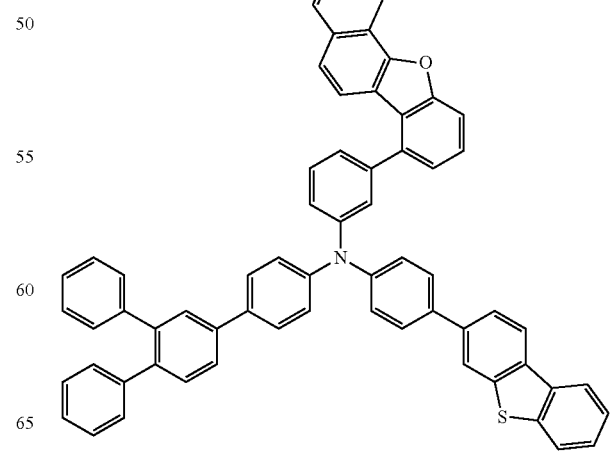

789
-continued
790
-continued
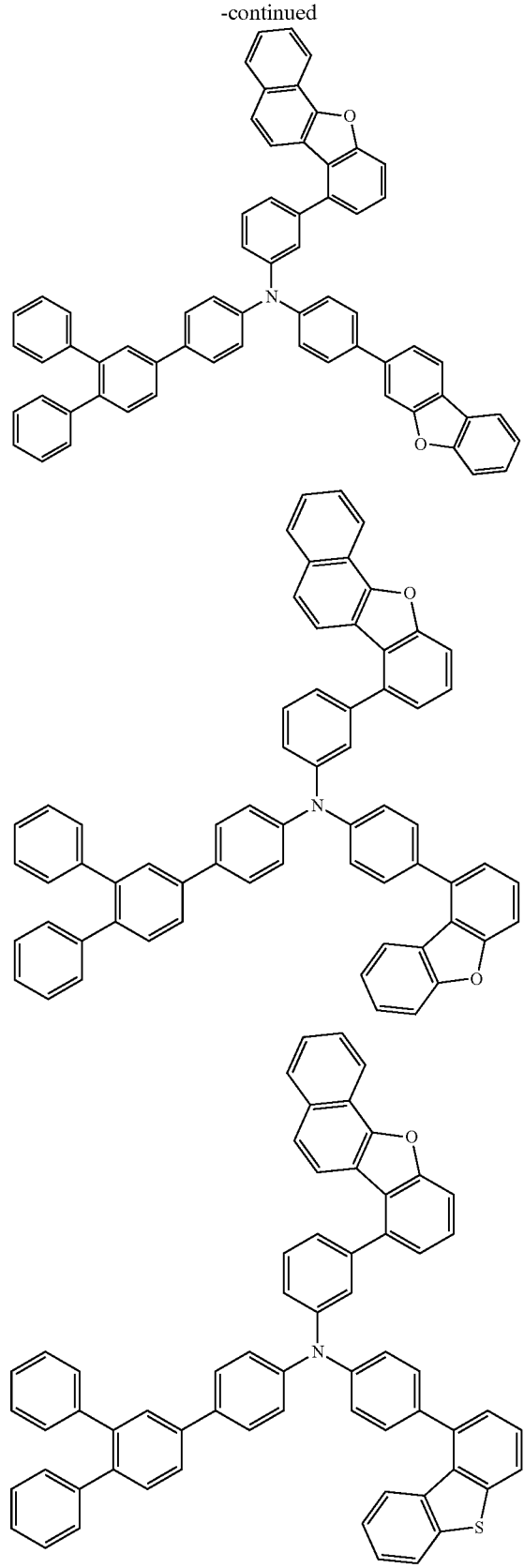
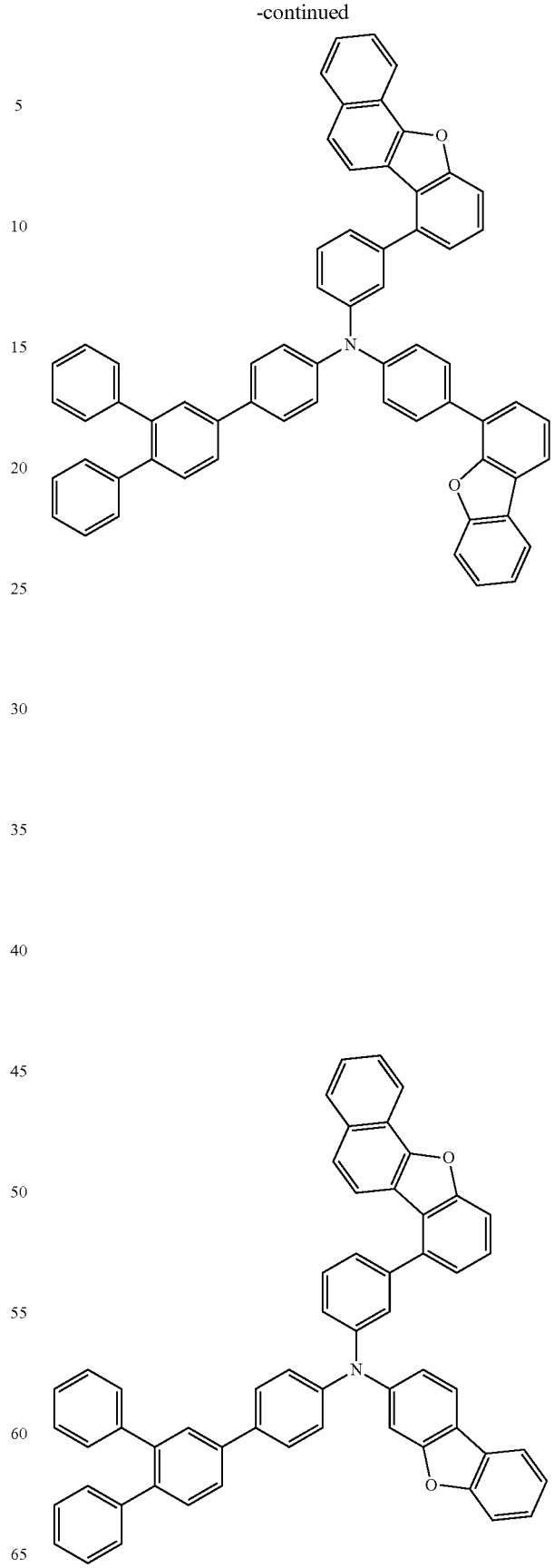

791
-continued
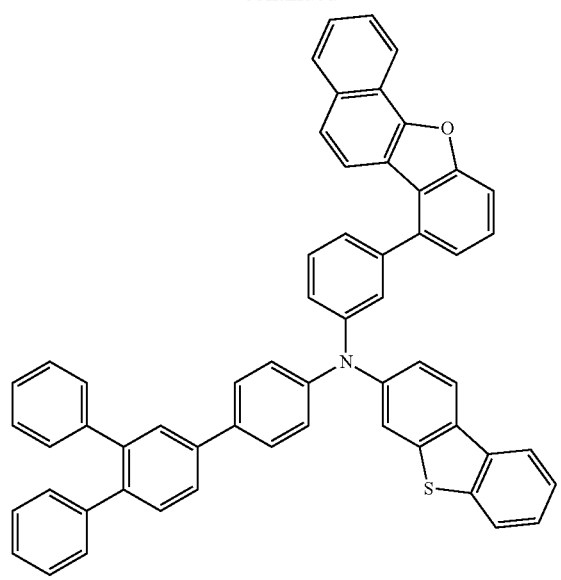
[Chem. 271]
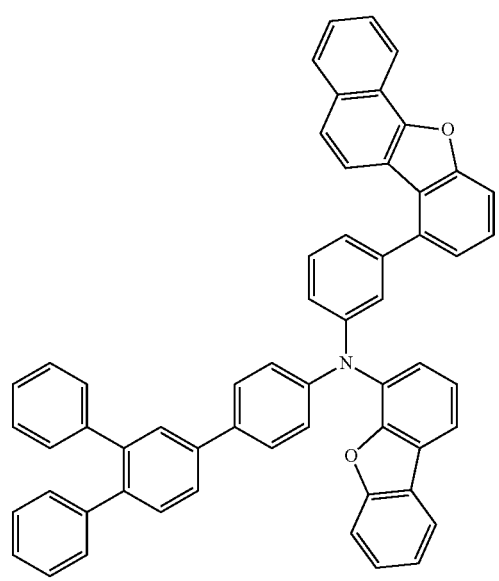
792
-continued
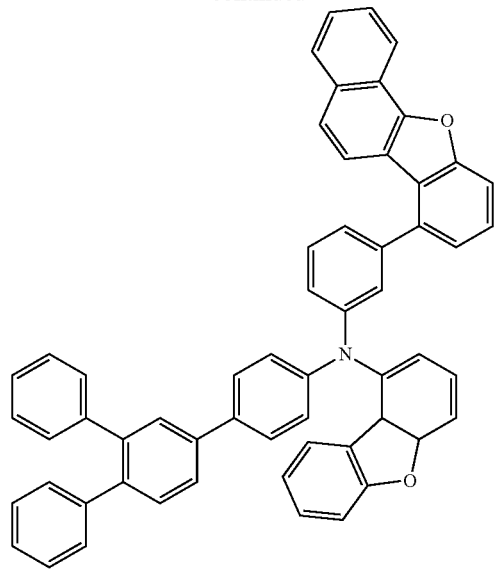
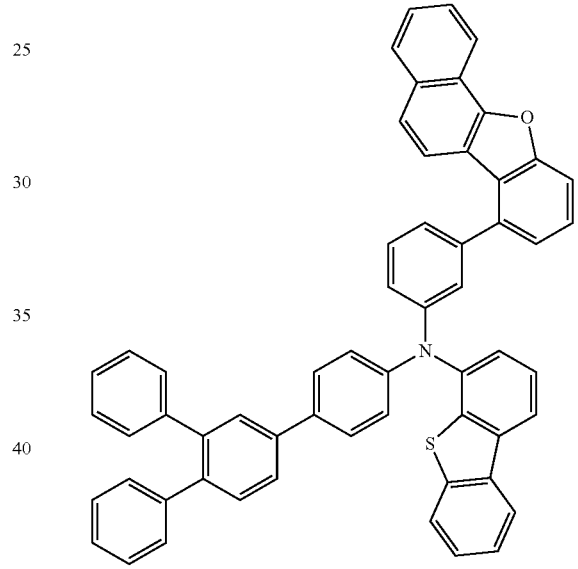
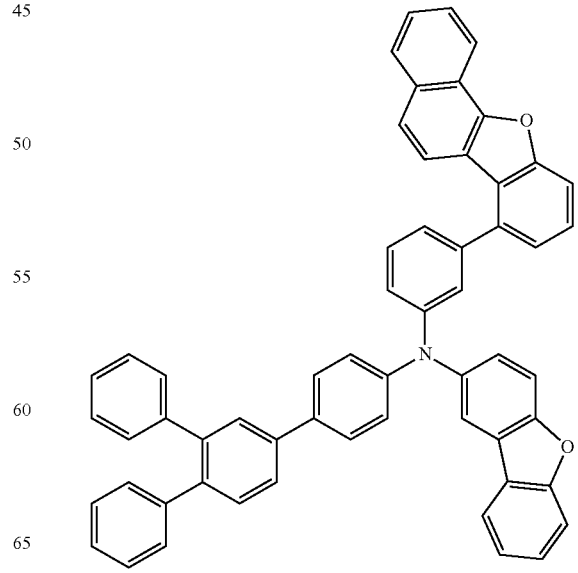

793
-continued
794
-continued
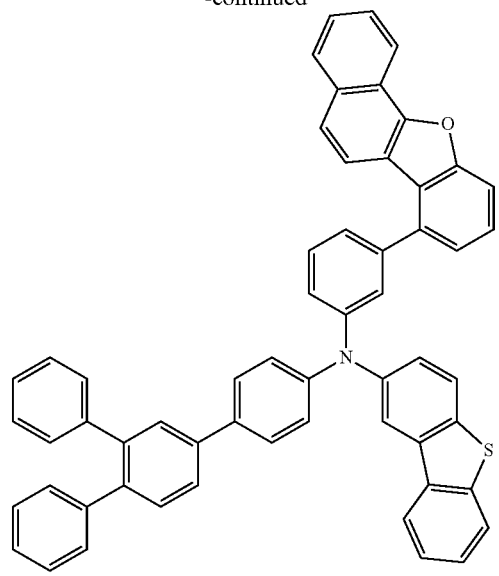
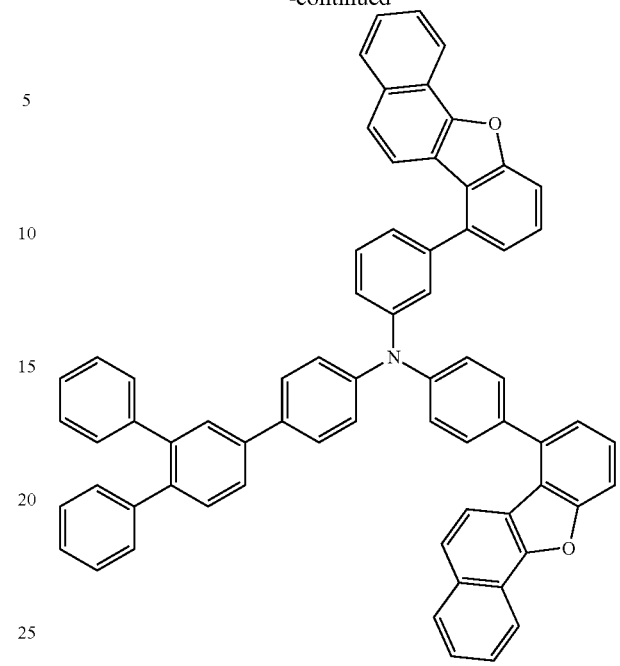

795
-continued
[Chem. 272]
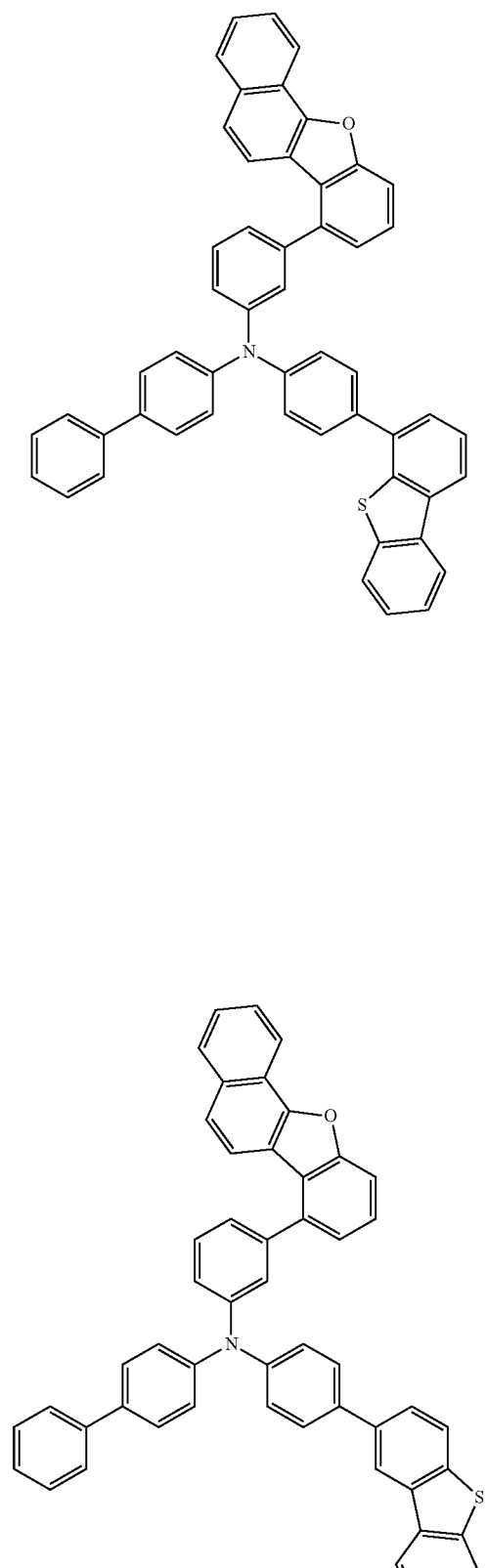
796
-continued
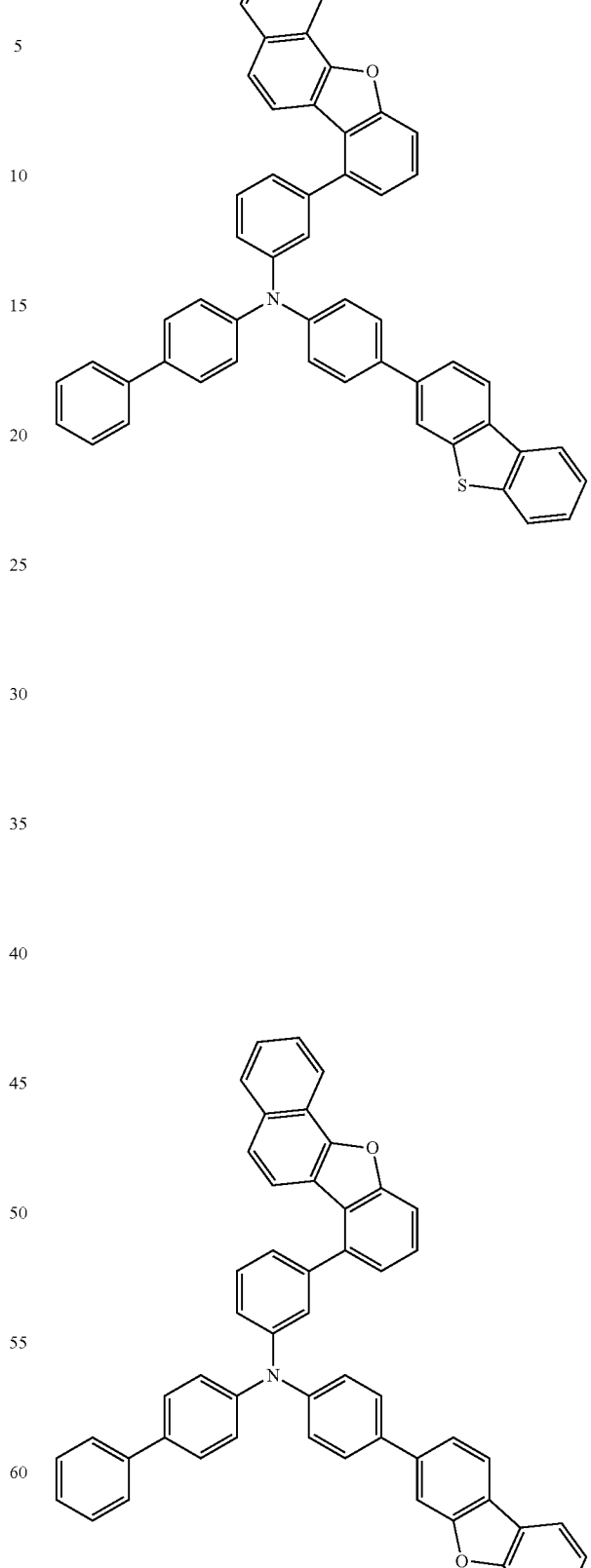

797
798
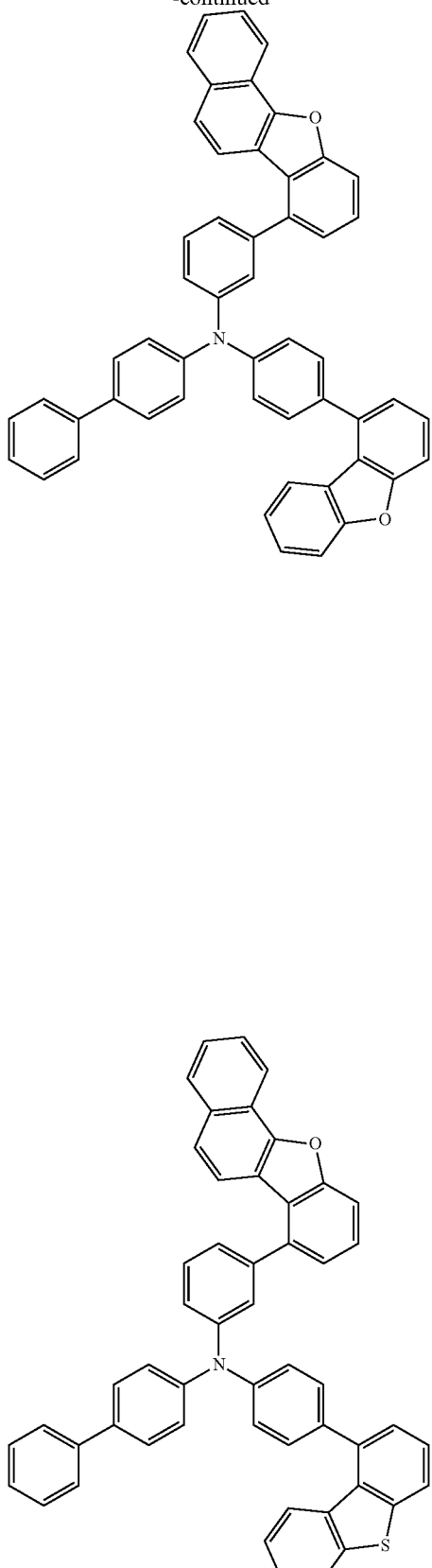
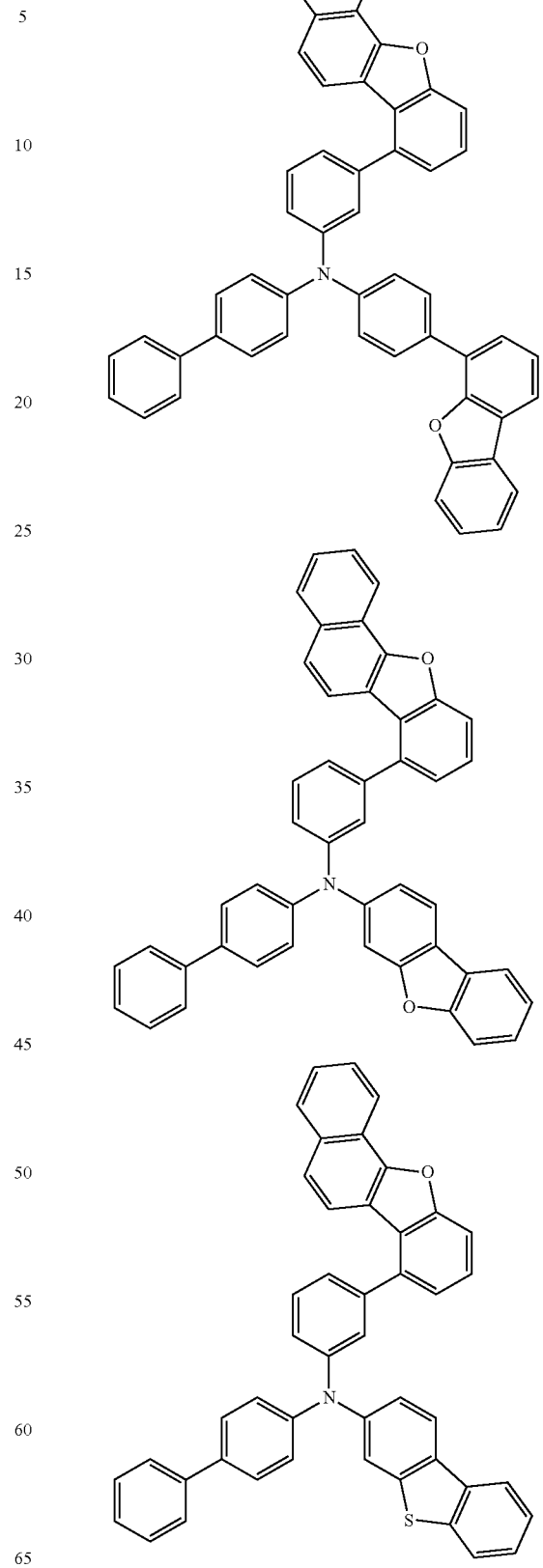

799
-continued

800
-continued

[Chem. 273]

801
-continued
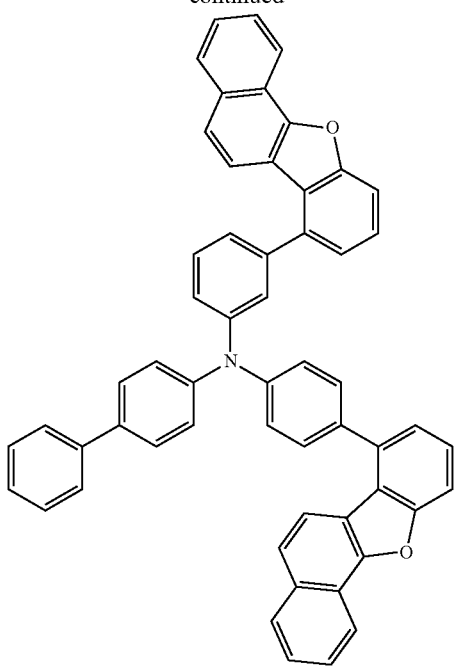
802
-continued
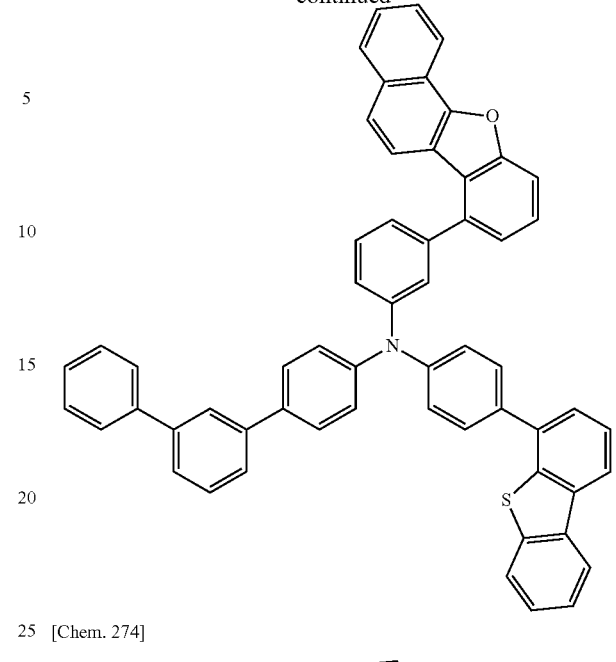
[Chem. 274]
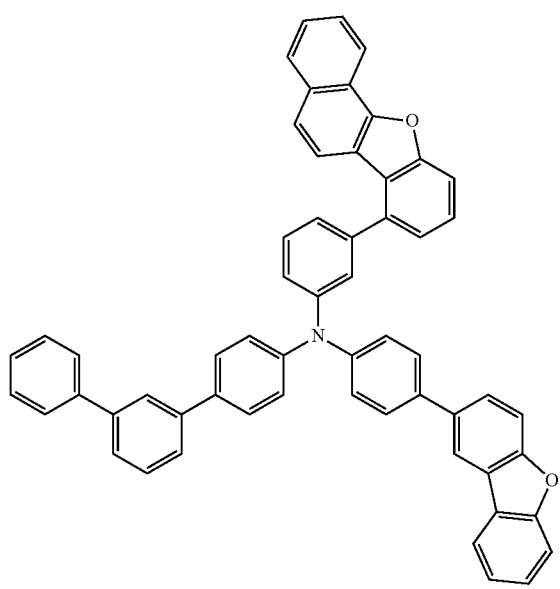
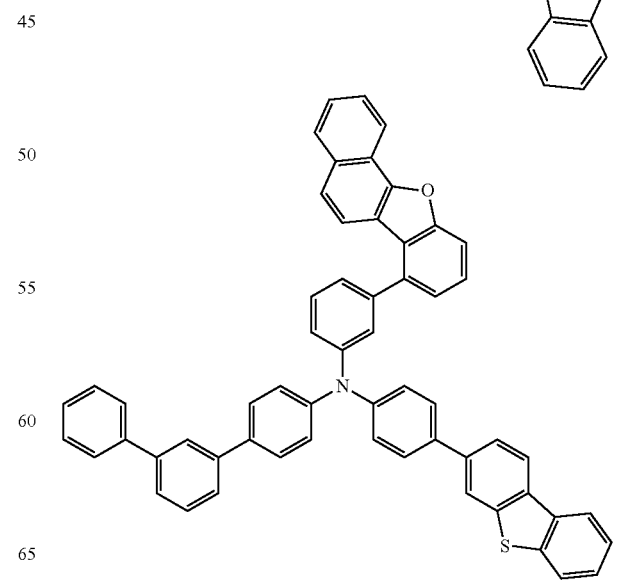

803
-continued
804
-continued
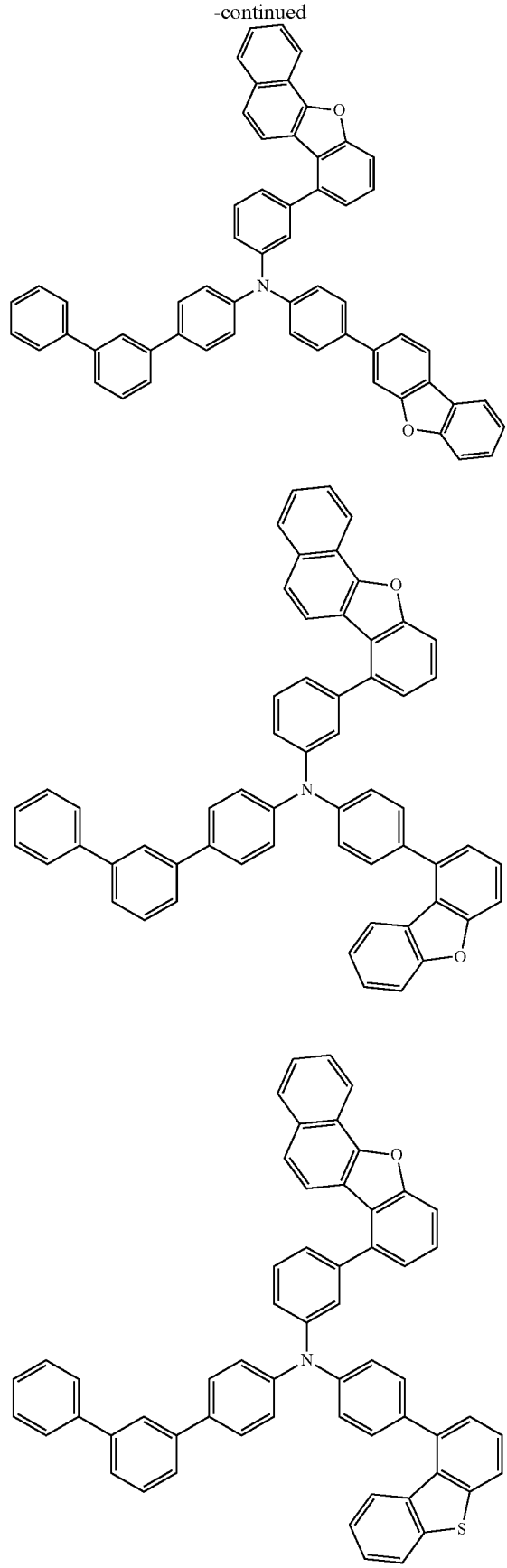
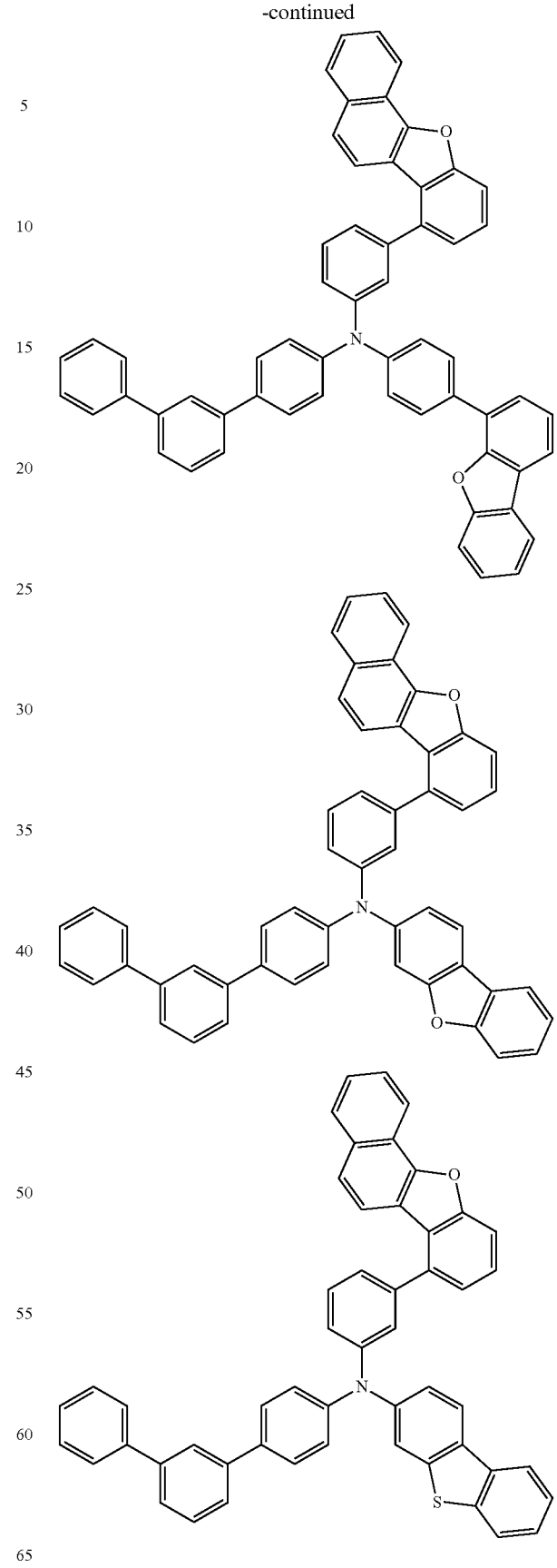

805
-continued
[Chem. 275]
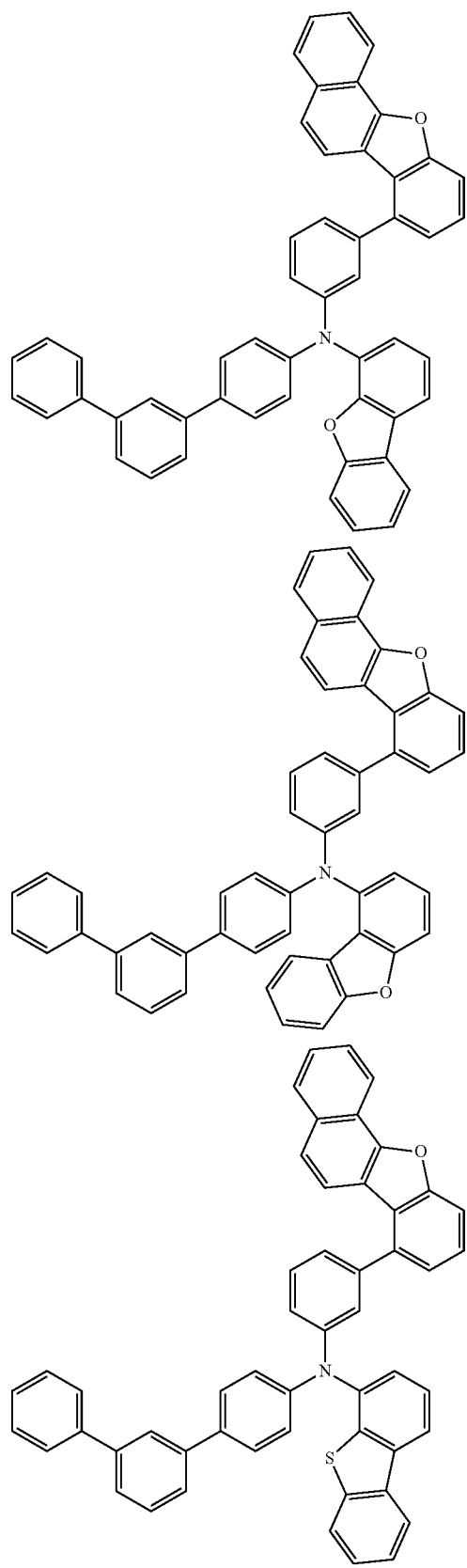
806
-continued
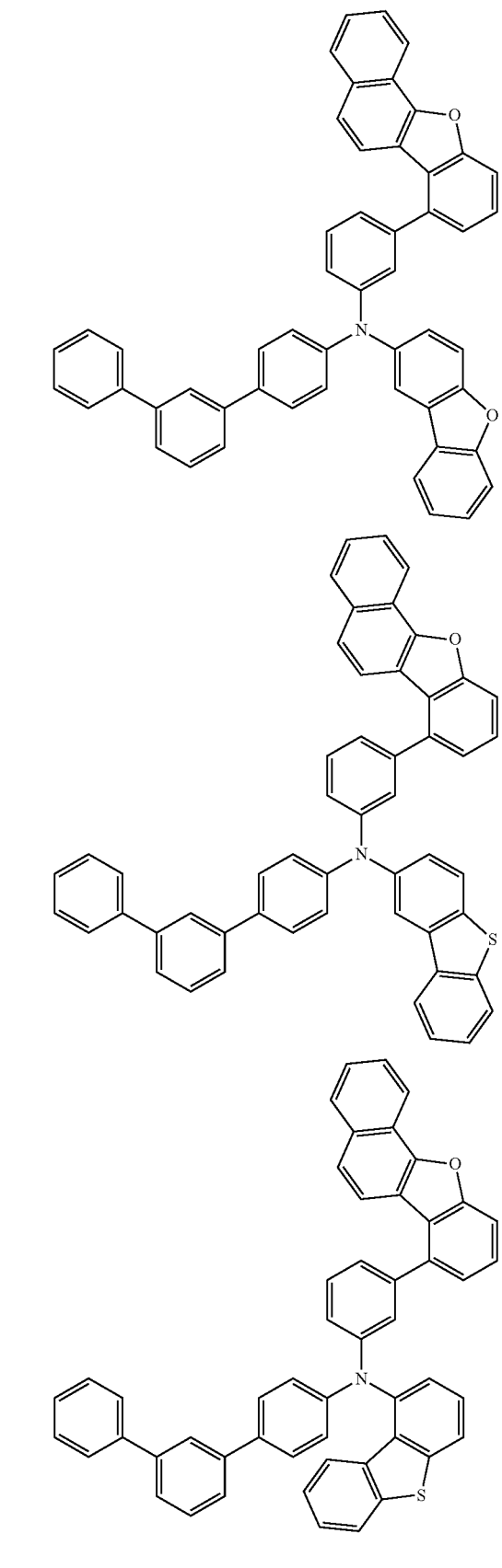

807
-continued
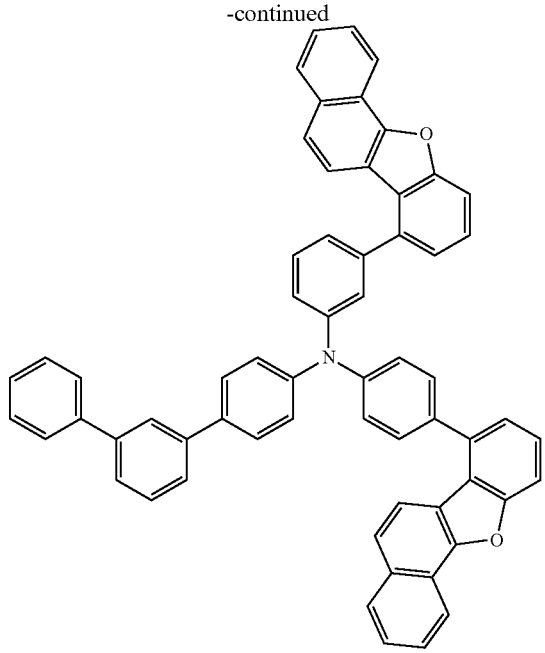
808
-continued
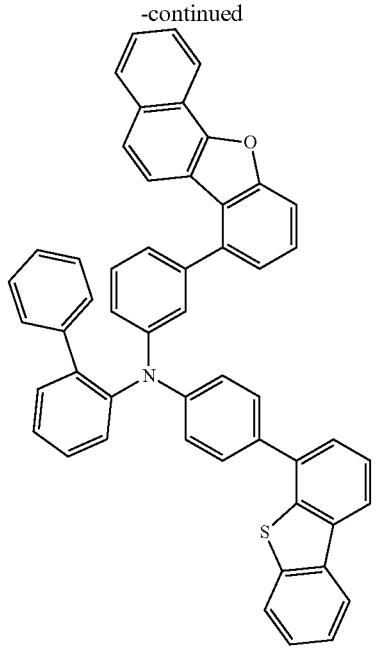
[Chem. 276]
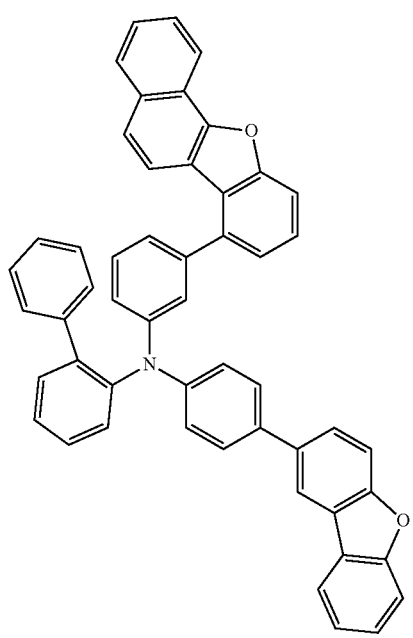
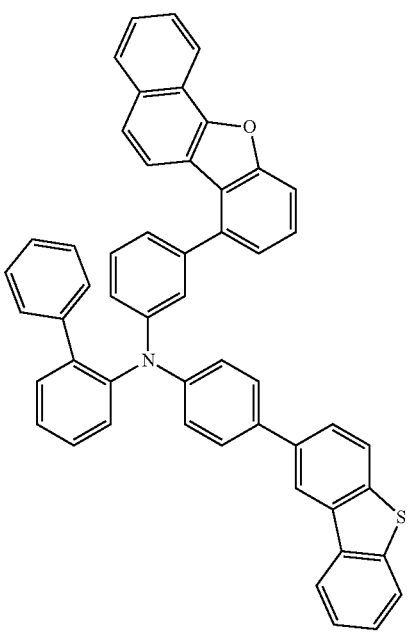

809
-continued
810
-continued
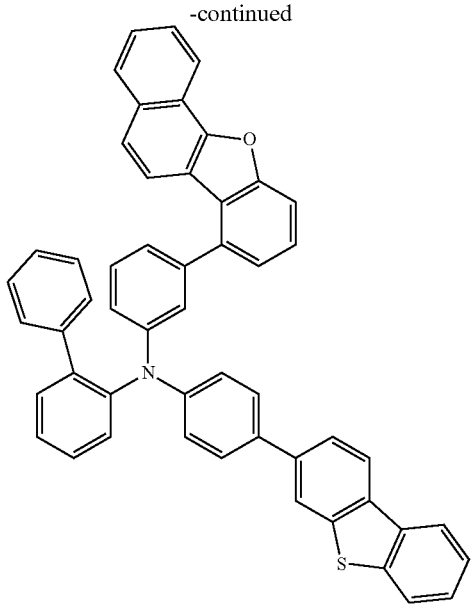
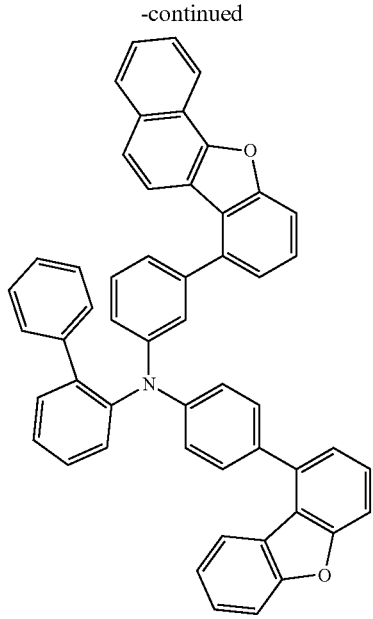

811
-continued
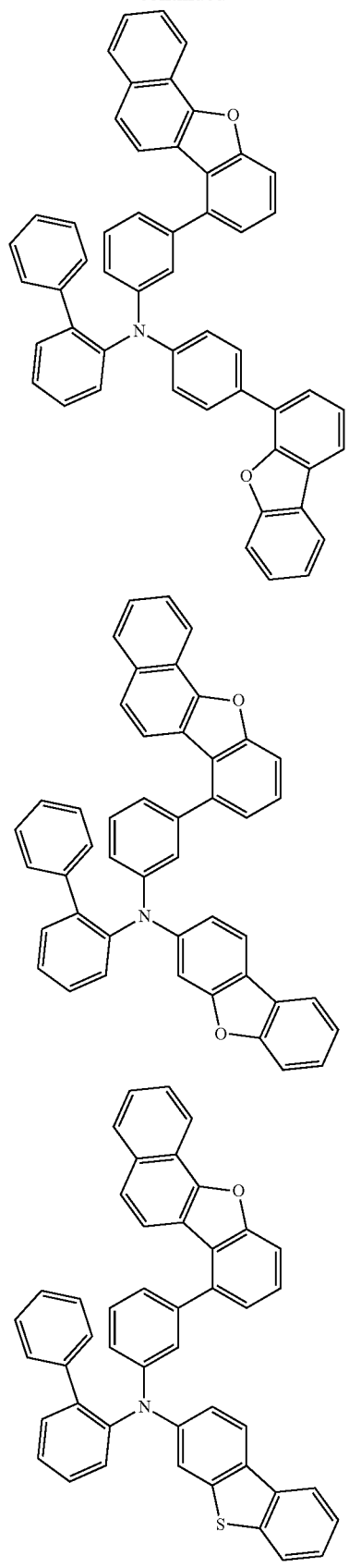
812
-continued
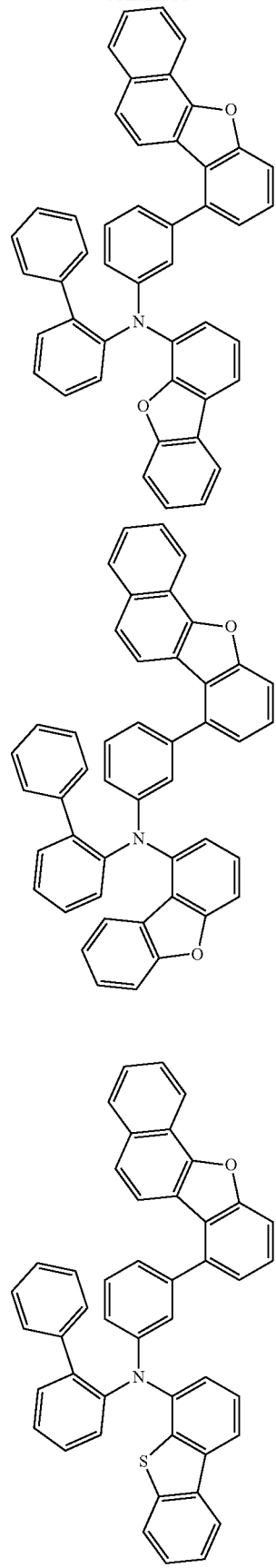
[Chem. 277]

813
-continued
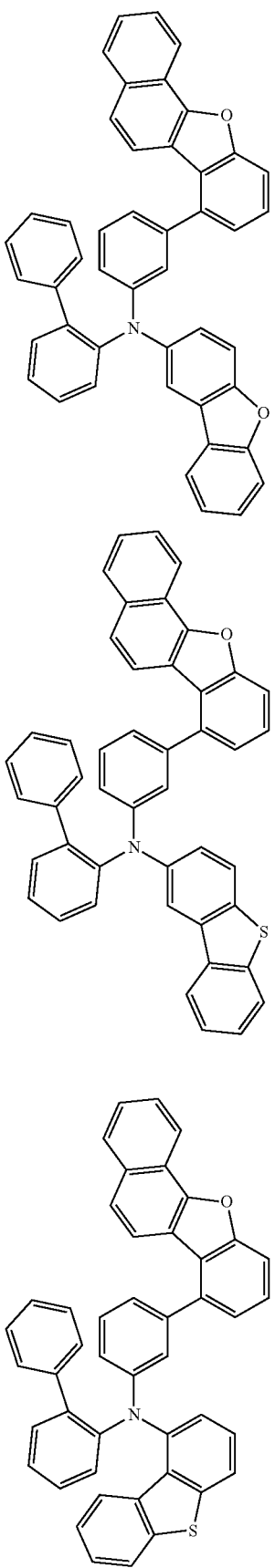
814
-continued
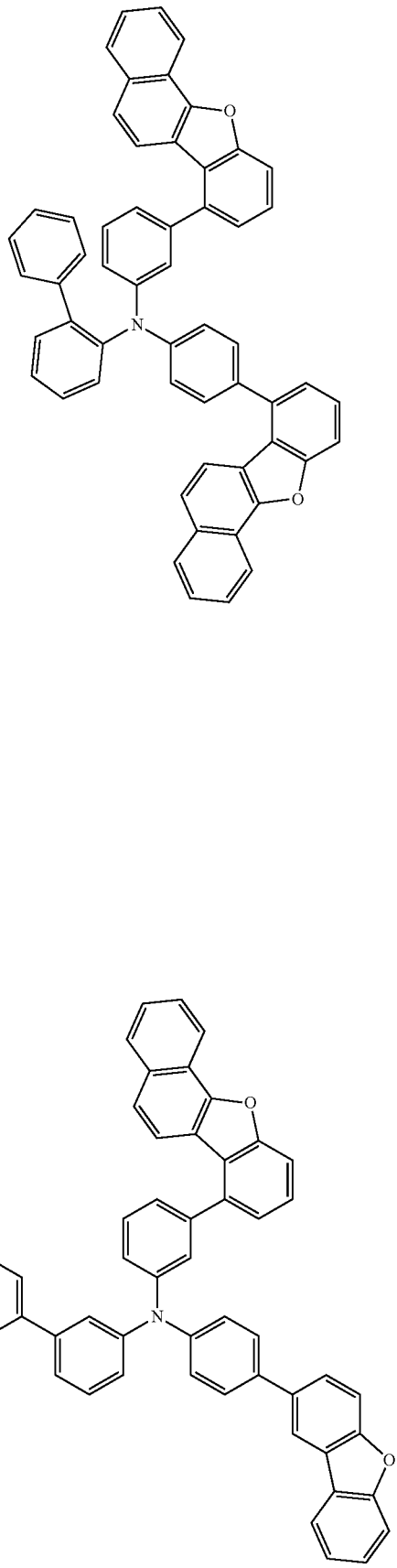

815
-continued
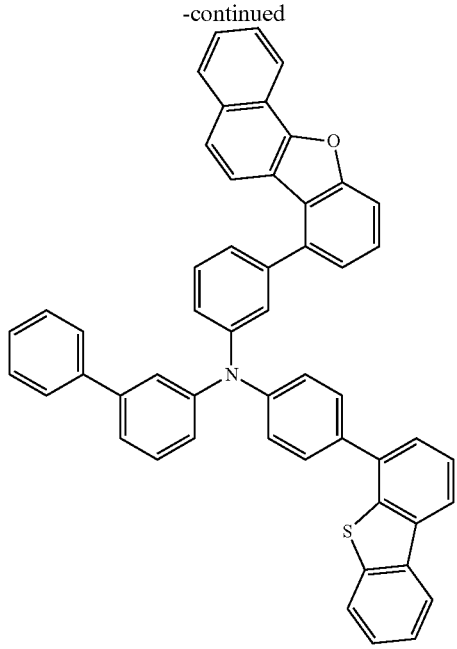
816
-continued
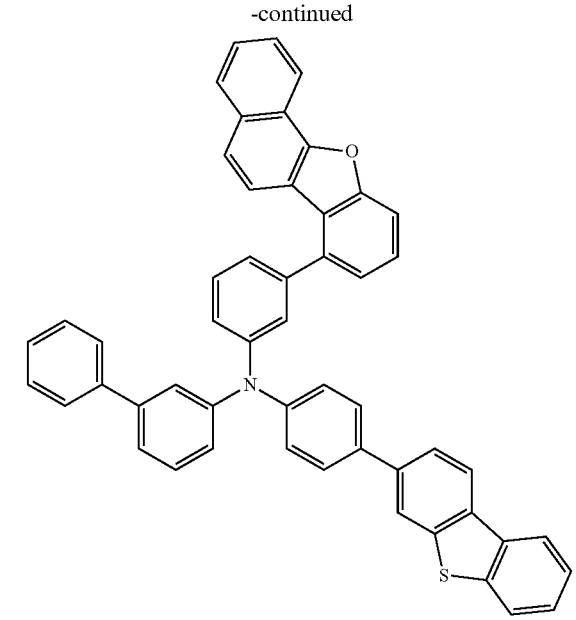
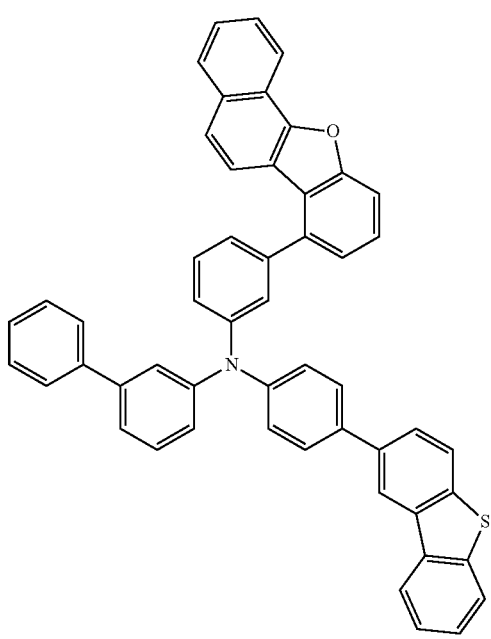
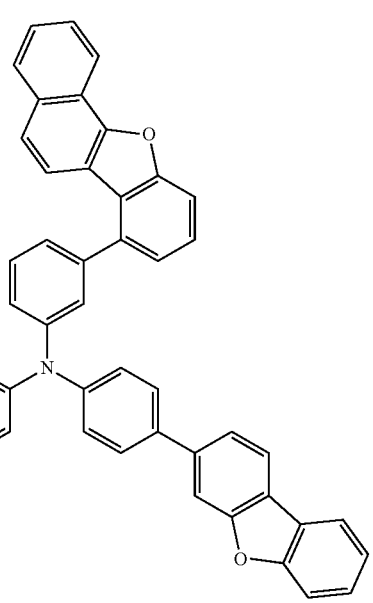

817
-continued
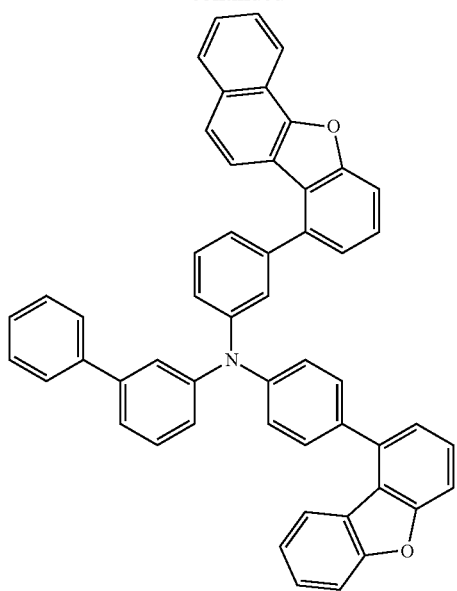
818
-continued
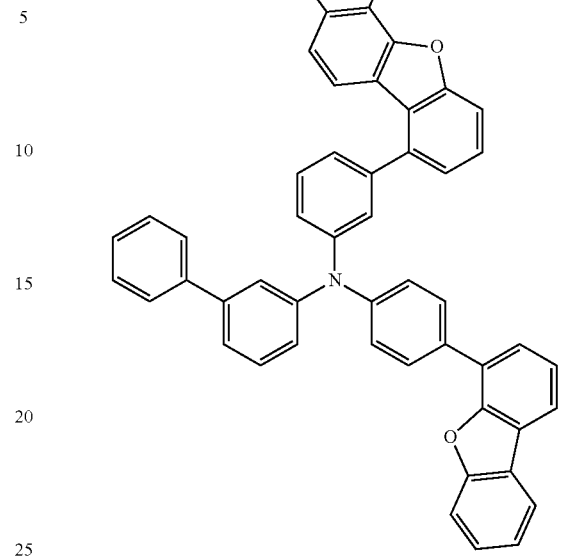
[Chem. 278]
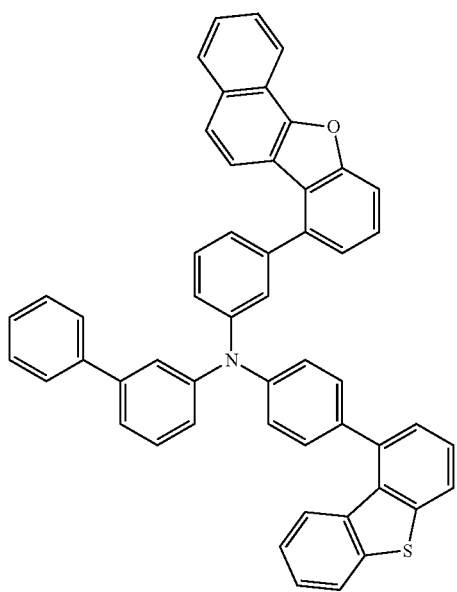
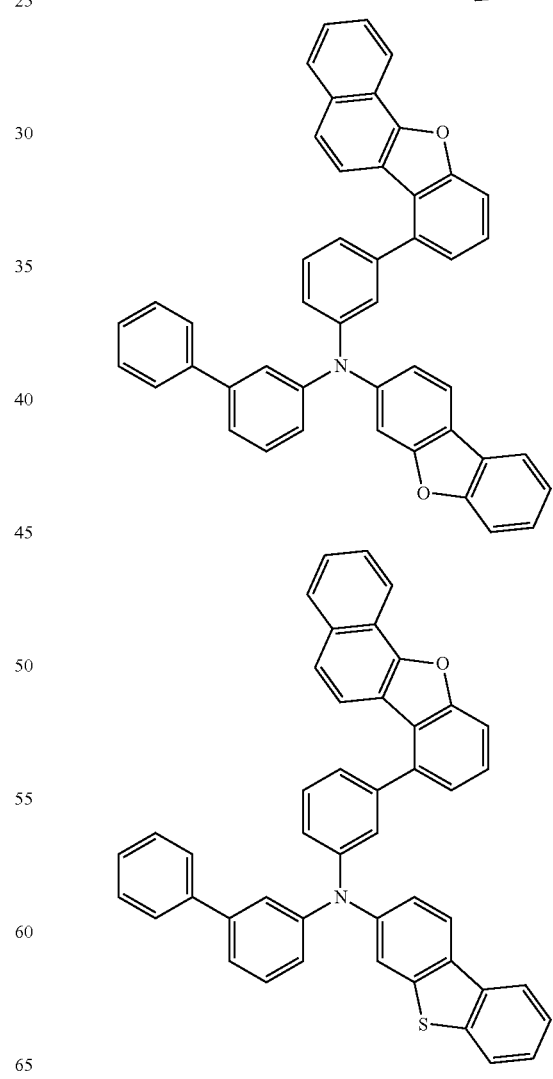

819
-continued
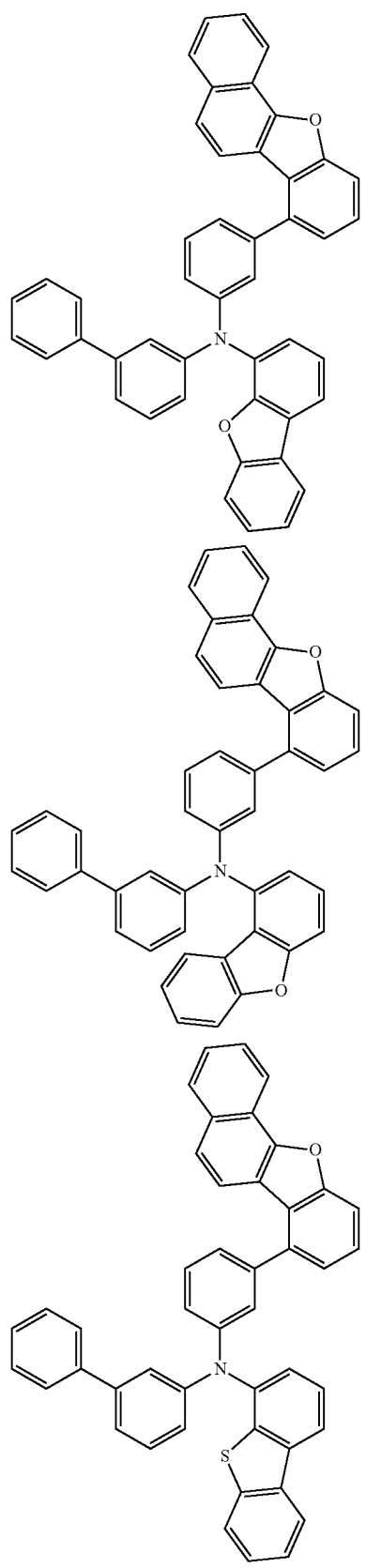
820
-continued
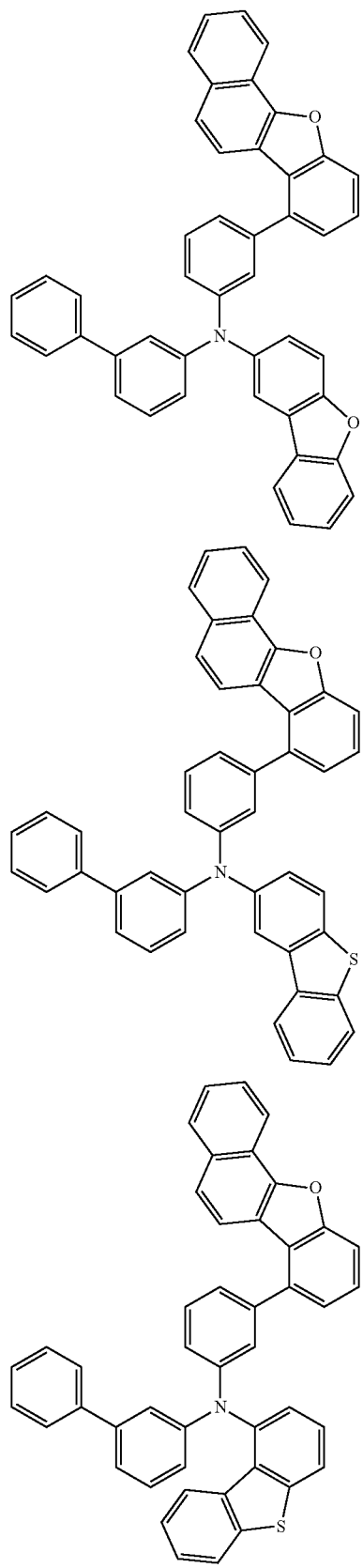

821
-continued
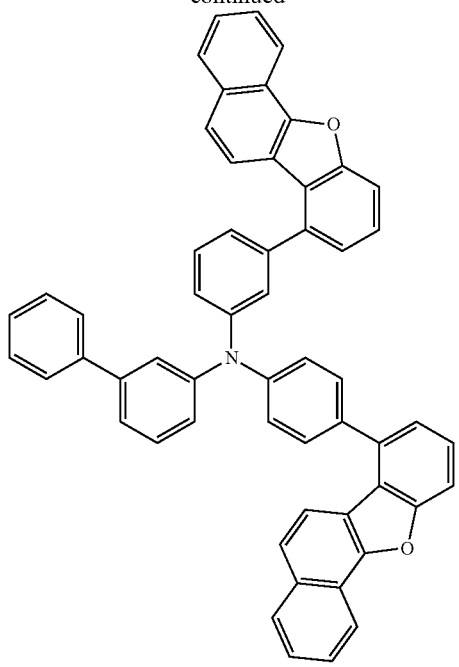
[Chem. 279]
822
-continued
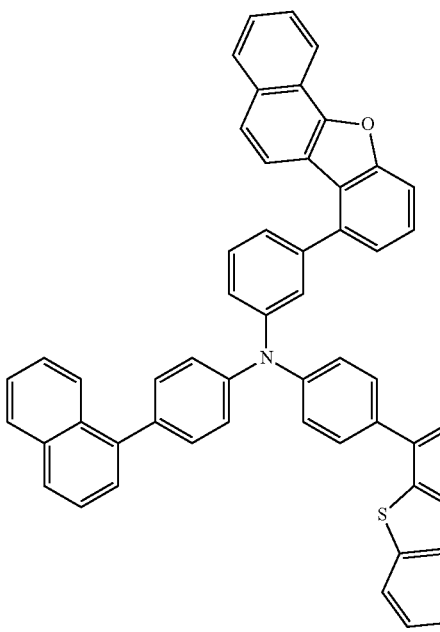
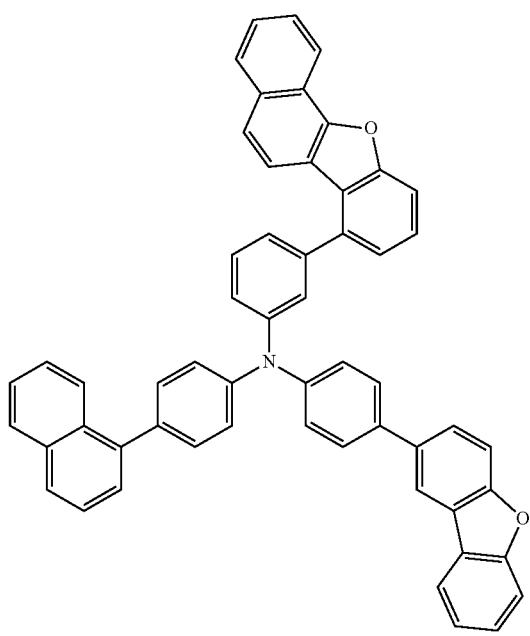
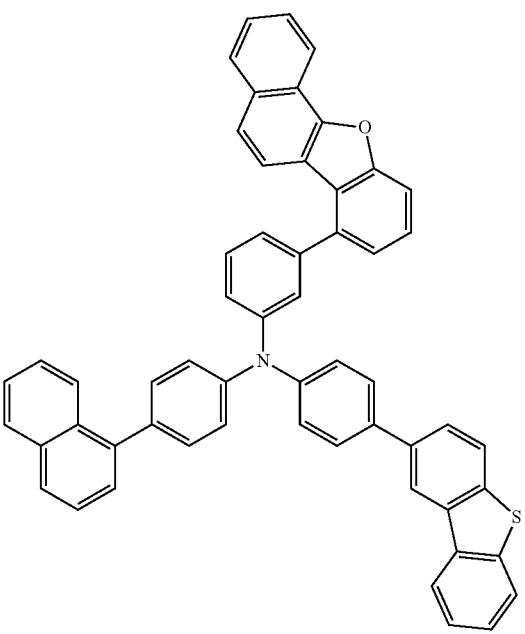

823
-continued
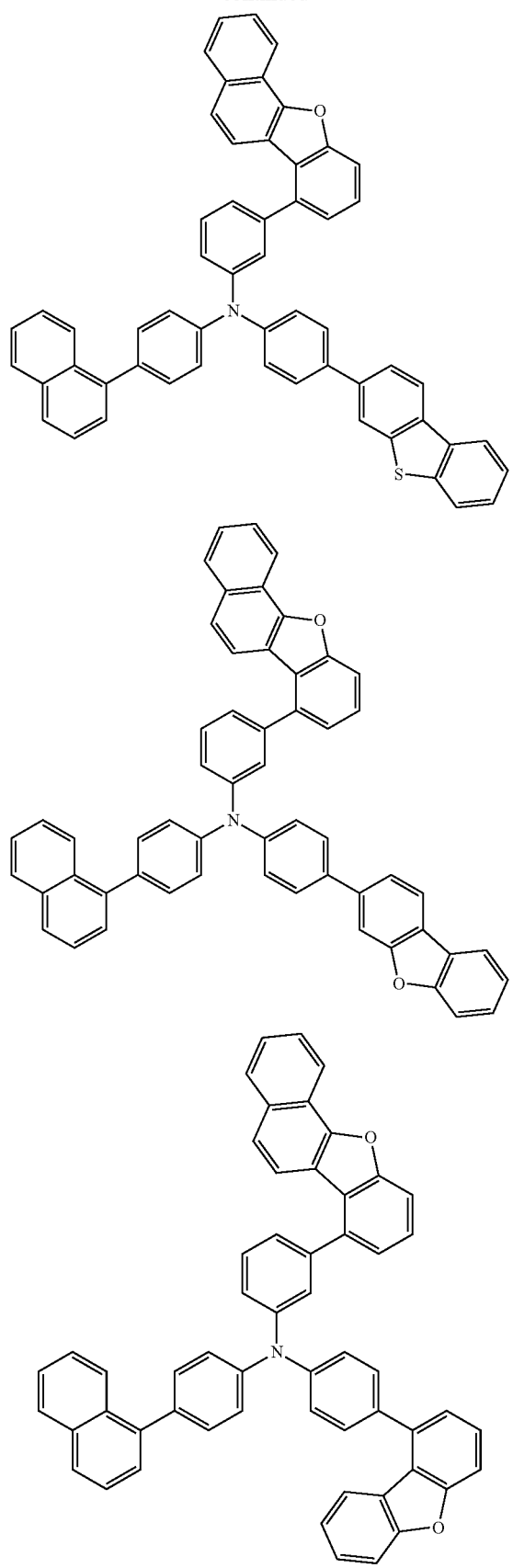
824
-continued
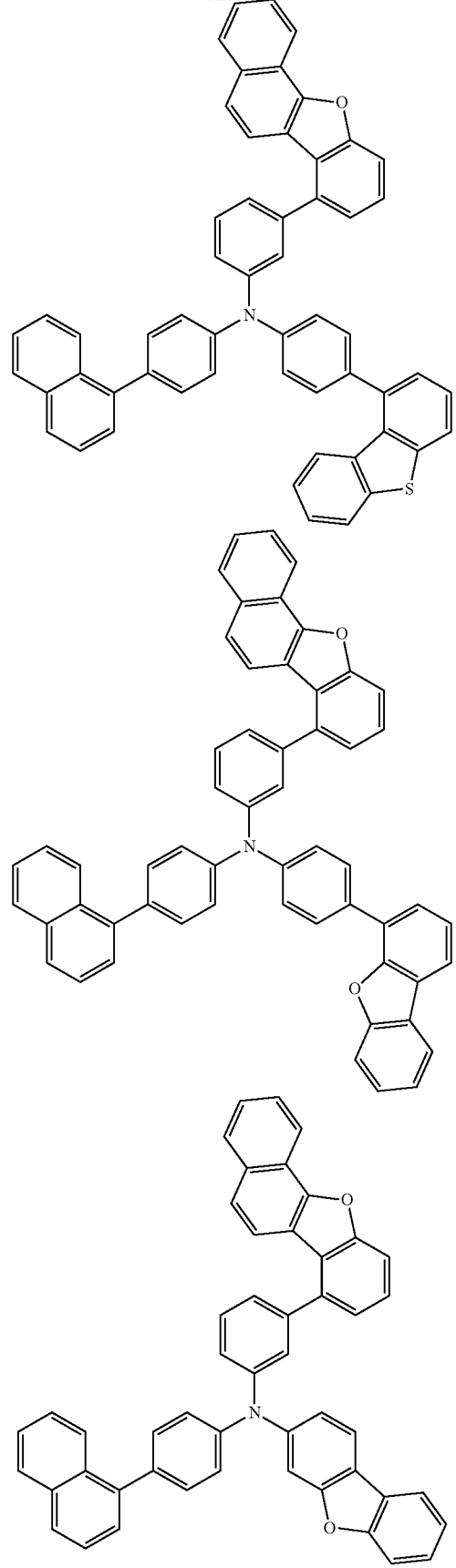

825
-continued
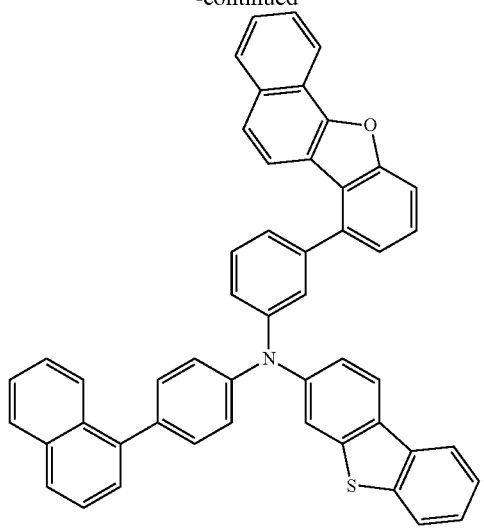
[Chem. 280]
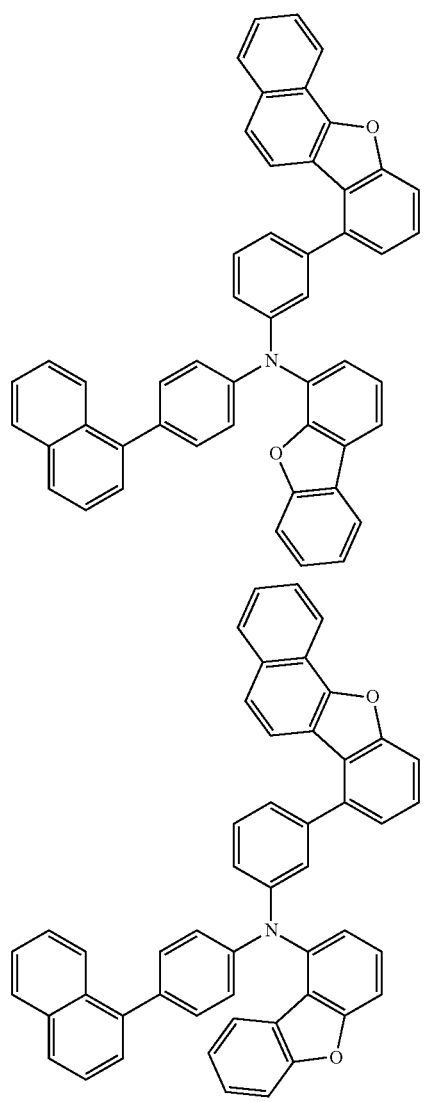
826
-continued
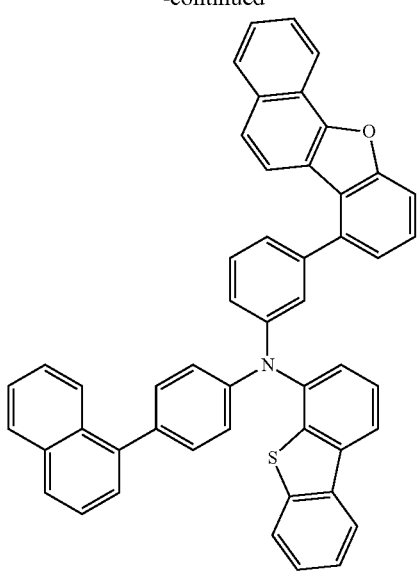
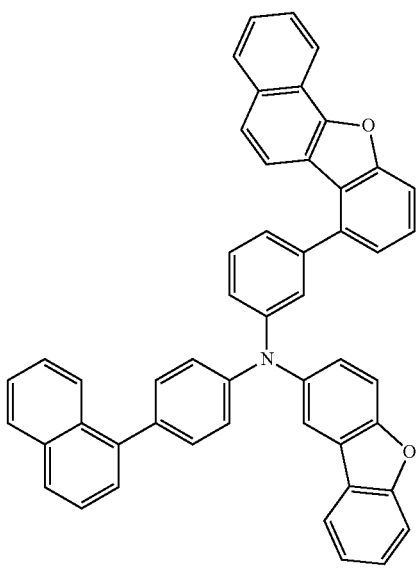
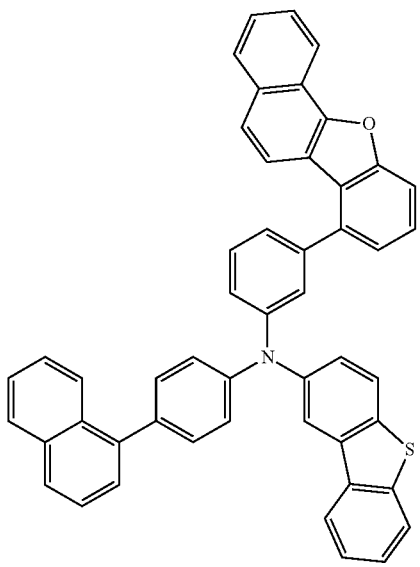

827
-continued
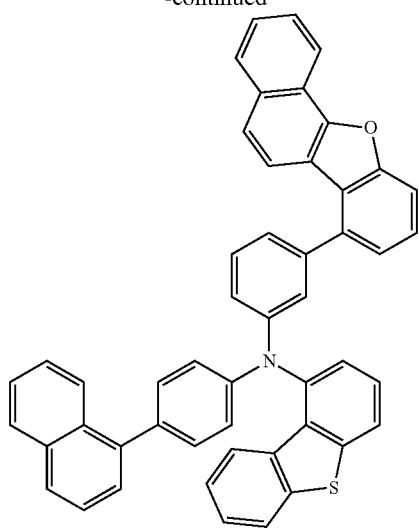
828
-continued
[Chem. 281]
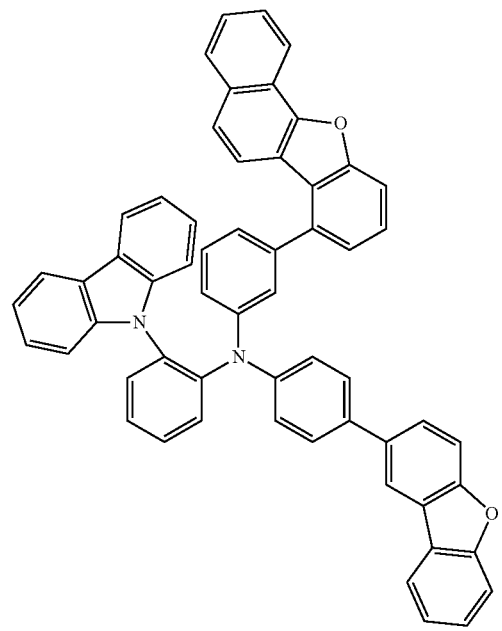
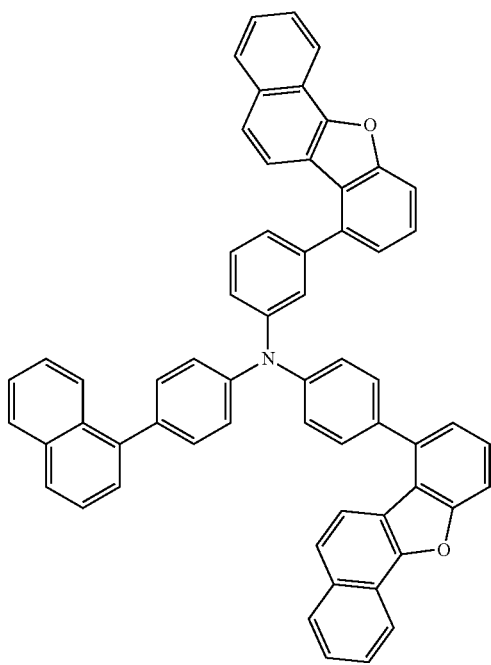
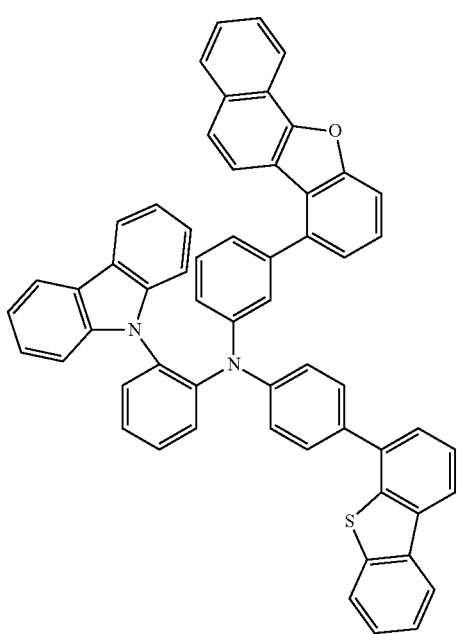

829
-continued
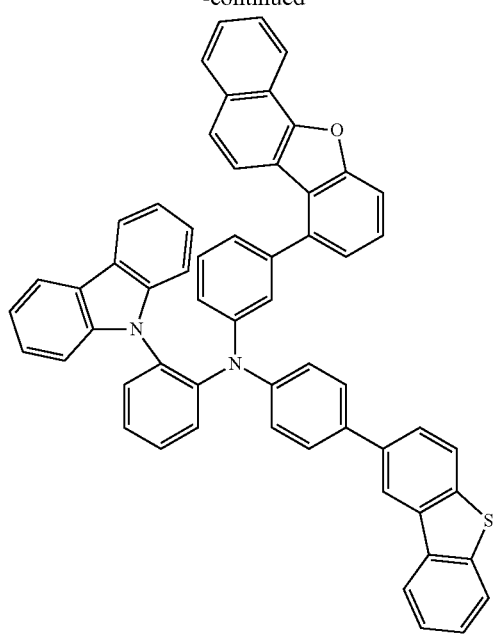
830
-continued
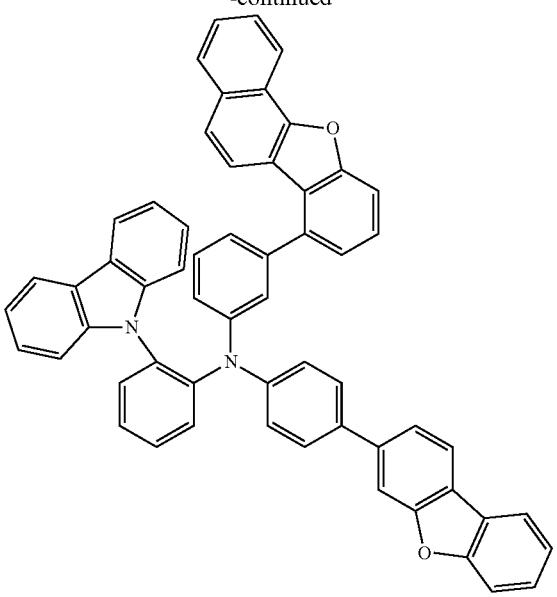
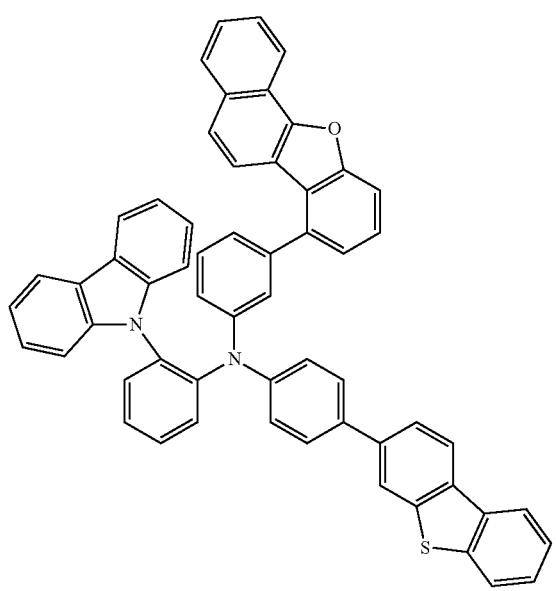
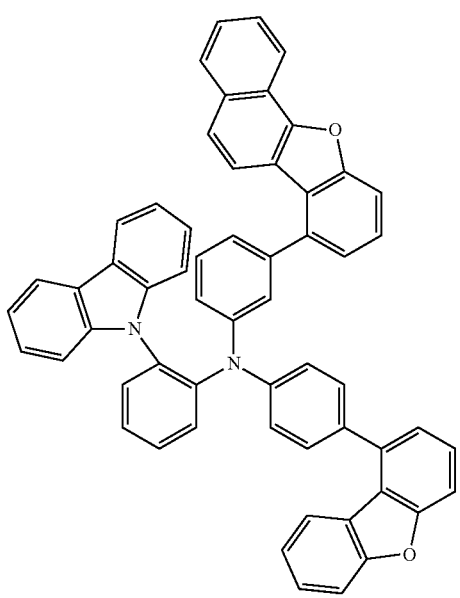

831
-continued
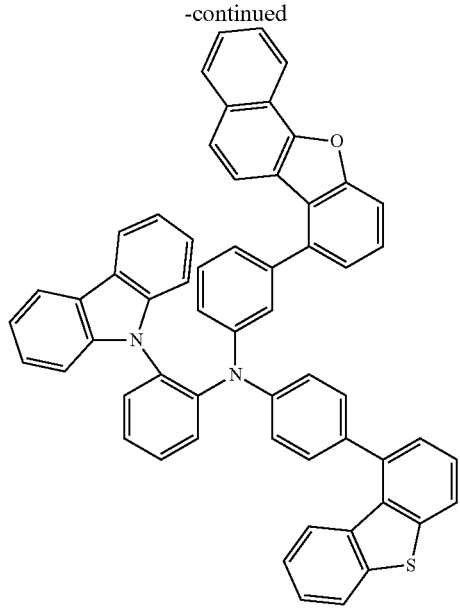
832
-continued
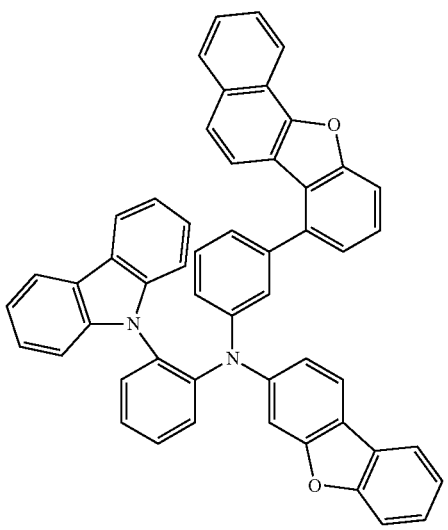
[Chem. 282]
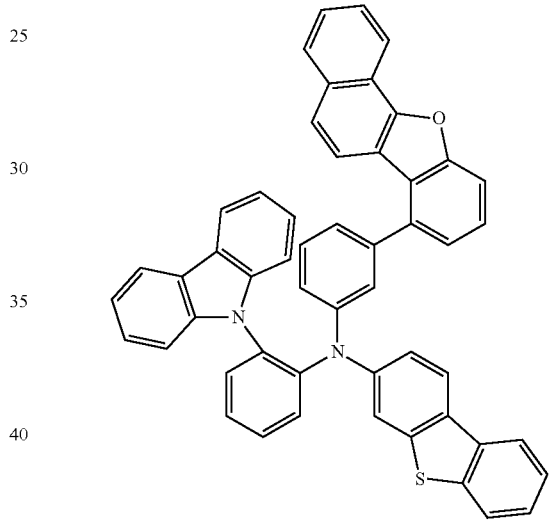
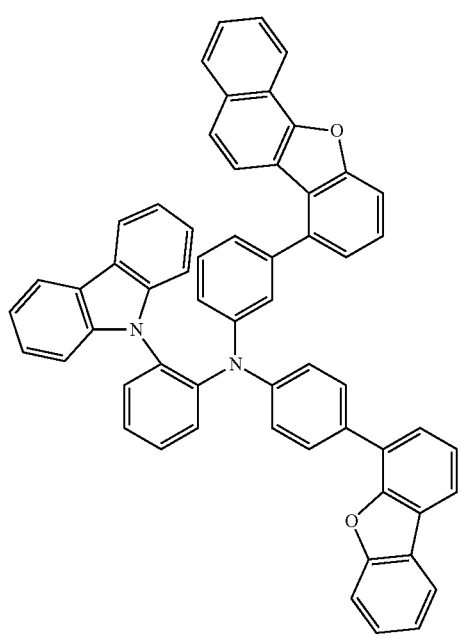
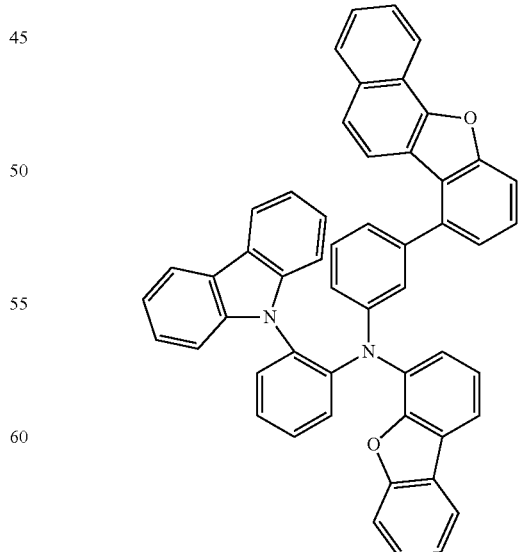

833
-continued

834
-continued

835
-continued
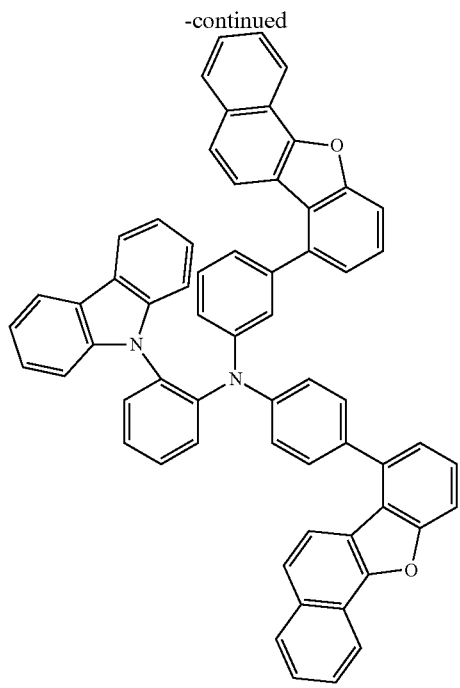
836
-continued
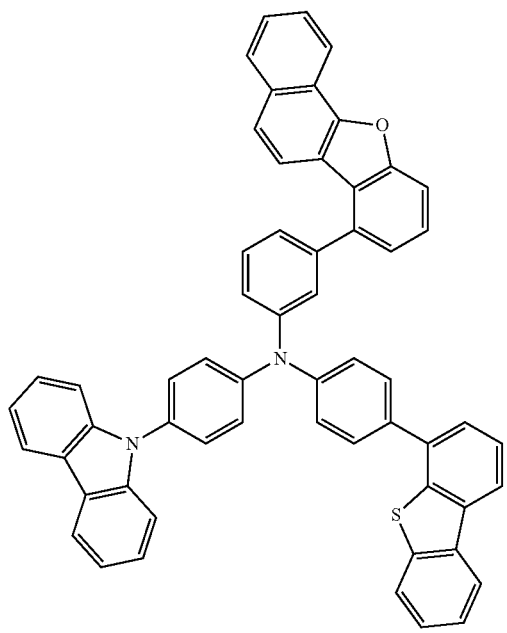
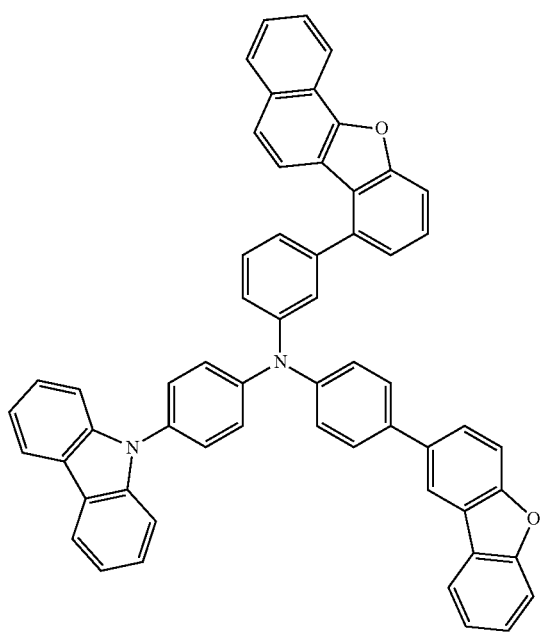
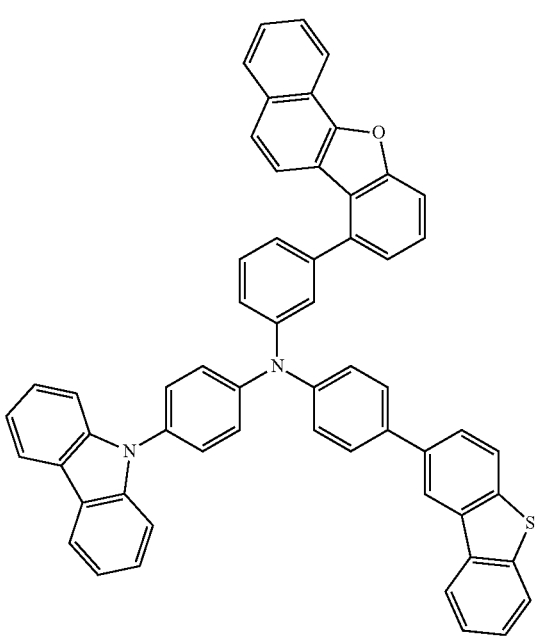

837
-continued
838
-continued
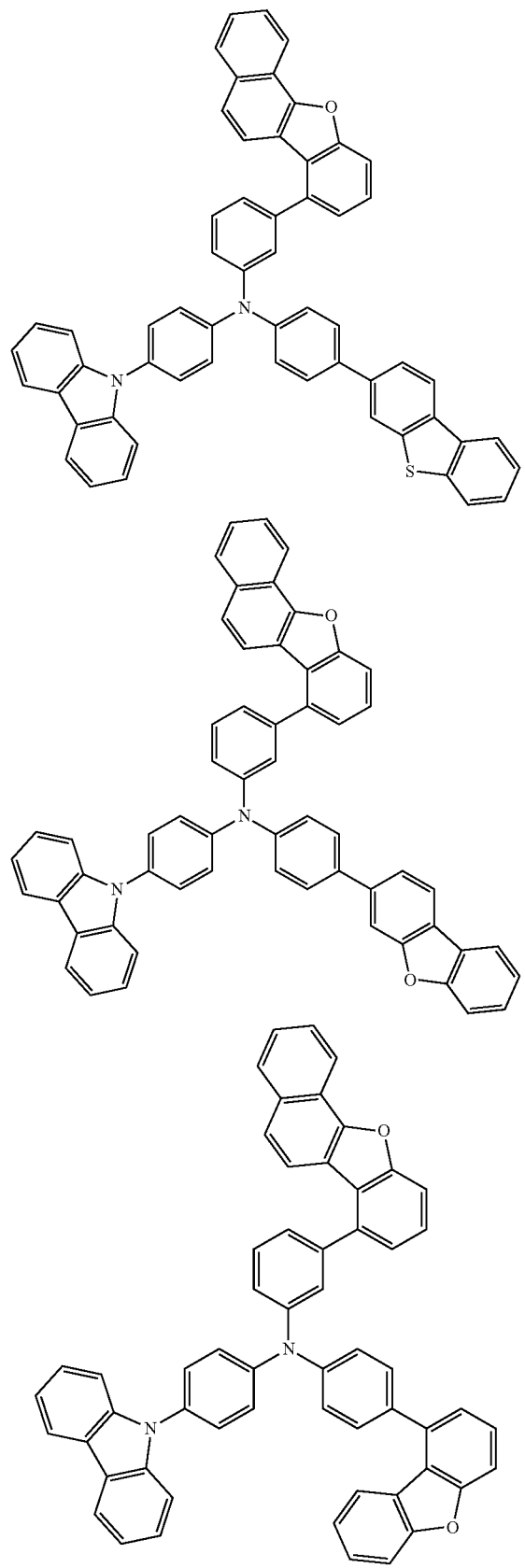
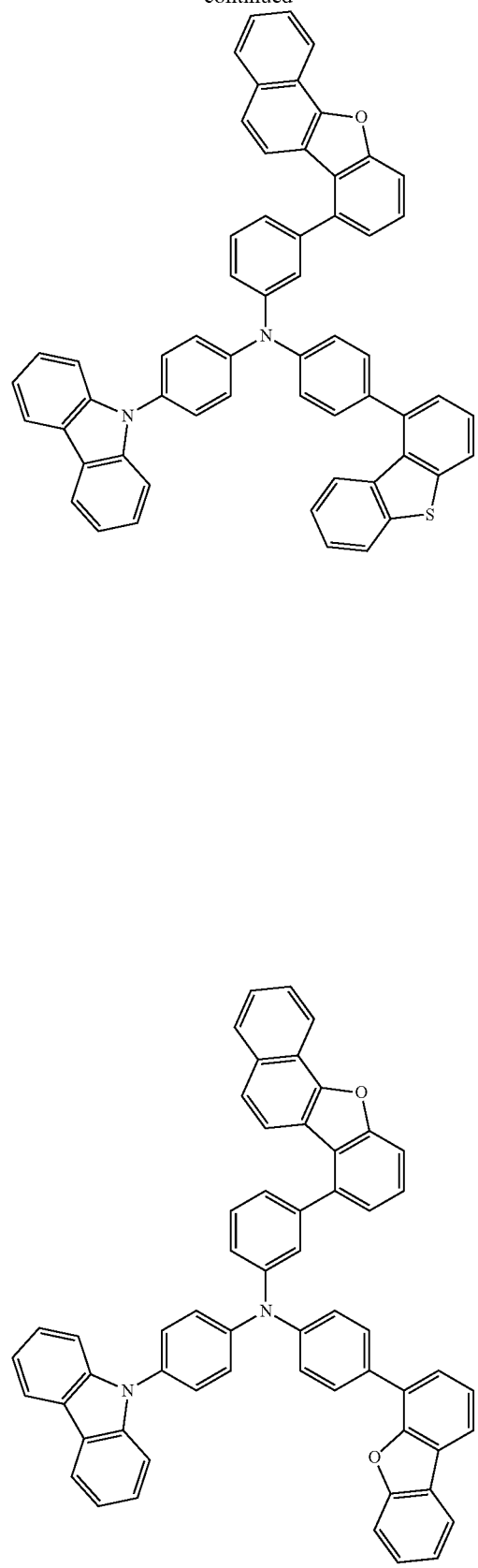

839
-continued
840
-continued
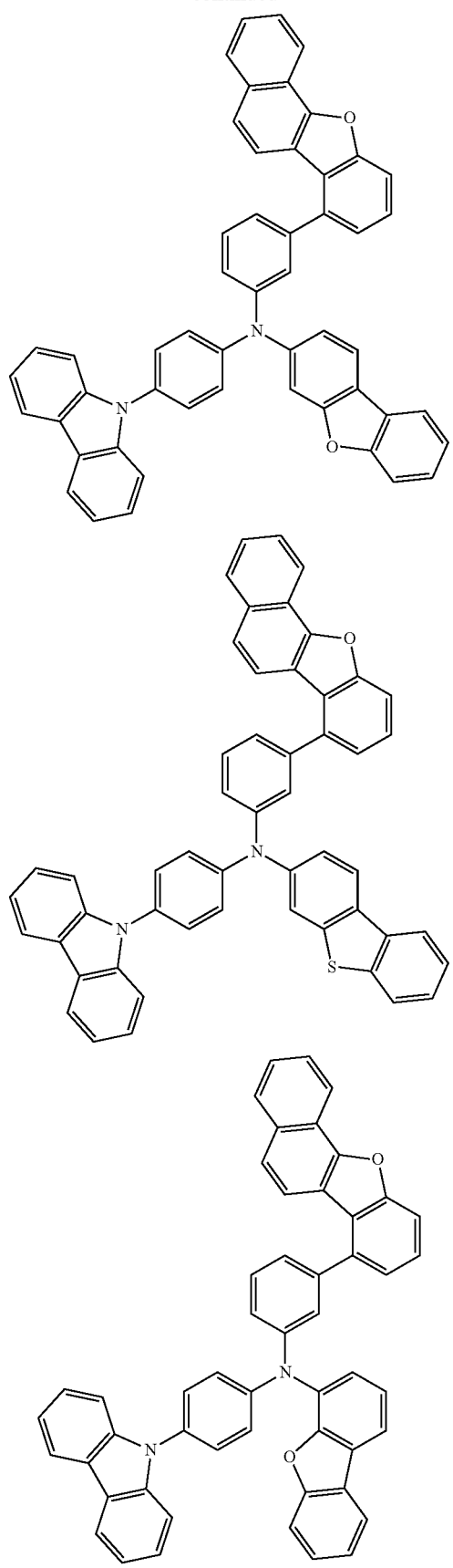
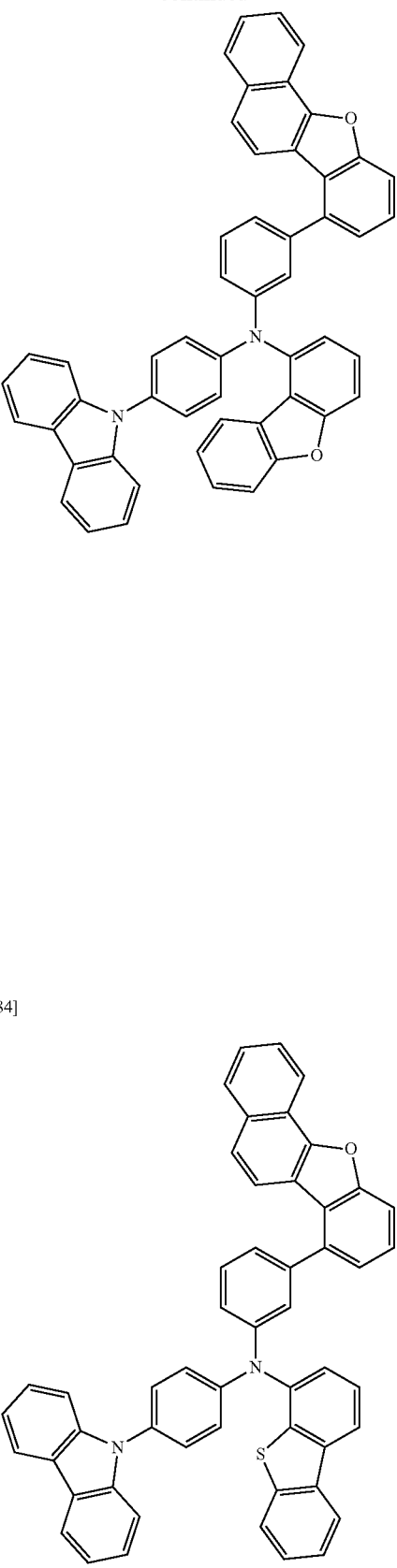
[Chem. 284]

841
-continued
842
-continued
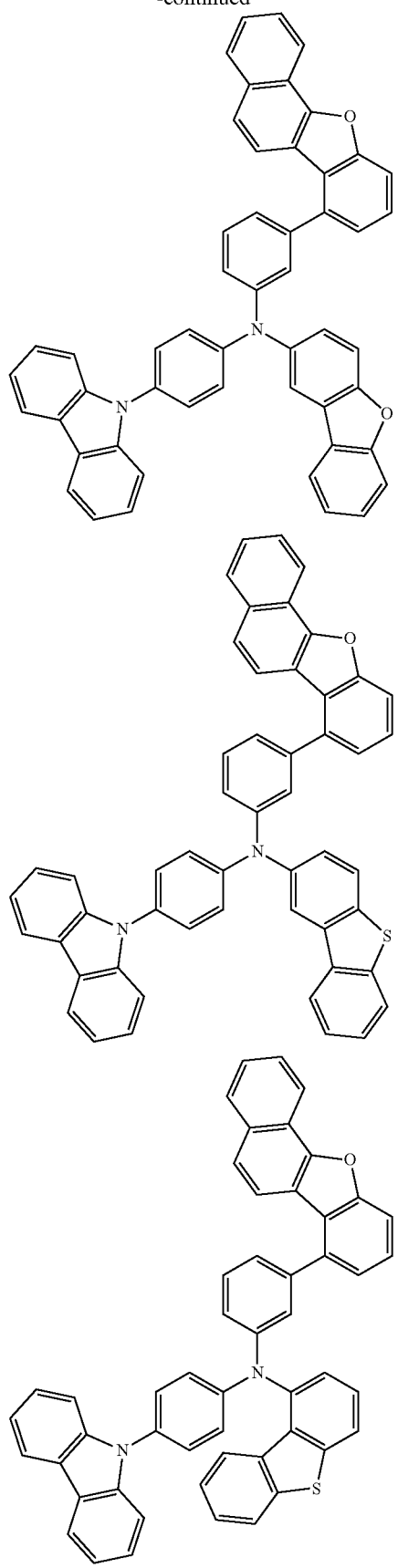
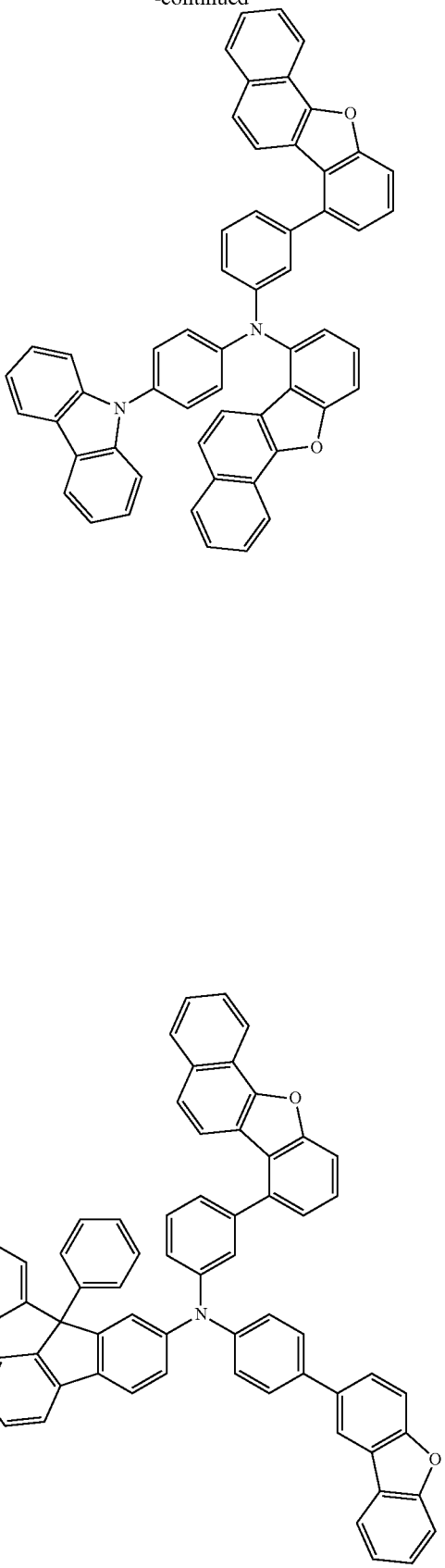

843
-continued
844
-continued
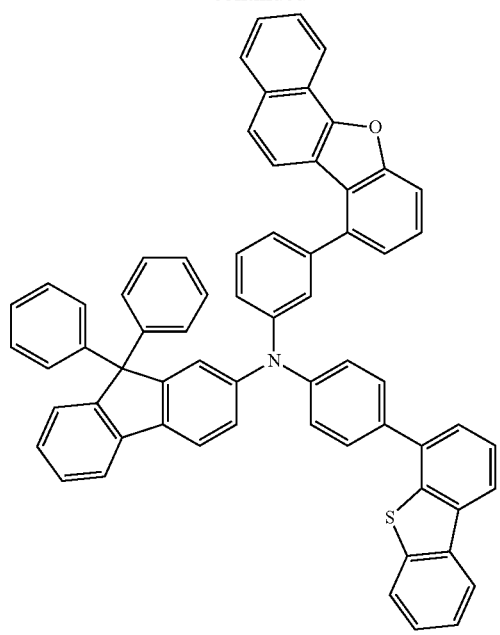
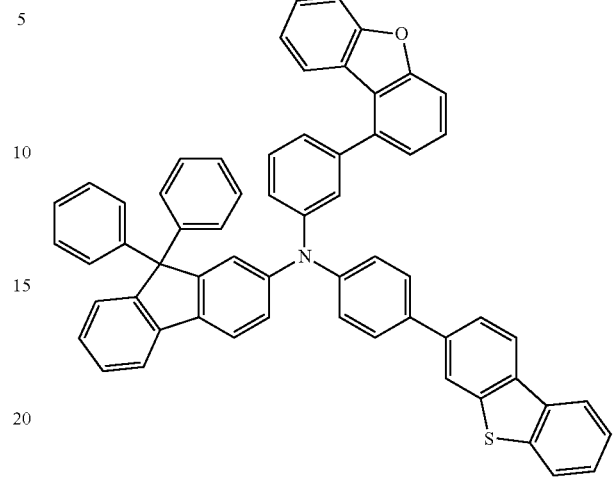
[Chem. 285]
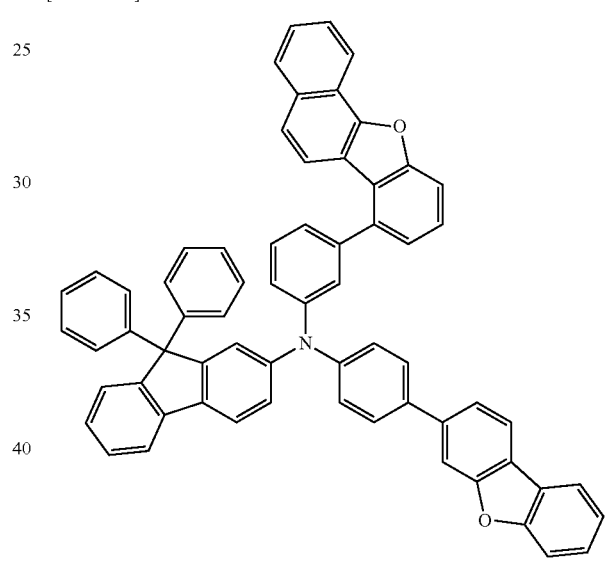
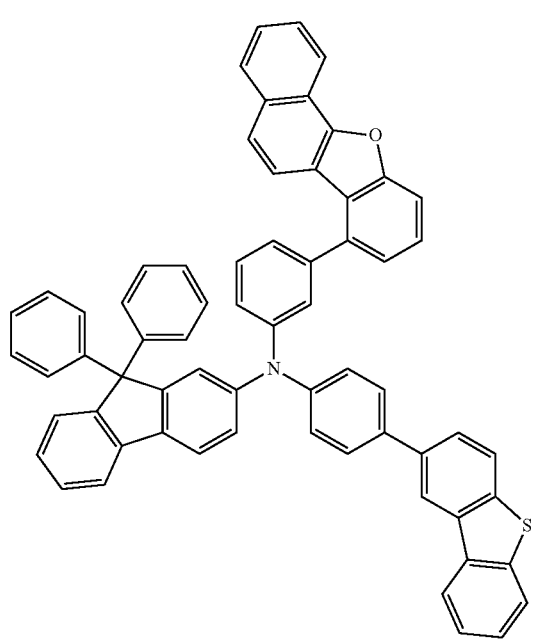

845
-continued
846
-continued
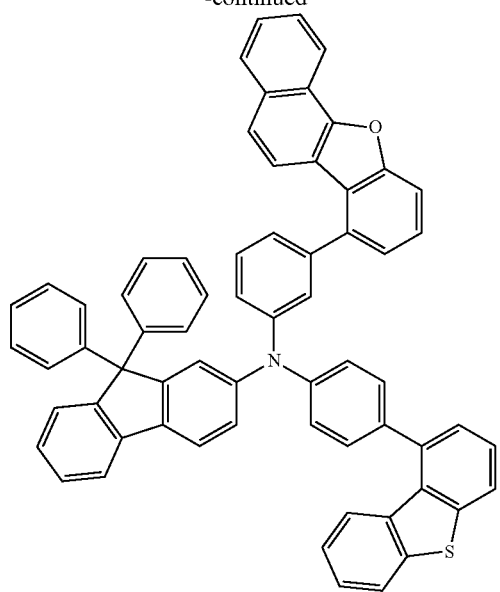
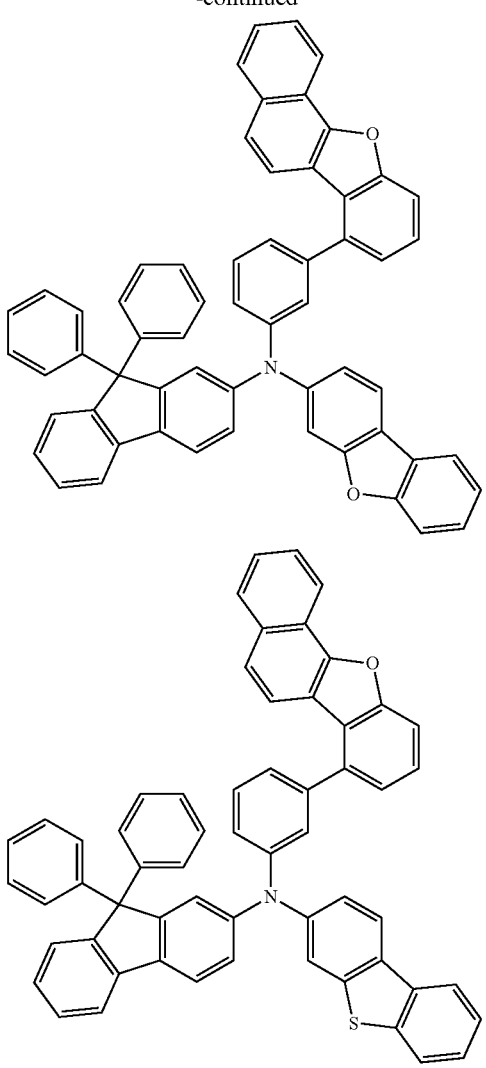
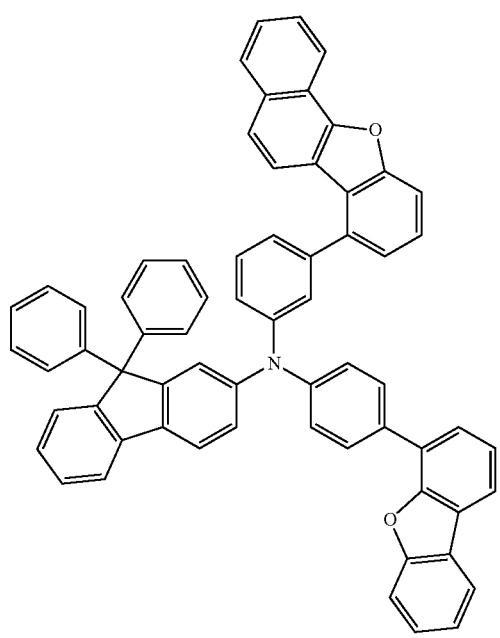
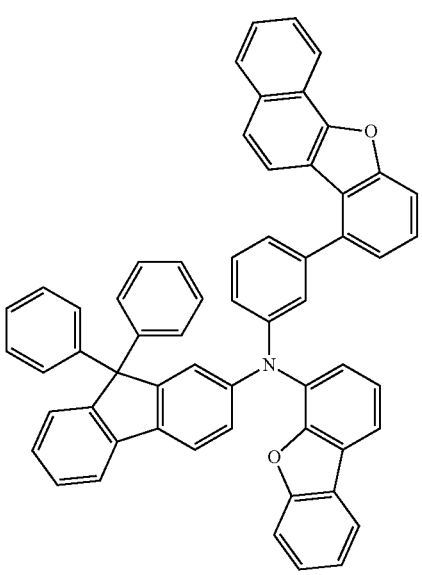

847
-continued
[Chem. 286]
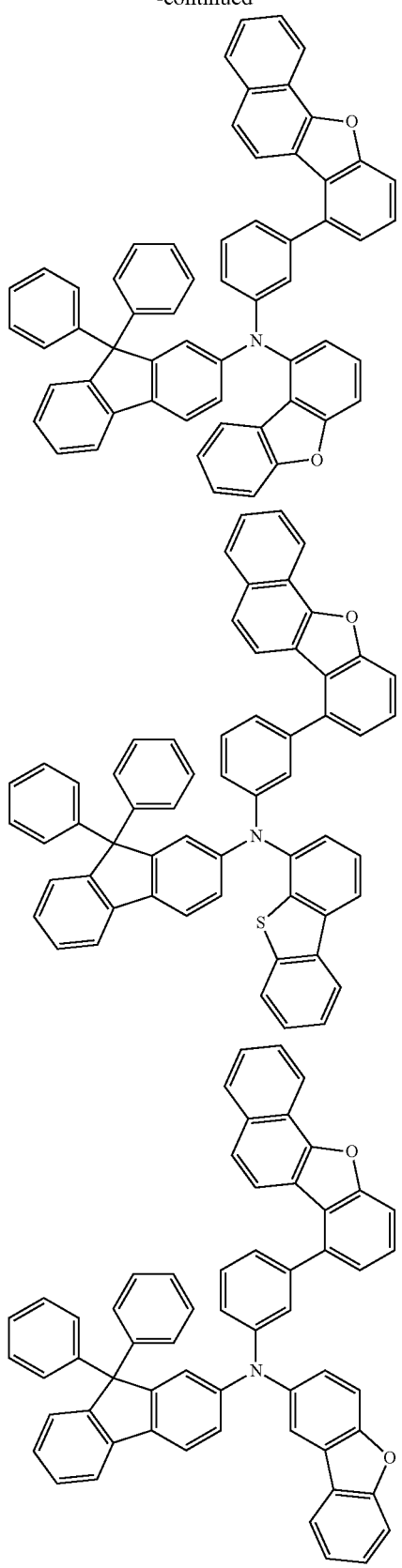
848
-continued

849
-continued
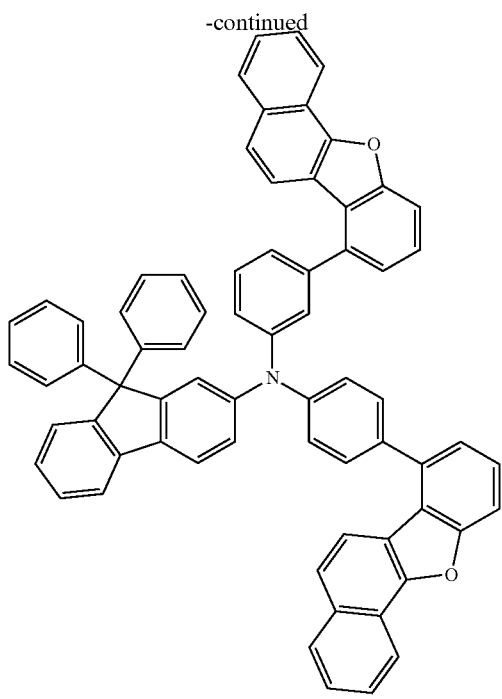
850
-continued
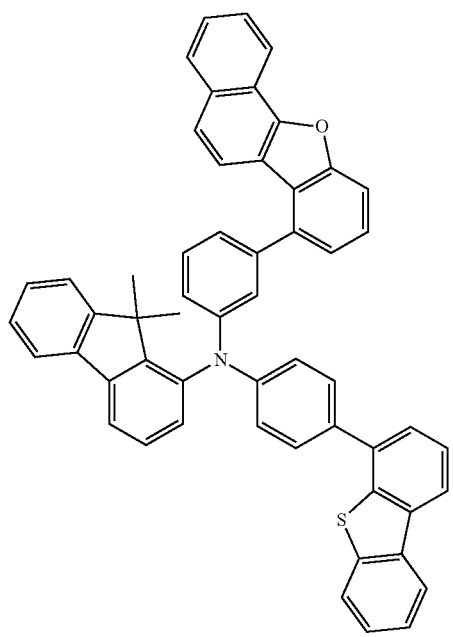
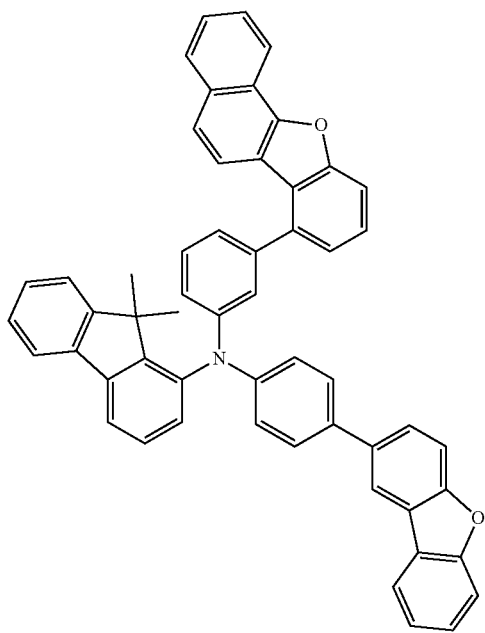

851
-continued
852
-continued
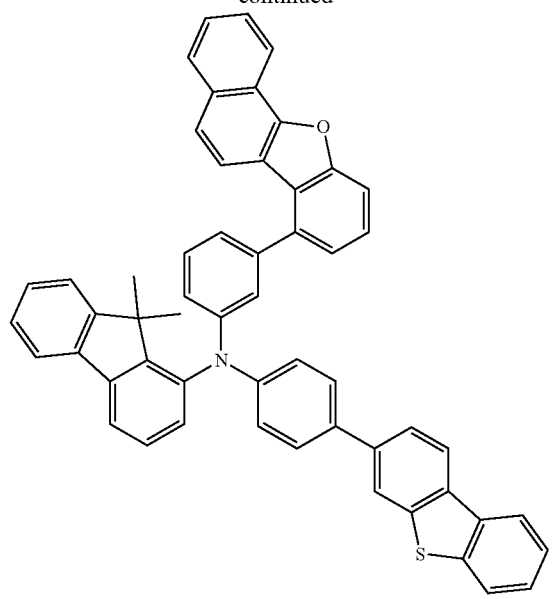
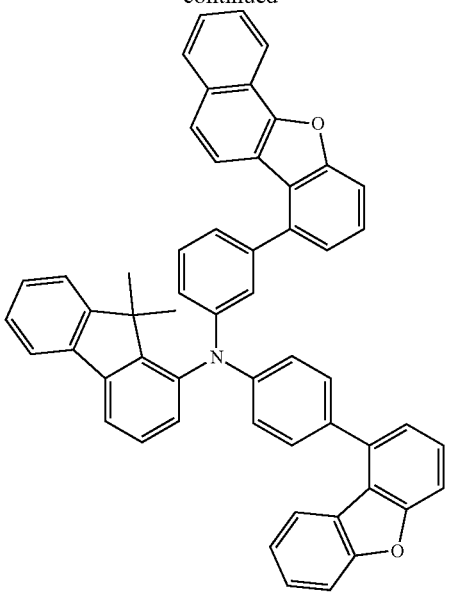

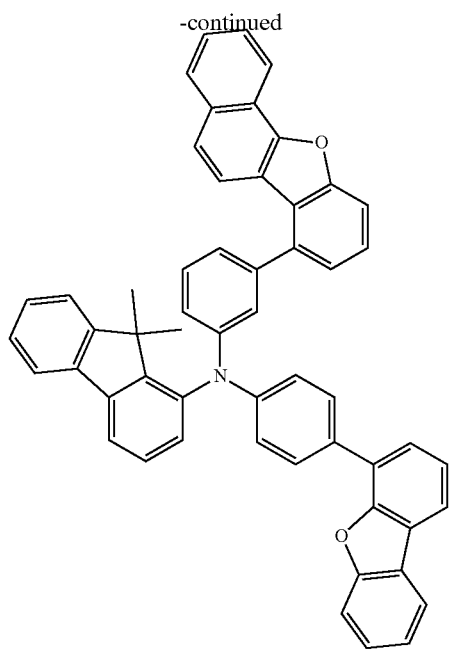
[Chem. 287]
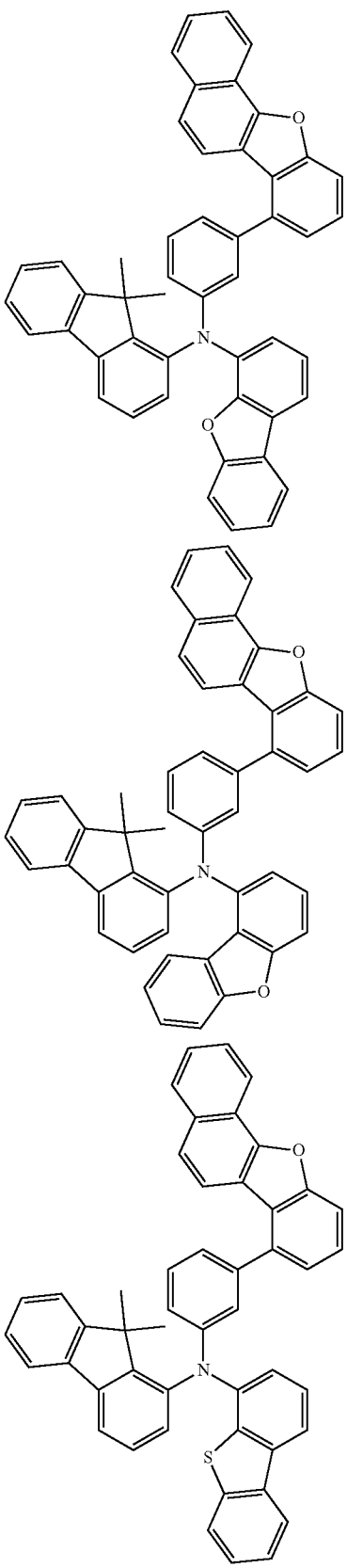

855
-continued
856
-continued
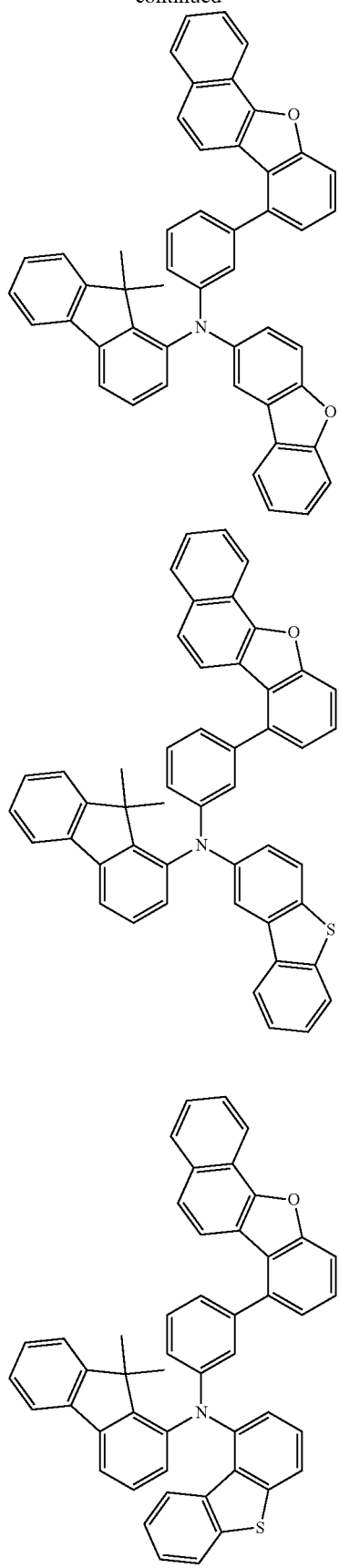
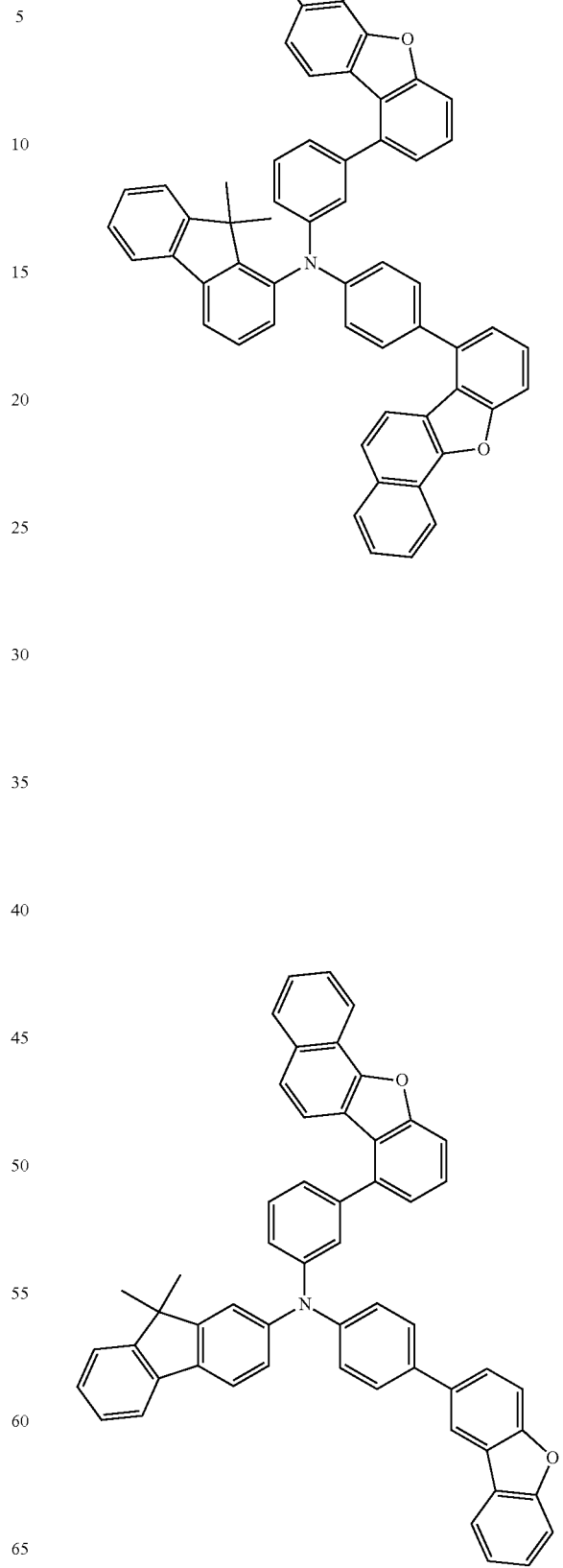

857
-continued
858
-continued
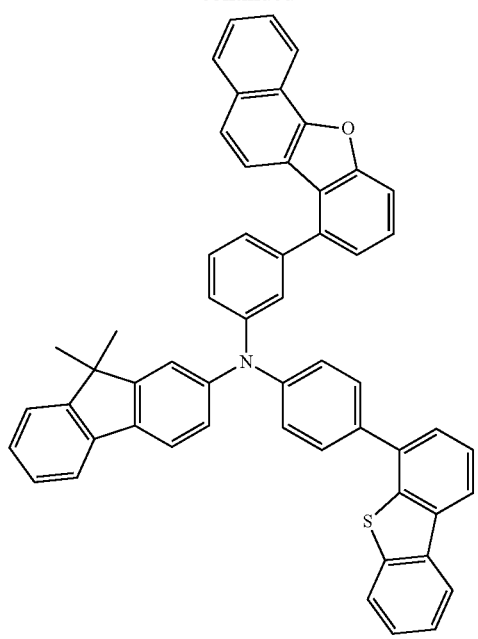
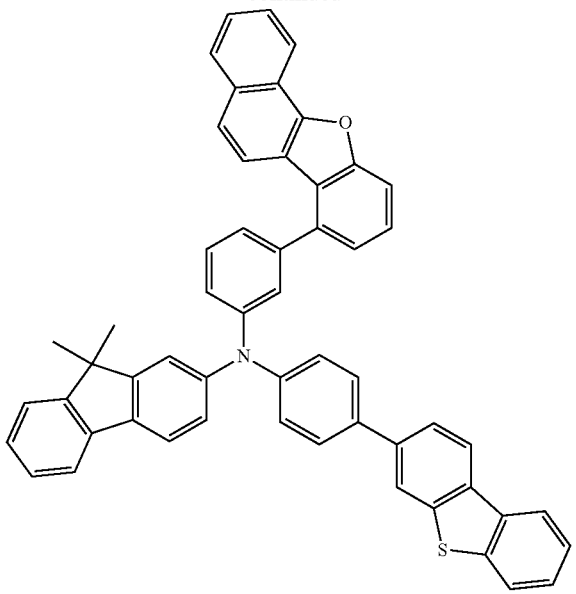
[Chem. 288]
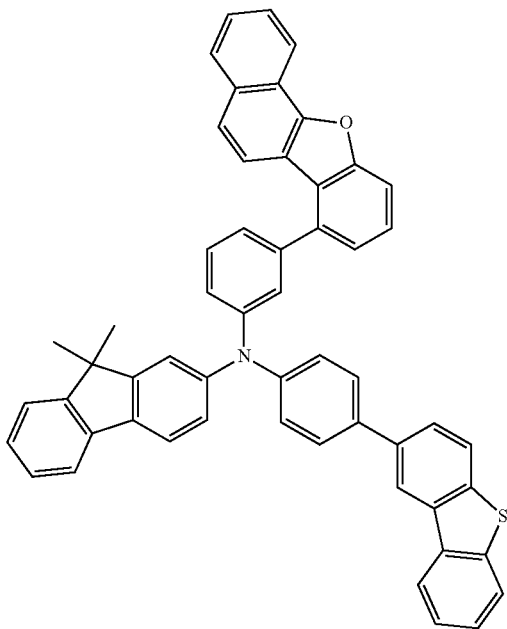

859
-continued
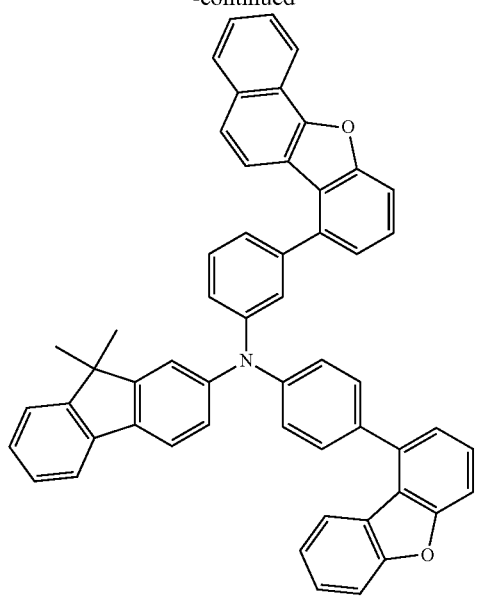
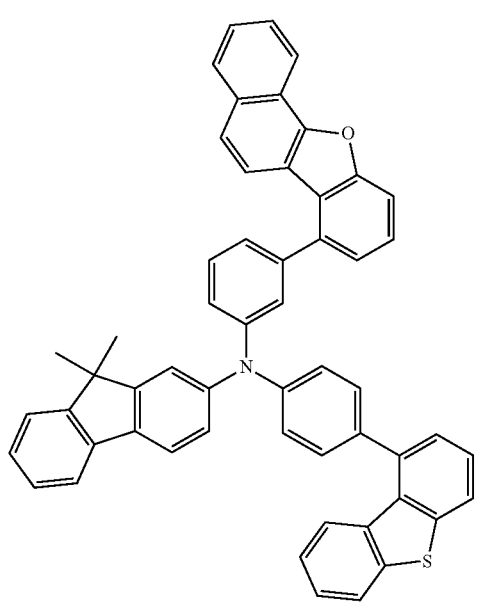
860
-continued
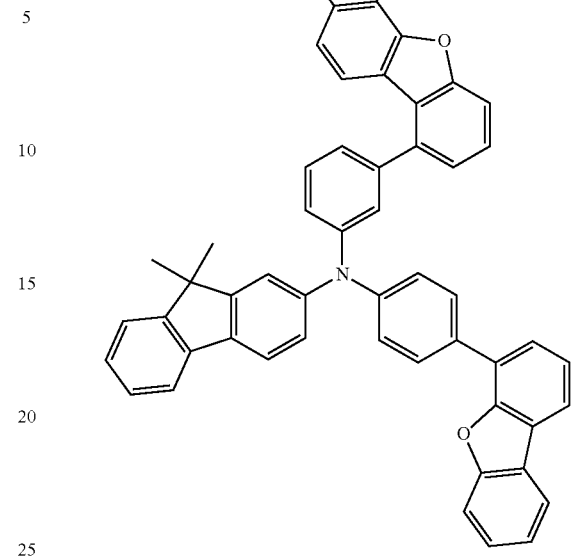
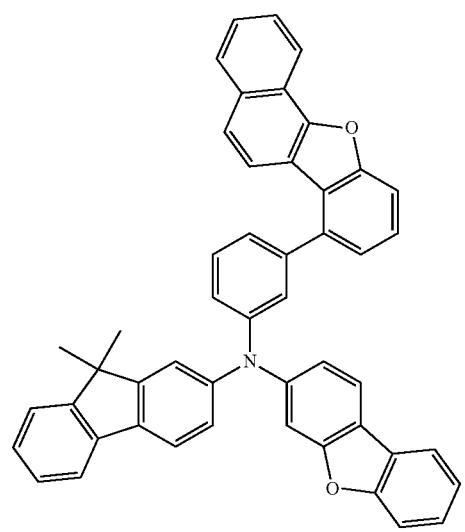
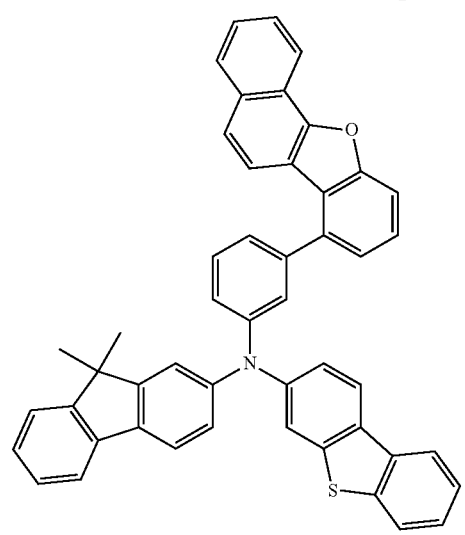

861
-continued
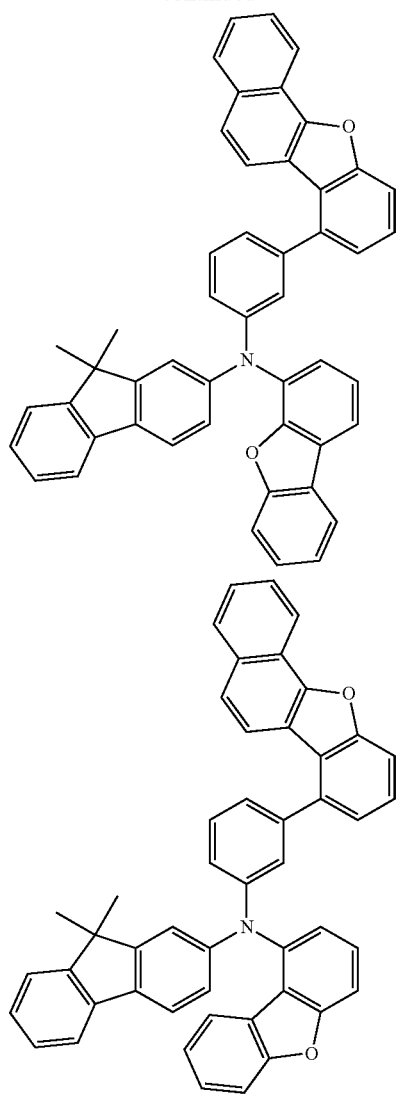
[Chem. 289]
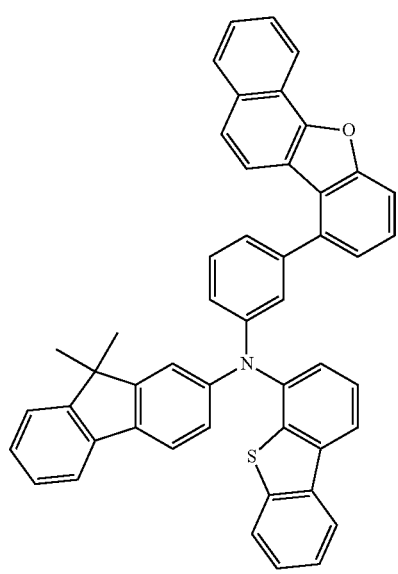
862
-continued
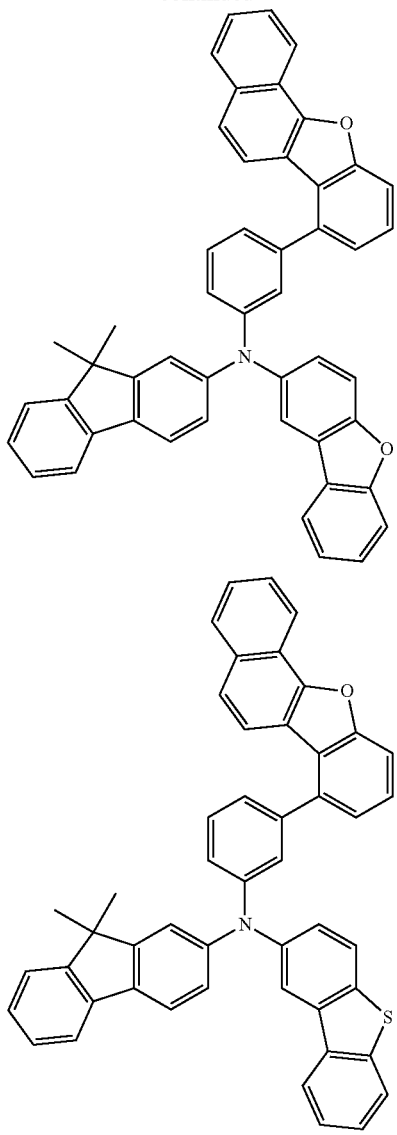

863
-continued
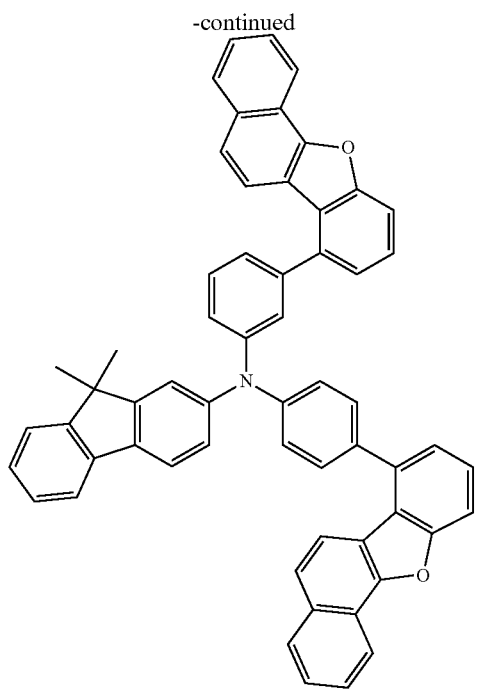
864
-continued
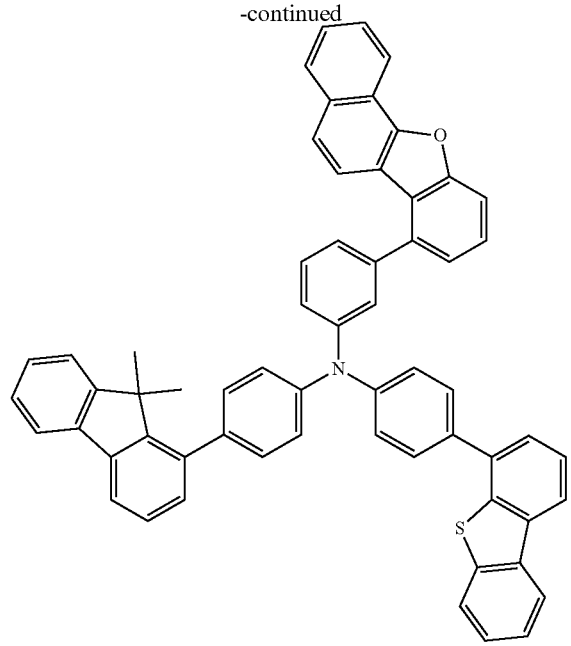
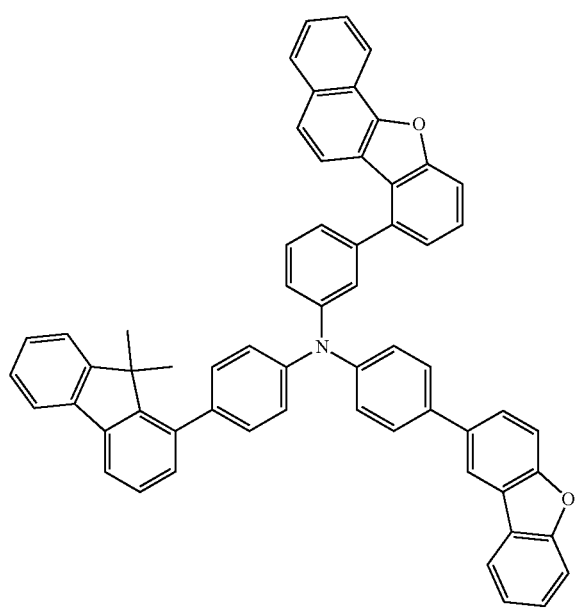
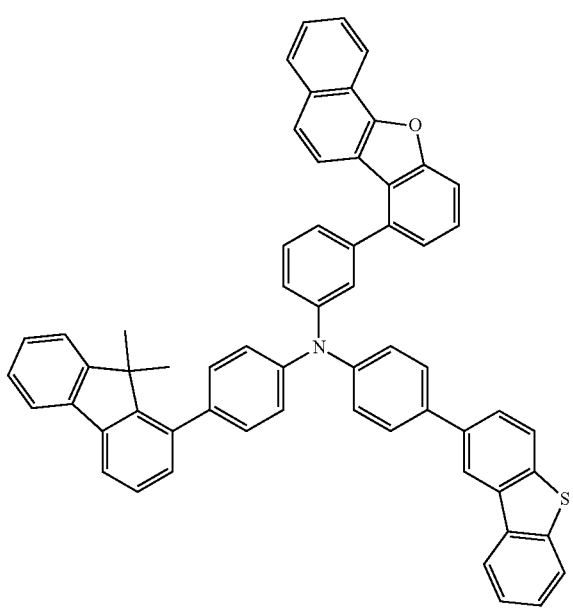

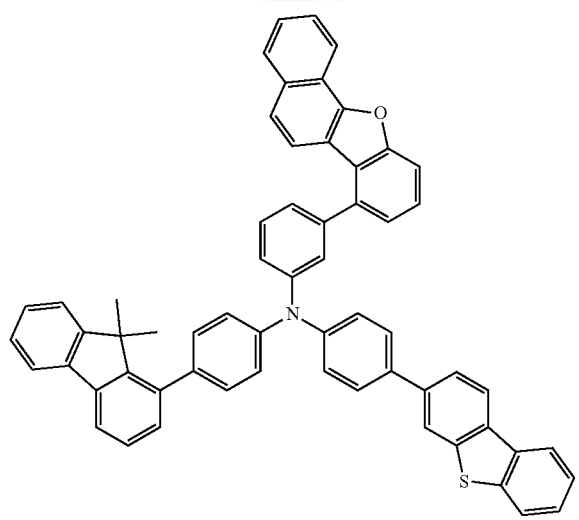
[Chem. 290]
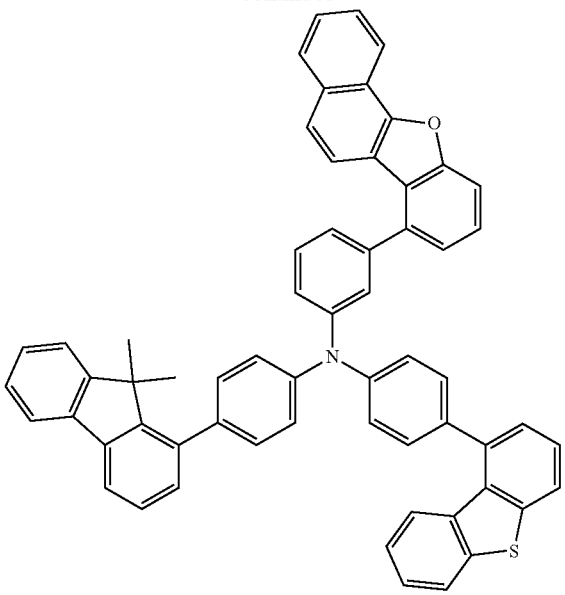
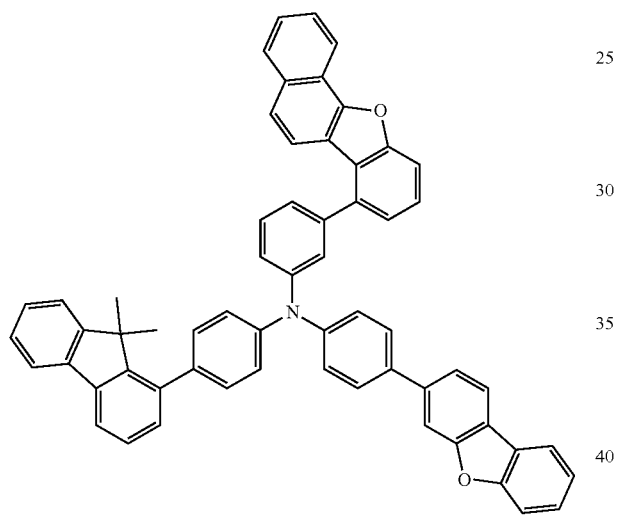
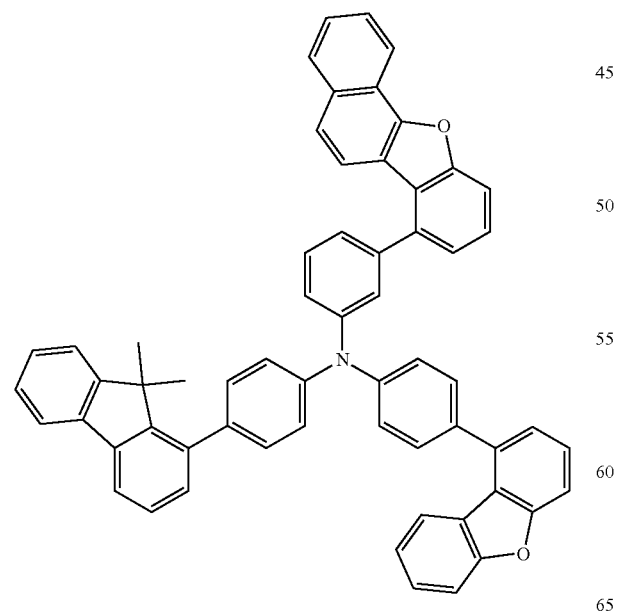
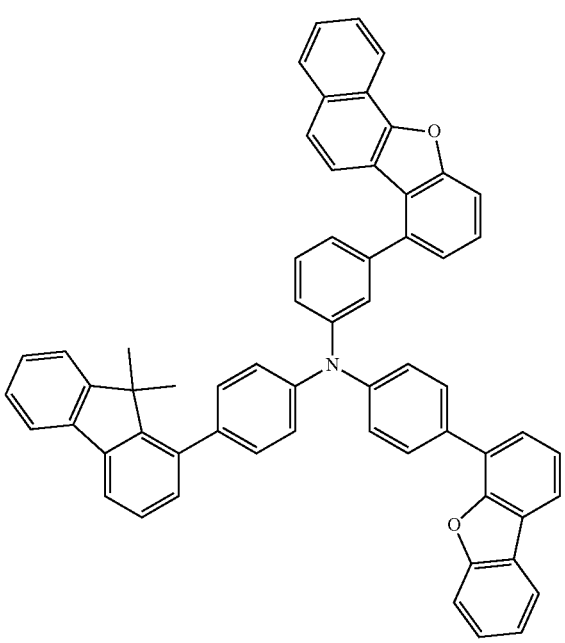

867
-continued

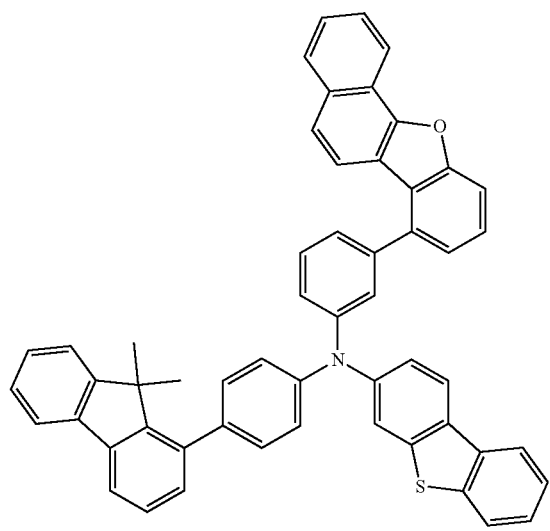
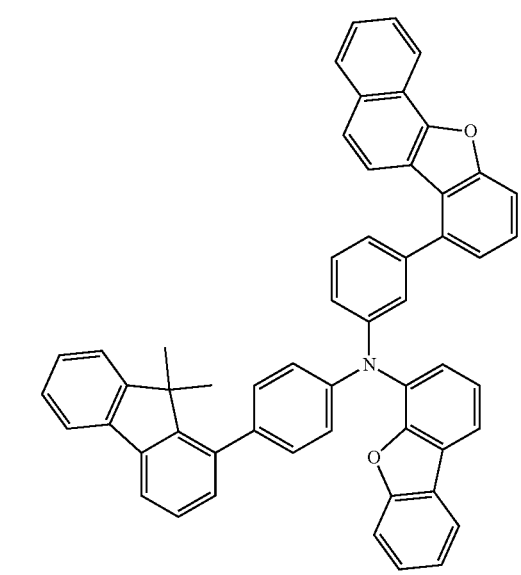
868
-continued
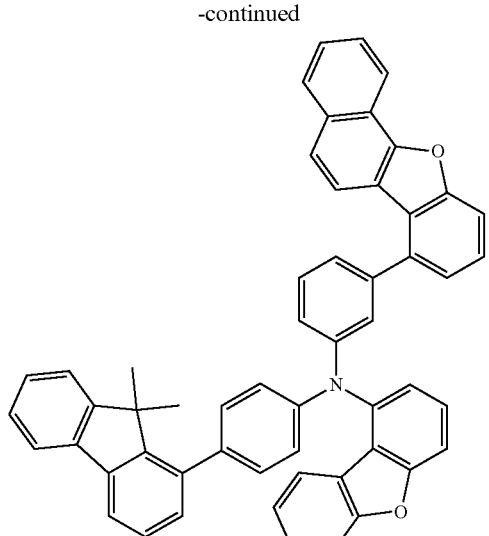
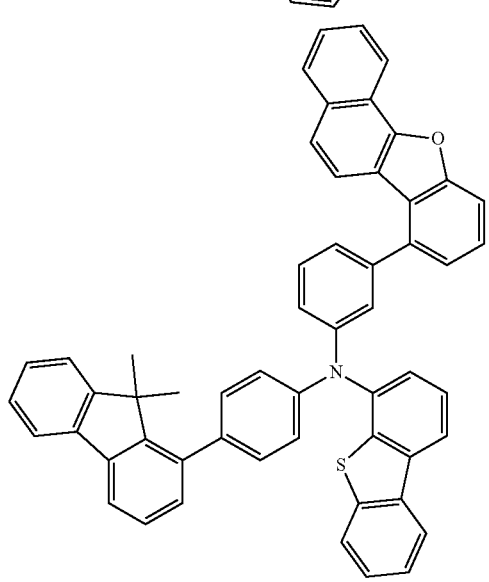
[Chem. 291]
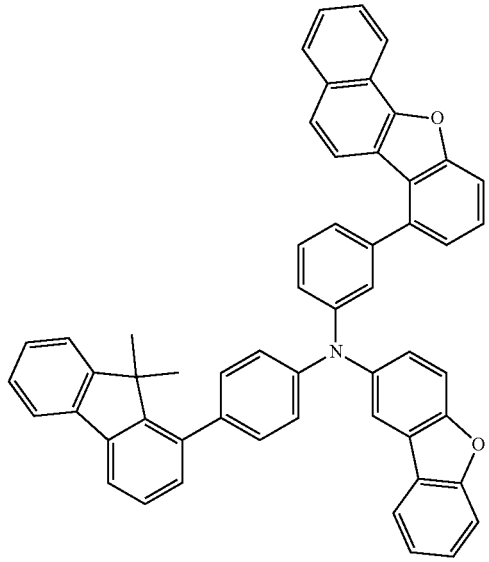

-continued
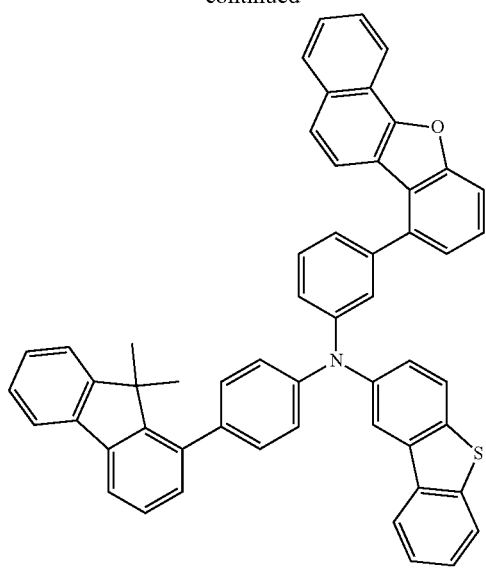
-continued
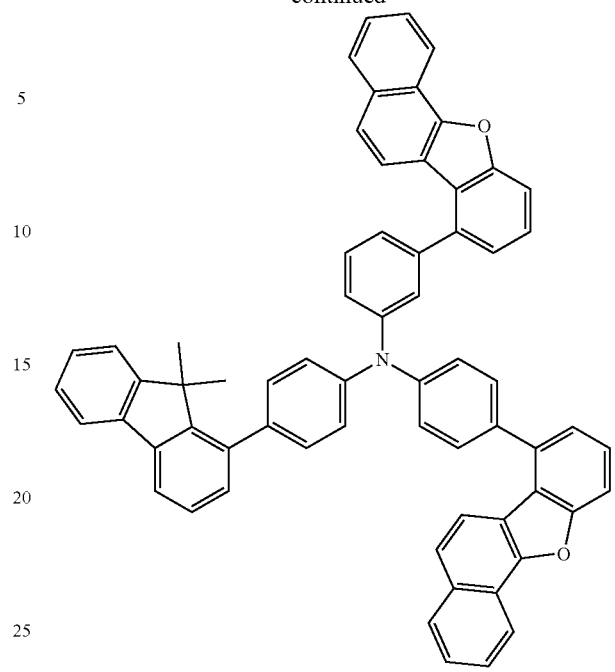
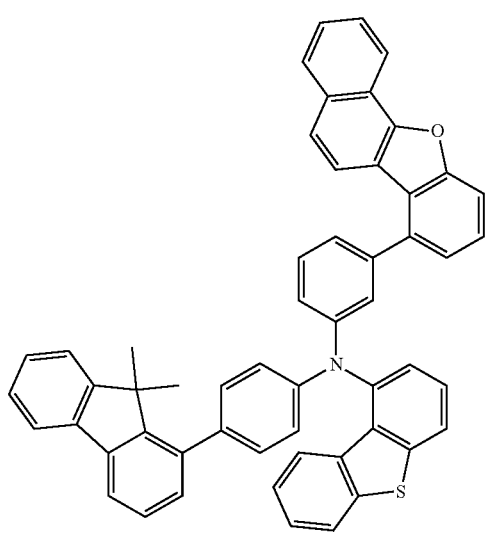
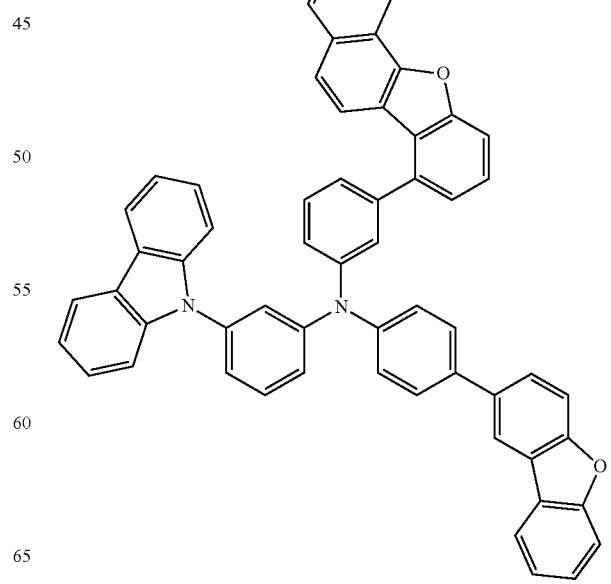

871
-continued
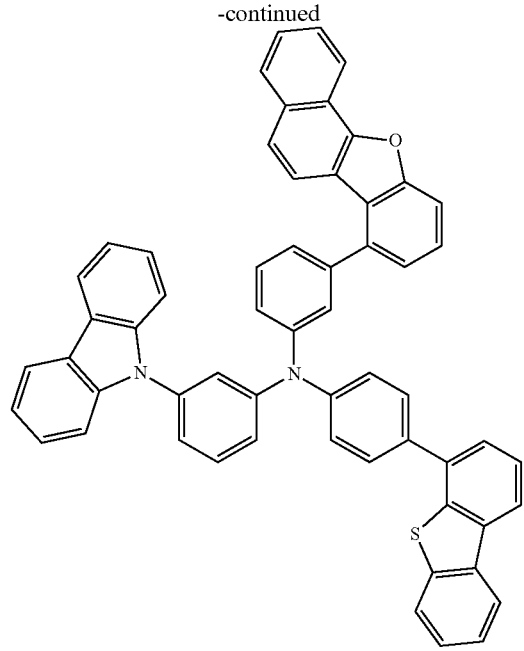
872
-continued
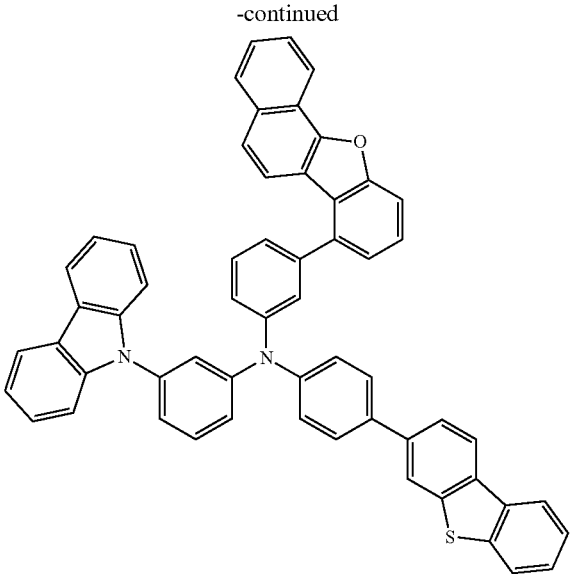
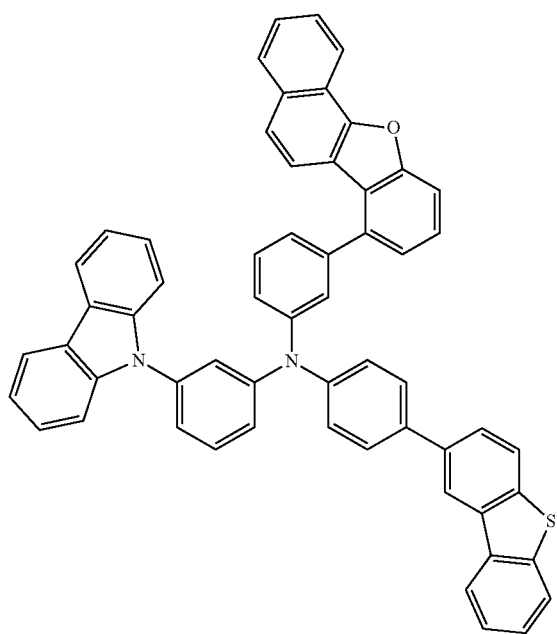
[Chem. 292]
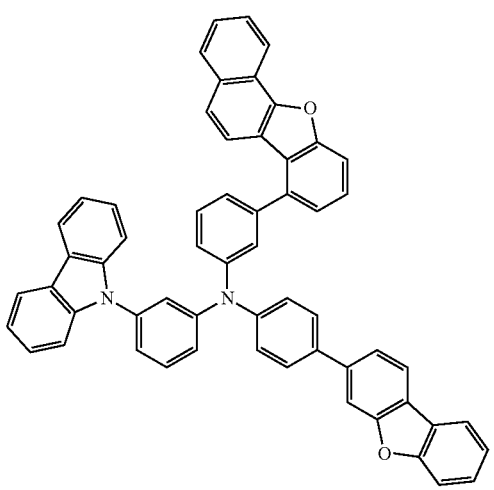

873
-continued
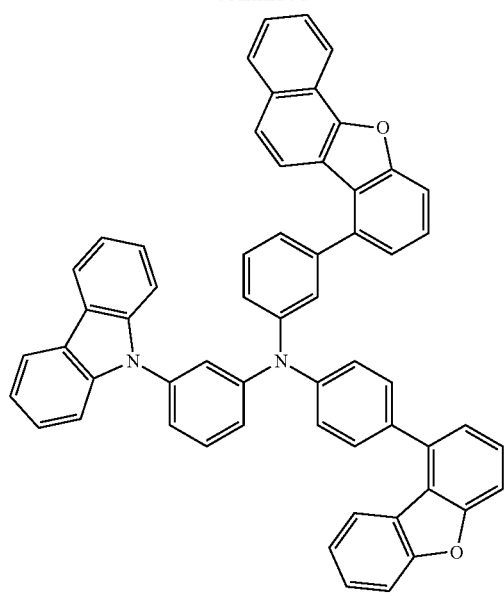
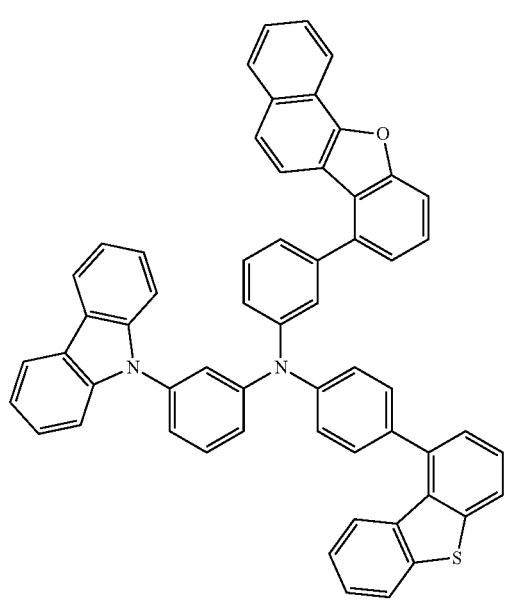
874
-continued
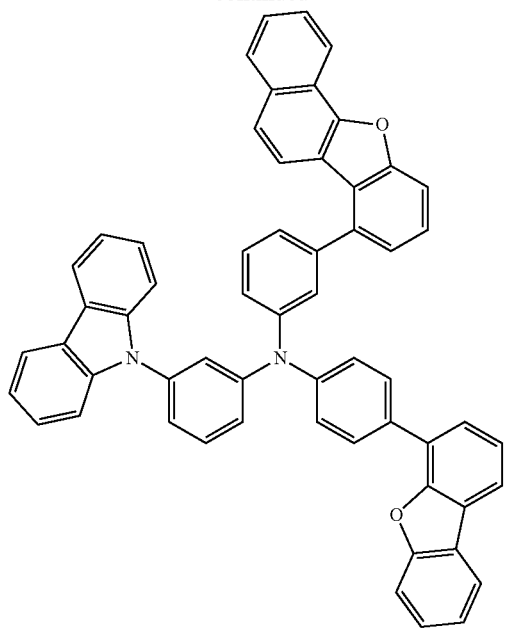
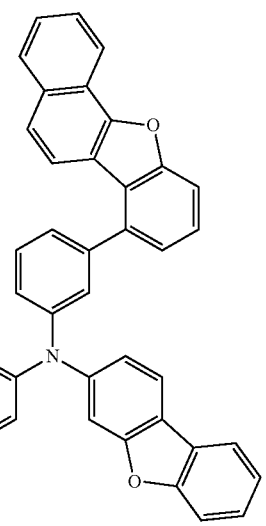
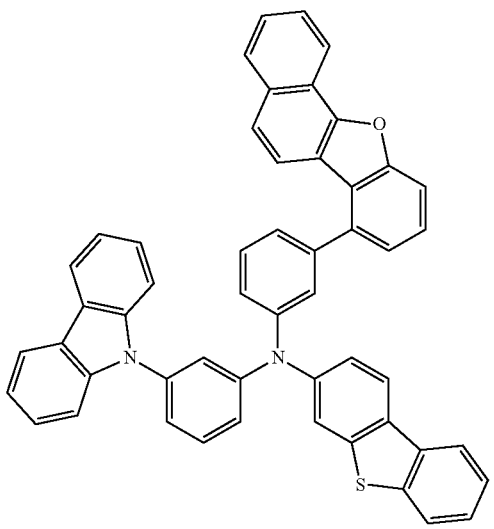

875
-continued
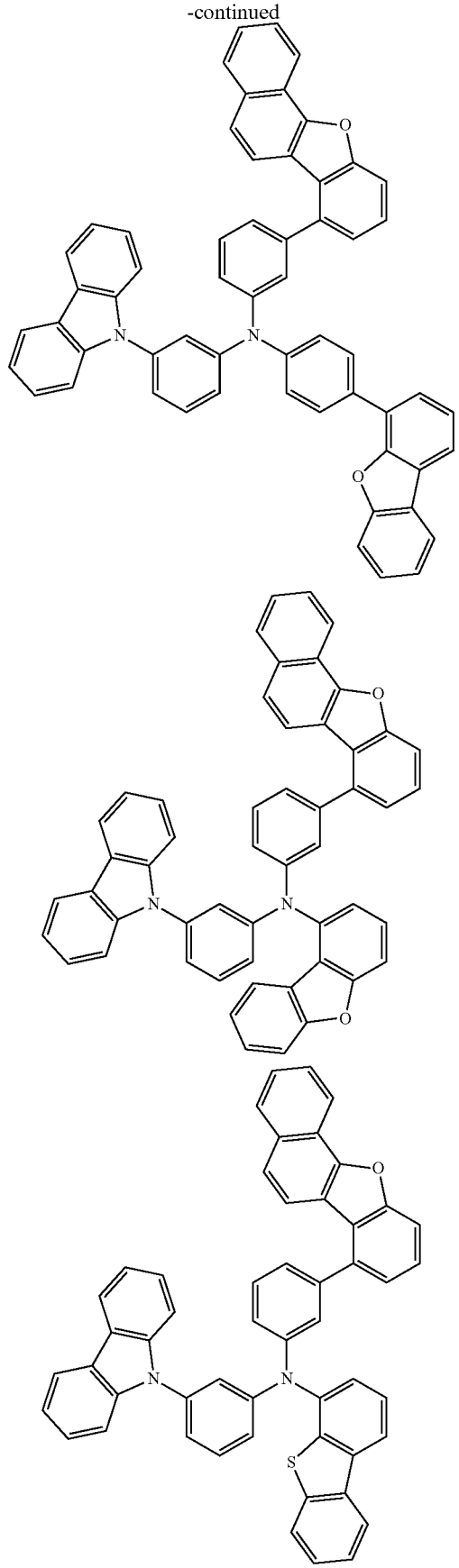
876
-continued
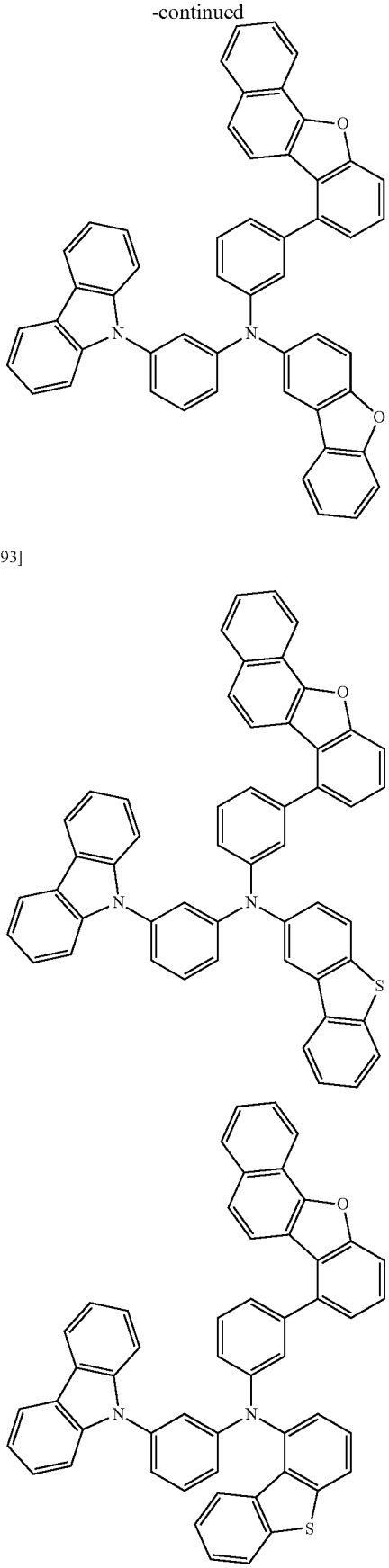
[Chem. 293]

877
-continued
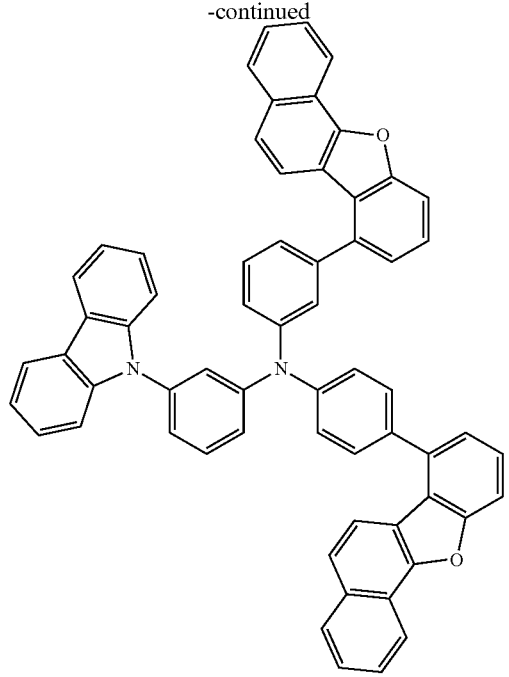
878
-continued
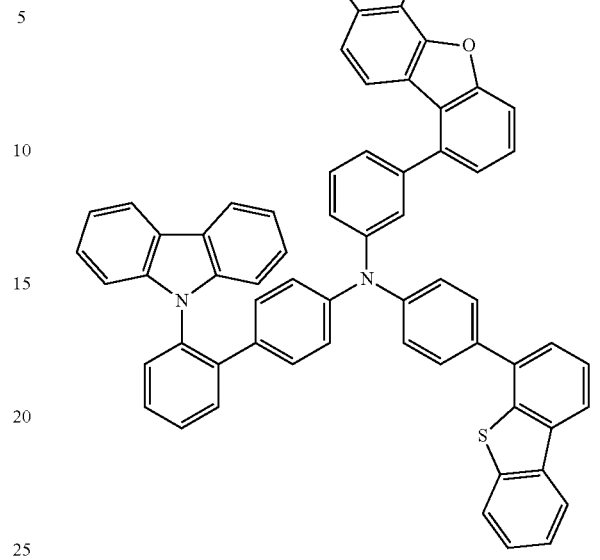
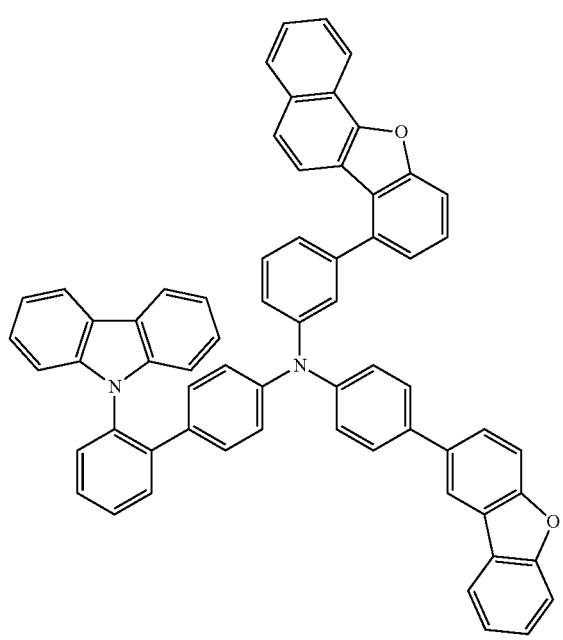
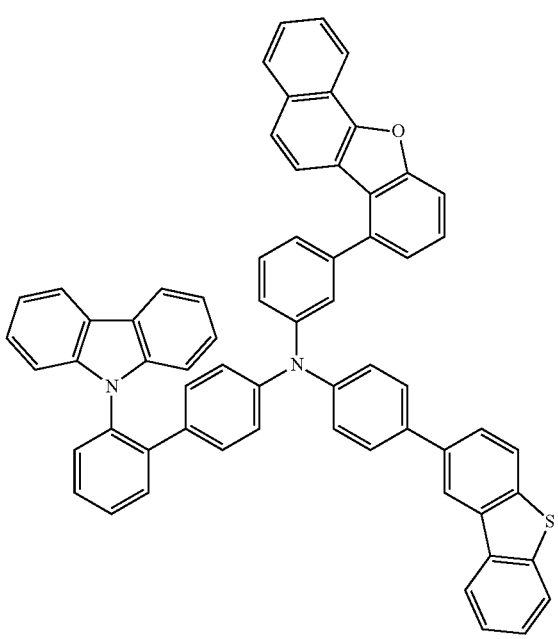

879
-continued
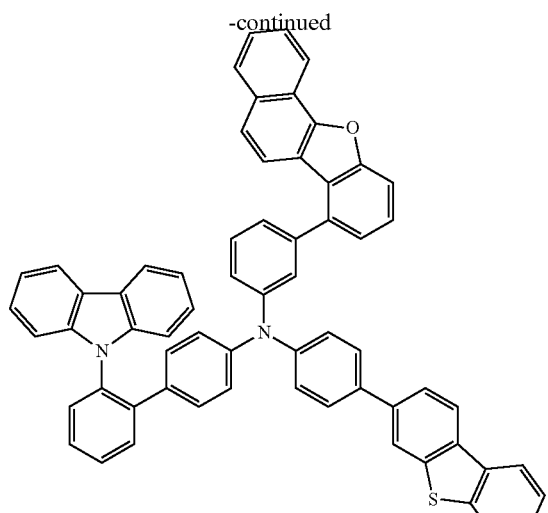
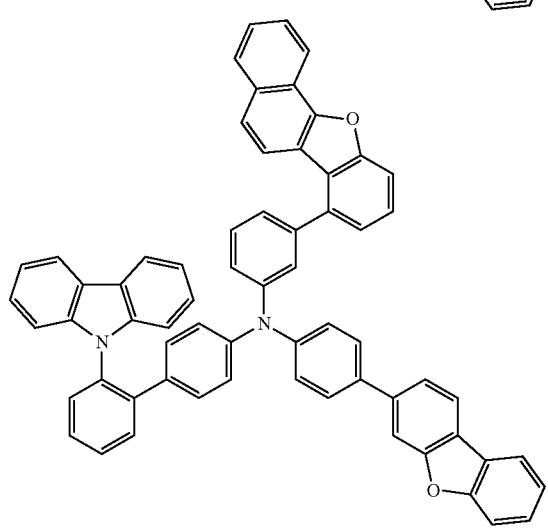
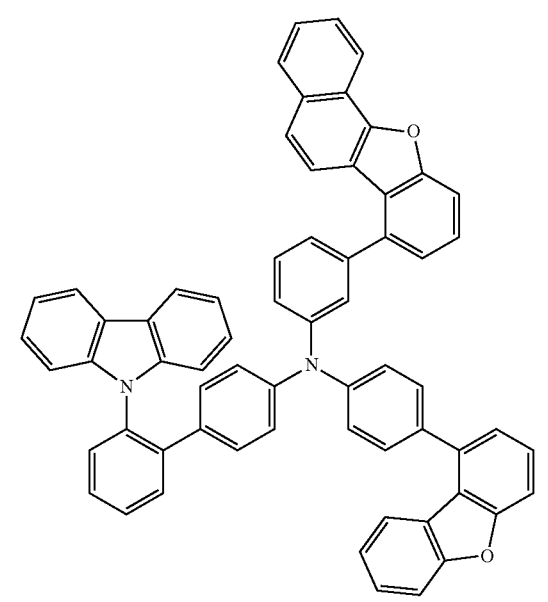
880
-continued
[Chem. 294]
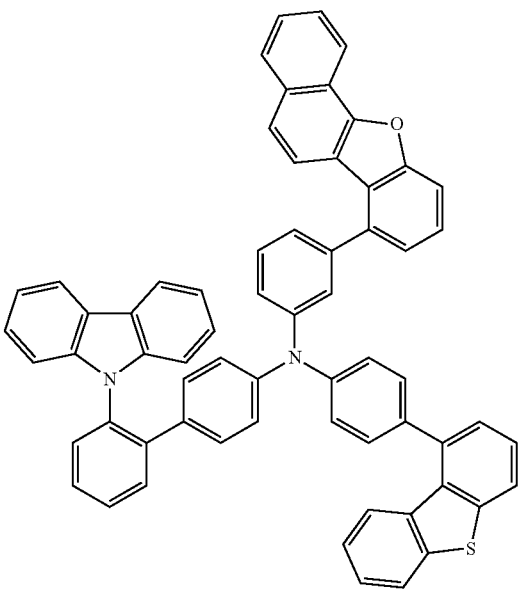
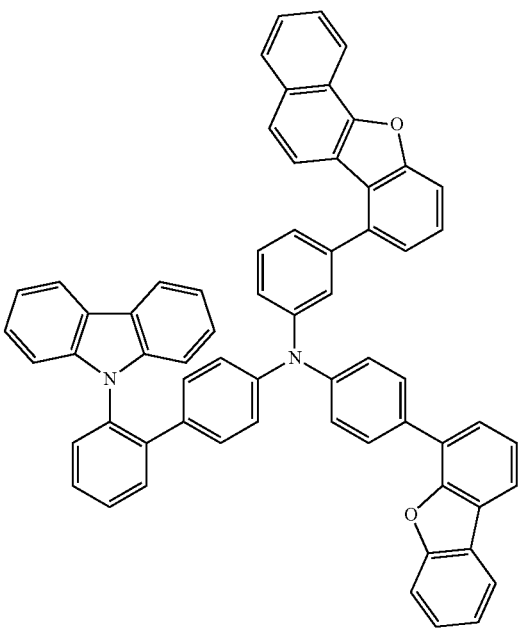

881
-continued
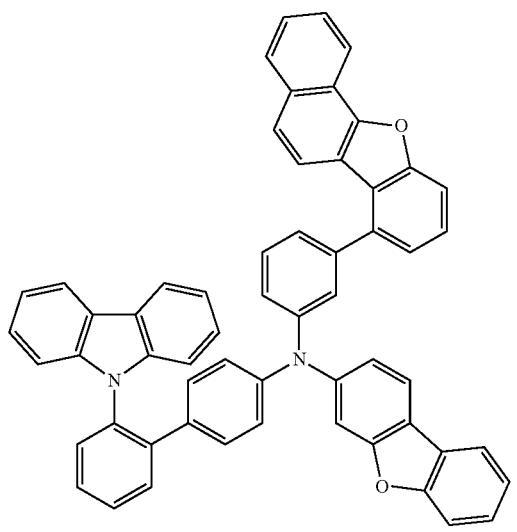
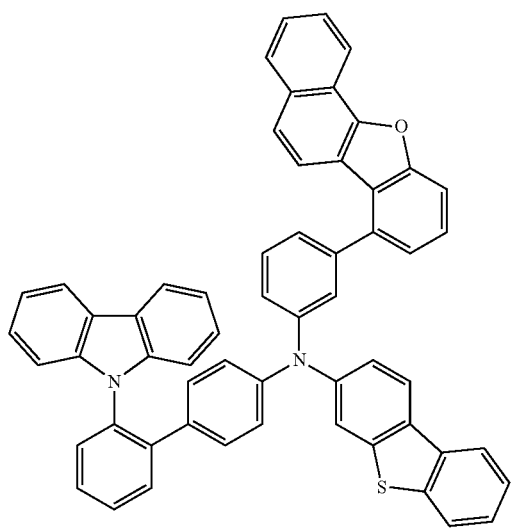
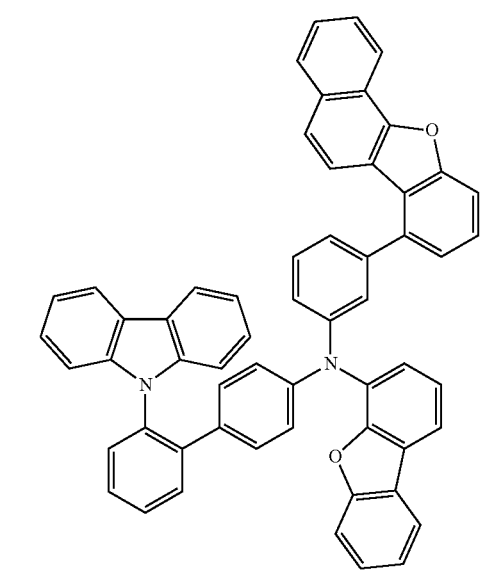
882
-continued
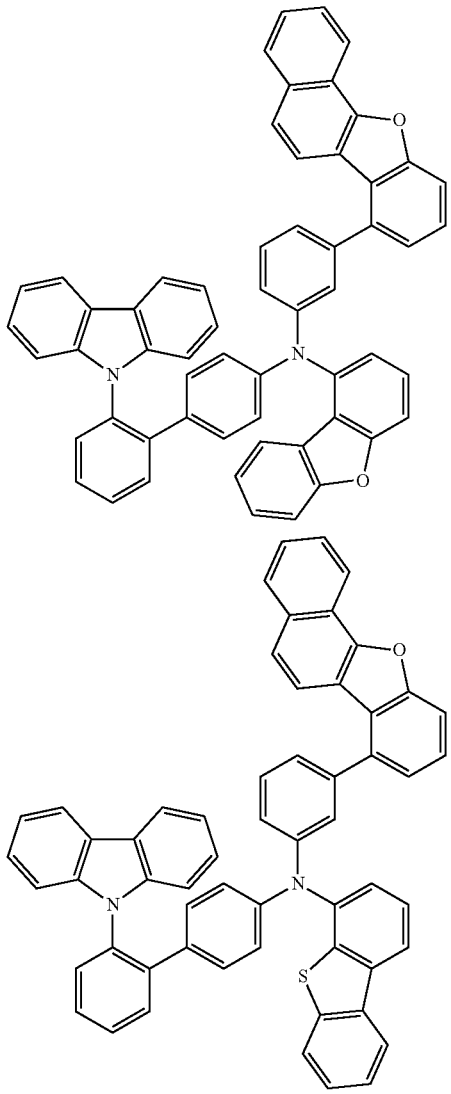
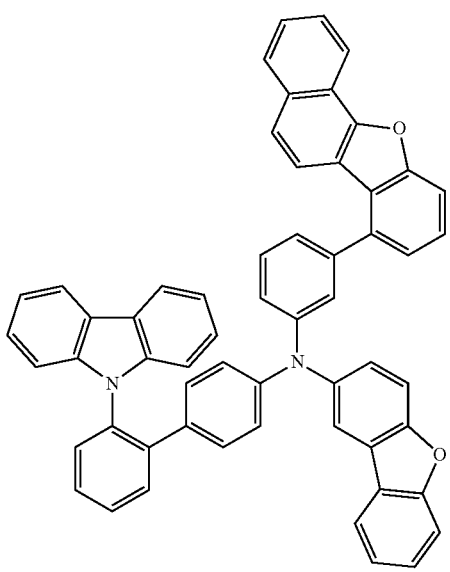

883
-continued
884
-continued
[Chem. 295]
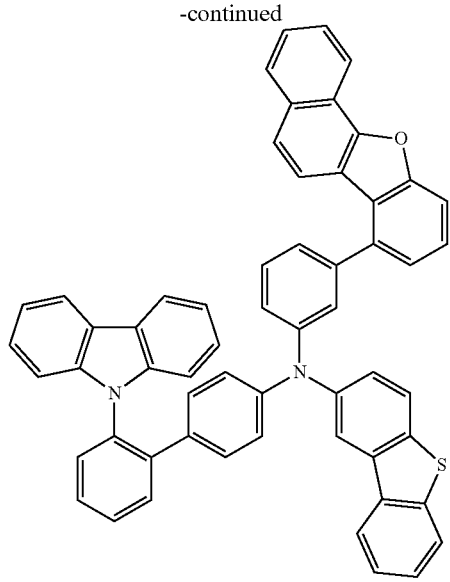
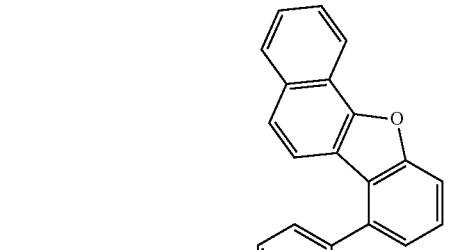
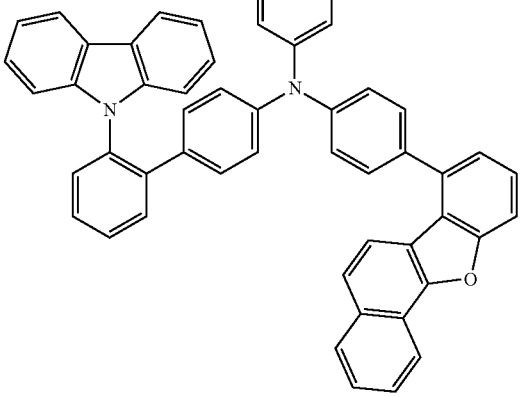
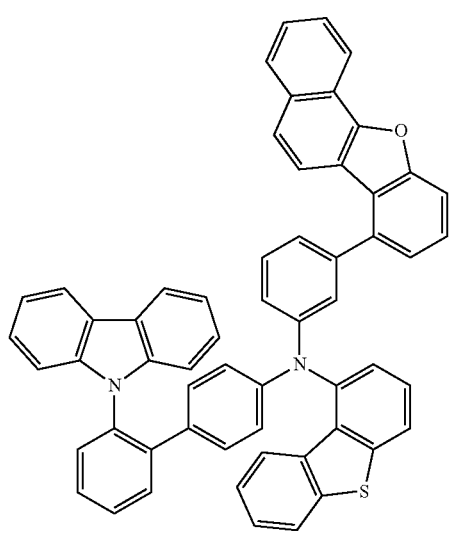
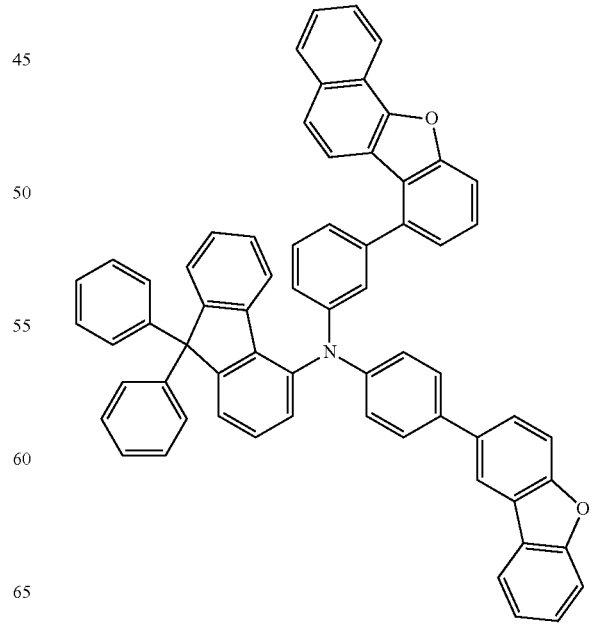

-continued
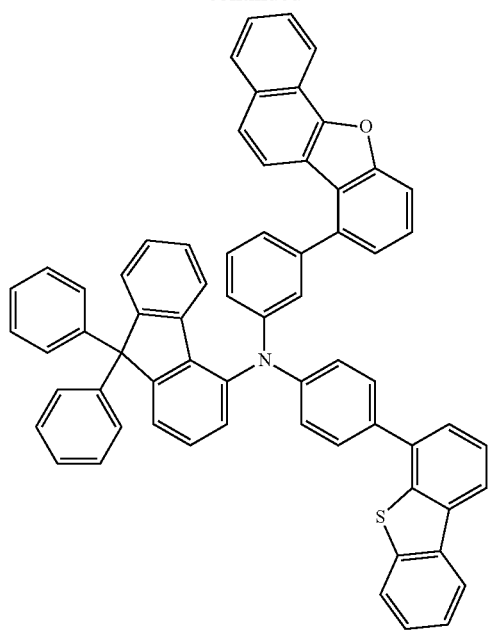
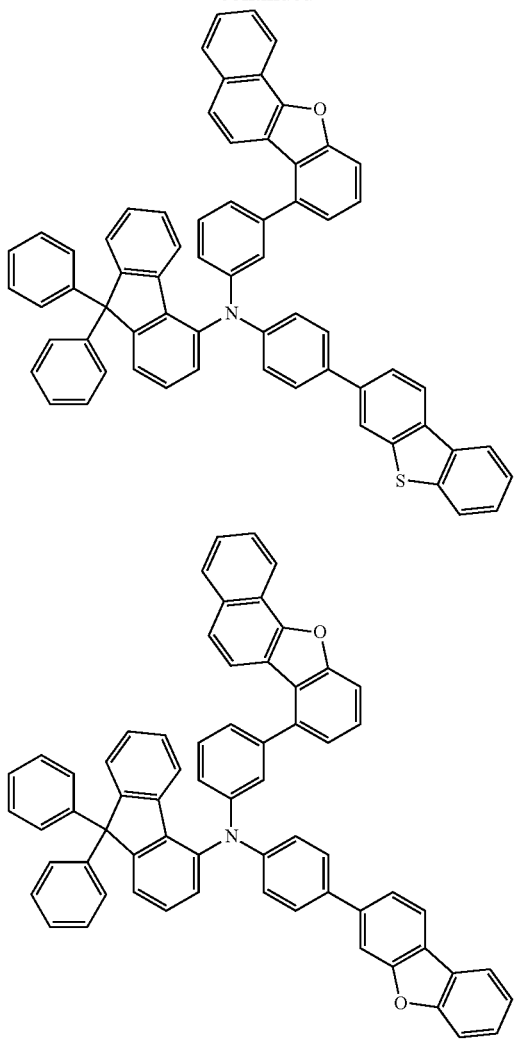
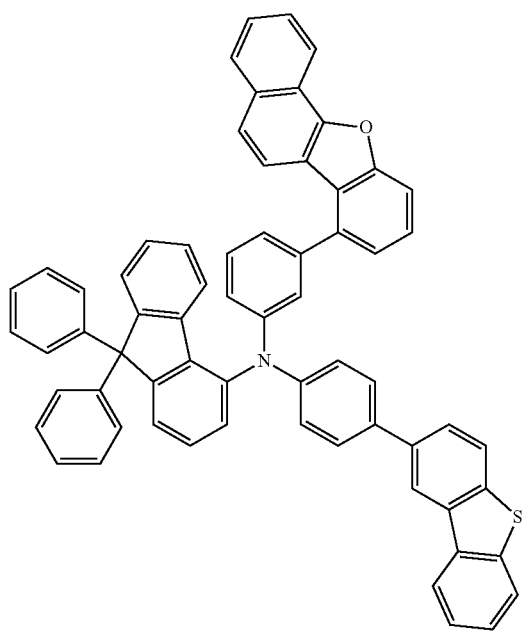

887
-continued
888
-continued
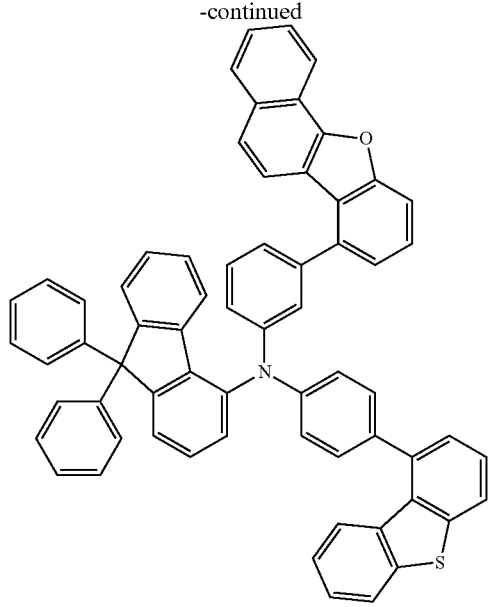
[Chem. 296]
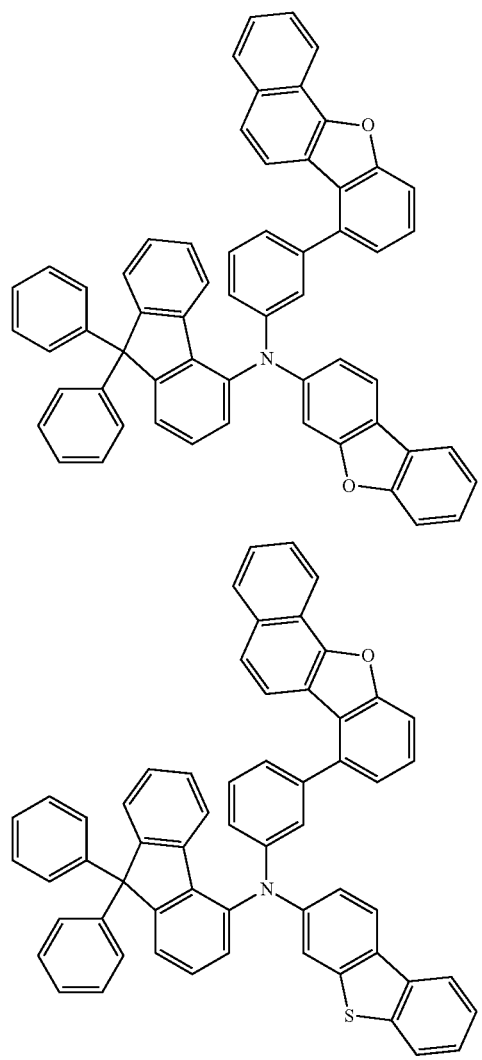
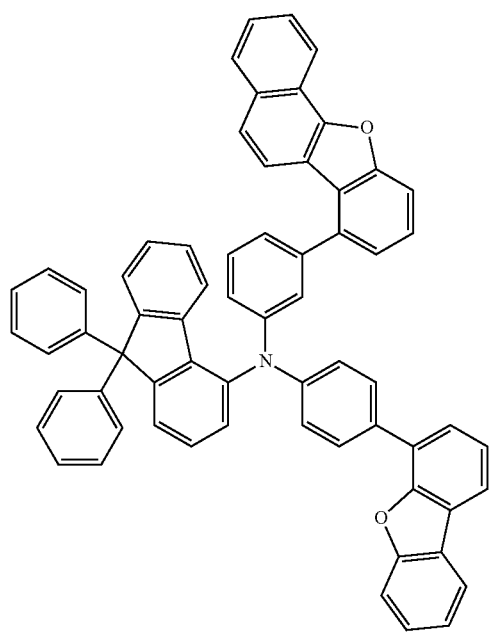

889
-continued
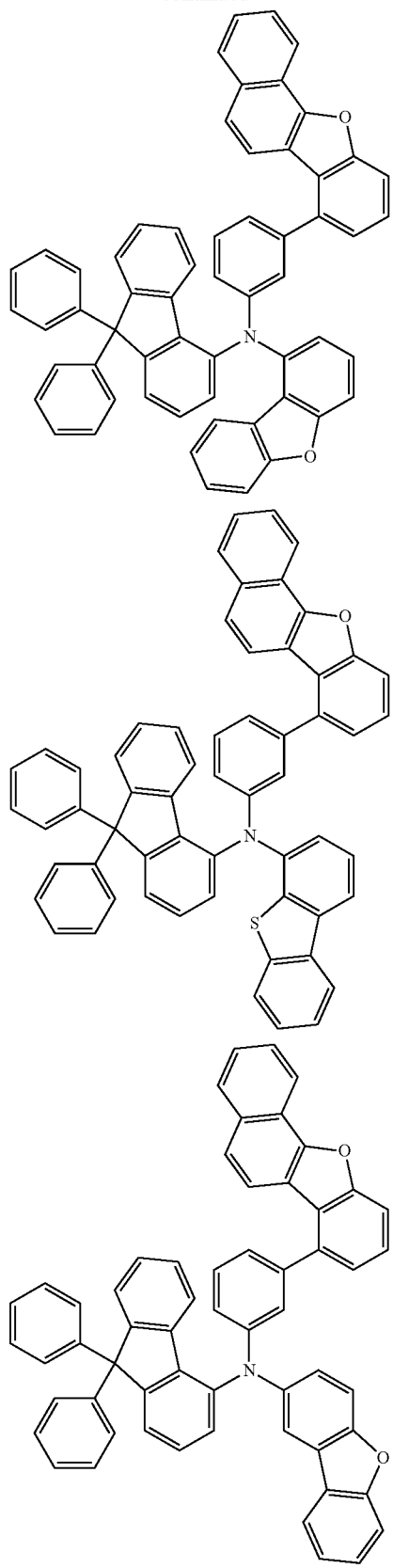
890
-continued

891
-continued
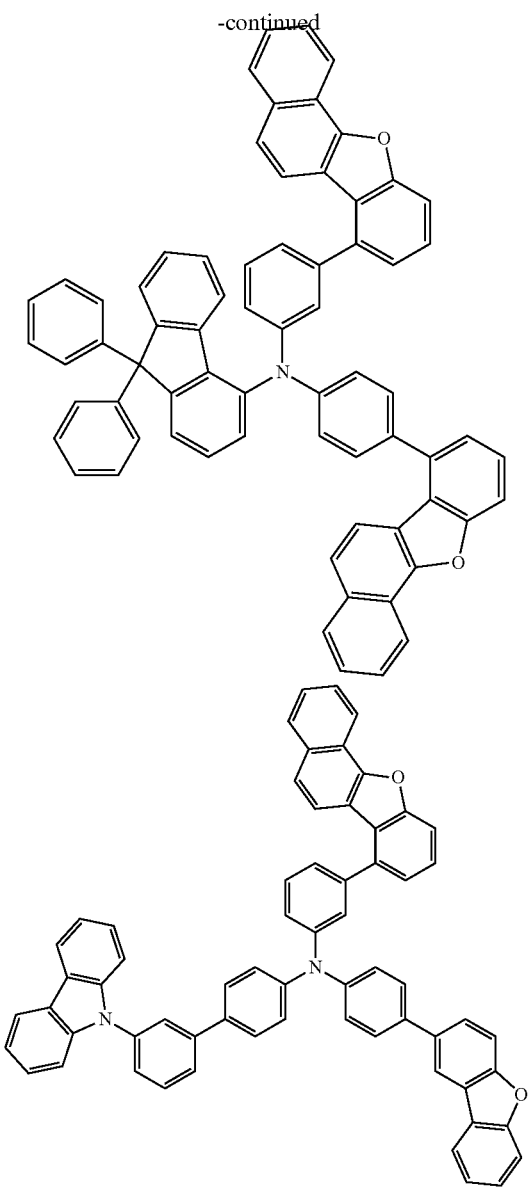
[Chem. 297]
892
-continued
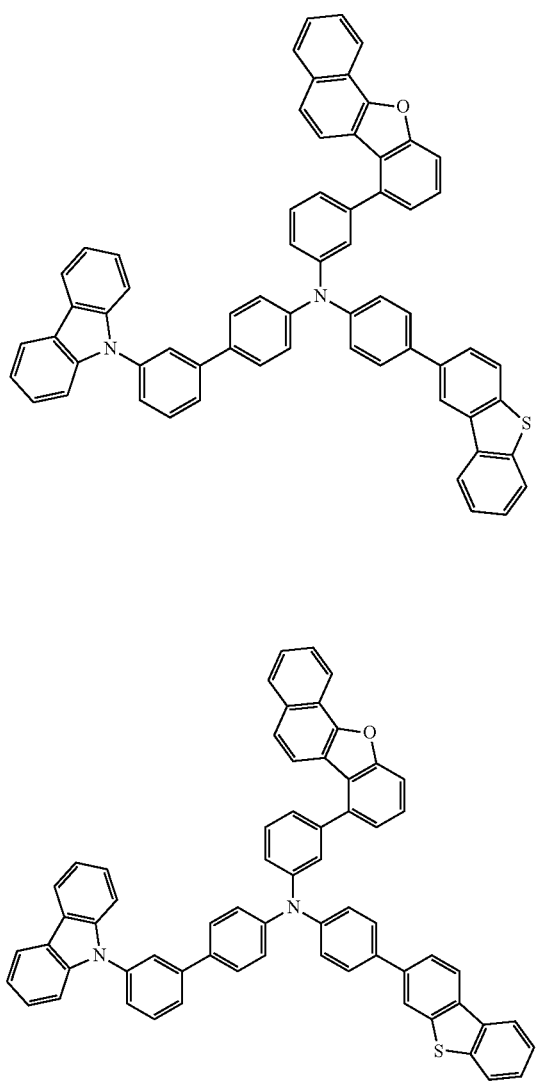
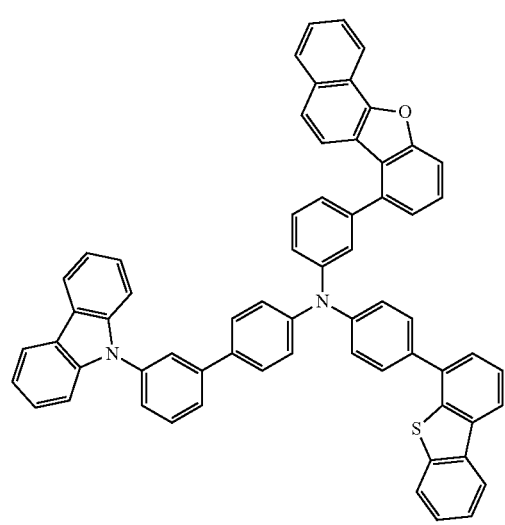

893
-continued
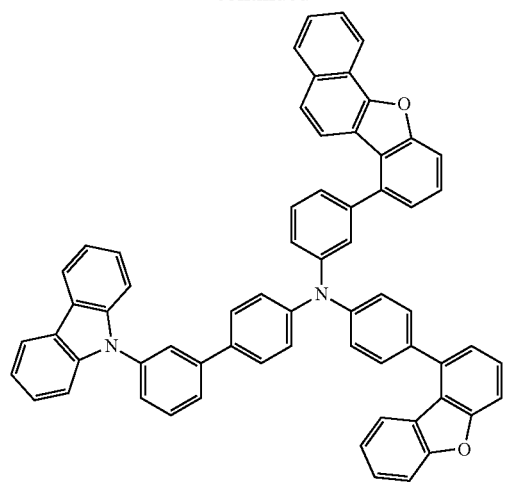
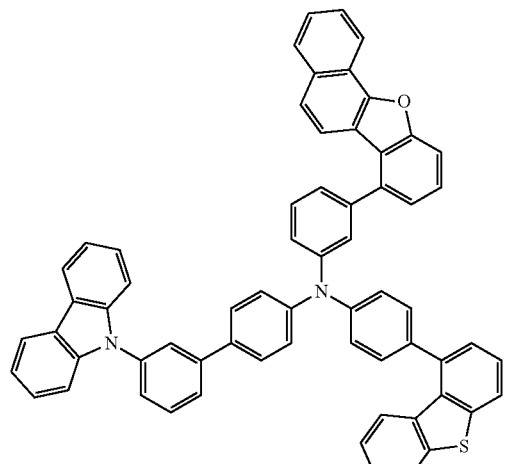
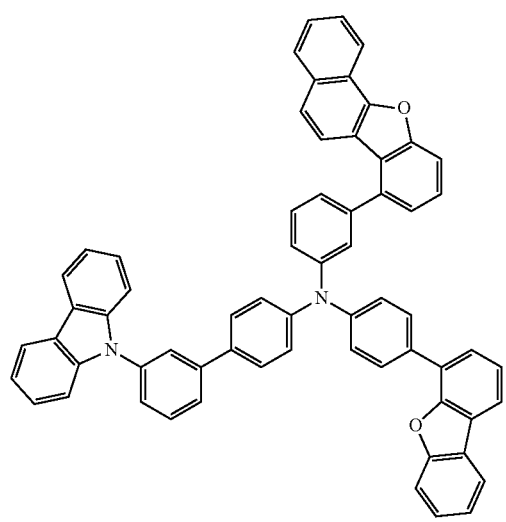
894
-continued
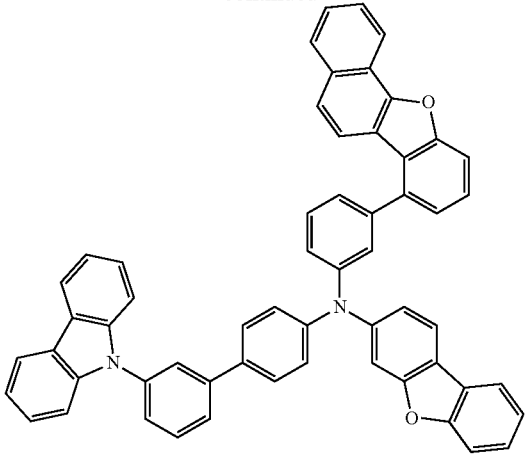
[Chem. 298]
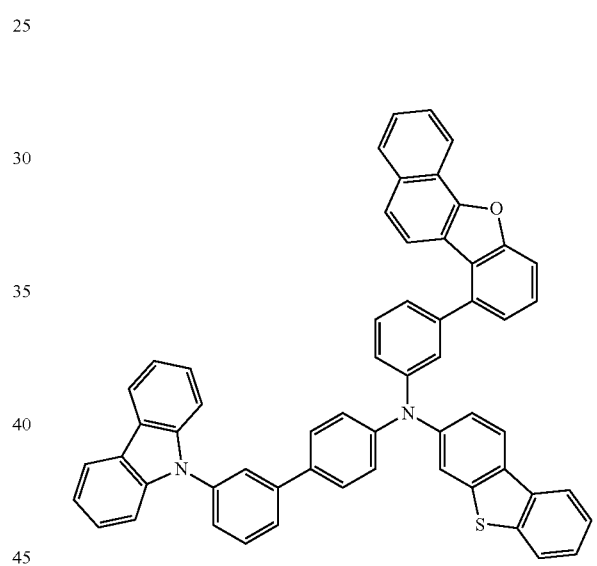
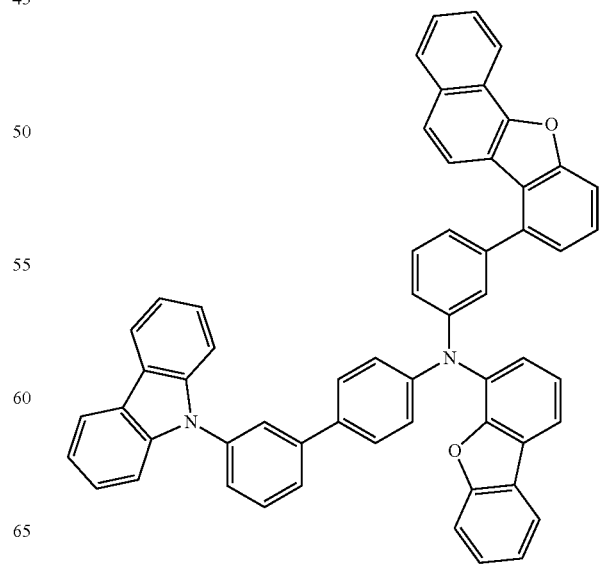

895
-continued
896
-continued
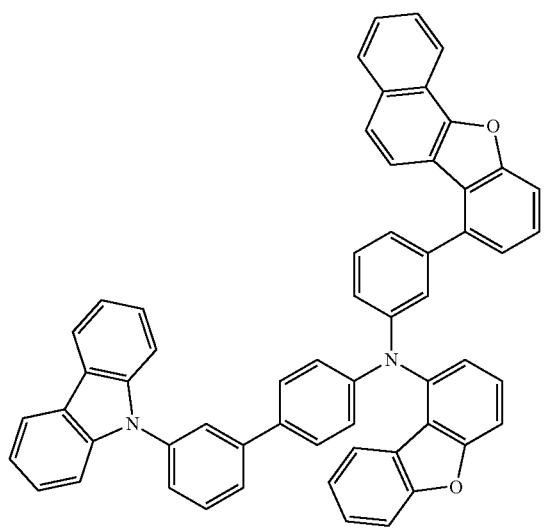
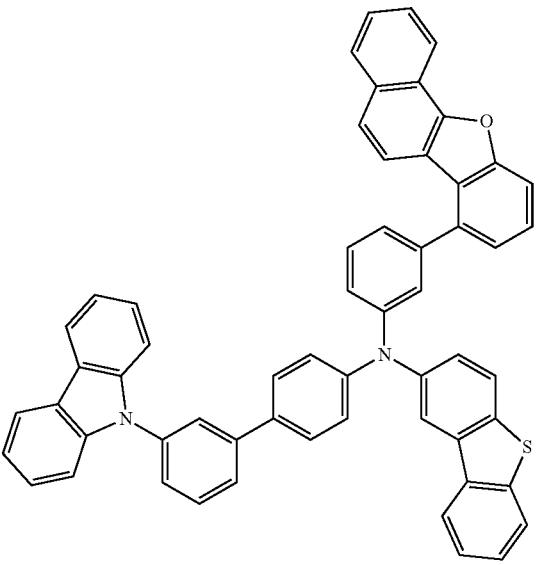

-continued
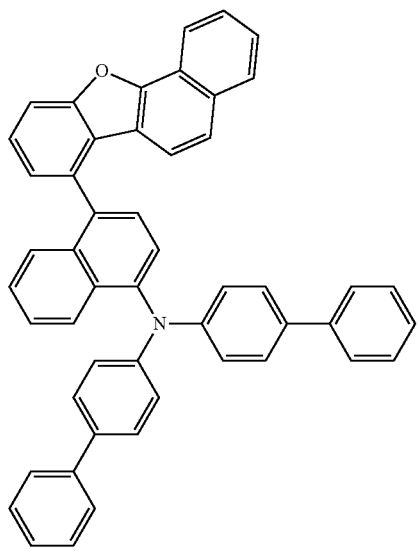
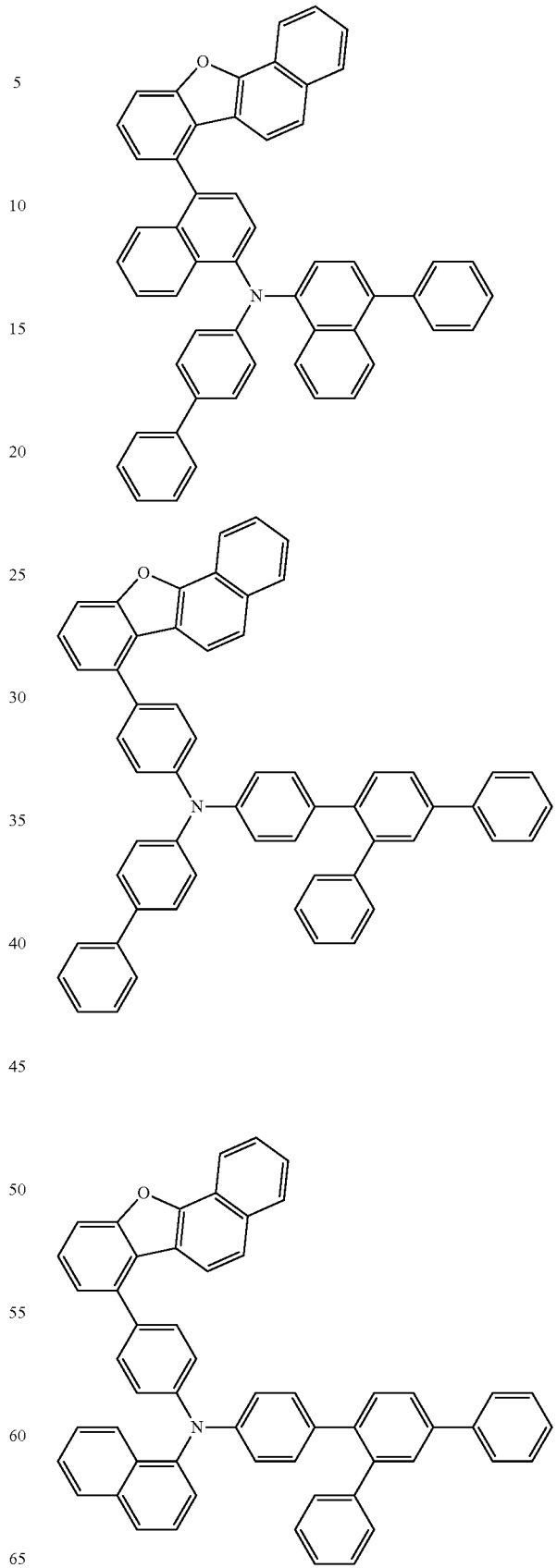

899
-continued
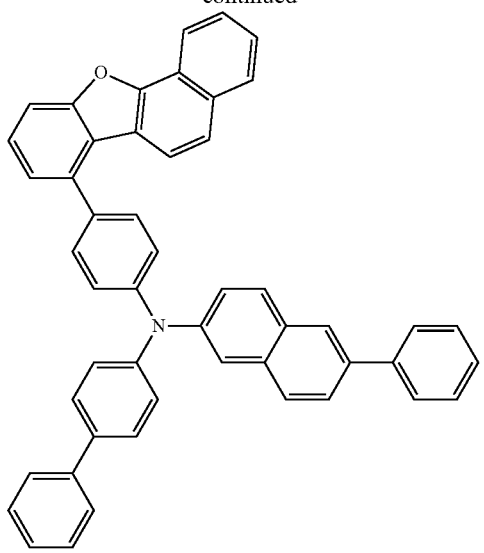
[Chem. 300]
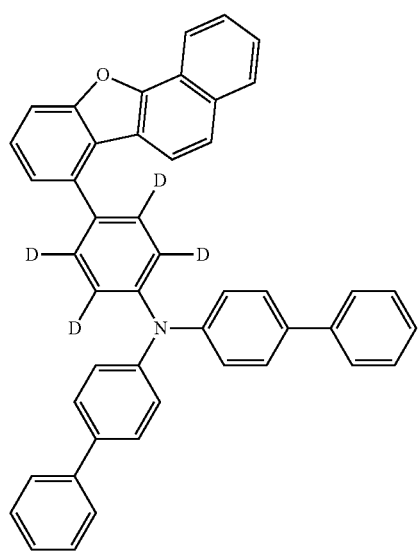
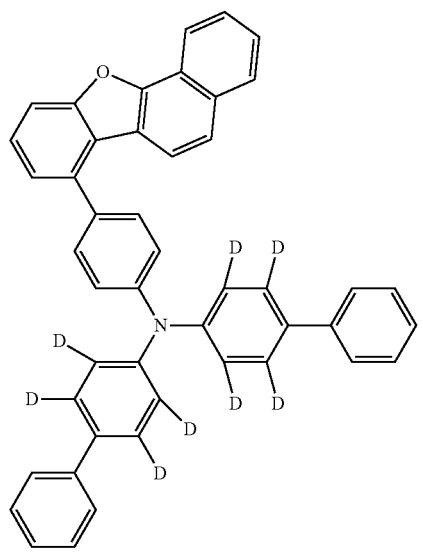
900
-continued
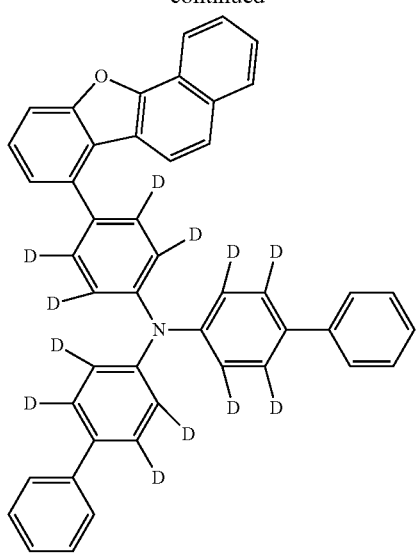
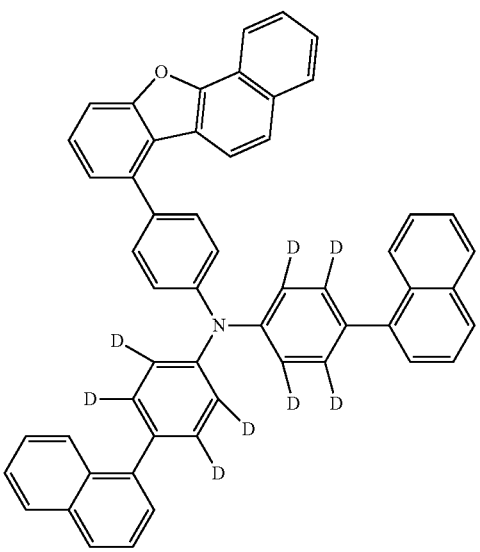
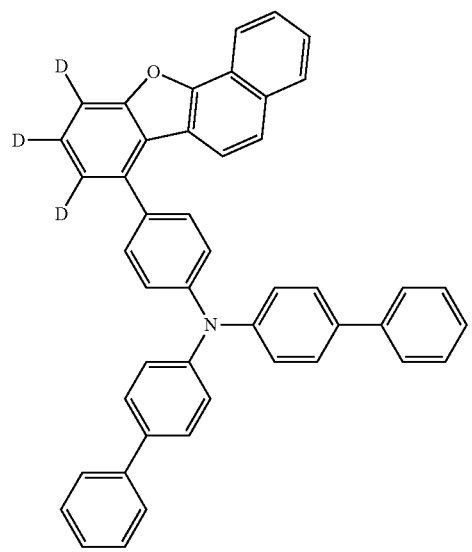

901
-continued
902
-continued
[Chem. 301]
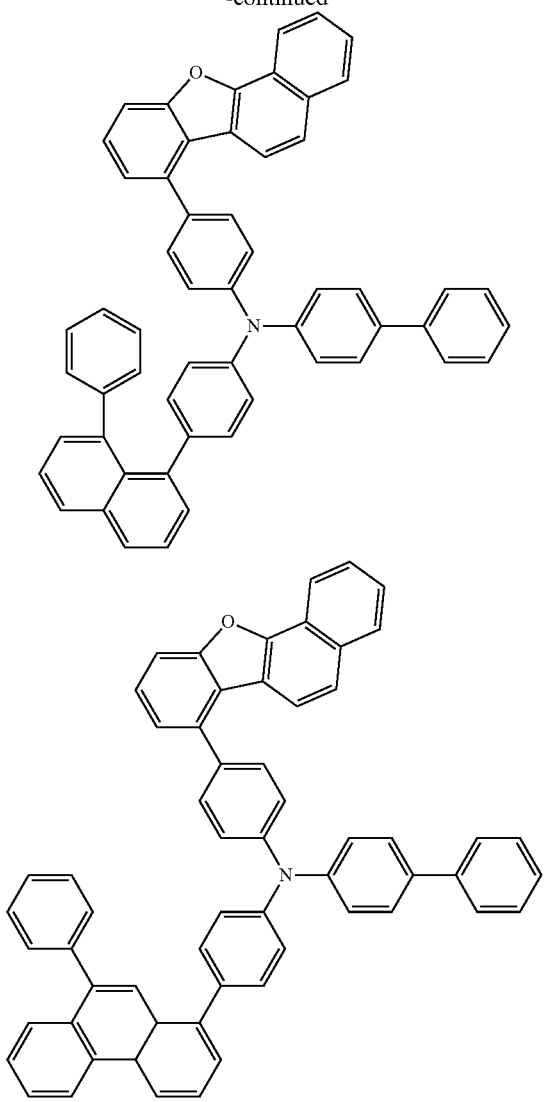
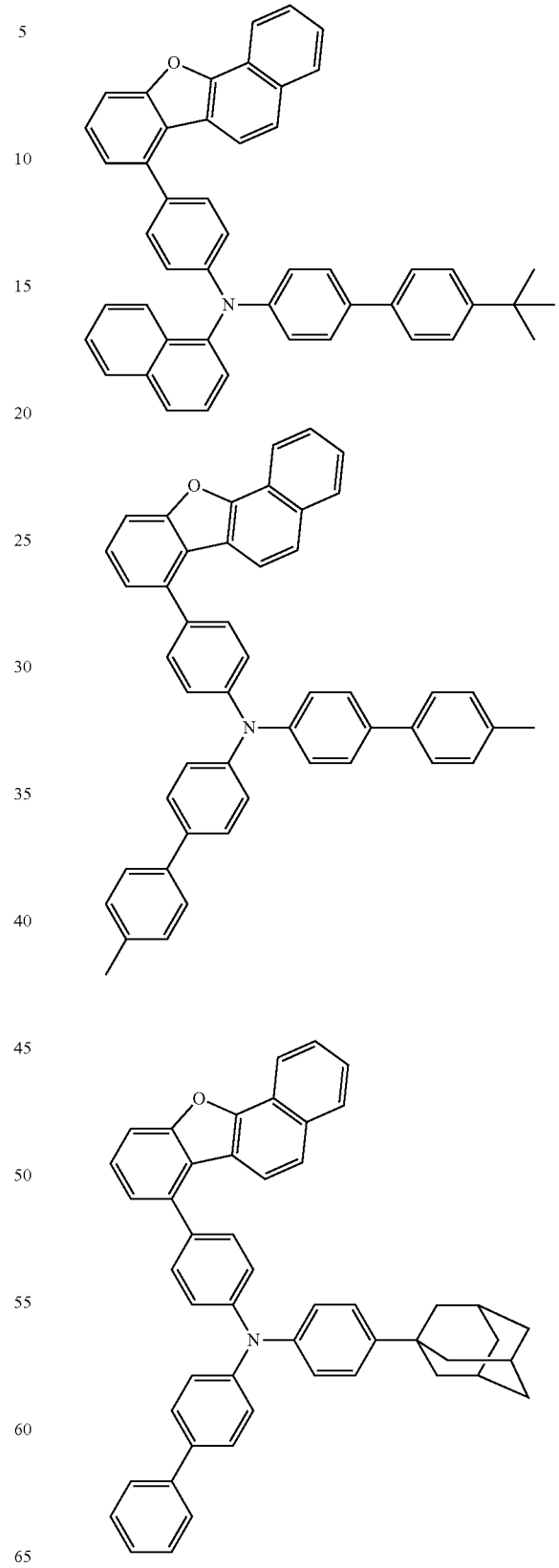

903
-continued
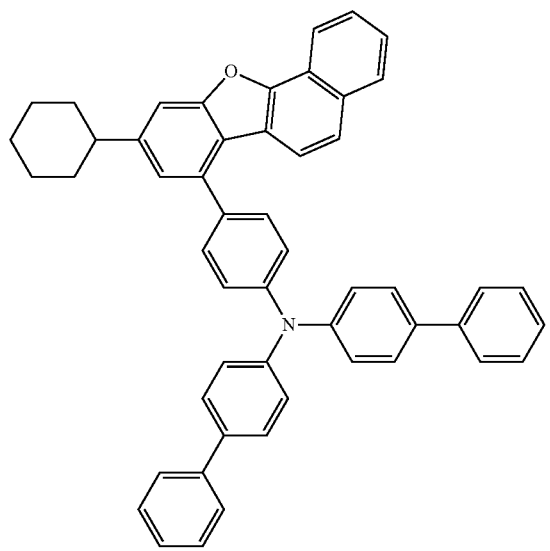
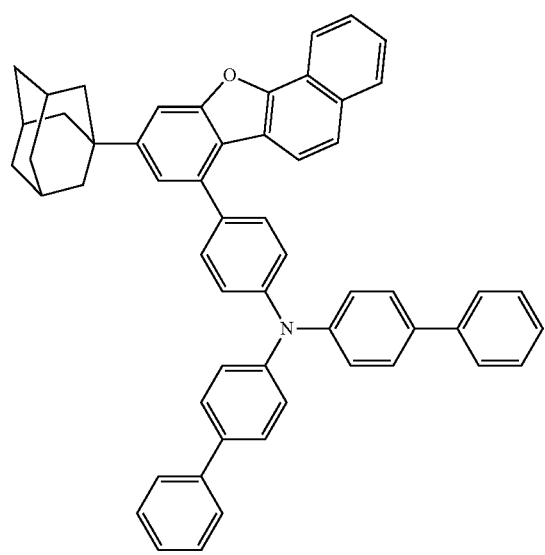
[Chem. 302]
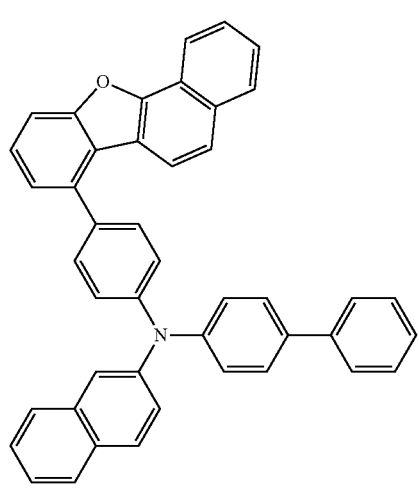
904
-continued
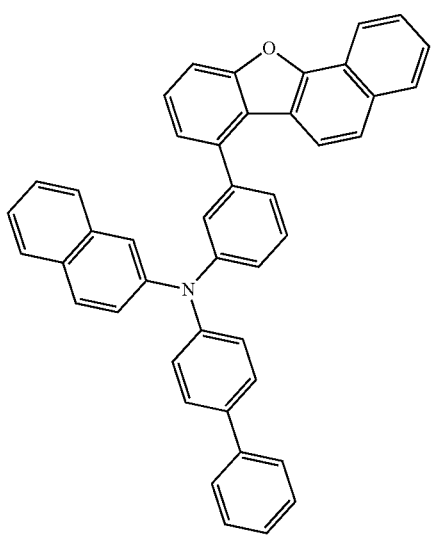
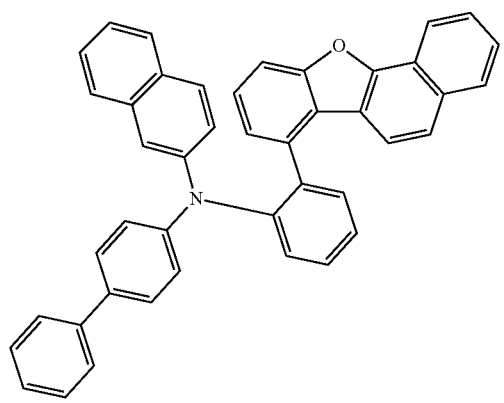
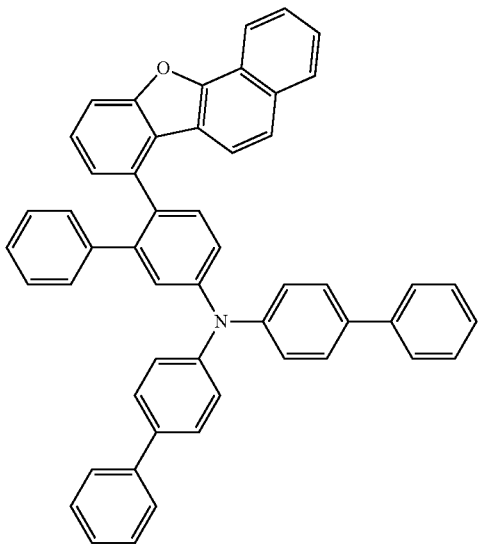

905
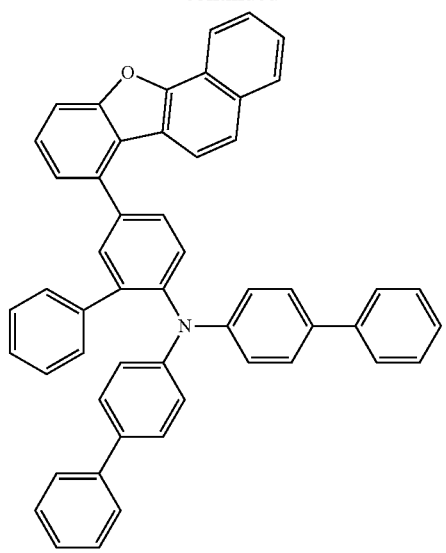
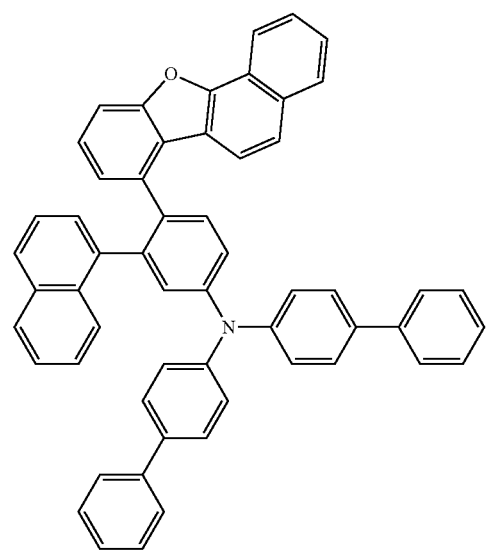
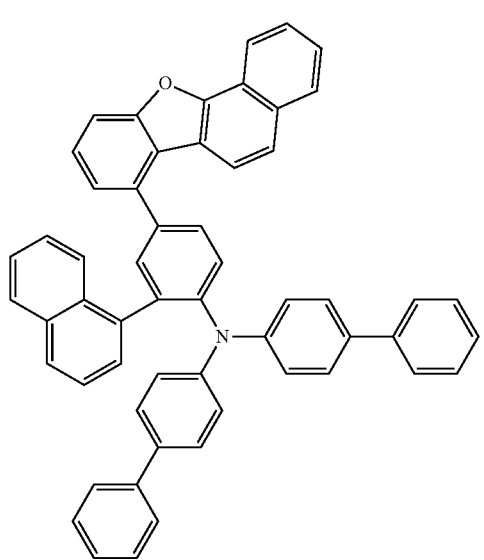
906
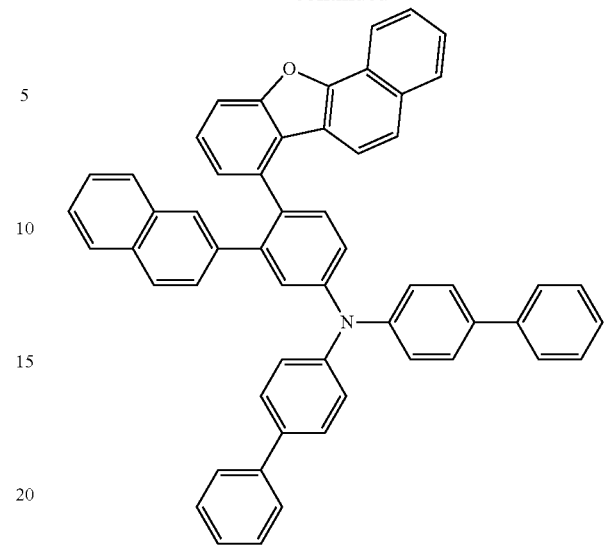
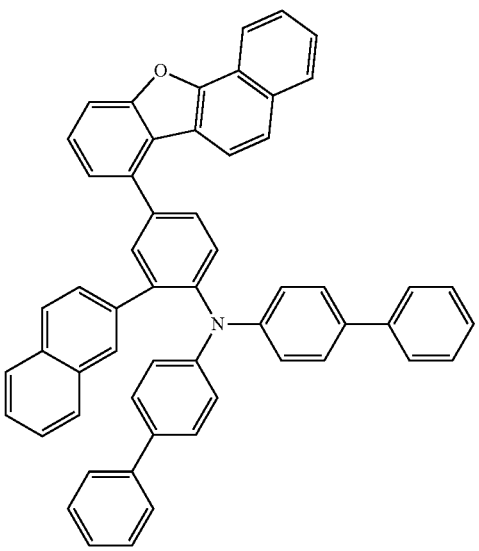

907
-continued
[Chem. 303]
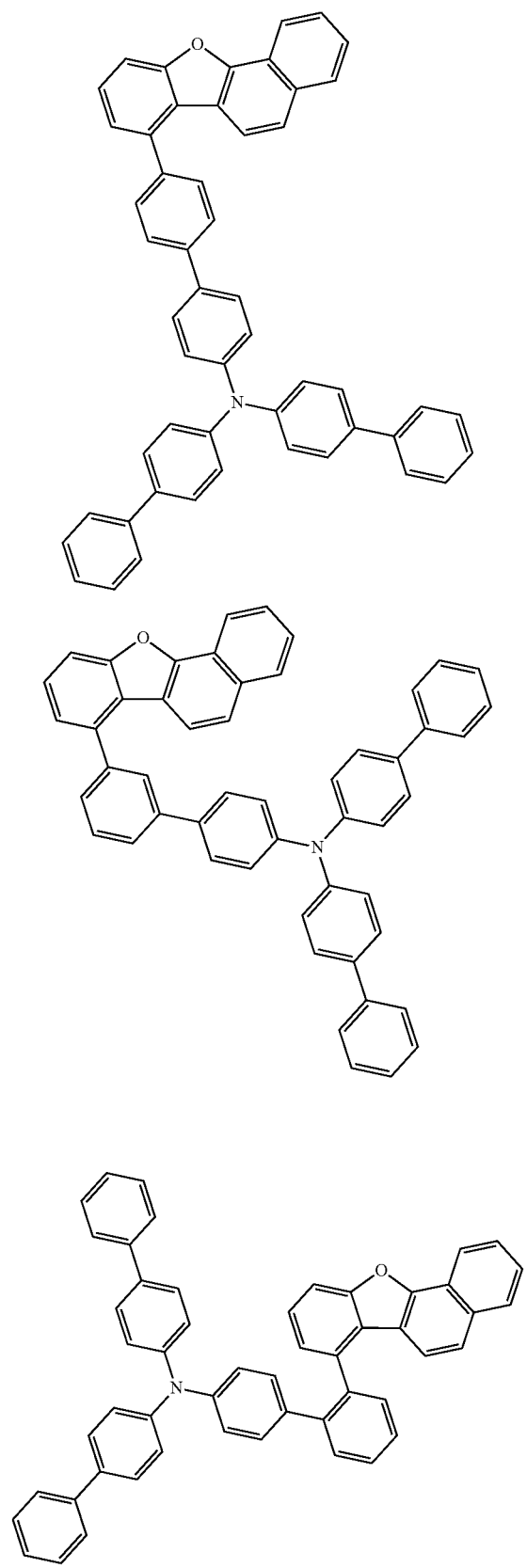
908
-continued
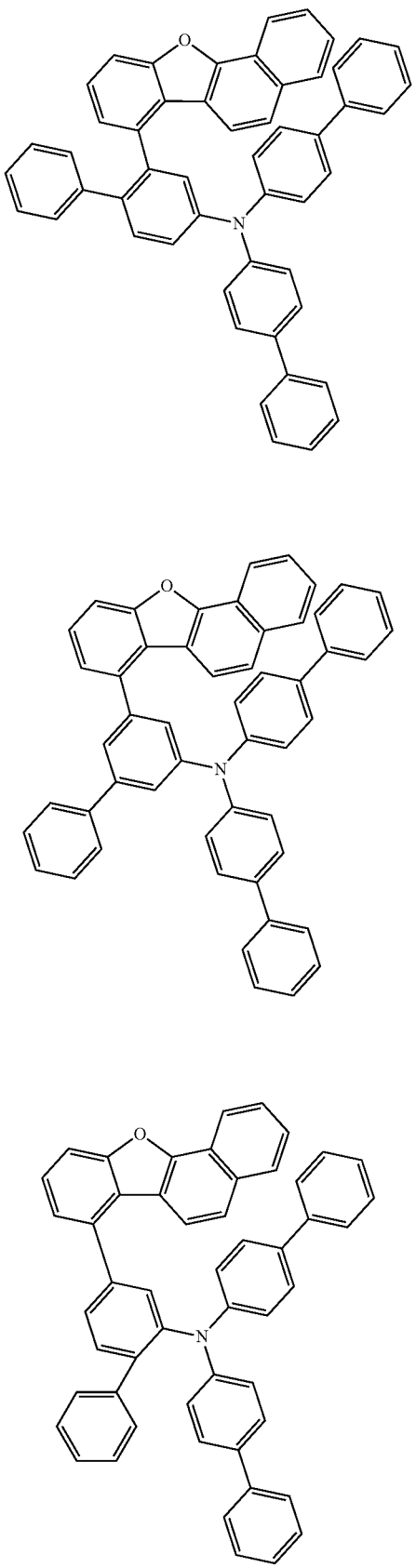

909
-continued
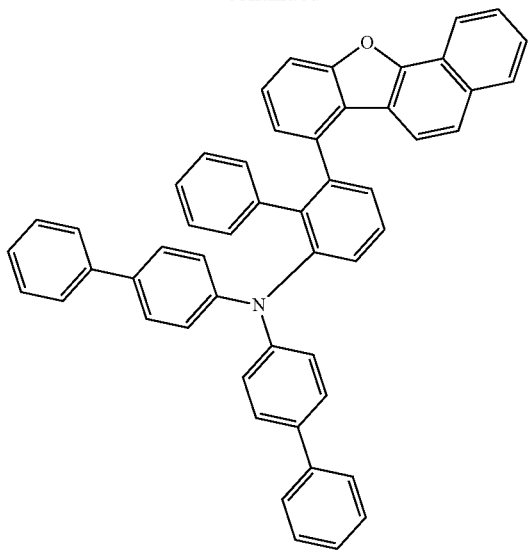
[Chem. 304]
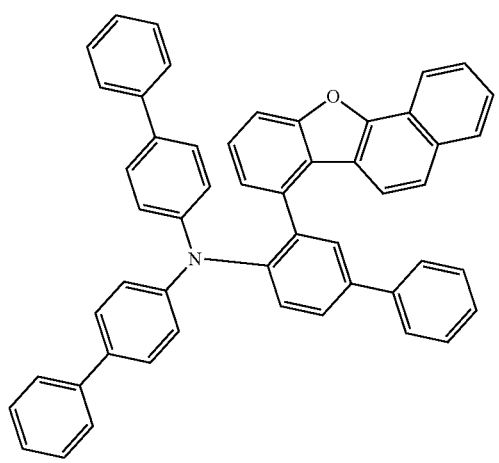
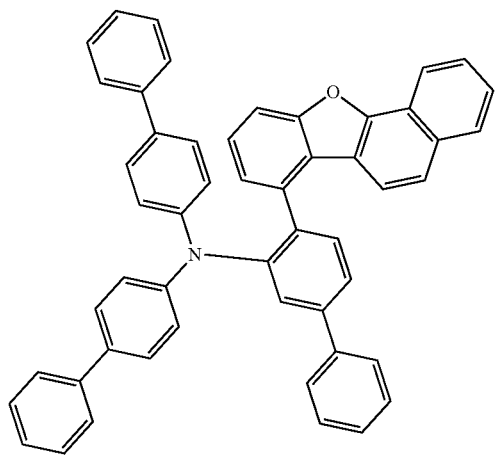
910
-continued
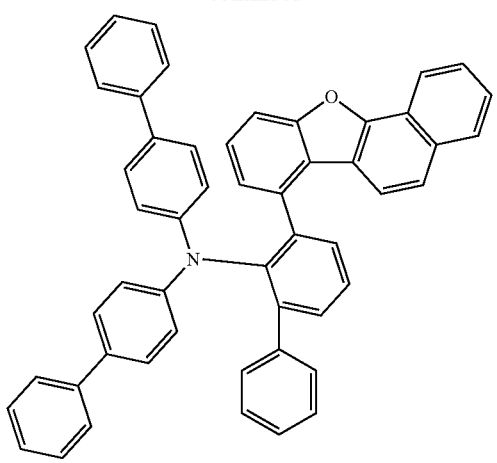
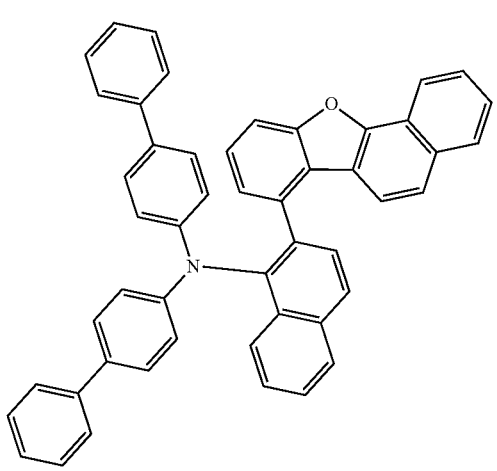
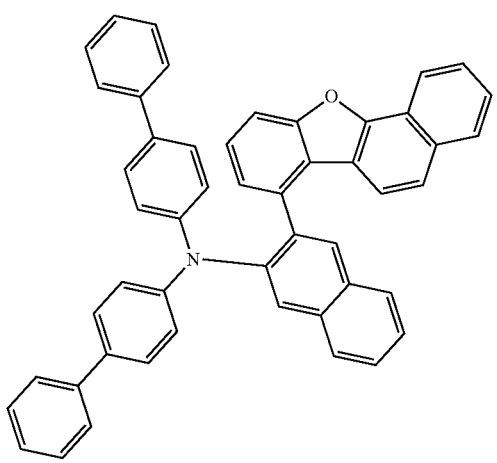

911
-continued
912
-continued
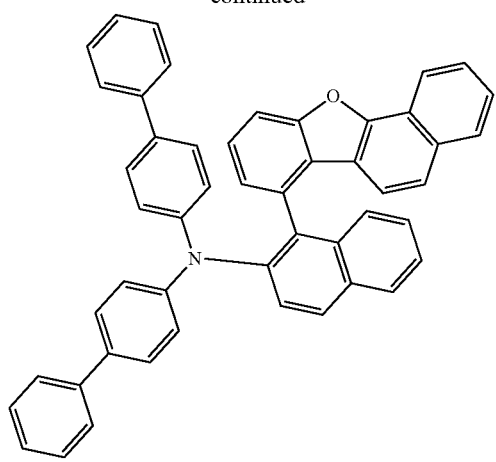
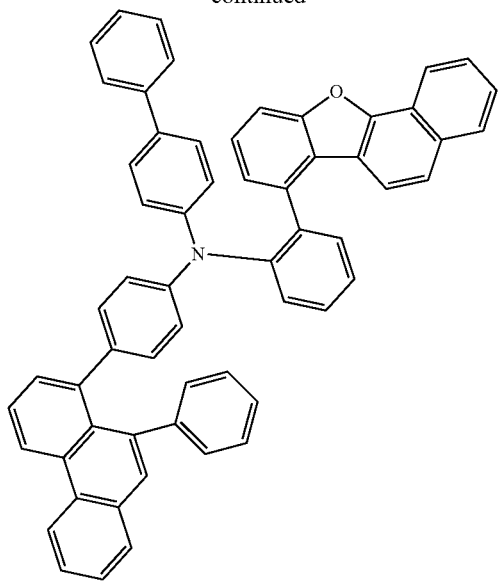
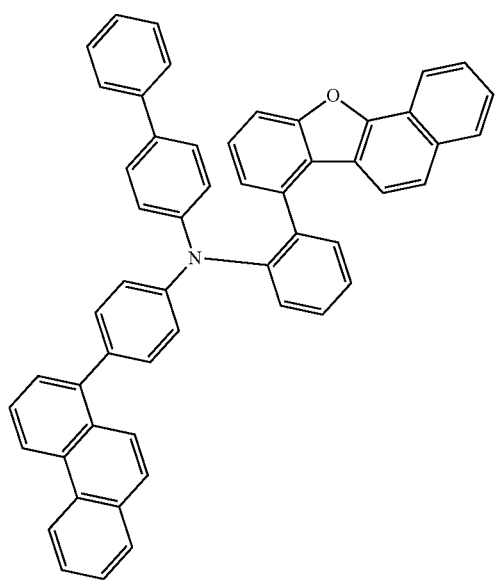
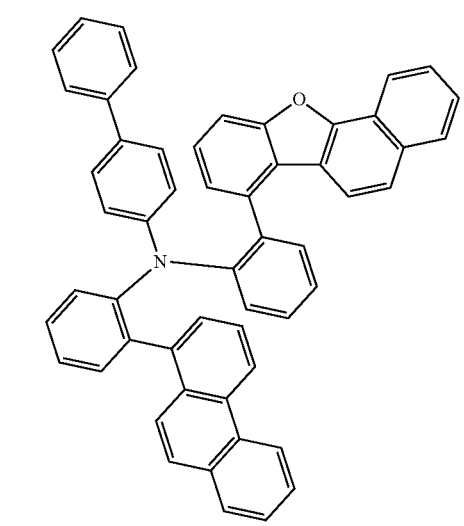
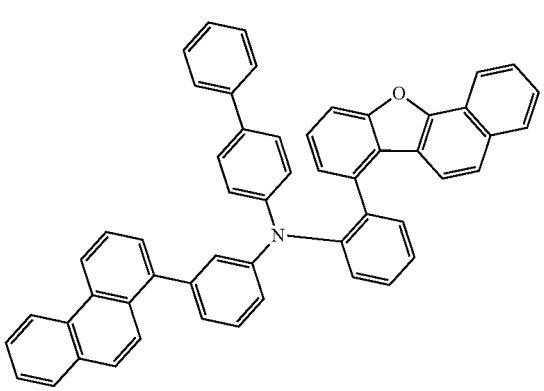
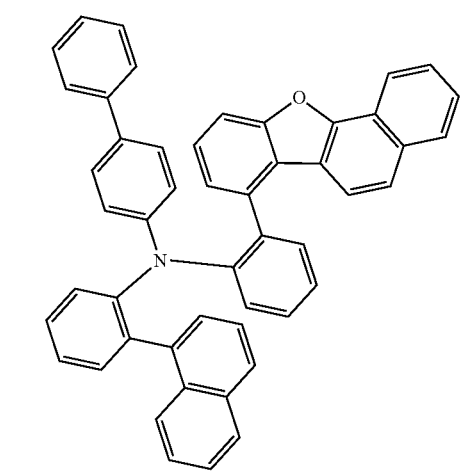

913
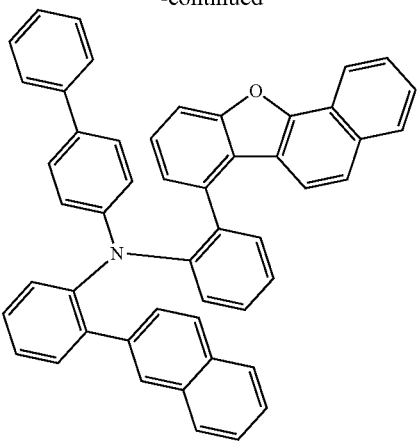
[Chem. 305]
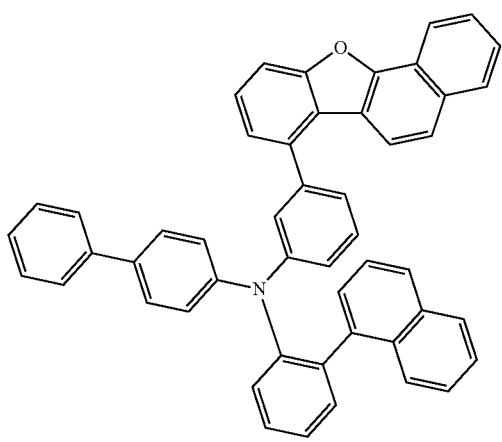
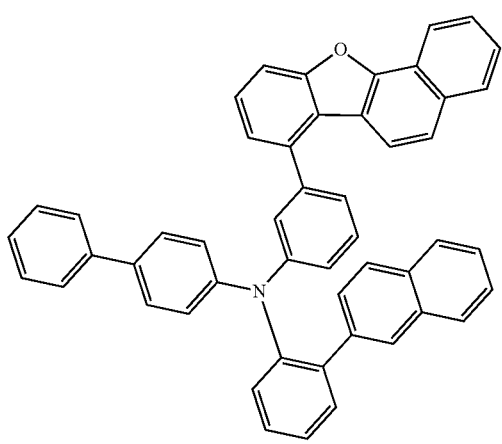
914
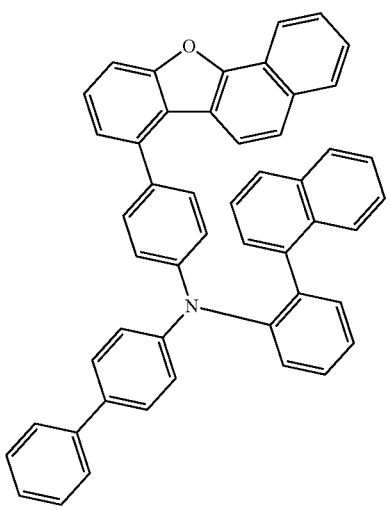
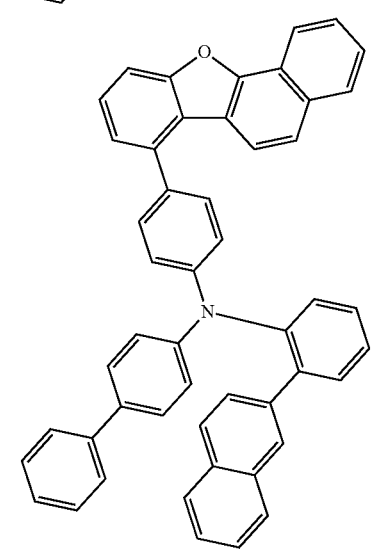
[Chem. 306]
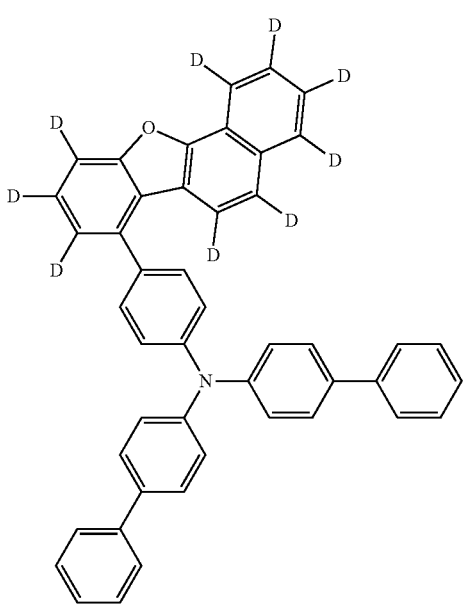

915
-continued
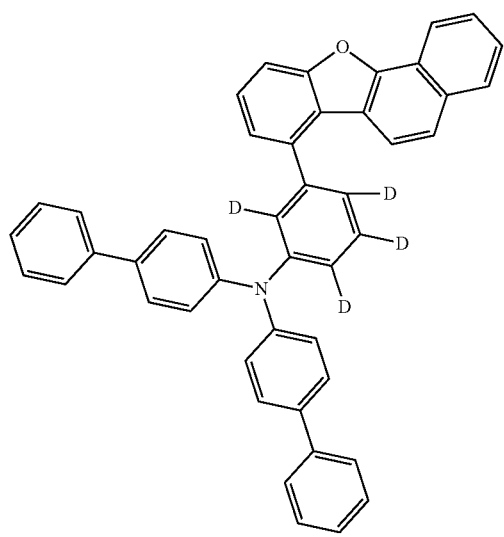
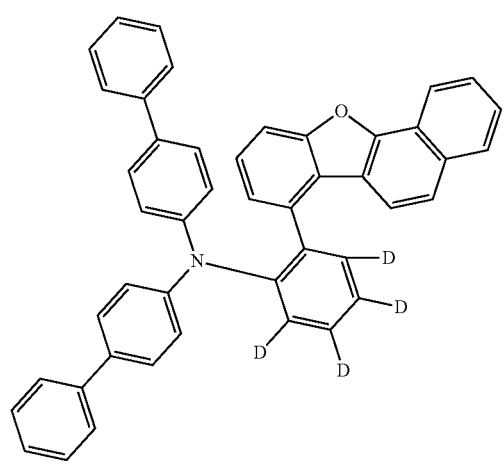
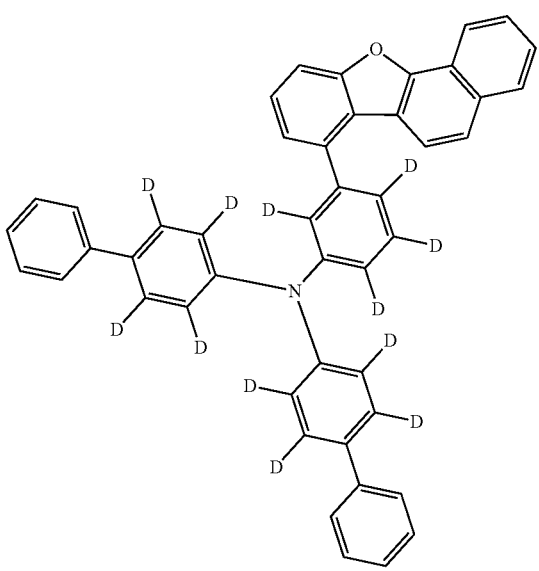
916
-continued
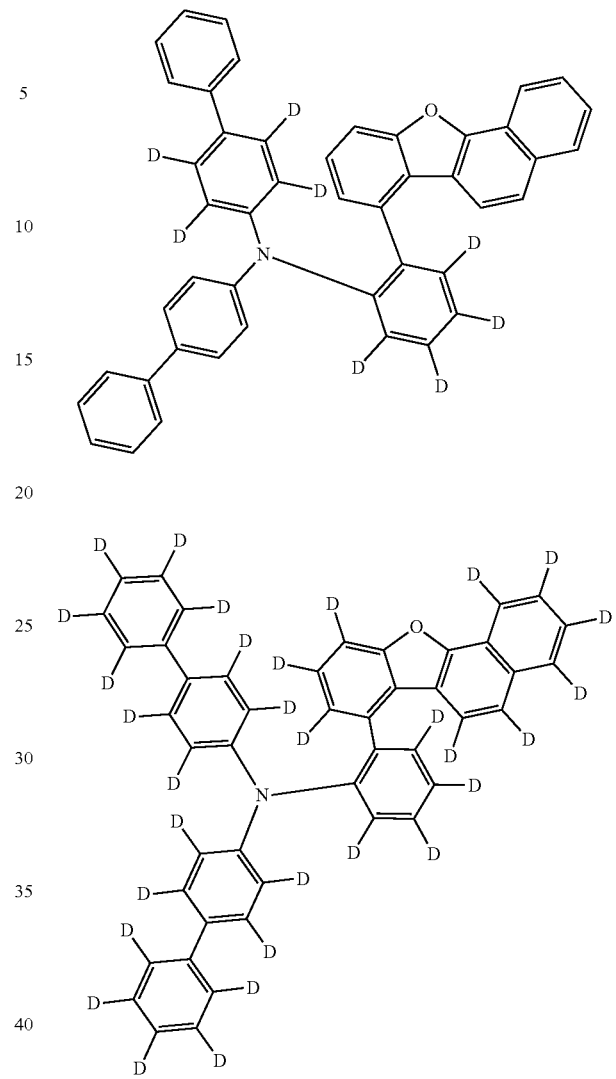
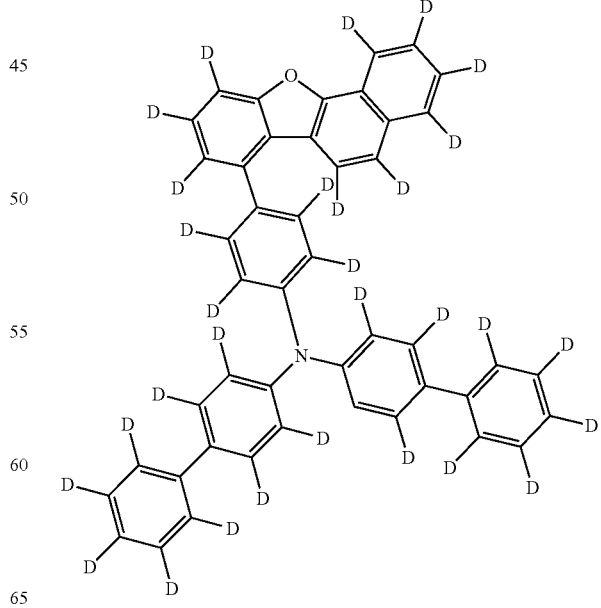

917
-continued
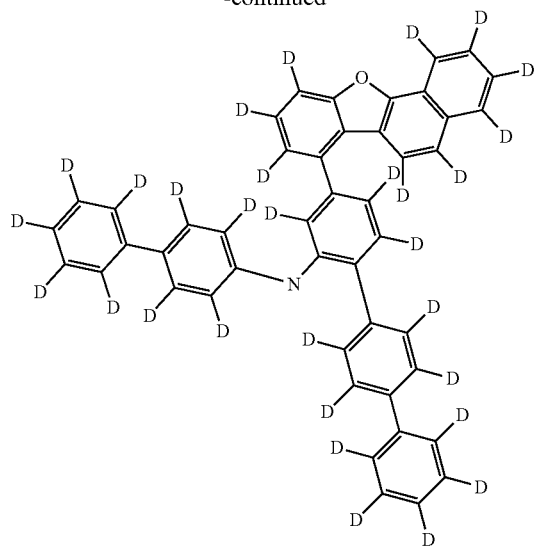
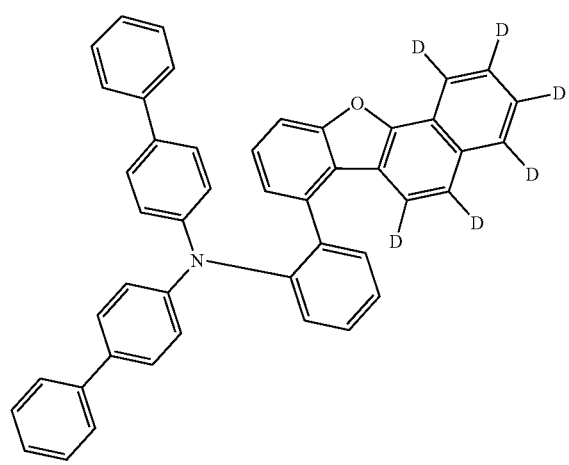
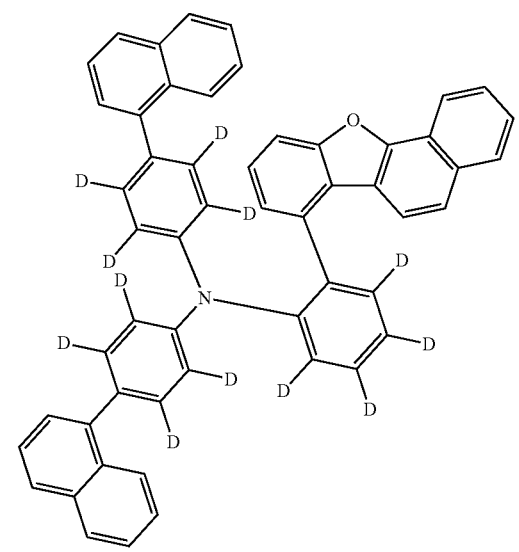
918
-continued
[Chem. 307]
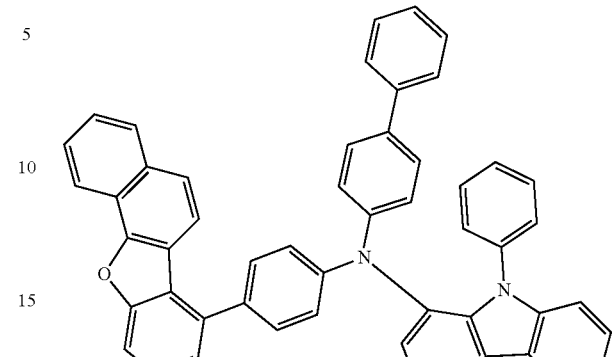
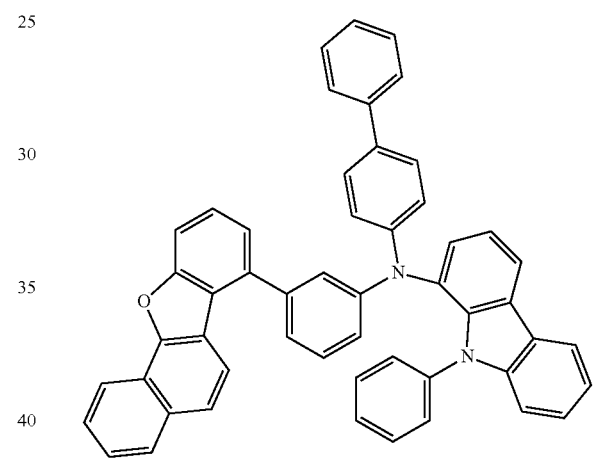
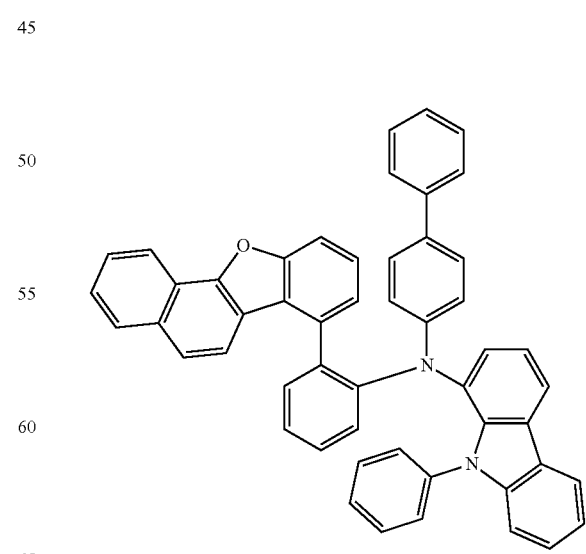

919
-continued
920
-continued
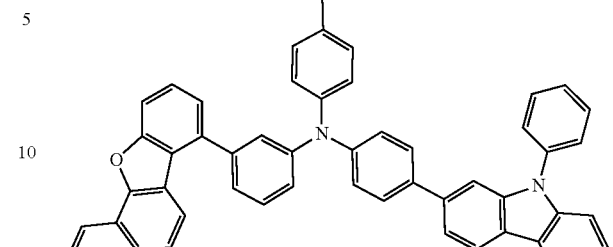
[Chem. 308]
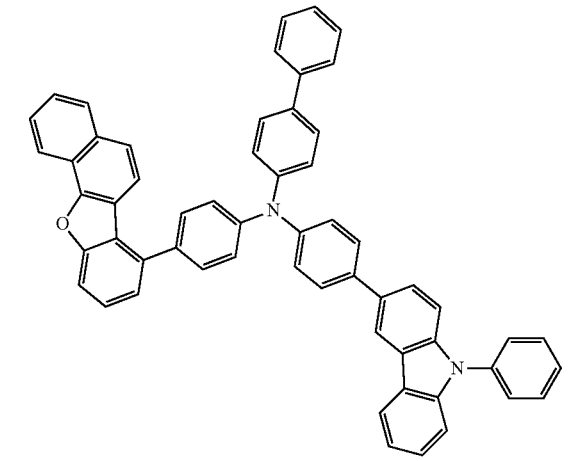
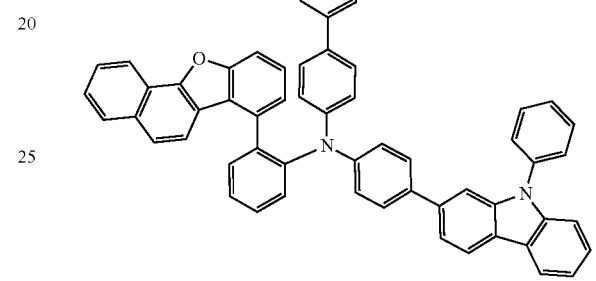
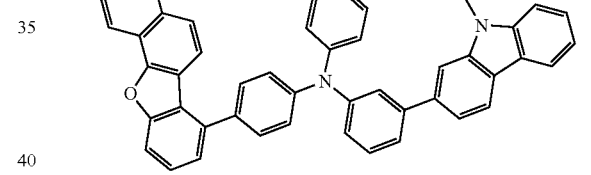
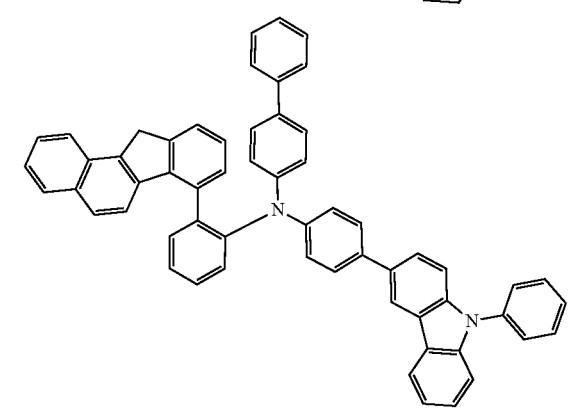
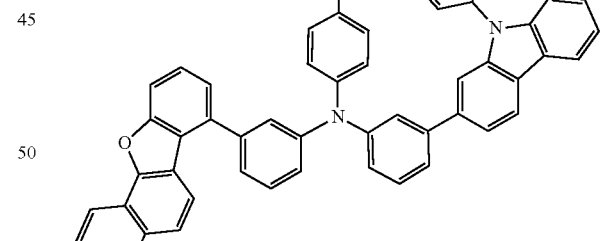
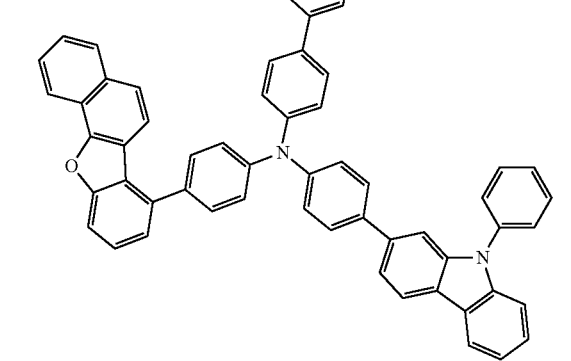
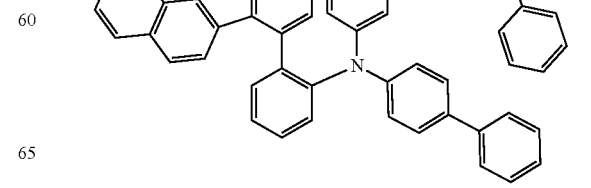
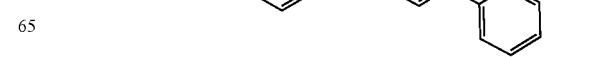

921
-continued
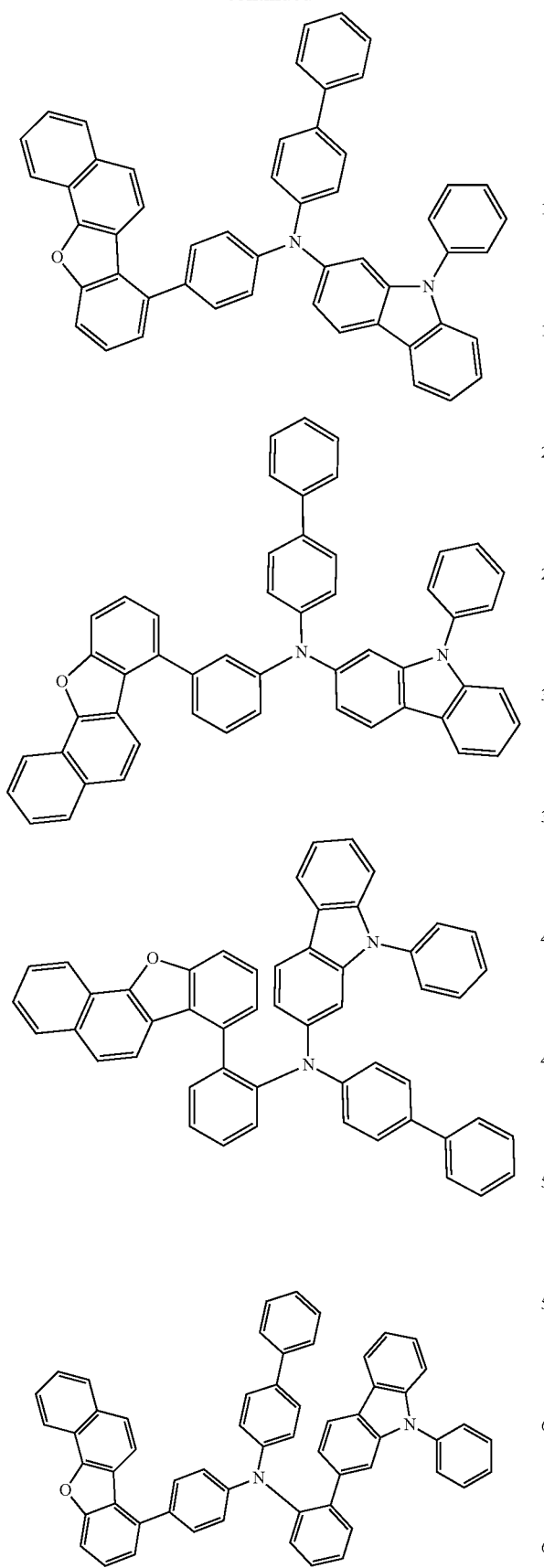
922
-continued
[Chem. 309]

923
-continued
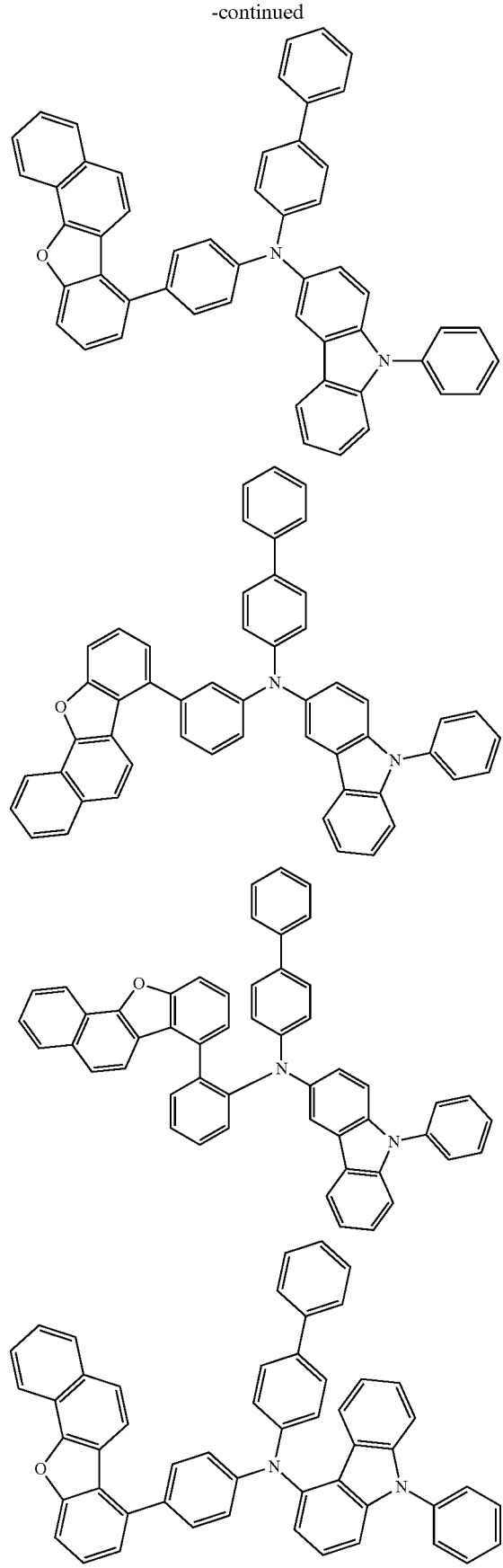
924
-continued
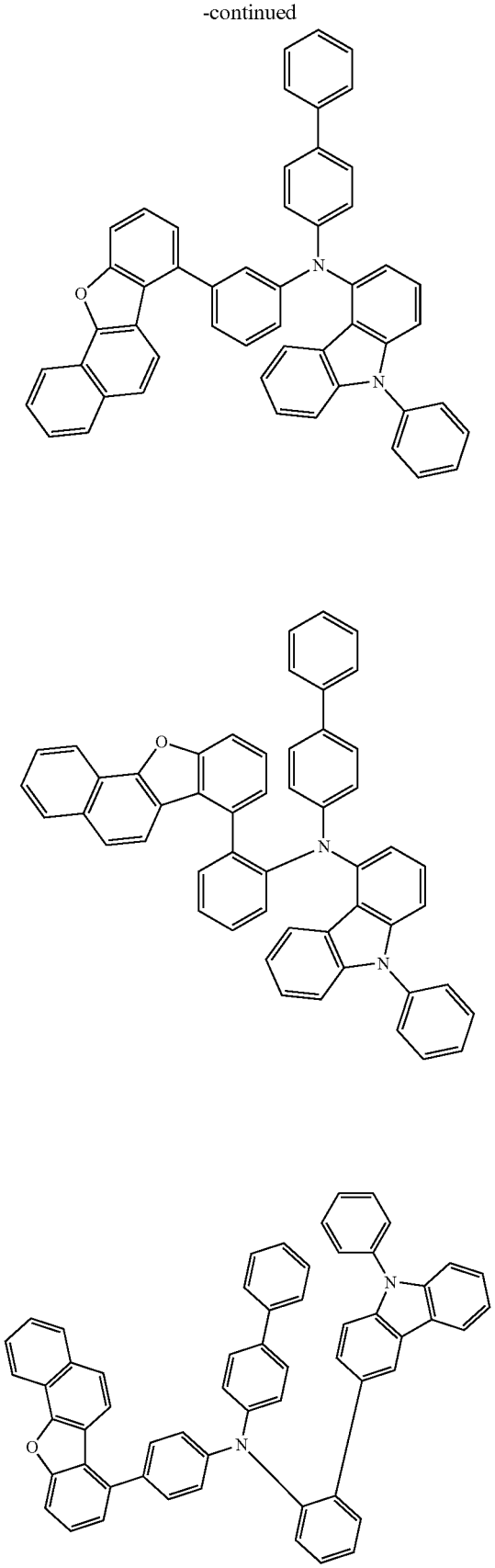

925
-continued
[Chem. 310]
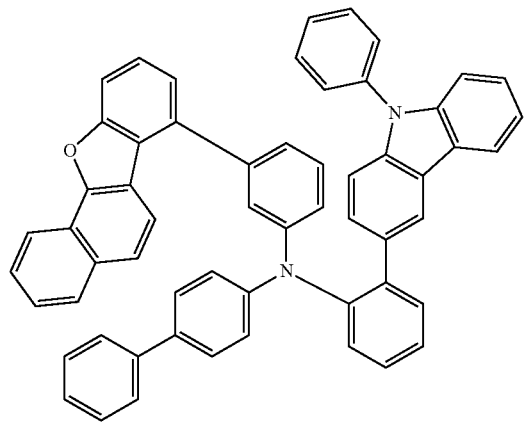
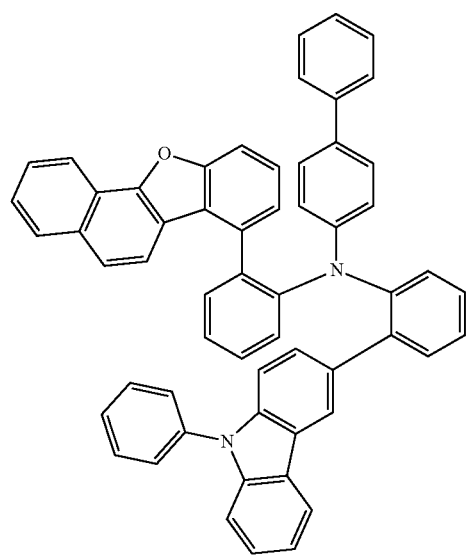
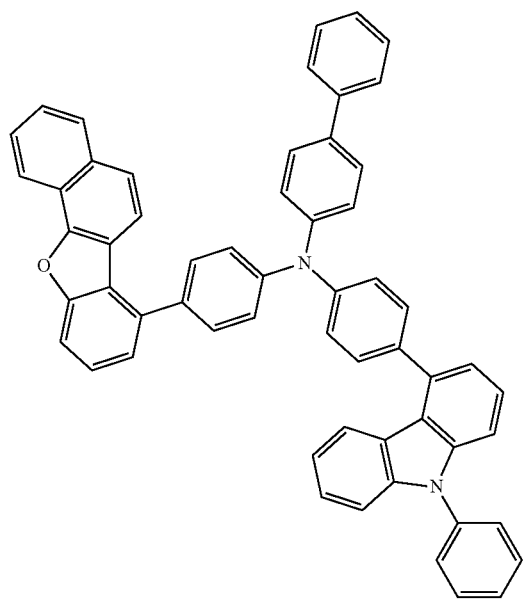
926
-continued
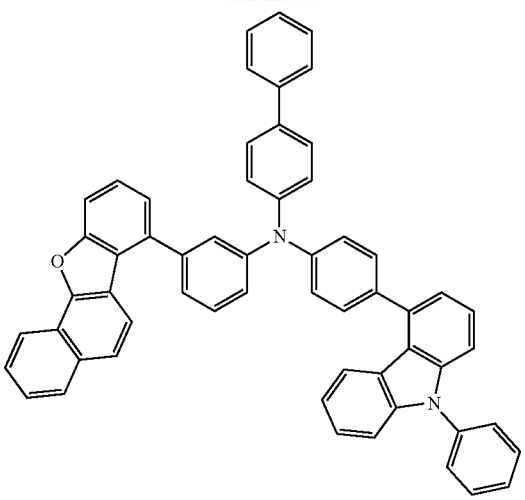
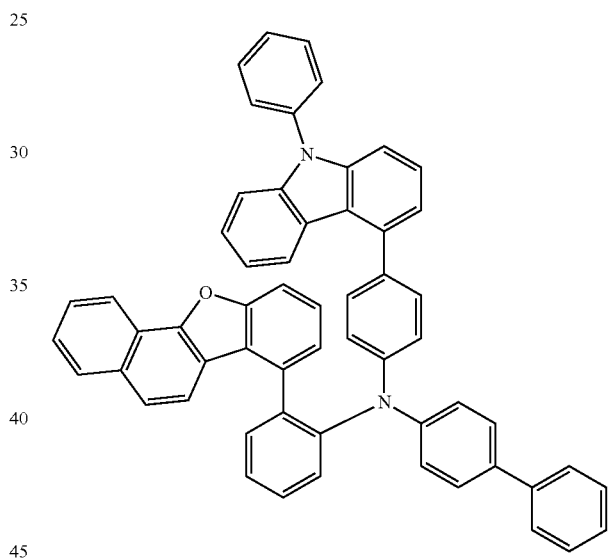
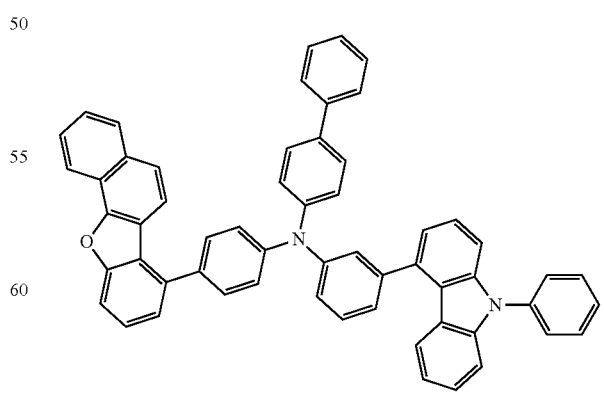

927
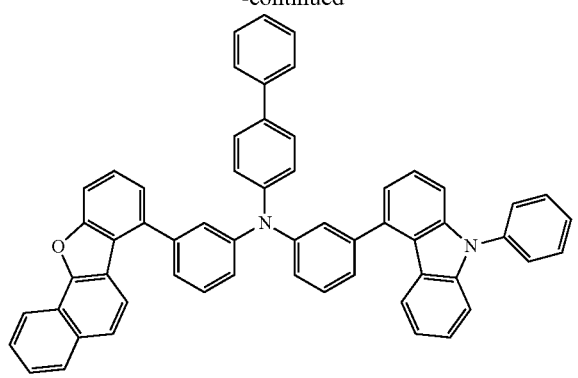
[Chem. 311]
928
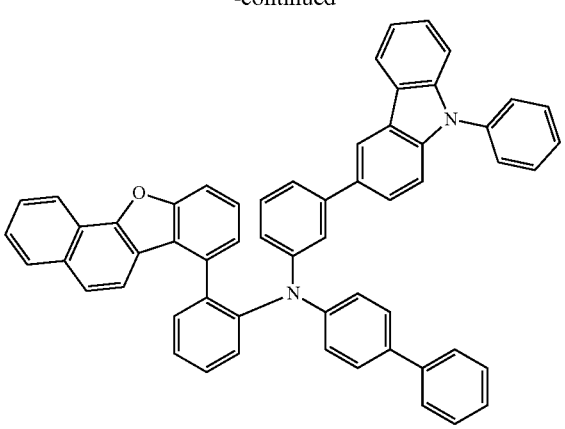
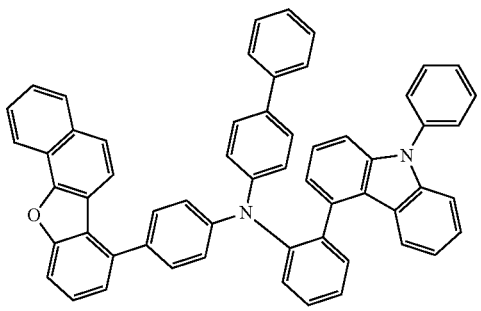
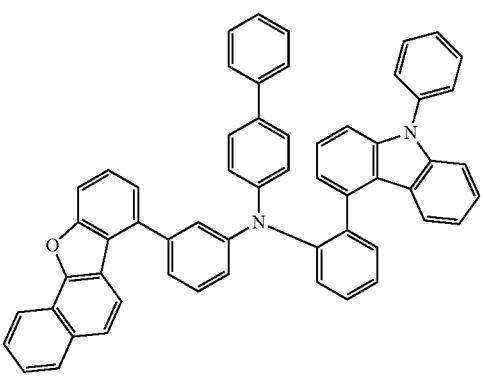
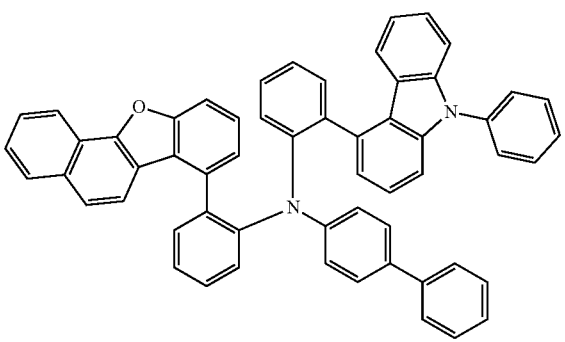

929
-continued
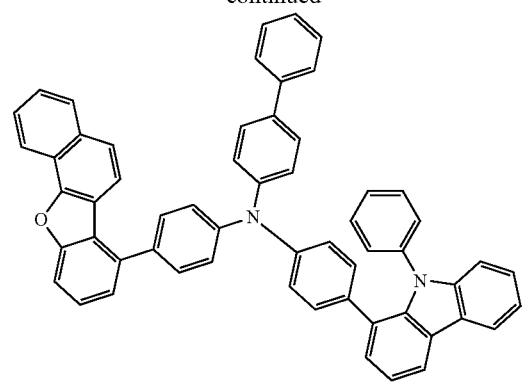
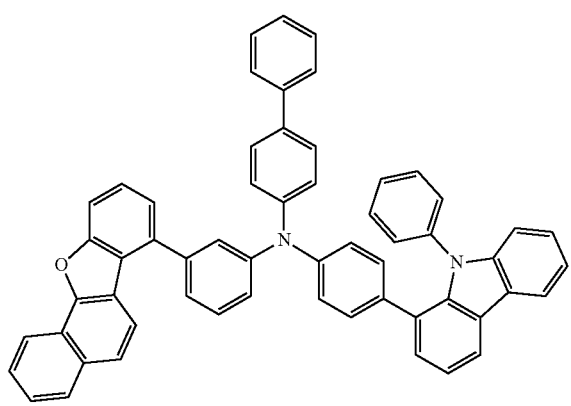
[Chem. 312]
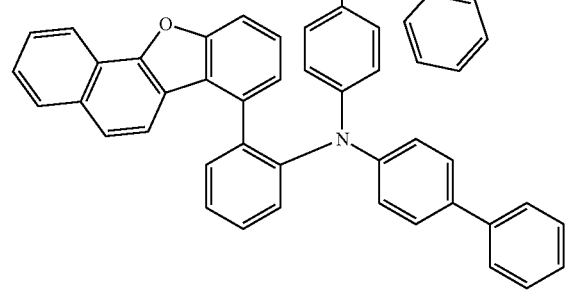
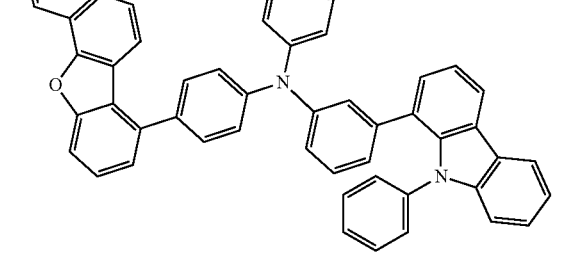
930
-continued
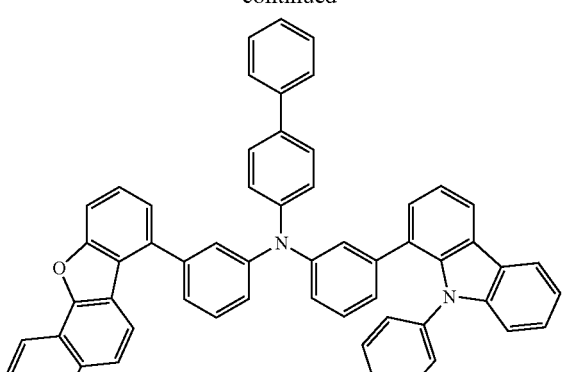
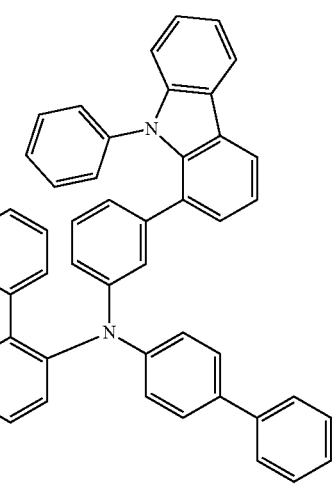
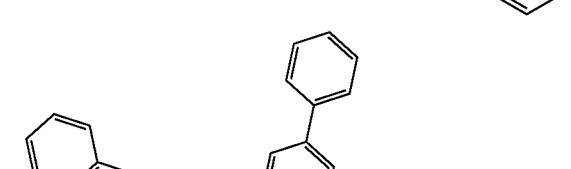

931
-continued
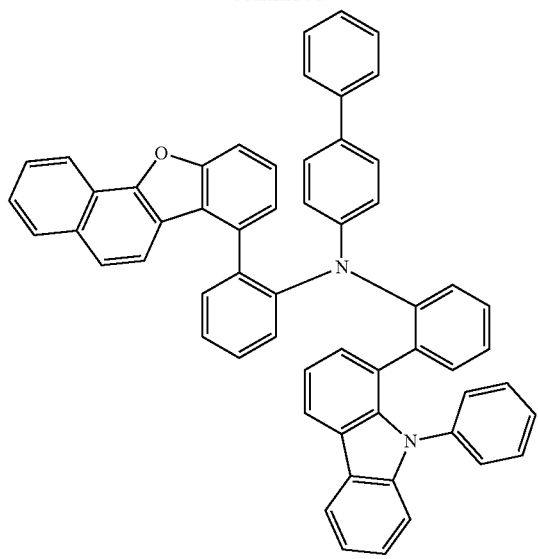
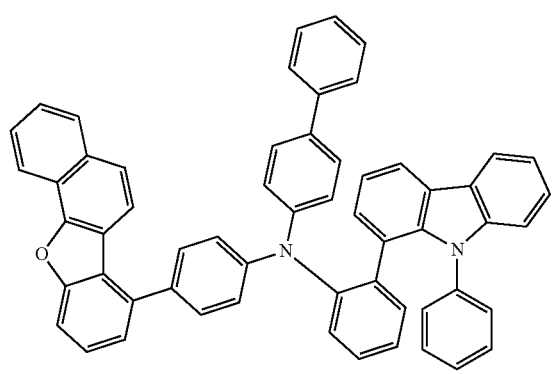
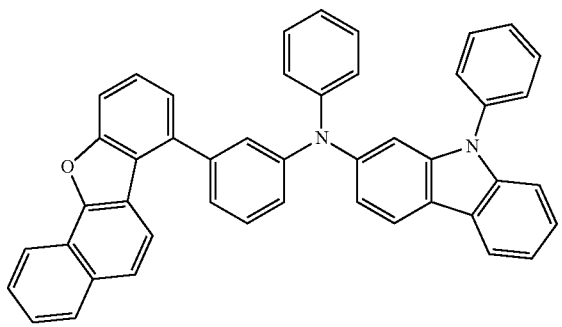
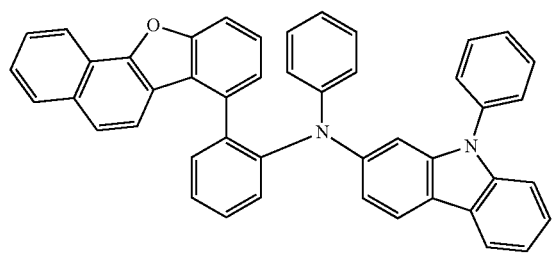
932
-continued
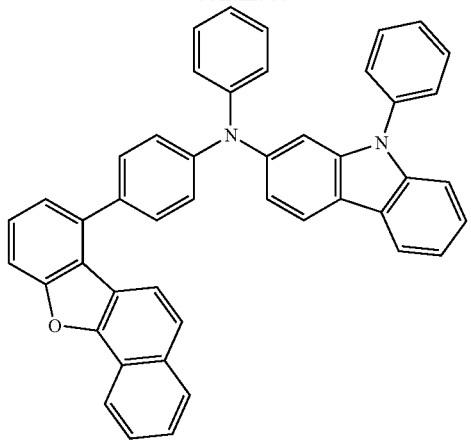
[Chem. 313]
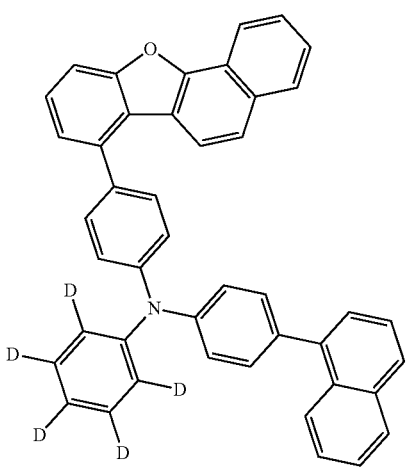
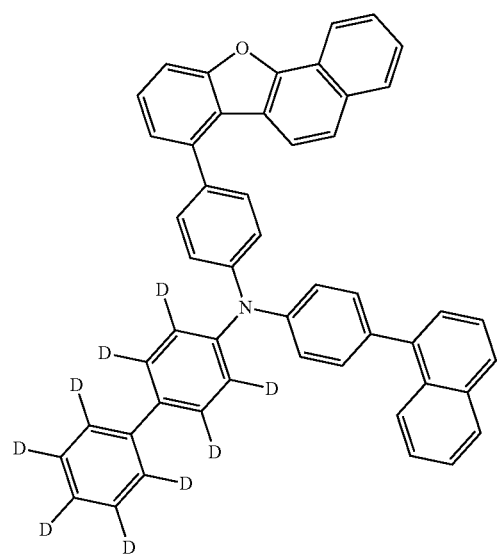

933
-continued
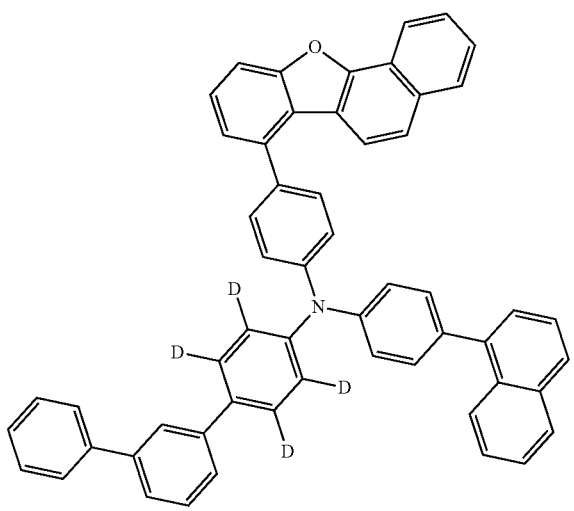
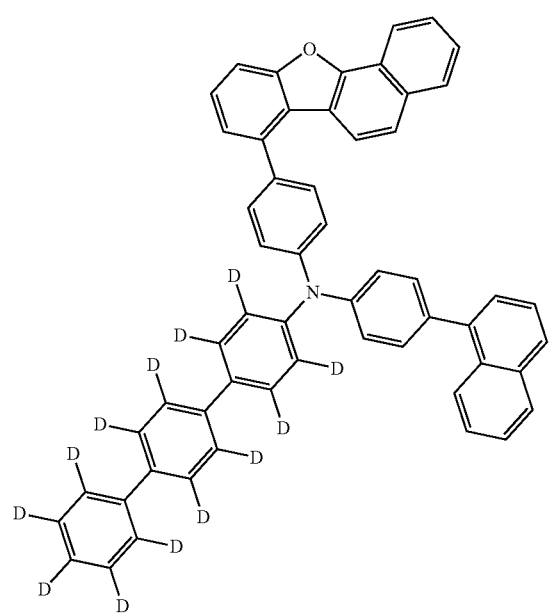
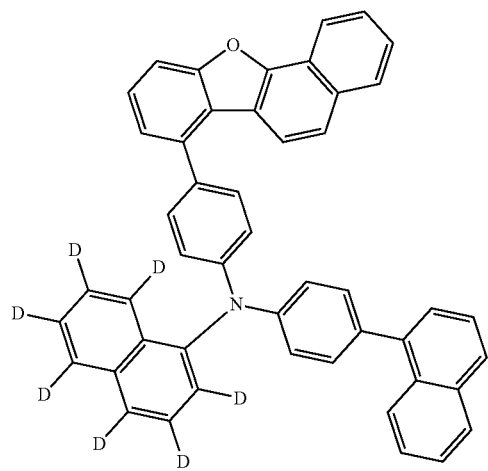
934
-continued
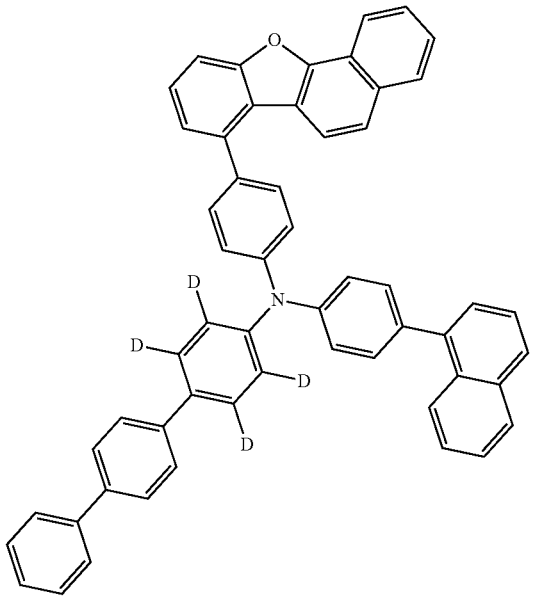
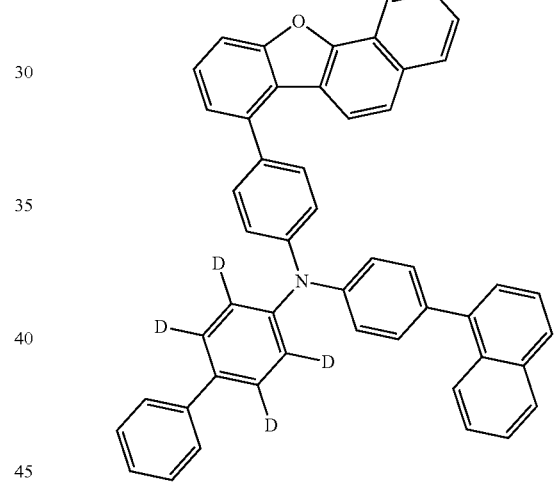
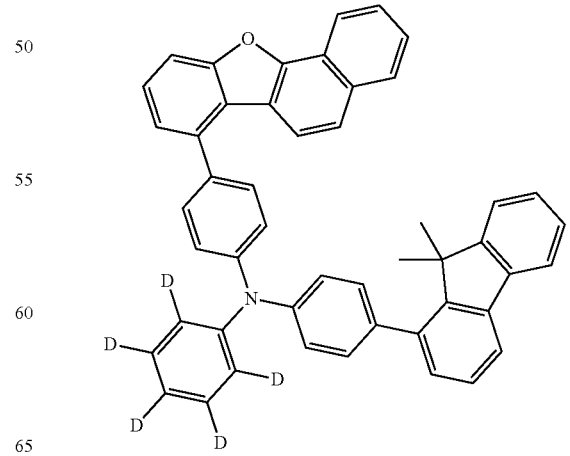

935
-continued
[Chem. 314]
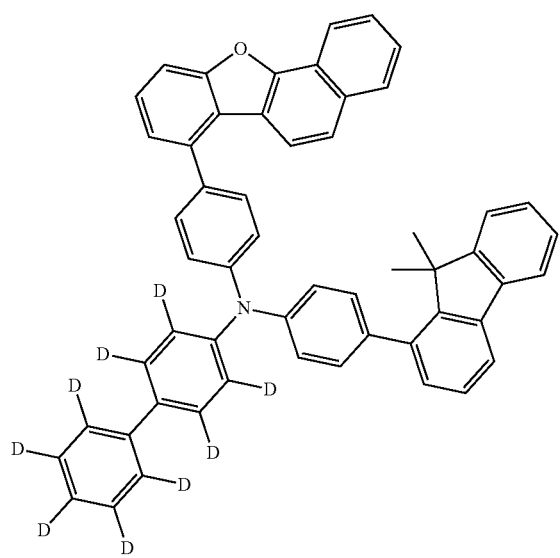
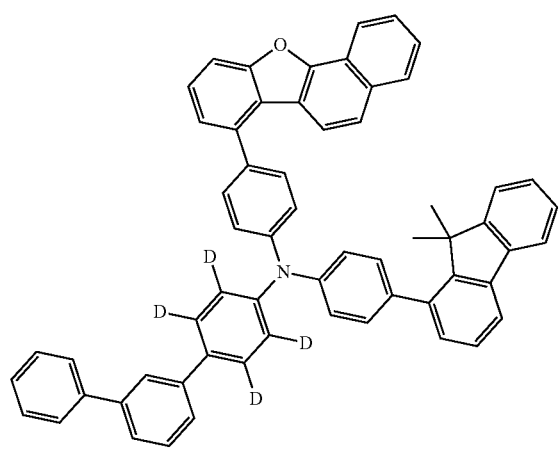
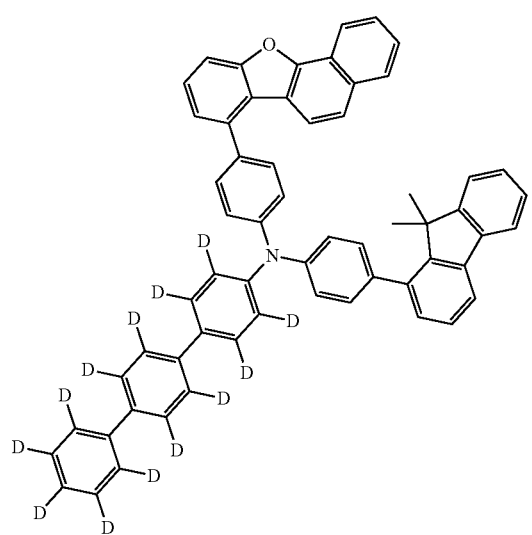
936
-continued
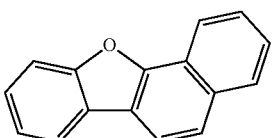
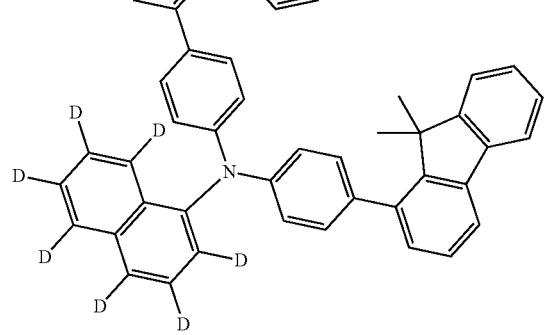
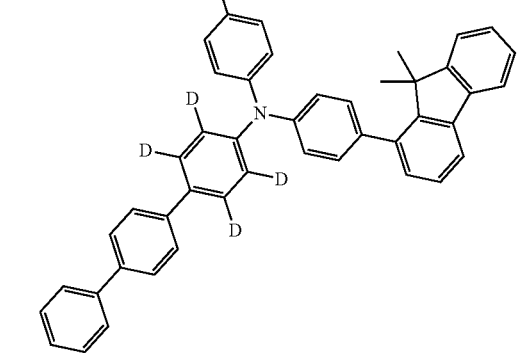
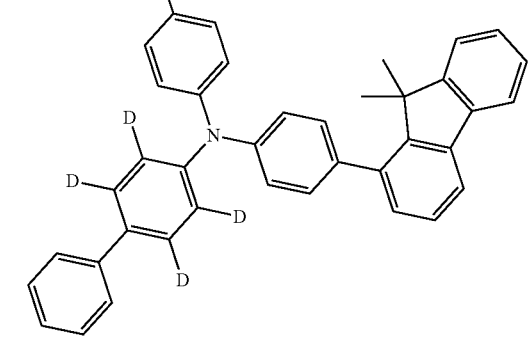

937
-continued
938
-continued
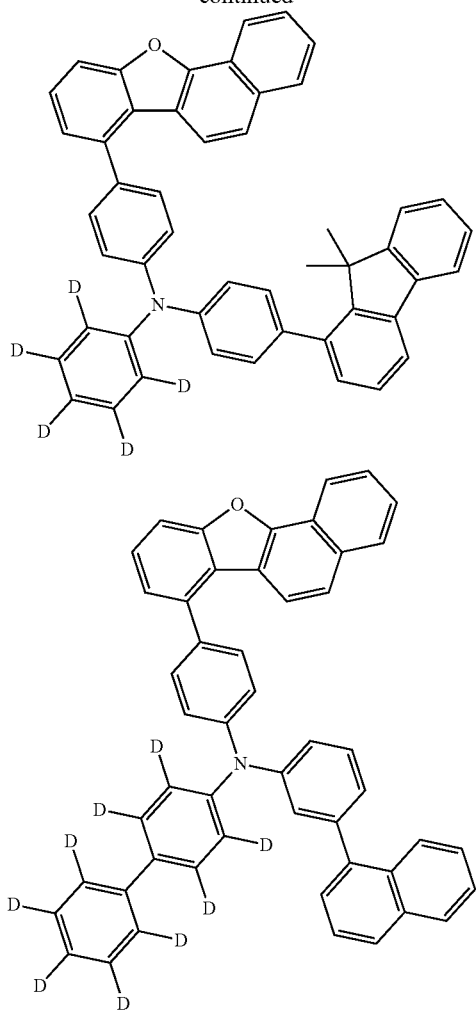
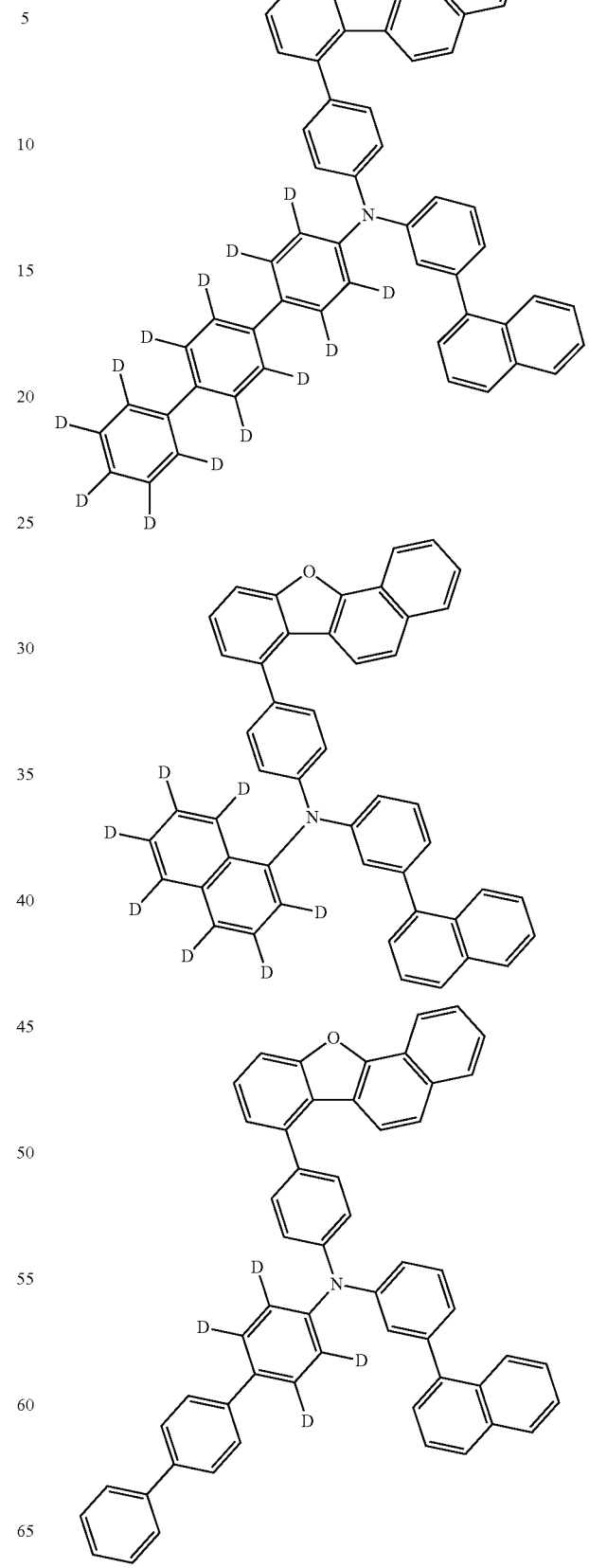
[Chem. 315]
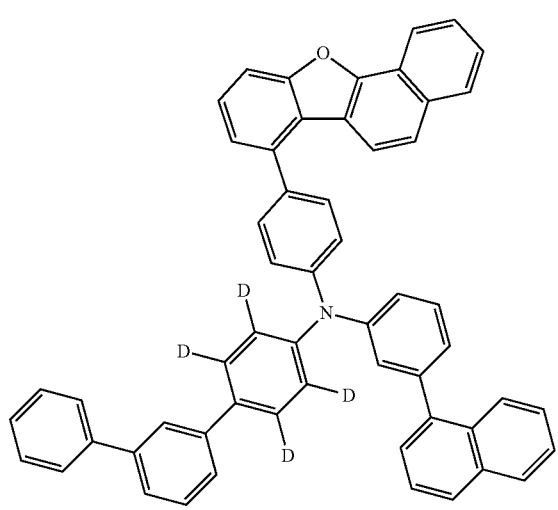

939
-continued
940
-continued
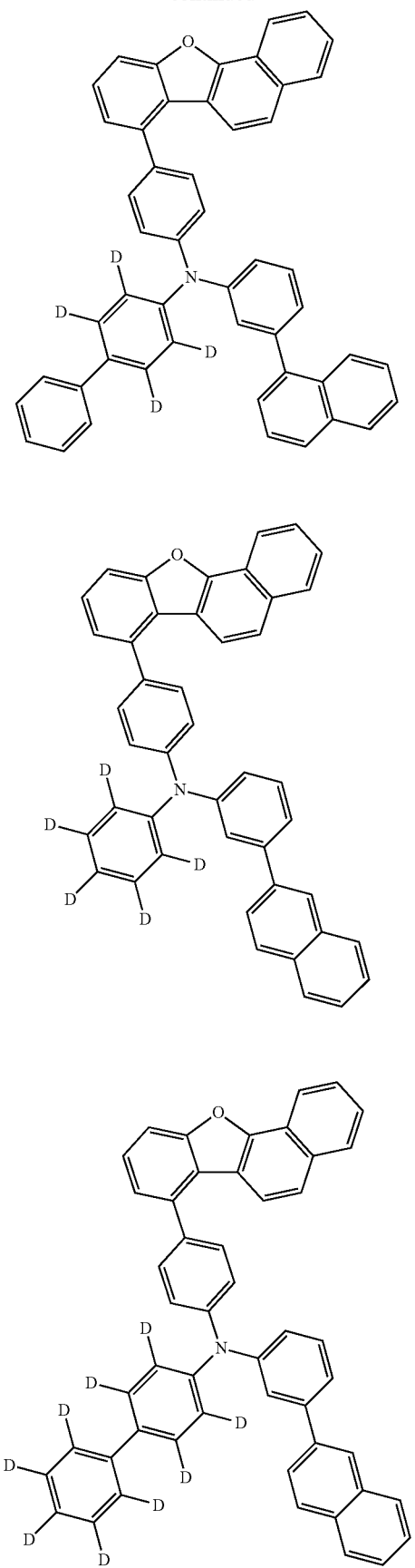
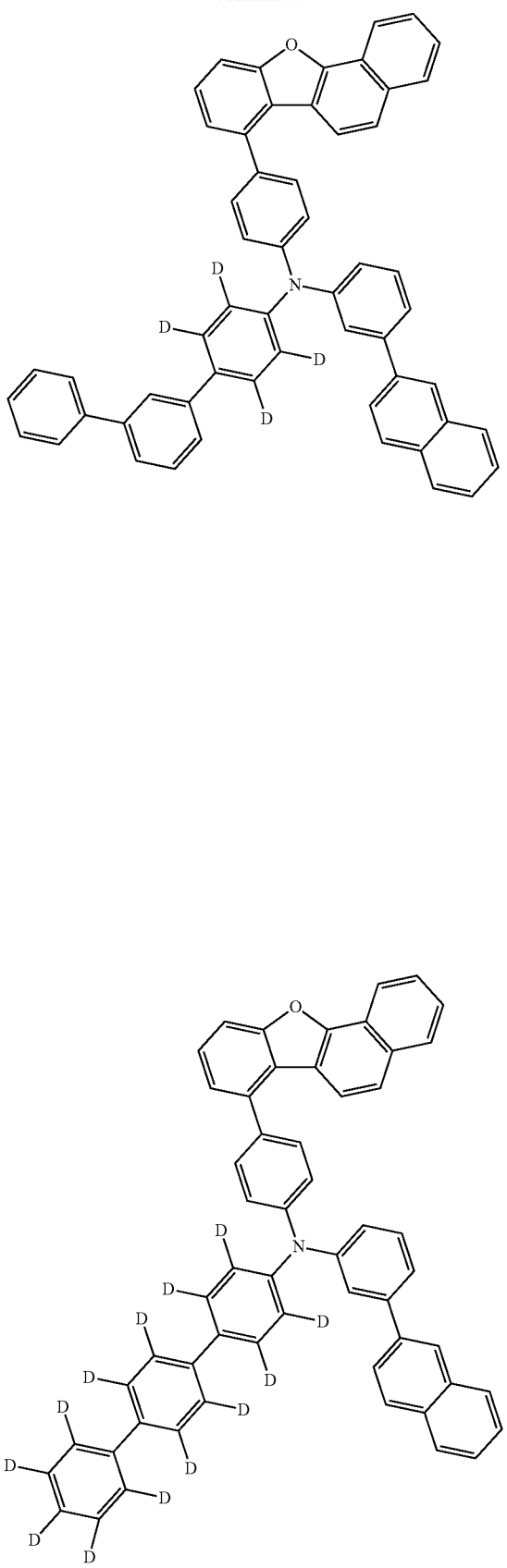

941
-continued
[Chem. 316]
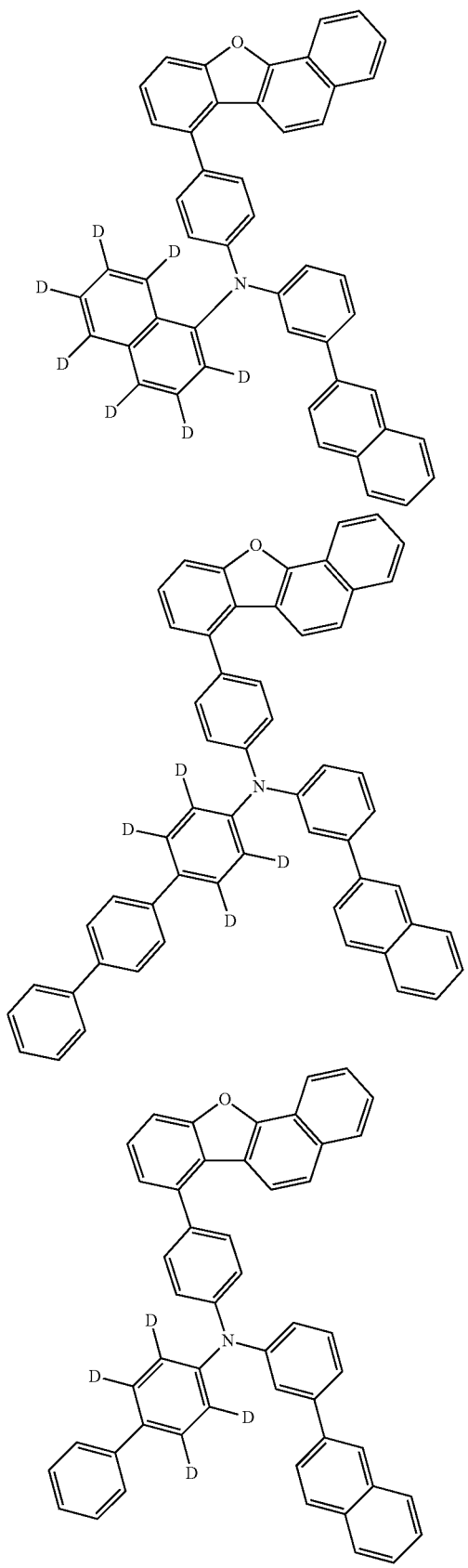
942
-continued
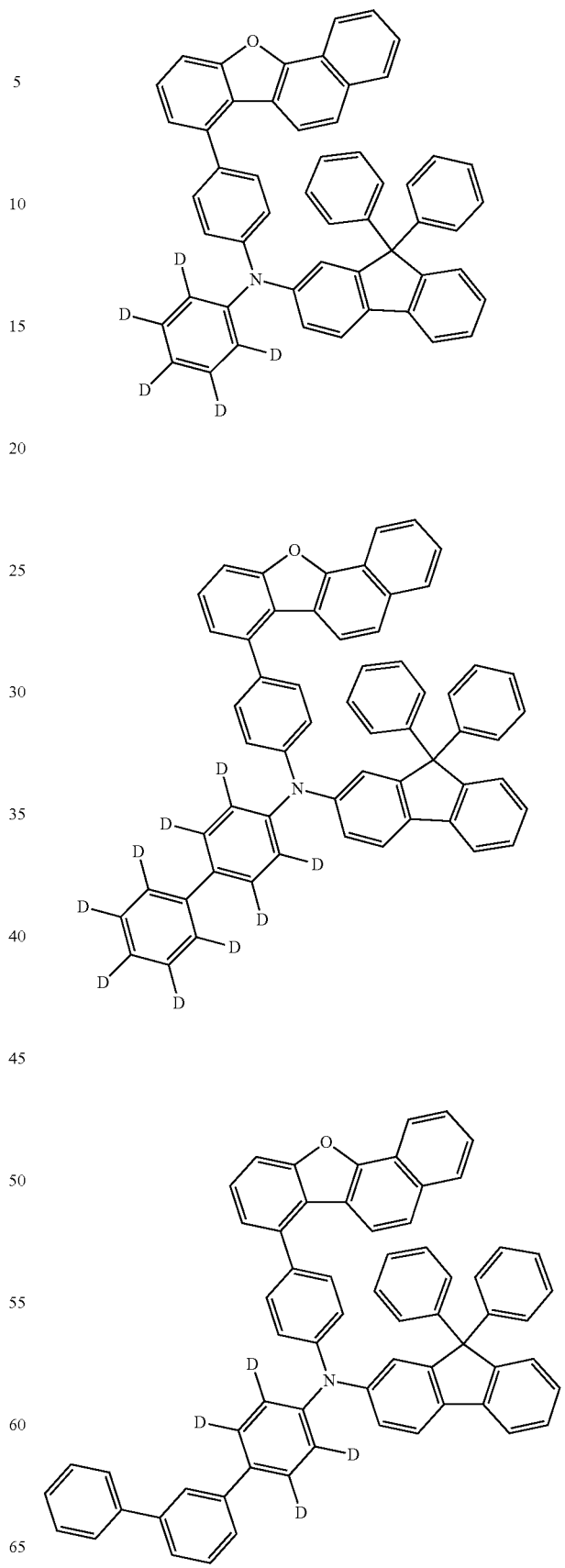

943
-continued
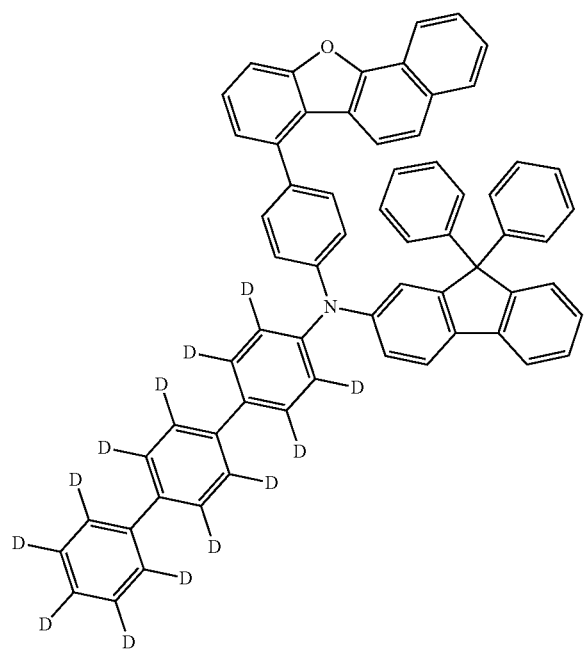
944
-continued
[Chem. 317]
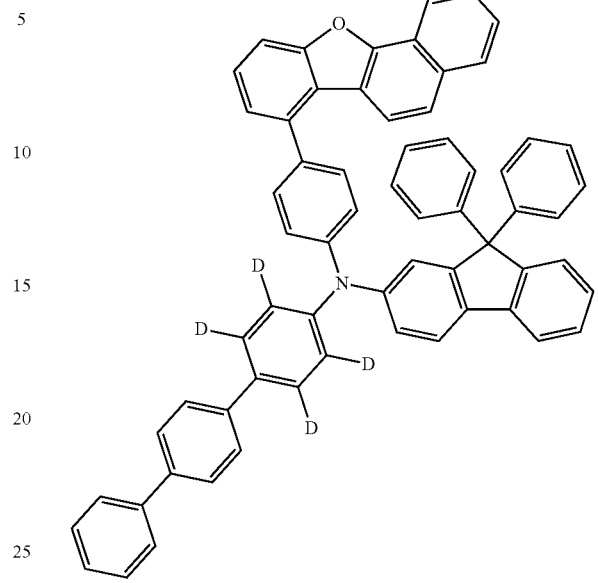
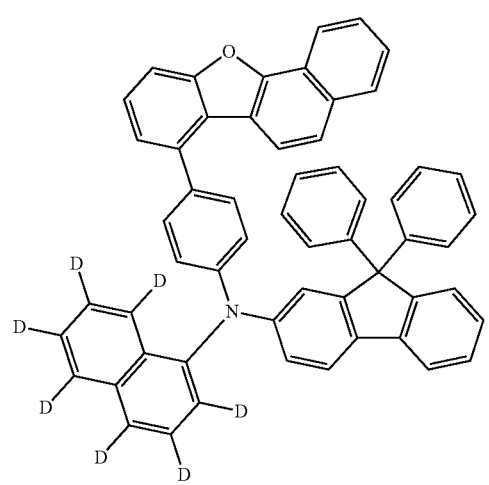
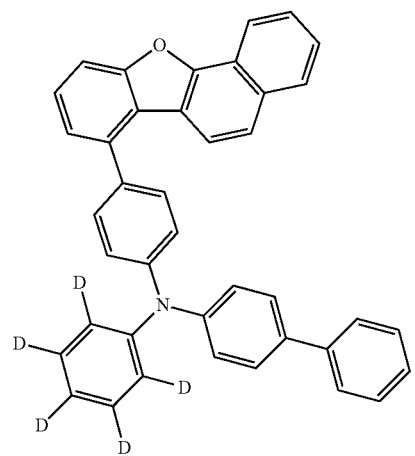

945
946
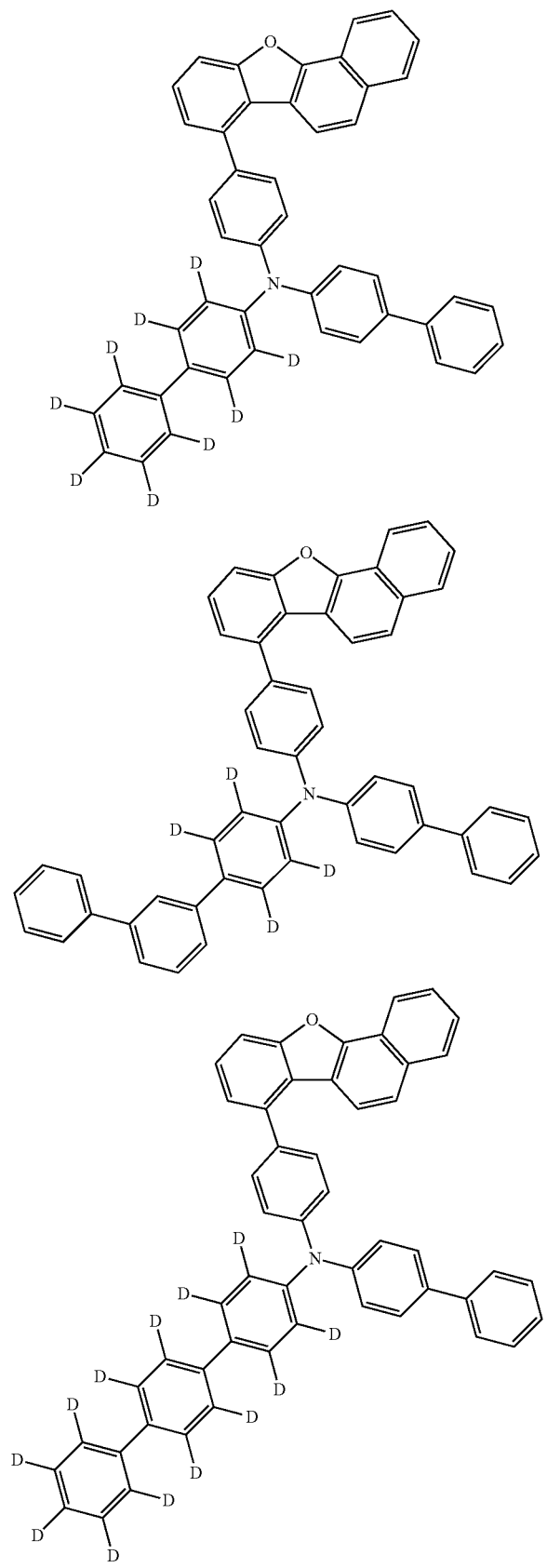
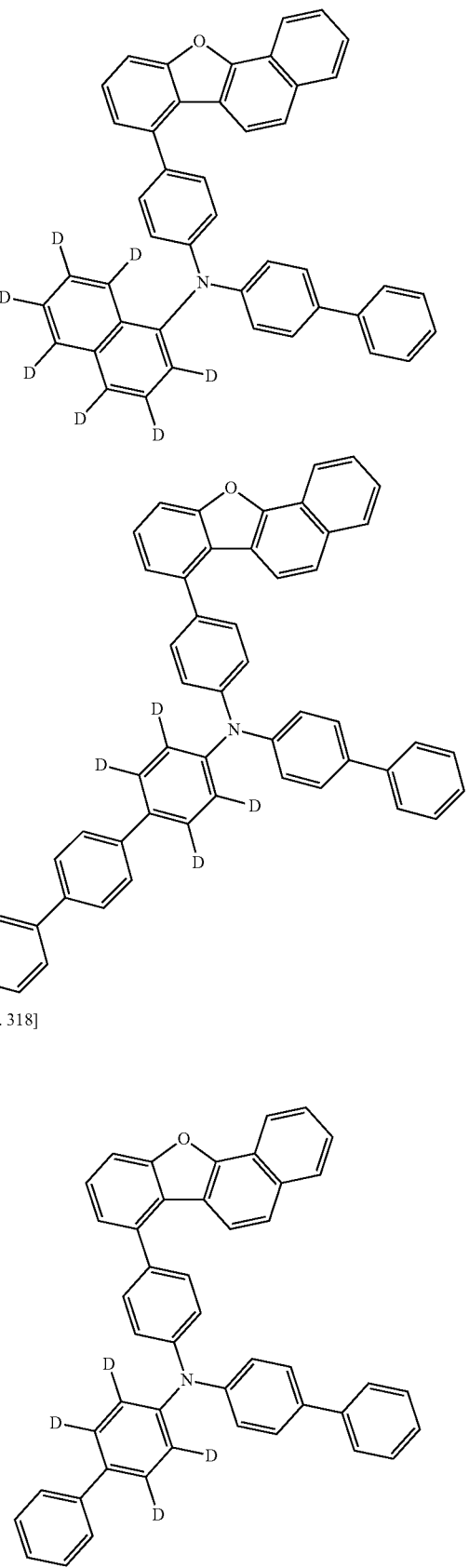
[Chem. 318]

947
-continued
948
-continued
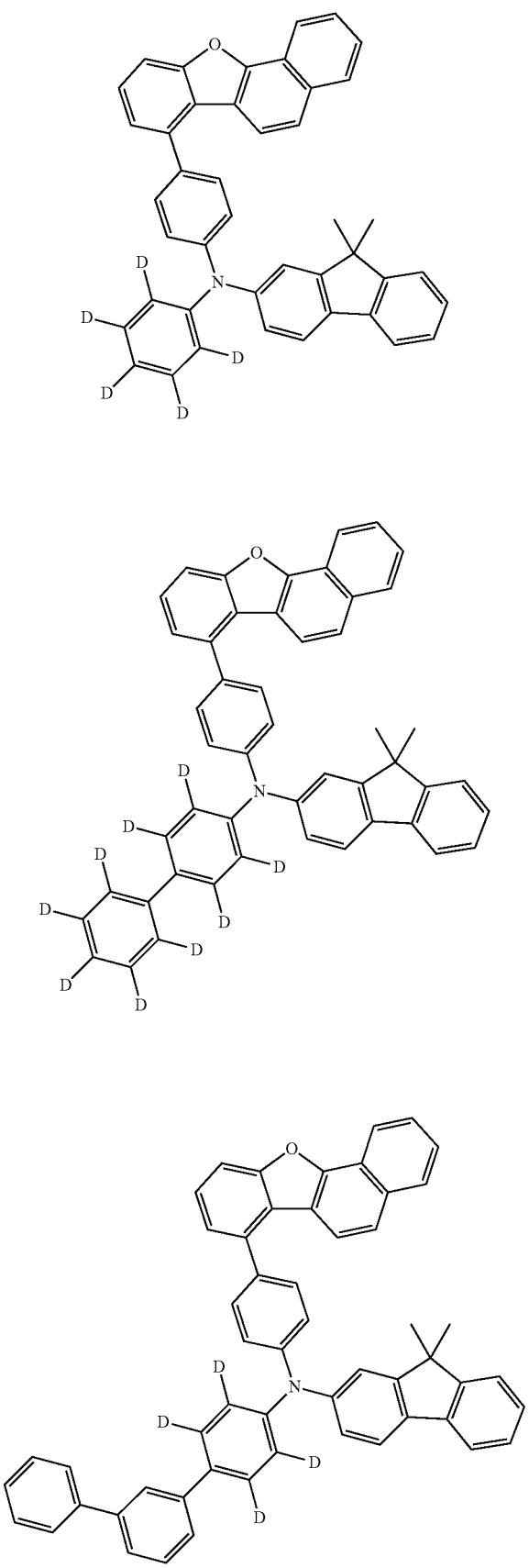
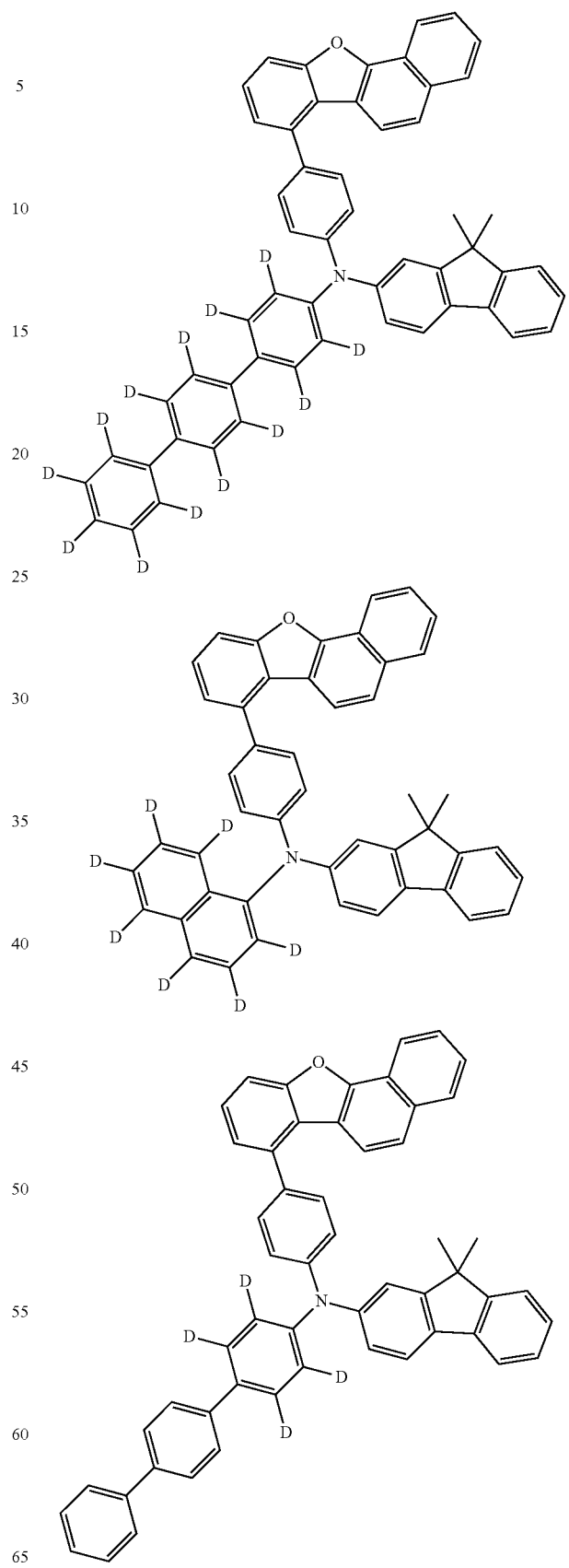

949
-continued
950
-continued
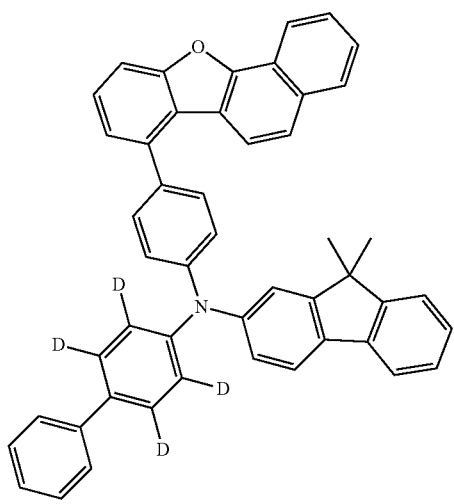
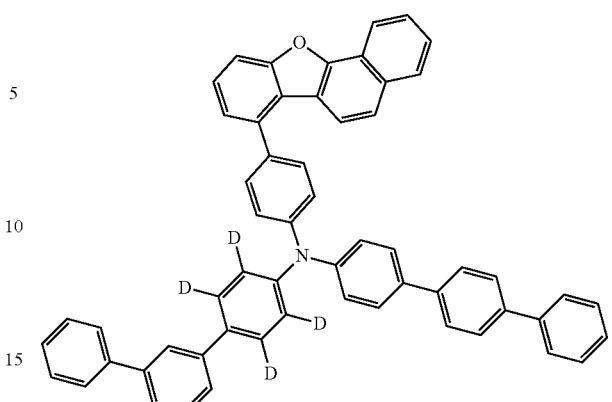
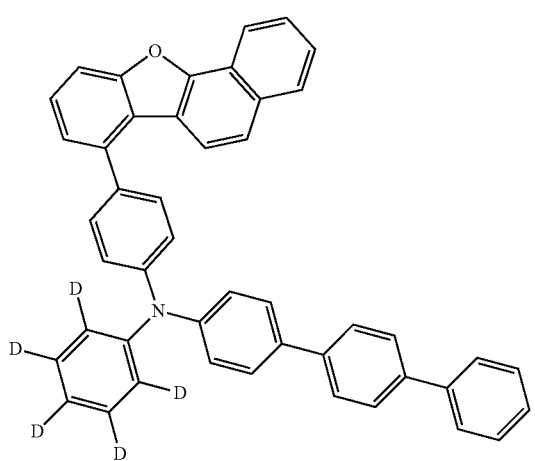
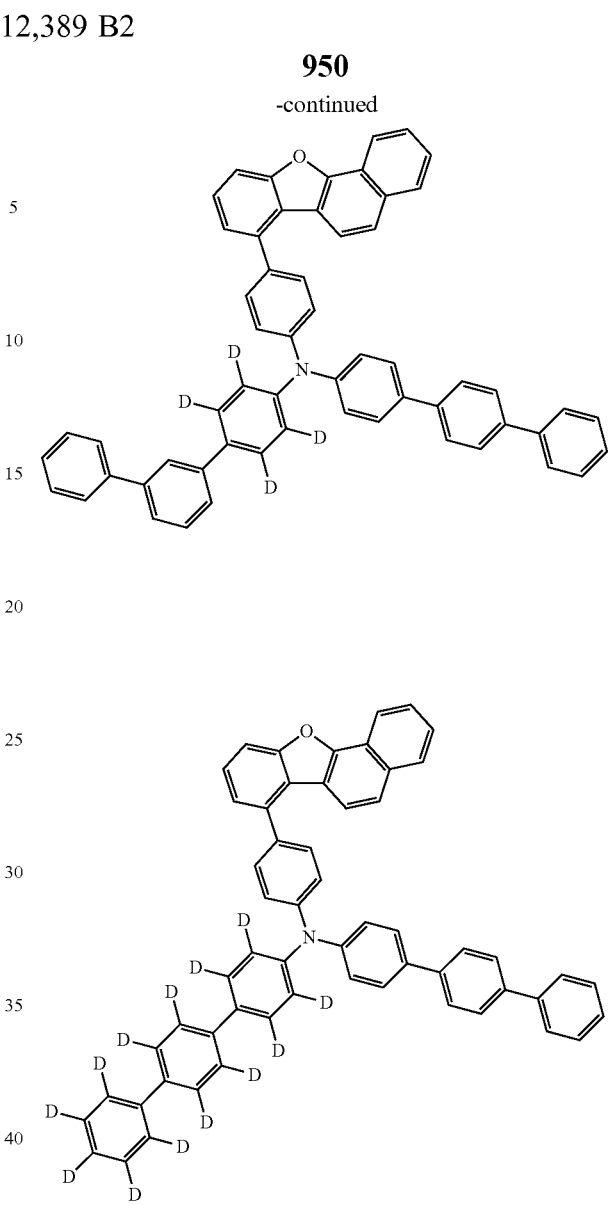
[Chem. 319]
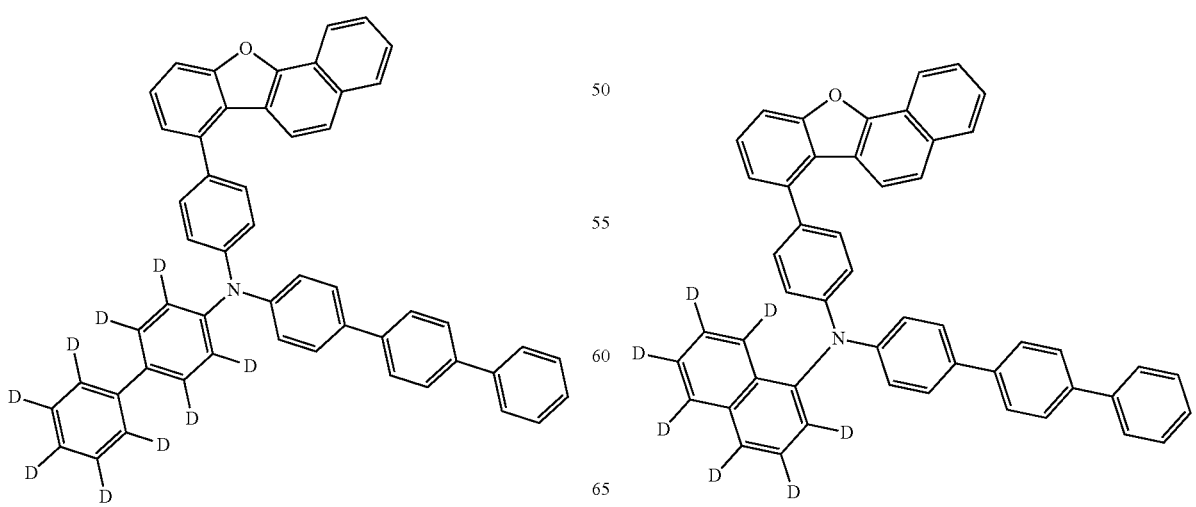

951
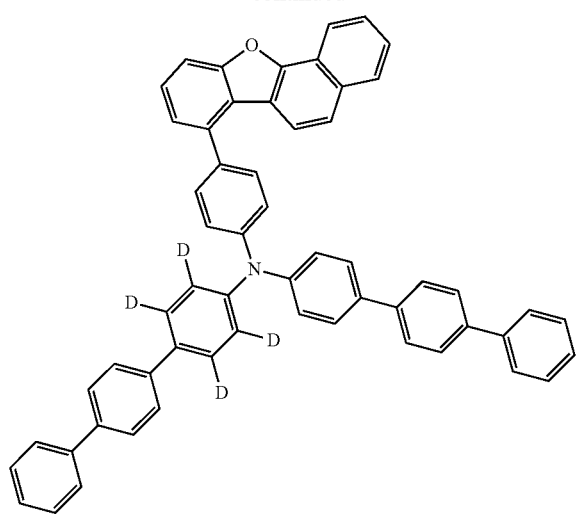
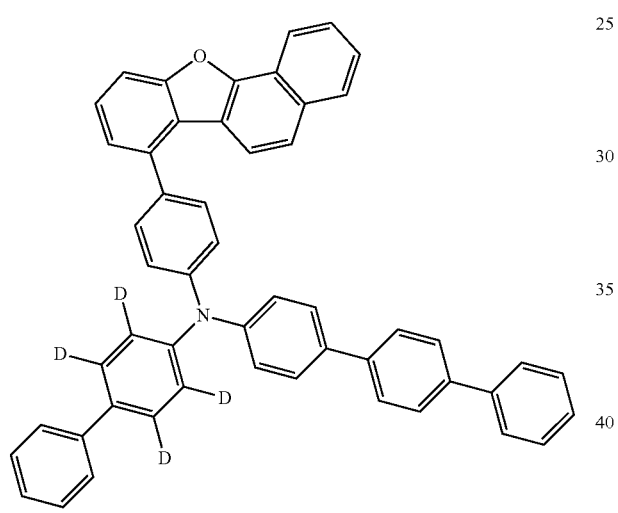
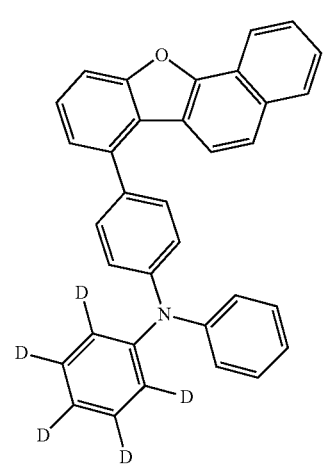
952
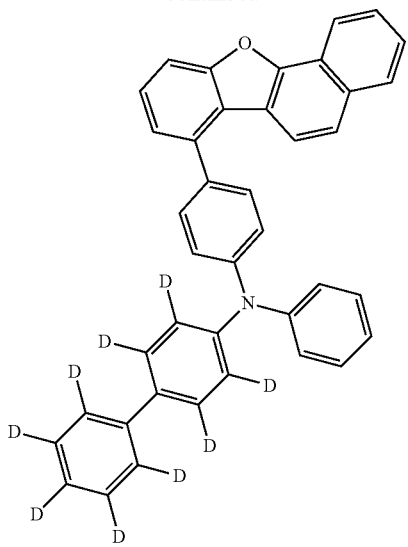
[Chem. 320]
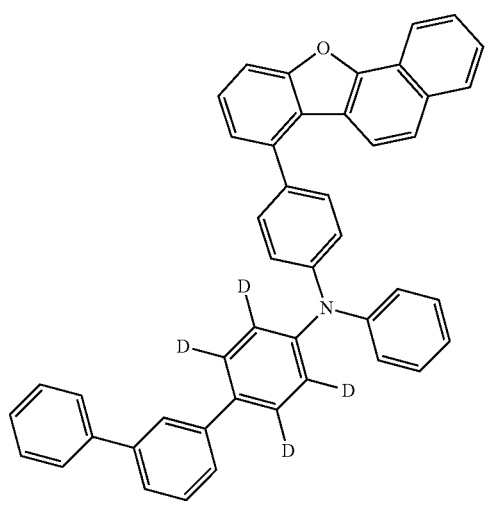
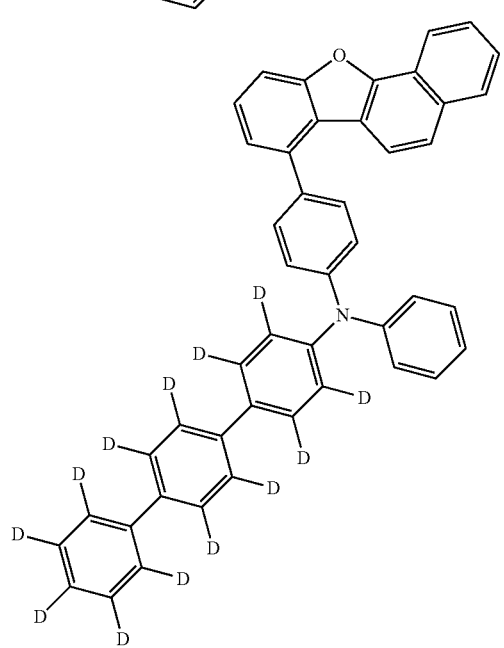

953
-continued
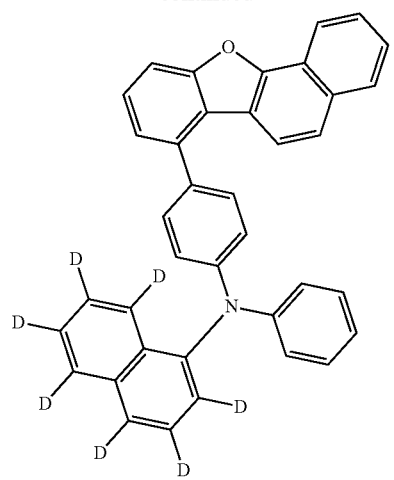
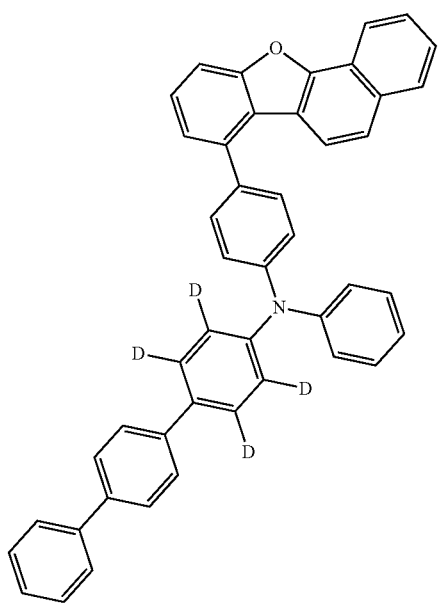
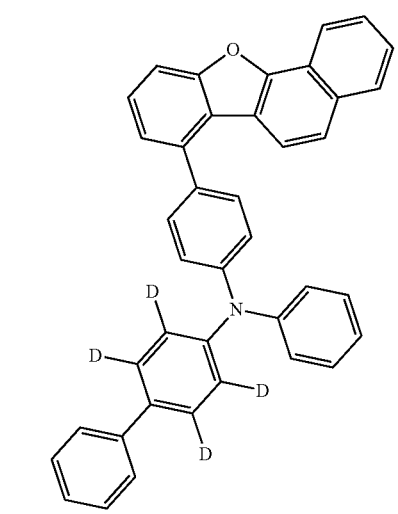
954
-continued
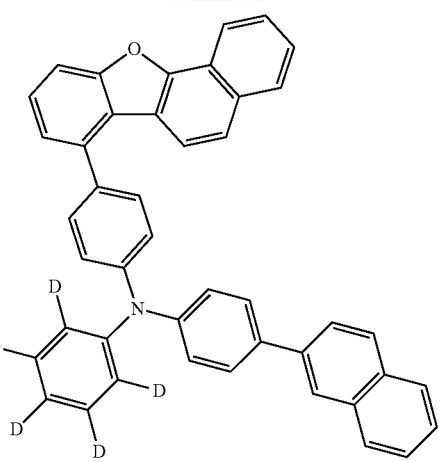
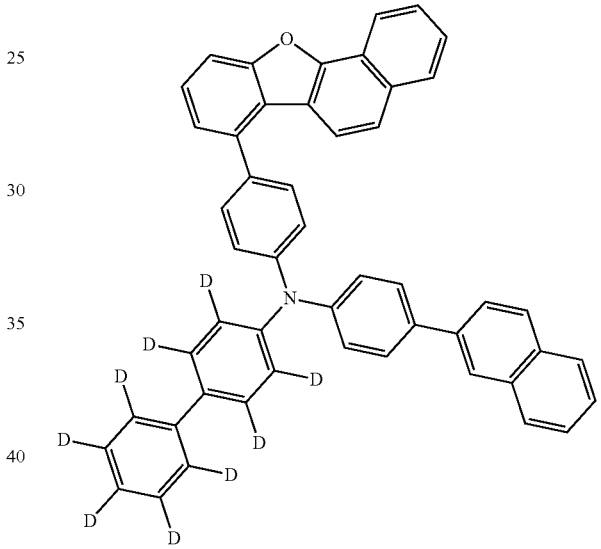
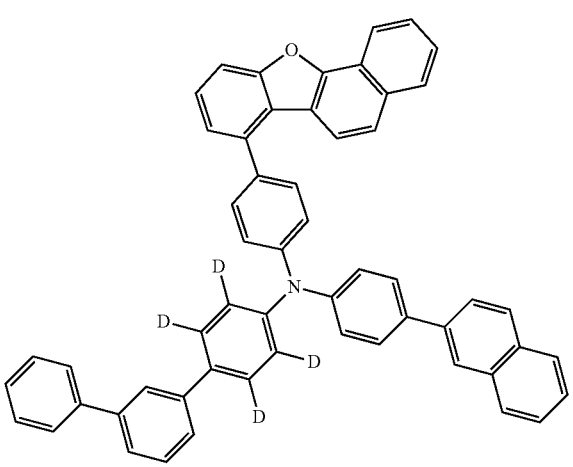

955
-continued
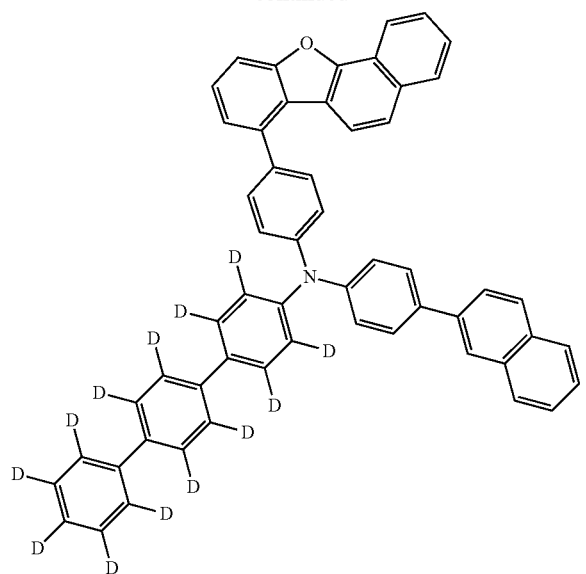
[Chem. 321]
956
-continued
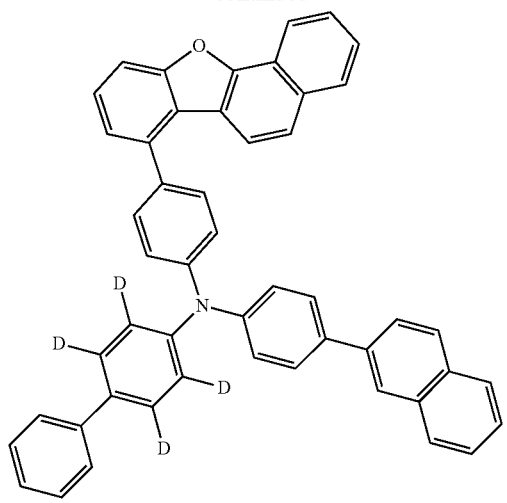
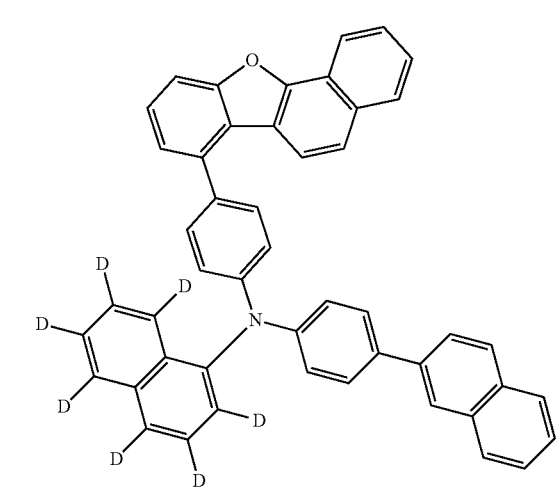
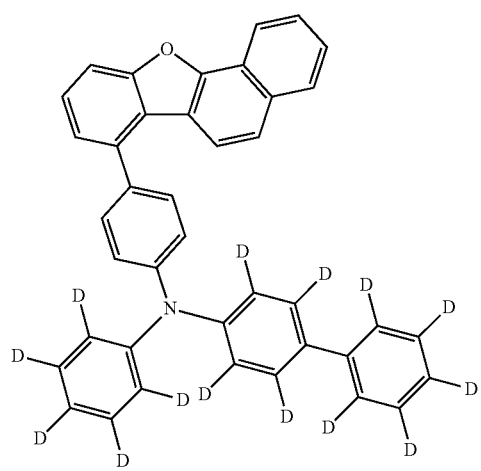

957
-continued
958
-continued
[Chem. 322]
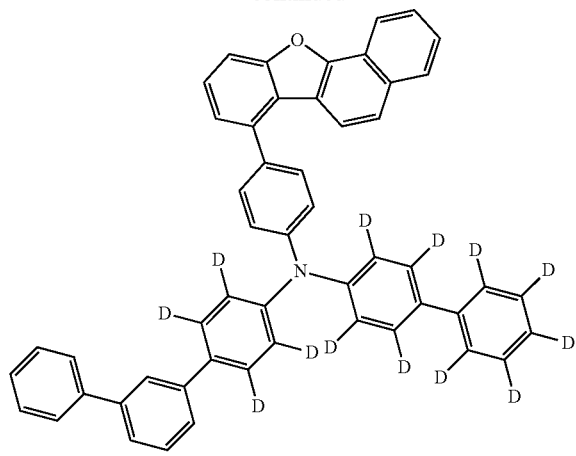
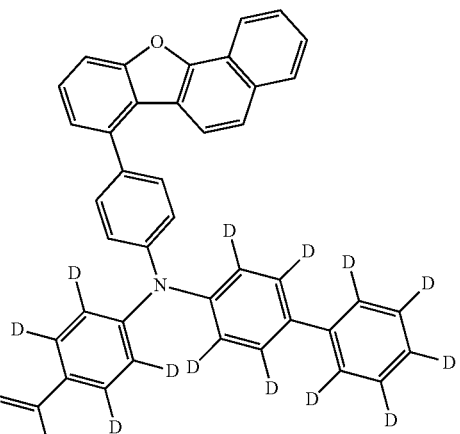
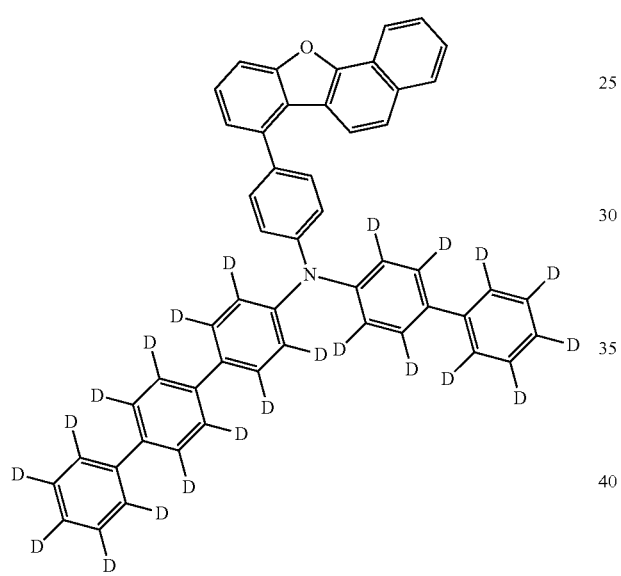
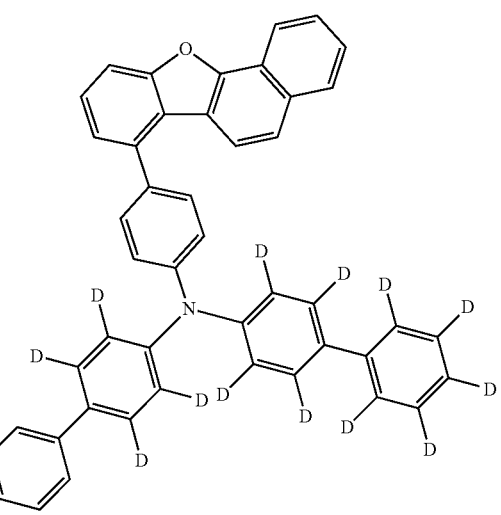
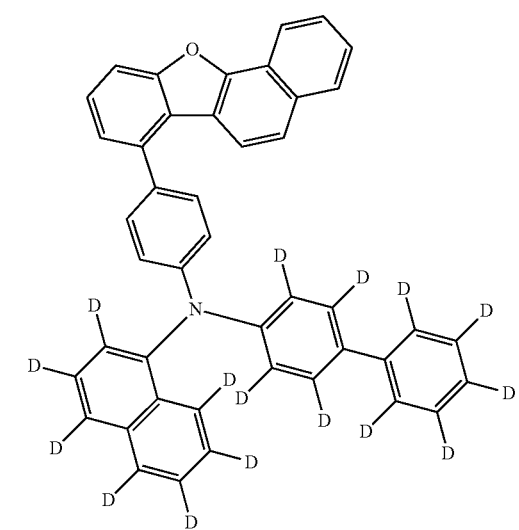

959
-continued
960
-continued
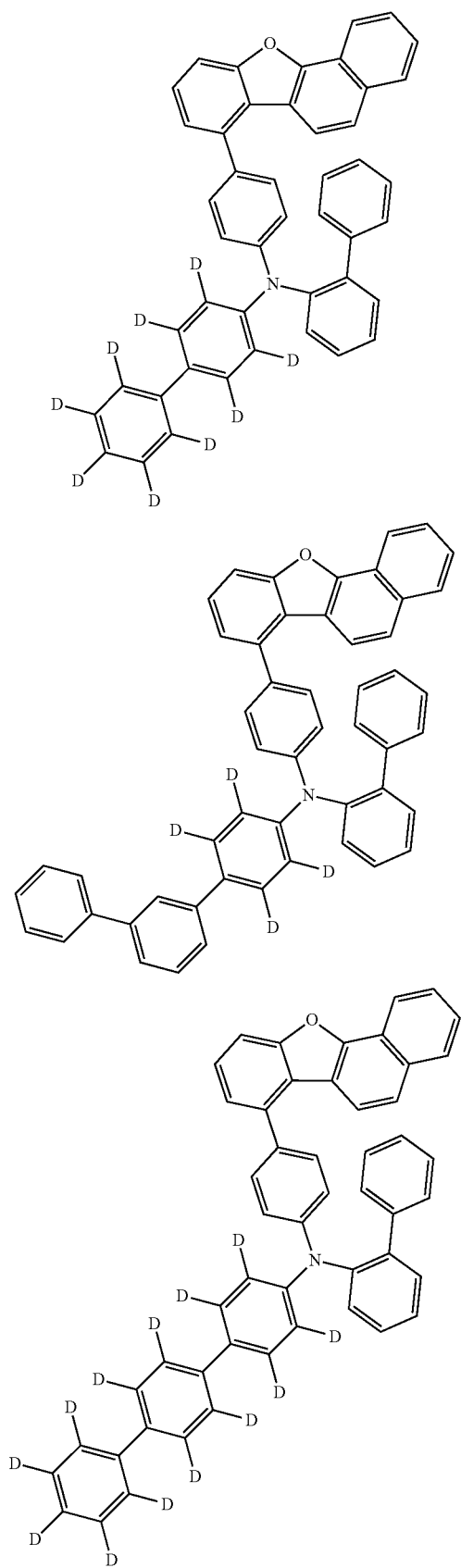
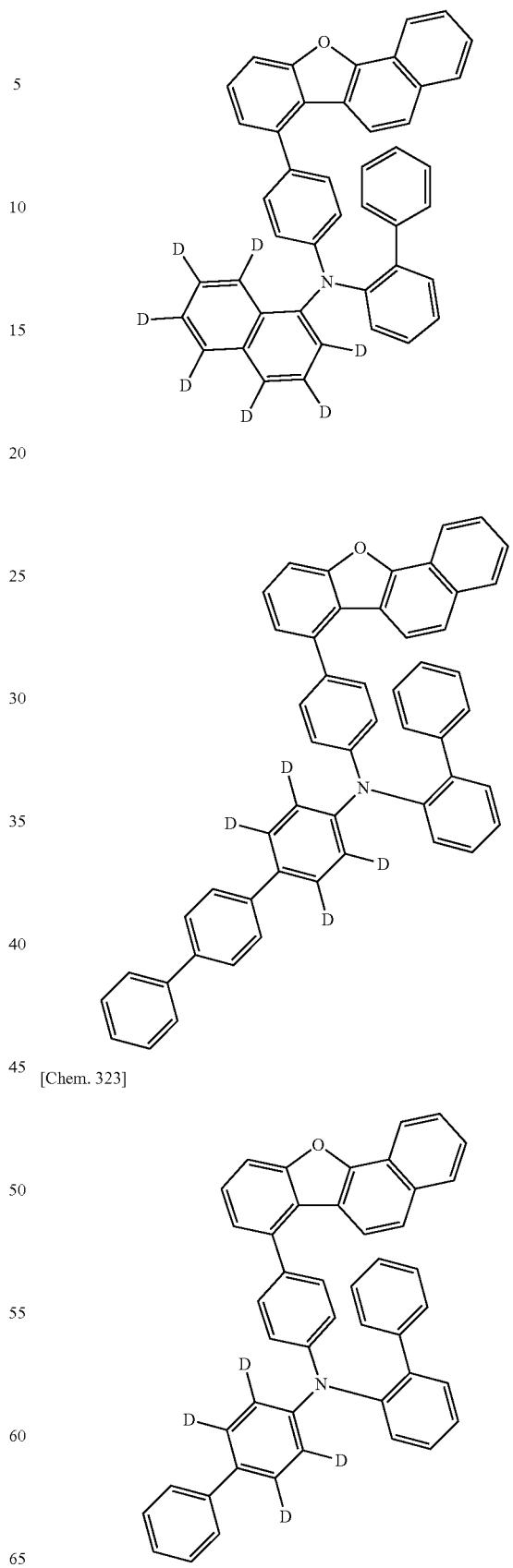
[Chem. 323]

961
-continued
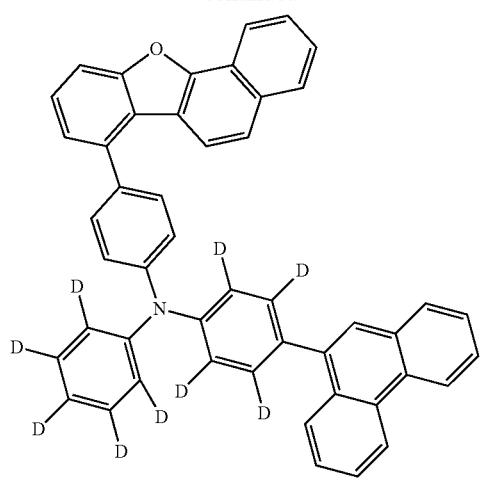
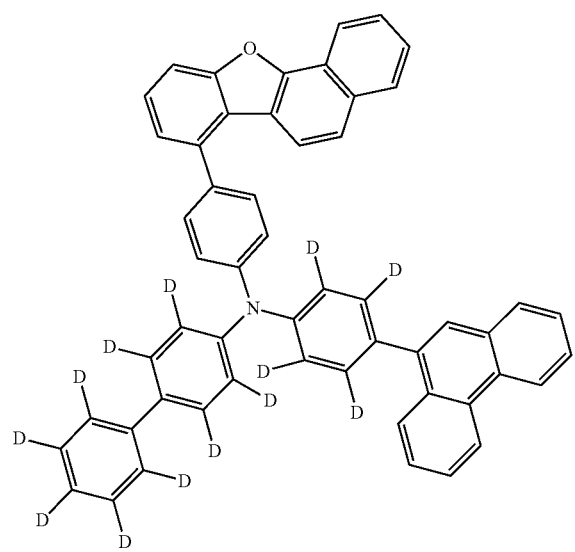
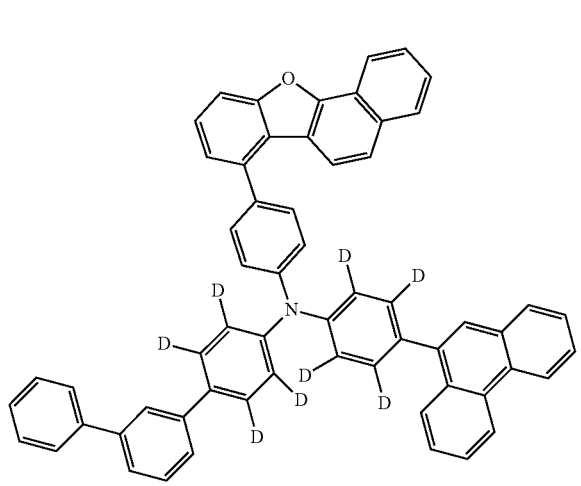
962
-continued
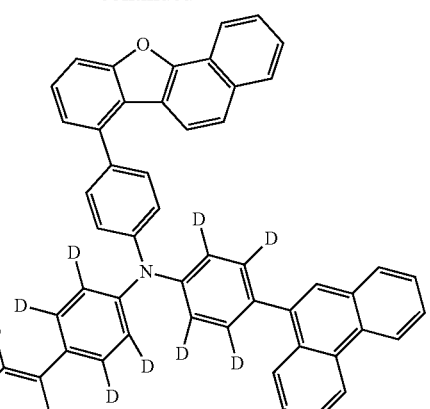
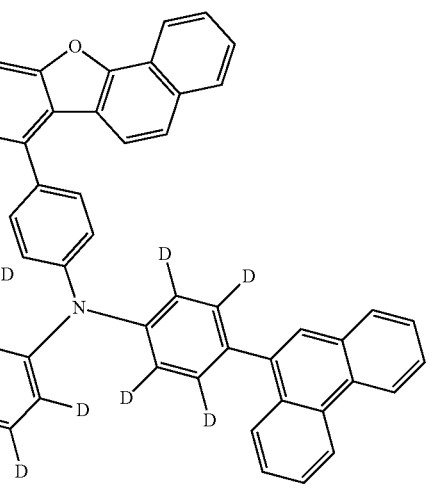
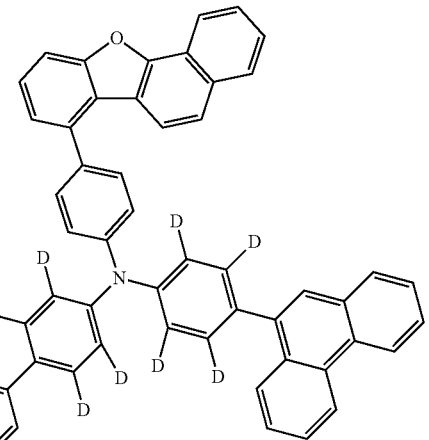

963
-continued
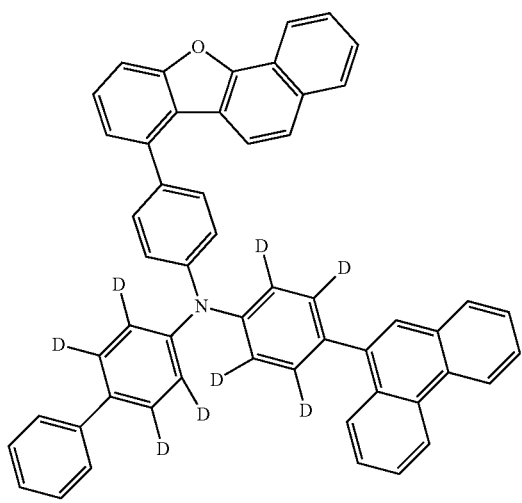
[Chem. 324]
964
-continued
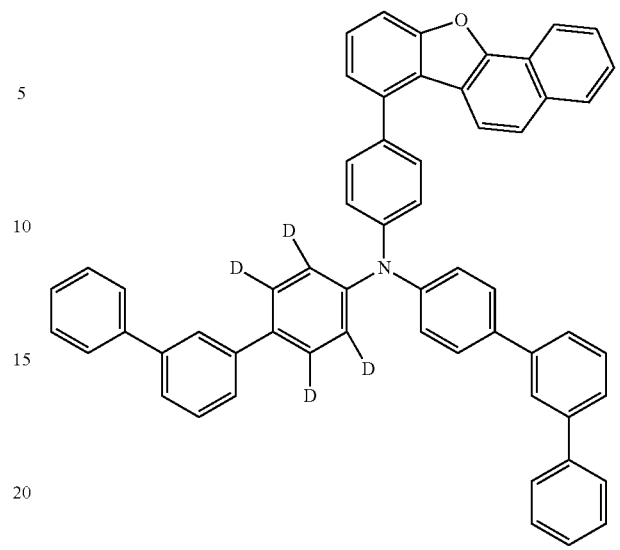
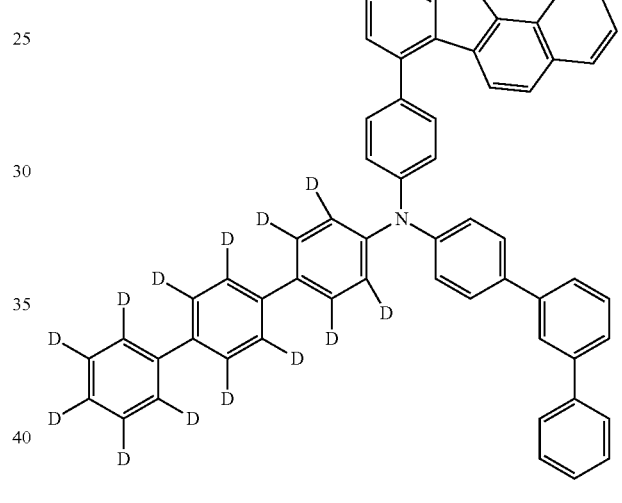
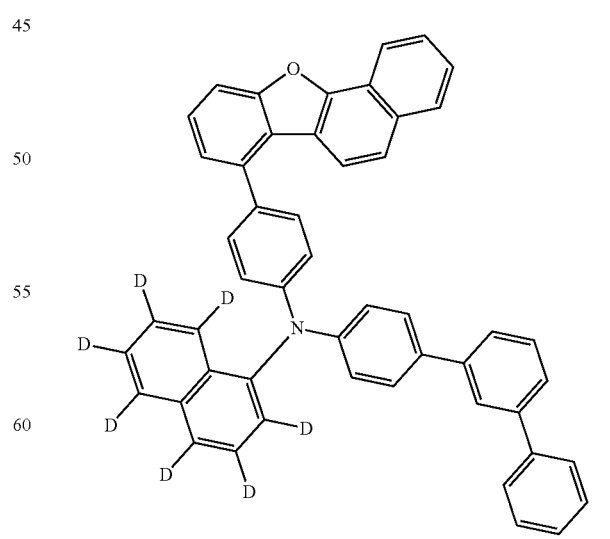

965
-continued
966
-continued
[Chem. 325]
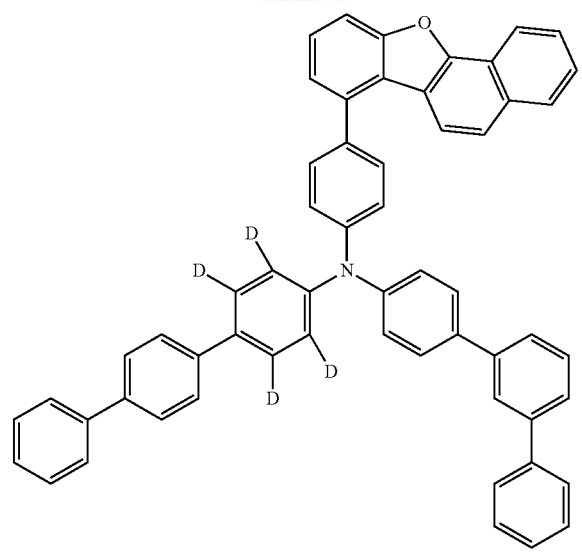
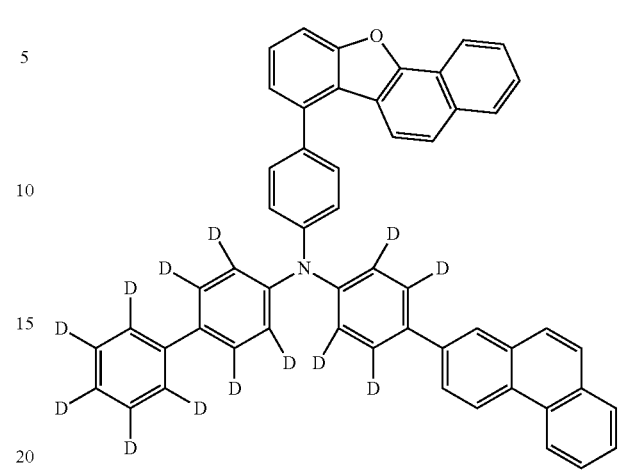
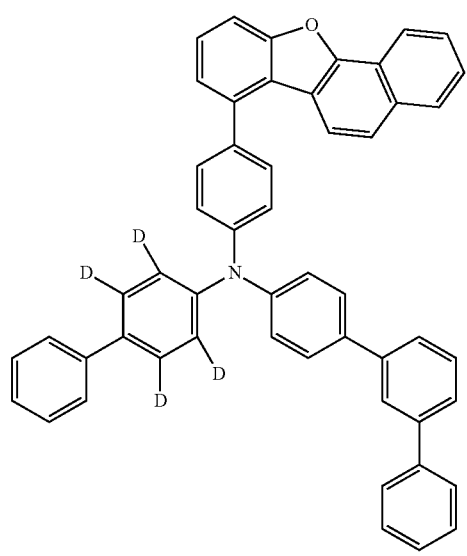
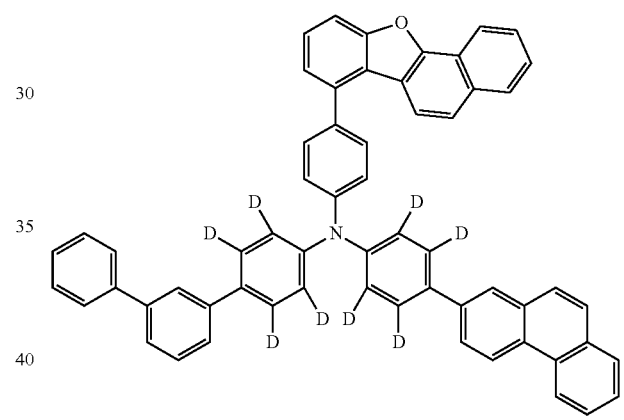
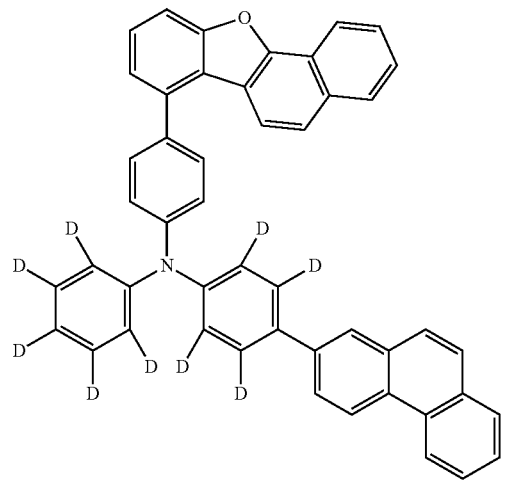
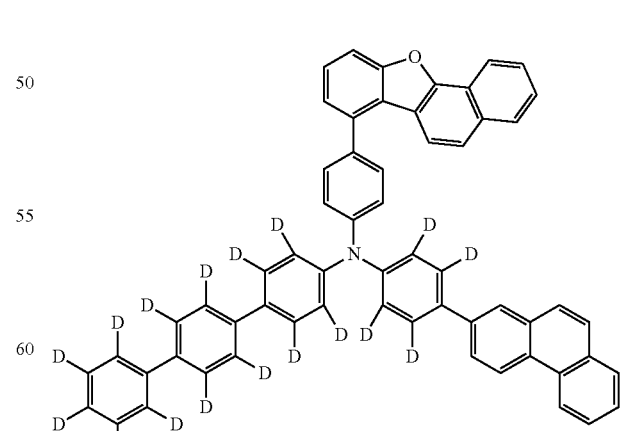

967
-continued
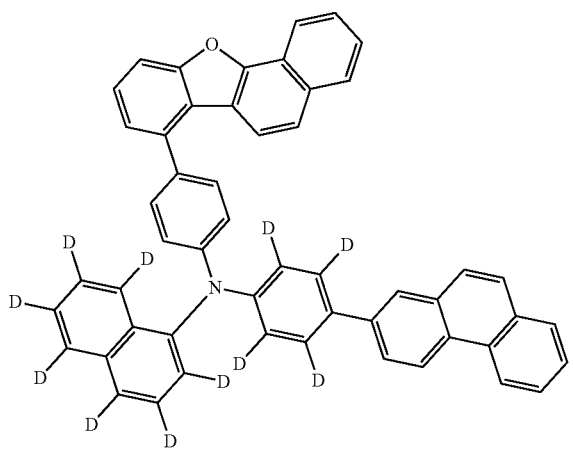
968
-continued
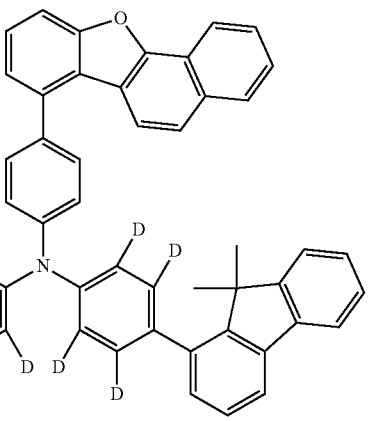
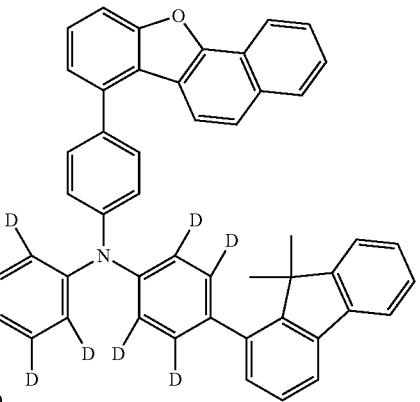
[Chem. 326]
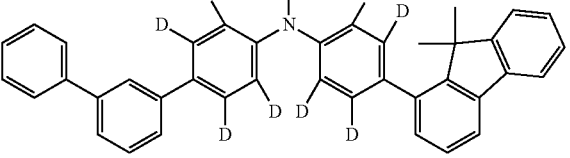
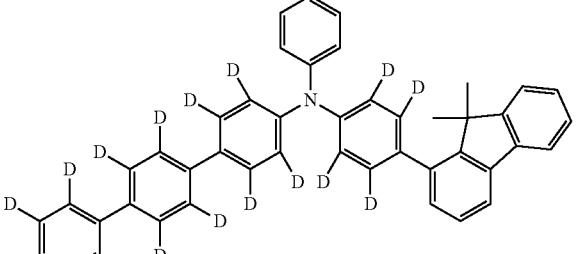

969
-continued
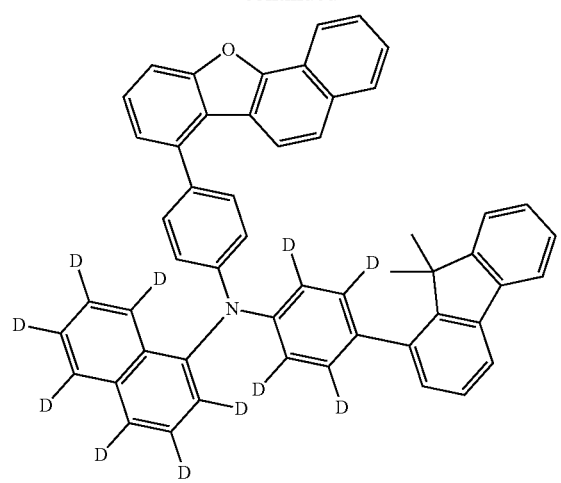
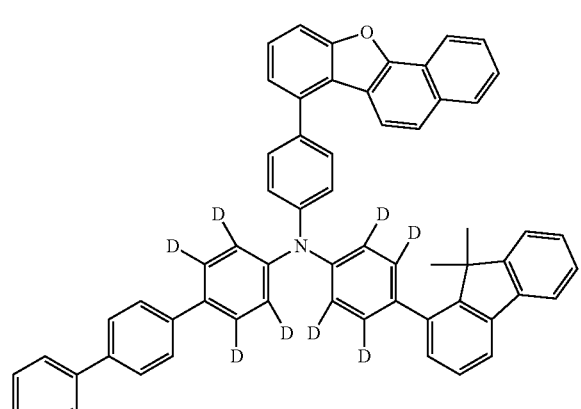
970
-continued
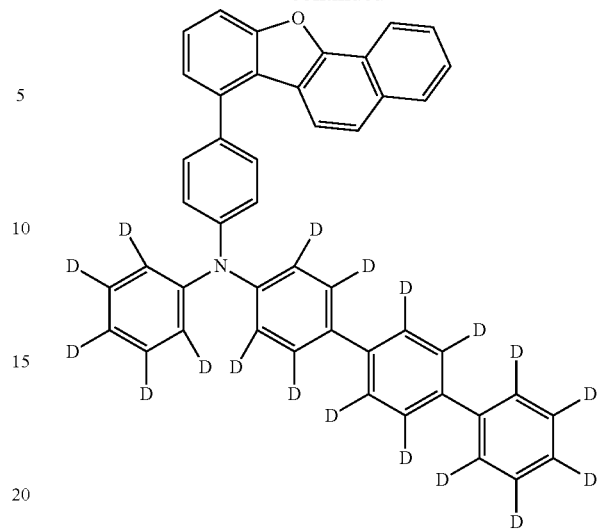
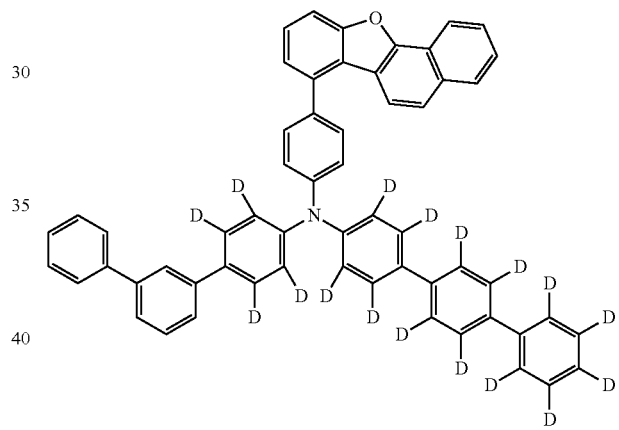
[Chem. 327]
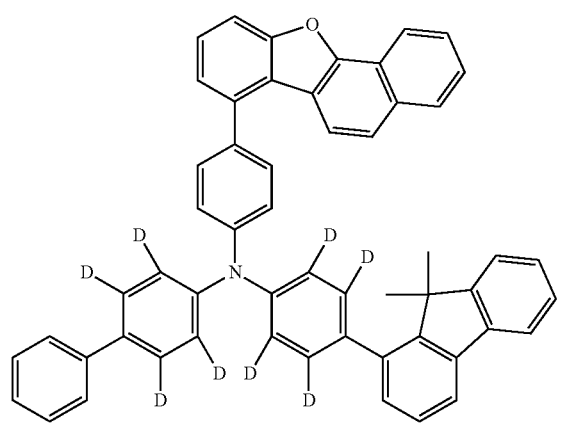
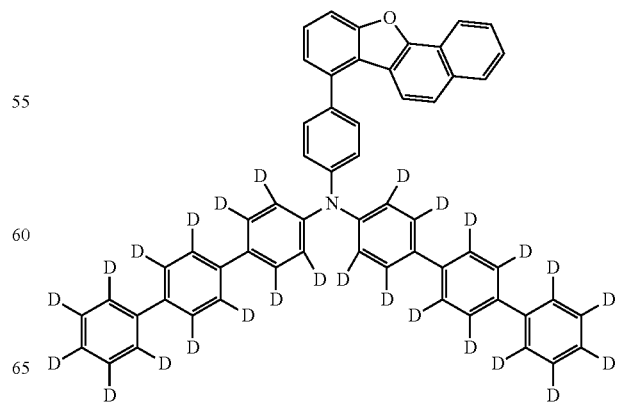

971
-continued
972
-continued
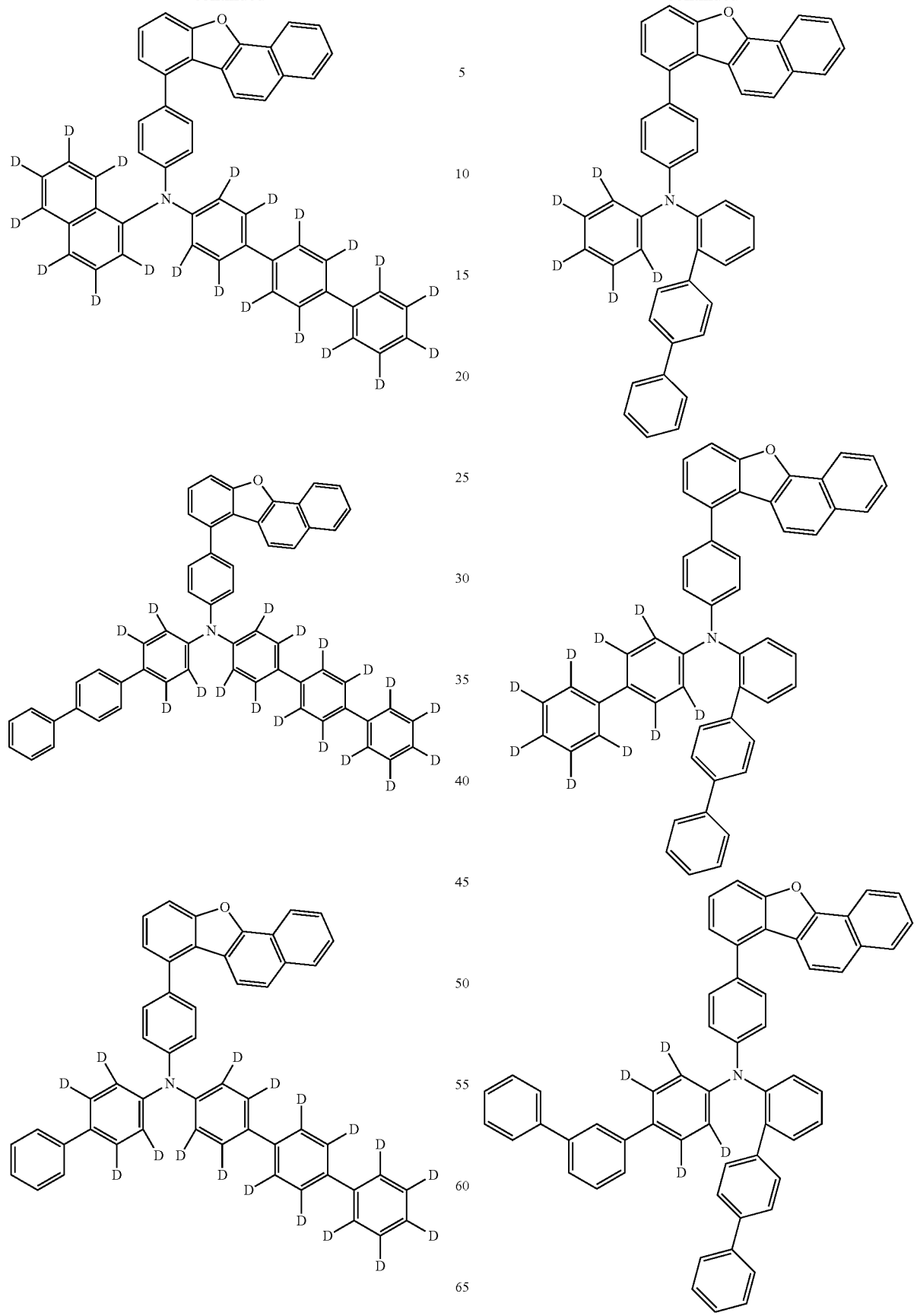

973
-continued
974
-continued
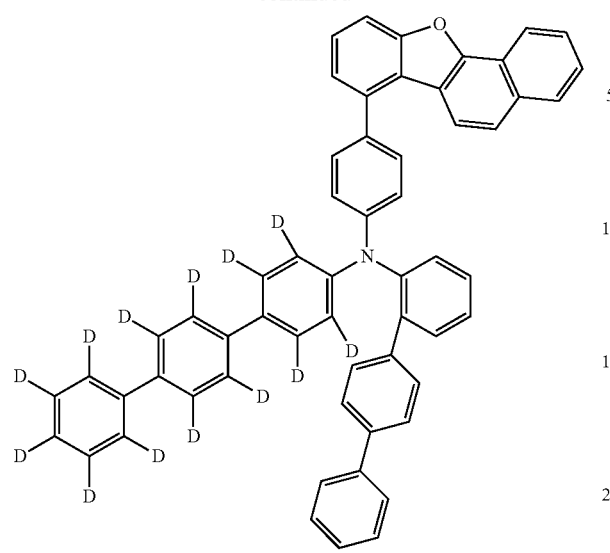
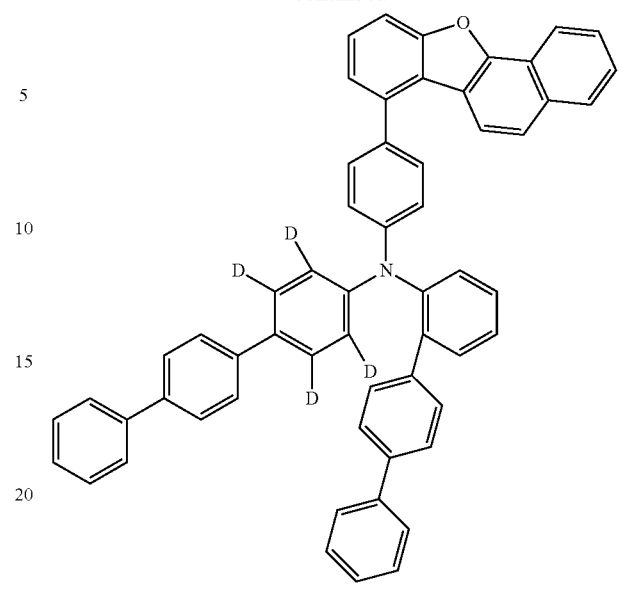
[Chem. 328]
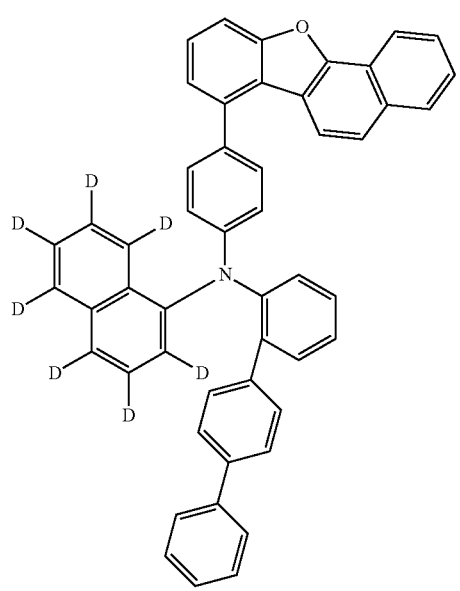

975
-continued
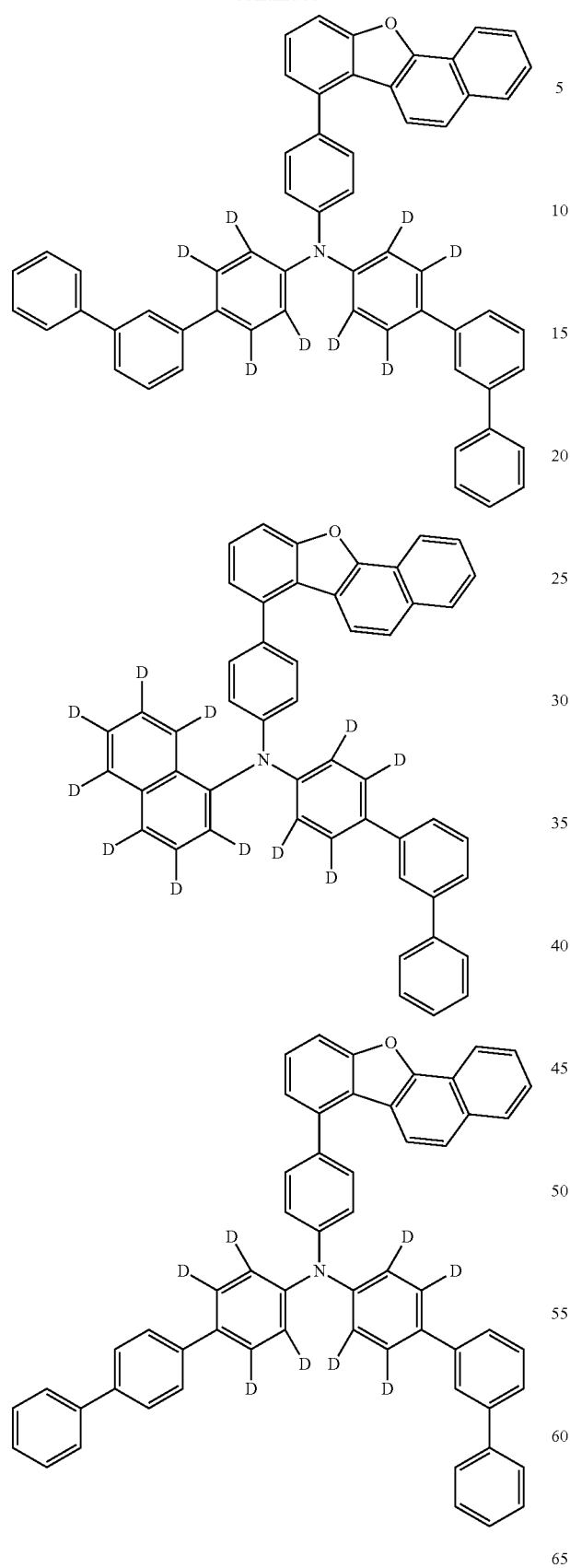
976
-continued
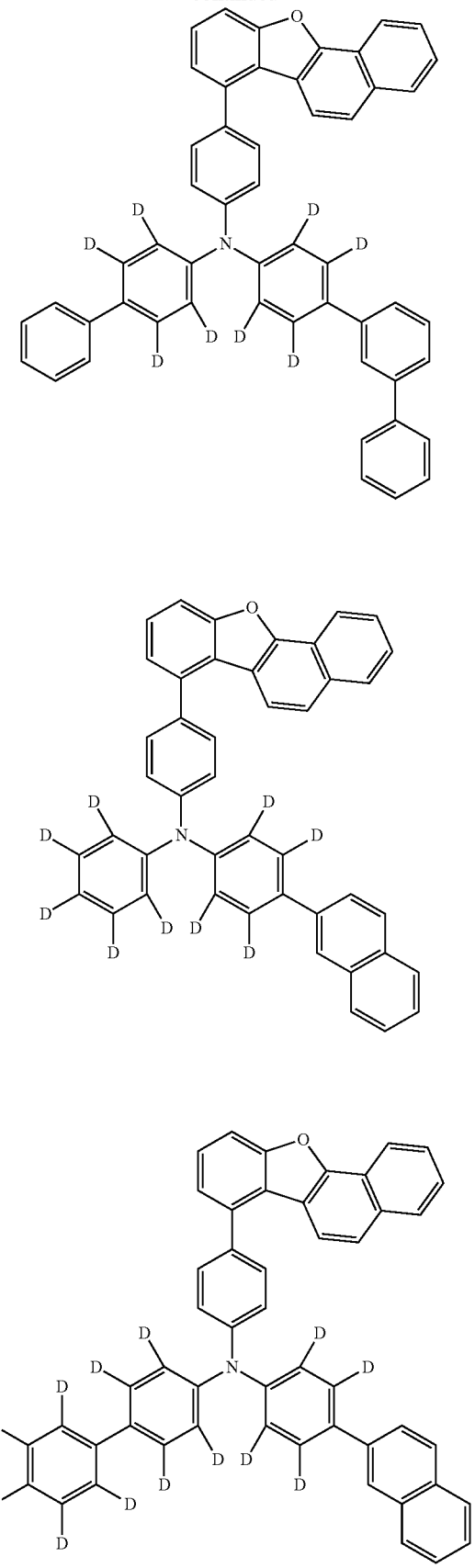

977
-continued
[Chem. 329]
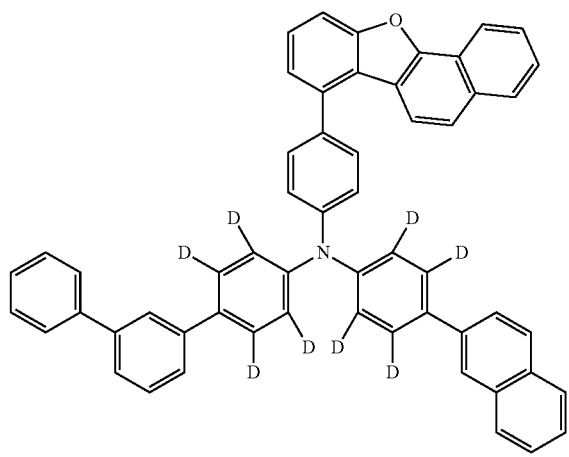
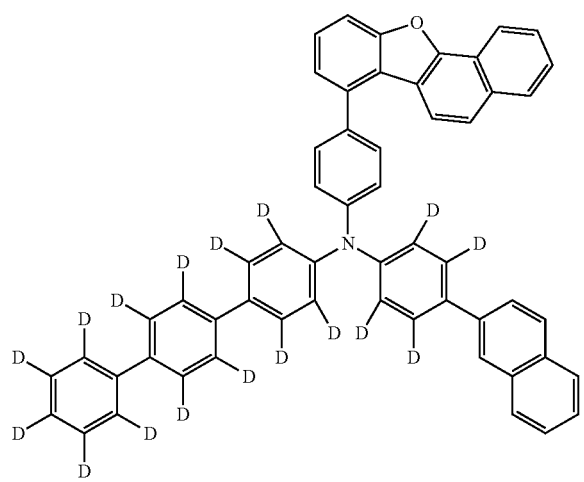
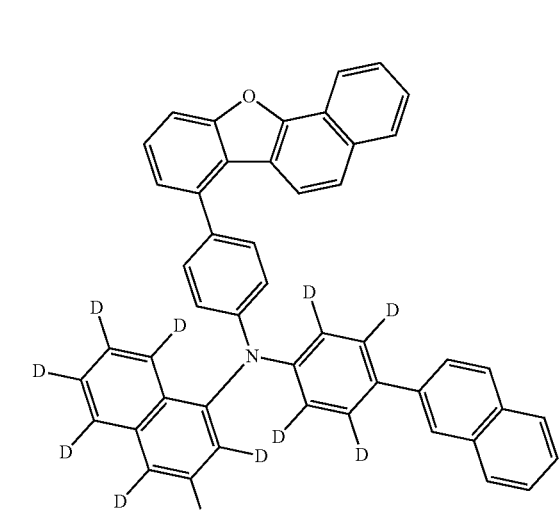
978
-continued
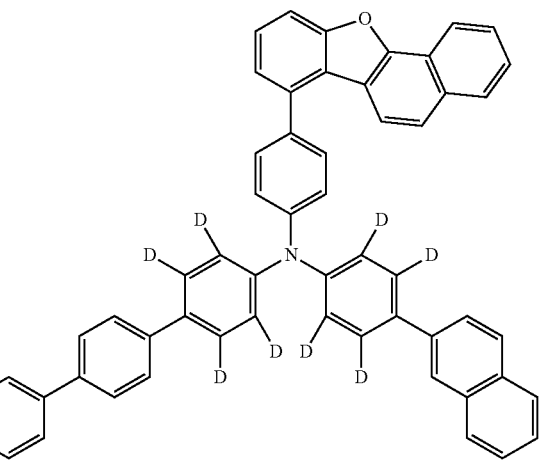
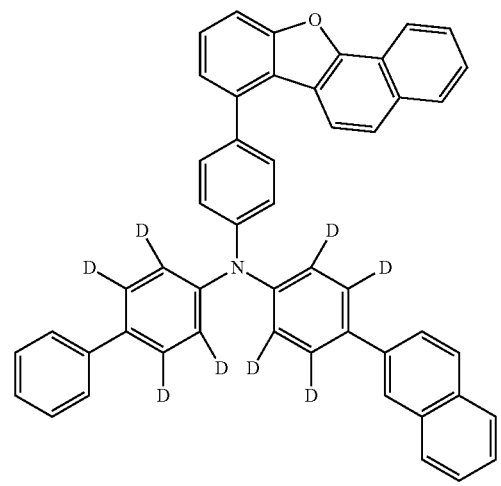
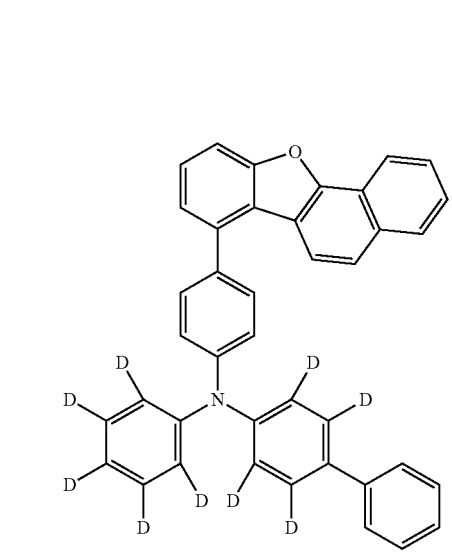

979
-continued
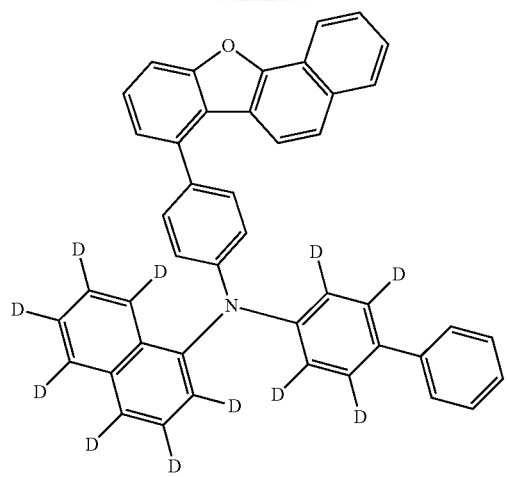
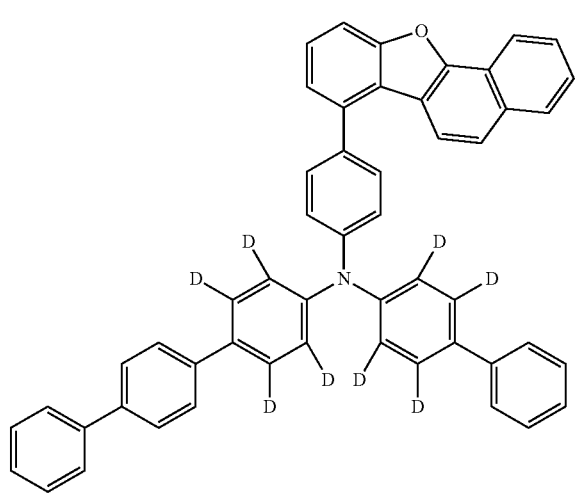
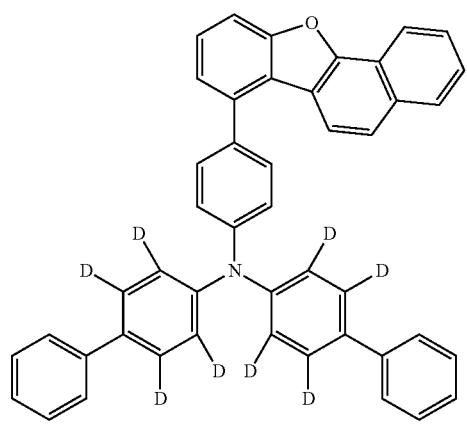
980
-continued
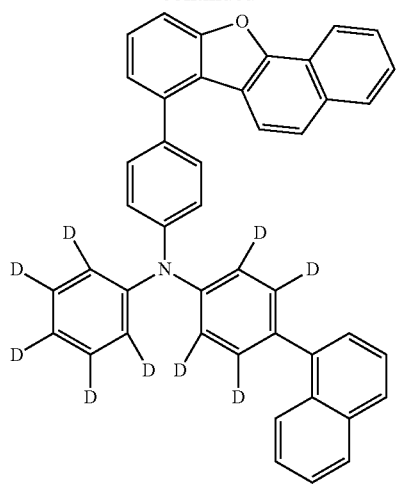
[Chem. 330]
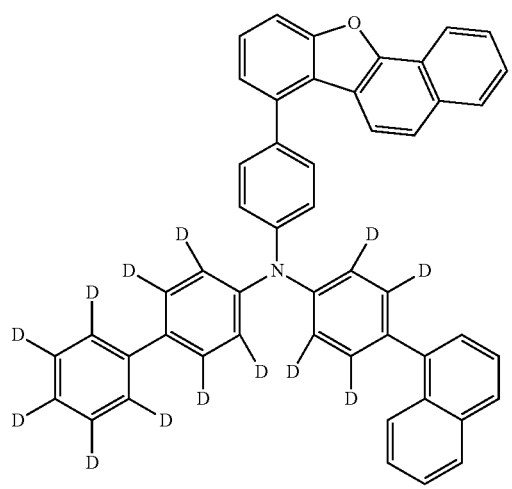
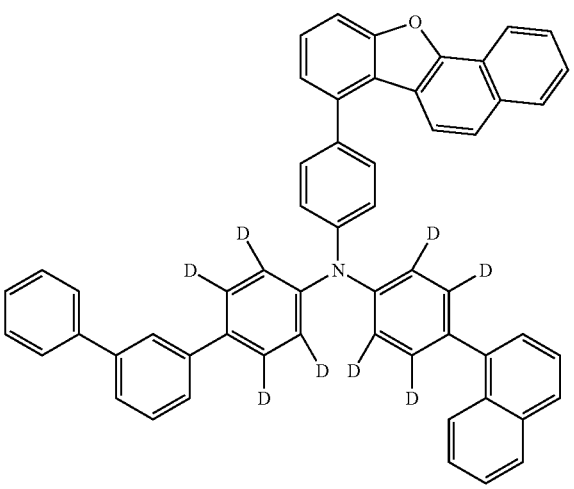

981
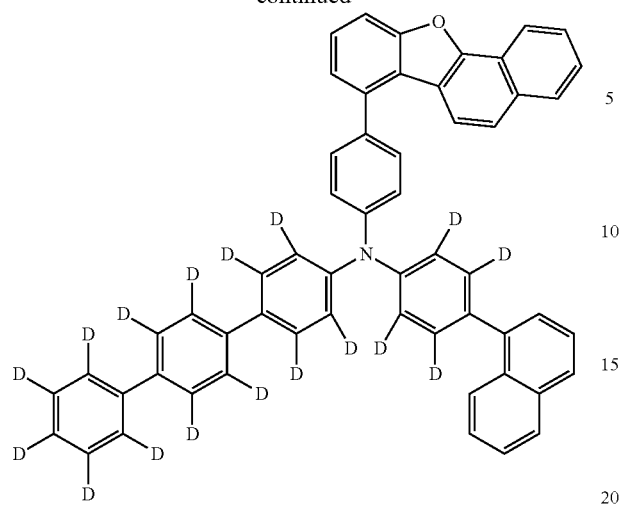
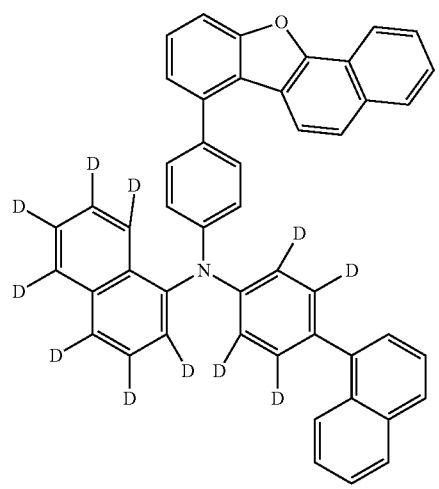
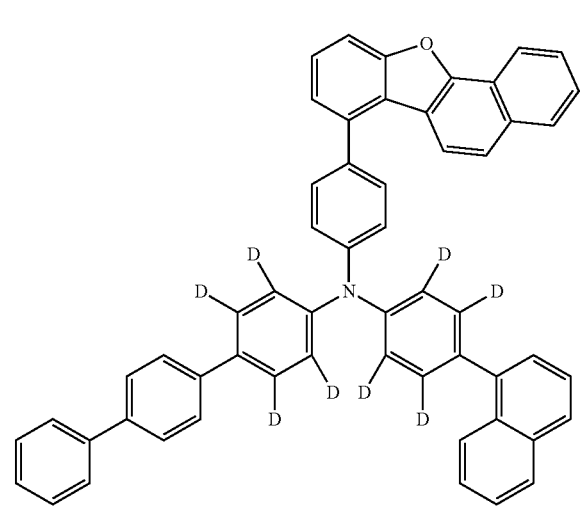
982
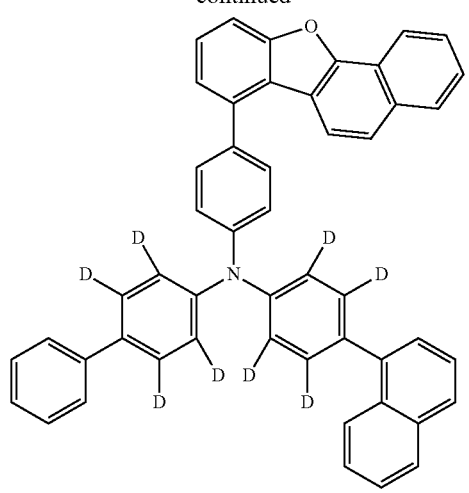
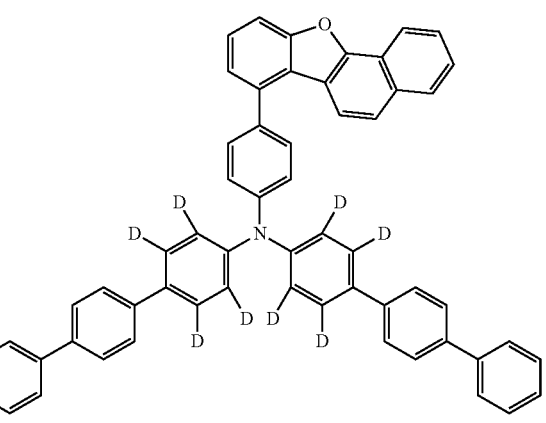
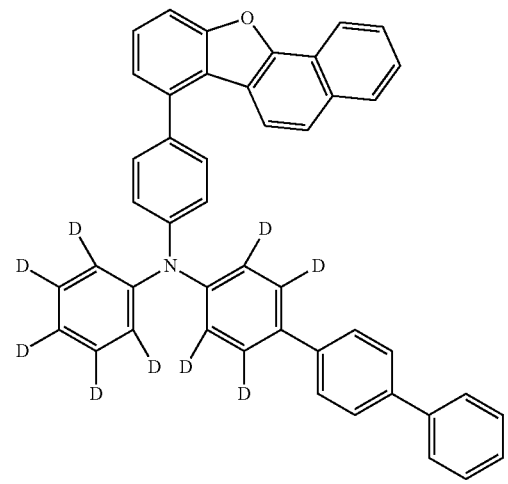

983
-continued
984
-continued
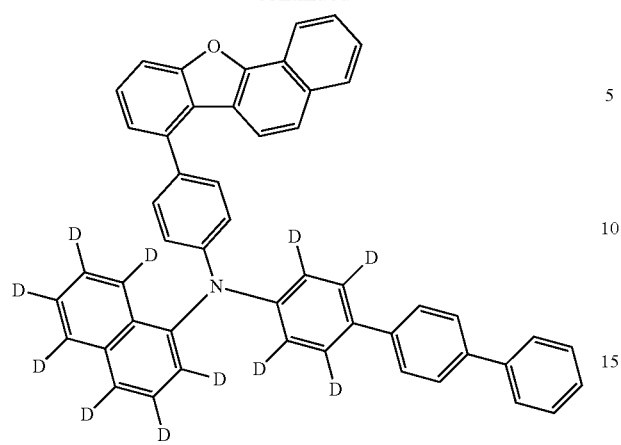
[Chem. 331]
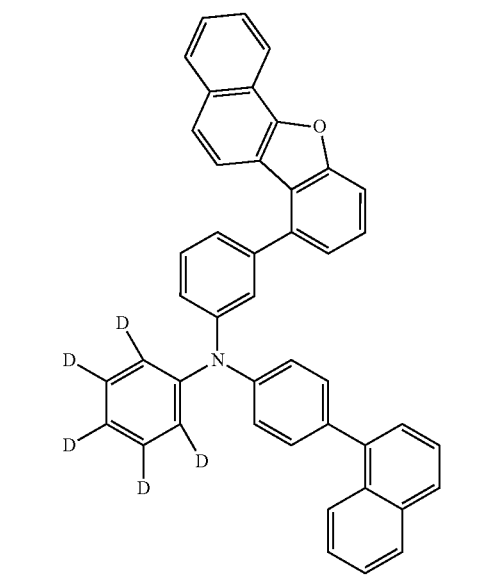
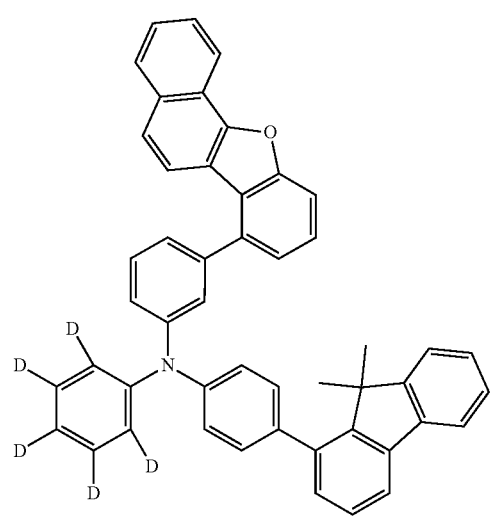
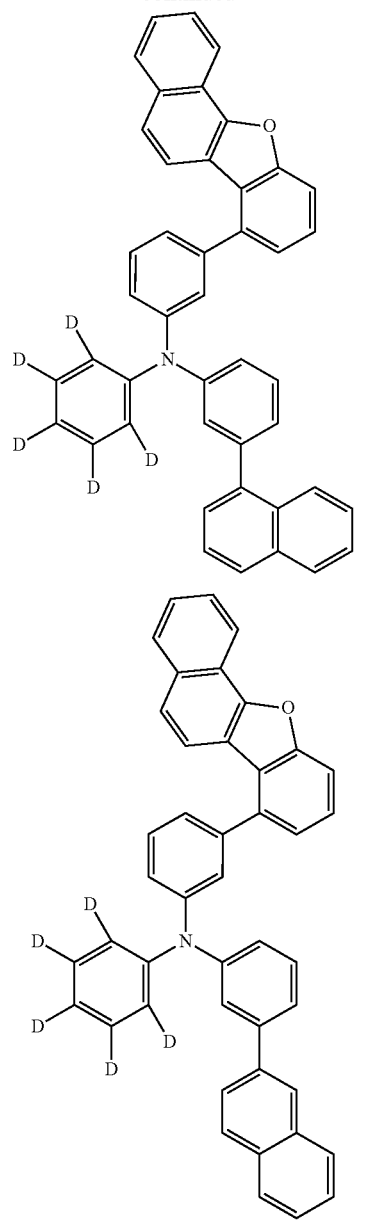
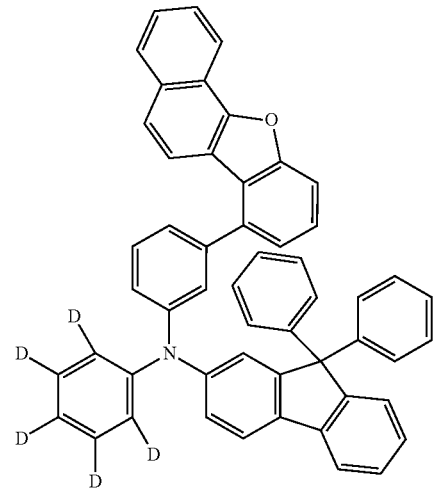

985
-continued
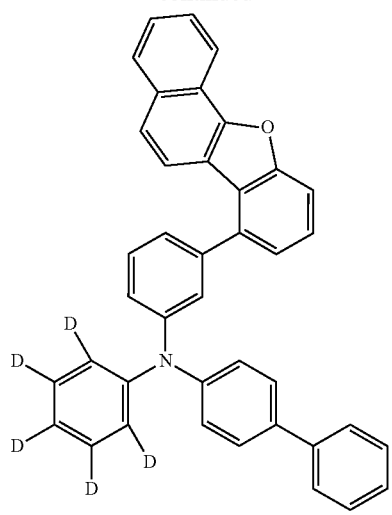
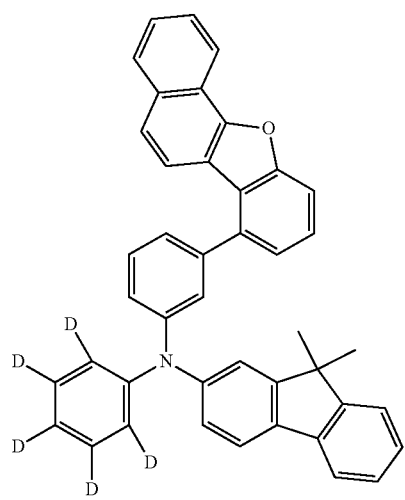
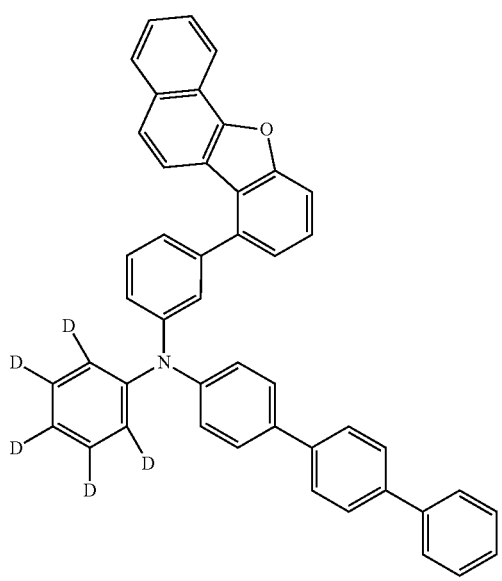
986
-continued
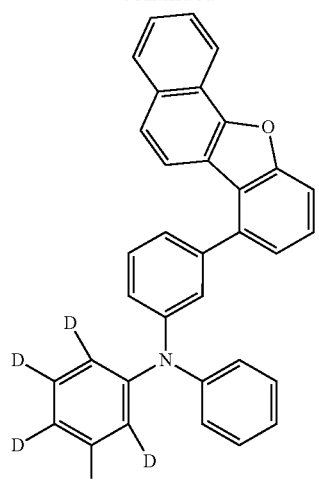
[Chem. 332]
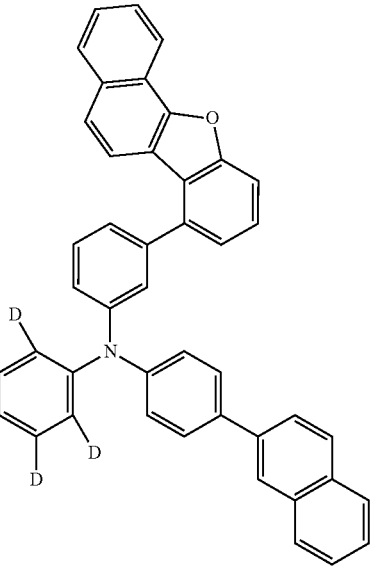
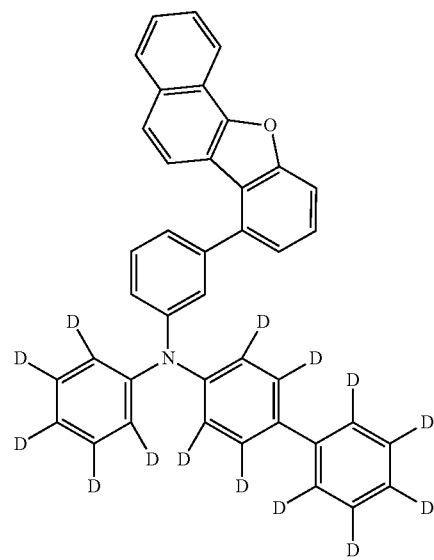

987 988
-continued -continued
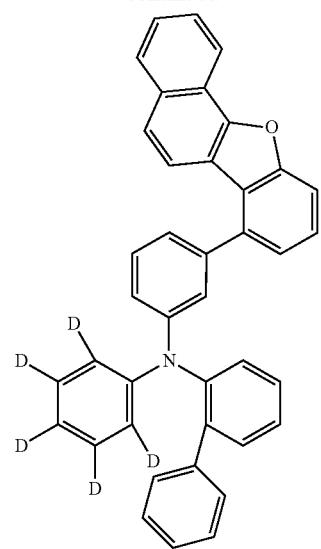
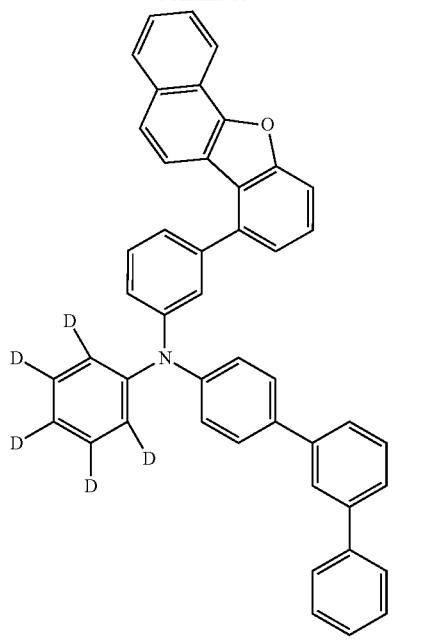
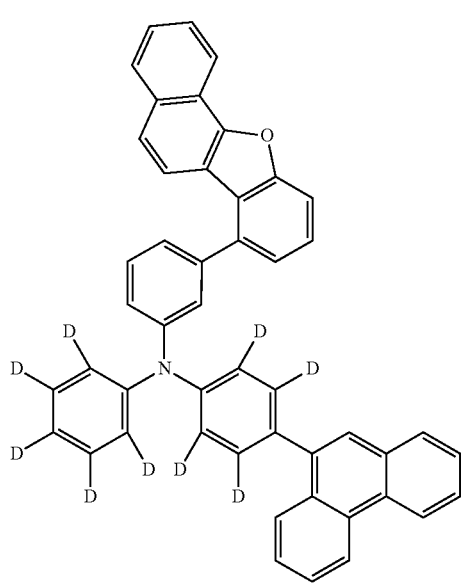
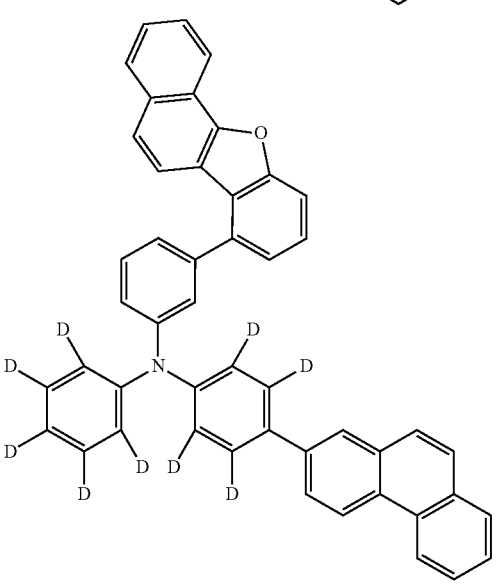
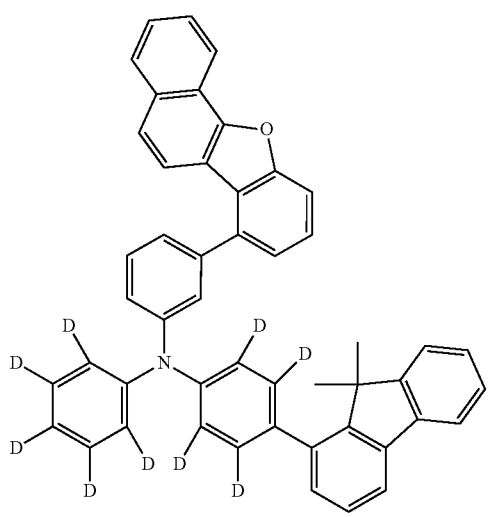

989
-continued
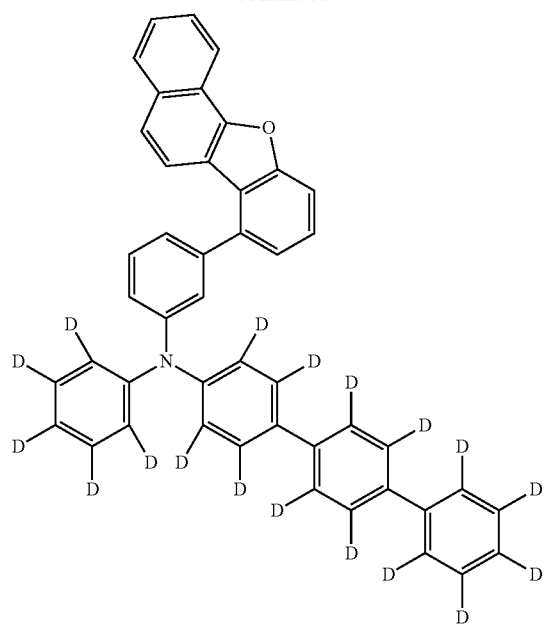
990
-continued
[Chem. 333]
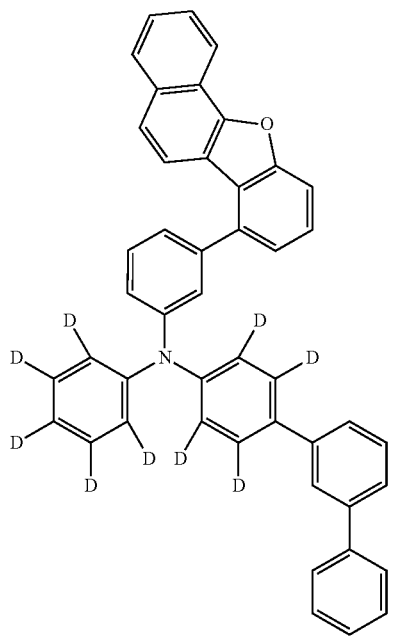
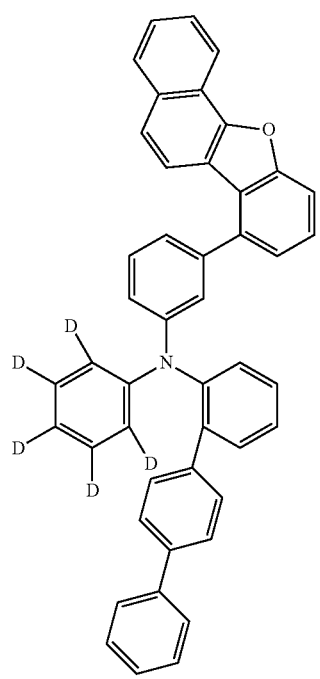
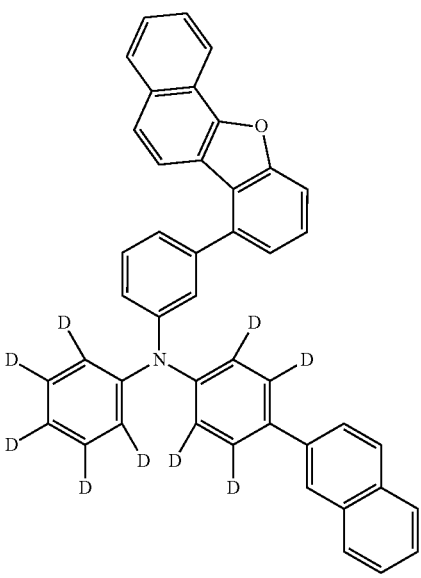

991
-continued
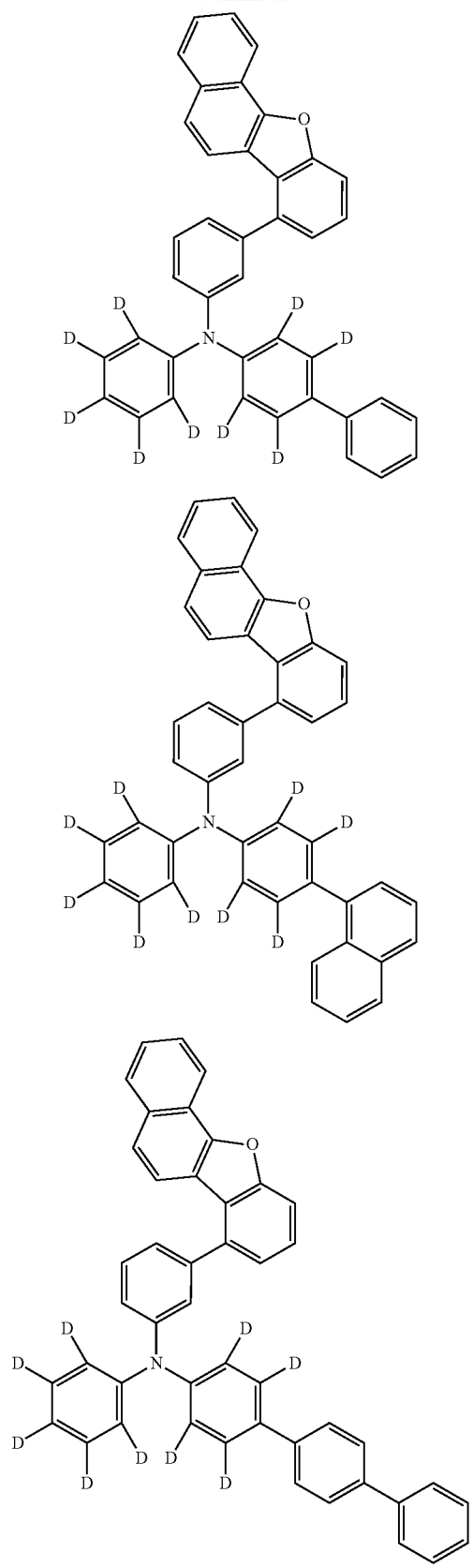
992
-continued
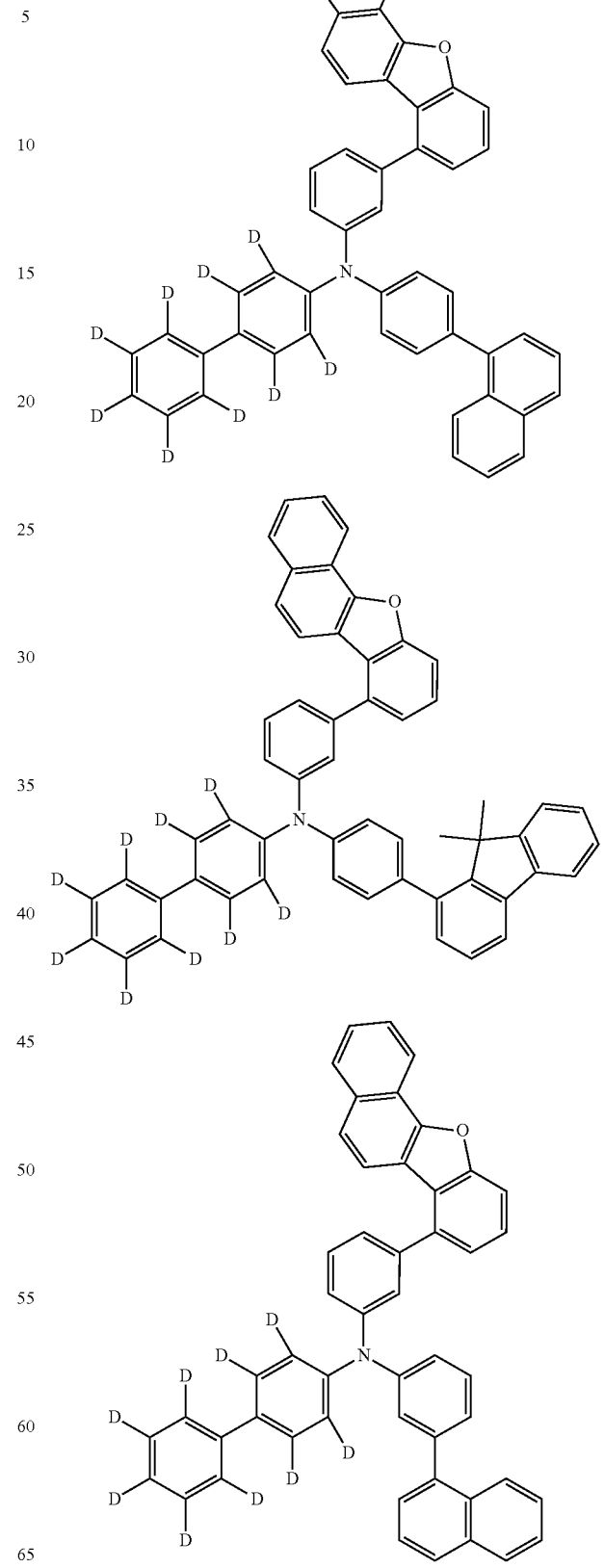

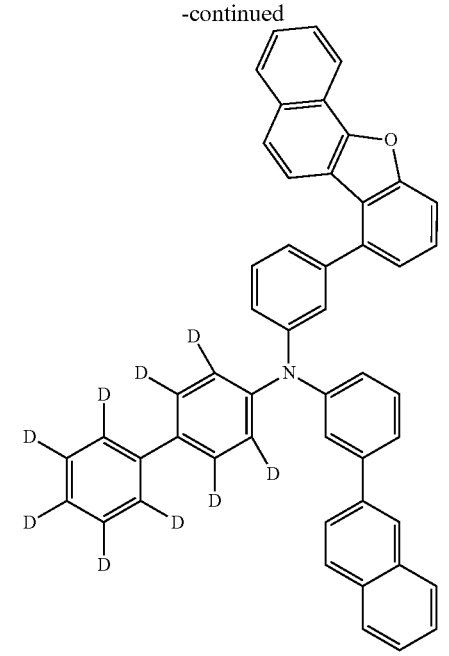
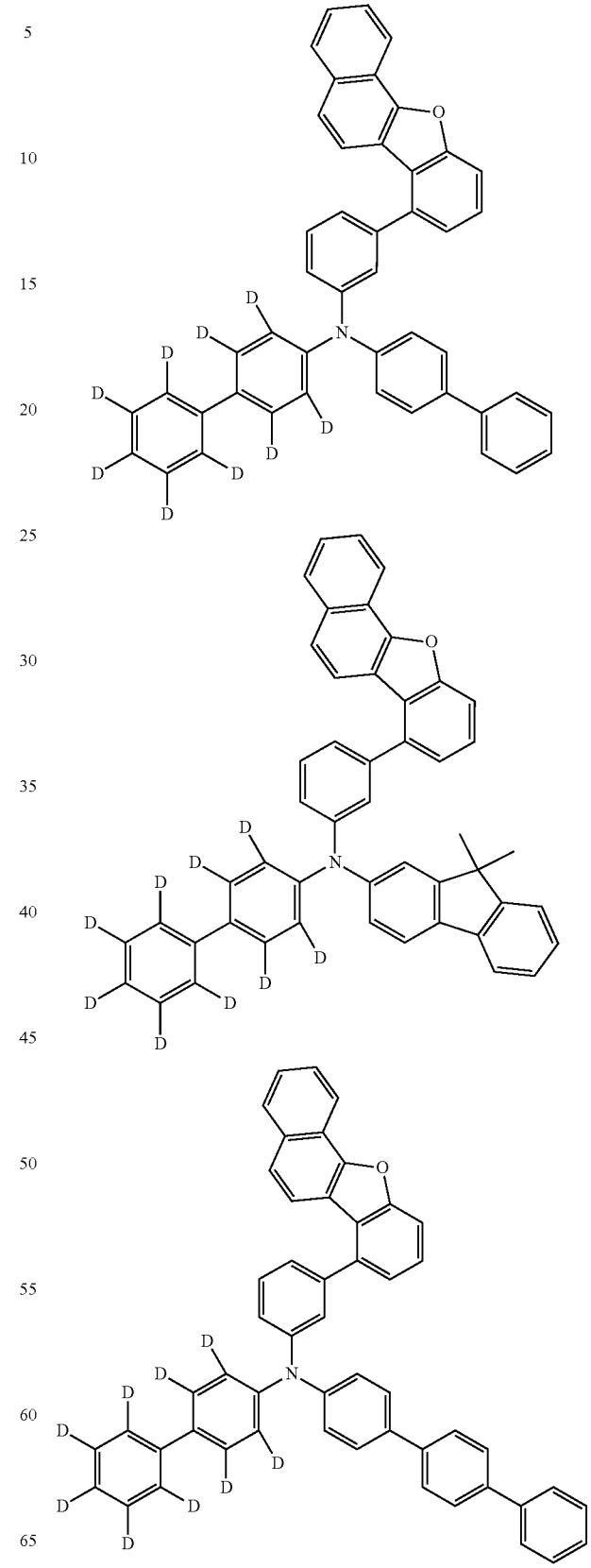
[Chem. 334]

995
-continued
996
-continued
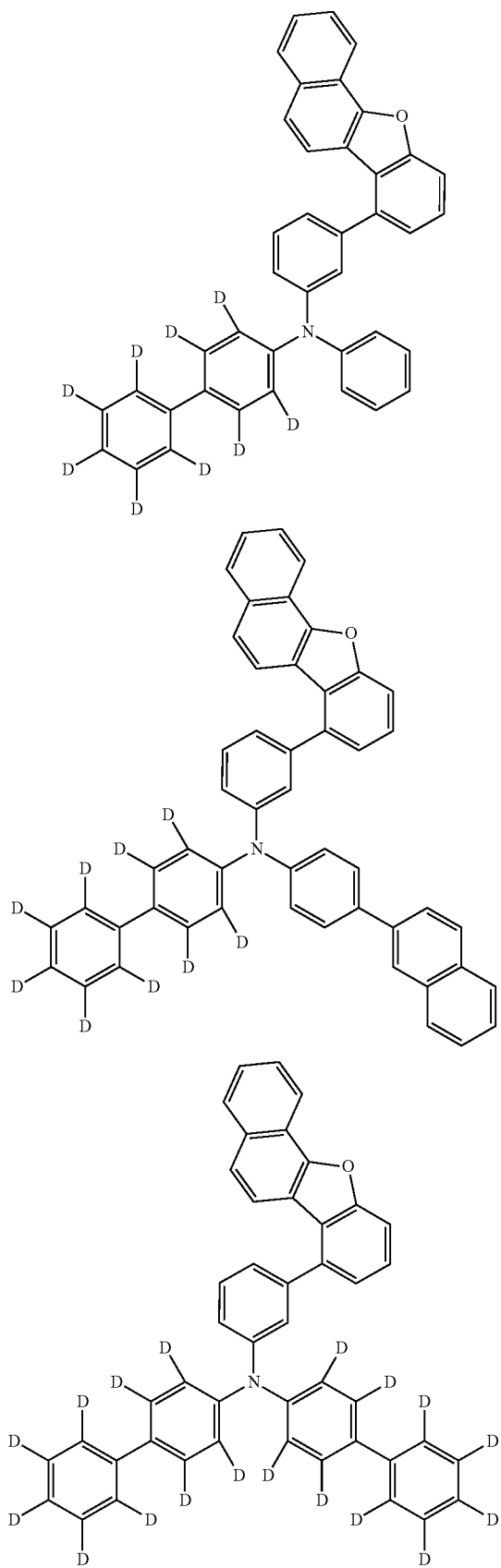
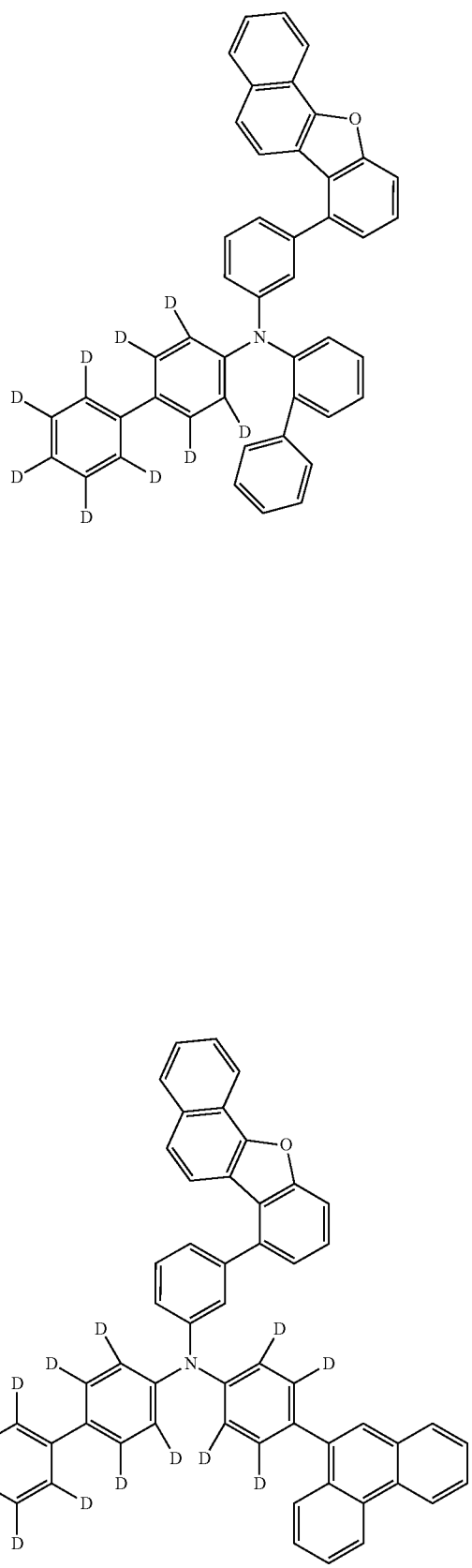

997
-continued
[Chem. 335]
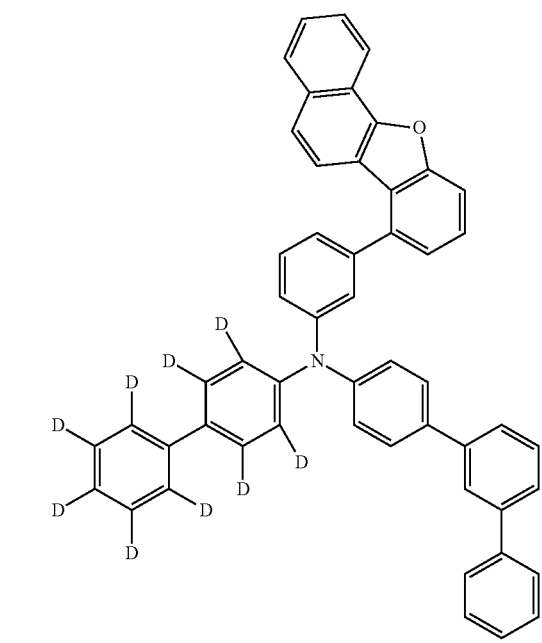
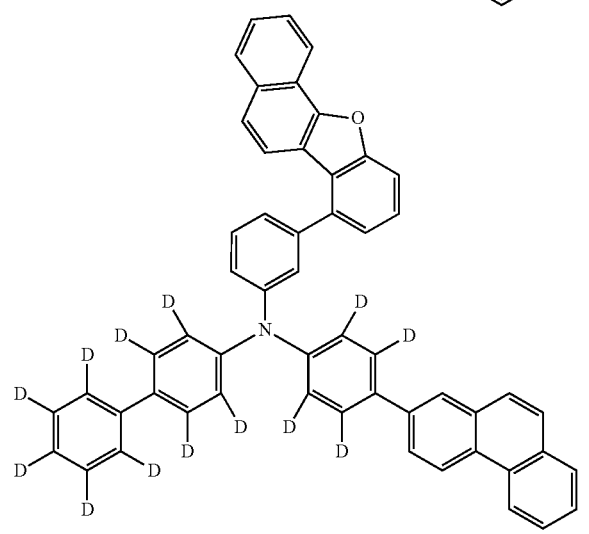
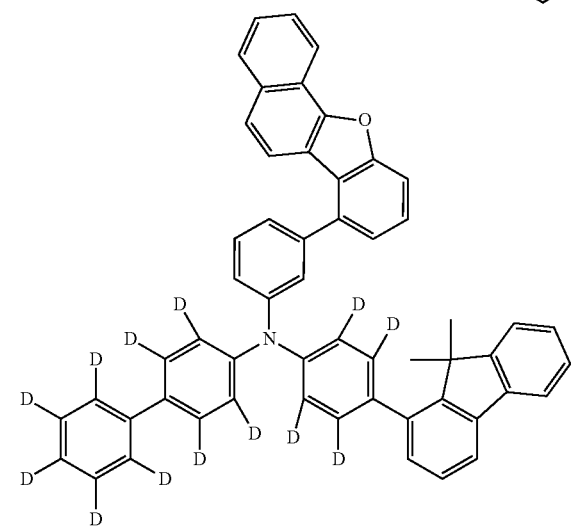
998
-continued
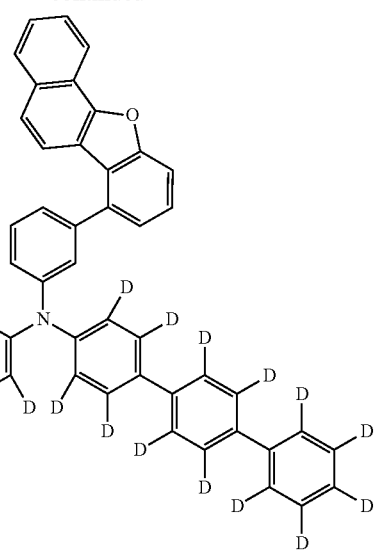
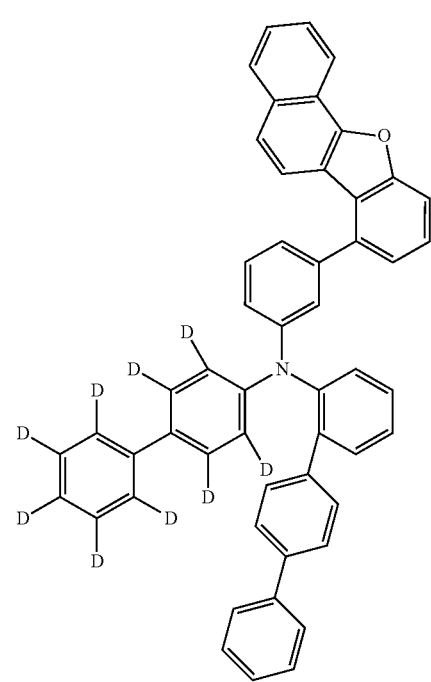

999
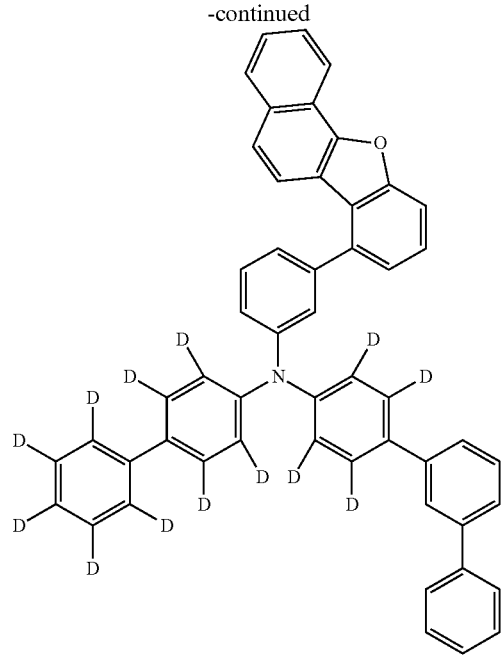
[Chem. 336]
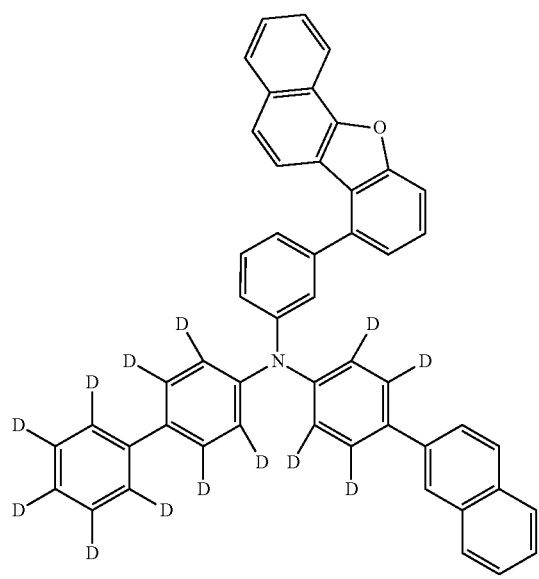
1000
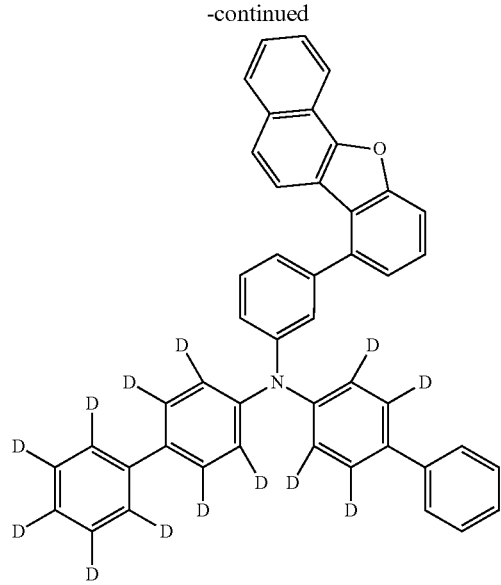
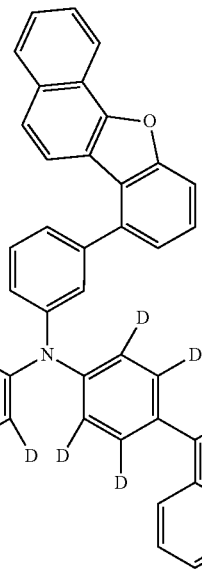
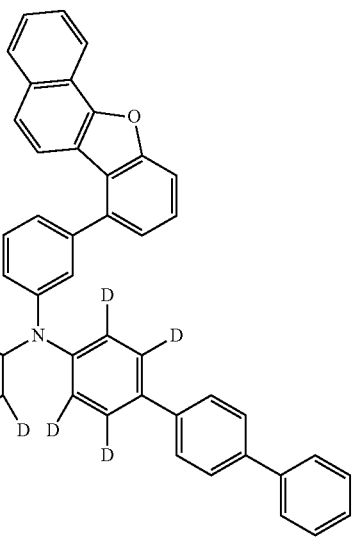

1001
-continued
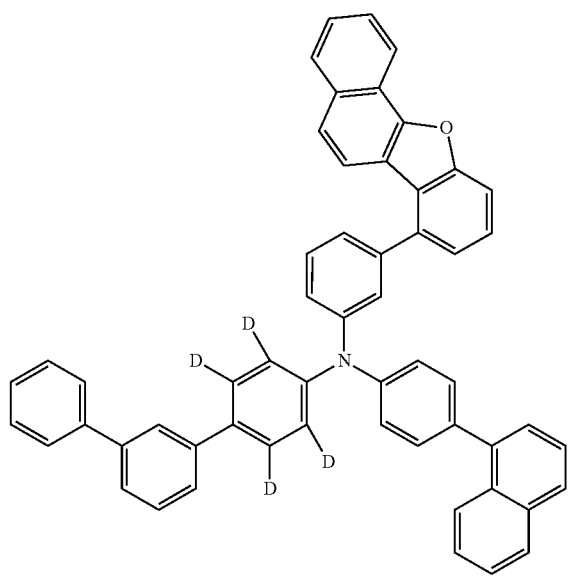
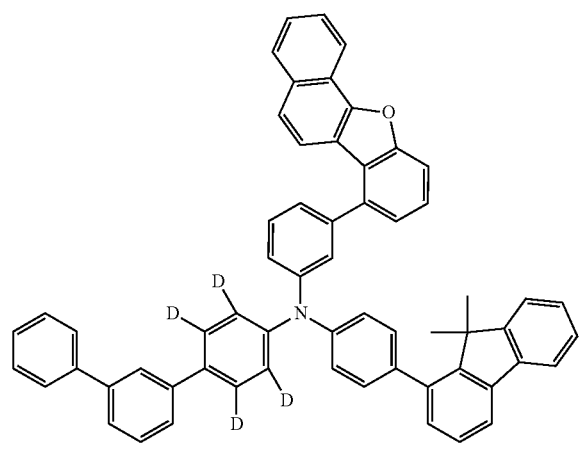
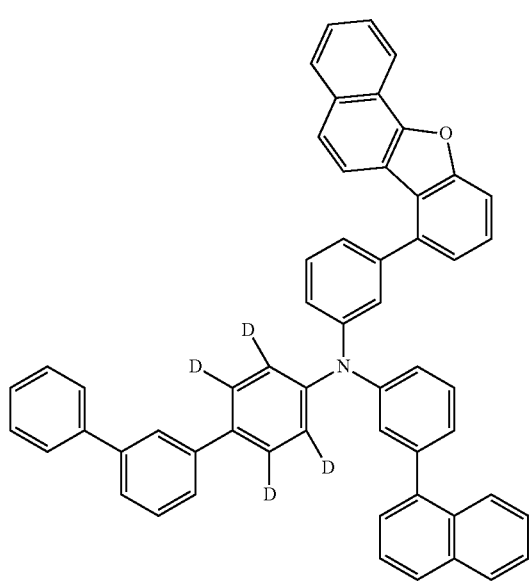
1002
-continued
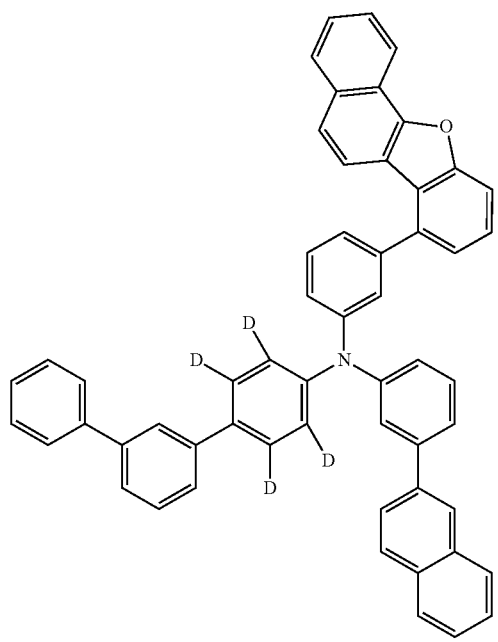
[Chem. 337]
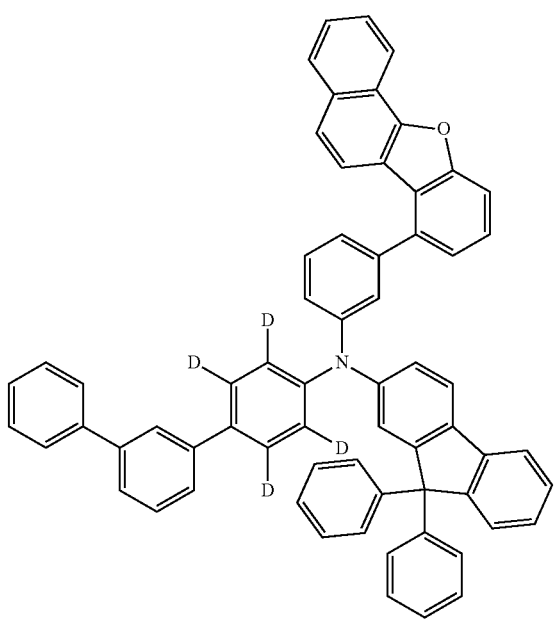

1003
-continued
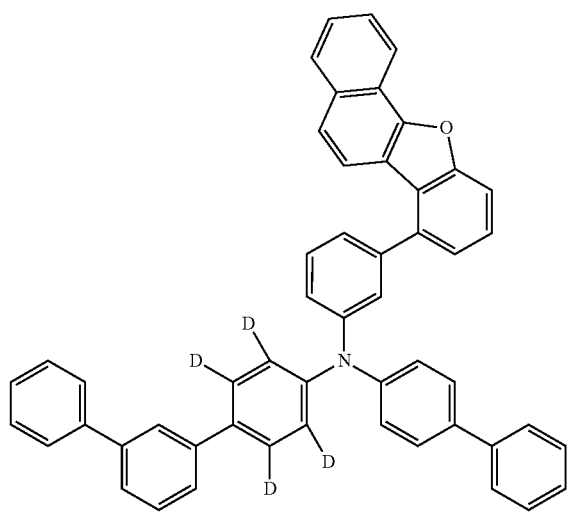
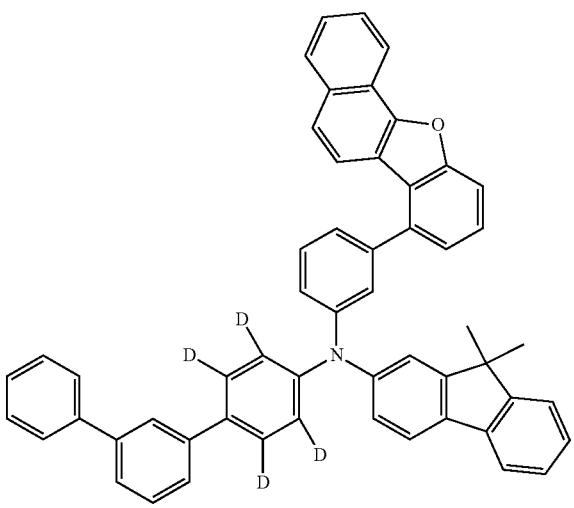
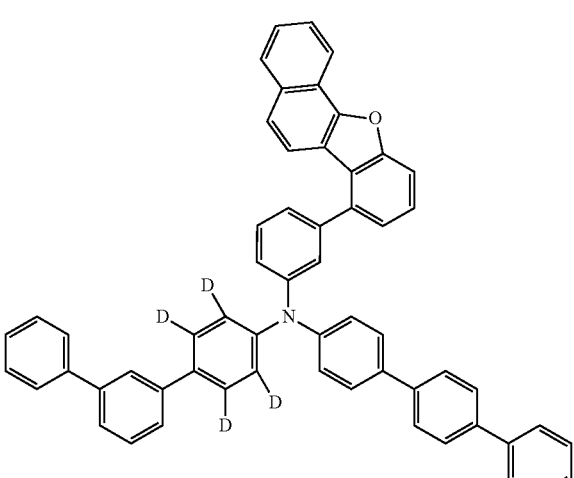
1004
-continued
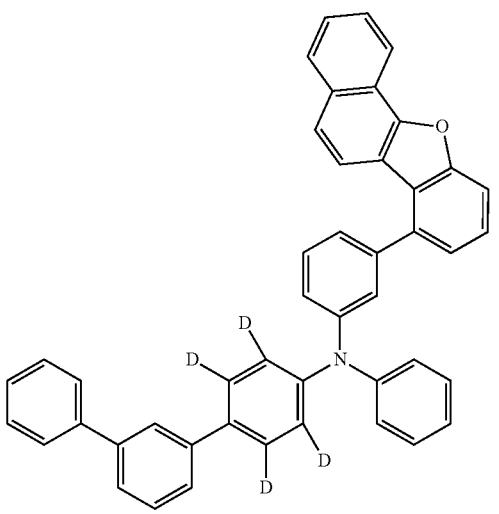
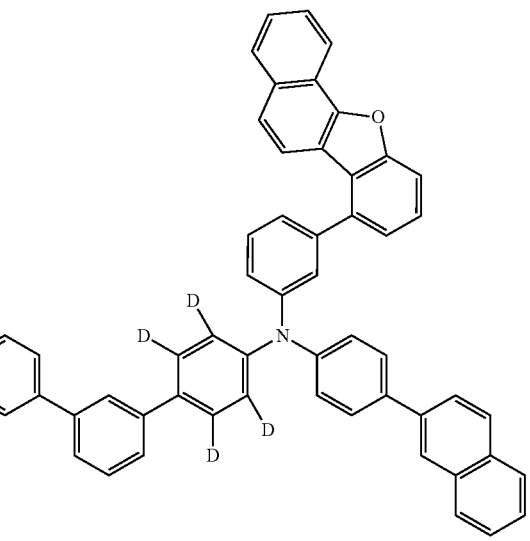
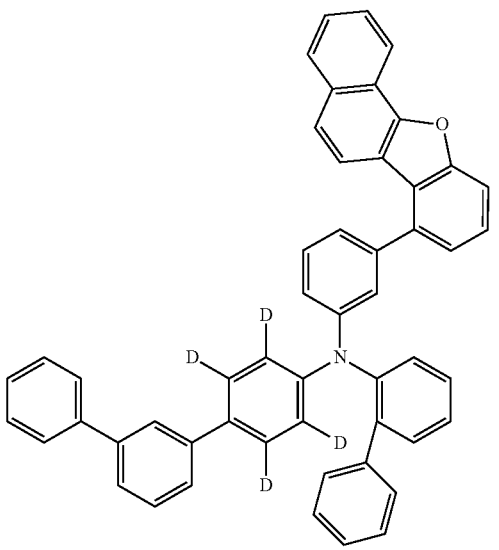

1005
-continued
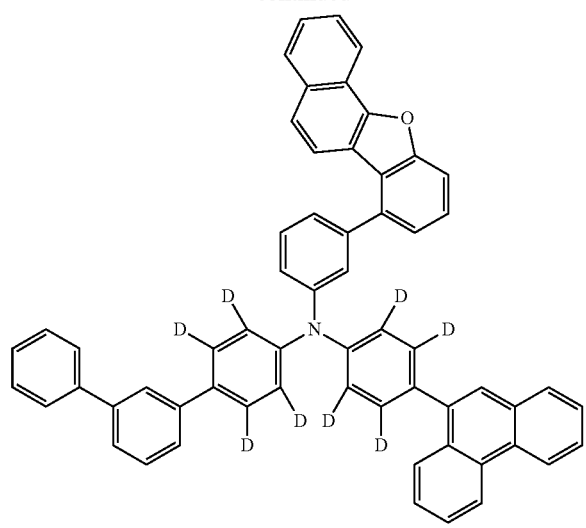
[Chem. 338]
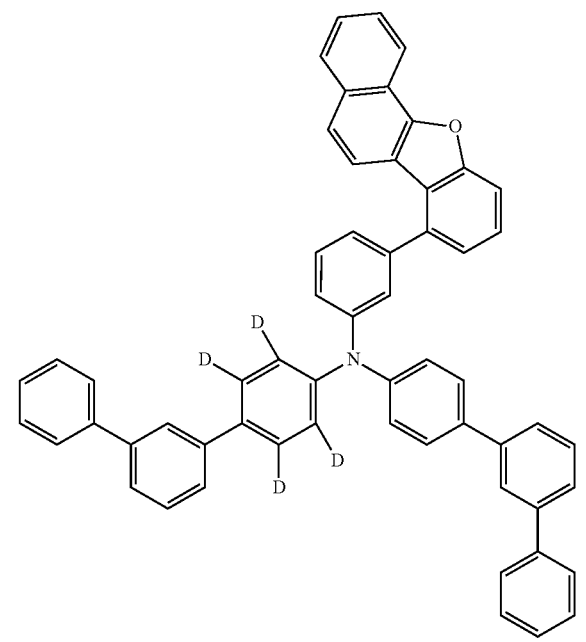
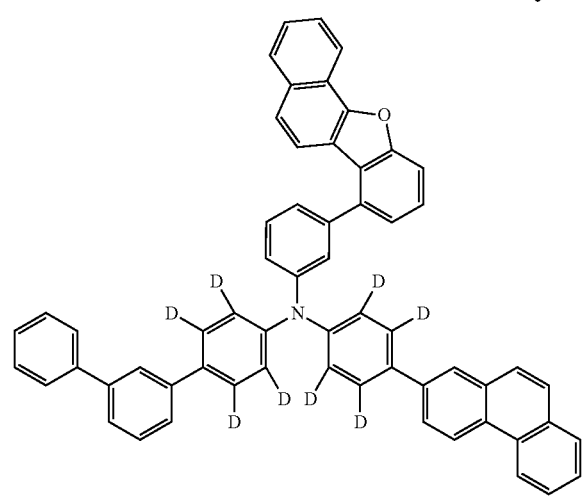
1006
-continued
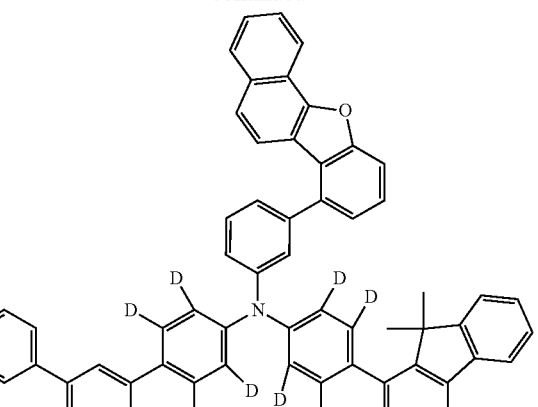
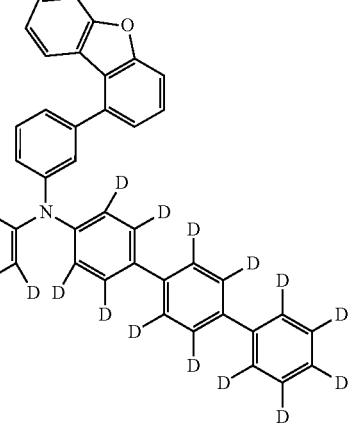
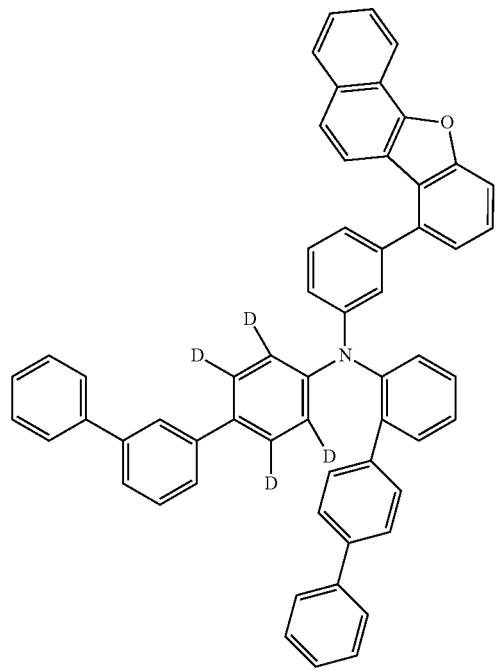

1007
-continued
1008
[Chem. 339]
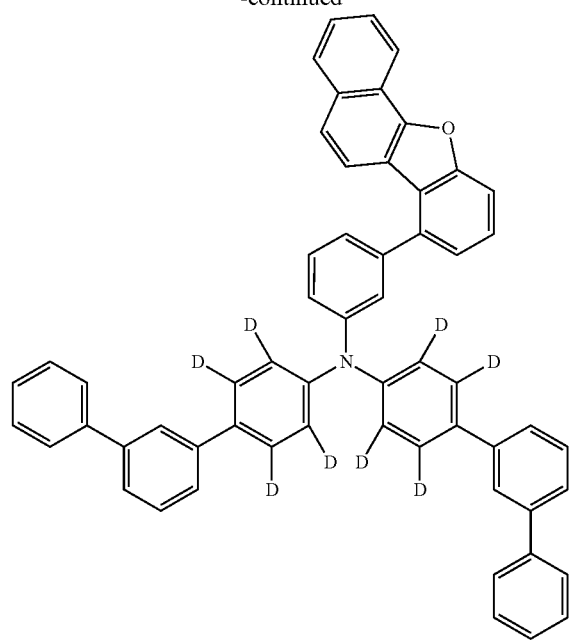
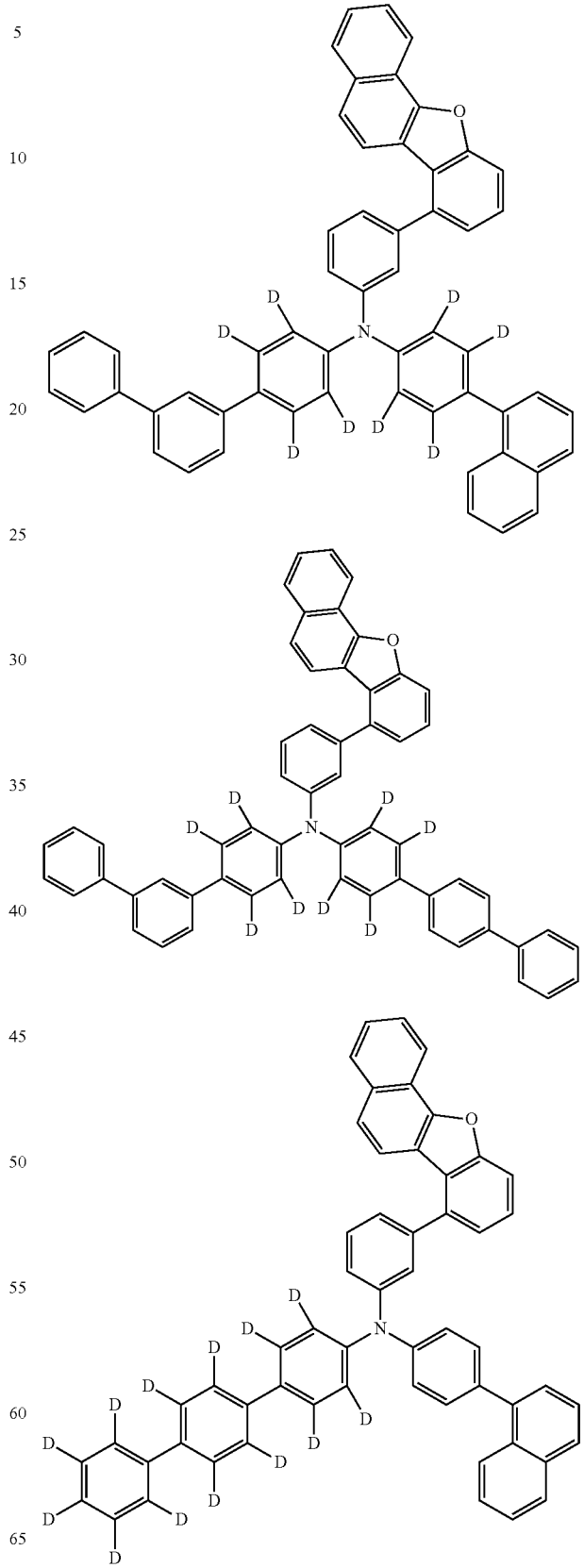

1009
-continued
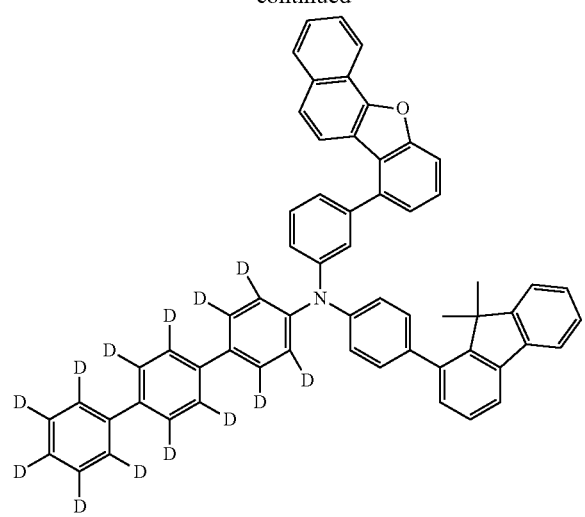
1010
-continued
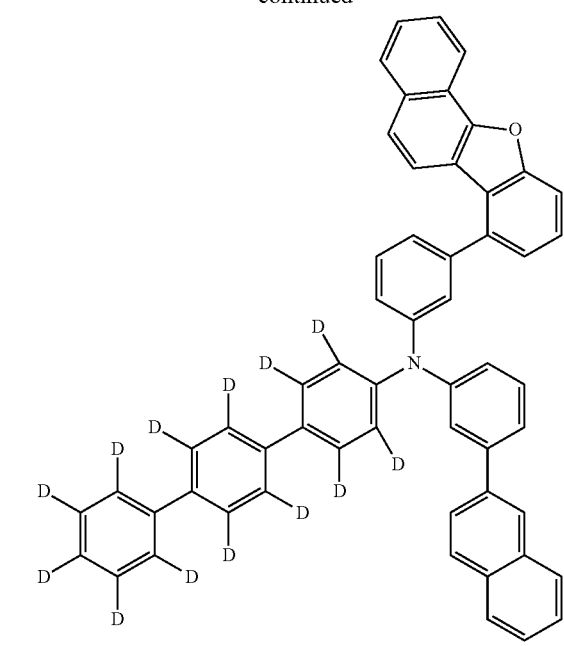
[Chem. 340]
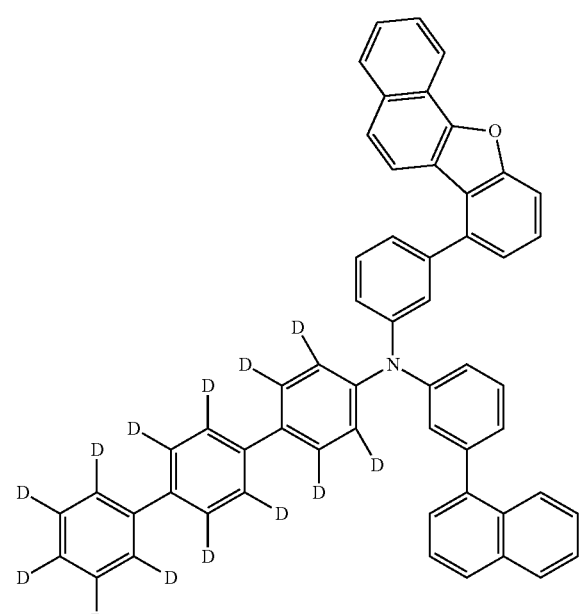
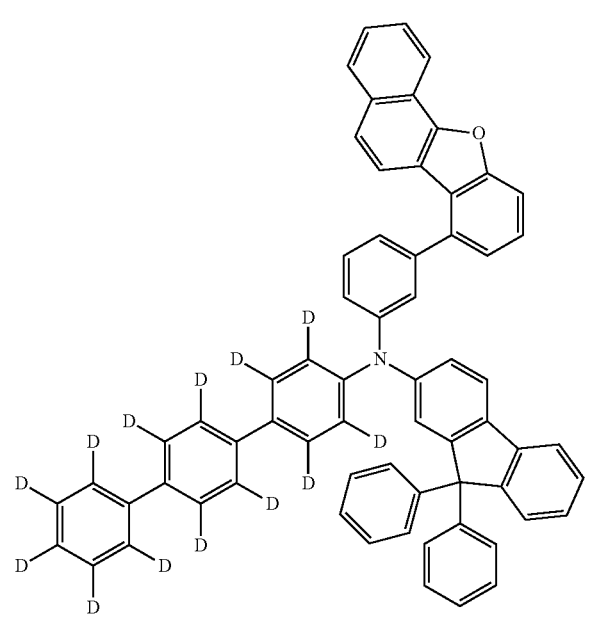

1011
-continued
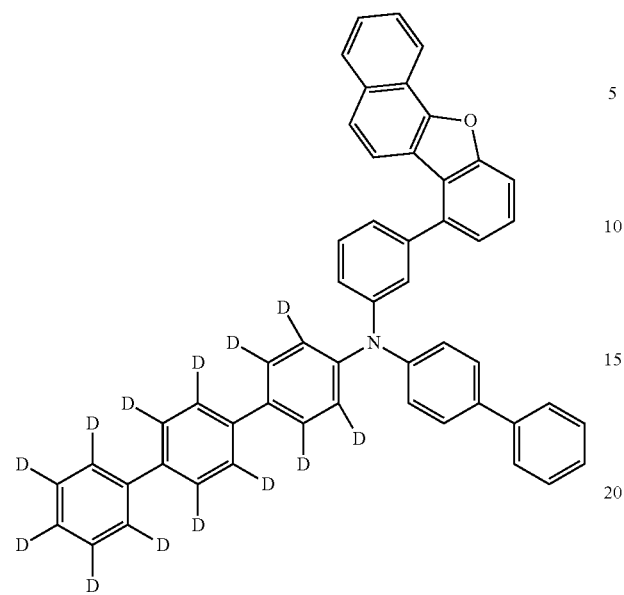
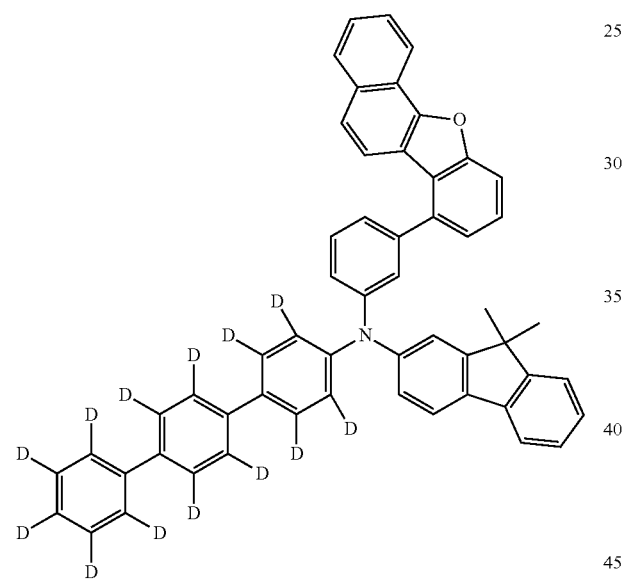
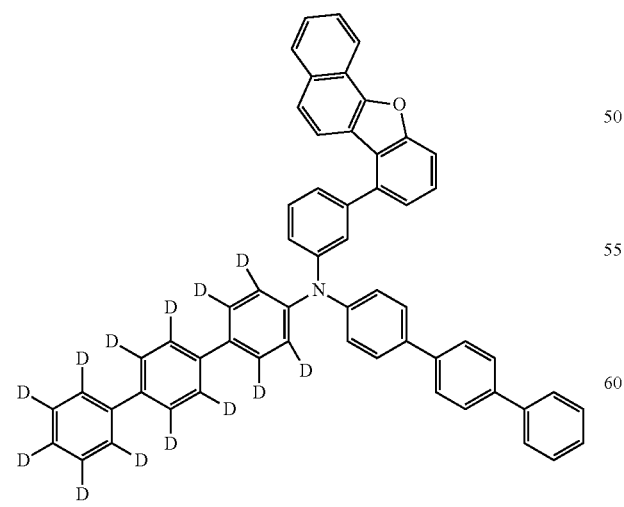
1012
-continued
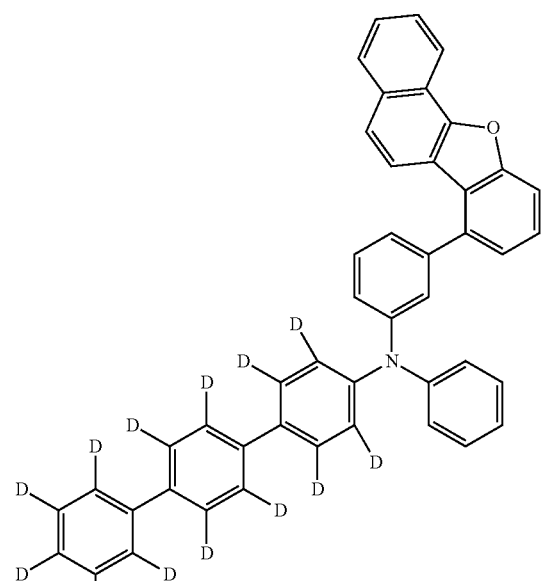
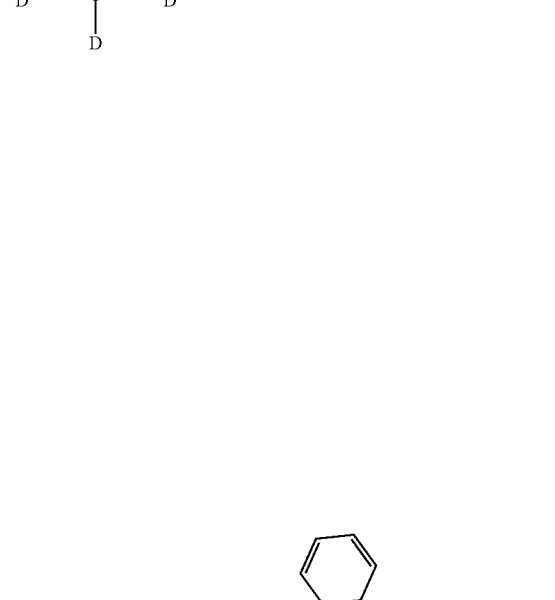
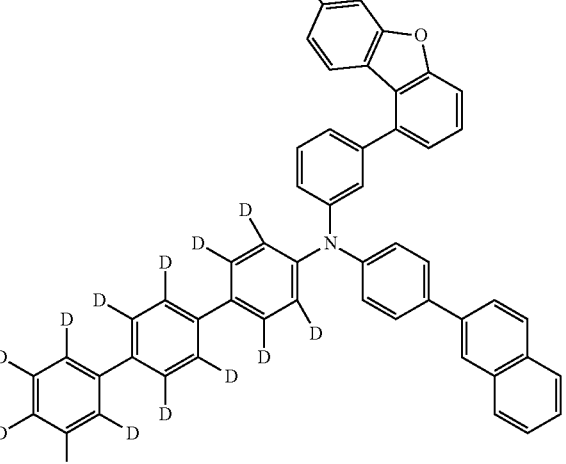

1013
-continued
[Chem. 341]
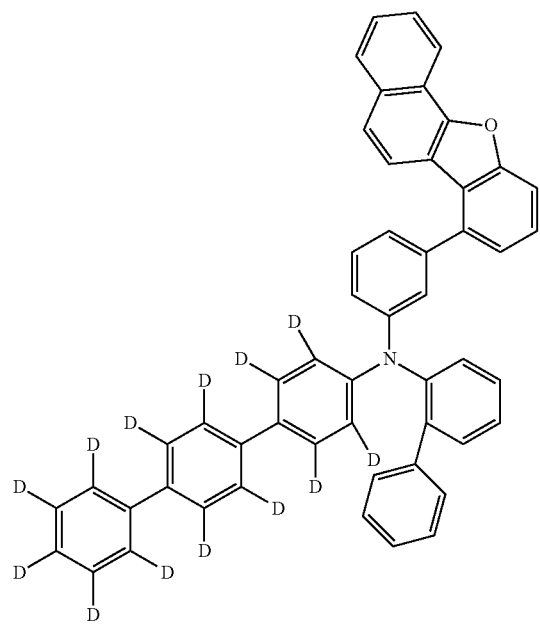
1014
-continued
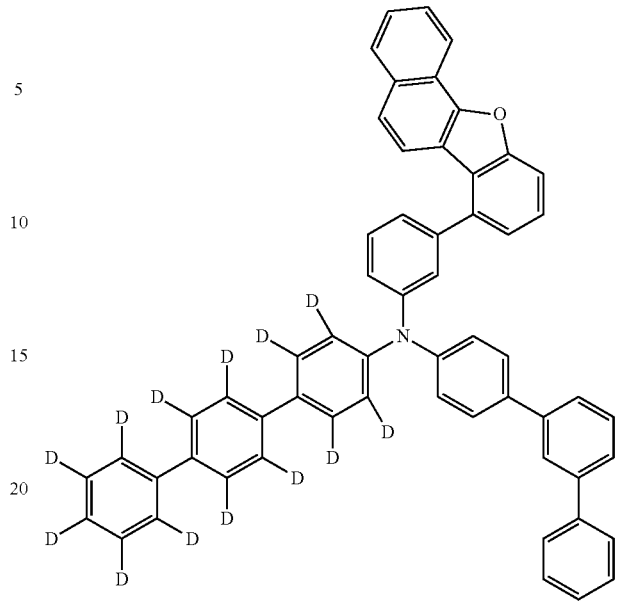
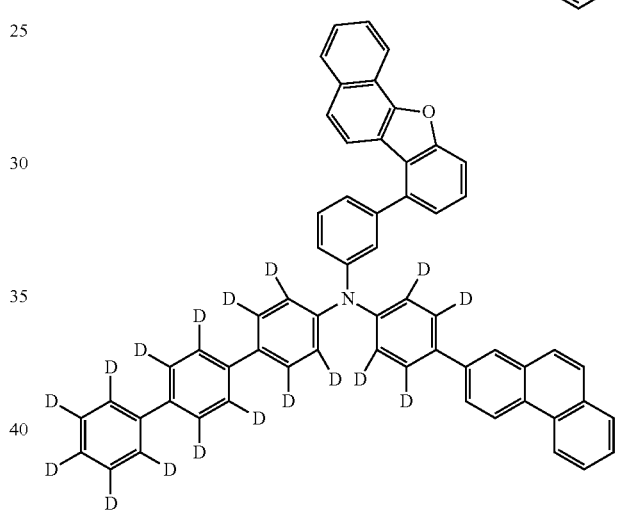
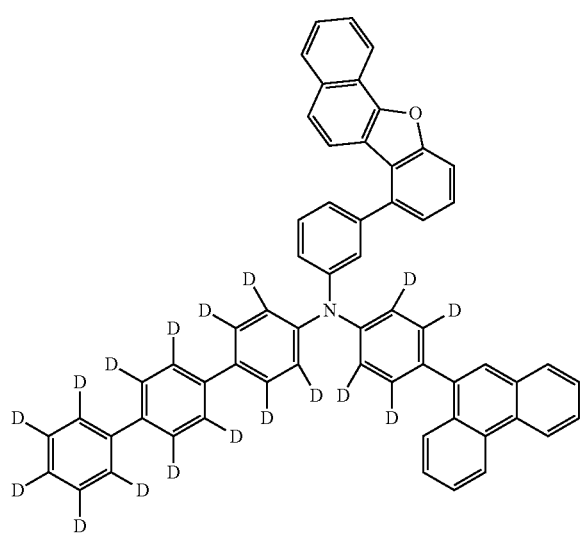
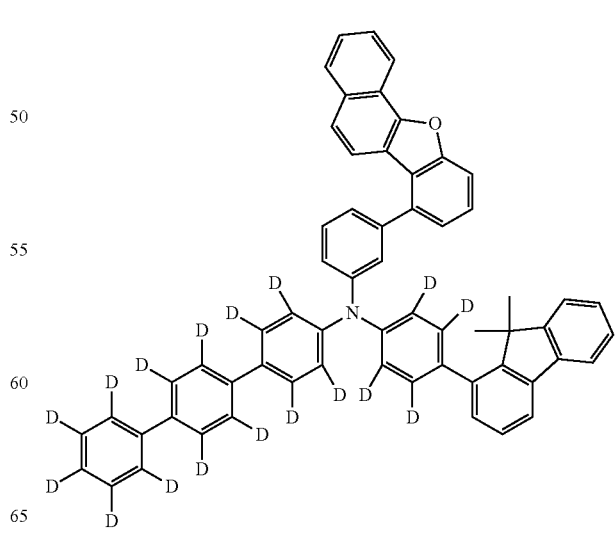

1015
-continued
[Chem. 342]
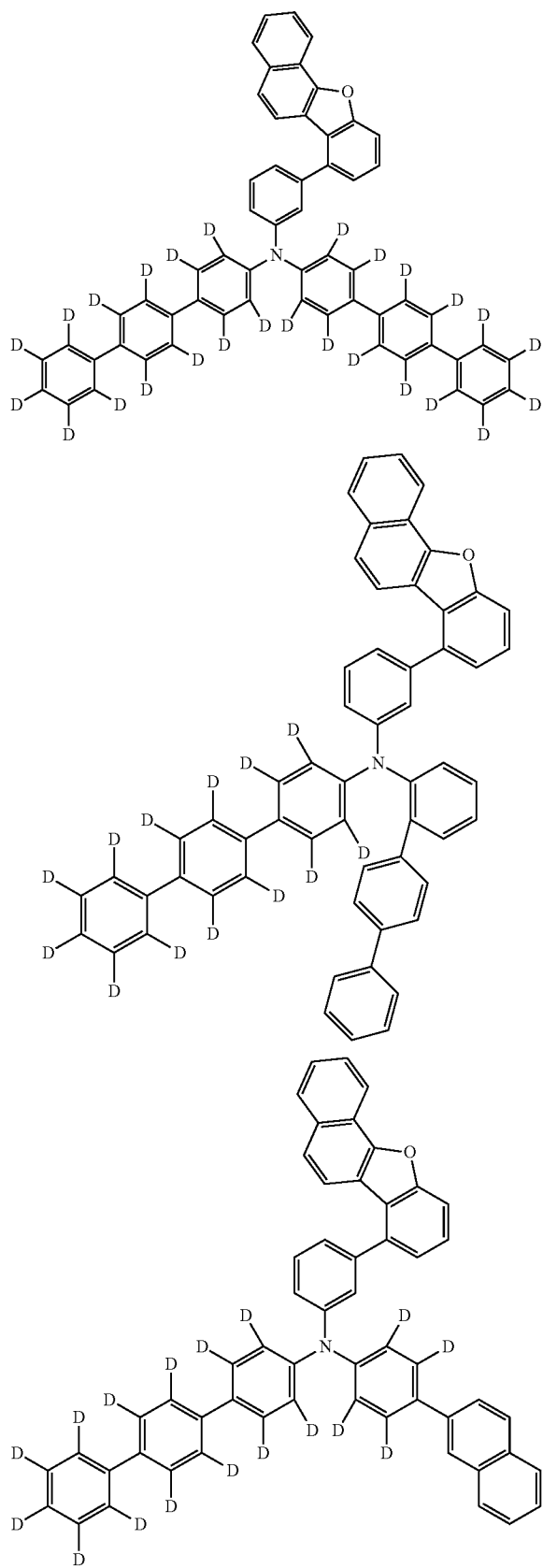
1016
-continued
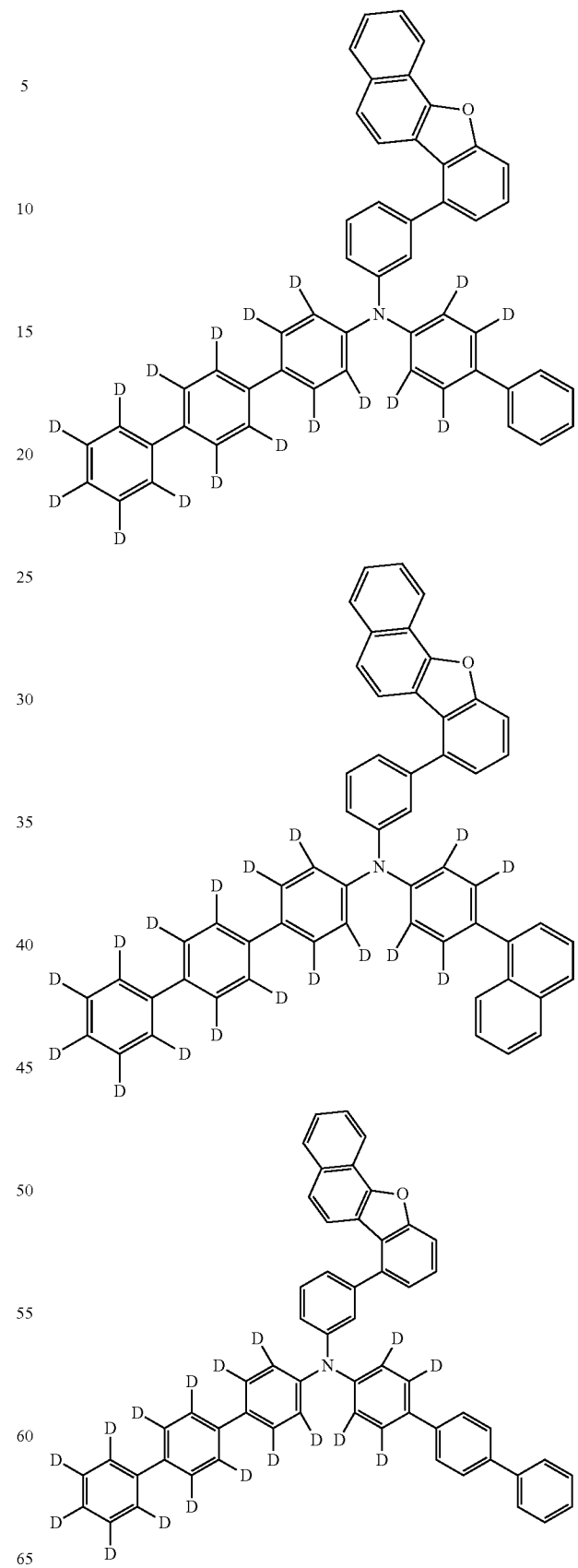

1017
-continued
[Chem. 343]
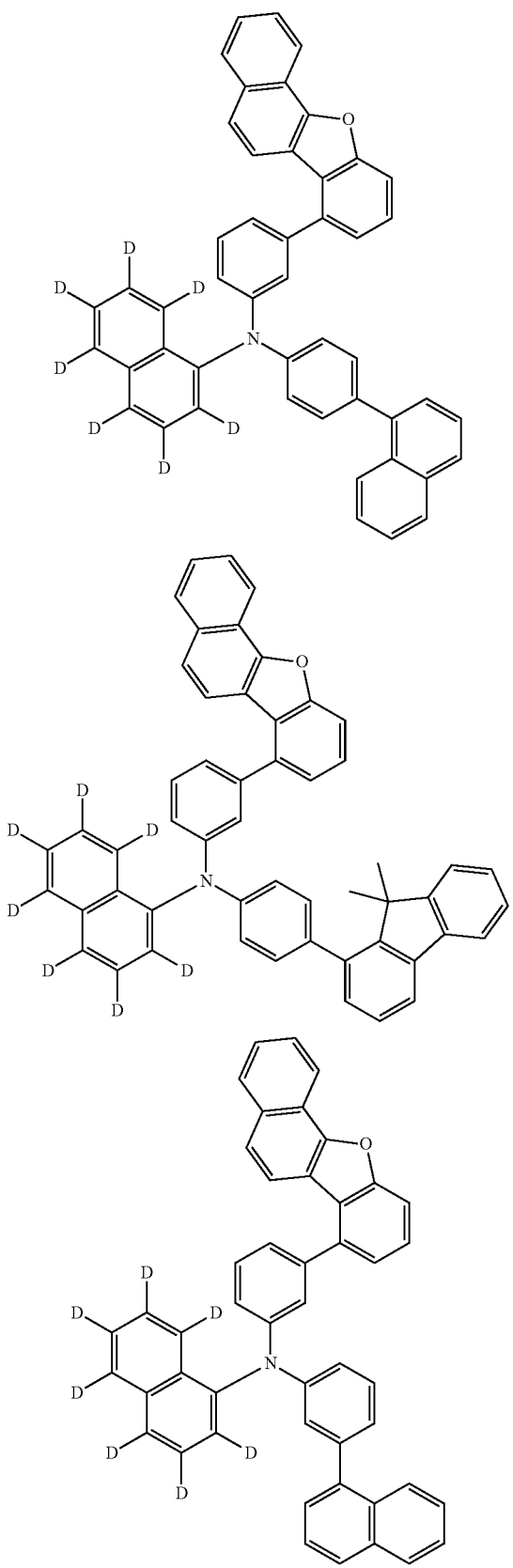
1018
-continued
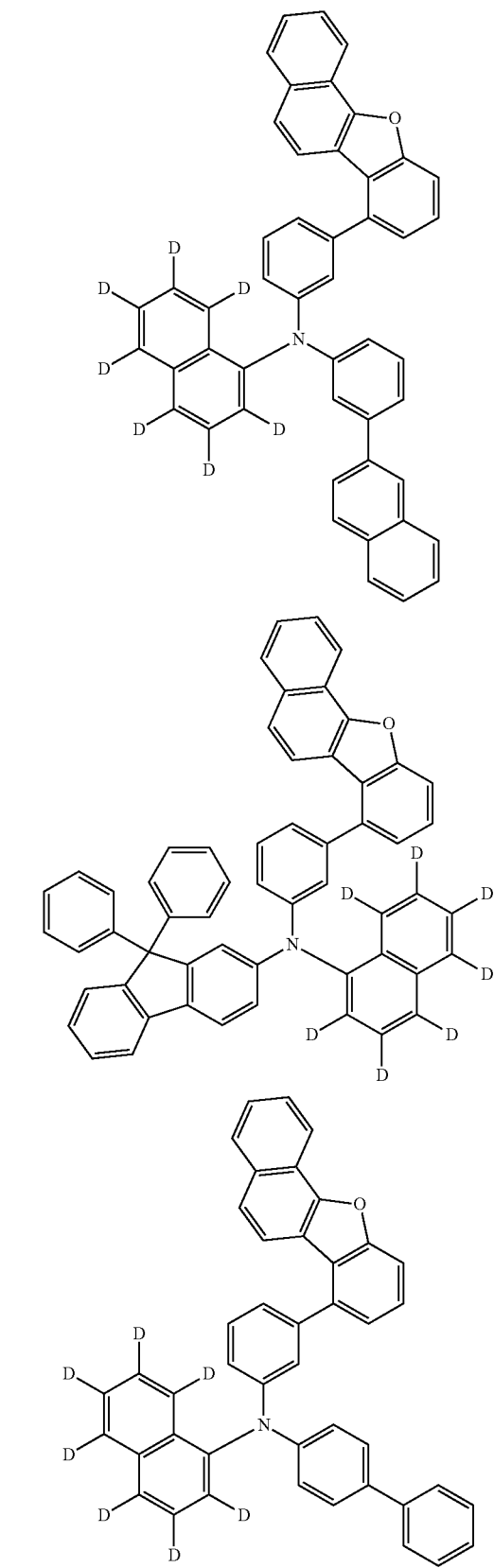

1019
-continued
1020
-continued
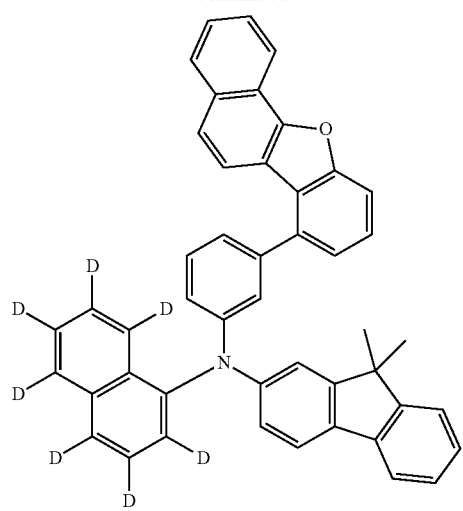
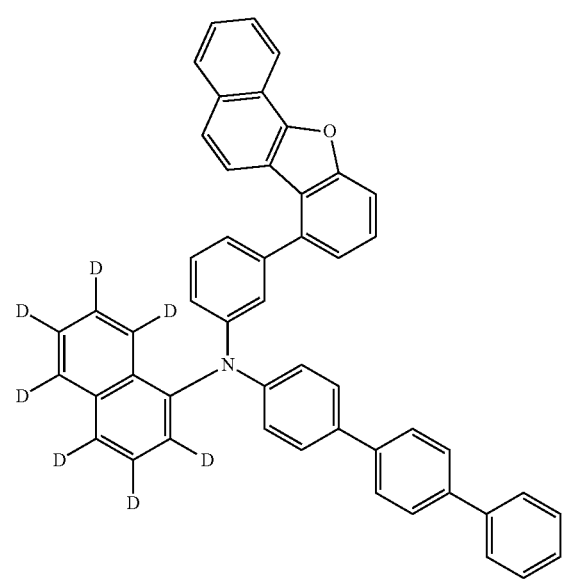
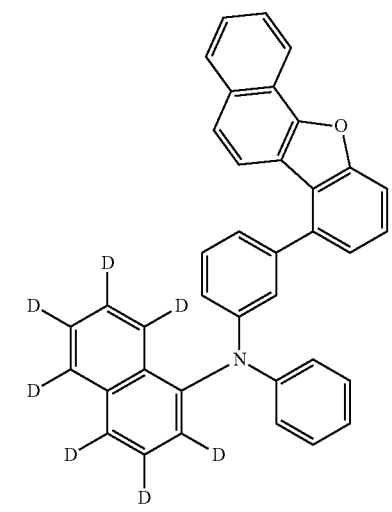
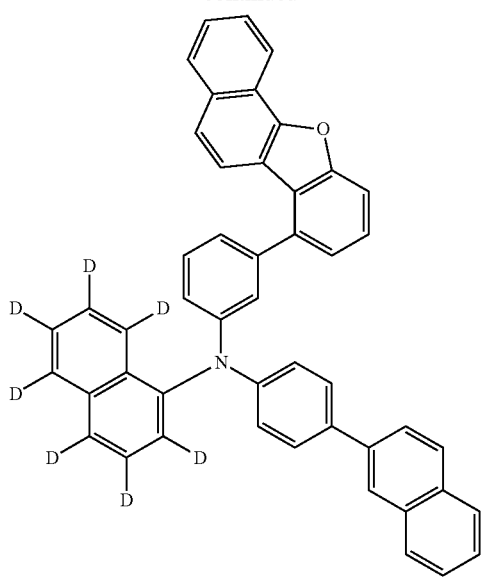
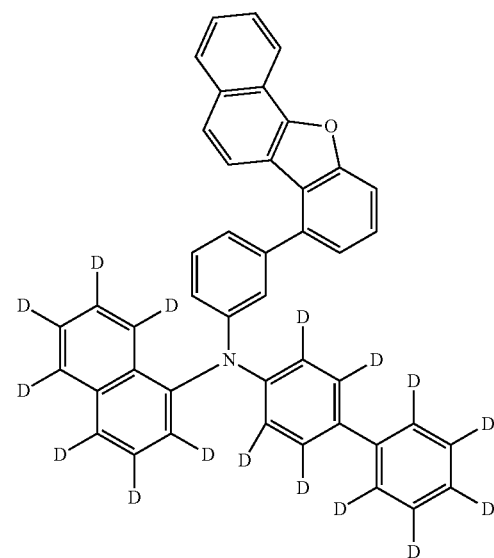
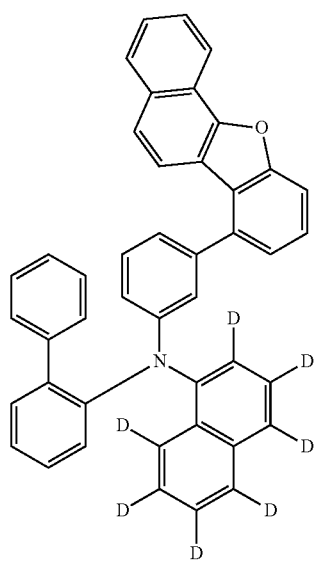

1021
-continued
[Chem. 344]
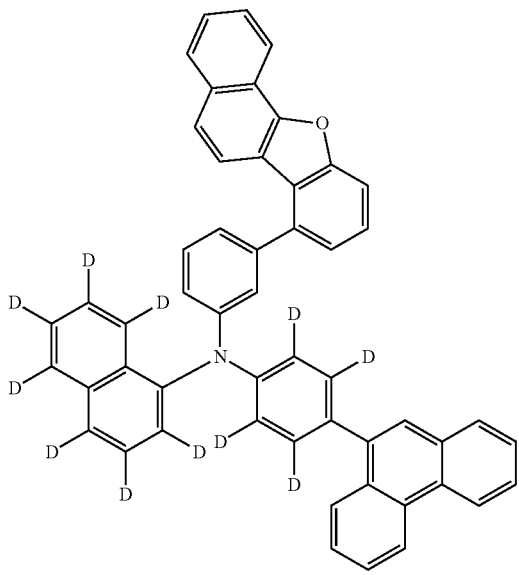
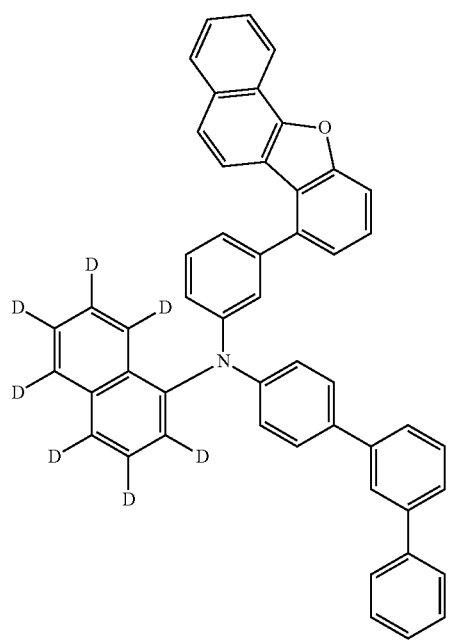
1022
-continued
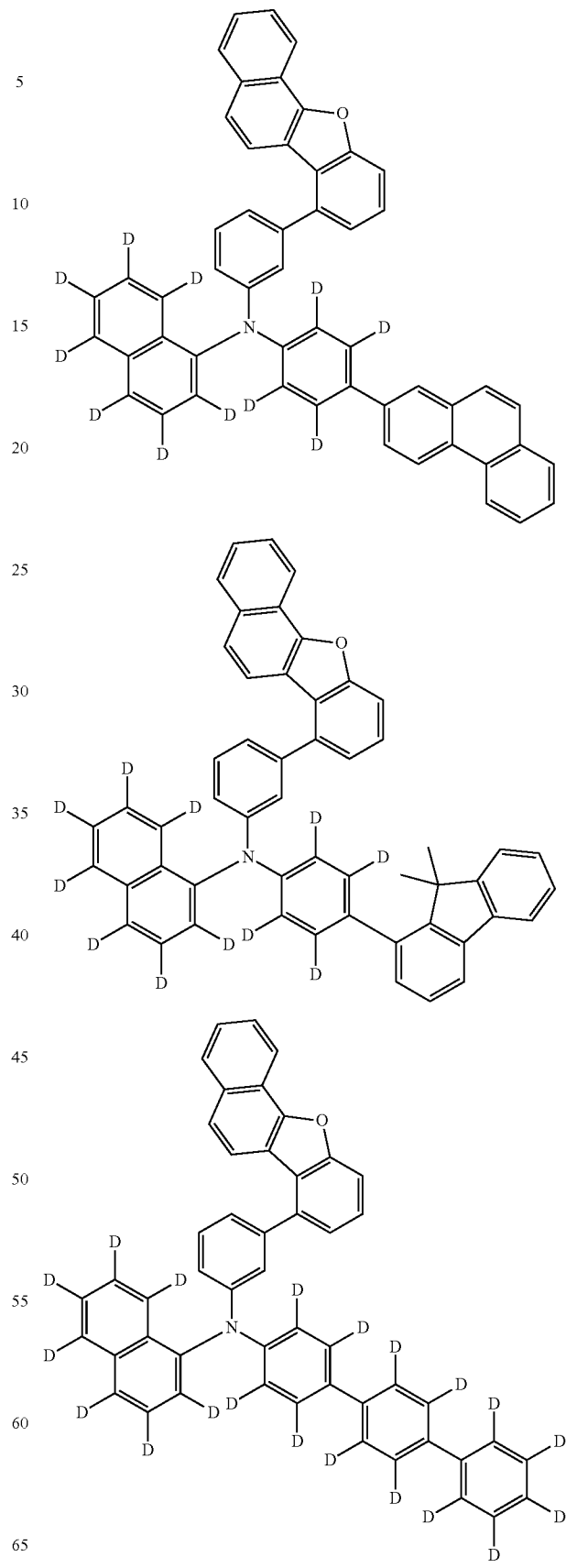

1023
-continued
1024
-continued
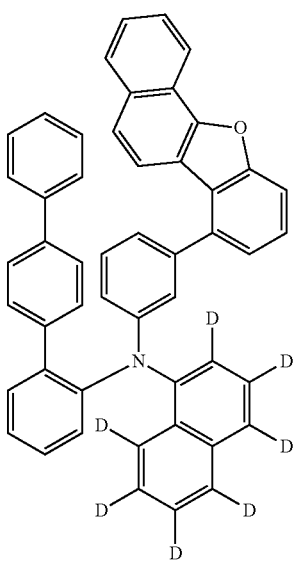
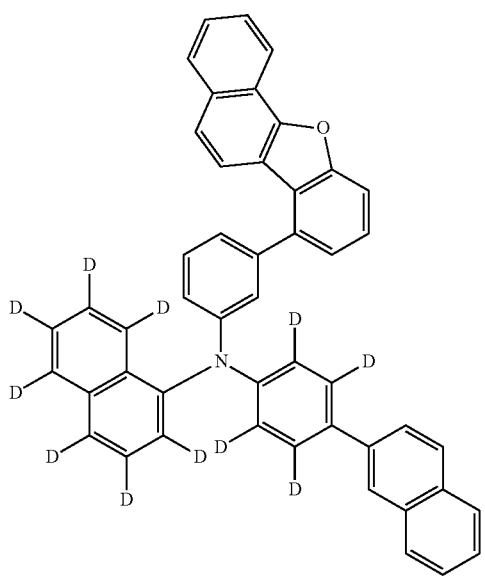
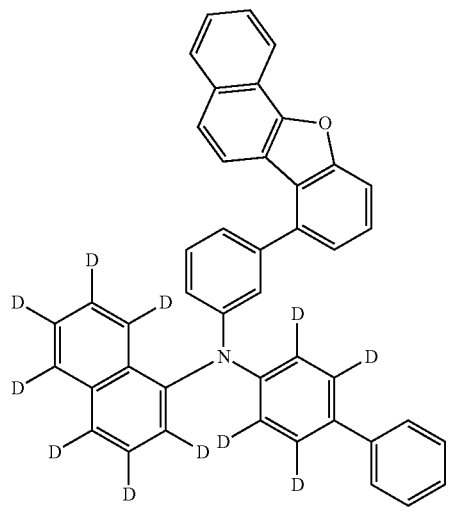
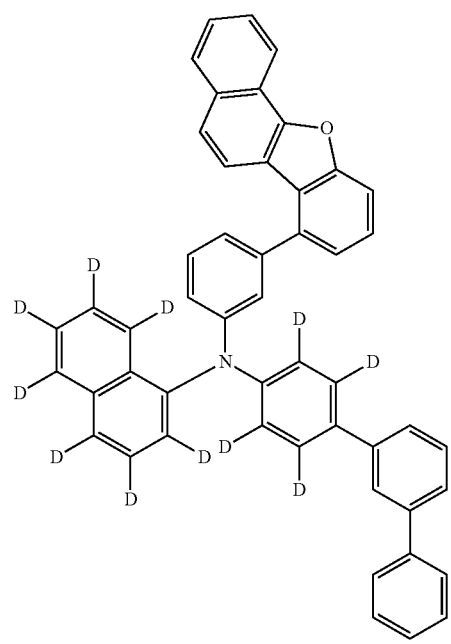
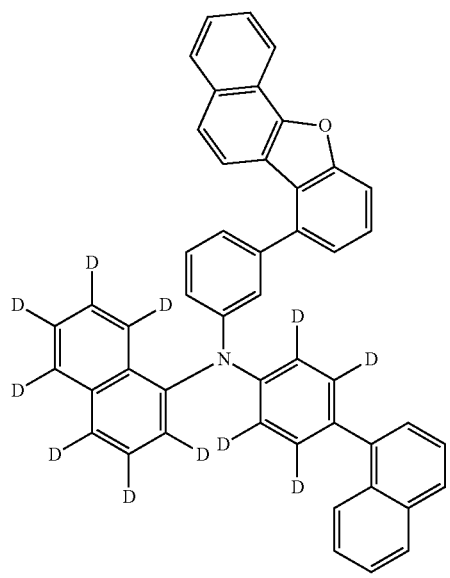

1025
-continued
[Chem. 345]
1026
-continued
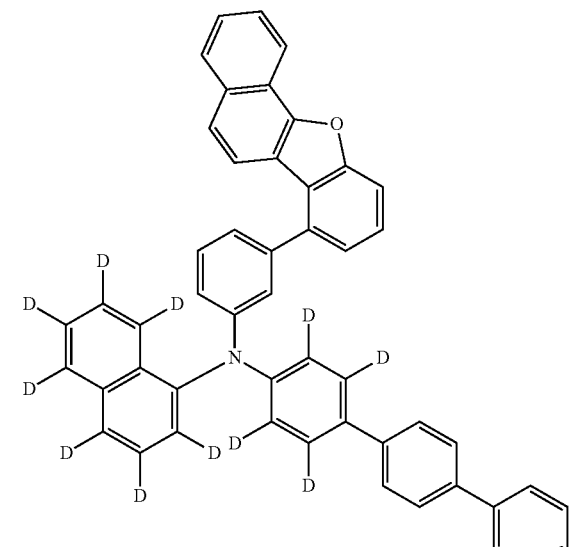
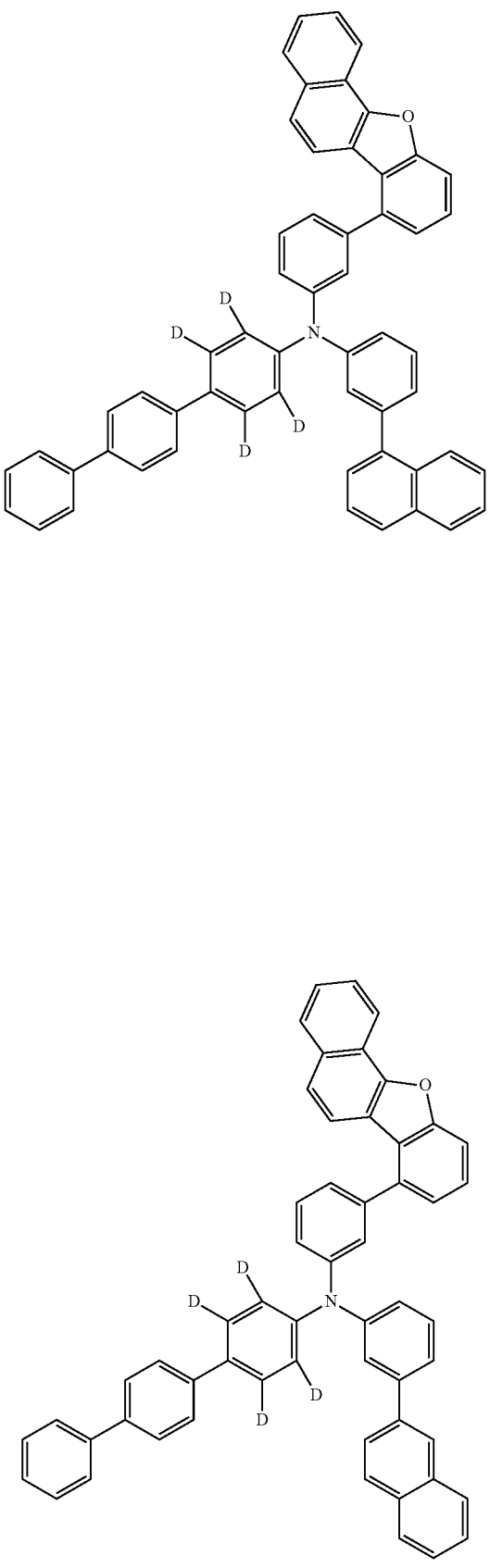

1027
-continued
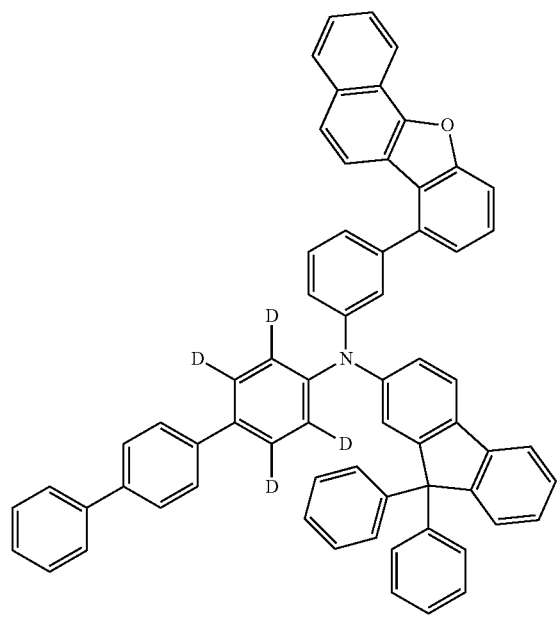
1028
-continued
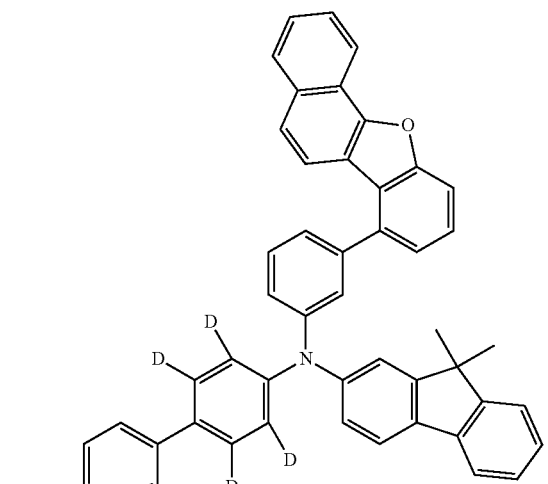
[Chem. 346]
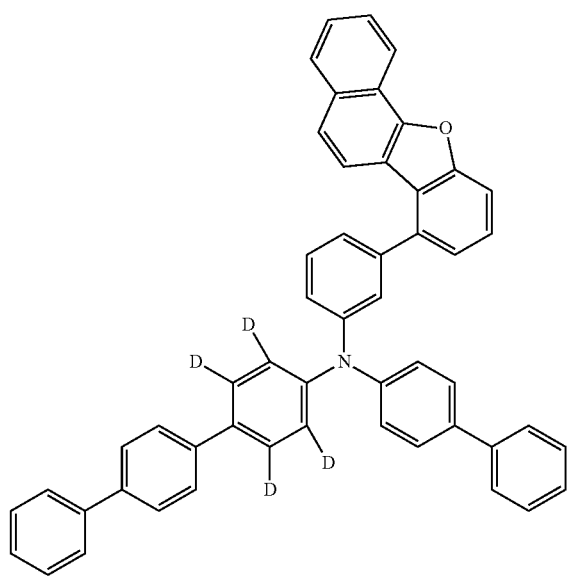
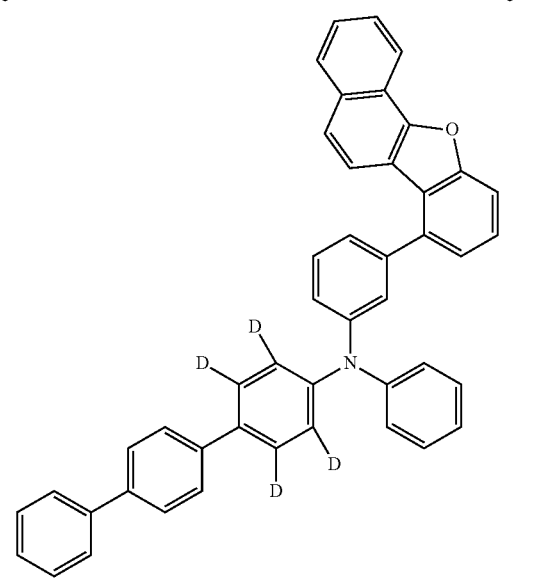

1029
-continued
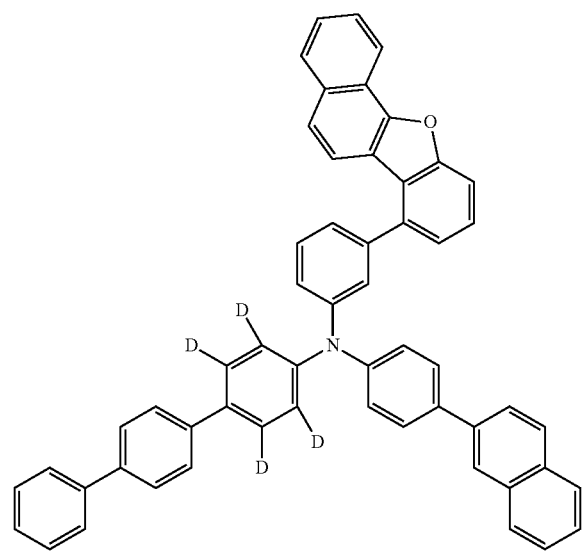
1030
-continued
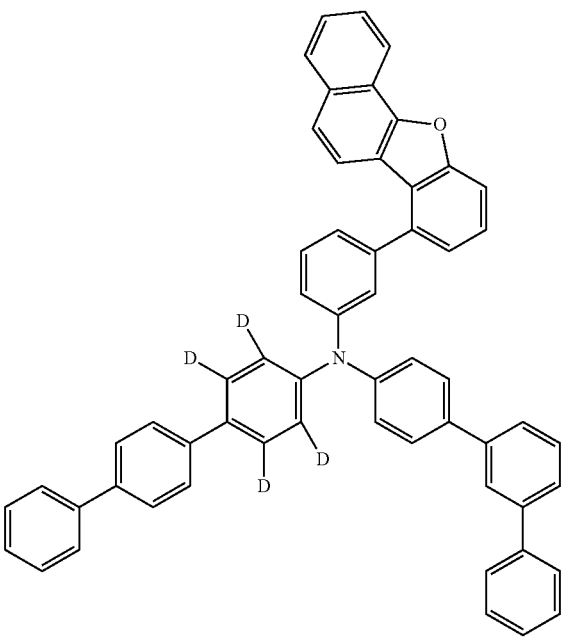
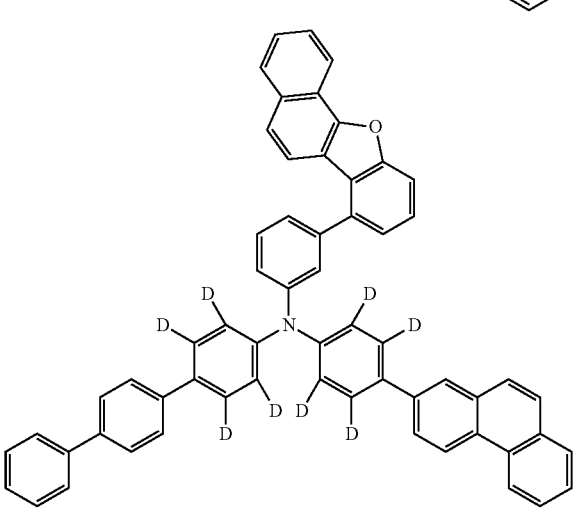
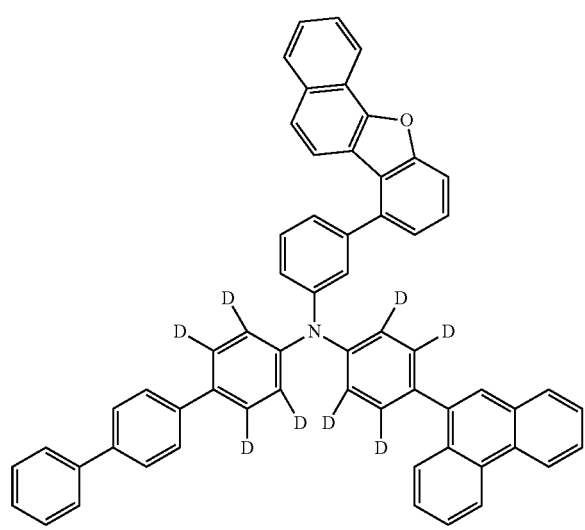
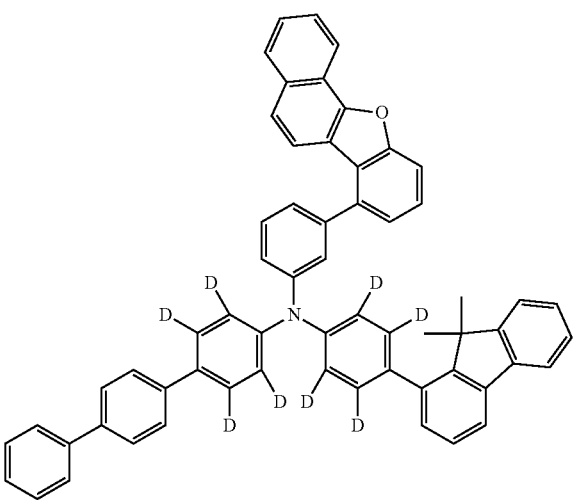

1031
-continued
[Chem. 347]
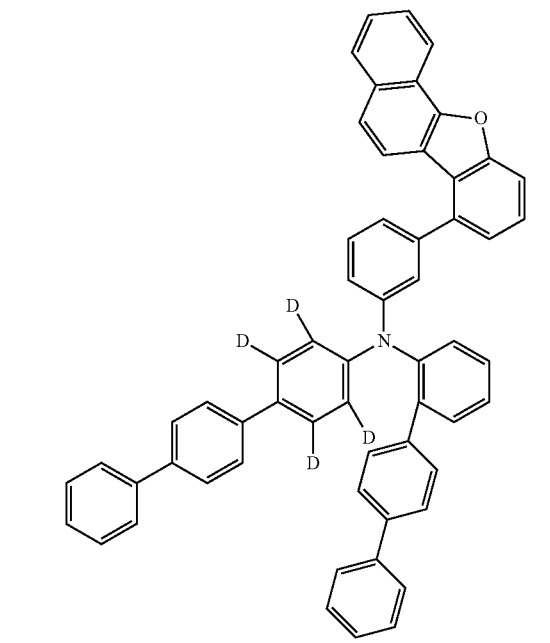
1032
-continued
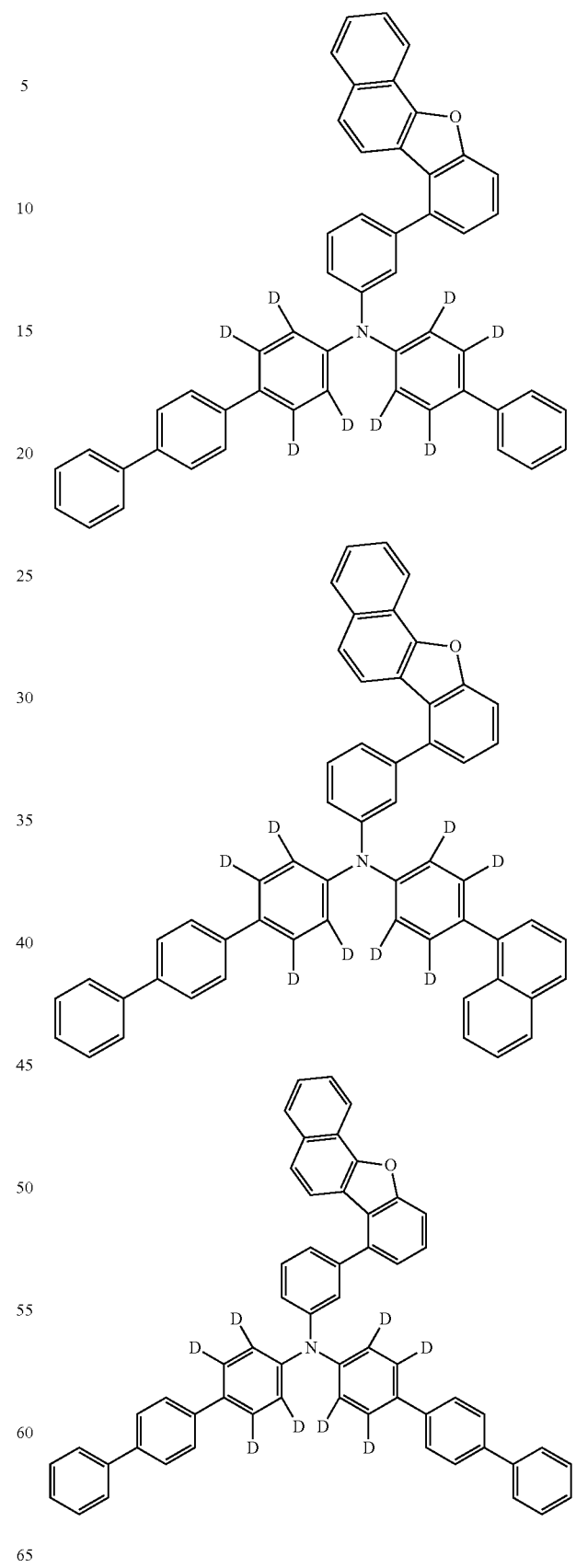

1033
-continued
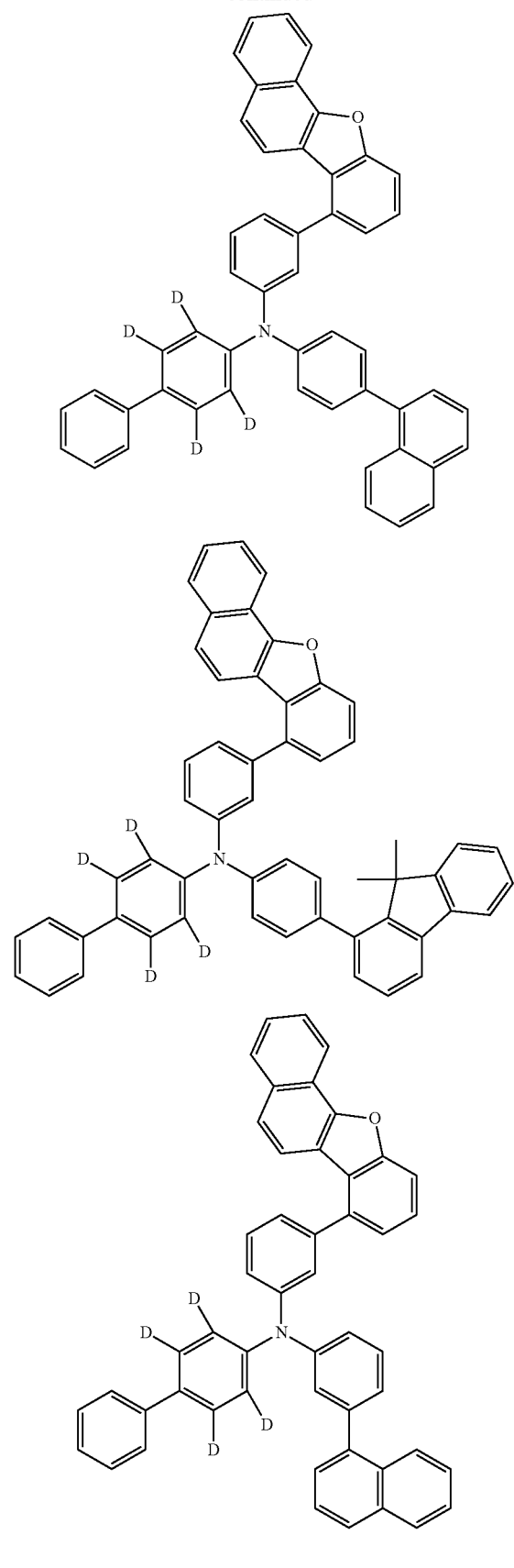
1034
-continued
[Chem. 348]

1035
-continued
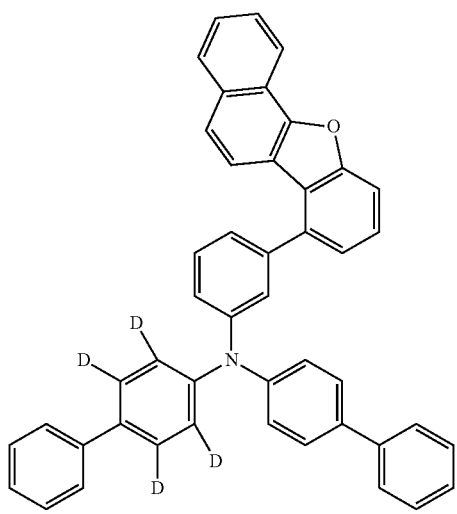
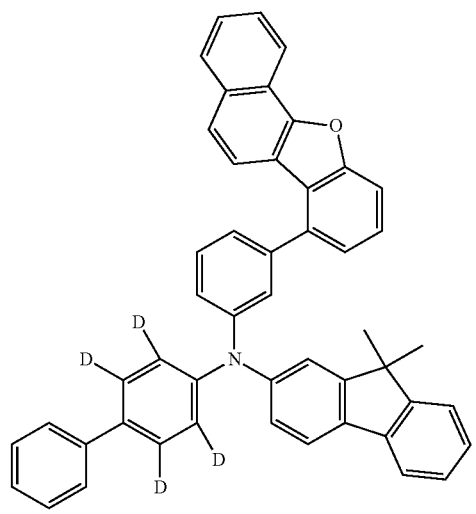
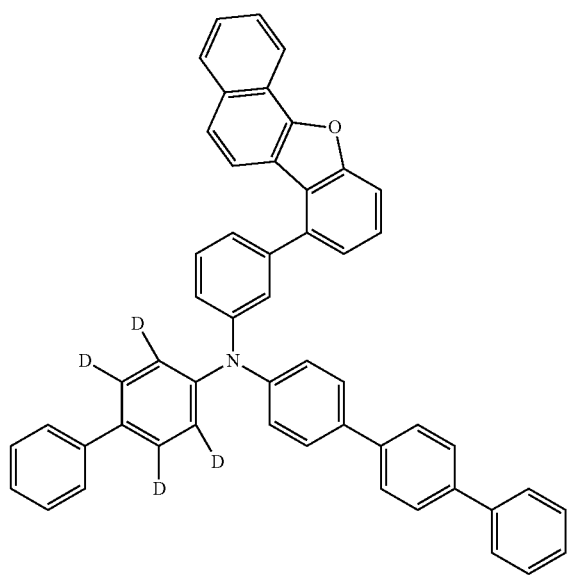
1036
-continued
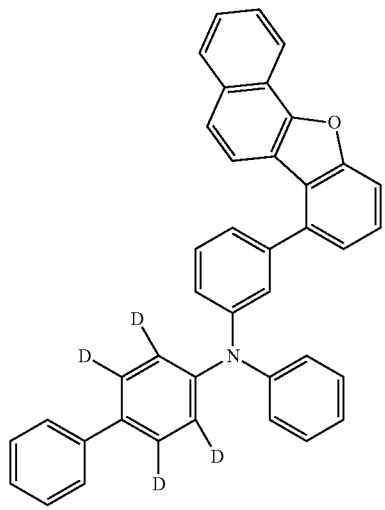
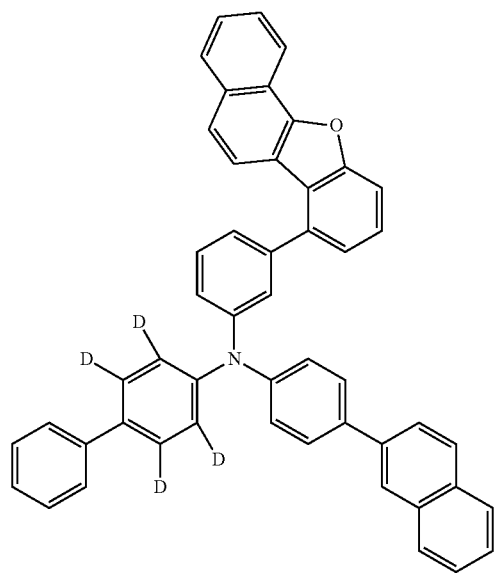
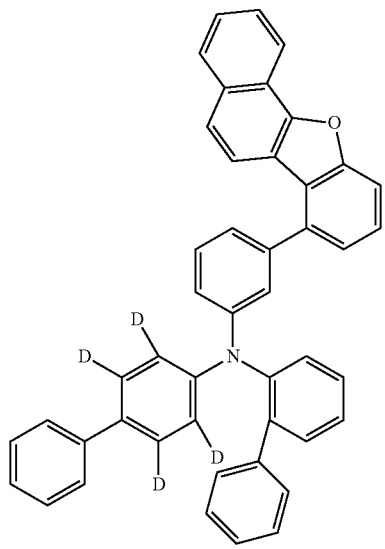

1037
-continued
1038
-continued
[Chem. 349]
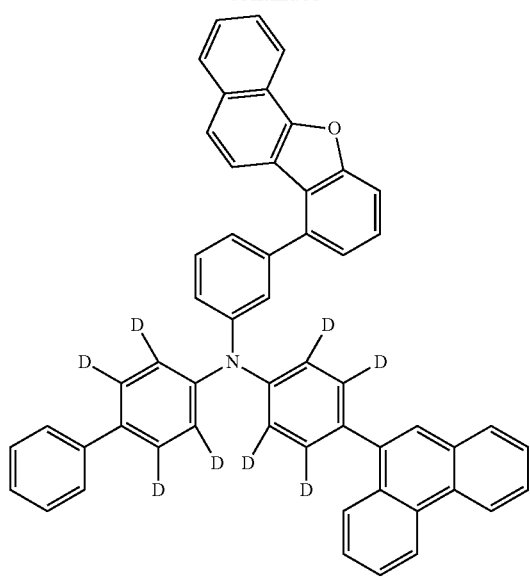
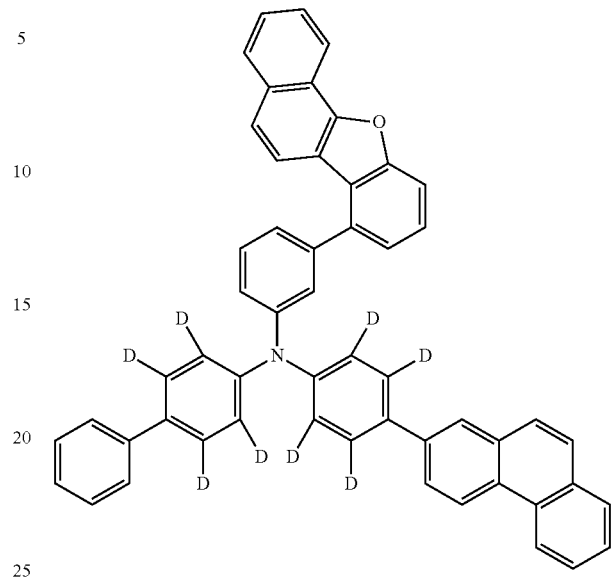
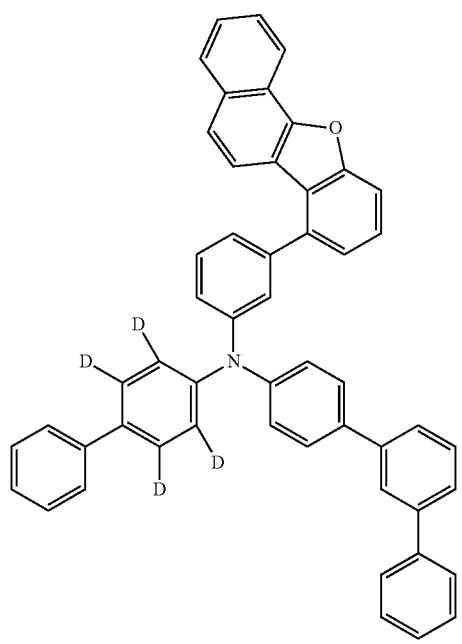
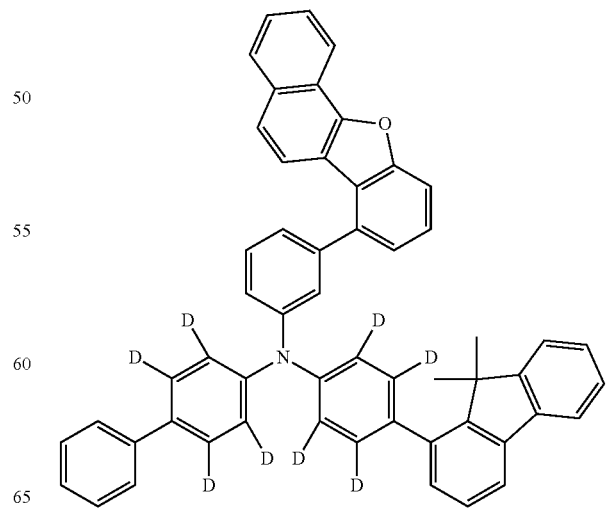

1039
-continued
1040
-continued
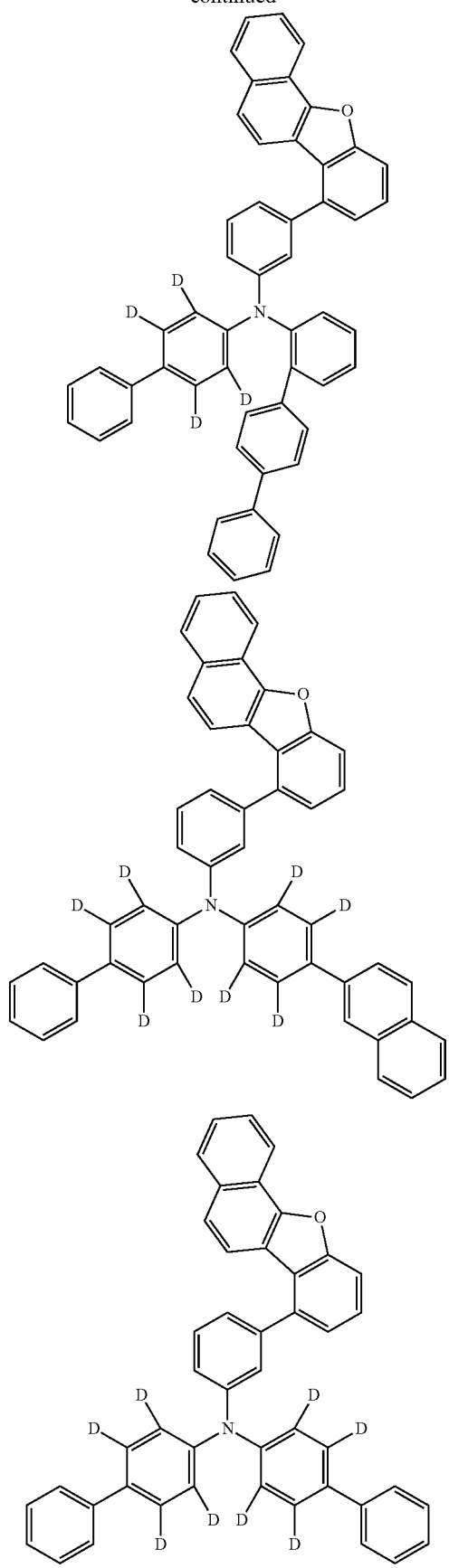
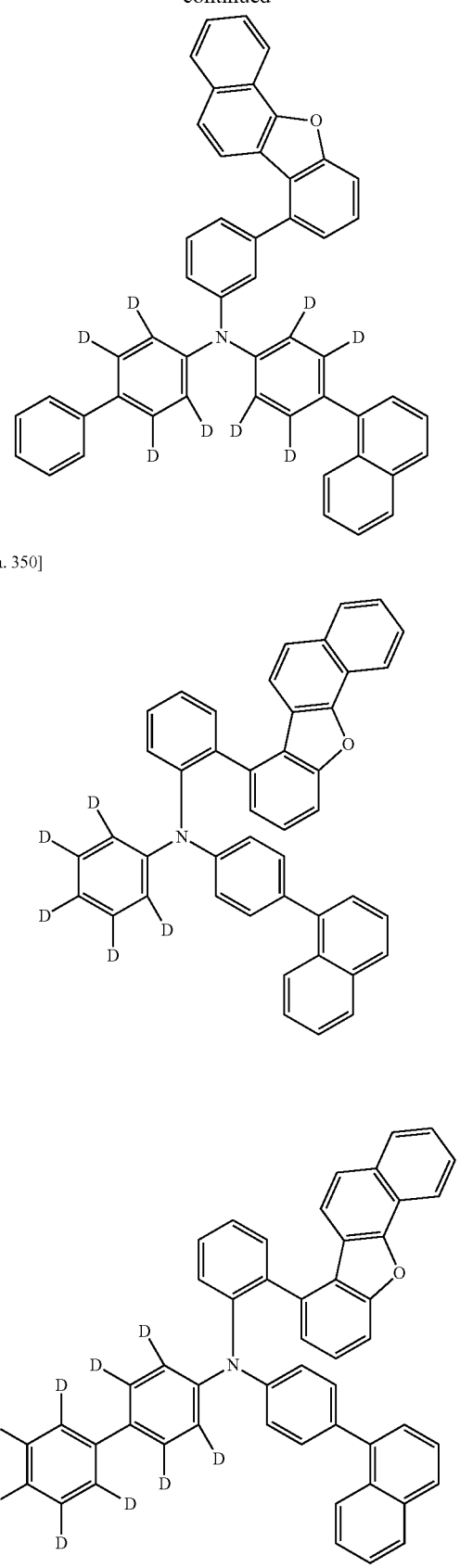
[Chem. 350]

1041
-continued
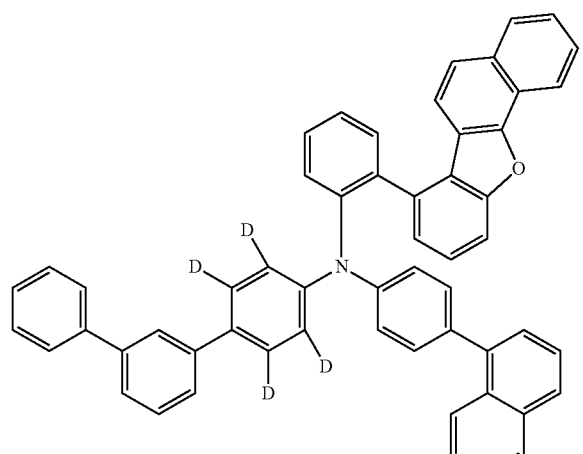
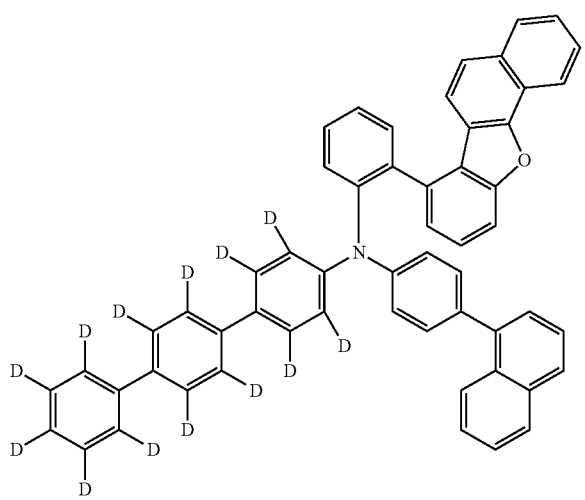
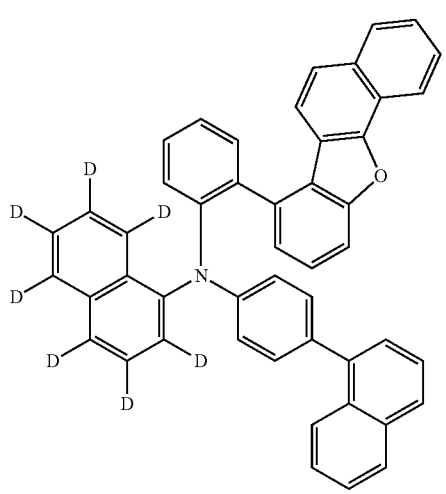
1042
-continued
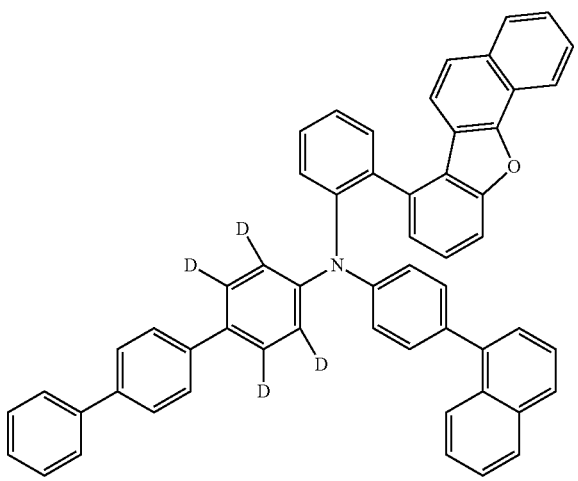
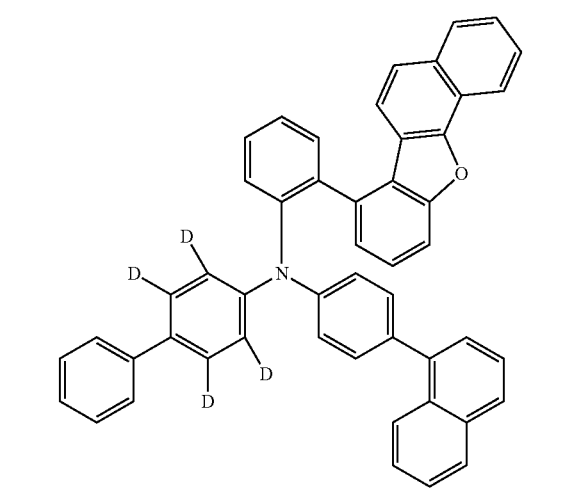

1043
-continued
[Chem. 351]
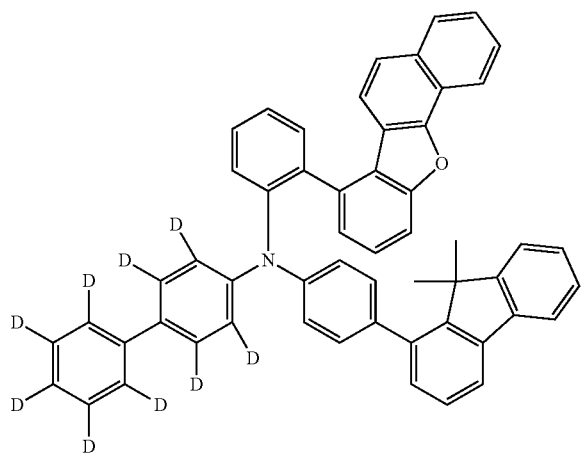
1044
-continued
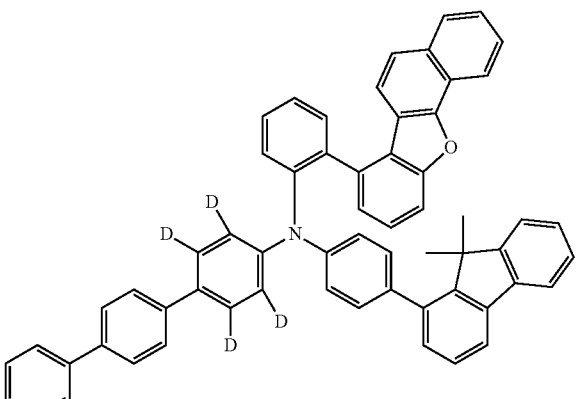

1045
-continued
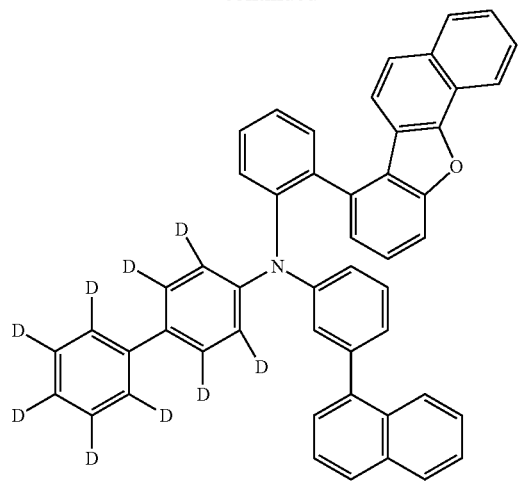
[Chem. 352]
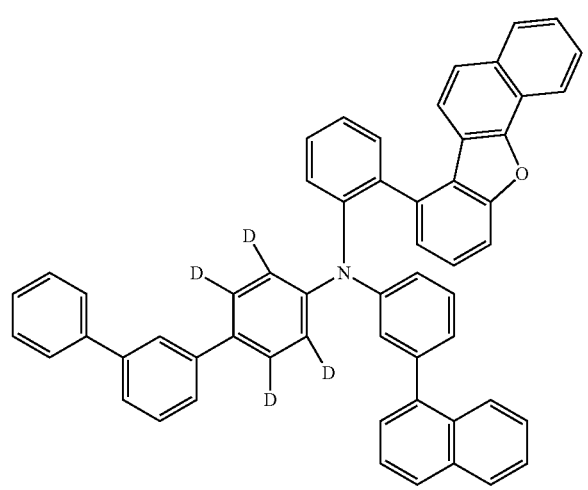
1046
-continued
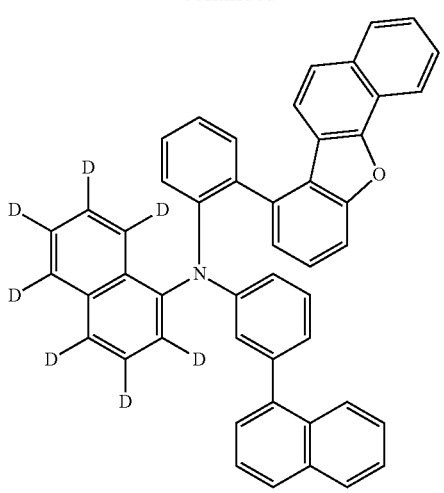
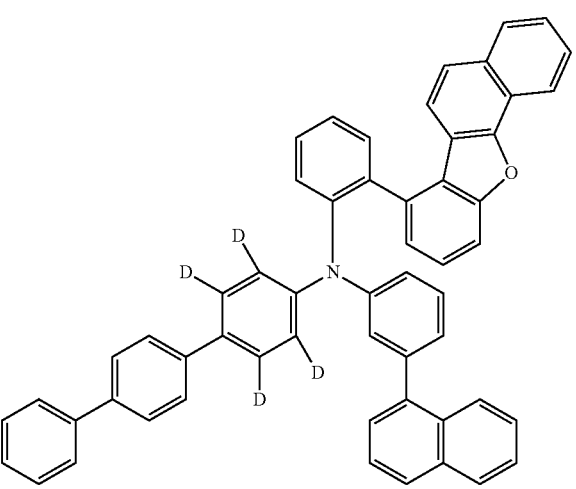
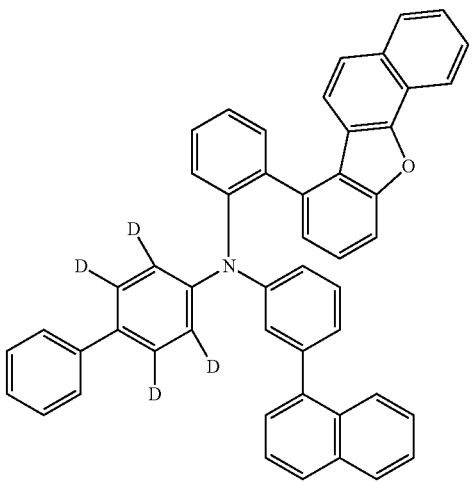

1047
-continued
1048
-continued
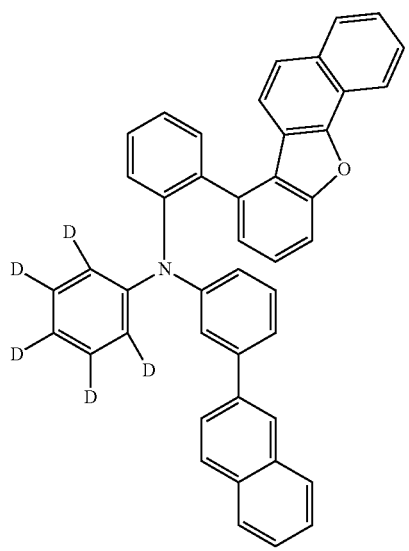
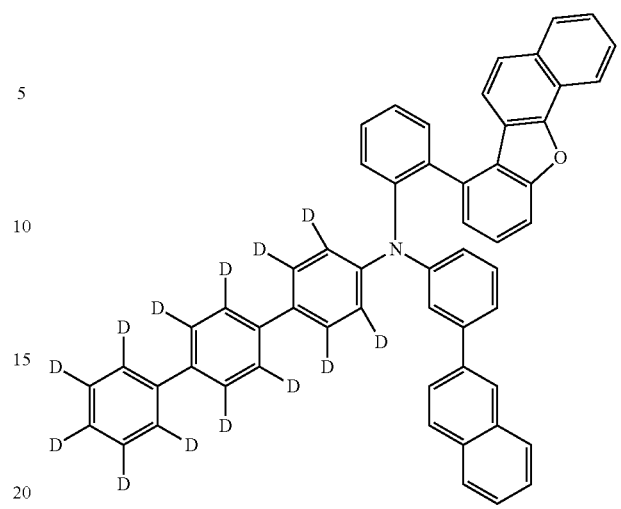
[Chem. 353]
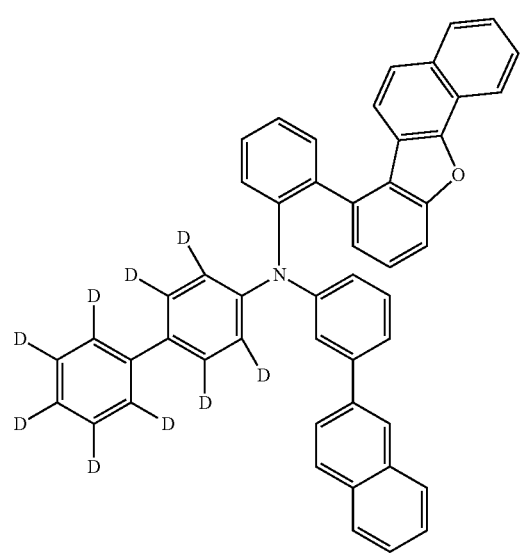
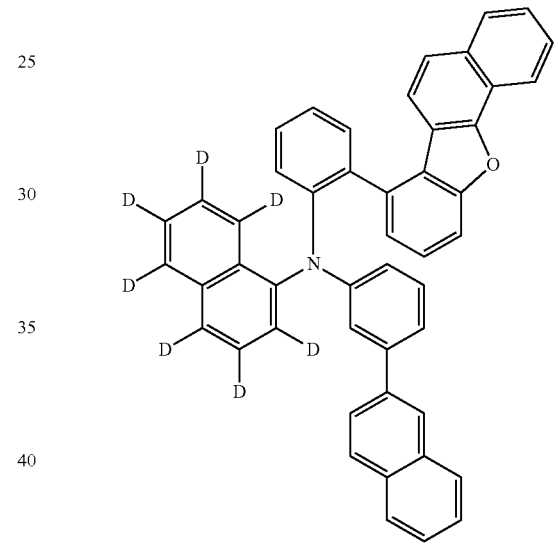
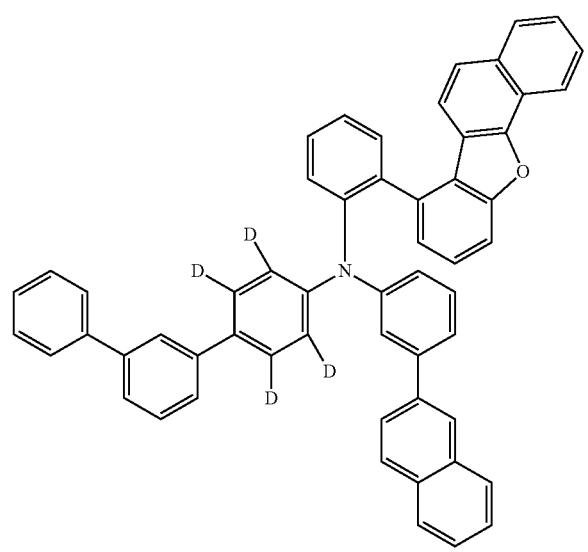
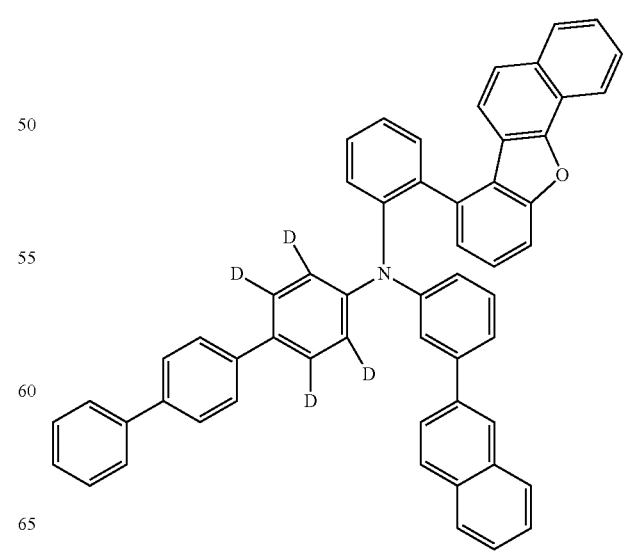

1049
-continued
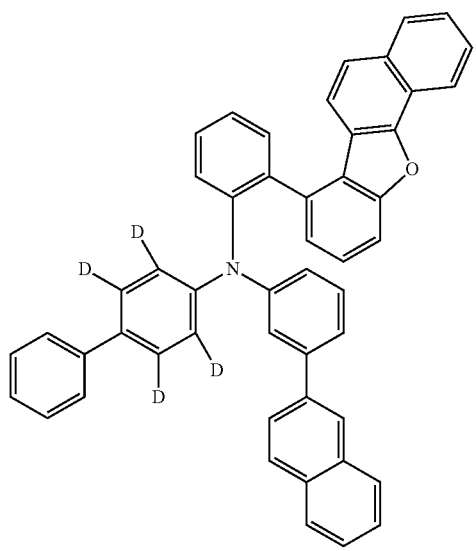
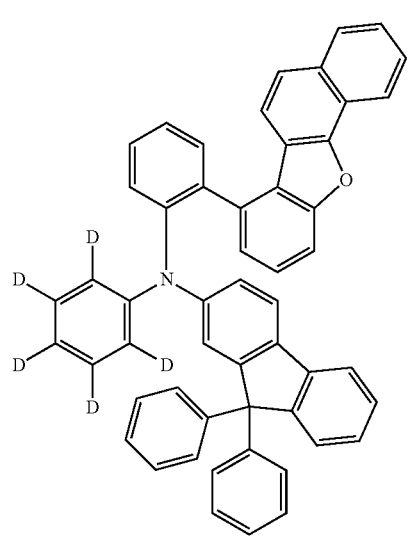
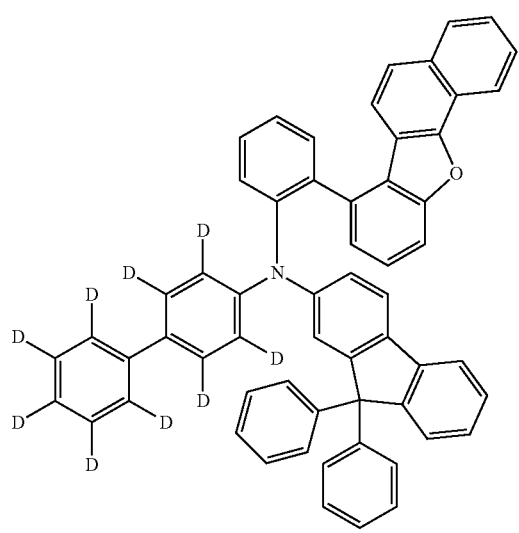
1050
-continued
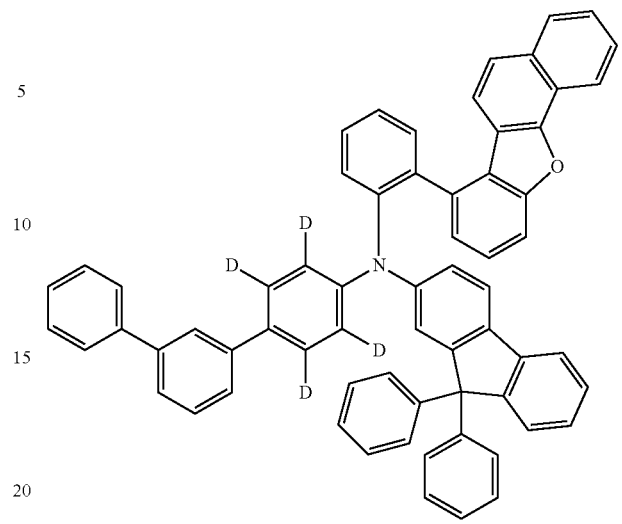
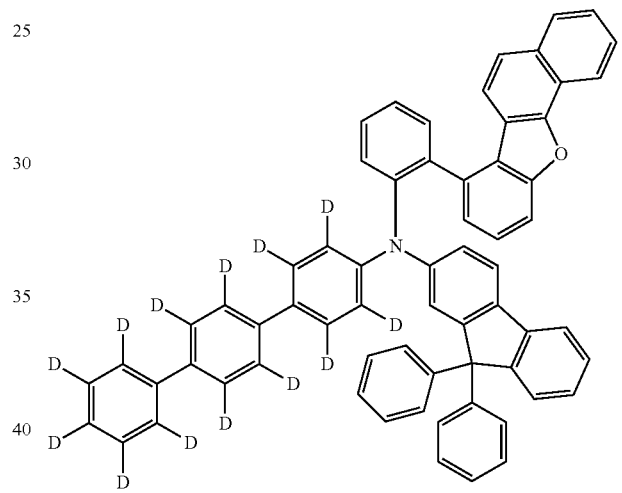
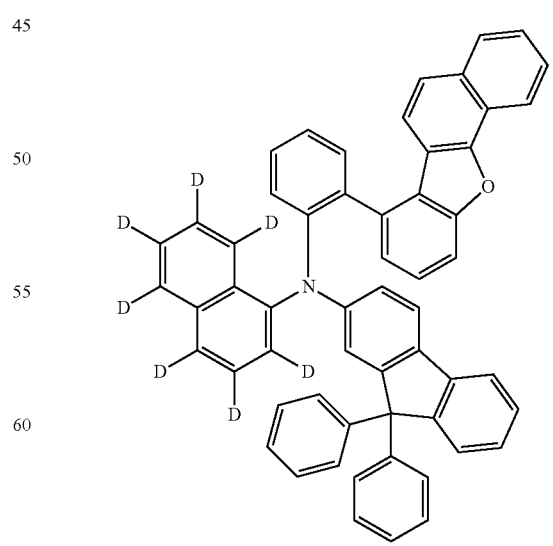

1051
-continued
[Chem. 354]
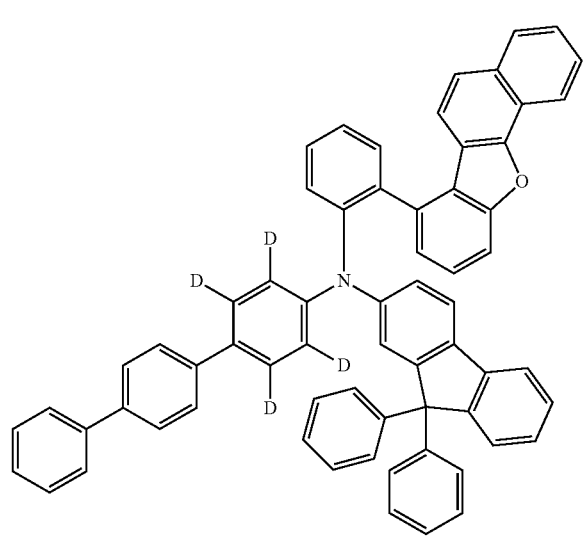
1052
-continued
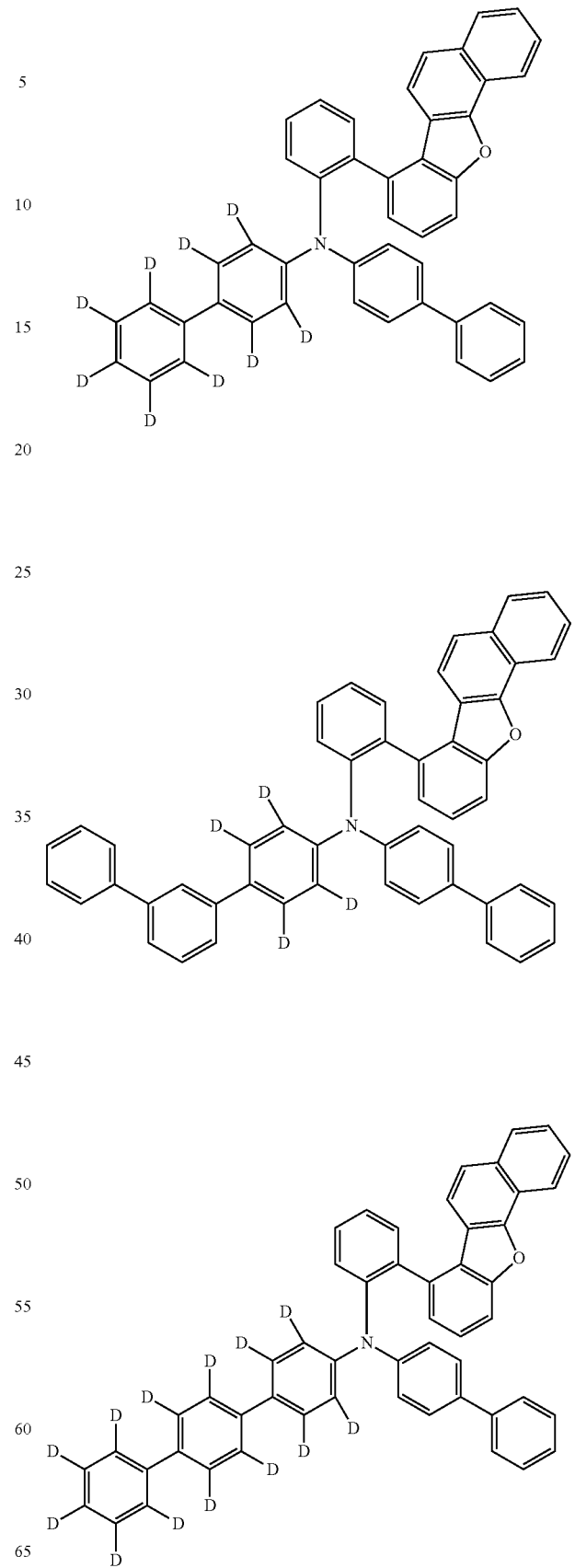

1053
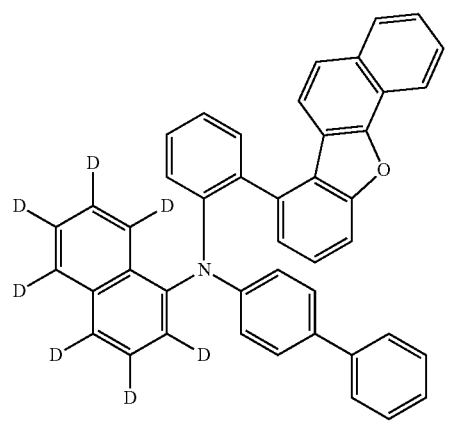
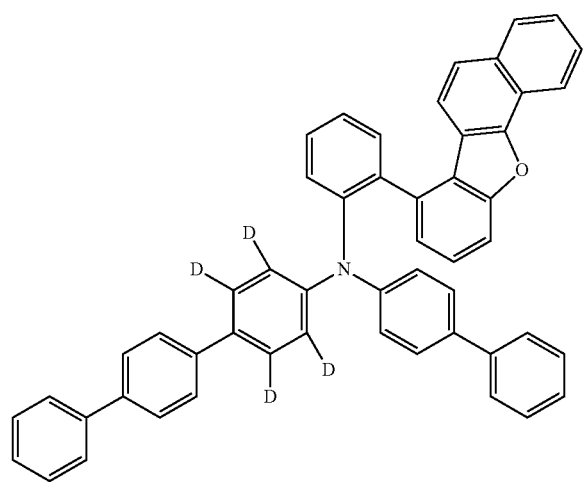
[Chem. 355]
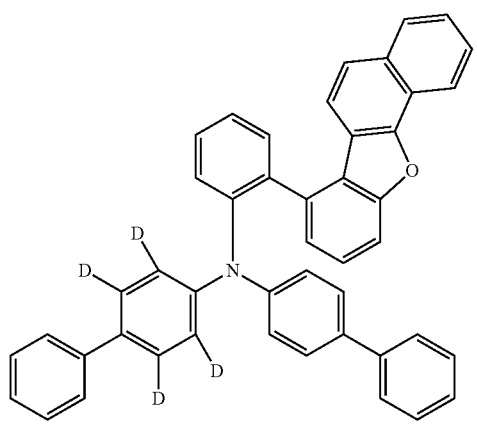
1054
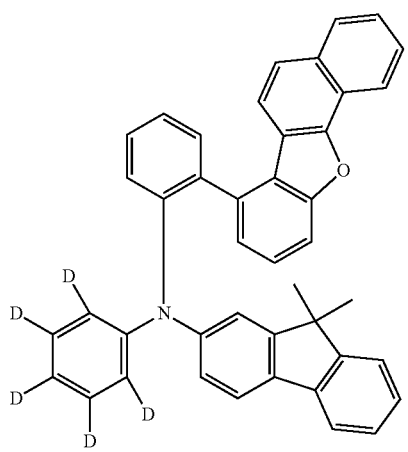
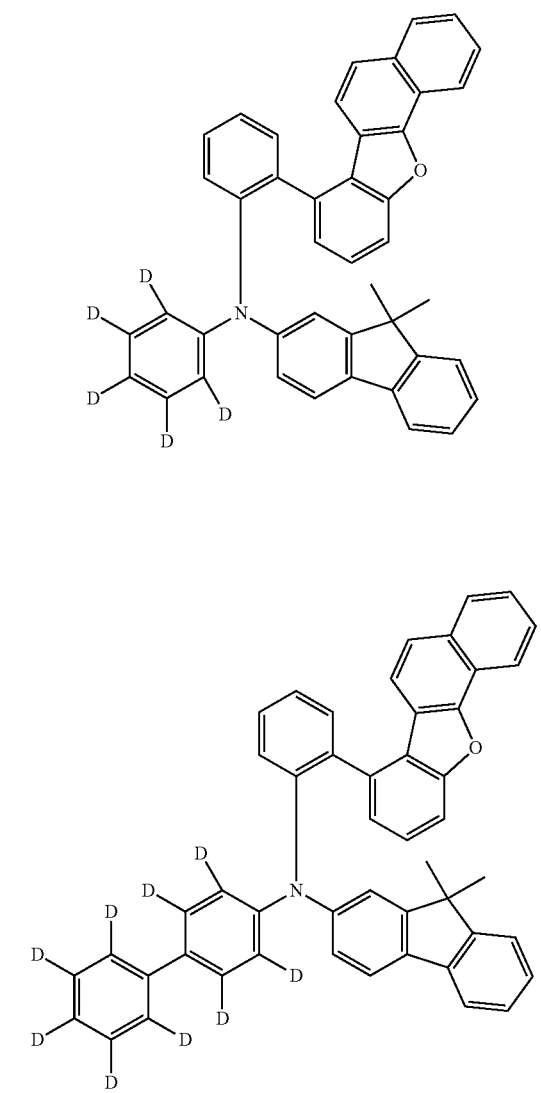
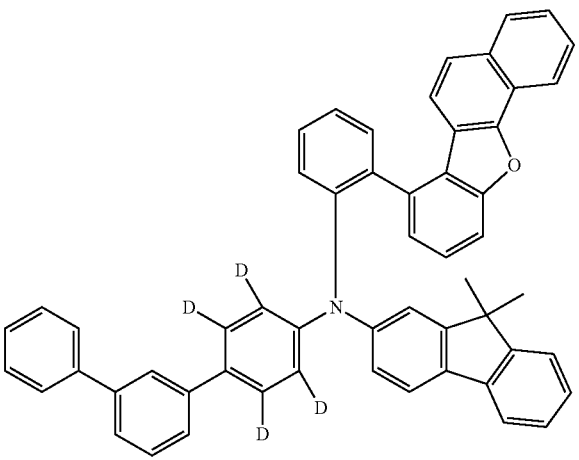

1055
-continued
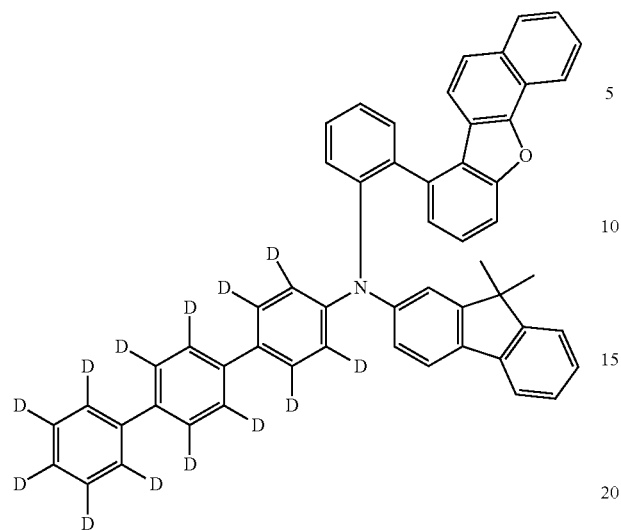
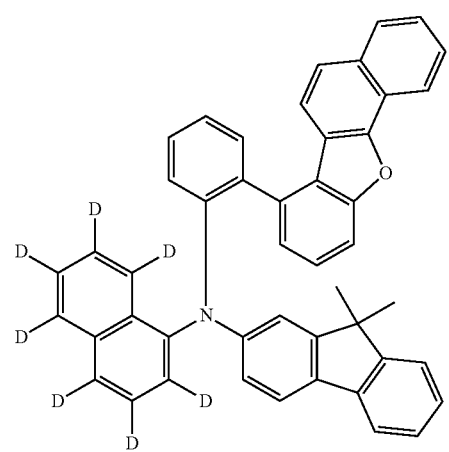
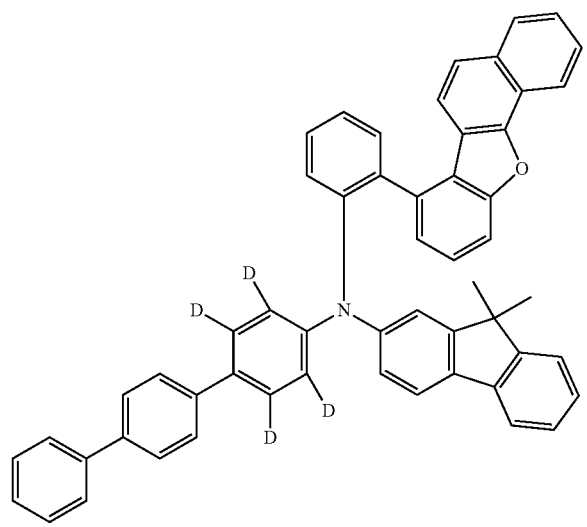
1056
-continued
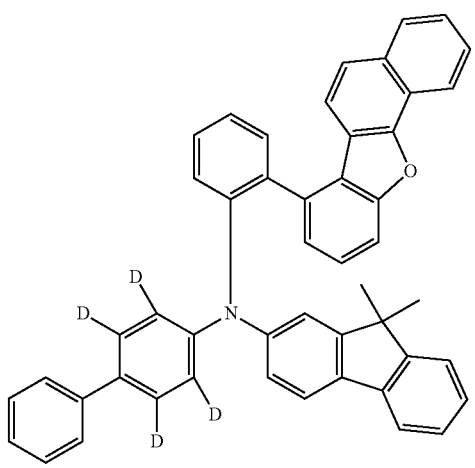
[Chem. 356]
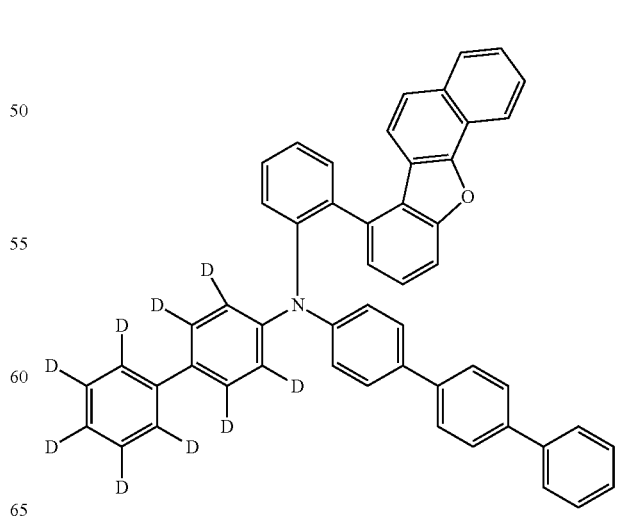

1057
-continued
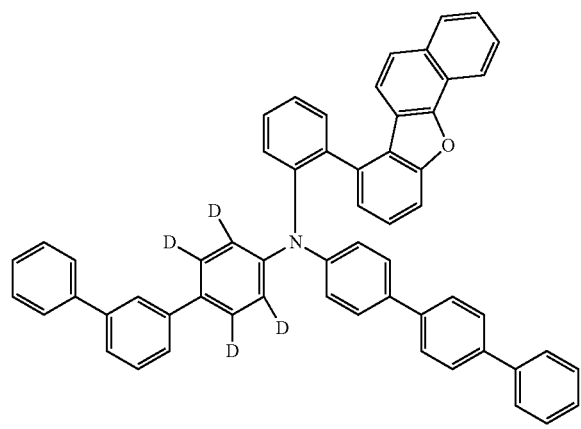
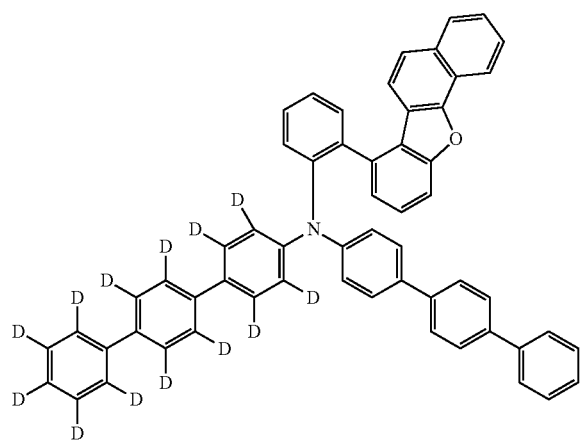
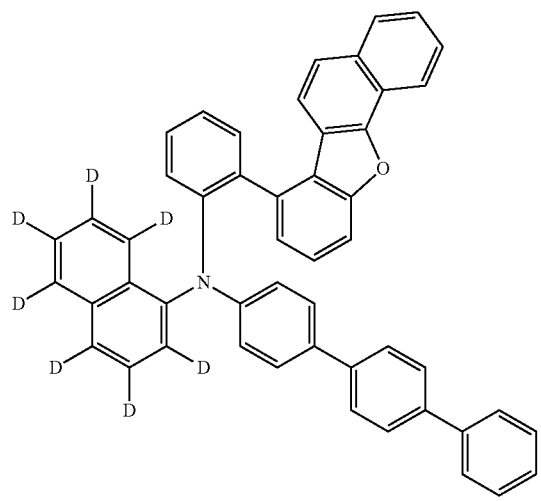
1058
-continued
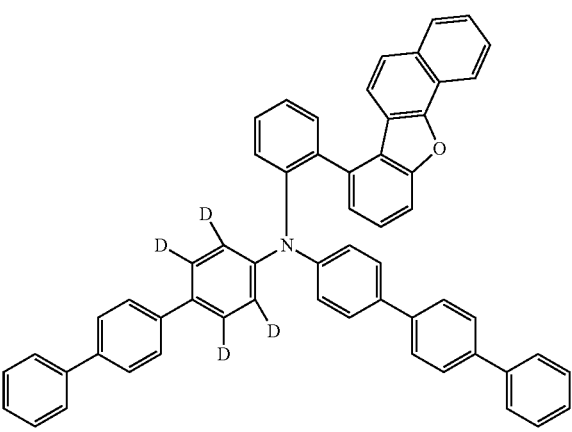
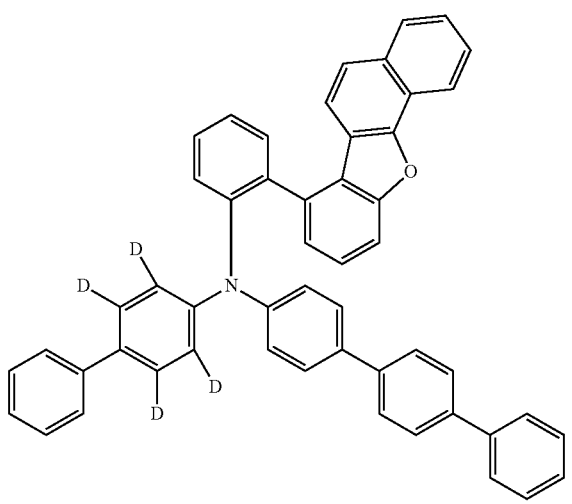
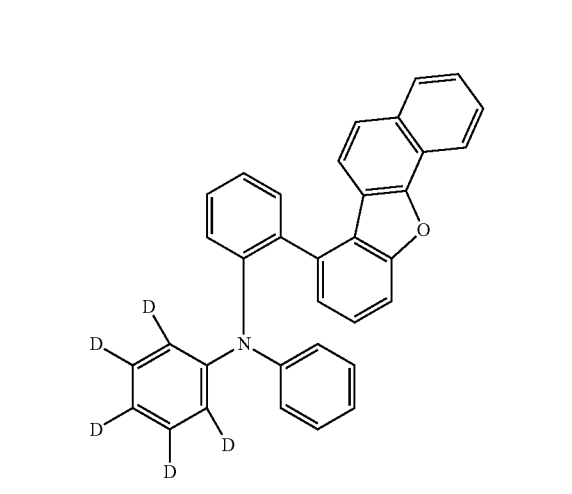

1059
-continued
1060
-continued
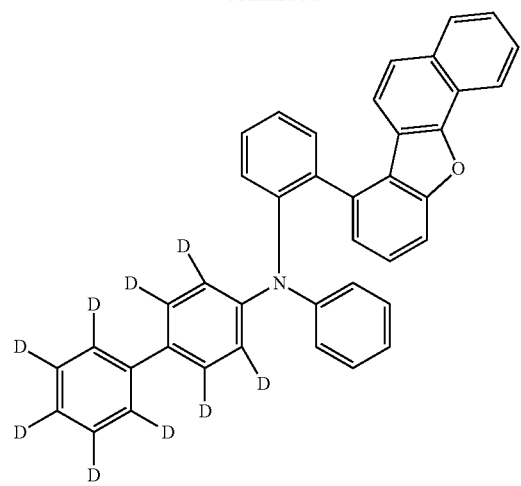
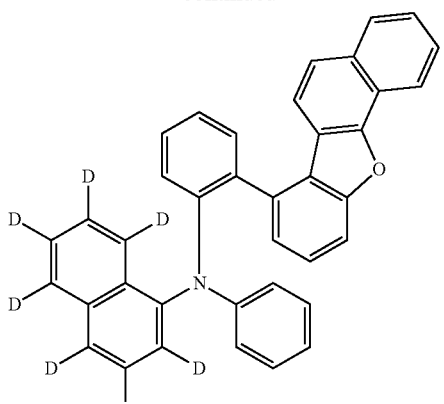
[Chem. 357]
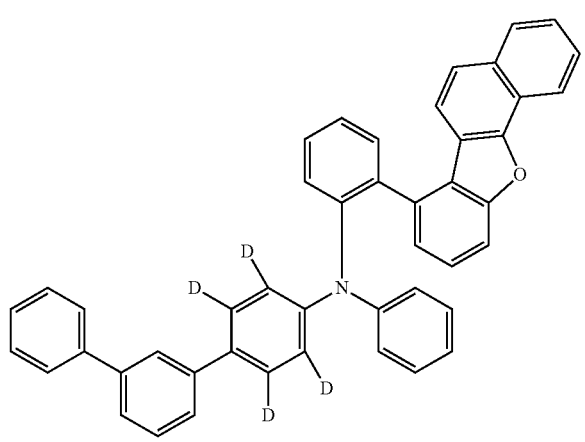
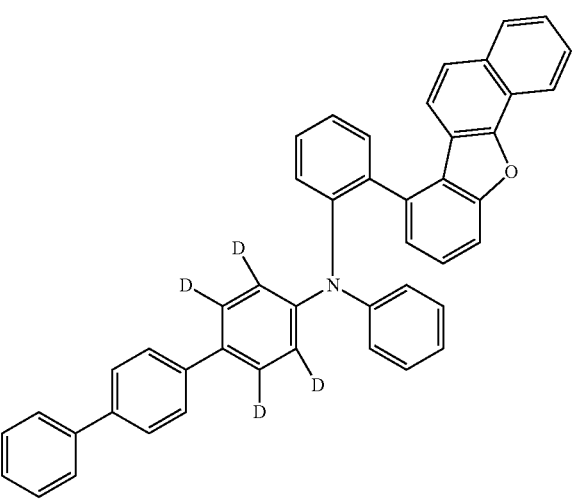
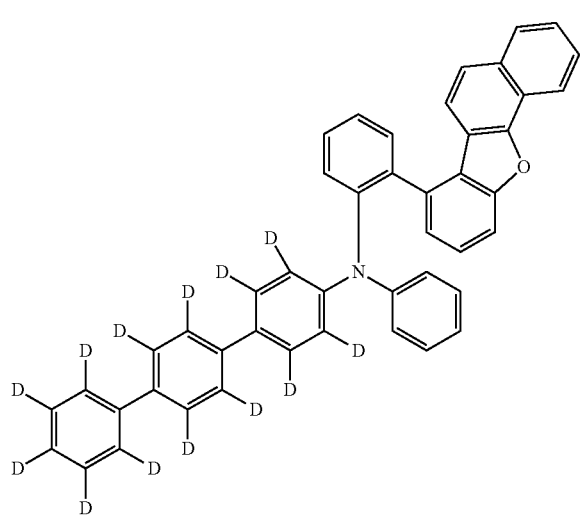
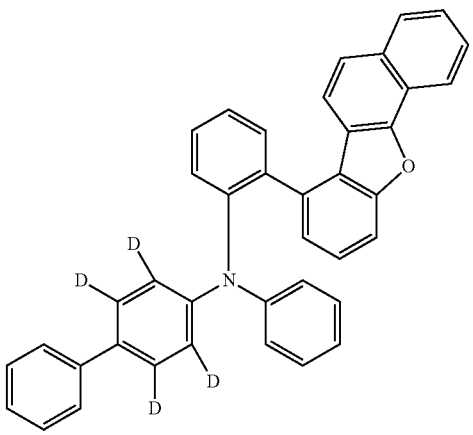

1061
-continued
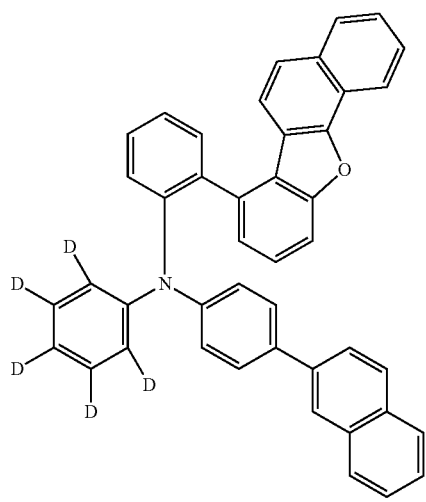
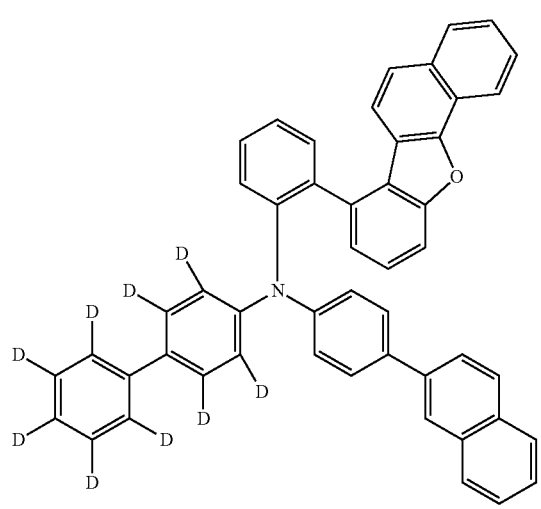
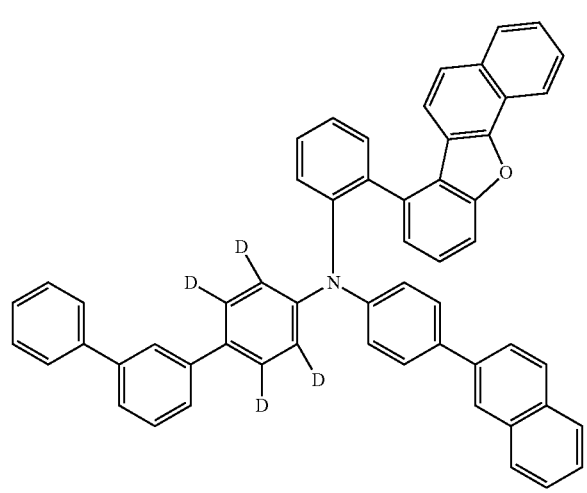
1062
-continued
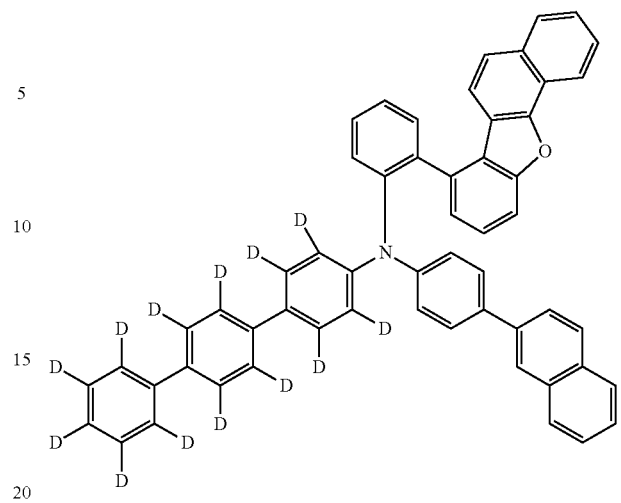
[Chem. 358]
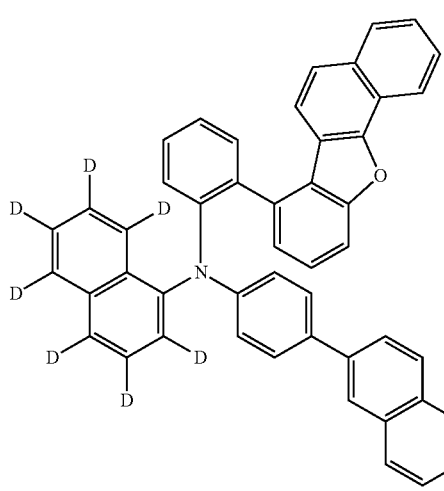
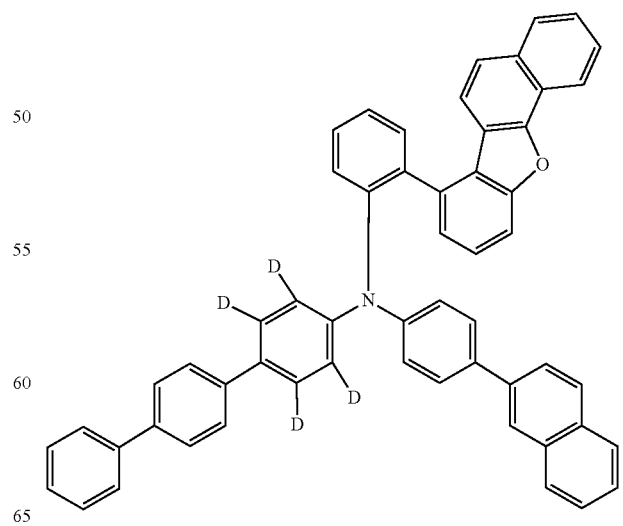

1063
1064
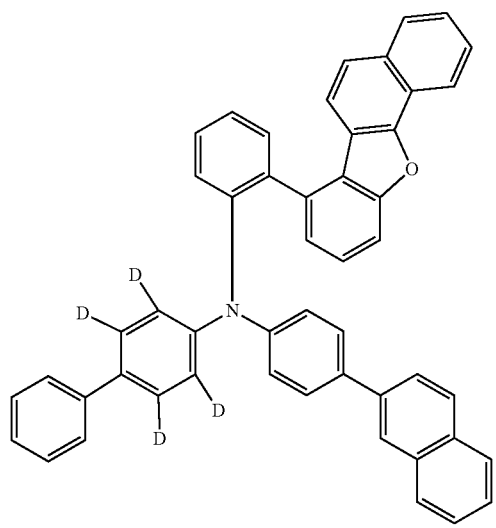
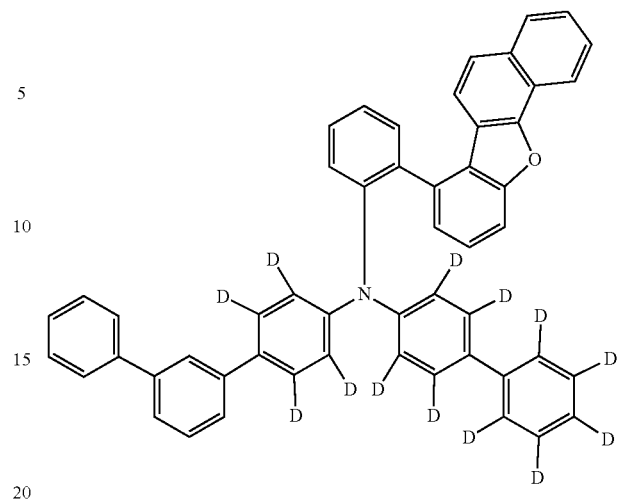
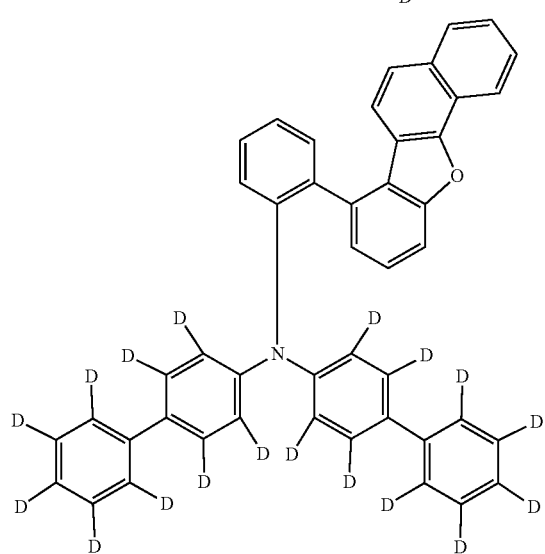
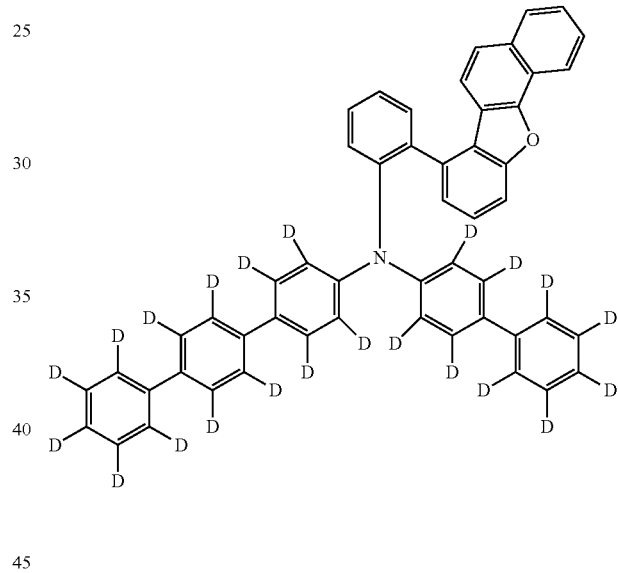
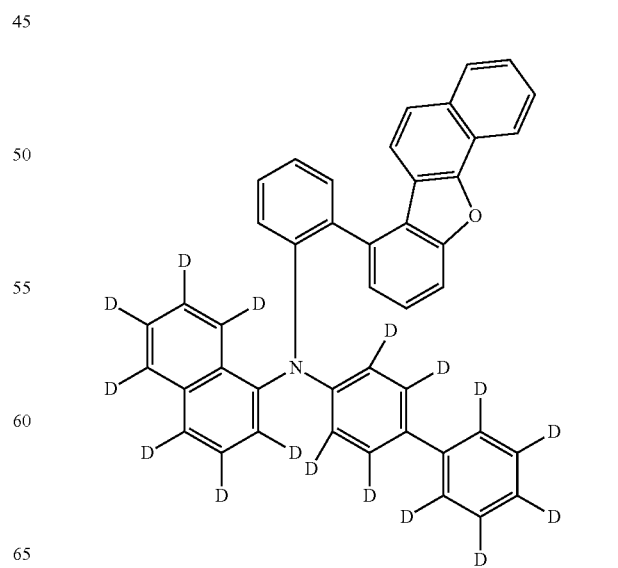

1065
-continued
[Chem. 359]
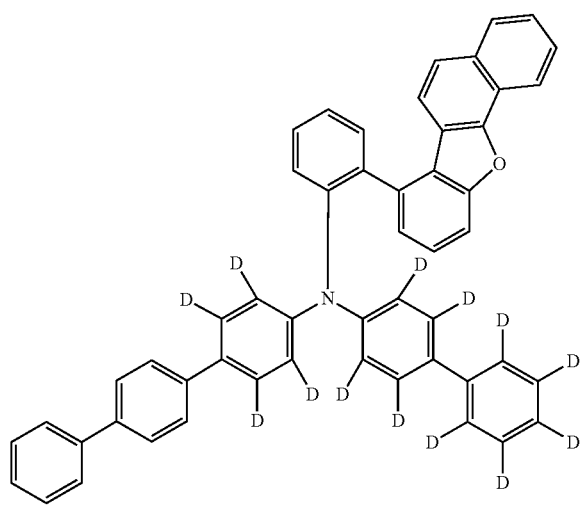
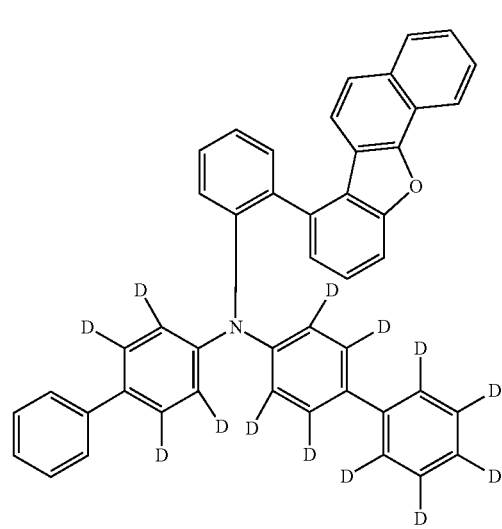
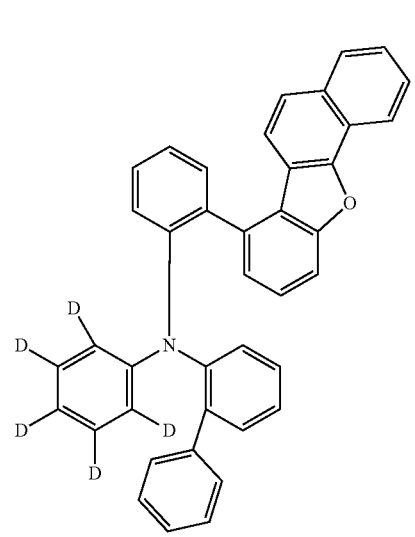
1066
-continued
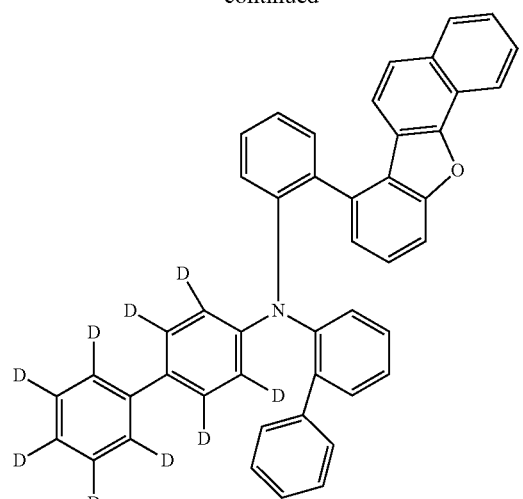
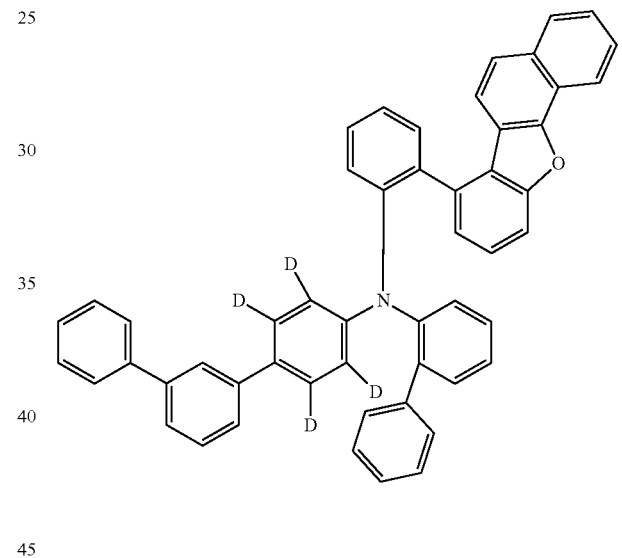
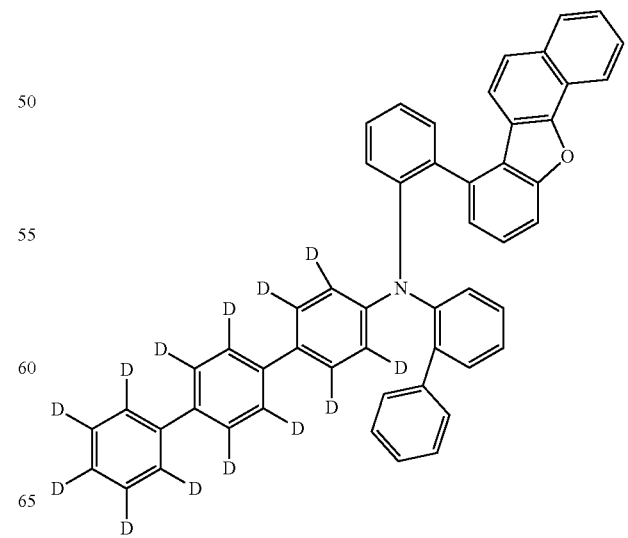

1067
-continued
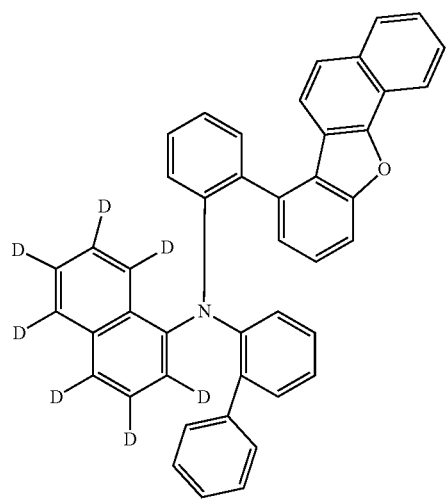
[Chem. 360]
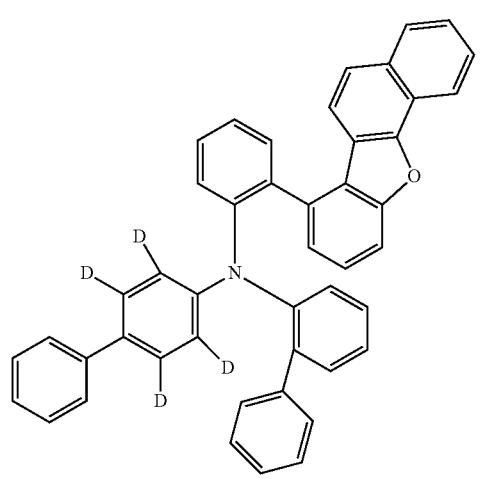
1068
-continued
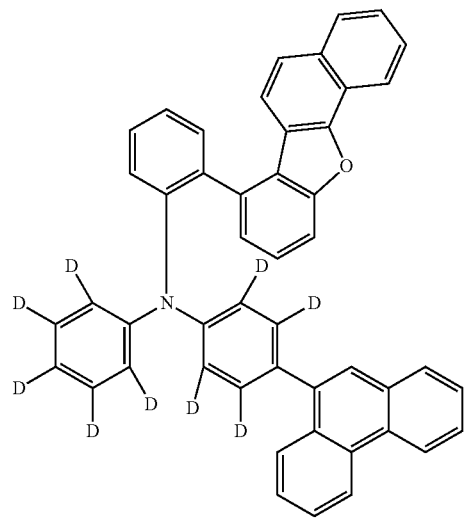
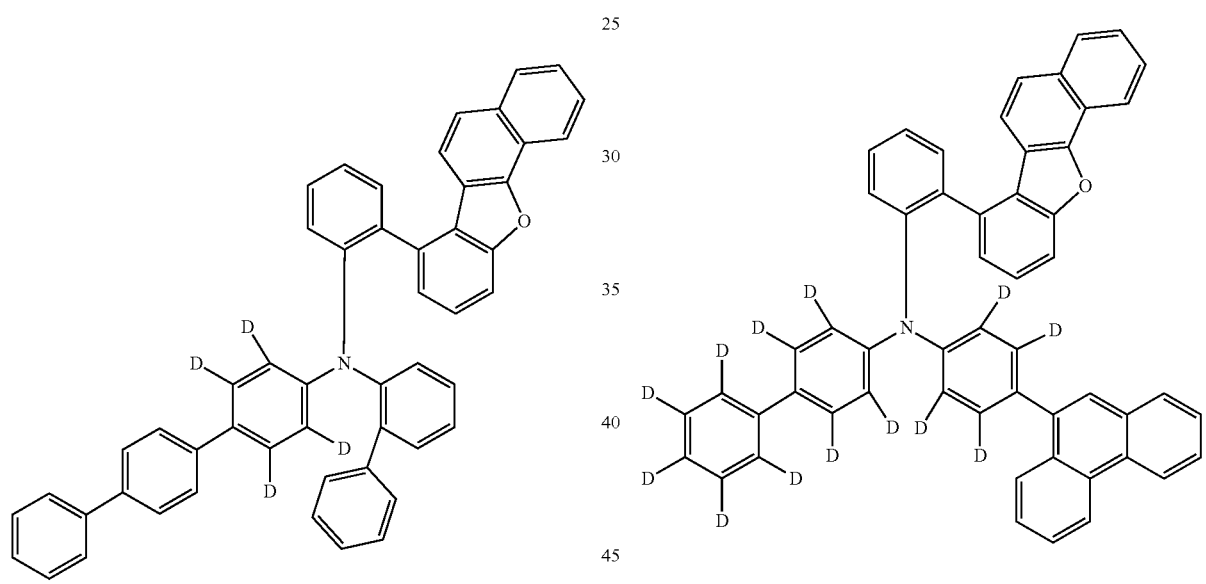
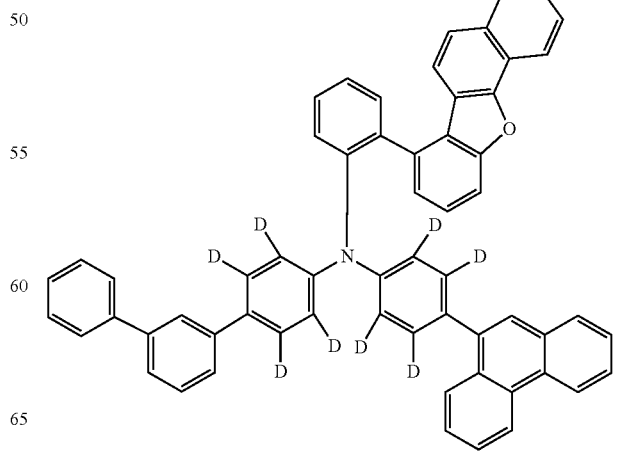

1069
-continued
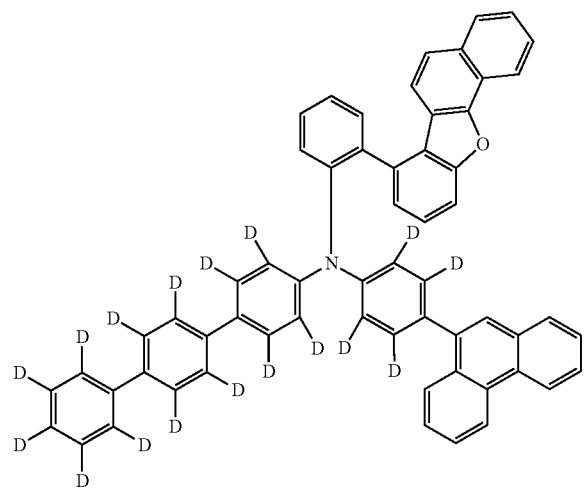
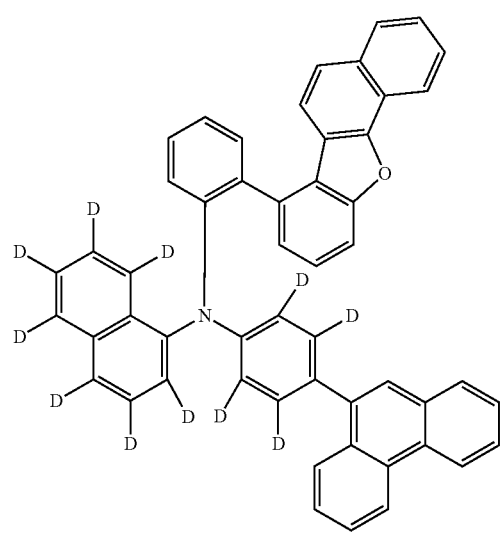
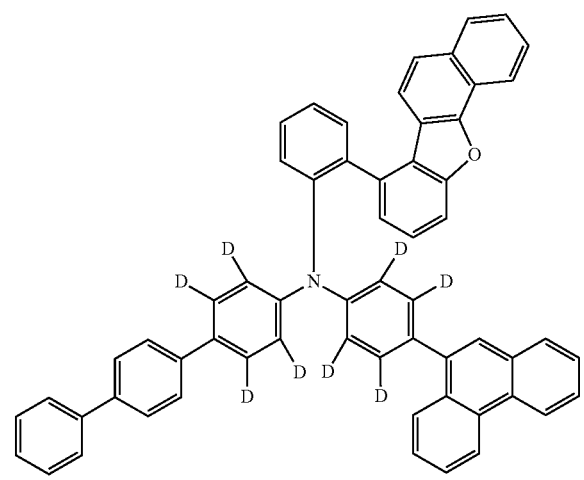
1070
-continued
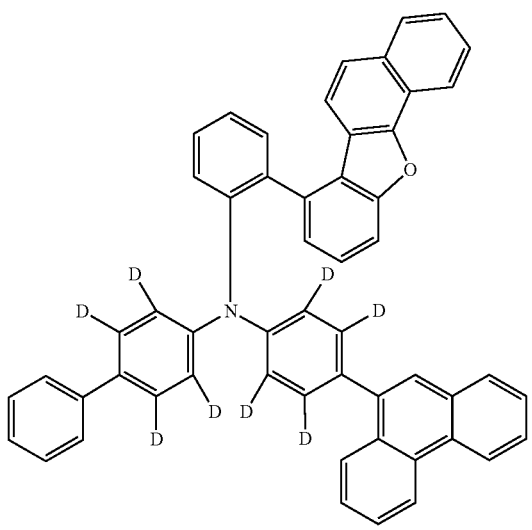
[Chem. 361]
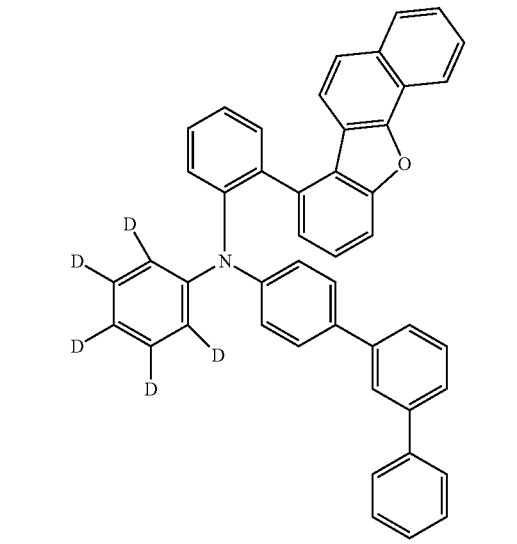
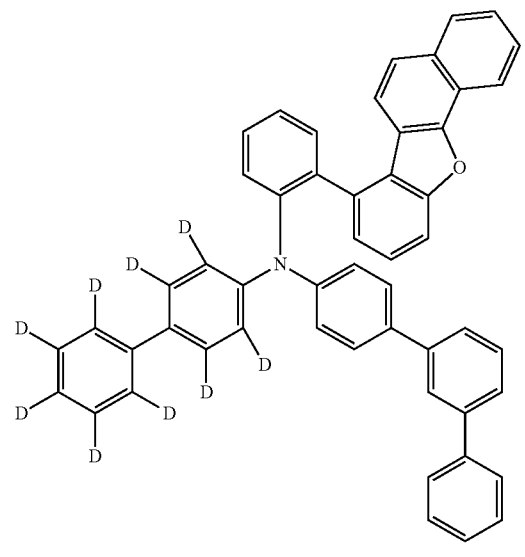

1071
-continued
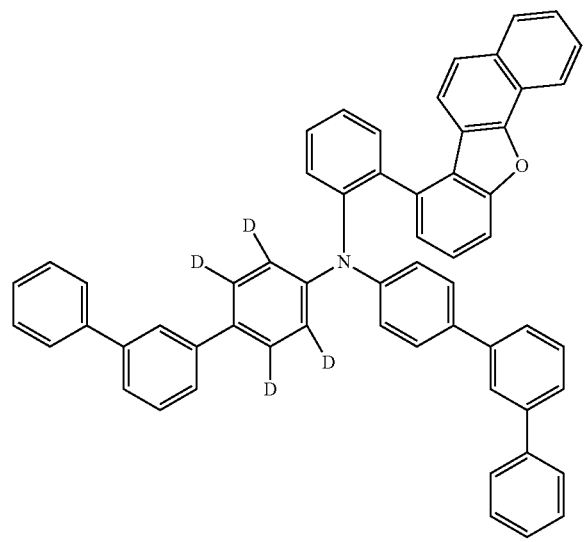
1072
-continued
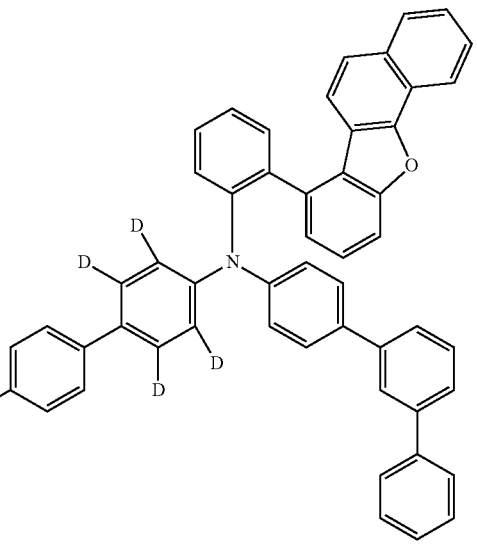
[Chem. 362]
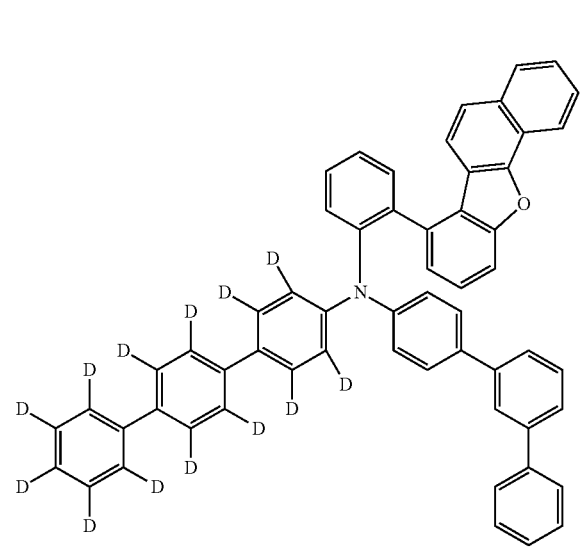
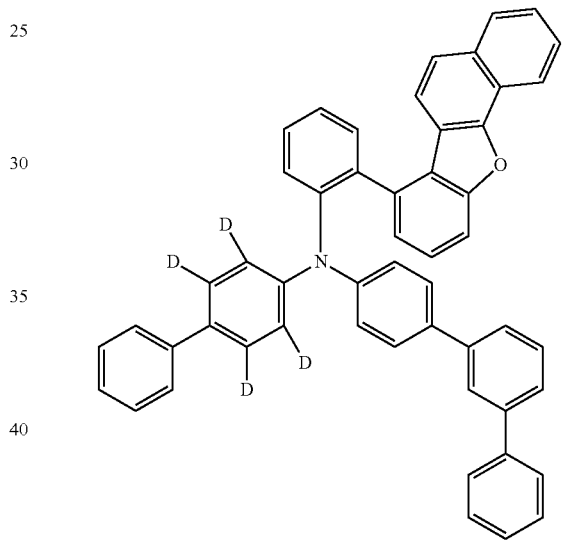
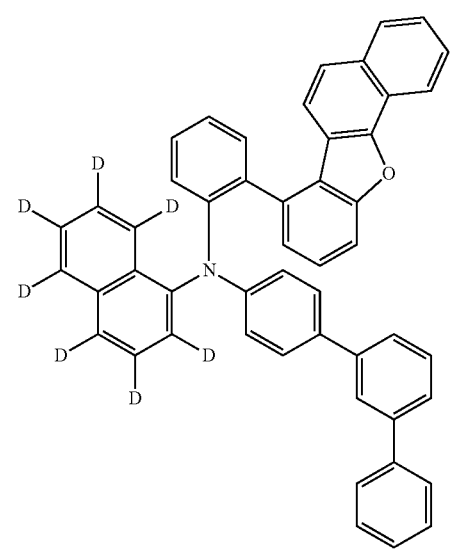
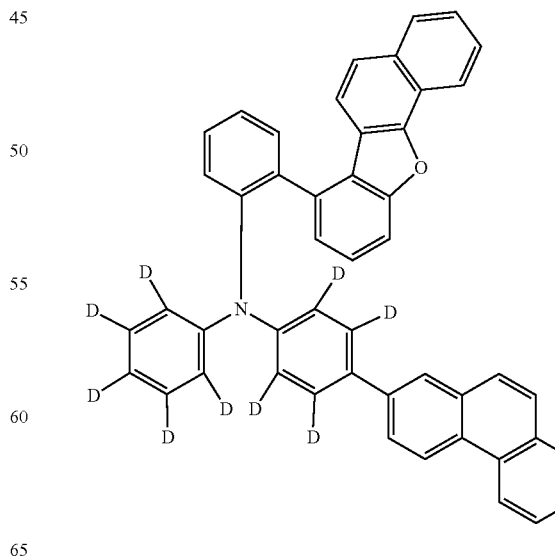

1073
-continued
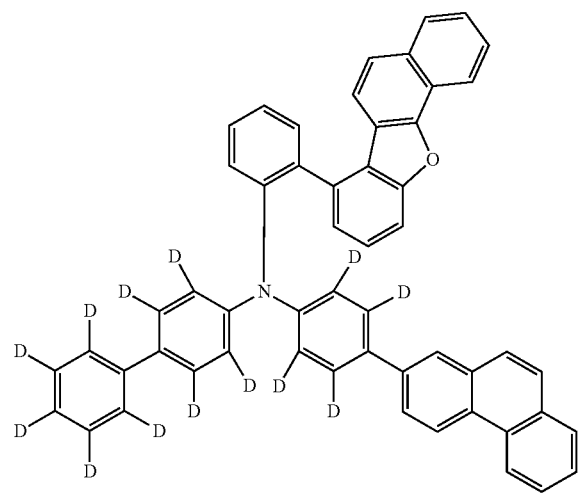
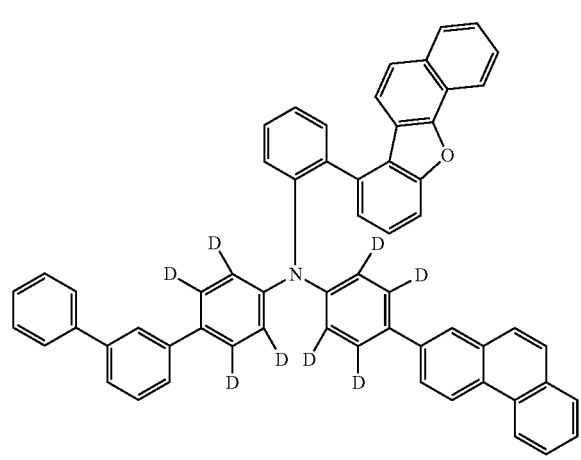
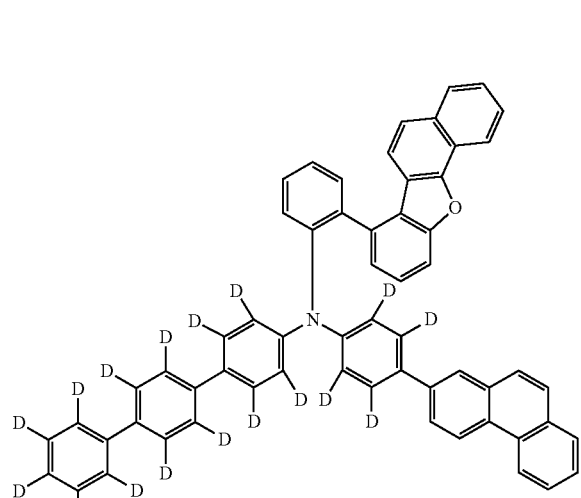
1074
-continued
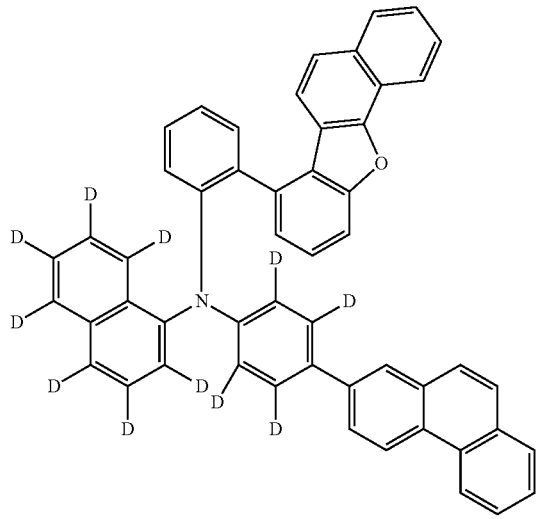
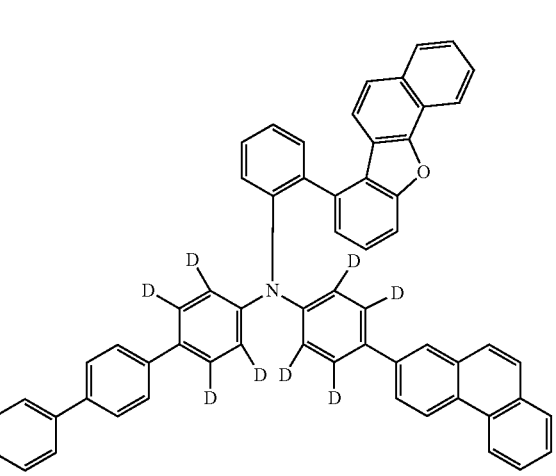
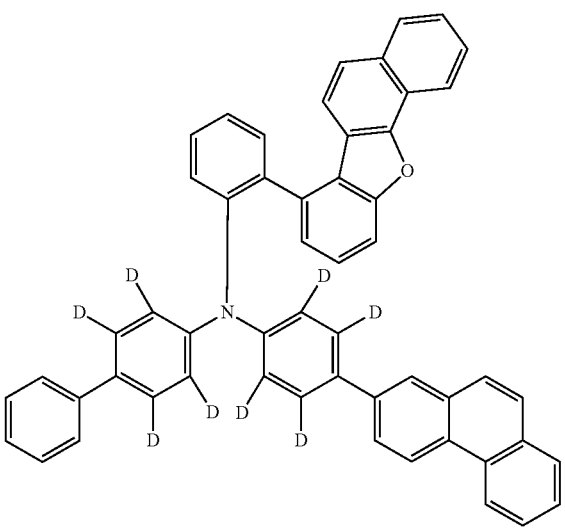

1075
-continued
[Chem. 363]
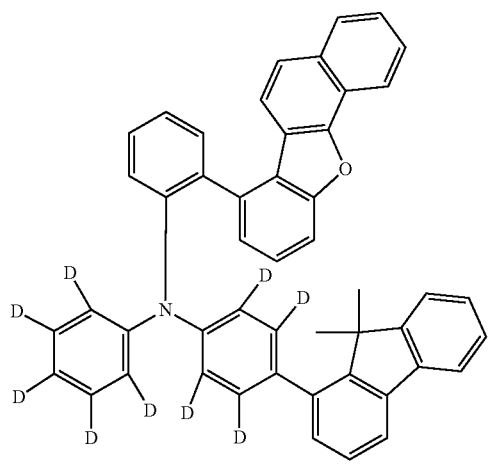
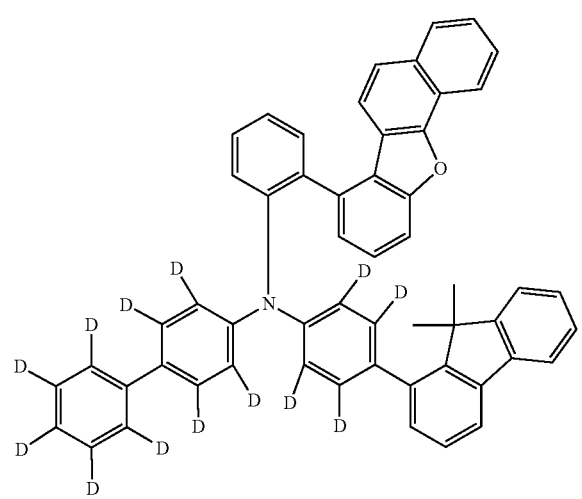
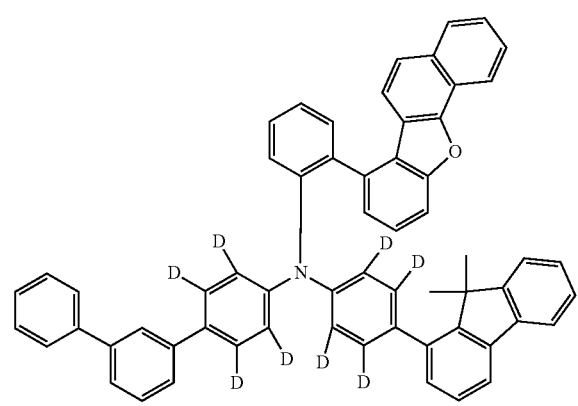
1076
-continued
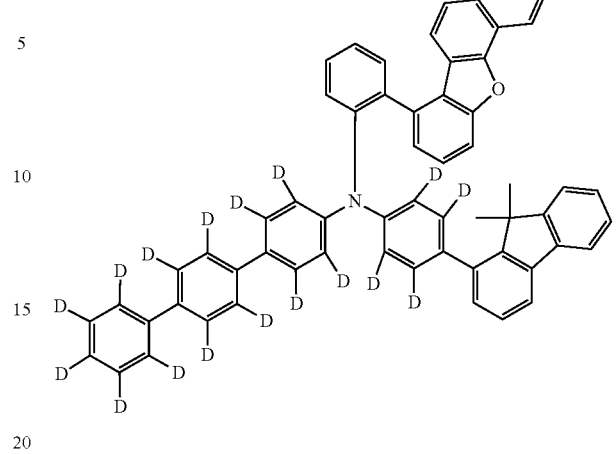
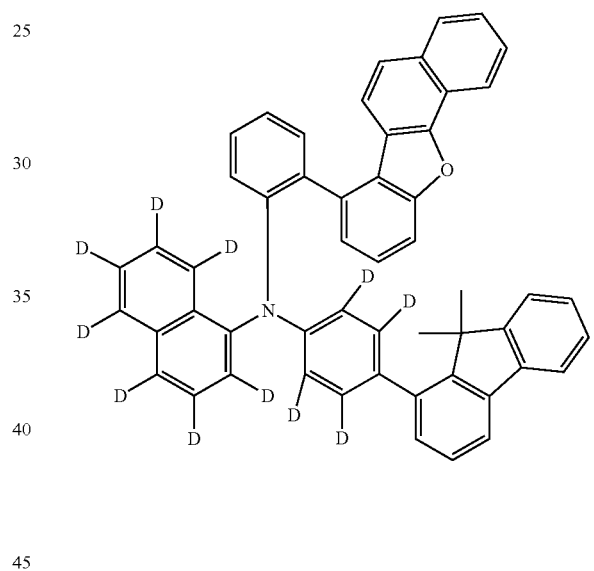
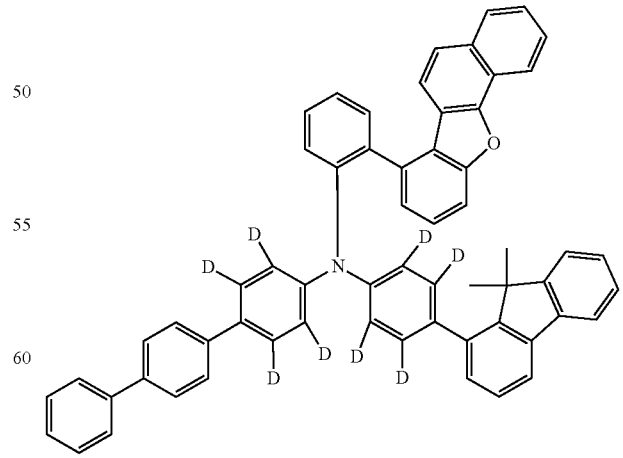

1077
-continued
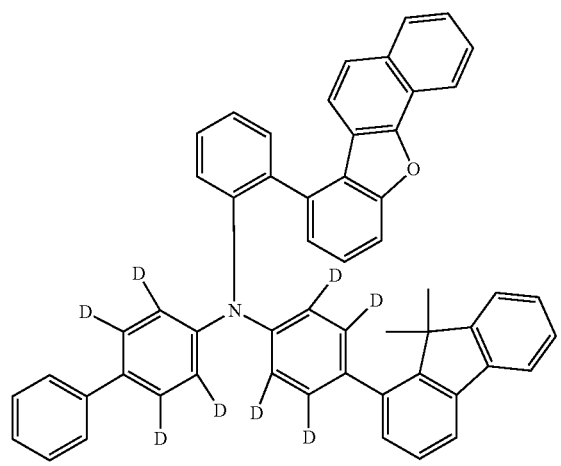
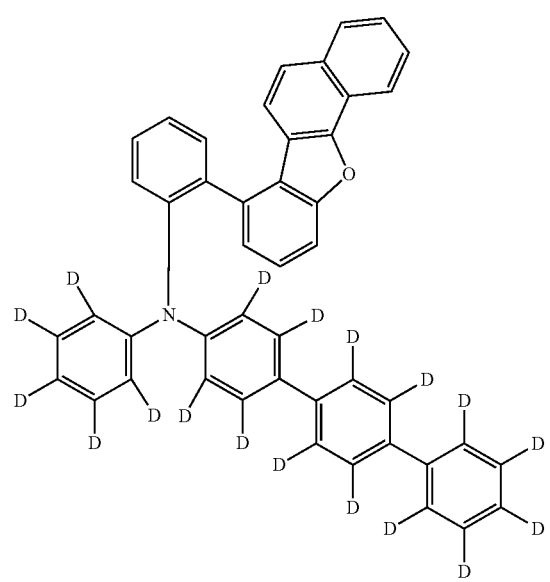
[Chem. 364]
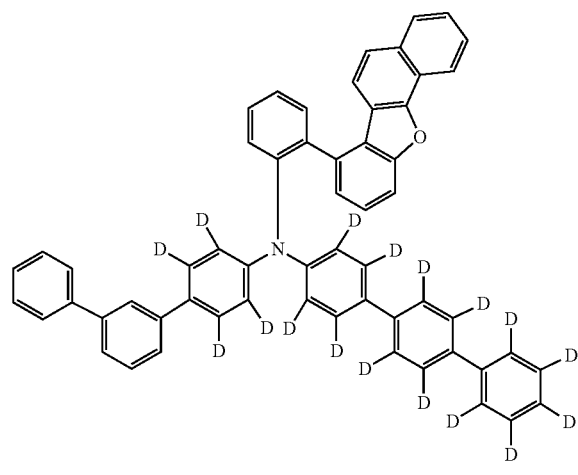
1078
-continued
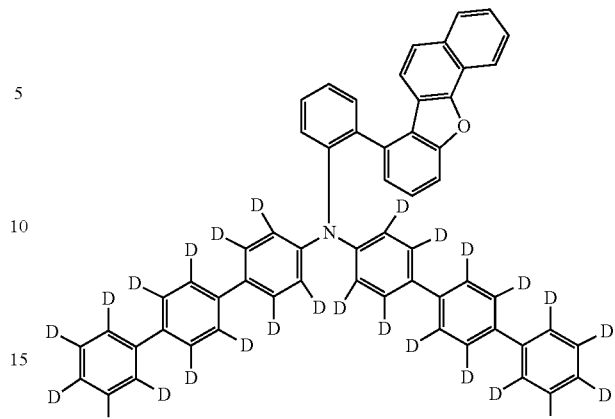
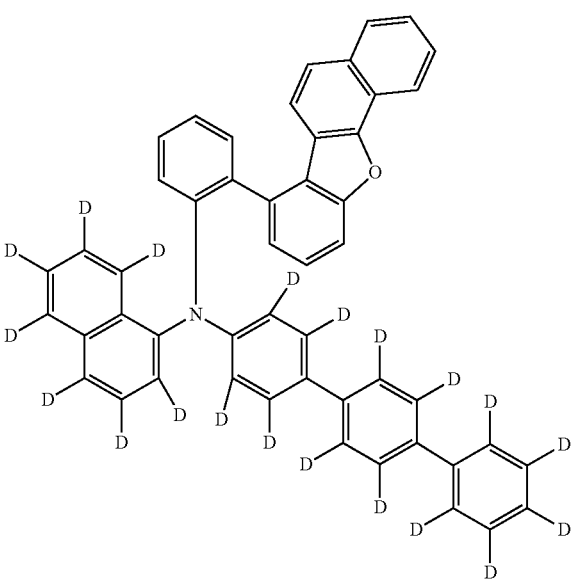
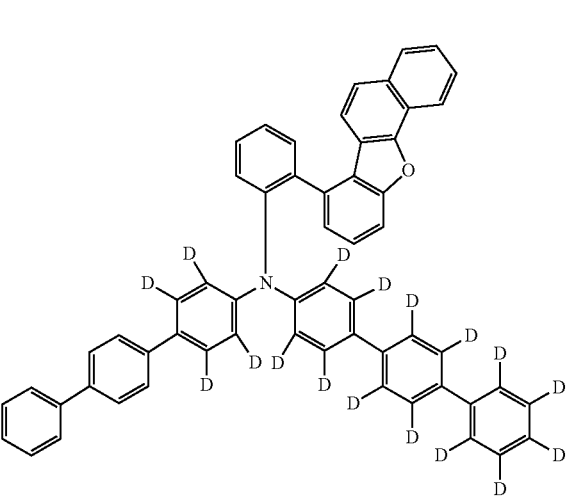

1079
-continued
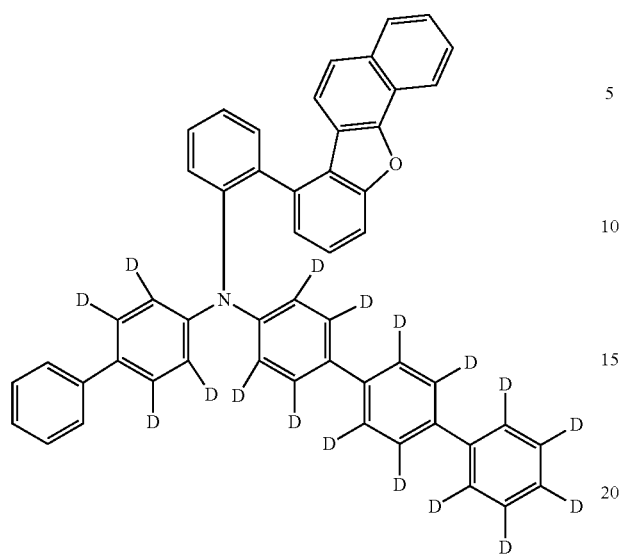
1080
-continued
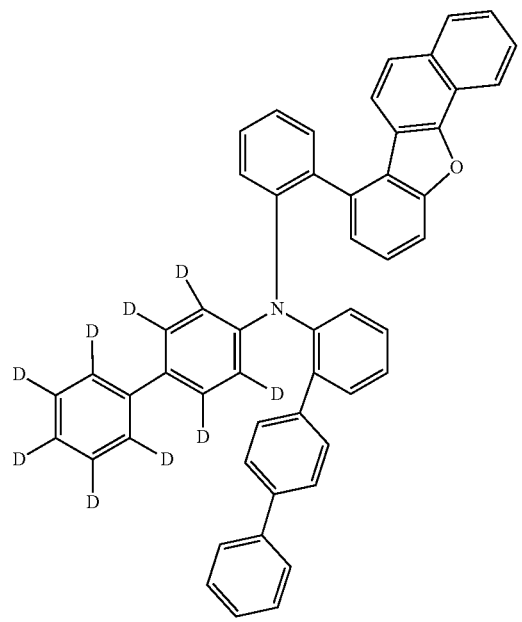
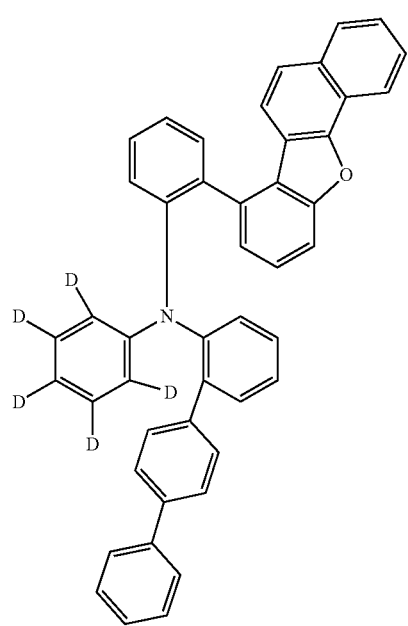
[Chem. 365]
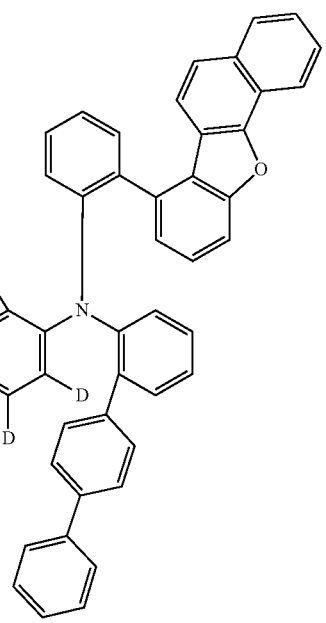

1081
-continued
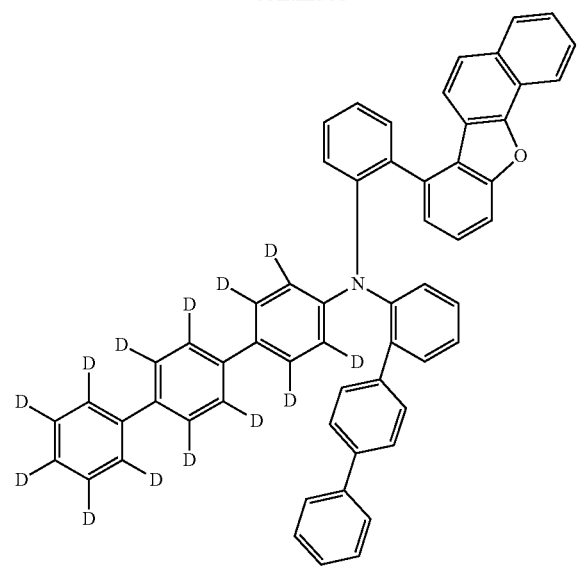
1082
-continued
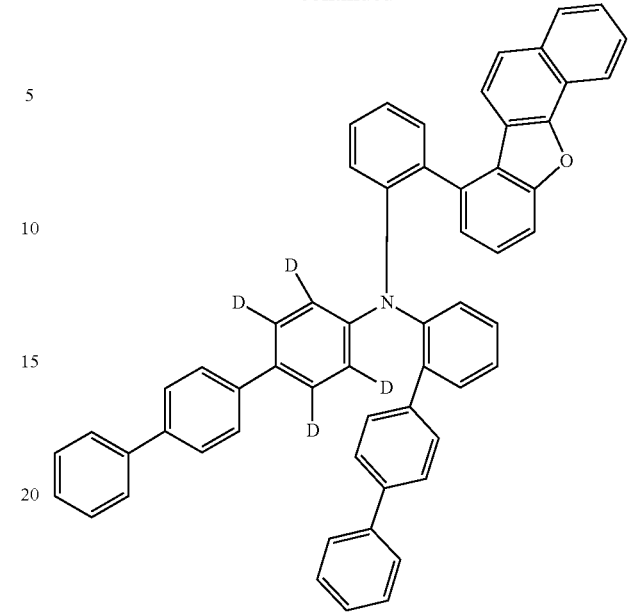
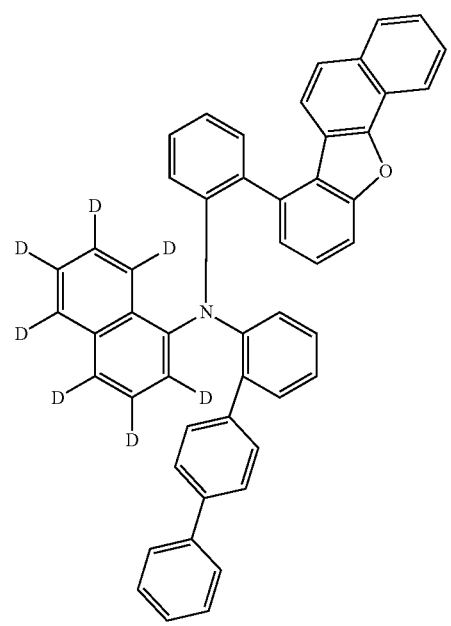
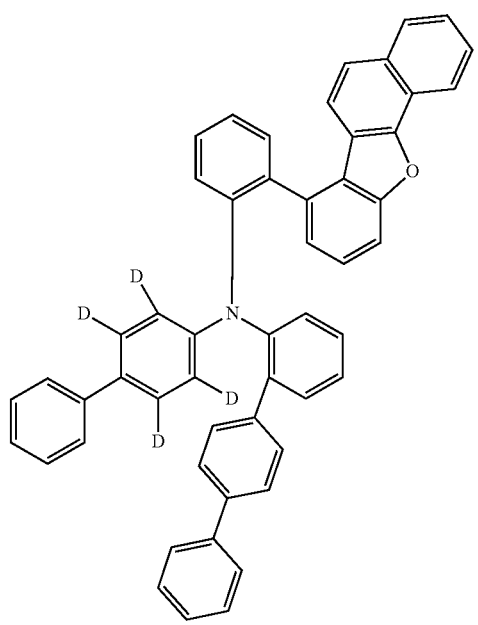

1083
-continued
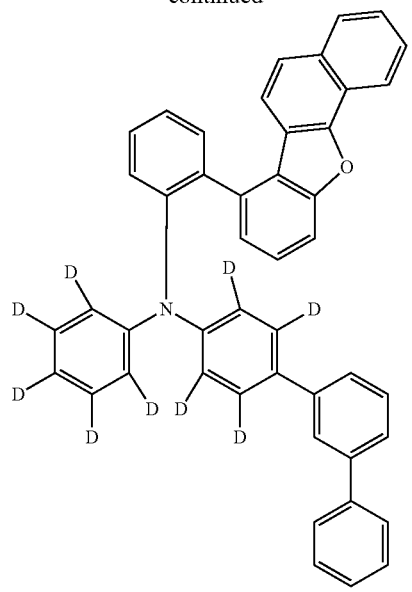
1084
-continued
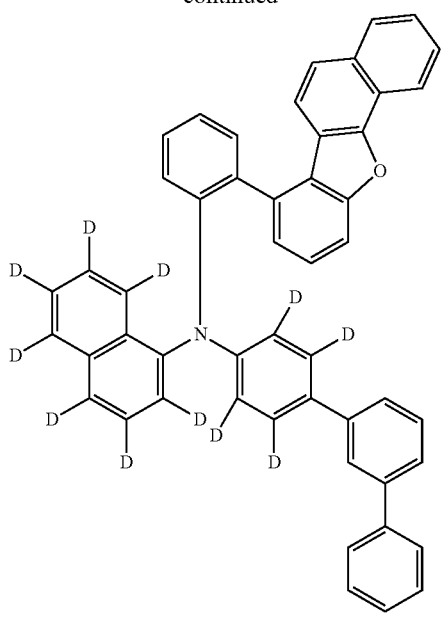
[Chem. 366]
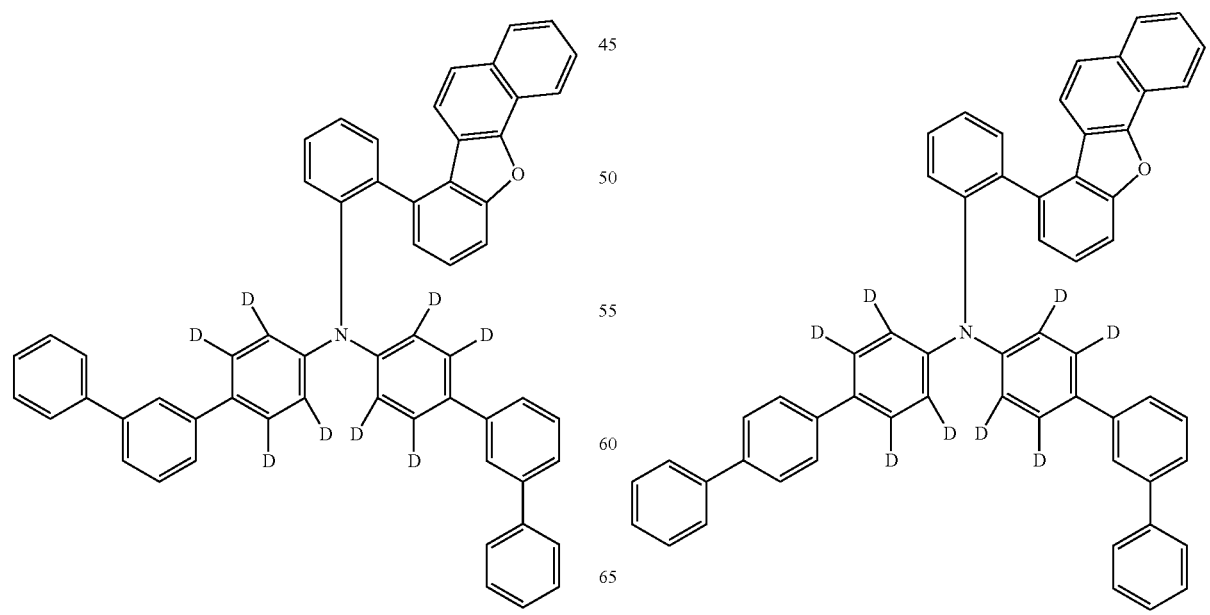

1085
-continued
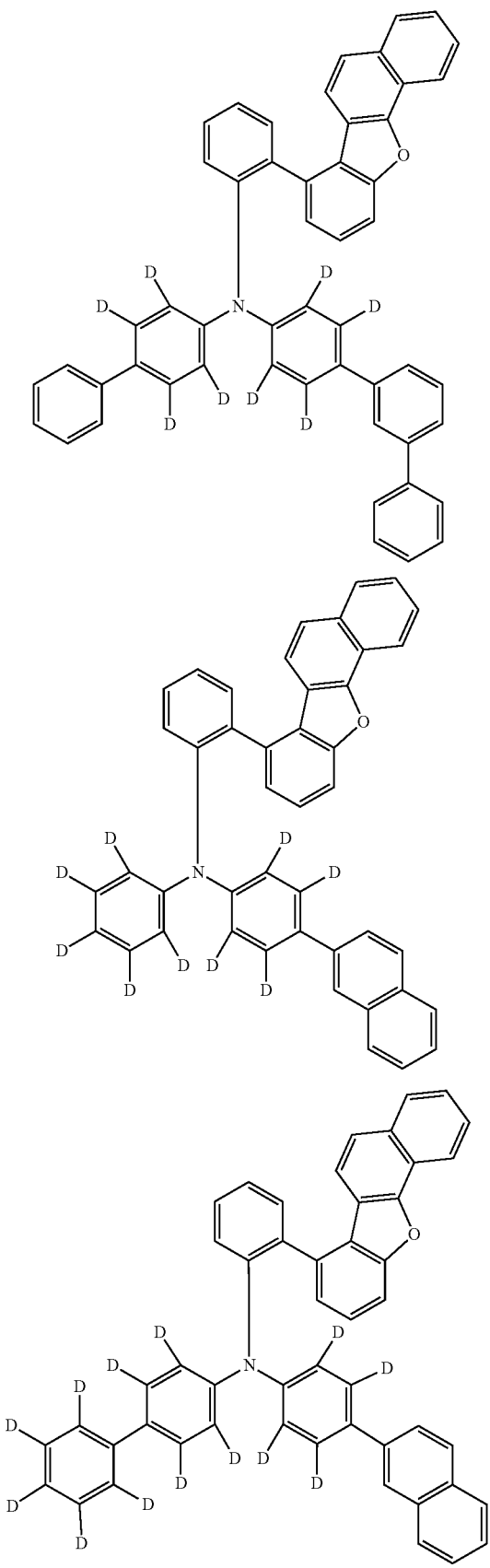
1086
-continued
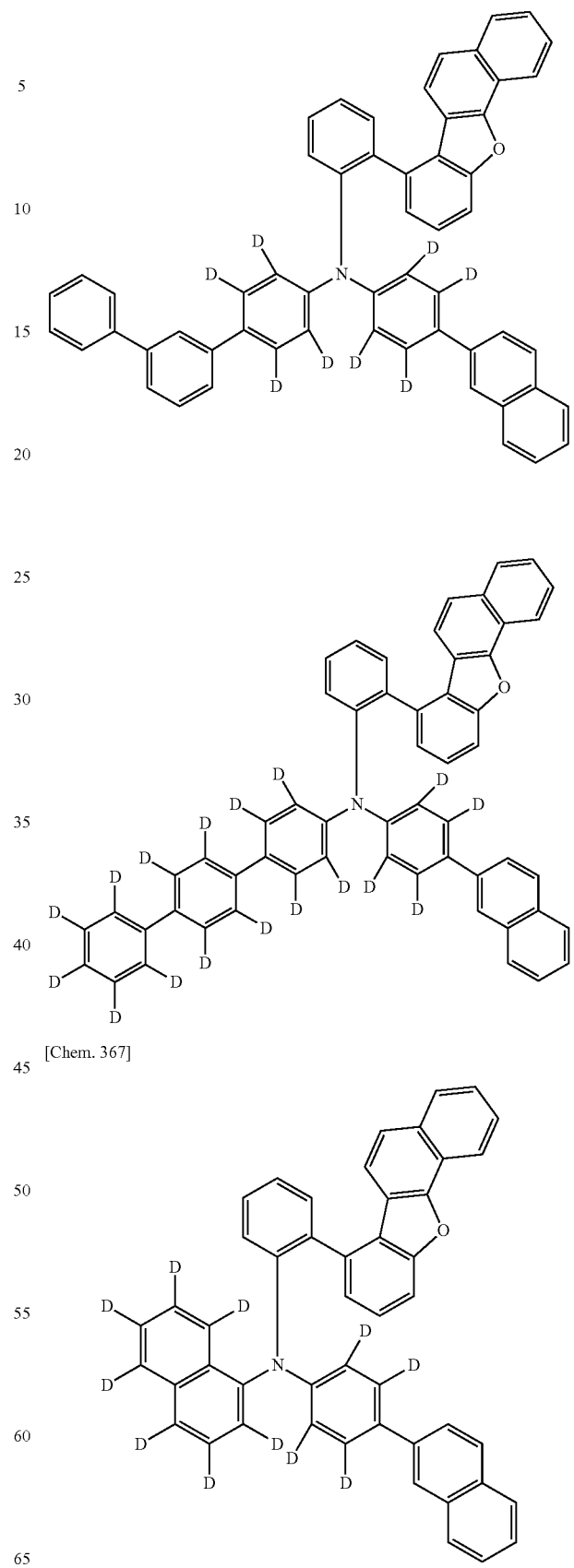
[Chem. 367]

1087
-continued
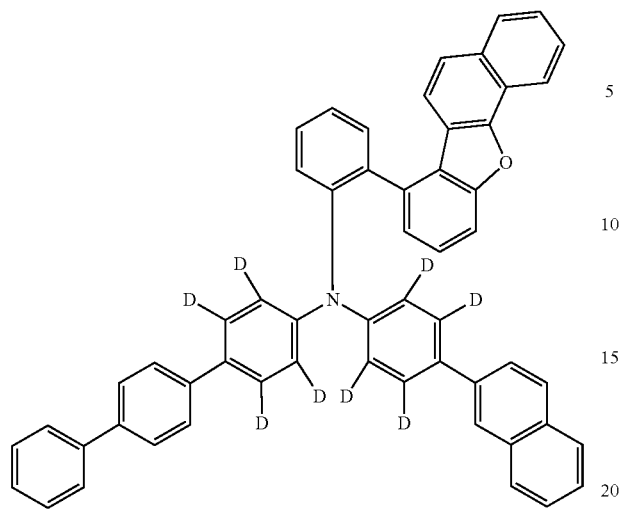
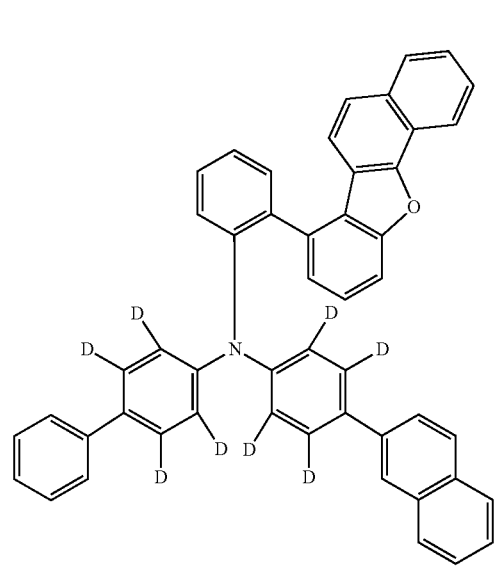
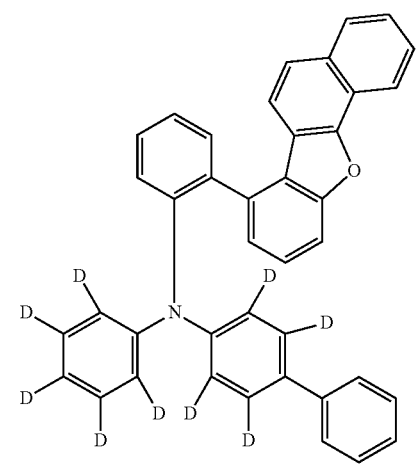
1088
-continued
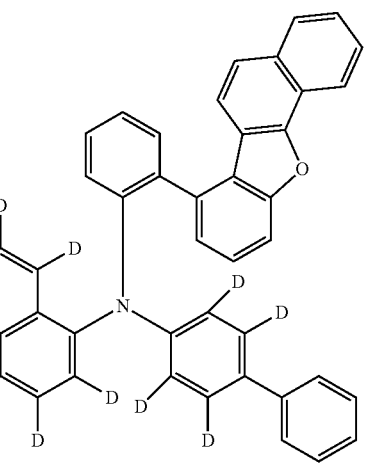
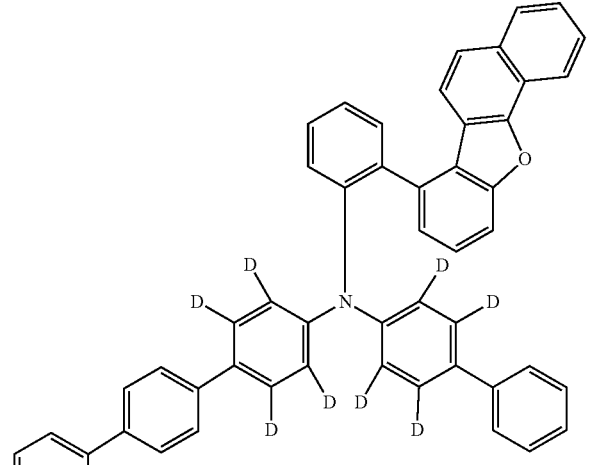
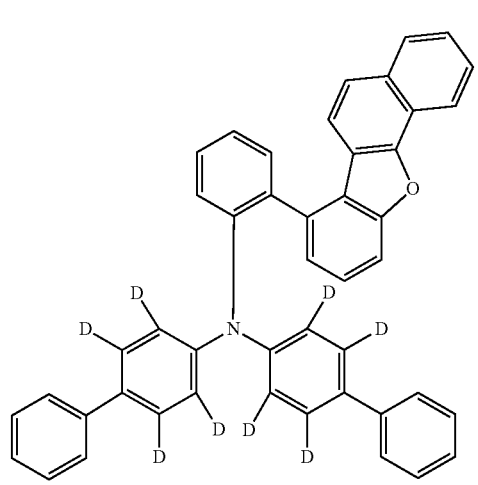

1089
-continued
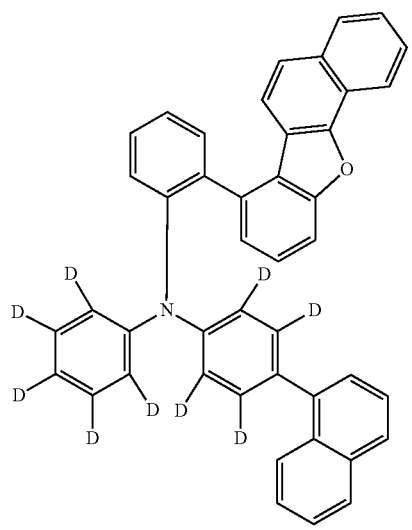
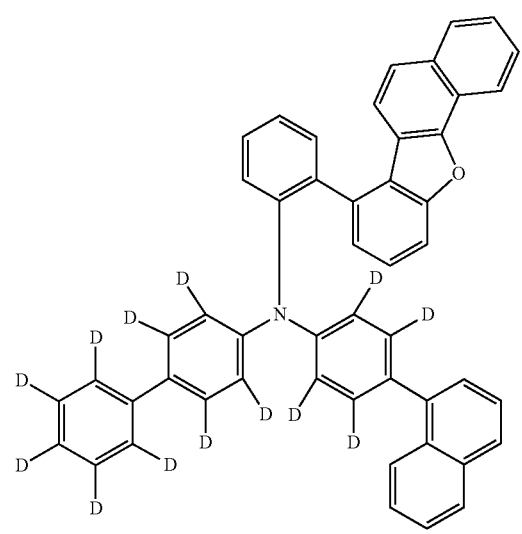
[Chem. 368]
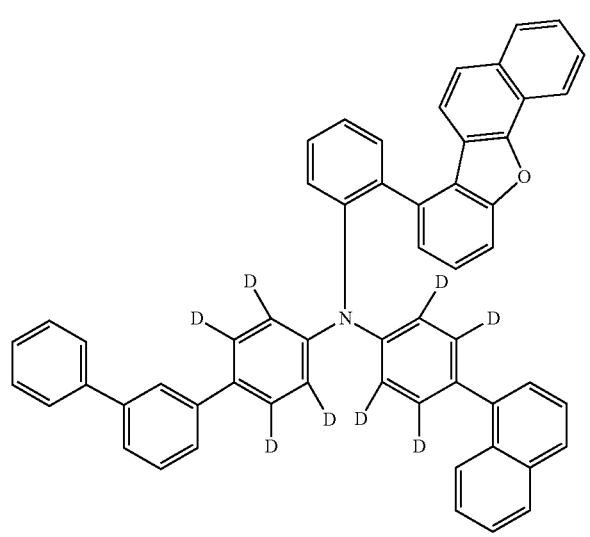
1090
-continued
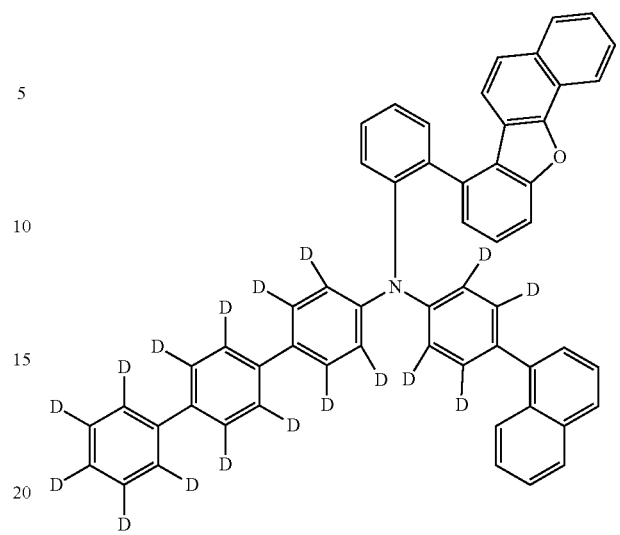
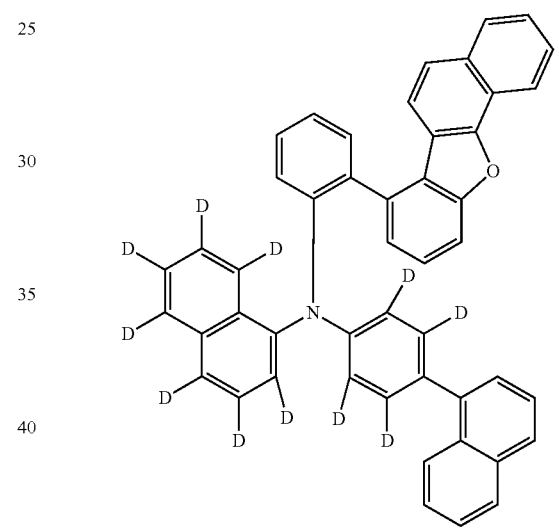
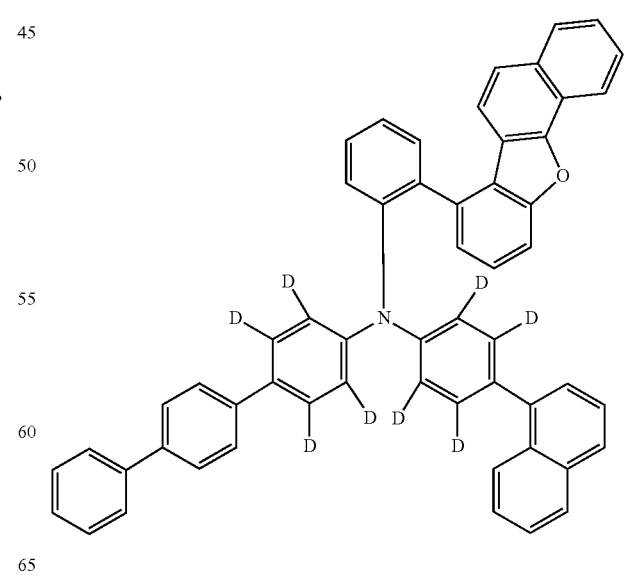

1091
-continued
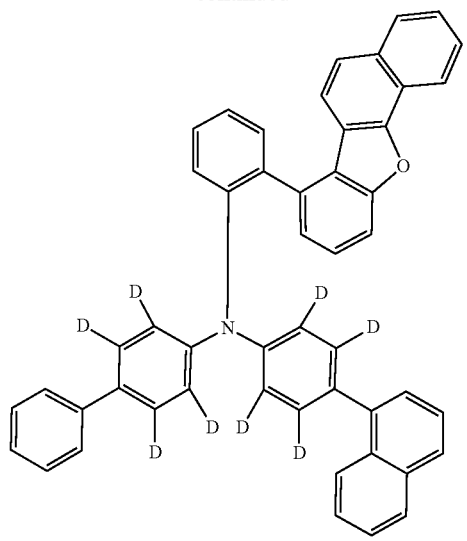
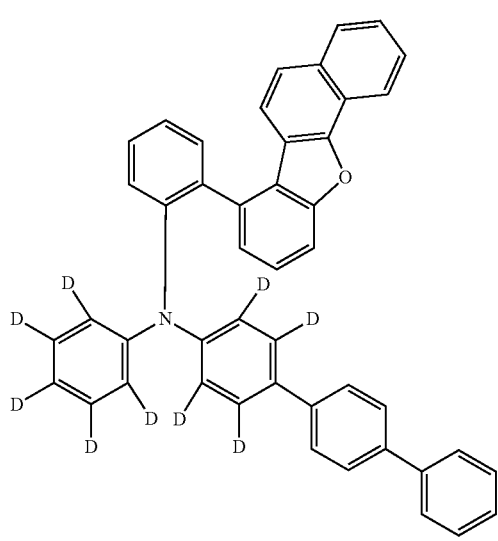
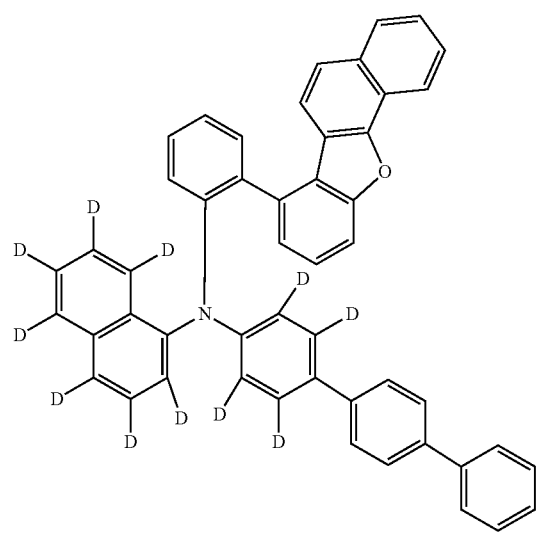
1092
-continued
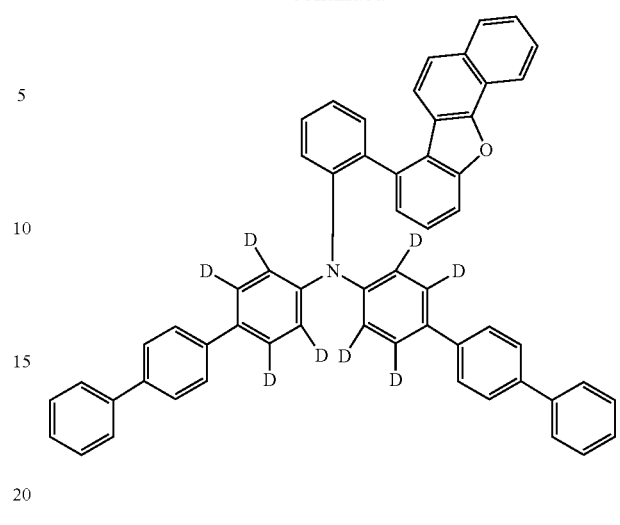
[Chem. 369]
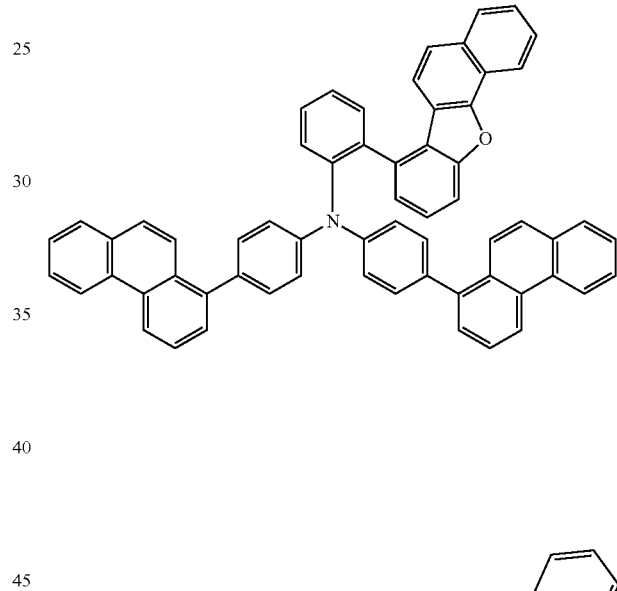
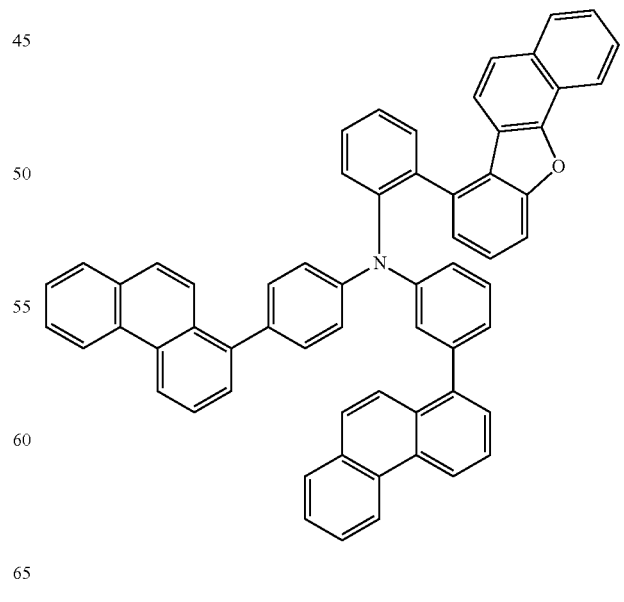

1093
-continued
1094
-continued
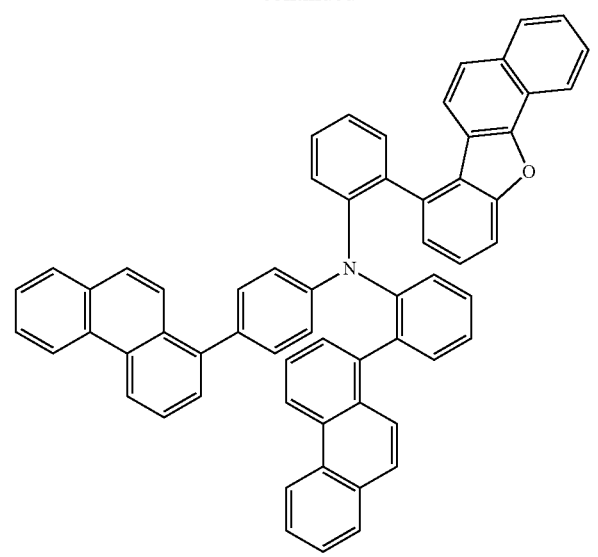
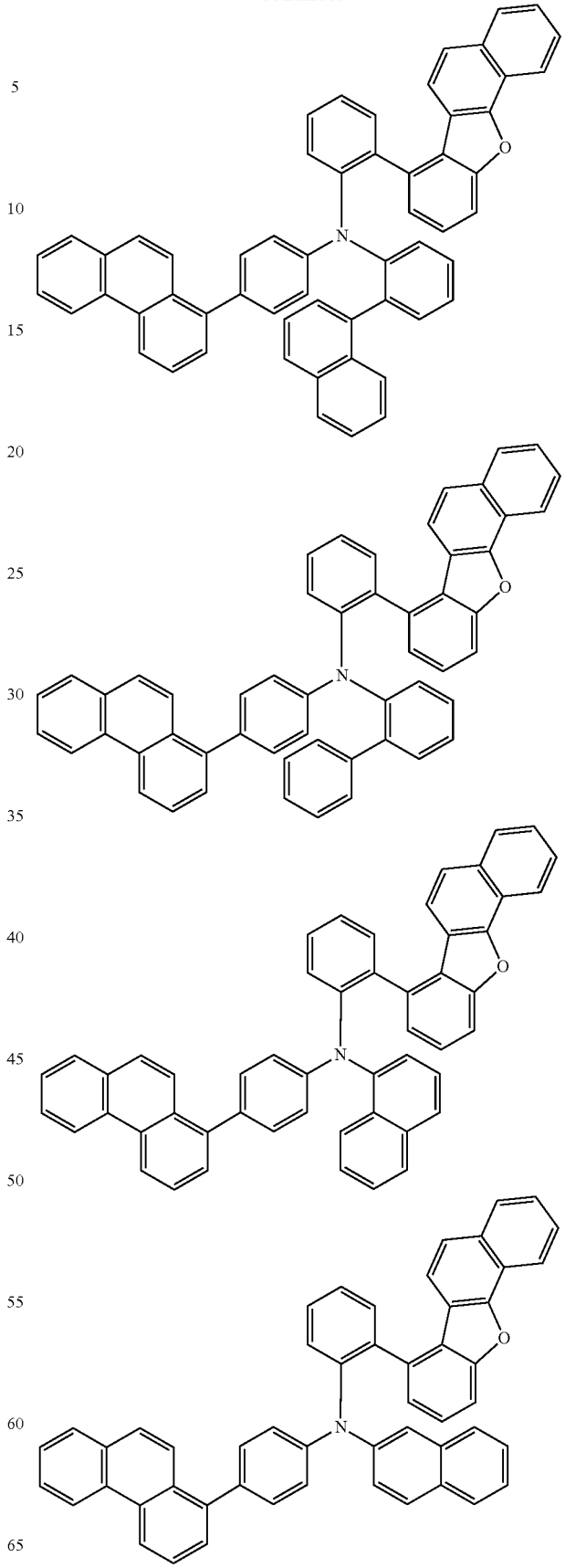

1095
-continued
[Chem. 370]
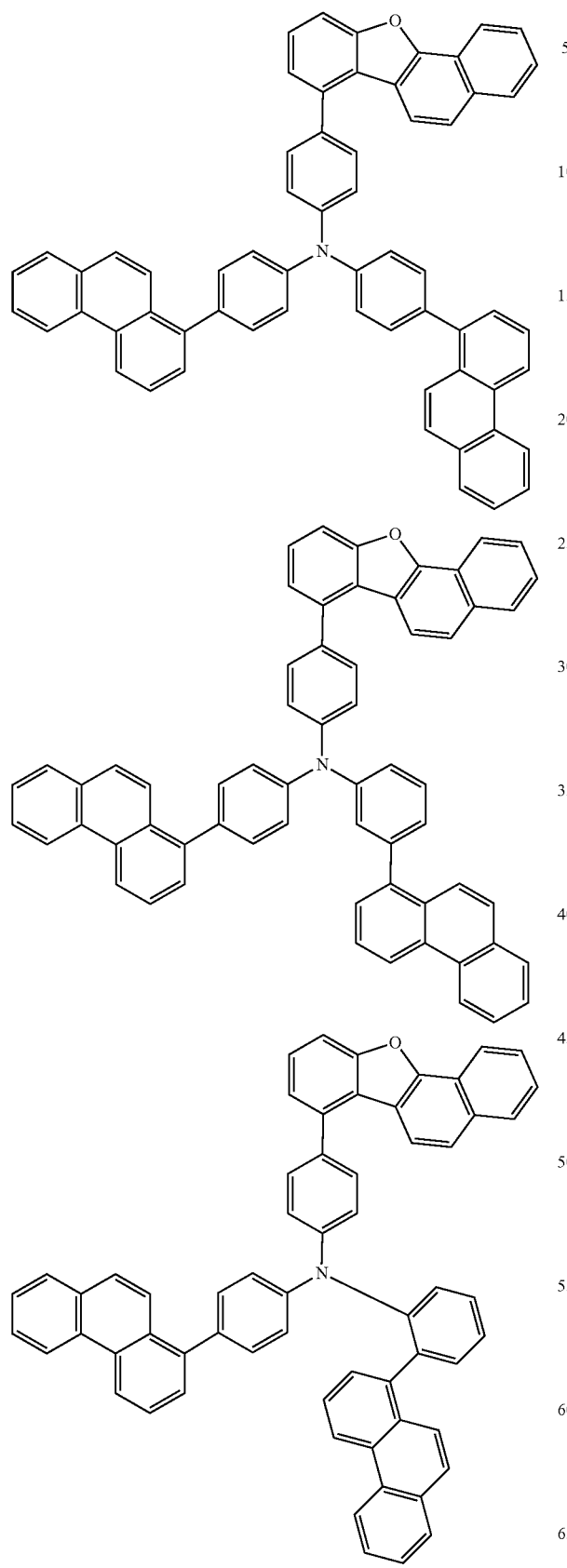
1096
-continued
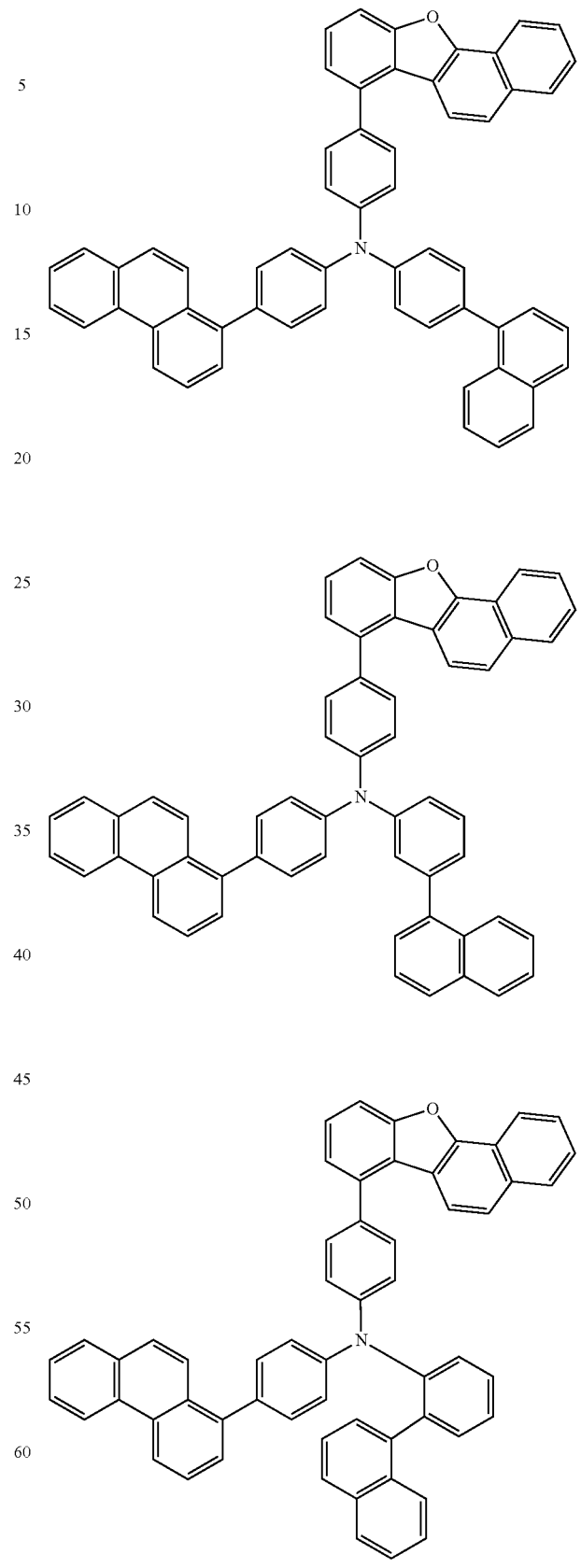

1097
-continued
1098
-continued
[Chem. 371]
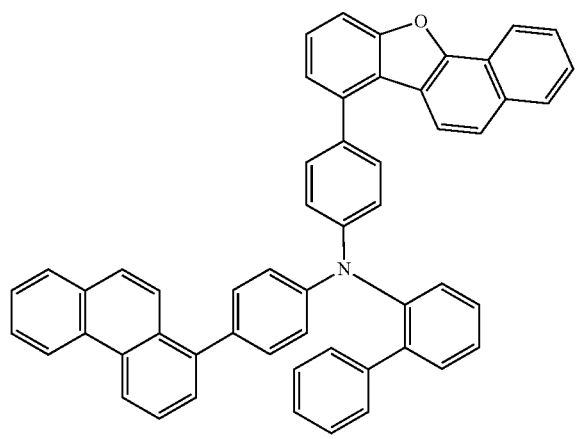
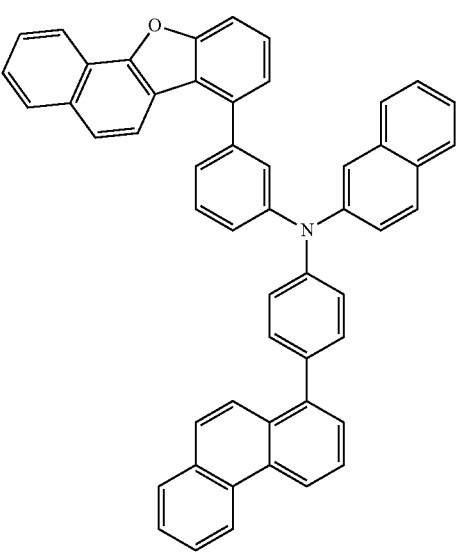
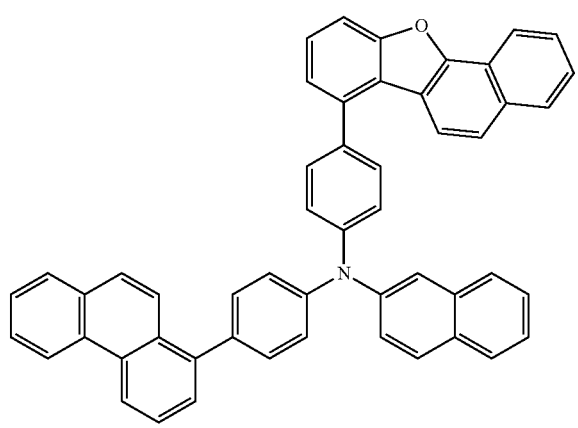
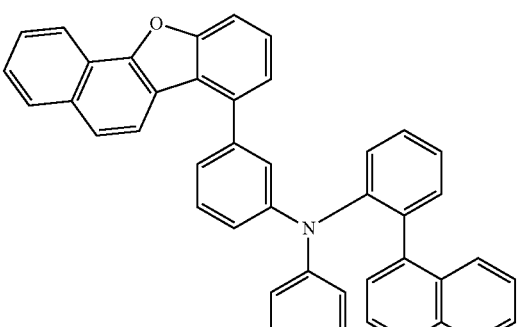
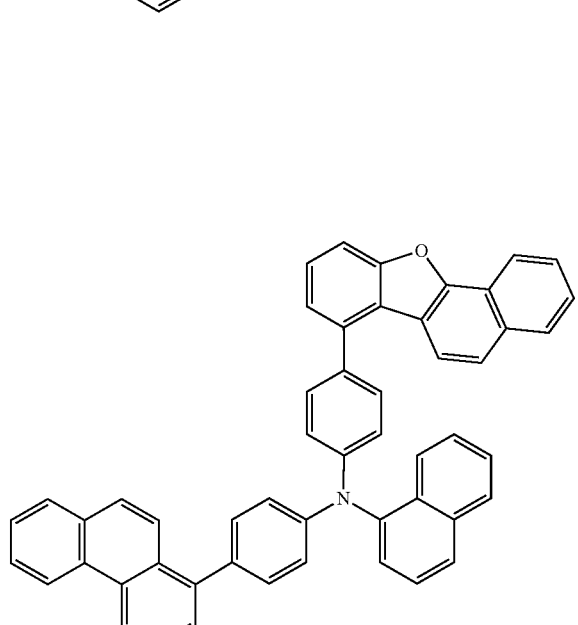
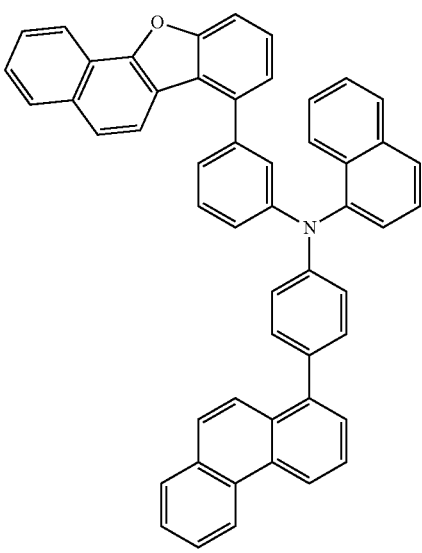

1099
-continued
1100
-continued
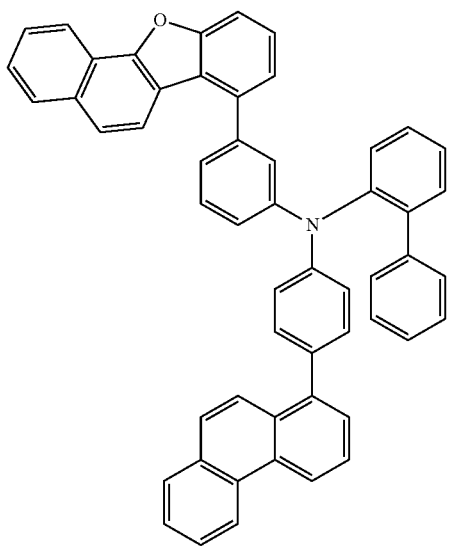
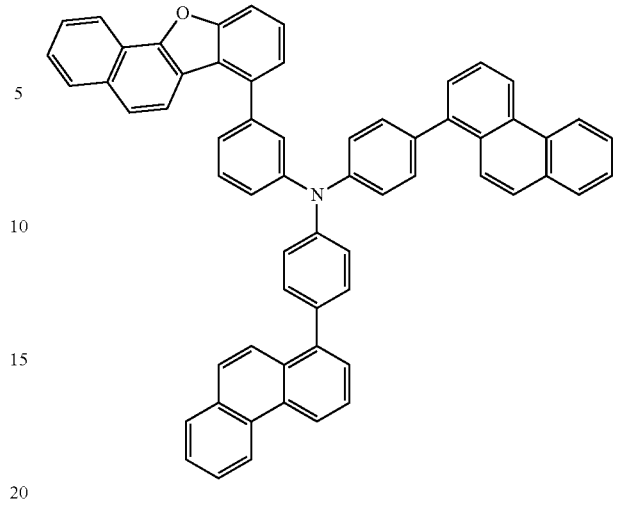
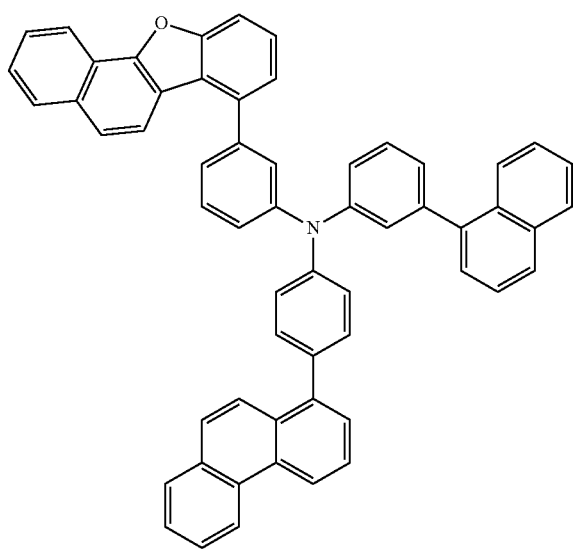
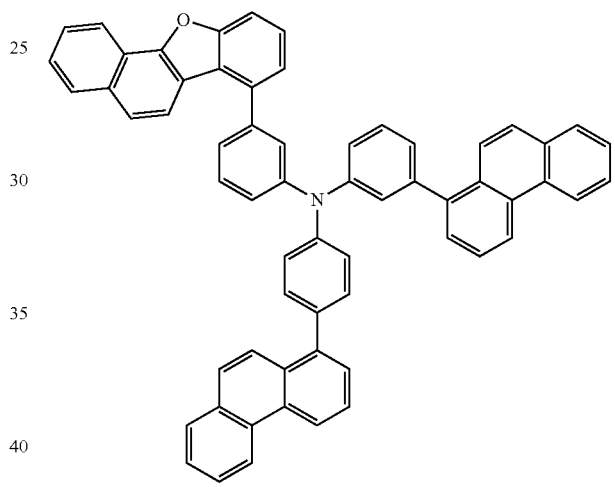
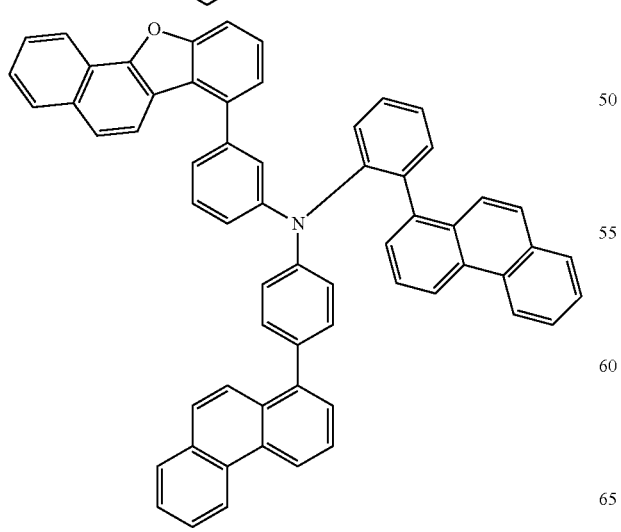

1101
-continued
[Chem. 372]
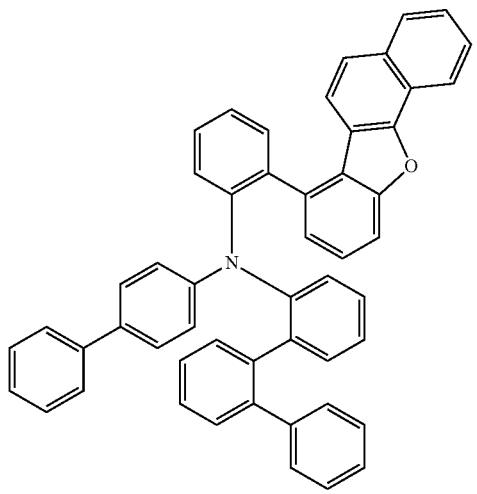
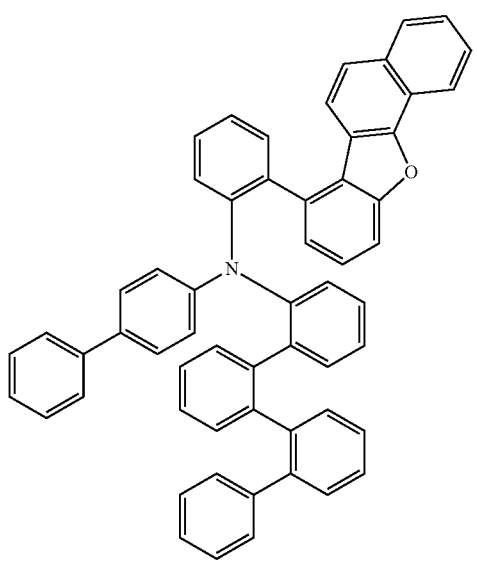
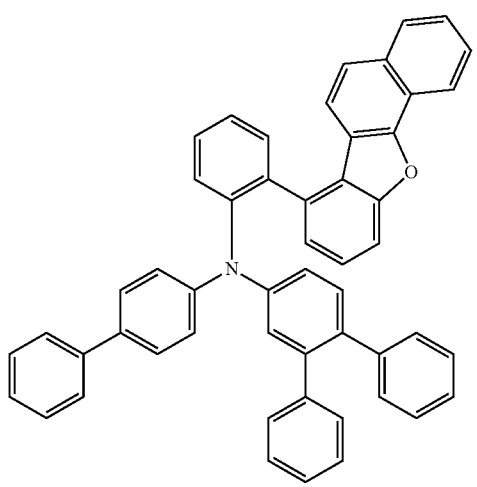
1102
-continued
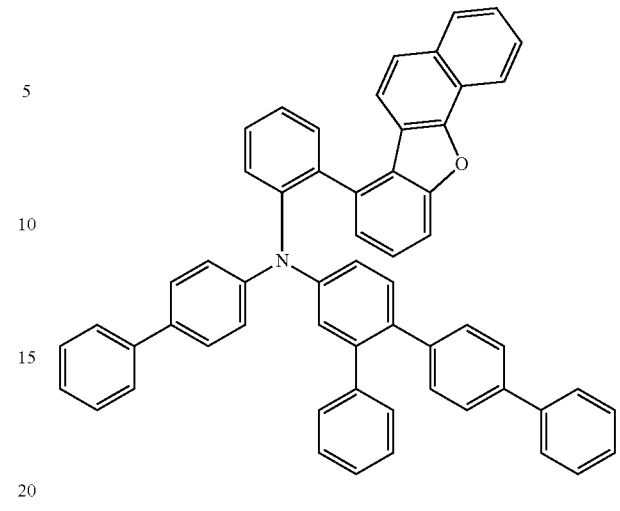
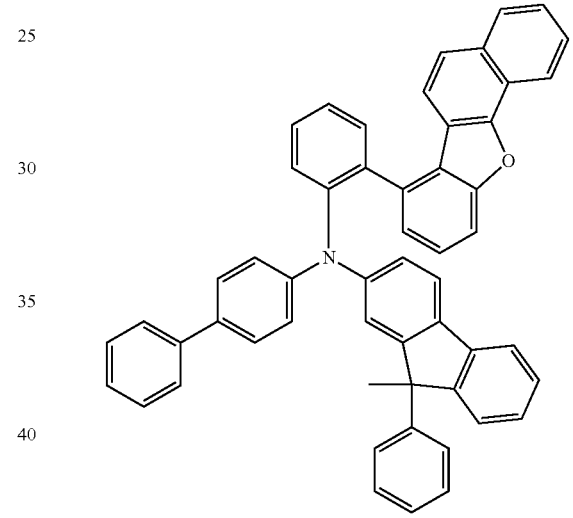
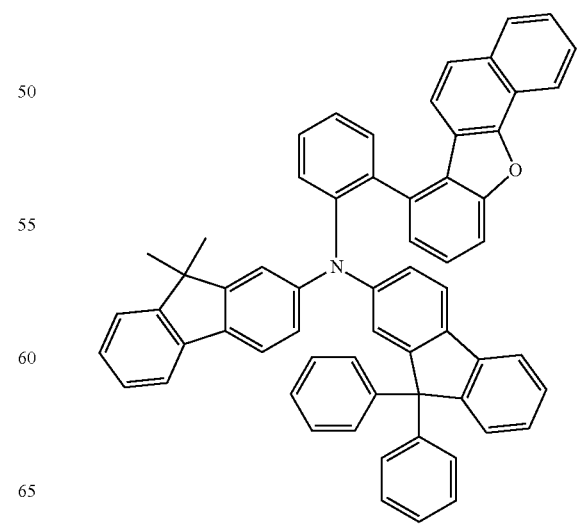

1103
-continued
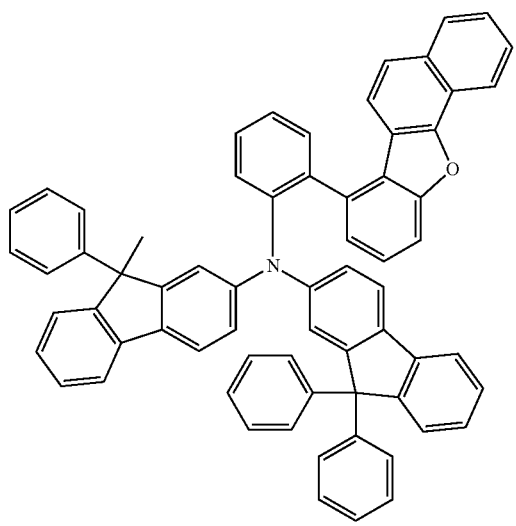
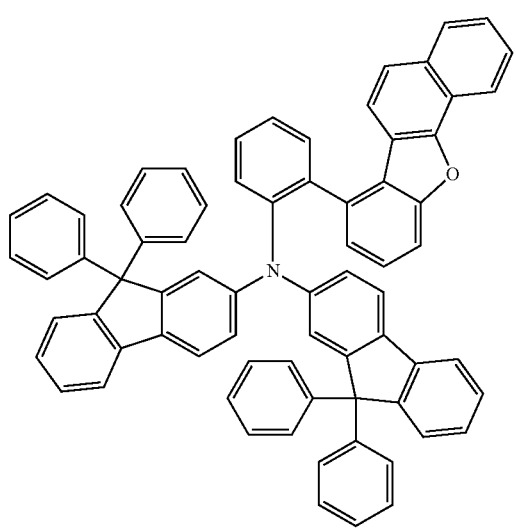
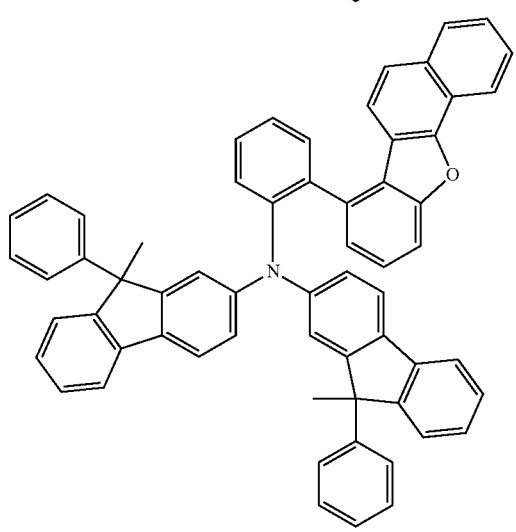
1104
-continued
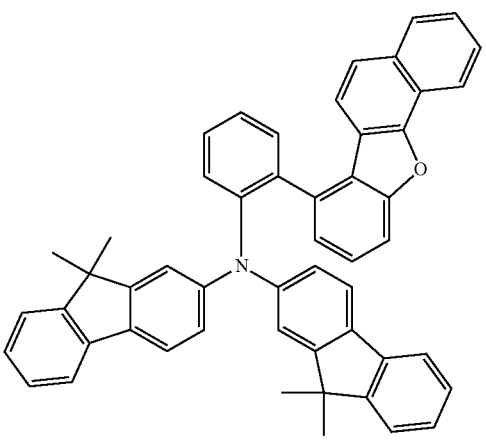
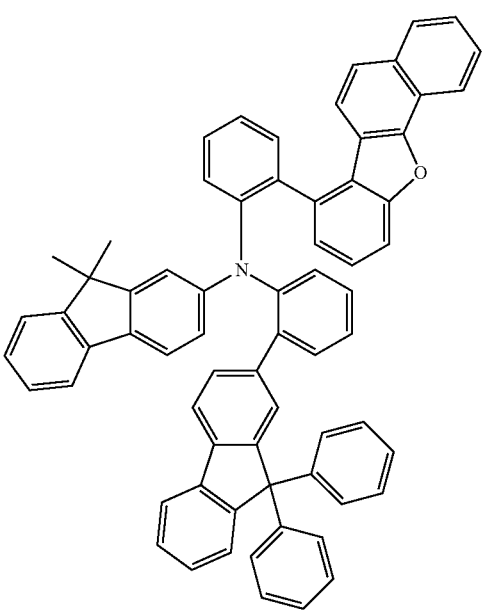
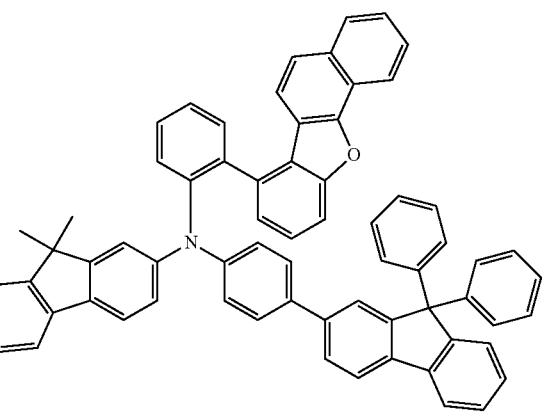

1105
-continued
1106
-continued
[Chem. 373]
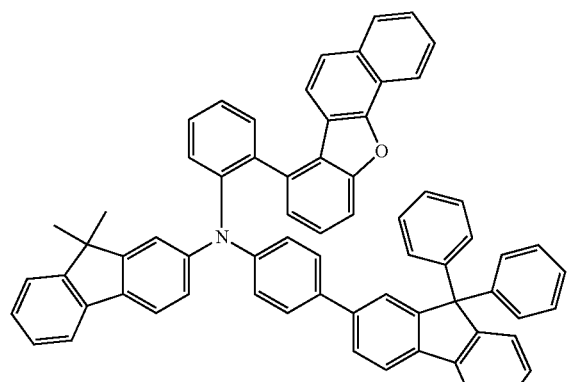
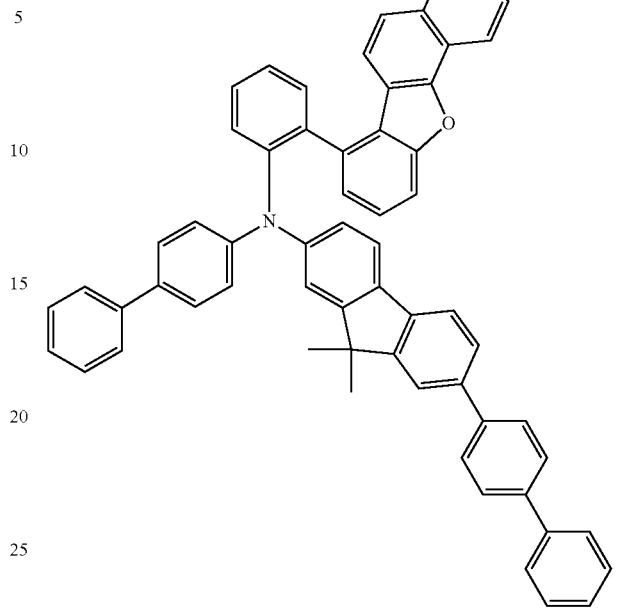
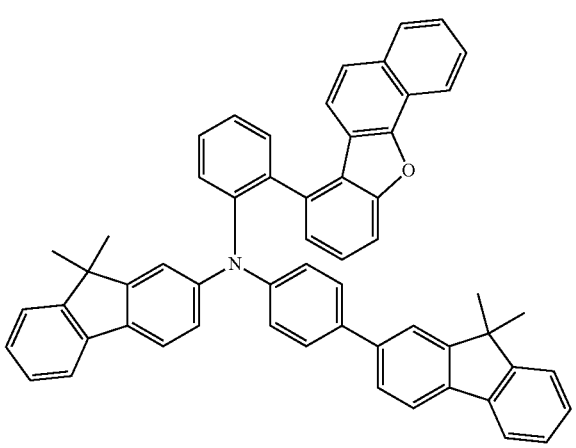
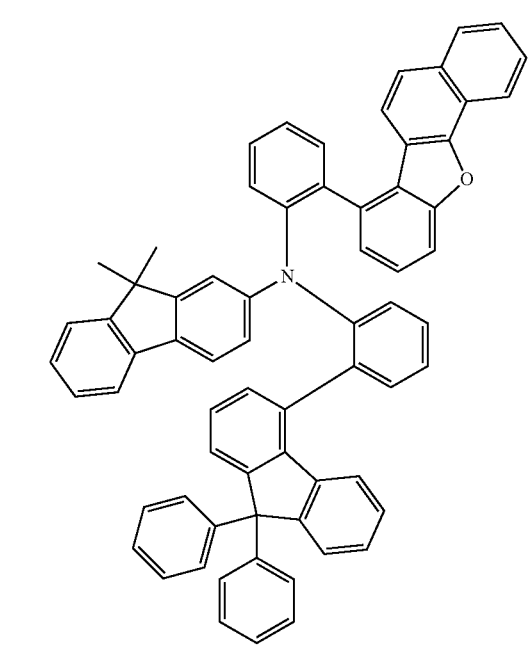
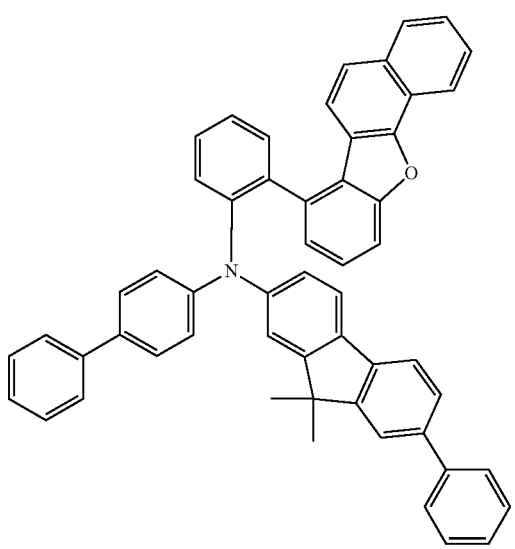

1107
-continued
1108
-continued
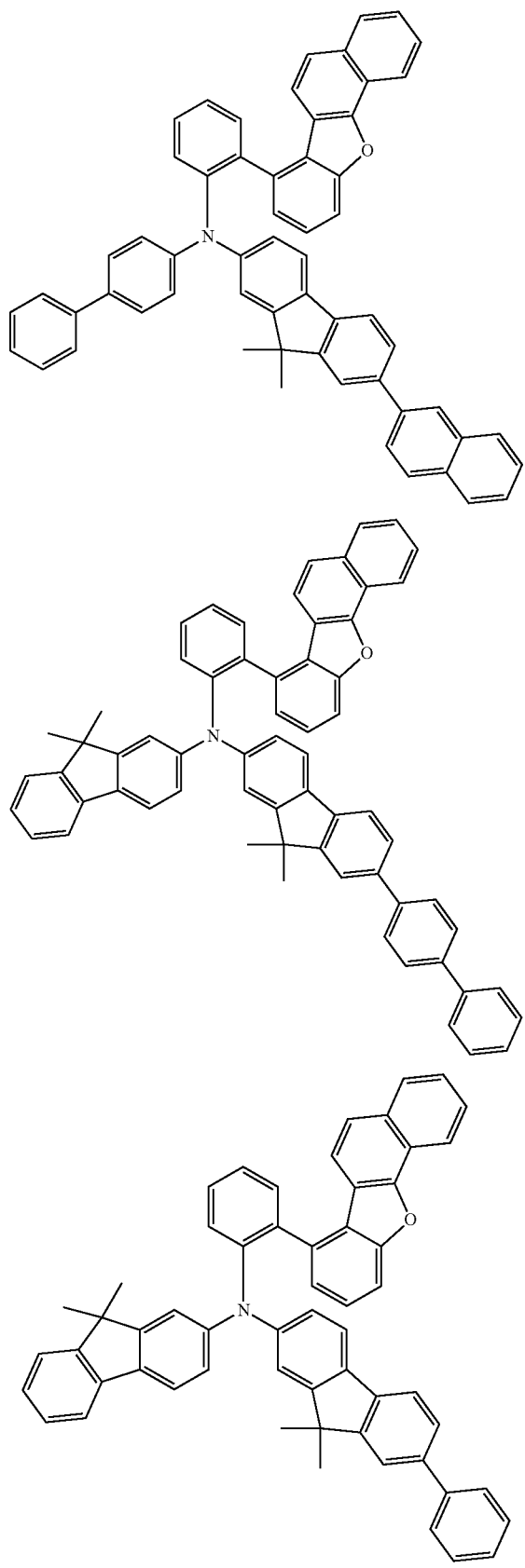
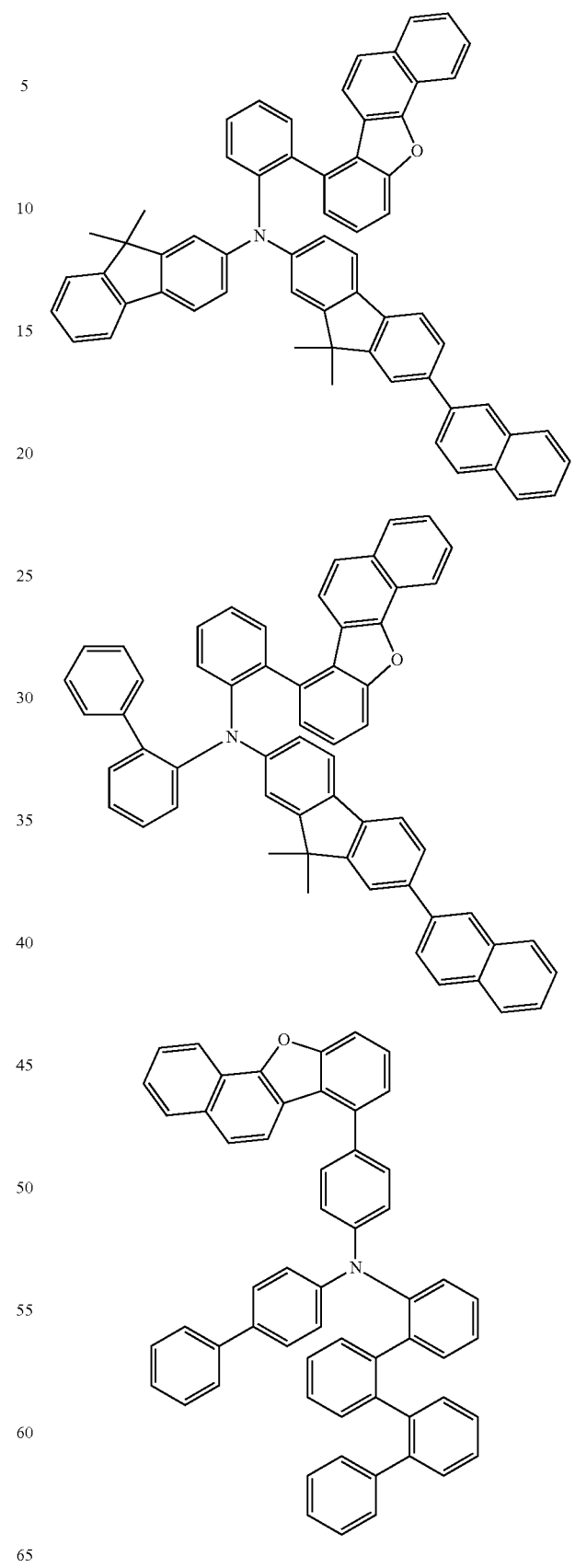

1109
-continued
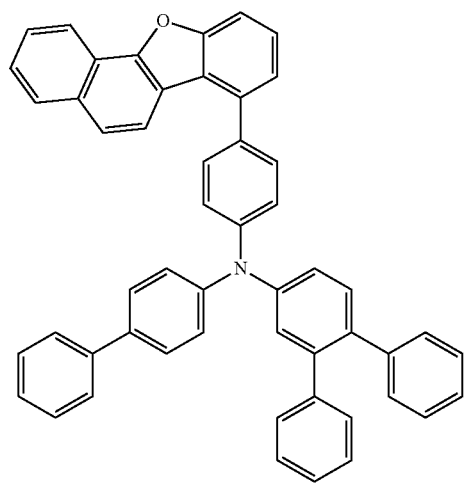
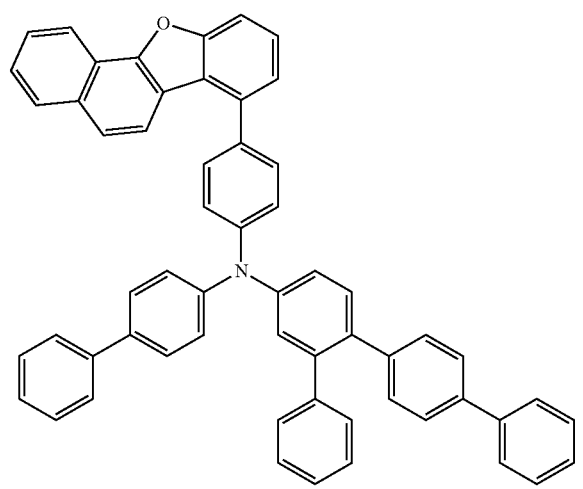
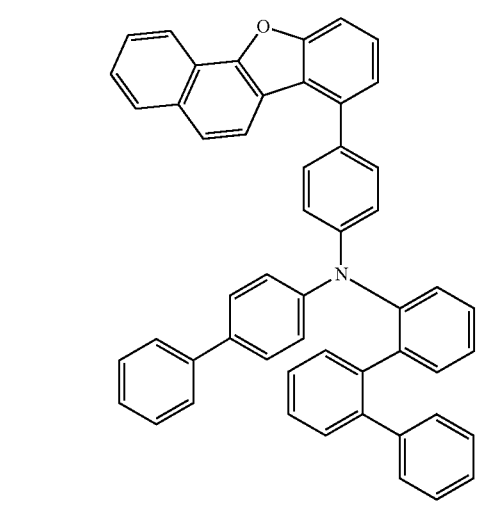
1110
-continued
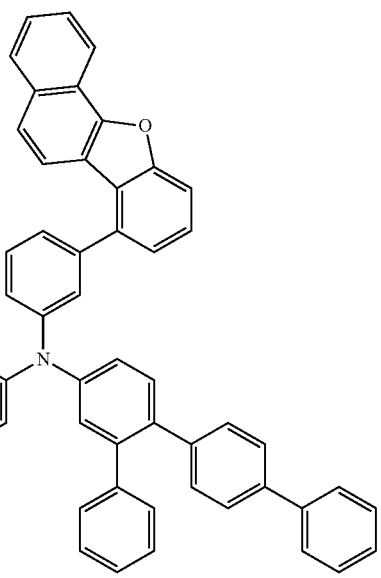
[Chem. 374]
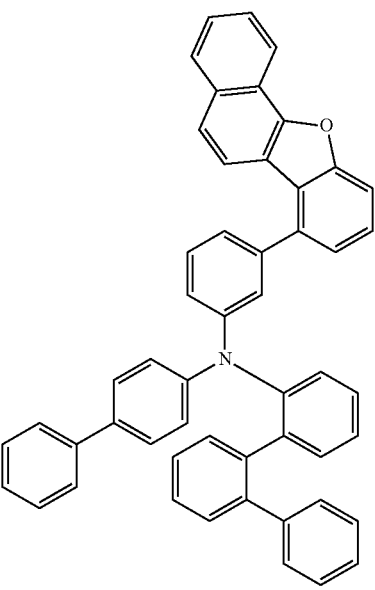

1111
-continued
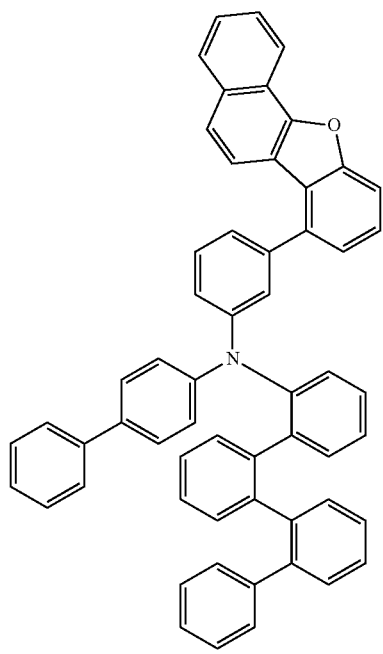
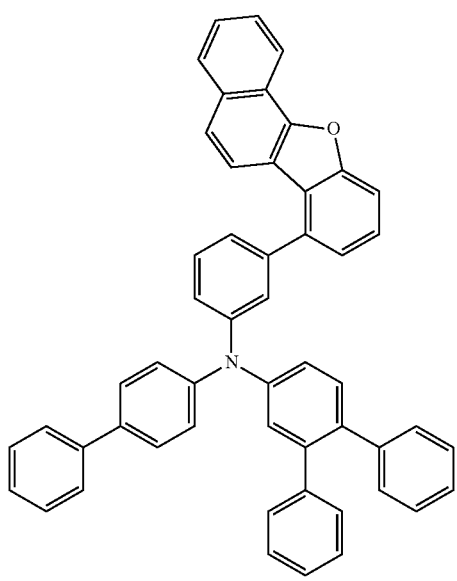
1112
-continued
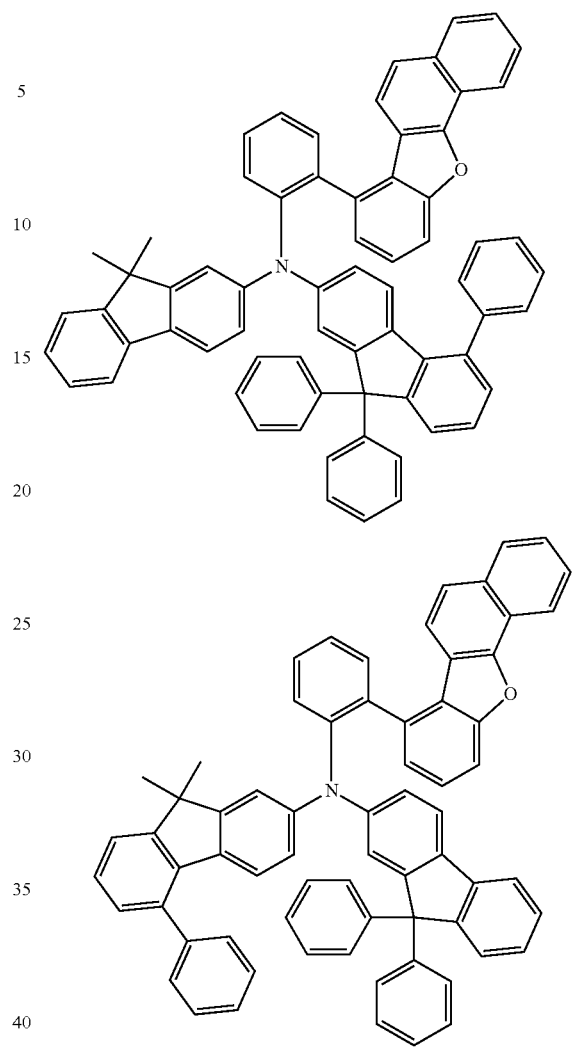
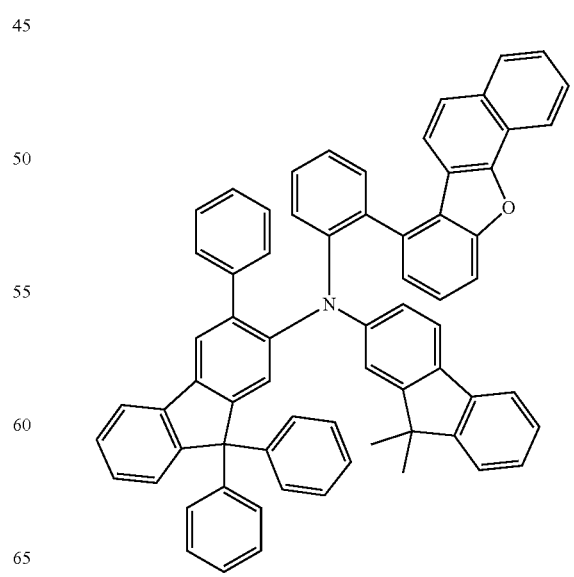

| 1113 -continued | 1114 -continued |
|---|---|
| 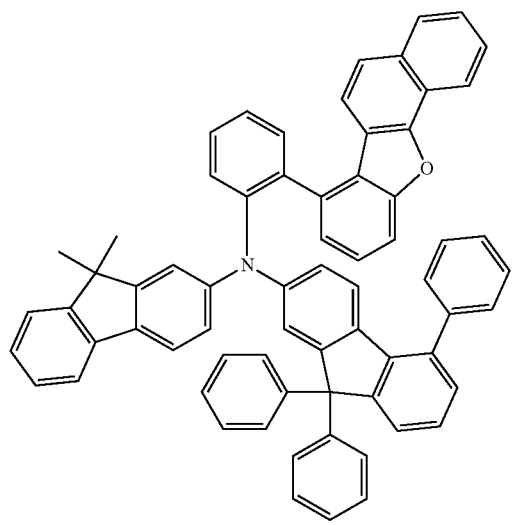 | 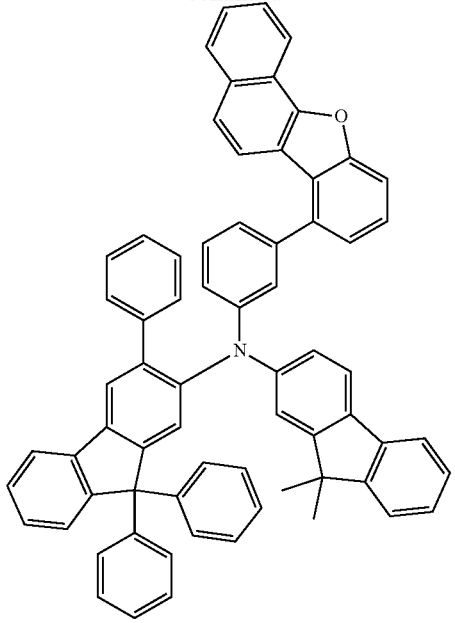 |
| 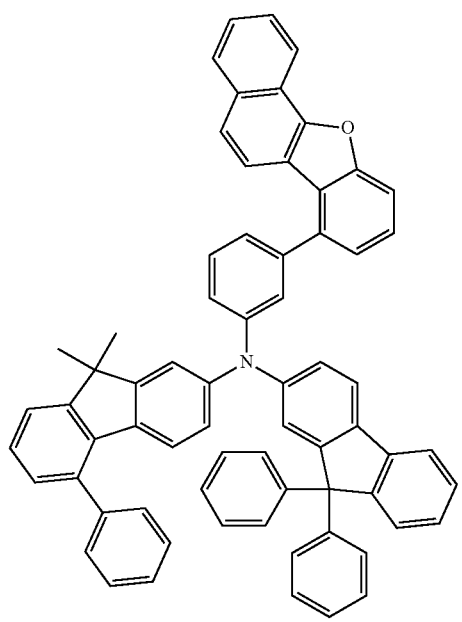 | 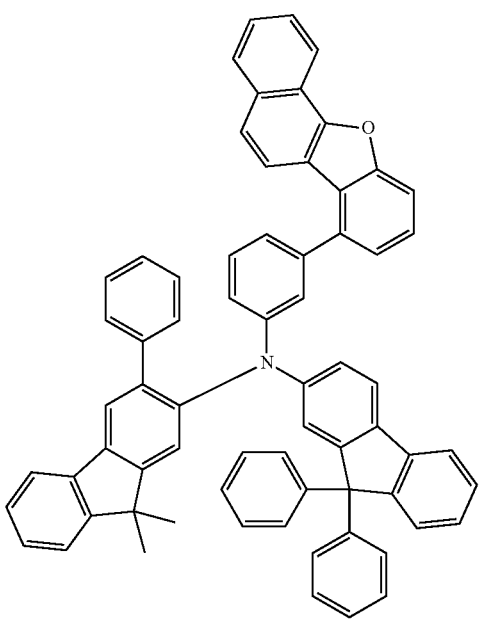 |

1115
-continued
1116
-continued
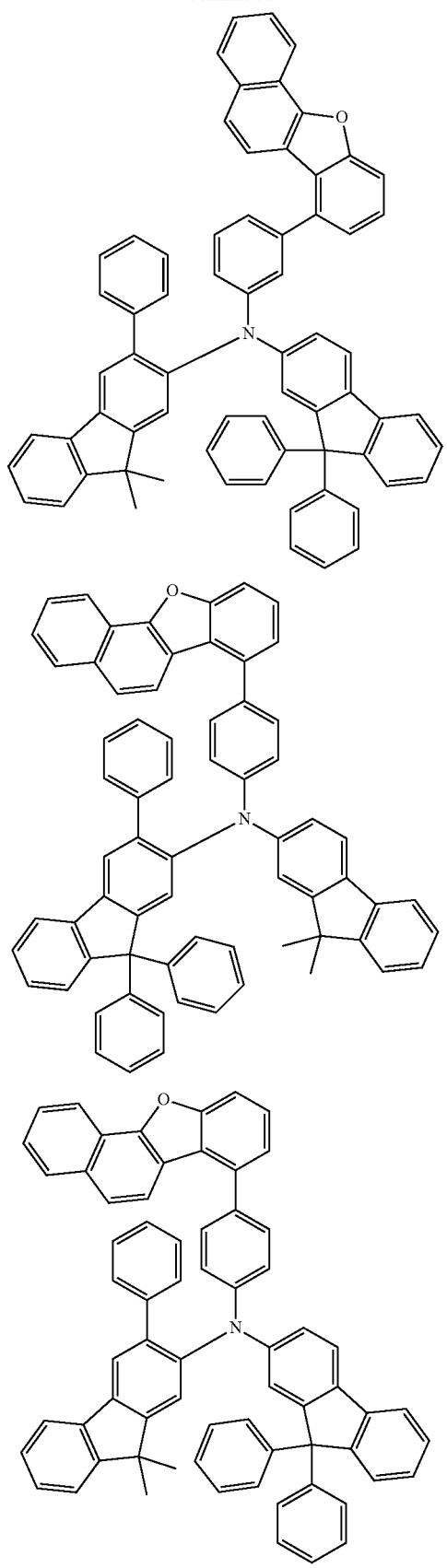
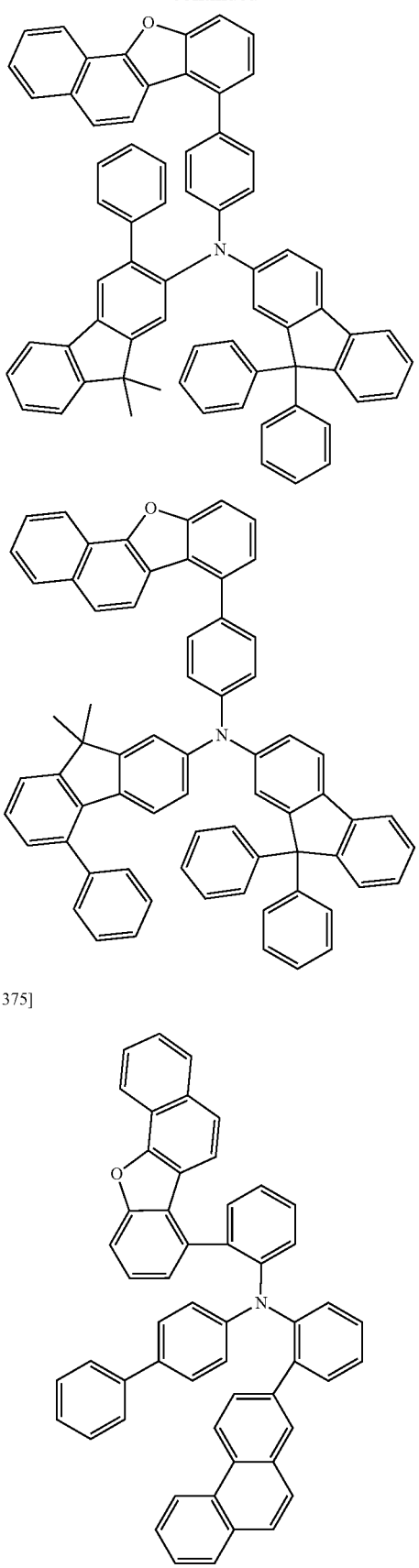
[Chem. 375]

1117
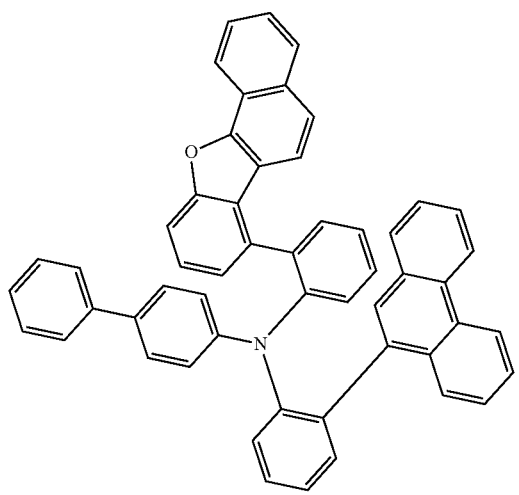
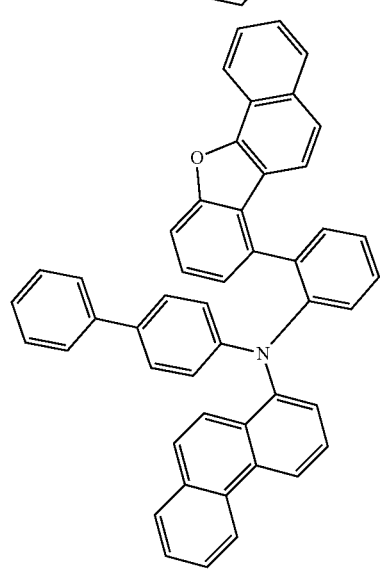
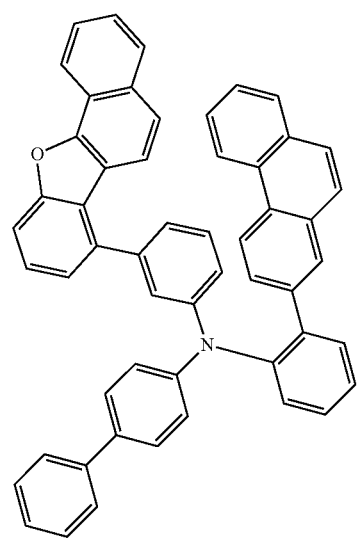
1118
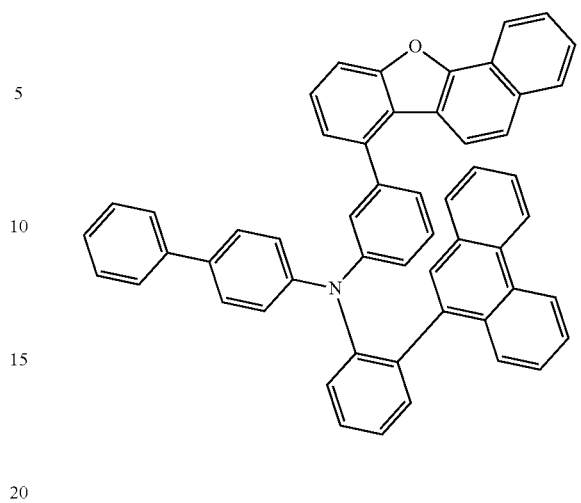
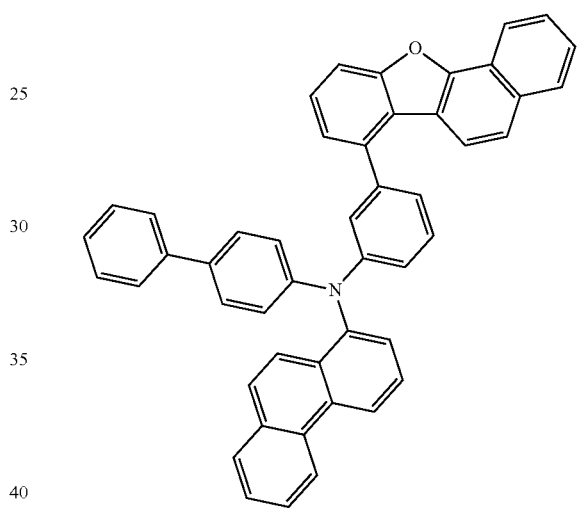
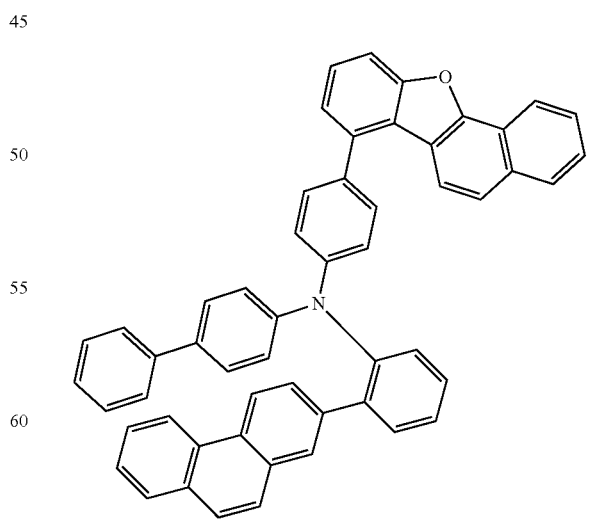

1119
-continued
1120
-continued
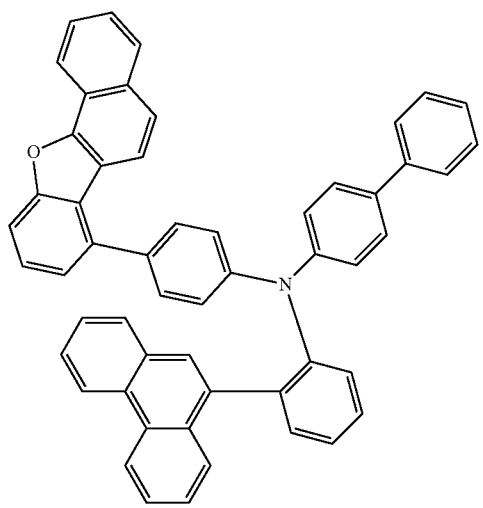
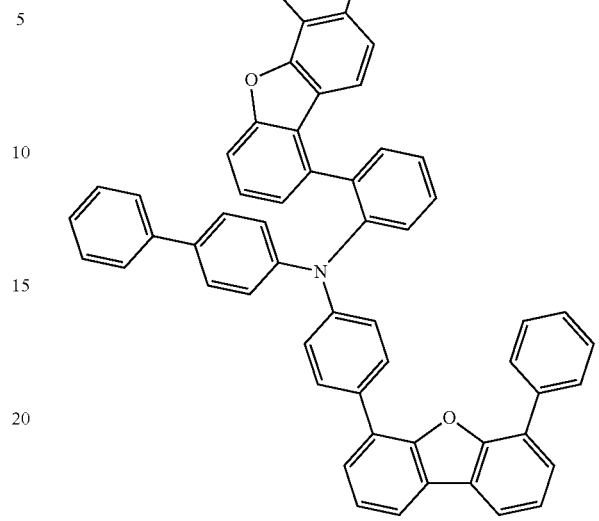
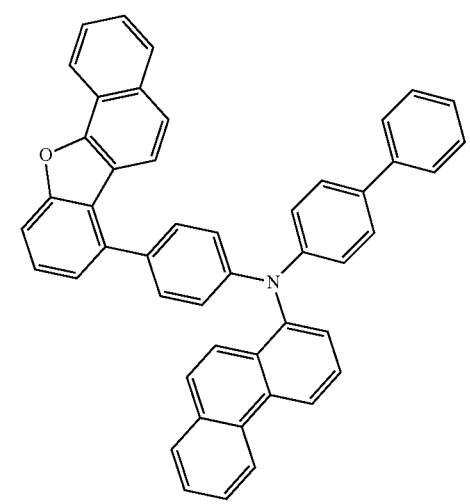
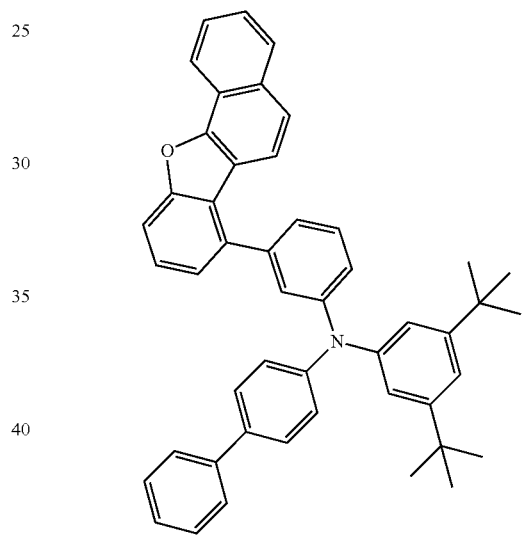
[Chem. 376]
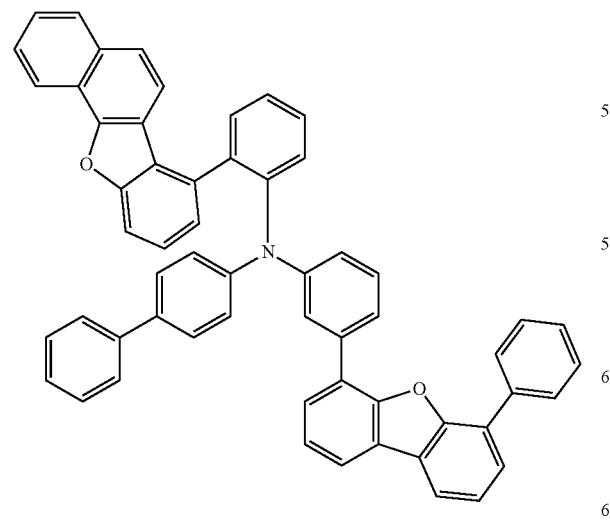
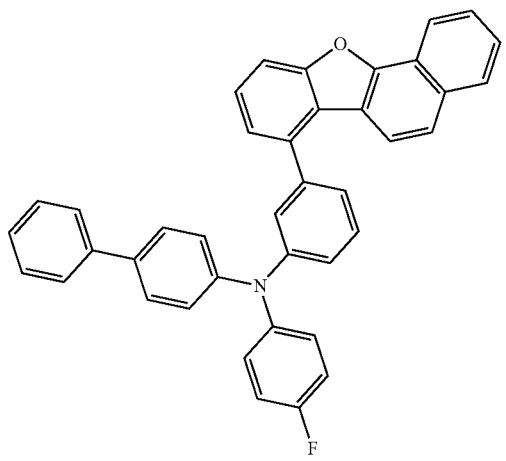

1121
-continued

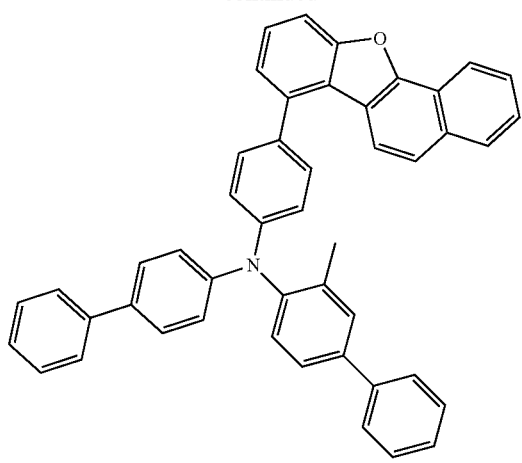

[Chem. 377]

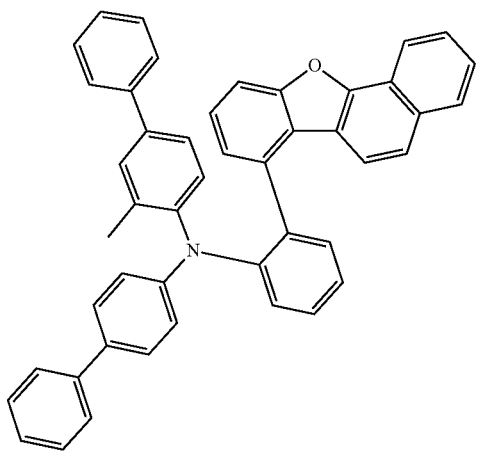

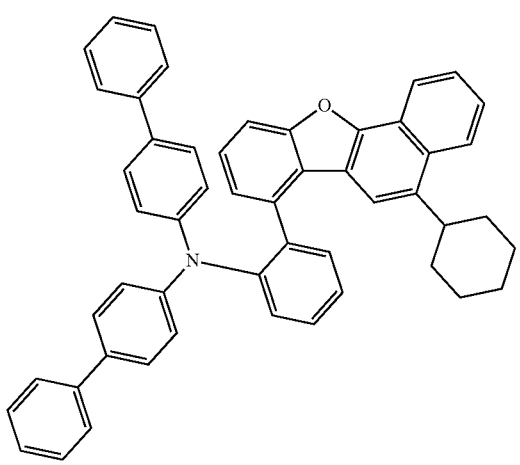

1122
-continued

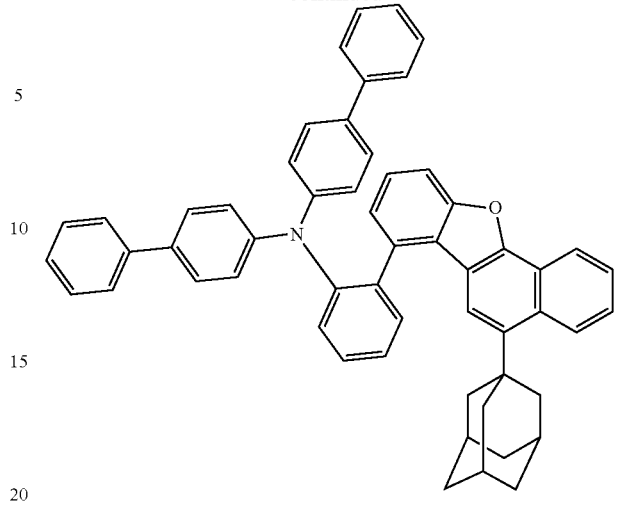

[Material for Organic EL Devices]

The material for organic EL devices as an aspect of the present invention contains the inventive compound. The content of the inventive compound in the material for organic EL devices is 1% by mass or more (including 100%), preferably 10% by mass or more (including 100%), more preferably 50% by mass or more (including 100%), further preferably 80% by mass or more (including 100%), and particularly preferably 90% by mass or more (including 100%). The material for organic EL devices as an aspect of the present invention is useful for production of an organic EL device.

Organic EL Device

The organic EL device as an aspect of the present invention includes an anode, a cathode, and organic layers disposed between the anode and the cathode. The organic layers include a light emitting layer and at least one of the organic layers contains the inventive compound.

Examples of the organic layer containing the inventive compound include, but not limited to, a hole transporting zone (hole injecting layer, hole transporting layer, electron blocking layer, exciton blocking layer, etc.) provided between the anode and the light emitting layer, the light emitting layer, a space layer, an electron transporting zone (electron injecting layer, electron transporting layer, hole blocking layer, etc.) provided between the cathode and the light emitting layer. The inventive compound is preferably used as a material for the hole transporting zone or light emitting layer, more preferably as a material for the hole transporting zone, further preferably as a material for the hole injecting layer, hole transporting layer, electron blocking layer, or exciton blocking layer, and particularly preferably as a material for the hole injecting layer or hole transporting layer, of a fluorescent or phosphorescent EL device.

The organic EL device as an aspect of the present invention may be a fluorescence or phosphorescence emission type monochromatic luminescent device, a fluorescence/phosphorescence hybrid type white luminescent device, a simple type having a single light emitting unit, or a tandem type having two or more light emitting units, and is preferably a fluorescence emission type device. Here, the "light emitting unit" refers to a minimum unit that includes organic layers, at least one of which is a light emitting layer, and that emits light by recombination of injected holes and injected electrons.

An example of a typical device configuration of the simple type organic EL device is the following device configuration.

(1) Anode/Light Emitting Unit/Cathode

The light emitting unit may be a multilayer type having two or more phosphorescence emitting layers and fluorescence emitting layers, and in this case, a space layer may be provided between the light emitting layers for the purpose of preventing excitons generated in the phosphorescence emitting layers from diffusing into the fluorescence emitting layers. A typical layer configuration of the simple type light emitting unit is shown below. The layers in parentheses are optional.

(a) (hole injecting layer/) hole transporting layer/fluorescence emitting layer/electron transporting layer (/electron injecting layer)

(b) (hole injecting layer/) hole transporting layer/phosphorescence emitting layer electron transporting layer (/electron injecting layer)

(c) (hole injecting layer/) hole transporting layer/first fluorescence emitting layer/second fluorescence emitting layer/electron transporting layer (/electron injecting layer)

(d) (hole injecting layer/) hole transporting layer/first phosphorescence emitting layer/second phosphorescence emitting layer/electron transporting layer (/electron injecting layer)

(e) (hole injecting layer/) hole transporting layer/phosphorescence emitting layer/space layer/fluorescence emitting layer/electron transporting layer (/electron injecting layer)

(f) (hole injecting layer/) hole transporting layer/first phosphorescence emitting layer/second phosphorescence emitting layer/space layer/fluorescence emitting layer/electron transporting layer (/electron injecting layer)

(g) (hole injecting layer/) hole transporting layer/first phosphorescence emitting layer/space layer/second phosphorescence emitting layer/space layer/fluorescence emitting layer/electron transporting layer (/electron injecting layer)

(h) (hole injecting layer/) hole transporting layer/phosphorescence emitting layer/space layer/first fluorescence emitting layer/second fluorescence emitting layer/electron transporting layer (/electron injecting layer)

(i) (hole injecting layer/) hole transporting layer/electron blocking layer/fluorescence emitting layer/electron transporting layer (/electron injecting layer)

(j) (hole injecting layer/) hole transporting layer/electron blocking layer/phosphorescence emitting layer/electron transporting layer (/electron injecting layer)

(k) (hole injecting layer/) hole transporting layer/exciton blocking layer/fluorescence emitting layer/electron transporting layer (/electron injecting layer)

(l) (hole injecting layer/) hole transporting layer/exciton blocking layer/phosphorescence emitting layer/electron transporting layer (/electron injecting layer)

(m) (hole injecting layer/) first hole transporting layer/second hole transporting layer/fluorescence emitting layer/electron transporting layer (/electron injecting layer)

(n) (hole injecting layer/) first hole transporting layer/second hole transporting layer/phosphorescence emitting layer/electron transporting layer (/electron injecting layer)

(o) (hole injecting layer/) first hole transporting layer/second hole transporting layer/fluorescence emitting layer/first electron transporting layer/second electron transporting layer (/electron injecting layer)

(p) (hole injecting layer/) first hole transporting layer/second hole transporting layer/phosphorescence emitting layer/first electron transporting layer/second electron transporting layer (/electron injecting layer)

(q) (hole injecting layer/) hole transporting layer/fluorescence emitting layer/hole blocking layer/electron transporting layer (/electron injecting layer)

(r) (hole injecting layer/) hole transporting layer/phosphorescence emitting layer/hole blocking layer/electron transporting layer (/electron injecting layer)

(s) (hole injecting layer/) hole transporting layer/fluorescence emitting layer/exciton blocking layer/electron transporting layer (/electron injecting layer)

(t) (hole injecting layer/) hole transporting layer/phosphorescence emitting layer/exciton blocking layer/electron transporting layer (/electron injecting layer)

The phosphorescence or fluorescence emitting layers described above can exhibit luminescent colors different from one another. A specific example of the layer configuration is a layer configuration in the light emitting unit (f) of (hole injecting layer/) hole transporting layer/first phosphorescence emitting layer (red light emission)/second phosphorescence emitting layer (green light emission)/space layer/fluorescence emitting layer (blue light emission)/electron transporting layer.

An electron blocking layer may be appropriately provided between each light emitting layer and a hole transporting layer or a space layer. In addition, a hole blocking layer may be appropriately provided between each light emitting layer and an electron transporting layer. By providing an electron blocking layer or hole blocking layer, electrons or holes can be trapped inside the light emitting layer to increase the probability of recombination of charges in the light emitting layer, thus enhancing the light emitting efficiency.

An example of a typical device configuration of the tandem type organic EL device is the following device configuration.

(2) Anode/First Light Emitting Unit/Intermediate Layer/Second Light Emitting Unit/Cathode Here, the first light emitting unit and the second light emitting unit can each be independently selected, for example, from the light emitting units as described above.

The intermediate layer is generally also referred to as intermediate electrode, intermediate conductive layer, charge generating layer, electron withdrawing layer, connection layer, or intermediate insulating layer, and a known material configuration in which electrons are supplied to the first light emitting unit and holes are supplied to the second light emitting unit can be used.

FIG. 1 is a schematic diagram illustrating an example of the configuration of the organic EL device according to an aspect of the present invention. An organic EL device 1 includes a substrate 2, an anode 3, a cathode 4, and a light emitting unit 10 disposed between the anode 3 and the cathode 4. The light emitting unit 10 includes a light emitting layer 5. The organic EL device 1 includes a hole transporting zone 6 (hole injecting layer, hole transporting layer, etc.) between the light emitting layer 5 and the anode 3, and an electron transporting zone 7 (electron injecting layer, electron transporting layer, etc.) between the light emitting layer 5 and the cathode 4. In addition, an electron blocking layer (not shown) may be provided on the anode 3 side of the light emitting layer 5 and a hole blocking layer (not shown) may be provided on the cathode 4 side of the light emitting layer 5. This enables to trap electrons or holes in the light emitting layer 5 to further increase the efficiency of generating excitons in the light emitting layer 5.

Figure 2:
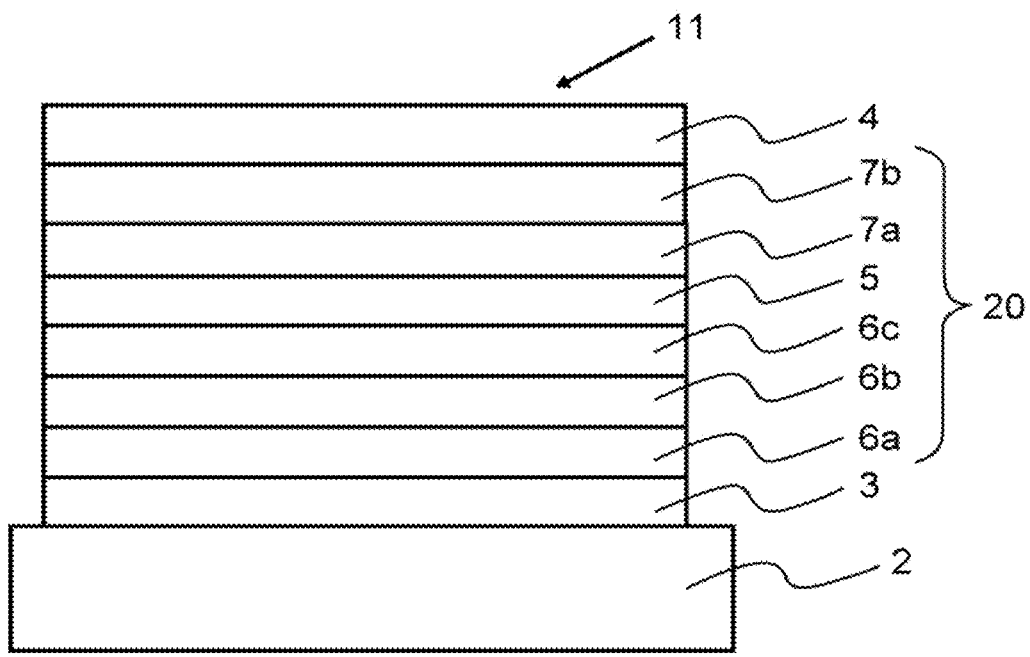
FIG. 2 is a schematic diagram illustrating another example of the layer configuration of the organic EL device according to an aspect of the present invention.

FIG. 2 is a schematic diagram illustrating another configuration of the organic EL device according to an aspect of the present invention. An organic EL device 11 includes the substrate 2, the anode 3, the cathode 4, and a light emitting unit 20 disposed between the anode 3 and the cathode 4. The light emitting unit 20 includes the light emitting layer 5. A hole transporting zone disposed between the anode 3 and the light emitting layer 5 is formed of a hole injecting layer 6a, a first hole transporting layer 6b, and a second hole transporting layer 6c. The electron transporting zone disposed between the light emitting layer 5 and the cathode 4 is formed of a first electron transporting layer 7a and a second electron transporting layer 7b.

In the present invention, a host combined with a fluorescent dopant (fluorescence emitting material) is referred to as a fluorescent host, and a host combined with a phosphorescent dopant is referred to as a phosphorescent host. The fluorescent host and the phosphorescent host are not distinguished only by the molecular structure. In other words, the phosphorescent host means a material that forms a phosphorescence emitting layer containing a phosphorescent dopant, and does not mean that it cannot be used as a material that forms a fluorescence emitting layer. The same applies to the fluorescent host.

Substrate

The substrate is used as a support of the organic EL device. As the substrate, for example, a plate of glass, quartz, or a plastic can be used. A flexible substrate may be used. An example of the flexible substrate is a plastic substrate of polycarbonate, polyarylate, polyethersulfone, polypropylene, polyester, polyvinyl fluoride, or polyvinyl chloride. An inorganic vapor deposition film can also be used.

Anode

For the anode formed on the substrate, a metal, an alloy an electrically conductive compound, a mixture thereof, or the like that has a high work function (specifically 4.0 eV or more) is preferably used. Specific examples thereof include indium oxide-tin oxide (ITO: indium tin oxide), indium oxide-tin oxide containing silicon or silicon oxide, indium oxide-zinc oxide, indium oxide containing tungsten oxide and zinc oxide, and graphene. Other examples include gold (Au), platinum (Pt), nickel (Ni), tungsten (W), chromium (Cr), molybdenum (Mo), iron (Fe), cobalt (Co), cupper (Cu), palladium (Pd), titanium (Ti), and nitride of the metals (for example, titanium nitride).

A film of such a material is generally formed by a spattering method. For example, indium oxide-zinc oxide can be formed by a spattering method by using a target obtained by adding to indium oxide 1 to 10 wt % of zinc oxide based on the indium oxide, and indium oxide containing tungsten oxide and zinc oxide can be formed by a spattering method by using a target obtained by adding to indium oxide 0.5 to 5 wt % of tungsten oxide and 0.1 to 1 wt % of zinc oxide based on the indium oxide. Alternatively a film of such a material may be produced by a vacuum vapor deposition method, a coating method, an inkjet method, a spin-coating method, or the like.

The hole injecting layer formed in contact with the anode is, regardless of the work function of the anode, formed by using a material in which hole injection is easy and thus a material that is generally used as an electrode material (for example, a metal, an alloy an electrically conductive compound, or a mixture thereof, or an element belonging to the group 1 or 2 in the periodic table) can be used.

An element belonging to the group 1 or 2 in the periodic table which is a material having a small work function, specifically an alkali metal, such as lithium (Li) or cesium (Cs), or an alkaline earth metal, such as magnesium (Mg), calcium (Ca), or strontium (Sr), and an alloy containing them (for example, MgAg, AlLi), a rare earth metal, such as europium (Eu) or ytterbium (Yb), or an alloy containing them, or the like, can be used. When the anode is formed using an alkali metal, an alkaline earth metal, or an alloy containing them, a vacuum vapor deposition method or a spattering method can be adopted. When silver paste or the like is used, a coating method, an inkjet method, or the like can be adopted.

Hole Injecting Layer

The hole injecting layer is a layer containing a material having a high hole injecting capability (hole injecting material), and is formed between the anode and the light emitting layer, or between a hole transporting layer, if present, and the anode.

As a hole injecting material other than the inventive compound, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, or the like can be used.

Other examples of a material for the hole injecting layer include aromatic amine compounds, such as 4,4',4"-tris(N, N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphtyl)-N-(9-phenylcarbazol-3-yl)amino]-9-phenylcarbazole (abbreviation: PCzPCN1), which are low-molecular weight organic compounds.

A high-molecular weight compound (oligomer, dendrimer, polymer, or the like) can also be used. Examples of the high-molecular weight compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: Poly-TPD). A high-molecular weight compound with an acid, such as poly(3,4-ethylenedioxythiophene)/poly(styrenesulfonic acid) (PEDOT/PSS) or polyaniline/poly(styrenesulfonic acid) (PAni/PSS), added thereto can also be used.

Furthermore, an acceptor material, such as a hexaazatriphenylene (HAT) compound represented by the following formula (K), is also preferably used.

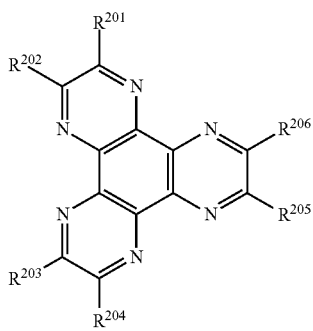

(K)

(In the formula, $R^{201}$ to $R^{206}$ each independently represent a cyano group, —$CONH_2$, a carboxy group, or —$COOR^{207}$ ($R^{207}$ represents an alkyl group having 1 to 20 carbon atoms or a cycloalkyl group having 3 to 20 carbon atoms). Adjacent two selected from $R^{201}$ and $R^{202}$, $R^{203}$ and $R^{204}$, and $R^{205}$ and $R^{206}$ may be bonded to each other to form a group represented by —CO—O—CO—.)

Examples of $R^{207}$ include a methyl group, an ethyl group, an n-propyl group, an isopropyl group, an n-butyl group, an isobutyl group, a t-butyl group, a cyclopentyl group, and a cyclohexyl group.

Hole Transporting Layer

The hole transporting layer is a layer containing a material having a high hole transporting capability (hole transporting material), and is formed between the anode and the light emitting layer or between a hole injecting layer, if present, and the light emitting layer. The inventive compound may be used, for the hole transporting layer, alone or in combination with the following compound.

The hole transporting layer may have a monolayer structure or a multilayer structure including two or more layers. For example, the hole transporting layer may have a two-layer structure including a first hole transporting layer (anode side) and a second hole transporting layer (cathode side). In an embodiment of the present invention, the hole transporting layer of the monolayer structure is preferably adjacent to the light emitting layer, and the hole transporting layer that is the nearest to the cathode in the multilayer structure, for example, the second hole transporting layer in the two-layer structure, is preferably adjacent to the light emitting layer. In another embodiment of the present invention, an electron blocking layer as described later or the like may be interposed between the hole transporting layer of the monolayer structure and the light emitting layer or between the hole transporting layer that is the nearest to the light emitting layer in the multilayer structure and the light emitting layer.

In the hole transporting layer of the two-layer configuration, the inventive compound may be contained in one of the first hole transporting layer and the second hole transporting layer, or may be contained in the both.

In an embodiment of the present invention, the inventive compound is preferably contained only in the first hole transporting layer, in another embodiment, the inventive compound is preferably contained only in the second hole transporting layer, and in still another embodiment, the inventive compound is preferably contained in the first hole transporting layer and the second hole transporting layer.

In an embodiment of the present invention, the inventive compound contained in one or both of the first hole transporting layer and the second hole transporting layer is preferably a light hydrogen form from the viewpoint of the production cost.

The light hydrogen form refers to the inventive compound in which all the hydrogen atoms are a light hydrogen atom.

Accordingly the organic EL device as an aspect of the present invention is preferably an organic EL device in which one or both of the first hole transporting layer and the second hole transporting layer contains the inventive compound essentially constituted only of light hydrogen forms. "The inventive compound essentially constituted only of light hydrogen forms" means that the content of the light hydrogen form based on the total amount of the inventive compound is 90% by mole or more, preferably 95% by mole or more, and more preferably 99% by mole or more (each including 100%).

As a material for the hole transporting layer other than the inventive compound, for example, an aromatic amine compound, a carbazole derivative, an anthracene derivative, or the like can be used.

Examples of the aromatic amine compound include 4,4'-bis[N-(1-naphtyl)-N-phenylamino]biphenyl (abbreviation: NPB) and N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB). The compounds have a hole mobility of $10^{-6}$ $cm^2/Vs$ or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphtyl)anthracene (abbreviation: t-BuDNA), 9,10-di(2-naphtyl)anthracene (abbreviation: DNA), and 9,10-diphenylanthracene (abbreviation: DPAnth).

A high-molecular weight compound, such as poly(N-vinylcarbazole) (abbreviation: PVK) or poly(4-vinyltriphenylamine) (abbreviation: PVTPA), can also be used.

However, compounds other than those mentioned above may be used so long as they are materials higher in the hole transporting capability rather than in the electron transporting capability.

Dopant Material for Light Emitting Layer

The light emitting layer is a layer containing a material having a high light emitting capability (dopant material), and various materials can be used. For example, a fluorescence emitting material or a phosphorescence emitting material can be used as the dopant material. A fluorescence emitting material is a compound that emits light from the singlet excited state, and a phosphorescence emitting material is a compound that emits light from the triplet excited state.

As a blue fluorescence emitting material that can be used for the light emitting layer, a pyrene derivative, a styrylamine derivative, a chrysene derivative, a fluoranthene derivative, a fluoran derivative, a diamine derivative, or a triarylamine derivative can be used. Specific examples thereof include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA).

As the green fluorescence emitting material that can be used in the light emitting layer, an aromatic amine derivative or the like can be used. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracene-2-amine (abbreviation: 2YGABPhA), and N,N,9-triphenylanthracene-9-amine (abbreviation: DPhAPhA).

As a red fluorescence emitting material that can be used in the light emitting layer, a tetracene derivative, a diamine derivative, or the like can be used. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acetonaphtho[1,2-a]fluoranthene-3,10-diamine (abbreviation: p-mPhAFD).

As a blue phosphorescence emitting material that can be used in the light emitting layer, a metal complex, such as an iridium complex, an osmium complex, or a platinum complex, is used. Specific examples thereof include bis[2-(4',6'-difluorophenyl)pyridinato-N,C2']iridium(III) tetrakis(1-pyrazolyl)borate (abbreviation: FIr6), bis[2-(4',6'-difluorophenyl)pyridinato-N,C2']iridium(III) picolinate (abbreviation: FIrpic), bis[2-(3',5'-bistrifluoromethylphenyl)pyridinato-N,C2']iridium(III) picolinate (abbreviation: Ir(CF3ppy)2(pic)), and bis[2-(4',6'-difluorophenyl)pyridinato-N,C2']iridium(III) acetylacetonate (abbreviation: FIracac).

As a green phosphorescence emitting material that can be used in the light emitting layer, an iridium complex or the like is used. Examples thereof include tris(2-phenylpyridinato-N,C2')iridium(III) (abbreviation: Ir(ppy)3), bis(2-phenylpyridinato-N,C2')iridium(III) acetylacetonate (abbreviation: Ir(ppy)2(acac)), bis(1,2-diphenyl-1H-benzimidazolato)iridium(III) acetylacetonate (abbreviation: Ir(pbi)2(acac)), and bis(benzo[h]quinolato)iridium(III) acetylacetonate (abbreviation: Ir(bzq)2(acac)).

As a red phosphorescence emitting material that can be used in the light emitting layer, a metal complex, such as an iridium complex, a platinum complex, a terbium complex, or a europium complex, is used. Specific examples thereof include organic metal complexes, such as bis[2-(2'-benzo[4,5-α]thienyl)pyridinato-N,C3']iridium(III) acetylacetonate (abbreviation: Ir(btp)2(acac)), bis(1-phenylisoquinolinato-N,C2')iridium(III) acetylacetonate (abbreviation: Ir(piq)2(acac)), (acetylacetonato)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrin platinum (II) (abbreviation: PtOEP).

In addition, a rare earth metal complex, such as tris (acetylacetonate)(monophenanthroline)terbium(III) (abbreviation: Tb(acac)3(Phen)), tris(1,3-diphenyl-1,3-propanedionato)(monophenanthroline)europium(III) (abbreviation: Eu(DBM)3(Phen)), or tris[1-(2-thenoyl)-3,3,3-trifluoroacetonato](monophenanthroline)europium(III) (abbreviation: Eu(TTA)3(Phen)), emits light from rare earth metal ions (electron transition between different multiplicities) and thus, can be used as a phosphorescence emitting material.

Host Material for Light Emitting Layer

The light emitting layer may have a configuration in which such a dopant material as described above is dispersed in another material (host material). A material that has a higher lowest unoccupied molecular orbital level (LUMO level) and a lower highest occupied molecular orbital level (HOMO level) than the dopant material is preferably used.

As the host material, for example,
(1) a metal complex, such as an aluminum complex, a beryllium complex, or a zinc complex,
(2) a heterocyclic compound, such as an oxadiazole derivative, a benzimidazole derivative, or a phenanthroline derivative,
(3) a condensed aromatic compound, such as a carbazole derivative, an anthracene derivative, a phenanthrene derivative, a pyrene derivative, or a chrysene derivative, or
(4) an aromatic amine compound, such as a triarylamine derivative or a condensed polycyclic aromatic amine derivative is used.

For example, a metal complex, such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ);

a heterocyclic compound, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), or bathocuproine (abbreviation: BCP);

a condensed aromatic compound, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis (3,5-diphenylphenyl)anthracene (abbreviation: DPPA), 9,10-di(2-naphtyl)anthracene (abbreviation: DNA), 2-tert-butyl-9,10-di(2-naphtyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrrane (abbreviation: TPB3), 9,10-diphenylanthracene (abbreviation: DPAnth), or 6,12-dimethoxy-5,11-diphenylchrysene; and an aromatic amine compound, such as N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl] phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphtyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), or 4,4'- bis[N-(spiro-9,9'-bifluoren-2-yl)-N-phenylamino]bi-phenyl (abbreviation: BSPB), can be used. Two or more host materials may be used.
In particular, in the case of the blue fluorescence device, the following anthracene compounds are preferably used as a host material.
[Chem. 379]
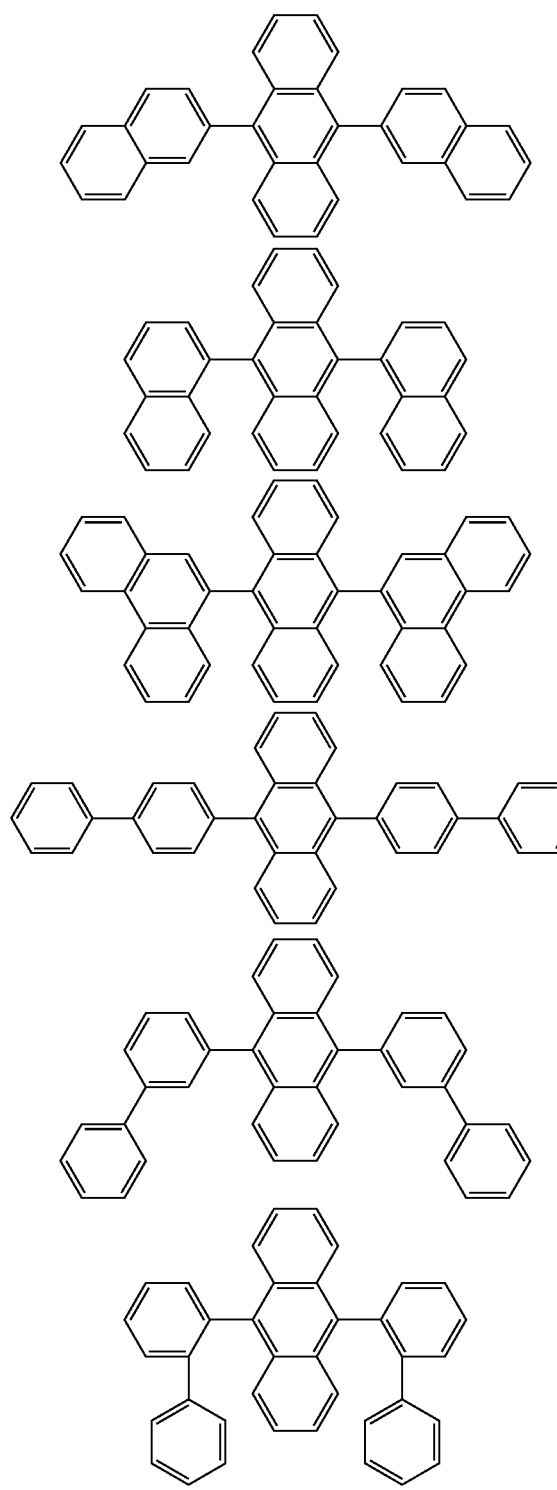
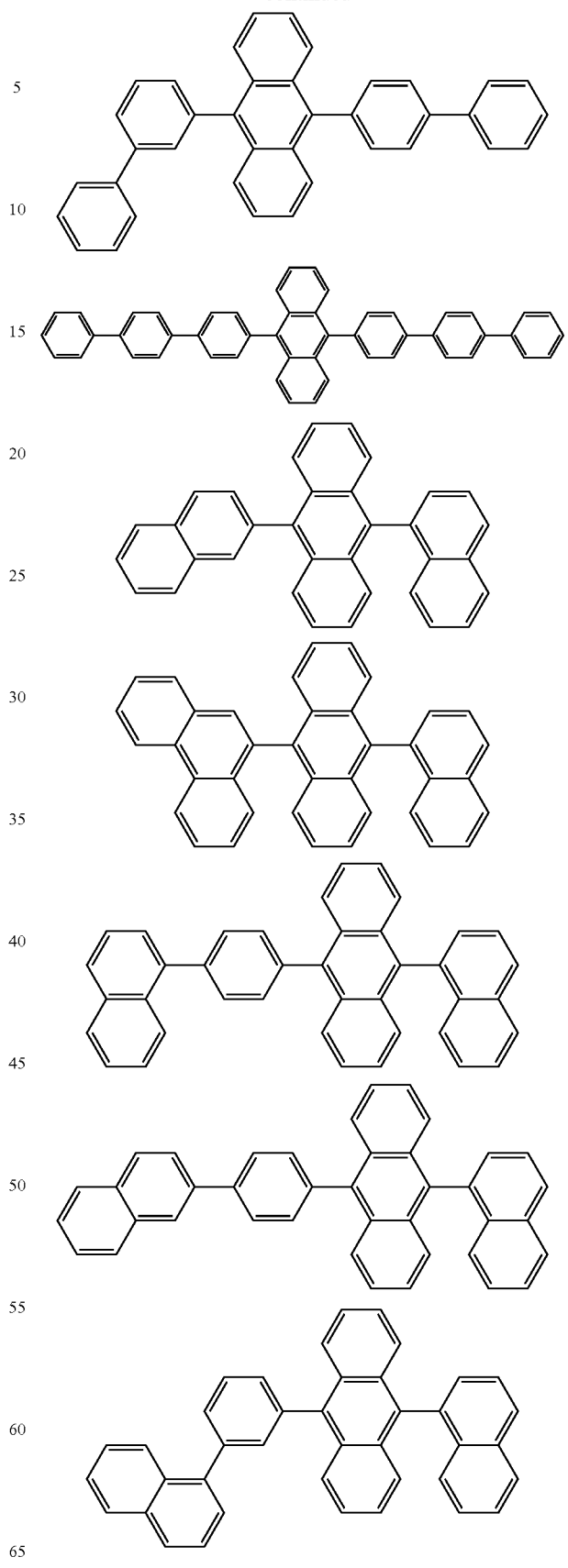

1133
-continued
1134
-continued
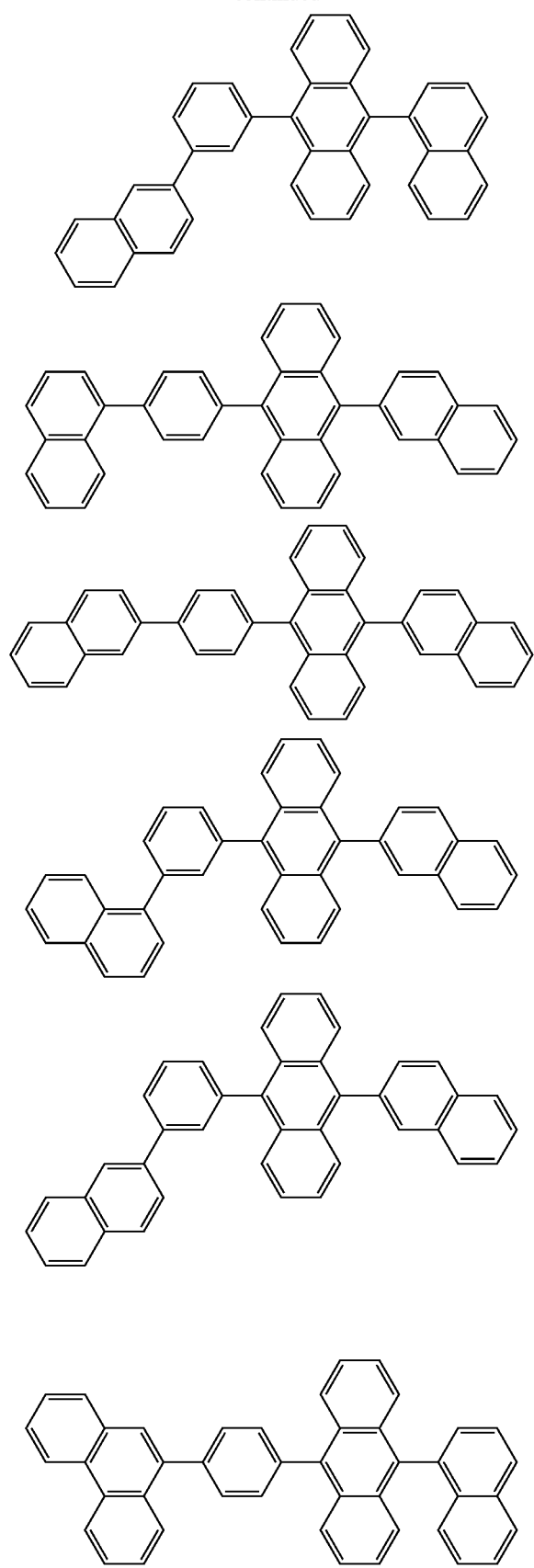
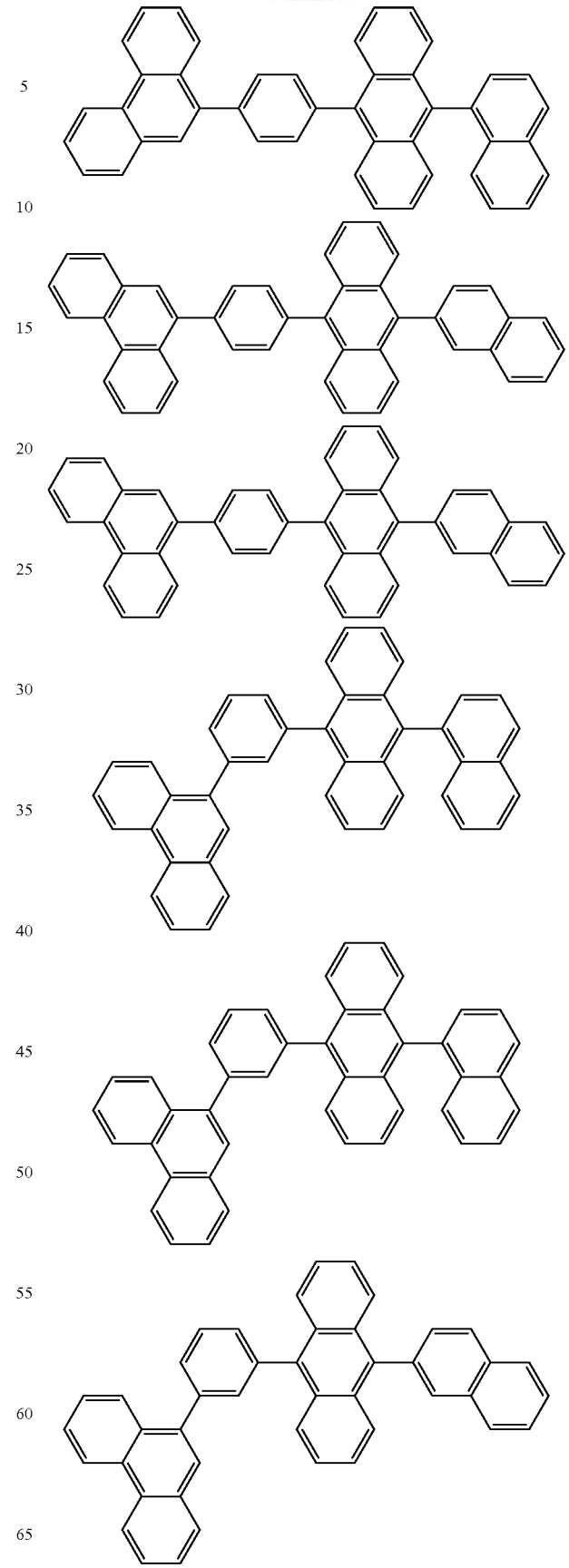

1135
-continued
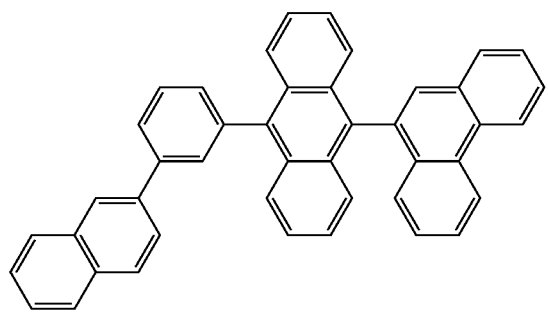
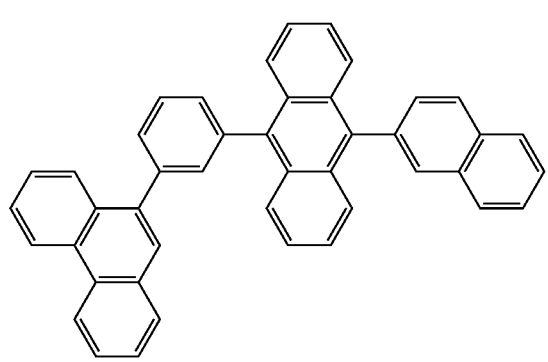
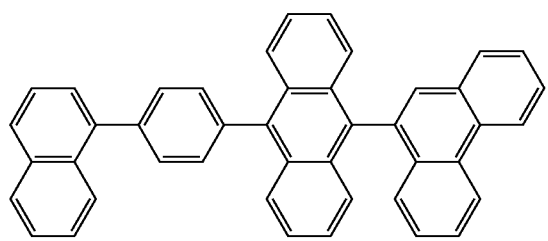
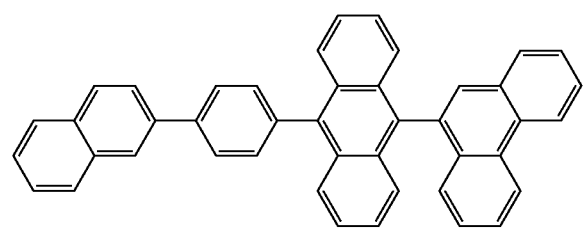
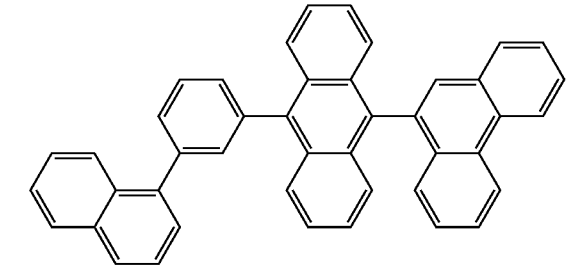
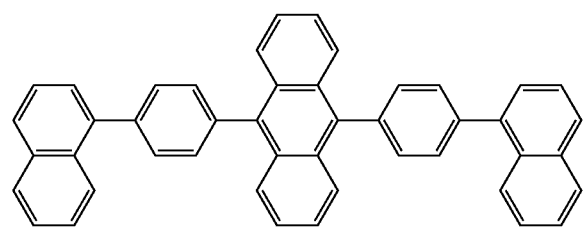
1136
-continued
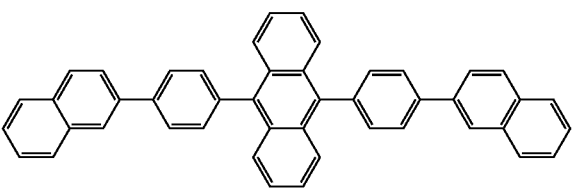
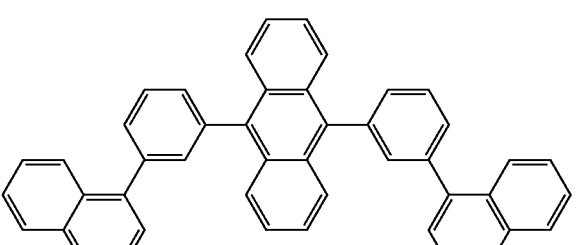
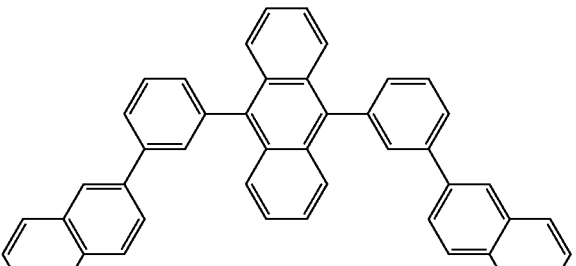
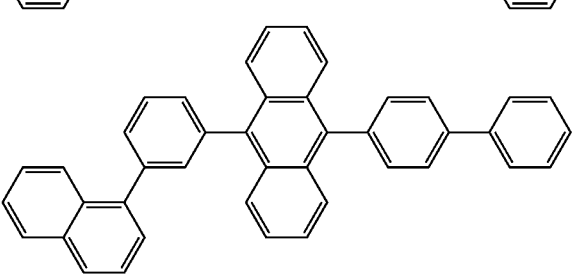
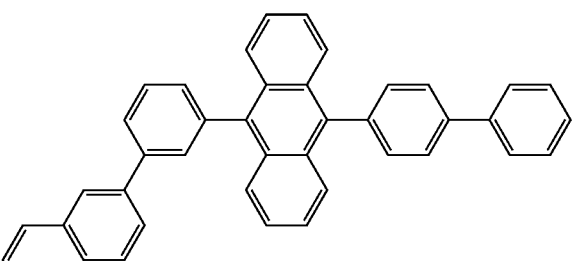
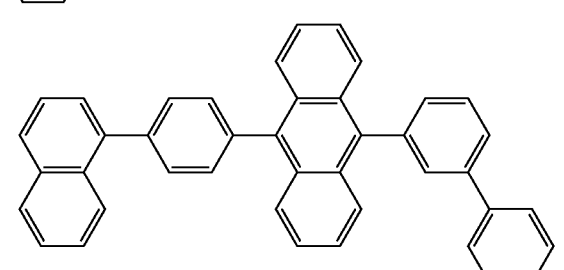

1137
-continued
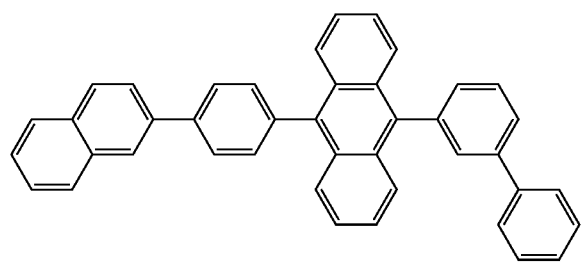
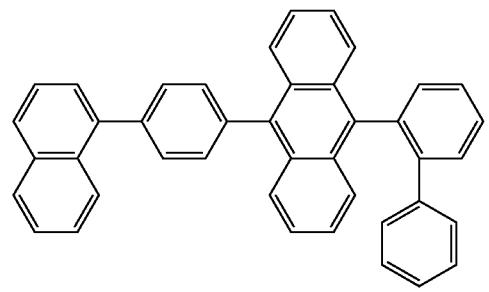
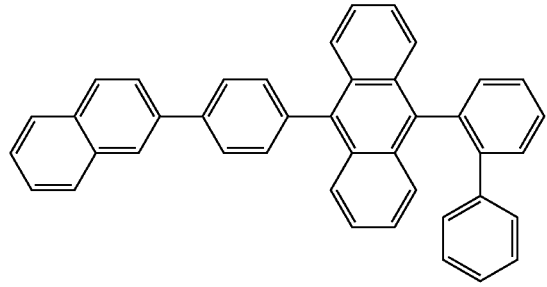
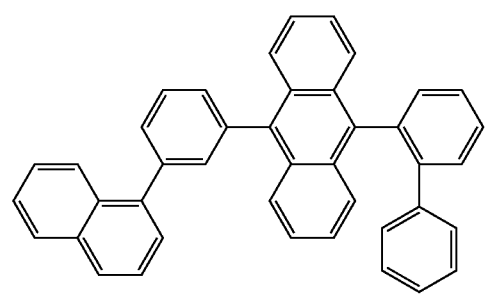
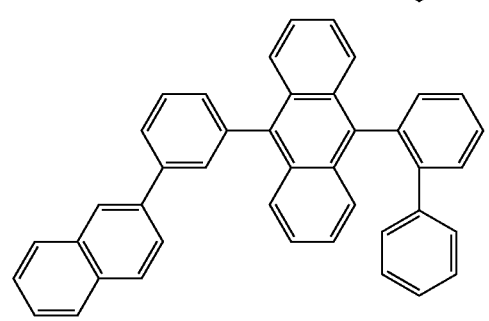
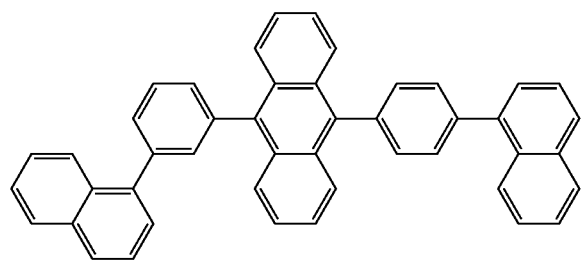
1138
-continued
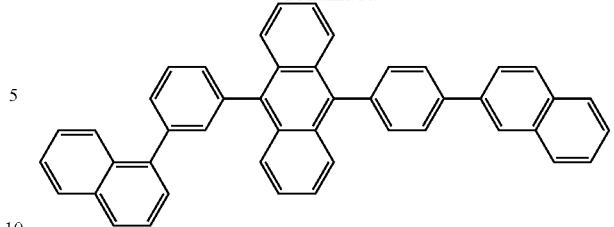
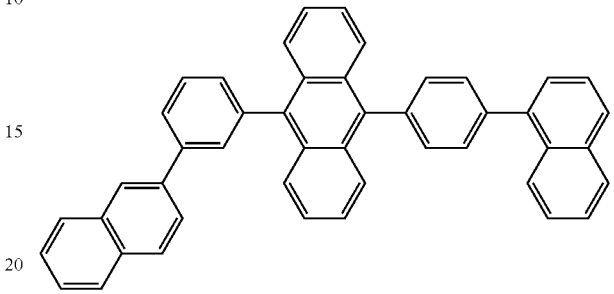
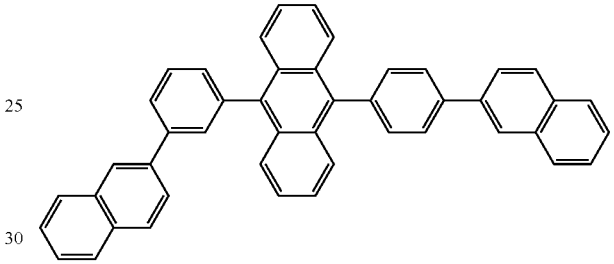
[Chem. 380]
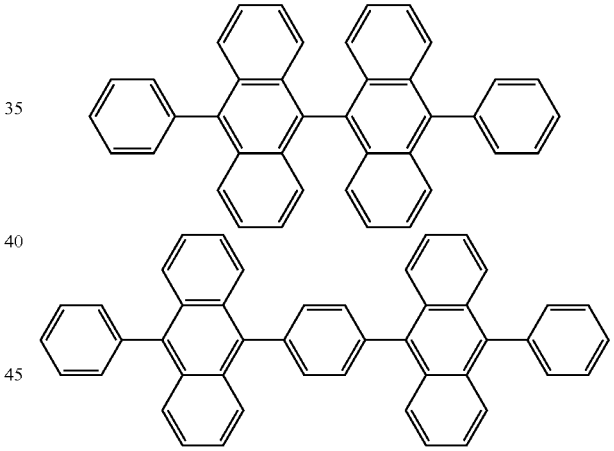
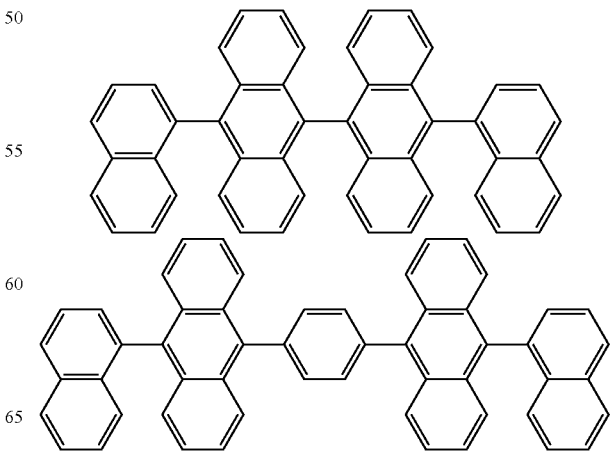

1139
-continued

1140
-continued

1141
-continued
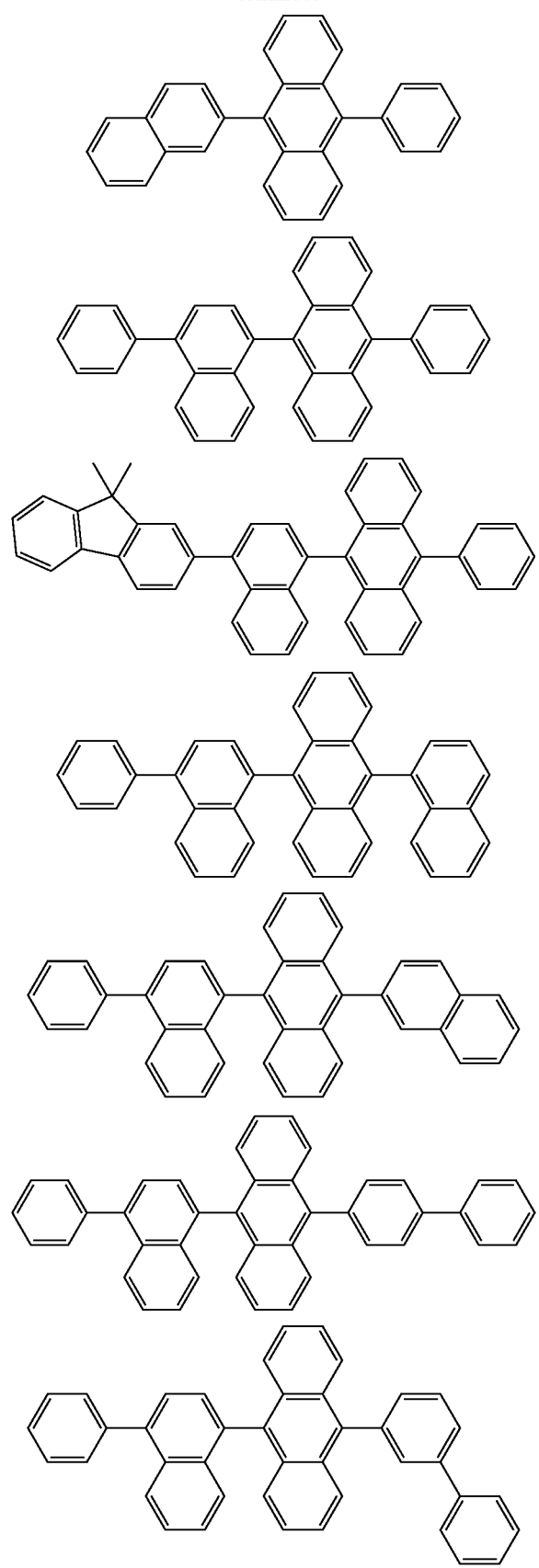
1142
-continued
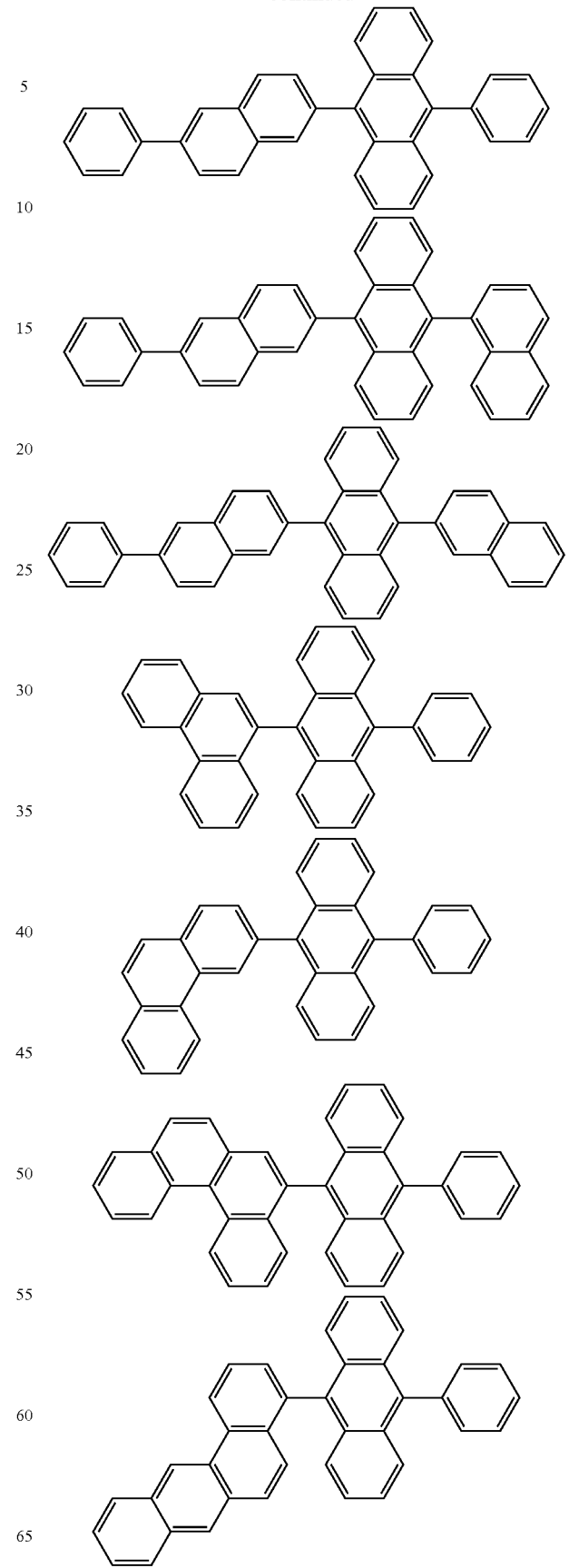

1143
-continued
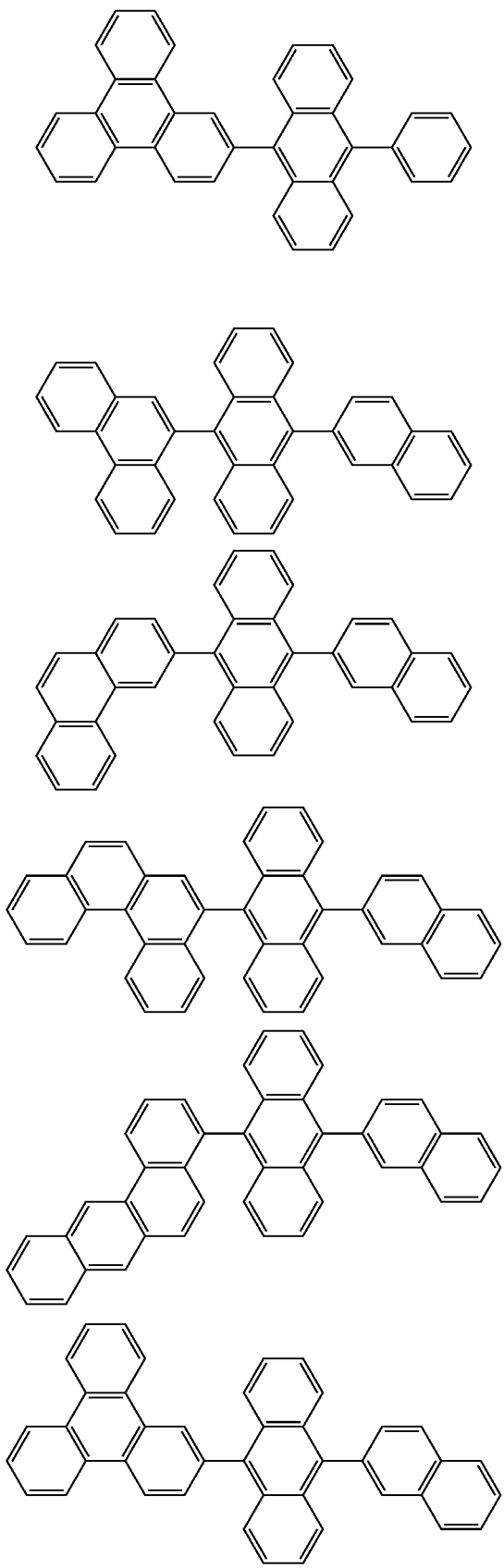
1144
-continued
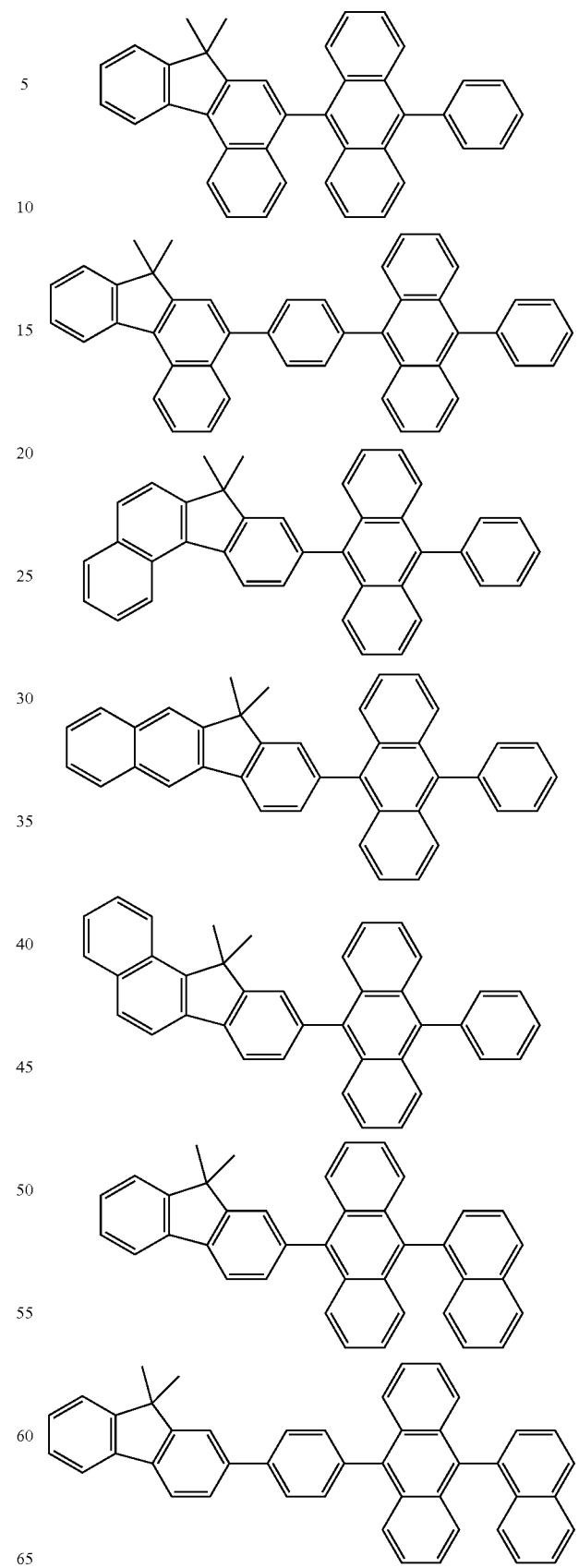

1145
-continued
1146
-continued
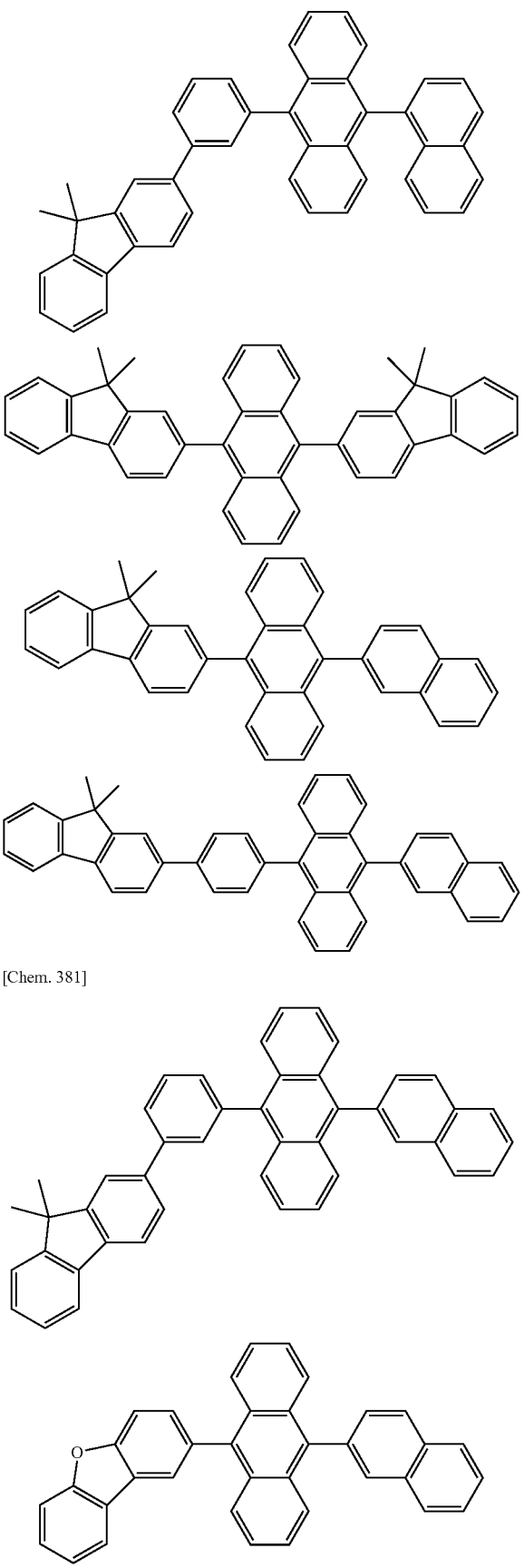
[Chem. 381]
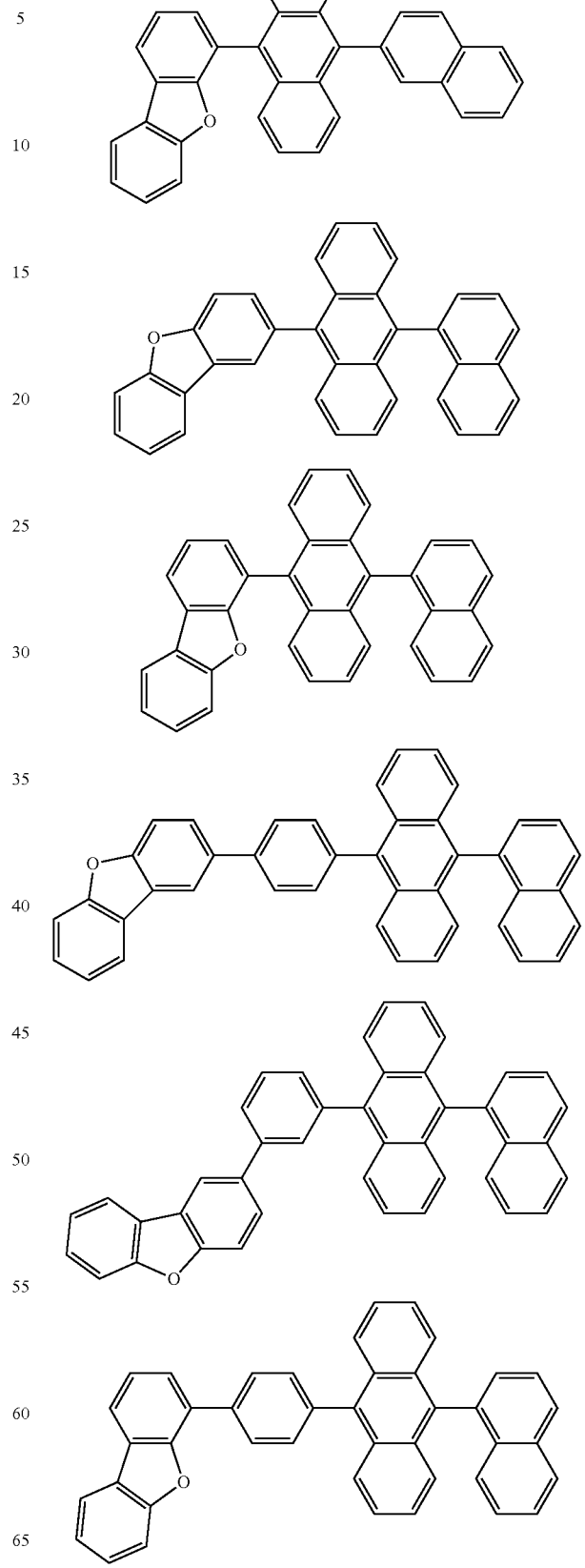

1147
-continued
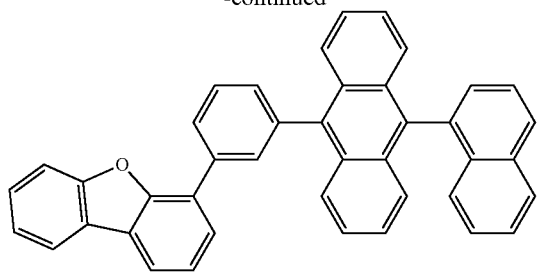
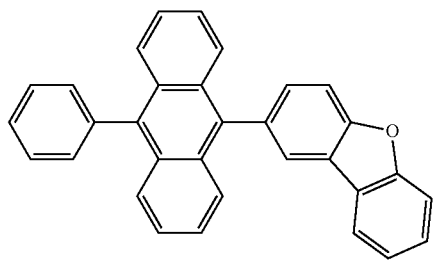
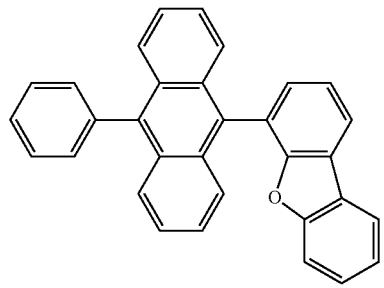
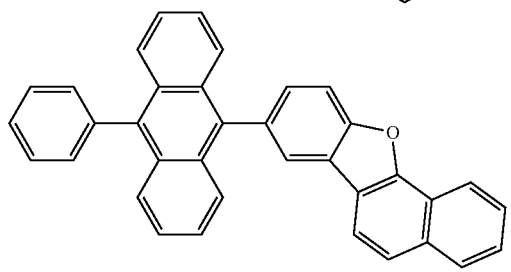
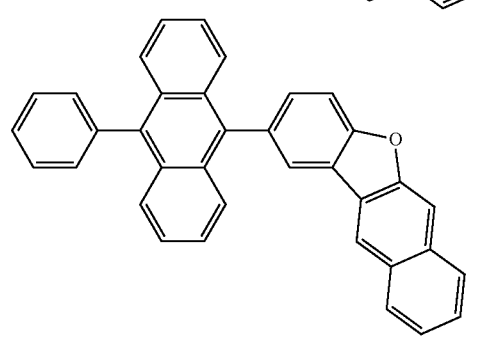
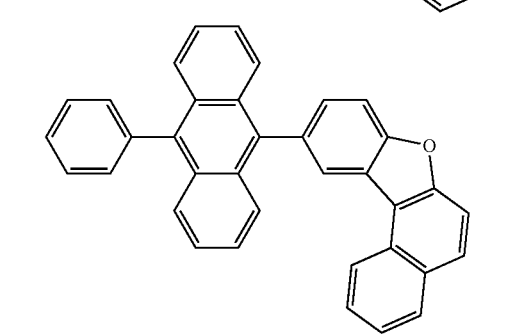
1148
-continued
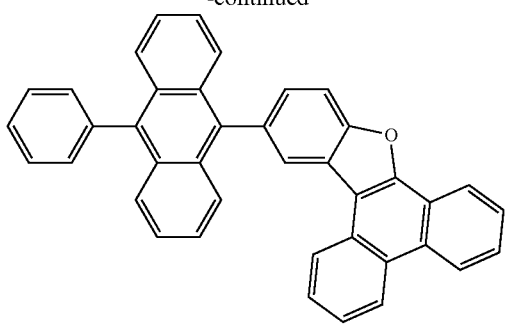
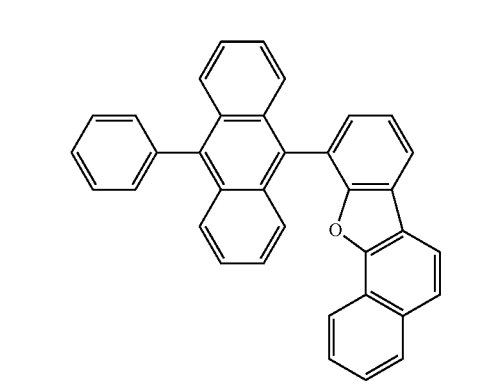
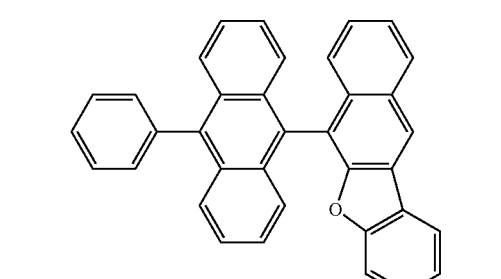
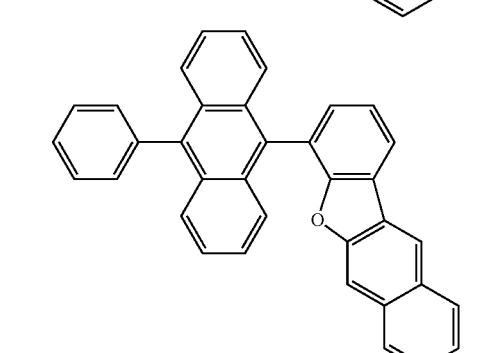
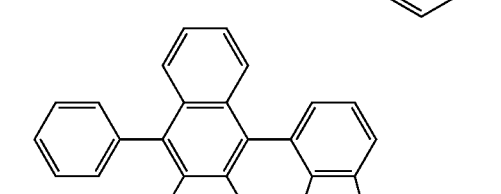
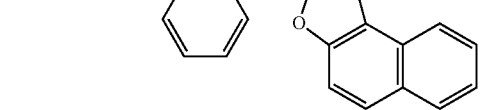

1149
-continued
1150
-continued
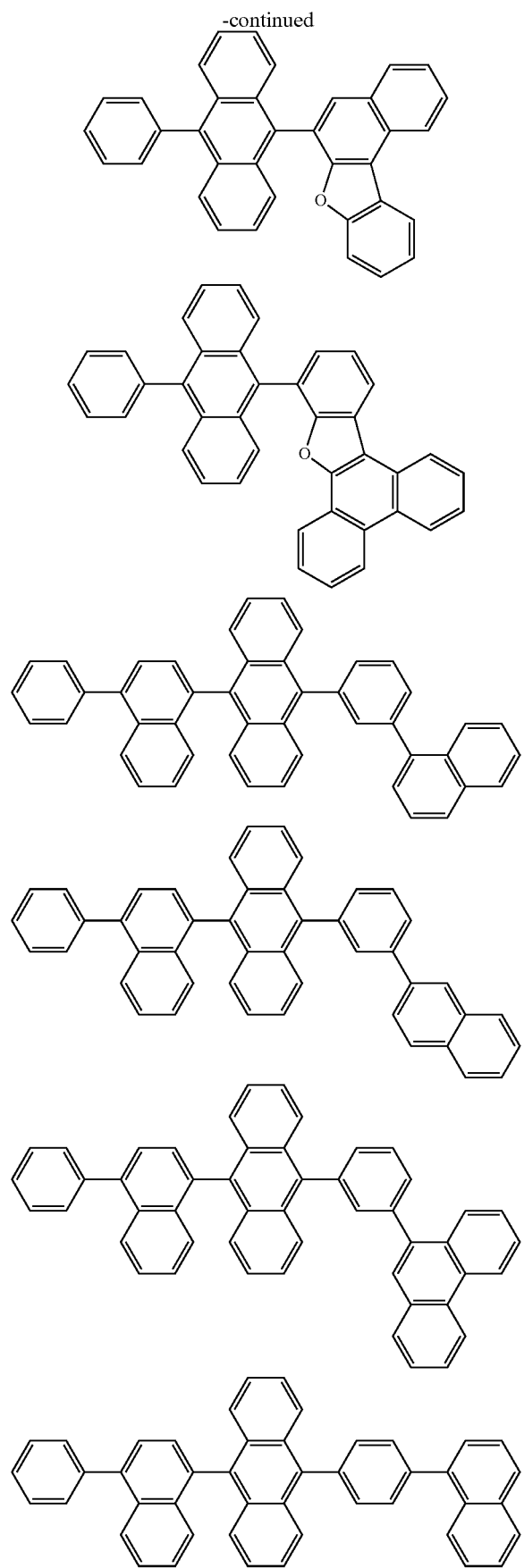
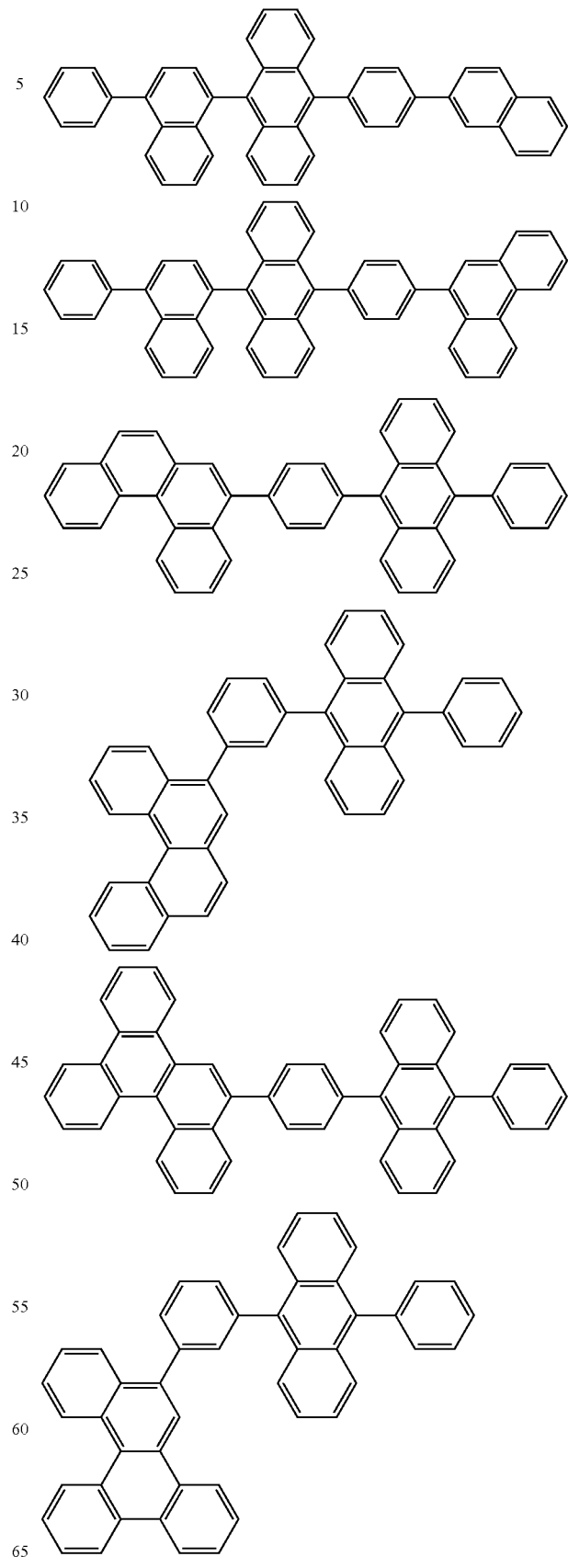

-continued

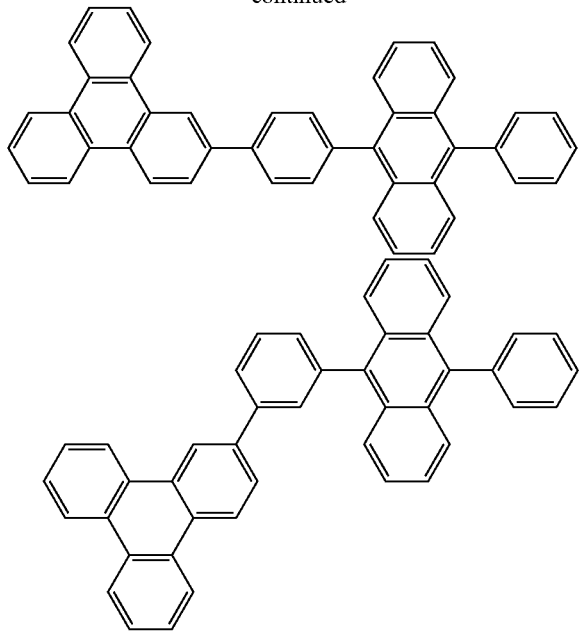

Electron Transporting Layer

The electron transporting layer is a material having a high electron transporting capability (electron transporting material), and is formed between the light emitting layer and the cathode or between an electron injecting layer, if present, and the light emitting layer.

The electron transporting layer may have a monolayer structure or a multilayer structure including two or more layers. For example, the electron transporting layer may have a two-layer structure including a first electron transporting layer (anode side) and a second electron transporting layer (cathode side). In an embodiment of the present invention, the electron transporting layer in the monolayer structure is preferably adjacent to the light emitting layer, and the electron transporting layer that is the nearest to the anode in the multilayer configuration, for example, the first electron transporting layer of the two-layer structure, is preferably adjacent to the light emitting layer. In another embodiment of the present invention, a hole blocking layer as described later or the like may be interposed between the electron transporting layer of the monolayer structure and the light emitting layer or between the electron transporting layer that is the nearest to the light emitting layer in the multilayer structure and the light emitting layer.

For the electron transporting layer, for example,
(1) a metal complex, such as an aluminum complex, a beryllium complex, or a zinc complex,
(2) a heteroaromatic compound, such as an imidazole derivative, a benzimidazole derivative, an azine derivative, a carbazole derivative, or a phenanthroline derivative, or
(3) a high-molecular weight compound can be used.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl)stilbene (abbreviation: BzOs).

Examples of the high-molecular weight compound include poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy).

The materials are materials having an electron mobility of $10^{-6}$ cm$^2$/Vs or more. Materials other than those as mentioned above may be used for the electron transporting layer so long as they are materials higher in the electron transporting capability rather than in the hole transporting capability.

Electron Injecting Layer

The electron injecting layer is a layer containing a material having a high electron injecting capability. In the electron injecting layer, an alkali metal, such as lithium (Li) or cesium (Cs), an alkaline earth metal, such as magnesium (Mg), calcium (Ca), or strontium (Sr), a rare earth metal, such as europium (Eu) or ytterbium (Yb), and a compound containing them can be used. Examples of the compound include an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. In addition, two or more of the compounds can be used in mixture.

Besides, a material in which an alkali metal, an alkaline earth metal, or a compound thereof is contained in a material having electron transporting capability specifically, a material in which magnesium (Mg) is contained in Alq, or the like, may be used. In this case, electron injection from the cathode can be more efficiently achieved.

Alternatively a composite material obtained by mixing an organic compound with an electron donor may be used in the injecting layer. Such a composite material is excellent in the electron injecting capability and the electron transporting capability because the organic compound receives electrons from the electron donor. In this case, the organic compound is preferably a material excellent in transporting received electrons, and specifically a material constituting the aforementioned electron transporting layer (such as a metal complex or a heteroaromatic compound) can be used. As the electron donor, a material having an electron donation capability for an organic compound can be used. Specifically an alkali metal, an alkaline earth metal, and a rare earth metal are preferred, and examples thereof include lithium, cesium, magnesium, calcium, erbium, and ytterbium. An alkali metal oxide or an alkaline earth metal oxide is also preferred, and examples thereof include lithium oxide, calcium oxide, and barium oxide. A Lewis base, such as magnesium oxide, can also be used. An organic compound, such as tetrathiafulvalene (abbreviation: TTF), can also be used.

Cathode

A metal, an alloy an electrically conductive compound, or a mixture thereof that has a low work function (specifically 3.8 eV or less) is preferably used for the cathode. Specific examples of such a cathode material include elements belonging to the group 1 or 2 of the periodic table, that is, an alkali metal, such as lithium (Li) or cesium (Cs), an alkaline earth metal, such as magnesium (Mg), calcium (Ca), or strontium (Sr), and an alloy containing them (for example, MgAg, AlLi), and a rare earth metal, such as europium (Eu) or ytterbium (Yb), and an alloy containing them.

When the cathode is formed by using an alkali metal, an alkaline earth metal, and an alloy containing them, a vacuum vapor deposition method or a sputtering method can be adopted. When silver paste or the like is used, a coating method, an inkjet method, or the like can be adopted.

By providing the electron injecting layer, the cathode can be formed using various conductive materials, such as Al, Ag, ITO, graphene, and indium oxide-tin oxide containing silicon or silicon oxide, regardless of the magnitude of the work function. A film of such a conductive material can be formed by using a sputtering method, an inkjet method, a spin-coating method, or the like.

Insulating Layer

The organic EL device applies an electric field to an ultrathin film, and thus, pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of them may also be used.

Space Layer

The space layer is, for example, a layer provided between a fluorescence emitting layer and a phosphorescence emitting layer for the purpose of preventing excitons generated in the phosphorescence emitting layer from diffusing into the fluorescence emitting layer, or adjusting the carrier balance, in the case where the fluorescence emitting layers and the phosphorescence emitting layers are stacked. The space layer can also be provided between two or more phosphorescence emitting layers.

Since the space layer is provided between the light emitting layers, a material having both an electron transporting capability and a hole transporting capability is preferred. In addition, one having a triplet energy of 2.6 eV or more is preferred in order to prevent diffusion of the triplet energy in the adjacent phosphorescence emitting layers. Examples of a material used for the space layer include the same as those used for the hole transporting layer as described above.

Blocking Layer

A blocking layer, such as an electron blocking layer, a hole blocking layer, or an exciton blocking layer, may be provided adjacent to the light emitting layer. The electron blocking layer is a layer that prevents electrons from leaking from the light emitting layer to a hole transporting layer, and the hole blocking layer is a layer that prevents holes from leaking from the light emitting layer to an electron transporting layer. The exciton blocking layer functions to prevent excitons generated in the light emitting layer from diffusing into the surrounding layers to trap the excitons within the light emitting layer.

Each layer of the organic EL device can be formed by a conventionally known vapor deposition method, a coating method, or the like. For example, each layer can be formed by a known technique by a vapor deposition method, such as a vacuum vapor deposition method or a molecular beam vapor deposition method (MBE method), or a coating method using a solution of a compound for forming a layer, such as a dipping method, a spin-coating method, a casting method, a bar-coating method, and a roll-coating method.

The film thickness of each layer is not particularly limited, but is typically 5 nm to 10 μm, and more preferably 10 nm to 0.2 μm because in general, when the film thickness is too small, defects such as pinholes are likely to occur, and conversely when the film thickness is too large, a high driving voltage is required and the efficiency decreases.

The organic EL device can be suitably used in an electronic instrument, such as a display component of an organic EL panel module or the like, a display apparatus of a television, a mobile phone, a personal computer, or the like, and a luminescent apparatus of a lighting or a vehicular lamp.

EXAMPLES

The present invention will be described in more detail below by reference to Examples, but the present invention is not to be limited to the following Examples.

Inventive Compounds Used for Production of Organic EL Devices of Examples 1 to 2

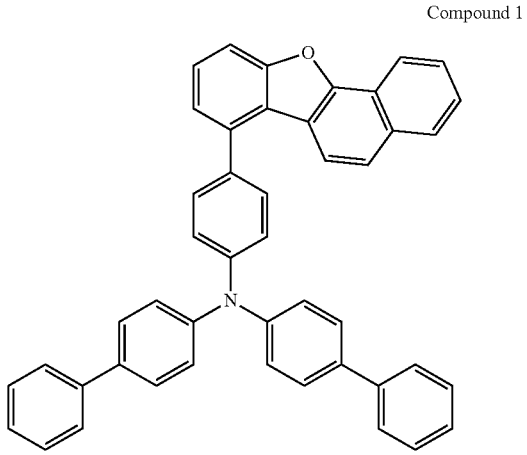

Compound 1

Compound 2
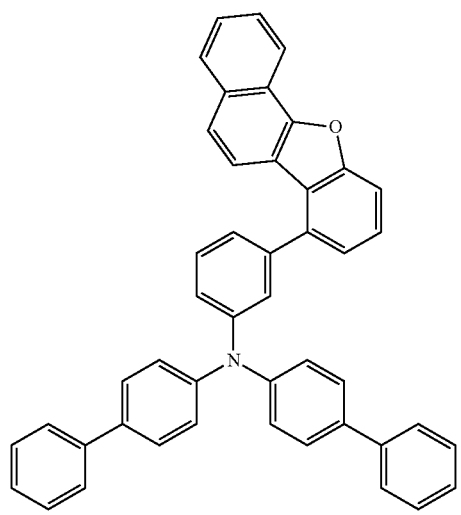
Compound 1, Compound 2
Comparative Compound Used for Production of Organic EL Device of Comparative Example 1
Comparative Compound 1
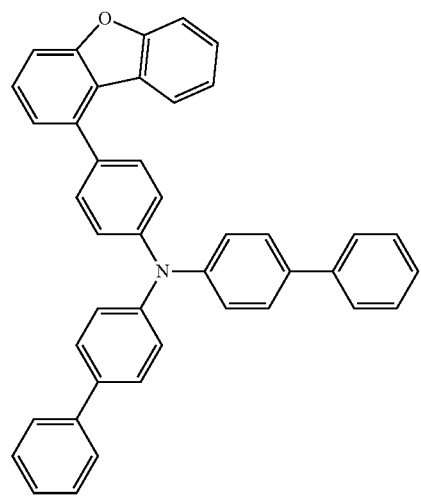
Other Compounds Used for Production of Organic EL Devices of Examples 1 to 2 and Comparative Example 1
HA
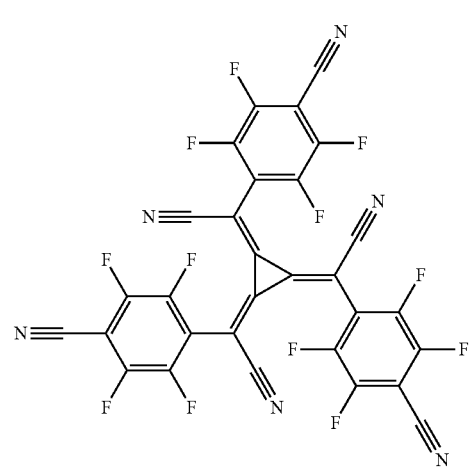
HT-1
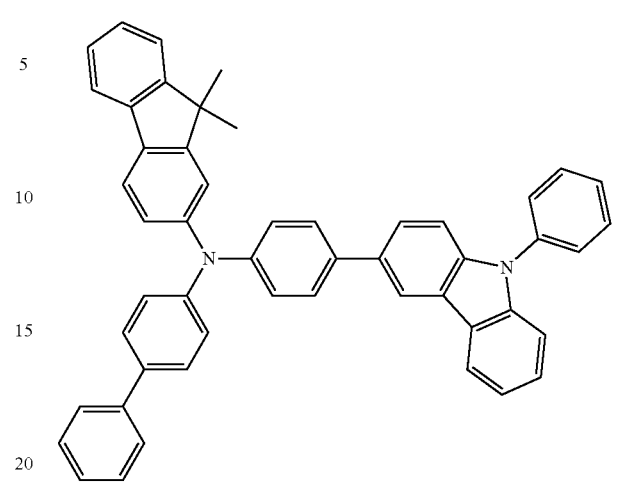
BH-1
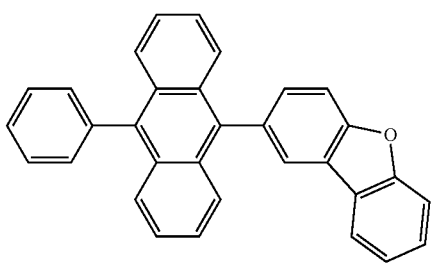
BD-1
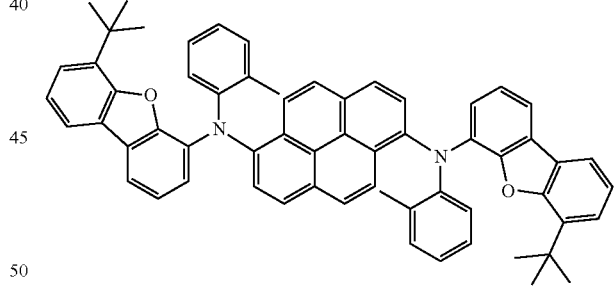
ET-1
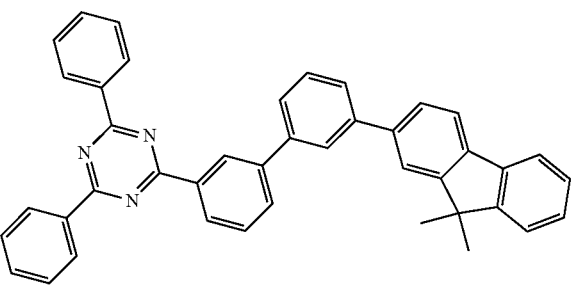

ET-2
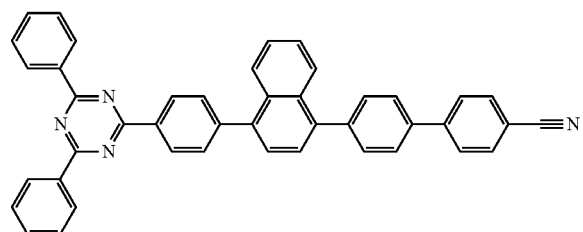
Inventive Compounds Used for Production of Organic EL Devices of Examples 3 to 13
Compound 6
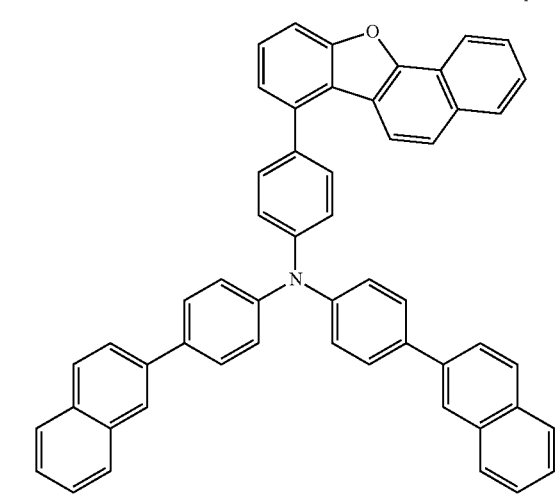
Compound 7
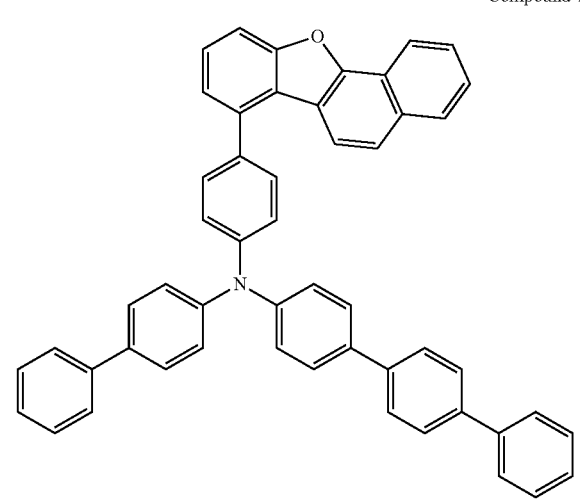
Compound 8
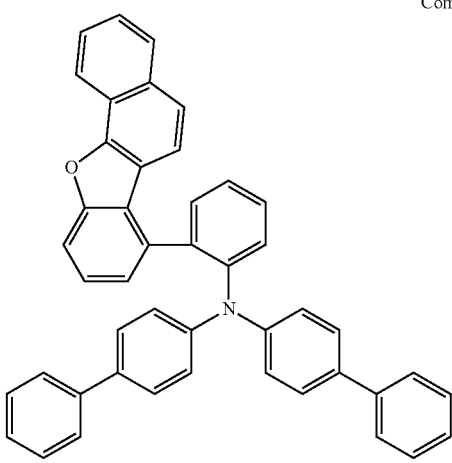
Compound 9
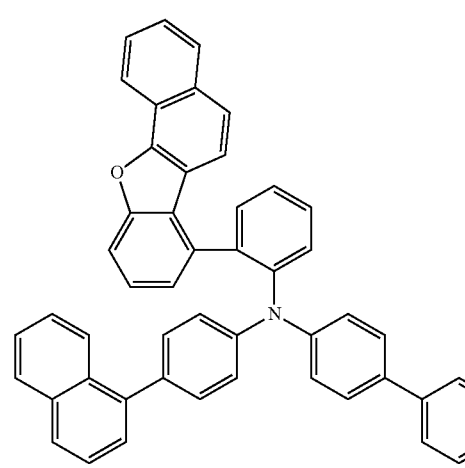
Compound 10
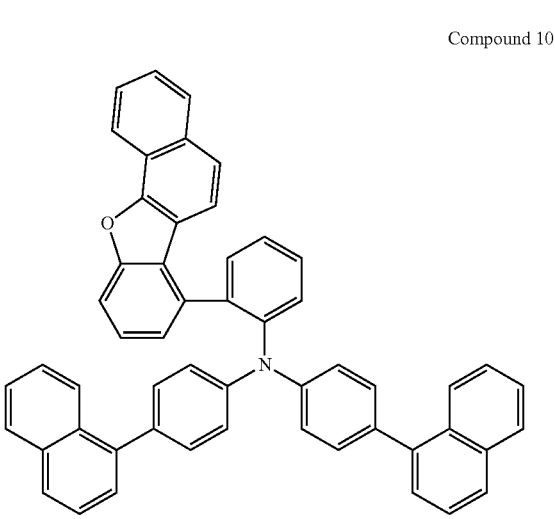

Compound 11
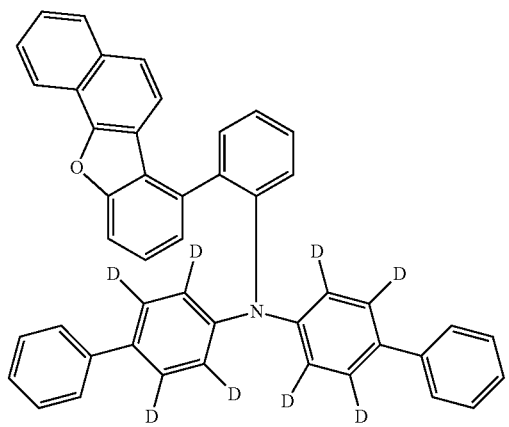
Compound 14
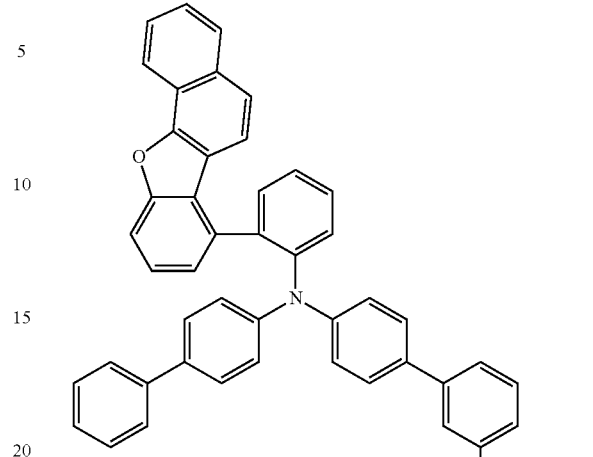
Compound 12
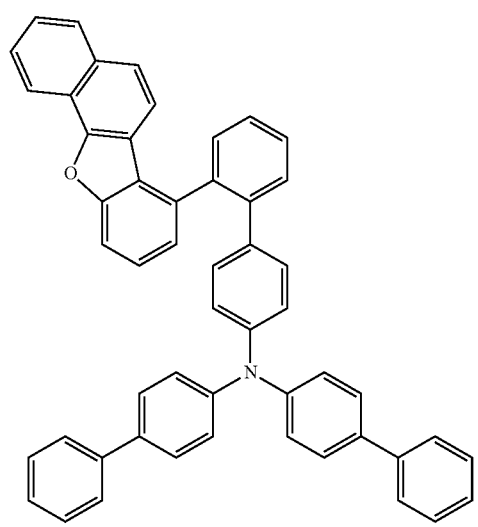
Compound 15
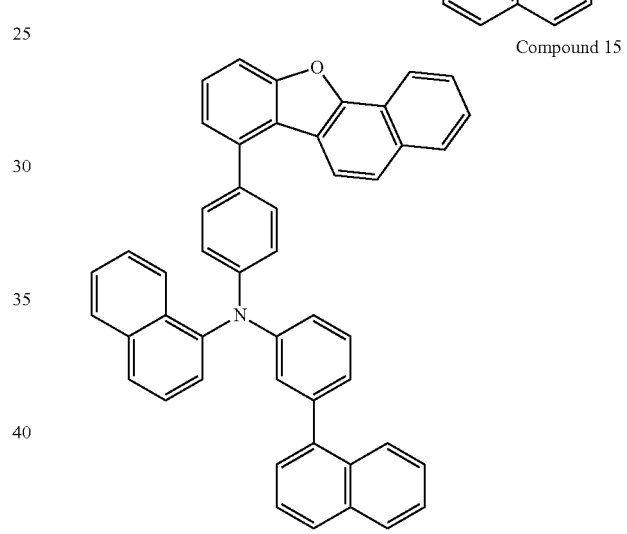
Compound 13
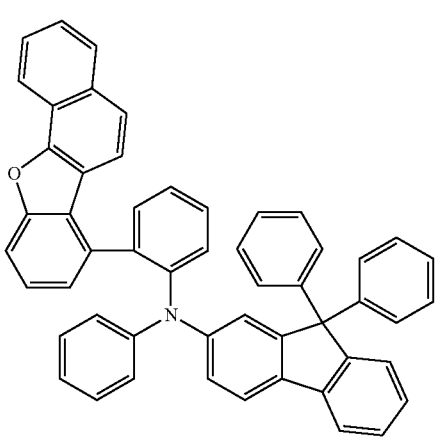
Compound 16
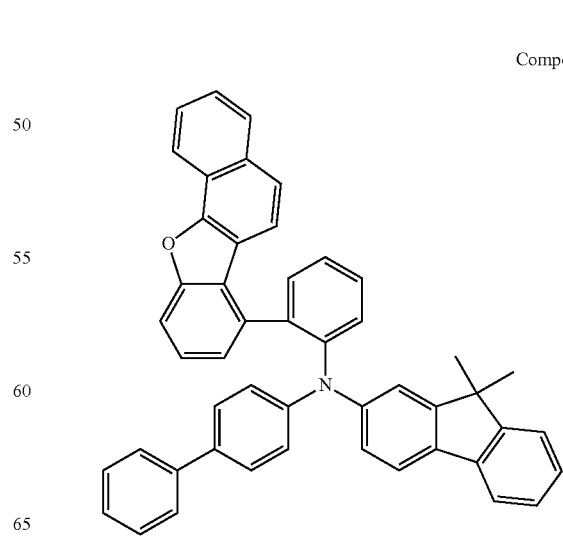

Comparative Compounds Used for Production of Organic EL Devices of Comparative Examples 2 to 4
Comparative Compound 2
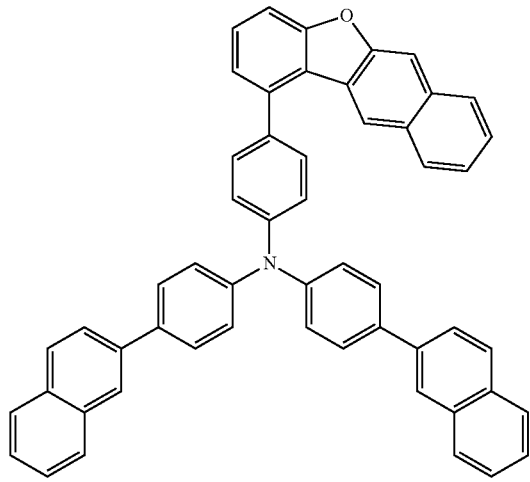
Comparative Compound 3
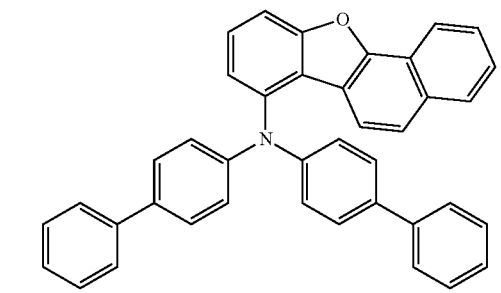
Comparative Compound 4
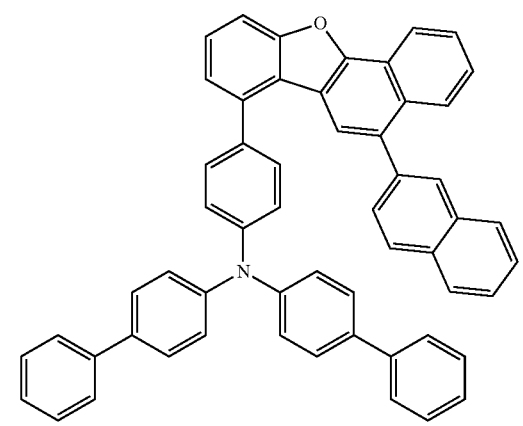
Other Compounds Used for Production of Organic EL Devices of Examples 3 to 13 and Comparative Examples 2 to 4
HA
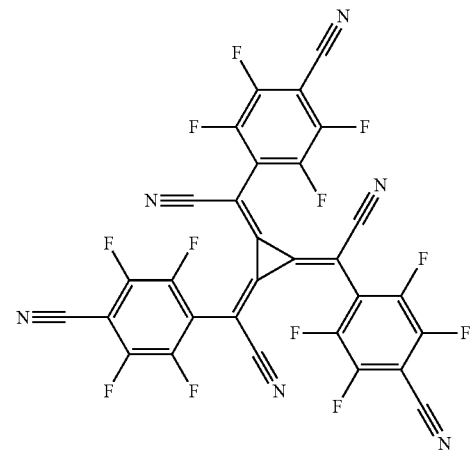
HT-2
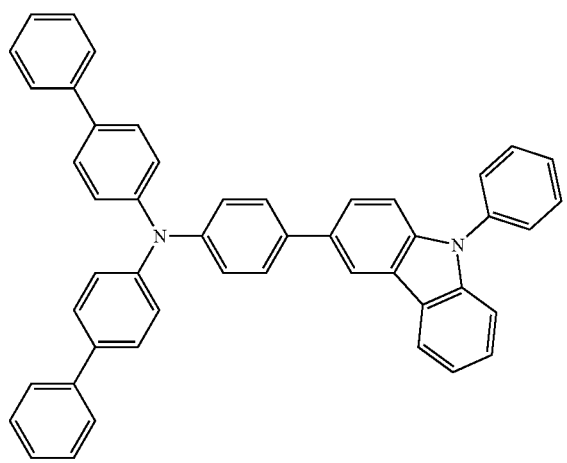
BH-2
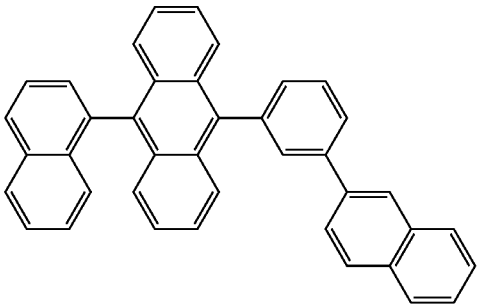
BD-2
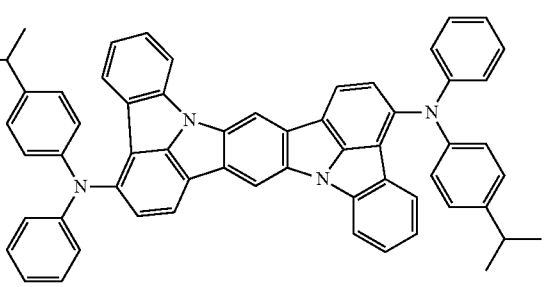

ET-1
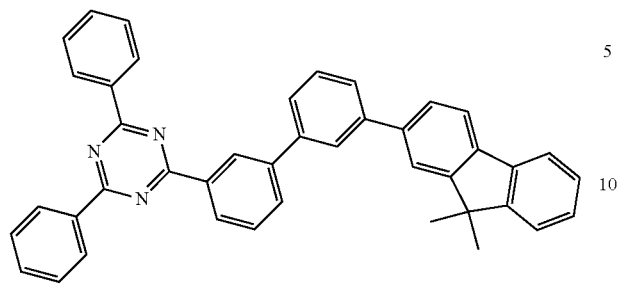
ET-3
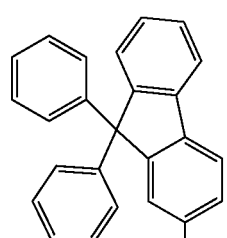
Liq
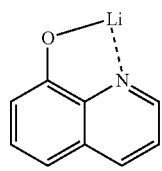
Inventive Compounds Used for Production of Organic EL Devices of Examples 14 to 19
Compound 3
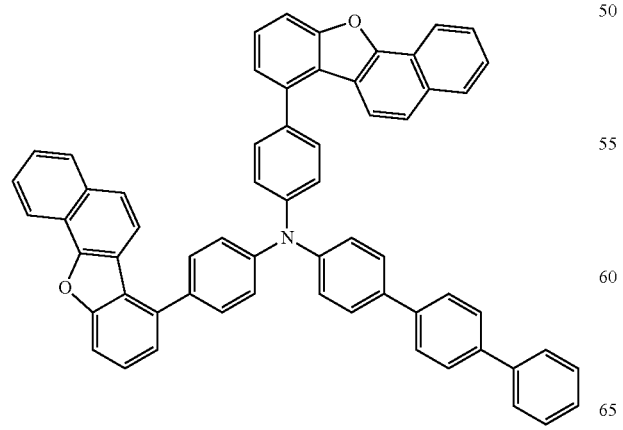
Compound 4
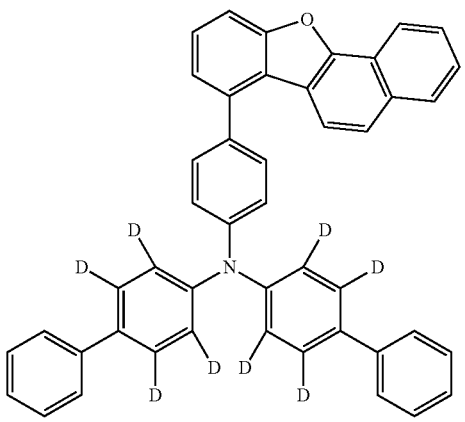
Compound 5
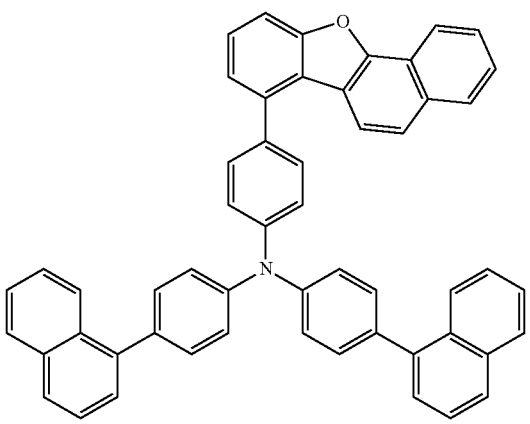
Compound 16
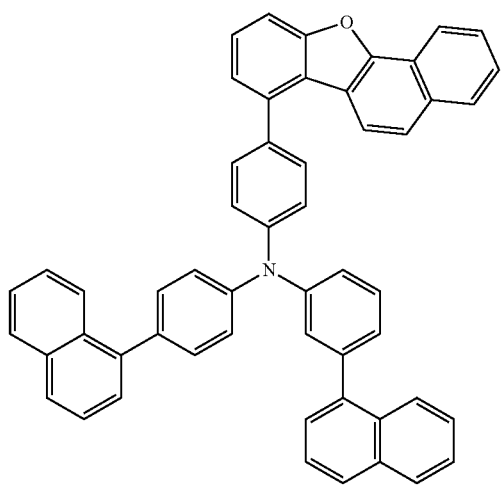

Compound 17
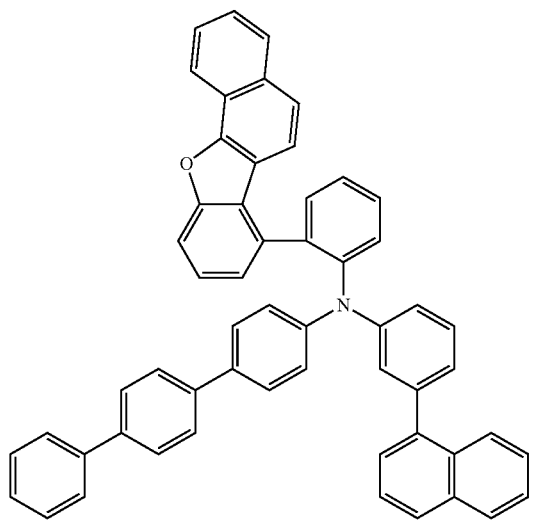
Compound 18
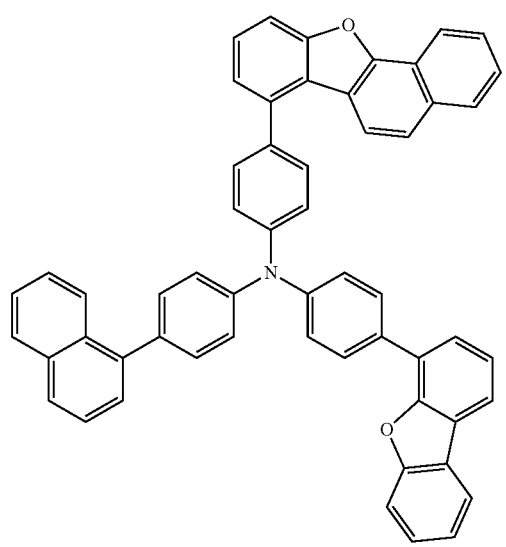
Comparative Compound Used for Production of Organic EL Device of Comparative Example 5
Comparative Compound 5
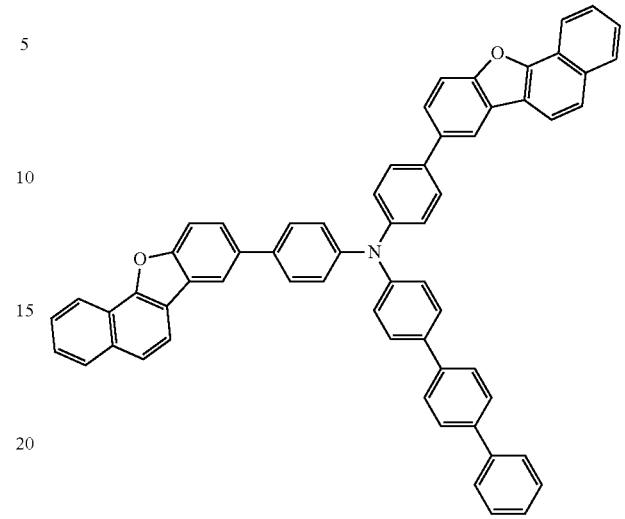
Other Compounds Used for Production of Organic EL Devices of Examples 14 to 19 and Comparative Example 5
HA
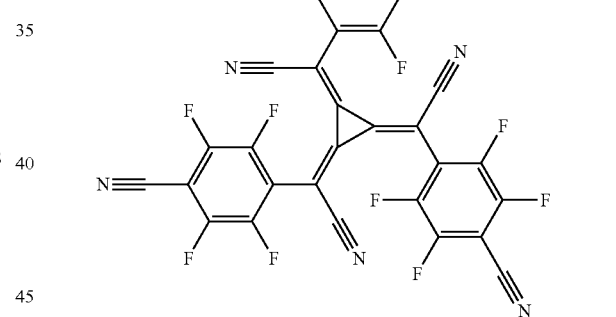
HT-3
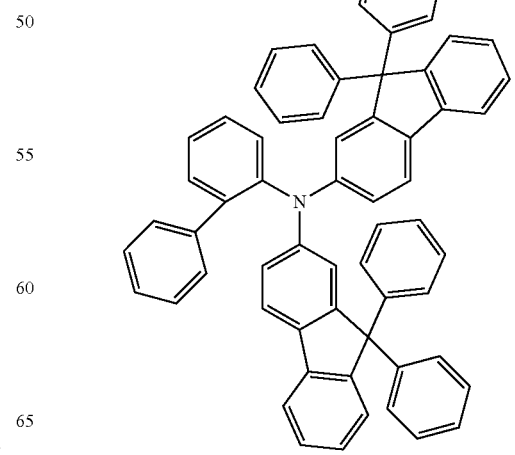

-continued

BH-1
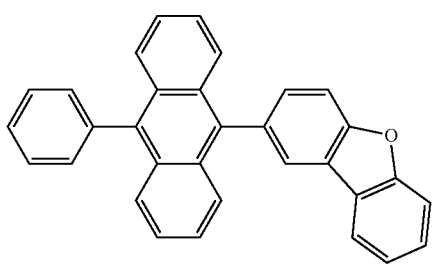

BD-1
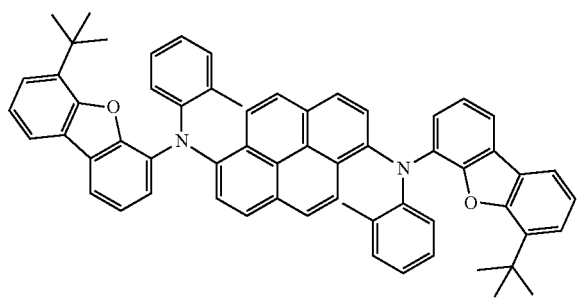

ET-1
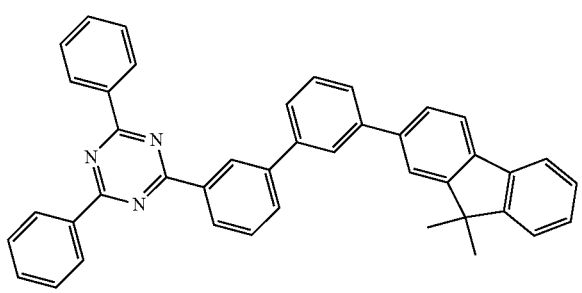

ET-2
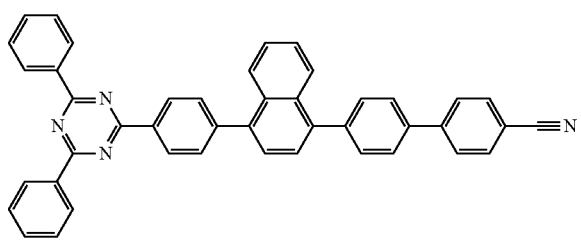

Liq
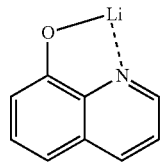

Production of Organic EL Device

Example 1

A glass substrate of 25 mm×75 mm×1.1 mm with an ITO transparent electrode (anode) (manufactured by GEO-MATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate with the transparent electrode was mounted on a substrate holder of a vacuum vapor deposition apparatus, and firstly Compound HT-1 and Compound HA were vapor co-deposited on the surface having the transparent electrode formed thereon so as to cover the transparent electrode, thus forming a hole injecting layer with a film thickness of 10 nm. The mass ratio of Compound HT-1 and Compound HA was 97:3.

Subsequently on the hole injecting layer, Compound HT-1 was vapor deposited to form a first hole transporting layer with a film thickness of 80 nm.

Subsequently on this first hole transporting layer, Compound 1 was vapor deposited to form a second hole transporting layer with a film thickness of 10 nm.

Subsequently on this second hole transporting layer, Compound BH-1 (host material) and Compound BD-1 (dopant material) were vapor co-deposited to form a light emitting layer with a film thickness of 25 nm. The mass ratio of Compound BH-1 and Compound BD-1 (BH-1:BD-1) was 96:4.

Subsequently on this light emitting layer, Compound ET-1 was vapor deposited to form a first electron transporting layer with a film thickness of 5 nm.

Subsequently on this first electron transporting layer, Compound ET-2 and Liq were vapor co-deposited to form a second electron transporting layer with a film thickness of 20 nm. The mass ratio of Compound ET-2 and Liq (ET-2:Liq) was 50:50.

Subsequently on this second electron transporting layer, LiF was vapor deposited to form an electron injecting electrode with a film thickness of 1 nm.

Then, on this electron injecting electrode, metal Al was vapor deposited to form a metal cathode with a film thickness of 50 nm.

The layer configuration of the organic EL device of Example 1 thus obtained was as follows.

$$ITO(130)/(HT\text{-}1{:}HA=97{:}3)(10)/HT\text{-}1(80)/Compound1$$
$$(10)/(BH\text{-}1{:}BD\text{-}1=96{:}4)(25)/ET\text{-}1(5)/(ET\text{-}2{:}$$
$$Liq=50{:}50)(20)/LiF(1)/Al \qquad (50)$$

In the layer configuration, the numerals in parentheses each indicate the film thickness (nm), and the ratios are each a mass ratio Measurement of Device Lifetime (LT95)

The resulting organic EL device was driven with direct current at a current density of 50 mA/cm², and the period of time until the luminance was reduced to 95% of the initial luminance was measured, and was defined as 95% lifetime (LT95). The result is shown in Table 1.

Examples 2 and Comparative Example 1

An organic EL device was produced in the same manner as in Example 1 except for changing the material of the second hole transporting layer to Compound 2 (Example 2) or Comparative Compound 1 (Comparative Example 1), and LT95 was measured. The results are shown in Table 1.

TABLE 1

|  | Material of second hole transporting layer | LT95 (h) at 50 mA/cm² |
|---|---|---|
| Example 1 | Compound 1 | 84 |
| Example 2 | Compound 2 | 77 |
| Comparative Example 1 | Comparative Compound 1 | 59 |

As apparent from the results in Table 1, the organic EL devices respectively containing the inventive compounds (compounds 1 and 2) have a longer lifetime than the organic EL device containing Comparative Compound 1.

Examples 3

A glass substrate of 25 mm×75 mm×1.1 mm with an ITO transparent electrode (anode) (manufactured by GEO-MATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate with the transparent electrode was mounted on a substrate holder of a vacuum vapor deposition apparatus, and firstly Compound HT-2 and Compound HA were vapor co-deposited on the surface having the transparent electrode formed thereon so as to cover the transparent electrode, thus forming a hole injecting layer with a film thickness of 10 nm. The mass ratio of Compound HT-2 and Compound HA (HT-2:Compound HA) was 97:3.

Subsequently on the hole injecting layer, Compound HT-2 was vapor deposited to form a first hole transporting layer with a film thickness of 75 nm.

Subsequently on this first hole transporting layer, Compound 6 was vapor deposited to form a second hole transporting layer with a film thickness of 10 nm.

Subsequently on this second hole transporting layer, Compound BH-2 (host material) and Compound BD-2 (dopant material) were vapor co-deposited to form a light emitting layer with a film thickness of 20 nm. The mass ratio of Compound BH-2 and Compound BD-2 (BH-2:BD-2) was 99:1.

Subsequently on this light emitting layer, Compound ET-1 was vapor deposited to form a first electron transporting layer with a film thickness of 5 nm.

Subsequently on this first electron transporting layer, Compound ET-3 and Liq were vapor co-deposited to form a second electron transporting layer with a film thickness of 25 nm. The mass ratio of Compound ET-3 and Liq (ET-3:Liq) was 50:50.

Subsequently on this second electron transporting layer, Yb was vapor deposited to form an electron injecting electrode with a film thickness of 1 nm.

Then, on this electron injecting electrode, metal Al was vapor deposited to form a metal cathode with a film thickness of 80 nm.

The layer configuration of the organic EL device of Example 1 thus obtained was as follows.

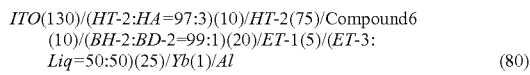
ITO(130)/(HT-2:HA=97:3)(10)/HT-2(75)/Compound6(10)/(BH-2:BD-2=99:1)(20)/ET-1(5)/(ET-3:Liq=50:50)(25)/Yb(1)/Al (80)

In the layer configuration, the numerals in parentheses each indicate the film thickness (nm), and the ratios are each a mass ratio.

LT95 of the resulting organic EL device was measured. The result is shown in Table 2.

Examples 4 to 13 and Comparative Examples 2 to 4

An organic EL device was produced in the same manner as in Example 3 except for changing the material of the second hole transporting layer to the compound shown in Table 2, and LT95 was measured in the same manner as in Example 1. The results are shown in Table 2.

TABLE 2

| | Material of second hole transporting layer | LT95 (h) at 50 mA/cm² |
|---|---|---|
| Example 3 | Compound 6 | 95 |
| Example 4 | Compound 7 | 97 |
| Example 5 | Compound 8 | 108 |
| Example 6 | Compound 9 | 105 |
| Example 7 | Compound 10 | 92 |
| Example 8 | Compound 11 | 119 |
| Example 9 | Compound 12 | 110 |
| Example 10 | Compound 13 | 94 |
| Example 11 | Compound 14 | 104 |
| Example 12 | Compound 15 | 90 |
| Example 13 | Compound 19 | 106 |
| Comparative Example 2 | Comparative Compound 2 | 78 |
| Comparative Example 3 | Comparative Compound 3 | 80 |
| Comparative Example 4 | Comparative Compound 4 | 63 |

As apparent from the results in Table 2, the organic EL devices containing the inventive compounds (compound 6 to 15 and 19) have a longer lifetime than the organic EL devices containing Comparative Compounds 2 to 4.

Example 14

A glass substrate of 25 mm×75 mm×1.1 mm with an ITO transparent electrode (anode) (manufactured by GEO-MATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with the transparent electrode was mounted on a substrate holder of a vacuum vapor deposition apparatus, and firstly Compound HT-3 and Compound HA were vapor co-deposited on the surface having the transparent electrode formed thereon so as to cover the transparent electrode, thus forming a hole injecting layer with a film thickness of 10 nm. The mass ratio of Compound HT-3 and Compound HA (HT-3:HA) was 97:3.

Subsequently on the hole injecting layer, Compound HT-3 was vapor deposited to form a first hole transporting layer with a film thickness of 80 nm.

Subsequently on this first hole transporting layer, Compound 3 was vapor deposited to form a second hole transporting layer with a film thickness of 10 nm.

Subsequently on this second hole transporting layer, Compound BH-1 (host material) and Compound BD-1 (dopant material) were vapor co-deposited to form a light emitting layer with a film thickness of 25 nm. The mass ratio of Compound BH-1 and Compound BD-1 (BH-1:BD-1) was 96:4.

Subsequently on this light emitting layer, Compound ET-1 was vapor deposited to form a first electron transporting layer with a film thickness of 5 nm.

Subsequently on this first electron transporting layer, Compound ET-3 and Liq were vapor co-deposited to form a second electron transporting layer with a film thickness of 20 nm. The mass ratio of Compound ET-3 and Liq (ET-3:Liq) was 50:50.

Subsequently on this second electron transporting layer, LiF was vapor deposited to form an electron injecting electrode with a film thickness of 1 nm.

Then, on this electron injecting electrode, metal Al was vapor deposited to form a metal cathode with a film thickness of 50 nm.

The layer configuration of the organic EL device of Example 1 thus obtained was as follows.

ITO(130)/(HT-3:HA=97:3)(10)/HT-3(80)/Compound3 (10)/(BH-1:BD-1=96:4)(25)/ET-1(5)/(ET-3: Liq=50:50)(20)/LiF(1)/Al     (5)

In the layer configuration, the numerals in parentheses each indicate the film thickness (nm), and the ratios are each a mass ratio.

LT95 of the resulting organic EL device was measured. The result is shown in Table 2.

Examples 15 to 19 and Comparative Example 5

An organic EL device was produced in the same manner as in Example 14 except for changing the material of the second hole transporting layer to the compound shown in Table 3, and LT95 was measured in the same manner as in Example 1. The results are shown in Table 3.

TABLE 3

|  | Material of second hole transporting layer | LT95 (h) at 50 mA/cm$^2$ |
| --- | --- | --- |
| Example 14 | Compound 3 | 78 |
| Example 15 | Compound 4 | 103 |
| Example 16 | Compound 5 | 88 |
| Example 17 | Compound 16 | 81 |
| Example 18 | Compound 17 | 90 |
| Example 19 | Compound 18 | 84 |
| Comparative Example 5 | Comparative Compound 5 | 65 |

As apparent from the results in Table 3, the organic EL devices respectively containing the inventive compounds (compounds 3 to 5 and 16 to 18) have a longer lifetime than the organic EL device containing Comparative Compound 5.

Compounds 1 to 19 Synthesized in Synthetic Examples 1 to 19

Compound 1

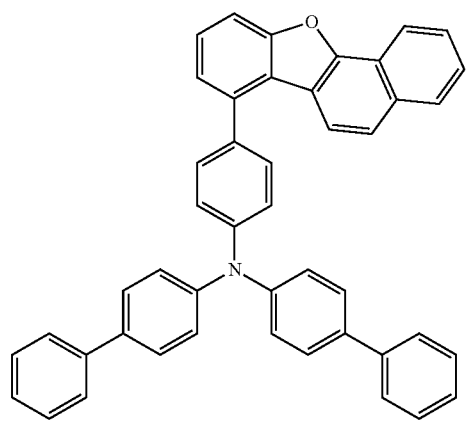

Compound 2

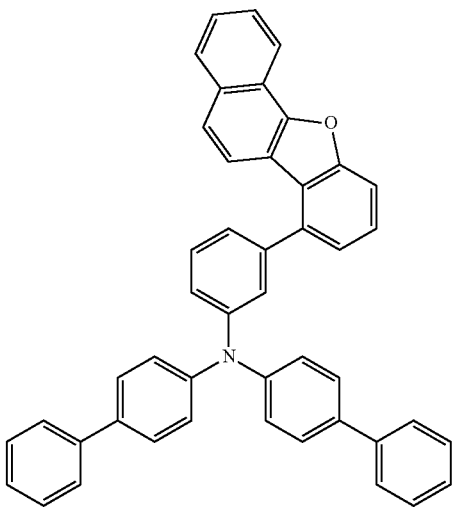

Compound 3

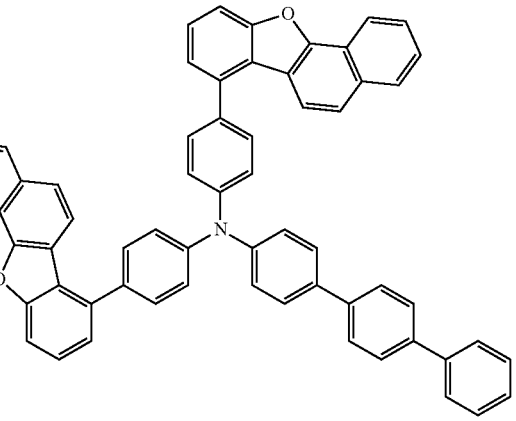

Compound 4

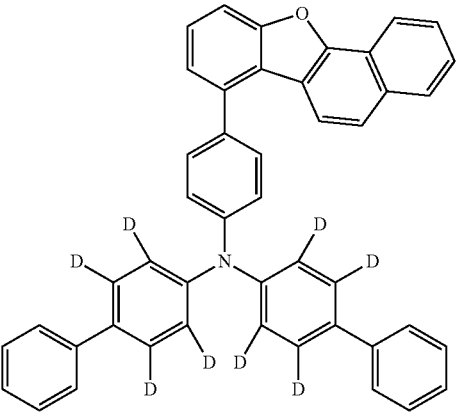

Compound 5
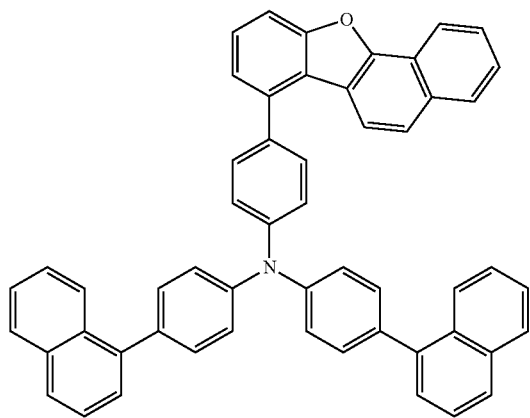
Compound 6
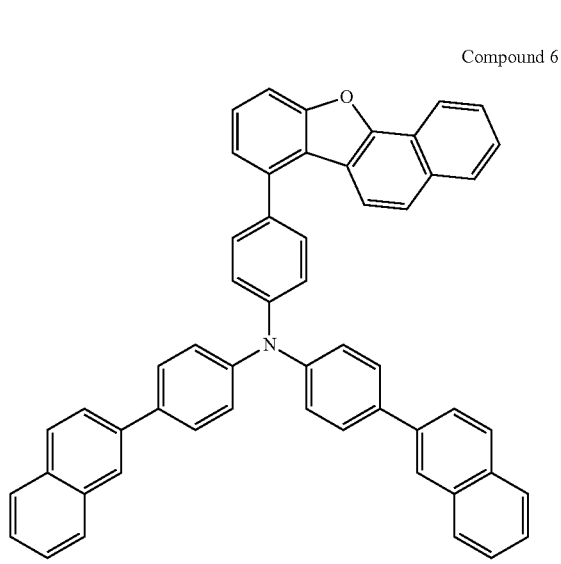
Compound 7
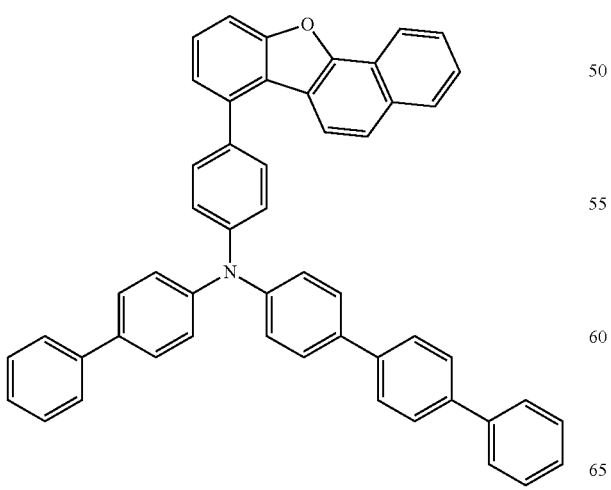
Compound 8
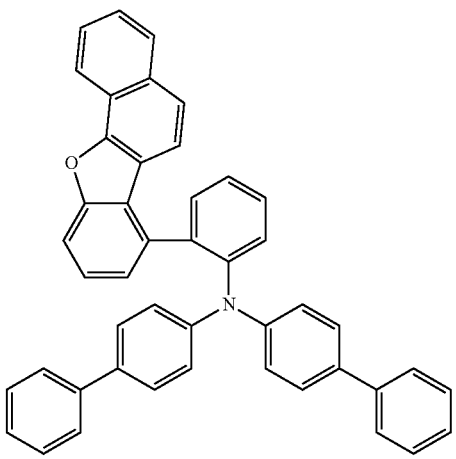
Compound 9
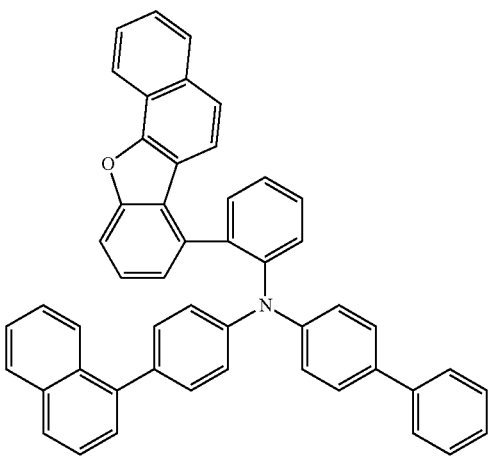
Compound 10
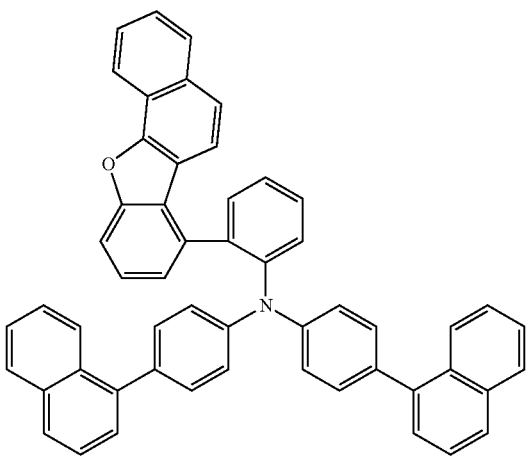

Compound 11
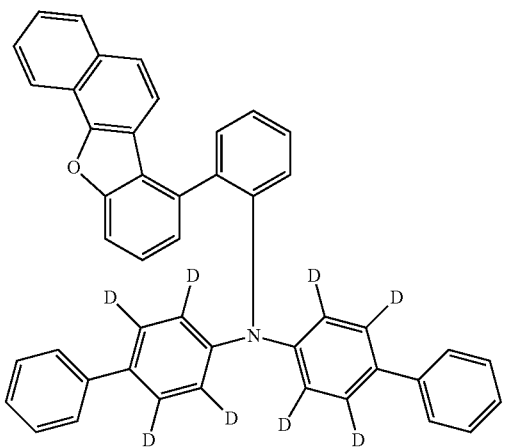
Compound 12
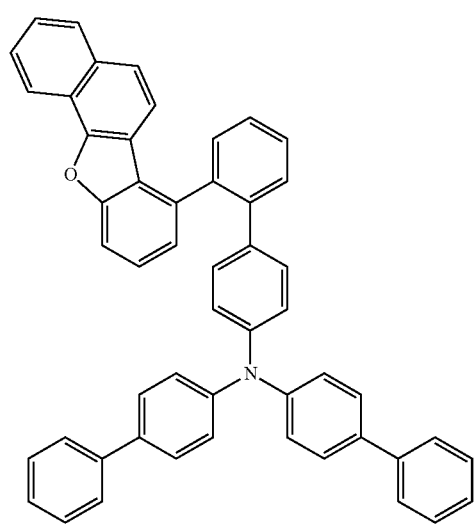
Compound 13
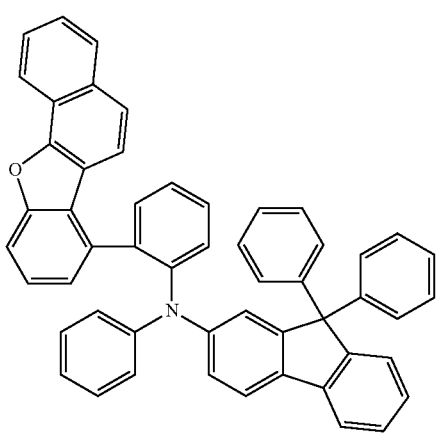
Compound 14
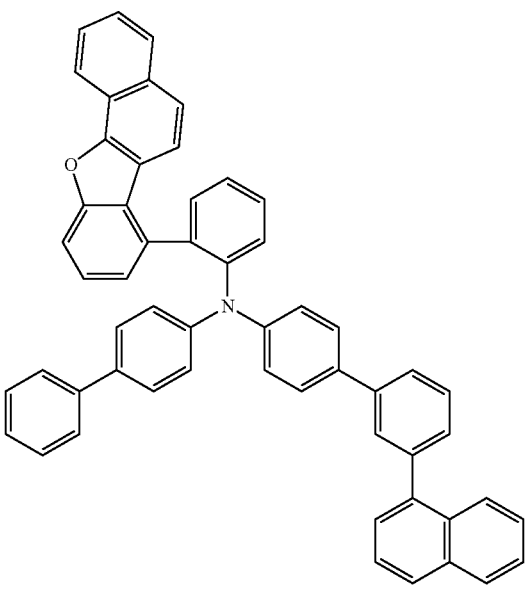
Compound 15
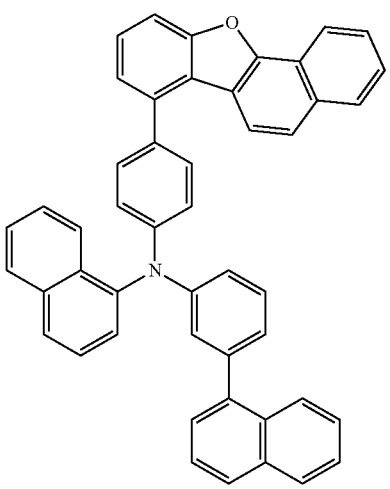
Compound 16
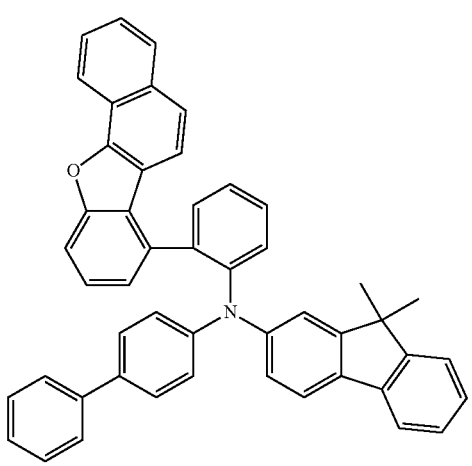

-continued
Compound 17
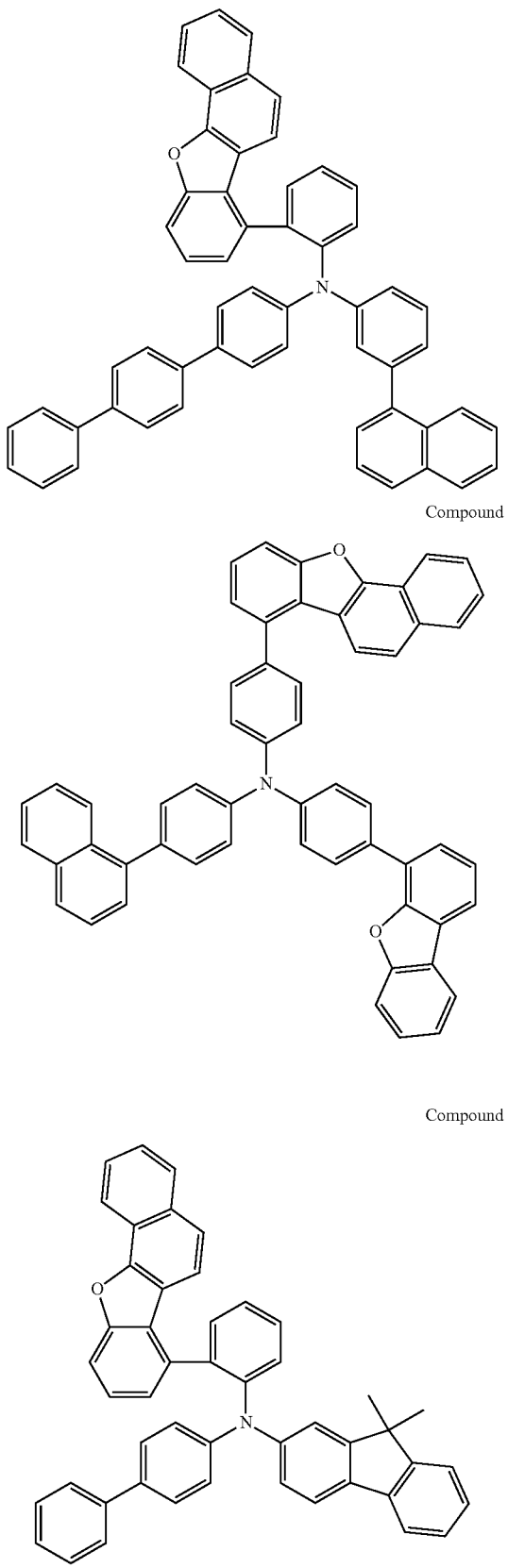
Compound 18
Compound 19
Intermediate Synthetic Example 1: Synthesis of Intermediate A
[Chem. 393]
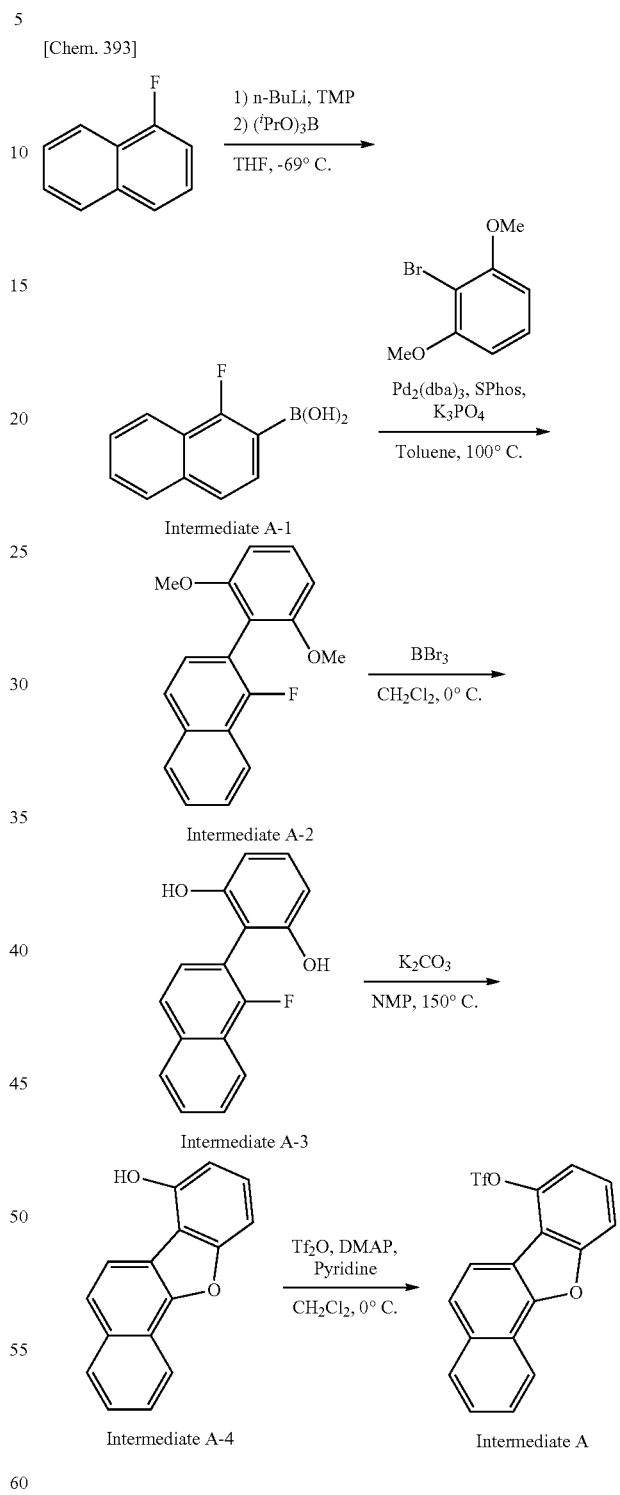
(1) Synthesis of Intermediate A-1
In an argon atmosphere, 7.2 g of 2,2,6,6-tetramethylpiperidine and 60 mL of tetrahydrofuran (dehydrated) were put in a flask, and were cooled to −43° C. To the flask, 33 mL of n-BuLi (1.55 M in hexane) was added, and the mixture was then stirred at −40° C. for 30 minutes. Next, the mixture was cooled to −69° C., and 16.0 mL of ($^i$PrO)$_3$B was added. After stirring at −78° C. for 5 minutes, 20 mL of a solution of 5.00 g of 1-fluoronaphthalene in THF was added dropwise, and the mixture was stirred in an ice bath for 10 hours. After completion of the reaction, 1N HCl aq. (100 mL) was added, and the mixture was stirred at room temperature for 1 hour. Then, the reaction mixture was transferred into a separating funnel, and was extracted with ethyl acetate. This solution was dried over anhydrous magnesium sulfate, then was concentrated and washed with hexane to obtain 6.13 g (yield 71%) of a white solid of (1-fluoronaphthalen-2-yl) boronic acid (Intermediate A-1).

(2) Synthesis of Intermediate A-2

In an argon atmosphere, 4.52 g of (1-fluoronaphthalen-2-yl)boronic acid (Intermediate A-1), 4.30 g of 2-bromo-1,3-dimethoxybenzene, 0.91 g of tris(dibenzylideneacetone)dipalladium(0), 0.81 g of 2-dicyclohexylphosphino-2',6'-dimethoxybiphenyl (SPhos), 12.6 g of tripotassium phosphate, and 10 mL of toluene (dehydrated) were put in a flask, and were heated under reflux with stirring for 7 hours. After cooling to room temperature, the reaction solution was extracted with toluene, the aqueous layer was removed, and then the organic layer was washed with saturated saline solution. The organic layer was dried over anhydrous sodium sulfate and was then concentrated. The residue was purified by silica gel chromatography to obtain 4.70 g (yield 84%) of 2-(2,6-dimethoxyphenyl)-1-fluoronaphthalene (Intermediate A-2).

(3) Synthesis of Intermediate A-3

In an argon atmosphere, 4.70 g of 2-(2,6-dimethoxyphenyl)-1-fluoronaphthalene (Intermediate A-2) and 210 mL of dichloromethane (dehydrated) were put in a flask and were cooled to 0° C. To the flask, 41 mL of a 1.0 mol/l boron tribromide dichloromethane solution was added, and then the mixture was stirred at room temperature for 4 hours. After completion of the reaction, the solution was cooled to −78° C., was carefully deactivated with methanol, and was further deactivated with a sufficient amount of water. The solution was transferred into a separating funnel, was extracted with dichloromethane, and was dried over anhydrous sodium sulfate. Then, the solution was allowed to pass through a silica gel short column to remove origin impurities, and the solution was concentrated. The resulting sample was dried in vacuum at room temperature for 3 hours to obtain 4.00 g (94%) of a transparent oily substance of 2-(3-fluoronaphthalen-2-yl)benzene-1,3-diol (Intermediate A-3).

(4) Synthesis of Intermediate A-4

In an argon atmosphere, 4.00 g of 2-(3-fluoronaphthalen-2-yl)benzene-1,3-diol (Intermediate A-3), 15 mL of N-methyl-2-pyrrolidinone (dehydrated), and 3.26 g of K$_2$CO$_3$ were put in a flask, and were then stirred at 150° C. for 2 hours. After completion of the reaction, the solution was cooled to room temperature, ethyl acetate (200 mL) was added, and the mixture was transferred into a separating funnel and was washed with water. The solution was dried over anhydrous sodium sulfate and was then purified by silica gel chromatography to obtain 1.25 g (yield 34%) of a white solid of naphtho[1,2-b]benzofuran-7-ol (Intermediate A-4).

(5) Synthesis of Intermediate 5

In an argon atmosphere, 1.25 g naphtho[1,2-b]benzofuran-7-ol (Intermediate A-4), 65 mg of N,N-dimethyl-4-aminopyridine, 1.08 mL of trifluoromethane sulfonic anhydride, and 27 mL of dichloromethane (dehydrated) were put in a flask and were cooled to 0° C. 10.6 mL of pyridine (dehydrated) was added dropwise, and then the mixture was stirred at room temperature for 2 hours. After completion of the reaction, the reaction mixture was deactivated with a sufficient amount of water. The solution was transferred into a separating funnel, was extracted with dichloromethane, and was dried over anhydrous sodium sulfate. Then, the solution was allowed to pass through a silica gel short column to remove origin impurities and the solution was concentrated. The resulting sample was dried in vacuum at room temperature for 3 hours to obtain 1.50 g (77%) of a white solid of naphtho[1,2-b]benzofuran-7-yl trifluoromethane sulfonate (Intermediate A).

Intermediate Synthetic Example 2: Synthesis of Intermediate B

[Chem. 394]

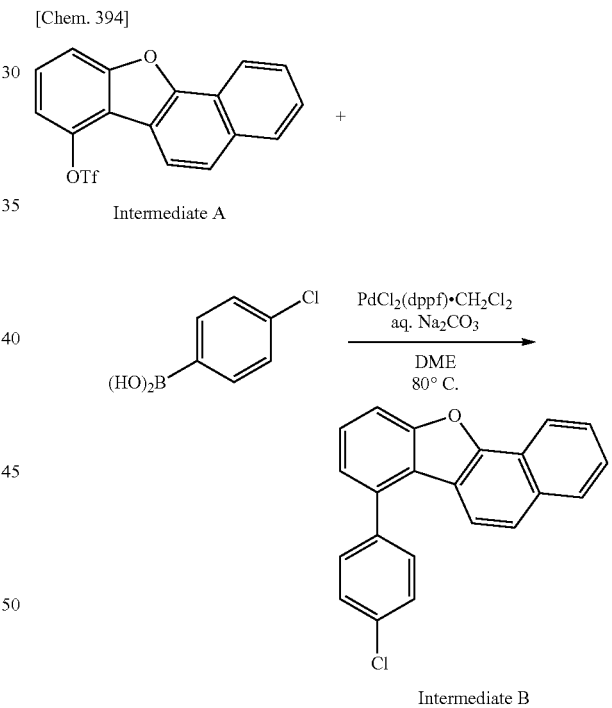

In an argon atmosphere, a mixture of 7.33 g (20.0 mmol) of Intermediate A, 3.75 g (24.0 mmol) of 4-chlorophenylboronic acid, 0.327 g (0.400 mmol) of [1,1'-bis(diphenylphosphino)ferrocene]palladium(II) dichloride dichloromethane additive, 20 mL (40.0 mmol) of 2 M aqueous sodium carbonate solution, and 66.7 mL of DME was stirred at 80° C. for 2 hours. The reaction solution was cooled to room temperature. Water was added thereto, followed by filtration. The resulting residue was purified by silica gel chromatography and recrystallization to obtain 6.07 g of a white solid. The yield was 92%.

Intermediate Synthetic Example 3: Synthesis of Intermediate C

[Chem. 395]

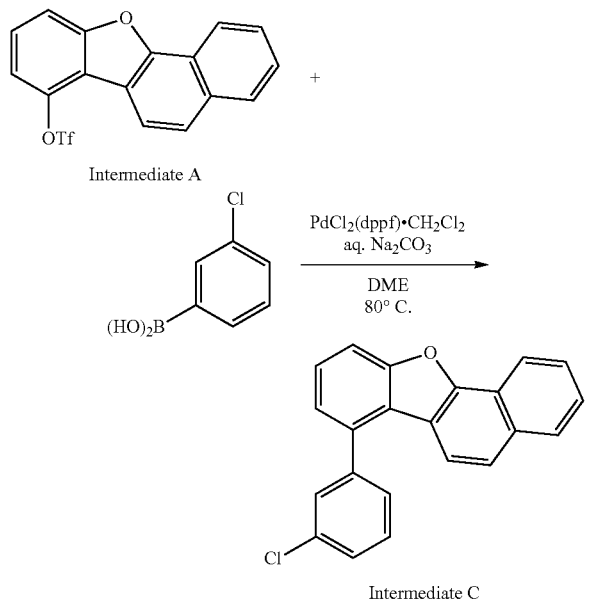

A white solid was obtained in the same manner as in Intermediate Synthetic Example 2 except for using 3-chlorophenylboronic acid instead of 4-chlorophenylboronic acid. The yield was 94%.

Intermediate Synthetic Example 4: Synthesis of Intermediate D

[Chem. 396]

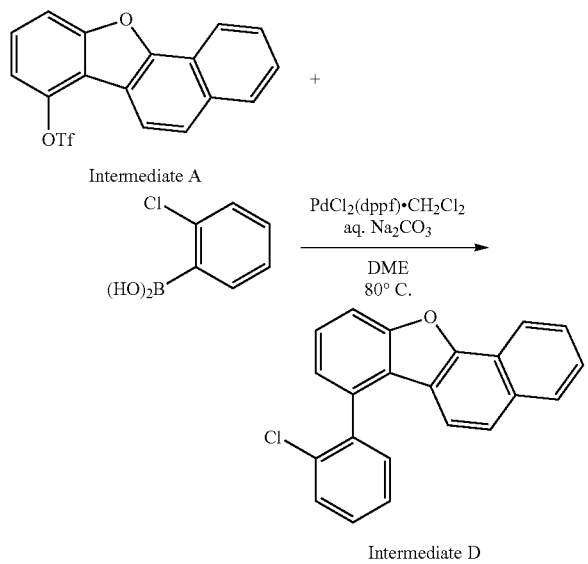

A white solid was obtained in the same manner as in Intermediate Synthetic Example 2 except for using 2-chlorophenylboronic acid instead of 4-chlorophenylboronic acid. The yield was 90%.

Intermediate Synthetic Example 5: Synthesis of Intermediate E

[Chem. 397]

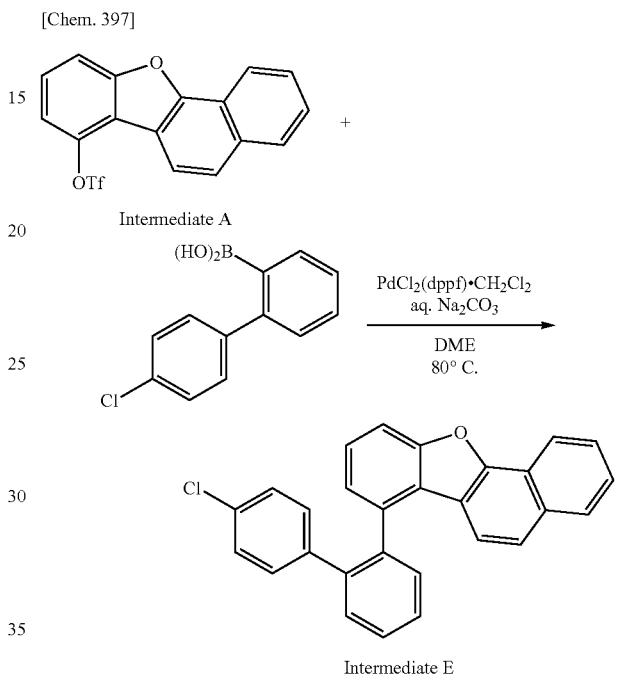

A white solid was obtained in the same manner as in Intermediate Synthetic Example 2 except for using (4'-chloro[1,1'-biphenyl]-2-yl)boronic acid instead of 4-chlorophenylboronic acid. The yield was 77%.

Intermediate Synthetic Example 6: Synthesis of Intermediate F

[Chem. 398]

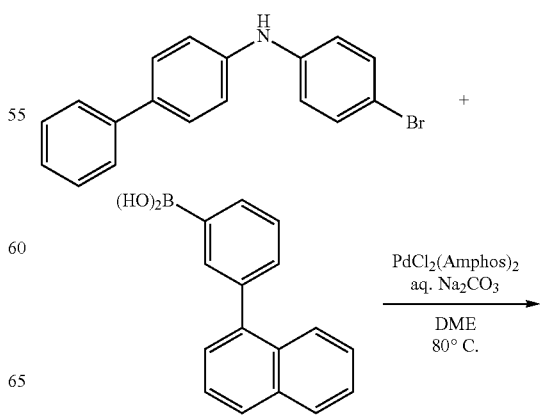

-continued

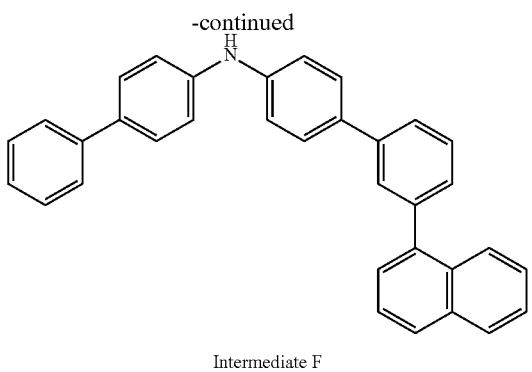

Intermediate F

In an argon atmosphere, a mixture of 9.73 g (30.0 mmol) of N-(4-bromophenyl)[1,1'-biphenyl]-4-amine, 8.19 g (33.0 mmol) of (3-(naphthalen-1-yl)phenyl)boronic acid, 0.425 g (0.60 mmol) of bis[di-tert-butyl(4-dimethylaminophenyl)phosphine]dichloropalladium(II), 30 mL (60.0 mmol) of 2 M aqueous sodium carbonate solution, and 150 mL of DME was stirred with heat at 80° C. for 4 hours. The reaction solution was cooled to room temperature, and then was concentrated under reduced pressure. The resulting residue was purified by silica gel chromatography to obtain 8.06 g of a white solid. The yield was 60%.

Intermediate Synthetic Example 7: Synthesis of Intermediate G

[Chem. 399]

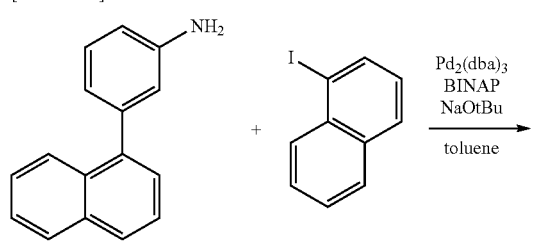

Intermediate G

In an argon atmosphere, a mixture of 5.68 g (25.9 mmol) of 3-(1-naphthalenyl)benzene amine, 6.58 g (25.9 mmol) of 1-iodonaphthalene, 0.474 g (0.518 mmol) of tris(dibenzylideneacetone)dipalladium(0), 0.645 g (1.04 mmol) of BINAP, 2.74 g (28.5 mmol) of sodium-t-butoxide, and 130 mL of toluene was stirred at 100° C. for 7 hours. The reaction solution was cooled to room temperature, and was then concentrated under reduced pressure. The resulting residue was purified by silica gel chromatography to obtain 8.95 g of a white solid. The yield was 84%.

Intermediate Synthetic Example 8: Synthesis of Intermediate H

[Chem. 400]

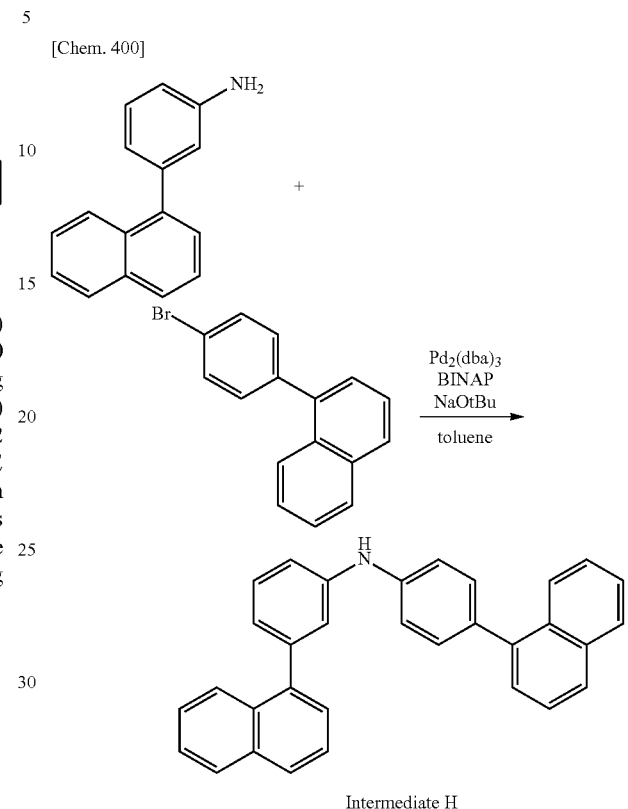

Intermediate H

A white solid was obtained in the same manner as in the Synthesis of Intermediate G except for using 1-(4-bromophenyl)naphthalene instead of 1-iodonaphthalene. The yield was 79%.

Synthetic Example 1: Synthesis of Compound 1

[Chem. 401]

1185

-continued

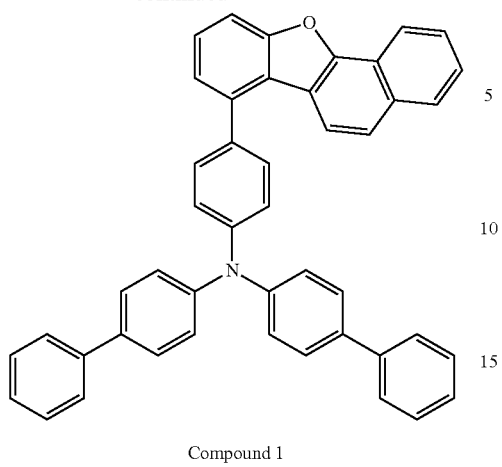

Compound 1

In an argon atmosphere, a mixture of 2.25 g (7.00 mmol) of N-[1,1'-biphenyl]-4-yl-[1,1'-biphenyl]-4-amine, 2.53 g (7.70 mmol) of Intermediate B, 0.128 g (0.140 mmol) of tris(dibenzylideneacetone)dipalladium(0), 0.162 g (0.56 mmol) of tri-t-butylphosphonium tetrafluoroborate, 0.942 g (9.80 mmol) of sodium-t-butoxide, and 70 mL of xylene was stirred at 110° C. for 2 hours. The reaction solution was cooled to room temperature, and was then concentrated under reduced pressure. The resulting residue was purified by silica gel chromatography and recrystallization to obtain 3.51 g of a white solid. The yield was 82%.

The resulting substance was revealed as Compound 1 by mass spectrometry, showing m/e=614 with respect to the molecular weight of 613.76.

Synthetic Example 2: Synthesis of Compound 2

[Chem. 402]

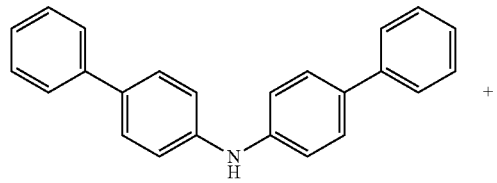

+

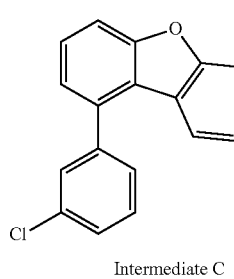

Intermediate C

1186

-continued

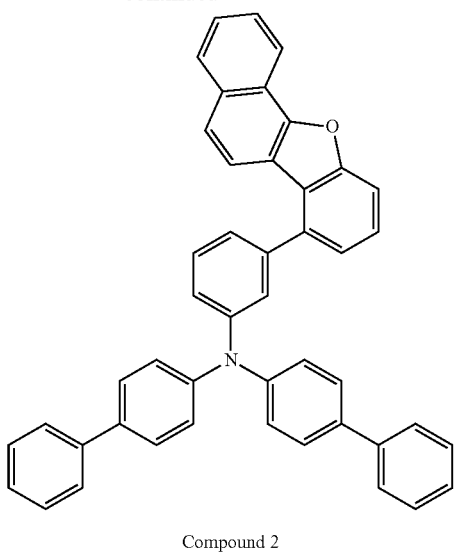

Compound 2

A white solid was obtained in the same manner as in Synthetic Example 1 except for using Intermediate C instead of Intermediate B. The yield was 92%.

The resulting substance was revealed as Compound 2 by mass spectrometry, showing m/e=614 with respect to the molecular weight of 613.76.

Synthetic Example 3: Synthesis of Compound 3

[Chem. 403]

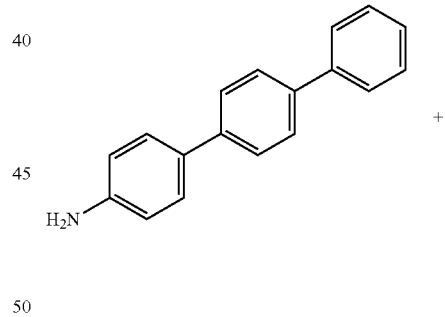

+

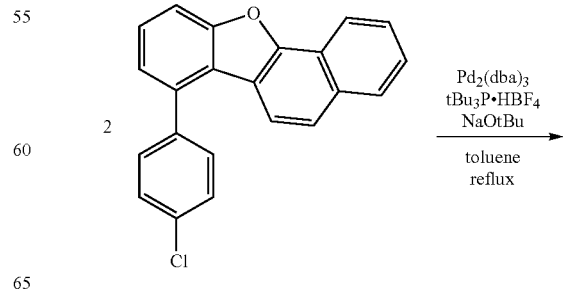

Intermediate B

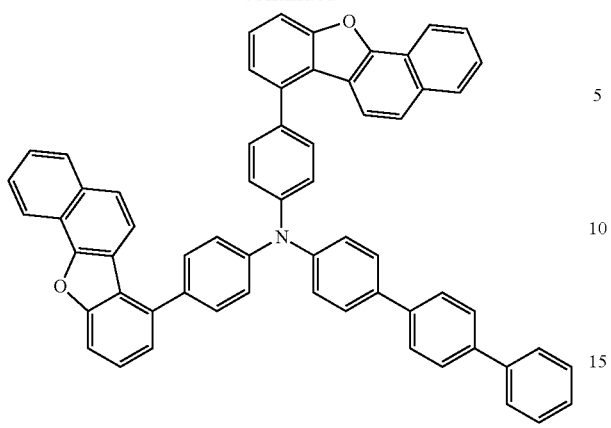

Compound 3

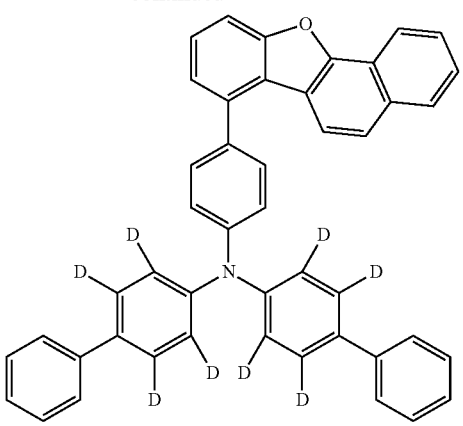

Compound 4

In an argon atmosphere, a mixture of 0.986 g (4.02 mmol) of [1,1':4',1''-terphenyl]-4-amine, 2.91 g (8.85 mmol) of Intermediate B, 0.110 g (0.121 mmol) of tris(dibenzylideneacetone)dipalladium(0), 0.140 g (0.482 mmol) of tri-t-butylphosphonium tetrafluoroborate, 1.08 g (11.3 mmol) of sodium-t-butoxide, and 80 mL of toluene was stirred under reflux at the boiling point for 2 hours. The reaction solution was cooled to room temperature, and was then concentrated under reduced pressure. The resulting residue was purified by recrystallization to obtain 2.35 g of a white solid. The yield was 70%.

The resulting substance was revealed as Compound 3 by mass spectrometry, showing m/e=830 with respect to the molecular weight of 830.00.

Synthetic Example 4: Synthesis of Compound 4

[Chem. 404]

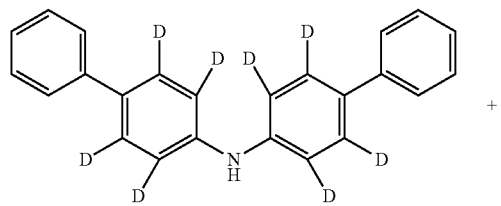

+

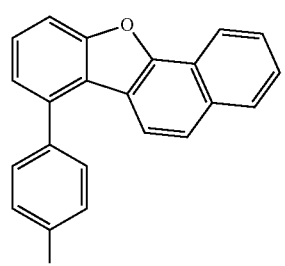

Intermediate B

Pd$_2$(dba)$_3$
tBu$_3$P•HBF$_4$
NaOtBu xylene
110° C.

⟶

A white solid was obtained in the same manner as in Synthetic Example 1 except for using N-([1,1'-biphenyl]-4-yl-2,3,5,6-d4)-[1,1'-biphenyl-2,3,5,6-d4]-4-amine instead of N-[1,1'-biphenyl]-4-yl-[1,1'-biphenyl]-4-amine. The yield was 81%.

The resulting substance was revealed as Compound 4 by mass spectrometry, showing m/e=622 with respect to the molecular weight of 621.81.

Synthetic Example 5: Synthesis of Compound 5

[Chem. 405]

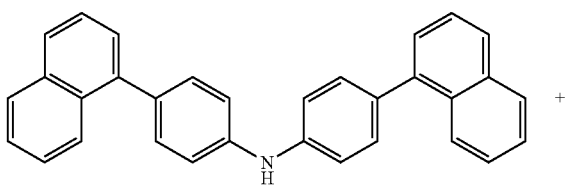

+

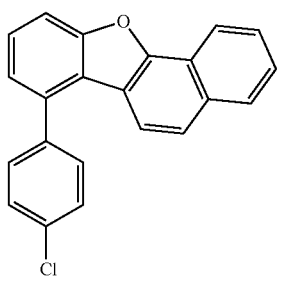

Intermediate B

Pd$_2$(dba)$_3$
tBu$_3$P•HBF$_4$
NaOtBu xylene
130° C.

⟶

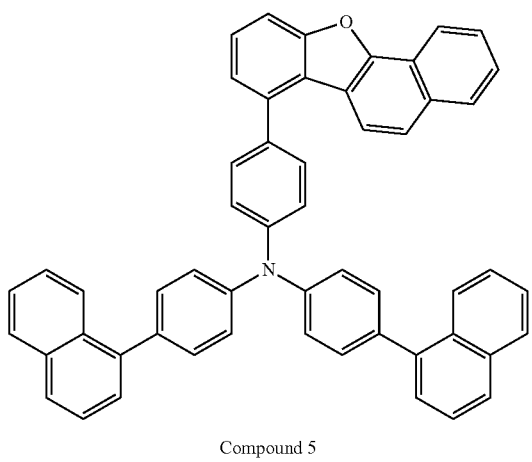

Compound 5

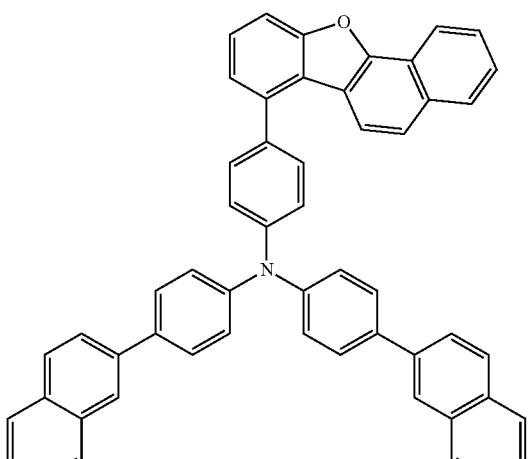

Compound 6

A white solid was obtained in the same manner as in Synthetic Example 1 except for using 4-(1-naphthalenyl)-N-[4-(1-naphthalenyl)phenyl]benzene amine instead of N-[1,1'-biphenyl]-4-yl-[1,1'-biphenyl]-4-amine and changing the reaction temperature to 130° C. The yield was 61%.

The resulting substance was revealed as Compound 5 by mass spectrometry, showing m/e=714 with respect to the molecular weight of 713.88.

Synthetic Example 6: Synthesis of Compound 6

[Chem. 406]

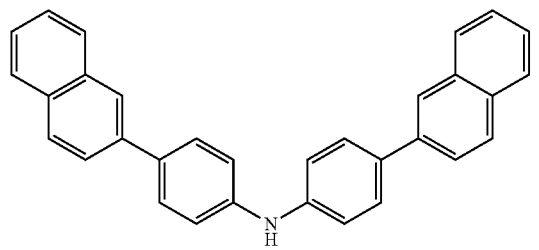

A white solid was obtained in the same manner as in Synthetic Example 1 except for using 4-(2-naphthalenyl)-N-[4-(2-naphthalenyl)phenyl]benzene amine instead of N-[1,1'-biphenyl]-4-yl-[1,1'-biphenyl]-4-amine and changing the reaction temperature to 120° C. The yield was 61%.

The resulting substance was revealed as Compound 6 by mass spectrometry, showing m/e=714 with respect to the molecular weight of 713.88.

Synthetic Example 7: Synthesis of Compound 7

[Chem. 407]

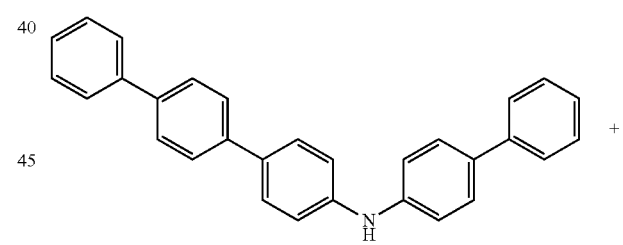

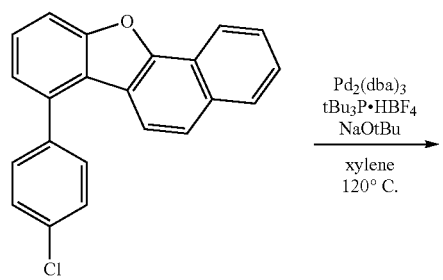

Intermediate B

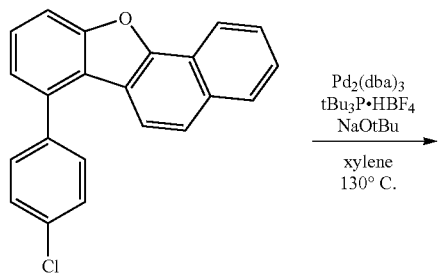

Intermediate B

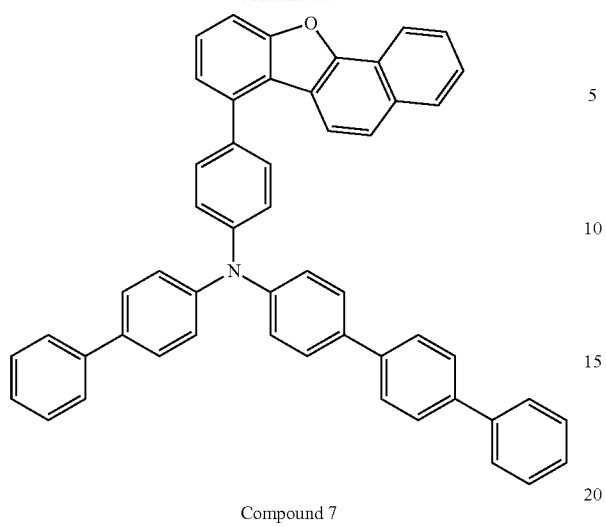

Compound 7

A white solid was obtained in the same manner as in Synthetic Example 1 except for using N-[1,1'-biphenyl]-4-yl-[1,1':4',1''-terphenyl]-4-amine instead of N-[1,1'-biphenyl]-4-yl-[1,1'-biphenyl]-4-amine and changing the reaction temperature to 130° C. The yield was 63%.

The resulting substance was revealed as Compound 7 by mass spectrometry, showing m/e=690 with respect to the molecular weight of 689.86.

Synthetic Example 8: Synthesis of Compound 8

[Chem. 408]

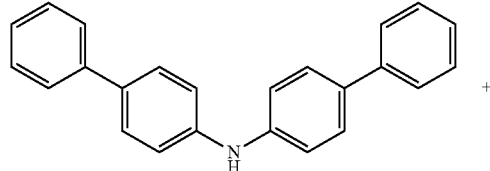

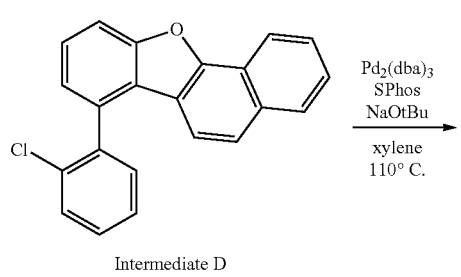

Intermediate D

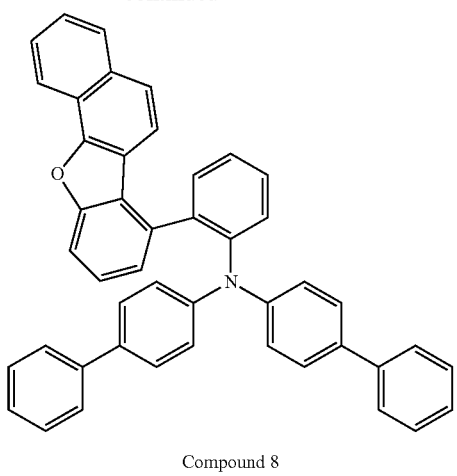

Compound 8

A white solid was obtained in the same manner as in Synthetic Example except for using Intermediate D instead of Intermediate B and using SPhos instead of tri-t-butylphosphonium tetrafluoroborate. The yield was 83%.

The resulting substance was revealed as Compound 8 by mass spectrometry, showing m/e=614 with respect to the molecular weight of 613.76.

Synthetic Example 9: Synthesis of Compound 9

[Chem. 409]

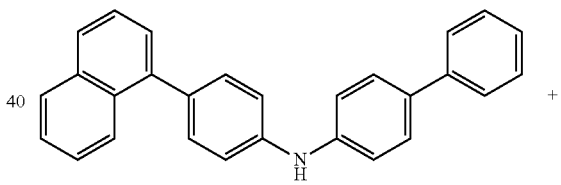

+

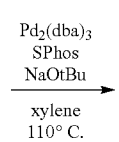

Intermediate D

1193

-continued

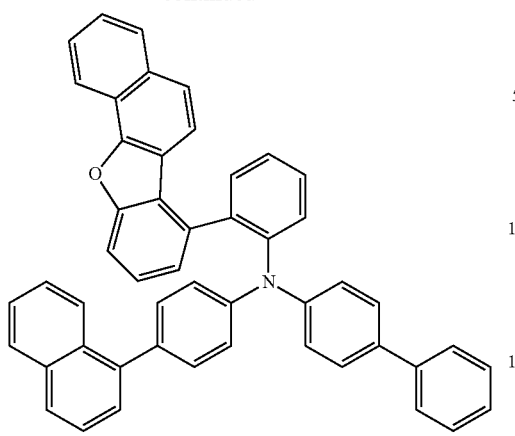

Compound 9

A white solid was obtained in the same manner as in Synthetic Example 8 except for using N-[4-(1-naphthalenyl)phenyl][1,1'-biphenyl]-4-amine instead of N-[1,1'-biphenyl]-4-yl-[1,1'-biphenyl]-4-amine. The yield was 89%.

The resulting substance was revealed as Compound 9 by mass spectrometry, showing m/e=664 with respect to the molecular weight of 663.82.

Synthetic Example 10: Synthesis of Compound 10

[Chem. 410]

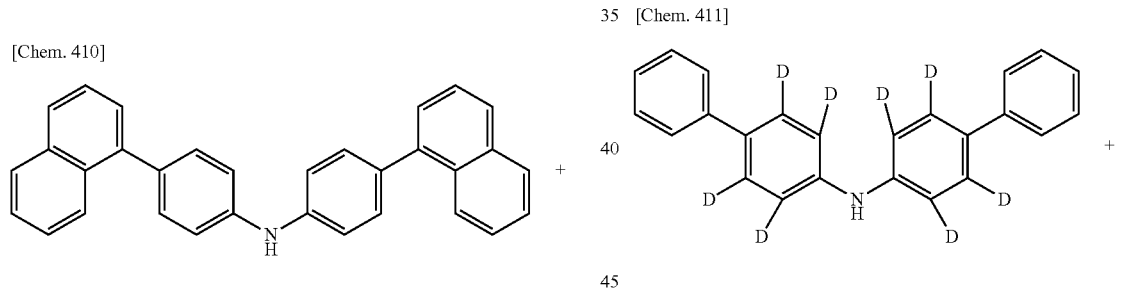

1194

-continued

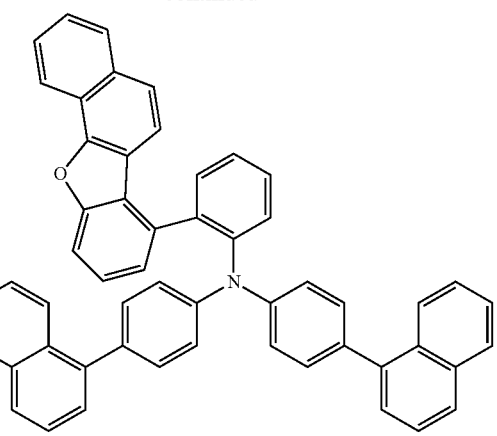

Compound 10

A white solid was obtained in the same manner as in Synthetic Example 8 except for using 4-(1-naphthalenyl)-N-[4-(1-naphthalenyl)phenyl]benzene amine instead of N-[1,1'-biphenyl]-4-yl-[1,1'-biphenyl]-4-amine. The yield was 64%. The resulting substance was revealed as Compound 10 by mass spectrometry, showing m/e=714 with respect to the molecular weight of 713.88.

Synthetic Example 11: Synthesis of Compound 11

[Chem. 411]

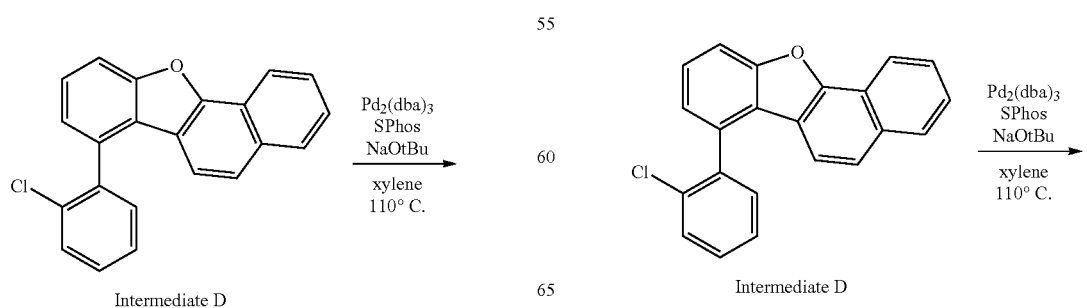

1195
-continued

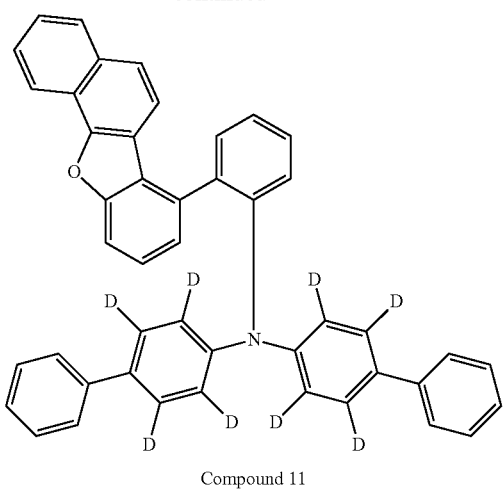
Compound 11

A white solid was obtained in the same manner as in Synthetic Example 8 except for using N-([1,1'-biphenyl]-4-yl-2,3,5,6-d4)-[1,1'-biphenyl-2,3,5,6-d4]-4-amine instead of N-[1,1'-biphenyl]-4-yl-[1,1'-biphenyl]-4-amine. The yield was 71%. The resulting substance was revealed as Compound 11 by mass spectrometry, showing m/e=622 with respect to the molecular weight of 621.81.

Synthetic Example 12: Synthesis of Compound 12

[Chem. 412]

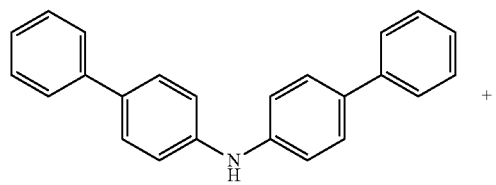
+

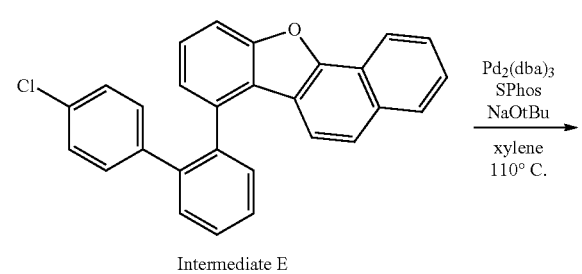
Intermediate E

1196
-continued

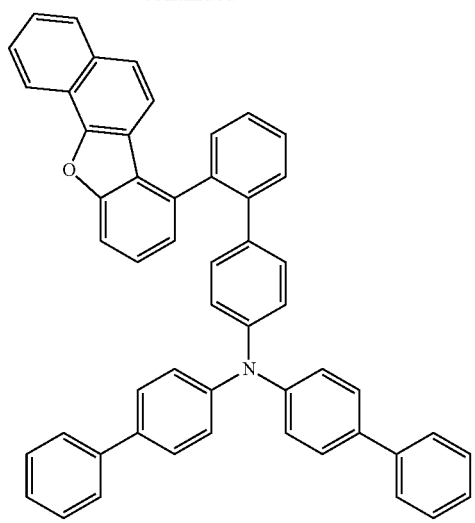
Compound 12

A white solid was obtained in the same manner as in Synthetic Example 8 except for using Intermediate E instead of Intermediate D. The yield was 91%.

The resulting substance was revealed as Compound 12 by mass spectrometry, showing m/e=690 with respect to the molecular weight of 689.86.

Synthetic Example 13: Synthesis of Compound 13

[Chem. 413]

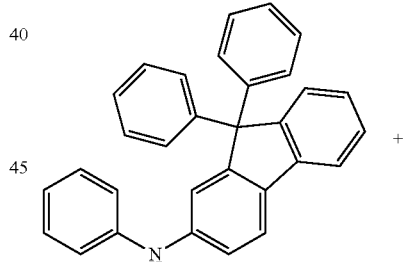
+

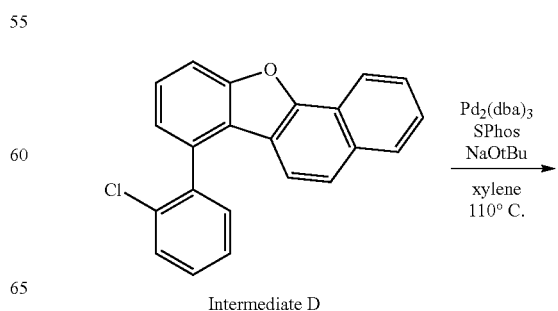
Intermediate D

-continued

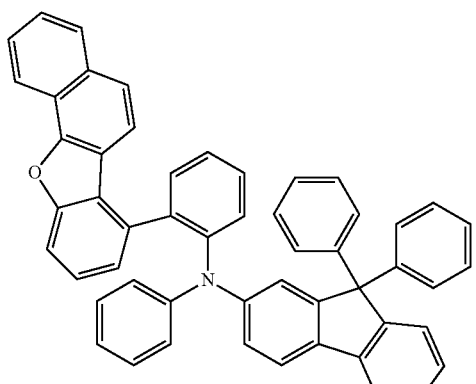

Compound 13

A white solid was obtained in the same manner as in Synthetic Example 8 except for using N,9,9-triphenyl-9H-fluoren-2-amine instead of N-[1,1'-biphenyl]-4-yl-[1,1'-biphenyl]-4-amine. The yield was 47%. The resulting substance was revealed as Compound 13 by mass spectrometry, showing m/e=702 with respect to the molecular weight of 701.87.

Synthetic Example 14: Synthesis of Compound 14

[Chem. 414]

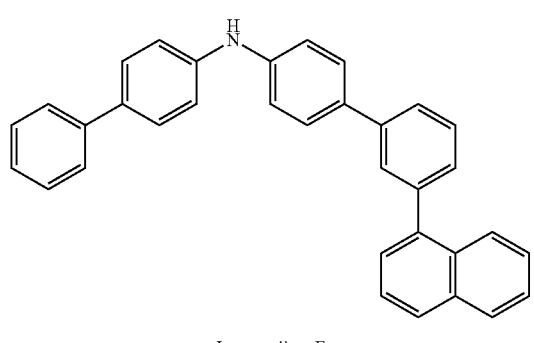

Intermediate F

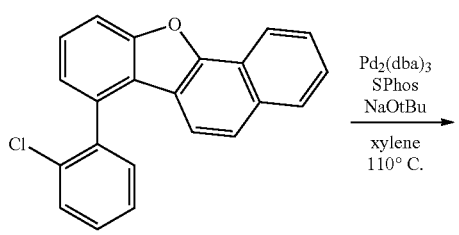

Intermediate D

-continued

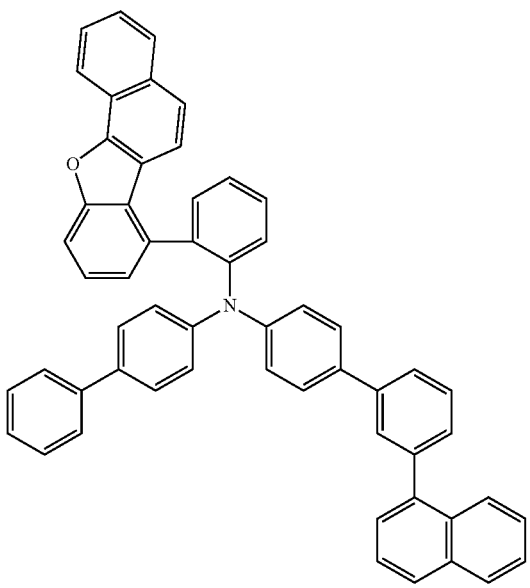

Compound 14

A white solid was obtained in the same manner as in Synthetic Example 8 except for using Intermediate F instead of N-[1,1'-biphenyl]-4-yl-[1,1'-biphenyl]-4-amine. The yield was 75%.

The resulting substance was revealed as Compound 14 by mass spectrometry, showing m/e=740 with respect to the molecular weight of 739.92.

Synthetic Example 15: Synthesis of Compound 15

[Chem. 415]

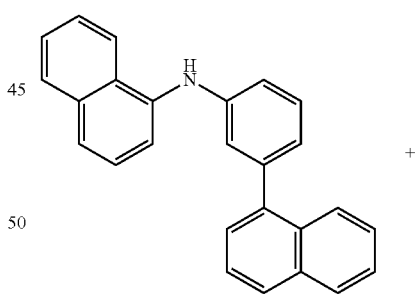

Intermediate G

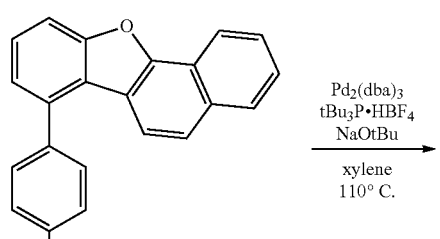

Intermediate B

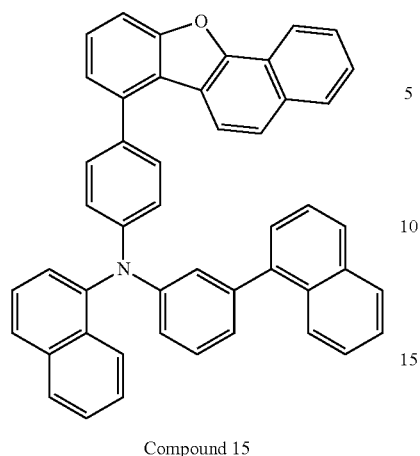

Compound 15

A white solid was obtained in the same manner as in Synthetic Example 1 except for using Intermediate G instead of N-[1,1'-biphenyl]-4-yl-[1,1'-biphenyl]-4-amine. The yield was 68%.

The resulting substance was revealed as Compound 15 by mass spectrometry, showing m/e=638 with respect to the molecular weight of 637.78.

Synthetic Example 16: Synthesis of Compound 16

[Chem. 416]

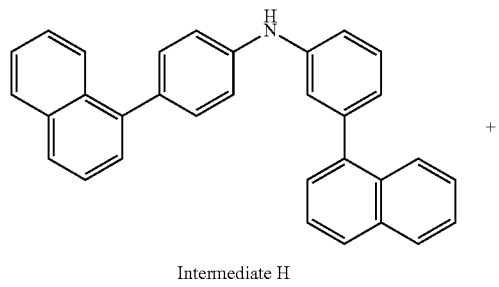

Intermediate H

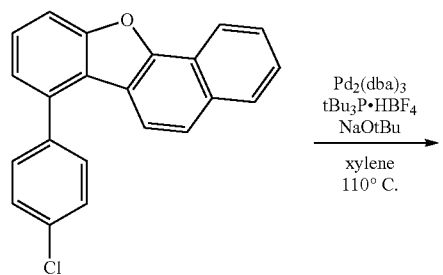

Intermediate B

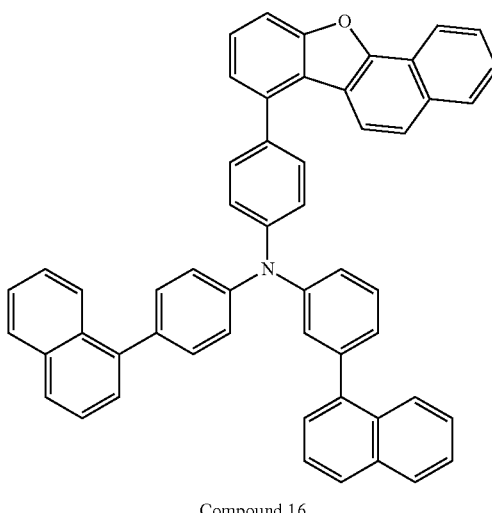

Compound 16

A white solid was obtained in the same manner as in Synthetic Example 1 except for using Intermediate H instead of N-[1,1'-biphenyl]-4-yl-[1,1'-biphenyl]-4-amine. The yield was 62%.

The resulting substance was revealed as Compound 16 by mass spectrometry, showing m/e=714 with respect to the molecular weight of 713.88.

Synthetic Example 17: Synthesis of Compound 17

[Chem. 417]

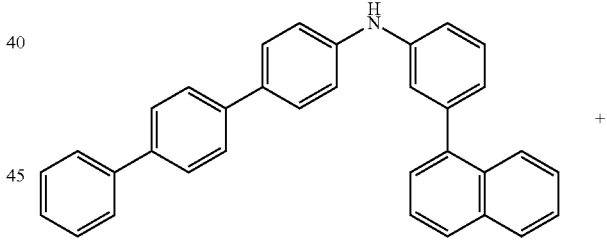

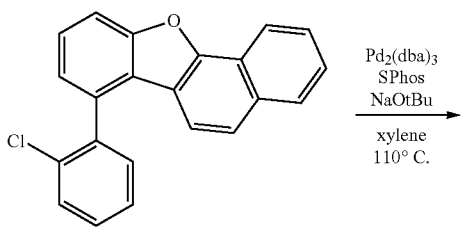

Intermediate D

1201
-continued

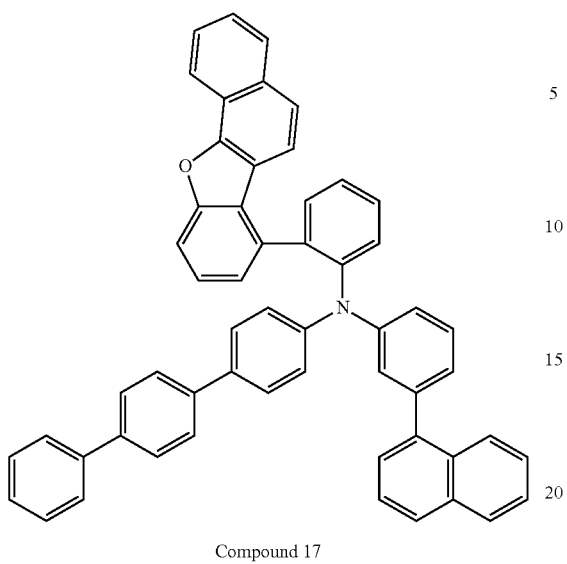

Compound 17

A white solid was obtained in the same manner as in Synthetic Example 8 except for using N-[3-(1-naphthalenyl)phenyl][1,1':4',1"-terphenyl]-4-amine instead of N-[1,1'-biphenyl]-4-yl-[1,1'-biphenyl]-4-amine. The yield was 75%.

The resulting substance was revealed as Compound 17 by mass spectrometry, showing m/e=740 with respect to the molecular weight of 739.92.

Synthetic Example 18: Synthesis of Compound 18

[Chem. 418]

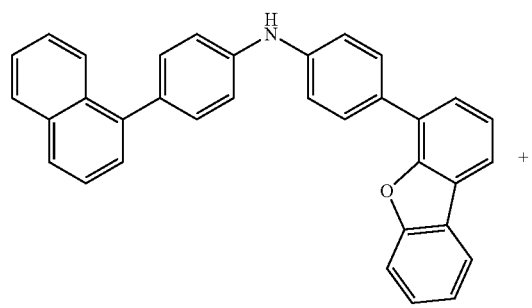

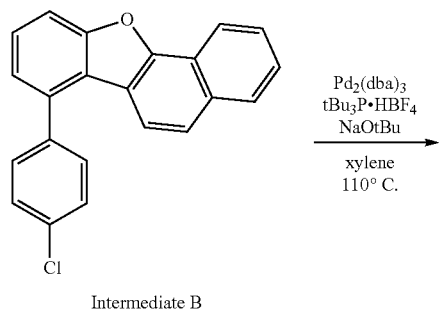

Intermediate B

1202
-continued

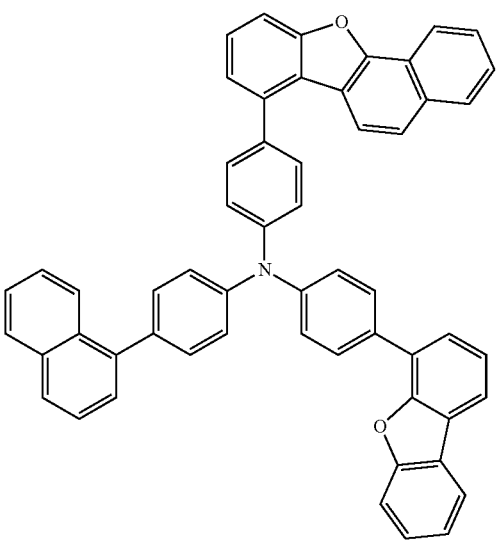

Compound 18

A white solid was obtained in the same manner as in Synthetic Example 1 except for using 4-(4-dibenzofuranyl)-N-[4-(1-naphthalenyl)phenyl]benzene amine instead of N-[1,1'-biphenyl]-4-yl-[1,1'-biphenyl]-4-amine. The yield was 66%.

The resulting substance was revealed as Compound 16 by mass spectrometry, showing m/e=754 with respect to the molecular weight of 753.90.

Synthetic Example 19: Synthesis of Compound 19

[Chem. 419]

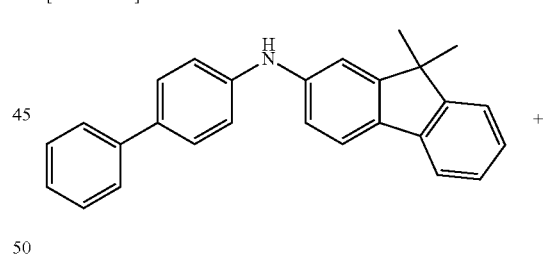

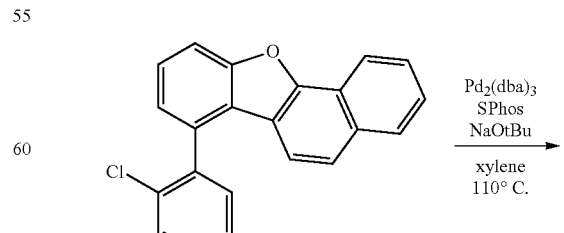

Intermediate D

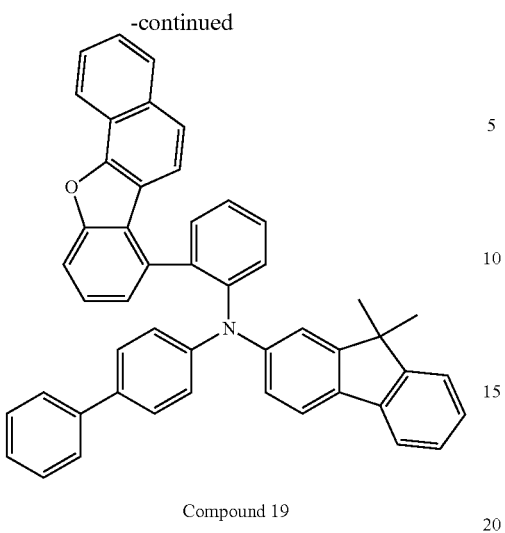

Compound 19

A white solid was obtained in the same manner as in Synthetic Example 8 except for using N-[1,1'-biphenyl]-4-yl-9,9-dimethyl-9H-fluoren-2-amine instead of N-[1,1'-biphenyl]-4-yl-[1,1'-biphenyl]-4-amine. The yield was 61%.

The resulting substance was Compound 19 by mass spectrometry, showing m/e=654 with respect to the molecular weight of 653.83.

REFERENCE SIGNS LIST

1, 11: Organic EL device
2: Substrate
3: Anode
4: Cathode
5: Light emitting layer
6: Hole transporting zone (hole transporting layer)
6a: Hole injecting layer
6b: First hole transporting layer
6c: Second hole transporting layer
7: Electron transporting zone (Electron transporting layer)
7a: First electron transporting layer
7b: Second electron transporting layer
10, 20: Light emitting unit

The invention claimed is:
1. A compound represented by the following formula (1):

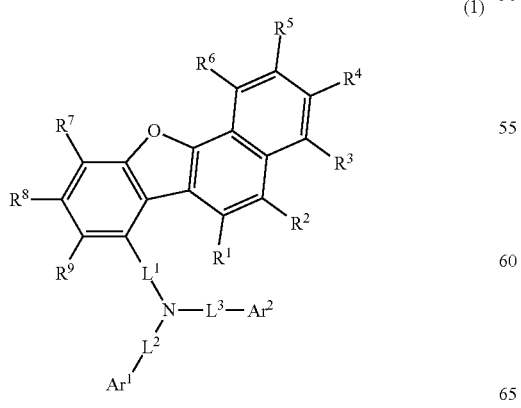

(1)

wherein
$R^1$ to $R^9$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, or a substituted or unsubstituted heterocyclic group having 5 to 50 ring atoms,
provided that adjacent two selected from $R^1$ to $R^9$ are not bonded to each other, thus forming no ring structure,
$L^1$ is an arylene group represented by the following formula (TEMP-43) or (TEMP-44);

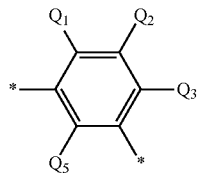

(TEMP-43)

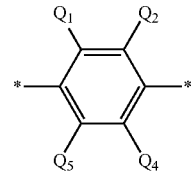

(TEMP-44)

wherein
each * represents a bonding site to the carbon atom or the central nitrogen atom, and
$Q_1$ to $Q_5$ are each independently a hydrogen atom, a substituted or unsubstituted alkyl group having 1 to 6 carbon atoms, a substituted or unsubstituted aryl group having 6 to 18 ring carbon atoms, or a substituted or unsubstituted heterocyclic group having 5 to 18 ring atoms,
combinations of adjacent two selected from $Q_1$ to $Q_5$ may or may not each independently be bonded to each other to form a substituted or unsubstituted ring structure, and
$L^2$ and $L^3$ are each independently a single bond, a substituted or unsubstituted divalent heterocyclic group having 5 to 30 ring atoms, or a group represented by any of the following formulae (i) to (iii):

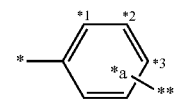

(i)

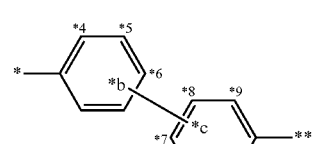

(ii)

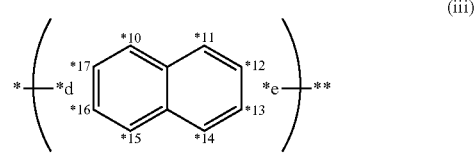

(iii)

wherein
*a is bonded to one selected from the carbon atoms *1 to *3,
*b is bonded to one selected from the carbon atoms *4 to *6,
*c is bonded to one selected from the carbon atoms *7 to *9,
*d is bonded to one selected from the carbon atoms *10 to *17, *e is bonded to another one selected from the carbon atoms *10 to *17,
* represents a bonding site to the central nitrogen atom, and
** represents a bonding site to $Ar^1$ or $Ar^2$,
$Ar^1$ and $Ar^2$ are each independently a group represented by any of the following formulae (a) to (e):

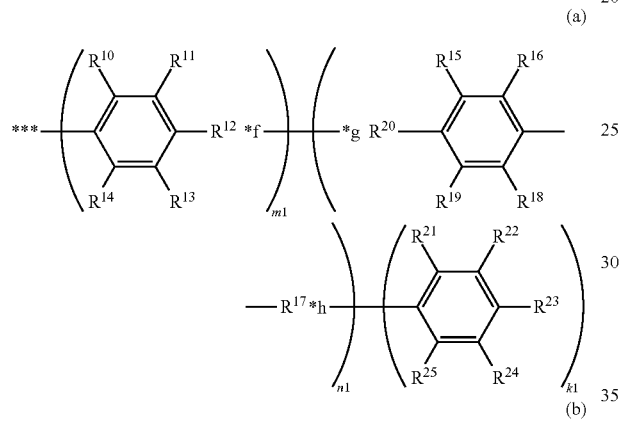

(a)

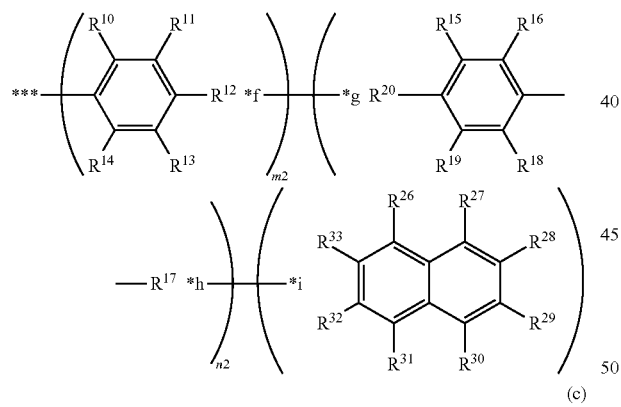

(b)

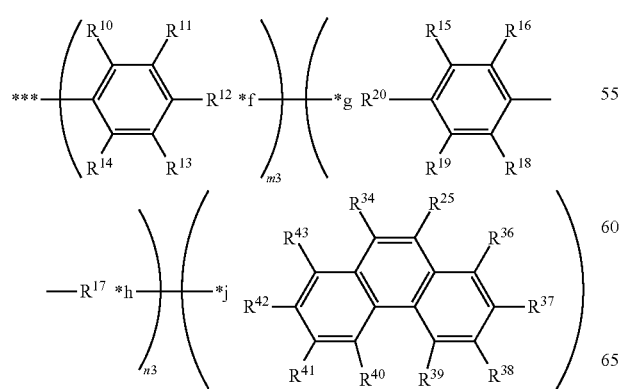

(c)

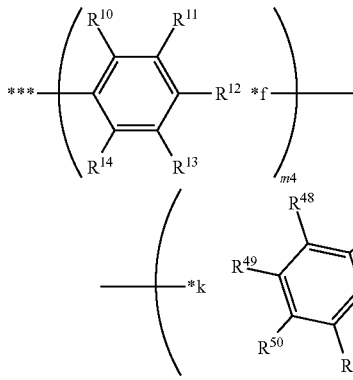

(d)

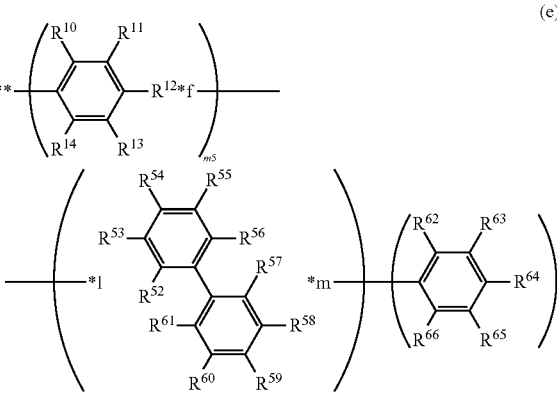

(e)

in the formula (a),
$R^{10}$ to $R^{25}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms,
provided that
one selected from $R^{10}$ to $R^{14}$ is a single bond bonded to *f,
one selected from $R^{15}$ to $R^{20}$ is a single bond bonded to *g, another one selected from $R^{15}$ to $R^{20}$ is a single bond bonded to *h,
*** represents a bonding site to $L^2$ or $L^3$,
m1 is 0 or 1, n1 is 0 or 1,
when m1 is 0 and n1 is 0, *h is bonded to $L^2$ or $L^3$,
when m1 is 0 and n1 is 1, *f is bonded to $L^2$ or $L^3$,
when m1 is 1 and n1 is 0, one selected from $R^{10}$ to $R^{14}$ is a single bond bonded to *h,
k1 is 1 or 2, and
adjacent two selected from $R^{10}$ to $R^{14}$ at are not the single bond are, and adjacent two selected from $R^{15}$ to $R^{20}$ that are not either of the single bonds are, not bonded to each other, thus forming no ring structure;
in the formula (b),
$R^{10}$ to $R^{20}$, *f *g, *h, and *** are the same as described above,
$R^{26}$ to $R^{33}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, provided that one selected from $R^{26}$ to $R^{33}$ is a single bond bonded to *i, m2 is 0 or 1, n2 is 0 or 1, when m2 is 0 and n2 is 0, *h is bonded to $L^2$ or $L^3$, when m2 is 0 and n2 is 1, *f is bonded to $L^2$ or $L^3$, when m2 is 1 and n2 is 0, one selected from $R^{10}$ to $R^{14}$ is a single bond bonded to *h, and adjacent two selected from $R^{10}$ to $R^{14}$ that are not the single bond are, and adjacent two selected from $R^{15}$ to $R^{20}$ that are not either of the single bonds are, not bonded to each other, thus forming no ring structure;

in the formula (c), $R^{10}$ to $R^{20}$, *f, *g, *h, and *** are the same as described above, $R^{34}$ to $R^{43}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, provided that one selected from $R^{34}$ to $R^{43}$ is a single bond bonded to *j, m3 is 0 or 1, n3 is 0 or 1, when m3 is 0 and n3 is 0, *h is bonded to $L^2$ or $L^3$, when m3 is 0 and n3 is 1, *f is bonded to $L^2$ or $L^3$, when m3 is 1 and n2 is 0, one selected from $R^{10}$ to $R^{14}$ is a single bond bonded to *h, and adjacent two selected from $R^{10}$ to $R^{14}$ that are not the single bond are, adjacent two selected from $R^{15}$ to $R^{20}$ that are not either of the single bonds are, and $R^{34}$ and $R^{35}$ are, not bonded to each other, thus forming no ring structure;

in the formula (d), $R^{10}$ to $R^{14}$, *f, and *** are the same as described above, $R^{44}$ to $R^{51}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, X is an oxygen atom, a sulfur atom, $CR^aR^b$, or $NR^c$, $R^a$, $R^b$, and $R^c$ are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms, provided that one selected from $R^{44}$ to $R^{51}$ and $R^c$ is a single bond bonded to *k, m4 is 0 or 1, when m4 is 0, *f is bonded to $L^2$ or $L^3$, combinations of adjacent two selected from $R^{44}$ to $R^{51}$ that are not the single bond may each independently be bonded to each other to form a substituted or unsubstituted ring structure, $R^{46}$ and $R^{47}$, and $R^{48}$ and $R^{49}$, are not bonded to each other, thus forming no ring structure, and $R^a$ and $R^b$ are not crosslinked;

in the formula (e), $R^{10}$ to $R^{14}$, *f, and *** are the same as described above, $R^{52}$ to $R^{66}$ are each independently a hydrogen atom, a substituted or unsubstituted alkyl group having 1 to 50 carbon atoms, a substituted or unsubstituted cycloalkyl group having 3 to 50 ring carbon atoms, a halogen atom, a cyano group, a nitro group, a substituted or unsubstituted aryl group having 6 to 30 ring carbon atoms constituted only of 6-membered rings, or a substituted or unsubstituted heterocyclic group having 5 to 50 ring atoms, provided that one selected from $R^{52}$ to $R^{56}$ is a single bond bonded to *l, another one selected from $R^{52}$ to $R^{56}$ is a single bond bonded to *m, m5 is 0 or 1, when m5 is 0, *f is bonded to $L^2$ or $L^3$, adjacent two selected from $R^{10}$ to $R^{14}$ that are not the single bond are, adjacent two selected from $R^{52}$ to $R^{56}$ that are not either of the single bonds are, $R^{52}$ and $R^{61}$ are, and $R^{56}$ and $R^{57}$ are, not bonded to each other, thus forming no ring structure.

2. The compound according to claim 1, wherein $Ar^1$ and $Ar^2$ are each independently a group represented by any of the formulae (a-1) to (e-1):

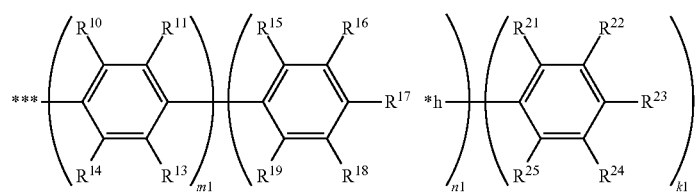

(a-1)

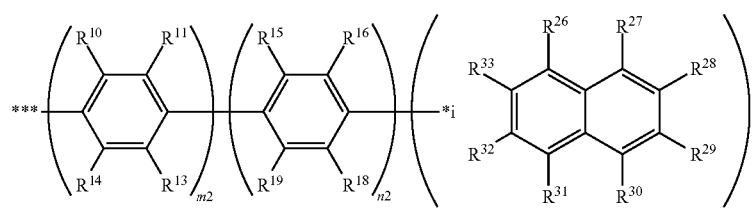

(b-1)

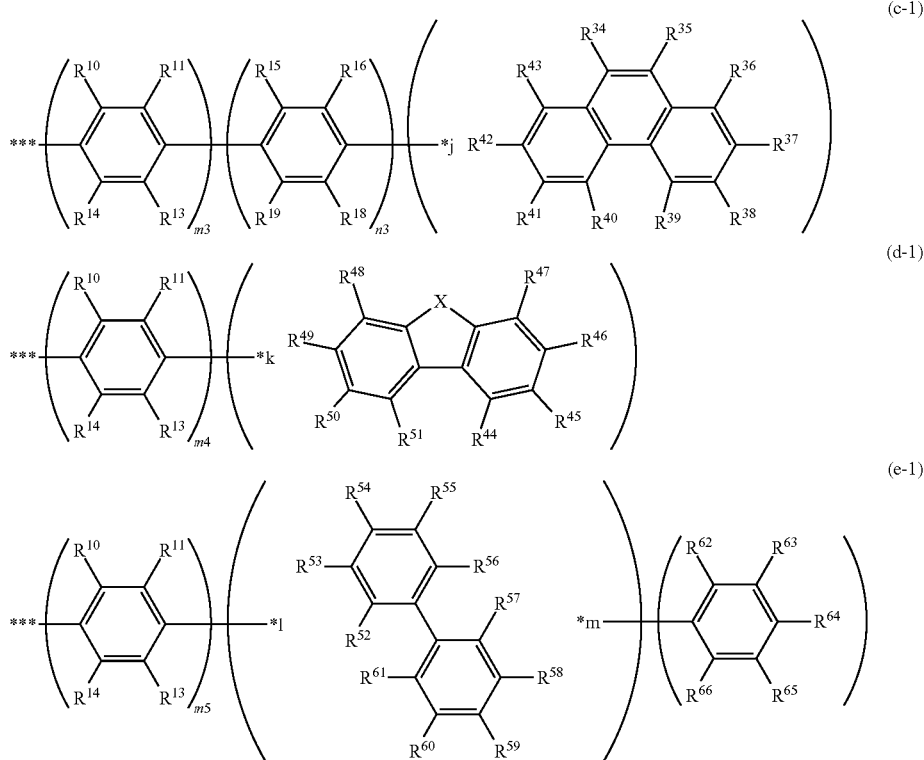

wherein
$R^{10}$, $R^{11}$, $R^{13}$, $R^{14}$, $R^{15}$ to $R^{19}$, $R^{21}$ to $R^{66}$, X, *i, *j, *k, *l, *m, m1, n1, k1, m2, n2, m3, n3, m4, and m5 are as defined in the formula (1).

3. The compound according to claim 1, wherein at least one of $Ar^1$ and $Ar^2$ is a group represented by the formula (a).

4. The compound according to claim 1, wherein $L^2$ and $L^3$ are each independently a single bond, a group represented by the formula (i) or (ii).

5. The compound according to claim 1, wherein *a is bonded to the carbon atom *3.

6. The compound according to claim 1, wherein *b is bonded to the carbon atom *6.

7. The compound according to claim 1, wherein *c is bonded to the carbon atom *7.

8. The compound according to claim 1, wherein X is an oxygen atom, $CR^aR^b$, or $NR^c$.

9. The compound according to claim 1, wherein $R^{34}$ or $R^{37}$ is a single bond bonded to *j.

10. The compound according to claim 1, wherein $R^{53}$ is a single bond bonded to *l and $R^{56}$ is a single bond bonded to *m.

11. The compound according to claim 1, wherein all of $R^1$ to $R^9$ are each a hydrogen atom.

12. The compound according to claim 1, wherein in the formula (a), all of $R^{10}$ to $R^{14}$ at are not the single bond bonded to *f are each a hydrogen atom.

13. The compound according to claim 1, wherein in the formula (a), all of $R^{15}$ to $R^{20}$ that are not the single bond bonded to *g nor the single bond bonded to *h are each a hydrogen atom.

14. The compound according to claim 1, wherein all of $R^{21}$ to $R^{25}$ are each a hydrogen atom.

15. The compound according to claim 1, wherein in the formula (b), all of $R^{10}$ to $R^{14}$ at are not the single bond bonded to *f are each a hydrogen atom.

16. The compound according to claim 1, wherein in the formula (b), all of $R^{15}$ to $R^{20}$ that are not the single bond bonded to *g nor the single bond bonded to *h are each a hydrogen atom.

17. The compound according to claim 1, wherein all of $R^{26}$ to $R^{33}$ that are not the single bond bonded to *i are each a hydrogen atom.

18. The compound according to claim 1, wherein in the formula (c), all of $R^{10}$ to $R^{14}$ at are not the single bond bonded to *f are each a hydrogen atom.

19. The compound according to claim 1, wherein in the formula (c), all of $R^{15}$ to $R^{20}$ that are not the single bond bonded to *g nor the single bond bonded to *h are each a hydrogen atom.

20. The compound according to claim 1, wherein all of $R^{34}$ to $R^{43}$ that are not the single bond bonded to *j are each a hydrogen atom.

21. The compound according to claim 1, wherein in the formula (d), all of $R^{10}$ to $R^{14}$ at are not the single bond bonded to *f are each a hydrogen atom.

22. The compound according to claim 1, wherein all of $R^{44}$ to $R^{51}$ that are not the single bond bonded to *k are each a hydrogen atom.

23. The compound according to claim 1, wherein in the formula (e), all of $R^{10}$ to $R^{14}$ at are not the single bond bonded to *f are each a hydrogen atom.

24. The compound according to claim 1, wherein all of $R^{52}$ to $R^{56}$ that are not the single bond bonded to *l nor the single bond bonded to *m are each a hydrogen atom.

25. The compound according to claim 1, wherein all of $R^{57}$ to $R^{61}$ are each a hydrogen atom.

26. The compound according to claim 1, wherein all of $R^{62}$ to $R^{66}$ are each a hydrogen atom.

27. The compound according to claim 1, wherein the compound represented by the formula (1) comprises at least one deuterium atom.

28. A material for organic electroluminescence devices, the material comprising the compound according claim 1.

29. An organic electroluminescence device comprising a cathode, an anode, and an organic layer between the cathode and the anode, the organic layer comprising a light emitting layer, and at least one layer of the organic layer comprising the compound according claim 1.

30. The organic electroluminescence device according to claim 29, wherein the organic layer comprises a hole transporting zone between the anode and the light emitting layer, the hole transporting zone comprising the compound.

31. The organic electroluminescence device according to claim 30, wherein the hole transporting zone comprises a first hole transporting layer on an anode side and a second hole transporting layer on a cathode side, and at least one of the first hole transporting layer and the second hole transporting layer, or the both containing comprises the compound.

32. The organic electroluminescence device according to claim 31, wherein the second hole transporting layer comprises the compound.

33. The organic electroluminescence device according to claim 31, wherein the second hole transporting layer is adjacent to the light emitting layer.

34. The organic electroluminescence device according to claim 29, wherein the light emitting layer comprises a fluorescent dopant material.

35. The organic electroluminescence device according to claim 29, wherein the light emitting layer comprises a phosphorescent dopant material.

36. An electronic instrument comprising the organic electroluminescence device according to claim 29.

\* \* \* \* \*

UNITED STATES PATENT AND TRADEMARK OFFICE
CERTIFICATE OF CORRECTION

PATENT NO. : 12,012,389 B2  
APPLICATION NO. : 18/329687  
DATED : June 18, 2024  
INVENTOR(S) : Yusuke Takahashi et al.

Page 1 of 2

It is certified that error appears in the above-identified patent and that said Letters Patent is hereby corrected as shown below:

In the Claims

In Column 1205, Claim 1, beginning at Line 51, delete the following formula (c)

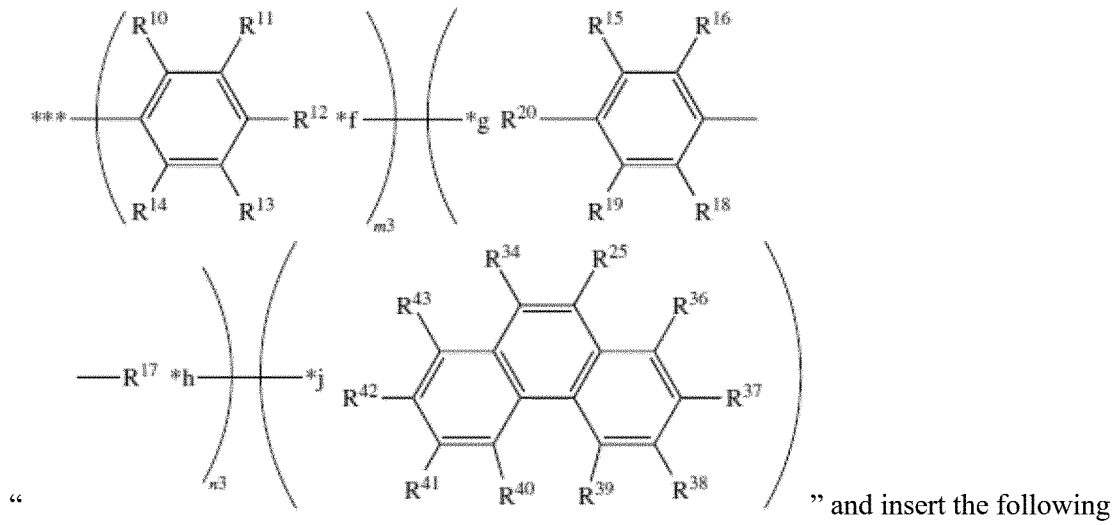

" and insert the following formula (c) therefor

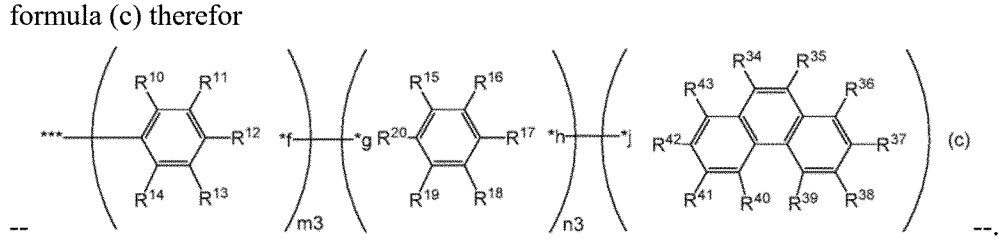

In Column 1206, Claim 1, Line 57, delete "at" and insert -- that --, therefor.

Signed and Sealed this  
First Day of October, 2024

Katherine Kelly Vidal  
*Director of the United States Patent and Trademark Office*

CERTIFICATE OF CORRECTION (continued)
U.S. Pat. No. 12,012,389 B2

In Column 1209, Claim 12, Line 60, delete "at" and insert -- that --, therefor.

In Column 1210, Claim 15, Line 34, delete "at" and insert -- that --, therefor.

In Column 1210, Claim 18, Line 45, delete "at" and insert -- that --, therefor.

In Column 1210, Claim 21, Line 55, delete "at" and insert -- that --, therefor.

In Column 1210, Claim 23, Line 61, delete "at" and insert -- that --, therefor.

In Column 1212, Claim 31, Line 3, delete ", or the both containing".